US012435070B2

(12) United States Patent
Parham et al.

(10) Patent No.: US 12,435,070 B2

(45) Date of Patent: Oct. 7, 2025

(54) COMPOSITION FOR ORGANIC ELECTRONIC DEVICES

(71) Applicant: Merck Patent GmbH, Darmstadt (DE)

(72) Inventors: Amir Parham, Frankfurt am Main (DE); Jonas Kroeber, Frankfurt am Main (DE); Tobias Grossmann, Shanghai (CN); Anja Jatsch, Darmstadt (DE); Christian Eickhoff, Darmstadt (DE); Christian Ehrenreich, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 126 days.

(21) Appl. No.: 18/090,711

(22) Filed: Dec. 29, 2022

(65) Prior Publication Data

US 2023/0150987 A1 May 18, 2023

Related U.S. Application Data

(63) Continuation of application No. 16/628,280, filed as application No. PCT/EP2018/067732 on Jul. 2, 2018, now Pat. No. 11,591,320.

(30) Foreign Application Priority Data

Jul. 5, 2017 (EP) .................................... 17179775
Oct. 5, 2017 (EP) .................................... 17195036

(51) Int. Cl.

| | |
|---|---|
| ***H01L 51/50*** | (2006.01) |
| ***C07D 405/14*** | (2006.01) |
| ***H10K 71/10*** | (2023.01) |
| ***H10K 85/60*** | (2023.01) |
| *H10K 50/11* | (2023.01) |
| *H10K 50/16* | (2023.01) |
| *H10K 50/17* | (2023.01) |
| *H10K 101/10* | (2023.01) |

(52) U.S. Cl.

CPC ........... *C07D 405/14* (2013.01); *H10K 71/10* (2023.02); *H10K 85/654* (2023.02); *H10K 85/6572* (2023.02); *H10K 85/6574* (2023.02); *H10K 50/11* (2023.02); *H10K 50/16* (2023.02); *H10K 50/171* (2023.02); *H10K 2101/10* (2023.02)

(58) Field of Classification Search

None

See application file for complete search history.

(56) References Cited

U.S. PATENT DOCUMENTS

| | | | |
|---|---|---|---|
| 6,392,250 | B1 | 5/2002 | Aziz et al. |
| 6,803,720 | B2 | 10/2004 | Kwong et al. |
| 9,266,851 | B2 | 2/2016 | Yoshida et al. |
| 9,334,260 | B2 | 5/2016 | Parham et al. |
| 9,601,698 | B2 | 3/2017 | Cho et al. |
| 10,355,223 | B2 | 7/2019 | Parham et al. |
| 2014/0158992 | A1 | 6/2014 | Xia et al. |
| 2015/0001488 | A1 | 1/2015 | Min et al. |
| 2015/0318487 | A1 | 11/2015 | Ito et al. |
| 2016/0181548 | A1 | 6/2016 | Parham et al. |
| 2017/0186965 | A1 | 6/2017 | Parham et al. |
| 2018/0090689 | A1 | 3/2018 | Kim et al. |
| 2019/0006590 | A1 | 1/2019 | Park et al. |

FOREIGN PATENT DOCUMENTS

| | | | |
|---|---|---|---|
| EP | 3336159 | A1 | 6/2018 |
| KR | 10-1744248 | B1 | 6/2017 |
| KR | 10-2017-0113320 | A | 10/2017 |
| WO | 2009/069442 | A1 | 6/2009 |
| WO | 2011/046182 | A1 | 4/2011 |
| WO | 2011/057706 | A2 | 5/2011 |
| WO | 2015/014434 | A1 | 2/2015 |
| WO | 2015/156587 | A1 | 10/2015 |
| WO | 2015/165563 | A1 | 11/2015 |
| WO | 2015/169412 | A1 | 11/2015 |
| WO | 2018/101691 | A1 | 6/2018 |

OTHER PUBLICATIONS

International Preliminary Report on Patentability received for PCT Patent Application No. PCT/EP2018/067732, mailed on Jan. 16, 2020, 17 pages (11 pages of English Translation and 6 pages of Original Document).

International Search Report for PCT/EP2018/067732 mailed Aug. 30, 2018.

Written Opinion of the International Searching Authority for PCT/EP2018/067732 mailed Aug. 30, 2018.

Yang, J., et al., "Correlation of the molecular structure of host materials with lifetime and efficiency of blue phosphorescent organic light-emitting diodes", Physical Chemistry Chemical Physics, 2015, vol. 17, pp. 24468-24474.

*Primary Examiner* — Gregory D Clark

(74) *Attorney, Agent, or Firm* — Faegre Drinker Biddle & Reath LLP

(57) ABSTRACT

The present invention relates to a composition which comprises an electron-transporting host and a hole-transporting host, to the use thereof in electronic devices and to electronic devices containing this composition. The electron-transporting host is particularly preferably selected from the class of the triazine-dibenzofuran-carbazole systems or the class of the triazine-dibenzothiophene-carbazole systems. The hole-transporting host is preferably selected from the class of the biscarbazoles.

20 Claims, No Drawings

COMPOSITION FOR ORGANIC ELECTRONIC DEVICES

CROSS-REFERENCE TO RELATED APPLICATIONS

This application is a continuation of U.S. application Ser. No. 16/628,280, filed Jan. 3, 2020, which is a National stage application (under 35 U.S.C. § 371) of PCT/EP2018/067732, filed Jul. 2, 2018, which claims benefit of European Application Nos. 17179775.6, filed Jul. 5, 2017, and 17195036.3, filed Oct. 5, 2017, all of which are incorporated herein by reference in their entirety.

The present invention relates to a composition which comprises an electron-transporting host and a hole-transporting host, to the use thereof in electronic devices and to electronic devices containing this composition. The electron-transporting host is particularly preferably selected from the class of the triazine-dibenzofuran-carbazole systems or the class of the triazine-dibenzothiophene-carbazole systems. The hole-transporting host is preferably selected from the class of the biscarbazoles.

The structure of organic electroluminescent devices (for example OLEDs—organic light-emitting diodes, or OLECs—organic light-emitting electrochemical cells) in which organic semiconductors are employed as functional materials is described, for example, in U.S. Pat. Nos. 4,539,507, 5,151,629, EP 0676461 and WO 98/27136. The emitting materials employed here, besides fluorescent emitters, are increasingly organometallic complexes which exhibit phosphorescence instead of fluorescence (M. A. Baldo et al., Appl. Phys. Lett. 1999, 75, 4-6). For quantum-mechanical reasons, an up to four-fold increase in energy and power efficiency is possible using organometallic compounds as phosphorescence emitters. In general, however, there is still a need for improvement, for example with respect to efficiency, operating voltage and lifetime, in the case of OLEDs, in particular also in the case of OLEDs which exhibit triplet emission (phosphorescence).

The properties of organic electroluminescent devices are not determined only by the emitters employed. Of particular importance here are also, in particular, the other materials used, such as host and matrix materials, hole-blocking materials, electron-transport materials, hole-transport materials and electron- or exciton-blocking materials, and of these in particular the host or matrix materials. Improvements in these materials can result in significant improvements in electroluminescent devices.

Host materials for use in organic electronic devices are well known to the person skilled in the art. The term matrix material is frequently also used in the prior art to mean a host material for phosphorescent emitters. This use of the term also applies to the present invention. In the meantime, a multiplicity of host materials have been developed, both for fluorescent and for phosphorescent electronic devices.

According to the prior art, use is made, inter alia, of ketones (for example in accordance with WO 2004/093207 or WO 2010/006680) or phosphine oxides (for example in accordance with WO 2005/003253) as matrix materials for phosphorescent emitters. Further matrix materials in accordance with the prior art are triazines (for example WO 2008/056746, EP 0906947, EP 0908787, EP 0906948) and lactams (for example WO 2011/116865 or WO 2011/137951). Furthermore, use is made in accordance with the prior art of, inter alia, carbazole derivatives (for example in accordance with WO 2005/039246, US 2005/0069729 or WO 2014/015931), indolocarbazole derivatives (for example in accordance with WO 2007/063754 or WO 2008/056746) or indenocarbazole derivatives (for example in accordance with WO 2010/136109 or WO 2011/000455), in particular those which are substituted by electron-deficient heteroaromatic groups, such as triazine, as matrix materials for phosphorescent emitters. WO 2011/057706 discloses carbazole derivatives which are substituted by two triphenyltriazine groups. WO 2011/046182 discloses carbazol-arylene-triazine derivatives which are substituted on the triazine by a fluorenyl group. WO 2009/069442 discloses tricyclic compounds, such as carbazole, dibenzofuran or dibenzothiophene, which are substituted to a high degree by electron-deficient heteroaromatic groups (for example pyridine, pyrimidine ortriazine), as host materials. WO 2011/057706, WO 2015/014434 and WO 2015/169412 disclose further host materials which comprise, inter alia, triazine-dibenzofuran-carbazole derivatives and triazine-dibenzothiophene-carbazole derivatives, where the triazine is optionally bonded to the dibenzofuran or dibenzothiophene by means of a linker.

A further possibility for improving the performance data of electronic devices, in particular of organic electroluminescent devices, consists in using combinations of two or more materials, in particular host materials or matrix materials.

U.S. Pat. No. 6,392,250 B1 discloses the use of a mixture consisting of an electron-transport material, a hole-transport material and a fluorescent emitter in the emission layer of an OLED. With the aid of this mixture, it has been possible to improve the lifetime of the OLED compared with the prior art.

U.S. Pat. No. 6,803,720 B1 discloses the use of a mixture comprising a phosphorescent emitter and a hole-transport material and an electron-transport material in the emission layer of an OLED. Both the hole-transport material and the electron-transport material are small organic molecules.

U.S. Pat. No. 9,601,698 discloses the use of a mixture of two host materials and a phosphorescent emitter, for example a mixture of a pyridine-carbazole-dibenzothiophene derivative, with a triarylamino-substituted biscarbazole in the emitting layer of an OLED.

According to WO 2015/156587, specific carbazole derivatives in a mixture with biscarbazoles can be used as host materials.

According to WO 2015/169412, triazine-dibenzofuran-carbazole derivatives and triazine-dibenzothiophene-carbazole derivatives, for example, can likewise be used in a mixture. Thus, for example, the production of the OLED with the designation E34, which comprises the host materials EG1, IC6 and the phosphorescent emitter TEG1 in the emitting layer, is described. The structures of the compounds used are shown below:

EG1

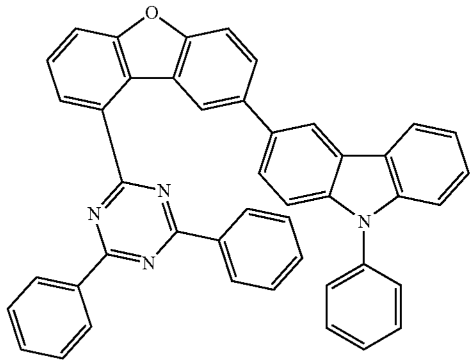

-continued

IC6

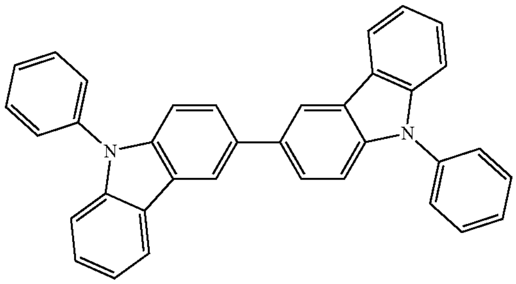

TEG1

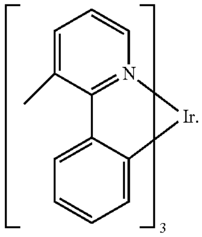

The patent KR101744248 B1 describes a specific sequence of two emitting layers in a device, where each emitting layer comprises two host materials. The first emitting layer comprises host 1-1 and host 1-2. The second emitting layer comprises host 2-1 and host 2-2, where host 1-2 and host 2-1 are the same materials. Claim 7 describes specific 1-2 host materials. Claim 10 describes the compound, abbreviated to EG1 above, as 2-2 host material.

According to the patent application KR20170113320, which was published after the priority date of the present application, the compound abbreviated to EG1 above, mentioned in document H-6, can be used in a mixture together with a di(1,3-biphenyl)-substituted biscarbazole. The corresponding biscarbazole (3-(9'-1,3-biphenyl-9H-carbazol-3'-yl)-9-(1,3-biphenyl)-9H-carbazole) is called H-2 in the document.

However, there is still a need for improvement, in particular in relation to the lifetime of the organic electronic device, on use of these materials or on use of mixtures of the materials.

The object of the present invention is therefore the provision of materials which are suitable for use in an organic electronic device, in particular in an organic electroluminescent device, and in particular in a fluorescent or phosphorescent OLED, and lead to good device properties, in particular with respect to an improved lifetime, and the provision of the corresponding electronic device.

It is now been found that compositions which comprise compounds of the formula (1), for example particularly preferably triazine-dibenzofuran-carbazole derivatives or triazine-dibenzothiophene-carbazole derivatives, and a hole-transporting host of the formula (2), preferably biscarbazoles, achieve this object and overcome the disadvantages from the prior art.

Compositions of this type lead to very good properties of organic electronic devices, in particular organic electroluminescent devices, in particular with respect to the lifetime and in particular also in the presence of a light-emitting component in the emission layer at concentrations between 2 and 15% by weight.

The present invention therefore relates firstly to a composition comprising at least one compound of the formula (1) and at least one compound of the formula (2)

formula (1)

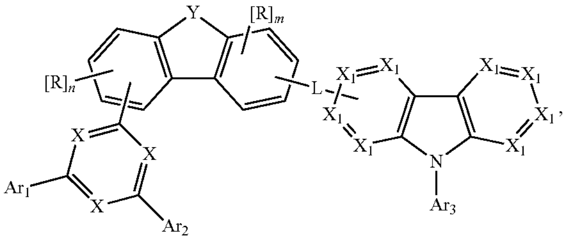

formula (2)

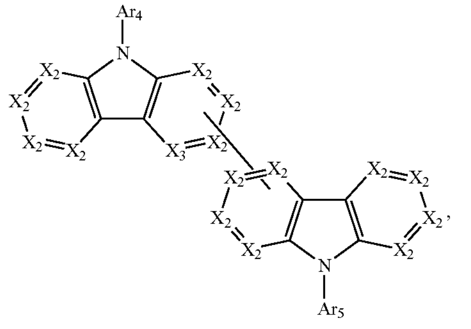

where the following applies to the symbols and indices used:

X is on each occurrence, identically or differently, $CR^0$ or N, with the proviso that at least one group X stands for N;

$X_1$ is on each occurrence, identically or differently, CR or N;

$X_2$ is on each occurrence, identically or differently, $CR^1$ or N;

Y is selected from O or S;

L is on each occurrence, identically or differently, a single bond or an aromatic or heteroaromatic ring system having 5 to 30 aromatic ring atoms, which may be substituted by one or more radicals $R^3$, preferably an aromatic or heteroaromatic ring system having 6 to 18 C atoms, which may be substituted by one or more radicals $R^3$ $Ar_1$, $Ar_2$ are in each case, independently of one another on each occurrence, an aryl or heteroaryl group having 5 to 40 aromatic ring atoms, which may be substituted by one or more radicals $R^3$;

$Ar_3$ is an aromatic ring system having 6 to 40 aromatic ring atoms or a heteroaromatic ring system having 10 to 40 aromatic ring atoms, which may be substituted by one or more radicals $R^3$;

$Ar_4$ and $Ar_5$ are in each case, independently of one another, an aromatic ring system having 6 to 40 aromatic ring atoms or a heteroaromatic ring system having 10 to 40 aromatic ring atoms, which may be substituted by one or more radicals $R^3$, with the proviso that $Ar_4$ and $Ar_5$ cannot simultaneously be phenyl;

$R^0$, R, $R^1$ are selected on each occurrence, identically or differently, from the group consisting of H, D, F, Cl, Br, I, CN, $NO_2$, $N(Ar)_2$, $N(R^2)_2$, C(═O)Ar, $C(═O)R^2$, $P(═O)(Ar)_2$, $P(Ar)_2$, $B(Ar)_2$, $Si(Ar)_3$, $Si(R^2)_3$, a straight-chain alkyl, alkoxy or thioalkyl group having 1 to 20 C atoms or a branched or cyclic alkyl, alkoxy or thioalkyl group having 3 to 20 C atoms or an alkenyl group having 2 to 20 C atoms, which may in each case be substituted by one or more radicals $R^2$, where one or more nonadjacent $CH_2$ groups may be replaced by $R^2C{=}CR^2$, $Si(R^2)_2$, C═O, C═S, $C{=}NR^2$, $P({=}O)(R^2)$, SO, $SO_2$, $NR^2$, O, S or $CONR^2$ and where one or more H atoms may be replaced by D, F, Cl, Br, I, CN or $NO_2$, an aromatic or heteroaromatic ring system having 5 to 40 aromatic ring atoms, which may in each case be substituted by one or more radicals $R^2$, or an aryloxy or heteroaryloxy group having 5 to 40 aromatic ring atoms, which may be substituted by one or more radicals $R^2$, or an aralkyl or heteroaralkyl group having 5 to 40 aromatic ring atoms, which may be substituted by one or more radicals $R^2$; two substituents $R^0$ and/or R and/or $R^1$ which are bonded to the same carbon atom or to adjacent carbon atoms may optionally form a monocyclic or polycyclic, aliphatic, aromatic or heteroaromatic ring system, which may be substituted by one or more radicals $R^2$;

$R^2$ is selected on each occurrence, identically or differently, from the group consisting of H, D, F, Cl, Br, I, CN, $NO_2$, $N(Ar)_2$, $NH_2$, $N(R^3)_2$, C(═O)Ar, C(═O)H, $C({=}O)R^3$, $P({=}O)(Ar)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, which may in each case be substituted by one or more radicals $R^3$, where one or more non-adjacent $CH_2$ groups may be replaced by HC═CH, $R^3C{=}CR^3$, C≡C, $Si(R^3)_2$, $Ge(R^3)_2$, $Sn(R^3)_2$, C═O, C═S, C═Se, $C{=}NR^3$, $P({=}O)(R^3)$, SO, $SO_2$, NH, $NR^3$, O, S, CONH or $CONR^3$ and where one or more H atoms may be replaced by D, F, Cl, Br, I, CN or $NO_2$, an aromatic or heteroaromatic ring system having 5 to 60 aromatic ring atoms, which may in each case be substituted by one or more radicals $R^3$, or an aryloxy or heteroaryloxy group having 5 to 60 aromatic ring atoms, which may be substituted by one or more radicals $R^3$, or a combination of these systems, where two or more adjacent substituents $R^2$ may optionally form a monocyclic or polycyclic, aliphatic, aromatic or heteroaromatic ring system, which may be substituted by one or more radicals $R^3$;

$R^3$ is selected on each occurrence, identically or differently, from the group consisting of H, D, F, CN, an aliphatic hydrocarbon radical having 1 to 20 C atoms or an aromatic or heteroaromatic ring system having 5 to 30 aromatic ring atoms, in which one or more H atoms may be replaced by D, F, Cl, Br, I or CN and which may be substituted by one or more alkyl groups, each having 1 to 4 carbon atoms; two or more adjacent substituents $R^3$ may form a mono- or polycyclic, aliphatic ring system with one another;

Ar is on each occurrence, identically or differently, an aromatic or heteroaromatic ring system having 5 to 30 aromatic ring atoms, which may be substituted by one or more non-aromatic radicals $R^3$; two radicals Ar which are bonded to the same N atom, P atom or B atom may also be bridged to one another by a single bond or a bridge selected from $N(R^3)$, $C(R^3)_2$, O or S, and n and m, independently of one another, denote 0, 1, 2 or 3.

L is in accordance with the invention preferably an aromatic or heteroaromatic ring system having 6 to 18 C atoms, which may be substituted by one or more radicals $R^3$. The aromatic or heteroaromatic ring system having 6 to 18 C atoms is preferably a linker selected from L-1 to L-40 as described below, which may be substituted by one or more radicals $R^3$. L is in accordance with the invention particularly preferably an aromatic ring system having 6 to 18 C atoms, which may be substituted by one or more radicals $R^3$, very particularly preferably selected from phenylene, naphthylene, biphenylene, phenanthrenylene or triphenylenylene, where the bonding to the other substituents is not restricted. The aromatic ring system having 6 to 18 C atoms is preferably phenylene, where the bonding to the other substituents is not restricted. Phenylene here can be linked to the dibenzofuran/dibenzothiophene unit and the carbazole unit in the ortho, meta or para position. L as phenylene is preferably linked in the meta position.

The invention furthermore relates to formulations which comprise compositions of this type, to the use of these compositions in an organic electronic device, to organic electronic devices, preferably electroluminescent devices, which contain compositions of this type, and preferably contain the composition in a layer, and to a process for the production of devices of this type. The present invention likewise relates to the corresponding preferred embodiments, as described below. The surprising and advantageous effects are achieved by specific selection of known materials, in particular relating to the choice of electron-conducting materials of the formula (1) and hole-transporting materials of the formula (2).

The layer which comprises the composition comprising at least one compound of the formula (1) and at least one compound of the formula (2), as described above or preferably described below, is, in particular, an emitting layer (EML), an electron-transport layer (ETL), an electron-injection layer (EIL) and/or a hole-blocking layer (HBL).

In the case of an emitting layer, this is preferably a phosphorescent layer which is characterised in that it comprises a phosphorescent emitter in addition to the composition comprising the matrix materials of the formula (1) and formula (2), as described above.

Adjacent carbon atoms in the sense of the present invention are carbon atoms which are linked directly to one another.

The formulation that two or more radicals can form a ring with one another is, for the purposes of the present description, intended to be taken to mean, inter alia, that the two radicals are linked to one another by a chemical bond with formal elimination of two hydrogen atoms. This is illustrated by the following scheme:

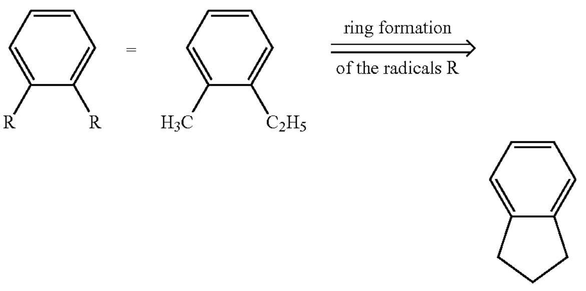

Furthermore, however, the above-mentioned formulation is also intended to be taken to mean that, in the case where one of the two radicals represents hydrogen, the second radical is bonded at the position at which the hydrogen atom was bonded, with formation of a ring. This is intended to be illustrated by the following scheme:

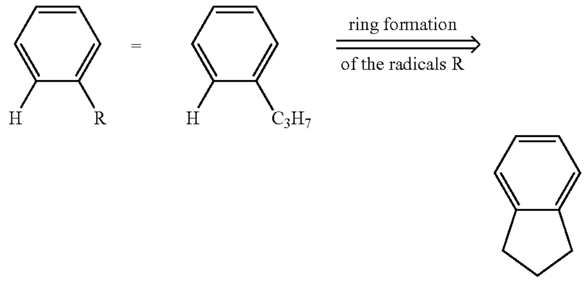

An aryl group in the sense of this invention contains 6 to 40 aromatic ring atoms, preferably C atoms. A heteroaryl group in the sense of this invention contains 5 to 40 aromatic ring atoms, where the ring atoms include C atoms and at least one heteroatom, with the proviso that the sum of C atoms and heteroatoms is at least 5. The heteroatoms are preferably selected from N, O and/or S. An aryl group or heteroaryl group here is either a simple aromatic ring, i.e. phenyl, derived from benzene, or a simple heteroaromatic ring, for example derived from pyridine, pyrimidine or thiophene, or a condensed aryl or heteroaryl group, for example derived from naphthalene, anthracene, phenanthrene, quinoline or isoquinoline. An aryl group having 6 to 10 C atoms is therefore preferably phenyl or naphthyl, where the bonding of the aryl group as substituent is not restricted. An arylene group having 6 to 10 C atoms is therefore preferably phenylene or naphthylene, where the linking of the arylene group as linker is not restricted.

An aromatic ring system in the sense of this invention contains 6 to 40 C atoms in the ring system and may be substituted by one or more radicals $R^3$, where $R^3$ has a meaning described below. An aromatic ring system also contains aryl groups, as described above.

A heteroaromatic ring system in the sense of this invention contains 5 to 40 ring atoms and at least one heteroatom and may be substituted by one or more radicals $R^3$, where $R^3$ has a meaning described below. A preferred heteroaromatic ring system has 10 to 40 ring atoms and at least one heteroatom and may be substituted by one or more radicals $R^3$, where $R^3$ has a meaning described below. A heteroaromatic ring system also contains heteroaryl groups, as described above. The heteroatoms in the heteroaromatic ring system are preferably selected from N, O and/or S. An aromatic or heteroaromatic ring system in the sense of this invention is taken to mean a system which does not necessarily contain only aryl or heteroaryl groups, but instead in which, in addition, a plurality of aryl or heteroaryl groups may be interrupted by a non-aromatic unit (preferably less than 10% of the atoms other than H), such as, for example, a C, N or O atom or a carbonyl group. Thus, for example, systems such as 9,9'-spirobifluorene, 9,9-diarylfluorene, triarylamine, diaryl ether, stilbene, etc. are intended to be taken to be aromatic or heteroaromatic ring systems in the sense of this invention, as are systems in which two or more aryl groups are interrupted, for example, by a linear or cyclic alkyl group or by a silyl group. Furthermore, systems in which two or more aryl or heteroaryl groups are bonded directly to one another, such as, for example, biphenyl, terphenyl, quaterphenyl or bipyridine, are likewise covered by the definition of the aromatic or heteroaromatic ring system.

An aromatic or heteroaromatic ring system having 5-40 aromatic ring atoms, which may also in each case be substituted by the said radicals $R^3$ and which may be linked to the aromatic or heteroaromatic ring system via any desired positions, is taken to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

The abbreviation Ar is on each occurrence, identically or differently, an aromatic or heteroaromatic ring system having 5 to 30 aromatic ring atoms, which may be substituted by one or more non-aromatic radicals $R^3$; two radicals Ar which are bonded to the same N atom, P atom or B atom may also be bridged to one another by a single bond or a bridge selected from $N(R^3)$, $C(R^3)_2$, O or S. The substituent $R^3$ has been described above or is preferably described below.

A cyclic alkyl, alkoxy or thioalkoxy group in the sense of this invention is taken to mean a monocyclic, bicyclic or polycyclic group.

For the purposes of the present invention, a $C_1$- to $C_{20}$-alkyl group, in which, in addition, individual H atoms or $CH_2$ groups may be substituted by the above-mentioned groups, is taken to mean, for example, the radicals methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl)cyclohex-1-yl, 1-(n-hexyl)cyclohex-1-yl, 1-(n-octyl)cyclohex-1-yl and 1-(n-decyl)cyclohex-1-yl.

An alkenyl group is taken to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl.

An alkynyl group is taken to mean, for example, ethynyl, propynyl, butynyl, pentynyl, hexynyl, heptynyl or octynyl.

A $C_1$- to $C_{20}$-alkoxy group is taken to mean, for example, methoxy, trifluoromethoxy, ethoxy, n-propoxy, i-propoxy, n-butoxy, i-butoxy, s-butoxy, t-butoxy or 2-methylbutoxy.

A $C_1$- to $C_{20}$-thioalkyl group is taken to mean, for example, S-alkyl groups, for example thiomethyl, 1-thioethyl, 1-thio-i-propyl, 1-thio-n-propyl, 1-thio-i-butyl, 1-thio-n-butyl or 1-thio-t-butyl.

An aryloxy or heteroaryloxy group having 5 to 40 aromatic ring atoms denotes O-aryl or O-heteroaryl and means that the aryl or heteroaryl group respectively is bonded via an oxygen atom.

An aralkyl or heteroaralkyl group having 5 to 40 aromatic ring atoms means that an alkyl group, as described above, is substituted by an aryl group or heteroaryl group.

A phosphorescent emitter in the sense of the present invention is a compound which exhibits luminescence from an excited state having relatively high spin multiplicity, i.e. a spin state >1, in particular from an excited triplet state. For the purposes of this application, all luminescent complexes containing transition metals or lanthanides are to be regarded as phosphorescent emitters. A more precise definition is given below.

If the composition comprising at least one compound of the formula (1), as described above or preferably described below, and at least one compound of the formula (2), as described above or described below, is employed as matrix material for a phosphorescent emitter, its triplet energy is preferably not significantly less than the triplet energy of the phosphorescent emitter. The following preferably applies to the triplet level: $T_1$(emitter)$-T_1$(matrix)$\leq$0.2 eV, particularly preferably $\leq$0.15 eV, very particularly preferably $\leq$0.1 eV. $T_1$(matrix) here is the triplet level of the matrix material in the emission layer, where this condition applies to each of the two matrix materials, and $T_1$(emitter) is the triplet level of the phosphorescent emitter. If the emission layer comprises more than two matrix materials, the abovementioned relationship preferably also applies to each further matrix material.

Electron-Transporting Hosts of the Formula (1):

In an embodiment of the invention, compounds of the formula (1) are selected in which Y is selected from O or S and the substituent

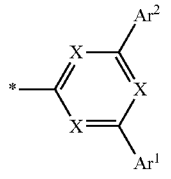

is bonded in position 1, 2, 3 or 4 of the dibenzofuran or dibenzothiophene, where X, $X_1$, Y, L, $Ar_1$, $Ar_2$, $Ar_3$, R, n and m have a meaning indicated above or a meaning indicated below and * denotes the linking site to the dibenzofuran or dibenzothiophene.

The symbol $X_1$ in compounds of the formula (1) preferably stands twice for N, particularly preferably once for N, and the remaining groups $X_1$ then stand for CR, where R in each case, independently of one another, has a meaning indicated above or preferably indicated below. $X_1$ in compounds of the formula (1) is very particularly preferably CR.

Compounds of the formula (1) in which $X_1$ on each occurrence, identically or differently, denotes CR and the substituent

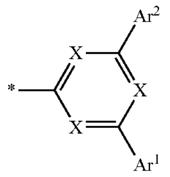

is located in position 1 or 2 of the dibenzofuran or dibenzothiophene are represented by the formulae (1a) and (1b), formula (1a)

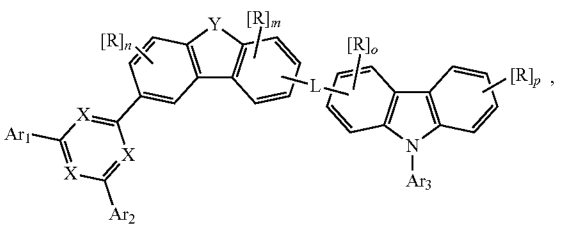

formula (1b)

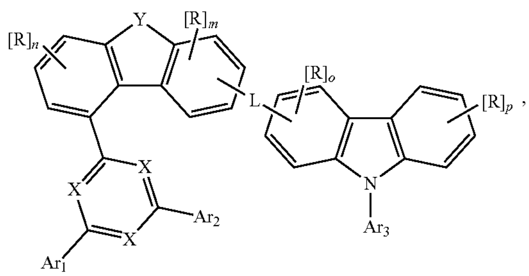

where X, Y, L, $Ar_1$, $Ar_2$, $Ar_3$, R, n and m have a meaning indicated above or a meaning indicated below and p and o in each case, independently of one another, denote 0, 1, 2 or 3.

Compounds of the formula (1) in which $X_1$ on each occurrence, identically or differently, denotes CR and the substituent

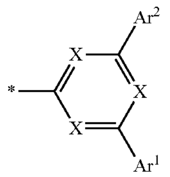

is located in position 3 or 4 of the dibenzofuran or dibenzothiophene are represented by the formulae (1c) and (1d), formula (1c)

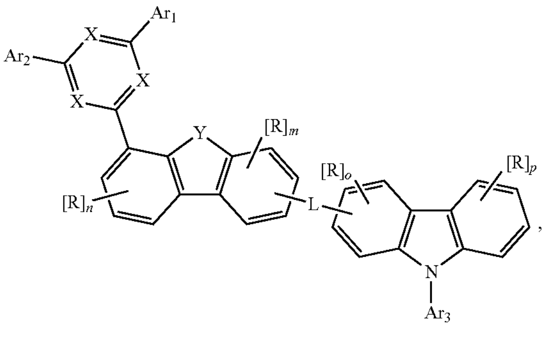

formula (1d)

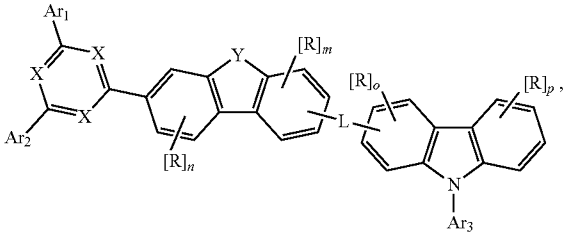

where X, Y, L, $Ar_1$, $Ar_2$, $Ar_3$, R, n and m have a meaning indicated above or a meaning indicated below and p and o in each case, independently of one another, denote 0, 1, 2 or 3.

At least one compound of the formula (1a), having substituents described above or preferably described below, is preferably selected for the composition.

At least one compound of the formula (1b), having substituents described above or preferably described below, is preferably selected for the composition.

At least one compound of the formula (1c), having substituents described above or preferably described below, is preferably selected for the composition.

At least one compound of the formula (1d), having substituents described above or preferably described below, is preferably selected for the composition.

The invention accordingly furthermore relates to a composition, as described above, where the compound of the formula (1) corresponds to the compound of the formula (1a), (1b), (1c) or (1d), preferably the formula (1b) or (1c).

The symbol X in compounds of the formula (1), (1a), (1 b), (1c) or (1d) preferably stands at least once for N, particularly preferably twice for N, and very particularly preferably all symbols X stand for N. The remaining groups X then stand for $CR^0$, in particular for CH.

$R^0$ is preferably selected on each occurrence, identically or differently, from the group consisting of H, D, F or an aromatic or heteroaromatic ring system having 5 to 40 aromatic ring atoms. $R^0$ is on each occurrence particularly preferably H.

Accordingly, a compound of the formula (1), (1a), (1b), (1c) or (1d) in which the substituent

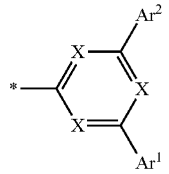

denotes a triazine is particularly preferably selected for the composition.

In this embodiment, compounds of the formula (1e), formula (1e)

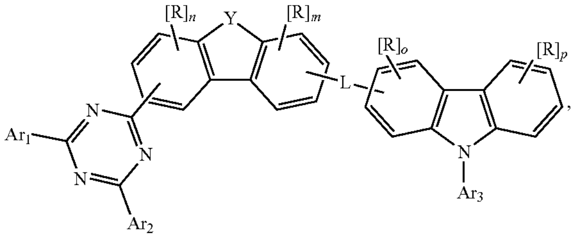

where Y, L, $Ar_1$, $Ar_2$, $Ar_3$, R, n and m have a meaning indicated above or a meaning indicated below, the triazine substituent is linked in position 1, 2, 3 or 4 and p and o in each case, independently of one another, denote 0, 1, 2 or 3, are preferably selected for the composition.

In compounds of the formula (1), (1a), (1b), (1c), (1d) or (1e) or preferably described compounds of the formula (1), (1a), (1b), (1c), (1d) or (1e), $Ar_1$ and $Ar_2$ in each case, independently of one another, preferably stand for an aryl group having 6 to 40 C atoms, as described or preferably described above, which may be substituted by one or more radicals $R^3$. Particularly preferably, at least one $Ar_1$ or $Ar_2$ stands for phenyl and the other aromatic substituent stands for an aryl group having 6 to 40 C atoms, which may be substituted by one or more radicals $R^3$. Particularly preferably, at least one $Ar_1$ or $Ar_2$ stands for phenyl and the other aromatic substituent stands for a phenyl group, which may be substituted by one or more radicals $R^3$. Very particularly preferably, the two groups $Ar_1$ and $Ar_2$ are identical. Very particularly preferably, both groups $Ar_1$ and $Ar_2$ stand for phenyl.

If $Ar_1$ and $Ar_2$, as described or preferably described above, in compounds of the formula (1), (1a), (1b), (1c), (1d) or (1e) or preferably described compounds of the formula (1), (1a), (1b), (1c), (1d) or (1e) denote an aryl or heteroaryl group which is substituted by one or more radicals $R^3$, the substituent $R^3$ is preferably selected on each occurrence, identically or differently, from the group consisting of D, F or an aromatic or heteroaromatic ring system having 5 to 40 aromatic ring atoms. For this/these substituent/s $R^3$, the heteroaromatic ring system having 5 to 40 aromatic ring atoms is preferably derived from dibenzofuran or dibenzothiophene. For this/these substituent/s $R^3$, the aromatic ring system having 6 to 40 aromatic ring atoms is preferably phenyl, biphenyl or terphenyl, particularly preferably phenyl or [1,1',2',1"]-terphenyl-5'-yl. The aryl group or heteroaryl group in $Ar_1$ and $Ar_2$ is in each case, independently of one another, preferably monosubstituted by $R^3$. The aryl group or heteroaryl group in $Ar_1$ or $Ar_2$ is particularly preferably monosubstituted by $R^3$. The aryl group or heteroaryl group in $Ar_1$ and $Ar_2$ is very particularly preferably unsubstituted.

In compounds of the formula (1), (1a), (1b), (1c), (1d) or (1e) or preferably described compounds of the formula (1), (1a), (1b), (1c), (1d) or (1e), Y is selected from O or S. Y particularly preferably stands for O.

In compounds of the formula (1), (1a), (1b), (1c), (1d) or (1e) or preferably described compounds of the formula (1), (1a), (1b), (1c), (1d) or (1e), n is preferably 0 or 1, where R has a meaning indicated above or a meaning indicated below. n is particularly preferably 0.

In compounds of the formula (1), (1a), (1b), (1c), (1d) or (1e) or in preferably described compounds of the formula (1), (1a), (1b), (1c), (1d) or (1e), m is preferably 0 or 1, where R has a meaning indicated above or a meaning indicated below. m is particularly preferably 0.

In compounds of the formula (1), (1a), (1b), (1c), (1d) or (1e) or in preferably described compounds of the formula (1), (1a), (1b), (1c), (1d) or (1e), the sum of n and m, abbreviated to (n+m), is preferably 0, 1 or 2, where R has a meaning indicated above or a meaning indicated below. (n+m) is particularly preferably 0 or 1. (n+m) is very particularly preferably 0.

If n and m are greater than 0 or n or m is greater than 0 in compounds of the formula (1), (1a), (1b), (1c), (1d) or (1e) or in preferably described compounds of the formula (1), (1a), (1b), (1c), (1d) or (1e), the substituent R is preferably selected on each occurrence, identically or differently, from the group consisting of D, F, an alkyl group having 1 to 40 C atoms or an aromatic or heteroaromatic ring system having 5 to 40 aromatic ring atoms. For this substituent R, the heteroaromatic ring system having 5 to 40 aromatic ring atoms is preferably derived from dibenzofuran or dibenzothiophene. For this substituent R, the aromatic ring system having 6 to 40 aromatic ring atoms is preferably phenyl, biphenyl or terphenyl, particularly preferably phenyl or [1,1',2',1"]-terphenyl-5'-yl. For this substituent R, the alkyl group having 1 to 40 C atoms is preferably a linear or branched alkyl group having 1 to 4 C atoms, particularly preferably methyl, ethyl, n-propyl or n-butyl, very particularly preferably methyl.

In compounds of the formula (1), (1a), (1b), (1c), (1d) or (1e) or preferably described compounds of the formula (1), (1a), (1b), (1c), (1d) or (1e), L is preferably on each occurrence, identically or differently, a single bond or an aromatic or heteroaromatic ring system having 6 to 18 C atoms, which may be substituted by one or more radicals $R^3$.

In compounds of the formula (1), (1a), (1b), (1c), (1d) or (1e) or preferably described compounds of the formula (1), (1a), (1b), (1c), (1d) or (1e), L is particularly preferably an aromatic or heteroaromatic ring system having 6 to 18 C atoms, which may be substituted by one or more radicals $R^3$.

In compounds of the formula (1), (1a), (1b), (1c), (1d) or (1e) or preferably described compounds of the formula (1), (1a), (1b), (1c), (1d) or (1e), L is very particularly preferably an aromatic ring system having 6 to 18 C atoms, which may be substituted by one or more radicals $R^3$. $R^3$ here is preferably selected from the group consisting of D or phenyl.

The aromatic or heteroaromatic ring system having 6 to 18 C atoms is preferably a linker selected from L-1 to L-40, which are unsubstituted or may be substituted by $R^3$, as described above:

L-1

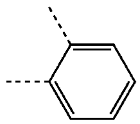

L-2

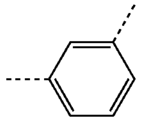

L-3

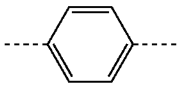

L-4

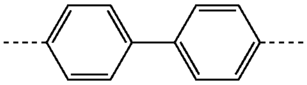

L-5

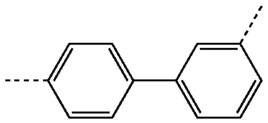

L-6

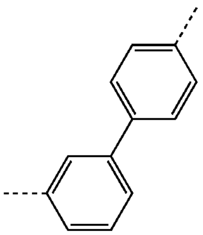

L-7

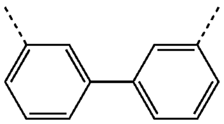

L-8

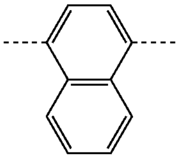

L-9

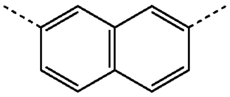

L-10

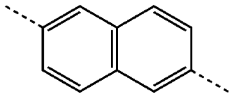

L-11

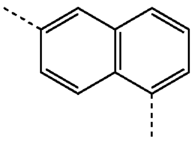

-continued
L-12
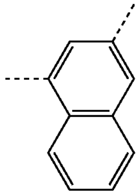
L-13
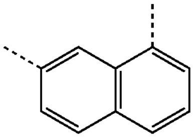
L-14
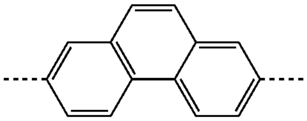
L-15
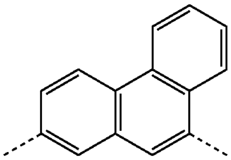
L-16
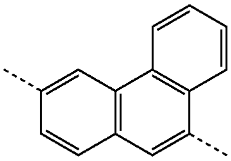
L-17
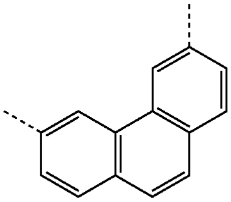
L-18
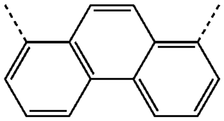
L-19
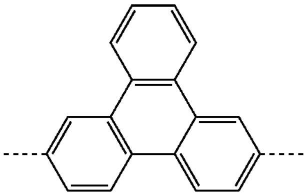
L-20
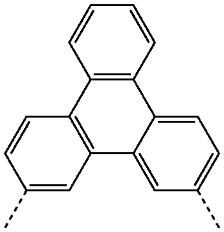
-continued
L-21
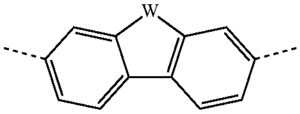
L-22
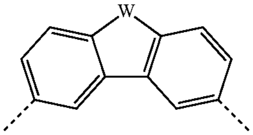
L-23
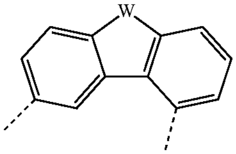
L-24
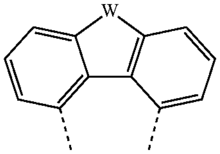
L-25
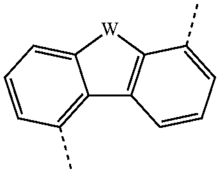
L-26
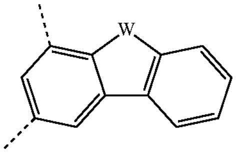
L-27
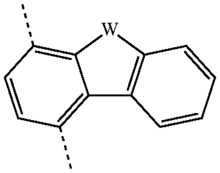
L-28
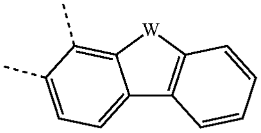
L-29
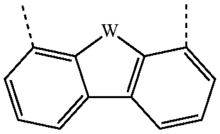
L-30
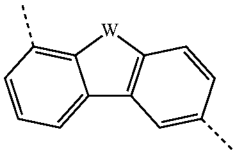

-continued

L-31

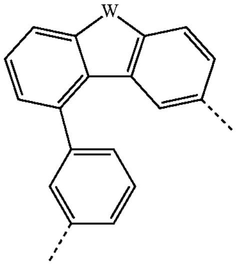

L-32

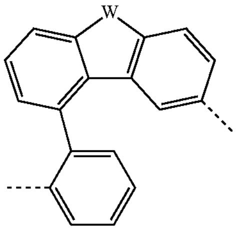

L-33

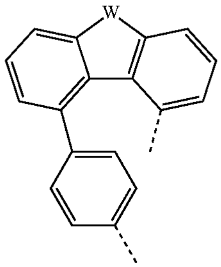

L-34

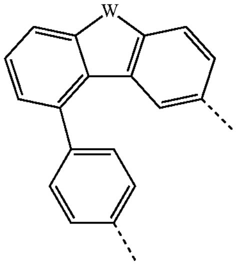

L-35

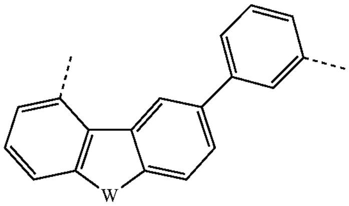

L-36

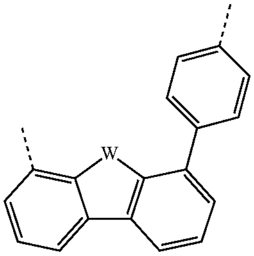

-continued

L-37

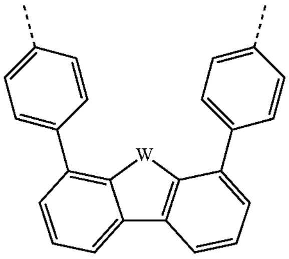

L-38

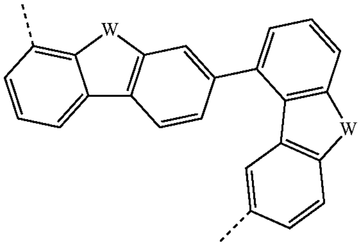

L-39

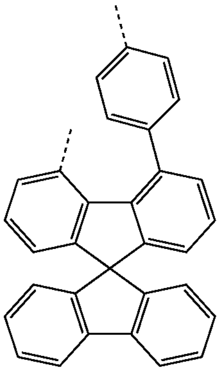

L-40

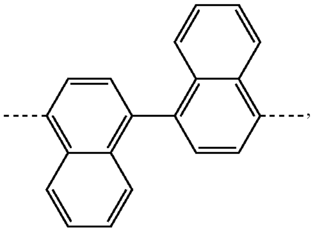

where W denotes N—$R^0$, O, S or $C(R^0)_2$ and $R^0$ has a meaning indicated or preferably indicated above. W is preferably O or S. W is particularly preferably $C(R^0)_2$, where $R^0$ particularly preferably denotes methyl or phenyl.

The aromatic ring system having 6 to 18 C atoms and thus the linker L is particularly preferably selected from phenylene, naphthylene, biphenylene, phenanthrenylene or triphenylenylene, where bonding to the other substituents is not restricted. The aromatic ring system having 6 to 18 C atoms especially phenylene, where the bonding to the other substituents is not restricted. Phenylene can be linked to the dibenzofuran/dibenzothiophene unit and carbazole unit here in the ortho, meta or para position. L as phenylene is preferably linked in the meta position.

L or one of the linkers L-1 to L-40 is preferably unsubstituted.

In compounds of the formula (1), (1a), (1b), (1c), (1d) or (1e) or preferably described compounds of the formula (1), (1a), (1b), (1c), (1d) or (1e), L can be linked in position 6, 7, 8 or 9 of the dibenzofuran ring or dibenzothiophene ring. L, as described above or as preferably described, is preferably linked in position 6 or position 8 of the dibenzofuran ring or dibenzothiophene ring. L, as described above or as preferably described, is particularly preferably linked in position 8 of the dibenzofuran ring or dibenzothiophene ring.

In this embodiment, if L is linked at position 8 of the dibenzofuran ring or dibenzothiophene ring, compounds of the formula (1f), formula (1f)

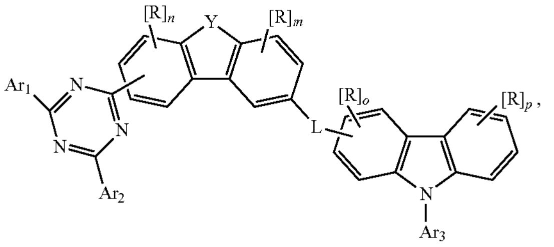

where Y, L, $Ar_1$, $Ar_2$, n and m have a meaning indicated or preferably indicated above, R has a meaning indicated above or below, the triazine substituent is linked in position 1, 2, 3 or 4, $Ar_3$ has a meaning indicated above or described as preferred below and p and o in each case, independently of one another, denote 0, 1, 2 or 3, are preferably selected for the composition.

If L is a single bond, compounds of the formula (1g), formula (1g)

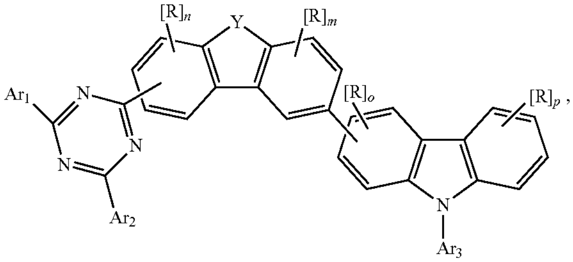

where Y, $Ar_1$, $Ar_2$, n and m have a meaning indicated or preferably indicated above, R has a meaning indicated above or below, the triazine substituent is linked in position 1, 2, 3 or 4, $Ar_3$ has a meaning indicated above or described as preferred below and p and o in each case, independently of one another, denote 0, 1, 2 or 3, are preferably selected for the composition.

In compounds of the formula (1), (1a), (1b), (1c), (1d), (1e), (1f) or (1g) or preferably described compounds of the formula (1), (1a), (1b), (1c), (1d), (1e), (1f) or (1g), L can be bonded to the heteroaryl, preferably the carbazole, in any desired position. L, as described above or as preferably described, is preferably linked in position 3 of the carbazole.

In this embodiment, compounds of the formula (1 h), formula (1h)

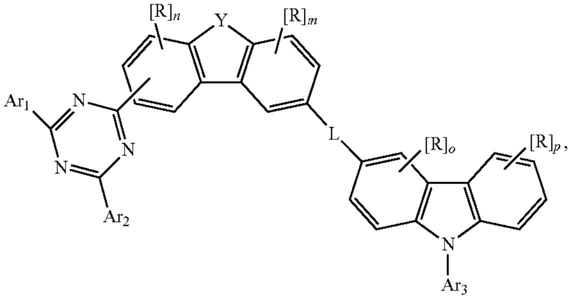

where Y, $Ar_1$, $Ar_2$, L, n and m have a meaning indicated or preferably indicated above, R has a meaning indicated above or below, the triazine substituent is linked in position 1, 2, 3 or 4, $Ar_3$ has a meaning indicated above or described as preferred below and p and o in each case, independently of one another, denote 0, 1, 2 or 3, are preferably selected for the composition.

Particularly preferably selected compounds of the formula (1), as described above or as preferably described, correspond to the formula (1i), formula (1i)

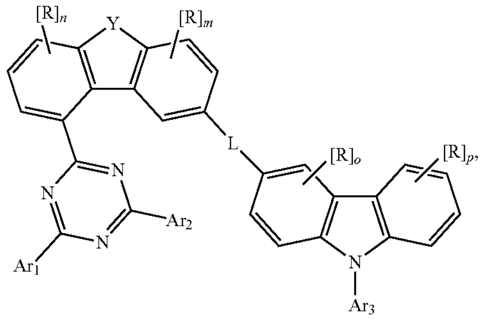

where Y, $Ar_1$, $Ar_2$, L, n and m have a meaning indicated or preferably indicated above, R has a meaning indicated above or below, $Ar_3$ has a meaning indicated above or described as preferred below and p and o in each case, independently of one another, denote 0, 1, 2 or 3.

Particularly preferably selected compounds of the formula (1), as described above or as preferably described, correspond to the formula (1j), formula (1j)

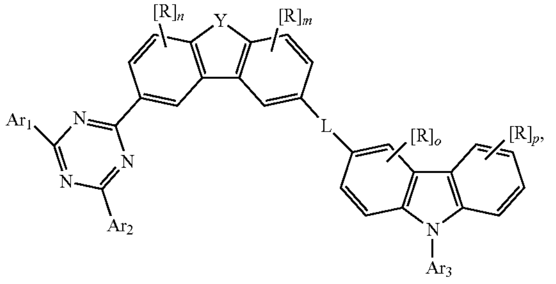

where Y, $Ar_1$, $Ar_2$, L, n and m have a meaning indicated or preferably indicated above, R has a meaning indicated above or below, $Ar_3$ has a meaning indicated above or described as preferred below and p and o in each case, independently of one another, denote 0, 1, 2 or 3.

Particularly preferably selected compounds of the formula (1), as described above or as preferably described, correspond to the formula (1k), formula (1k)

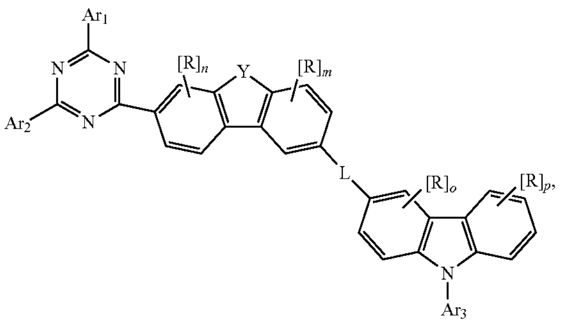

where Y, $Ar_1$, $Ar_2$, L, n and m have a meaning indicated or preferably indicated above, R has a meaning indicated above or below, $Ar_3$ has a meaning indicated above or described as preferred below and p and o in each case, independently of one another, denote 0, 1, 2 or 3.

Particularly preferably selected compounds of the formula (1), as described above or as preferably described, correspond to the formula (1l), formula (1l)

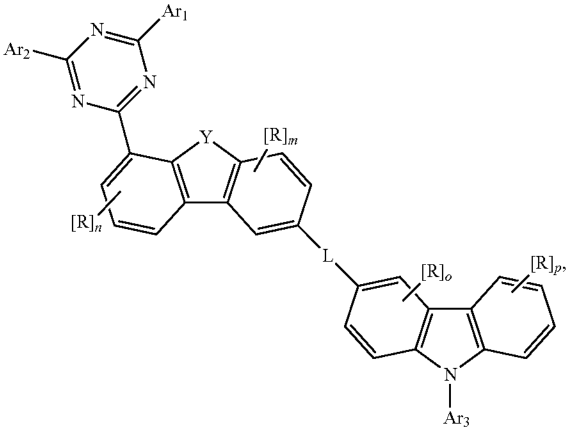

where Y, $Ar_1$, $Ar_2$, L, n and m have a meaning indicated or preferably indicated above, R has a meaning indicated above or below, $Ar_3$ has a meaning indicated above or described as preferred below and p and o in each case, independently of one another, denote 0, 1, 2 or 3.

In compounds of the formula (1), (1a), (1b), (1c), (1d), (1e), (1f), (1g), (1h), (1i), (1j), (1k) or (1l) or preferably described compounds of the formula (1), (1a), (1b), (1c), (1d), (1e), (1f), (1g), (1h), (1i), (1j), (1k) or (1l), o is preferably 0 or 1, where R has a meaning indicated above or a meaning indicated below. o is particularly preferably 0.

In compounds of the formula (1), (1a), (1b), (1c), (1d), (1e), (1f), (1g), (1h), (1i), (1j), (1k) or (1l) or preferably described compounds of the formula (1), (1a), (1b), (1c), (1d), (1e), (1f), (1g), (1h), (1i), (1j), (1k) or (1l), p is preferably 0, 1 or 2, where R in each case, independently of one another, has a meaning indicated above or a meaning indicated below. p is particularly preferably 0 or 1. p is very particularly preferably 0.

If p is greater than 0 in compounds of the formula (1), (1a), (1b), (1c), (1d), (1e), (1f), (1g), (1h), (1i), (1j), (1k) or (1l) or preferably described compounds of the formula (1), (1a), (1b), (1c), (1d), (1e), (1f), (1g), (1h), (1i), (1j), (1k) or (1l), the substituent R is preferably selected on each occurrence, identically or differently, from the group consisting of D, F, an alkyl group having 1 to 40 C atoms or an aromatic or heteroaromatic ring system having 5 to 40 aromatic ring atoms or two substituents R which are bonded to adjacent carbon atoms form an aromatic or heteroaromatic ring system. The aromatic or heteroaromatic ring system having 5 to 40 aromatic ring atoms in this R preferably corresponds to $Ar_3$. Preferred meanings of $Ar_3$ are described below. The aromatic or heteroaromatic ring system formed by two substituents R particularly preferably corresponds to a spirobifluorene.

If p is greater than 0 in compounds of the formula (1), (1a), (1b), (1c), (1d), (1e), (1f), (1g), (1h), (1i), (1j), (1k) or (1l) or preferably described compounds of the formula (1), (1a), (1b), (1c), (1d), (1e), (1f), (1g), (1h), (1i), (1j), (1k) or (1l), the substituent R is on each occurrence, identically or differently, particularly preferably derived from aromatic or heteroaromatic ring systems from the group carbazole, 9-phenylcarbazole, dibenzofuran, dibenzothiophene, fluorene, terphenyl or spirobifluorene, very particularly preferably from the group 9-phenylcarbazole and spirobifluorene.

Two substituents R on the carbazole which together form an aromatic or heteroaromatic ring system preferably correspond to the formula (A), formula (A)

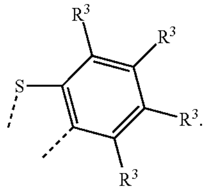

In compounds of the formula (1), (1a), (1b), (1c), (1d), (1e), (1f), (1g), (1h), (1i), (1j), (1k) or (1l) or preferably described compounds of the formula (1), (1a), (1b), (1c), (1d), (1e), (1f), (1g), (1h), (1i), (1j), (1k) or (1l), $Ar_3$ is preferably selected from an aromatic ring system having 6 to 40 aromatic ring atoms or a heteroaromatic ring system having 10 to 40 aromatic ring atoms, which may be substituted by one or more radicals $R^3$, with the exception of heteroaromatic ring systems having 10 to 40 aromatic ring atoms containing N.

In compounds of the formula (1), (1a), (1b), (1c), (1d), (1e), (1f), (1g), (1h), (1i), (1j), (1k) or (1l) or preferably described compounds of the formula (1), (1a), (1b), (1c), (1d), (1e), (1f), (1g), (1h), (1i), (1j), (1k) or (1l), $Ar_3$ is preferably selected from the aromatic or heteroaromatic ring systems Ar-1 to Ar-22, Ar-1

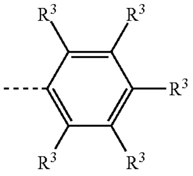

Ar-2

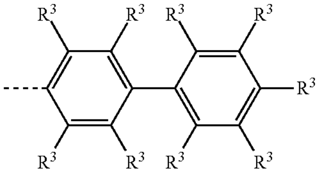

Ar-3

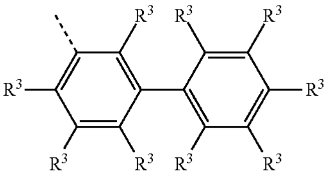

Ar-4

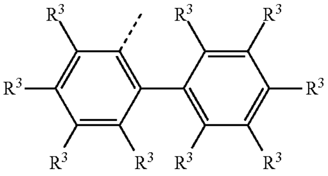

-continued

Ar-5

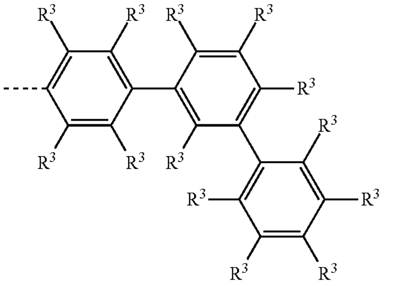

Ar-6

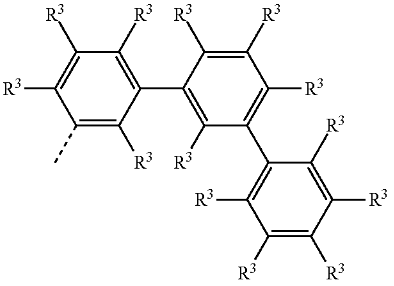

Ar-7

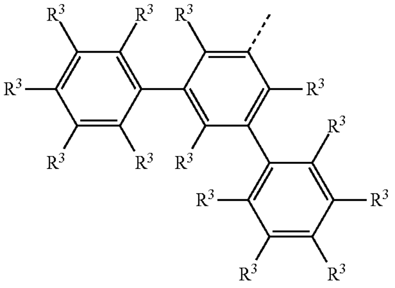

Ar-8

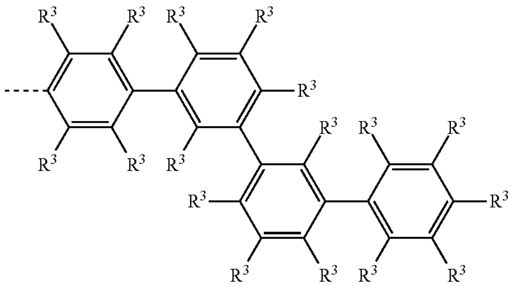

Ar-9

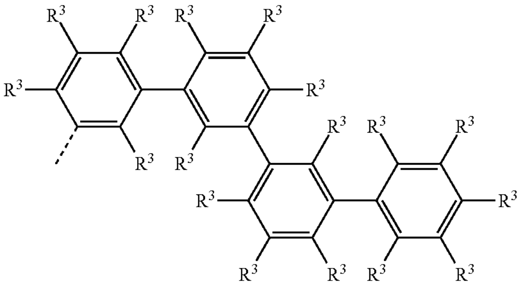

-continued
Ar-10
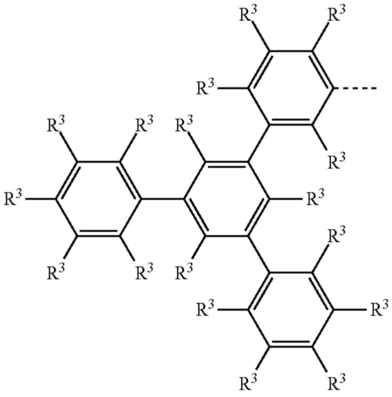
Ar-11
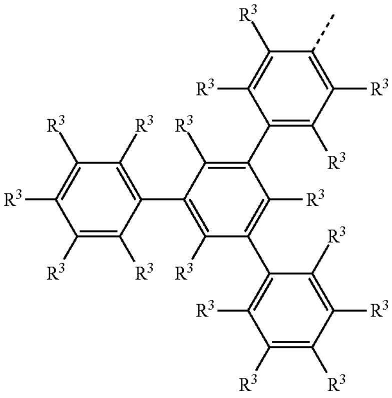
Ar-12
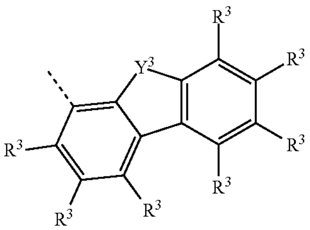
Ar-13
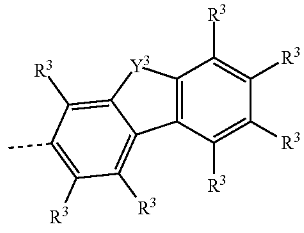
Ar-14
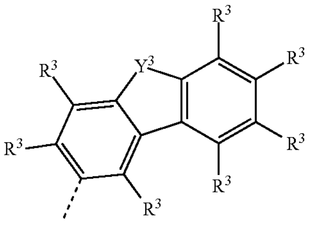
-continued
Ar-15
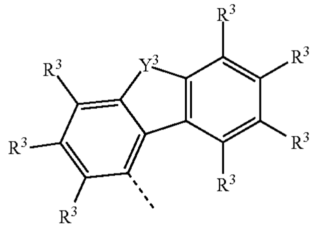
Ar-16
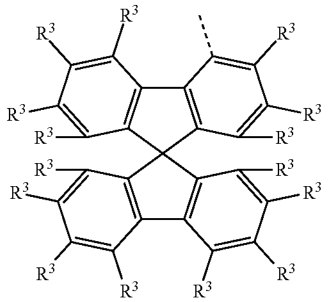
Ar-17
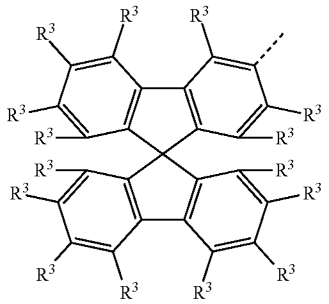
Ar-18
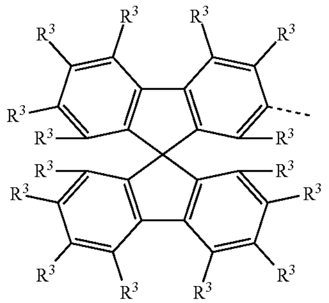
Ar-19
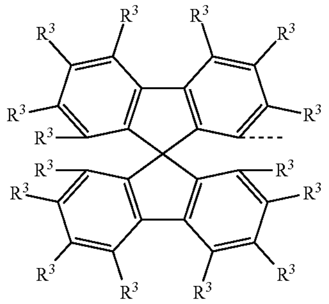

-continued

Ar-20

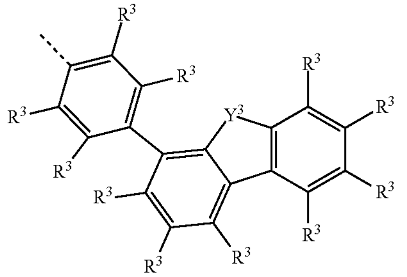

Ar-21

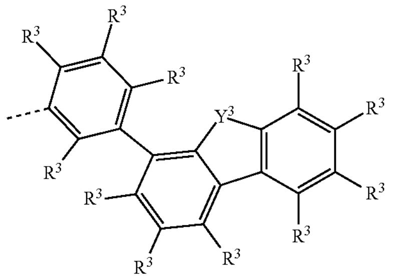

Ar-22

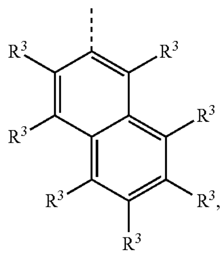

where $Y^3$ on each occurrence, identically or differently, denotes O, S or $C(R^{\#})_2$, where $R^3$ has the meaning given above or a preferred meaning below and the dashed bond represents the bond to the N atom and where $R^3$ as substituent for $Ar_3$ does not include a heteroaromatic ring system having 5 to 30 aromatic ring atoms.

The radical $R^{\#}$ is on each occurrence, identically or differently, H, D, F, Cl, Br, I, CN, $NO_2$, $N(Ar)_2$, $N(R^2)_2$, C(═O)Ar, C(═O)$R^2$, P(═O)$(Ar)_2$, $P(Ar)_2$, $B(Ar)_2$, $Si(Ar)_3$, $Si(R^2)_3$, a straight-chain alkyl, alkoxy or thioalkyl group having 1 to 20 C atoms or a branched or cyclic alkyl, alkoxy or thioalkyl group having 3 to 20 C atoms or an alkenyl group having 2 to 20 C atoms, which may in each case be substituted by one or more radicals $R^2$, where one or more non-adjacent $CH_2$ groups may be replaced by $R^2C$═$CR^2$, $Si(R^2)_2$, C═O, C═S, C═$NR^2$, P(═O)($R^2$), SO, $SO_2$, $NR^2$, O, S or $CONR^2$ and where one or more H atoms may be replaced by D, F, Cl, Br, I, CN or $NO_2$, an aromatic or heteroaromatic ring system having 5 to 40 aromatic ring atoms, which may in each case be substituted by one or more radicals $R^2$, or an aryloxy or heteroaryloxy group having 5 to 40 aromatic ring atoms, which may be substituted by one or more radicals $R^2$, or an aralkyl or heteroaralkyl group having 5 to 40 aromatic ring atoms, which may be substituted by one or more radicals $R^2$; two substituents $R^{\#}$ which are bonded to the same carbon atom or to adjacent carbon atoms may optionally form a mono-cyclic or polycyclic, aliphatic, aromatic or heteroaromatic ring system, which may be substituted by one or more radicals $R^2$.

$Y^3$ is preferably O, S or $C(CH_3)_2$. $Y^3$ is particularly preferably O. $Y^3$ is very particularly preferably $C(CH_3)_2$.

The substituent $R^3$ in structures Ar-1 to Ar-22 is selected on each occurrence, identically or differently, from the group consisting of H, D, F, CN, an aliphatic hydrocarbon radical having 1 to 20 C atoms or an aromatic ring system having 6 to 30 aromatic ring atoms, in which one or more H atoms may be replaced by D, F, Cl, Br, I or CN and which may be substituted by one or more alkyl groups, each having 1 to 4 carbon atoms; two or more adjacent substituents $R^3$ may form a mono- or polycyclic, aliphatic ring system with one another. The substituent $R^3$ in structures Ar-1 to Ar-22 is preferably selected on each occurrence, identically or differently, from the group consisting of H, F, CN, an aliphatic hydrocarbon radical having 1 to 10 C atoms or an aromatic ring system having 6 to 30 aromatic ring atoms. The substituent $R^3$ in structures Ar-1 to Ar-22 is preferably selected on each occurrence, identically or differently, from the group consisting of H or an aromatic ring system having 6 to 30 aromatic ring atoms, as described above, but preferably dibenzofuran, dibenzothiophene or spirobifluorene.

Two substituents R and $R^3$, R has substituent on the carbazole and $R^3$ as substituent on $Ar_3$, may likewise together form an aromatic or heteroaromatic ring system, where they are correspondingly connected to one another via a linker, for example via —O—, —S— or —$C(R^0)_2$—, where $R^0$ has a meaning indicated above or a preferred meaning, preferably via —O— or —$C(CH_3)_2$—.

The substituent $R^3$ in structures Ar-1 to Ar-22 is particularly preferably on each occurrence H.

In compounds of the formula (1), (1a), (1b), (1c), (1d), (1e), (1f), (1g), (1h), (1i), (1j), (1k) or (1l) or preferably described compounds of the formula (1), (1a), (1b), (1c), (1d), (1e), (1f), (1g), (1h), (1i), (1j), (1k) or (1l), $Ar_3$ is particularly preferably selected from the aromatic or heteroaromatic ring systems Ar-1, Ar-2, Ar-3, Ar-7, Ar-10, Ar-11, Ar-14, Ar-15, Ar-20, Ar-21 and Ar-22, where the substituents $R^3$ and $Y^3$ have a meaning given above or described as preferred.

Examples of particularly suitable compounds which are selected in accordance with the invention are compounds of the formula (1f), (1h) or (1i), where L has a preferably or particularly preferably indicated meaning.

Examples of particularly suitable compounds which are selected in accordance with the invention are compounds of the formula (1i), where L has a preferably or particularly preferably indicated meaning.

Examples of suitable compounds of the formula (1), (1a), (1b), (1c), (1d), (1e), (1f), (1g), (1h), (1i), (1j), (1k) or (1l) which are selected in accordance with the invention are the structures given below in Tables 1, 2, 3 and 4.

TABLE 1
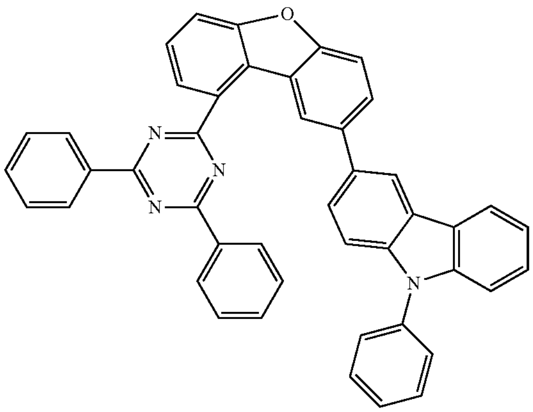
1
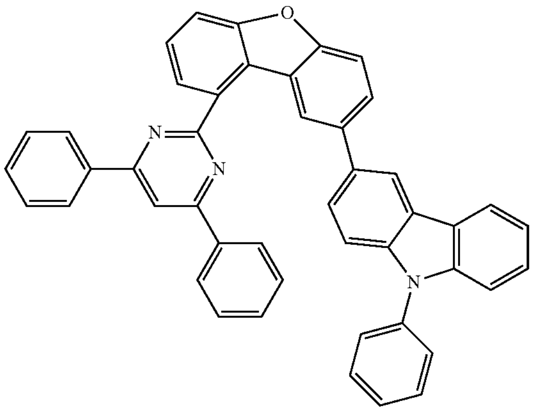 [SMILES: c1ccc(-c2cc(-c3ccccc3)nc(-c3cccc4oc5ccc(-c6ccc7c(c6)c6ccccc6n7-c6ccccc6)cc5c34)n2)cc1]
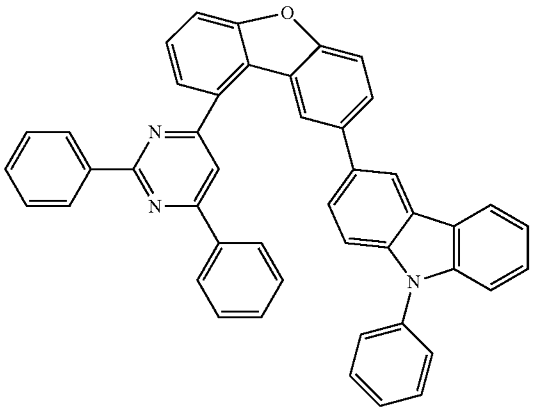

TABLE 1-continued
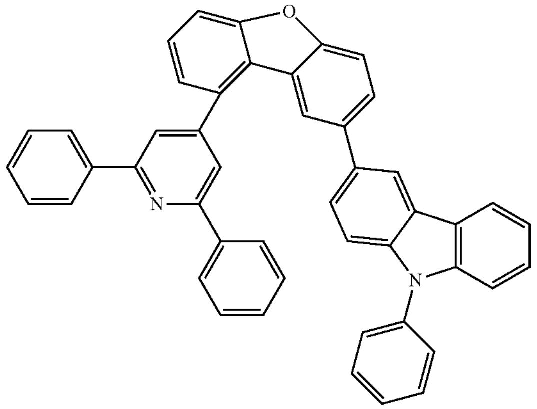 [SMILES: c1ccc(-c2cc(-c3cccc4oc5ccc(-c6ccc7c(c6)c6ccccc6n7-c6ccccc6)cc5c34)cc(-c3ccccc3)n2)cc1]
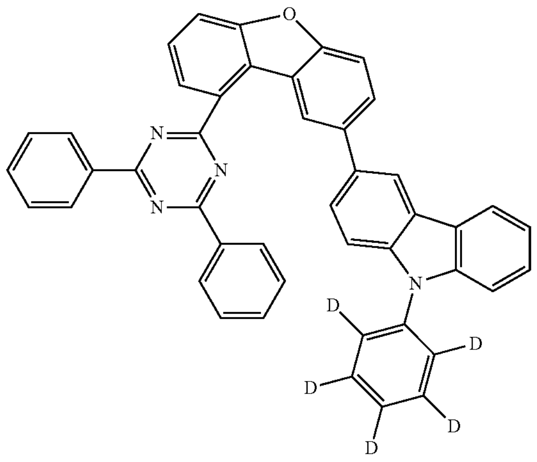 [SMILES: [2H]c1c([2H])c([2H])c(-n2c3ccccc3c3cc(-c4ccc5oc6cccc(-c7nc(-c8ccccc8)nc(-c8ccccc8)n7)c6c5c4)ccc32)c([2H])c1[2H]]
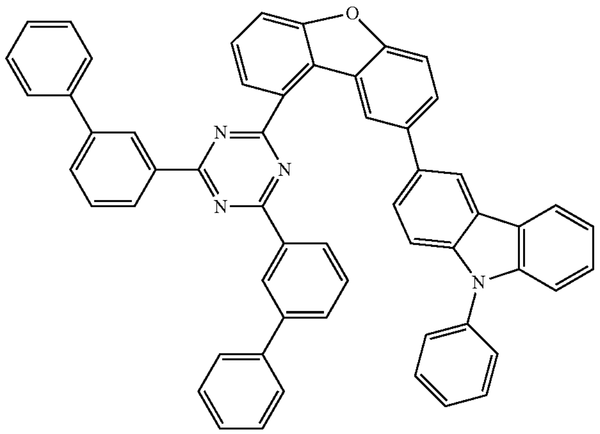

TABLE 1-continued
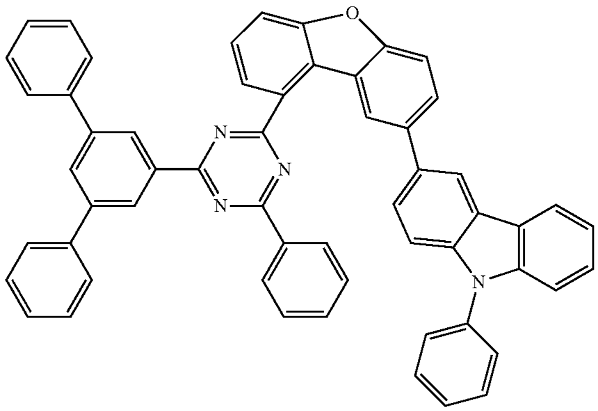
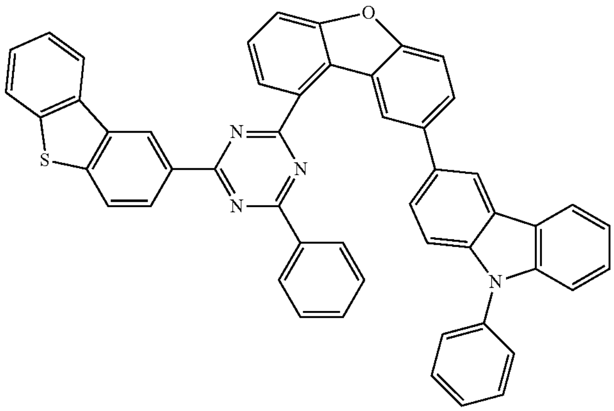
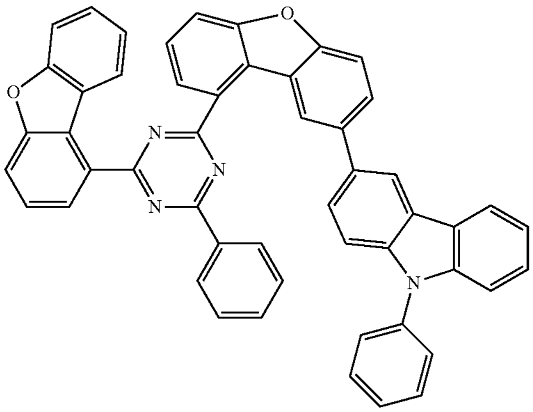

TABLE 1-continued
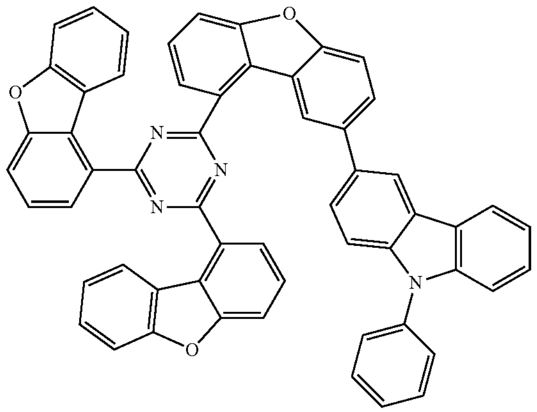
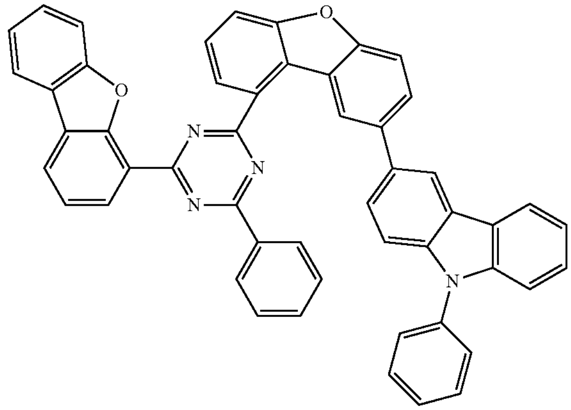 [SMILES: c1ccc(-c2nc(-c3cccc4c3oc3ccccc34)nc(-c3cccc4oc5ccc(-c6ccc7c(c6)c6ccccc6n7-c6ccccc6)cc5c34)n2)cc1]
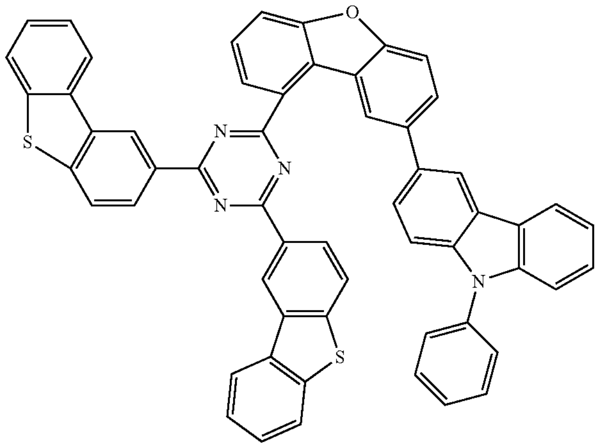 [SMILES: c1ccc(-n2c3ccccc3c3cc(-c4ccc5oc6cccc(-c7nc(-c8ccc9sc%10ccccc%10c9c8)nc(-c8ccc9sc%10ccccc%10c9c8)n7)c6c5c4)ccc32)cc1]

TABLE 1-continued
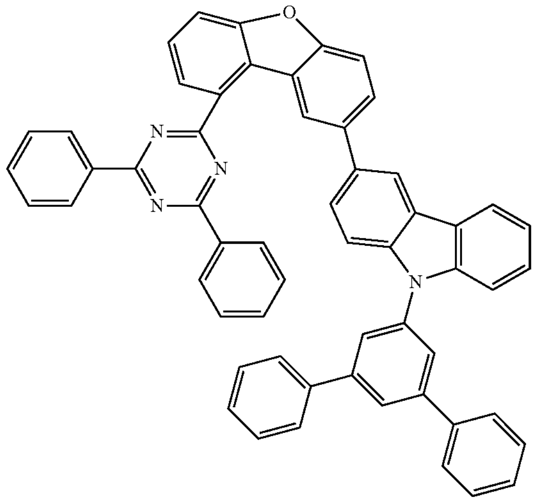 [SMILES: c1ccc(-c2cc(-c3ccccc3)cc(-n3c4ccccc4c4cc(-c5ccc6oc7cccc(-c8nc(-c9ccccc9)nc(-c9ccccc9)n8)c7c6c5)ccc43)c2)cc1]
2
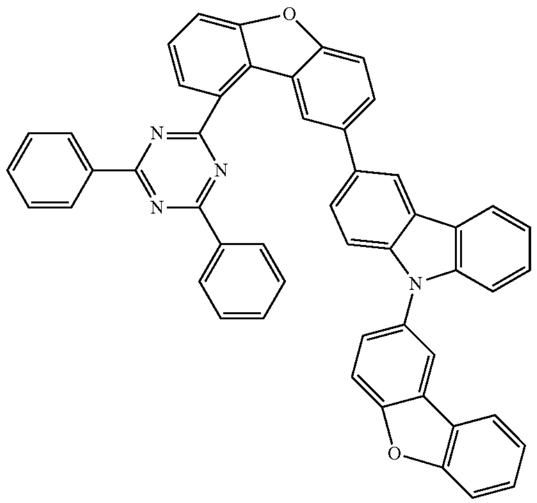 [SMILES: c1ccc(-c2nc(-c3ccccc3)nc(-c3cccc4oc5ccc(-c6ccc7c(c6)c6ccccc6n7-c6ccc7oc8ccccc8c7c6)cc5c34)n2)cc1]
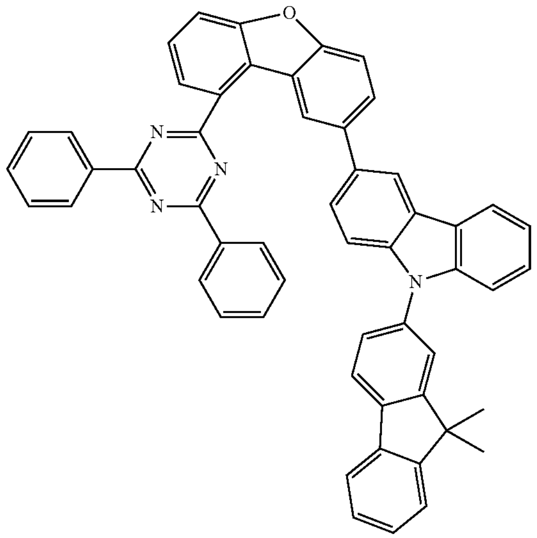 [SMILES: CC1(C)c2ccccc2-c2ccc(-n3c4ccccc4c4cc(-c5ccc6oc7cccc(-c8nc(-c9ccccc9)nc(-c9ccccc9)n8)c7c6c5)ccc43)cc21]

TABLE 1-continued
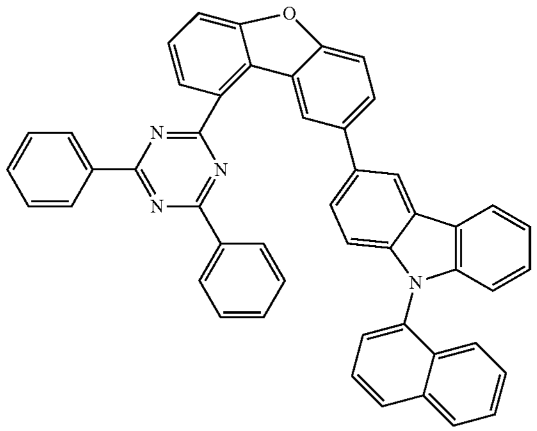 [SMILES: c1ccc(-c2nc(-c3ccccc3)nc(-c3cccc4oc5ccc(-c6ccc7c(c6)c6ccccc6n7-c6cccc7ccccc67)cc5c34)n2)cc1]
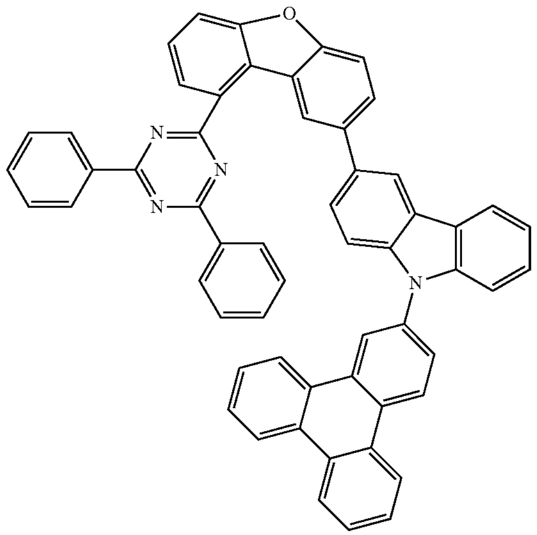 [SMILES: c1ccc(-c2nc(-c3ccccc3)nc(-c3cccc4oc5ccc(-c6ccc7c(c6)c6ccccc6n7-c6ccc7c8ccccc8c8ccccc8c7c6)cc5c34)n2)cc1]
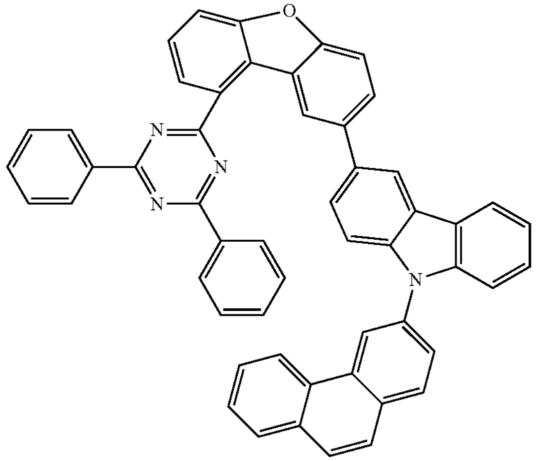 [SMILES: c1ccc(-c2nc(-c3ccccc3)nc(-c3cccc4oc5ccc(-c6ccc7c(c6)c6ccccc6n7-c6ccc7ccc8ccccc8c7c6)cc5c34)n2)cc1]

TABLE 1-continued
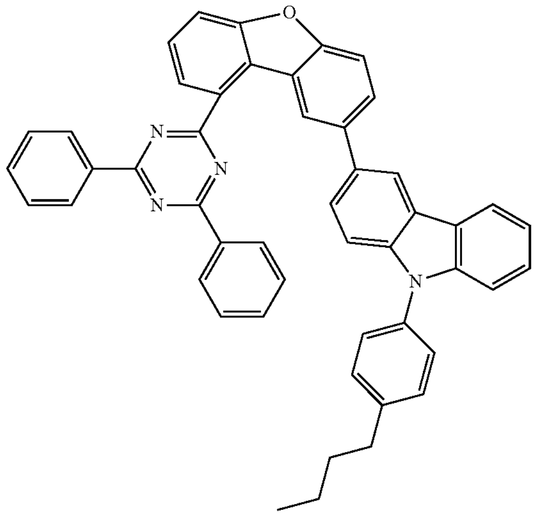 [SMILES: CCCCc1ccc(-n2c3ccccc3c3cc(-c4ccc5oc6cccc(-c7nc(-c8ccccc8)nc(-c8ccccc8)n7)c6c5c4)ccc32)cc1]
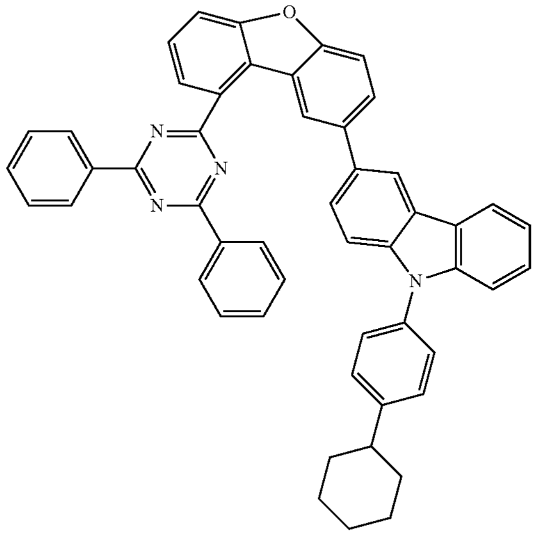 [SMILES: c1ccc(-c2nc(-c3ccccc3)nc(-c3cccc4oc5ccc(-c6ccc7c(c6)c6ccccc6n7-c6ccc(C7CCCCC7)cc6)cc5c34)n2)cc1]
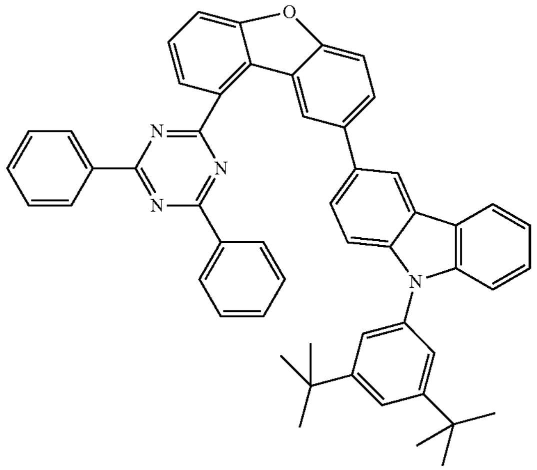 [SMILES: CC(C)(C)c1cc(-n2c3ccccc3c3cc(-c4ccc5oc6cccc(-c7nc(-c8ccccc8)nc(-c8ccccc8)n7)c6c5c4)ccc32)cc(C(C)(C)C)c1]

TABLE 1-continued
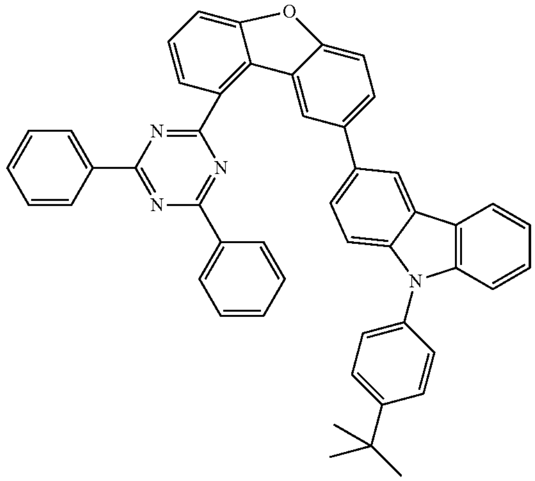 [SMILES: CC(C)(C)c1ccc(-n2c3ccccc3c3cc(-c4ccc5oc6cccc(-c7nc(-c8ccccc8)nc(-c8ccccc8)n7)c6c5c4)ccc32)cc1]
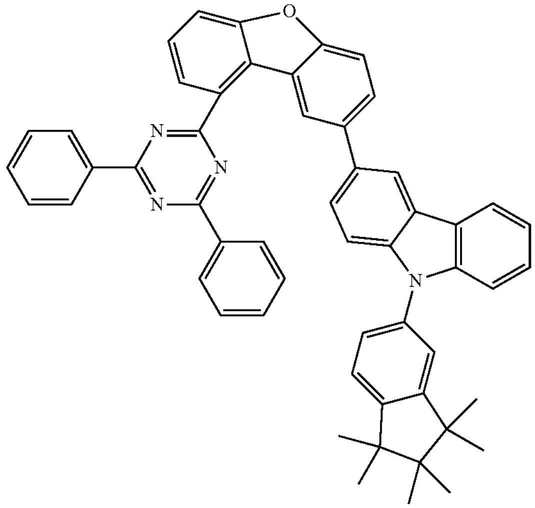 [SMILES: CC1(C)c2ccc(-n3c4ccccc4c4cc(-c5ccc6oc7cccc(-c8nc(-c9ccccc9)nc(-c9ccccc9)n8)c7c6c5)ccc43)cc2C(C)(C)C1(C)C]
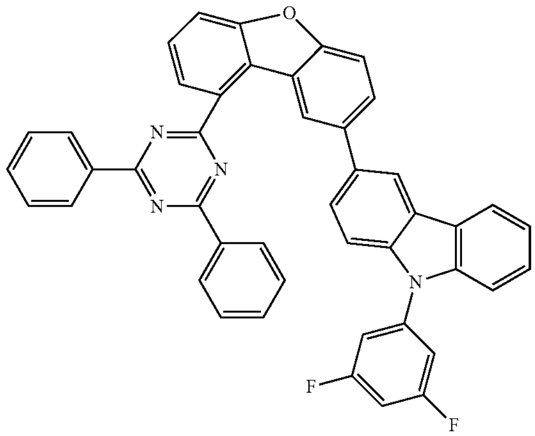 [SMILES: Fc1cc(F)cc(-n2c3ccccc3c3cc(-c4ccc5oc6cccc(-c7nc(-c8ccccc8)nc(-c8ccccc8)n7)c6c5c4)ccc32)c1]

TABLE 1-continued
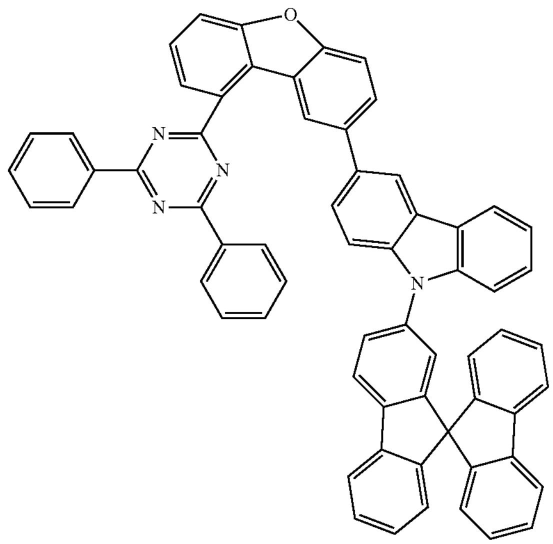 [SMILES: c1ccc(-c2nc(-c3ccccc3)nc(-c3cccc4oc5ccc(-c6ccc7c(c6)c6ccccc6n7-c6ccc7c(c6)C6(c8ccccc8-c8ccccc86)c6ccccc6-7)cc5c34)n2)cc1]
3
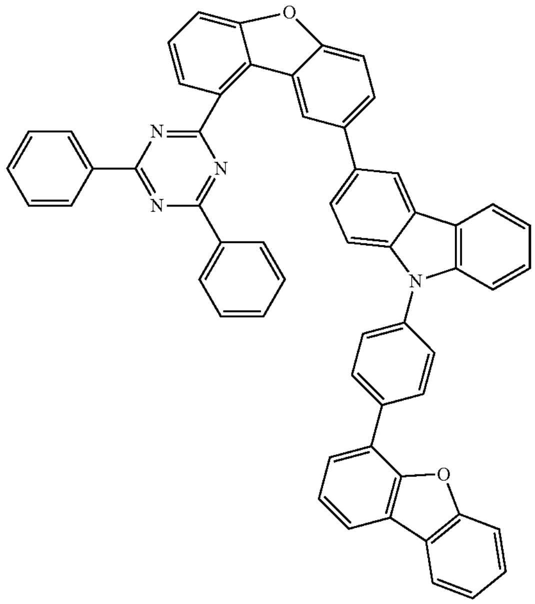 [SMILES: c1ccc(-c2nc(-c3ccccc3)nc(-c3cccc4oc5ccc(-c6ccc7c(c6)c6ccccc6n7-c6ccc(-c7cccc8c7oc7ccccc78)cc6)cc5c34)n2)cc1]
4

TABLE 1-continued
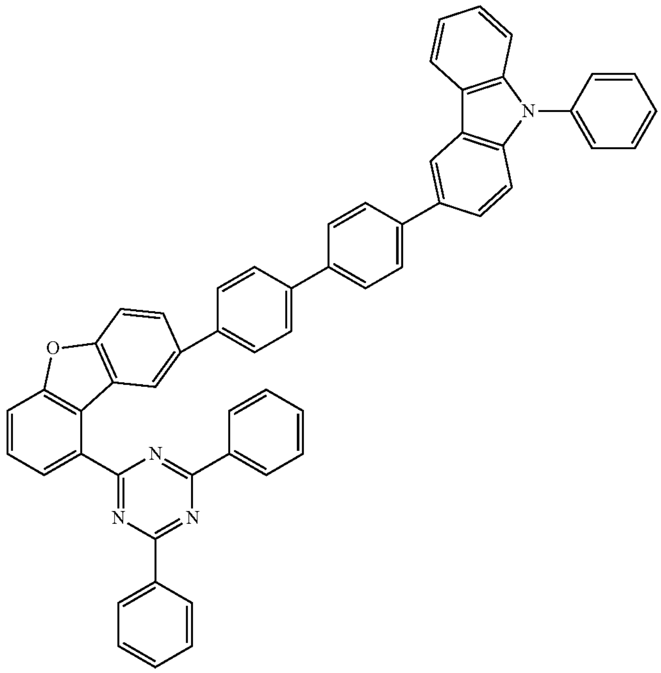 [SMILES: c1ccc(-c2nc(-c3ccccc3)nc(-c3cccc4oc5ccc(-c6ccc(-c7ccc(-c8ccc9c(c8)c8ccccc8n9-c8ccccc8)cc7)cc6)cc5c34)n2)cc1]
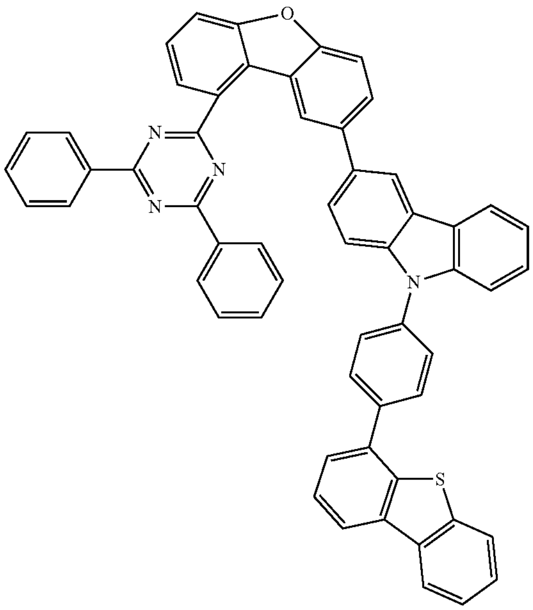 [SMILES: c1ccc(-c2nc(-c3ccccc3)nc(-c3cccc4oc5ccc(-c6ccc7c(c6)c6ccccc6n7-c6ccc(-c7cccc8c7sc7ccccc78)cc6)cc5c34)n2)cc1]

TABLE 1-continued
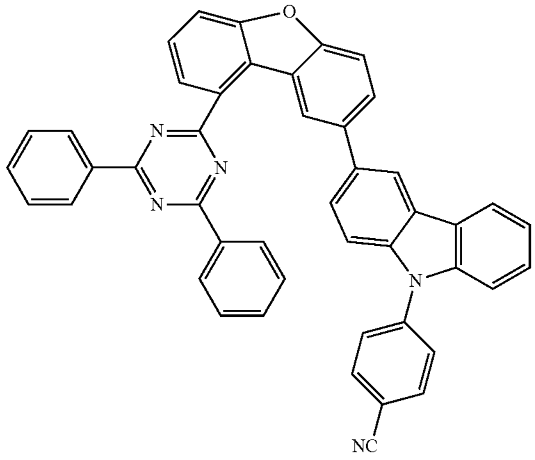 [SMILES: N#Cc1ccc(-n2c3ccccc3c3cc(-c4ccc5oc6cccc(-c7nc(-c8ccccc8)nc(-c8ccccc8)n7)c6c5c4)ccc32)cc1]
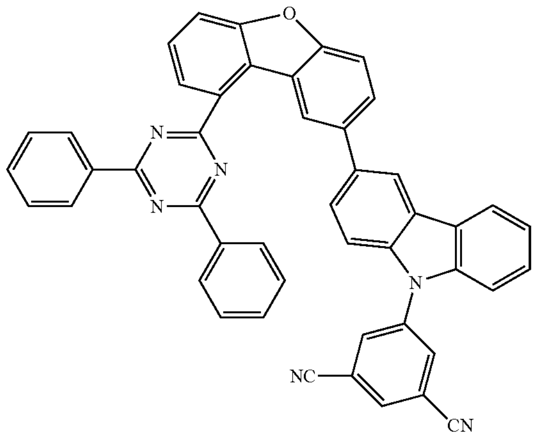 [SMILES: N#Cc1cc(C#N)cc(-n2c3ccccc3c3cc(-c4ccc5oc6cccc(-c7nc(-c8ccccc8)nc(-c8ccccc8)n7)c6c5c4)ccc32)c1]
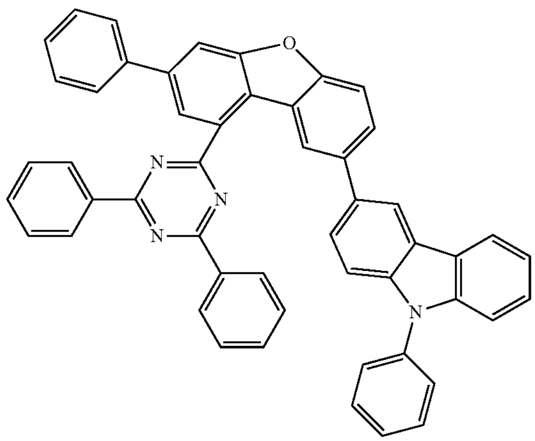 [SMILES: c1ccc(-c2cc(-c3nc(-c4ccccc4)nc(-c4ccccc4)n3)c3c(c2)oc2ccc(-c4ccc5c(c4)c4ccccc4n5-c4ccccc4)cc23)cc1]

TABLE 1-continued
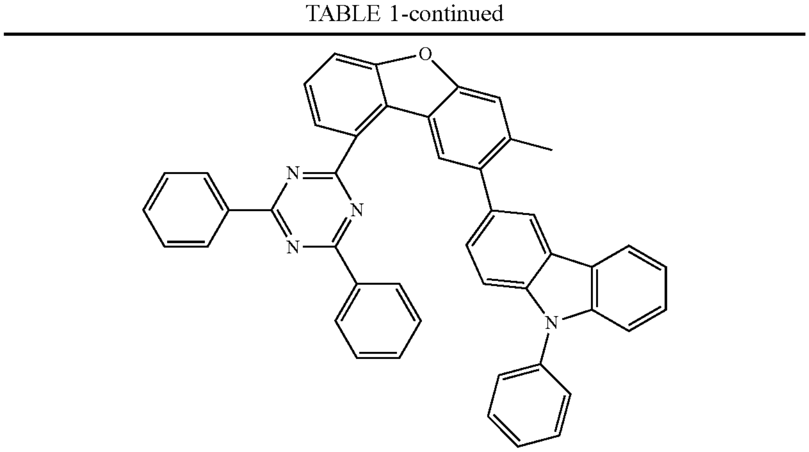
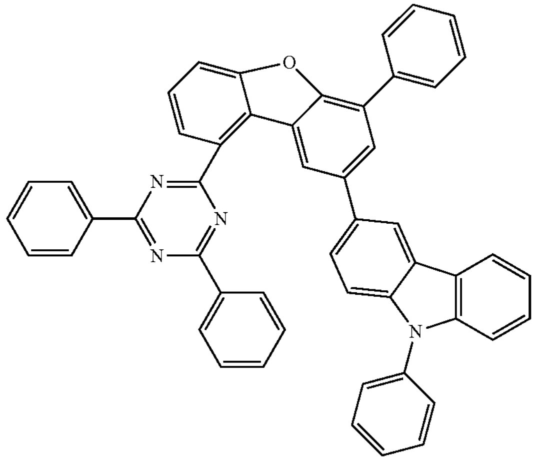 [SMILES: c1ccc(-c2nc(-c3ccccc3)nc(-c3cccc4oc5c(-c6ccccc6)cc(-c6ccc7c(c6)c6ccccc6n7-c6ccccc6)cc5c34)n2)cc1]
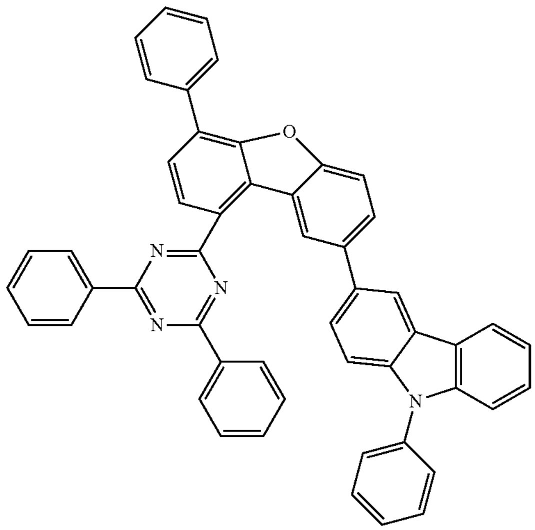 [SMILES: c1ccc(-c2nc(-c3ccccc3)nc(-c3ccc(-c4ccccc4)c4oc5ccc(-c6ccc7c(c6)c6ccccc6n7-c6ccccc6)cc5c34)n2)cc1]

TABLE 1-continued
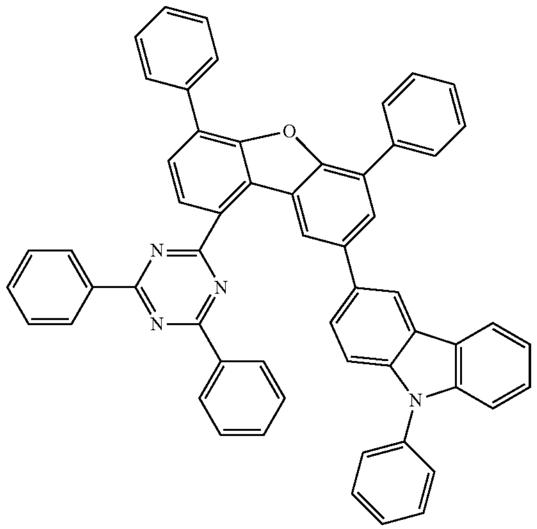 [SMILES: c1ccc(-c2nc(-c3ccccc3)nc(-c3ccc(-c4ccccc4)c4oc5c(-c6ccccc6)cc(-c6ccc7c(c6)c6ccccc6n7-c6ccccc6)cc5c34)n2)cc1]
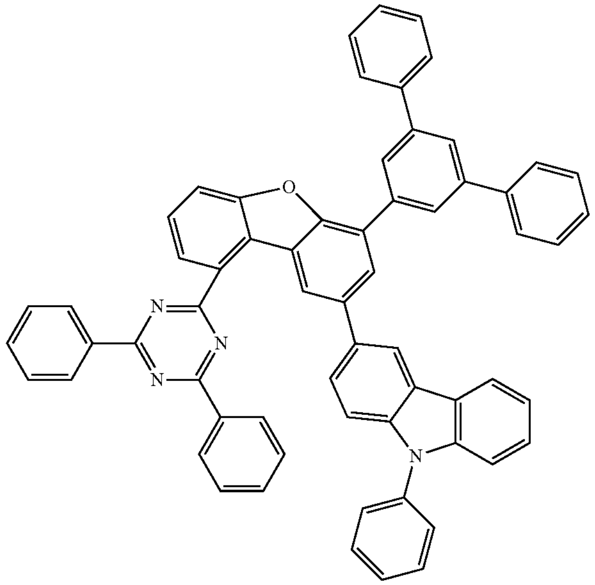 [SMILES: c1ccc(-c2cc(-c3ccccc3)cc(-c3cc(-c4ccc5c(c4)c4ccccc4n5-c4ccccc4)cc4c3oc3cccc(-c5nc(-c6ccccc6)nc(-c6ccccc6)n5)c34)c2)cc1]
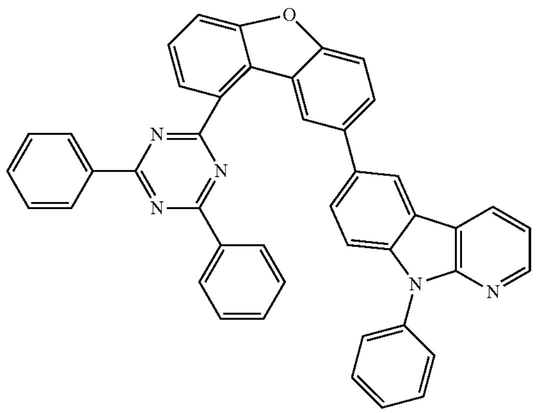 [SMILES: c1ccc(-c2nc(-c3ccccc3)nc(-c3cccc4oc5ccc(-c6ccc7c(c6)c6cccnc6n7-c6ccccc6)cc5c34)n2)cc1]

TABLE 1-continued
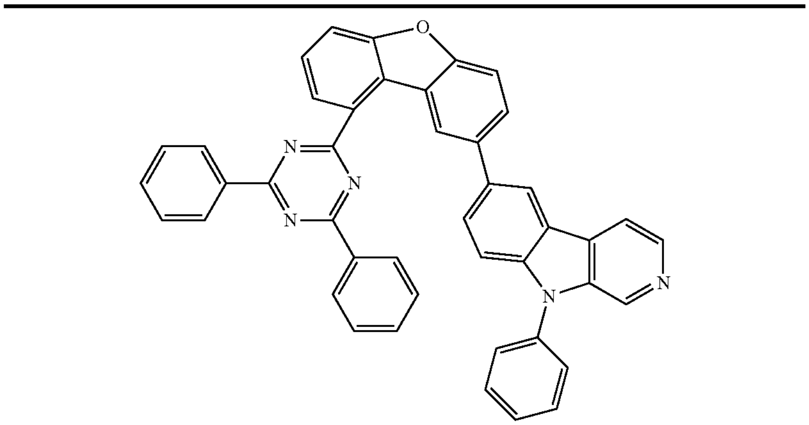
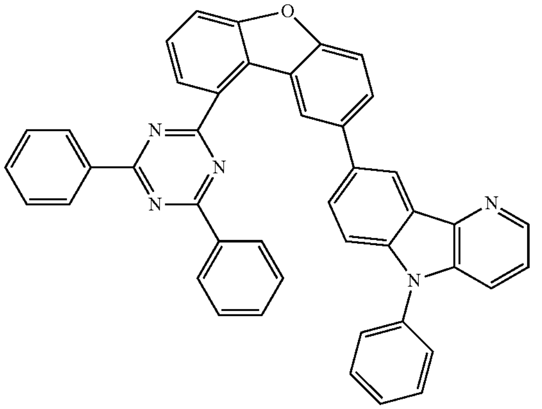
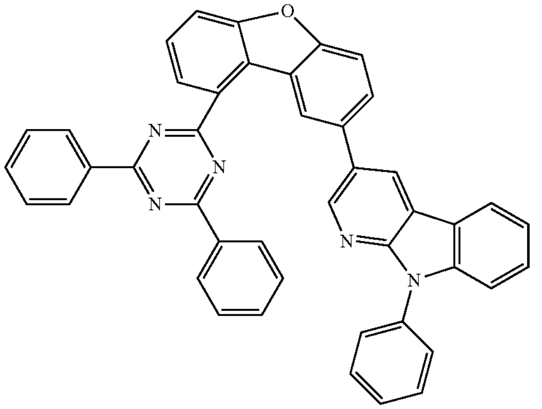
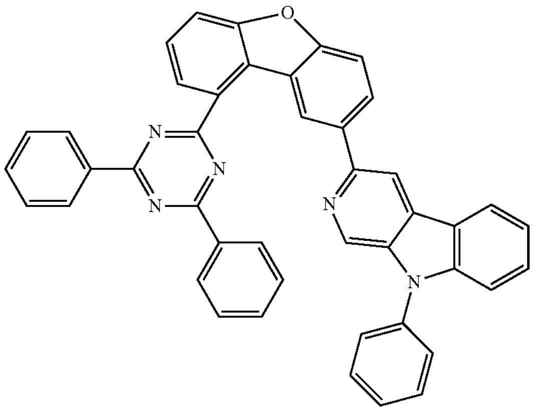

TABLE 1-continued
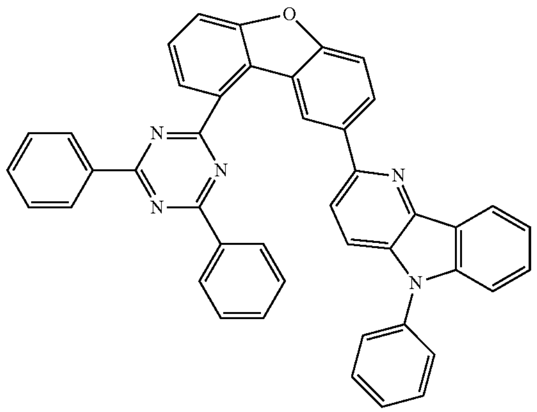
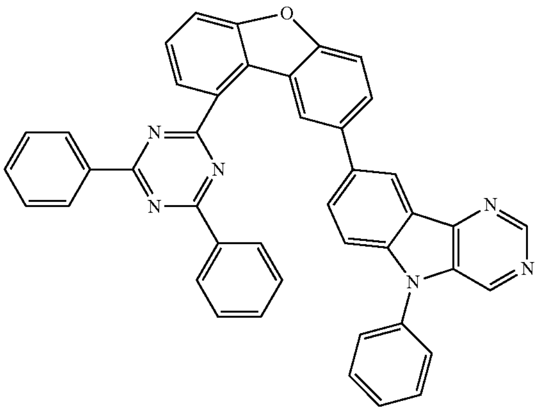
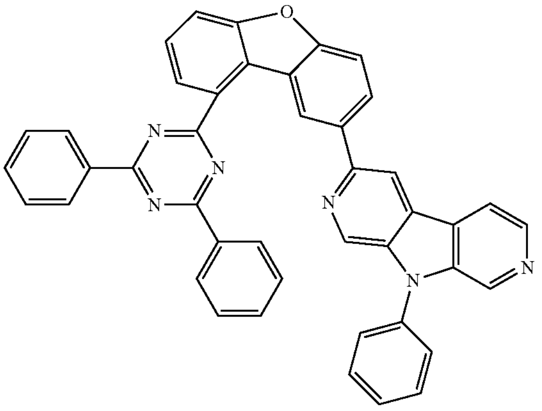 [SMILES: c1ccc(-c2nc(-c3ccccc3)nc(-c3cccc4oc5ccc(-c6ccc7c(c6)c6ccncc6n7-c6ccccc6)cc5c34)n2)cc1]

TABLE 1-continued
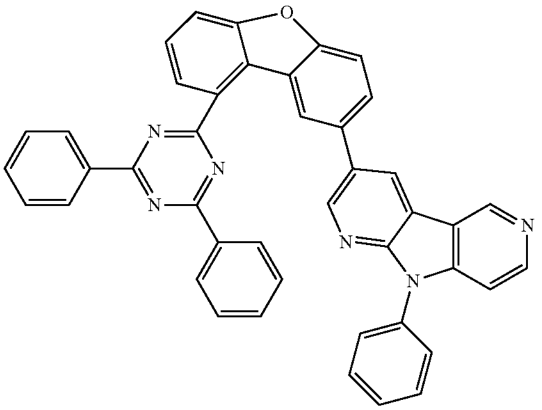 [SMILES: c1ccc(-c2nc(-c3ccccc3)nc(-c3cccc4oc5ccc(-c6cnc7c(c6)c6cnccc6n7-c6ccccc6)cc5c34)n2)cc1]
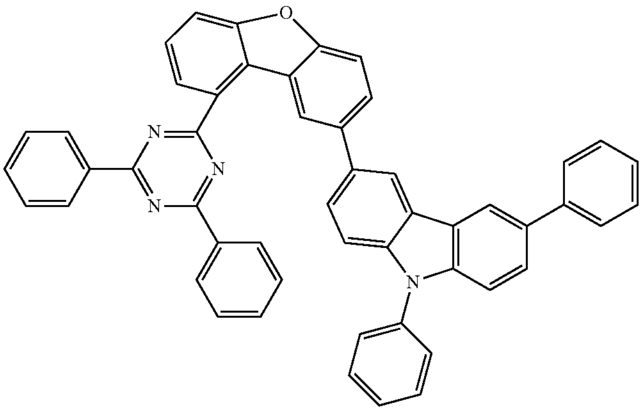 [SMILES: c1ccc(-c2ccc3c(c2)c2cc(-c4ccc5oc6cccc(-c7nc(-c8ccccc8)nc(-c8ccccc8)n7)c6c5c4)ccc2n3-c2ccccc2)cc1]
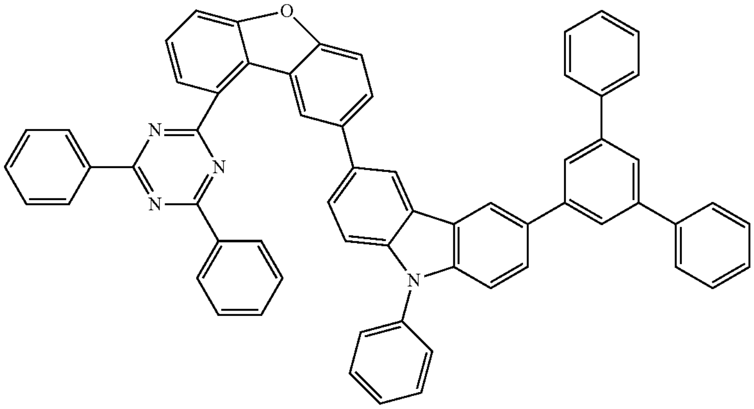 [SMILES: c1ccc(-c2cc(-c3ccccc3)cc(-c3ccc4c(c3)c3cc(-c5ccc6oc7cccc(-c8nc(-c9ccccc9)nc(-c9ccccc9)n8)c7c6c5)ccc3n4-c3ccccc3)c2)cc1]

TABLE 1-continued
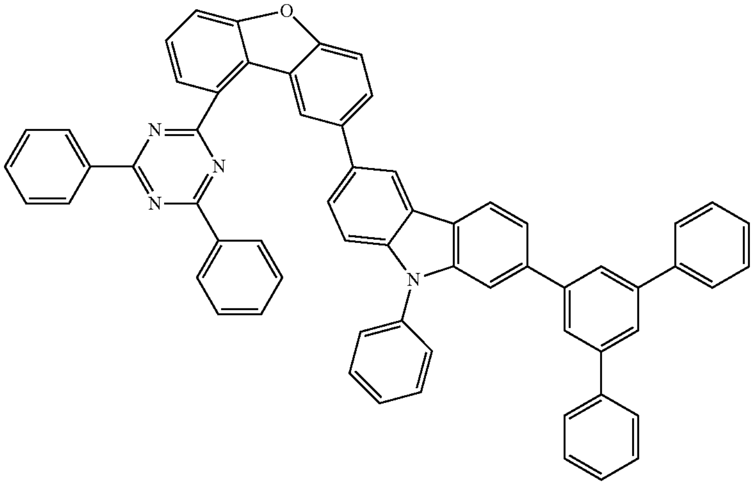 [SMILES: c1ccc(-c2cc(-c3ccccc3)cc(-c3ccc4c5cc(-c6ccc7oc8cccc(-c9nc(-c%10ccccc%10)nc(-c%10ccccc%10)n9)c8c7c6)ccc5n(-c5ccccc5)c4c3)c2)cc1]
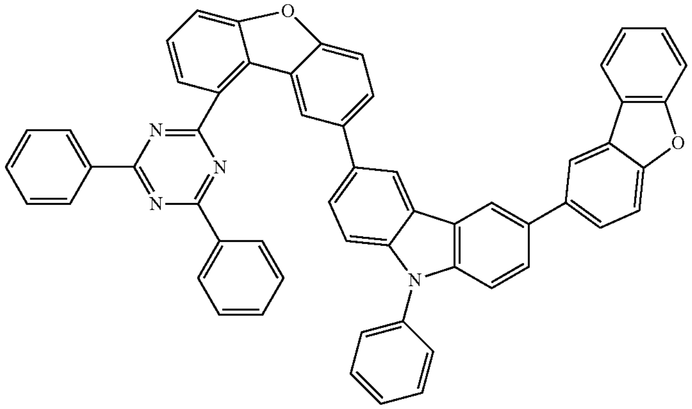 [SMILES: c1ccc(-c2nc(-c3ccccc3)nc(-c3cccc4oc5ccc(-c6ccc7c(c6)c6cc(-c8ccc9oc%10ccccc%10c9c8)ccc6n7-c6ccccc6)cc5c34)n2)cc1]
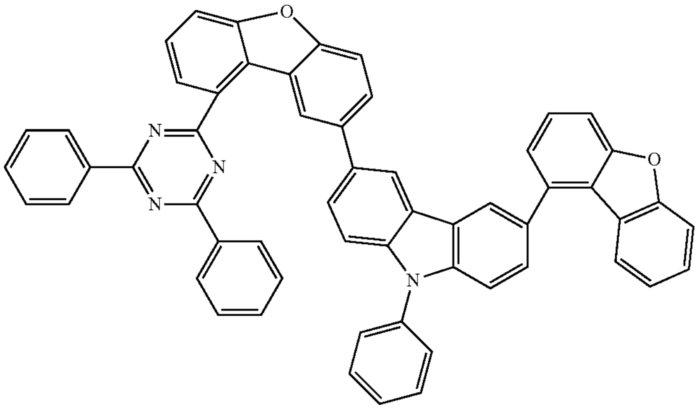 [SMILES: c1ccc(-c2nc(-c3ccccc3)nc(-c3cccc4oc5ccc(-c6ccc7c(c6)c6cc(-c8cccc9oc%10ccccc%10c89)ccc6n7-c6ccccc6)cc5c34)n2)cc1]

TABLE 1-continued
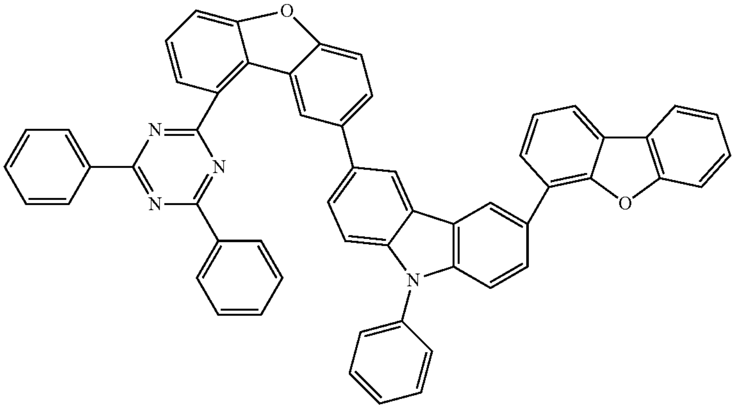 [SMILES: c1ccc(-c2nc(-c3ccccc3)nc(-c3cccc4oc5ccc(-c6ccc7c(c6)c6cc(-c8cccc9c8oc8ccccc89)ccc6n7-c6ccccc6)cc5c34)n2)cc1]
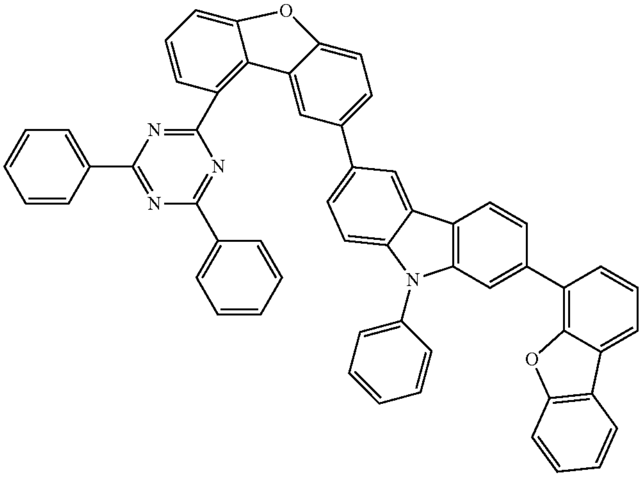 [SMILES: c1ccc(-c2nc(-c3ccccc3)nc(-c3cccc4oc5ccc(-c6ccc7c(c6)c6ccc(-c8cccc9c8oc8ccccc89)cc6n7-c6ccccc6)cc5c34)n2)cc1]
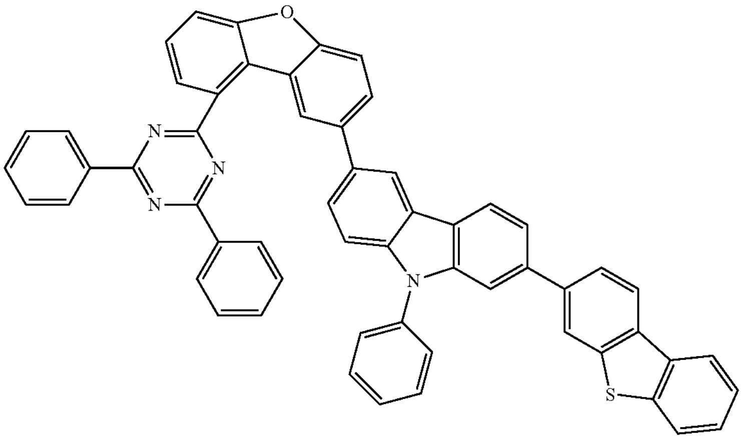 [SMILES: c1ccc(-c2nc(-c3ccccc3)nc(-c3cccc4oc5ccc(-c6ccc7c(c6)c6ccc(-c8ccc9c(c8)sc8ccccc89)cc6n7-c6ccccc6)cc5c34)n2)cc1]

TABLE 1-continued
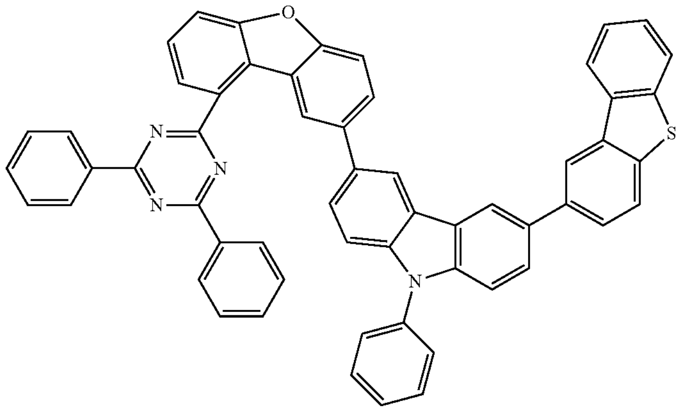 [SMILES: c1ccc(-c2nc(-c3ccccc3)nc(-c3cccc4oc5ccc(-c6ccc7c(c6)c6cc(-c8ccc9sc%10ccccc%10c9c8)ccc6n7-c6ccccc6)cc5c34)n2)cc1]
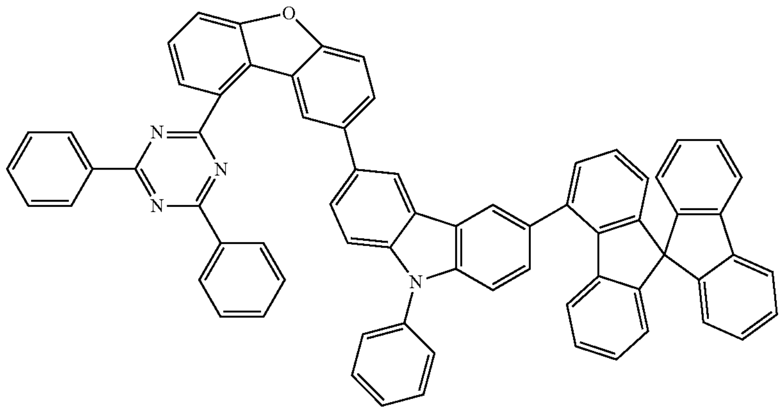 [SMILES: c1ccc(-c2nc(-c3ccccc3)nc(-c3cccc4oc5ccc(-c6ccc7c(c6)c6cc(-c8cccc9c8-c8ccccc8C98c9ccccc9-c9ccccc98)ccc6n7-c6ccccc6)cc5c34)n2)cc1]
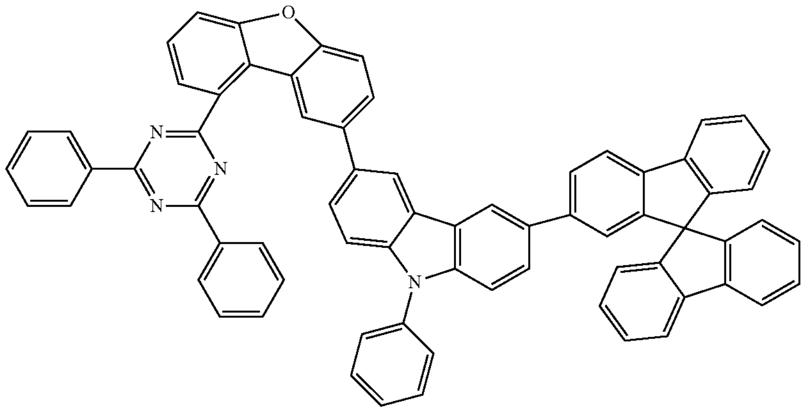 [SMILES: c1ccc(-c2nc(-c3ccccc3)nc(-c3cccc4oc5ccc(-c6ccc7c(c6)c6cc(-c8ccc9c(c8)C8(c%10ccccc%10-c%10ccccc%108)c8ccccc8-9)ccc6n7-c6ccccc6)cc5c34)n2)cc1]

TABLE 1-continued
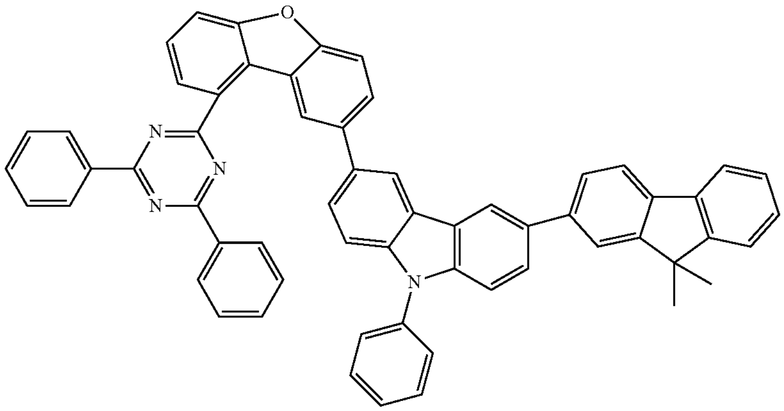 [SMILES: CC1(C)c2ccccc2-c2ccc(-c3ccc4c(c3)c3cc(-c5ccc6oc7cccc(-c8nc(-c9ccccc9)nc(-c9ccccc9)n8)c7c6c5)ccc3n4-c3ccccc3)cc21]
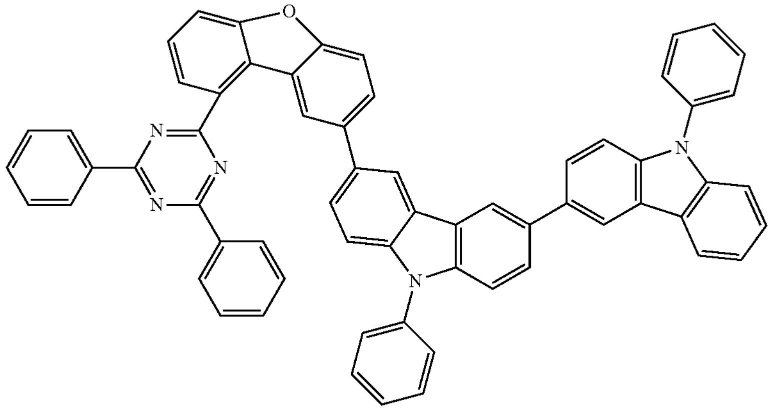 [SMILES: c1ccc(-c2nc(-c3ccccc3)nc(-c3cccc4oc5ccc(-c6ccc7c(c6)c6cc(-c8ccc9c(c8)c8ccccc8n9-c8ccccc8)ccc6n7-c6ccccc6)cc5c34)n2)cc1]
6
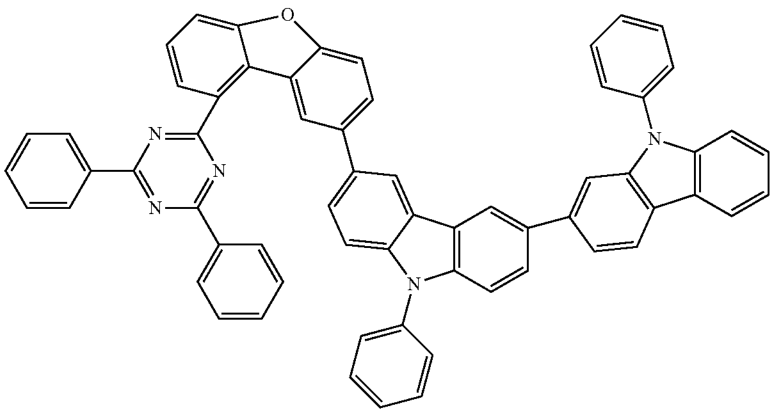 [SMILES: c1ccc(-c2nc(-c3ccccc3)nc(-c3cccc4oc5ccc(-c6ccc7c(c6)c6cc(-c8ccc9c%10ccccc%10n(-c%10ccccc%10)c9c8)ccc6n7-c6ccccc6)cc5c34)n2)cc1]

TABLE 1-continued
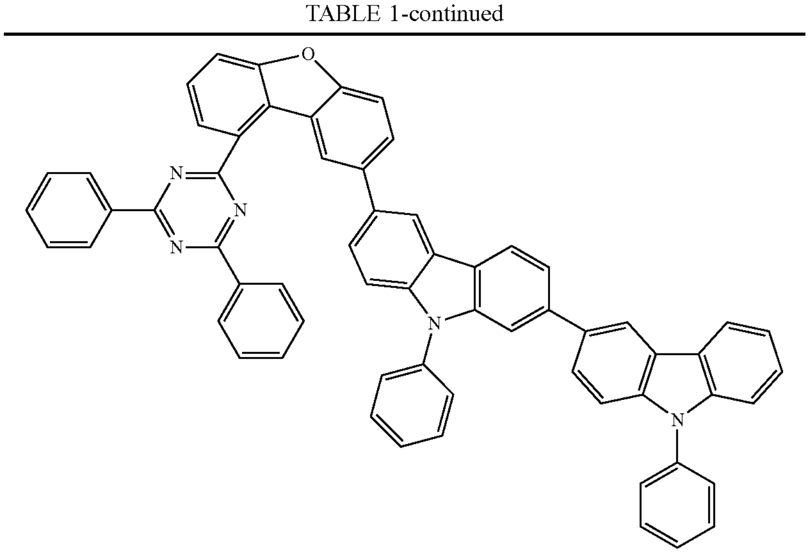
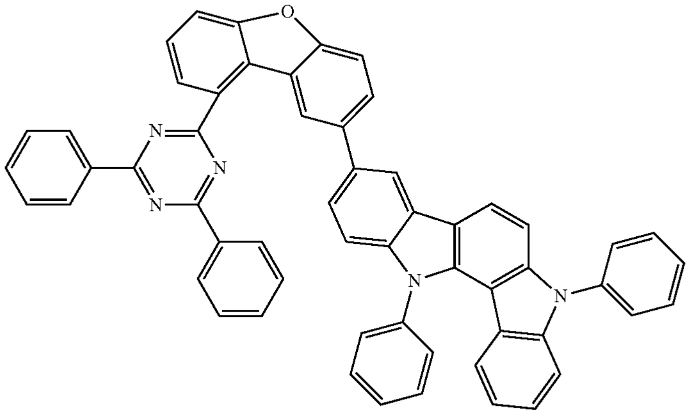 [SMILES: c1ccc(-c2nc(-c3ccccc3)nc(-c3cccc4oc5ccc(-c6ccc7c(c6)c6ccc8c(c9ccccc9n8-c8ccccc8)c6n7-c6ccccc6)cc5c34)n2)cc1]
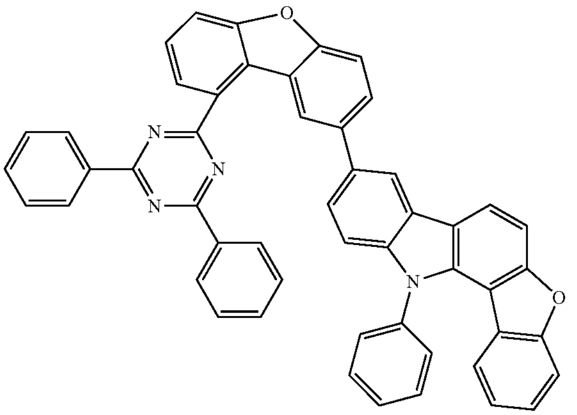 [SMILES: c1ccc(-c2nc(-c3ccccc3)nc(-c3cccc4sc5ccc(-c6ccc7c(c6)c6ccc8oc9ccccc9c8c6n7-c6ccccc6)cc5c34)n2)cc1]

TABLE 1-continued
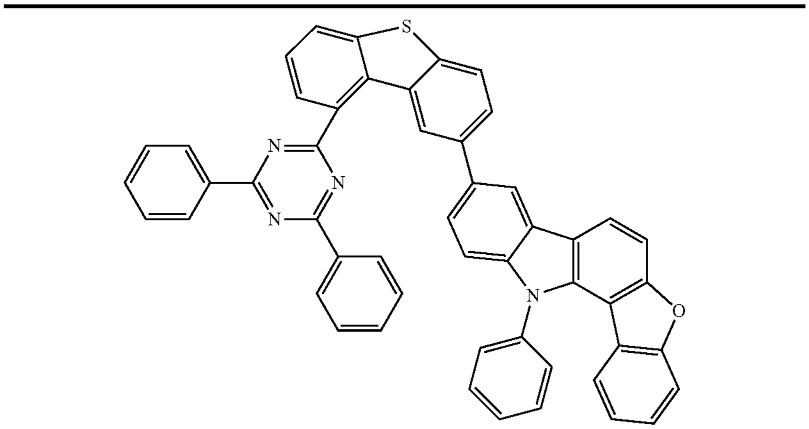
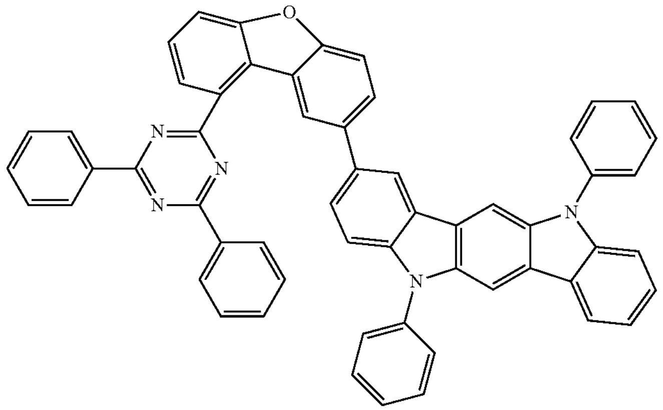 [SMILES: c1ccc(-c2nc(-c3ccccc3)nc(-c3cccc4oc5ccc(-c6ccc7c(c6)c6cc8c(cc6n7-c6ccccc6)c6ccccc6n8-c6ccccc6)cc5c34)n2)cc1]
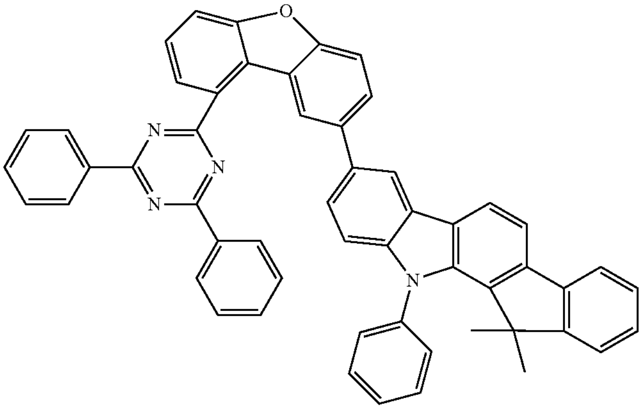 [SMILES: CC1(C)c2ccccc2-c2ccc3c4cc(-c5ccc6oc7cccc(-c8nc(-c9ccccc9)nc(-c9ccccc9)n8)c7c6c5)ccc4n(-c4ccccc4)c3c21]
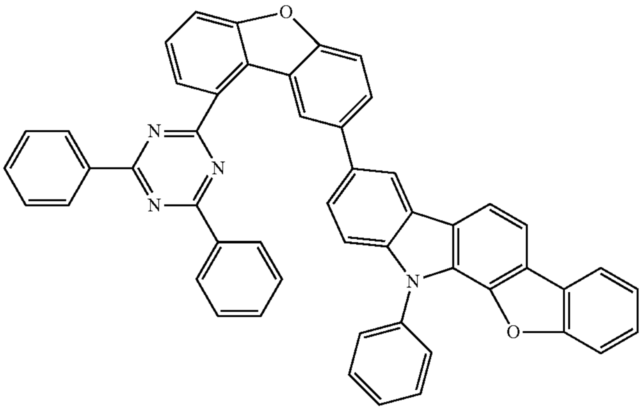 [SMILES: c1ccc(-c2nc(-c3ccccc3)nc(-c3cccc4oc5ccc(-c6ccc7c(c6)c6ccc8c9ccccc9oc8c6n7-c6ccccc6)cc5c34)n2)cc1]

TABLE 1-continued
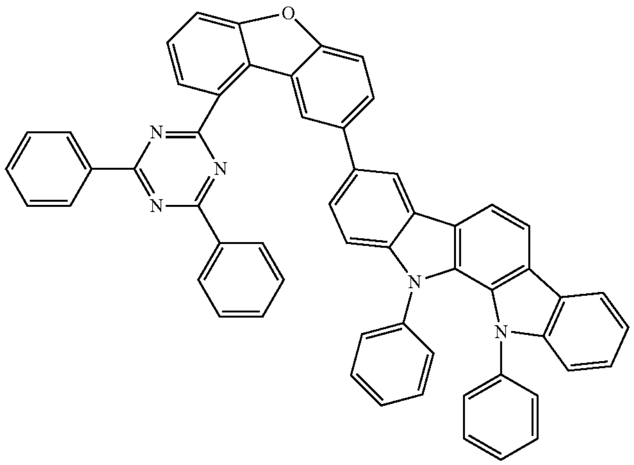 [SMILES: c1ccc(-c2nc(-c3ccccc3)nc(-c3cccc4oc5ccc(-c6ccc7c(c6)c6ccc8c9ccccc9n(-c9ccccc9)c8c6n7-c6ccccc6)cc5c34)n2)cc1]
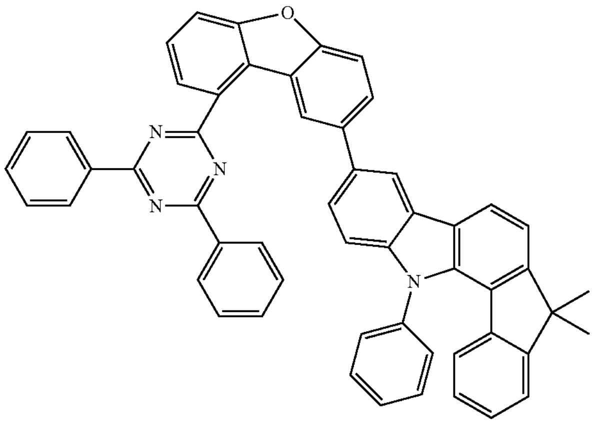 [SMILES: CC1(C)c2ccccc2-c2c1ccc1c3cc(-c4ccc5oc6cccc(-c7nc(-c8ccccc8)nc(-c8ccccc8)n7)c6c5c4)ccc3n(-c3ccccc3)c21]
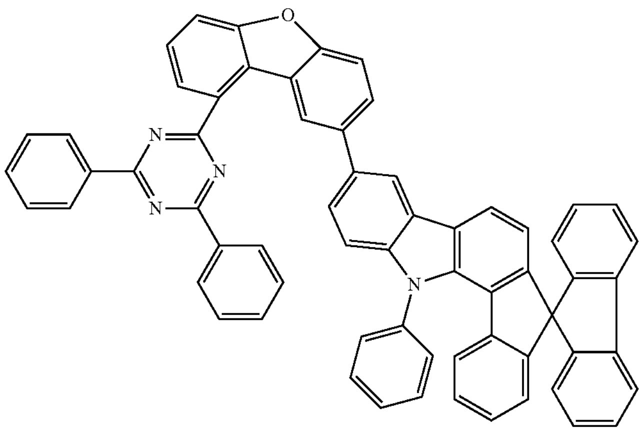
7

TABLE 1-continued
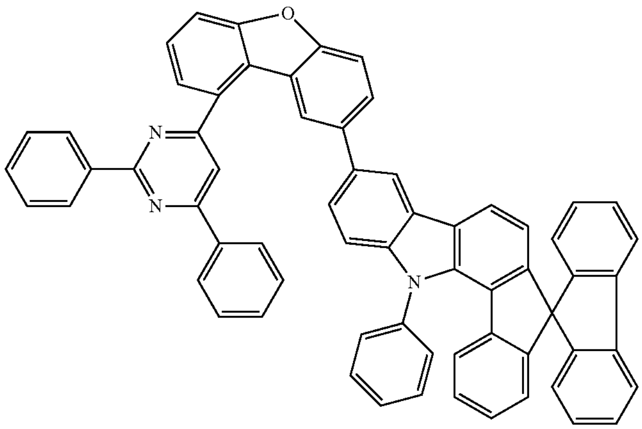 [SMILES: c1ccc(-c2cc(-c3cccc4oc5ccc(-c6ccc7c(c6)c6ccc8c(c6n7-c6ccccc6)-c6ccccc6C86c7ccccc7-c7ccccc76)cc5c34)nc(-c3ccccc3)n2)cc1]
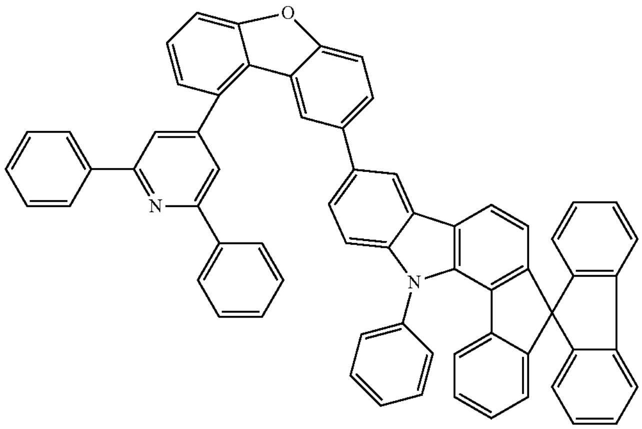 [SMILES: c1ccc(-c2cc(-c3cccc4oc5ccc(-c6ccc7c(c6)c6ccc8c(c6n7-c6ccccc6)-c6ccccc6C86c7ccccc7-c7ccccc76)cc5c34)cc(-c3ccccc3)n2)cc1]
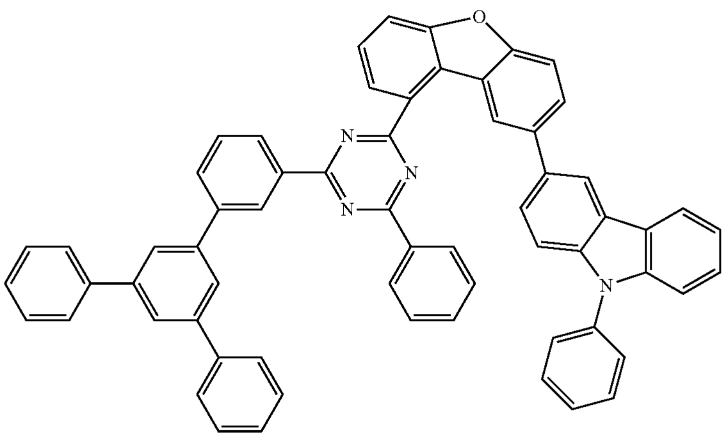 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8ccccc8)cc7c56)n4)c3)c2)cc1]

TABLE 1-continued
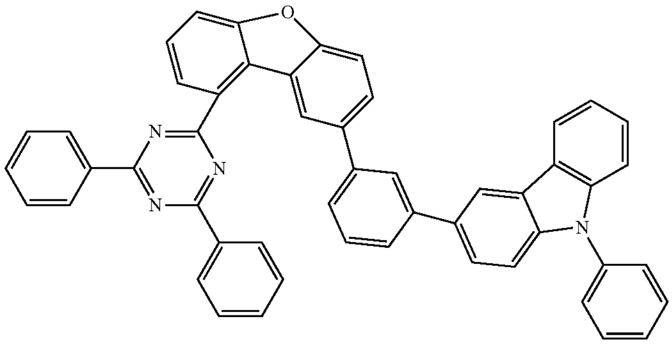 [SMILES: c1ccc(-c2nc(-c3ccccc3)nc(-c3cccc4oc5ccc(-c6cccc(-c7ccc8c(c7)c7ccccc7n8-c7ccccc7)c6)cc5c34)n2)cc1]
9
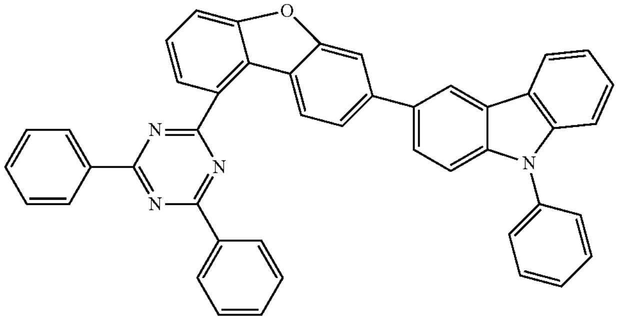 [SMILES: c1ccc(-c2nc(-c3ccccc3)nc(-c3cccc4oc5cc(-c6ccc7c(c6)c6ccccc6n7-c6ccccc6)ccc5c34)n2)cc1]
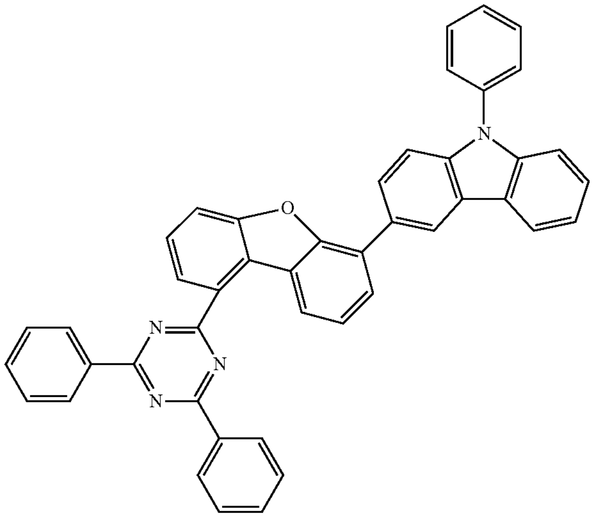 [SMILES: c1ccc(-c2nc(-c3ccccc3)nc(-c3cccc4oc5c(-c6ccc7c(c6)c6ccccc6n7-c6ccccc6)cccc5c34)n2)cc1]
10

TABLE 1-continued
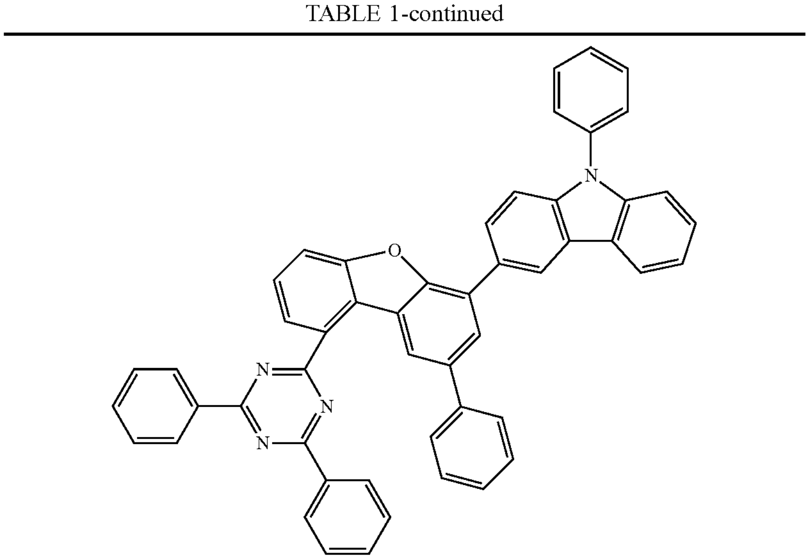
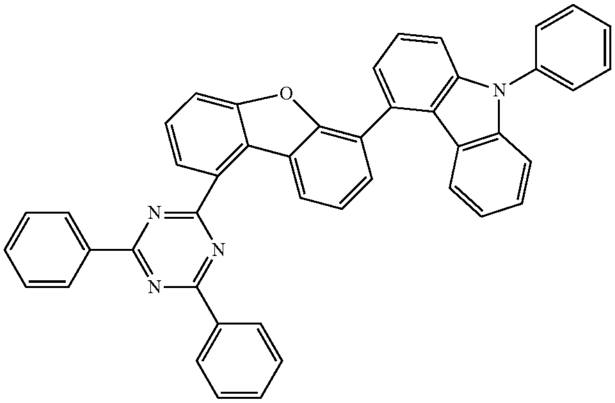 [SMILES: c1ccc(-c2nc(-c3ccccc3)nc(-c3cccc4oc5c(-c6cccc7c6c6ccccc6n7-c6ccccc6)cccc5c34)n2)cc1]
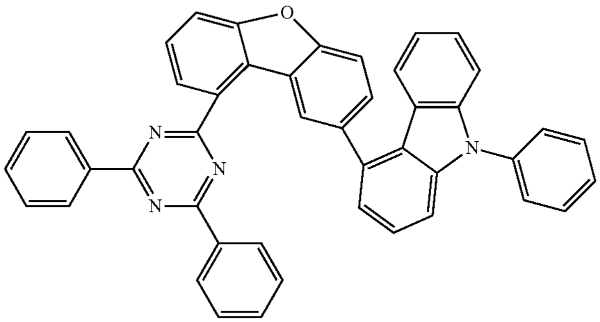 [SMILES: c1ccc(-c2nc(-c3ccccc3)nc(-c3cccc4oc5ccc(-c6cccc7c6c6ccccc6n7-c6ccccc6)cc5c34)n2)cc1]
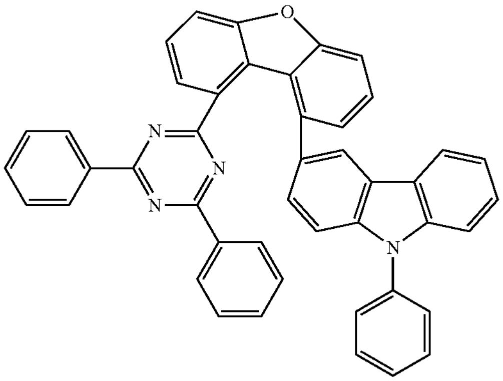 [SMILES: c1ccc(-c2nc(-c3ccccc3)nc(-c3cccc4oc5cccc(-c6ccc7c(c6)c6ccccc6n7-c6ccccc6)c5c34)n2)cc1]

TABLE 1-continued
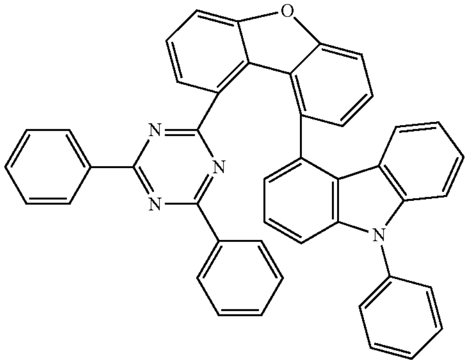 [SMILES: c1ccc(-c2nc(-c3ccccc3)nc(-c3cccc4oc5cccc(-c6cccc7c6c6ccccc6n7-c6ccccc6)c5c34)n2)cc1]
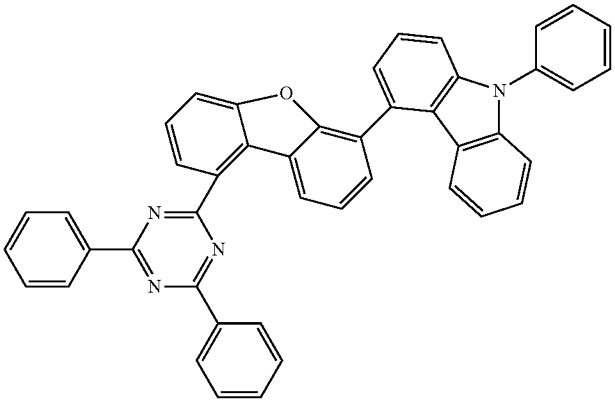 [SMILES: c1ccc(-c2nc(-c3ccccc3)nc(-c3cccc4oc5c(-c6cccc7c6c6ccccc6n7-c6ccccc6)cccc5c34)n2)cc1]
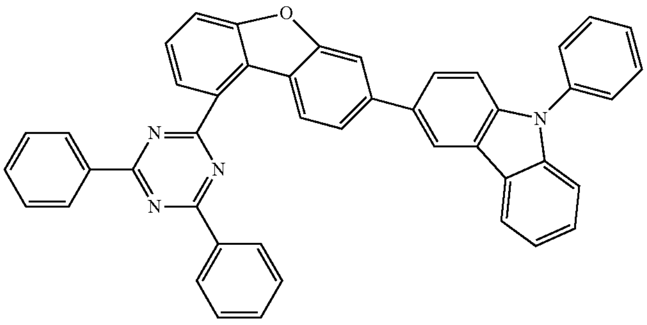 [SMILES: c1ccc(-c2nc(-c3ccccc3)nc(-c3cccc4oc5cc(-c6ccc7c(c6)c6ccccc6n7-c6ccccc6)ccc5c34)n2)cc1]
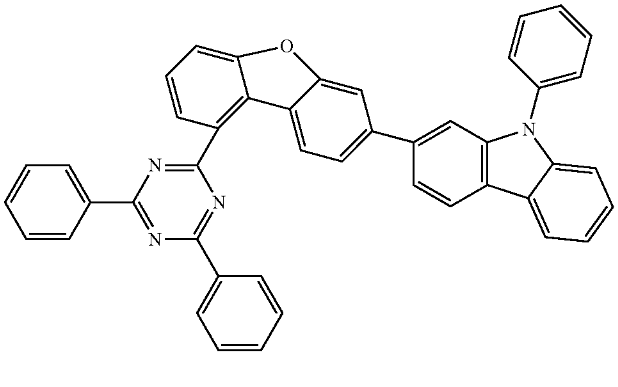 [SMILES: c1ccc(-c2nc(-c3ccccc3)nc(-c3cccc4oc5cc(-c6ccc7c8ccccc8n(-c8ccccc8)c7c6)ccc5c34)n2)cc1]

TABLE 1-continued
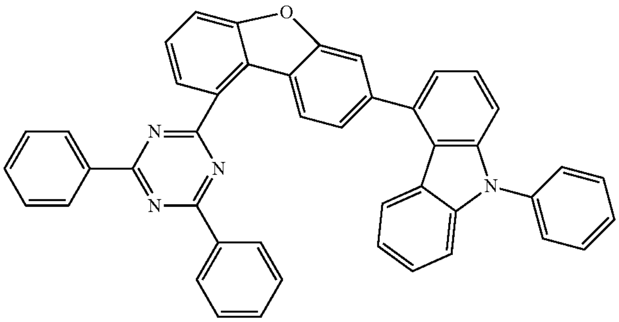 [SMILES: c1ccc(-c2nc(-c3ccccc3)nc(-c3cccc4oc5cc(-c6cccc7c6c6ccccc6n7-c6ccccc6)ccc5c34)n2)cc1]
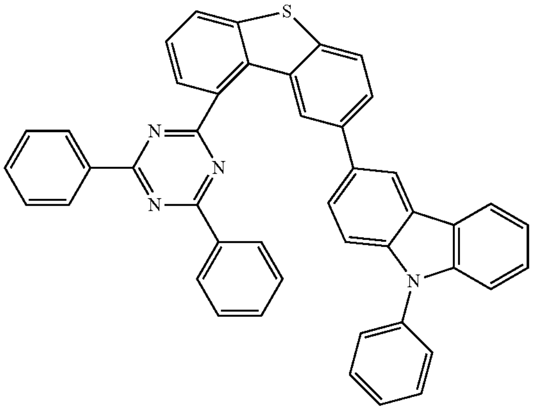 [SMILES: c1ccc(-c2nc(-c3ccccc3)nc(-c3cccc4sc5ccc(-c6ccc7c(c6)c6ccccc6n7-c6ccccc6)cc5c34)n2)cc1]
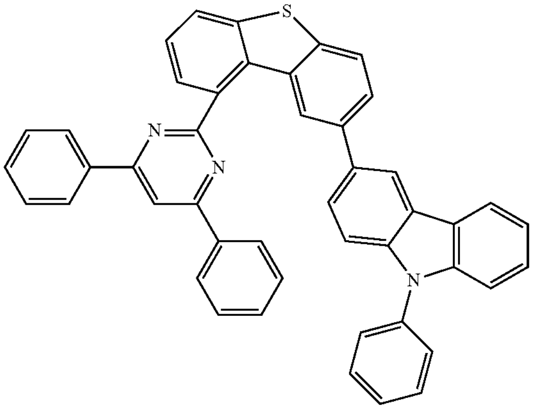 [SMILES: c1ccc(-c2cc(-c3ccccc3)nc(-c3cccc4sc5ccc(-c6ccc7c(c6)c6ccccc6n7-c6ccccc6)cc5c34)n2)cc1]
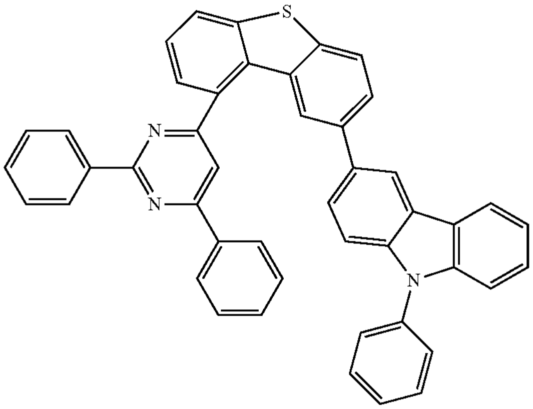 [SMILES: c1ccc(-c2cc(-c3cccc4sc5ccc(-c6ccc7c(c6)c6ccccc6n7-c6ccccc6)cc5c34)nc(-c3ccccc3)n2)cc1]

TABLE 1-continued
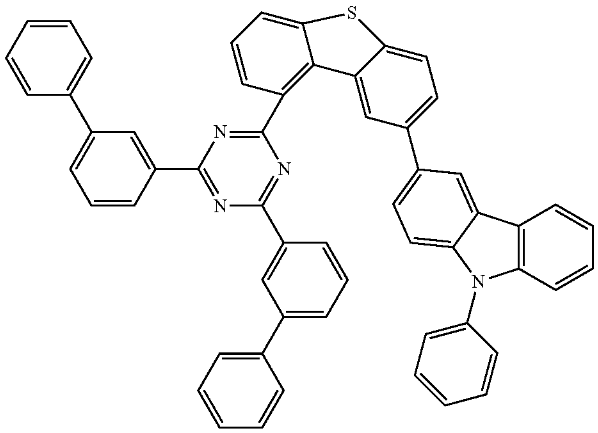
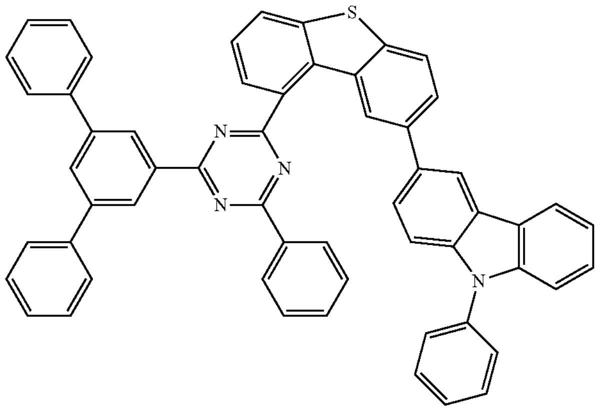
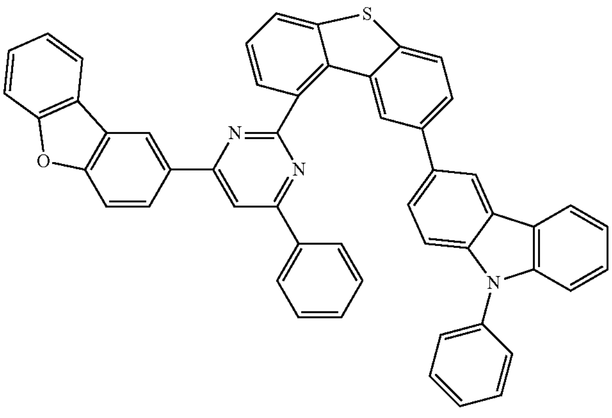 [SMILES: c1ccc(-c2cc(-c3ccc4oc5ccccc5c4c3)nc(-c3cccc4sc5ccc(-c6ccc7c(c6)c6ccccc6n7-c6ccccc6)cc5c34)n2)cc1]

TABLE 1-continued
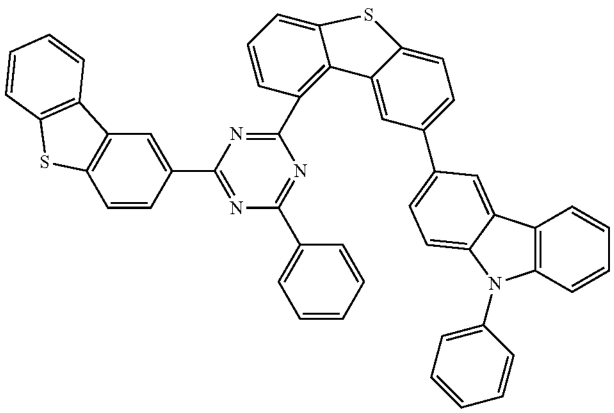 [SMILES: c1ccc(-c2nc(-c3ccc4sc5ccccc5c4c3)nc(-c3cccc4sc5ccc(-c6ccc7c(c6)c6ccccc6n7-c6ccccc6)cc5c34)n2)cc1]
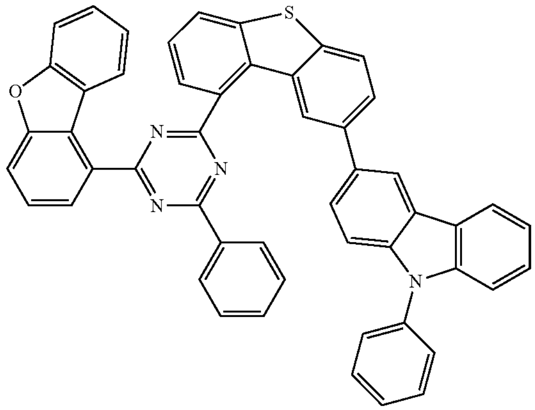 [SMILES: c1ccc(-c2nc(-c3cccc4oc5ccccc5c34)nc(-c3cccc4sc5ccc(-c6ccc7c(c6)c6ccccc6n7-c6ccccc6)cc5c34)n2)cc1]
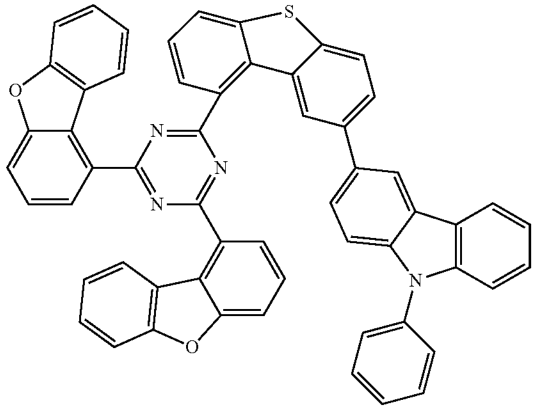 [SMILES: c1ccc(-n2c3ccccc3c3cc(-c4ccc5sc6cccc(-c7nc(-c8cccc9oc%10ccccc%10c89)nc(-c8cccc9oc%10ccccc%10c89)n7)c6c5c4)ccc32)cc1]

TABLE 1-continued
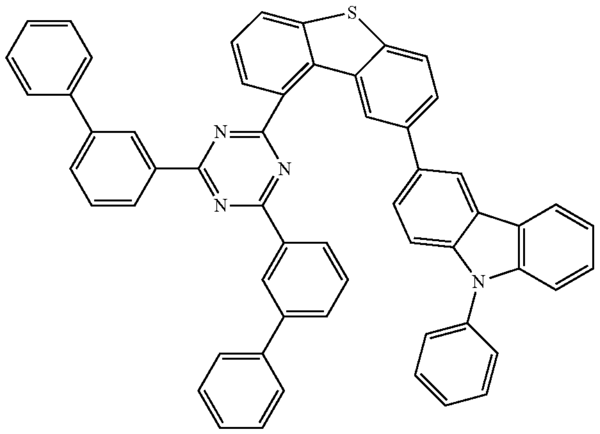 [SMILES: c1ccc(-c2cccc(-c3nc(-c4cccc(-c5ccccc5)c4)nc(-c4cccc5sc6ccc(-c7ccc8c(c7)c7ccccc7n8-c7ccccc7)cc6c45)n3)c2)cc1]
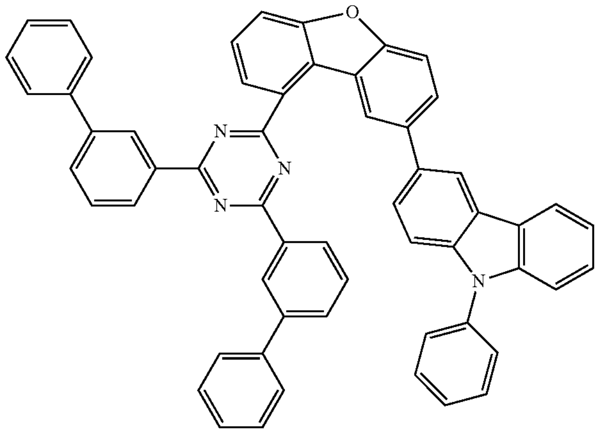 [SMILES: c1ccc(-c2cccc(-c3nc(-c4cccc(-c5ccccc5)c4)nc(-c4cccc5oc6ccc(-c7ccc8c(c7)c7ccccc7n8-c7ccccc7)cc6c45)n3)c2)cc1]
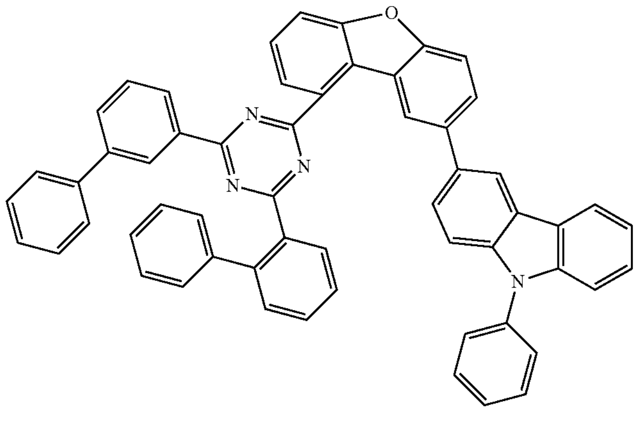 [SMILES: c1ccc(-c2cccc(-c3nc(-c4ccccc4-c4ccccc4)nc(-c4cccc5oc6ccc(-c7ccc8c(c7)c7ccccc7n8-c7ccccc7)cc6c45)n3)c2)cc1]

TABLE 1-continued
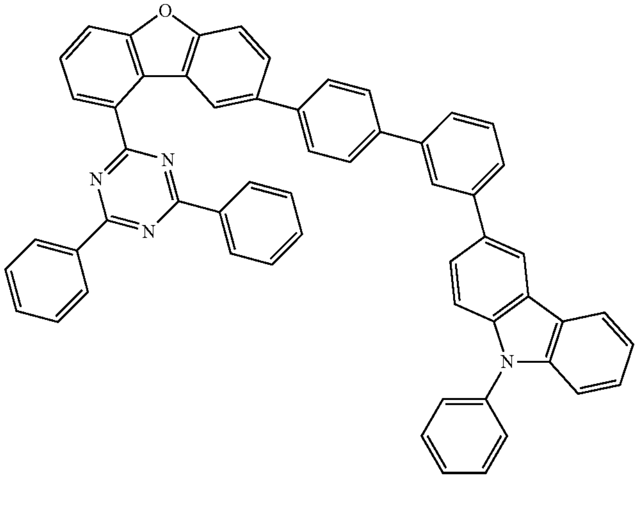 [SMILES: c1ccc(-c2nc(-c3ccccc3)nc(-c3cccc4oc5ccc(-c6ccc(-c7cccc(-c8ccc9c(c8)c8ccccc8n9-c8ccccc8)c7)cc6)cc5c34)n2)cc1]
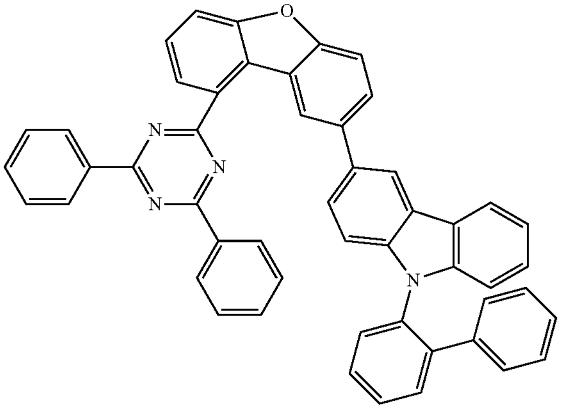 [SMILES: c1ccc(-c2nc(-c3ccccc3)nc(-c3cccc4oc5ccc(-c6ccc7c(c6)c6ccccc6n7-c6ccccc6-c6ccccc6)cc5c34)n2)cc1]
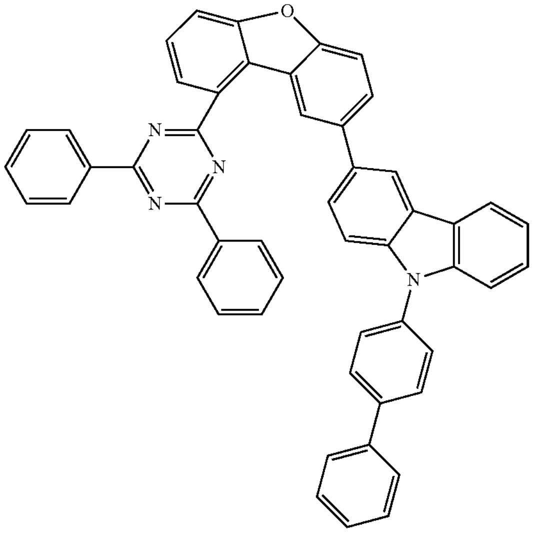

TABLE 1-continued
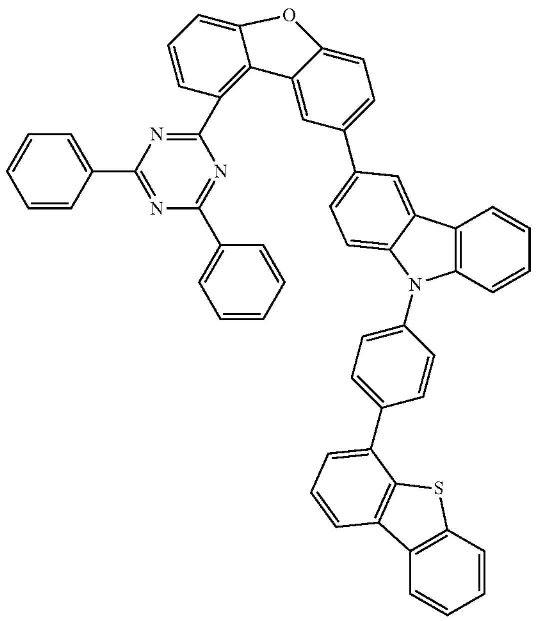 [SMILES: c1ccc(-c2nc(-c3ccccc3)nc(-c3cccc4oc5ccc(-c6ccc7c(c6)c6ccccc6n7-c6ccc(-c7cccc8c7sc7ccccc78)cc6)cc5c34)n2)cc1]
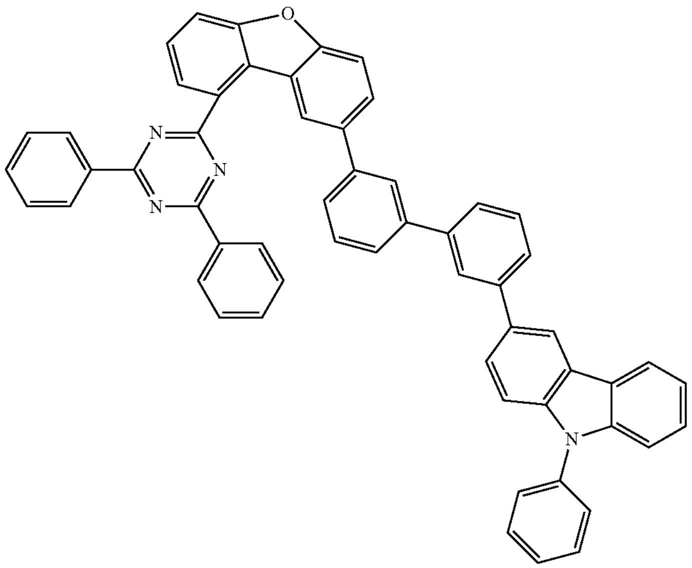
19

TABLE 1-continued
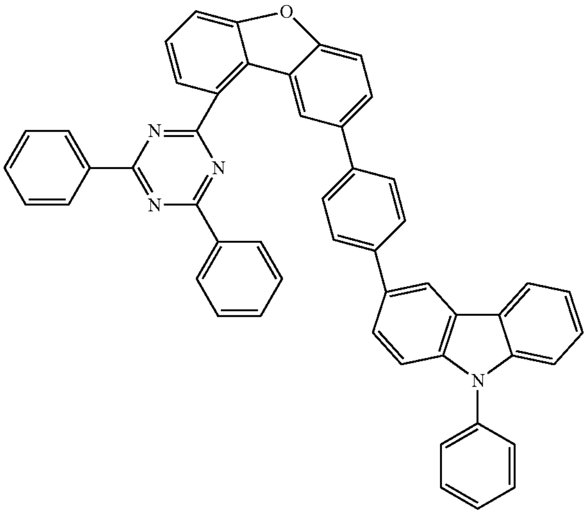 [SMILES: c1ccc(-c2nc(-c3ccccc3)nc(-c3cccc4oc5ccc(-c6ccc(-c7ccc8c(c7)c7ccccc7n8-c7ccccc7)cc6)cc5c34)n2)cc1]
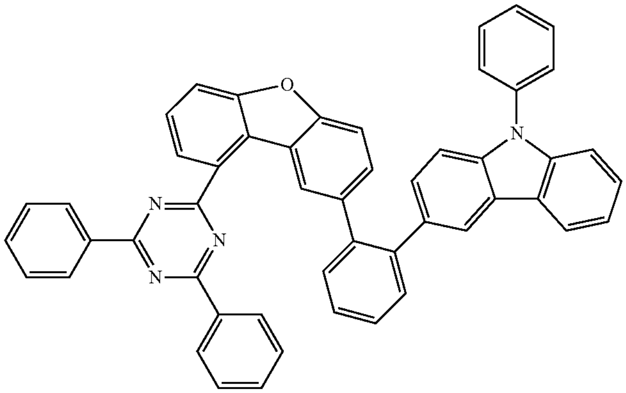 [SMILES: c1ccc(-c2nc(-c3ccccc3)nc(-c3cccc4oc5ccc(-c6ccccc6-c6ccc7c(c6)c6ccccc6n7-c6ccccc6)cc5c34)n2)cc1]
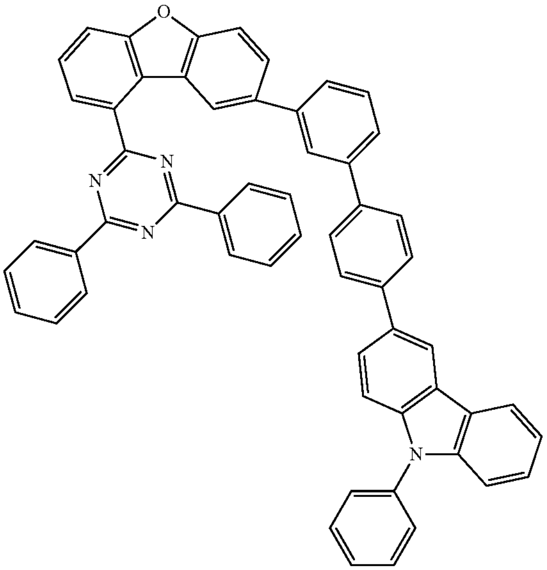 [SMILES: c1ccc(-c2nc(-c3ccccc3)nc(-c3cccc4oc5ccc(-c6cccc(-c7ccc(-c8ccc9c(c8)c8ccccc8n9-c8ccccc8)cc7)c6)cc5c34)n2)cc1]

TABLE 1-continued
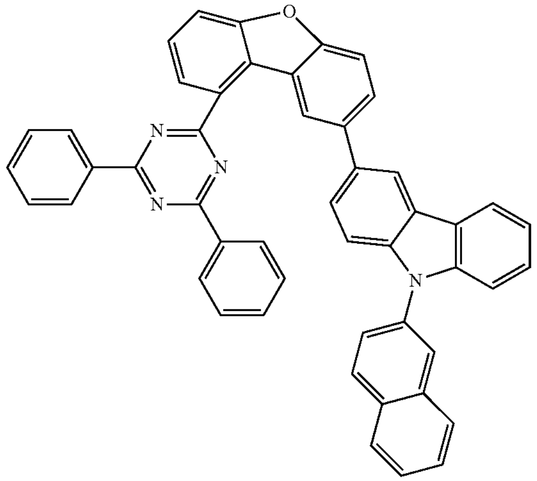
12
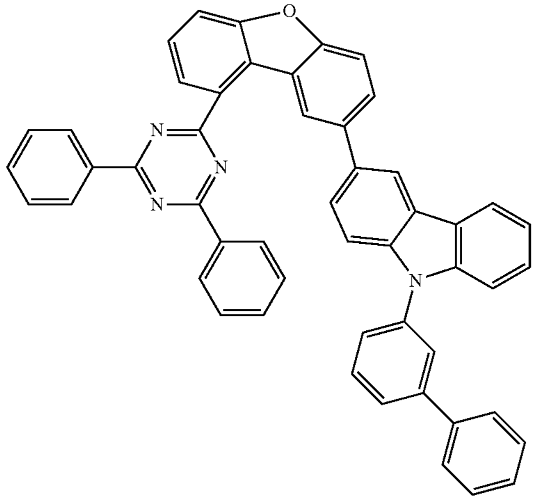
13
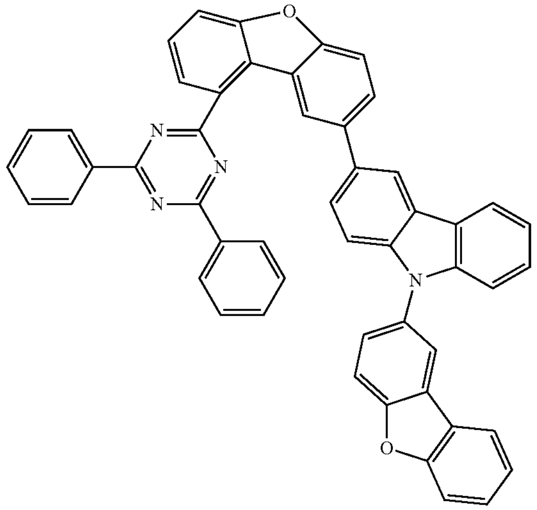
14

TABLE 1-continued
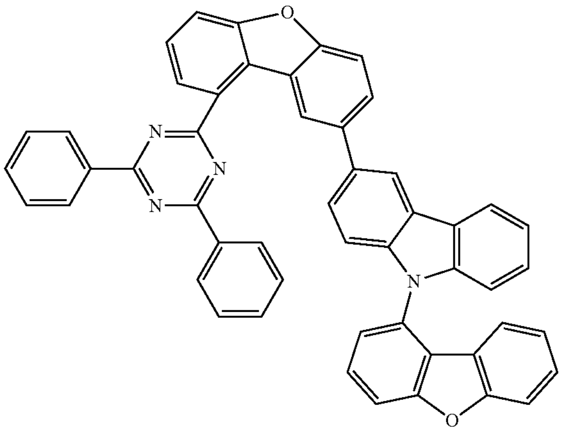
15
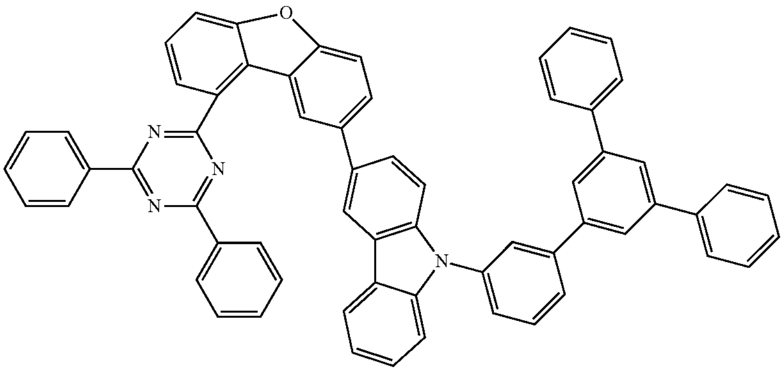
16
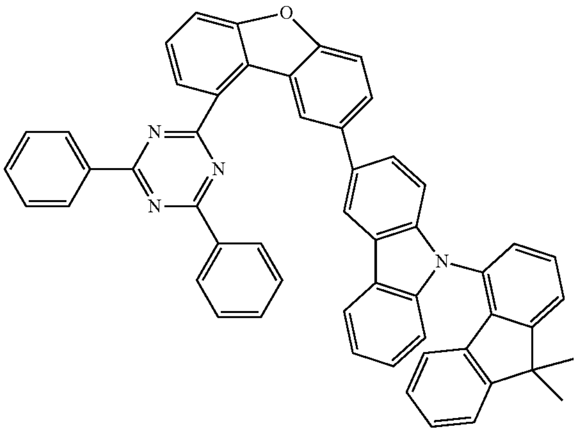
17

TABLE 1-continued
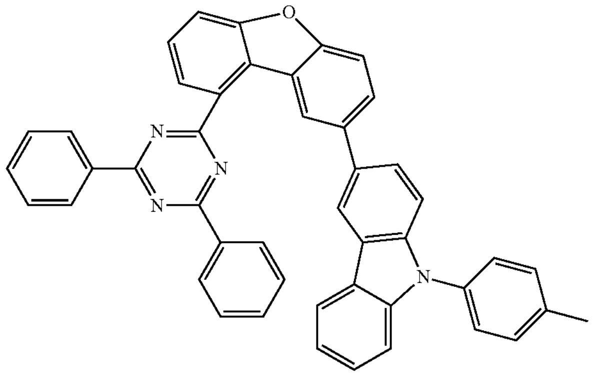
18
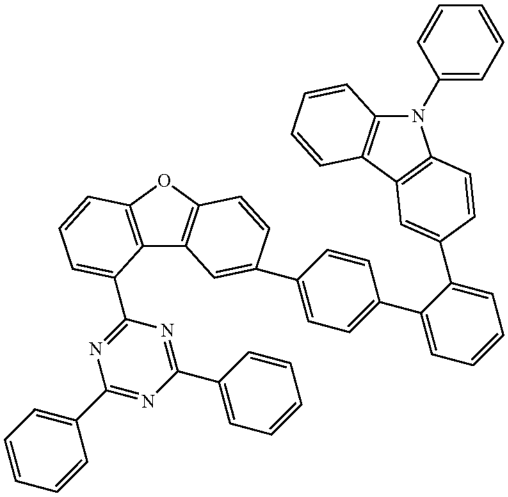 [SMILES: c1ccc(-c2nc(-c3ccccc3)nc(-c3cccc4oc5ccc(-c6ccc(-c7ccccc7-c7ccc8c(c7)c7ccccc7n8-c7ccccc7)cc6)cc5c34)n2)cc1]
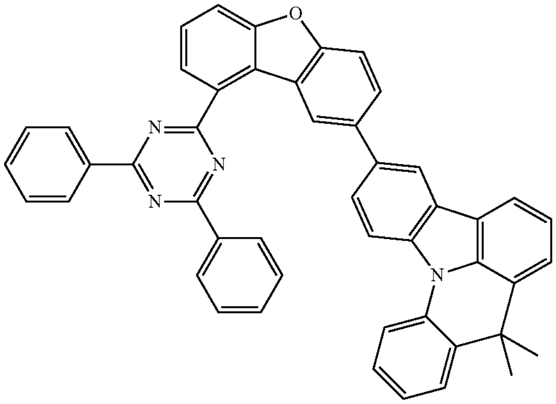
20

TABLE 1-continued
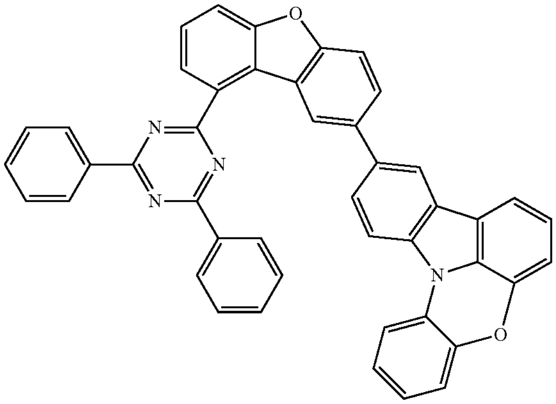
21
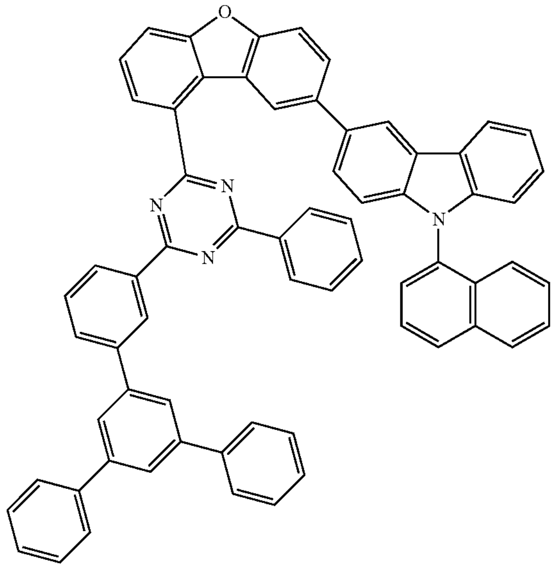 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8cccc9ccccc89)cc7c56)n4)c3)c2)cc1]
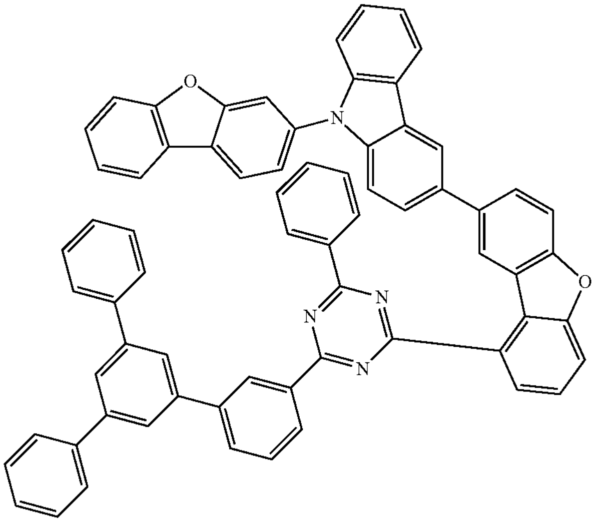 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8ccc9c(c8)oc8ccccc89)cc7c56)n4)c3)c2)cc1]

TABLE 1-continued
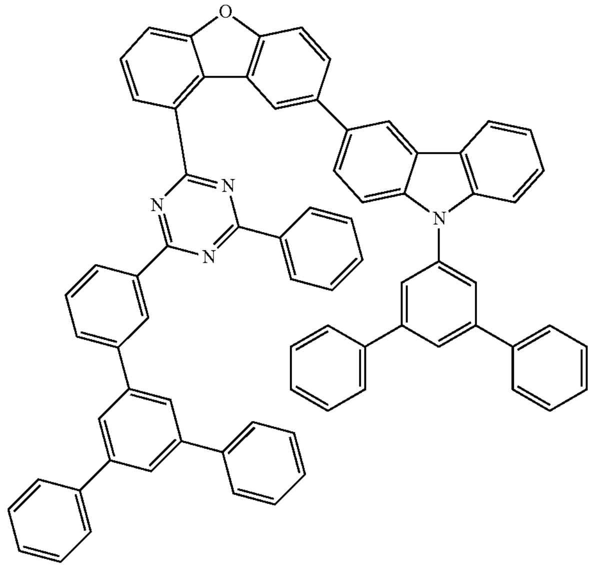 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8cc(-c9ccccc9)cc(-c9ccccc9)c8)cc7c56)n4)c3)c2)cc1]
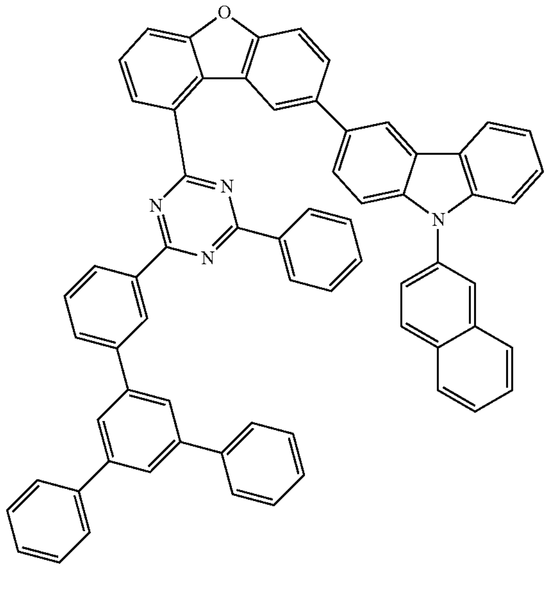 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8ccc9ccccc9c8)cc7c56)n4)c3)c2)cc1]

TABLE 1-continued
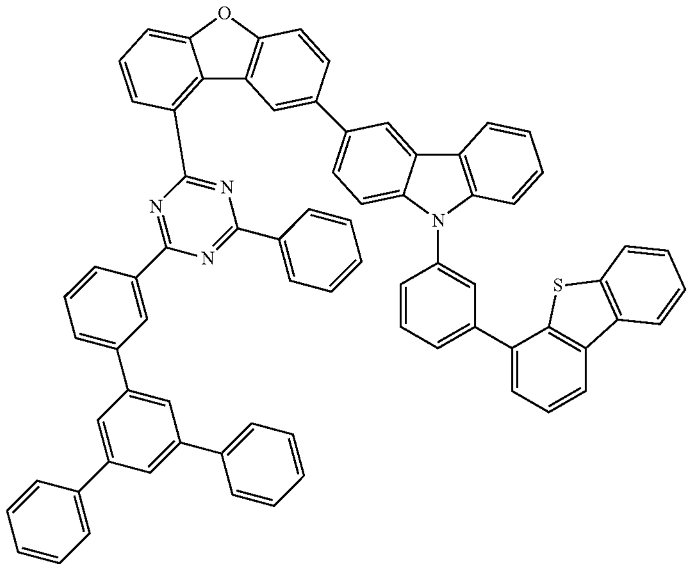 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8cccc(-c9cccc%10c9sc9ccccc9%10)c8)cc7c56)n4)c3)c2)cc1]
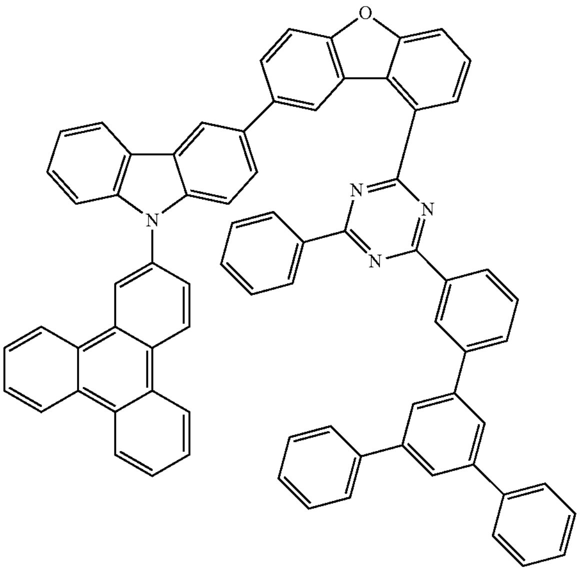 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8ccc9c%10ccccc%10c%10ccccc%10c9c8)cc7c56)n4)c3)c2)cc1]
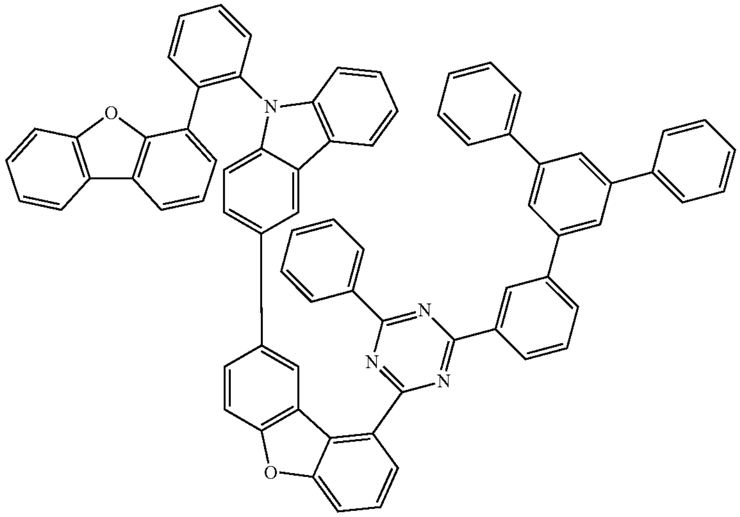 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8ccccc8-c8cccc9c8oc8ccccc89)cc7c56)n4)c3)c2)cc1]

TABLE 1-continued
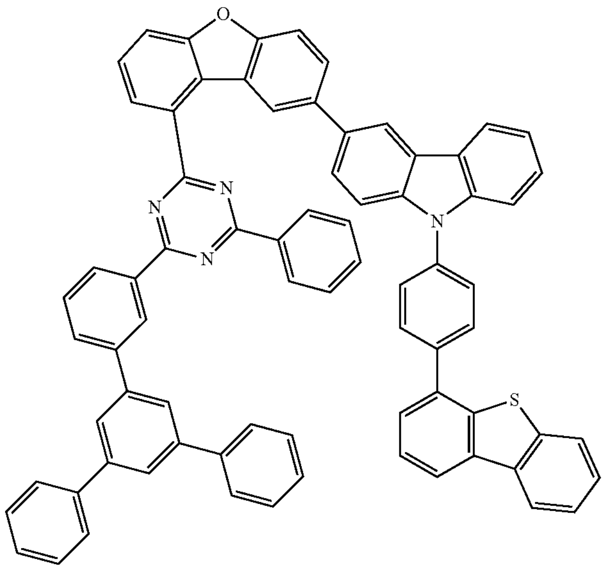 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8ccc(-c9cccc%10c9sc9ccccc9%10)cc8)cc7c56)n4)c3)c2)cc1]
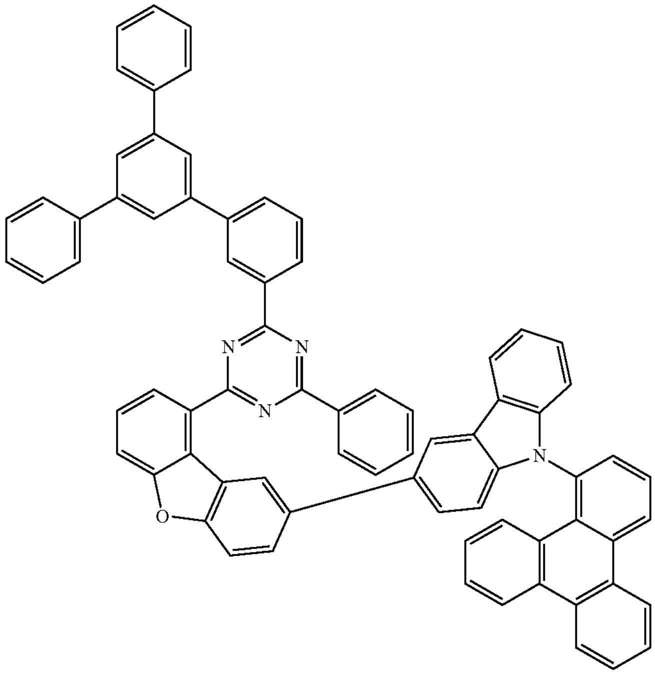 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8cccc9c%10ccccc%10c%10ccccc%10c89)cc7c56)n4)c3)c2)cc1]

TABLE 1-continued
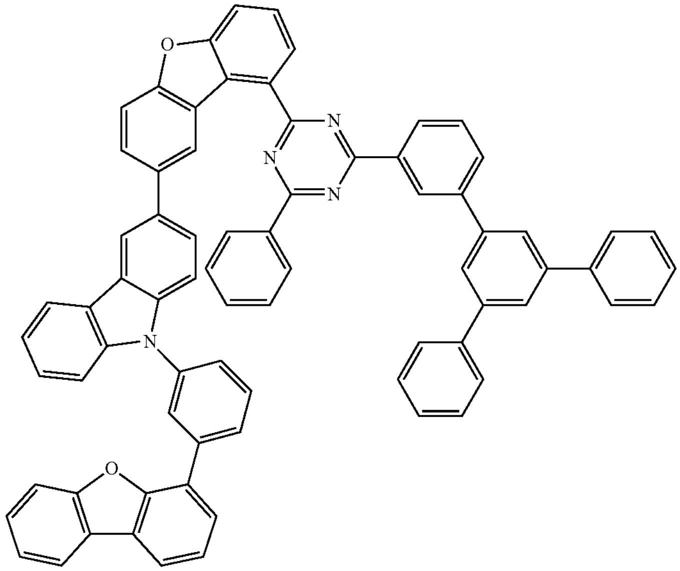 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8cccc(-c9cccc%10c9oc9ccccc9%10)c8)cc7c56)n4)c3)c2)cc1]
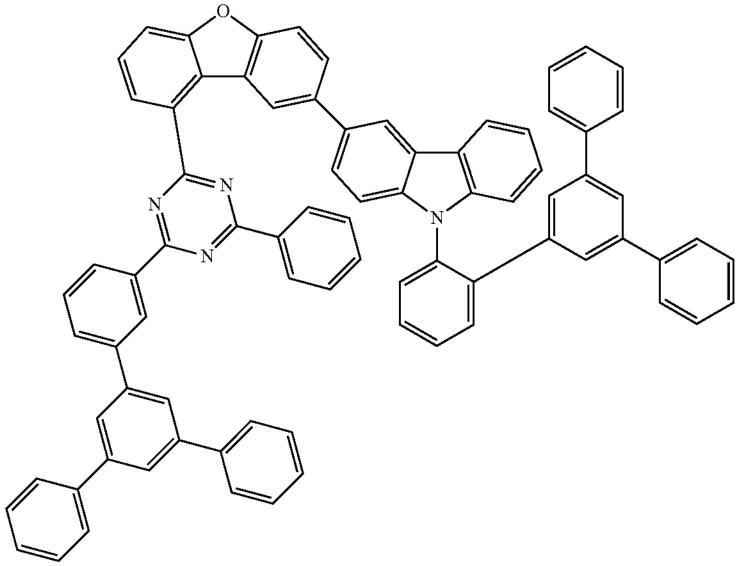 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8ccccc8-c8cc(-c9ccccc9)cc(-c9ccccc9)c8)cc7c56)n4)c3)c2)cc1]

TABLE 1-continued
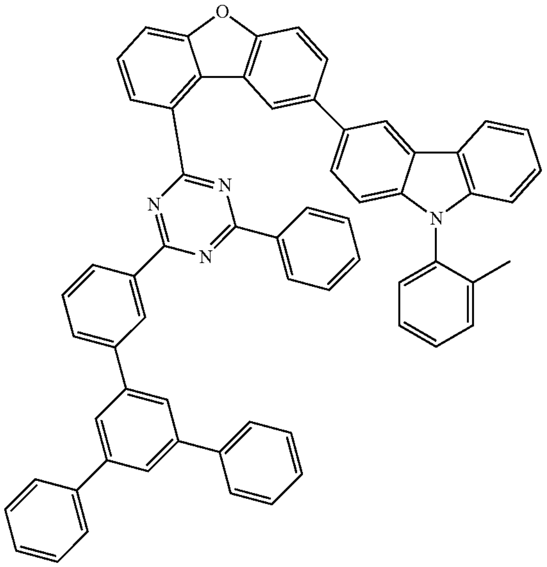 [SMILES: Cc1ccccc1-n1c2ccccc2c2cc(-c3ccc4oc5cccc(-c6nc(-c7ccccc7)nc(-c7cccc(-c8cc(-c9ccccc9)cc(-c9ccccc9)c8)c7)n6)c5c4c3)ccc21]
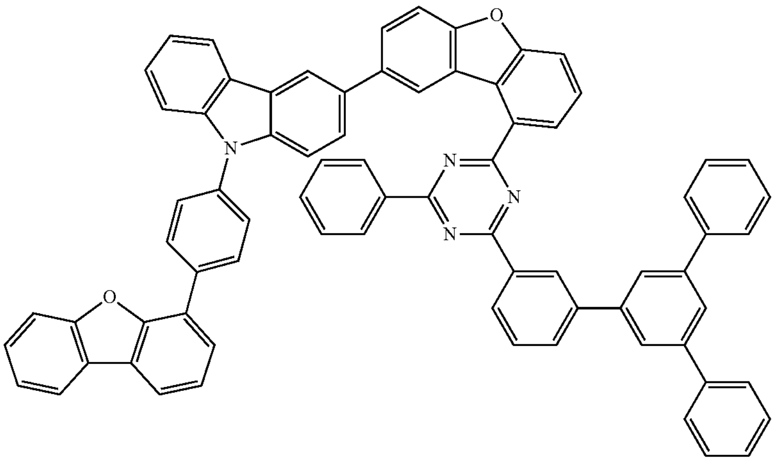 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8ccc(-c9cccc%10c9oc9ccccc9%10)cc8)cc7c56)n4)c3)c2)cc1]
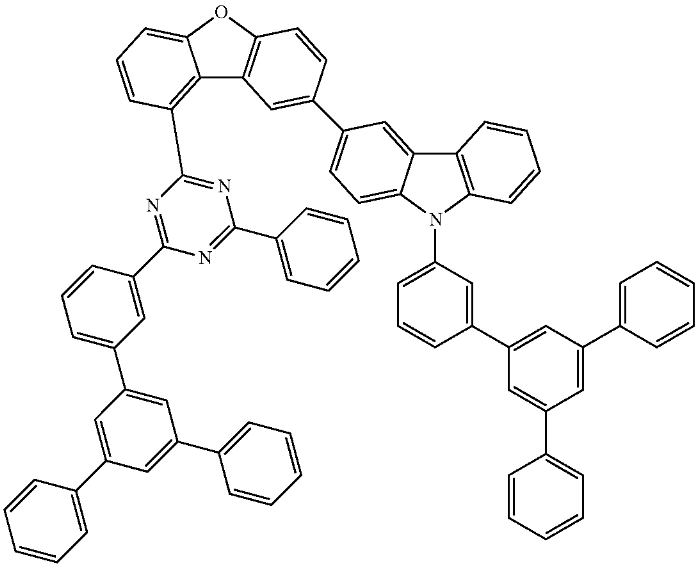 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8cccc(-c9cc(-c%10ccccc%10)cc(-c%10ccccc%10)c9)c8)cc7c56)n4)c3)c2)cc1]

TABLE 1-continued
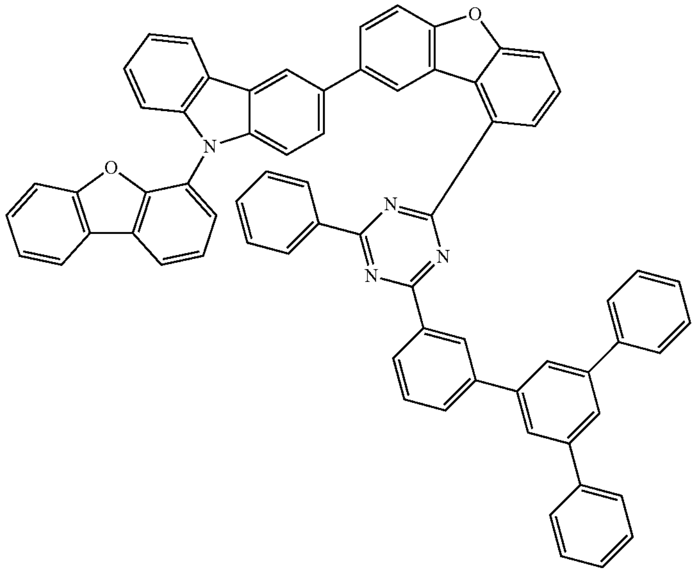 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8cccc9c8oc8ccccc89)cc7c56)n4)c3)c2)cc1]
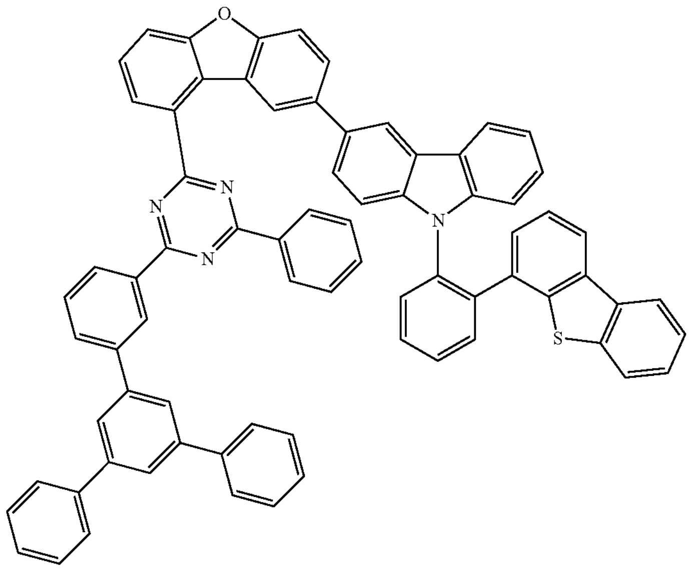 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8ccccc8-c8cccc9c8sc8ccccc89)cc7c56)n4)c3)c2)cc1]

TABLE 1-continued
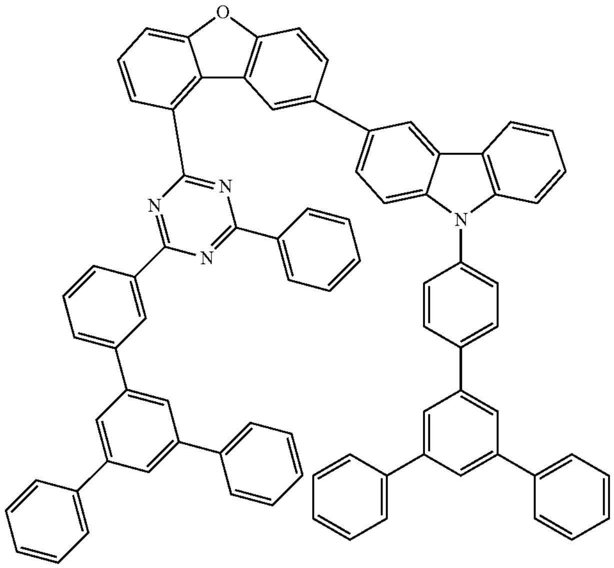 [SMILES: c1ccc(-c2cc(-c3ccccc3)cc(-c3ccc(-n4c5ccccc5c5cc(-c6ccc7oc8cccc(-c9nc(-c%10ccccc%10)nc(-c%10cccc(-c%11cc(-c%12ccccc%12)cc(-c%12ccccc%12)c%11)c%10)n9)c8c7c6)ccc54)cc3)c2)cc1]
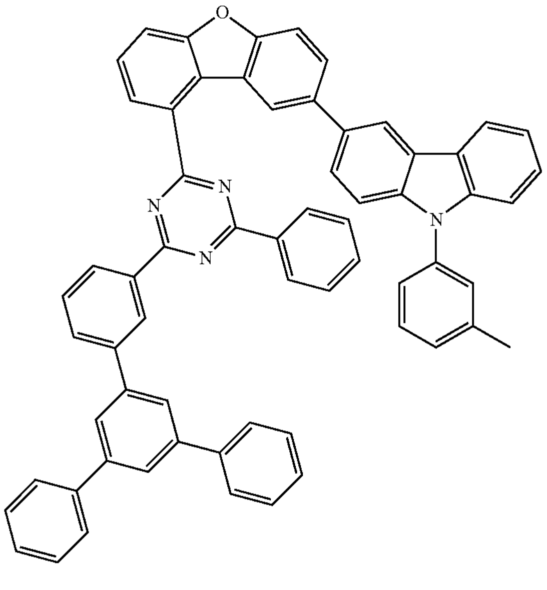 [SMILES: Cc1cccc(-n2c3ccccc3c3cc(-c4ccc5oc6cccc(-c7nc(-c8ccccc8)nc(-c8cccc(-c9cc(-c%10ccccc%10)cc(-c%10ccccc%10)c9)c8)n7)c6c5c4)ccc32)c1]

TABLE 1-continued
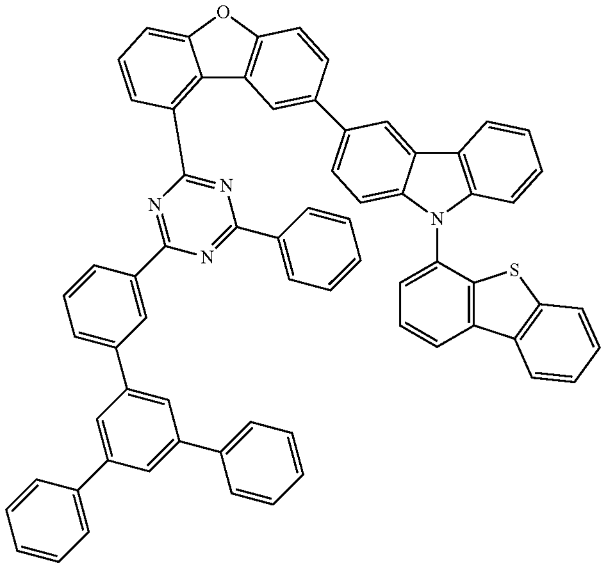 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8cccc9c8sc8ccccc89)cc7c56)n4)c3)c2)cc1]
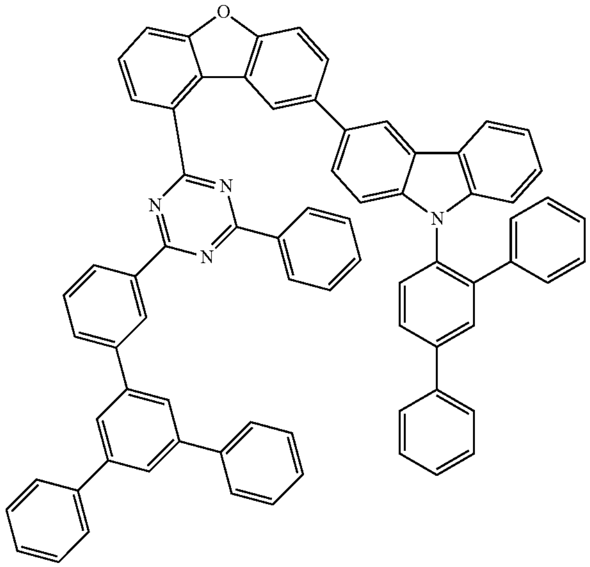 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8ccc(-c9ccccc9)cc8-c8ccccc8)cc7c56)n4)c3)c2)cc1]

TABLE 1-continued
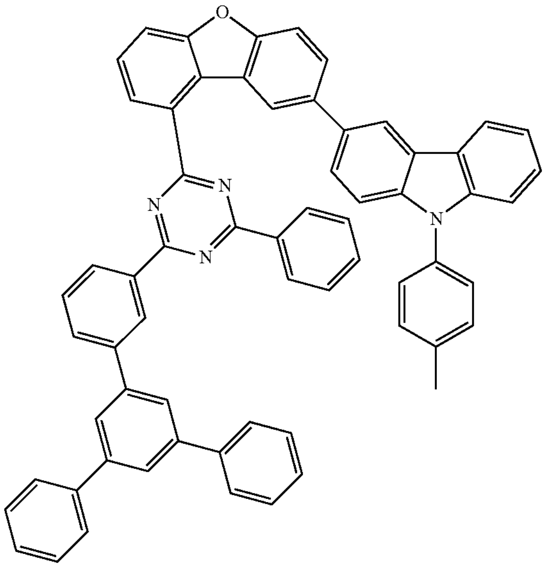 [SMILES: Cc1ccc(-n2c3ccccc3c3cc(-c4ccc5oc6cccc(-c7nc(-c8ccccc8)nc(-c8cccc(-c9cc(-c%10ccccc%10)cc(-c%10ccccc%10)c9)c8)n7)c6c5c4)ccc32)cc1]
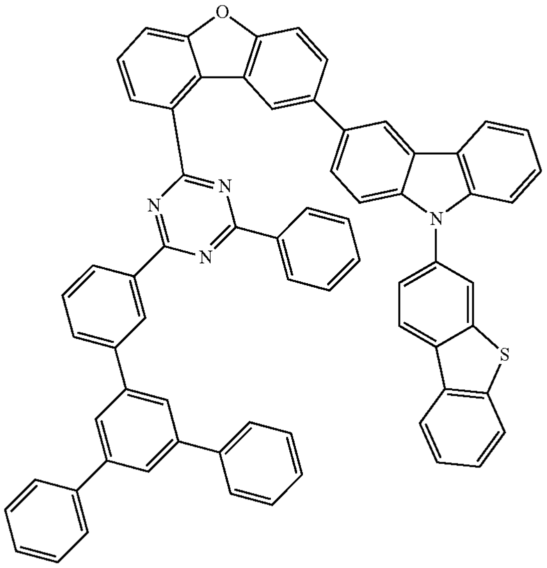 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8ccc9c(c8)sc8ccccc89)cc7c56)n4)c3)c2)cc1]
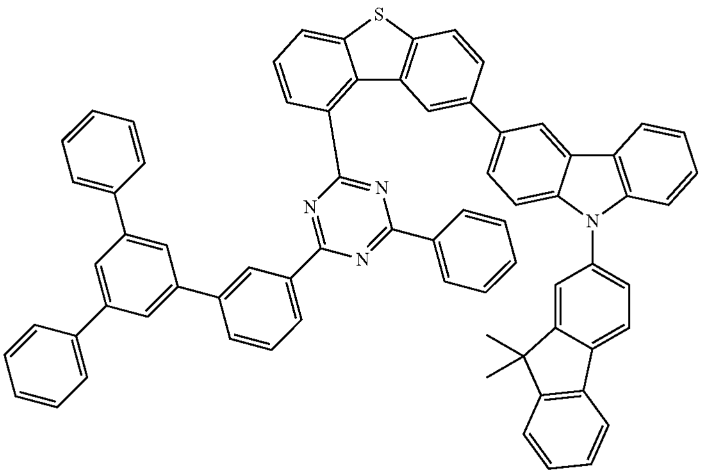 [SMILES: CC1(C)c2ccccc2-c2ccc(-n3c4ccccc4c4cc(-c5ccc6sc7cccc(-c8nc(-c9ccccc9)nc(-c9cccc(-c%10cc(-c%11ccccc%11)cc(-c%11ccccc%11)c%10)c9)n8)c7c6c5)ccc43)cc21]

TABLE 1-continued
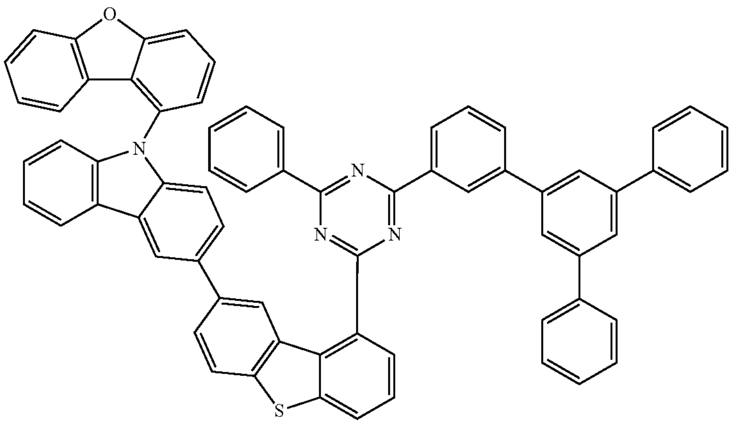 [SMILES: c1ccc(-c2cc(-c3ccccc3)cc(-c3cccc(-c4nc(-c5ccccc5)nc(-c5cccc6sc7ccc(-c8ccc9c(c8)c8ccccc8n9-c8cccc9oc%10ccccc%10c89)cc7c56)n4)c3)c2)cc1]
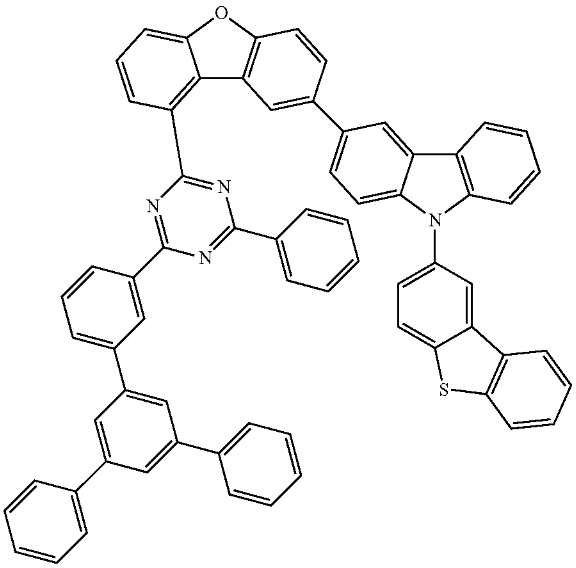 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8ccc9sc%10ccccc%10c9c8)cc7c56)n4)c3)c2)cc1]
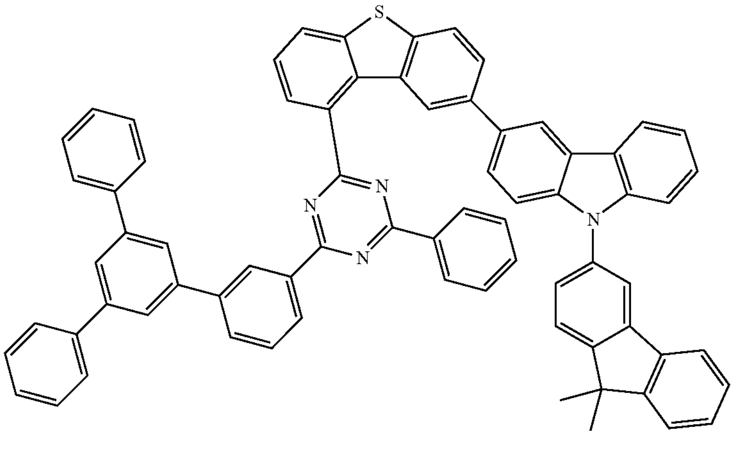 [SMILES: CC1(C)c2ccccc2-c2cc(-n3c4ccccc4c4cc(-c5ccc6sc7cccc(-c8nc(-c9ccccc9)nc(-c9cccc(-c%10cc(-c%11ccccc%11)cc(-c%11ccccc%11)c%10)c9)n8)c7c6c5)ccc43)ccc21]

TABLE 1-continued
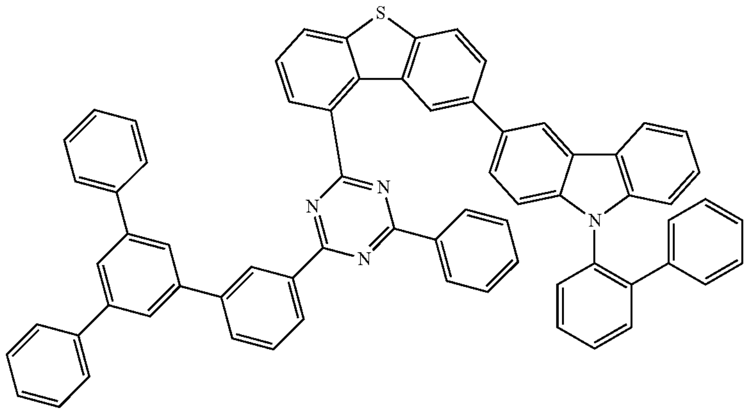 [SMILES: c1ccc(-c2cc(-c3ccccc3)cc(-c3cccc(-c4nc(-c5ccccc5)nc(-c5cccc6sc7ccc(-c8ccc9c(c8)c8ccccc8n9-c8ccccc8-c8ccccc8)cc7c56)n4)c3)c2)cc1]
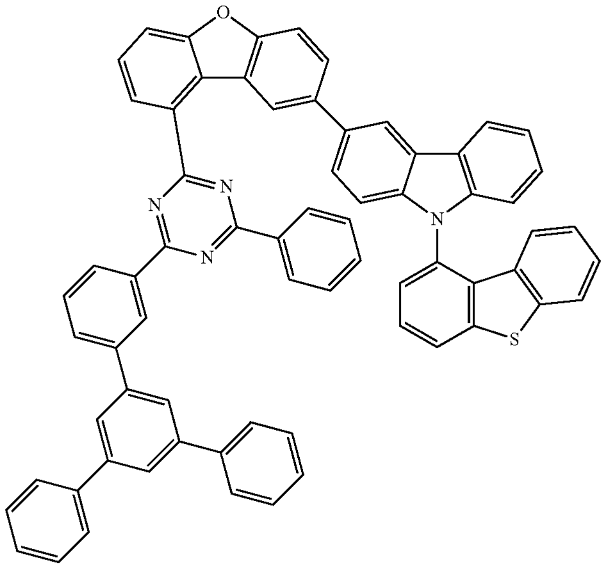 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8cccc9sc%10ccccc%10c89)cc7c56)n4)c3)c2)cc1]
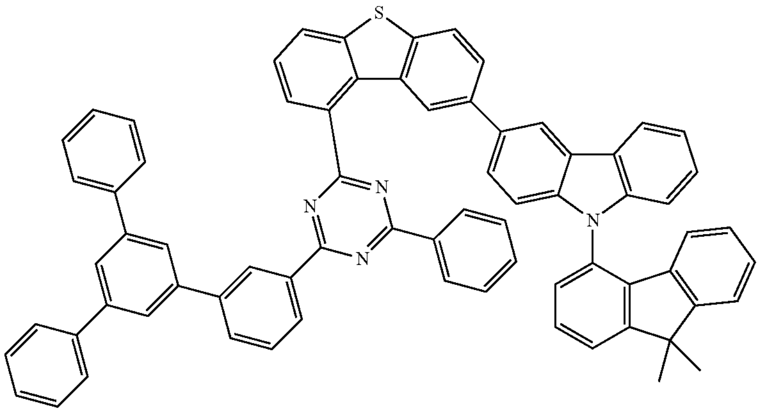 [SMILES: CC1(C)c2ccccc2-c2c(-n3c4ccccc4c4cc(-c5ccc6sc7cccc(-c8nc(-c9ccccc9)nc(-c9cccc(-c%10cc(-c%11ccccc%11)cc(-c%11ccccc%11)c%10)c9)n8)c7c6c5)ccc43)cccc21]

TABLE 1-continued
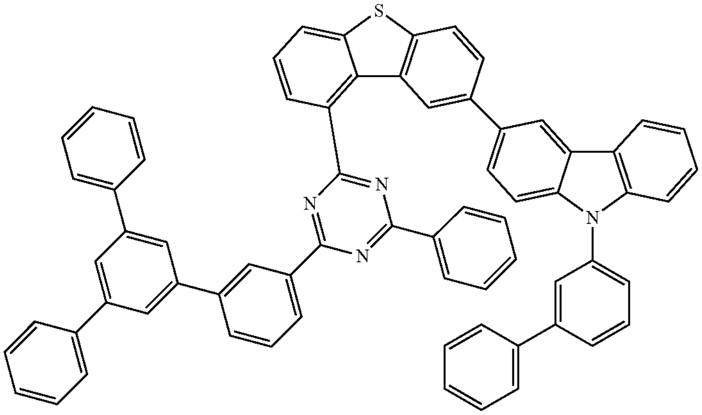 [SMILES: c1ccc(-c2cc(-c3ccccc3)cc(-c3cccc(-c4nc(-c5ccccc5)nc(-c5cccc6sc7ccc(-c8ccc9c(c8)c8ccccc8n9-c8cccc(-c9ccccc9)c8)cc7c56)n4)c3)c2)cc1]
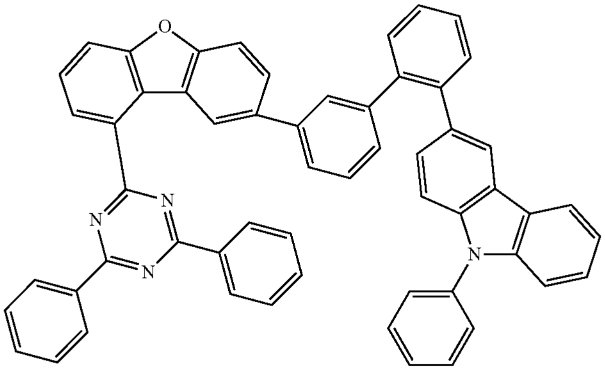 [SMILES: c1ccc(-c2nc(-c3ccccc3)nc(-c3cccc4oc5ccc(-c6cccc(-c7ccccc7-c7ccc8c(c7)c7ccccc7n8-c7ccccc7)c6)cc5c34)n2)cc1]
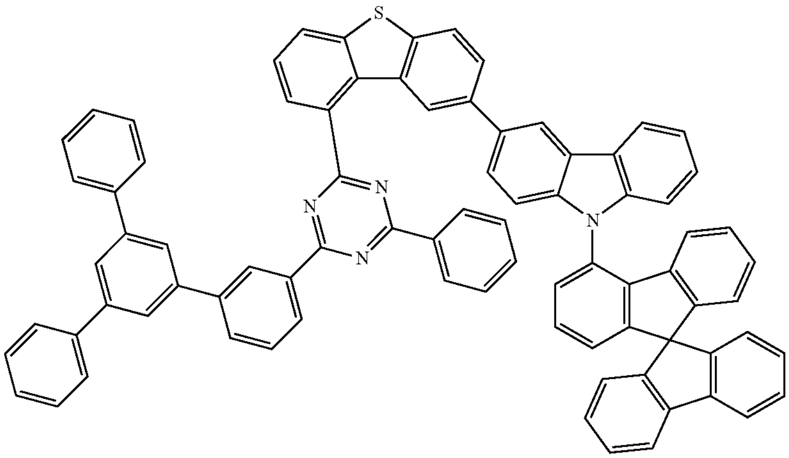 [SMILES: c1ccc(-c2cc(-c3ccccc3)cc(-c3cccc(-c4nc(-c5ccccc5)nc(-c5cccc6sc7ccc(-c8ccc9c(c8)c8ccccc8n9-c8cccc9c8-c8ccccc8C98c9ccccc9-c9ccccc98)cc7c56)n4)c3)c2)cc1]

TABLE 1-continued
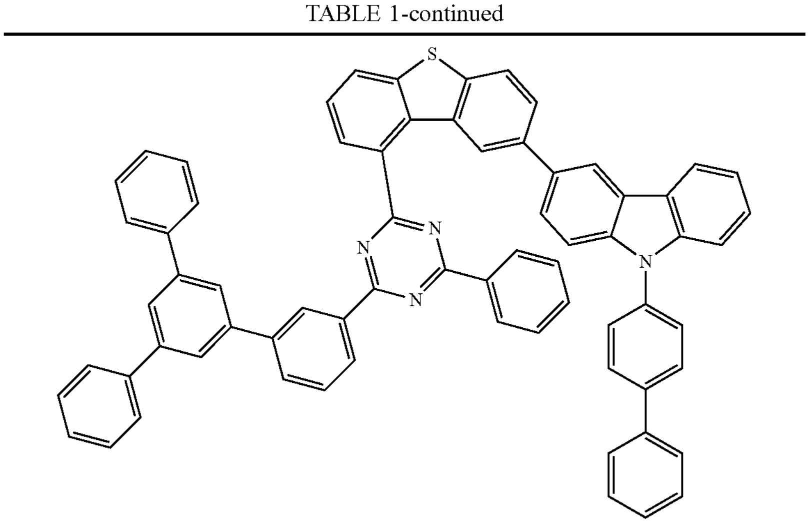
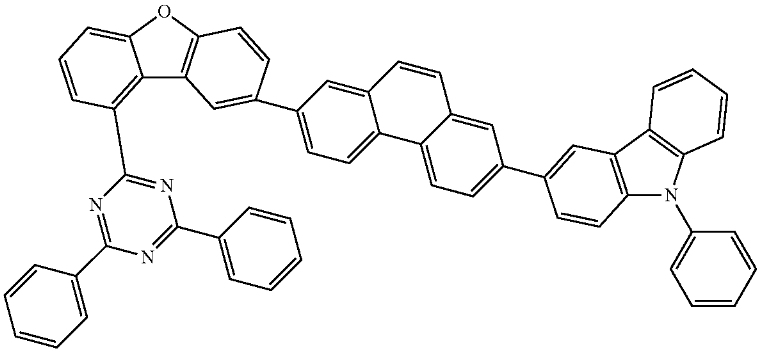 [SMILES: c1ccc(-c2nc(-c3ccccc3)nc(-c3cccc4oc5ccc(-c6ccc7c(ccc8cc(-c9ccc%10c(c9)c9ccccc9n%10-c9ccccc9)ccc87)c6)cc5c34)n2)cc1]
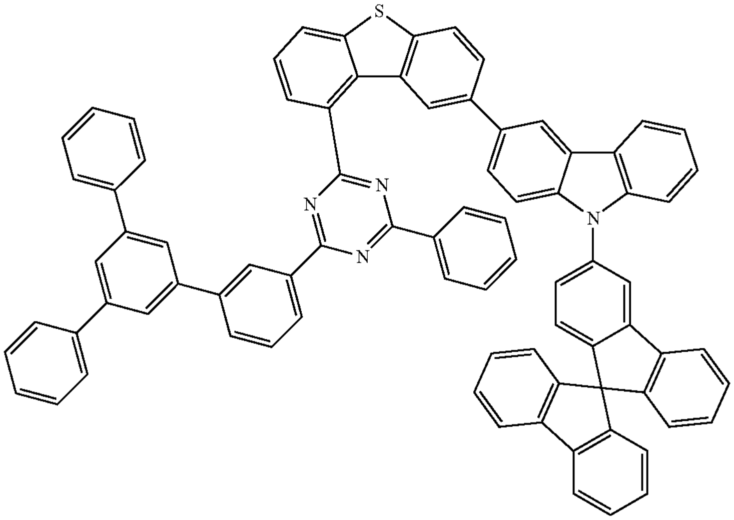 [SMILES: c1ccc(-c2cc(-c3ccccc3)cc(-c3cccc(-c4nc(-c5ccccc5)nc(-c5cccc6sc7ccc(-c8ccc9c(c8)c8ccccc8n9-c8ccc9c(c8)-c8ccccc8C98c9ccccc9-c9ccccc98)cc7c56)n4)c3)c2)cc1]

TABLE 1-continued
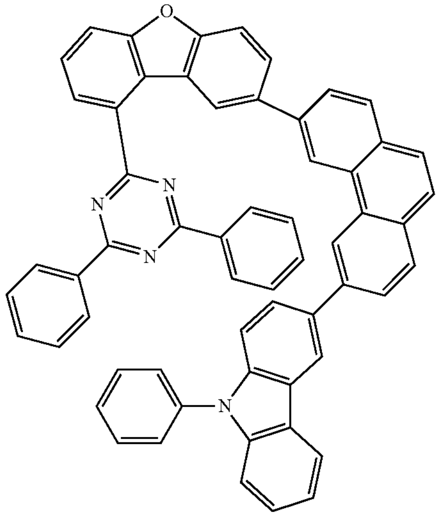 [SMILES: c1ccc(-c2nc(-c3ccccc3)nc(-c3cccc4oc5ccc(-c6ccc7ccc8ccc(-c9ccc%10c(c9)c9ccccc9n%10-c9ccccc9)cc8c7c6)cc5c34)n2)cc1]
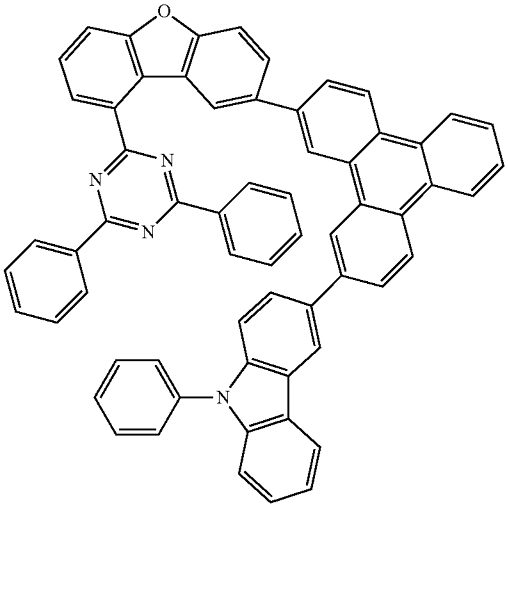 [SMILES: c1ccc(-c2nc(-c3ccccc3)nc(-c3cccc4oc5ccc(-c6ccc7c8ccccc8c8ccc(-c9ccc%10c(c9)c9ccccc9n%10-c9ccccc9)cc8c7c6)cc5c34)n2)cc1]

TABLE 1-continued
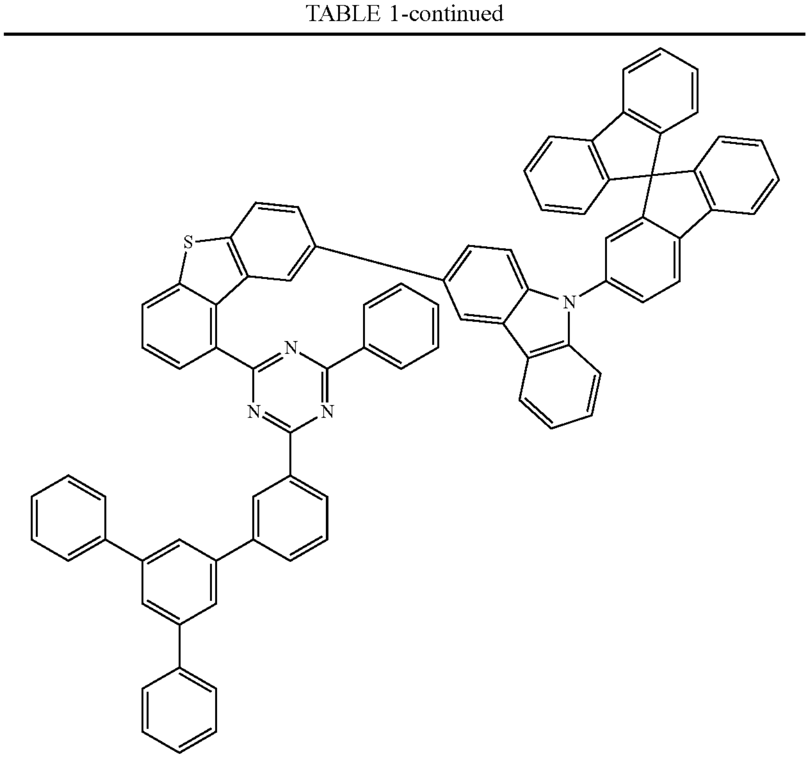
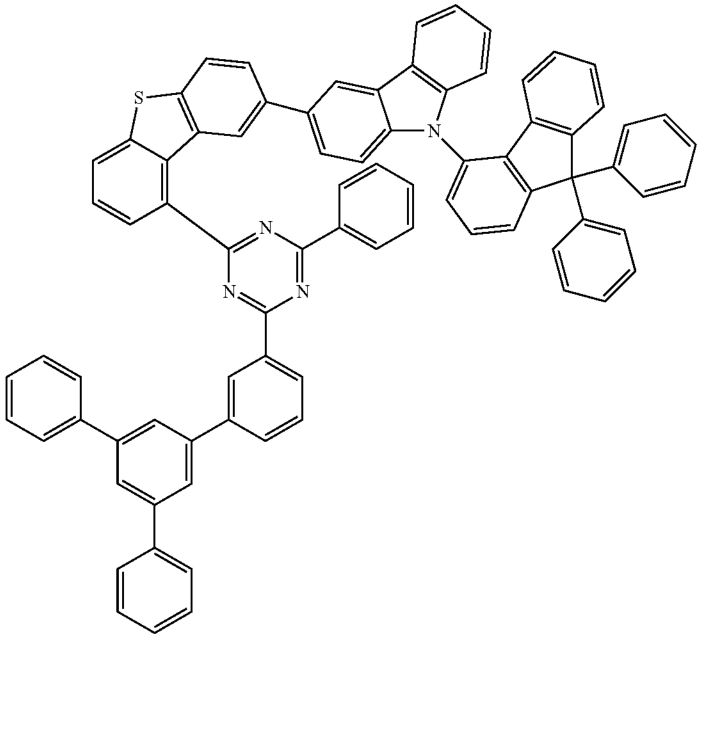 [SMILES: c1ccc(-c2cc(-c3ccccc3)cc(-c3cccc(-c4nc(-c5ccccc5)nc(-c5cccc6sc7ccc(-c8ccc9c(c8)c8ccccc8n9-c8cccc9c8-c8ccccc8C9(c8ccccc8)c8ccccc8)cc7c56)n4)c3)c2)cc1]

TABLE 1-continued
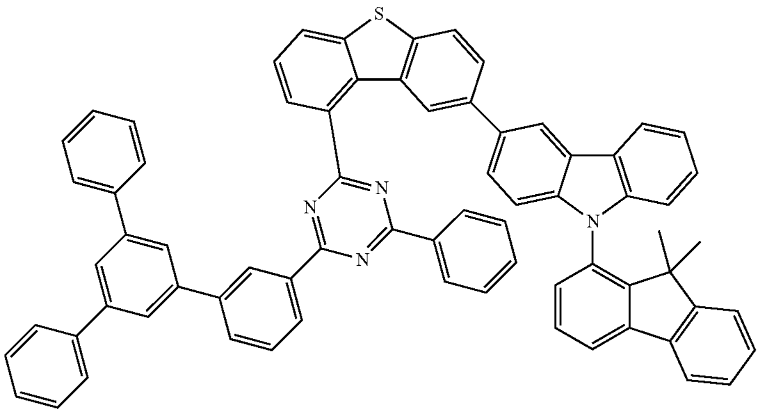 [SMILES: CC1(C)c2ccccc2-c2cccc(-n3c4ccccc4c4cc(-c5ccc6sc7cccc(-c8nc(-c9ccccc9)nc(-c9cccc(-c%10cc(-c%11ccccc%11)cc(-c%11ccccc%11)c%10)c9)n8)c7c6c5)ccc43)c21]
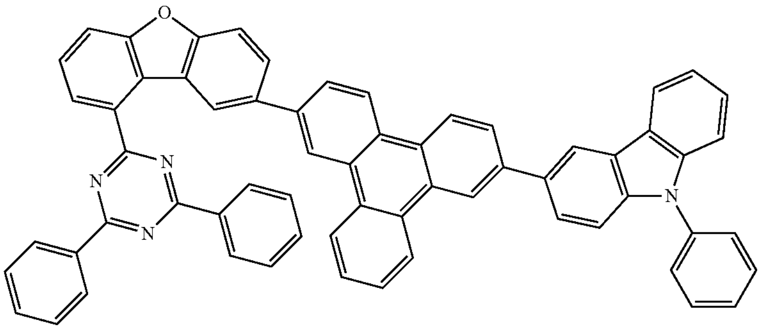 [SMILES: c1ccc(-c2nc(-c3ccccc3)nc(-c3cccc4oc5ccc(-c6ccc7c8ccc(-c9ccc%10c(c9)c9ccccc9n%10-c9ccccc9)cc8c8ccccc8c7c6)cc5c34)n2)cc1]
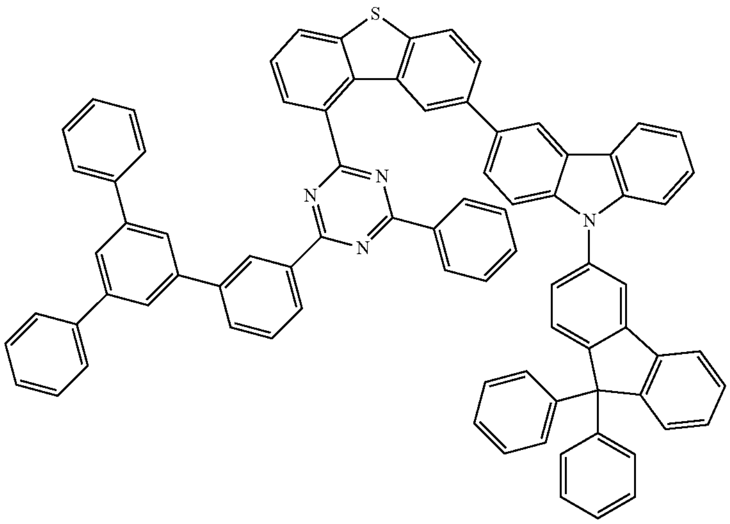 [SMILES: c1ccc(-c2cc(-c3ccccc3)cc(-c3cccc(-c4nc(-c5ccccc5)nc(-c5cccc6sc7ccc(-c8ccc9c(c8)c8ccccc8n9-c8ccc9c(c8)-c8ccccc8C9(c8ccccc8)c8ccccc8)cc7c56)n4)c3)c2)cc1]

TABLE 1-continued
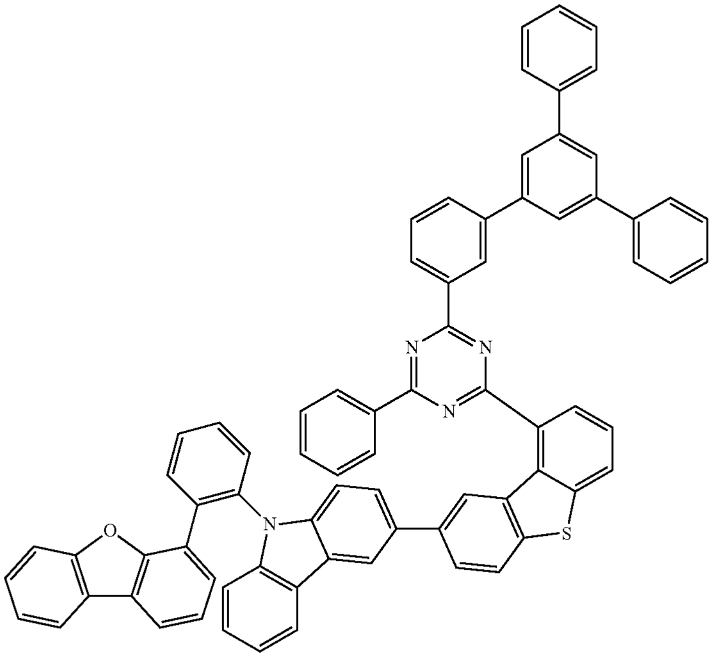 [SMILES: c1ccc(-c2cc(-c3ccccc3)cc(-c3cccc(-c4nc(-c5ccccc5)nc(-c5cccc6sc7ccc(-c8ccc9c(c8)c8ccccc8n9-c8ccccc8-c8cccc9c8oc8ccccc89)cc7c56)n4)c3)c2)cc1]
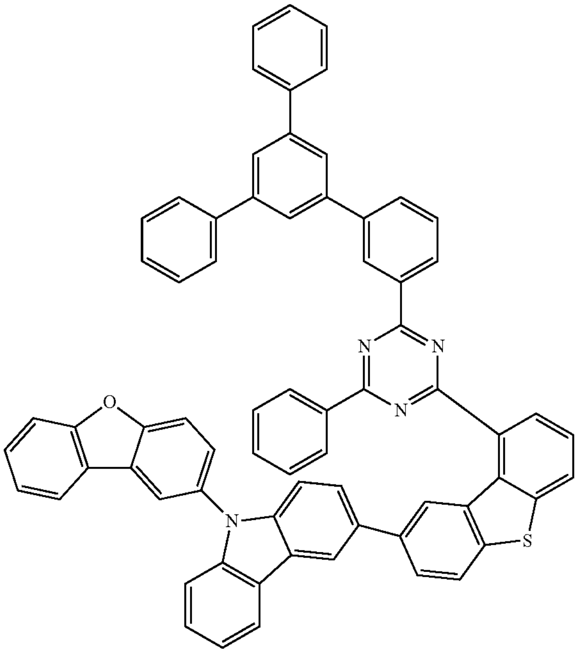

TABLE 1-continued
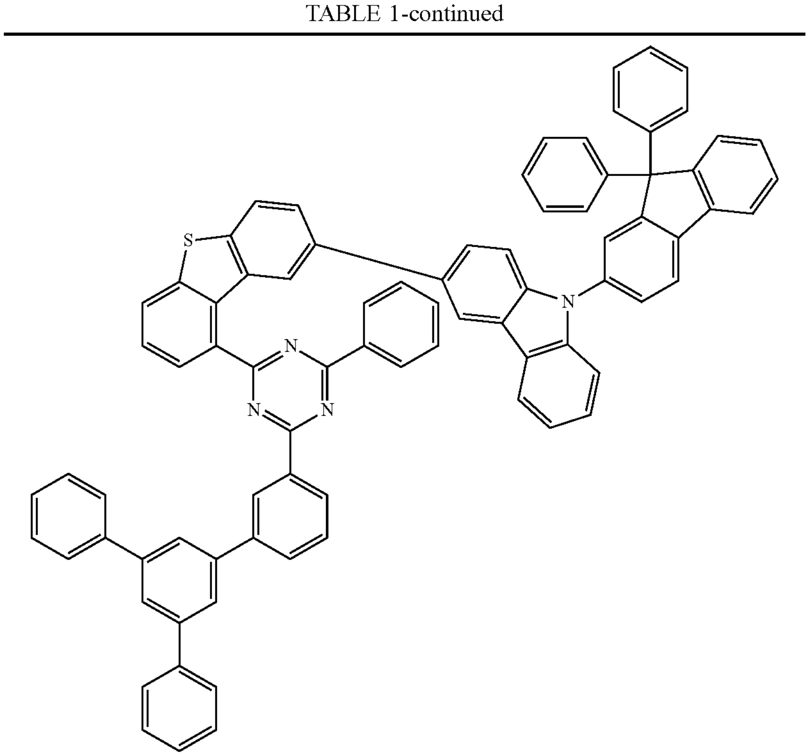
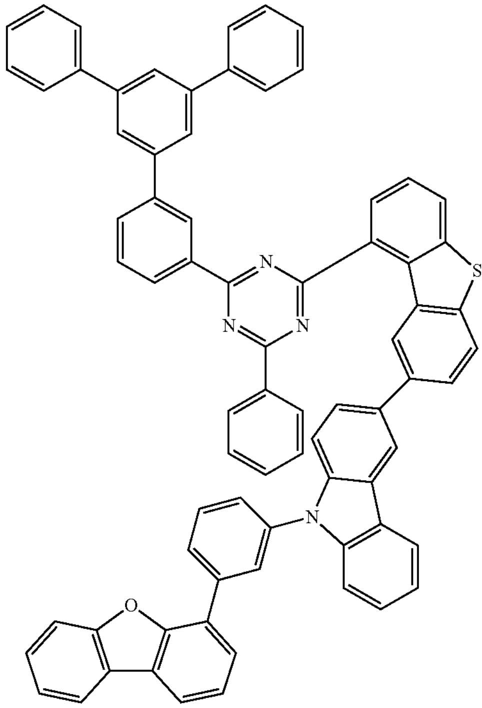 [SMILES: c1ccc(-c2cc(-c3ccccc3)cc(-c3cccc(-c4nc(-c5ccccc5)nc(-c5cccc6sc7ccc(-c8ccc9c(c8)c8ccccc8n9-c8cccc(-c9cccc%10c9oc9ccccc9%10)c8)cc7c56)n4)c3)c2)cc1]

TABLE 1-continued
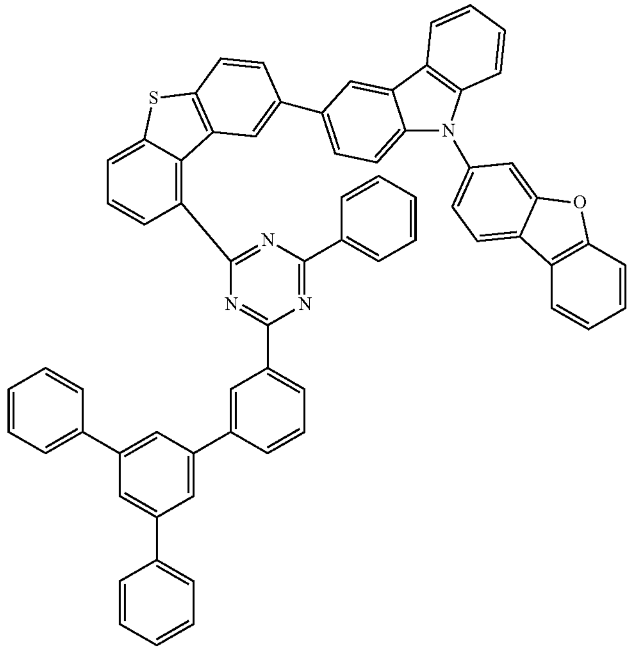 [SMILES: c1ccc(-c2cc(-c3ccccc3)cc(-c3cccc(-c4nc(-c5ccccc5)nc(-c5cccc6sc7ccc(-c8ccc9c(c8)c8ccccc8n9-c8ccc9c(c8)oc8ccccc89)cc7c56)n4)c3)c2)cc1]
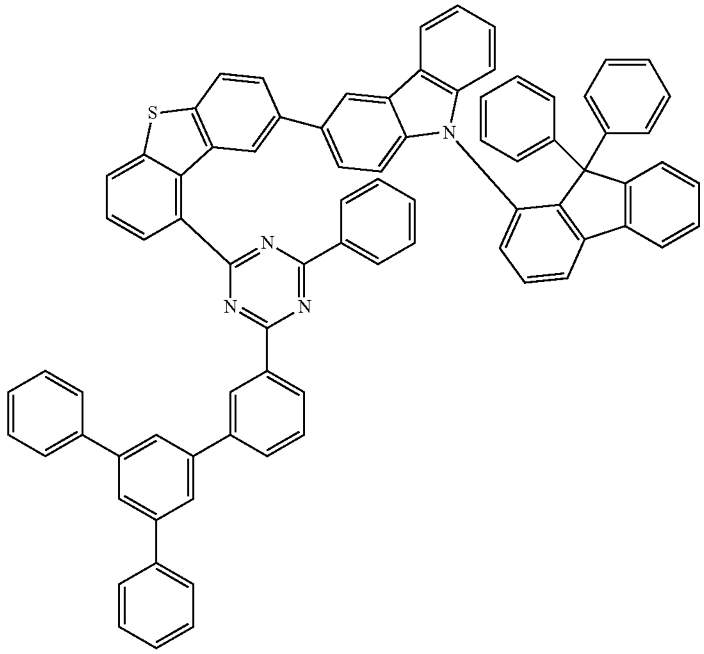 [SMILES: c1ccc(-c2cc(-c3ccccc3)cc(-c3cccc(-c4nc(-c5ccccc5)nc(-c5cccc6sc7ccc(-c8ccc9c(c8)c8ccccc8n9-c8cccc9c8C(c8ccccc8)(c8ccccc8)c8ccccc8-9)cc7c56)n4)c3)c2)cc1]

TABLE 1-continued
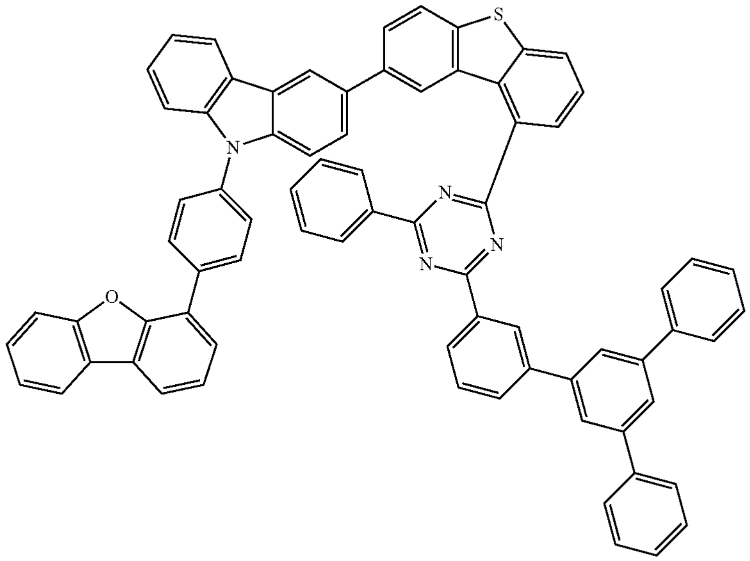
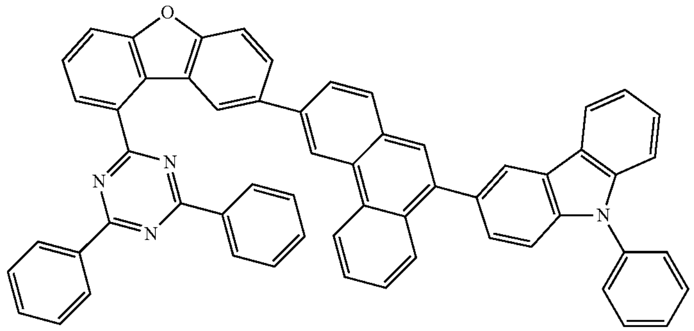 [SMILES: c1ccc(-c2nc(-c3ccccc3)nc(-c3cccc4oc5ccc(-c6ccc7cc(-c8ccc9c(c8)c8ccccc8n9-c8ccccc8)c8ccccc8c7c6)cc5c34)n2)cc1]
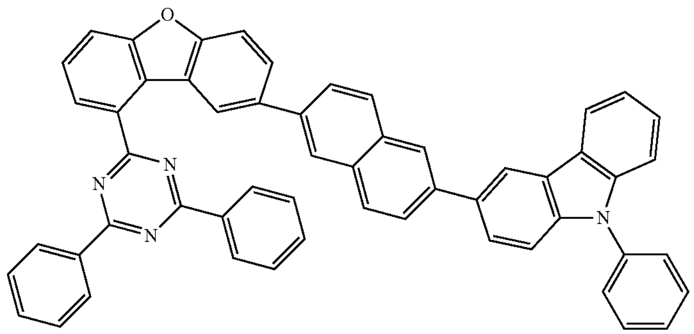 [SMILES: c1ccc(-c2nc(-c3ccccc3)nc(-c3cccc4oc5ccc(-c6ccc7cc(-c8ccc9c(c8)c8ccccc8n9-c8ccccc8)ccc7c6)cc5c34)n2)cc1]

TABLE 1-continued
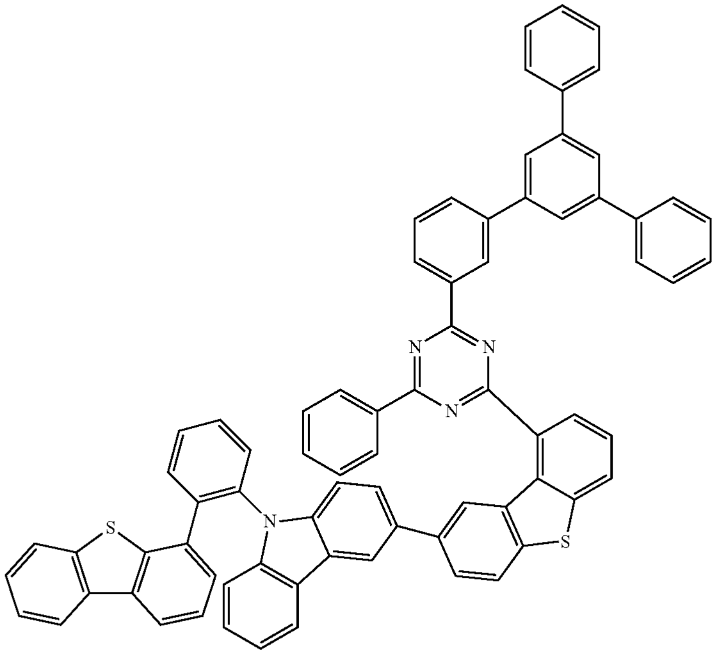 [SMILES: c1ccc(-c2cc(-c3ccccc3)cc(-c3cccc(-c4nc(-c5ccccc5)nc(-c5cccc6sc7ccc(-c8ccc9c(c8)c8ccccc8n9-c8ccccc8-c8cccc9c8sc8ccccc89)cc7c56)n4)c3)c2)cc1]
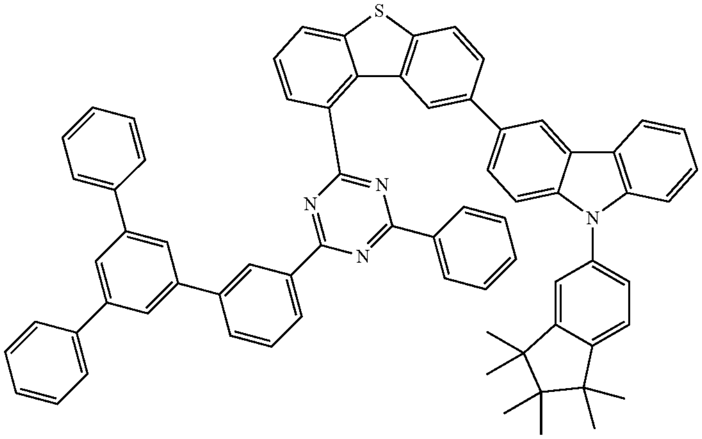 [SMILES: CC1(C)c2ccc(-n3c4ccccc4c4cc(-c5ccc6sc7cccc(-c8nc(-c9ccccc9)nc(-c9cccc(-c%10cc(-c%11ccccc%11)cc(-c%11ccccc%11)c%10)c9)n8)c7c6c5)ccc43)cc2C(C)(C)C1(C)C]

TABLE 1-continued
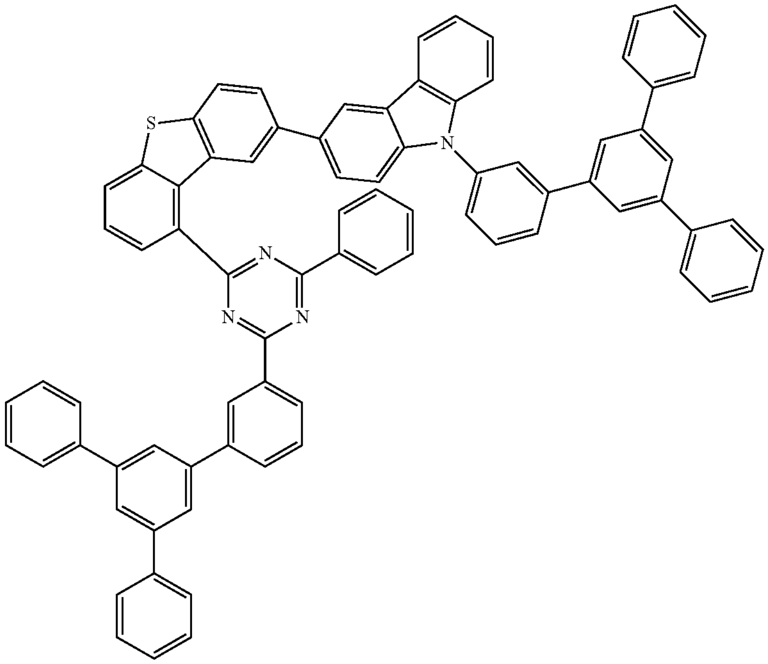 [SMILES: c1ccc(-c2cc(-c3ccccc3)cc(-c3cccc(-c4nc(-c5ccccc5)nc(-c5cccc6sc7ccc(-c8ccc9c(c8)c8ccccc8n9-c8cccc(-c9cc(-c%10ccccc%10)cc(-c%10ccccc%10)c9)c8)cc7c56)n4)c3)c2)cc1]
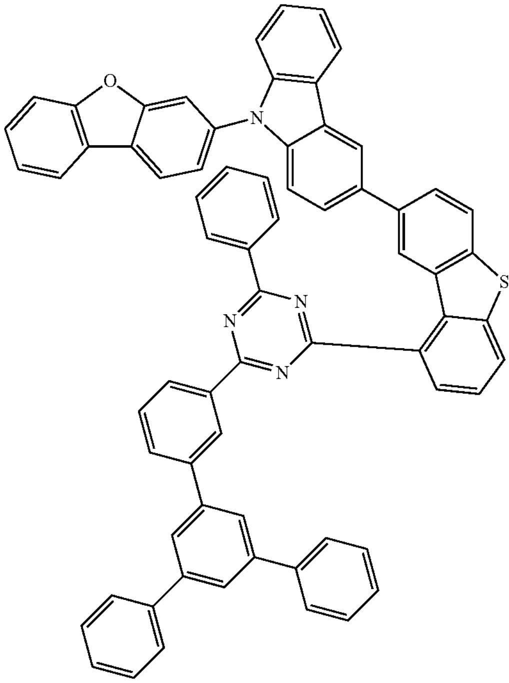 [SMILES: c1ccc(-c2cc(-c3ccccc3)cc(-c3cccc(-c4nc(-c5ccccc5)nc(-c5cccc6sc7ccc(-c8ccc9c(c8)c8ccccc8n9-c8ccc9c(c8)oc8ccccc89)cc7c56)n4)c3)c2)cc1]

TABLE 1-continued
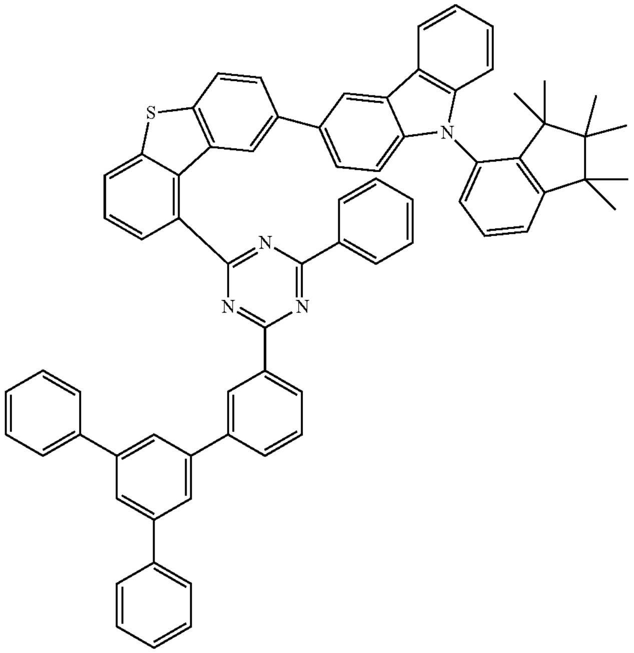 [SMILES: CC1(C)c2cccc(-n3c4ccccc4c4cc(-c5ccc6sc7cccc(-c8nc(-c9ccccc9)nc(-c9cccc(-c%10cc(-c%11ccccc%11)cc(-c%11ccccc%11)c%10)c9)n8)c7c6c5)ccc43)c2C(C)(C)C1(C)C]
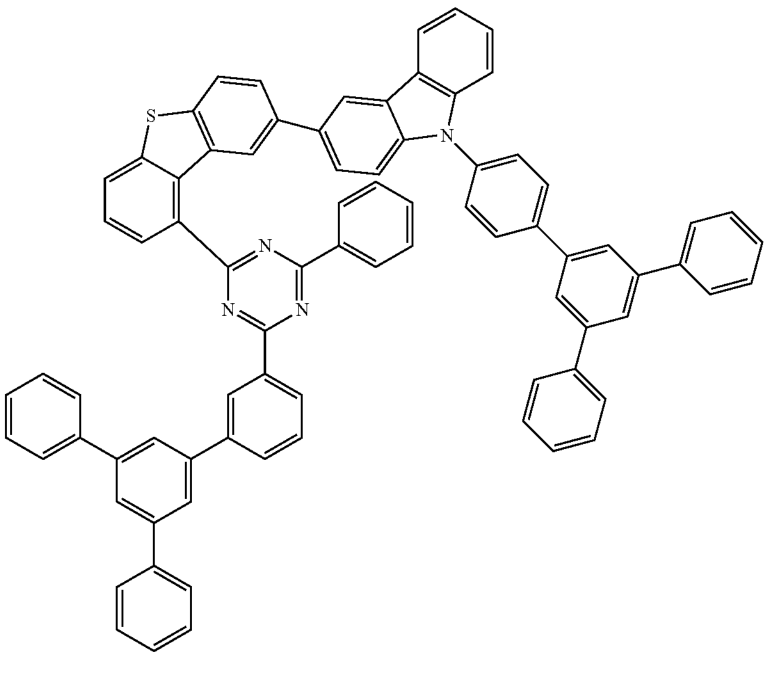 [SMILES: c1ccc(-c2cc(-c3ccccc3)cc(-c3ccc(-n4c5ccccc5c5cc(-c6ccc7sc8cccc(-c9nc(-c%10ccccc%10)nc(-c%10cccc(-c%11cc(-c%12ccccc%12)cc(-c%12ccccc%12)c%11)c%10)n9)c8c7c6)ccc54)cc3)c2)cc1]

TABLE 1-continued
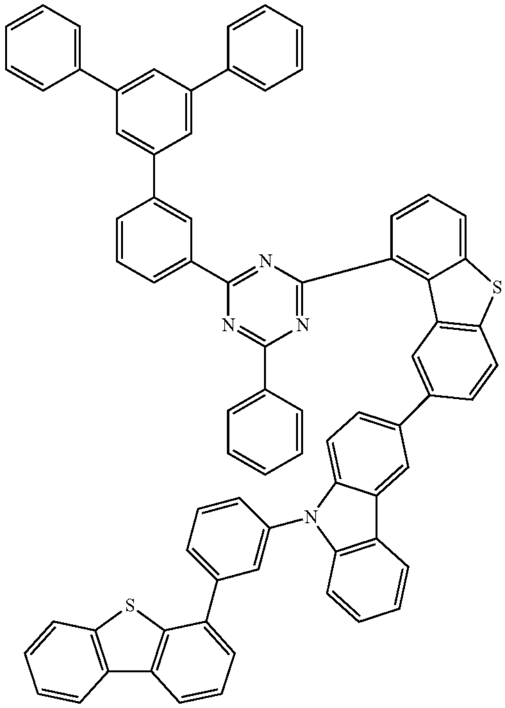 [SMILES: c1ccc(-c2cc(-c3ccccc3)cc(-c3cccc(-c4nc(-c5ccccc5)nc(-c5cccc6sc7ccc(-c8ccc9c(c8)c8ccccc8n9-c8cccc(-c9cccc%10c9sc9ccccc9%10)c8)cc7c56)n4)c3)c2)cc1]
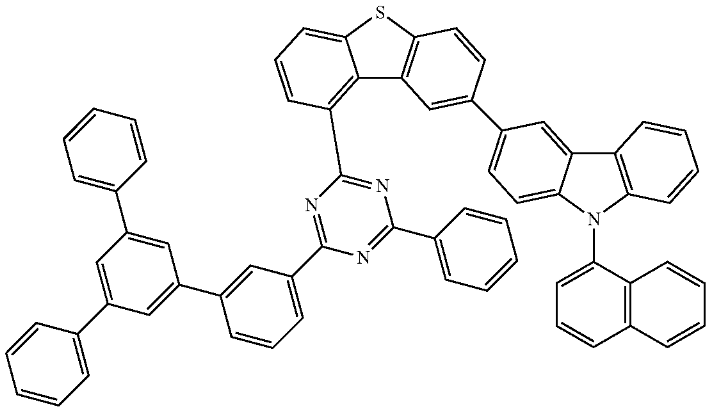 [SMILES: c1ccc(-c2cc(-c3ccccc3)cc(-c3cccc(-c4nc(-c5ccccc5)nc(-c5cccc6sc7ccc(-c8ccc9c(c8)c8ccccc8n9-c8cccc9ccccc89)cc7c56)n4)c3)c2)cc1]

TABLE 1-continued
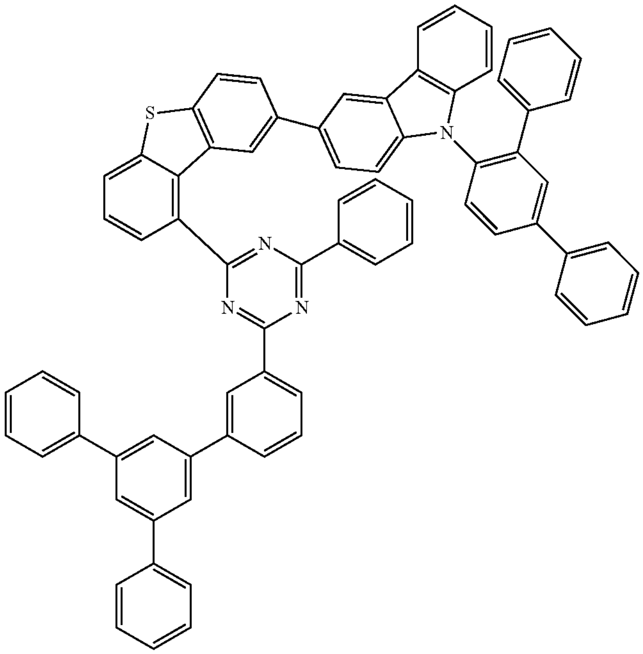 [SMILES: c1ccc(-c2cc(-c3ccccc3)cc(-c3cccc(-c4nc(-c5ccccc5)nc(-c5cccc6sc7ccc(-c8ccc9c(c8)c8ccccc8n9-c8ccc(-c9ccccc9)cc8-c8ccccc8)cc7c56)n4)c3)c2)cc1]
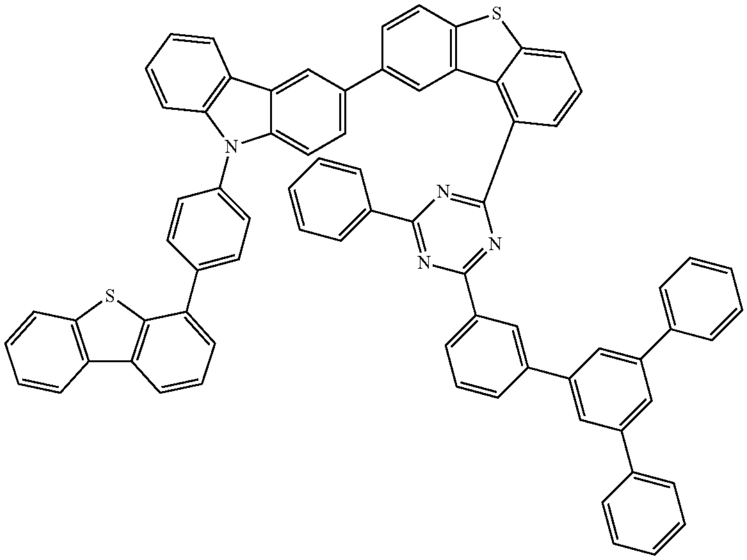 [SMILES: c1ccc(-c2cc(-c3ccccc3)cc(-c3cccc(-c4nc(-c5ccccc5)nc(-c5cccc6sc7ccc(-c8ccc9c(c8)c8ccccc8n9-c8ccc(-c9cccc%10c9sc9ccccc9%10)cc8)cc7c56)n4)c3)c2)cc1]
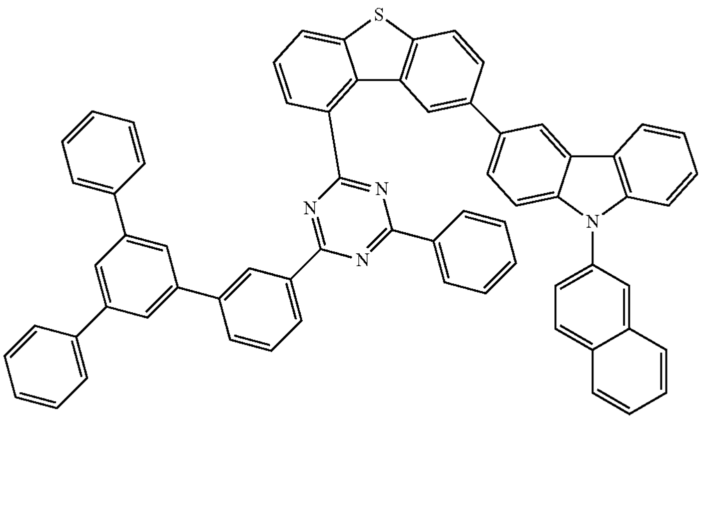 [SMILES: c1ccc(-c2cc(-c3ccccc3)cc(-c3cccc(-c4nc(-c5ccccc5)nc(-c5cccc6sc7ccc(-c8ccc9c(c8)c8ccccc8n9-c8ccc9ccccc9c8)cc7c56)n4)c3)c2)cc1]

TABLE 1-continued
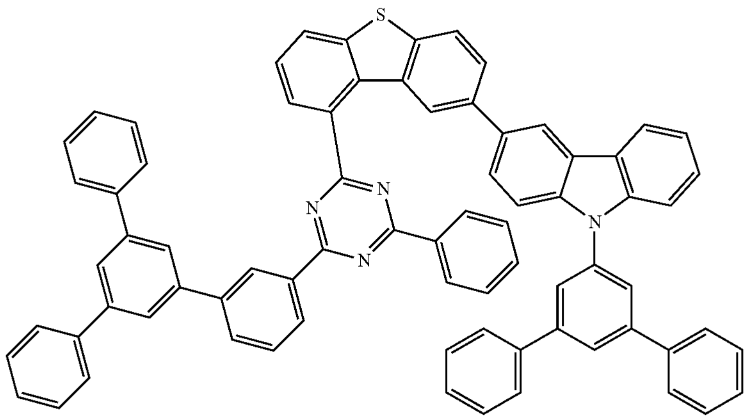 [SMILES: c1ccc(-c2cc(-c3ccccc3)cc(-c3cccc(-c4nc(-c5ccccc5)nc(-c5cccc6sc7ccc(-c8ccc9c(c8)c8ccccc8n9-c8cc(-c9ccccc9)cc(-c9ccccc9)c8)cc7c56)n4)c3)c2)cc1]
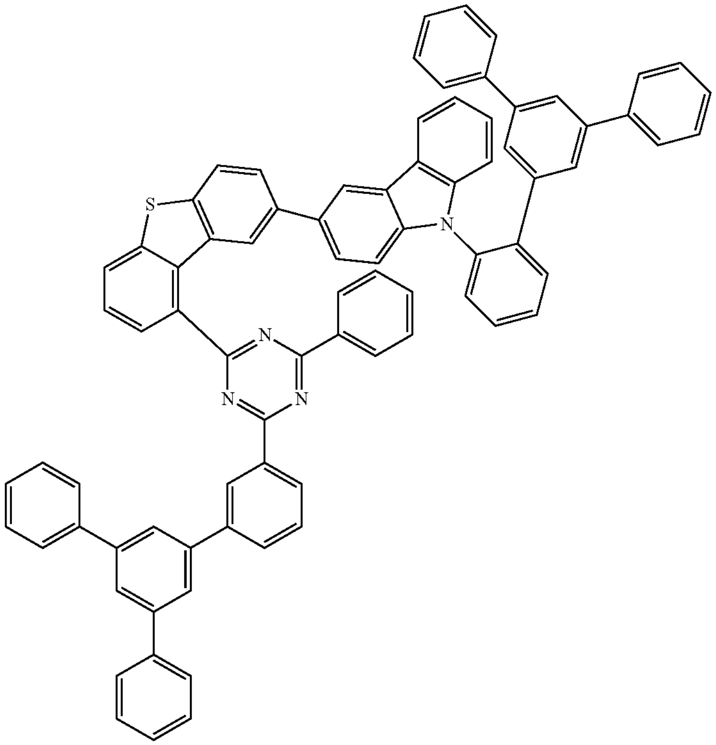 [SMILES: c1ccc(-c2cc(-c3ccccc3)cc(-c3cccc(-c4nc(-c5ccccc5)nc(-c5cccc6sc7ccc(-c8ccc9c(c8)c8ccccc8n9-c8ccccc8-c8cc(-c9ccccc9)cc(-c9ccccc9)c8)cc7c56)n4)c3)c2)cc1]

TABLE 1-continued
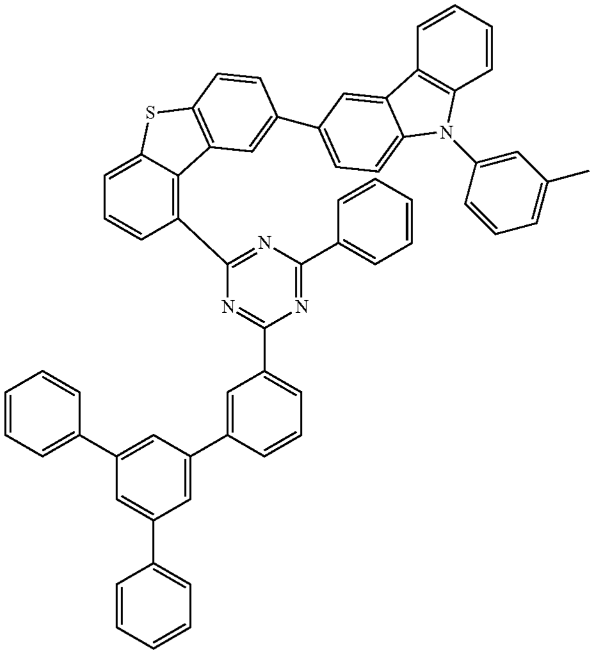 [SMILES: Cc1cccc(-n2c3ccccc3c3cc(-c4ccc5sc6cccc(-c7nc(-c8ccccc8)nc(-c8cccc(-c9cc(-c%10ccccc%10)cc(-c%10ccccc%10)c9)c8)n7)c6c5c4)ccc32)c1]
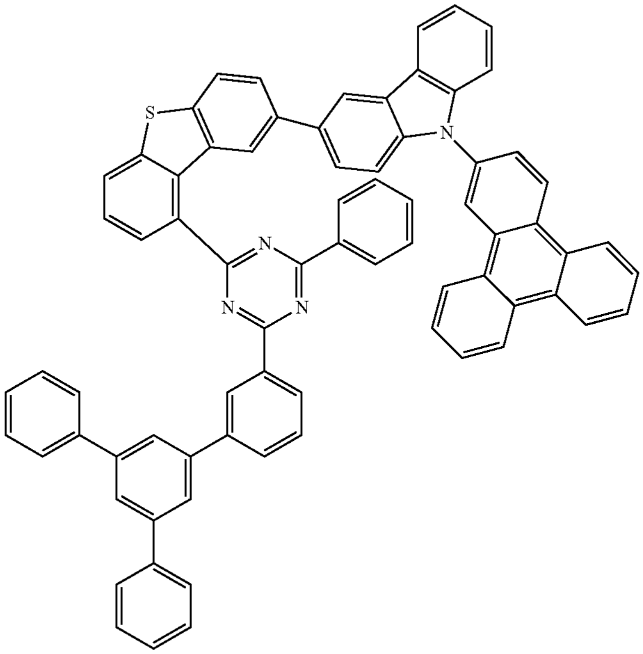 [SMILES: c1ccc(-c2cc(-c3ccccc3)cc(-c3cccc(-c4nc(-c5ccccc5)nc(-c5cccc6sc7ccc(-c8ccc9c(c8)c8ccccc8n9-c8ccc9c%10ccccc%10c%10ccccc%10c9c8)cc7c56)n4)c3)c2)cc1]

TABLE 1-continued
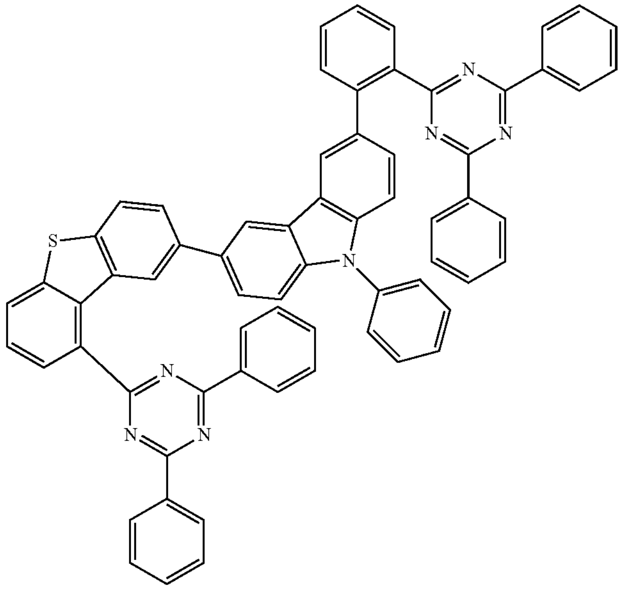 [SMILES: c1ccc(-c2nc(-c3ccccc3)nc(-c3ccccc3-c3ccc4c(c3)c3cc(-c5ccc6sc7cccc(-c8nc(-c9ccccc9)nc(-c9ccccc9)n8)c7c6c5)ccc3n4-c3ccccc3)n2)cc1]
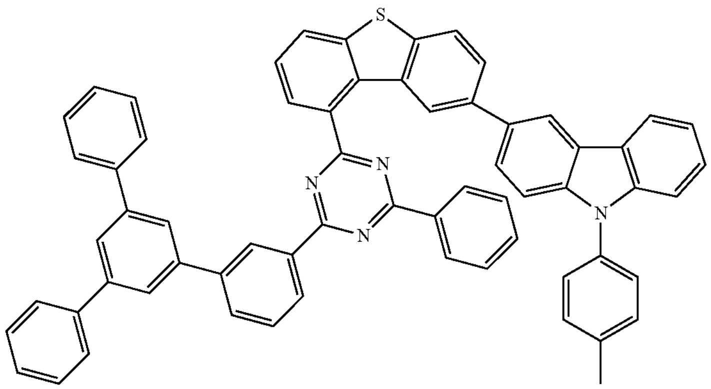 [SMILES: Cc1ccc(-n2c3ccccc3c3cc(-c4ccc5sc6cccc(-c7nc(-c8ccccc8)nc(-c8cccc(-c9cc(-c%10ccccc%10)cc(-c%10ccccc%10)c9)c8)n7)c6c5c4)ccc32)cc1]

TABLE 1-continued
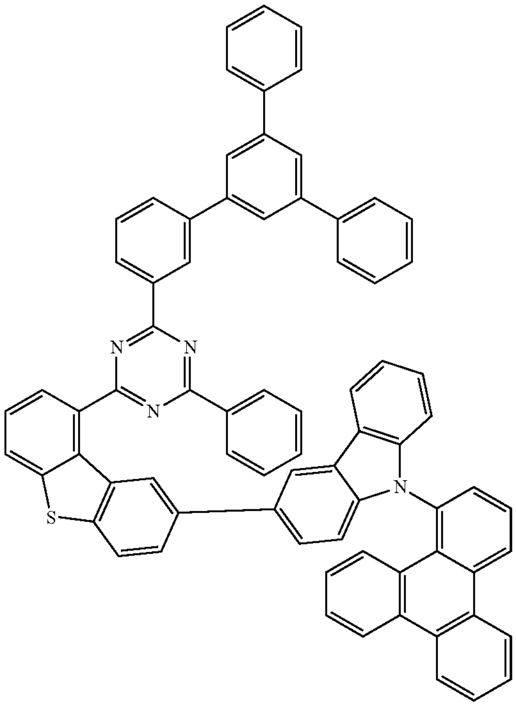 [SMILES: c1ccc(-c2cc(-c3ccccc3)cc(-c3cccc(-c4nc(-c5ccccc5)nc(-c5cccc6sc7ccc(-c8ccc9c(c8)c8ccccc8n9-c8cccc9c%10ccccc%10c%10ccccc%10c89)cc7c56)n4)c3)c2)cc1]
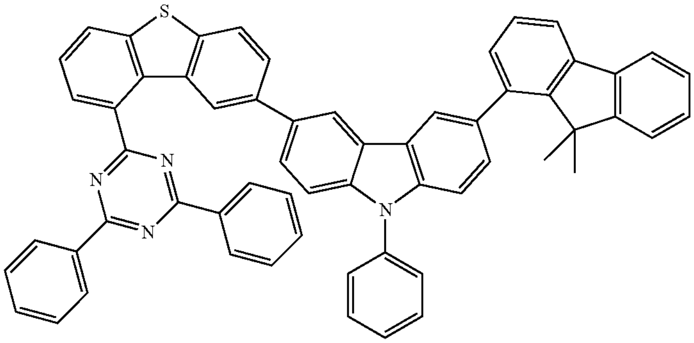 [SMILES: CC1(C)c2ccccc2-c2cccc(-c3ccc4c(c3)c3cc(-c5ccc6sc7cccc(-c8nc(-c9ccccc9)nc(-c9ccccc9)n8)c7c6c5)ccc3n4-c3ccccc3)c21]
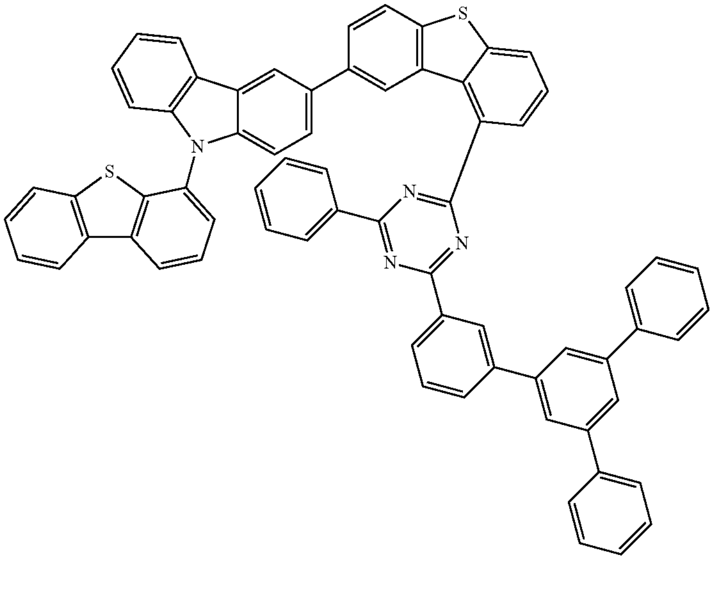 [SMILES: c1ccc(-c2cc(-c3ccccc3)cc(-c3cccc(-c4nc(-c5ccccc5)nc(-c5cccc6sc7ccc(-c8ccc9c(c8)c8ccccc8n9-c8cccc9c8sc8ccccc89)cc7c56)n4)c3)c2)cc1]

TABLE 1-continued
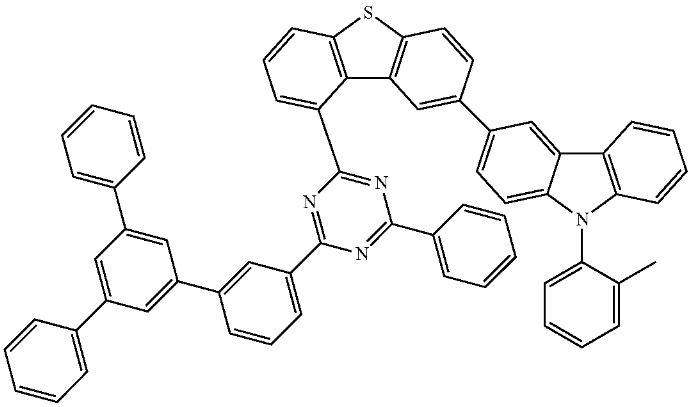 [SMILES: Cc1ccccc1-n1c2ccccc2c2cc(-c3ccc4sc5cccc(-c6nc(-c7ccccc7)nc(-c7cccc(-c8cc(-c9ccccc9)cc(-c9ccccc9)c8)c7)n6)c5c4c3)ccc21]
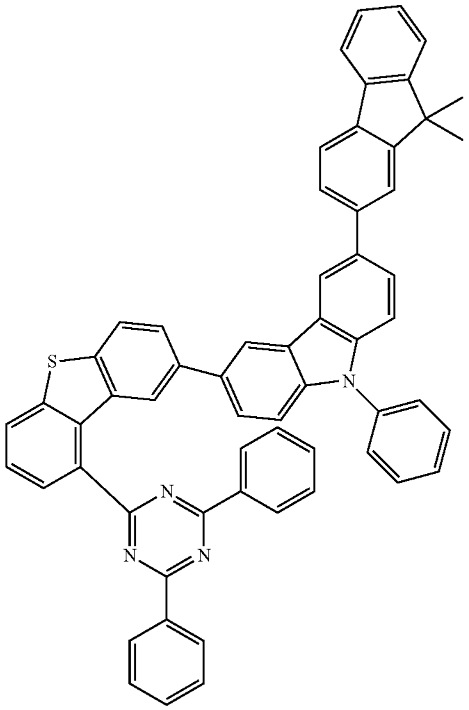 [SMILES: CC1(C)c2ccccc2-c2ccc(-c3ccc4c(c3)c3cc(-c5ccc6sc7cccc(-c8nc(-c9ccccc9)nc(-c9ccccc9)n8)c7c6c5)ccc3n4-c3ccccc3)cc21]

TABLE 1-continued
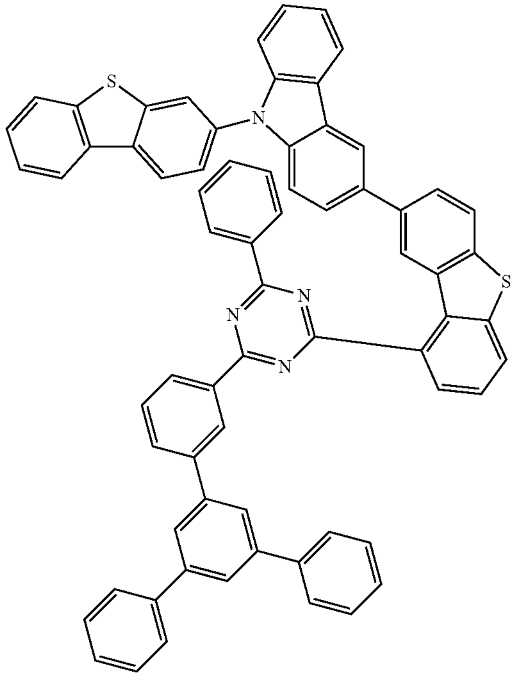 [SMILES: c1ccc(-c2cc(-c3ccccc3)cc(-c3cccc(-c4nc(-c5ccccc5)nc(-c5cccc6sc7ccc(-c8ccc9c(c8)c8ccccc8n9-c8ccc9c(c8)sc8ccccc89)cc7c56)n4)c3)c2)cc1]
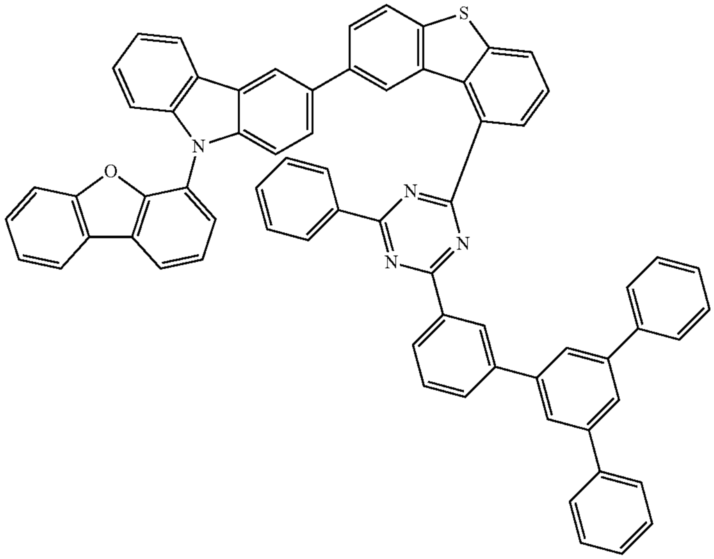
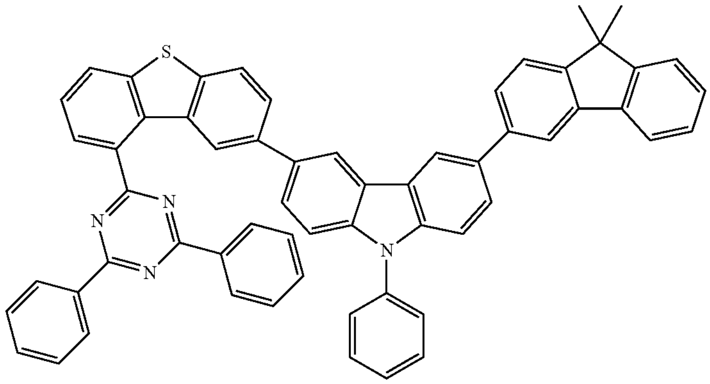 [SMILES: CC1(C)c2ccccc2-c2cc(-c3ccc4c(c3)c3cc(-c5ccc6sc7cccc(-c8nc(-c9ccccc9)nc(-c9ccccc9)n8)c7c6c5)ccc3n4-c3ccccc3)ccc21]

TABLE 1-continued
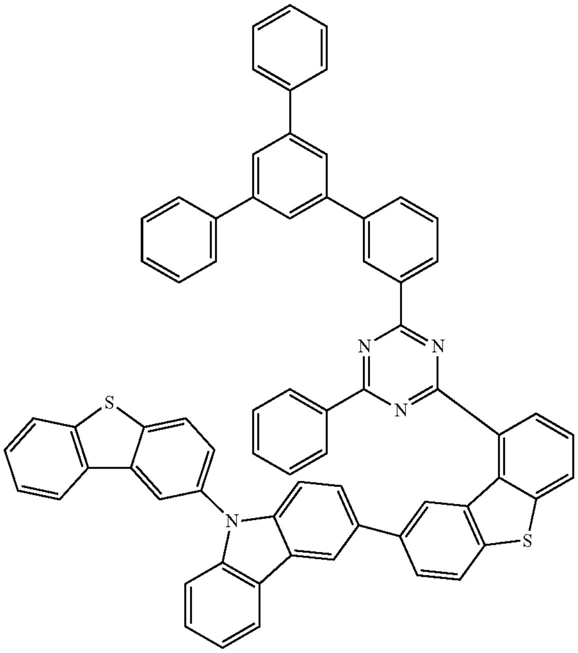 [SMILES: c1ccc(-c2cc(-c3ccccc3)cc(-c3cccc(-c4nc(-c5ccccc5)nc(-c5cccc6sc7ccc(-c8ccc9c(c8)c8ccccc8n9-c8ccc9sc%10ccccc%10c9c8)cc7c56)n4)c3)c2)cc1]
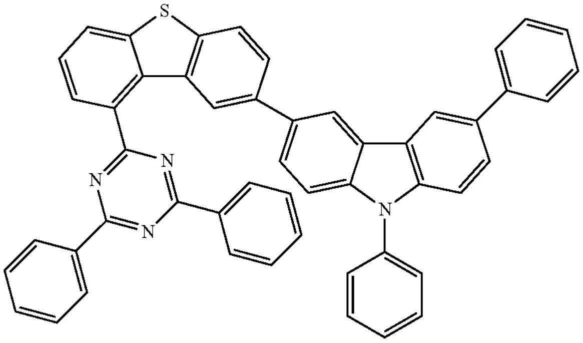 [SMILES: c1ccc(-c2ccc3c(c2)c2cc(-c4ccc5sc6cccc(-c7nc(-c8ccccc8)nc(-c8ccccc8)n7)c6c5c4)ccc2n3-c2ccccc2)cc1]
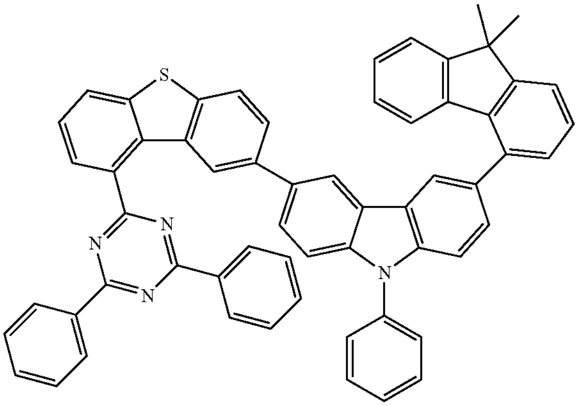 [SMILES: CC1(C)c2ccccc2-c2c(-c3ccc4c(c3)c3cc(-c5ccc6sc7cccc(-c8nc(-c9ccccc9)nc(-c9ccccc9)n8)c7c6c5)ccc3n4-c3ccccc3)cccc21]

TABLE 1-continued
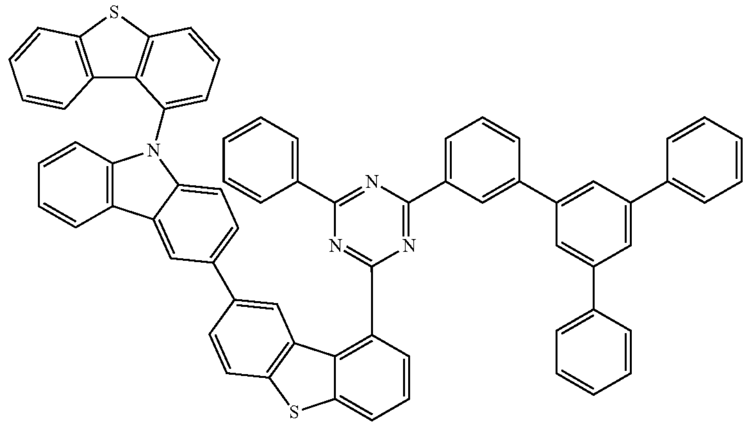 [SMILES: c1ccc(-c2cc(-c3ccccc3)cc(-c3cccc(-c4nc(-c5ccccc5)nc(-c5cccc6sc7ccc(-c8ccc9c(c8)c8ccccc8n9-c8cccc9sc%10ccccc%10c89)cc7c56)n4)c3)c2)cc1]
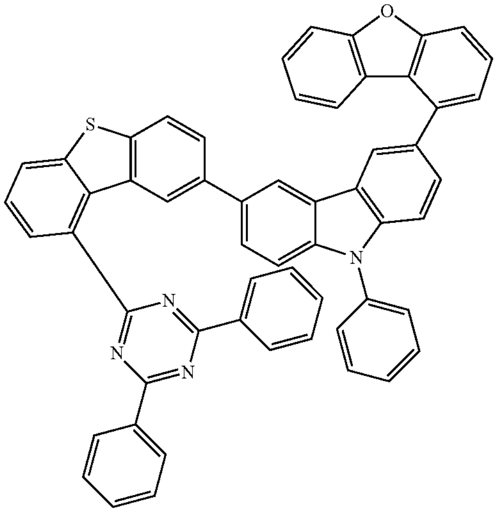
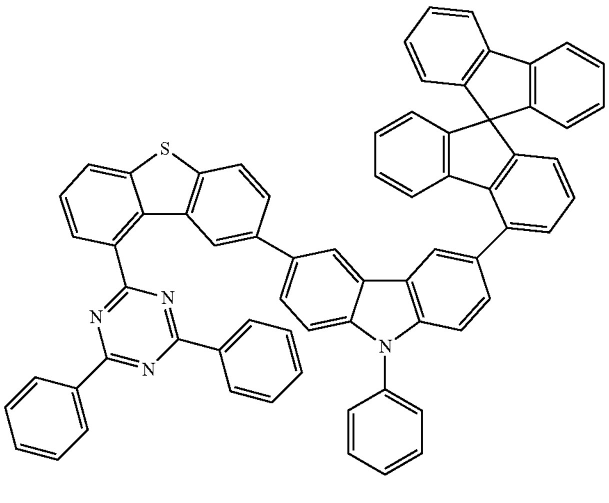 [SMILES: c1ccc(-c2nc(-c3ccccc3)nc(-c3cccc4sc5ccc(-c6ccc7c(c6)c6cc(-c8cccc9c8-c8ccccc8C98c9ccccc9-c9ccccc98)ccc6n7-c6ccccc6)cc5c34)n2)cc1]

TABLE 1-continued
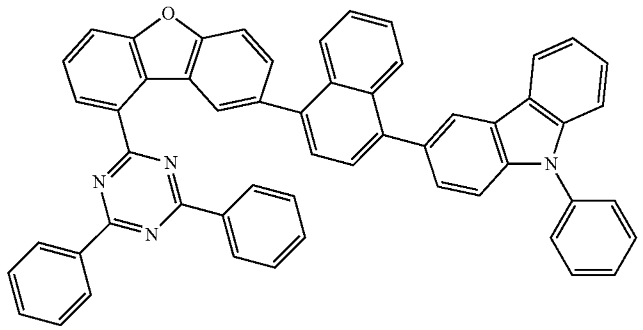 [SMILES: c1ccc(-c2nc(-c3ccccc3)nc(-c3cccc4oc5ccc(-c6ccc(-c7ccc8c(c7)c7ccccc7n8-c7ccccc7)c7ccccc67)cc5c34)n2)cc1]
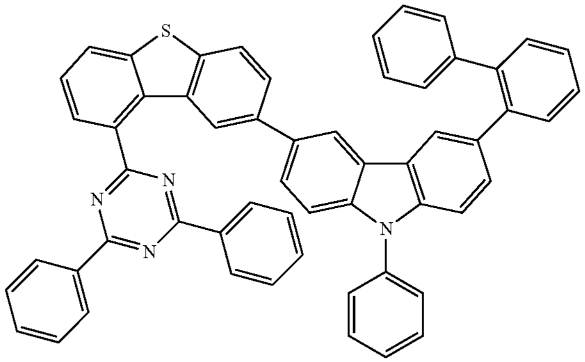 [SMILES: c1ccc(-c2nc(-c3ccccc3)nc(-c3cccc4sc5ccc(-c6ccc7c(c6)c6cc(-c8ccccc8-c8ccccc8)ccc6n7-c6ccccc6)cc5c34)n2)cc1]
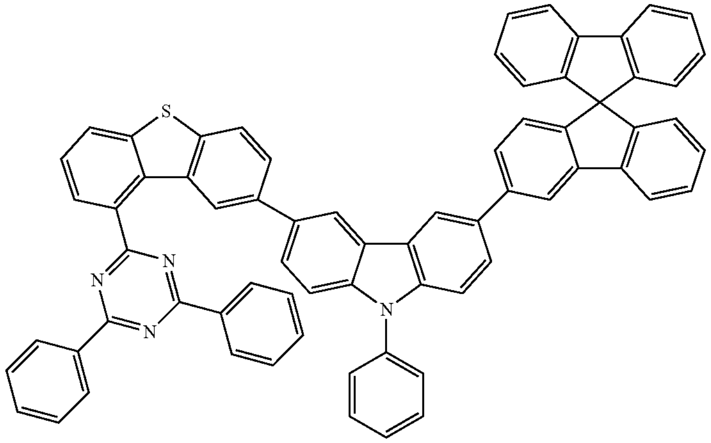 [SMILES: c1ccc(-c2nc(-c3ccccc3)nc(-c3cccc4sc5ccc(-c6ccc7c(c6)c6cc(-c8ccc9c(c8)-c8ccccc8C98c9ccccc9-c9ccccc98)ccc6n7-c6ccccc6)cc5c34)n2)cc1]
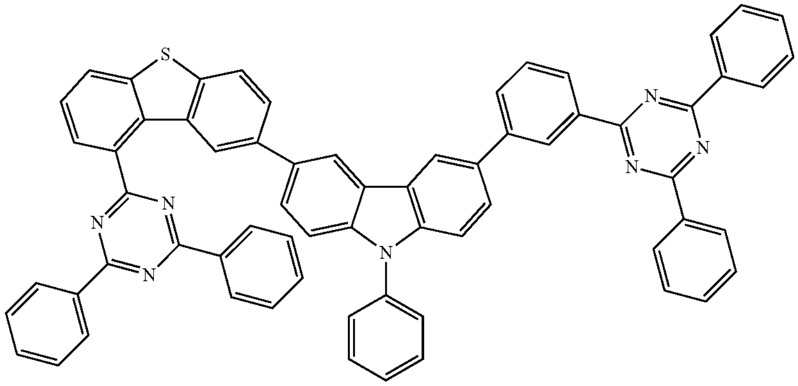

TABLE 1-continued
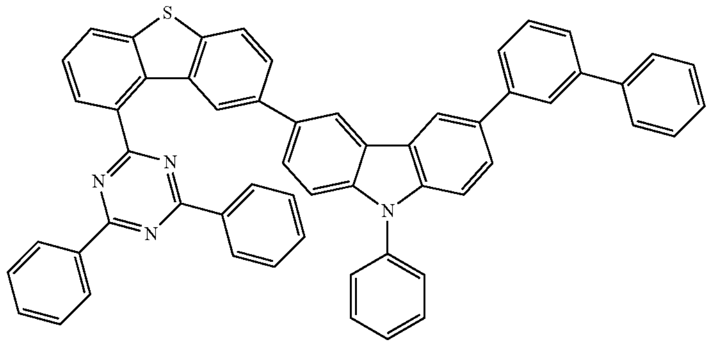
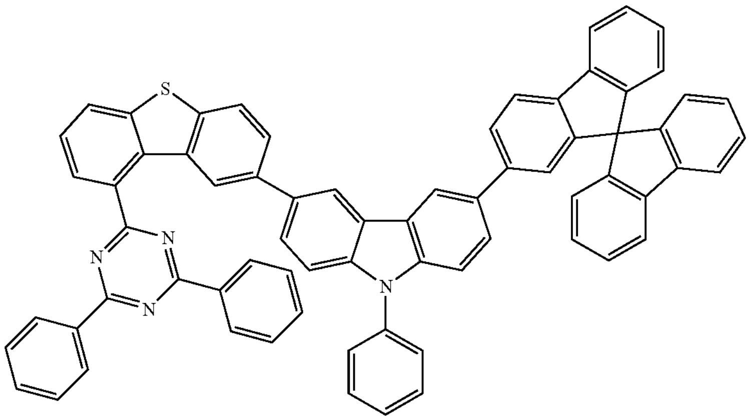 [SMILES: c1ccc(-c2nc(-c3ccccc3)nc(-c3cccc4sc5ccc(-c6ccc7c(c6)c6cc(-c8ccc9c(c8)C8(c%10ccccc%10-c%10ccccc%108)c8ccccc8-9)ccc6n7-c6ccccc6)cc5c34)n2)cc1]
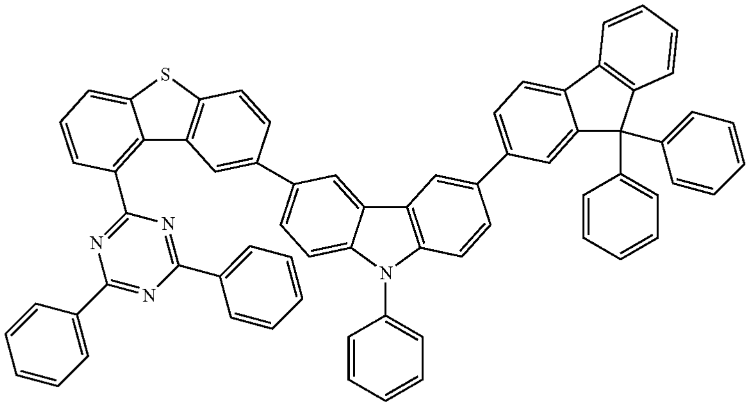 [SMILES: c1ccc(-c2nc(-c3ccccc3)nc(-c3cccc4sc5ccc(-c6ccc7c(c6)c6cc(-c8ccc9c(c8)C(c8ccccc8)(c8ccccc8)c8ccccc8-9)ccc6n7-c6ccccc6)cc5c34)n2)cc1]
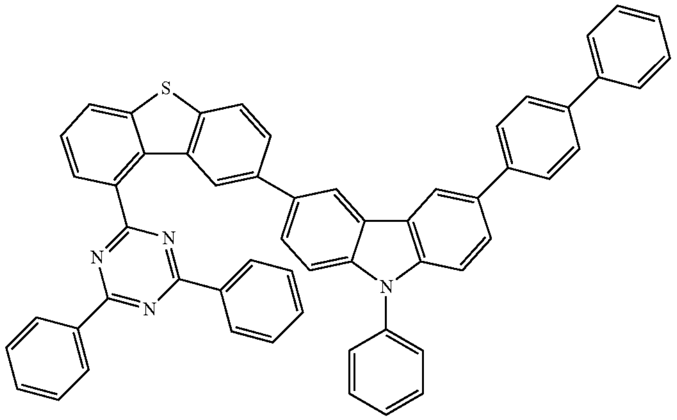 [SMILES: c1ccc(-c2ccc(-c3ccc4c(c3)c3cc(-c5ccc6sc7cccc(-c8nc(-c9ccccc9)nc(-c9ccccc9)n8)c7c6c5)ccc3n4-c3ccccc3)cc2)cc1]

TABLE 1-continued
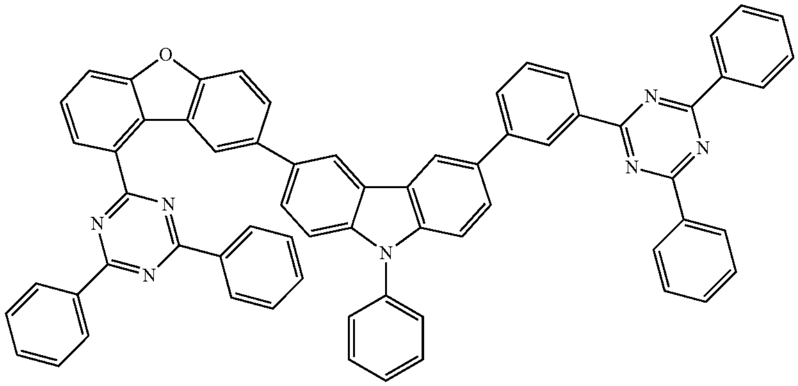
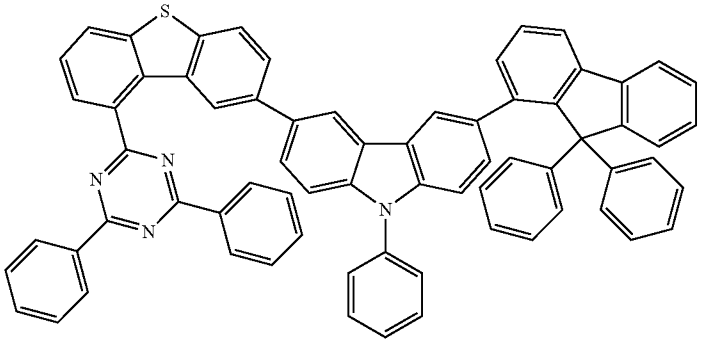 [SMILES: c1ccc(-c2nc(-c3ccccc3)nc(-c3cccc4sc5ccc(-c6ccc7c(c6)c6cc(-c8cccc9c8C(c8ccccc8)(c8ccccc8)c8ccccc8-9)ccc6n7-c6ccccc6)cc5c34)n2)cc1]
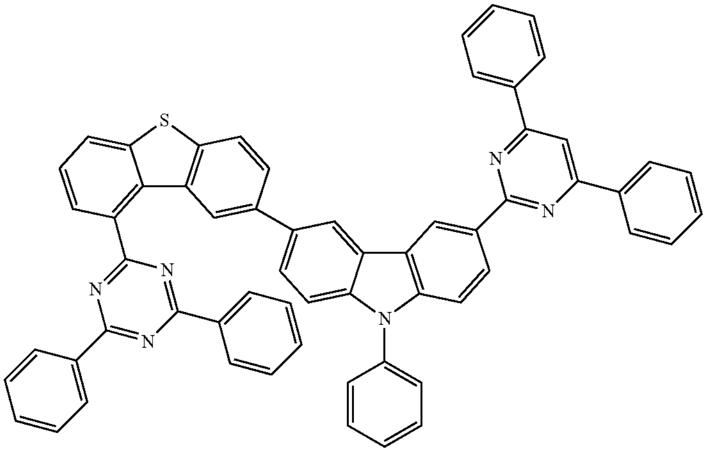 [SMILES: c1ccc(-c2cc(-c3ccccc3)nc(-c3ccc4c(c3)c3cc(-c5ccc6sc7cccc(-c8nc(-c9ccccc9)nc(-c9ccccc9)n8)c7c6c5)ccc3n4-c3ccccc3)n2)cc1]
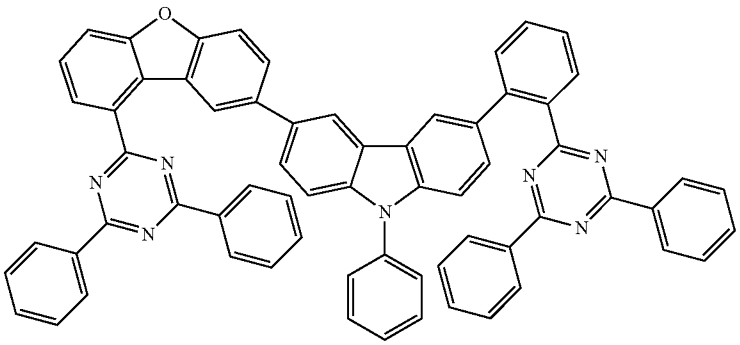 [SMILES: c1ccc(-c2nc(-c3ccccc3)nc(-c3ccccc3-c3ccc4c(c3)c3cc(-c5ccc6oc7cccc(-c8nc(-c9ccccc9)nc(-c9ccccc9)n8)c7c6c5)ccc3n4-c3ccccc3)n2)cc1]

TABLE 1-continued
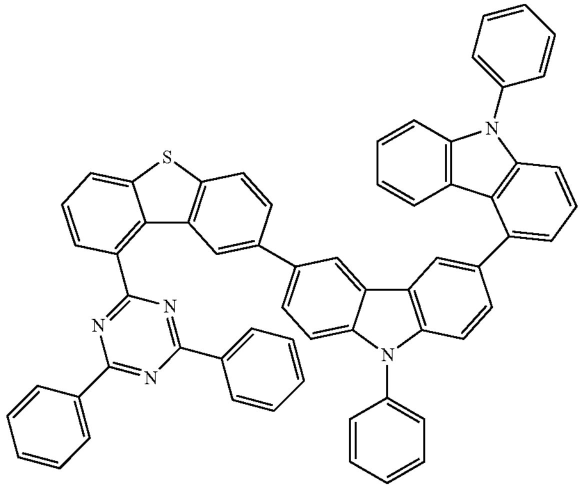
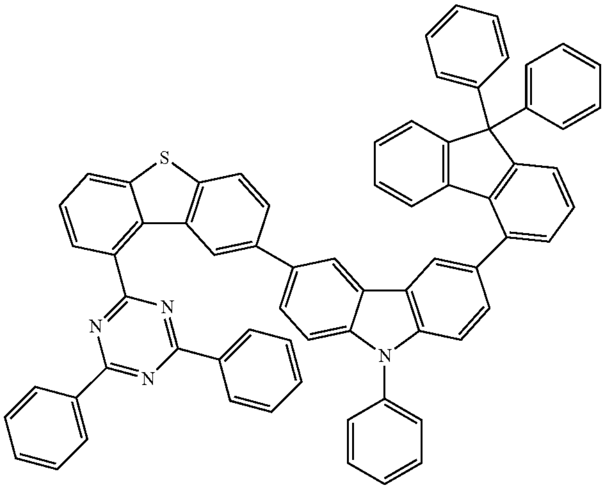 [SMILES: c1ccc(-c2nc(-c3ccccc3)nc(-c3cccc4sc5ccc(-c6ccc7c(c6)c6cc(-c8cccc9c8-c8ccccc8C9(c8ccccc8)c8ccccc8)ccc6n7-c6ccccc6)cc5c34)n2)cc1]
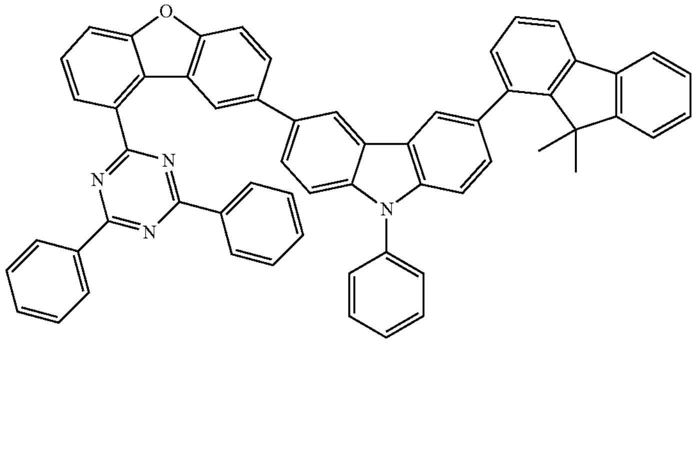 [SMILES: CC1(C)c2ccccc2-c2cccc(-c3ccc4c(c3)c3cc(-c5ccc6oc7cccc(-c8nc(-c9ccccc9)nc(-c9ccccc9)n8)c7c6c5)ccc3n4-c3ccccc3)c21]

TABLE 1-continued
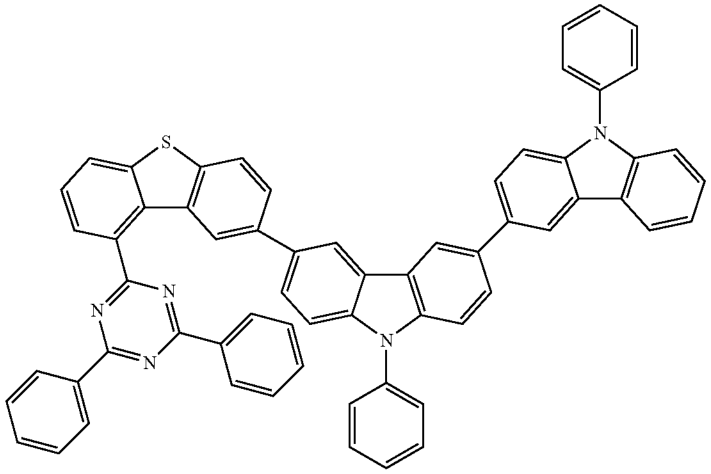 [SMILES: c1ccc(-c2nc(-c3ccccc3)nc(-c3cccc4sc5ccc(-c6ccc7c(c6)c6cc(-c8ccc9c(c8)c8ccccc8n9-c8ccccc8)ccc6n7-c6ccccc6)cc5c34)n2)cc1]
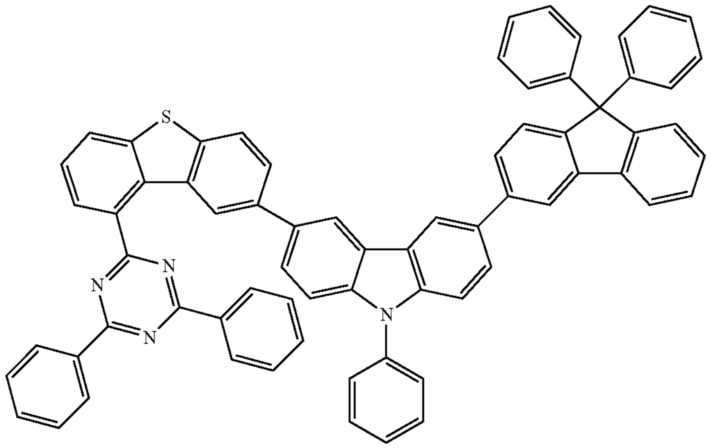
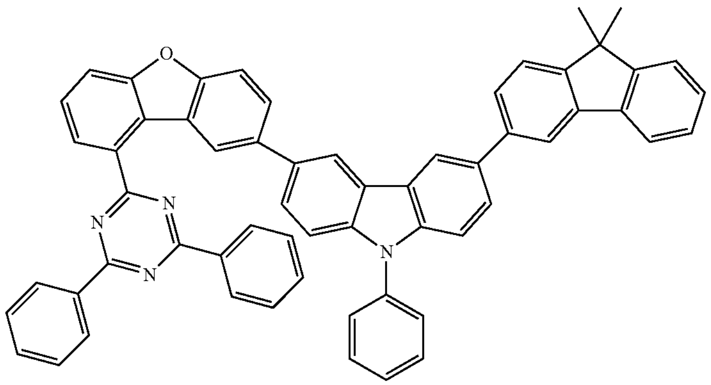 [SMILES: CC1(C)c2ccccc2-c2cc(-c3ccc4c(c3)c3cc(-c5ccc6oc7cccc(-c8nc(-c9ccccc9)nc(-c9ccccc9)n8)c7c6c5)ccc3n4-c3ccccc3)ccc21]

TABLE 1-continued
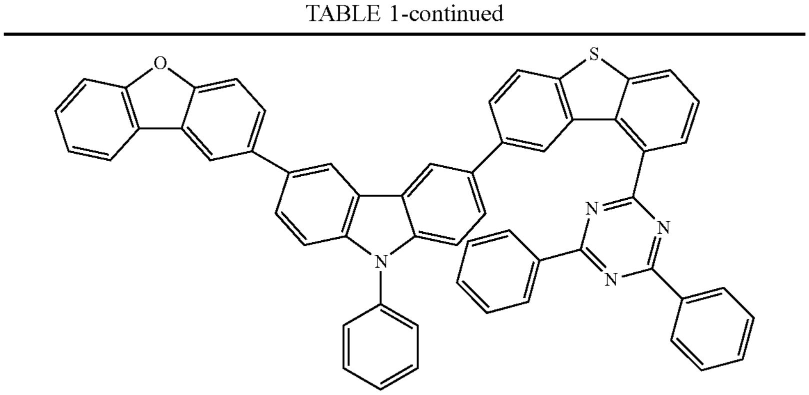
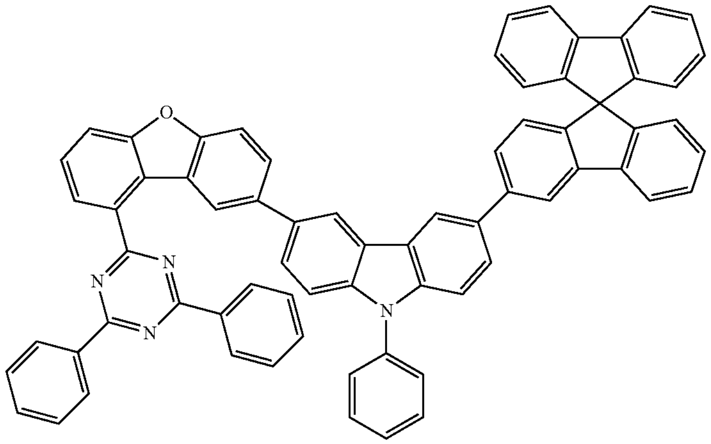
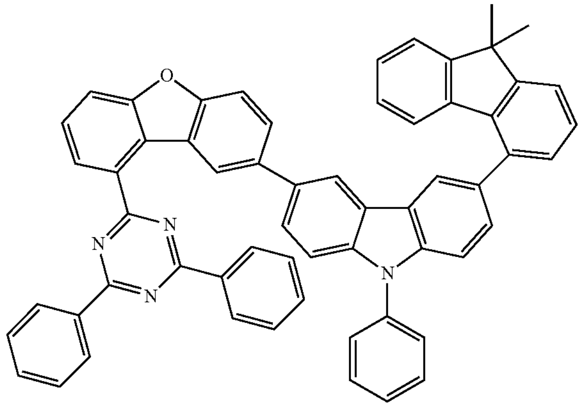 [SMILES: CC1(C)c2ccccc2-c2c(-c3ccc4c(c3)c3cc(-c5ccc6oc7cccc(-c8nc(-c9ccccc9)nc(-c9ccccc9)n8)c7c6c5)ccc3n4-c3ccccc3)cccc21]
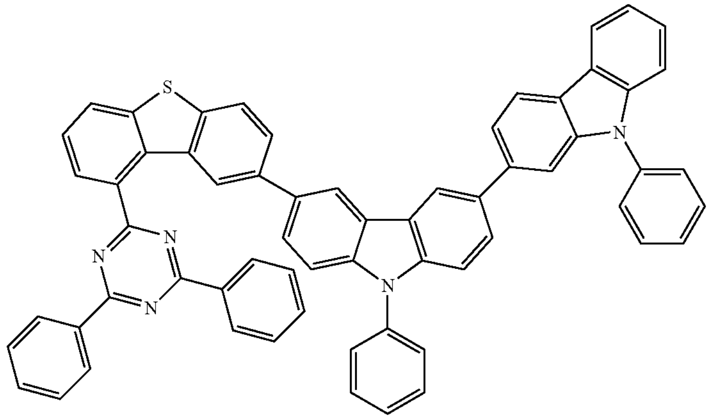 [SMILES: c1ccc(-c2nc(-c3ccccc3)nc(-c3cccc4sc5ccc(-c6ccc7c(c6)c6cc(-c8ccc9c%10ccccc%10n(-c%10ccccc%10)c9c8)ccc6n7-c6ccccc6)cc5c34)n2)cc1]

TABLE 1-continued
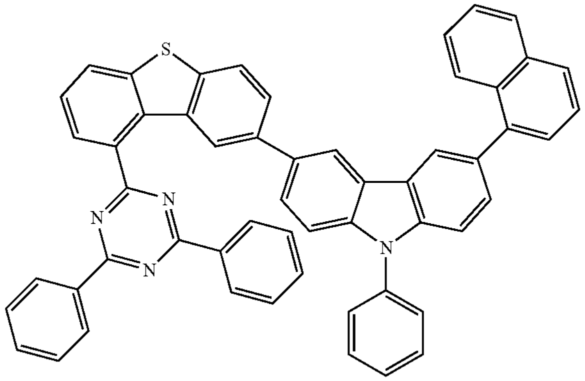 [SMILES: c1ccc(-c2nc(-c3ccccc3)nc(-c3cccc4sc5ccc(-c6ccc7c(c6)c6cc(-c8cccc9ccccc89)ccc6n7-c6ccccc6)cc5c34)n2)cc1]
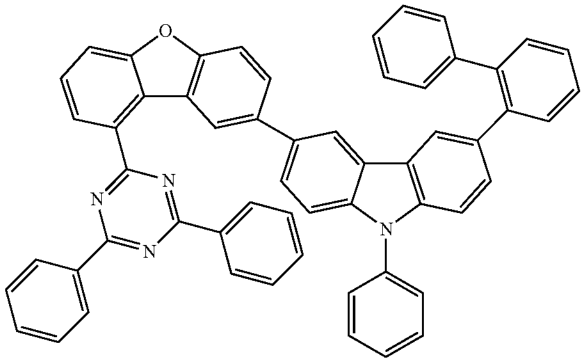 [SMILES: c1ccc(-c2nc(-c3ccccc3)nc(-c3cccc4oc5ccc(-c6ccc7c(c6)c6cc(-c8ccccc8-c8ccccc8)ccc6n7-c6ccccc6)cc5c34)n2)cc1]
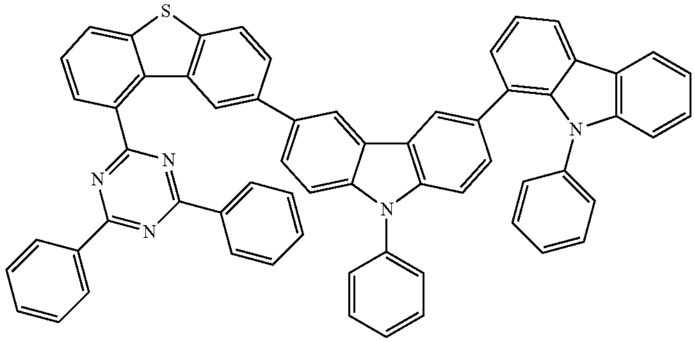
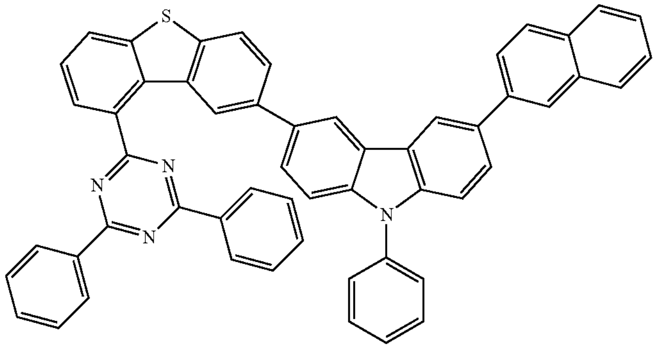

TABLE 1-continued
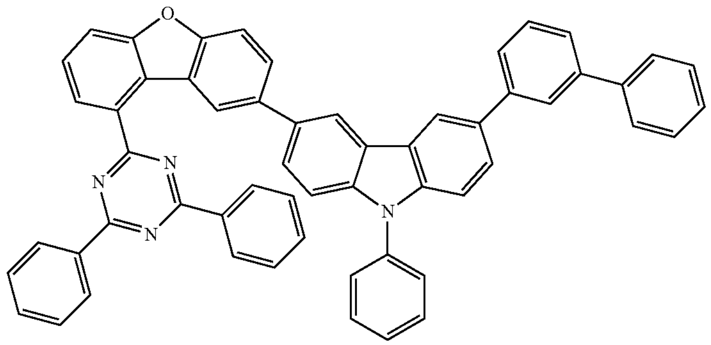 [SMILES: c1ccc(-c2cccc(-c3ccc4c(c3)c3cc(-c5ccc6oc7cccc(-c8nc(-c9ccccc9)nc(-c9ccccc9)n8)c7c6c5)ccc3n4-c3ccccc3)c2)cc1]
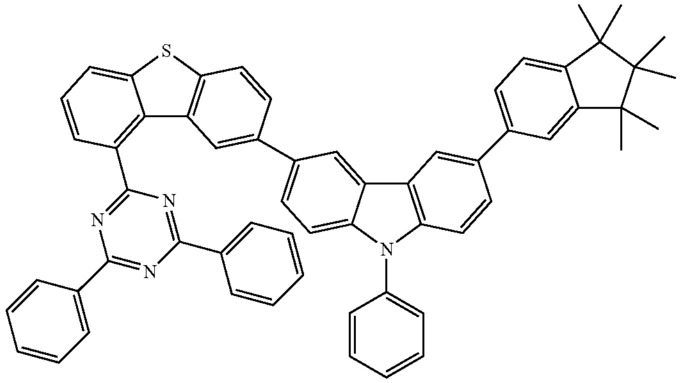 [SMILES: CC1(C)c2ccc(-c3ccc4c(c3)c3cc(-c5ccc6sc7cccc(-c8nc(-c9ccccc9)nc(-c9ccccc9)n8)c7c6c5)ccc3n4-c3ccccc3)cc2C(C)(C)C1(C)C]
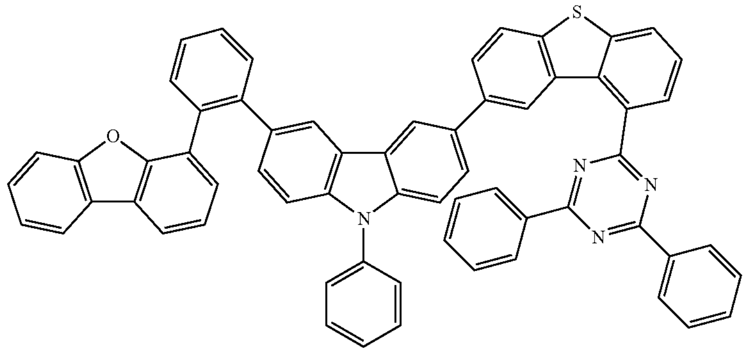 [SMILES: c1ccc(-c2nc(-c3ccccc3)nc(-c3cccc4sc5ccc(-c6ccc7c(c6)c6cc(-c8ccccc8-c8cccc9c8oc8ccccc89)ccc6n7-c6ccccc6)cc5c34)n2)cc1]
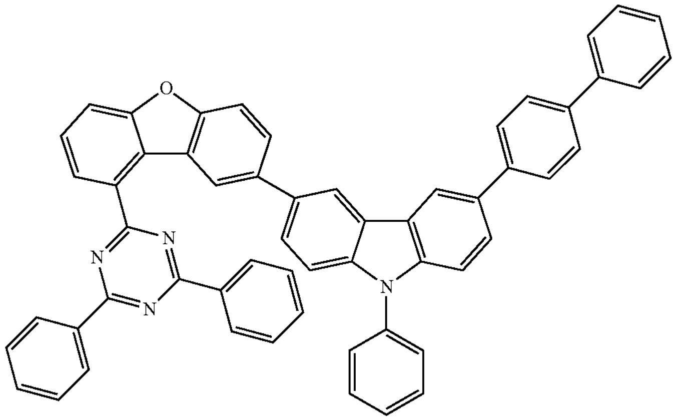

TABLE 1-continued
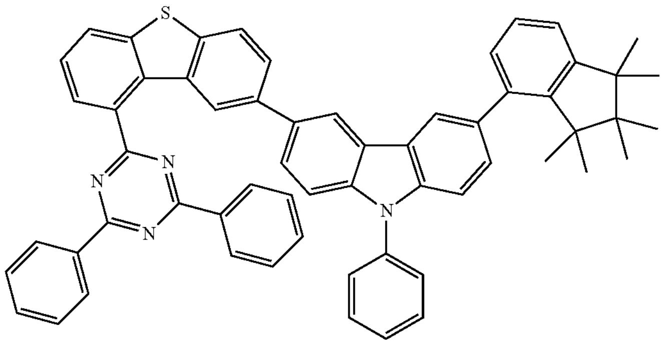 [SMILES: CC1(C)c2cccc(-c3ccc4c(c3)c3cc(-c5ccc6sc7cccc(-c8nc(-c9ccccc9)nc(-c9ccccc9)n8)c7c6c5)ccc3n4-c3ccccc3)c2C(C)(C)C1(C)C]
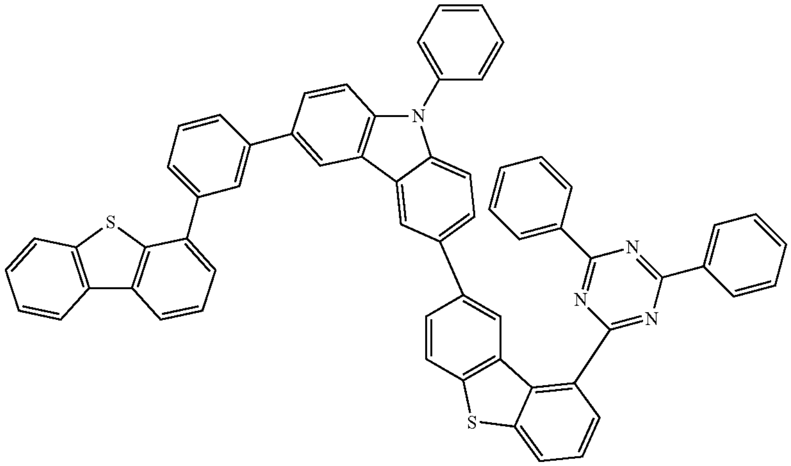 [SMILES: c1ccc(-c2nc(-c3ccccc3)nc(-c3cccc4sc5ccc(-c6ccc7c(c6)c6cc(-c8cccc(-c9cccc%10c9sc9ccccc9%10)c8)ccc6n7-c6ccccc6)cc5c34)n2)cc1]
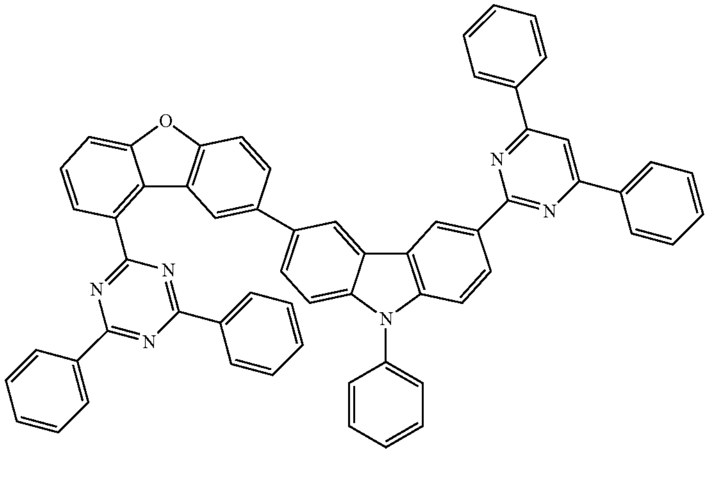

TABLE 1-continued
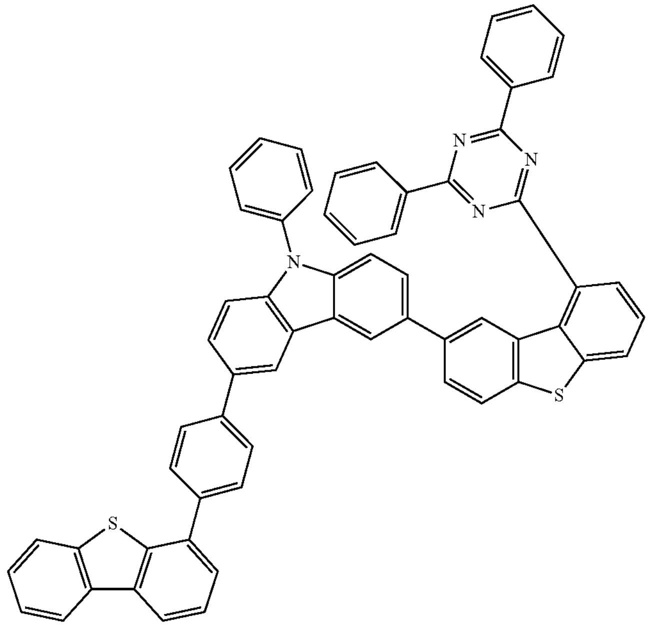 [SMILES: c1ccc(-c2nc(-c3ccccc3)nc(-c3cccc4sc5ccc(-c6ccc7c(c6)c6cc(-c8ccc(-c9cccc%10c9oc9ccccc9%10)cc8)ccc6n7-c6ccccc6)cc5c34)n2)cc1]
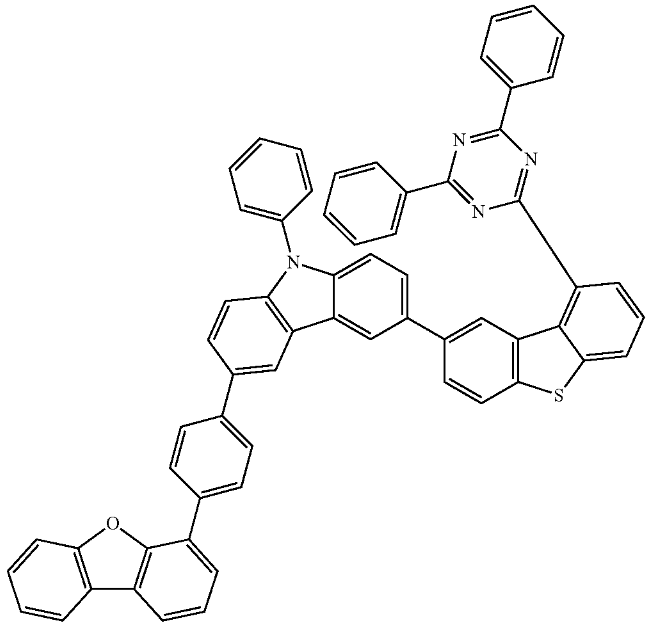

TABLE 1-continued
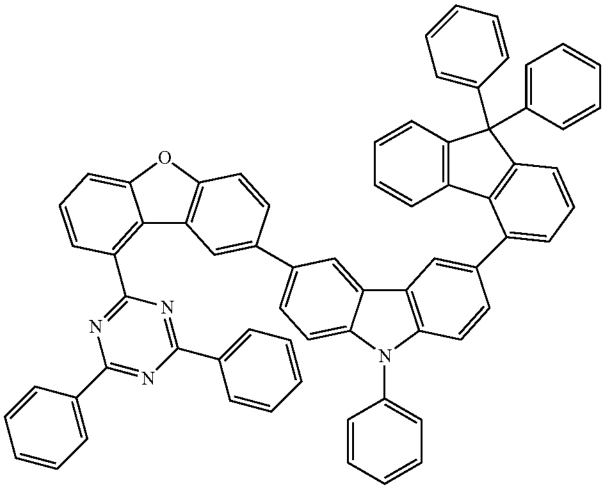
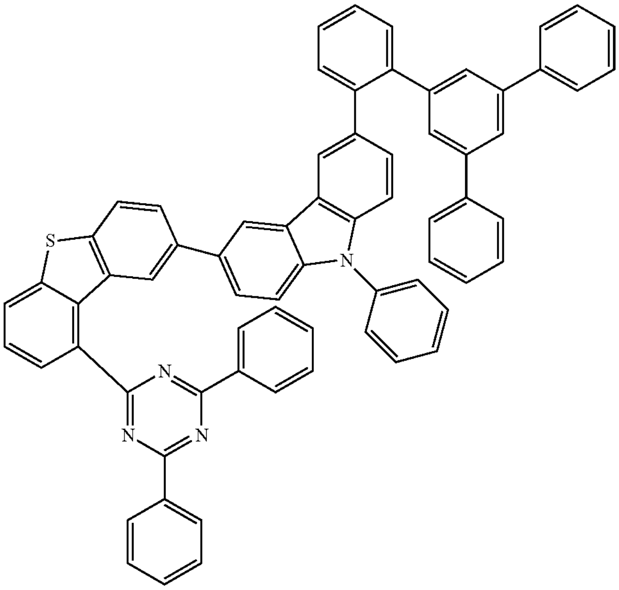 [SMILES: c1ccc(-c2cc(-c3ccccc3)cc(-c3ccccc3-c3ccc4c(c3)c3cc(-c5ccc6sc7cccc(-c8nc(-c9ccccc9)nc(-c9ccccc9)n8)c7c6c5)ccc3n4-c3ccccc3)c2)cc1]

TABLE 1-continued
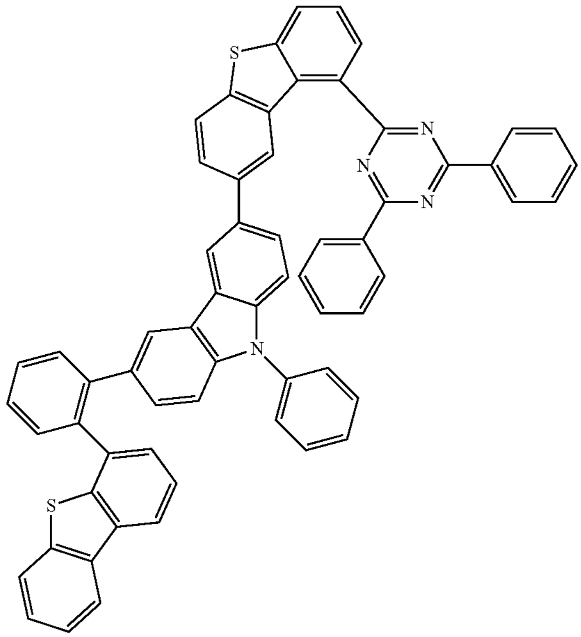 [SMILES: c1ccc(-c2nc(-c3ccccc3)nc(-c3cccc4sc5ccc(-c6ccc7c(c6)c6cc(-c8ccccc8-c8cccc9c8sc8ccccc89)ccc6n7-c6ccccc6)cc5c34)n2)cc1]
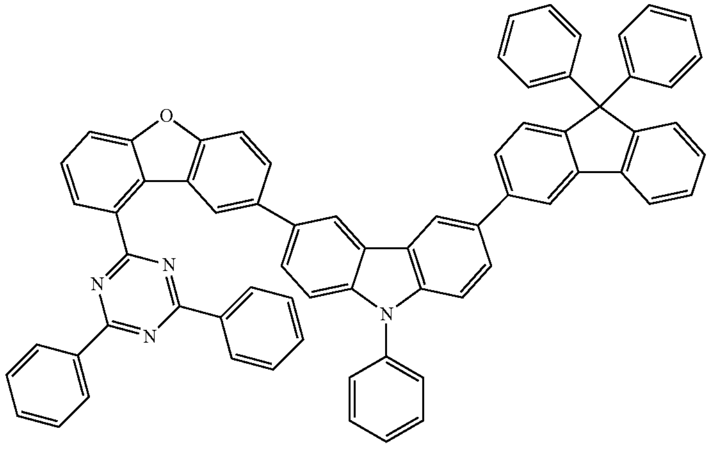
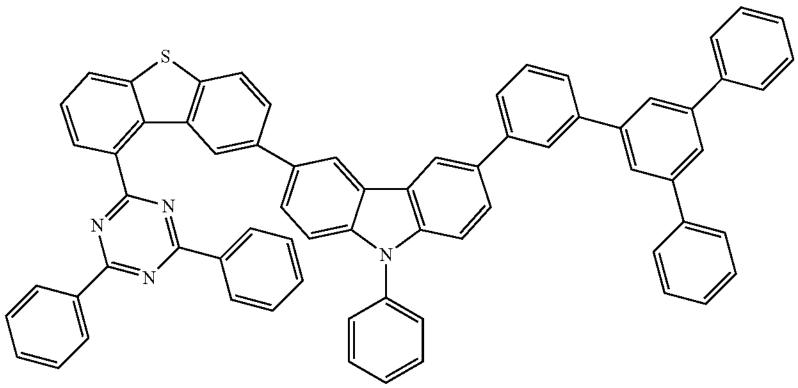

TABLE 1-continued
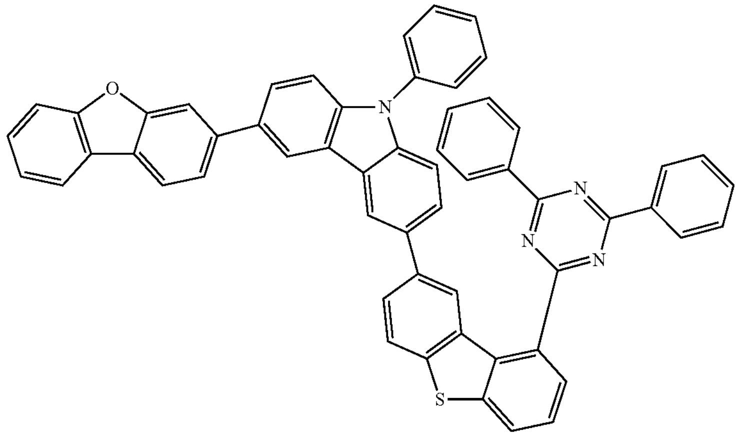 [SMILES: c1ccc(-c2nc(-c3ccccc3)nc(-c3cccc4sc5ccc(-c6ccc7c(c6)c6cc(-c8ccc9c(c8)oc8ccccc89)ccc6n7-c6ccccc6)cc5c34)n2)cc1]
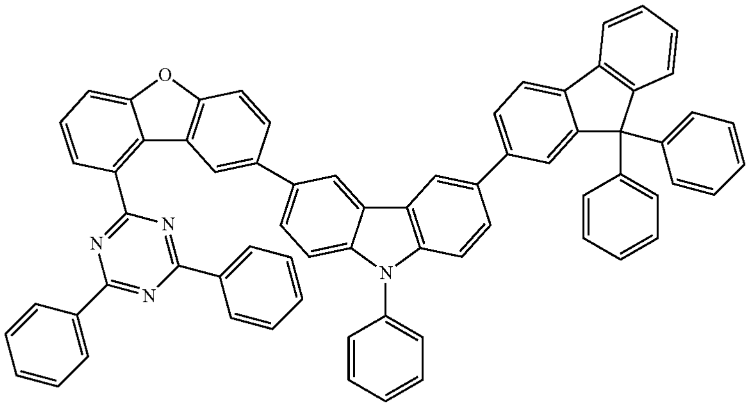
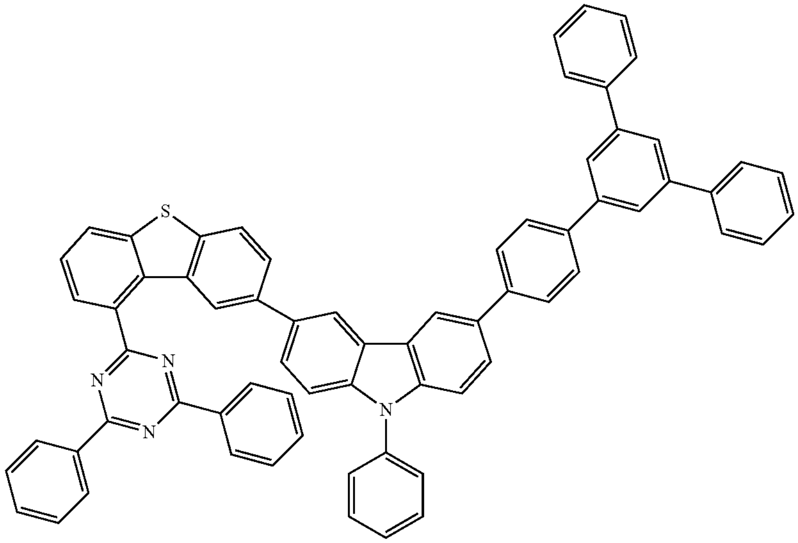

TABLE 1-continued
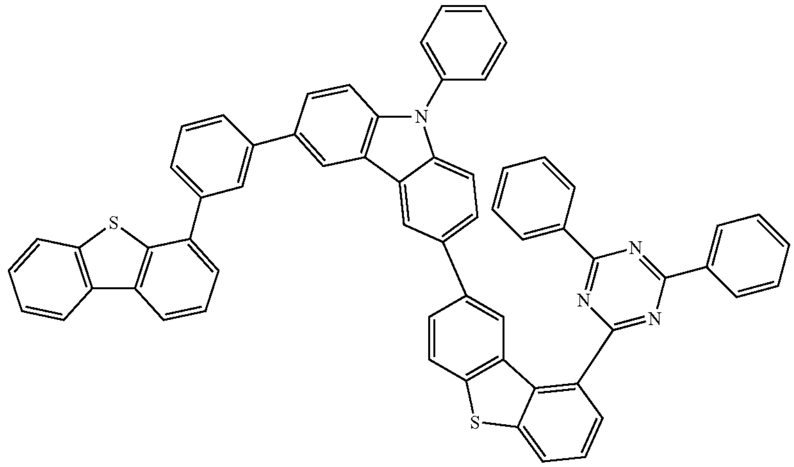 [SMILES: c1ccc(-c2nc(-c3ccccc3)nc(-c3cccc4sc5ccc(-c6ccc7c(c6)c6cc(-c8cccc(-c9cccc%10c9sc9ccccc9%10)c8)ccc6n7-c6ccccc6)cc5c34)n2)cc1]
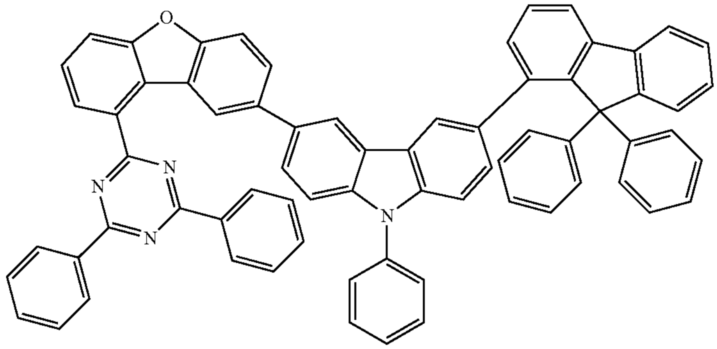 [SMILES: c1ccc(-c2nc(-c3ccccc3)nc(-c3cccc4oc5ccc(-c6ccc7c(c6)c6cc(-c8cccc9c8C(c8ccccc8)(c8ccccc8)c8ccccc8-9)ccc6n7-c6ccccc6)cc5c34)n2)cc1]
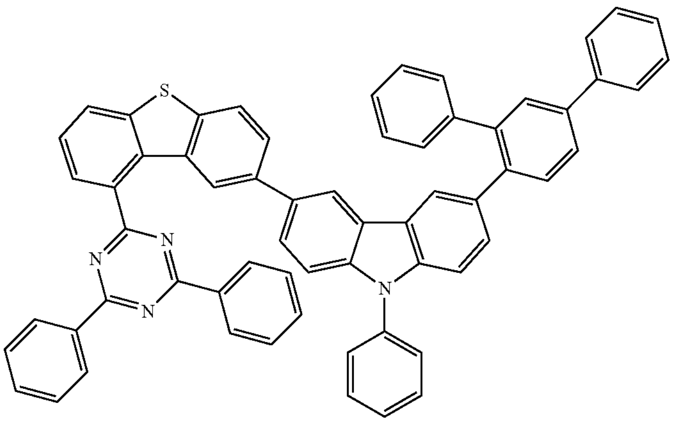 [SMILES: c1ccc(-c2ccc(-c3ccc4c(c3)c3cc(-c5ccc6sc7cccc(-c8nc(-c9ccccc9)nc(-c9ccccc9)n8)c7c6c5)ccc3n4-c3ccccc3)c(-c3ccccc3)c2)cc1]

TABLE 1-continued
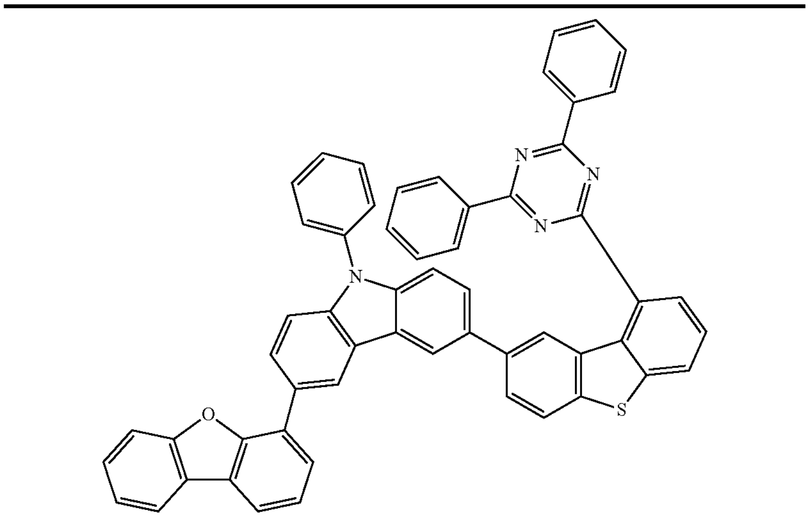
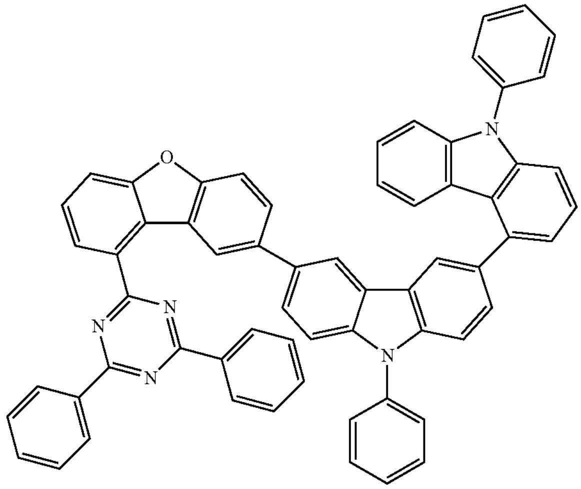 [SMILES: c1ccc(-c2nc(-c3ccccc3)nc(-c3cccc4oc5ccc(-c6ccc7c(c6)c6cc(-c8cccc9c8c8ccccc8n9-c8ccccc8)ccc6n7-c6ccccc6)cc5c34)n2)cc1]
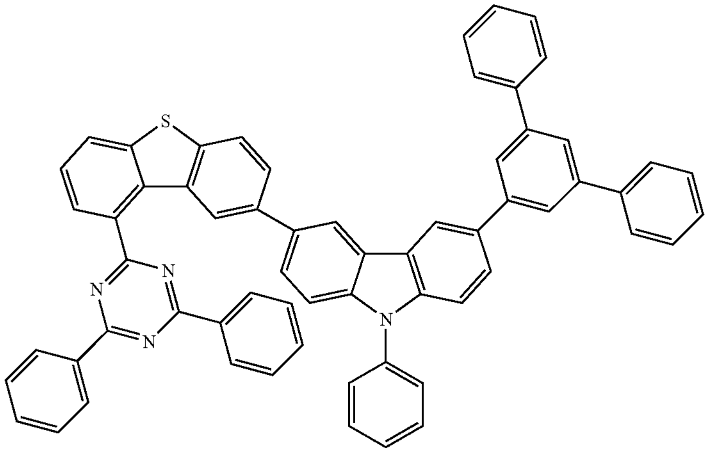

TABLE 1-continued
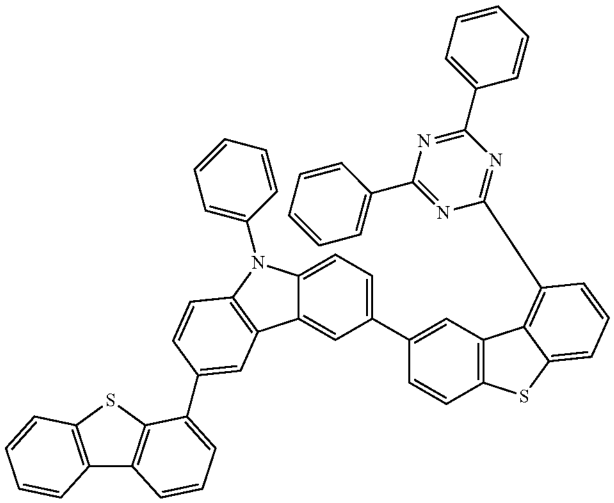 [SMILES: c1ccc(-c2nc(-c3ccccc3)nc(-c3cccc4sc5ccc(-c6ccc7c(c6)c6cc(-c8cccc9c8sc8ccccc89)ccc6n7-c6ccccc6)cc5c34)n2)cc1]
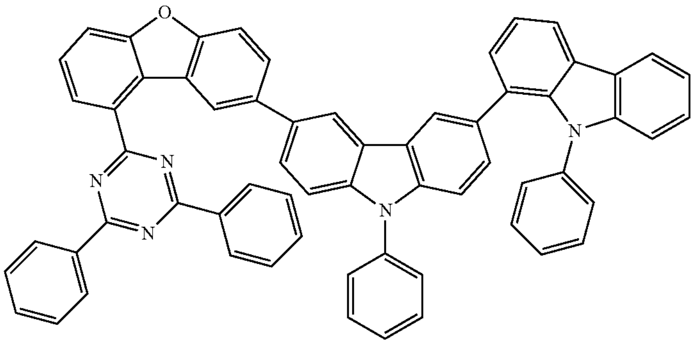 [SMILES: c1ccc(-c2nc(-c3ccccc3)nc(-c3cccc4oc5ccc(-c6ccc7c(c6)c6cc(-c8cccc9c%10ccccc%10n(-c%10ccccc%10)c89)ccc6n7-c6ccccc6)cc5c34)n2)cc1]
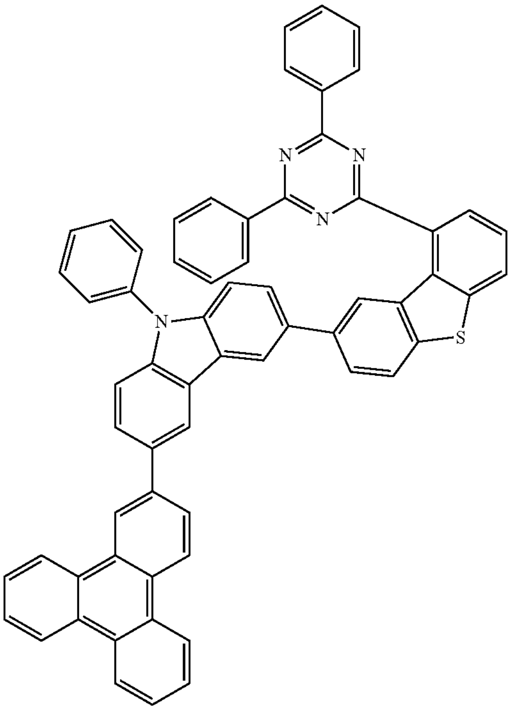 [SMILES: c1ccc(-c2nc(-c3ccccc3)nc(-c3cccc4sc5ccc(-c6ccc7c(c6)c6cc(-c8ccc9c%10ccccc%10c%10ccccc%10c9c8)ccc6n7-c6ccccc6)cc5c34)n2)cc1]

TABLE 1-continued
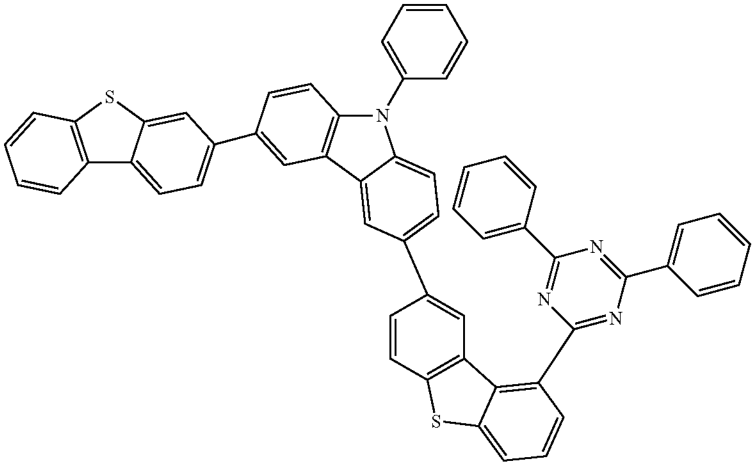 [SMILES: c1ccc(-c2nc(-c3ccccc3)nc(-c3cccc4sc5ccc(-c6ccc7c(c6)c6cc(-c8ccc9c(c8)sc8ccccc89)ccc6n7-c6ccccc6)cc5c34)n2)cc1]
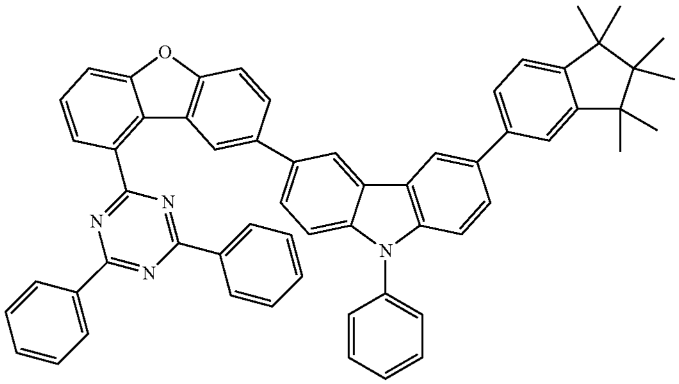
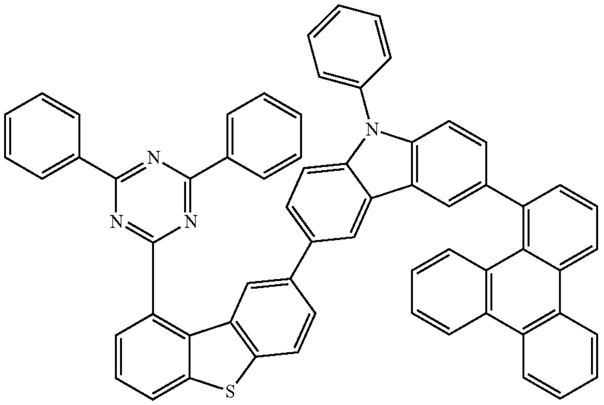 [SMILES: c1ccc(-c2nc(-c3ccccc3)nc(-c3cccc4sc5ccc(-c6ccc7c(c6)c6cc(-c8cccc9c%10ccccc%10c%10ccccc%10c89)ccc6n7-c6ccccc6)cc5c34)n2)cc1]
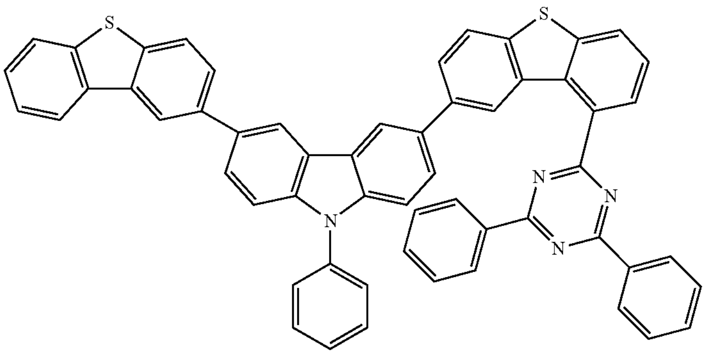 [SMILES: c1ccc(-c2nc(-c3ccccc3)nc(-c3cccc4sc5ccc(-c6ccc7c(c6)c6cc(-c8ccc9sc%10ccccc%10c9c8)ccc6n7-c6ccccc6)cc5c34)n2)cc1]

TABLE 1-continued
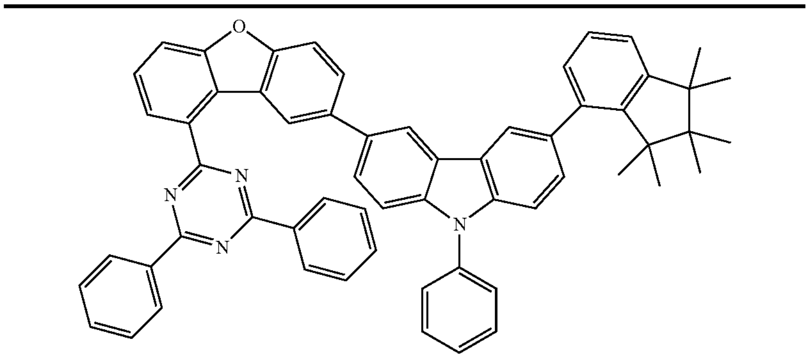
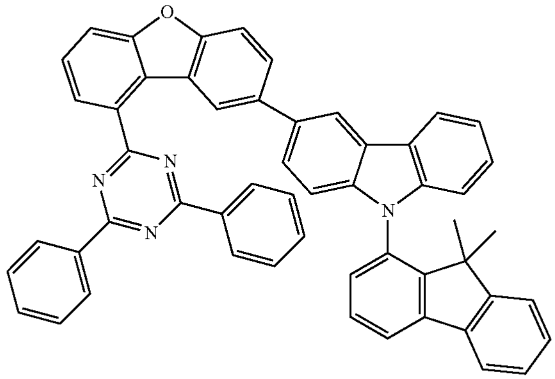 [SMILES: CC1(C)c2ccccc2-c2cccc(-n3c4ccccc4c4cc(-c5ccc6oc7cccc(-c8nc(-c9ccccc9)nc(-c9ccccc9)n8)c7c6c5)ccc43)c21]
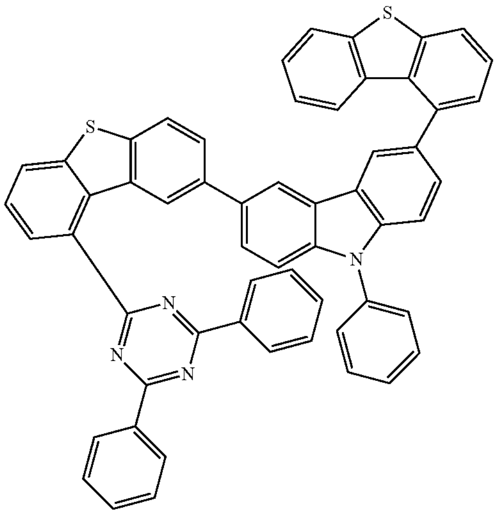 [SMILES: c1ccc(-c2nc(-c3ccccc3)nc(-c3cccc4sc5ccc(-c6ccc7c(c6)c6cc(-c8cccc9sc%10ccccc%10c89)ccc6n7-c6ccccc6)cc5c34)n2)cc1]
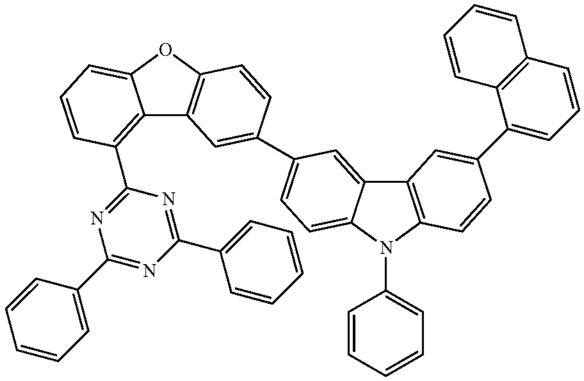

TABLE 1-continued
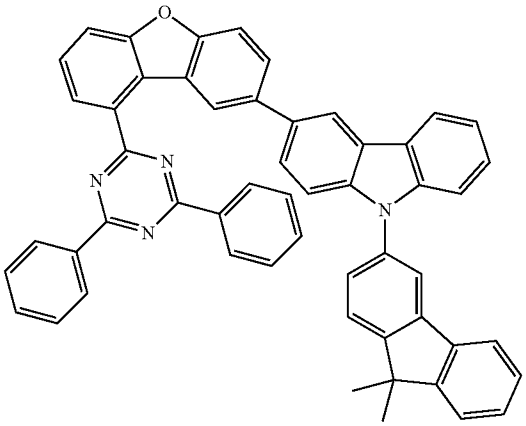
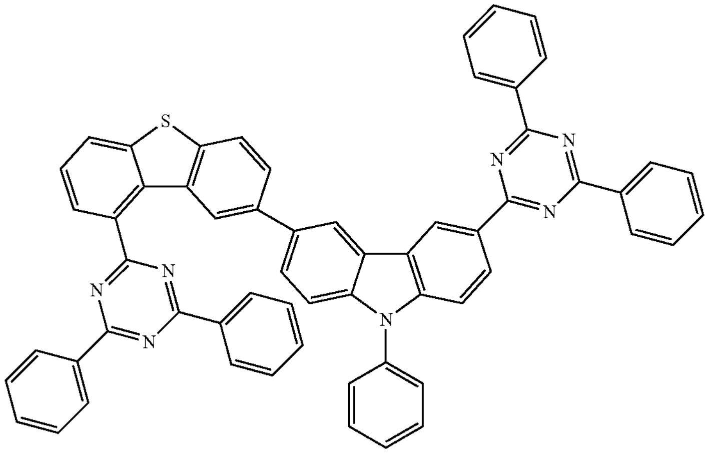
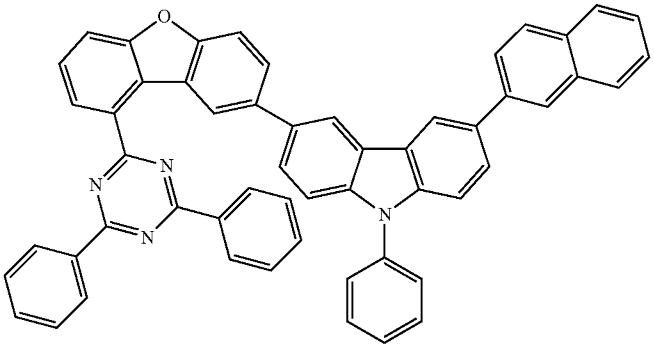 [SMILES: c1ccc(-c2nc(-c3ccccc3)nc(-c3cccc4oc5ccc(-c6ccc7c(c6)c6cc(-c8ccc9ccccc9c8)ccc6n7-c6ccccc6)cc5c34)n2)cc1]

TABLE 1-continued
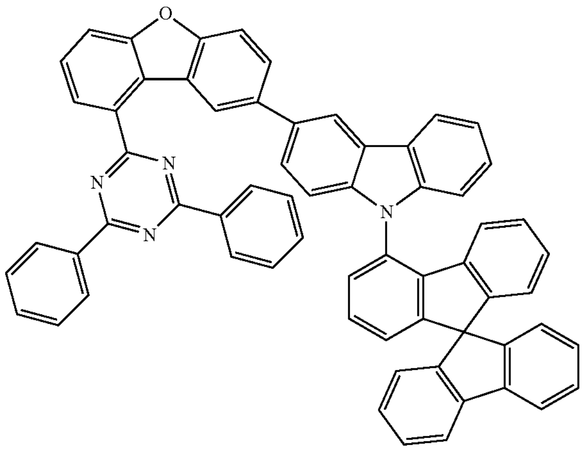 [SMILES: c1ccc(-c2nc(-c3ccccc3)nc(-c3cccc4oc5ccc(-c6ccc7c(c6)c6ccccc6n7-c6cccc7c6-c6ccccc6C76c7ccccc7-c7ccccc76)cc5c34)n2)cc1]
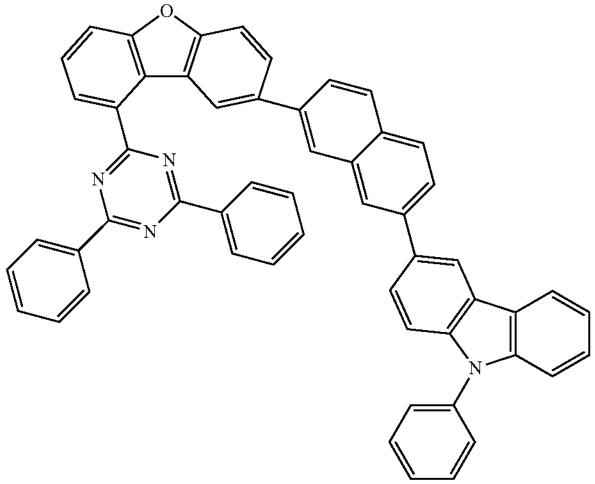 [SMILES: c1ccc(-c2nc(-c3ccccc3)nc(-c3cccc4oc5ccc(-c6ccc7ccc(-c8ccc9c(c8)c8ccccc8n9-c8ccccc8)cc7c6)cc5c34)n2)cc1]
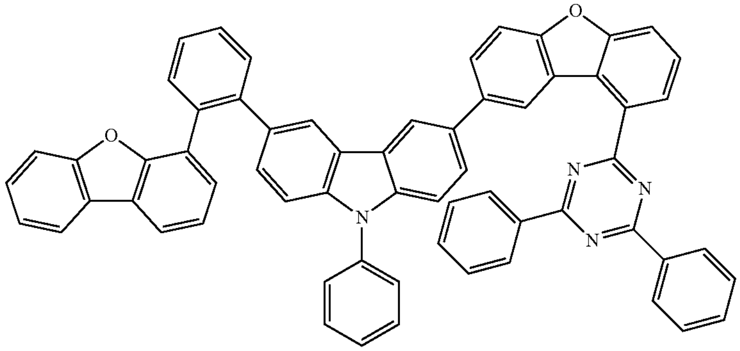 [SMILES: c1ccc(-c2nc(-c3ccccc3)nc(-c3cccc4oc5ccc(-c6ccc7c(c6)c6cc(-c8ccccc8-c8cccc9c8oc8ccccc89)ccc6n7-c6ccccc6)cc5c34)n2)cc1]

TABLE 1-continued
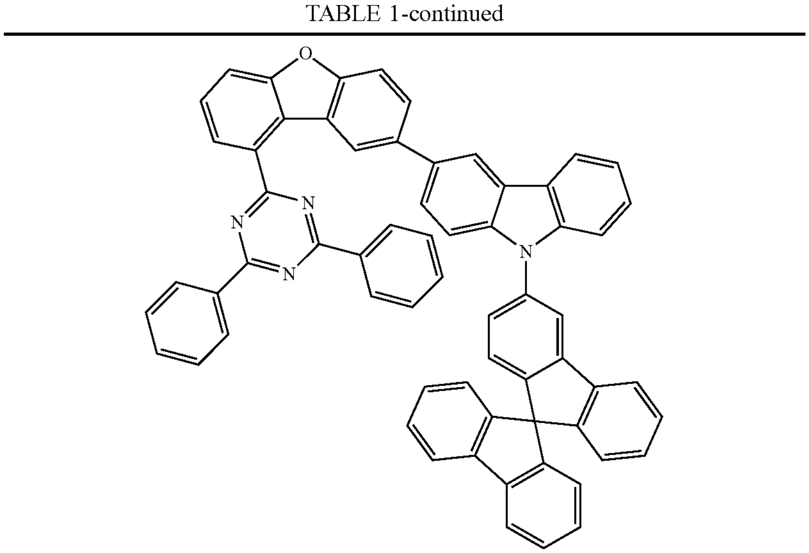
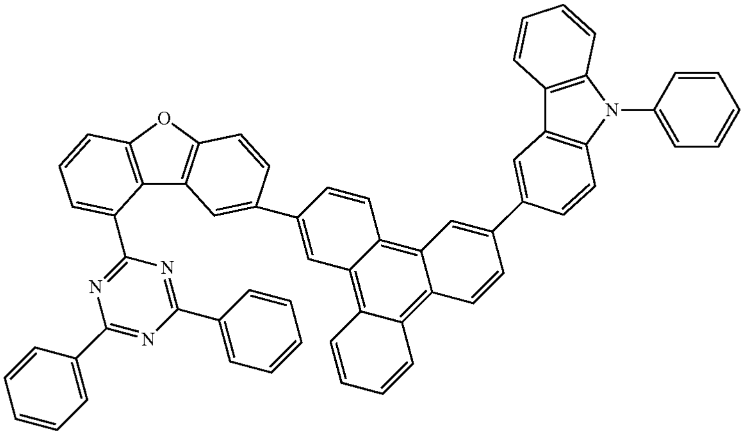 [SMILES: c1ccc(-c2nc(-c3ccccc3)nc(-c3cccc4oc5ccc(-c6ccc7c(c6)c6ccccc6c6ccc(-c8ccc9c(c8)c8ccccc8n9-c8ccccc8)cc67)cc5c34)n2)cc1]
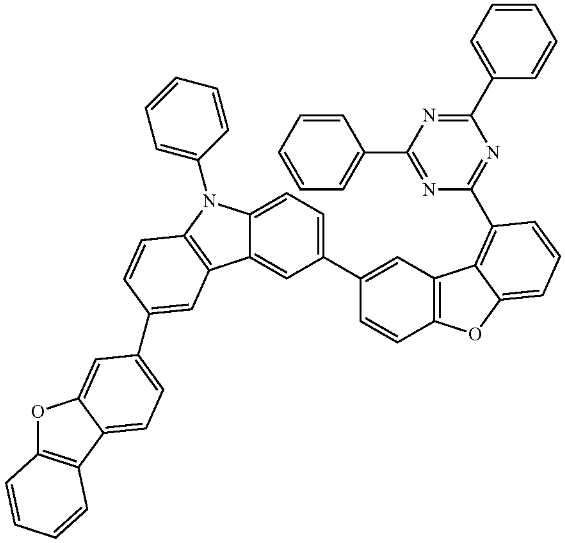 [SMILES: c1ccc(-c2nc(-c3ccccc3)nc(-c3cccc4oc5ccc(-c6ccc7c(c6)c6cc(-c8ccc9c(c8)oc8ccccc89)ccc6n7-c6ccccc6)cc5c34)n2)cc1]

TABLE 1-continued
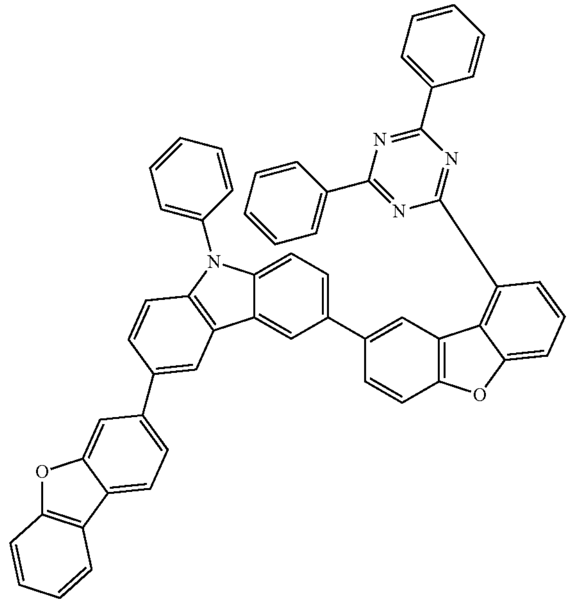 [SMILES: c1ccc(-c2nc(-c3ccccc3)nc(-c3cccc4oc5ccc(-c6ccc7c(c6)c6cc(-c8ccc9c(c8)oc8ccccc89)ccc6n7-c6ccccc6)cc5c34)n2)cc1]
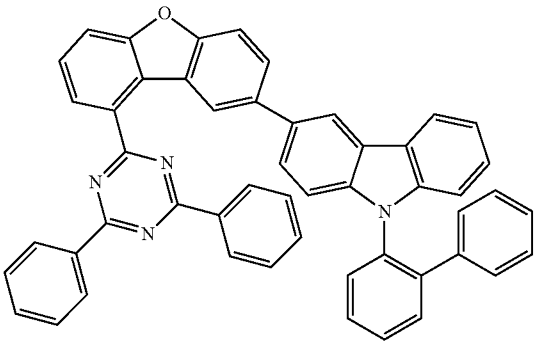 [SMILES: c1ccc(-c2nc(-c3ccccc3)nc(-c3cccc4oc5ccc(-c6ccc7c(c6)c6ccccc6n7-c6ccccc6-c6ccccc6)cc5c34)n2)cc1]
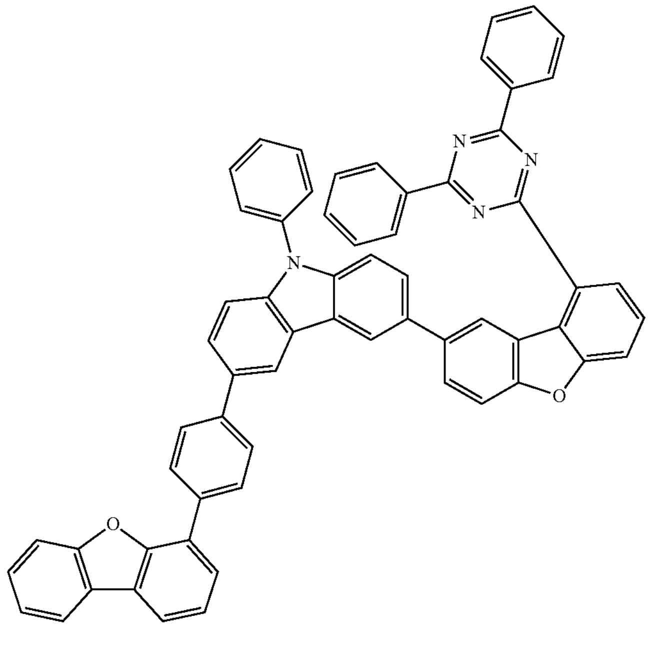 [SMILES: c1ccc(-c2nc(-c3ccccc3)nc(-c3cccc4oc5ccc(-c6ccc7c(c6)c6cc(-c8ccc(-c9cccc%10c9oc9ccccc9%10)cc8)ccc6n7-c6ccccc6)cc5c34)n2)cc1]

TABLE 1-continued
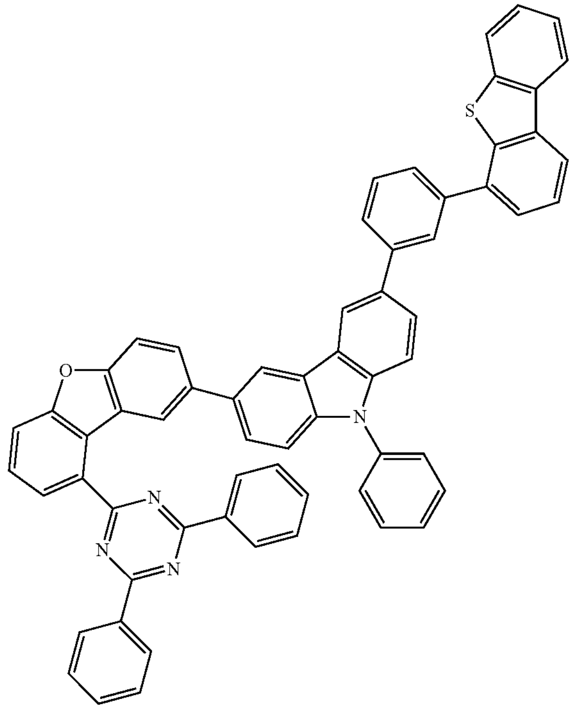 [SMILES: c1ccc(-c2nc(-c3ccccc3)nc(-c3cccc4oc5ccc(-c6ccc7c(c6)c6cc(-c8cccc(-c9cccc%10c9sc9ccccc9%10)c8)ccc6n7-c6ccccc6)cc5c34)n2)cc1]
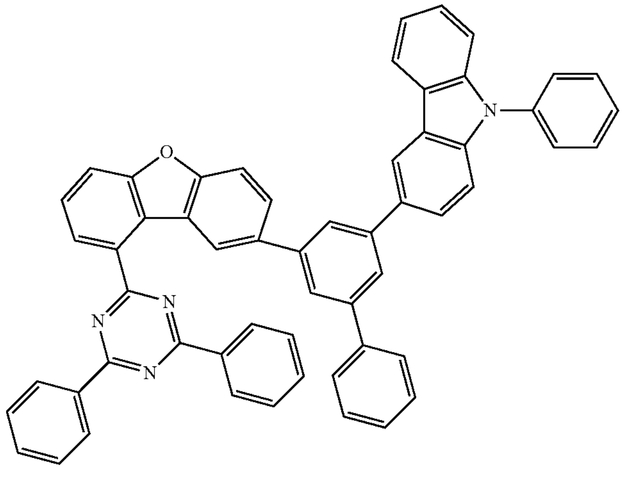 [SMILES: c1ccc(-c2cc(-c3ccc4oc5cccc(-c6nc(-c7ccccc7)nc(-c7ccccc7)n6)c5c4c3)cc(-c3ccc4c(c3)c3ccccc3n4-c3ccccc3)c2)cc1]
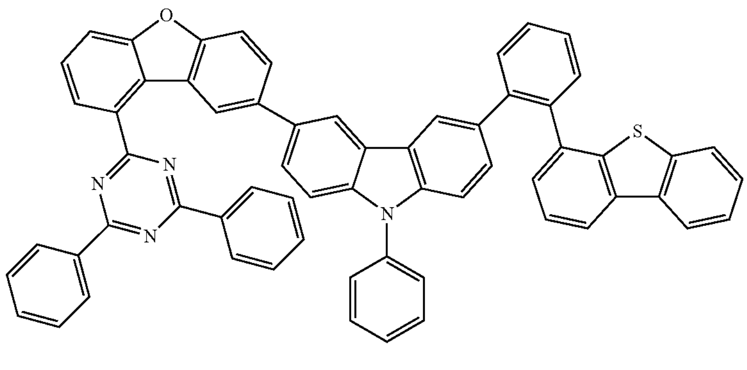 [SMILES: c1ccc(-c2nc(-c3ccccc3)nc(-c3cccc4oc5ccc(-c6ccc7c(c6)c6cc(-c8ccccc8-c8cccc9c8sc8ccccc89)ccc6n7-c6ccccc6)cc5c34)n2)cc1]

TABLE 1-continued
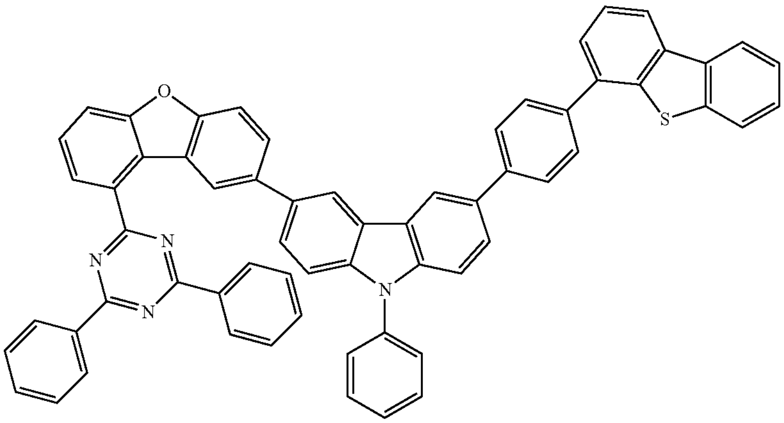 [SMILES: c1ccc(-c2nc(-c3ccccc3)nc(-c3cccc4oc5ccc(-c6ccc7c(c6)c6cc(-c8ccc(-c9cccc%10c9sc9ccccc9%10)cc8)ccc6n7-c6ccccc6)cc5c34)n2)cc1]
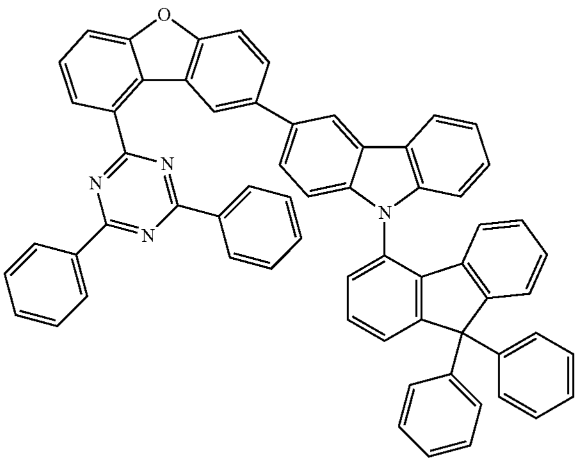
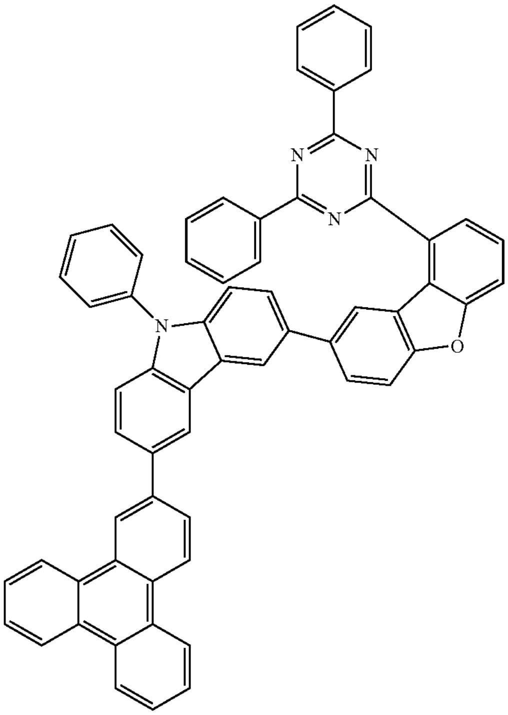 [SMILES: c1ccc(-c2nc(-c3ccccc3)nc(-c3cccc4oc5ccc(-c6ccc7c(c6)c6cc(-c8ccc9c%10ccccc%10c%10ccccc%10c9c8)ccc6n7-c6ccccc6)cc5c34)n2)cc1]

TABLE 1-continued
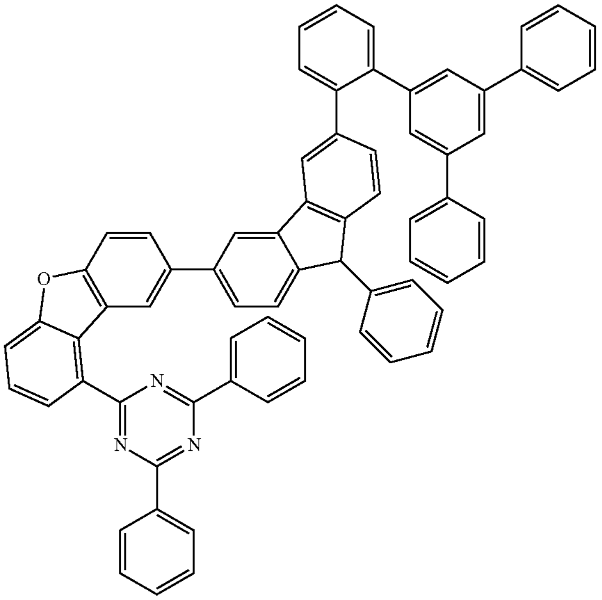 [SMILES: c1ccc(-c2cc(-c3ccccc3)cc(-c3ccccc3-c3ccc4c(c3)-c3cc(-c5ccc6oc7cccc(-c8nc(-c9ccccc9)nc(-c9ccccc9)n8)c7c6c5)ccc3C4c3ccccc3)c2)cc1]
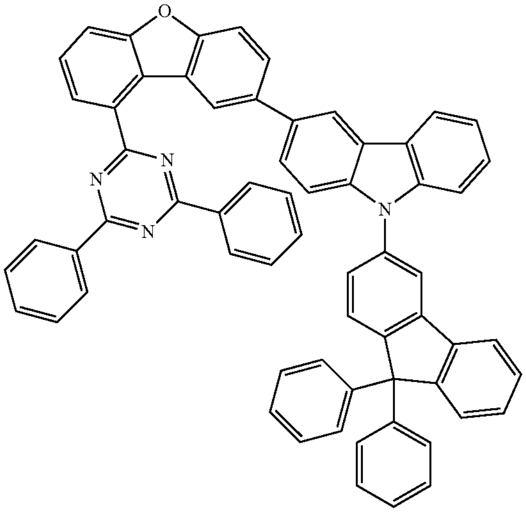 [SMILES: c1ccc(-c2nc(-c3ccccc3)nc(-c3cccc4oc5ccc(-c6ccc7c(c6)c6ccccc6n7-c6ccc7c(c6)-c6ccccc6C7(c6ccccc6)c6ccccc6)cc5c34)n2)cc1]
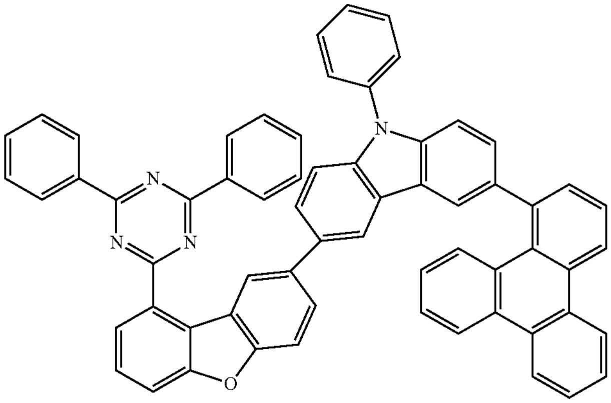 [SMILES: c1ccc(-c2nc(-c3ccccc3)nc(-c3cccc4oc5ccc(-c6ccc7c(c6)c6cc(-c8cccc9c%10ccccc%10c%10ccccc%10c89)ccc6n7-c6ccccc6)cc5c34)n2)cc1]

TABLE 1-continued
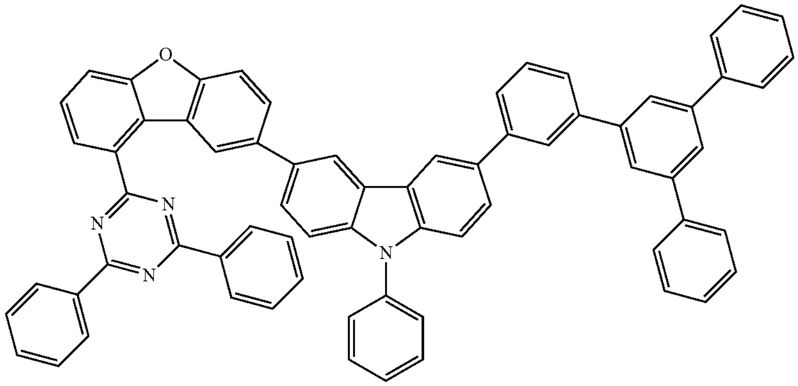 [SMILES: c1ccc(-c2cc(-c3ccccc3)cc(-c3cccc(-c4ccc5c(c4)c4cc(-c6ccc7oc8cccc(-c9nc(-c%10ccccc%10)nc(-c%10ccccc%10)n9)c8c7c6)ccc4n5-c4ccccc4)c3)c2)cc1]
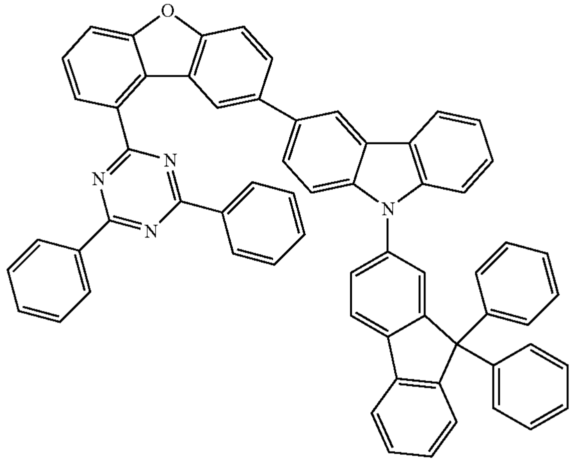 [SMILES: c1ccc(-c2nc(-c3ccccc3)nc(-c3cccc4oc5ccc(-c6ccc7c(c6)c6ccccc6n7-c6ccc7c(c6)C(c6ccccc6)(c6ccccc6)c6ccccc6-7)cc5c34)n2)cc1]
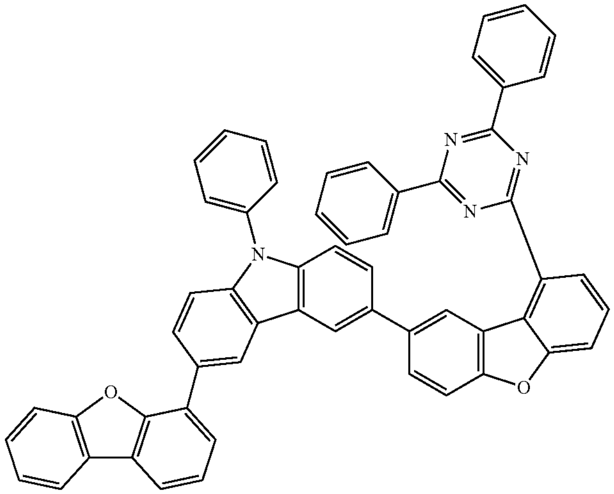 [SMILES: c1ccc(-c2nc(-c3ccccc3)nc(-c3cccc4oc5ccc(-c6ccc7c(c6)c6cc(-c8cccc9c8oc8ccccc89)ccc6n7-c6ccccc6)cc5c34)n2)cc1]

TABLE 1-continued
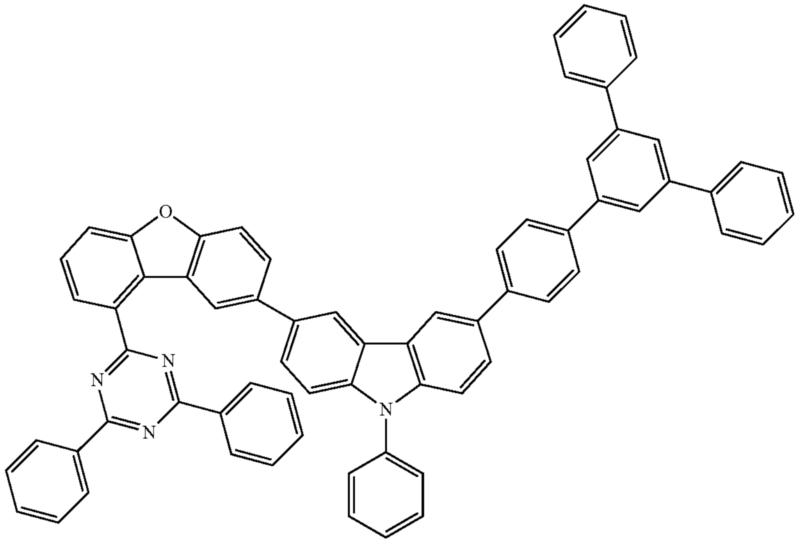 [SMILES: c1ccc(-c2cc(-c3ccccc3)cc(-c3ccc(-c4ccc5c(c4)c4cc(-c6ccc7oc8cccc(-c9nc(-c%10ccccc%10)nc(-c%10ccccc%10)n9)c8c7c6)ccc4n5-c4ccccc4)cc3)c2)cc1]
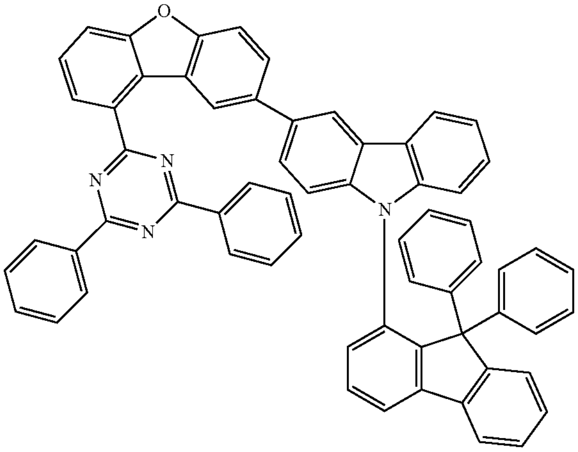 [SMILES: c1ccc(-c2nc(-c3ccccc3)nc(-c3cccc4oc5ccc(-c6ccc7c(c6)c6ccccc6n7-c6cccc7c6C(c6ccccc6)(c6ccccc6)c6ccccc6-7)cc5c34)n2)cc1]
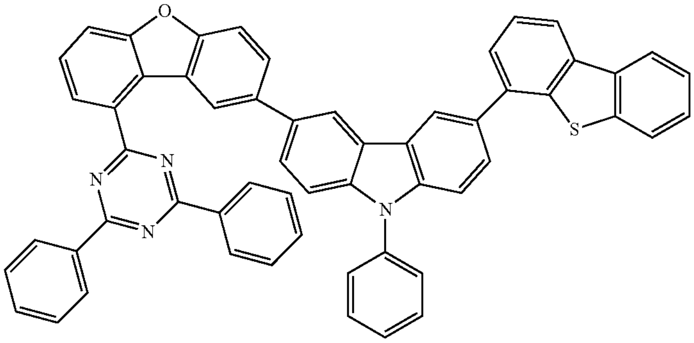 [SMILES: c1ccc(-c2nc(-c3ccccc3)nc(-c3cccc4oc5ccc(-c6ccc7c(c6)c6cc(-c8cccc9c8sc8ccccc89)ccc6n7-c6ccccc6)cc5c34)n2)cc1]

TABLE 1-continued
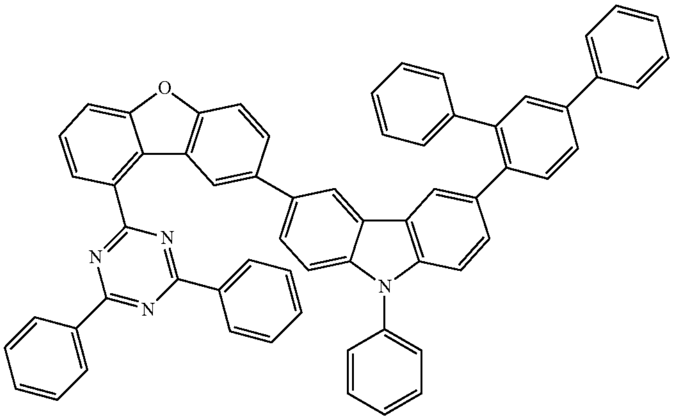
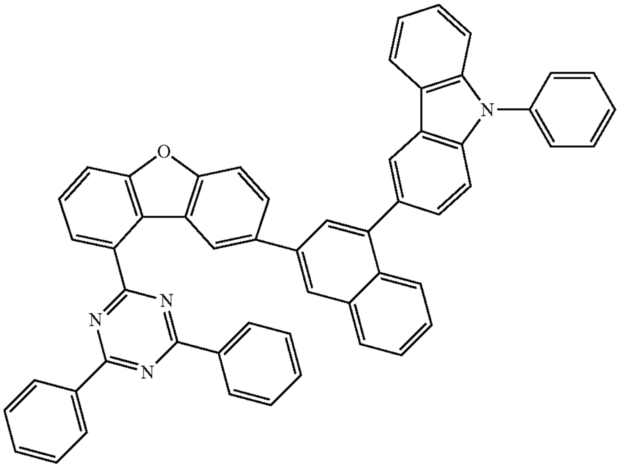 [SMILES: c1ccc(-c2nc(-c3ccccc3)nc(-c3cccc4oc5ccc(-c6cc(-c7ccc8c(c7)c7ccccc7n8-c7ccccc7)c7ccccc7c6)cc5c34)n2)cc1]
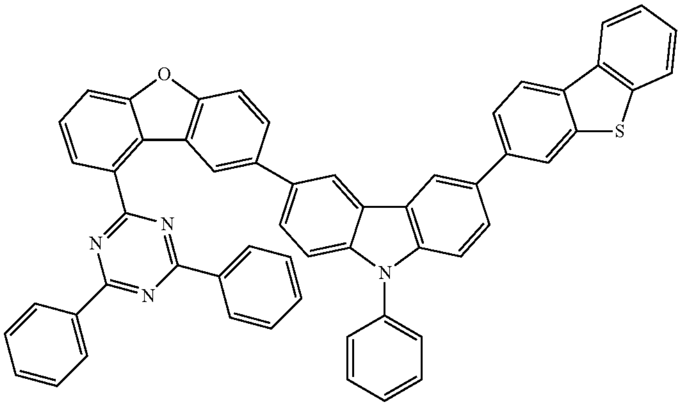 [SMILES: c1ccc(-c2nc(-c3ccccc3)nc(-c3cccc4oc5ccc(-c6ccc7c(c6)c6cc(-c8ccc9c(c8)sc8ccccc89)ccc6n7-c6ccccc6)cc5c34)n2)cc1]

TABLE 1-continued
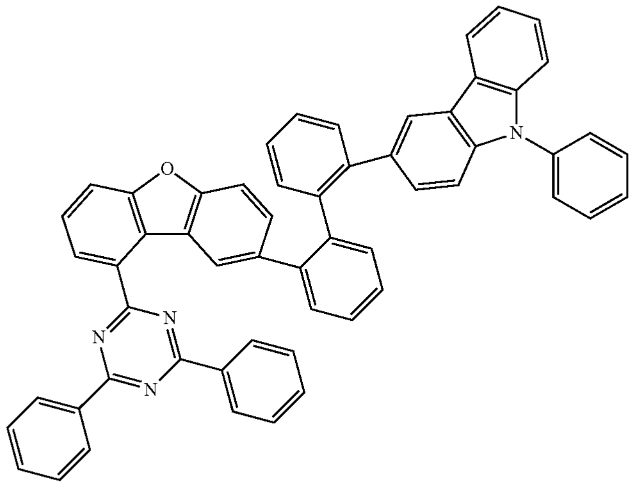 [SMILES: c1ccc(-c2nc(-c3ccccc3)nc(-c3cccc4oc5ccc(-c6ccccc6-c6ccccc6-c6ccc7c(c6)c6ccccc6n7-c6ccccc6)cc5c34)n2)cc1]
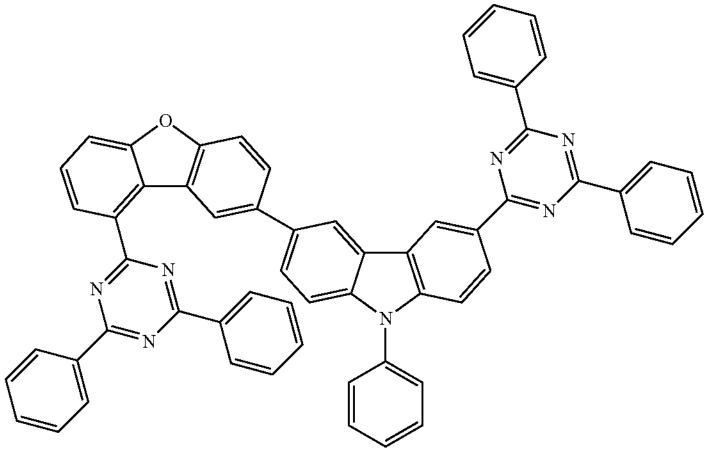
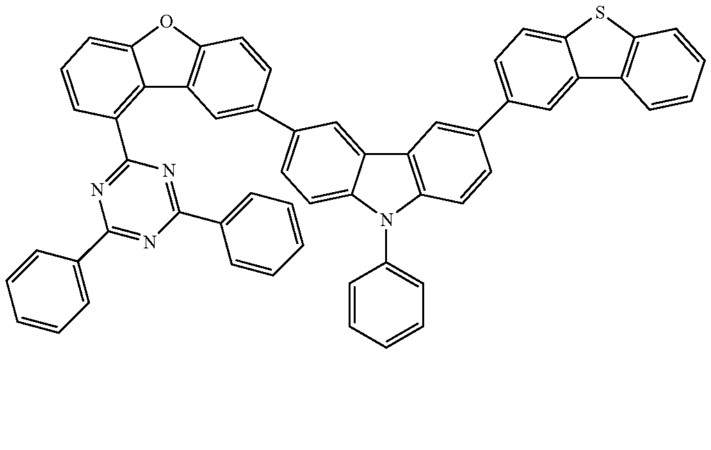 [SMILES: c1ccc(-c2nc(-c3ccccc3)nc(-c3cccc4oc5ccc(-c6ccc7c(c6)c6cc(-c8ccc9sc%10ccccc%10c9c8)ccc6n7-c6ccccc6)cc5c34)n2)cc1]

TABLE 1-continued
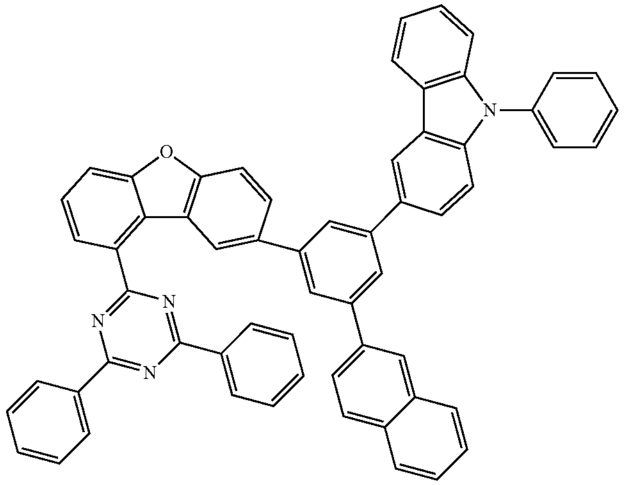 [SMILES: c1ccc(-c2nc(-c3ccccc3)nc(-c3cccc4oc5ccc(-c6cc(-c7ccc8ccccc8c7)cc(-c7ccc8c(c7)c7ccccc7n8-c7ccccc7)c6)cc5c34)n2)cc1]
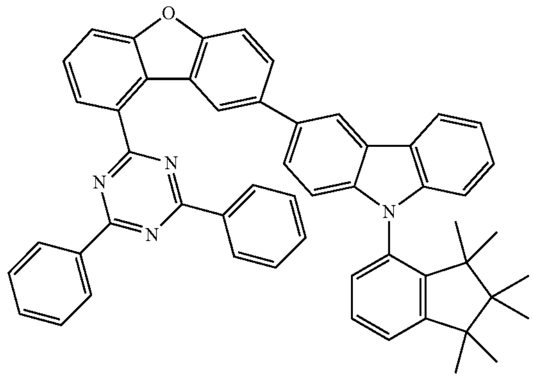
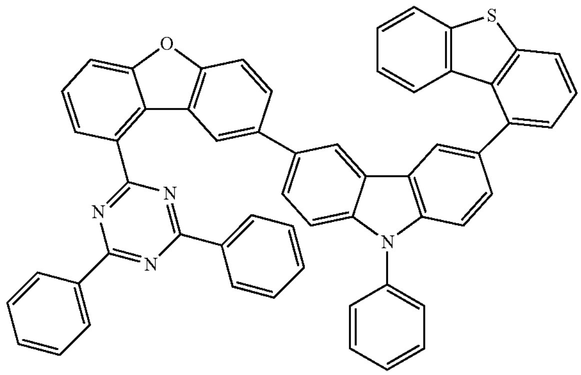 [SMILES: c1ccc(-c2nc(-c3ccccc3)nc(-c3cccc4oc5ccc(-c6ccc7c(c6)c6cc(-c8cccc9sc%10ccccc%10c89)ccc6n7-c6ccccc6)cc5c34)n2)cc1]

TABLE 1-continued
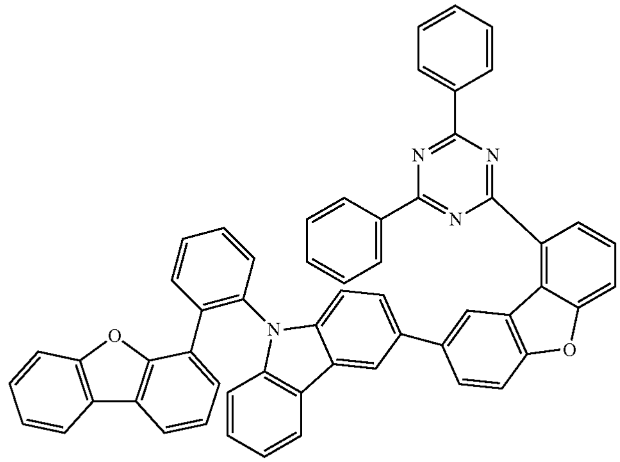 [SMILES: c1ccc(-c2nc(-c3ccccc3)nc(-c3cccc4oc5ccc(-c6ccc7c(c6)c6ccccc6n7-c6ccccc6-c6cccc7c6oc6ccccc67)cc5c34)n2)cc1]
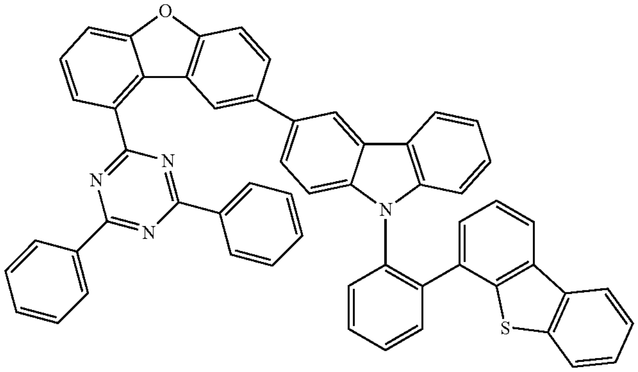 [SMILES: c1ccc(-c2nc(-c3ccccc3)nc(-c3cccc4oc5ccc(-c6ccc7c(c6)c6ccccc6n7-c6ccccc6-c6cccc7c6sc6ccccc67)cc5c34)n2)cc1]
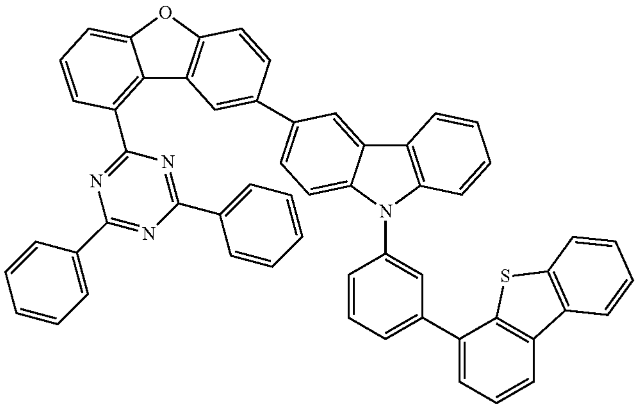 [SMILES: c1ccc(-c2nc(-c3ccccc3)nc(-c3cccc4oc5ccc(-c6ccc7c(c6)c6ccccc6n7-c6cccc(-c7cccc8c7sc7ccccc78)c6)cc5c34)n2)cc1]

TABLE 1-continued
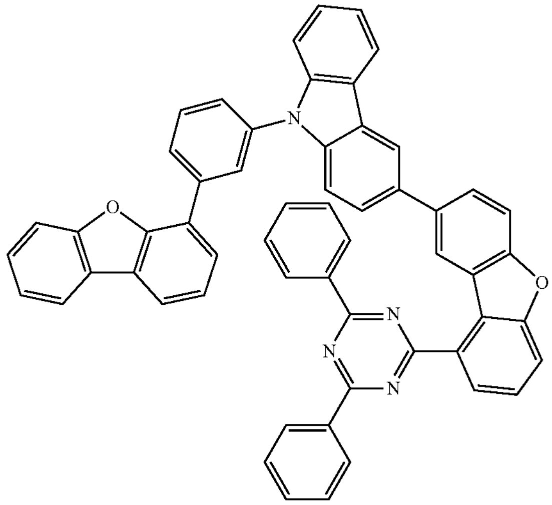 [SMILES: c1ccc(-c2nc(-c3ccccc3)nc(-c3cccc4oc5ccc(-c6ccc7c(c6)c6ccccc6n7-c6cccc(-c7cccc8c7oc7ccccc78)c6)cc5c34)n2)cc1]
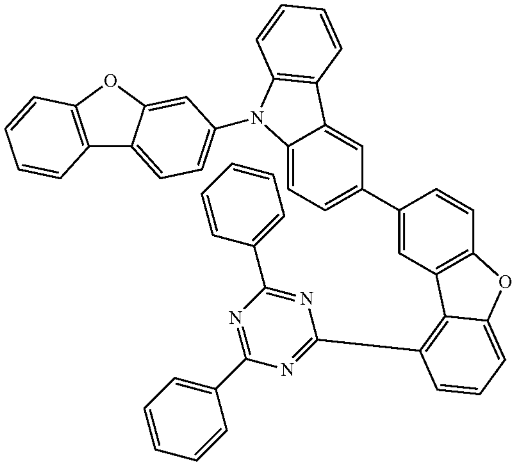 [SMILES: c1ccc(-c2nc(-c3ccccc3)nc(-c3cccc4oc5ccc(-c6ccc7c(c6)c6ccccc6n7-c6ccc7c(c6)oc6ccccc67)cc5c34)n2)cc1]
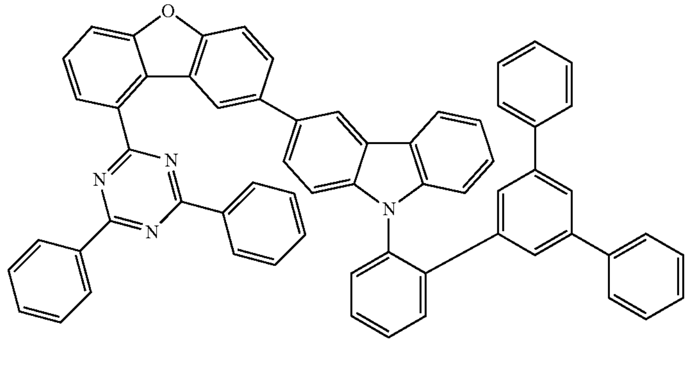 [SMILES: c1ccc(-c2cc(-c3ccccc3)cc(-c3ccccc3-n3c4ccccc4c4cc(-c5ccc6oc7cccc(-c8nc(-c9ccccc9)nc(-c9ccccc9)n8)c7c6c5)ccc43)c2)cc1]

TABLE 1-continued
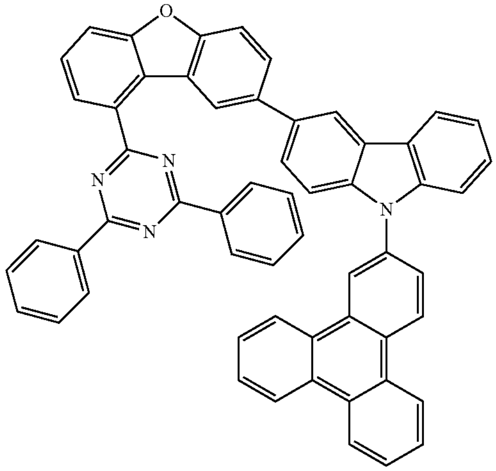
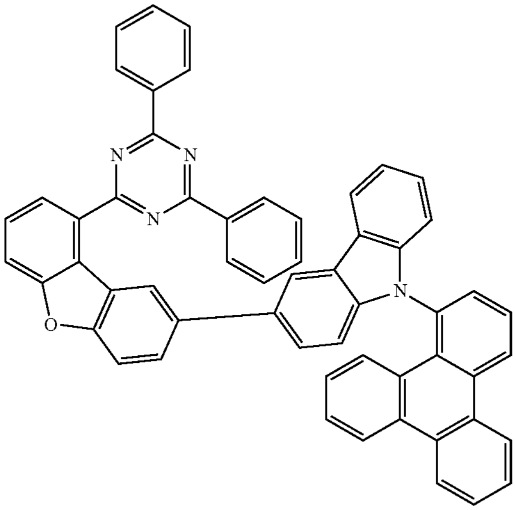 [SMILES: c1ccc(-c2nc(-c3ccccc3)nc(-c3cccc4oc5ccc(-c6ccc7c(c6)c6ccccc6n7-c6cccc7c8ccccc8c8ccccc8c67)cc5c34)n2)cc1]
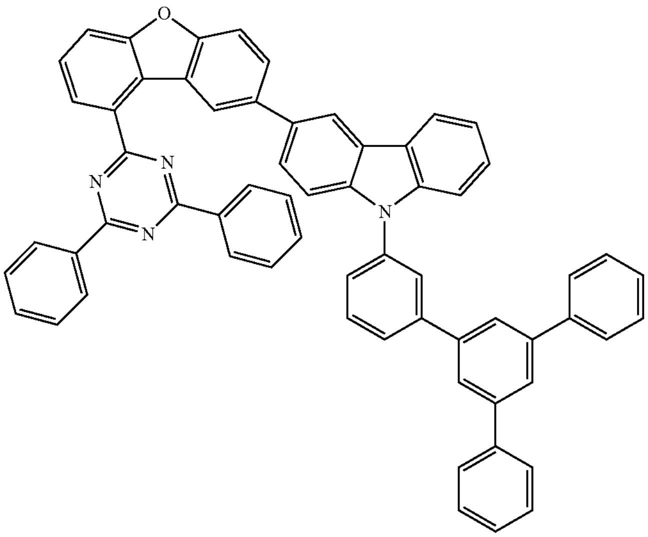

TABLE 1-continued
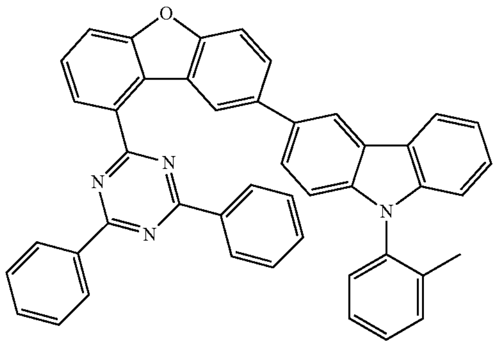 [SMILES: Cc1ccccc1-n1c2ccccc2c2cc(-c3ccc4oc5cccc(-c6nc(-c7ccccc7)nc(-c7ccccc7)n6)c5c4c3)ccc21]
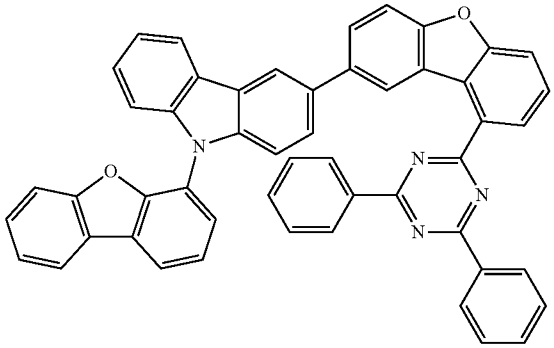 [SMILES: c1ccc(-c2nc(-c3ccccc3)nc(-c3cccc4oc5ccc(-c6ccc7c(c6)c6ccccc6n7-c6cccc7c6oc6ccccc67)cc5c34)n2)cc1]
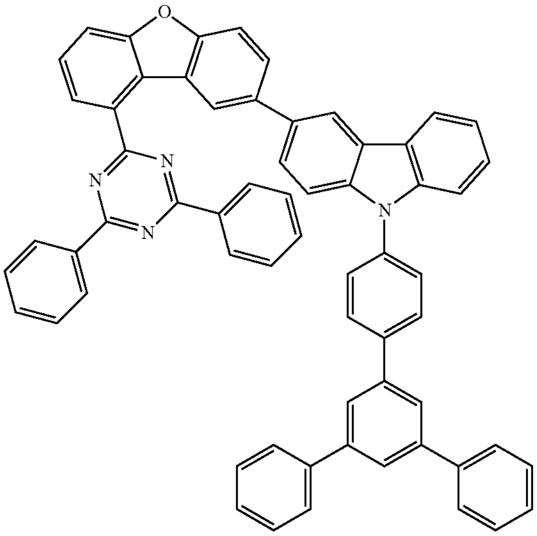 [SMILES: c1ccc(-c2cc(-c3ccccc3)cc(-c3ccc(-n4c5ccccc5c5cc(-c6ccc7oc8cccc(-c9nc(-c%10ccccc%10)nc(-c%10ccccc%10)n9)c8c7c6)ccc54)cc3)c2)cc1]
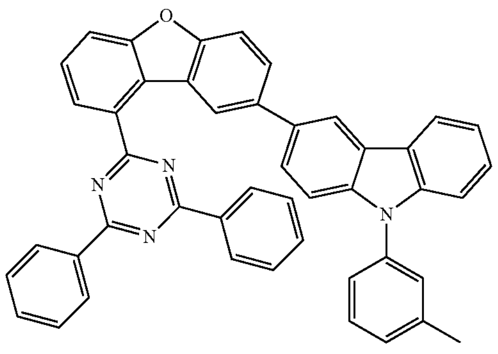

TABLE 1-continued
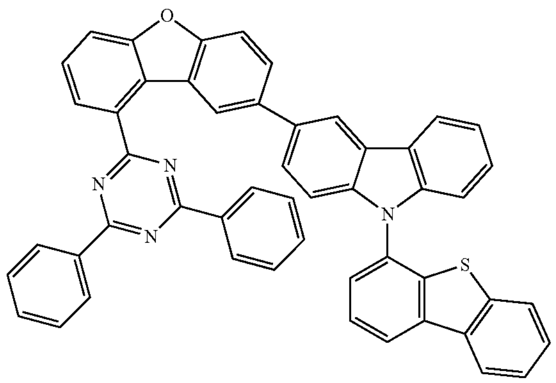 [SMILES: c1ccc(-c2nc(-c3ccccc3)nc(-c3cccc4oc5ccc(-c6ccc7c(c6)c6ccccc6n7-c6cccc7c6sc6ccccc67)cc5c34)n2)cc1]
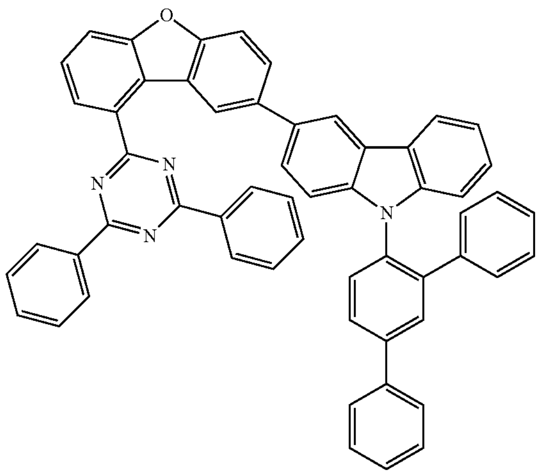 [SMILES: c1ccc(-c2ccc(-n3c4ccccc4c4cc(-c5ccc6oc7cccc(-c8nc(-c9ccccc9)nc(-c9ccccc9)n8)c7c6c5)ccc43)c(-c3ccccc3)c2)cc1]
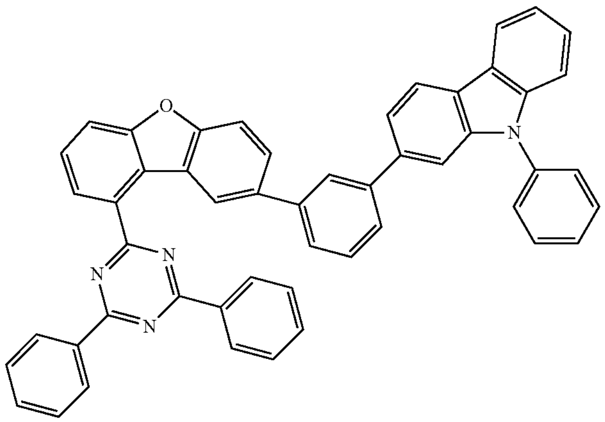 [SMILES: c1ccc(-c2nc(-c3ccccc3)nc(-c3cccc4oc5ccc(-c6cccc(-c7ccc8c9ccccc9n(-c9ccccc9)c8c7)c6)cc5c34)n2)cc1]

TABLE 1-continued
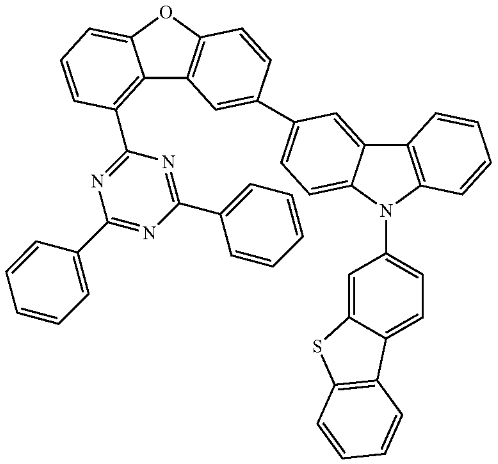 [SMILES: c1ccc(-c2nc(-c3ccccc3)nc(-c3cccc4oc5ccc(-c6ccc7c(c6)c6ccccc6n7-c6ccc7c(c6)sc6ccccc67)cc5c34)n2)cc1]
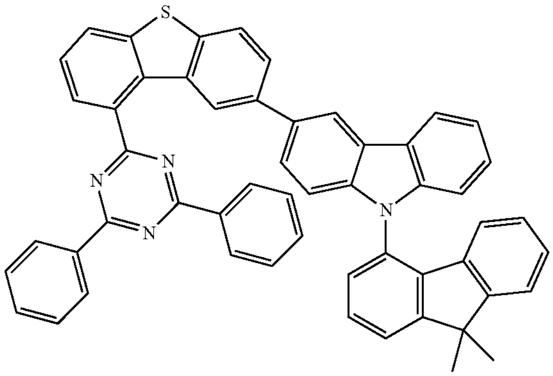 [SMILES: CC1(C)c2ccccc2-c2c(-n3c4ccccc4c4cc(-c5ccc6sc7cccc(-c8nc(-c9ccccc9)nc(-c9ccccc9)n8)c7c6c5)ccc43)cccc21]
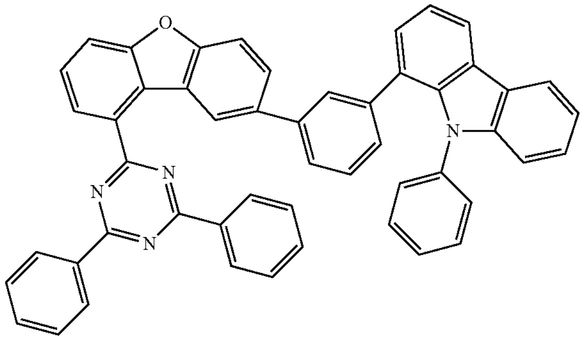 [SMILES: c1ccc(-c2nc(-c3ccccc3)nc(-c3cccc4oc5ccc(-c6cccc(-c7cccc8c9ccccc9n(-c9ccccc9)c78)c6)cc5c34)n2)cc1]
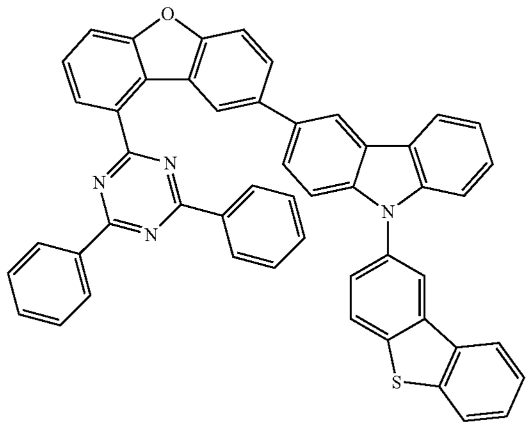 [SMILES: c1ccc(-c2nc(-c3ccccc3)nc(-c3cccc4oc5ccc(-c6ccc7c(c6)c6ccccc6n7-c6ccc7sc8ccccc8c7c6)cc5c34)n2)cc1]

TABLE 1-continued
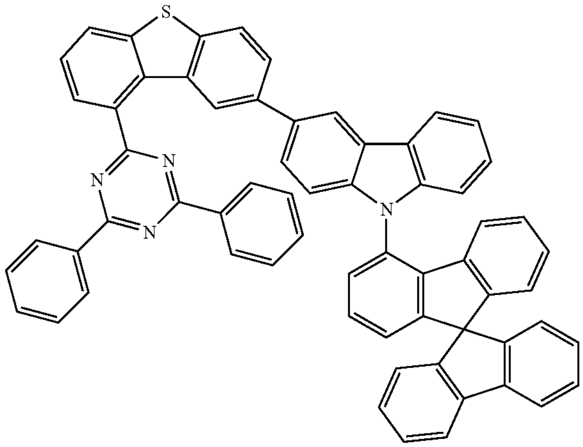 [SMILES: c1ccc(-c2nc(-c3ccccc3)nc(-c3cccc4sc5ccc(-c6ccc7c(c6)c6ccccc6n7-c6cccc7c6-c6ccccc6C76c7ccccc7-c7ccccc76)cc5c34)n2)cc1]
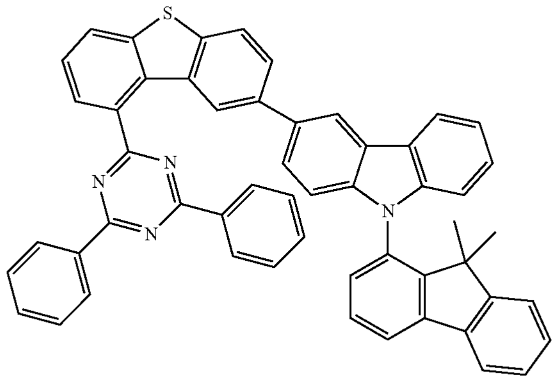
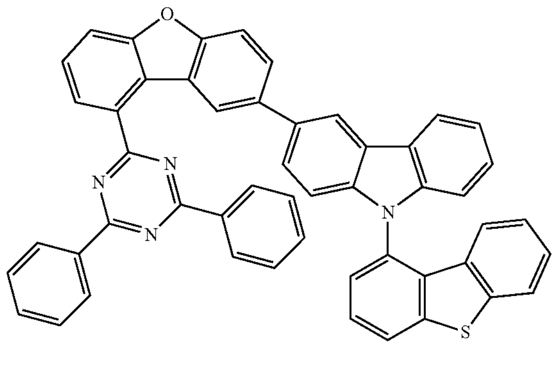 [SMILES: c1ccc(-c2nc(-c3ccccc3)nc(-c3cccc4oc5ccc(-c6ccc7c(c6)c6ccccc6n7-c6cccc7sc8ccccc8c67)cc5c34)n2)cc1]

TABLE 1-continued
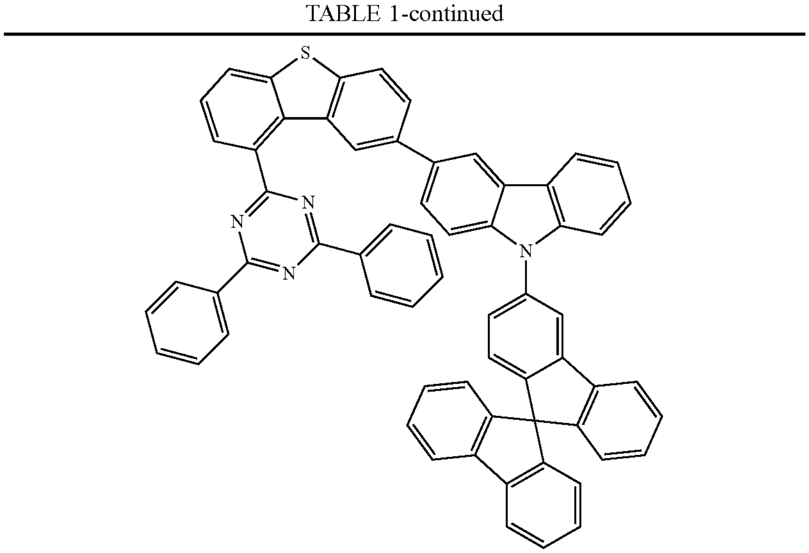
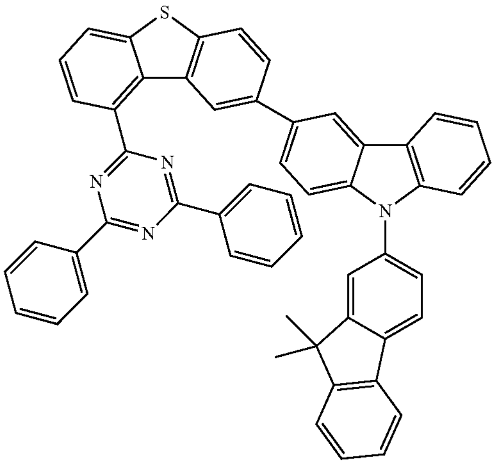 [SMILES: CC1(C)c2ccccc2-c2ccc(-n3c4ccccc4c4cc(-c5ccc6sc7cccc(-c8nc(-c9ccccc9)nc(-c9ccccc9)n8)c7c6c5)ccc43)cc21]
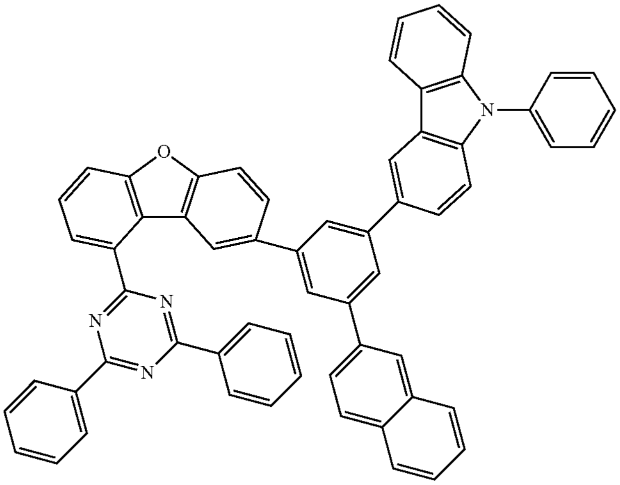 [SMILES: c1ccc(-c2nc(-c3ccccc3)nc(-c3cccc4oc5ccc(-c6cc(-c7ccc8ccccc8c7)cc(-c7ccc8c(c7)c7ccccc7n8-c7ccccc7)c6)cc5c34)n2)cc1]

TABLE 1-continued
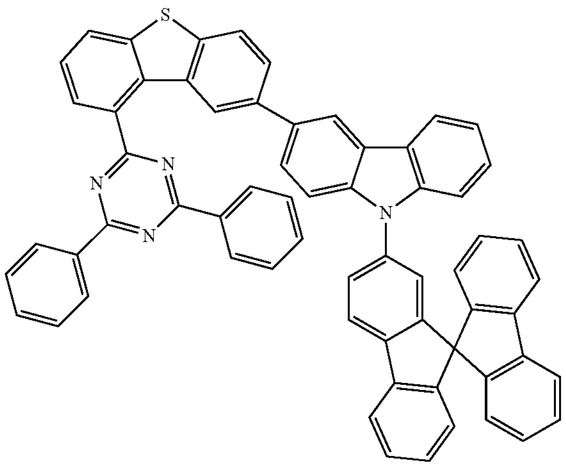 [SMILES: c1ccc(-c2nc(-c3ccccc3)nc(-c3cccc4sc5ccc(-c6ccc7c(c6)c6ccccc6n7-c6ccc7c(c6)C6(c8ccccc8-c8ccccc86)c6ccccc6-7)cc5c34)n2)cc1]
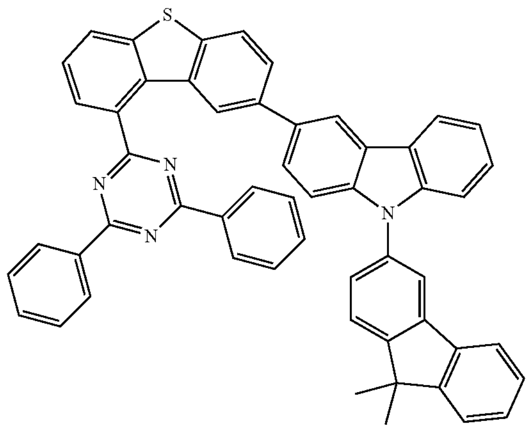 [SMILES: CC1(C)c2ccccc2-c2cc(-n3c4ccccc4c4cc(-c5ccc6sc7cccc(-c8nc(-c9ccccc9)nc(-c9ccccc9)n8)c7c6c5)ccc43)ccc21]
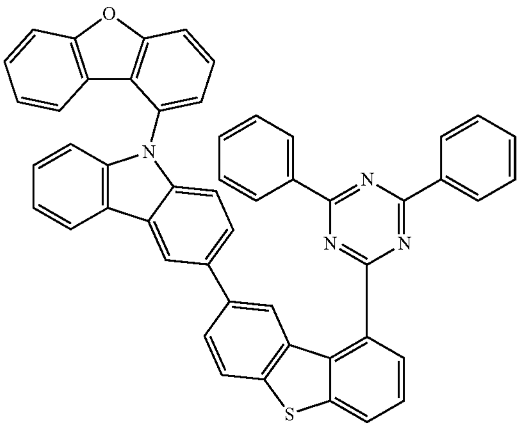 [SMILES: c1ccc(-c2nc(-c3ccccc3)nc(-c3cccc4sc5ccc(-c6ccc7c(c6)c6ccccc6n7-c6cccc7oc8ccccc8c67)cc5c34)n2)cc1]

TABLE 1-continued
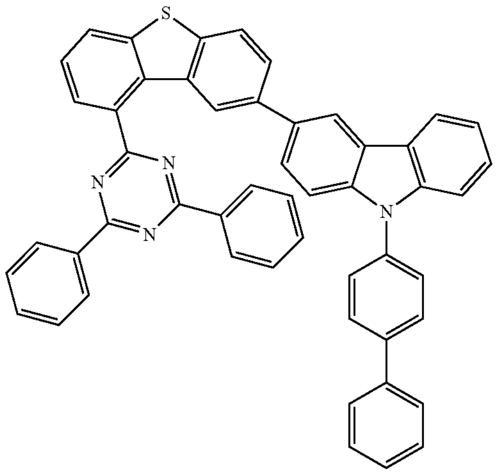 [SMILES: c1ccc(-c2ccc(-n3c4ccccc4c4cc(-c5ccc6sc7cccc(-c8nc(-c9ccccc9)nc(-c9ccccc9)n8)c7c6c5)ccc43)cc2)cc1]
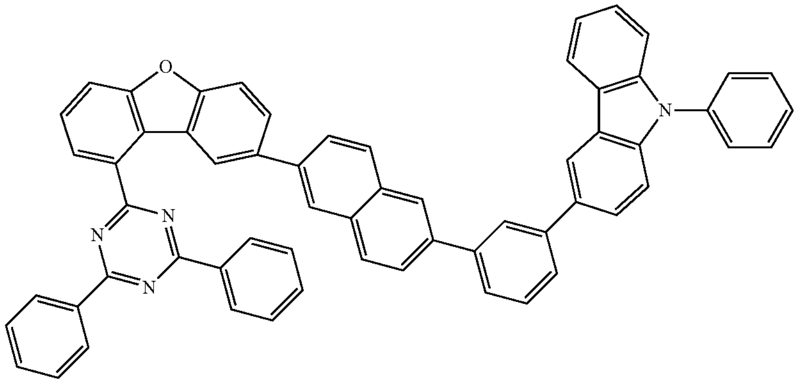 [SMILES: c1ccc(-c2nc(-c3ccccc3)nc(-c3cccc4oc5ccc(-c6ccc7cc(-c8cccc(-c9ccc%10c(c9)c9ccccc9n%10-c9ccccc9)c8)ccc7c6)cc5c34)n2)cc1]
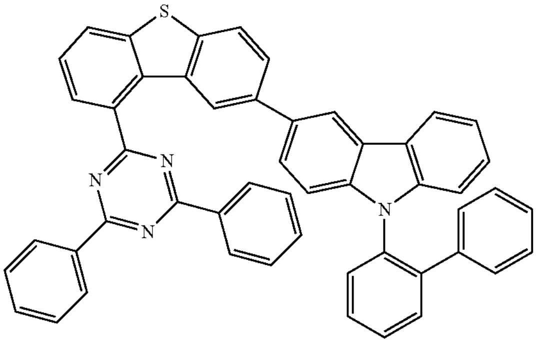
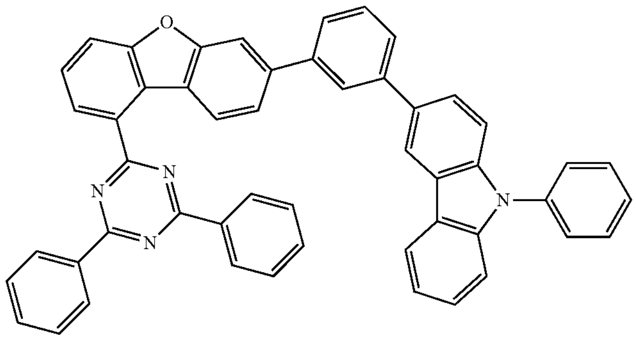 [SMILES: c1ccc(-c2nc(-c3ccccc3)nc(-c3cccc4oc5cc(-c6cccc(-c7ccc8c(c7)c7ccccc7n8-c7ccccc7)c6)ccc5c34)n2)cc1]

TABLE 1-continued
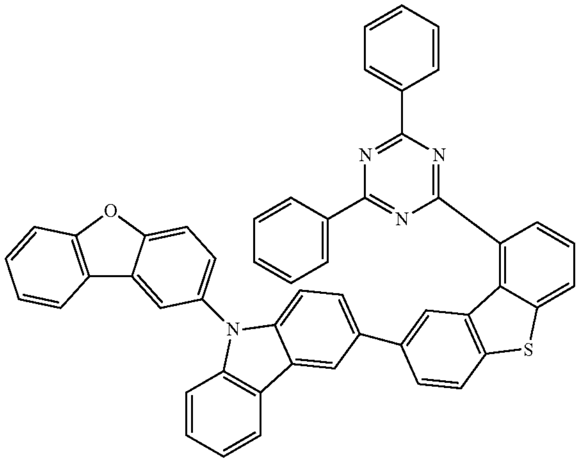 [SMILES: c1ccc(-c2nc(-c3ccccc3)nc(-c3cccc4sc5ccc(-c6ccc7c(c6)c6ccccc6n7-c6ccc7oc8ccccc8c7c6)cc5c34)n2)cc1]
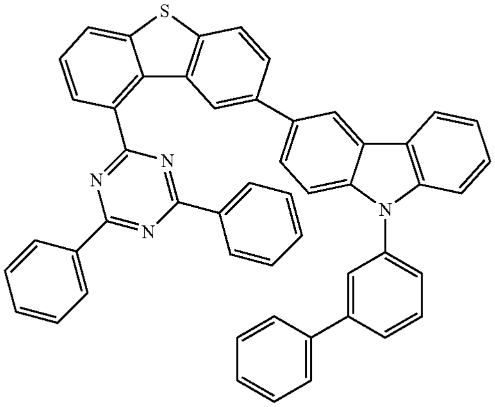 [SMILES: c1ccc(-c2cccc(-n3c4ccccc4c4cc(-c5ccc6sc7cccc(-c8nc(-c9ccccc9)nc(-c9ccccc9)n8)c7c6c5)ccc43)c2)cc1]
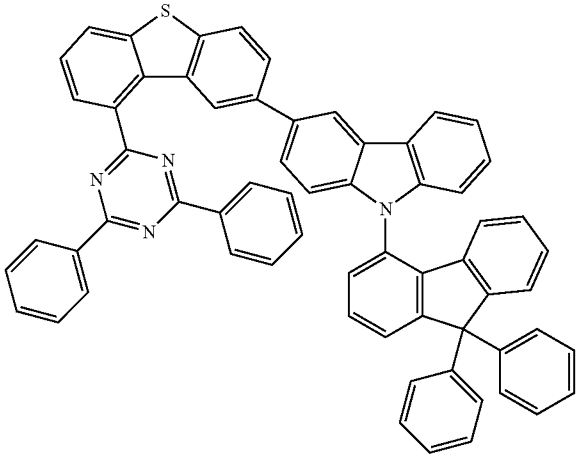 [SMILES: c1ccc(-c2nc(-c3ccccc3)nc(-c3cccc4sc5ccc(-c6ccc7c(c6)c6ccccc6n7-c6cccc7c6-c6ccccc6C7(c6ccccc6)c6ccccc6)cc5c34)n2)cc1]

TABLE 1-continued
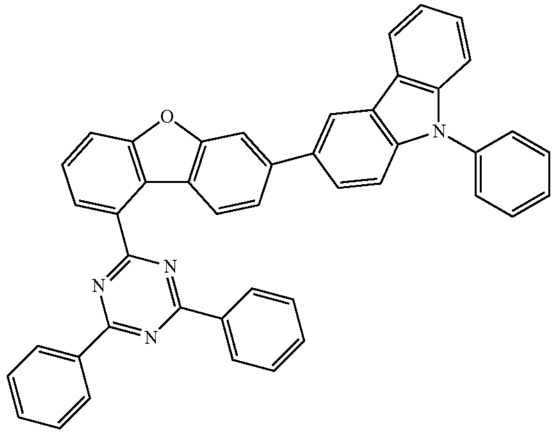 [SMILES: c1ccc(-c2nc(-c3ccccc3)nc(-c3cccc4oc5cc(-c6ccc7c(c6)c6ccccc6n7-c6ccccc6)ccc5c34)n2)cc1]
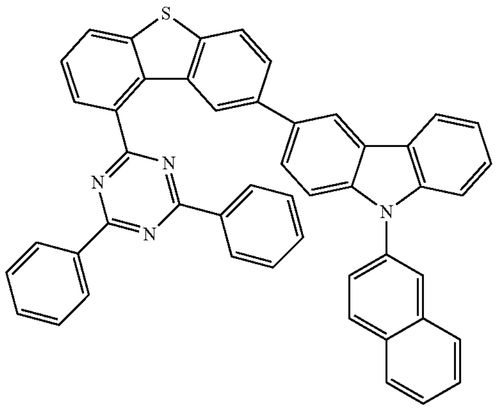 [SMILES: c1ccc(-c2nc(-c3ccccc3)nc(-c3cccc4sc5ccc(-c6ccc7c(c6)c6ccccc6n7-c6ccc7ccccc7c6)cc5c34)n2)cc1]
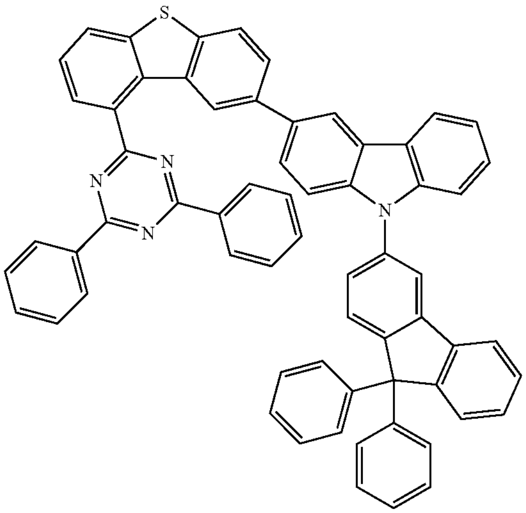 [SMILES: c1ccc(-c2nc(-c3ccccc3)nc(-c3cccc4sc5ccc(-c6ccc7c(c6)c6ccccc6n7-c6ccc7c(c6)-c6ccccc6C7(c6ccccc6)c6ccccc6)cc5c34)n2)cc1]

TABLE 1-continued
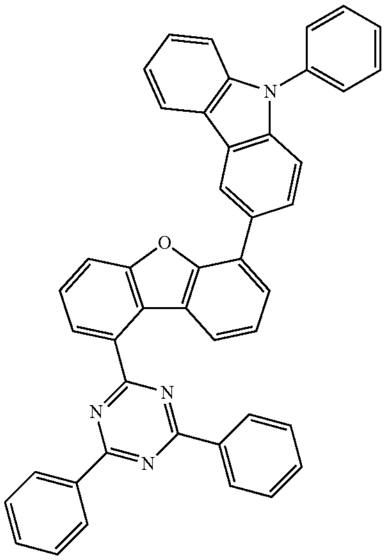 [SMILES: c1ccc(-c2nc(-c3ccccc3)nc(-c3cccc4oc5c(-c6ccc7c(c6)c6ccccc6n7-c6ccccc6)cccc5c34)n2)cc1]
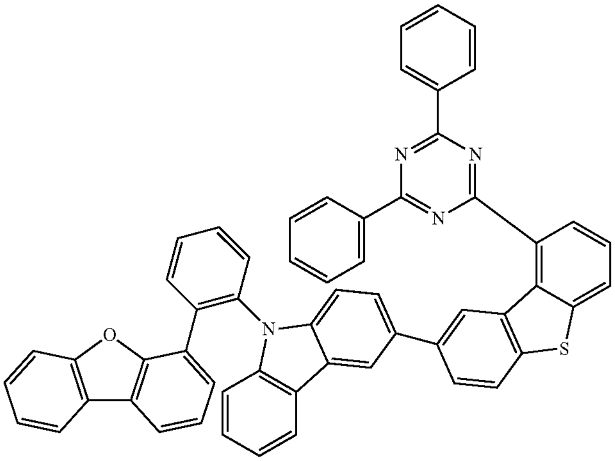 [SMILES: c1ccc(-c2nc(-c3ccccc3)nc(-c3cccc4sc5ccc(-c6ccc7c(c6)c6ccccc6n7-c6ccccc6-c6cccc7c6oc6ccccc67)cc5c34)n2)cc1]
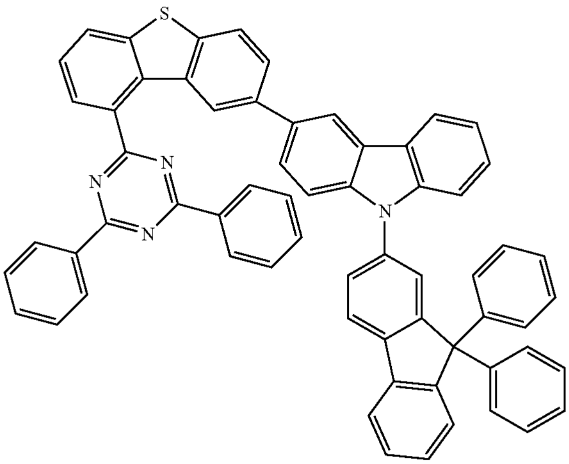

TABLE 1-continued
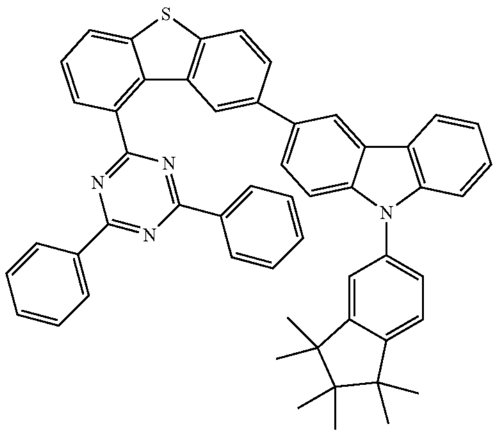 [SMILES: CC1(C)c2ccc(-n3c4ccccc4c4cc(-c5ccc6sc7cccc(-c8nc(-c9ccccc9)nc(-c9ccccc9)n8)c7c6c5)ccc43)cc2C(C)(C)C1(C)C]
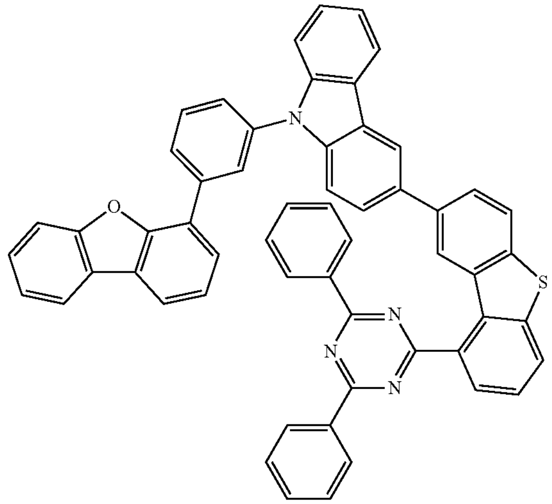 [SMILES: c1ccc(-c2nc(-c3ccccc3)nc(-c3cccc4sc5ccc(-c6ccc7c(c6)c6ccccc6n7-c6cccc(-c7cccc8c7oc7ccccc78)c6)cc5c34)n2)cc1]
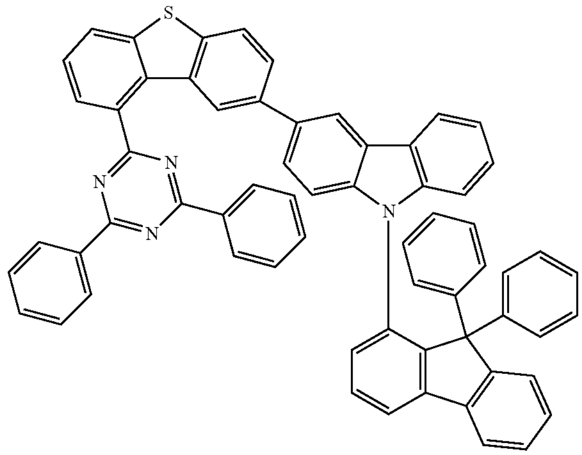 [SMILES: c1ccc(-c2nc(-c3ccccc3)nc(-c3cccc4sc5ccc(-c6ccc7c(c6)c6ccccc6n7-c6cccc7c6C(c6ccccc6)(c6ccccc6)c6ccccc6-7)cc5c34)n2)cc1]

TABLE 1-continued
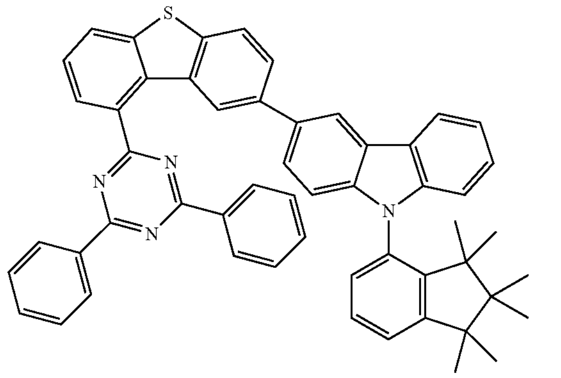 [SMILES: CC1(C)c2cccc(-n3c4ccccc4c4cc(-c5ccc6sc7cccc(-c8nc(-c9ccccc9)nc(-c9ccccc9)n8)c7c6c5)ccc43)c2C(C)(C)C1(C)C]
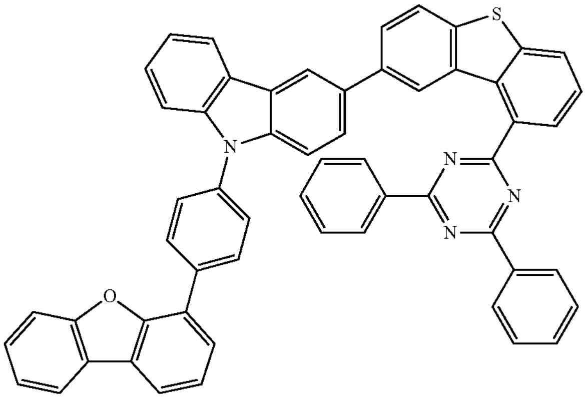 [SMILES: c1ccc(-c2nc(-c3ccccc3)nc(-c3cccc4sc5ccc(-c6ccc7c(c6)c6ccccc6n7-c6ccc(-c7cccc8c7oc7ccccc78)cc6)cc5c34)n2)cc1]
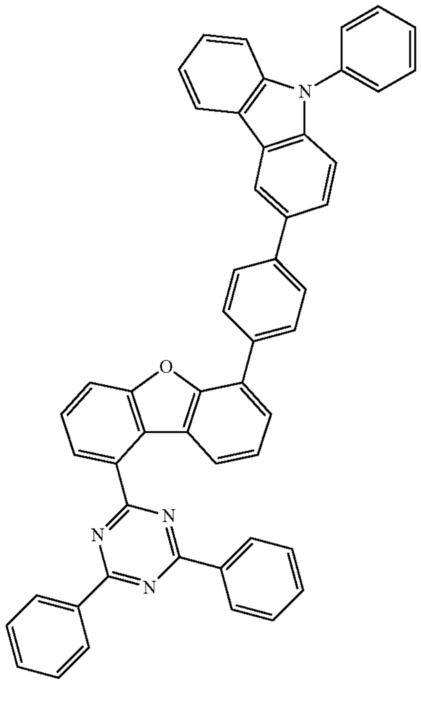 [SMILES: c1ccc(-c2nc(-c3ccccc3)nc(-c3cccc4oc5c(-c6ccc(-c7ccc8c(c7)c7ccccc7n8-c7ccccc7)cc6)cccc5c34)n2)cc1]

TABLE 1-continued
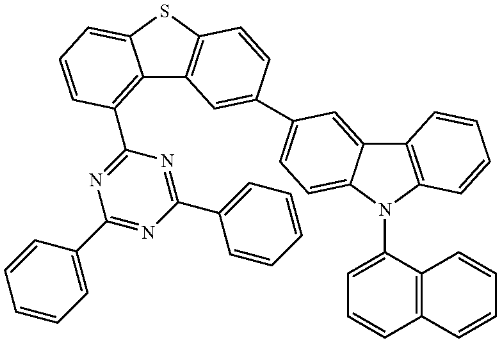 [SMILES: c1ccc(-c2nc(-c3ccccc3)nc(-c3cccc4sc5ccc(-c6ccc7c(c6)c6ccccc6n7-c6cccc7ccccc67)cc5c34)n2)cc1]
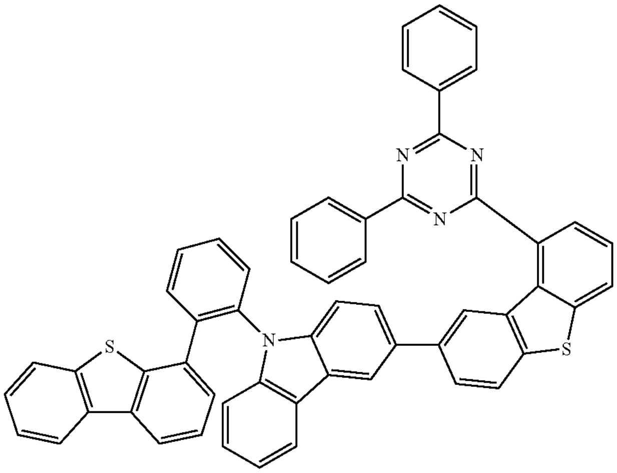 [SMILES: c1ccc(-c2nc(-c3ccccc3)nc(-c3cccc4sc5ccc(-c6ccc7c(c6)c6ccccc6n7-c6ccccc6-c6cccc7c6sc6ccccc67)cc5c34)n2)cc1]
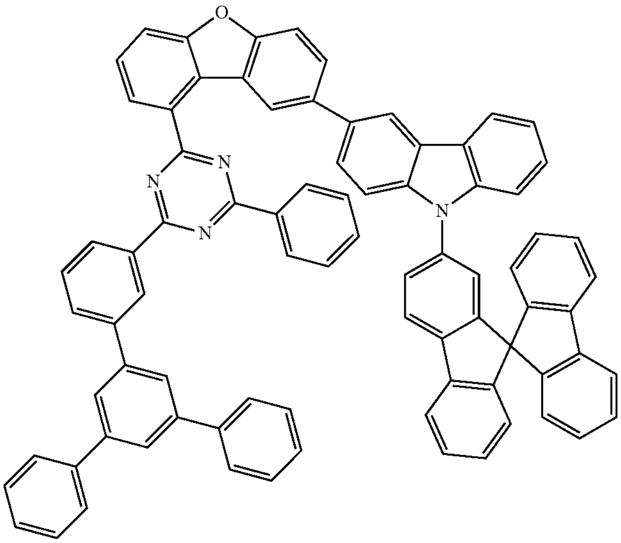 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8ccc9c(c8)C8(c%10ccccc%10-c%10ccccc%108)c8ccccc8-9)cc7c56)n4)c3)c2)cc1]

TABLE 1-continued
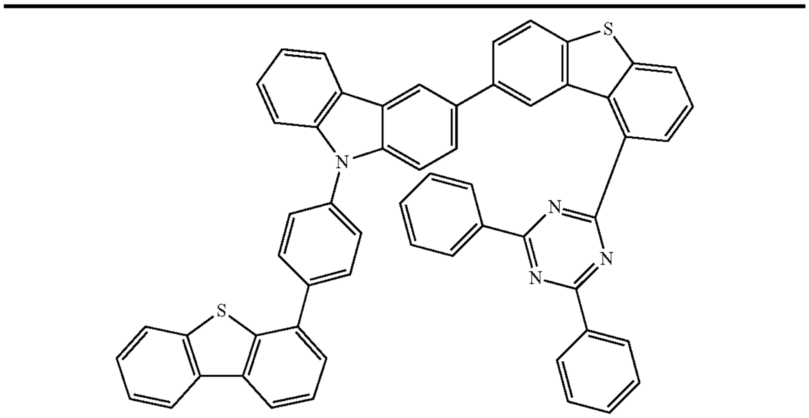
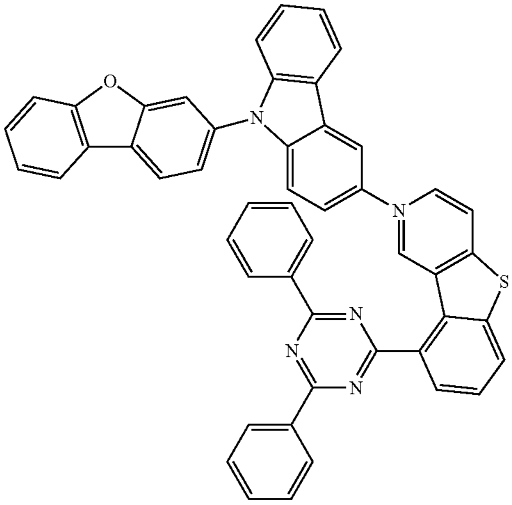
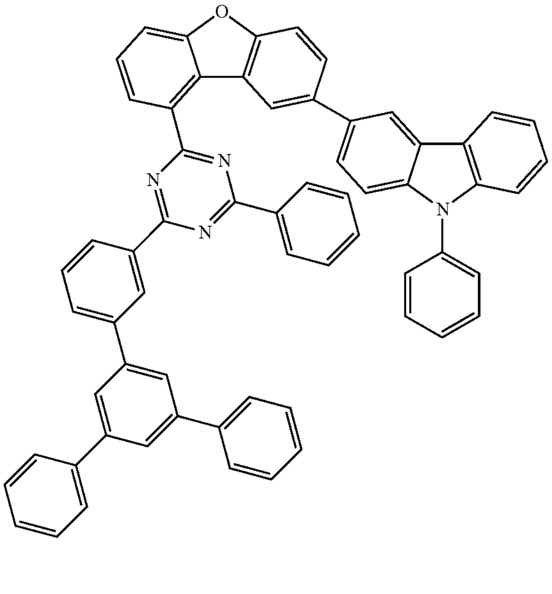 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8ccccc8)cc7c56)n4)c3)c2)cc1]

TABLE 1-continued
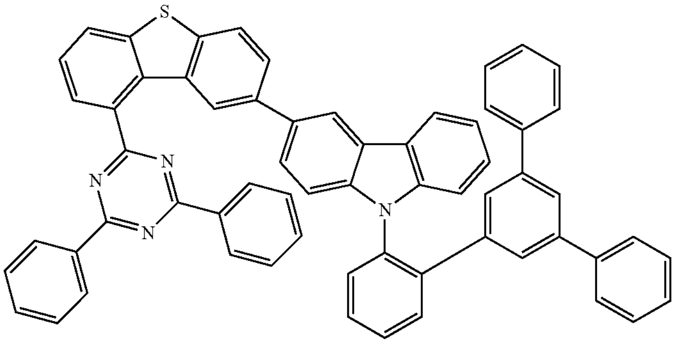 [SMILES: c1ccc(-c2cc(-c3ccccc3)cc(-c3ccccc3-n3c4ccccc4c4cc(-c5ccc6sc7cccc(-c8nc(-c9ccccc9)nc(-c9ccccc9)n8)c7c6c5)ccc43)c2)cc1]
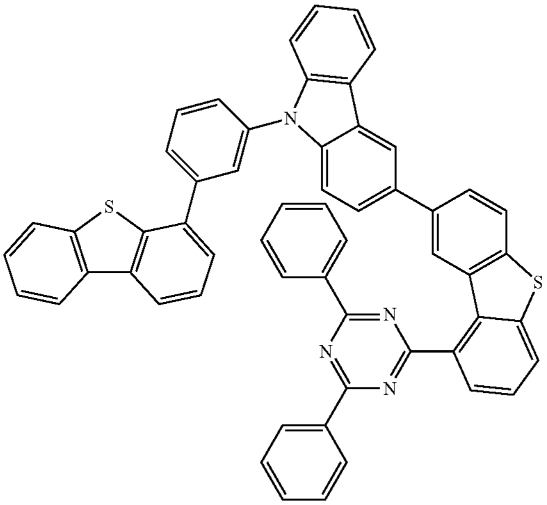
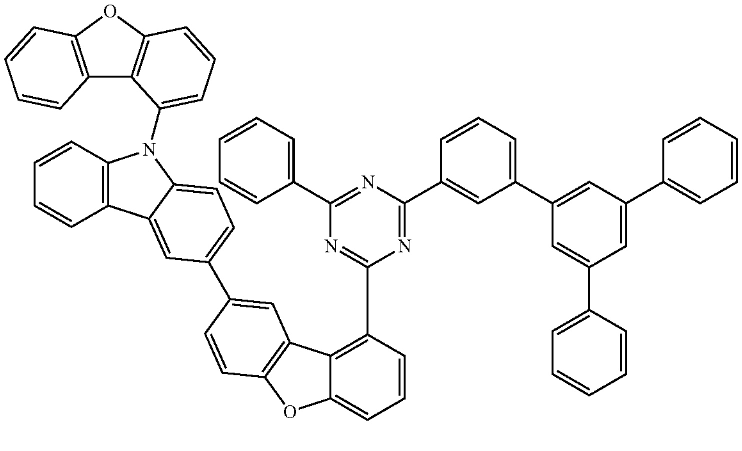 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8cccc9oc%10ccccc%10c89)cc7c56)n4)c3)c2)cc1]

TABLE 1-continued
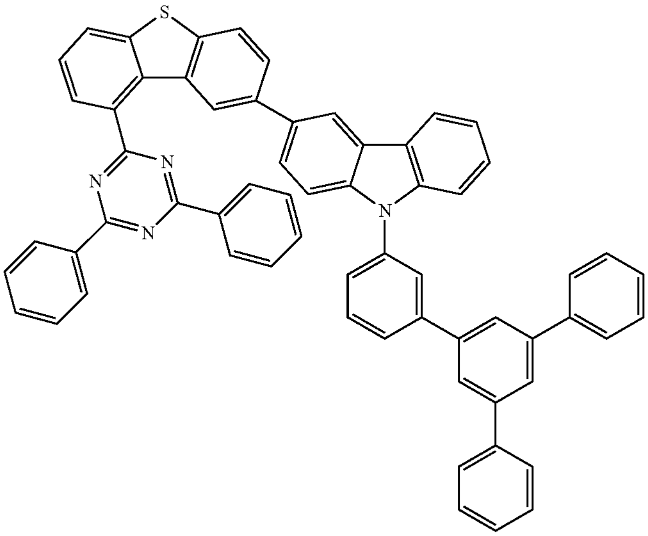 [SMILES: c1ccc(-c2cc(-c3ccccc3)cc(-c3cccc(-n4c5ccccc5c5cc(-c6ccc7sc8cccc(-c9nc(-c%10ccccc%10)nc(-c%10ccccc%10)n9)c8c7c6)ccc54)c3)c2)cc1]
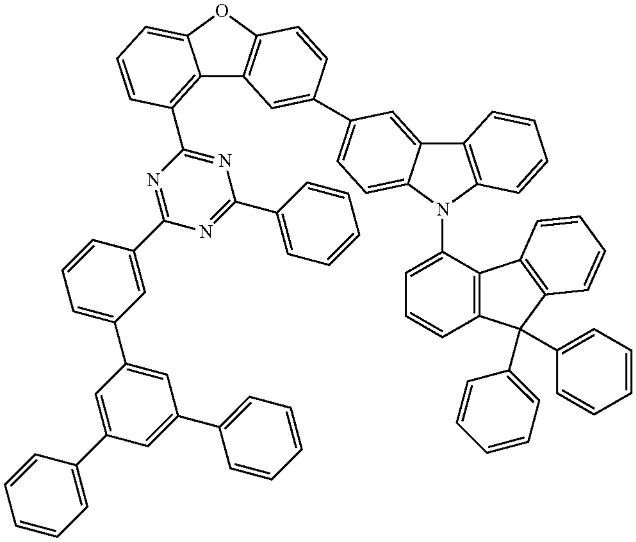 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8cccc9c8-c8ccccc8C9(c8ccccc8)c8ccccc8)cc7c56)n4)c3)c2)cc1]
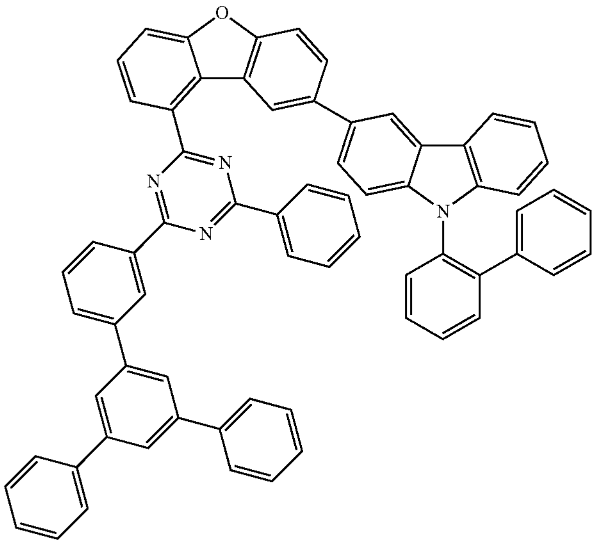 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8ccccc8-c8ccccc8)cc7c56)n4)c3)c2)cc1]

TABLE 1-continued
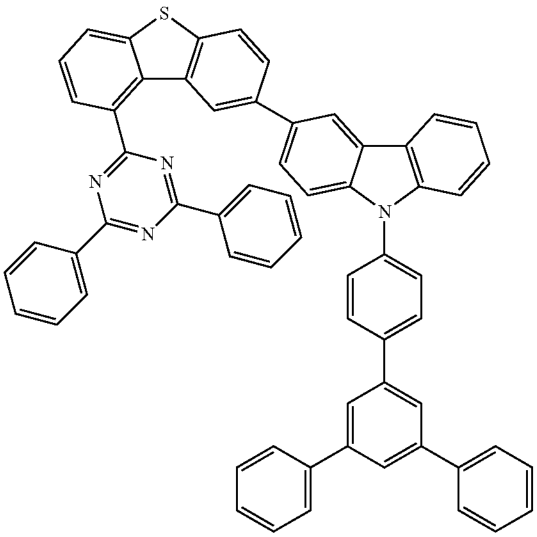
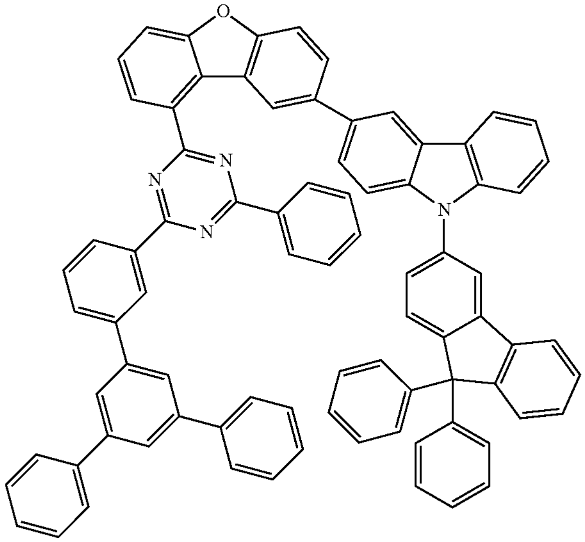 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8ccc9c(c8)-c8ccccc8C9(c8ccccc8)c8ccccc8)cc7c56)n4)c3)c2)cc1]
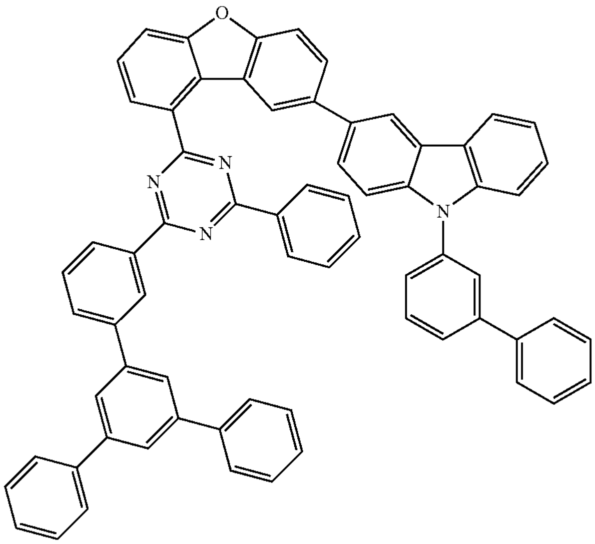 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8cccc(-c9ccccc9)c8)cc7c56)n4)c3)c2)cc1]

TABLE 1-continued
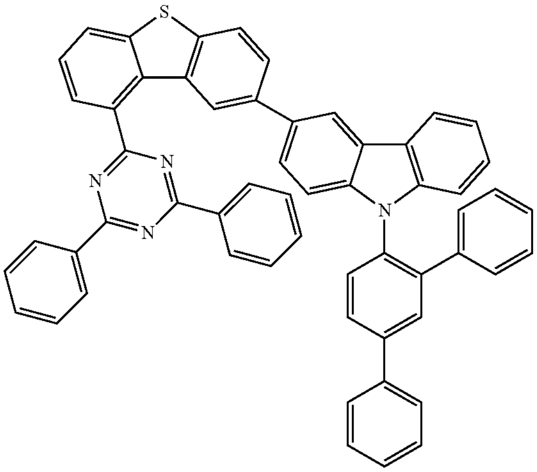
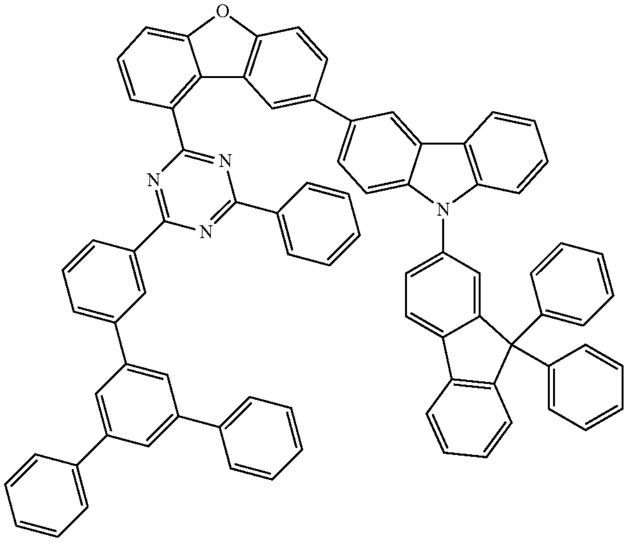 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8ccc9c(c8)C(c8ccccc8)(c8ccccc8)c8ccccc8-9)cc7c56)n4)c3)c2)cc1]
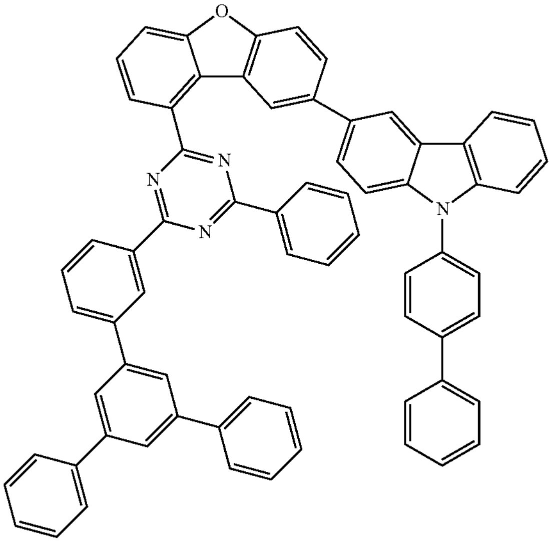 [SMILES: c1ccc(-c2ccc(-n3c4ccccc4c4cc(-c5ccc6oc7cccc(-c8nc(-c9ccccc9)nc(-c9cccc(-c%10cc(-c%11ccccc%11)cc(-c%11ccccc%11)c%10)c9)n8)c7c6c5)ccc43)cc2)cc1]

TABLE 1-continued
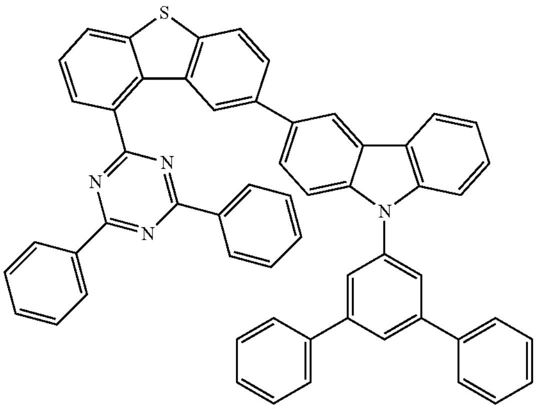 [SMILES: c1ccc(-c2cc(-c3ccccc3)cc(-n3c4ccccc4c4cc(-c5ccc6sc7cccc(-c8nc(-c9ccccc9)nc(-c9ccccc9)n8)c7c6c5)ccc43)c2)cc1]
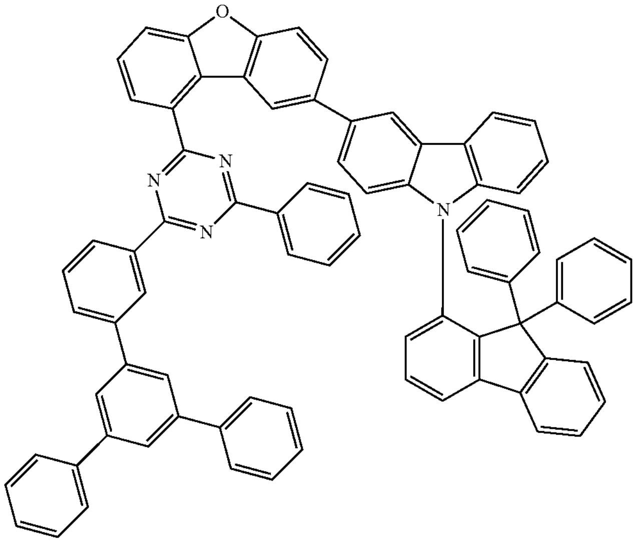 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8cccc9c8C(c8ccccc8)(c8ccccc8)c8ccccc8-9)cc7c56)n4)c3)c2)cc1]
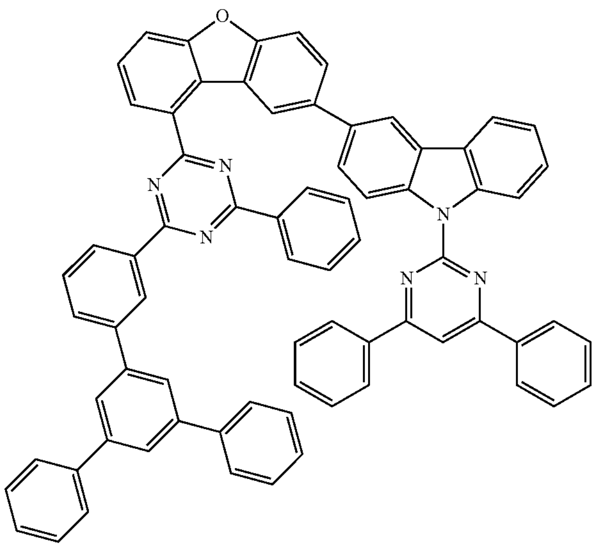 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8nc(-c9ccccc9)cc(-c9ccccc9)n8)cc7c56)n4)c3)c2)cc1]

TABLE 1-continued
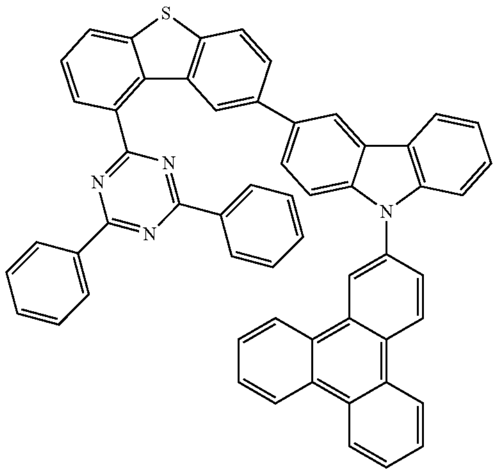 [SMILES: c1ccc(-c2nc(-c3ccccc3)nc(-c3cccc4sc5ccc(-c6ccc7c(c6)c6ccccc6n7-c6ccc7c8ccccc8c8ccccc8c7c6)cc5c34)n2)cc1]
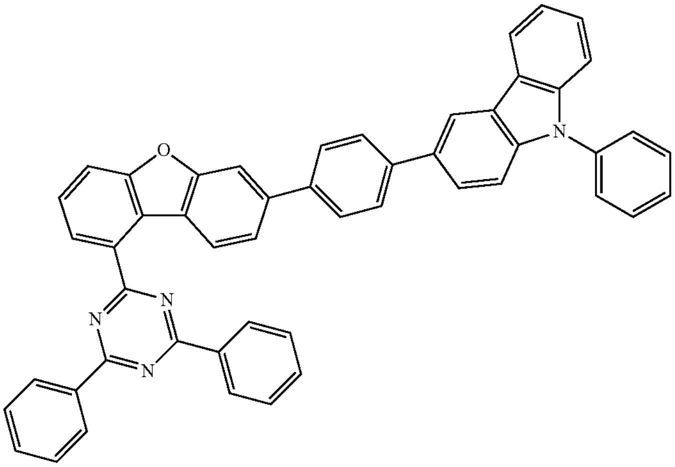 [SMILES: c1ccc(-c2nc(-c3ccccc3)nc(-c3cccc4oc5cc(-c6ccc(-c7ccc8c(c7)c7ccccc7n8-c7ccccc7)cc6)ccc5c34)n2)cc1]
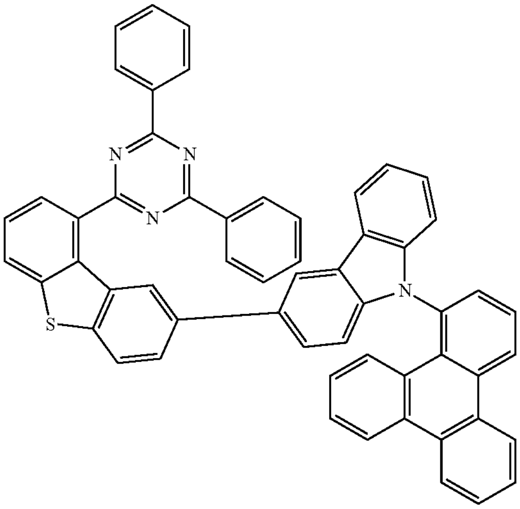 [SMILES: c1ccc(-c2nc(-c3ccccc3)nc(-c3cccc4sc5ccc(-c6ccc7c(c6)c6ccccc6n7-c6cccc7c8ccccc8c8ccccc8c67)cc5c34)n2)cc1]

TABLE 1-continued
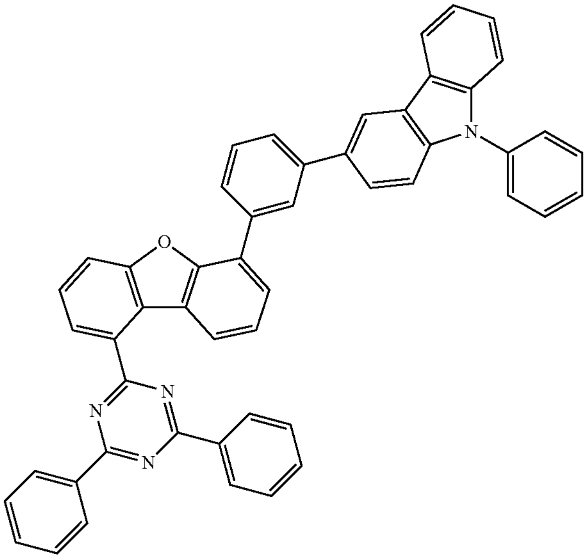 [SMILES: c1ccc(-c2nc(-c3ccccc3)nc(-c3cccc4oc5c(-c6cccc(-c7ccc8c(c7)c7ccccc7n8-c7ccccc7)c6)cccc5c34)n2)cc1]
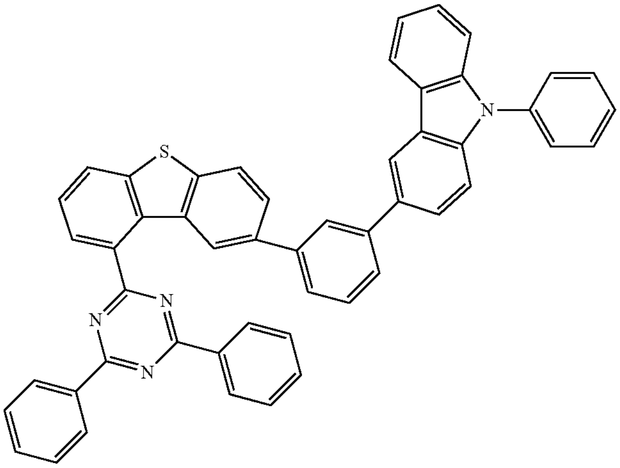 [SMILES: c1ccc(-c2nc(-c3ccccc3)nc(-c3cccc4sc5ccc(-c6cccc(-c7ccc8c(c7)c7ccccc7n8-c7ccccc7)c6)cc5c34)n2)cc1]
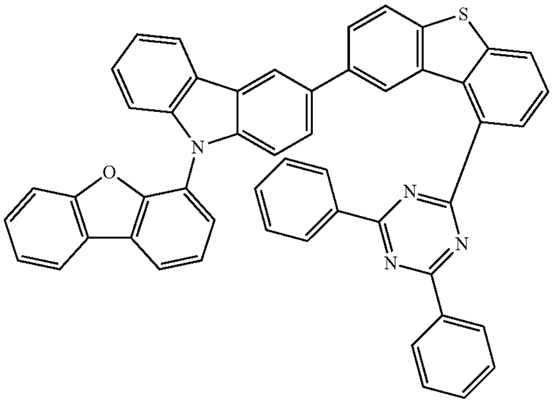

TABLE 1-continued
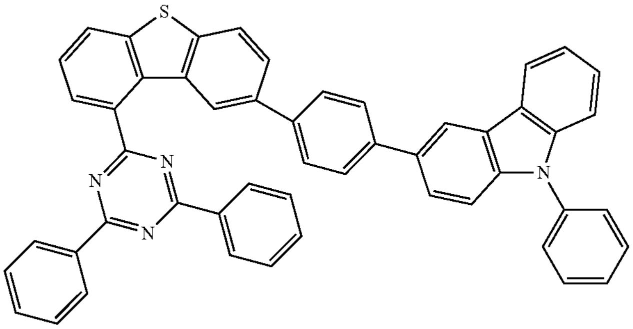 [SMILES: c1ccc(-c2nc(-c3ccccc3)nc(-c3cccc4sc5ccc(-c6ccc(-c7ccc8c(c7)c7ccccc7n8-c7ccccc7)cc6)cc5c34)n2)cc1]
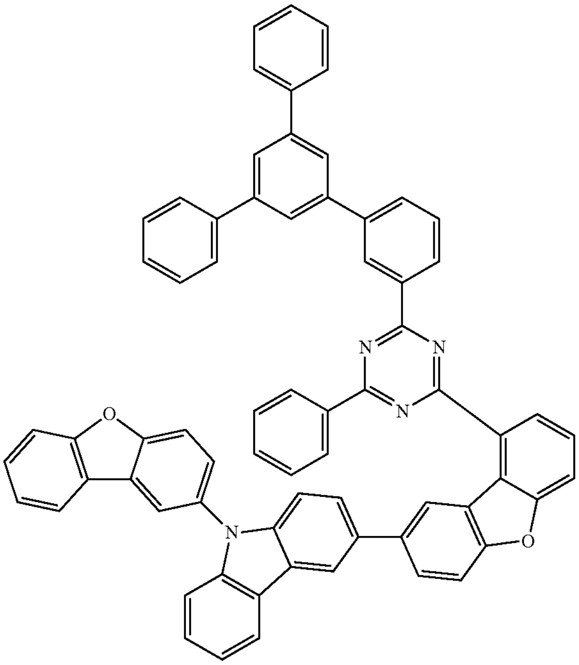 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8ccc9oc%10ccccc%10c9c8)cc7c56)n4)c3)c2)cc1]
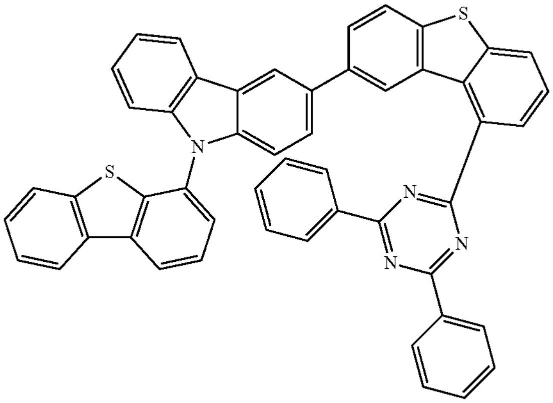 [SMILES: c1ccc(-c2nc(-c3ccccc3)nc(-c3cccc4sc5ccc(-c6ccc7c(c6)c6ccccc6n7-c6cccc7c6sc6ccccc67)cc5c34)n2)cc1]

TABLE 1-continued
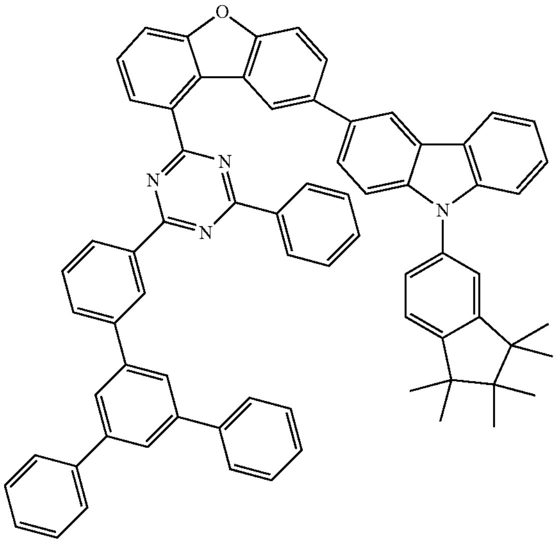 [SMILES: CC1(C)c2ccc(-n3c4ccccc4c4cc(-c5ccc6oc7cccc(-c8nc(-c9ccccc9)nc(-c9cccc(-c%10cc(-c%11ccccc%11)cc(-c%11ccccc%11)c%10)c9)n8)c7c6c5)ccc43)cc2C(C)(C)C1(C)C]
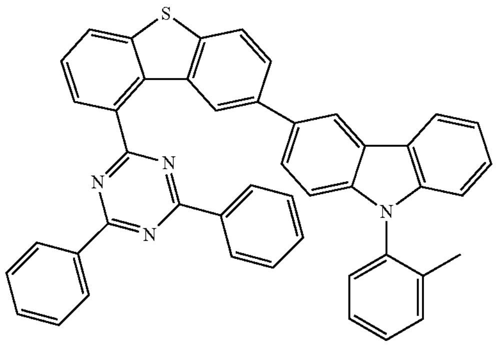
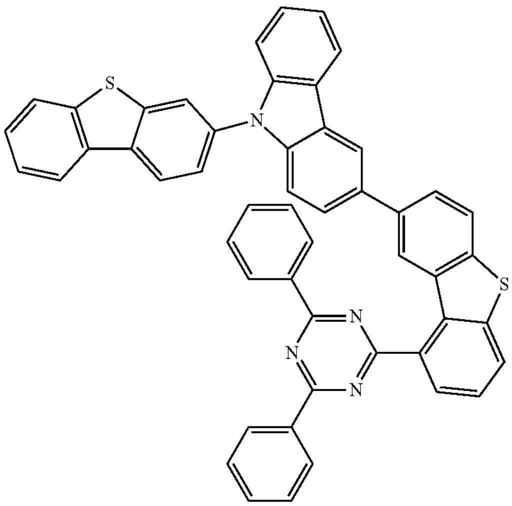 [SMILES: c1ccc(-c2nc(-c3ccccc3)nc(-c3cccc4sc5ccc(-c6ccc7c(c6)c6ccccc6n7-c6ccc7c(c6)sc6ccccc67)cc5c34)n2)cc1]

TABLE 1-continued
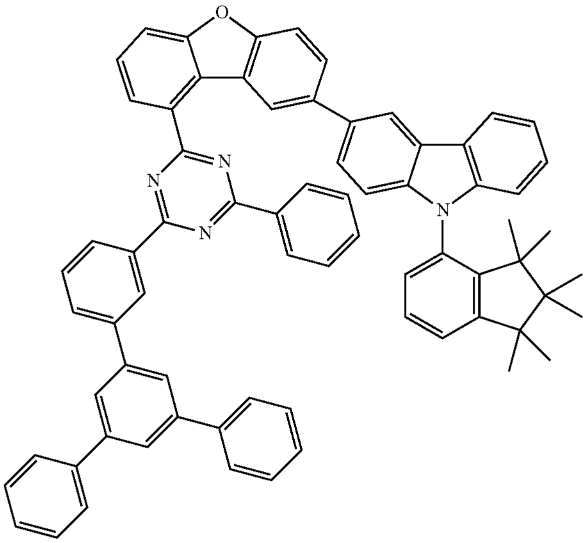 [SMILES: CC1(C)c2cccc(-n3c4ccccc4c4cc(-c5ccc6oc7cccc(-c8nc(-c9ccccc9)nc(-c9cccc(-c%10cc(-c%11ccccc%11)cc(-c%11ccccc%11)c%10)c9)n8)c7c6c5)ccc43)c2C(C)(C)C1(C)C]
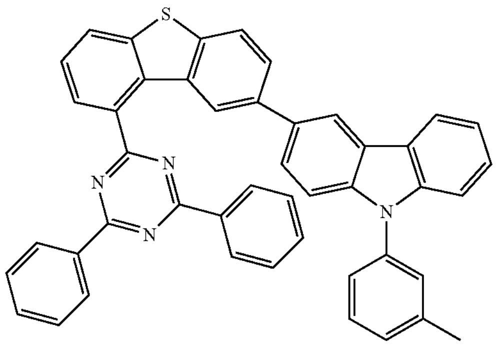 [SMILES: Cc1cccc(-n2c3ccccc3c3cc(-c4ccc5sc6cccc(-c7nc(-c8ccccc8)nc(-c8ccccc8)n7)c6c5c4)ccc32)c1]
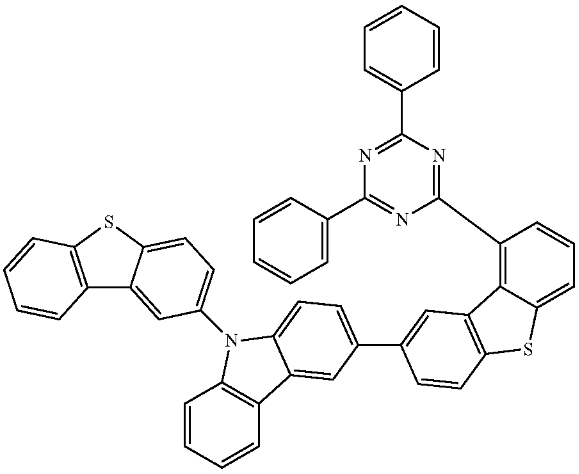 [SMILES: c1ccc(-c2nc(-c3ccccc3)nc(-c3cccc4sc5ccc(-c6ccc7c(c6)c6ccccc6n7-c6ccc7sc8ccccc8c7c6)cc5c34)n2)cc1]

TABLE 1-continued
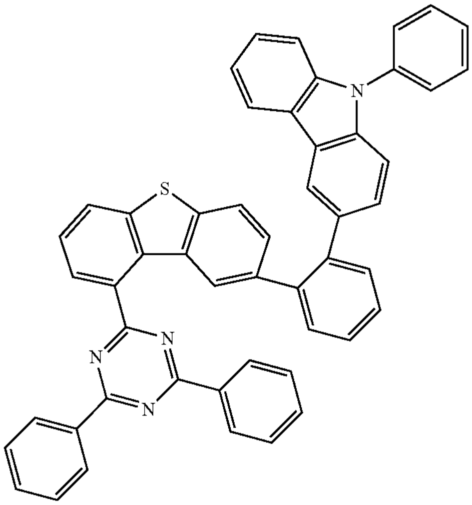 [SMILES: c1ccc(-c2nc(-c3ccccc3)nc(-c3cccc4sc5ccc(-c6ccccc6-c6ccc7c(c6)c6ccccc6n7-c6ccccc6)cc5c34)n2)cc1]
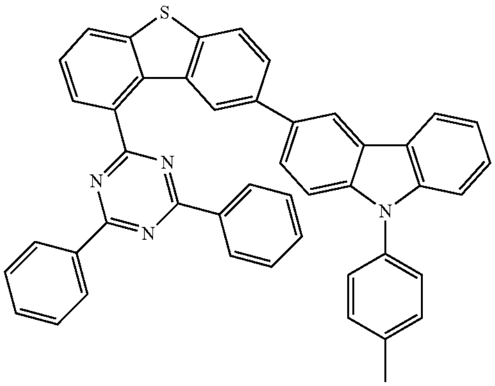 [SMILES: Cc1ccc(-n2c3ccccc3c3cc(-c4ccc5sc6cccc(-c7nc(-c8ccccc8)nc(-c8ccccc8)n7)c6c5c4)ccc32)cc1]
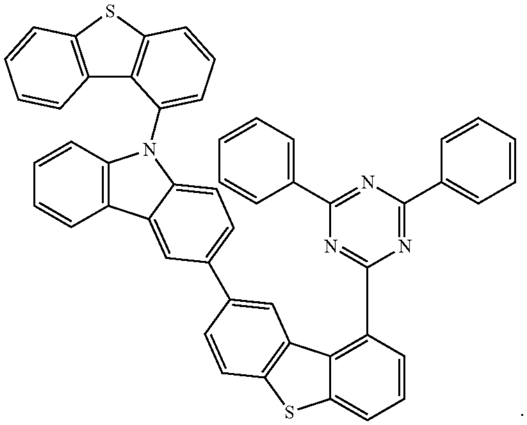 [SMILES: c1ccc(-c2nc(-c3ccccc3)nc(-c3cccc4sc5ccc(-c6ccc7c(c6)c6ccccc6n7-c6cccc7sc8ccccc8c67)cc5c34)n2)cc1]
.

TABLE 2
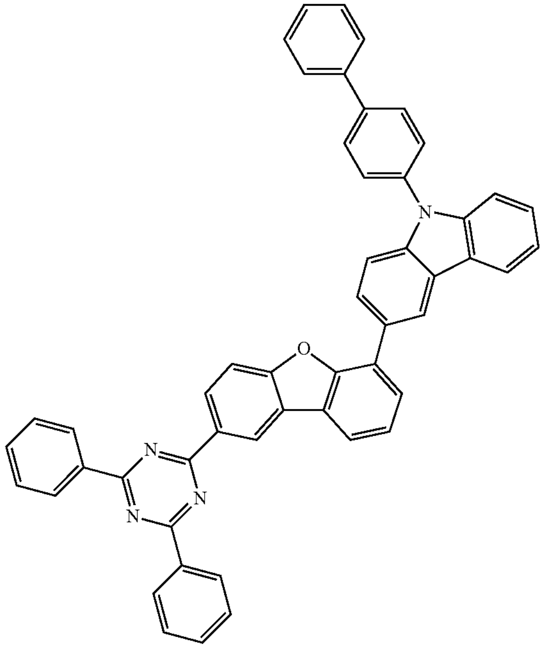
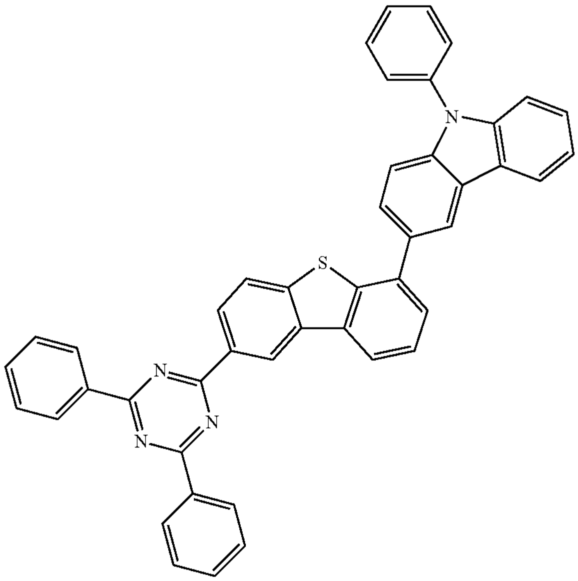 [SMILES: c1ccc(-c2nc(-c3ccccc3)nc(-c3ccc4sc5c(-c6ccc7c(c6)c6ccccc6n7-c6ccccc6)cccc5c4c3)n2)cc1]

TABLE 2-continued
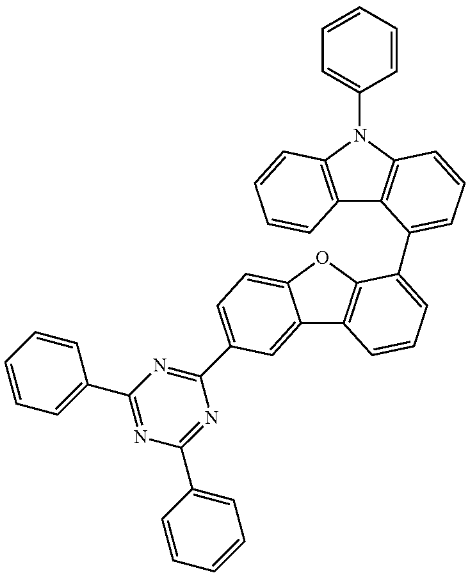 [SMILES: c1ccc(-c2nc(-c3ccccc3)nc(-c3ccc4oc5c(-c6cccc7c6c6ccccc6n7-c6ccccc6)cccc5c4c3)n2)cc1]
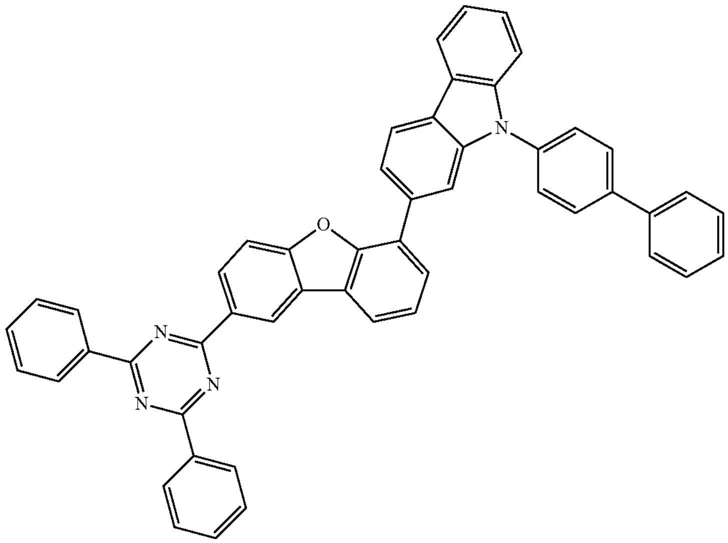

TABLE 2-continued
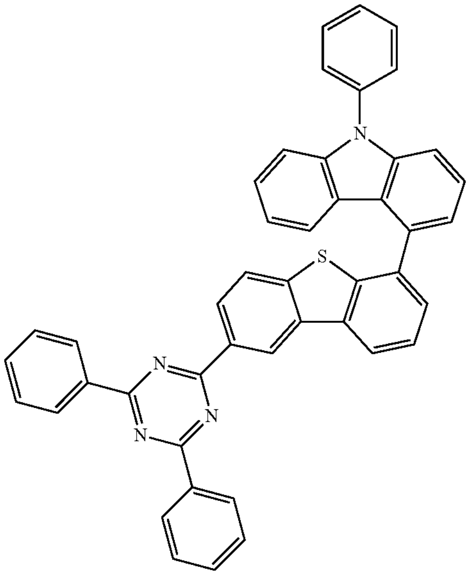 [SMILES: c1ccc(-c2nc(-c3ccccc3)nc(-c3ccc4sc5c(-c6cccc7c6c6ccccc6n7-c6ccccc6)cccc5c4c3)n2)cc1]
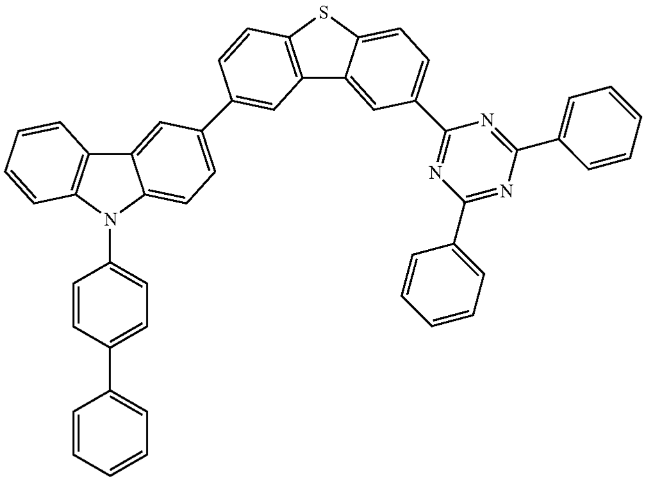 [SMILES: c1ccc(-c2ccc(-n3c4ccccc4c4cc(-c5ccc6sc7ccc(-c8nc(-c9ccccc9)nc(-c9ccccc9)n8)cc7c6c5)ccc43)cc2)cc1]

TABLE 2-continued
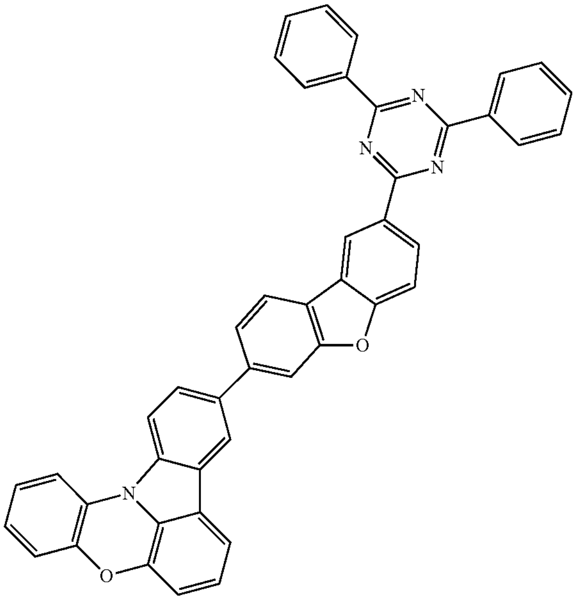 [SMILES: c1ccc(-c2nc(-c3ccccc3)nc(-c3ccc4oc5cc(-c6ccc7c(c6)c6cccc8c6n7-c6ccccc6O8)ccc5c4c3)n2)cc1]
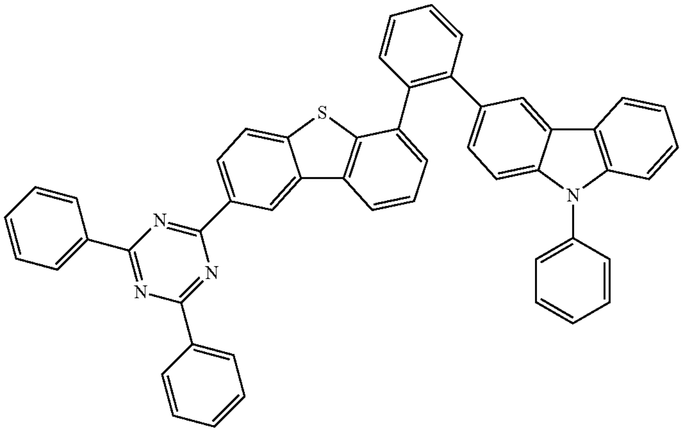
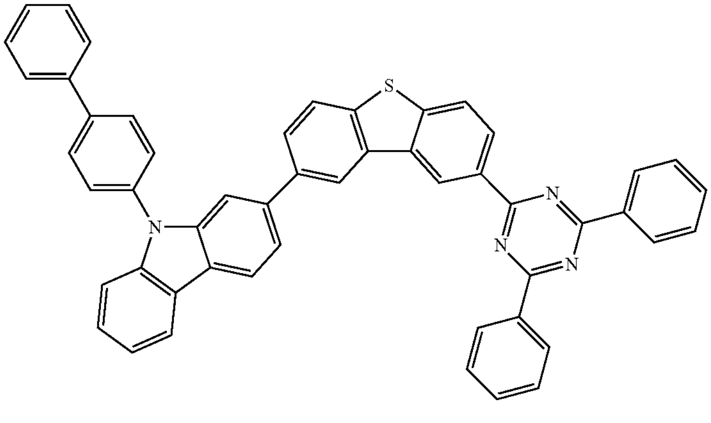 [SMILES: c1ccc(-c2ccc(-n3c4ccccc4c4ccc(-c5ccc6sc7ccc(-c8nc(-c9ccccc9)nc(-c9ccccc9)n8)cc7c6c5)cc43)cc2)cc1]

TABLE 2-continued
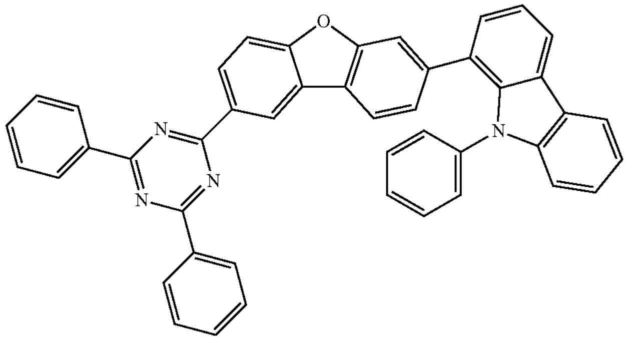
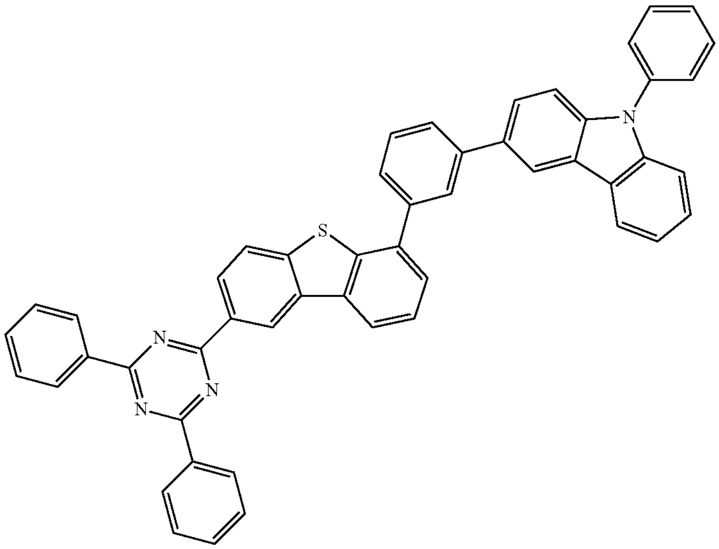
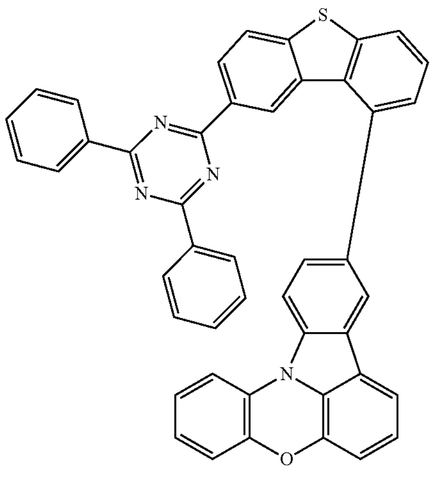 [SMILES: c1ccc(-c2nc(-c3ccccc3)nc(-c3ccc4sc5cccc(-c6ccc7c(c6)c6cccc8c6n7-c6ccccc6O8)c5c4c3)n2)cc1]

TABLE 2-continued
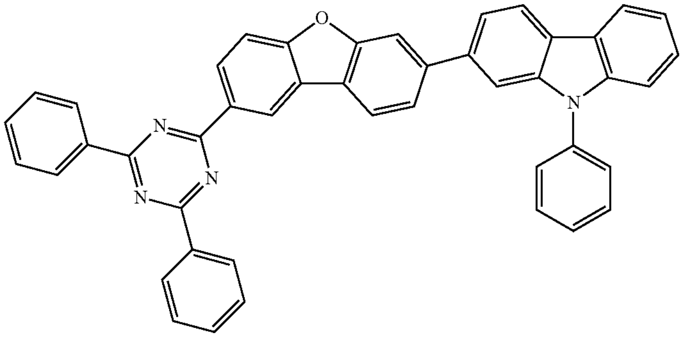
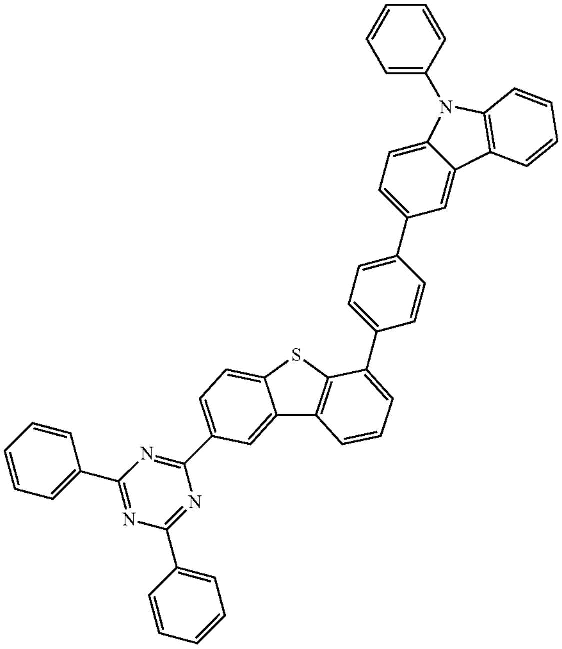
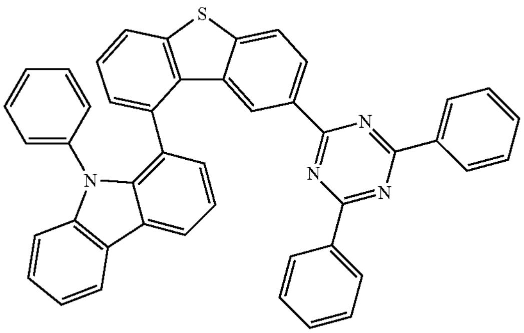 [SMILES: c1ccc(-c2nc(-c3ccccc3)nc(-c3ccc4sc5cccc(-c6cccc7c8ccccc8n(-c8ccccc8)c67)c5c4c3)n2)cc1]

TABLE 2-continued
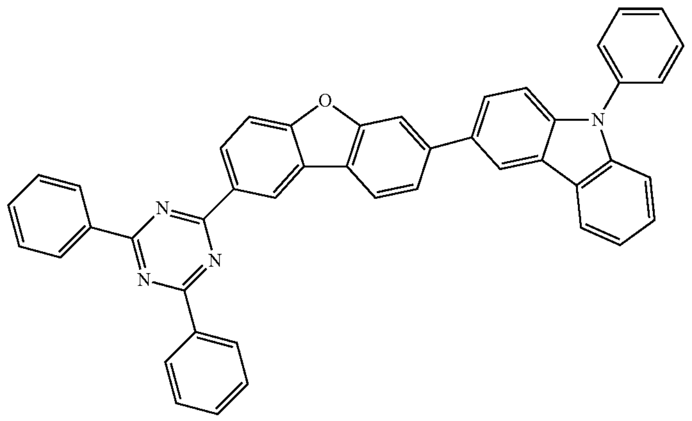
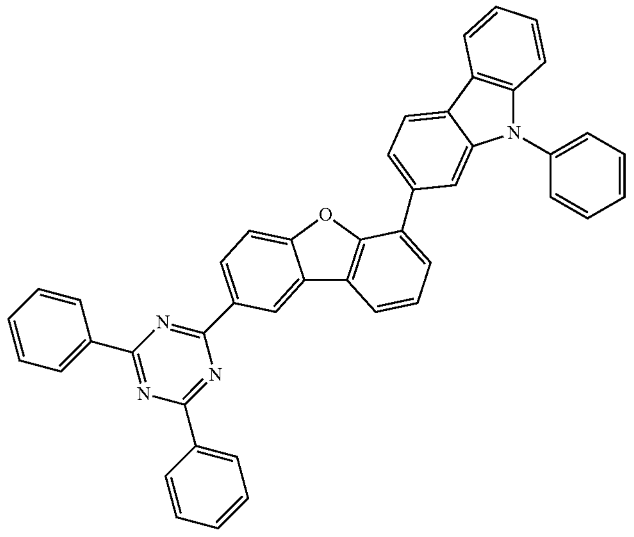 [SMILES: c1ccc(-c2nc(-c3ccccc3)nc(-c3ccc4oc5c(-c6ccc7c8ccccc8n(-c8ccccc8)c7c6)cccc5c4c3)n2)cc1]
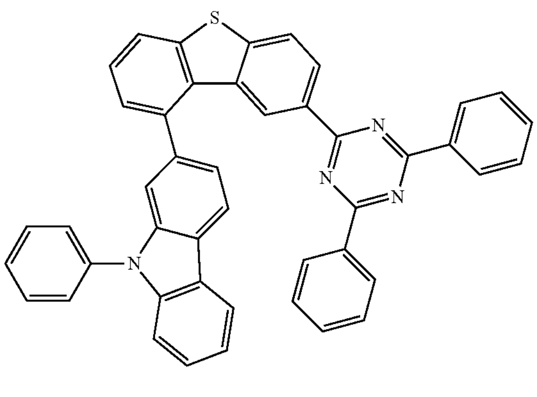 [SMILES: c1ccc(-c2nc(-c3ccccc3)nc(-c3ccc4sc5cccc(-c6ccc7c8ccccc8n(-c8ccccc8)c7c6)c5c4c3)n2)cc1]

TABLE 2-continued
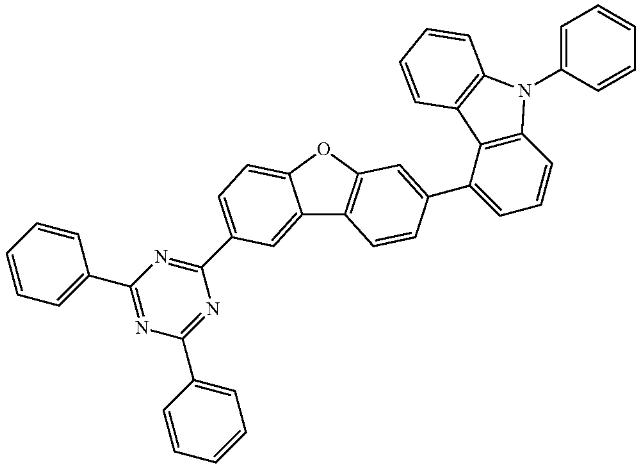
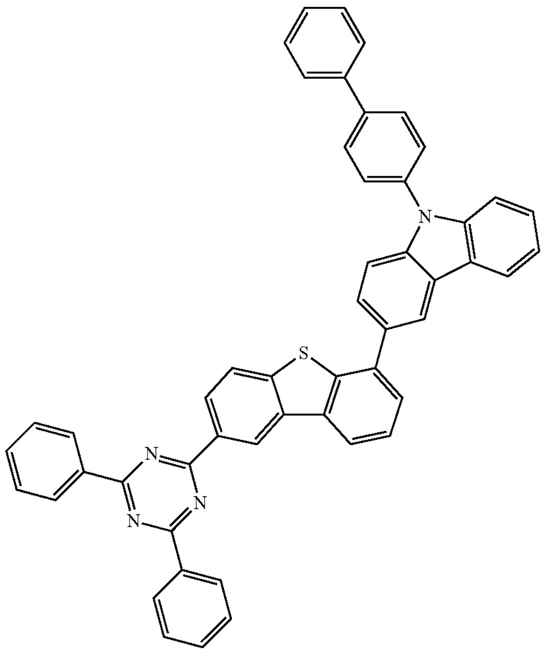 [SMILES: c1ccc(-c2ccc(-n3c4ccccc4c4cc(-c5cccc6c5sc5ccc(-c7nc(-c8ccccc8)nc(-c8ccccc8)n7)cc56)ccc43)cc2)cc1]
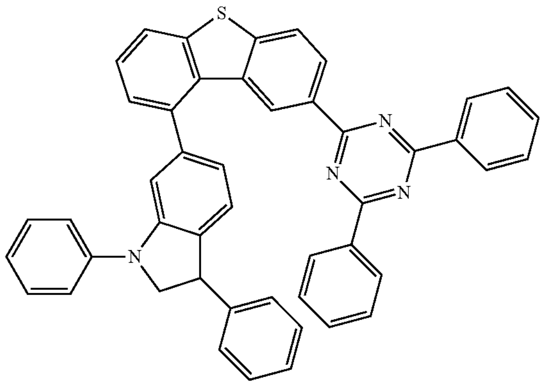 [SMILES: c1ccc(-c2nc(-c3ccccc3)nc(-c3ccc4sc5cccc(-c6ccc7c(c6)N(c6ccccc6)CC7c6ccccc6)c5c4c3)n2)cc1]

TABLE 2-continued
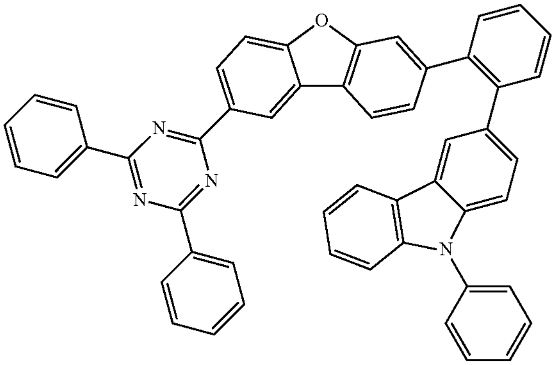 [SMILES: c1ccc(-c2nc(-c3ccccc3)nc(-c3ccc4oc5cc(-c6ccccc6-c6ccc7c(c6)c6ccccc6n7-c6ccccc6)ccc5c4c3)n2)cc1]
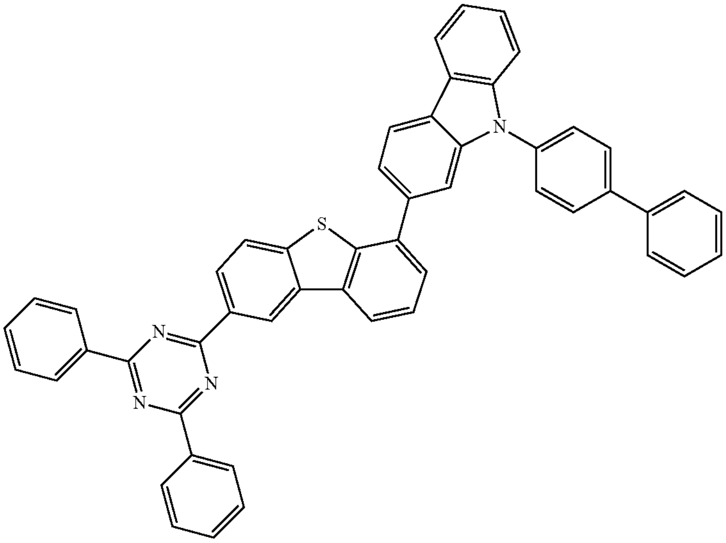 [SMILES: c1ccc(-c2ccc(-n3c4ccccc4c4ccc(-c5cccc6c5sc5ccc(-c7nc(-c8ccccc8)nc(-c8ccccc8)n7)cc56)cc43)cc2)cc1]
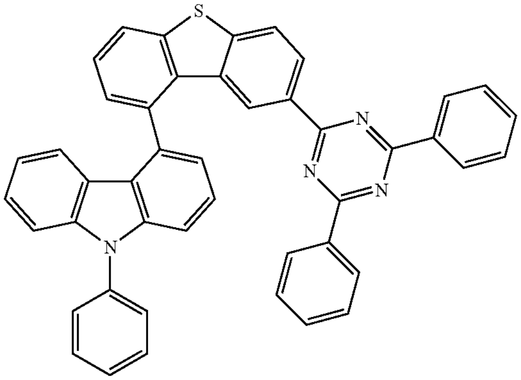

TABLE 2-continued
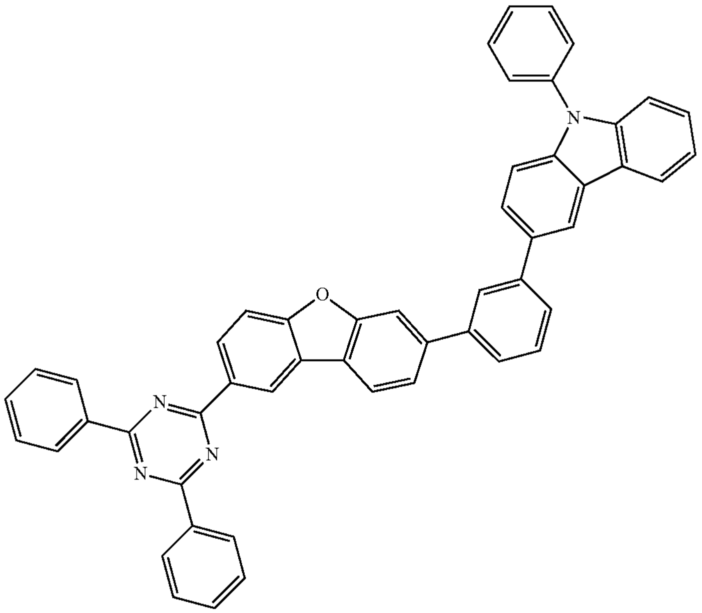 [SMILES: c1ccc(-c2nc(-c3ccccc3)nc(-c3ccc4oc5cc(-c6cccc(-c7ccc8c(c7)c7ccccc7n8-c7ccccc7)c6)ccc5c4c3)n2)cc1]
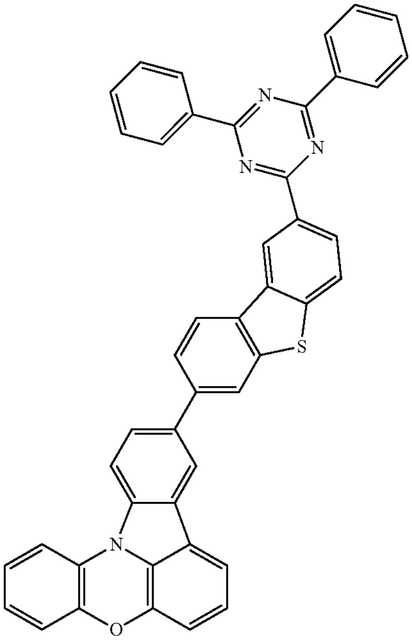 [SMILES: c1ccc(-c2nc(-c3ccccc3)nc(-c3ccc4sc5cc(-c6ccc7c(c6)c6cccc8c6n7-c6ccccc6O8)ccc5c4c3)n2)cc1]
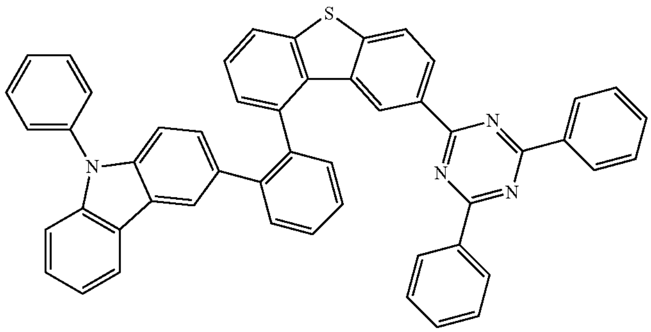 [SMILES: c1ccc(-c2nc(-c3ccccc3)nc(-c3ccc4sc5cccc(-c6ccccc6-c6ccc7c(c6)c6ccccc6n7-c6ccccc6)c5c4c3)n2)cc1]

TABLE 2-continued
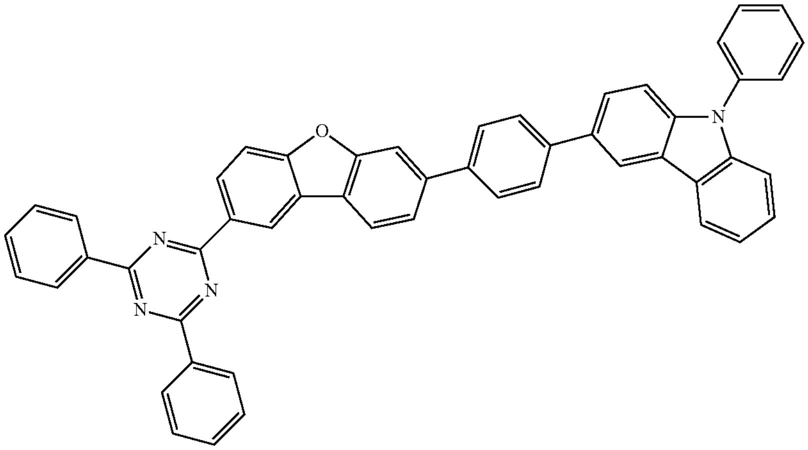 [SMILES: c1ccc(-c2nc(-c3ccccc3)nc(-c3ccc4oc5cc(-c6ccc(-c7ccc8c(c7)c7ccccc7n8-c7ccccc7)cc6)ccc5c4c3)n2)cc1]
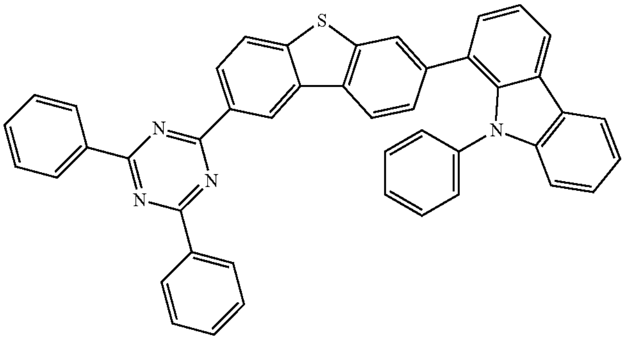 [SMILES: c1ccc(-c2nc(-c3ccccc3)nc(-c3ccc4sc5cc(-c6cccc7c8ccccc8n(-c8ccccc8)c67)ccc5c4c3)n2)cc1]
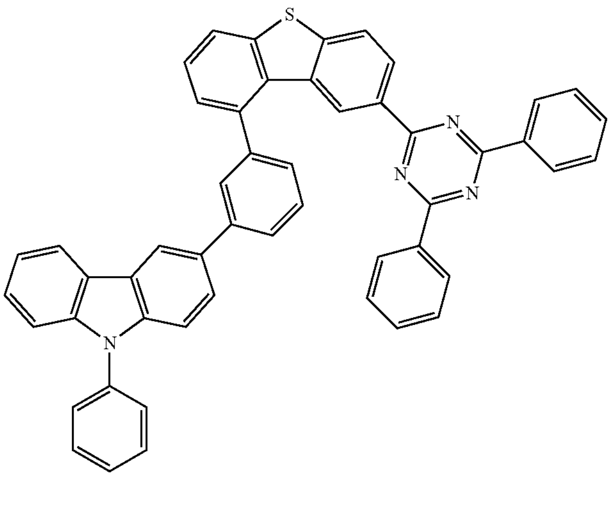 [SMILES: c1ccc(-c2nc(-c3ccccc3)nc(-c3ccc4sc5cccc(-c6cccc(-c7ccc8c(c7)c7ccccc7n8-c7ccccc7)c6)c5c4c3)n2)cc1]

TABLE 2-continued
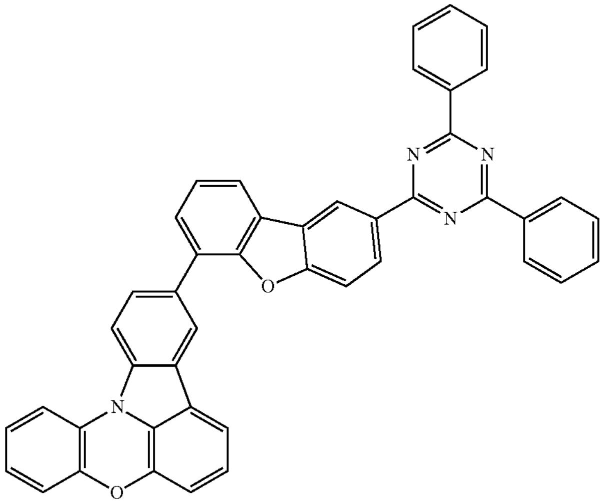 [SMILES: c1ccc(-c2nc(-c3ccccc3)nc(-c3ccc4oc5c(-c6ccc7c(c6)c6cccc8c6n7-c6ccccc6O8)cccc5c4c3)n2)cc1]
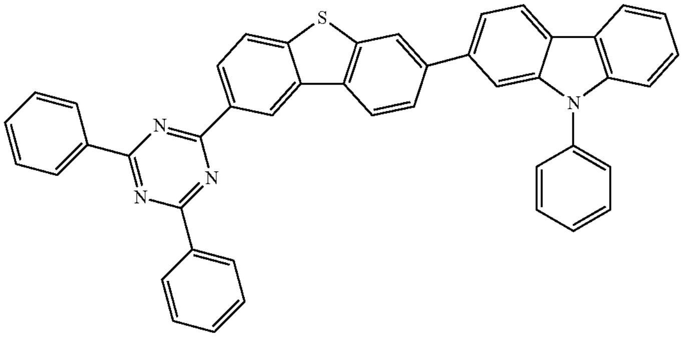 [SMILES: c1ccc(-c2nc(-c3ccccc3)nc(-c3ccc4sc5cc(-c6ccc7c8ccccc8n(-c8ccccc8)c7c6)ccc5c4c3)n2)cc1]
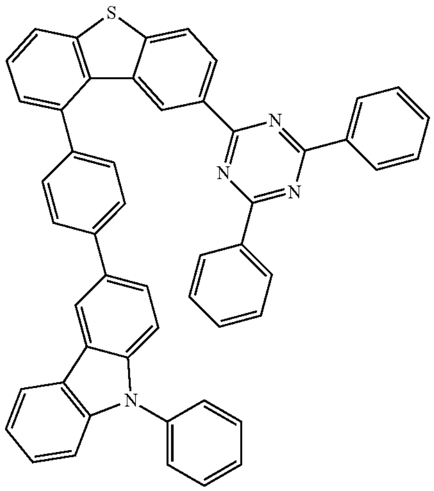

TABLE 2-continued
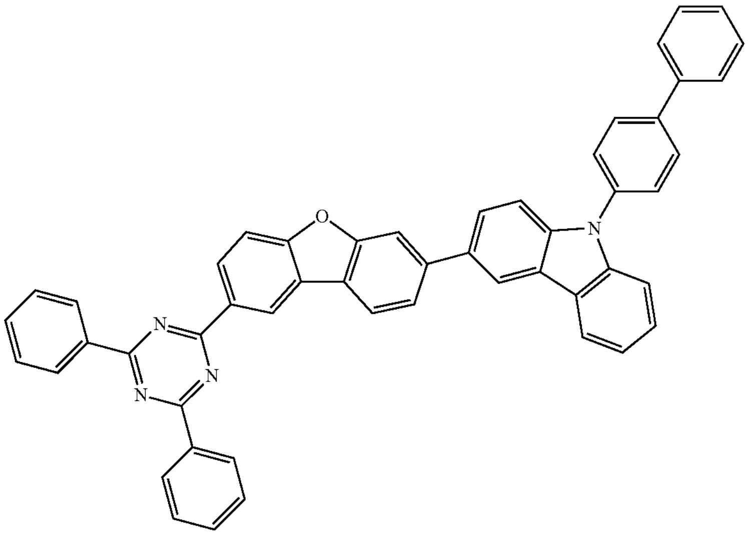
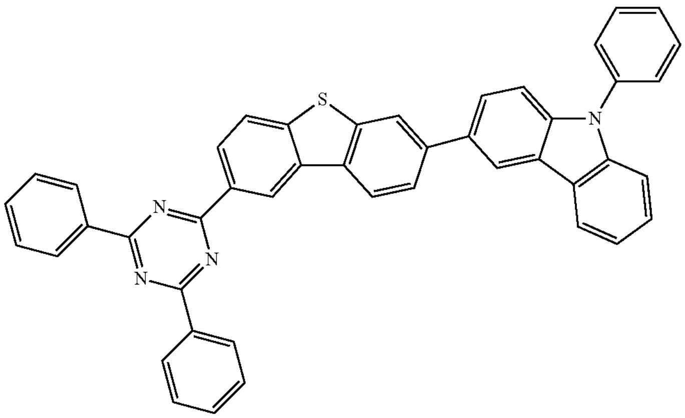
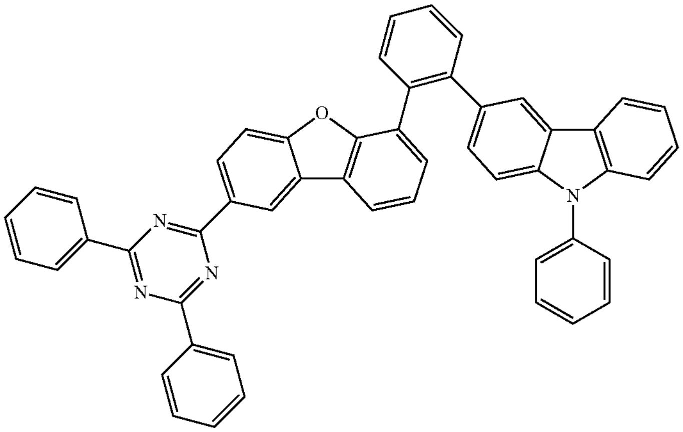

TABLE 2-continued
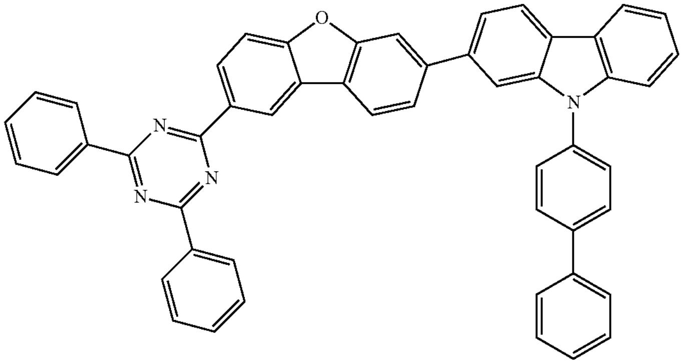 [SMILES: c1ccc(-c2ccc(-n3c4ccccc4c4ccc(-c5ccc6c(c5)oc5ccc(-c7nc(-c8ccccc8)nc(-c8ccccc8)n7)cc56)cc43)cc2)cc1]
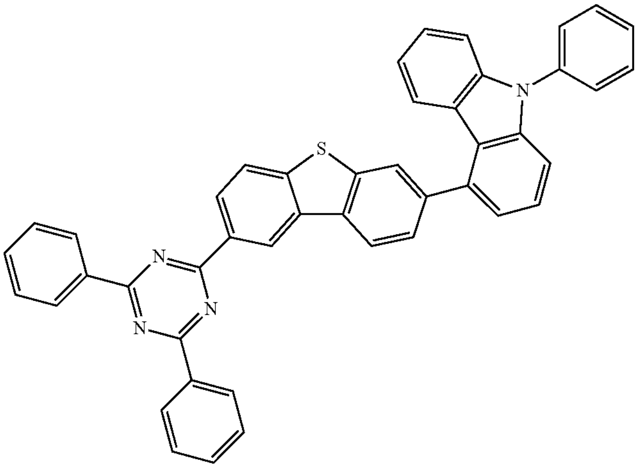 [SMILES: c1ccc(-c2nc(-c3ccccc3)nc(-c3ccc4sc5cc(-c6cccc7c6c6ccccc6n7-c6ccccc6)ccc5c4c3)n2)cc1]
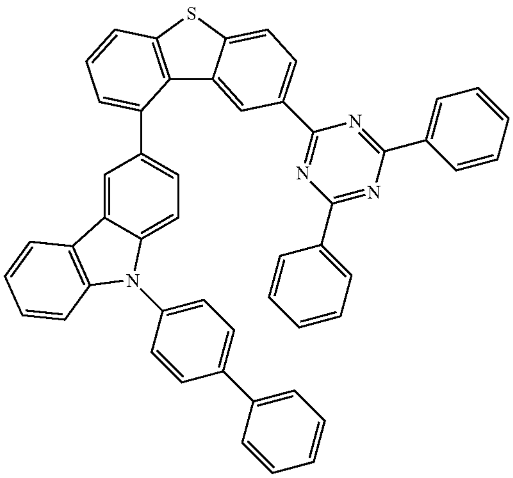 [SMILES: c1ccc(-c2ccc(-n3c4ccccc4c4cc(-c5cccc6sc7ccc(-c8nc(-c9ccccc9)nc(-c9ccccc9)n8)cc7c56)ccc43)cc2)cc1]

TABLE 2-continued
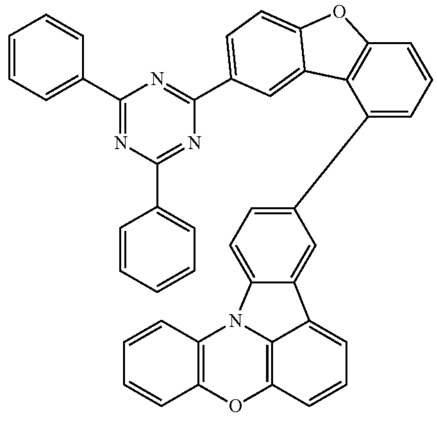 [SMILES: c1ccc(-c2nc(-c3ccccc3)nc(-c3ccc4oc5cccc(-c6ccc7c(c6)c6cccc8c6n7-c6ccccc6O8)c5c4c3)n2)cc1]
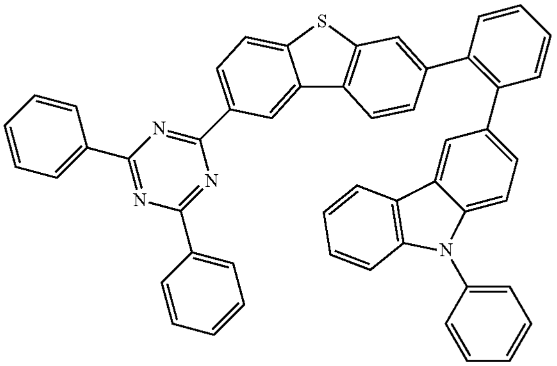 [SMILES: c1ccc(-c2nc(-c3ccccc3)nc(-c3ccc4sc5cc(-c6ccccc6-c6ccc7c(c6)c6ccccc6n7-c6ccccc6)ccc5c4c3)n2)cc1]
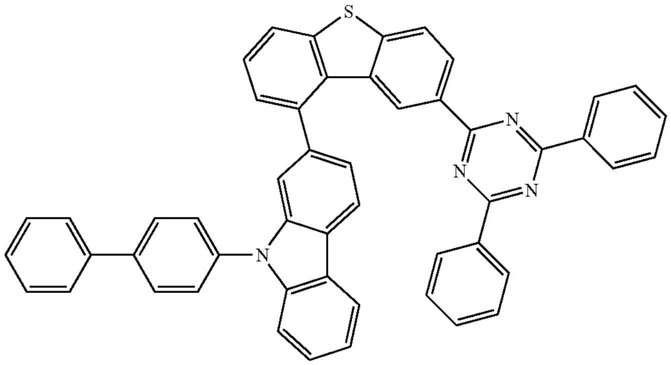 [SMILES: c1ccc(-c2ccc(-n3c4ccccc4c4ccc(-c5cccc6sc7ccc(-c8nc(-c9ccccc9)nc(-c9ccccc9)n8)cc7c56)cc43)cc2)cc1]
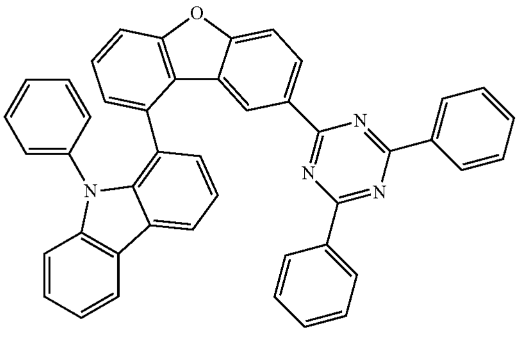 [SMILES: c1ccc(-c2nc(-c3ccccc3)nc(-c3ccc4oc5cccc(-c6cccc7c8ccccc8n(-c8ccccc8)c67)c5c4c3)n2)cc1]

TABLE 2-continued
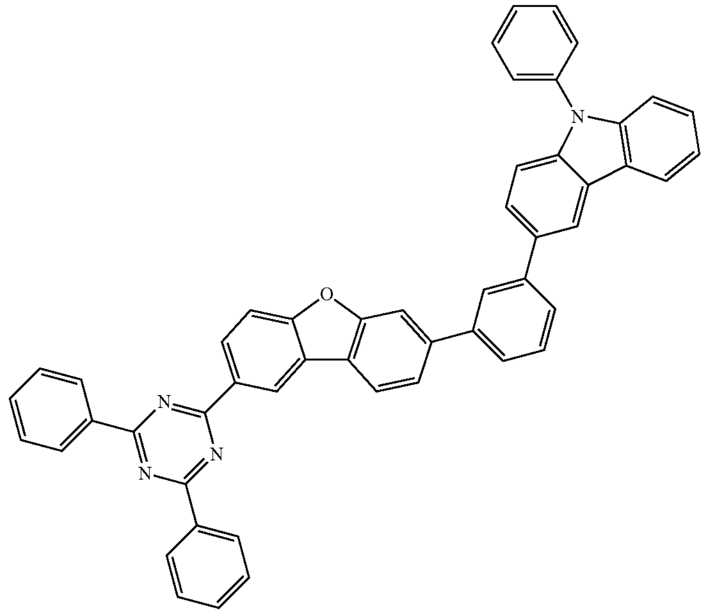 [SMILES: c1ccc(-c2nc(-c3ccccc3)nc(-c3ccc4oc5cc(-c6cccc(-c7ccc8c(c7)c7ccccc7n8-c7ccccc7)c6)ccc5c4c3)n2)cc1]
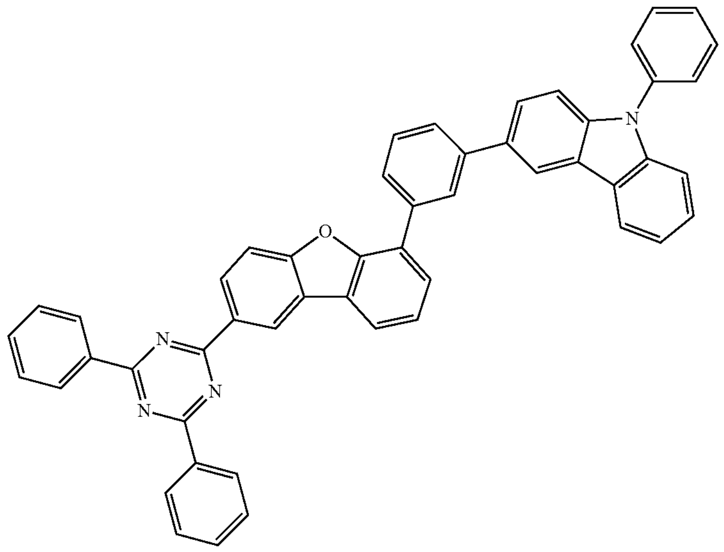 [SMILES: c1ccc(-c2nc(-c3ccccc3)nc(-c3ccc4oc5c(-c6cccc(-c7ccc8c(c7)c7ccccc7n8-c7ccccc7)c6)cccc5c4c3)n2)cc1]
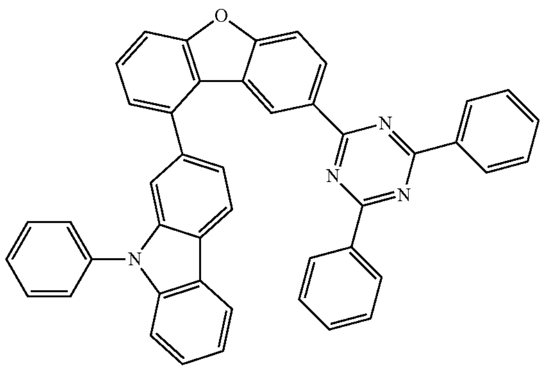 [SMILES: c1ccc(-c2nc(-c3ccccc3)nc(-c3ccc4oc5cccc(-c6ccc7c8ccccc8n(-c8ccccc8)c7c6)c5c4c3)n2)cc1]

TABLE 2-continued
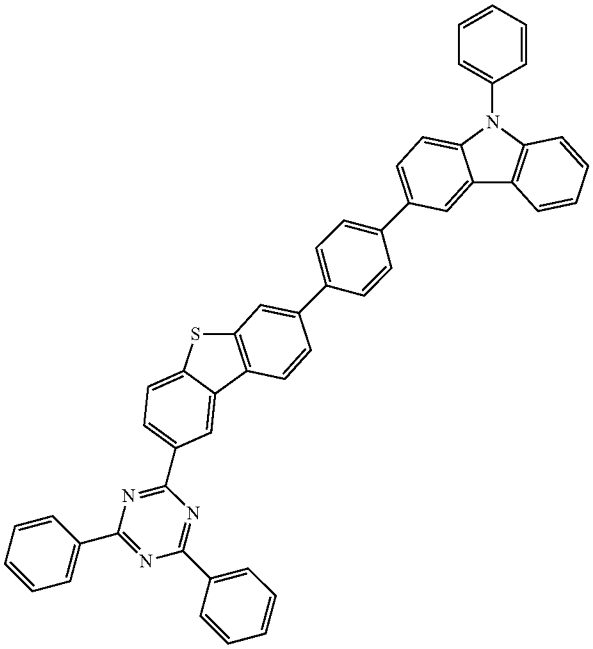 [SMILES: c1ccc(-c2nc(-c3ccccc3)nc(-c3ccc4sc5cc(-c6ccc(-c7ccc8c(c7)c7ccccc7n8-c7ccccc7)cc6)ccc5c4c3)n2)cc1]
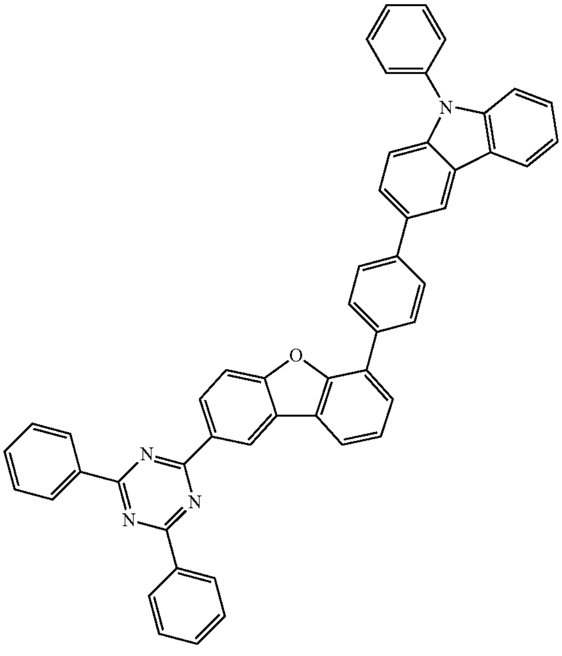 [SMILES: c1ccc(-c2nc(-c3ccccc3)nc(-c3ccc4oc5c(-c6ccc(-c7ccc8c(c7)c7ccccc7n8-c7ccccc7)cc6)cccc5c4c3)n2)cc1]

TABLE 2-continued
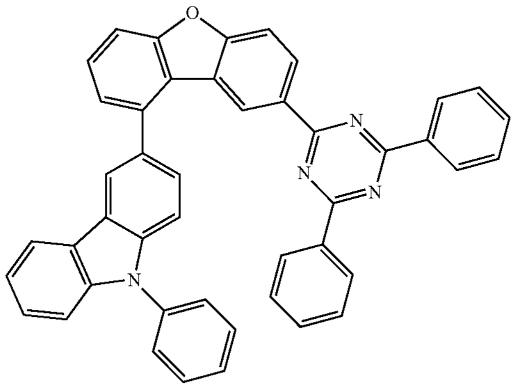 [SMILES: c1ccc(-c2nc(-c3ccccc3)nc(-c3ccc4oc5cccc(-c6ccc7c(c6)c6ccccc6n7-c6ccccc6)c5c4c3)n2)cc1]
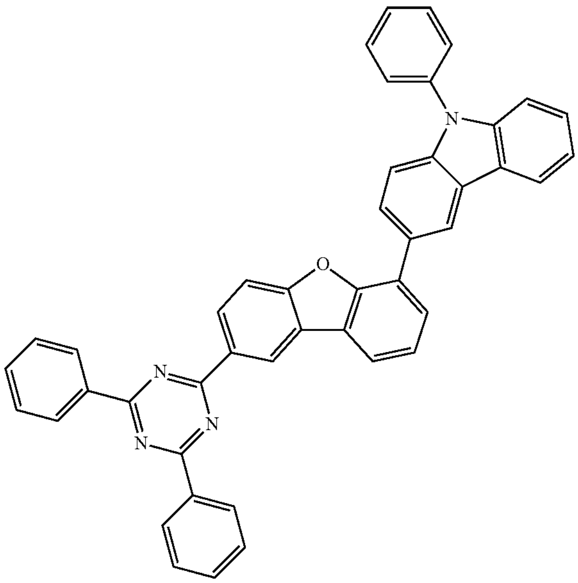
23
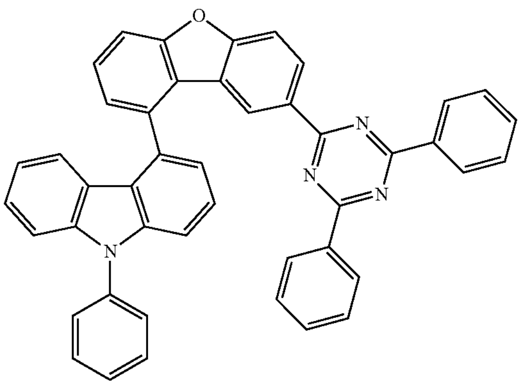 [SMILES: c1ccc(-c2nc(-c3ccccc3)nc(-c3ccc4oc5cccc(-c6cccc7c6c6ccccc6n7-c6ccccc6)c5c4c3)n2)cc1]

TABLE 2-continued
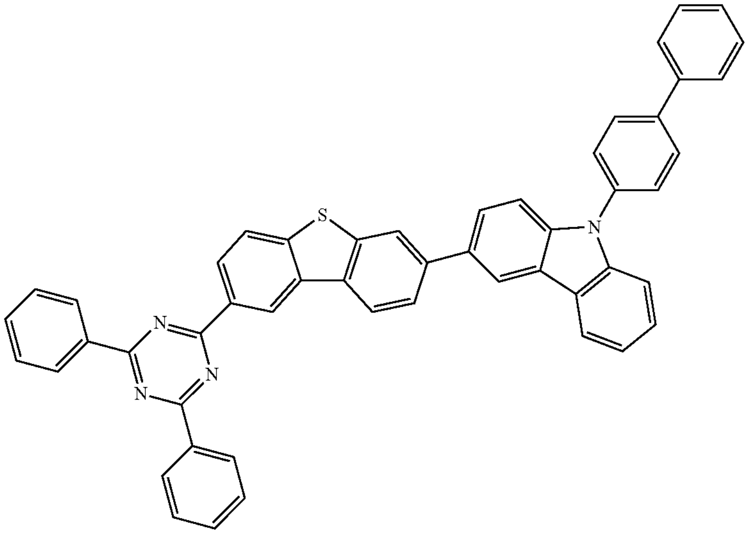 [SMILES: c1ccc(-c2ccc(-n3c4ccccc4c4cc(-c5ccc6c(c5)sc5ccc(-c7nc(-c8ccccc8)nc(-c8ccccc8)n7)cc56)ccc43)cc2)cc1]
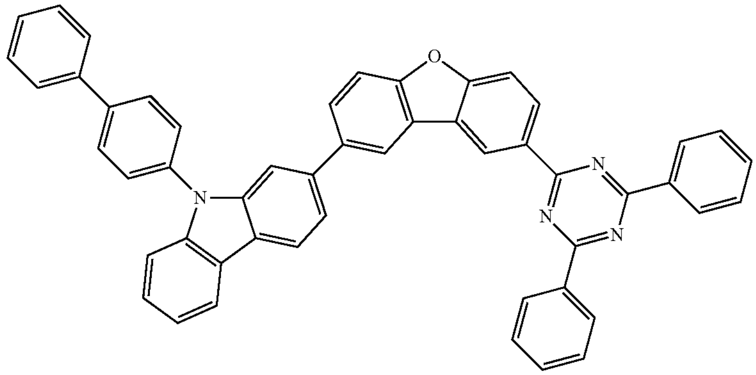 [SMILES: c1ccc(-c2ccc(-n3c4ccccc4c4ccc(-c5ccc6oc7ccc(-c8nc(-c9ccccc9)nc(-c9ccccc9)n8)cc7c6c5)cc43)cc2)cc1]
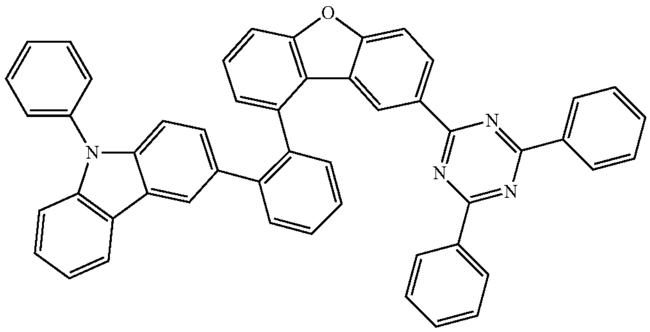 [SMILES: c1ccc(-c2nc(-c3ccccc3)nc(-c3ccc4oc5cccc(-c6ccccc6-c6ccc7c(c6)c6ccccc6n7-c6ccccc6)c5c4c3)n2)cc1]
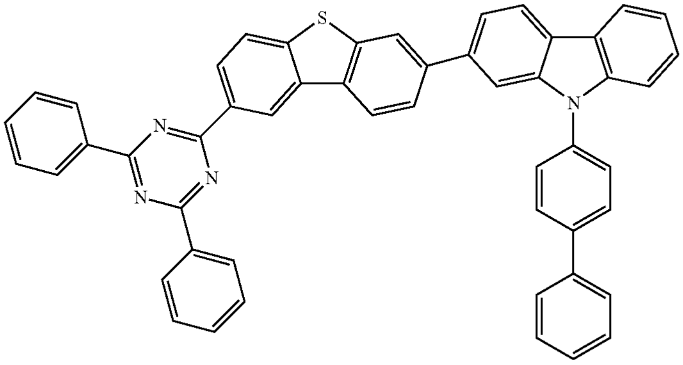

TABLE 2-continued
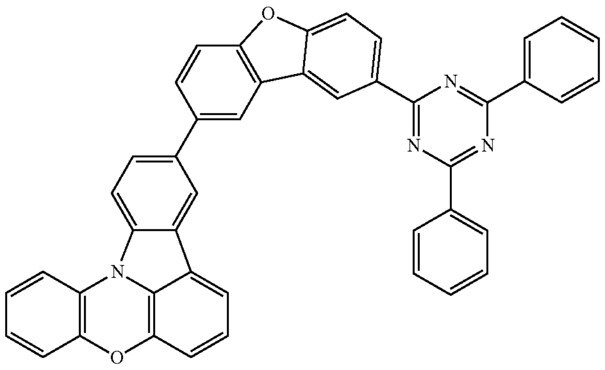
24
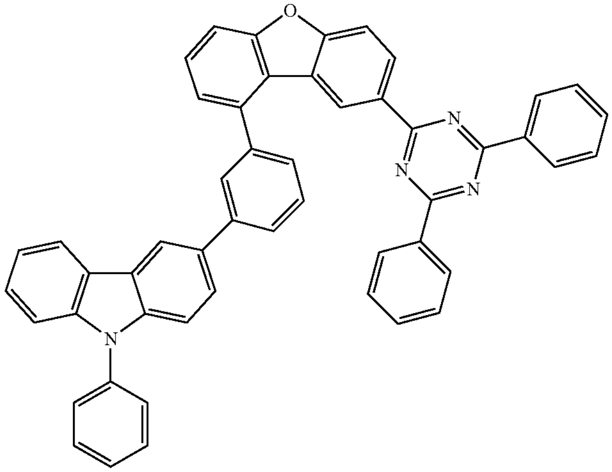 [SMILES: c1ccc(-c2nc(-c3ccccc3)nc(-c3ccc4oc5cccc(-c6cccc(-c7ccc8c(c7)c7ccccc7n8-c7ccccc7)c6)c5c4c3)n2)cc1]
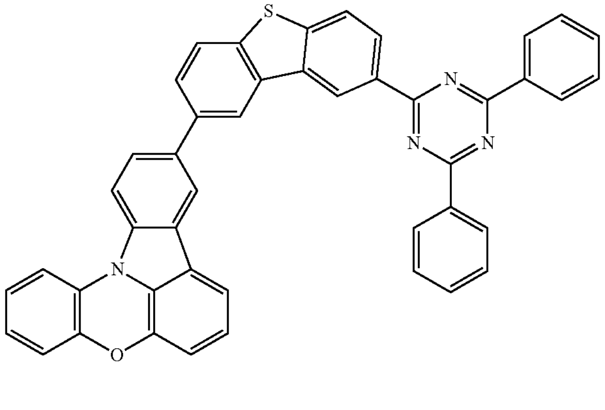 [SMILES: c1ccc(-c2nc(-c3ccccc3)nc(-c3ccc4sc5ccc(-c6ccc7c(c6)c6cccc8c6n7-c6ccccc6O8)cc5c4c3)n2)cc1]

TABLE 2-continued
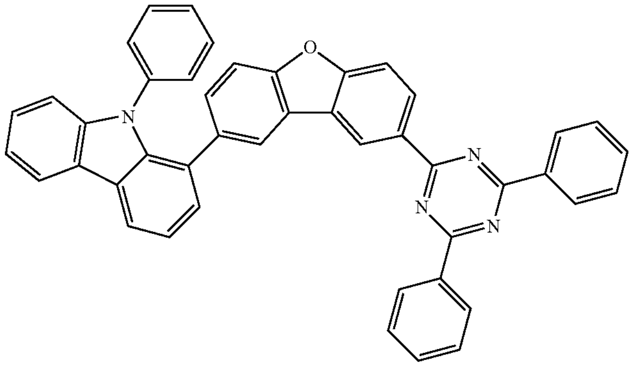 [SMILES: c1ccc(-c2nc(-c3ccccc3)nc(-c3ccc4sc5ccc(-c6cccc7c8ccccc8n(-c8ccccc8)c67)cc5c4c3)n2)cc1]
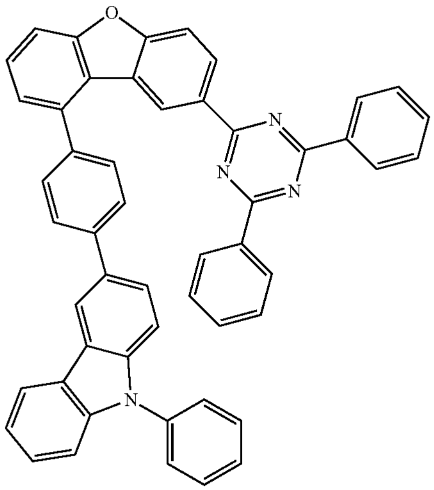
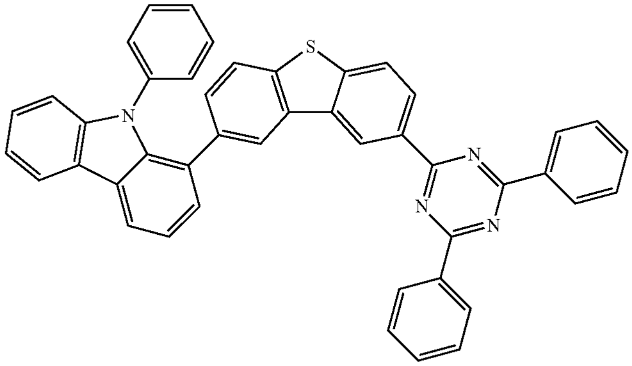
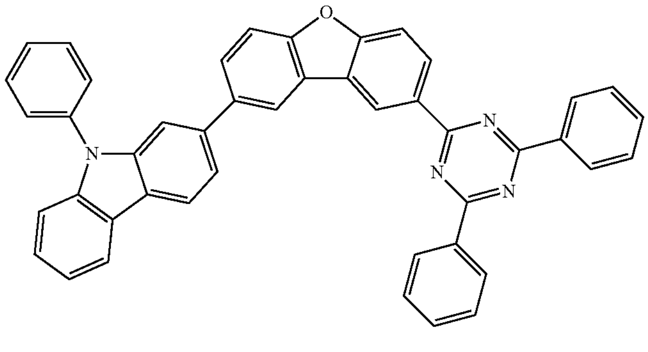 [SMILES: c1ccc(-c2nc(-c3ccccc3)nc(-c3ccc4oc5ccc(-c6ccc7c8ccccc8n(-c8ccccc8)c7c6)cc5c4c3)n2)cc1]

TABLE 2-continued
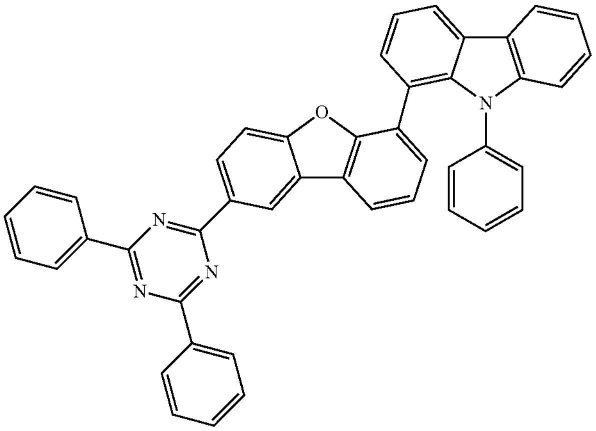
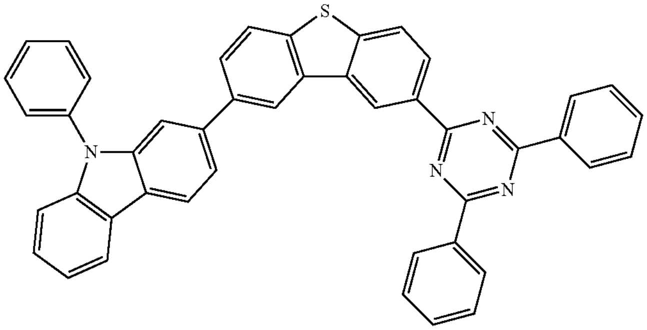 [SMILES: c1ccc(-c2nc(-c3ccccc3)nc(-c3ccc4sc5ccc(-c6ccc7c8ccccc8n(-c8ccccc8)c7c6)cc5c4c3)n2)cc1]
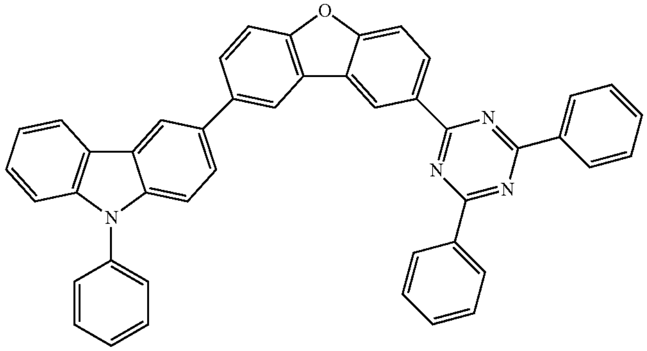

TABLE 2-continued
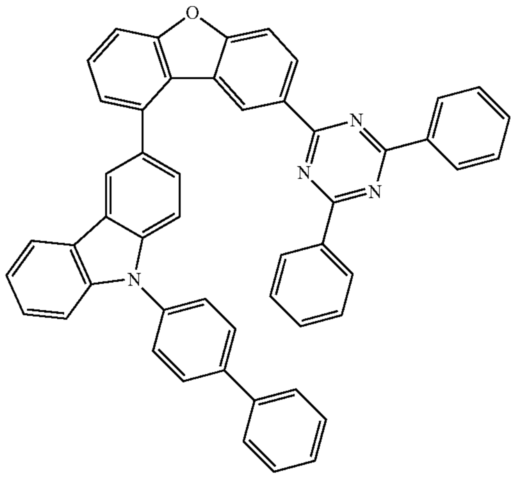 [SMILES: c1ccc(-c2ccc(-n3c4ccccc4c4cc(-c5cccc6oc7ccc(-c8nc(-c9ccccc9)nc(-c9ccccc9)n8)cc7c56)ccc43)cc2)cc1]
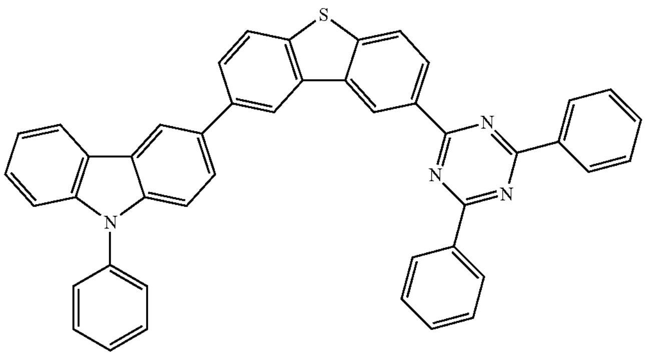 [SMILES: c1ccc(-c2nc(-c3ccccc3)nc(-c3ccc4sc5ccc(-c6ccc7c(c6)c6ccccc6n7-c6ccccc6)cc5c4c3)n2)cc1]
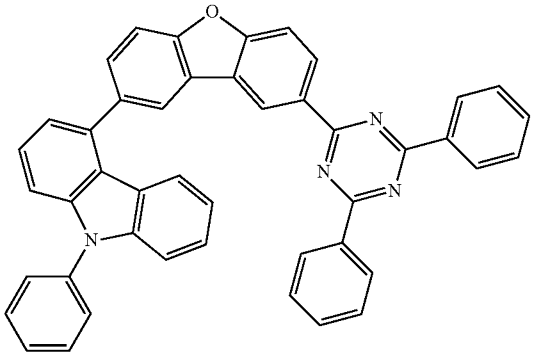 [SMILES: c1ccc(-c2nc(-c3ccccc3)nc(-c3ccc4oc5ccc(-c6cccc7c6c6ccccc6n7-c6ccccc6)cc5c4c3)n2)cc1]
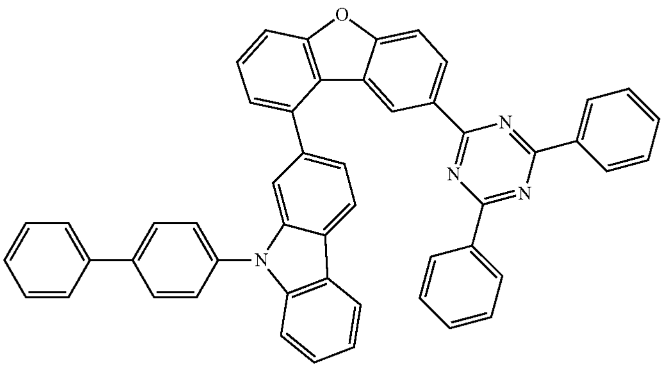 [SMILES: c1ccc(-c2ccc(-n3c4ccccc4c4ccc(-c5cccc6oc7ccc(-c8nc(-c9ccccc9)nc(-c9ccccc9)n8)cc7c56)cc43)cc2)cc1]

TABLE 2-continued
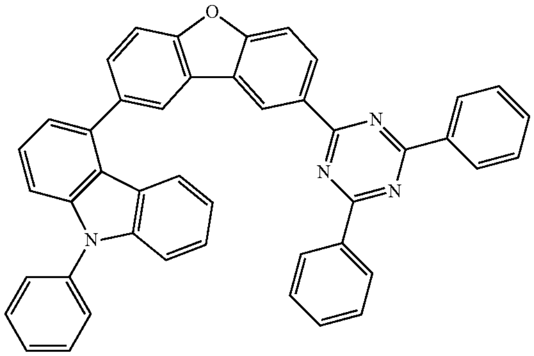 [SMILES: c1ccc(-c2nc(-c3ccccc3)nc(-c3ccc4oc5ccc(-c6cccc7c6c6ccccc6n7-c6ccccc6)cc5c4c3)n2)cc1]
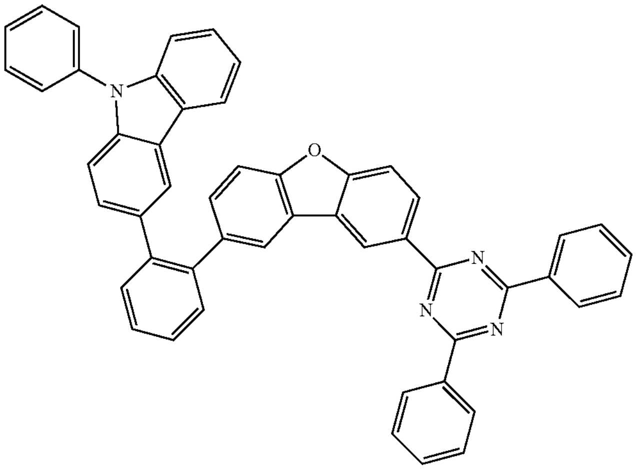 [SMILES: c1ccc(-c2nc(-c3ccccc3)nc(-c3ccc4oc5ccc(-c6ccccc6-c6ccc7c(c6)c6ccccc6n7-c6ccccc6)cc5c4c3)n2)cc1]
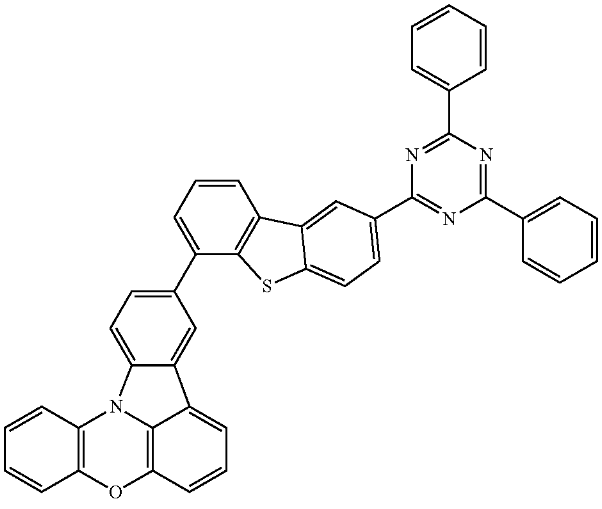

TABLE 2-continued
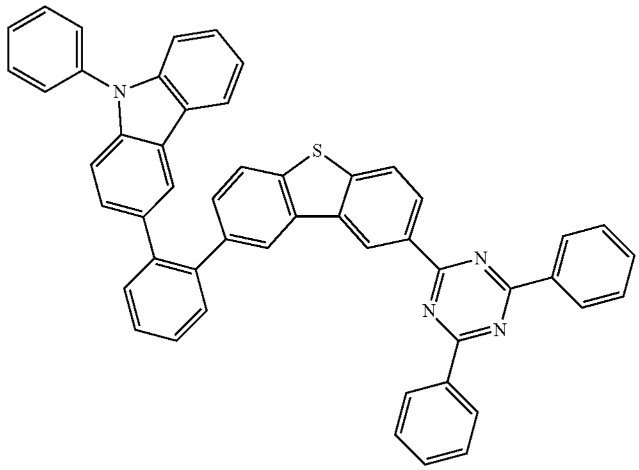
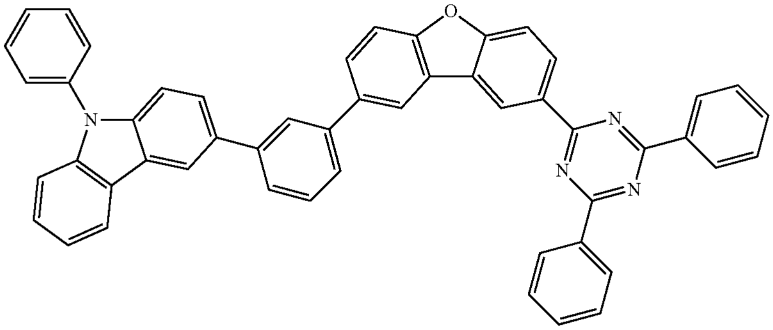
26
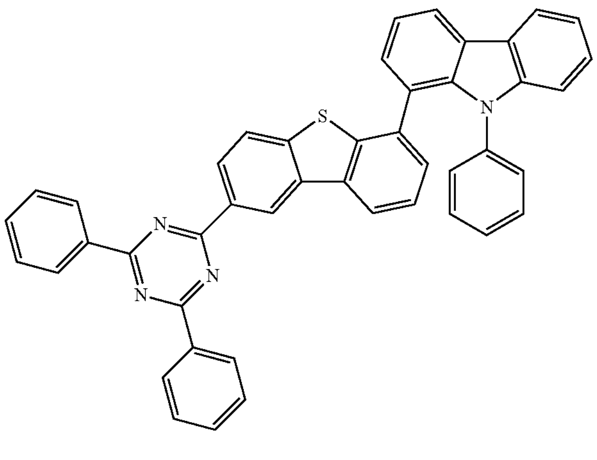 [SMILES: c1ccc(-c2nc(-c3ccccc3)nc(-c3ccc4sc5c(-c6cccc7c8ccccc8n(-c8ccccc8)c67)cccc5c4c3)n2)cc1]

TABLE 2-continued
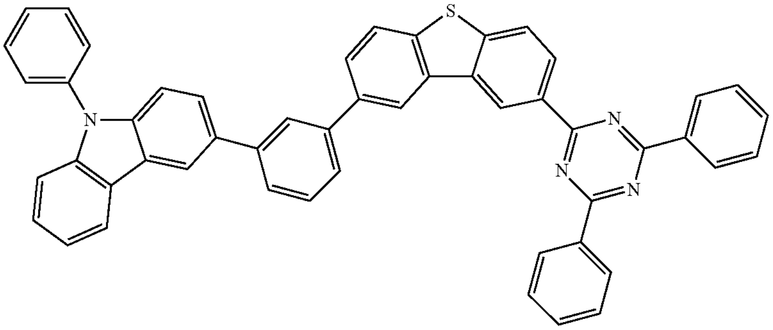
34
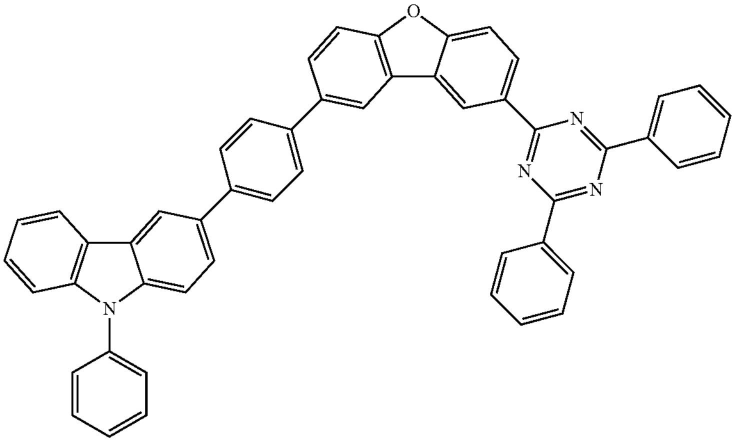
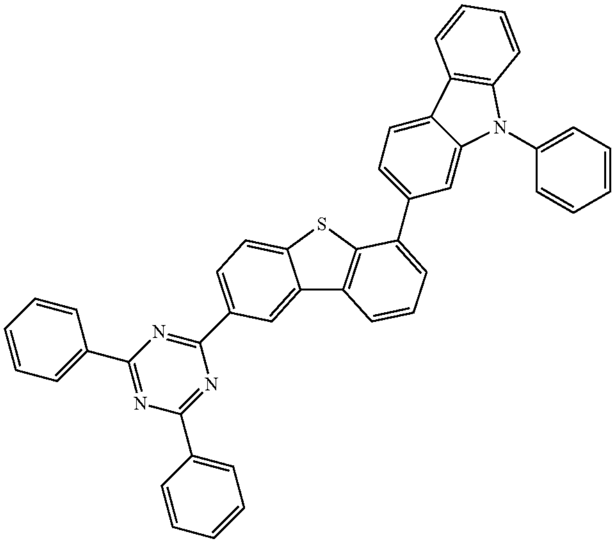 [SMILES: c1ccc(-c2nc(-c3ccccc3)nc(-c3ccc4sc5c(-c6ccc7c8ccccc8n(-c8ccccc8)c7c6)cccc5c4c3)n2)cc1]

TABLE 2-continued
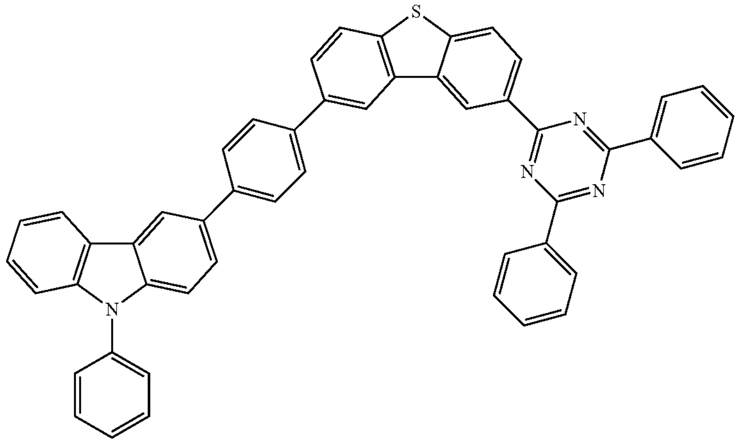 [SMILES: c1ccc(-c2nc(-c3ccccc3)nc(-c3ccc4sc5ccc(-c6ccc(-c7ccc8c(c7)c7ccccc7n8-c7ccccc7)cc6)cc5c4c3)n2)cc1]
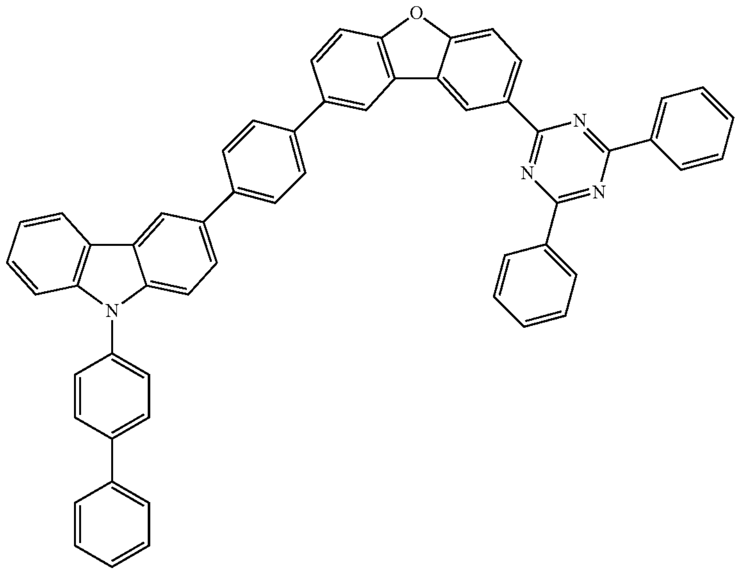
27
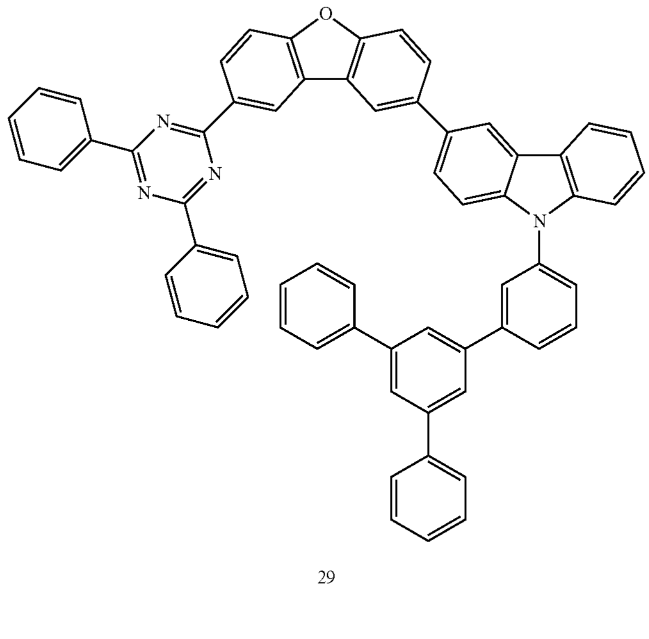 [SMILES: c1ccc(-c2cc(-c3ccccc3)cc(-c3cccc(-n4c5ccccc5c5cc(-c6ccc7oc8ccc(-c9nc(-c%10ccccc%10)nc(-c%10ccccc%10)n9)cc8c7c6)ccc54)c3)c2)cc1]
29

TABLE 2-continued
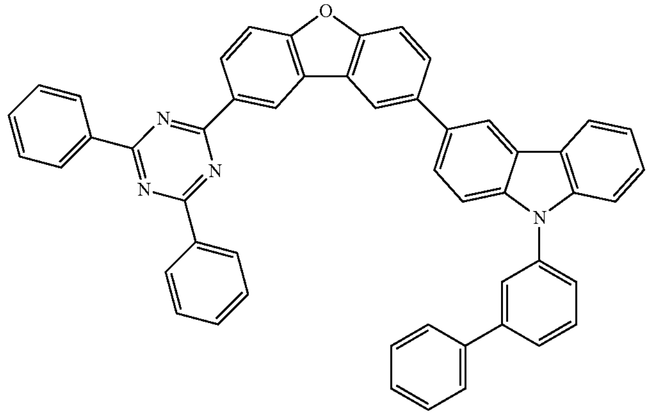
30
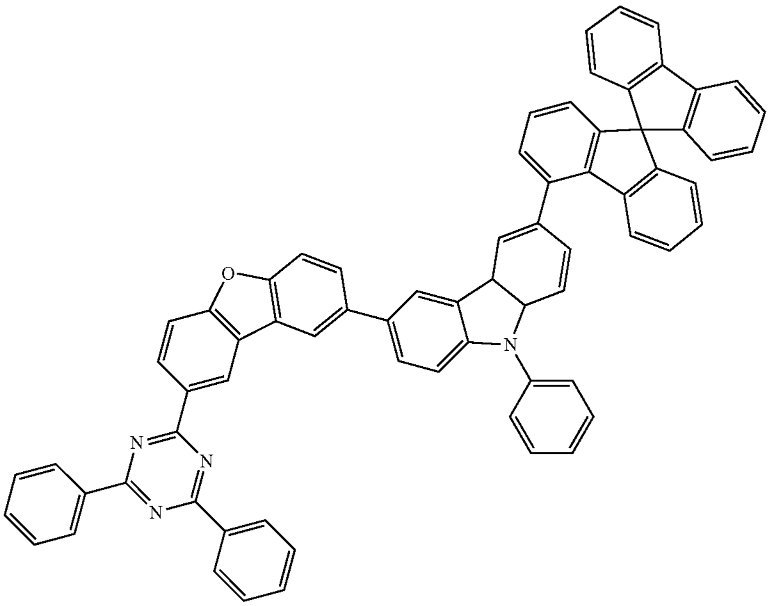
31
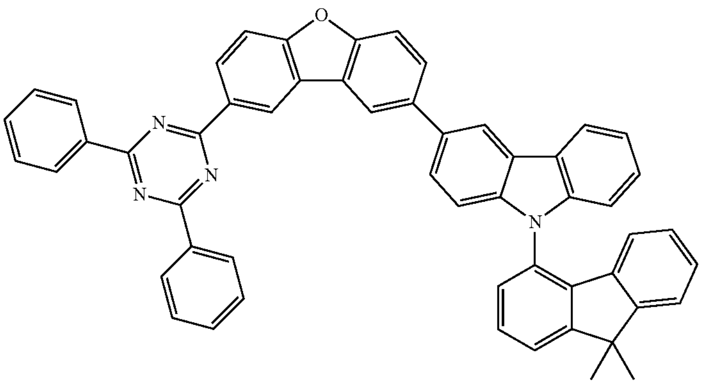
32

TABLE 2-continued
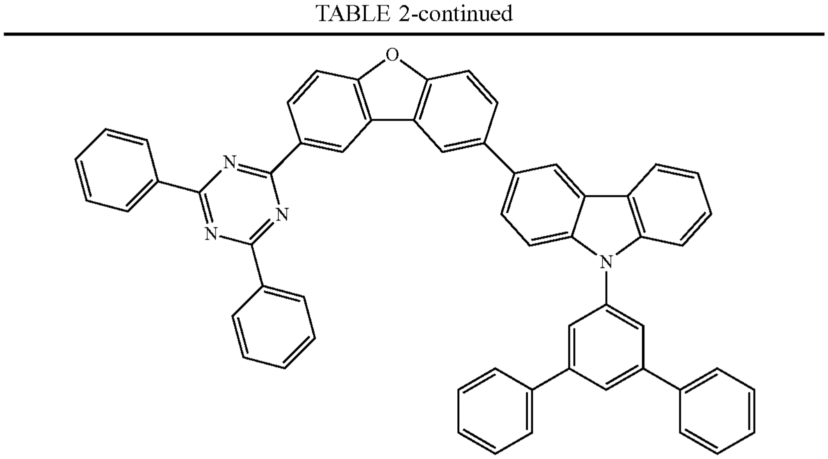
33
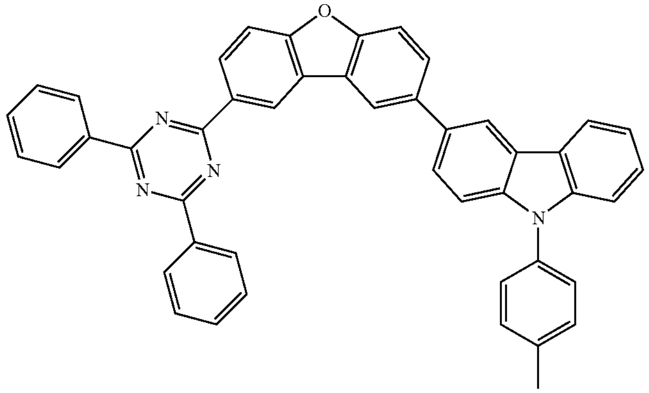
35
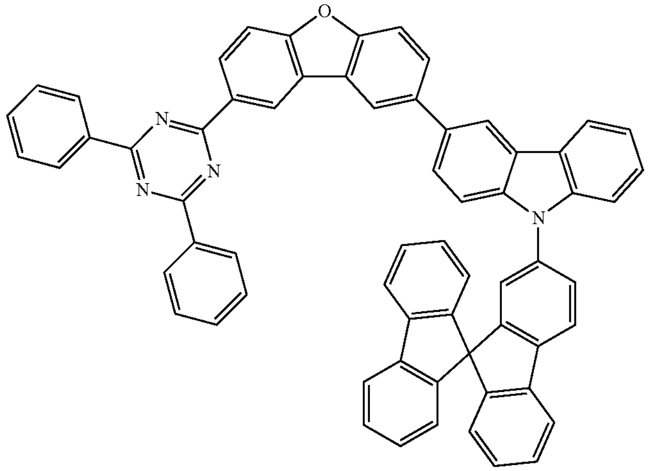
36

TABLE 2-continued
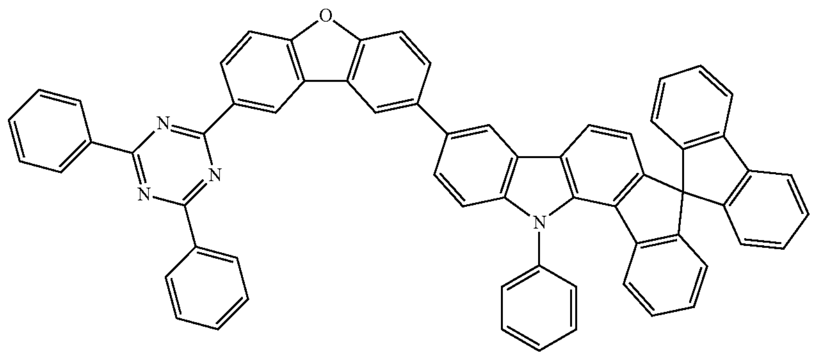
37
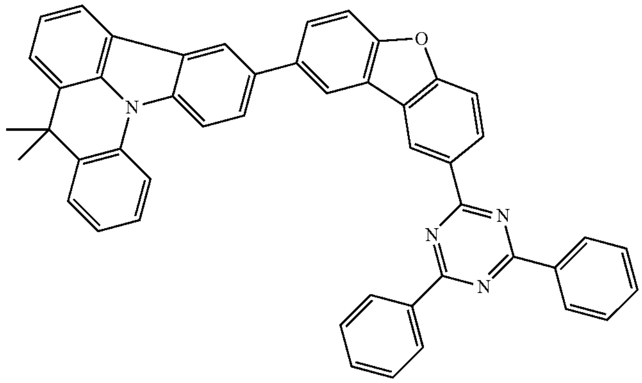
38
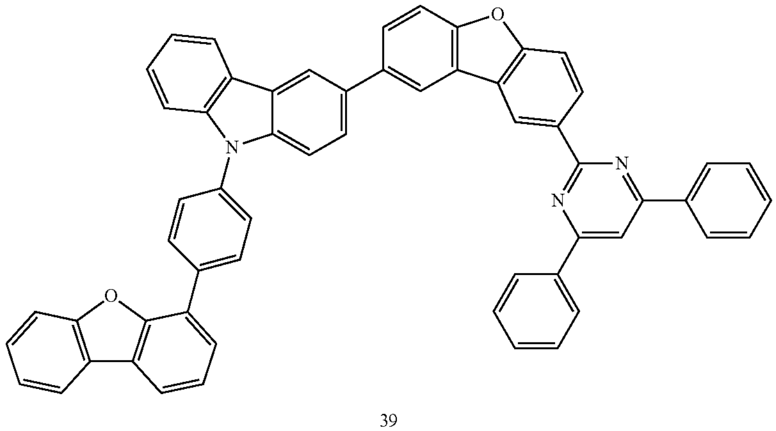 [SMILES: c1ccc(-c2cc(-c3ccccc3)nc(-c3ccc4oc5ccc(-c6ccc7c(c6)c6ccccc6n7-c6ccc(-c7cccc8c7oc7ccccc78)cc6)cc5c4c3)n2)cc1]
39

TABLE 2-continued
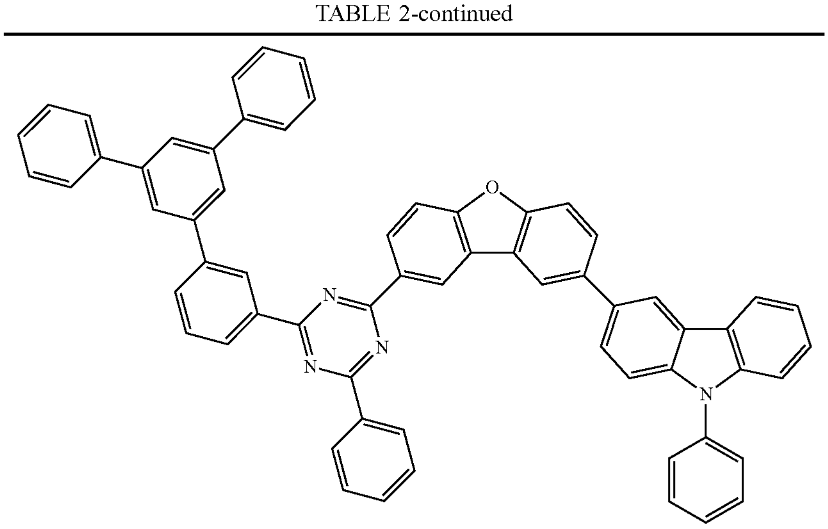
40
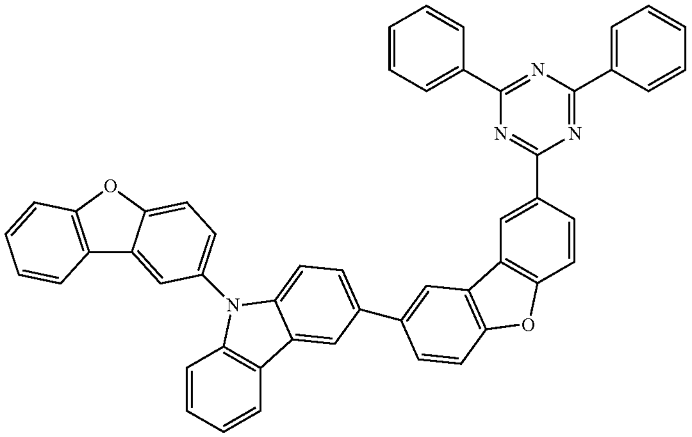
41
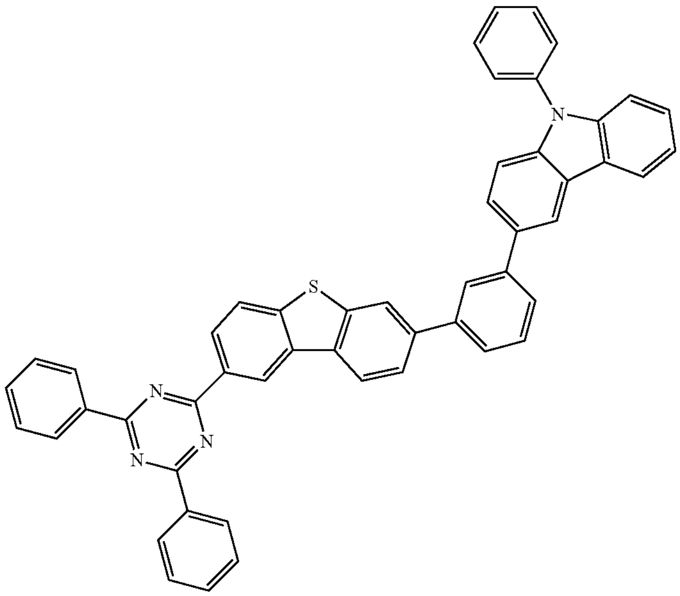
42

TABLE 2-continued
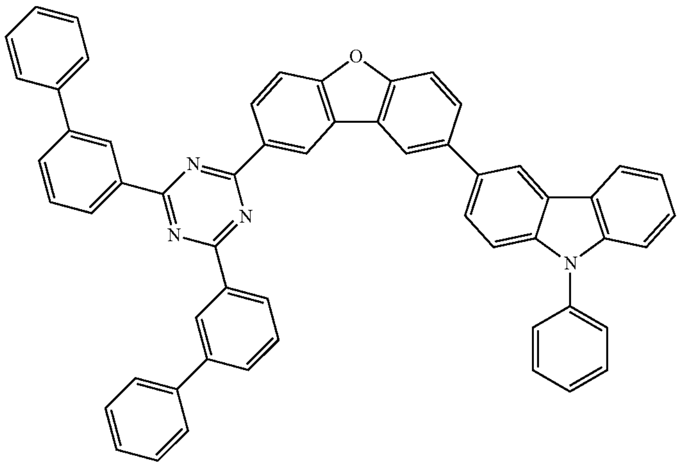
43
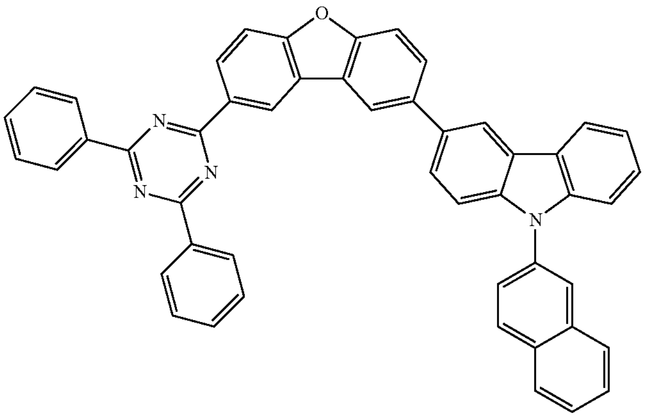
44
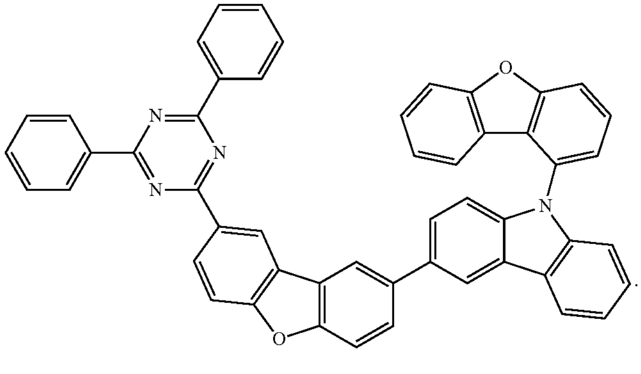
28

TABLE 3
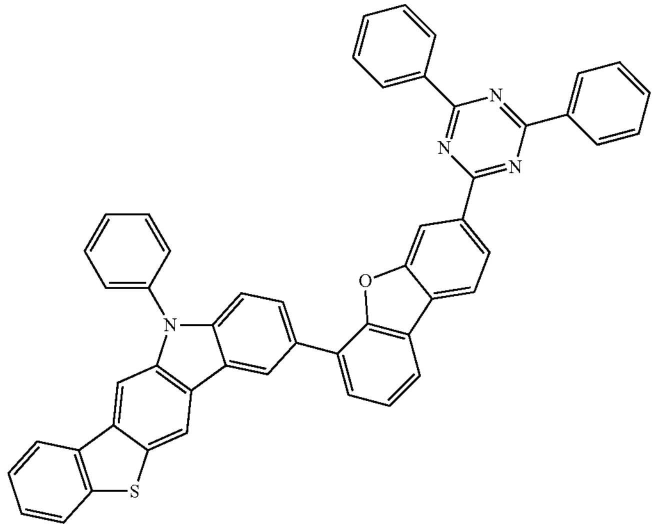 [SMILES: c1ccc(-c2nc(-c3ccccc3)nc(-c3ccc4c(c3)oc3c(-c5ccc6c(c5)c5cc7sc8ccccc8c7cc5n6-c5ccccc5)cccc34)n2)cc1]
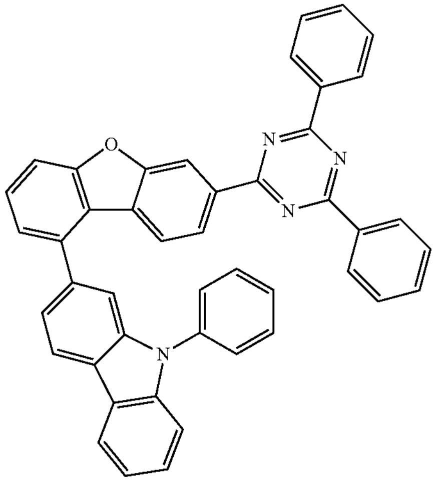
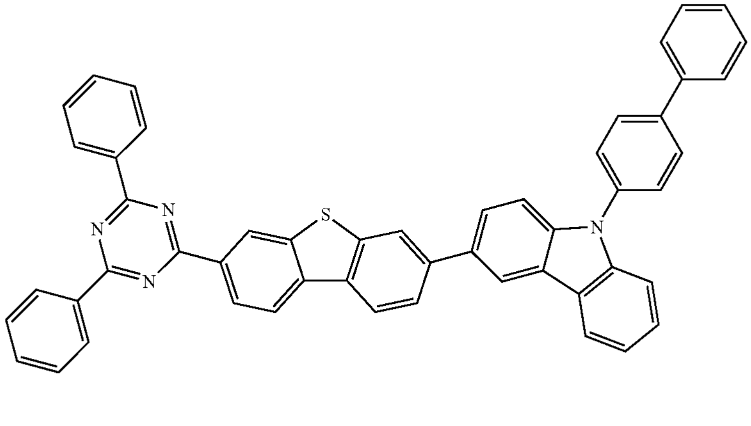 [SMILES: c1ccc(-c2ccc(-n3c4ccccc4c4cc(-c5ccc6c(c5)sc5cc(-c7nc(-c8ccccc8)nc(-c8ccccc8)n7)ccc56)ccc43)cc2)cc1]

TABLE 3-continued
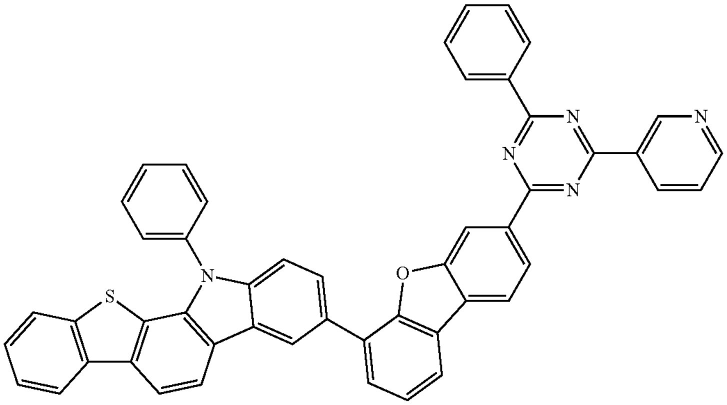 [SMILES: c1ccc(-c2nc(-c3cccnc3)nc(-c3ccc4c(c3)oc3c(-c5ccc6c(c5)c5ccc7c8ccccc8sc7c5n6-c5ccccc5)cccc34)n2)cc1]
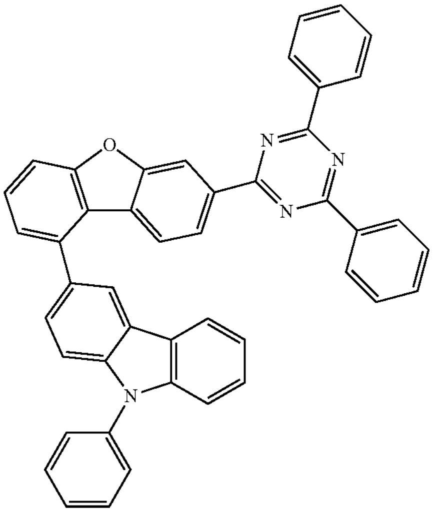 [SMILES: c1ccc(-c2nc(-c3ccccc3)nc(-c3ccc4c(c3)oc3cccc(-c5ccc6c(c5)c5ccccc5n6-c5ccccc5)c34)n2)cc1]
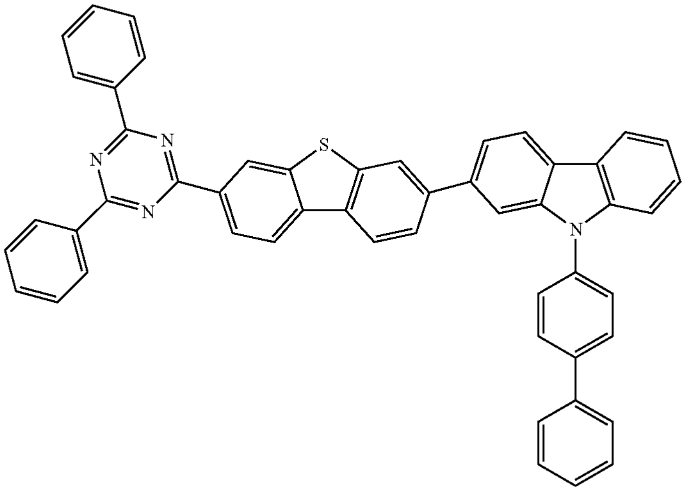 [SMILES: c1ccc(-c2ccc(-n3c4ccccc4c4ccc(-c5ccc6c(c5)sc5cc(-c7nc(-c8ccccc8)nc(-c8ccccc8)n7)ccc56)cc43)cc2)cc1]

TABLE 3-continued
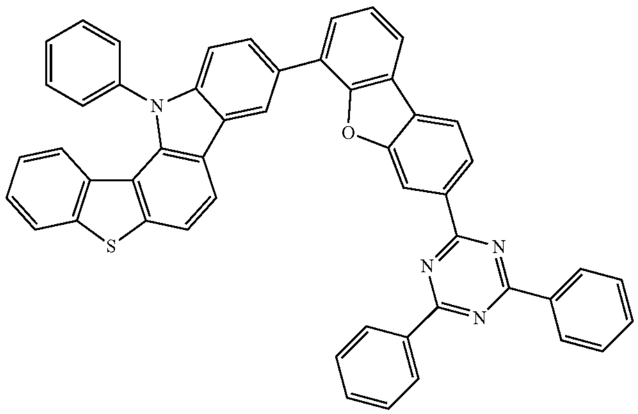 [SMILES: c1ccc(-c2nc(-c3ccccc3)nc(-c3ccc4c(c3)oc3c(-c5ccc6c(c5)c5ccc7sc8ccccc8c7c5n6-c5ccccc5)cccc34)n2)cc1]
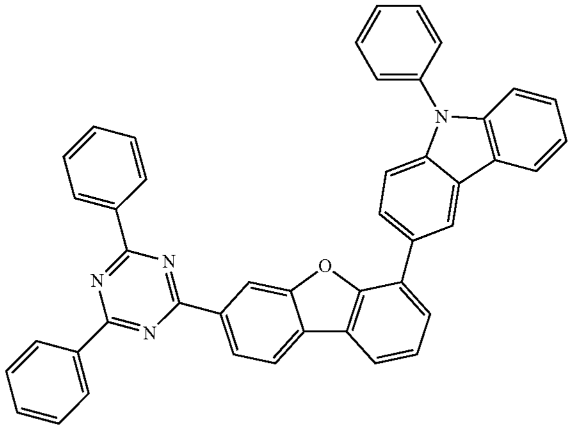
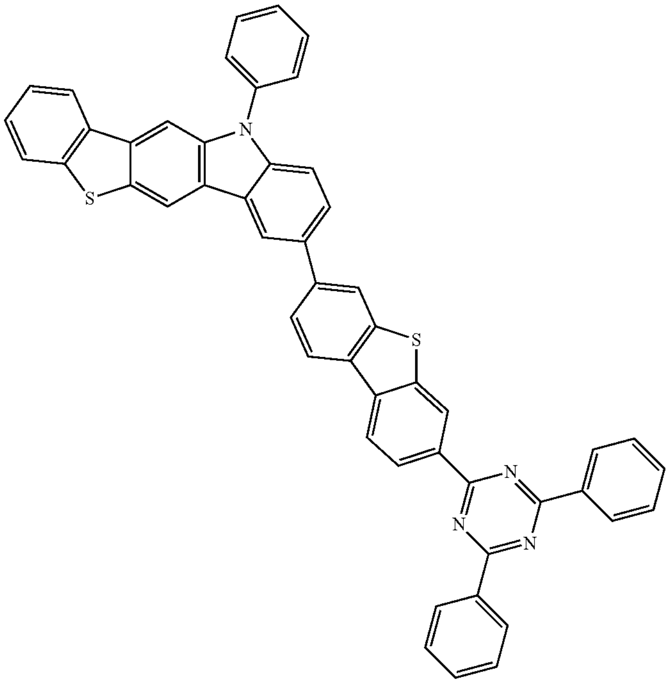 [SMILES: c1ccc(-c2nc(-c3ccccc3)nc(-c3ccc4c(c3)sc3cc(-c5ccc6c(c5)c5cc7sc8ccccc8c7cc5n6-c5ccccc5)ccc34)n2)cc1]

TABLE 3-continued
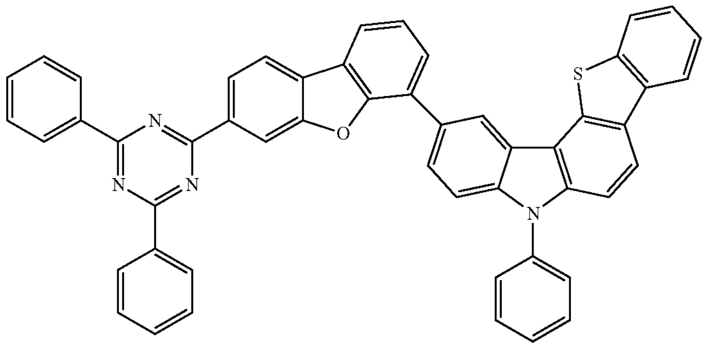 [SMILES: c1ccc(-c2nc(-c3ccccc3)nc(-c3ccc4c(c3)oc3c(-c5ccc6c(c5)c5c7sc8ccccc8c7ccc5n6-c5ccccc5)cccc34)n2)cc1]
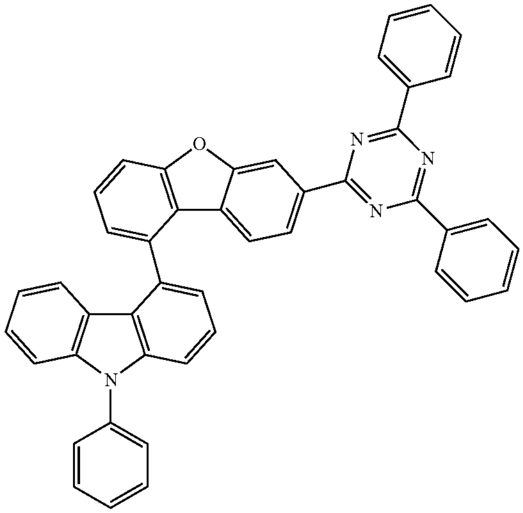
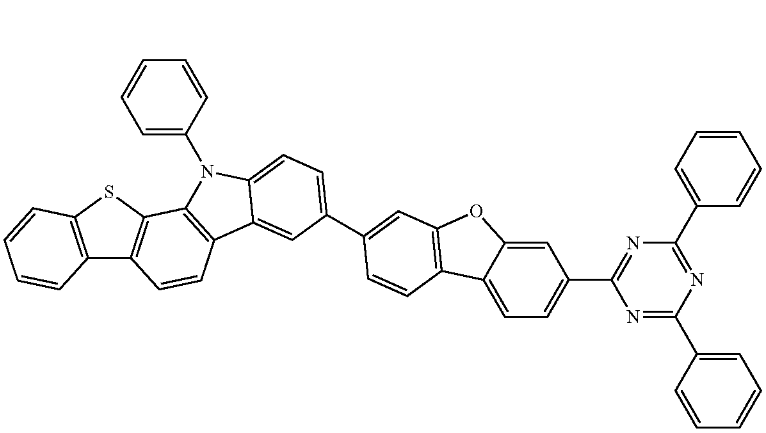 [SMILES: c1ccc(-c2nc(-c3ccccc3)nc(-c3ccc4c(c3)oc3cc(-c5ccc6c(c5)c5ccc7c8ccccc8sc7c5n6-c5ccccc5)ccc34)n2)cc1]

TABLE 3-continued
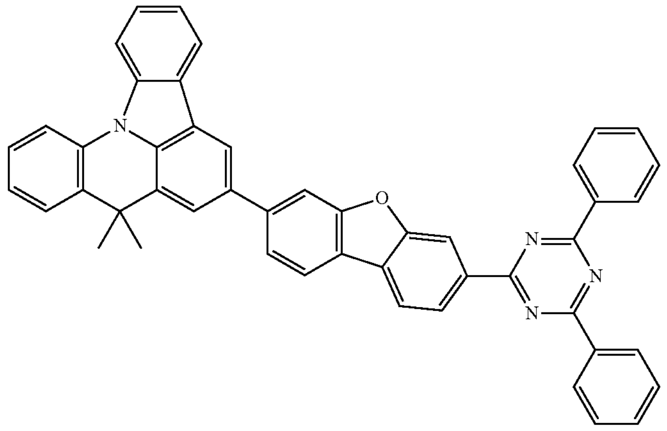 [SMILES: CC1(C)c2ccccc2-n2c3ccccc3c3cc(-c4ccc5c(c4)oc4cc(-c6nc(-c7ccccc7)nc(-c7ccccc7)n6)ccc45)cc1c32]
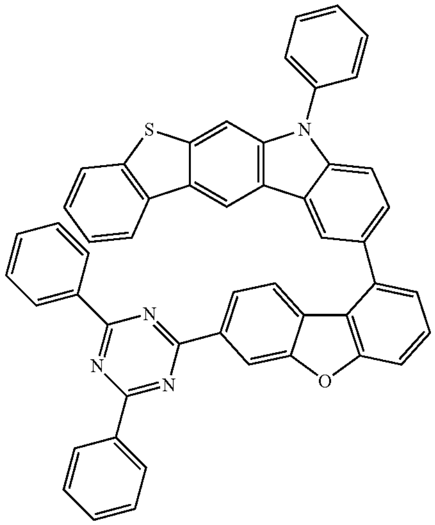 [SMILES: c1ccc(-c2nc(-c3ccccc3)nc(-c3ccc4c(c3)oc3cccc(-c5ccc6c(c5)c5cc7c(cc5n6-c5ccccc5)sc5ccccc57)c34)n2)cc1]
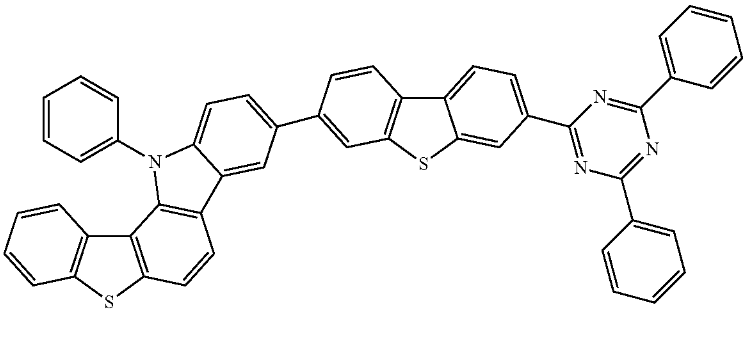

TABLE 3-continued
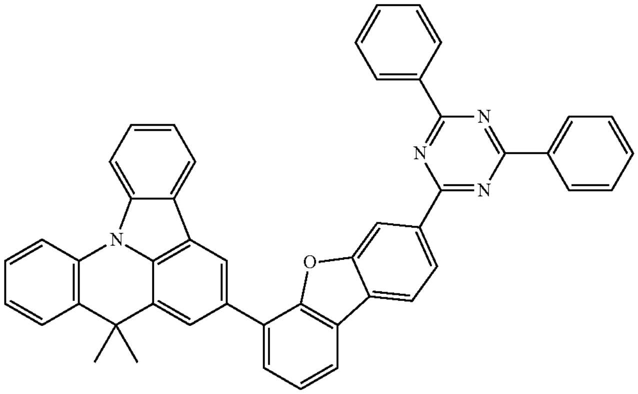 [SMILES: CC1(C)c2ccccc2-n2c3ccccc3c3cc(-c4cccc5c4oc4cc(-c6nc(-c7ccccc7)nc(-c7ccccc7)n6)ccc45)cc1c32]
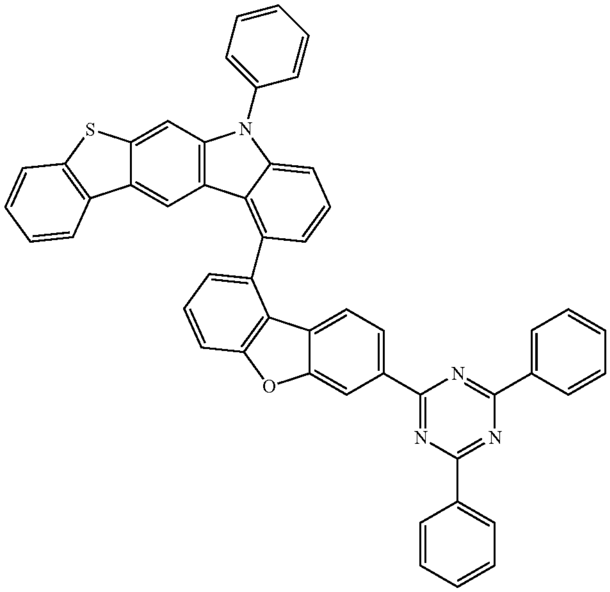 [SMILES: c1ccc(-c2nc(-c3ccccc3)nc(-c3ccc4c(c3)oc3cccc(-c5cccc6c5c5cc7c(cc5n6-c5ccccc5)sc5ccccc57)c34)n2)cc1]
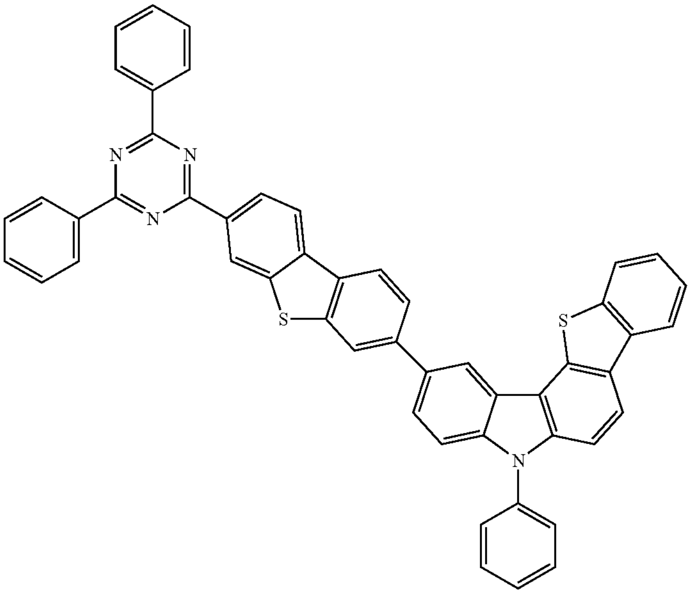 [SMILES: c1ccc(-c2nc(-c3ccccc3)nc(-c3ccc4c(c3)sc3cc(-c5ccc6c(c5)c5c7sc8ccccc8c7ccc5n6-c5ccccc5)ccc34)n2)cc1]

TABLE 3-continued
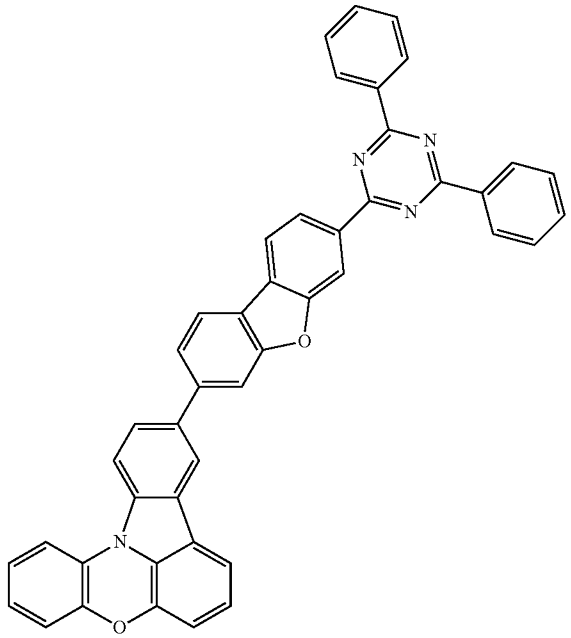 [SMILES: c1ccc(-c2nc(-c3ccccc3)nc(-c3ccc4c(c3)oc3cc(-c5ccc6c(c5)c5cccc7c5n6-c5ccccc5O7)ccc34)n2)cc1]
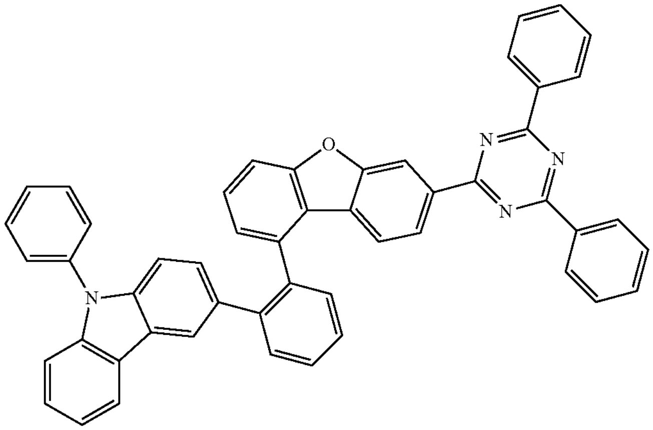 [SMILES: c1ccc(-c2nc(-c3ccccc3)nc(-c3ccc4c(c3)oc3cccc(-c5ccccc5-c5ccc6c(c5)c5ccccc5n6-c5ccccc5)c34)n2)cc1]
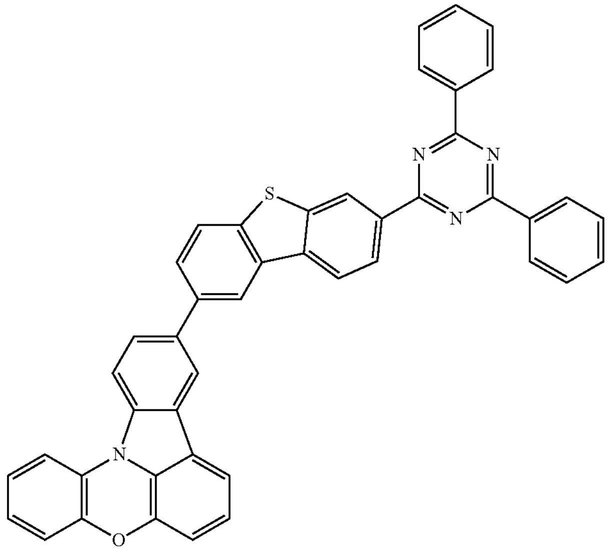 [SMILES: c1ccc(-c2nc(-c3ccccc3)nc(-c3ccc4c(c3)sc3ccc(-c5ccc6c(c5)c5cccc7c5n6-c5ccccc5O7)cc34)n2)cc1]

TABLE 3-continued
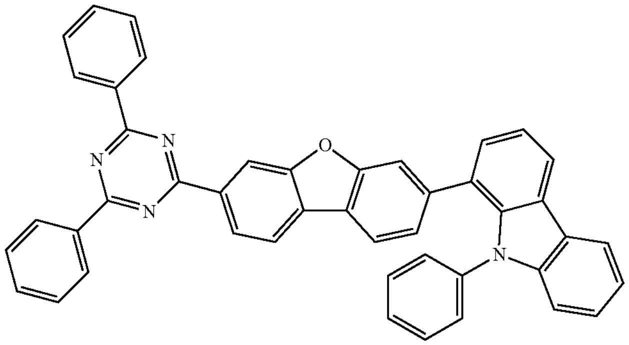
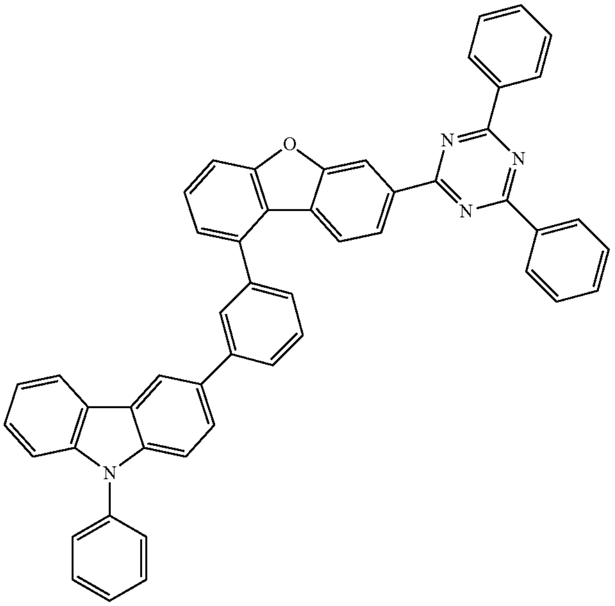
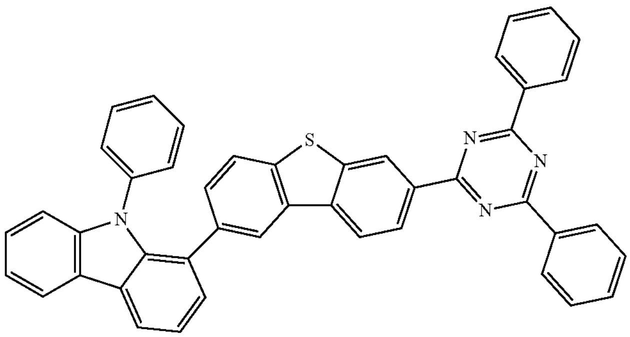 [SMILES: c1ccc(-c2nc(-c3ccccc3)nc(-c3ccc4c(c3)sc3ccc(-c5cccc6c7ccccc7n(-c7ccccc7)c56)cc34)n2)cc1]

TABLE 3-continued
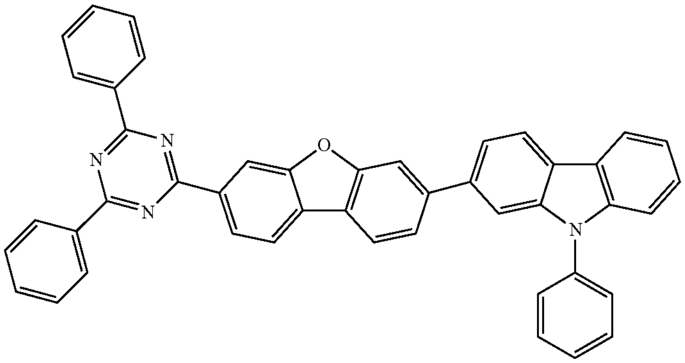
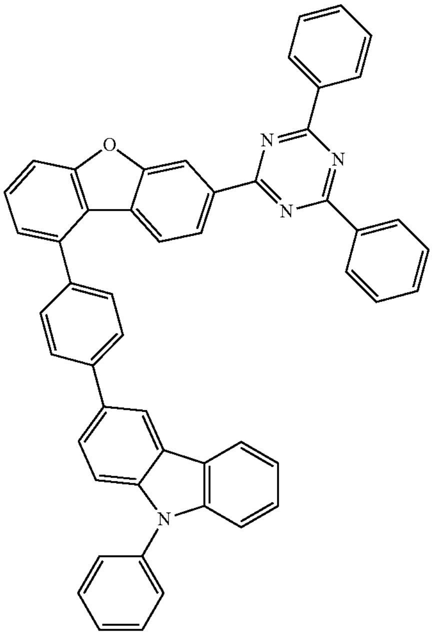 [SMILES: c1ccc(-c2nc(-c3ccccc3)nc(-c3ccc4c(c3)oc3cccc(-c5ccc(-c6ccc7c(c6)c6ccccc6n7-c6ccccc6)cc5)c34)n2)cc1]
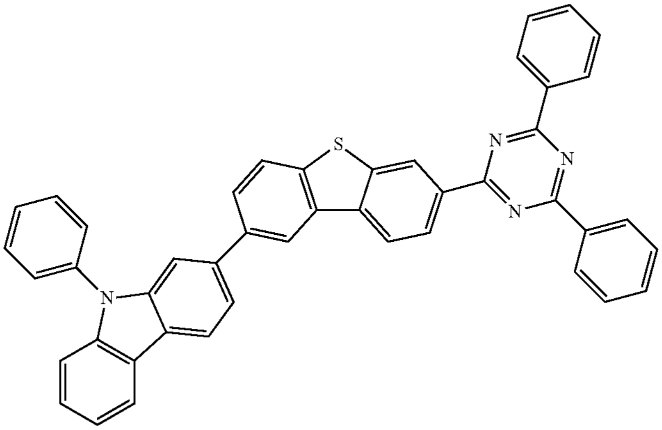 [SMILES: c1ccc(-c2nc(-c3ccccc3)nc(-c3ccc4c(c3)sc3ccc(-c5ccc6c7ccccc7n(-c7ccccc7)c6c5)cc34)n2)cc1]

TABLE 3-continued
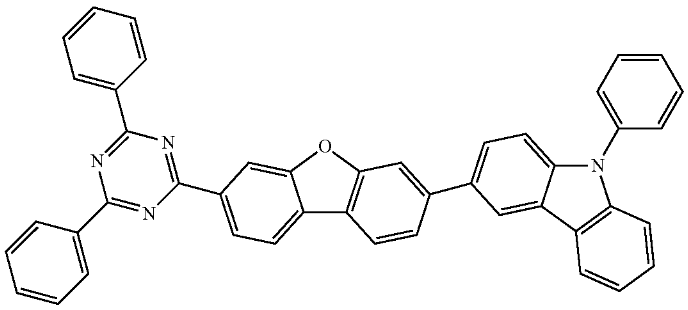
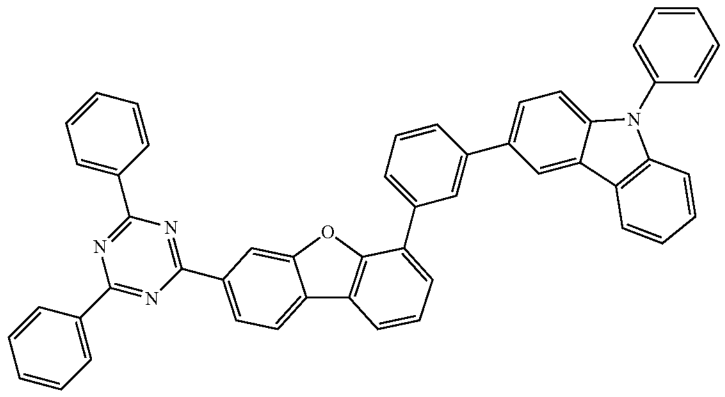 [SMILES: c1ccc(-c2nc(-c3ccccc3)nc(-c3ccc4c(c3)oc3c(-c5cccc(-c6ccc7c(c6)c6ccccc6n7-c6ccccc6)c5)cccc34)n2)cc1]
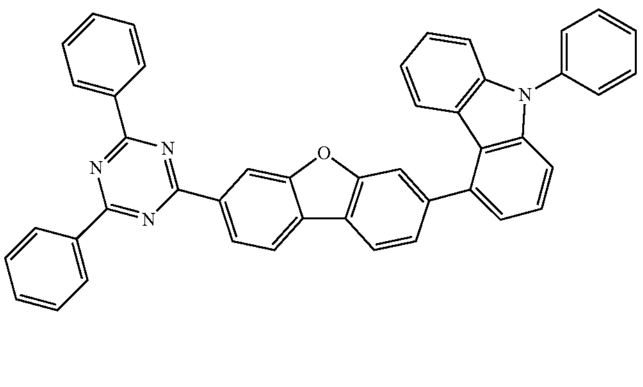

TABLE 3-continued
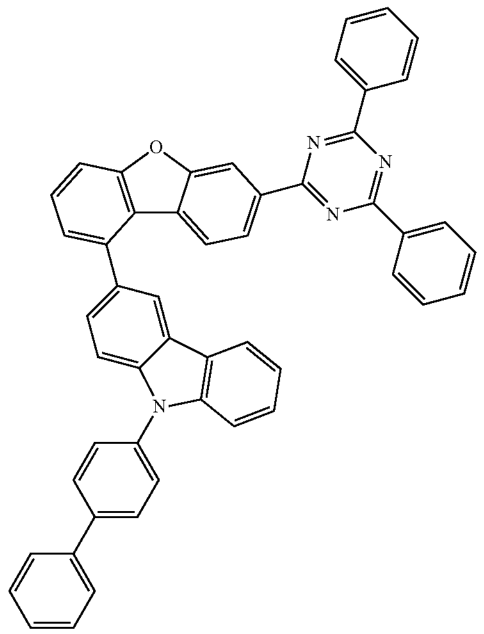 [SMILES: c1ccc(-c2ccc(-n3c4ccccc4c4cc(-c5cccc6oc7cc(-c8nc(-c9ccccc9)nc(-c9ccccc9)n8)ccc7c56)ccc43)cc2)cc1]
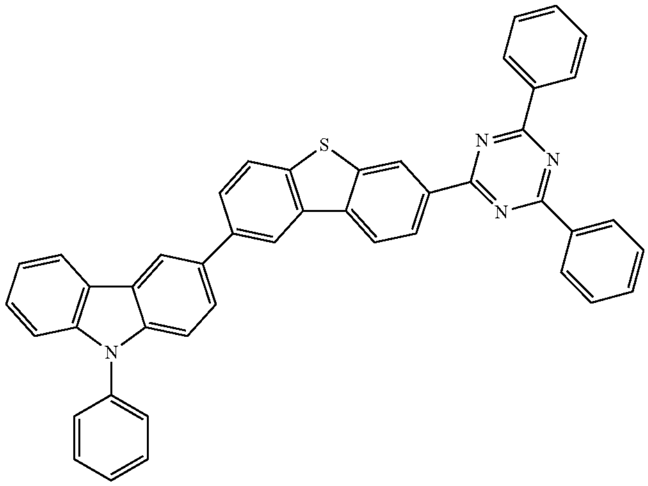 [SMILES: c1ccc(-c2nc(-c3ccccc3)nc(-c3ccc4c(c3)sc3ccc(-c5ccc6c(c5)c5ccccc5n6-c5ccccc5)cc34)n2)cc1]

TABLE 3-continued
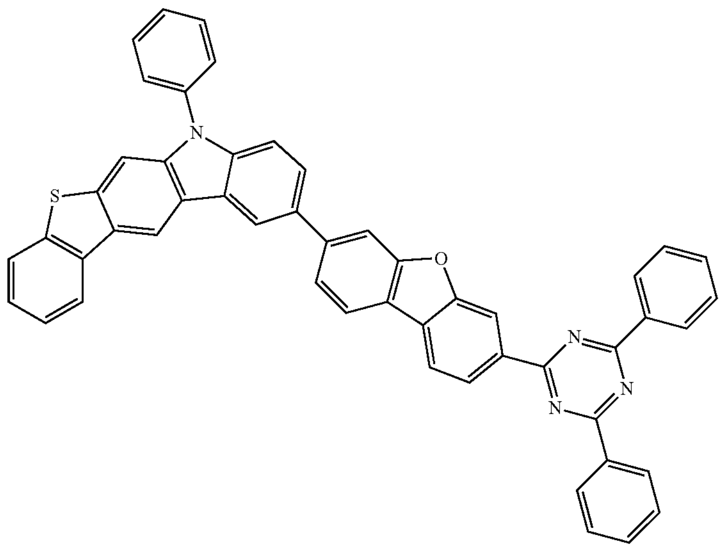 [SMILES: c1ccc(-c2nc(-c3ccccc3)nc(-c3ccc4c(c3)oc3cc(-c5ccc6c(c5)c5cc7c(cc5n6-c5ccccc5)sc5ccccc57)ccc34)n2)cc1]
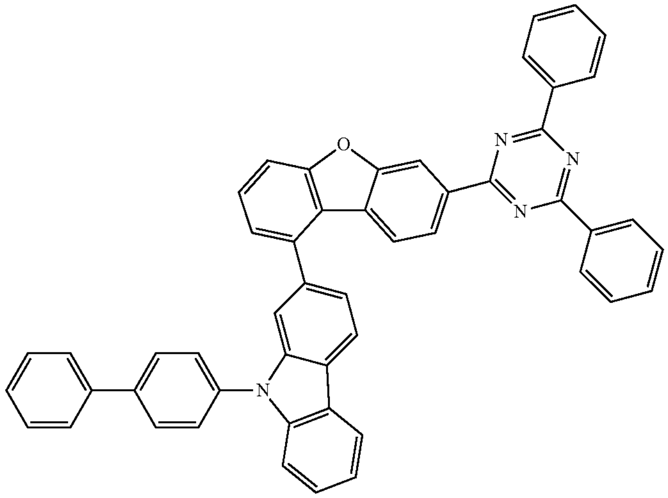 [SMILES: c1ccc(-c2ccc(-n3c4ccccc4c4ccc(-c5cccc6oc7cc(-c8nc(-c9ccccc9)nc(-c9ccccc9)n8)ccc7c56)cc43)cc2)cc1]
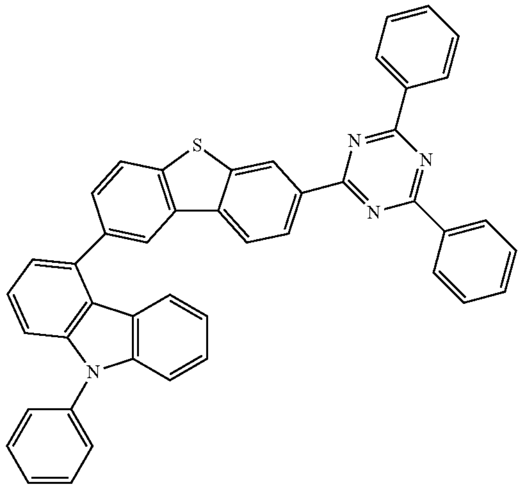 [SMILES: c1ccc(-c2nc(-c3ccccc3)nc(-c3ccc4c(c3)sc3ccc(-c5cccc6c5c5ccccc5n6-c5ccccc5)cc34)n2)cc1]

TABLE 3-continued
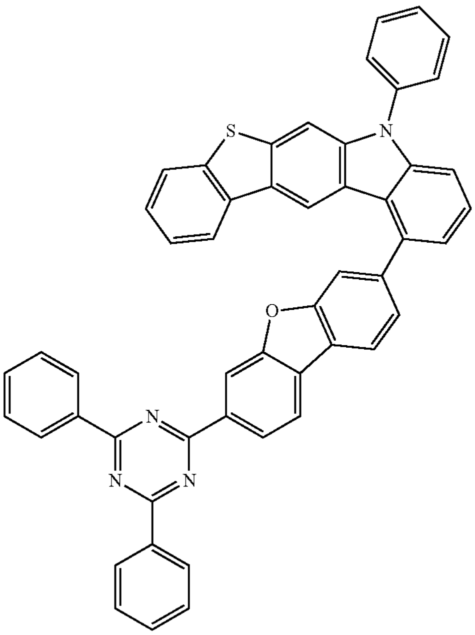 [SMILES: c1ccc(-c2nc(-c3ccccc3)nc(-c3ccc4c(c3)oc3cc(-c5cccc6c5c5cc7c(cc5n6-c5ccccc5)sc5ccccc57)ccc34)n2)cc1]
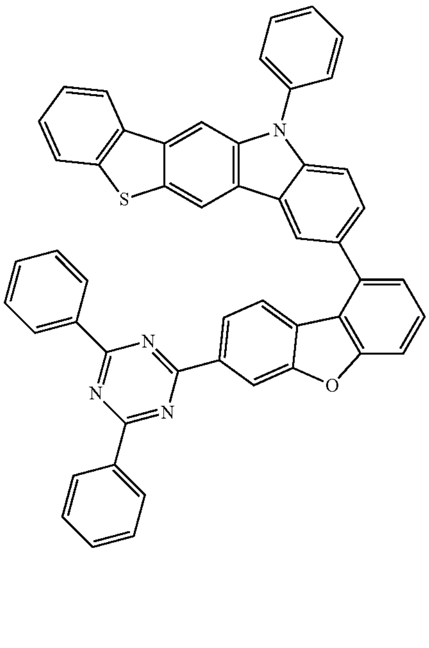 [SMILES: c1ccc(-c2nc(-c3ccccc3)nc(-c3ccc4c(c3)oc3cccc(-c5ccc6c(c5)c5cc7sc8ccccc8c7cc5n6-c5ccccc5)c34)n2)cc1]

TABLE 3-continued
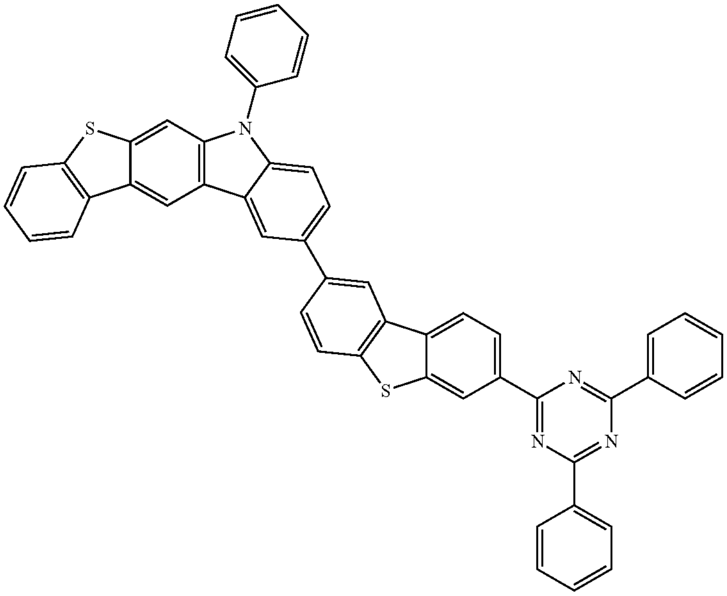 [SMILES: c1ccc(-c2nc(-c3ccccc3)nc(-c3ccc4c(c3)sc3ccc(-c5ccc6c(c5)c5cc7c(cc5n6-c5ccccc5)sc5ccccc57)cc34)n2)cc1]
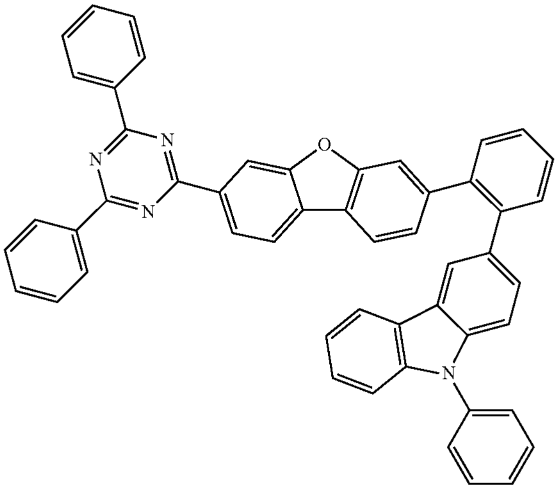
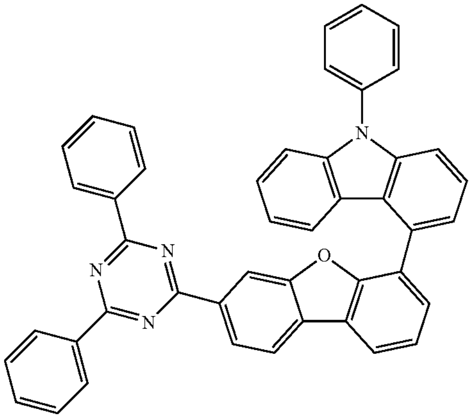 [SMILES: c1ccc(-c2nc(-c3ccccc3)nc(-c3ccc4c(c3)oc3c(-c5cccc6c5c5ccccc5n6-c5ccccc5)cccc34)n2)cc1]

TABLE 3-continued
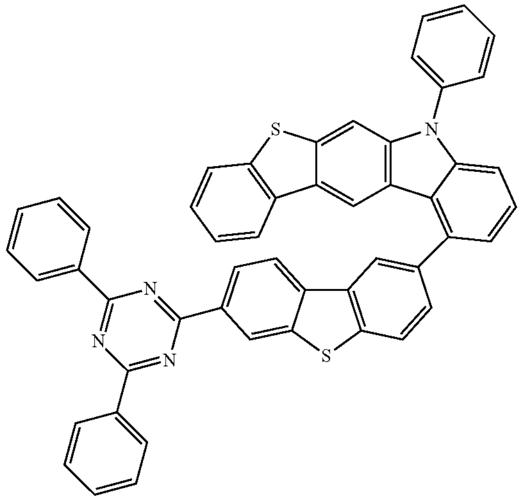 [SMILES: c1ccc(-c2nc(-c3ccccc3)nc(-c3ccc4c(c3)sc3ccc(-c5cccc6c5c5cc7c(cc5n6-c5ccccc5)sc5ccccc57)cc34)n2)cc1]
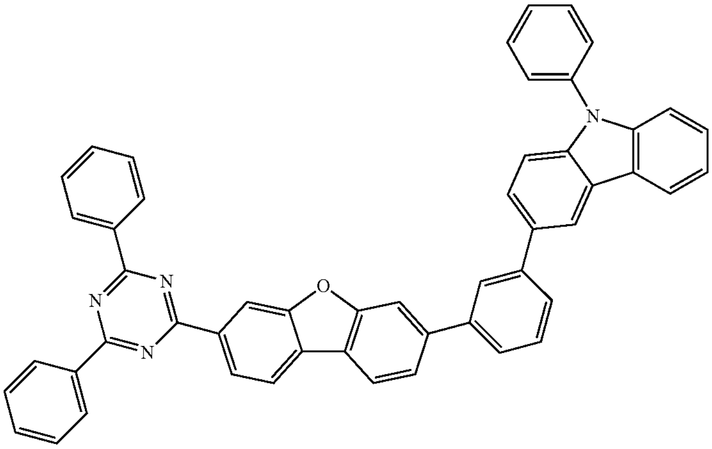 [SMILES: c1ccc(-c2nc(-c3ccccc3)nc(-c3ccc4c(c3)oc3cc(-c5cccc(-c6ccc7c(c6)c6ccccc6n7-c6ccccc6)c5)ccc34)n2)cc1]
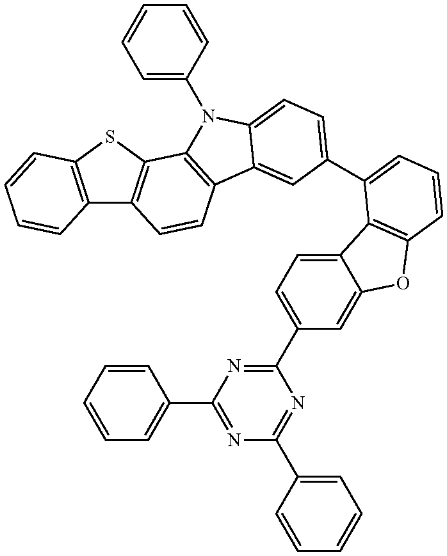

TABLE 3-continued
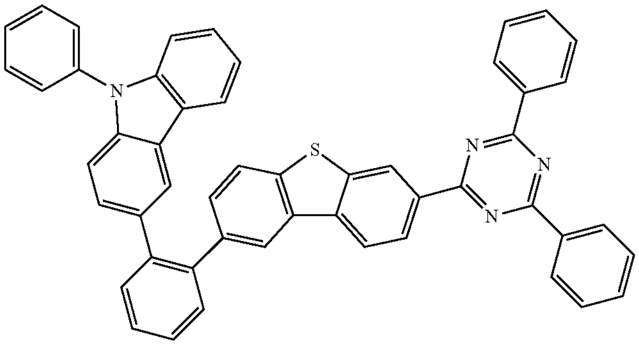 [SMILES: c1ccc(-c2nc(-c3ccccc3)nc(-c3ccc4c(c3)sc3ccc(-c5ccccc5-c5ccc6c(c5)c5ccccc5n6-c5ccccc5)cc34)n2)cc1]
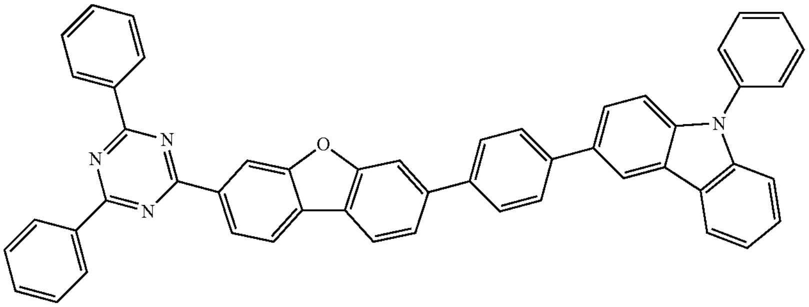 [SMILES: c1ccc(-c2nc(-c3ccccc3)nc(-c3ccc4c(c3)oc3cc(-c5ccc(-c6ccc7c(c6)c6ccccc6n7-c6ccccc6)cc5)ccc34)n2)cc1]
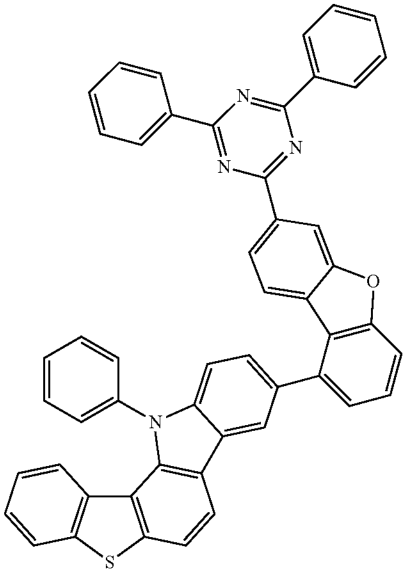 [SMILES: c1ccc(-c2nc(-c3ccccc3)nc(-c3ccc4c(c3)oc3cccc(-c5ccc6c(c5)c5ccc7sc8ccccc8c7c5n6-c5ccccc5)c34)n2)cc1]
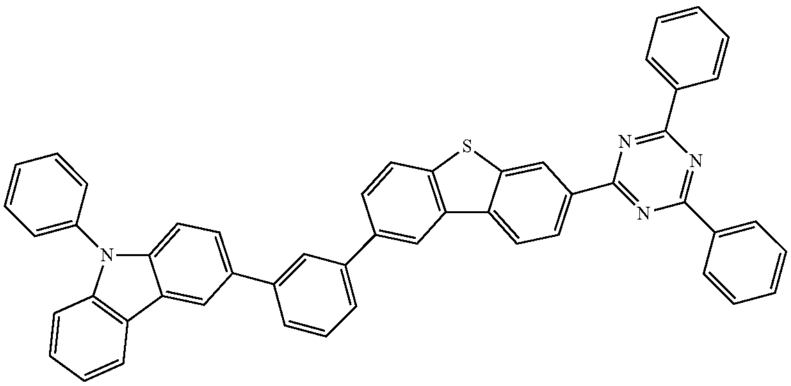 [SMILES: c1ccc(-c2nc(-c3ccccc3)nc(-c3ccc4c(c3)sc3ccc(-c5cccc(-c6ccc7c(c6)c6ccccc6n7-c6ccccc6)c5)cc34)n2)cc1]

TABLE 3-continued
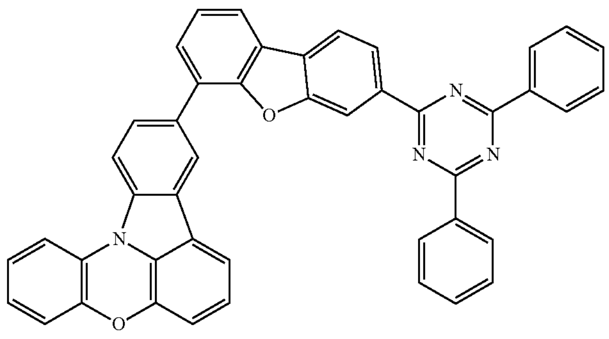 [SMILES: c1ccc(-c2nc(-c3ccccc3)nc(-c3ccc4c(c3)oc3c(-c5ccc6c(c5)c5cccc7c5n6-c5ccccc5O7)cccc34)n2)cc1]
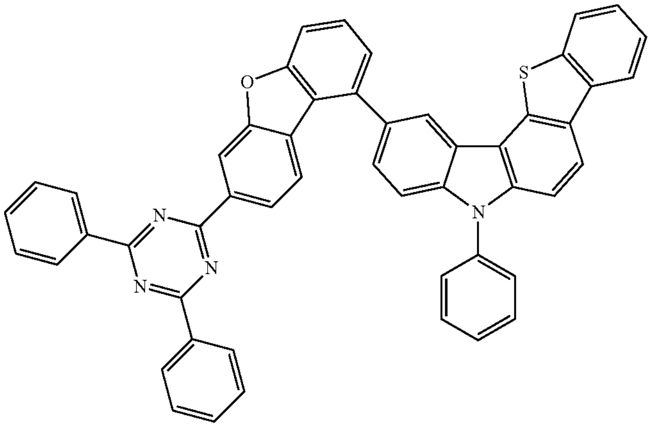 [SMILES: c1ccc(-c2nc(-c3ccccc3)nc(-c3ccc4c(c3)oc3cccc(-c5ccc6c(c5)c5c7sc8ccccc8c7ccc5n6-c5ccccc5)c34)n2)cc1]
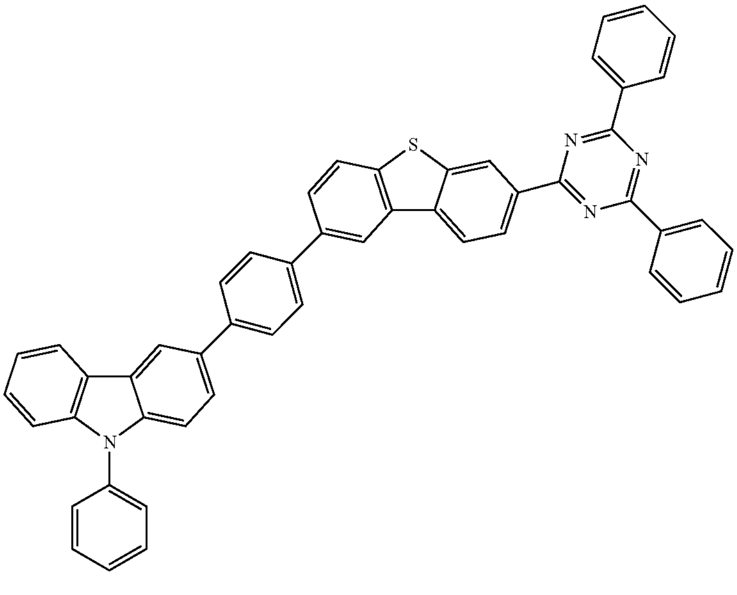 [SMILES: c1ccc(-c2nc(-c3ccccc3)nc(-c3ccc4c(c3)sc3ccc(-c5ccc(-c6ccc7c(c6)c6ccccc6n7-c6ccccc6)cc5)cc34)n2)cc1]

TABLE 3-continued
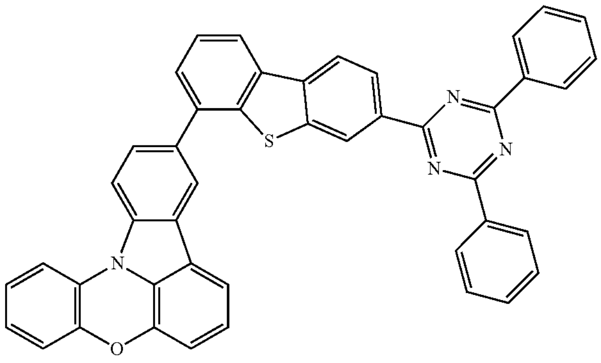 [SMILES: c1ccc(-c2nc(-c3ccccc3)nc(-c3ccc4c(c3)sc3c(-c5ccc6c(c5)c5cccc7c5n6-c5ccccc5O7)cccc34)n2)cc1]
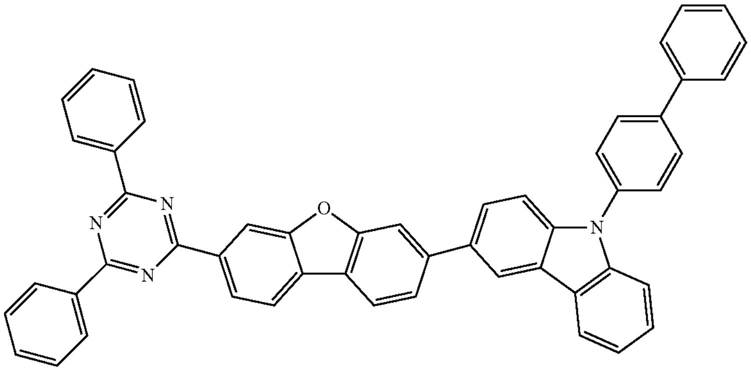 [SMILES: c1ccc(-c2ccc(-n3c4ccccc4c4cc(-c5ccc6c(c5)oc5cc(-c7nc(-c8ccccc8)nc(-c8ccccc8)n7)ccc56)ccc43)cc2)cc1]
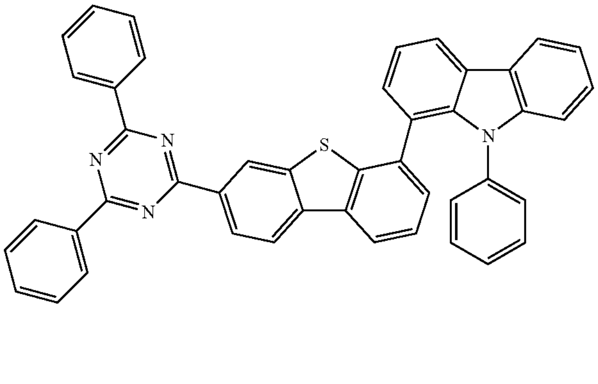 [SMILES: c1ccc(-c2nc(-c3ccccc3)nc(-c3ccc4c(c3)sc3c(-c5cccc6c7ccccc7n(-c7ccccc7)c56)cccc34)n2)cc1]

TABLE 3-continued
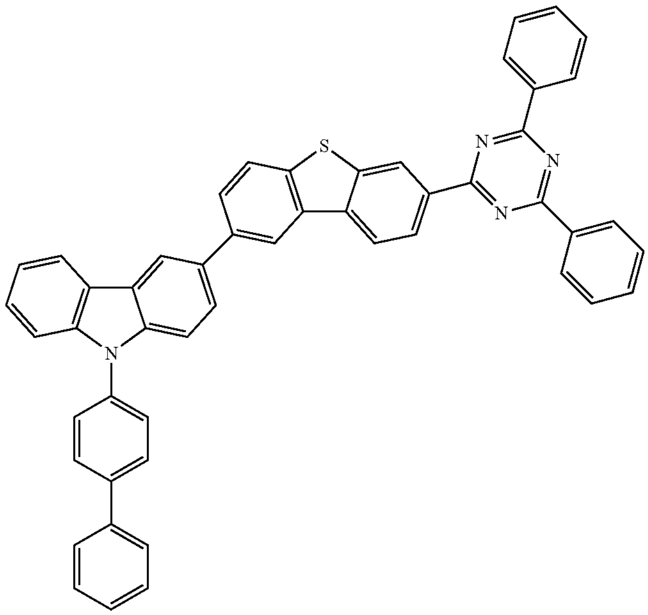 [SMILES: c1ccc(-c2ccc(-n3c4ccccc4c4cc(-c5ccc6sc7cc(-c8nc(-c9ccccc9)nc(-c9ccccc9)n8)ccc7c6c5)ccc43)cc2)cc1]
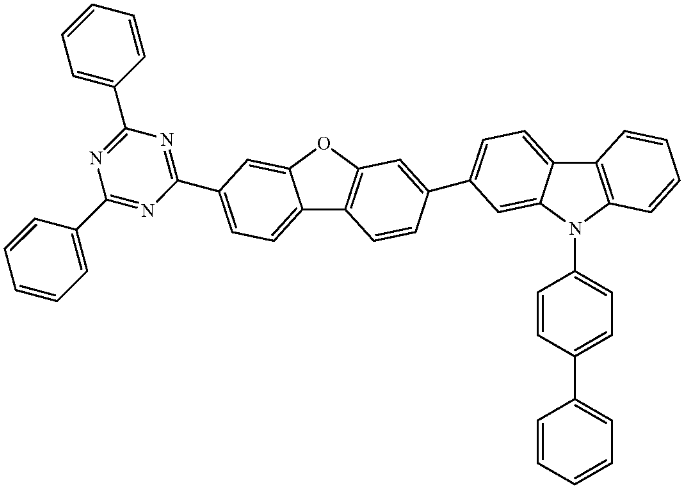
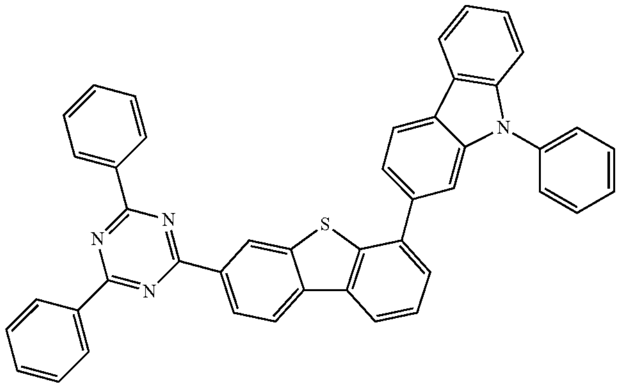

TABLE 3-continued
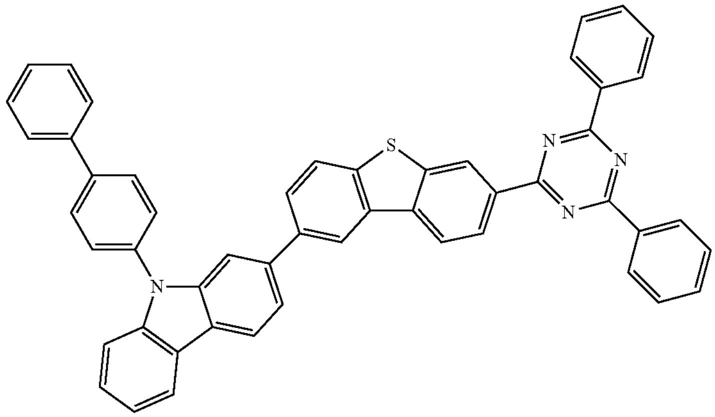
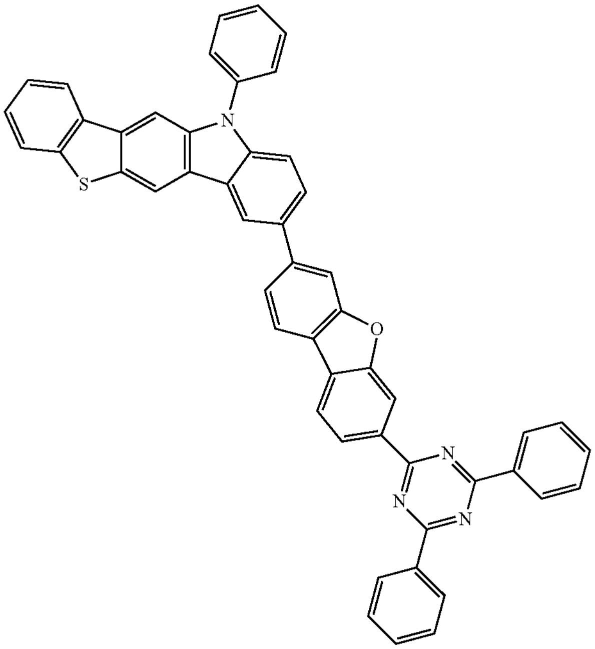 [SMILES: c1ccc(-c2nc(-c3ccccc3)nc(-c3ccc4c(c3)oc3cc(-c5ccc6c(c5)c5cc7sc8ccccc8c7cc5n6-c5ccccc5)ccc34)n2)cc1]
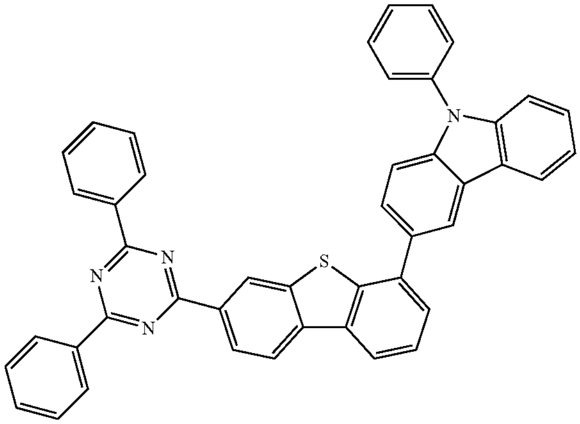 [SMILES: c1ccc(-c2nc(-c3ccccc3)nc(-c3ccc4c(c3)sc3c(-c5ccc6c(c5)c5ccccc5n6-c5ccccc5)cccc34)n2)cc1]

TABLE 3-continued
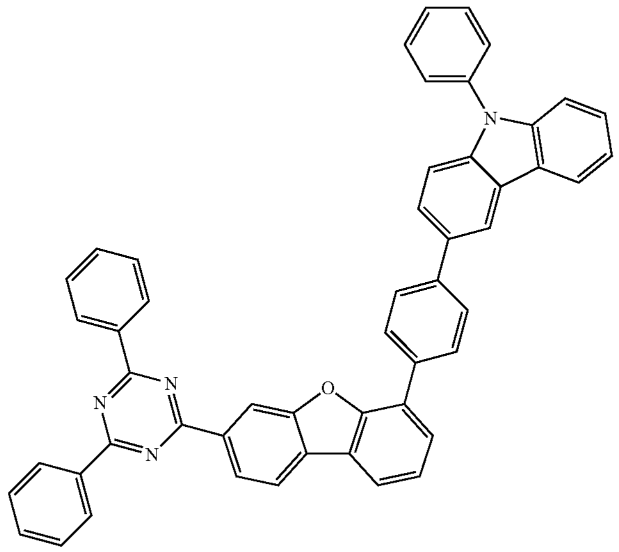
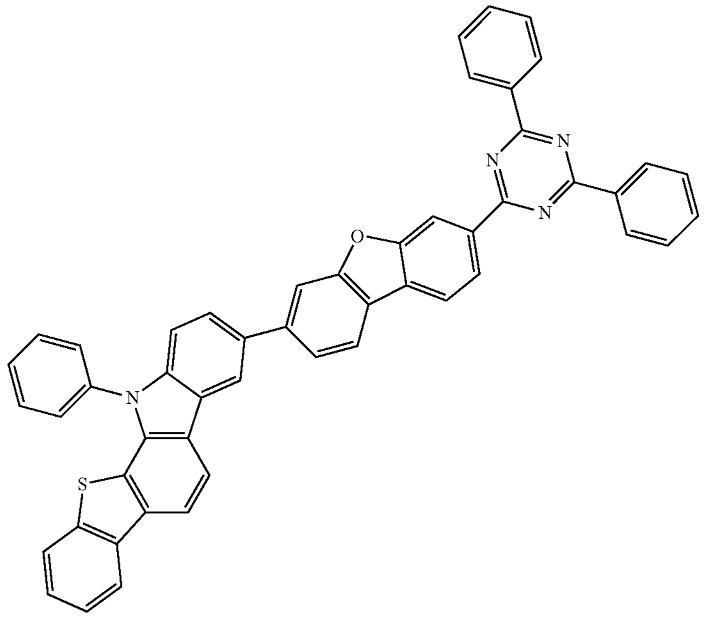 [SMILES: c1ccc(-c2nc(-c3ccccc3)nc(-c3ccc4c(c3)oc3cc(-c5ccc6c(c5)c5ccc7c8ccccc8sc7c5n6-c5ccccc5)ccc34)n2)cc1]
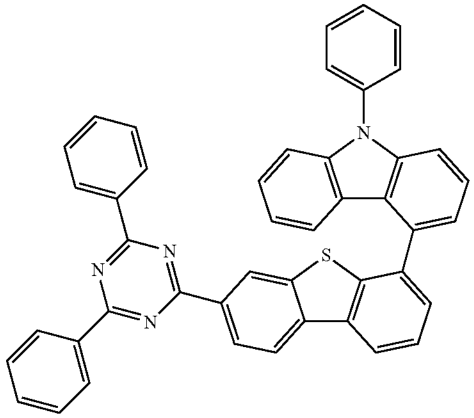

TABLE 3-continued
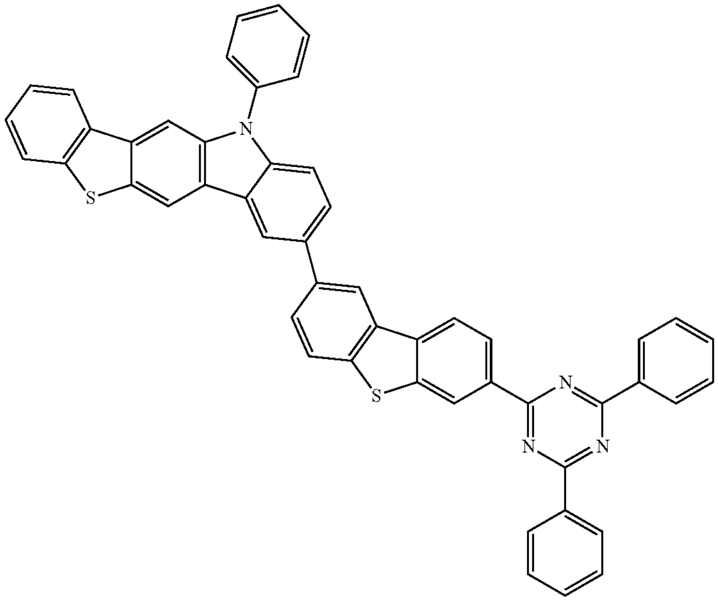 [SMILES: c1ccc(-c2nc(-c3ccccc3)nc(-c3ccc4c(c3)sc3ccc(-c5ccc6c(c5)c5cc7sc8ccccc8c7cc5n6-c5ccccc5)cc34)n2)cc1]
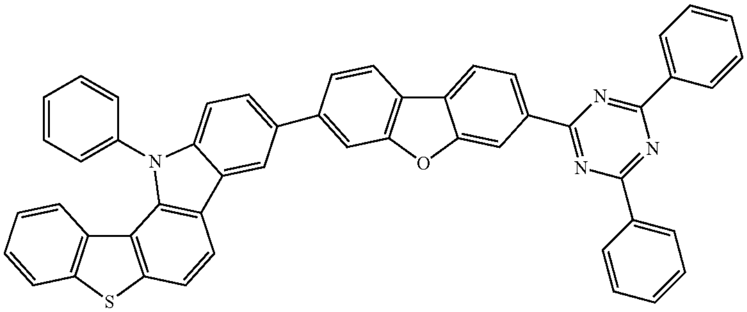 [SMILES: c1ccc(-c2nc(-c3ccccc3)nc(-c3ccc4c(c3)oc3cc(-c5ccc6c(c5)c5ccc7sc8ccccc8c7c5n6-c5ccccc5)ccc34)n2)cc1]
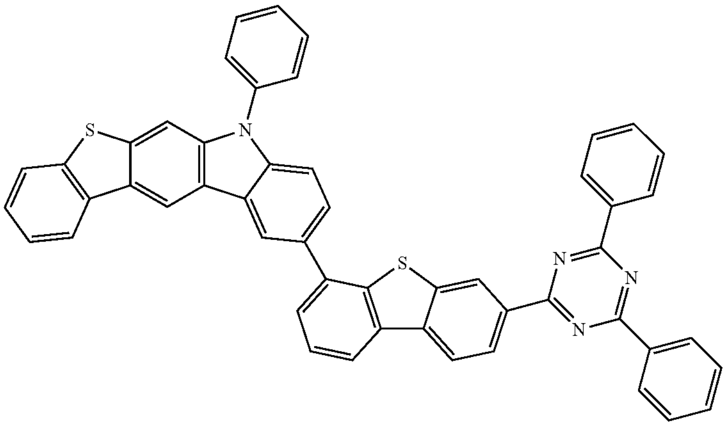 [SMILES: c1ccc(-c2nc(-c3ccccc3)nc(-c3ccc4c(c3)sc3c(-c5ccc6c(c5)c5cc7c(cc5n6-c5ccccc5)sc5ccccc57)cccc34)n2)cc1]

TABLE 3-continued
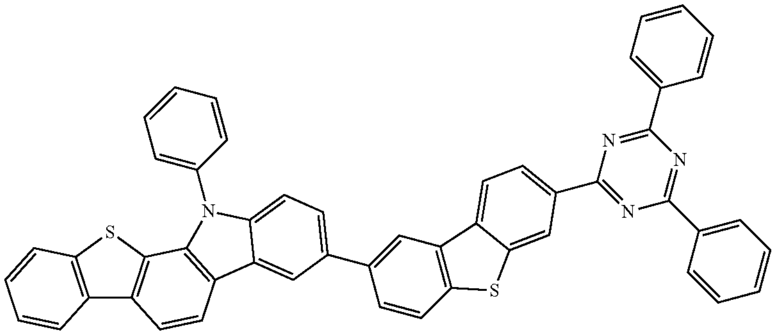 [SMILES: c1ccc(-c2nc(-c3ccccc3)nc(-c3ccc4c(c3)sc3ccc(-c5ccc6c(c5)c5ccc7c8ccccc8sc7c5n6-c5ccccc5)cc34)n2)cc1]
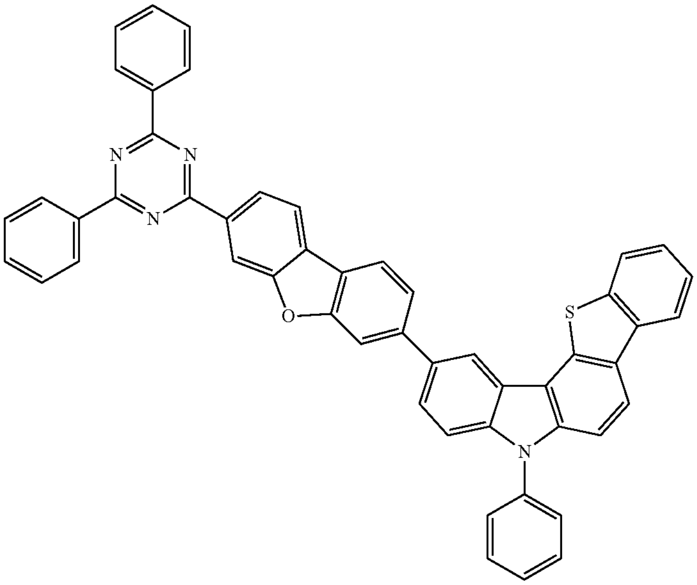 [SMILES: c1ccc(-c2nc(-c3ccccc3)nc(-c3ccc4c(c3)oc3cc(-c5ccc6c(c5)c5c7sc8ccccc8c7ccc5n6-c5ccccc5)ccc34)n2)cc1]
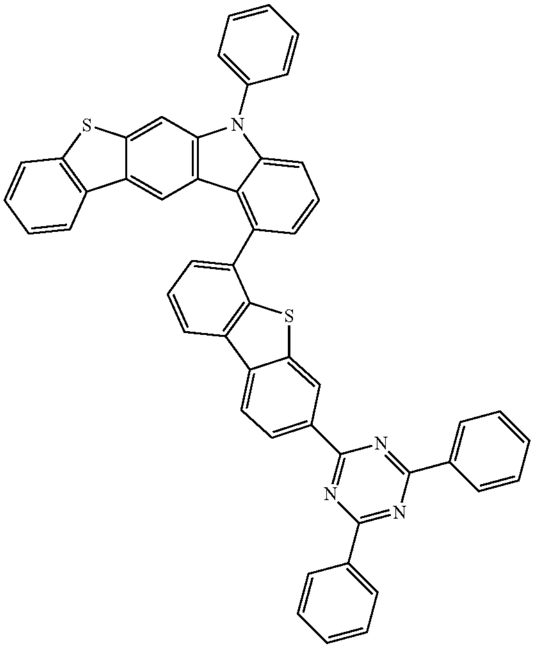 [SMILES: c1ccc(-c2nc(-c3ccccc3)nc(-c3ccc4c(c3)sc3c(-c5cccc6c5c5cc7c(cc5n6-c5ccccc5)sc5ccccc57)cccc34)n2)cc1]

TABLE 3-continued
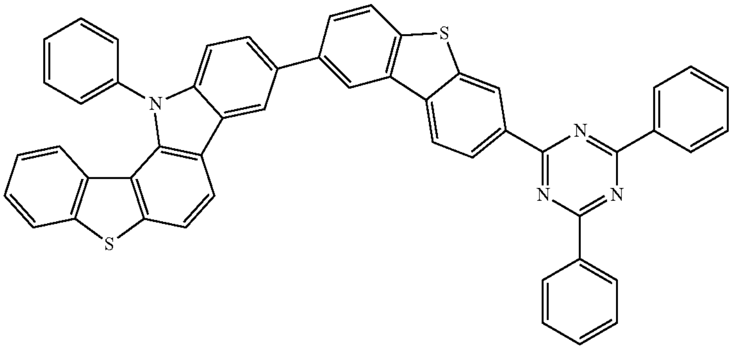 [SMILES: c1ccc(-c2nc(-c3ccccc3)nc(-c3ccc4c(c3)sc3ccc(-c5ccc6c(c5)c5ccc7sc8ccccc8c7c5n6-c5ccccc5)cc34)n2)cc1]
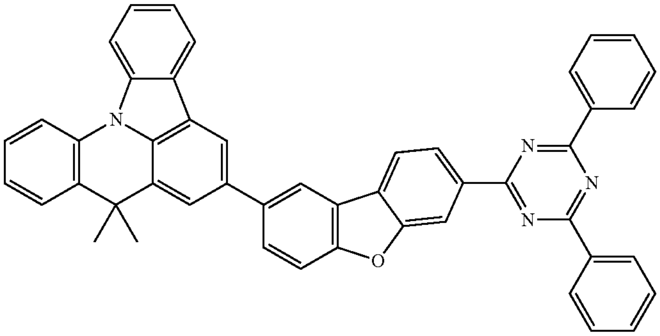 [SMILES: CC1(C)c2ccccc2-n2c3ccccc3c3cc(-c4ccc5oc6cc(-c7nc(-c8ccccc8)nc(-c8ccccc8)n7)ccc6c5c4)cc1c32]
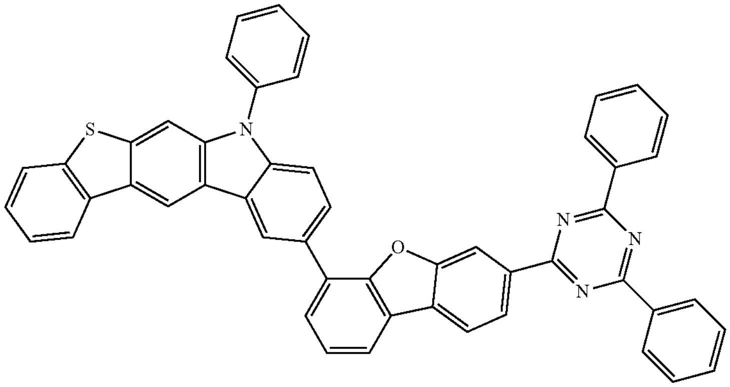 [SMILES: c1ccc(-c2nc(-c3ccccc3)nc(-c3ccc4c(c3)oc3c(-c5ccc6c(c5)c5cc7c(cc5n6-c5ccccc5)sc5ccccc57)cccc34)n2)cc1]
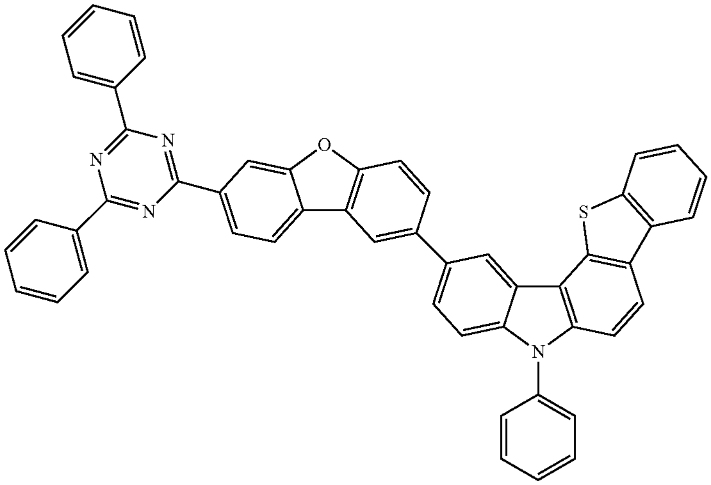 [SMILES: c1ccc(-c2nc(-c3ccccc3)nc(-c3ccc4c(c3)oc3ccc(-c5ccc6c(c5)c5c7sc8ccccc8c7ccc5n6-c5ccccc5)cc34)n2)cc1]

TABLE 3-continued
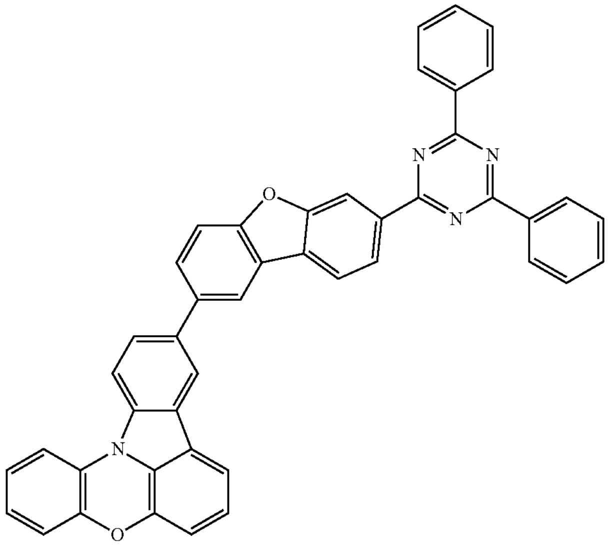
46
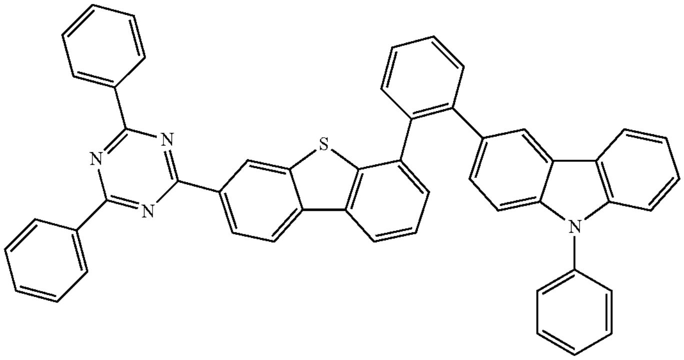
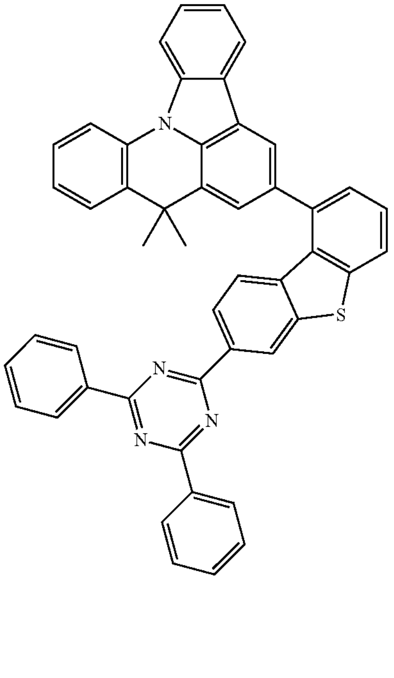 [SMILES: CC1(C)c2ccccc2-n2c3ccccc3c3cc(-c4cccc5sc6cc(-c7nc(-c8ccccc8)nc(-c8ccccc8)n7)ccc6c45)cc1c32]

TABLE 3-continued
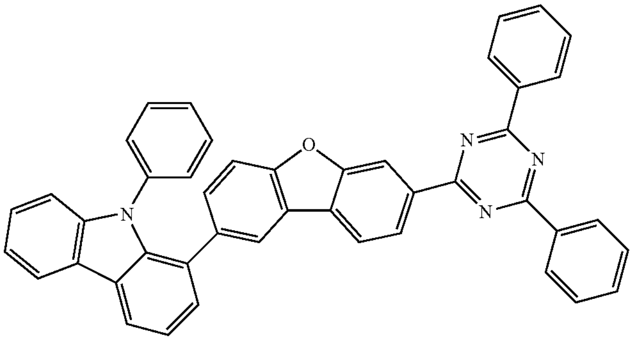 [SMILES: c1ccc(-c2nc(-c3ccccc3)nc(-c3ccc4c(c3)oc3ccc(-c5cccc6c7ccccc7n(-c7ccccc7)c56)cc34)n2)cc1]
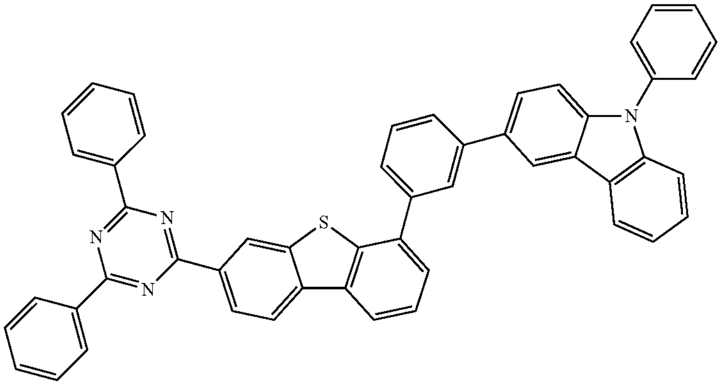 [SMILES: c1ccc(-c2nc(-c3ccccc3)nc(-c3ccc4c(c3)sc3c(-c5cccc(-c6ccc7c(c6)c6ccccc6n7-c6ccccc6)c5)cccc34)n2)cc1]
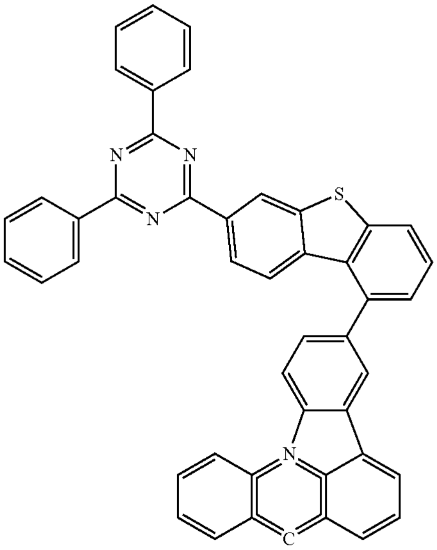
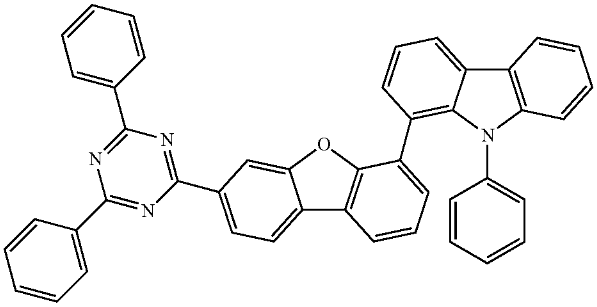 [SMILES: c1ccc(-c2nc(-c3ccccc3)nc(-c3ccc4c(c3)oc3c(-c5cccc6c7ccccc7n(-c7ccccc7)c56)cccc34)n2)cc1]

TABLE 3-continued
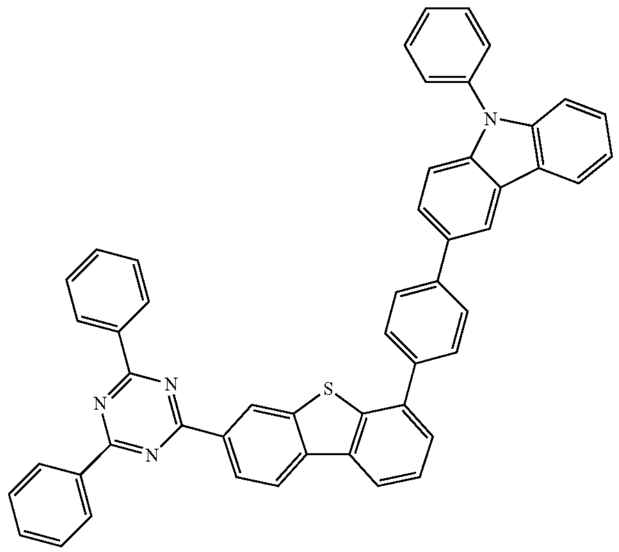 [SMILES: c1ccc(-c2nc(-c3ccccc3)nc(-c3ccc4c(c3)sc3c(-c5ccc(-c6ccc7c(c6)c6ccccc6n7-c6ccccc6)cc5)cccc34)n2)cc1]
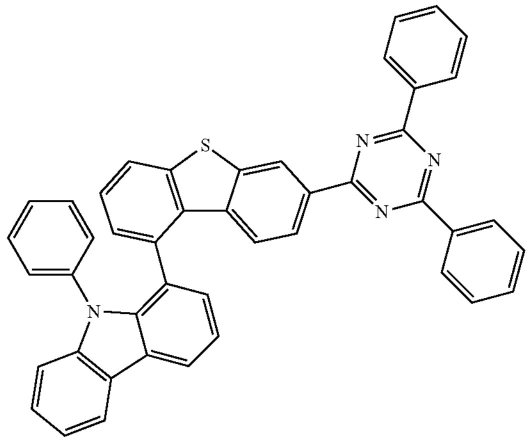 [SMILES: c1ccc(-c2nc(-c3ccccc3)nc(-c3ccc4c(c3)sc3cccc(-c5cccc6c7ccccc7n(-c7ccccc7)c56)c34)n2)cc1]
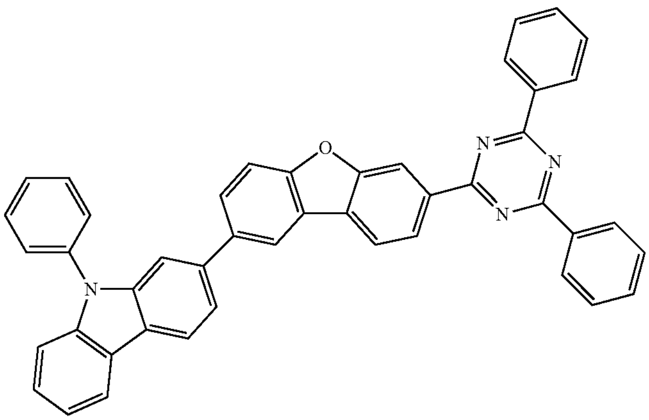 [SMILES: c1ccc(-c2nc(-c3ccccc3)nc(-c3ccc4c(c3)oc3ccc(-c5ccc6c7ccccc7n(-c7ccccc7)c6c5)cc34)n2)cc1]

TABLE 3-continued
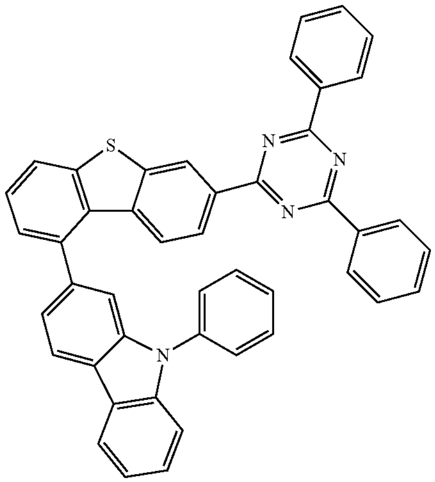
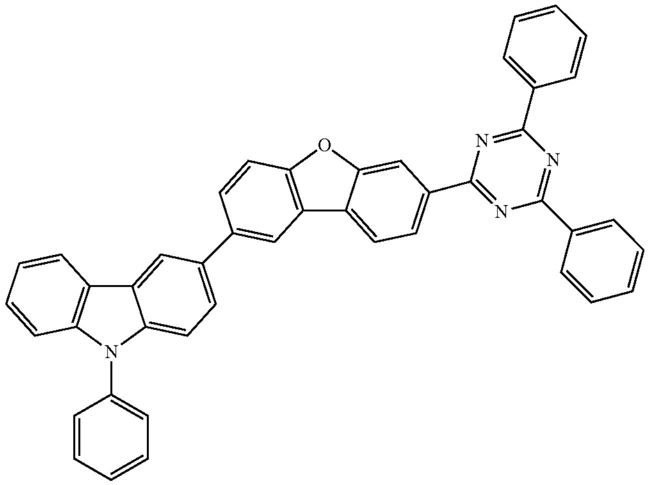
47
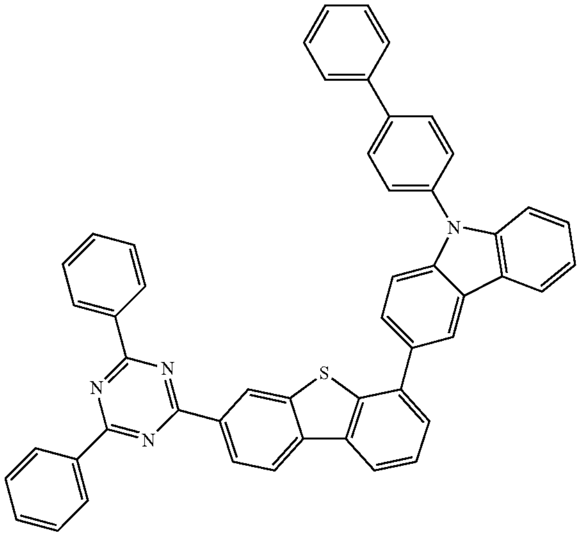

TABLE 3-continued
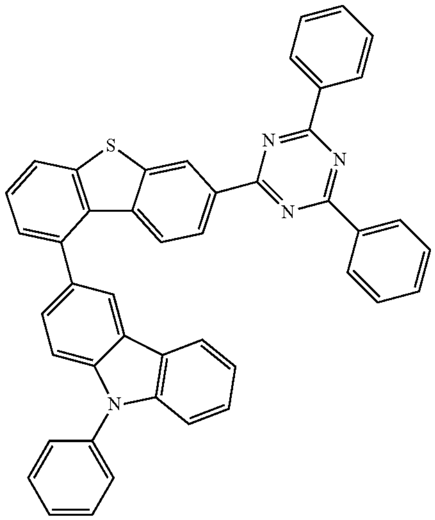 [SMILES: c1ccc(-c2nc(-c3ccccc3)nc(-c3ccc4c(c3)sc3cccc(-c5ccc6c(c5)c5ccccc5n6-c5ccccc5)c34)n2)cc1]
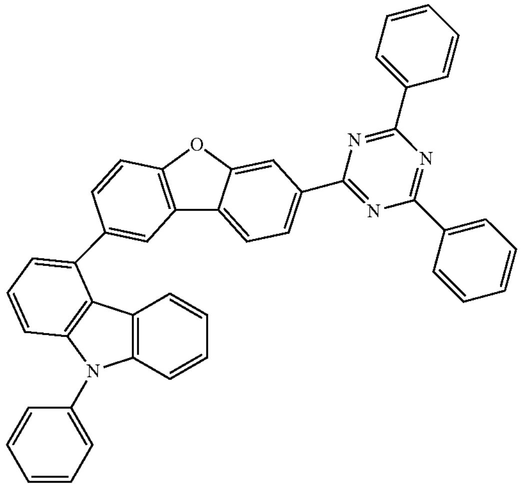
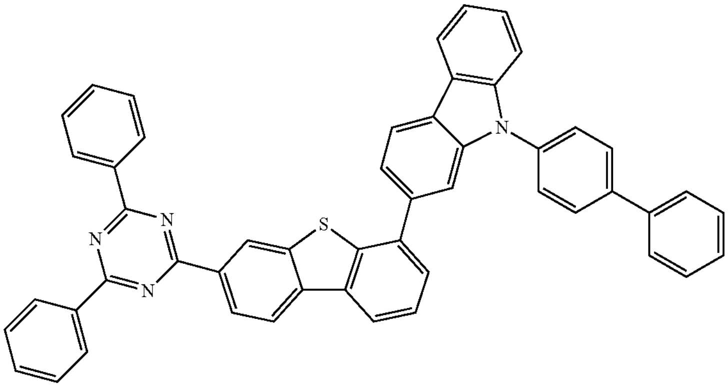

TABLE 3-continued
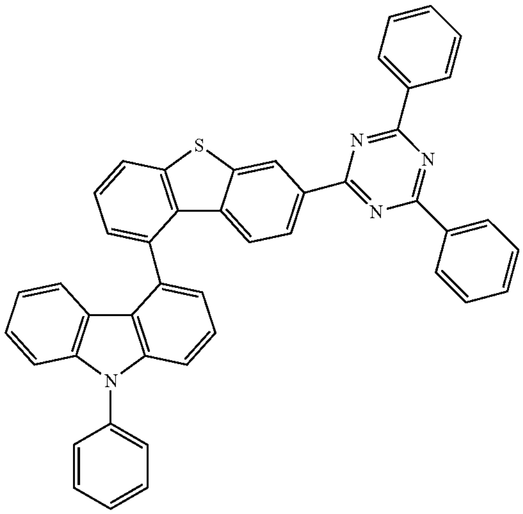 [SMILES: c1ccc(-c2nc(-c3ccccc3)nc(-c3ccc4c(c3)sc3cccc(-c5cccc6c5c5ccccc5n6-c5ccccc5)c34)n2)cc1]
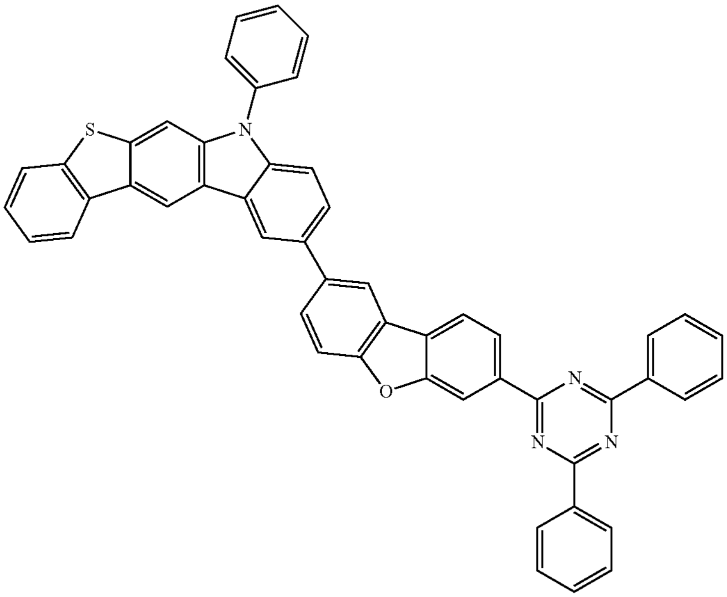
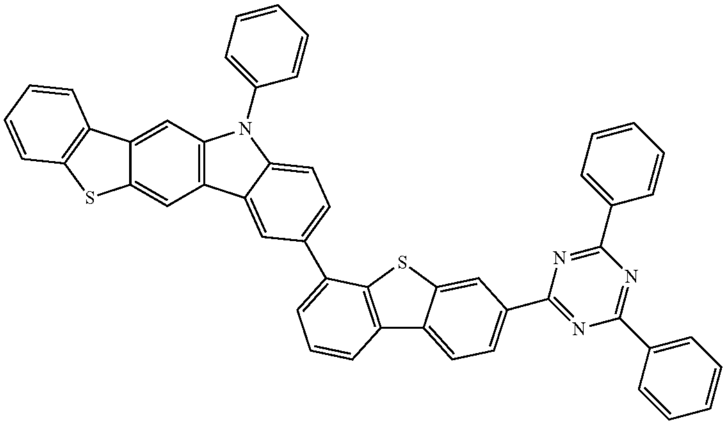 [SMILES: c1ccc(-c2nc(-c3ccccc3)nc(-c3ccc4c(c3)sc3c(-c5ccc6c(c5)c5cc7sc8ccccc8c7cc5n6-c5ccccc5)cccc34)n2)cc1]

TABLE 3-continued
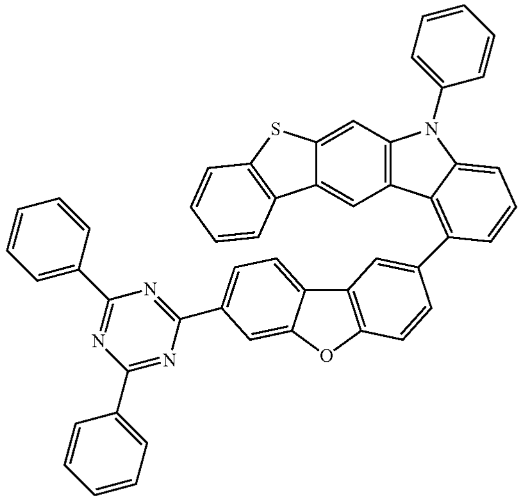
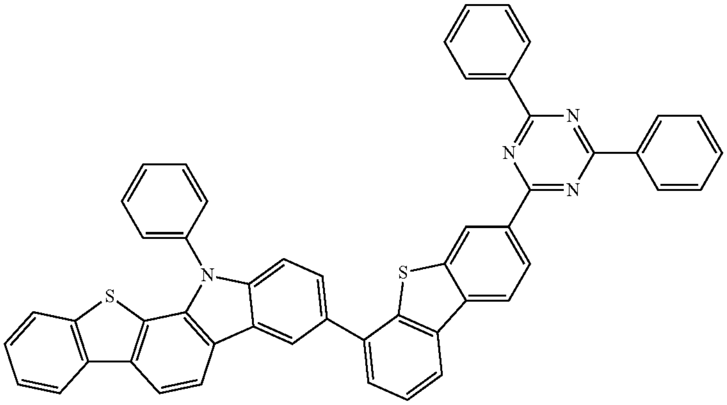
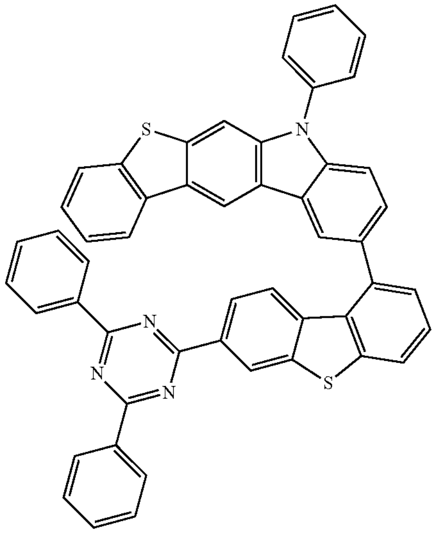 [SMILES: c1ccc(-c2nc(-c3ccccc3)nc(-c3ccc4c(c3)sc3cccc(-c5ccc6c(c5)c5cc7c(cc5n6-c5ccccc5)sc5ccccc57)c34)n2)cc1]

TABLE 3-continued
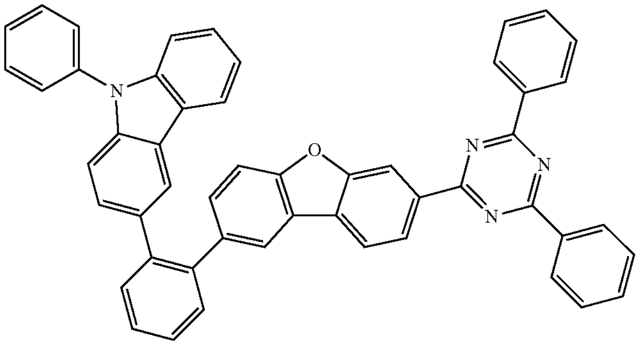 [SMILES: c1ccc(-c2nc(-c3ccccc3)nc(-c3ccc4c(c3)oc3ccc(-c5ccccc5-c5ccc6c(c5)c5ccccc5n6-c5ccccc5)cc34)n2)cc1]
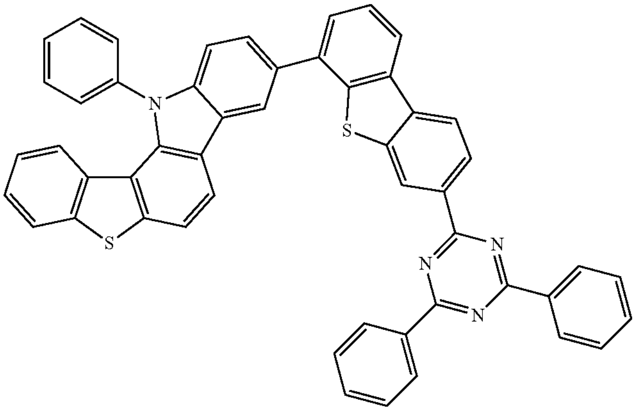 [SMILES: c1ccc(-c2nc(-c3ccccc3)nc(-c3ccc4c(c3)sc3c(-c5ccc6c(c5)c5ccc7sc8ccccc8c7c5n6-c5ccccc5)cccc34)n2)cc1]
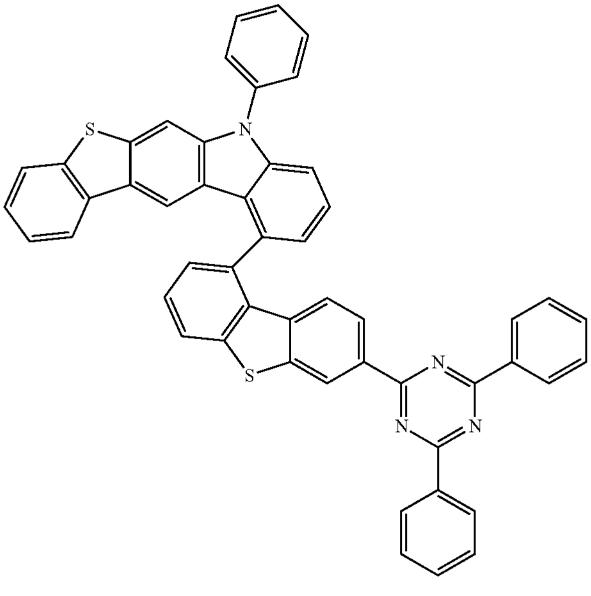 [SMILES: c1ccc(-c2nc(-c3ccccc3)nc(-c3ccc4c(c3)sc3cccc(-c5cccc6c5c5cc7c(cc5n6-c5ccccc5)sc5ccccc57)c34)n2)cc1]

TABLE 3-continued
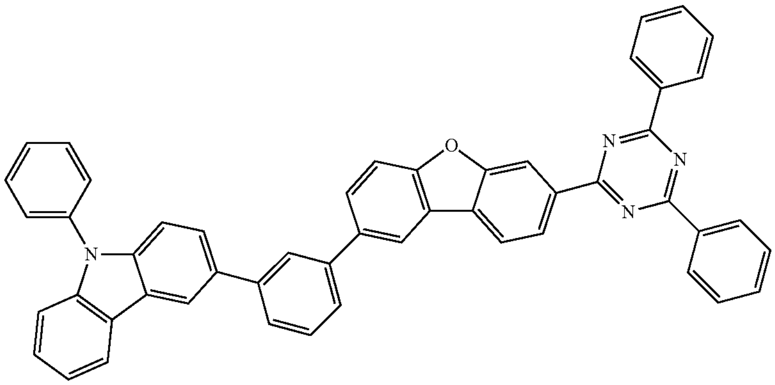
48
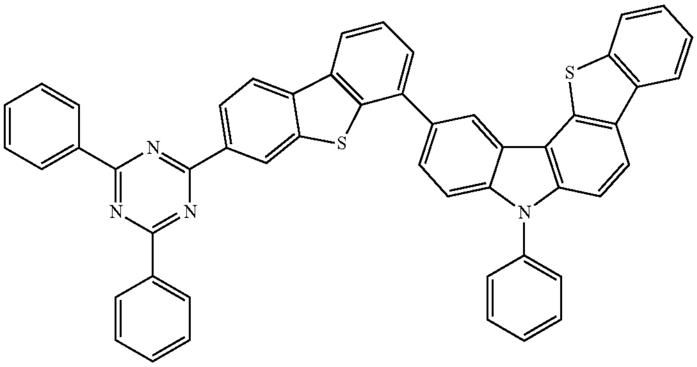 [SMILES: c1ccc(-c2nc(-c3ccccc3)nc(-c3ccc4c(c3)sc3c(-c5ccc6c(c5)c5c7sc8ccccc8c7ccc5n6-c5ccccc5)cccc34)n2)cc1]
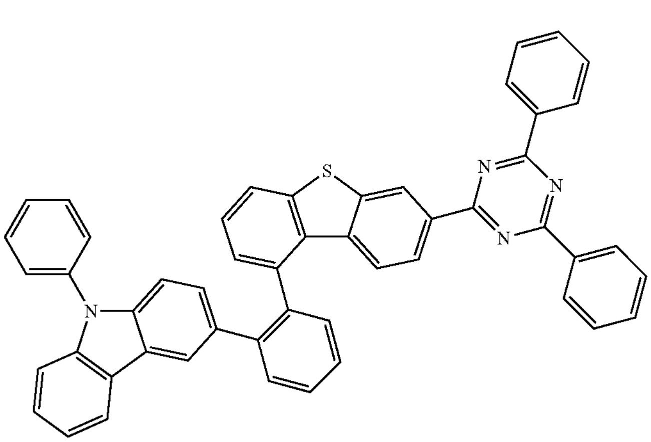 [SMILES: c1ccc(-c2nc(-c3ccccc3)nc(-c3ccc4c(c3)sc3cccc(-c5ccccc5-c5ccc6c(c5)c5ccccc5n6-c5ccccc5)c34)n2)cc1]

TABLE 3-continued
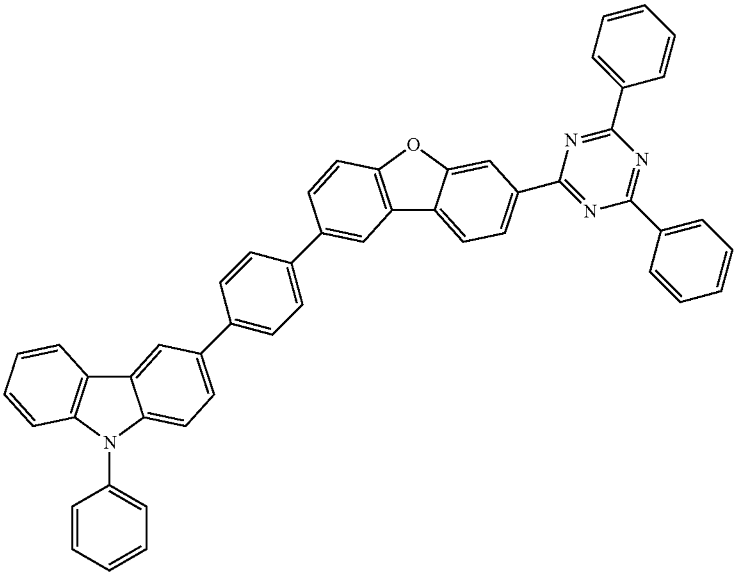
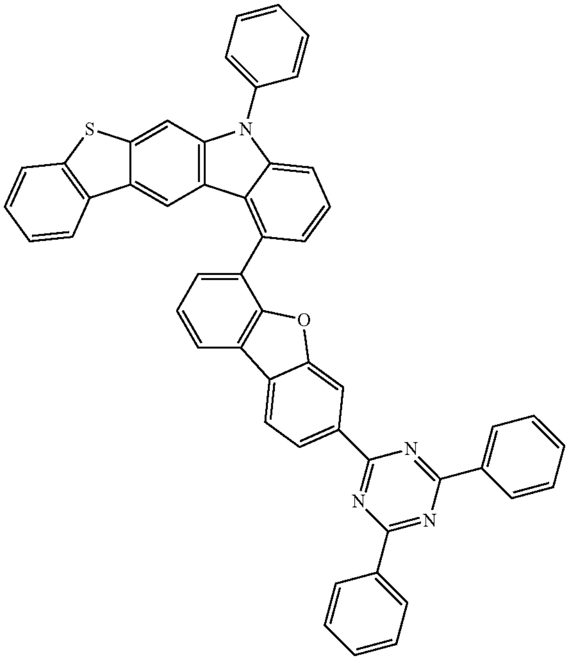 [SMILES: c1ccc(-c2nc(-c3ccccc3)nc(-c3ccc4c(c3)oc3c(-c5cccc6c5c5cc7c(cc5n6-c5ccccc5)sc5ccccc57)cccc34)n2)cc1]

TABLE 3-continued
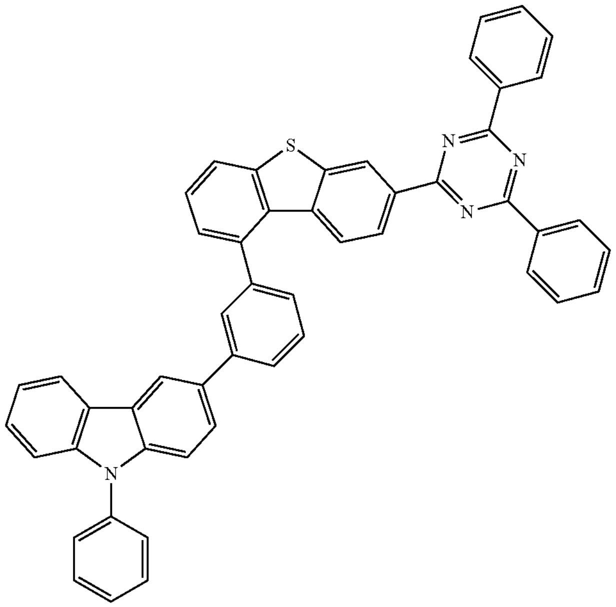 [SMILES: c1ccc(-c2nc(-c3ccccc3)nc(-c3ccc4c(c3)sc3cccc(-c5cccc(-c6ccc7c(c6)c6ccccc6n7-c6ccccc6)c5)c34)n2)cc1]
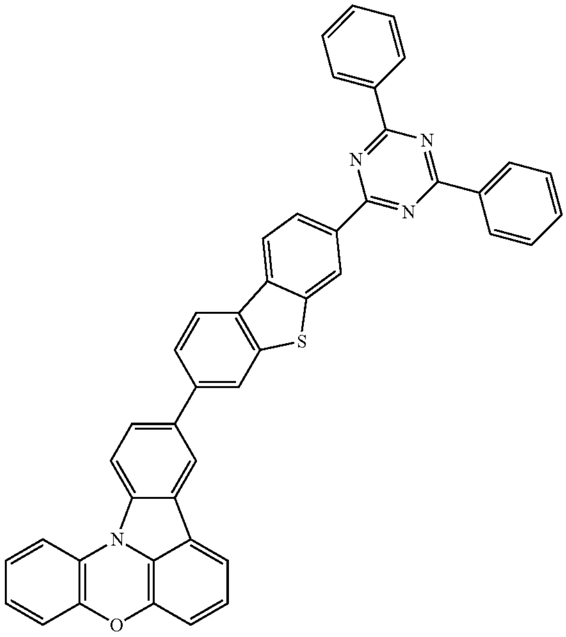 [SMILES: c1ccc(-c2nc(-c3ccccc3)nc(-c3ccc4c(c3)sc3cc(-c5ccc6c(c5)c5cccc7c5n6-c5ccccc5O7)ccc34)n2)cc1]

TABLE 3-continued
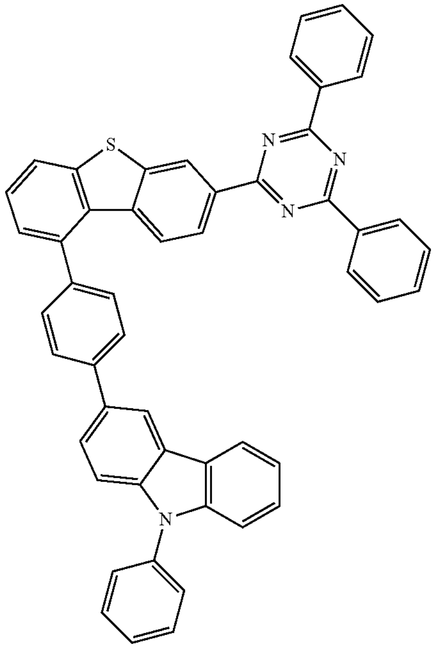 [SMILES: c1ccc(-c2nc(-c3ccccc3)nc(-c3ccc4c(c3)sc3cccc(-c5ccc(-c6ccc7c(c6)c6ccccc6n7-c6ccccc6)cc5)c34)n2)cc1]
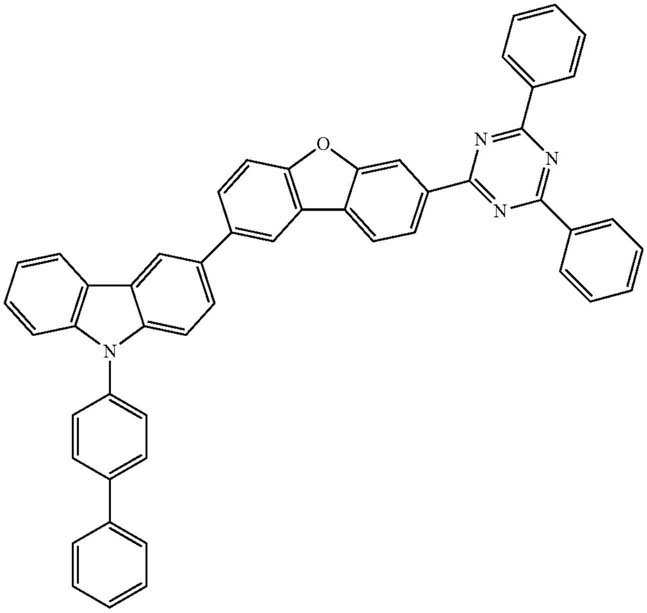
49
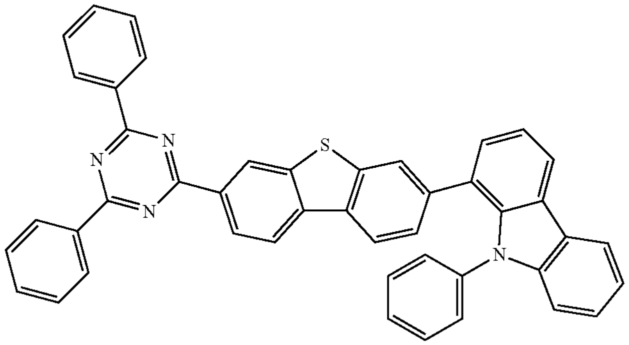 [SMILES: c1ccc(-c2nc(-c3ccccc3)nc(-c3ccc4c(c3)sc3cc(-c5cccc6c7ccccc7n(-c7ccccc7)c56)ccc34)n2)cc1]

TABLE 3-continued
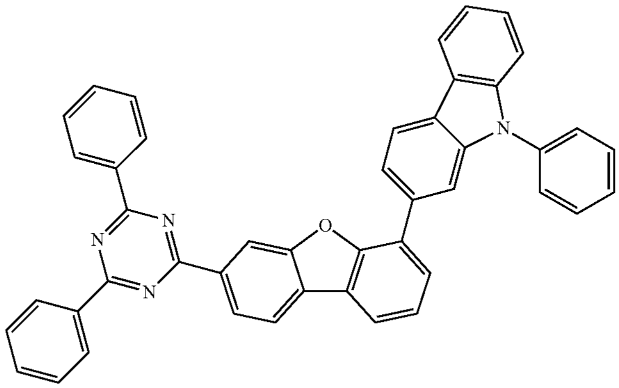 [SMILES: c1ccc(-c2nc(-c3ccccc3)nc(-c3ccc4c(c3)oc3c(-c5ccc6c7ccccc7n(-c7ccccc7)c6c5)cccc34)n2)cc1]
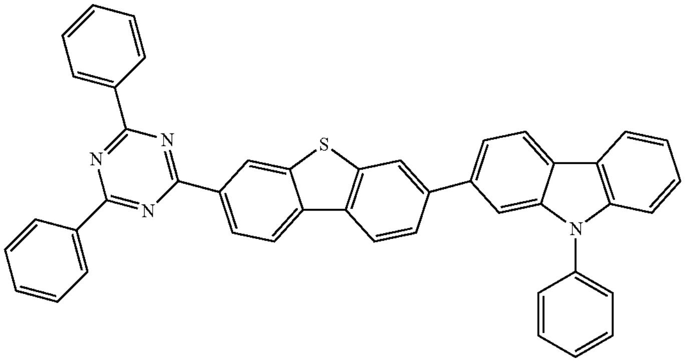 [SMILES: c1ccc(-c2nc(-c3ccccc3)nc(-c3ccc4c(c3)sc3cc(-c5ccc6c7ccccc7n(-c7ccccc7)c6c5)ccc34)n2)cc1]
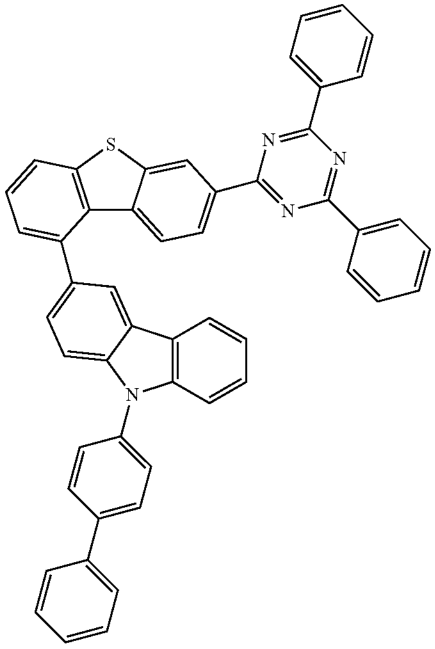 [SMILES: c1ccc(-c2ccc(-n3c4ccccc4c4cc(-c5cccc6sc7cc(-c8nc(-c9ccccc9)nc(-c9ccccc9)n8)ccc7c56)ccc43)cc2)cc1]

TABLE 3-continued
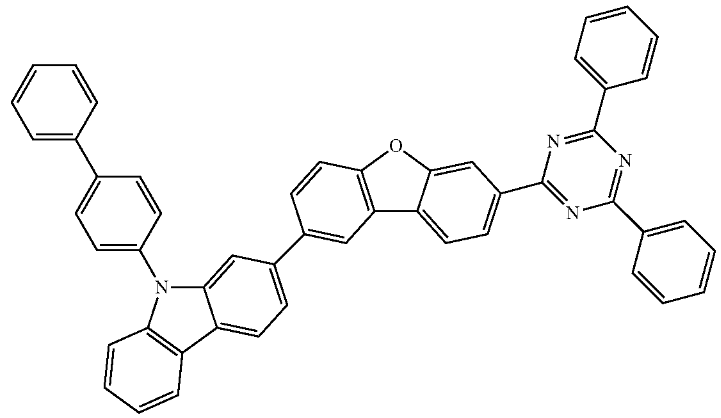 [SMILES: c1ccc(-c2ccc(-n3c4ccccc4c4ccc(-c5ccc6oc7cc(-c8nc(-c9ccccc9)nc(-c9ccccc9)n8)ccc7c6c5)cc43)cc2)cc1]
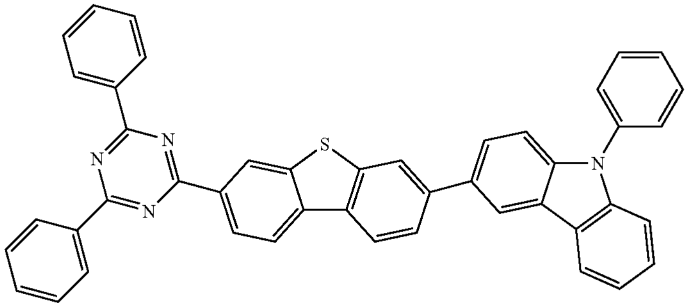 [SMILES: c1ccc(-c2nc(-c3ccccc3)nc(-c3ccc4c(c3)sc3cc(-c5ccc6c(c5)c5ccccc5n6-c5ccccc5)ccc34)n2)cc1]
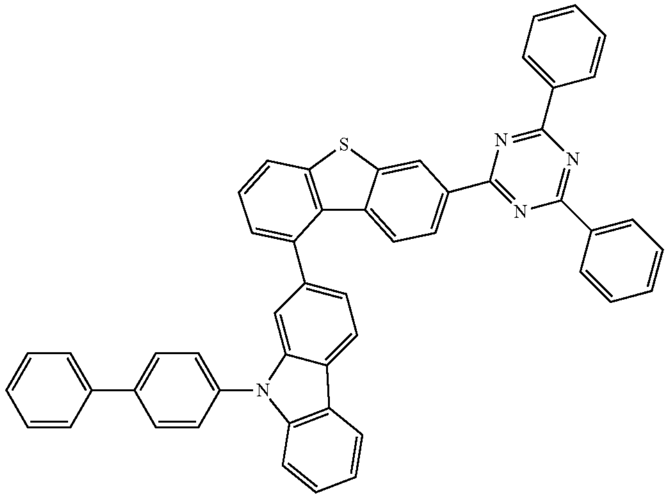 [SMILES: c1ccc(-c2ccc(-n3c4ccccc4c4ccc(-c5cccc6sc7cc(-c8nc(-c9ccccc9)nc(-c9ccccc9)n8)ccc7c56)cc43)cc2)cc1]

TABLE 3-continued
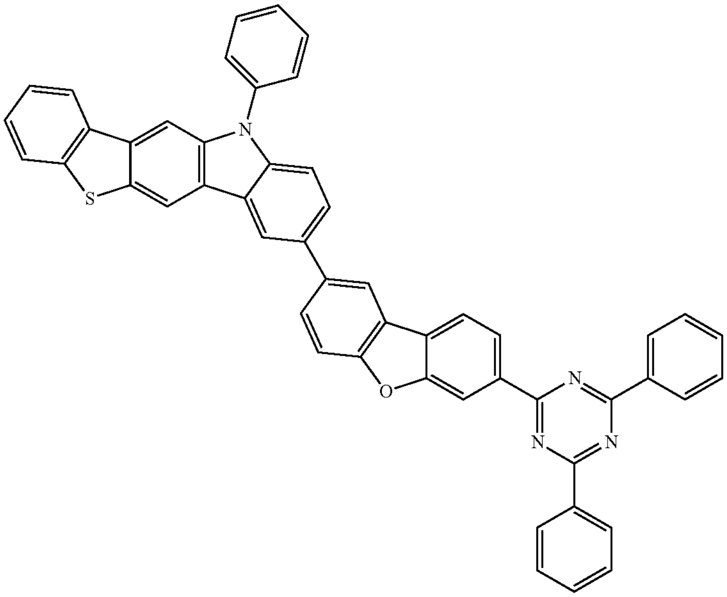 [SMILES: c1ccc(-c2nc(-c3ccccc3)nc(-c3ccc4c(c3)oc3ccc(-c5ccc6c(c5)c5cc7sc8ccccc8c7cc5n6-c5ccccc5)cc34)n2)cc1]
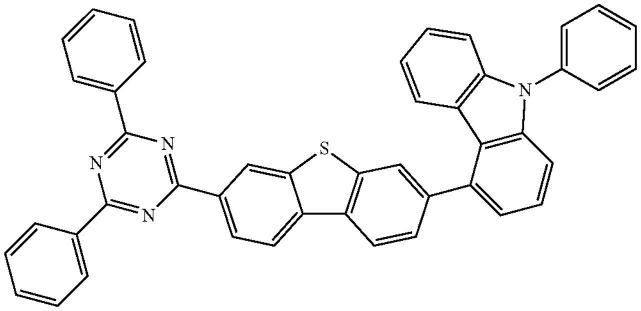 [SMILES: c1ccc(-c2nc(-c3ccccc3)nc(-c3ccc4c(c3)sc3cc(-c5cccc6c5c5ccccc5n6-c5ccccc5)ccc34)n2)cc1]
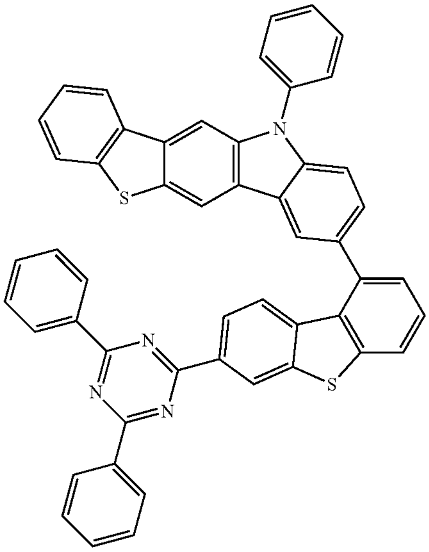 [SMILES: c1ccc(-c2nc(-c3ccccc3)nc(-c3ccc4c(c3)sc3cccc(-c5ccc6c(c5)c5cc7sc8ccccc8c7cc5n6-c5ccccc5)c34)n2)cc1]

TABLE 3-continued
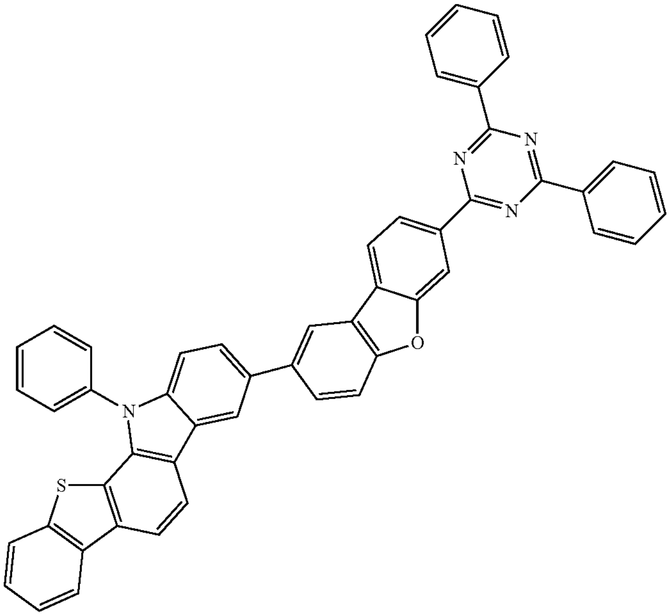 [SMILES: c1ccc(-c2nc(-c3ccccc3)nc(-c3ccc4c(c3)oc3ccc(-c5ccc6c(c5)c5ccc7c8ccccc8sc7c5n6-c5ccccc5)cc34)n2)cc1]
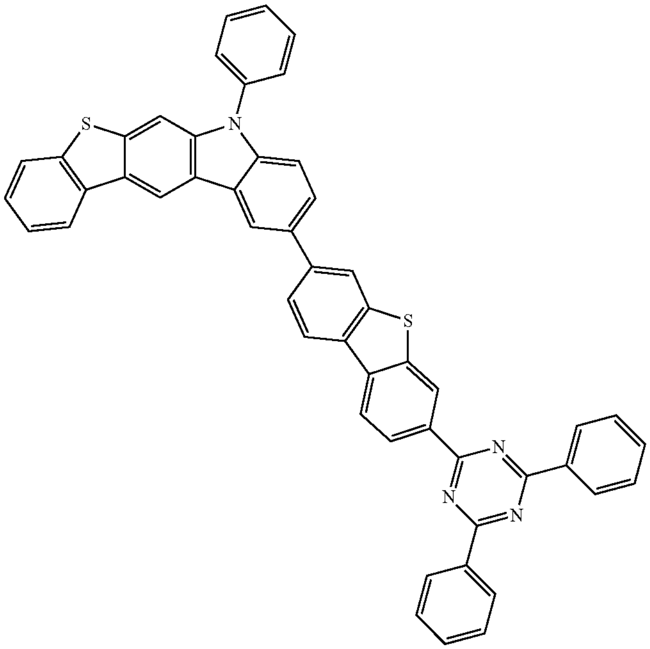 [SMILES: c1ccc(-c2nc(-c3ccccc3)nc(-c3ccc4c(c3)sc3cc(-c5ccc6c(c5)c5cc7c(cc5n6-c5ccccc5)sc5ccccc57)ccc34)n2)cc1]

TABLE 3-continued
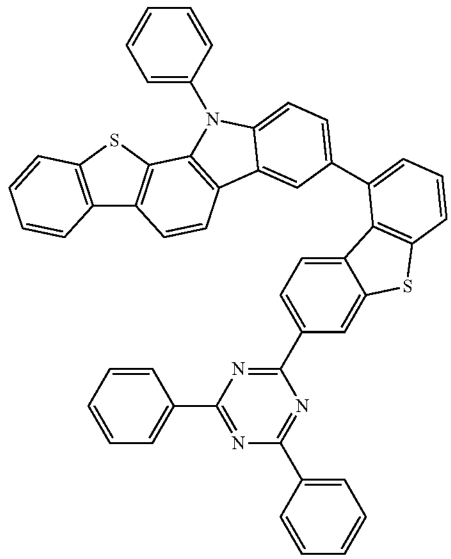 [SMILES: c1ccc(-c2nc(-c3ccccc3)nc(-c3ccc4c(c3)sc3cccc(-c5ccc6c(c5)c5ccc7c8ccccc8sc7c5n6-c5ccccc5)c34)n2)cc1]
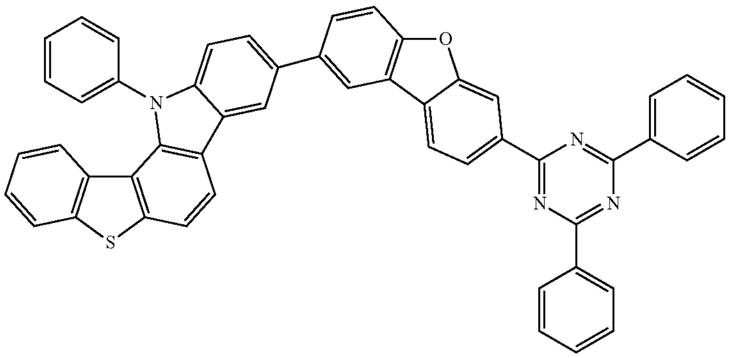 [SMILES: c1ccc(-c2nc(-c3ccccc3)nc(-c3ccc4c(c3)oc3ccc(-c5ccc6c(c5)c5ccc7sc8ccccc8c7c5n6-c5ccccc5)cc34)n2)cc1]
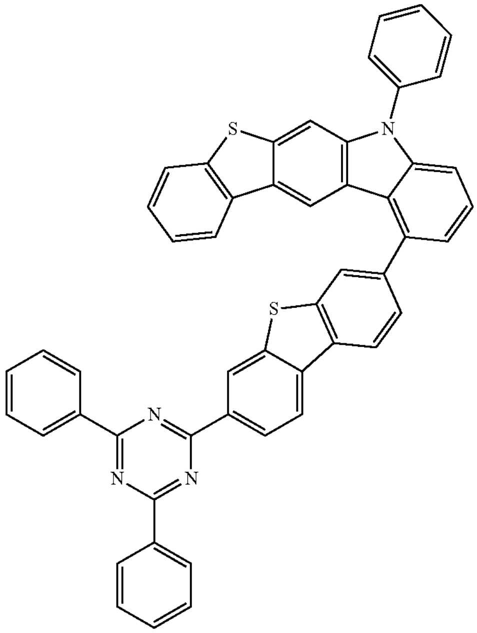 [SMILES: c1ccc(-c2nc(-c3ccccc3)nc(-c3ccc4c(c3)sc3cc(-c5cccc6c5c5cc7c(cc5n6-c5ccccc5)sc5ccccc57)ccc34)n2)cc1]

TABLE 3-continued
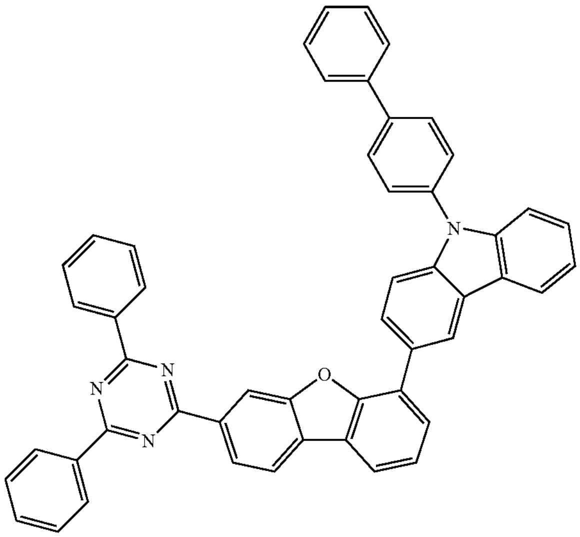 [SMILES: c1ccc(-c2ccc(-n3c4ccccc4c4cc(-c5cccc6c5oc5cc(-c7nc(-c8ccccc8)nc(-c8ccccc8)n7)ccc56)ccc43)cc2)cc1]
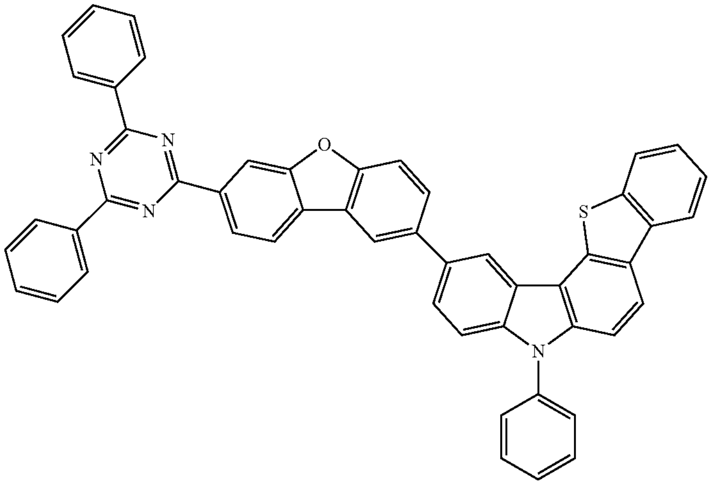 [SMILES: c1ccc(-c2nc(-c3ccccc3)nc(-c3ccc4c(c3)oc3ccc(-c5ccc6c(c5)c5c7sc8ccccc8c7ccc5n6-c5ccccc5)cc34)n2)cc1]
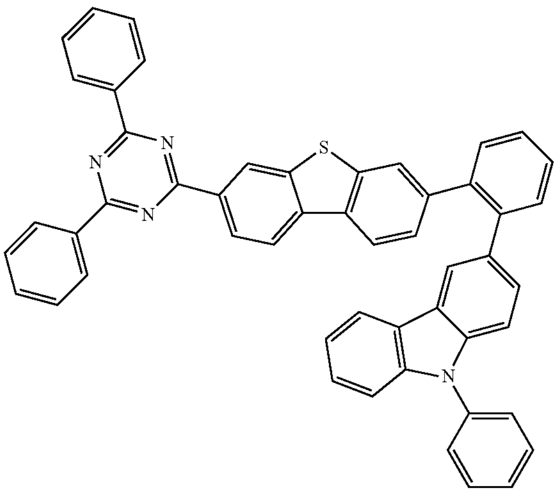 [SMILES: c1ccc(-c2nc(-c3ccccc3)nc(-c3ccc4c(c3)sc3cc(-c5ccccc5-c5ccc6c(c5)c5ccccc5n6-c5ccccc5)ccc34)n2)cc1]

TABLE 3-continued
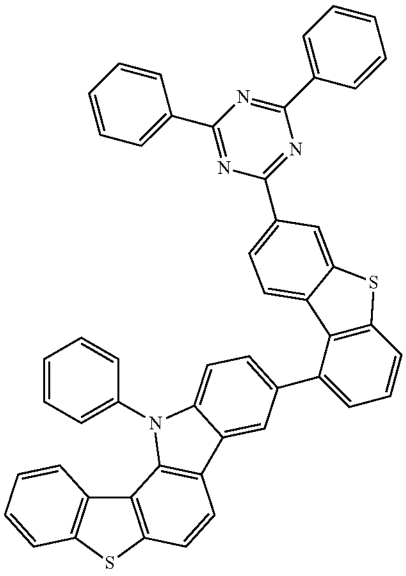
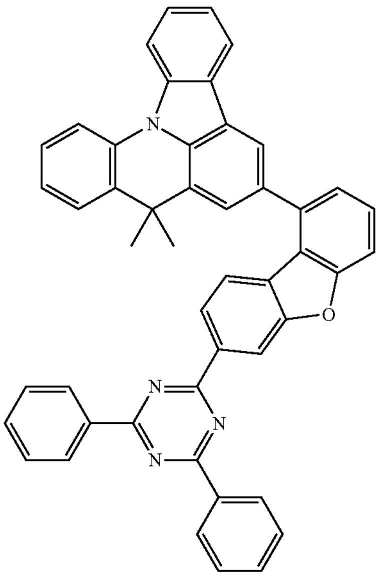 [SMILES: CC1(C)c2ccccc2-n2c3ccccc3c3cc(-c4cccc5oc6cc(-c7nc(-c8ccccc8)nc(-c8ccccc8)n7)ccc6c45)cc1c32]

TABLE 3-continued
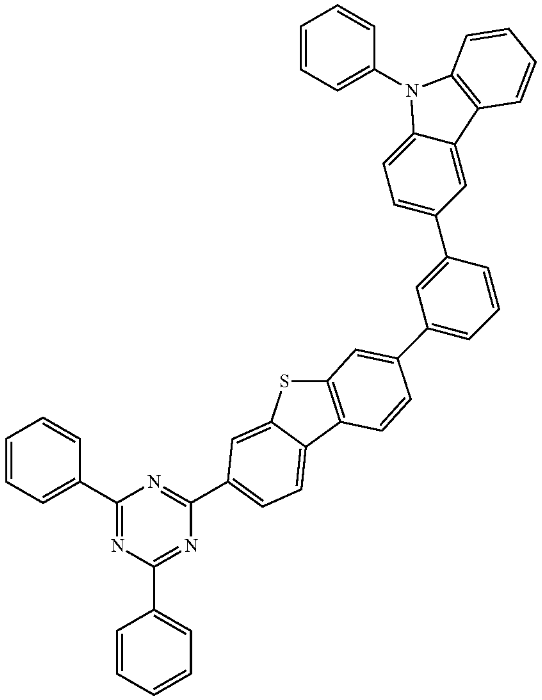
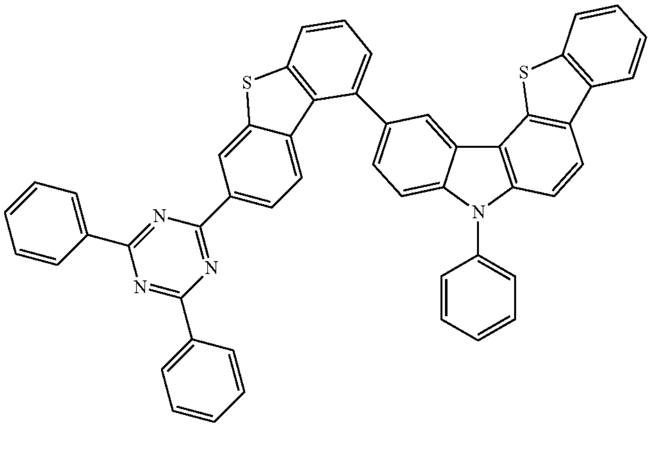 [SMILES: c1ccc(-c2nc(-c3ccccc3)nc(-c3ccc4c(c3)sc3cccc(-c5ccc6c(c5)c5c7sc8ccccc8c7ccc5n6-c5ccccc5)c34)n2)cc1]

TABLE 3-continued
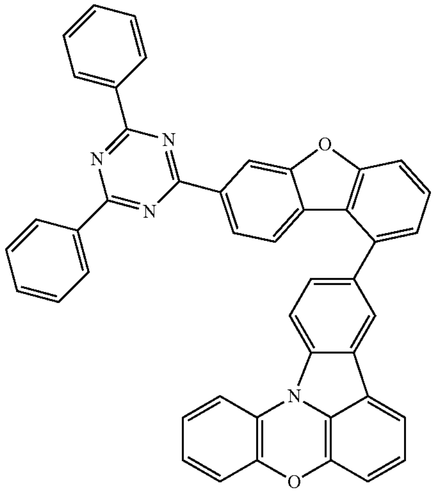 [SMILES: c1ccc(-c2nc(-c3ccccc3)nc(-c3ccc4c(c3)oc3cccc(-c5ccc6c(c5)c5cccc7c5n6-c5ccccc5O7)c34)n2)cc1]
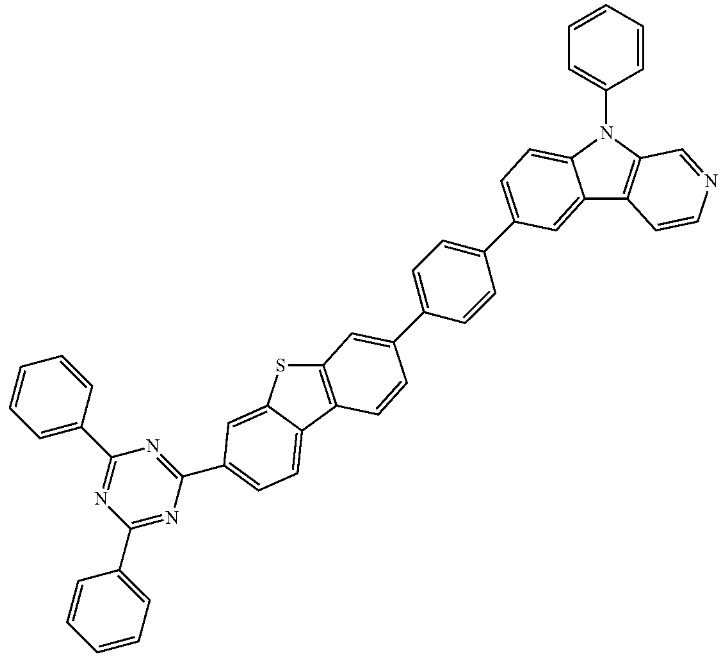 [SMILES: c1ccc(-c2nc(-c3ccccc3)nc(-c3ccc4c(c3)sc3cc(-c5ccc(-c6ccc7c(c6)c6ccncc6n7-c6ccccc6)cc5)ccc34)n2)cc1]
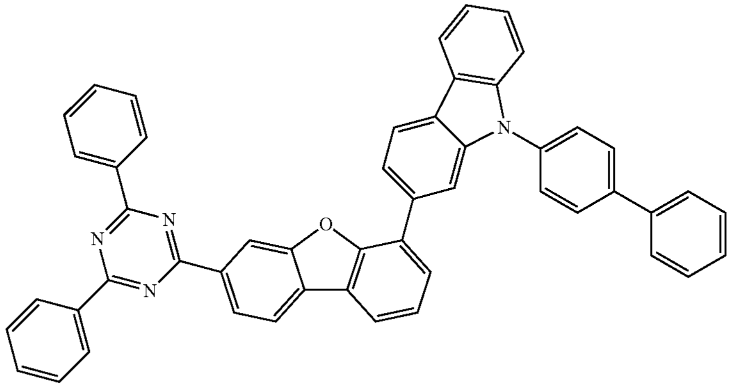 [SMILES: c1ccc(-c2ccc(-n3c4ccccc4c4ccc(-c5cccc6c5oc5cc(-c7nc(-c8ccccc8)nc(-c8ccccc8)n7)ccc56)cc43)cc2)cc1]

TABLE 3-continued
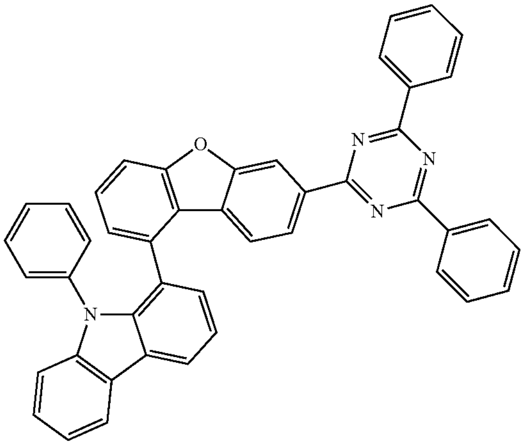 [SMILES: c1ccc(-c2nc(-c3ccccc3)nc(-c3ccc4c(c3)oc3cccc(-c5cccc6c7ccccc7n(-c7ccccc7)c56)c34)n2)cc1]
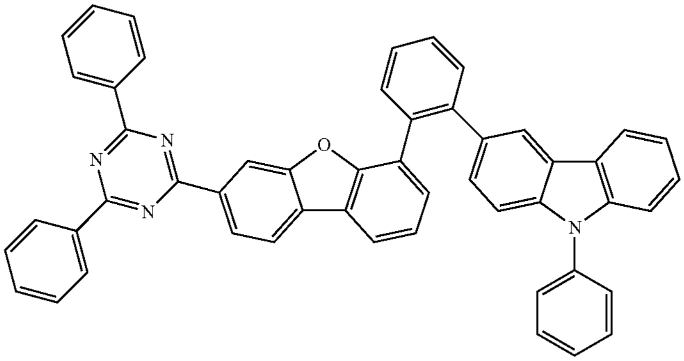 [SMILES: c1ccc(-c2nc(-c3ccccc3)nc(-c3ccc4c(c3)oc3c(-c5ccccc5-c5ccc6c(c5)c5ccccc5n6-c5ccccc5)cccc34)n2)cc1]
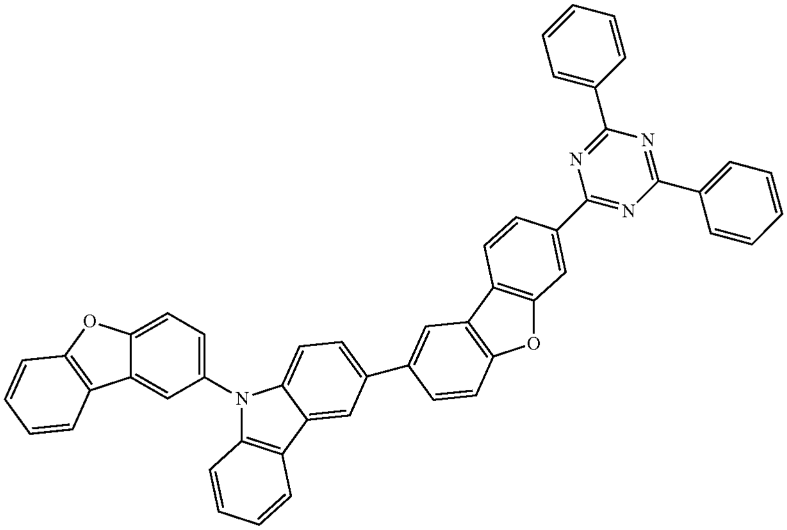

TABLE 3-continued
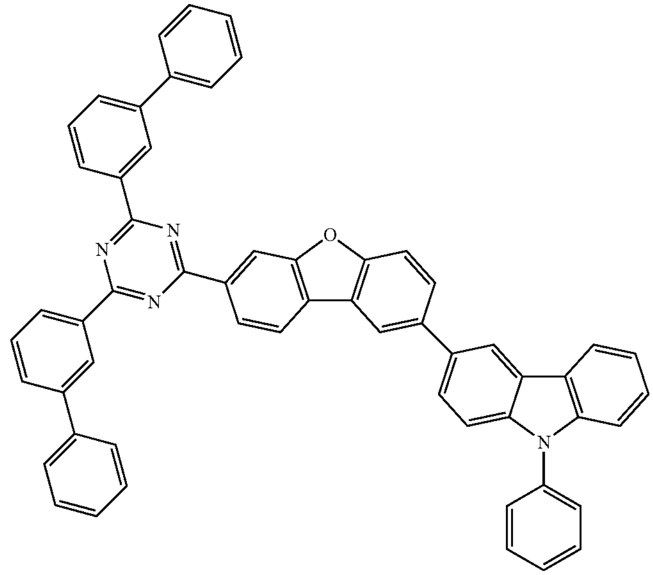
52
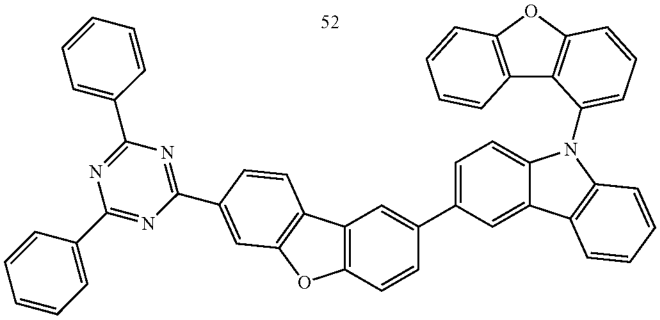
53
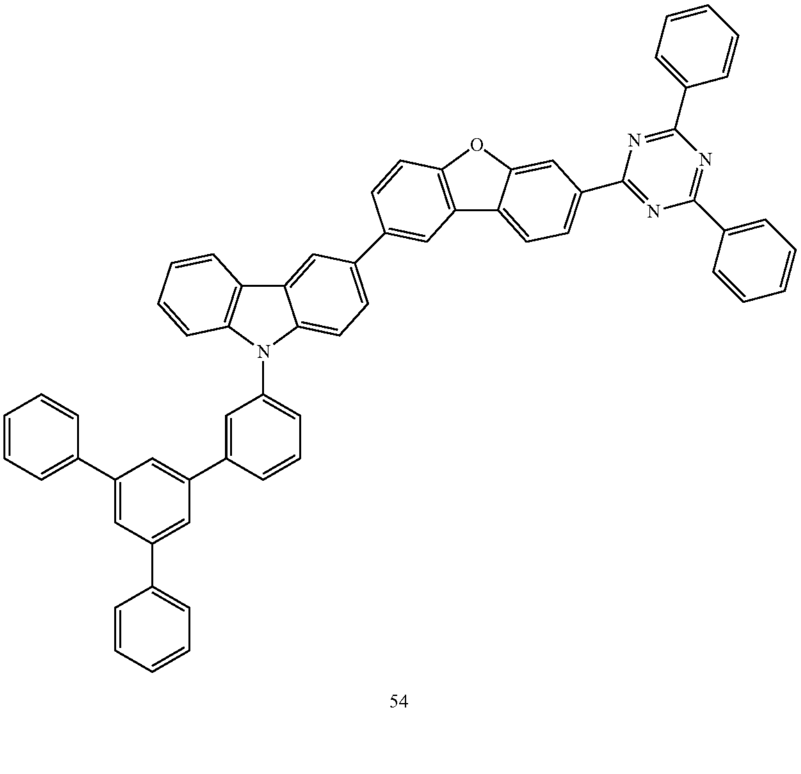 [SMILES: c1ccc(-c2cc(-c3ccccc3)cc(-c3cccc(-n4c5ccccc5c5cc(-c6ccc7oc8cc(-c9nc(-c%10ccccc%10)nc(-c%10ccccc%10)n9)ccc8c7c6)ccc54)c3)c2)cc1]
54

TABLE 3-continued
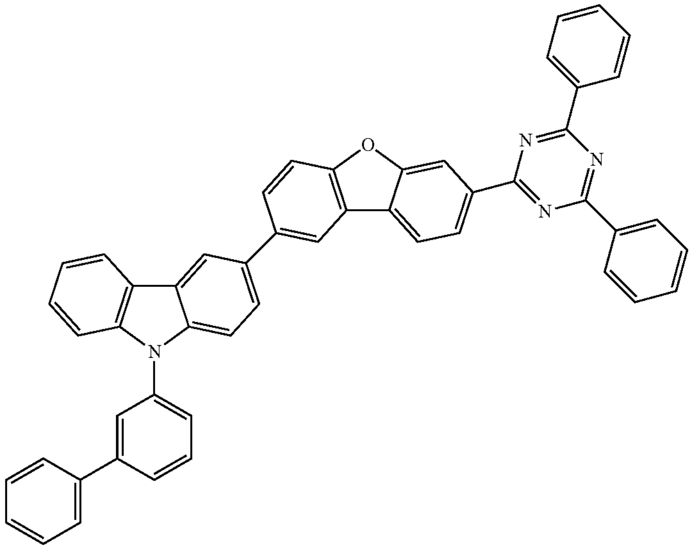
55
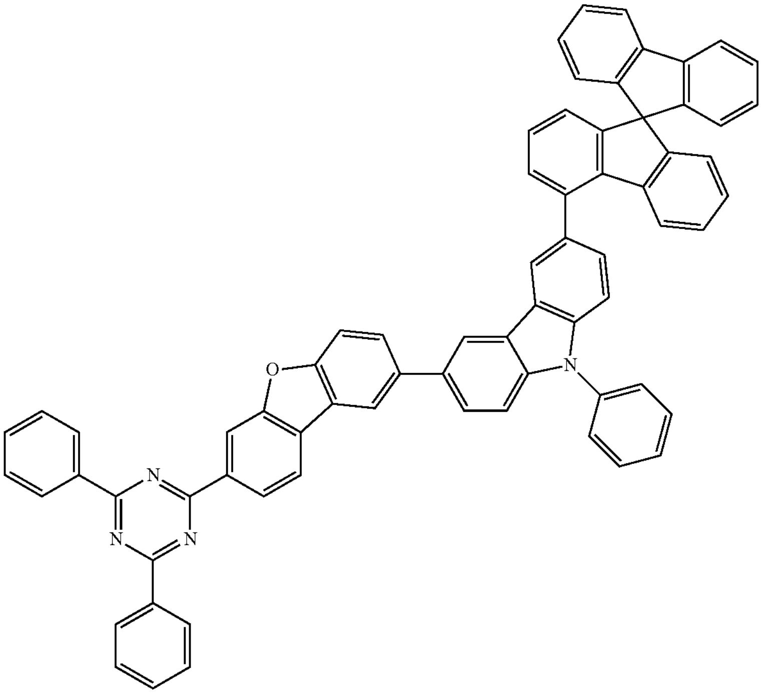
56

TABLE 3-continued
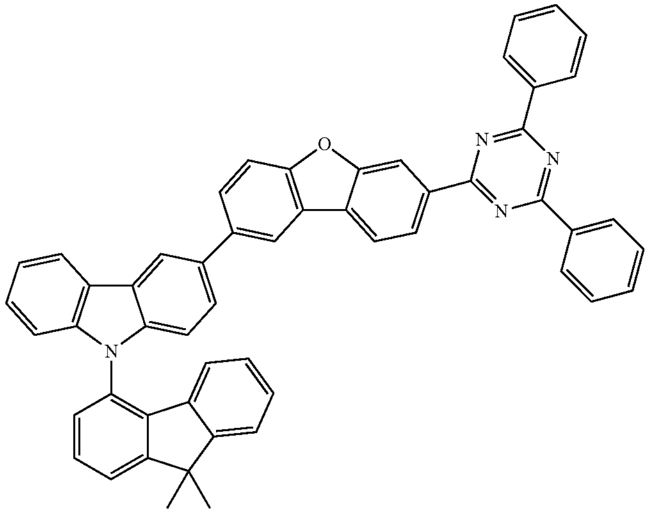
57
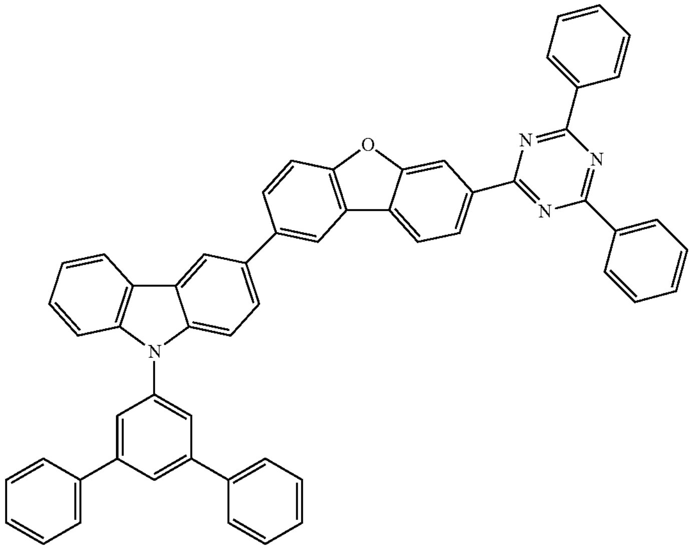
58

TABLE 3-continued
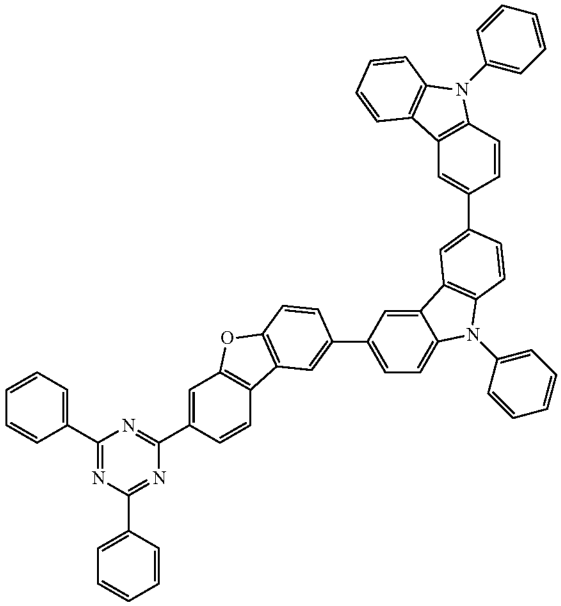
59
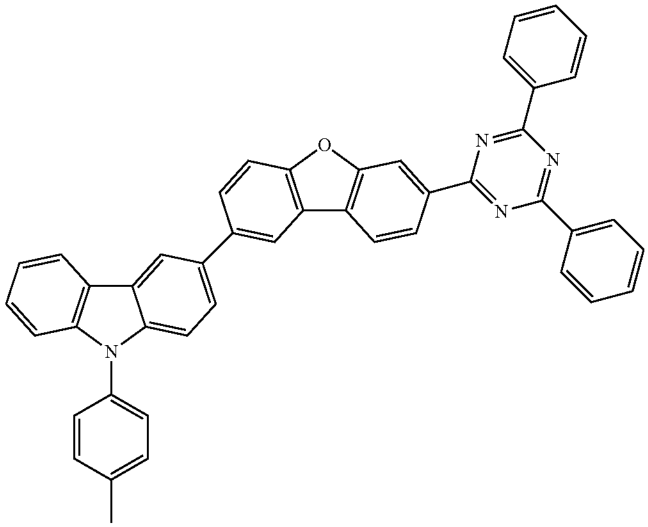
60

TABLE 3-continued
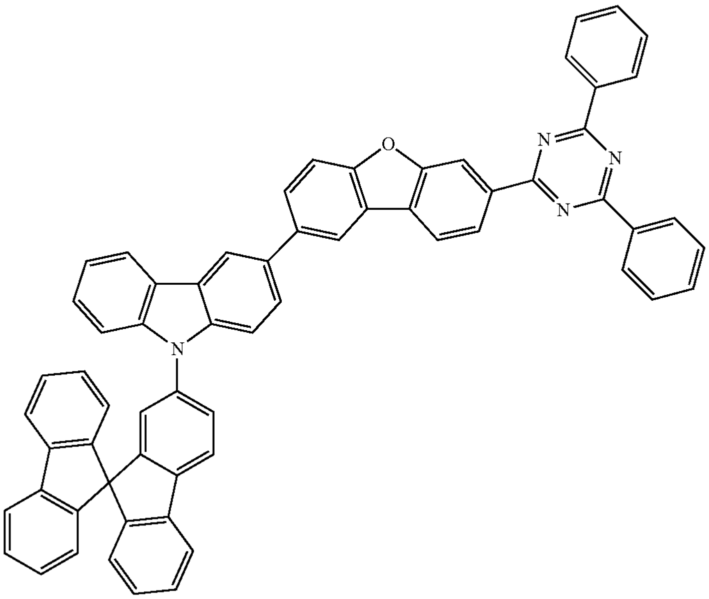
61
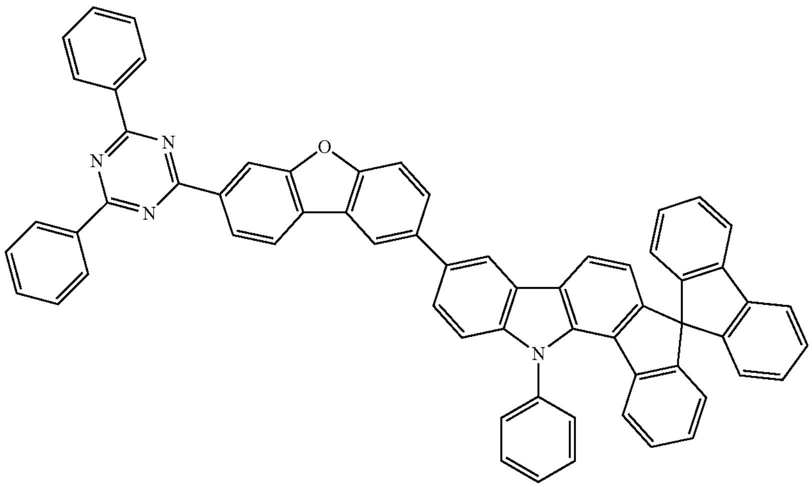
62

TABLE 3-continued
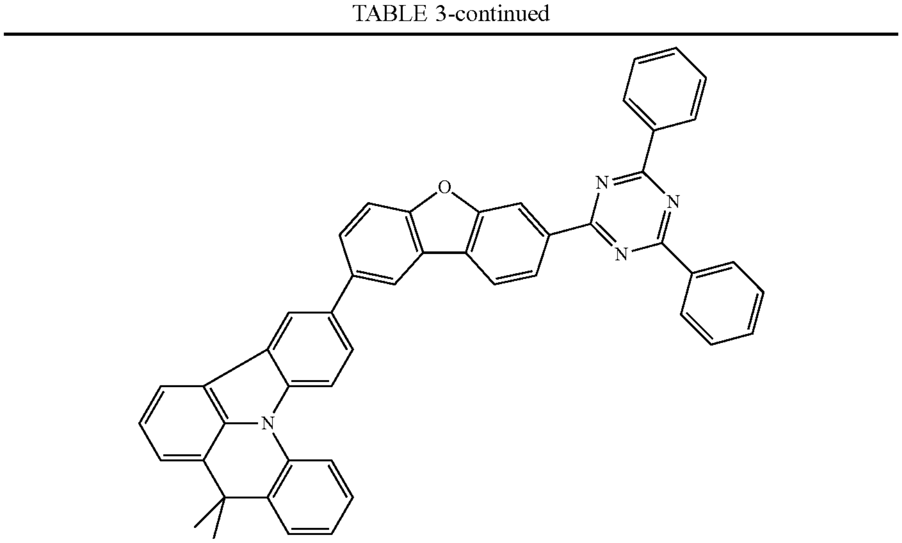
63
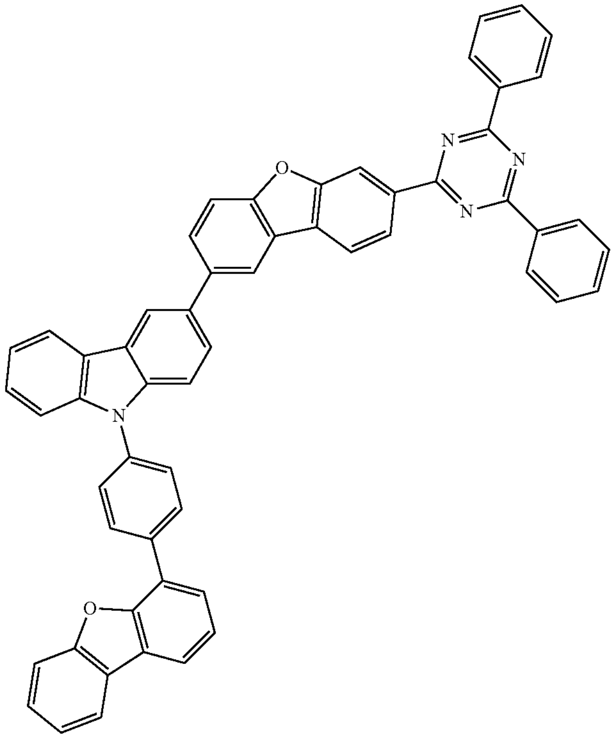
64

TABLE 3-continued
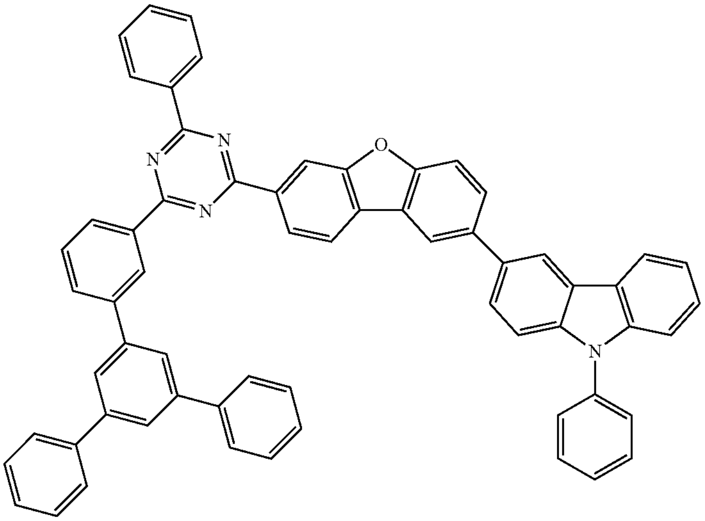
65
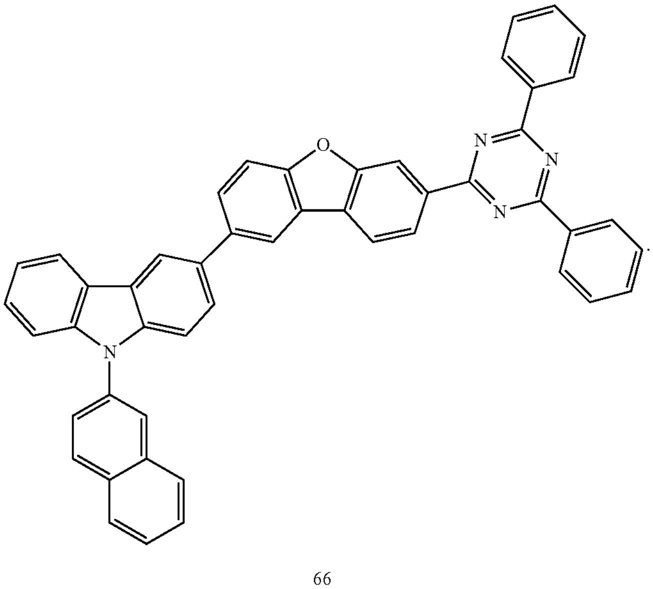 [SMILES: c1ccc(-c2nc(-c3ccccc3)nc(-c3ccc4c(c3)oc3ccc(-c5ccc6c(c5)c5ccccc5n6-c5ccc6ccccc6c5)cc34)n2)cc1]
66
TABLE 4
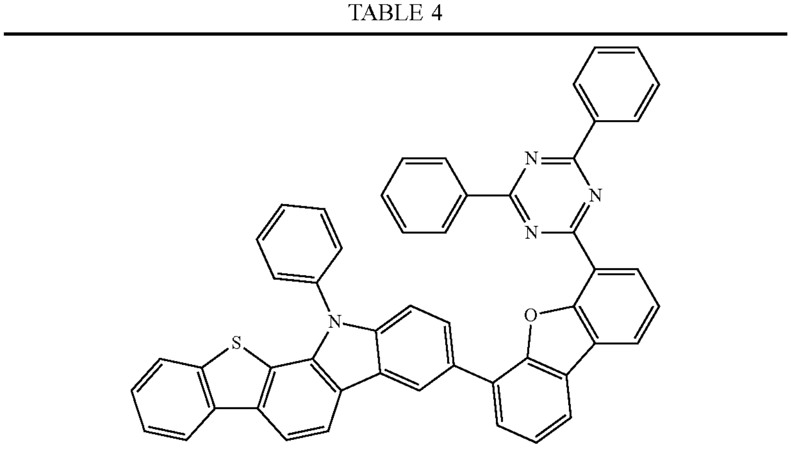

TABLE 4-continued
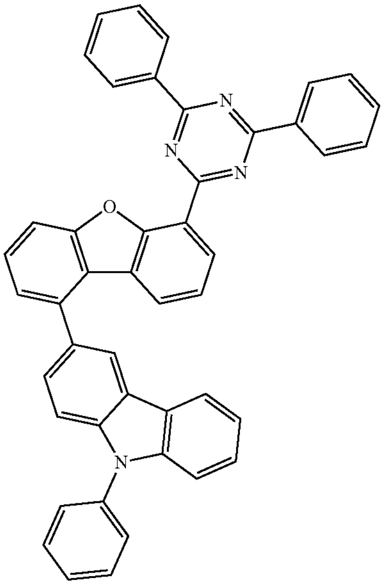 [SMILES: c1ccc(-c2nc(-c3ccccc3)nc(-c3cccc4c3oc3cccc(-c5ccc6c(c5)c5ccccc5n6-c5ccccc5)c34)n2)cc1]
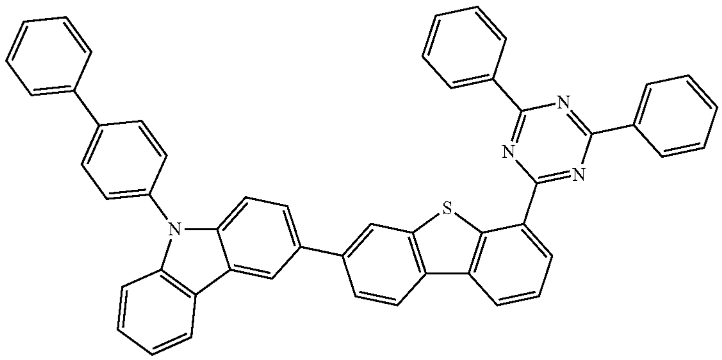 [SMILES: c1ccc(-c2ccc(-n3c4ccccc4c4cc(-c5ccc6c(c5)sc5c(-c7nc(-c8ccccc8)nc(-c8ccccc8)n7)cccc56)ccc43)cc2)cc1]
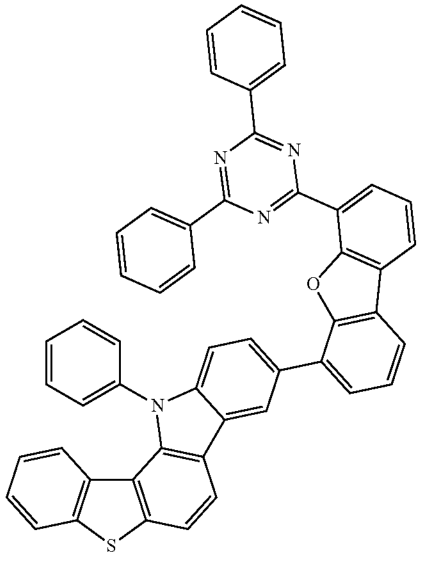 [SMILES: c1ccc(-c2nc(-c3ccccc3)nc(-c3cccc4c3oc3c(-c5ccc6c(c5)c5ccc7sc8ccccc8c7c5n6-c5ccccc5)cccc34)n2)cc1]

TABLE 4-continued
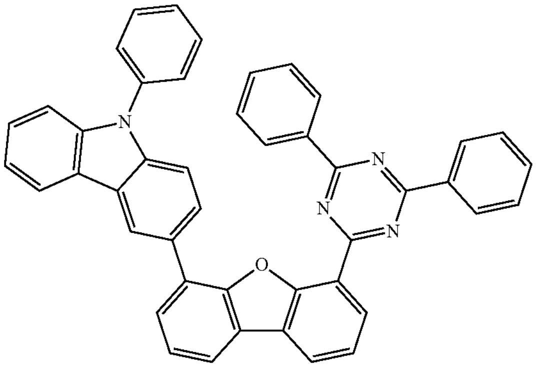
67
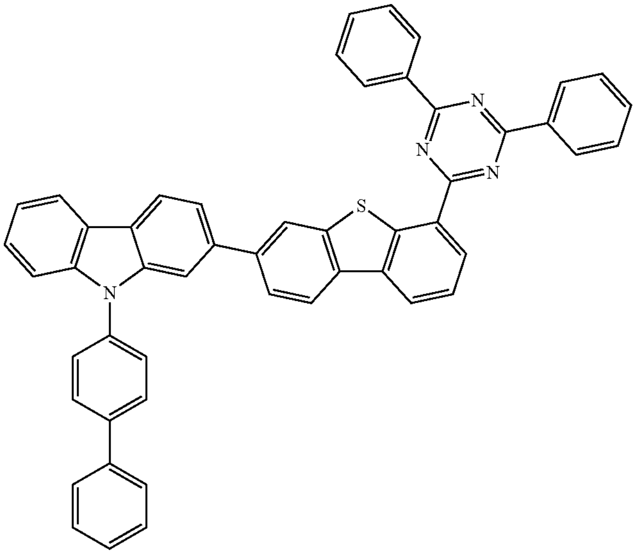
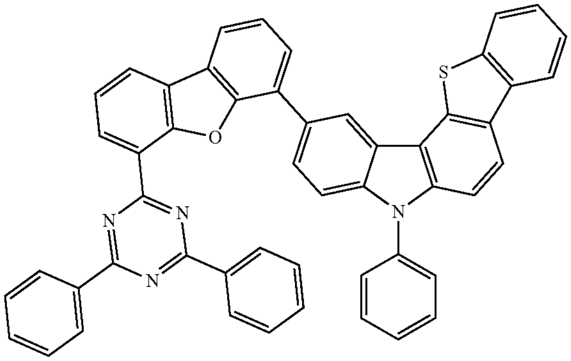 [SMILES: c1ccc(-c2nc(-c3ccccc3)nc(-c3cccc4c3oc3c(-c5ccc6c(c5)c5c7sc8ccccc8c7ccc5n6-c5ccccc5)cccc34)n2)cc1]

TABLE 4-continued
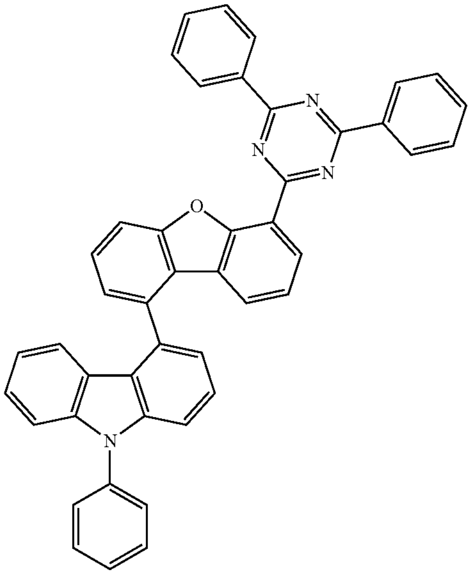 [SMILES: c1ccc(-c2nc(-c3ccccc3)nc(-c3cccc4c3oc3cccc(-c5cccc6c5c5ccccc5n6-c5ccccc5)c34)n2)cc1]
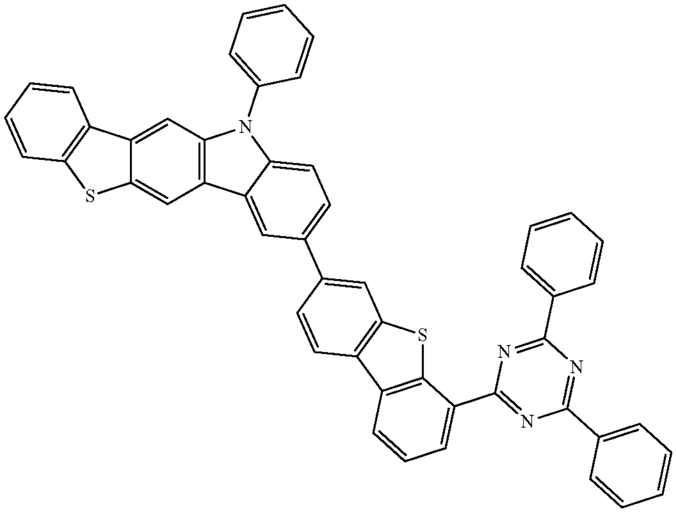 [SMILES: c1ccc(-c2nc(-c3ccccc3)nc(-c3cccc4c3sc3cc(-c5ccc6c(c5)c5cc7sc8ccccc8c7cc5n6-c5ccccc5)ccc34)n2)cc1]
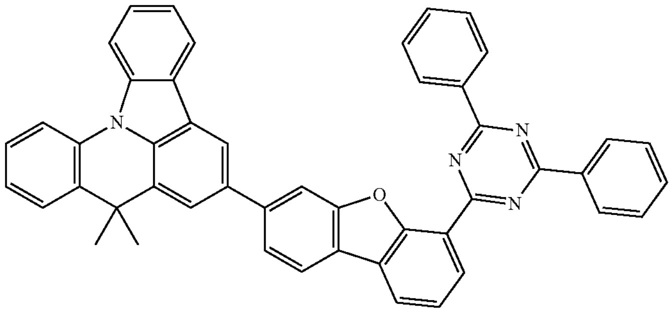 [SMILES: CC1(C)c2ccccc2-n2c3ccccc3c3cc(-c4ccc5c(c4)oc4c(-c6nc(-c7ccccc7)nc(-c7ccccc7)n6)cccc45)cc1c32]

TABLE 4-continued
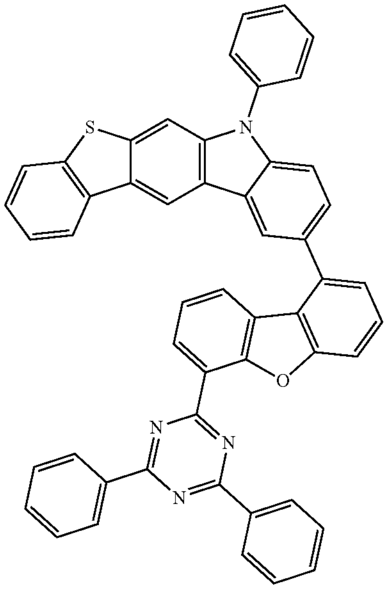
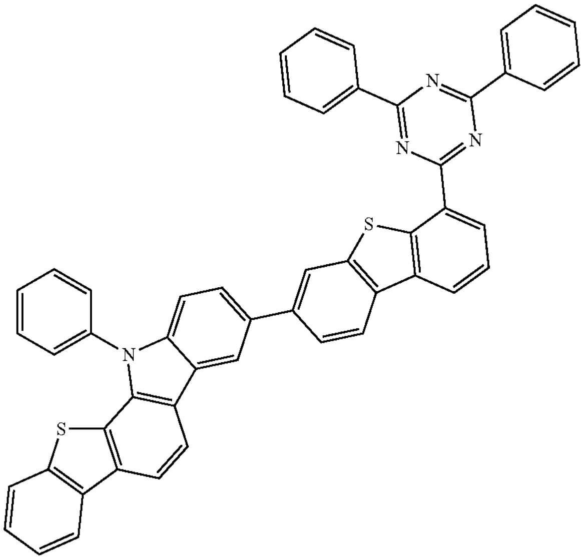 [SMILES: c1ccc(-c2nc(-c3ccccc3)nc(-c3cccc4c3sc3cc(-c5ccc6c(c5)c5ccc7c8ccccc8sc7c5n6-c5ccccc5)ccc34)n2)cc1]

TABLE 4-continued
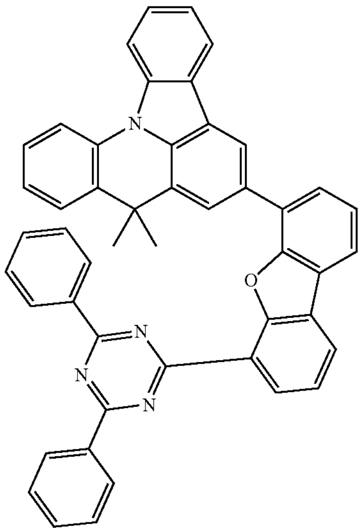 [SMILES: CC1(C)c2ccccc2-n2c3ccccc3c3cc(-c4cccc5c4oc4c(-c6nc(-c7ccccc7)nc(-c7ccccc7)n6)cccc45)cc1c32]
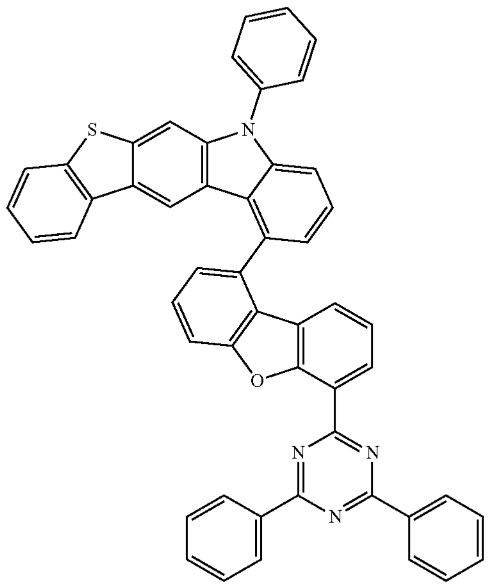 [SMILES: c1ccc(-c2nc(-c3ccccc3)nc(-c3cccc4c3oc3cccc(-c5cccc6c5c5cc7c(cc5n6-c5ccccc5)sc5ccccc57)c34)n2)cc1]
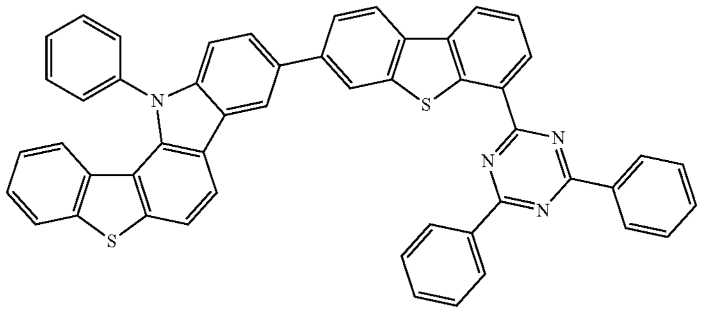 [SMILES: c1ccc(-c2nc(-c3ccccc3)nc(-c3cccc4c3sc3cc(-c5ccc6c(c5)c5ccc7sc8ccccc8c7c5n6-c5ccccc5)ccc34)n2)cc1]

TABLE 4-continued
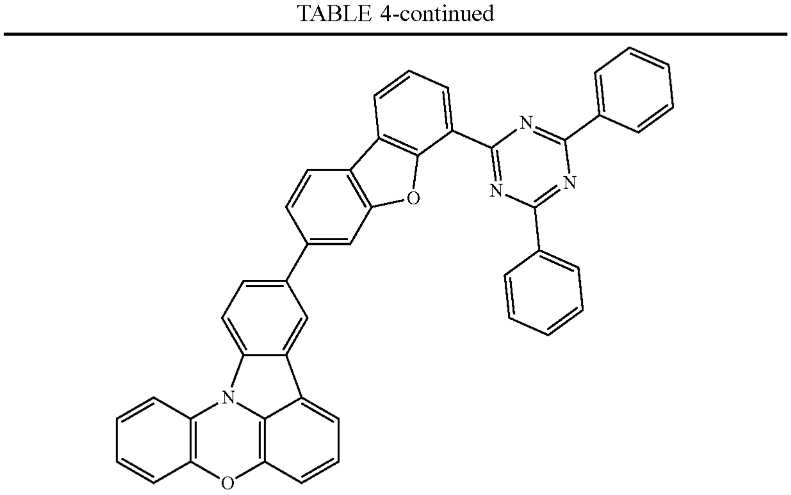
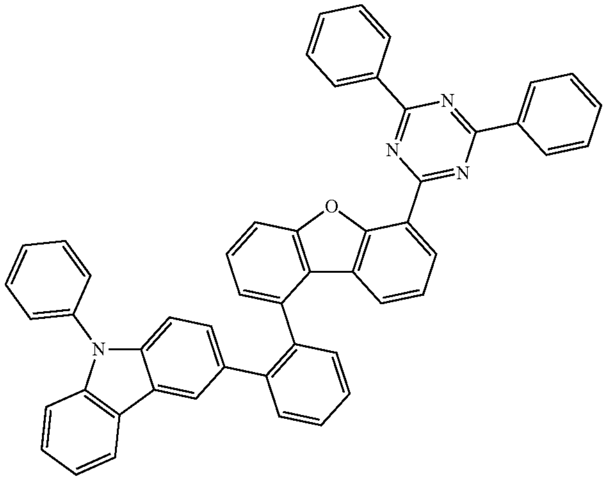
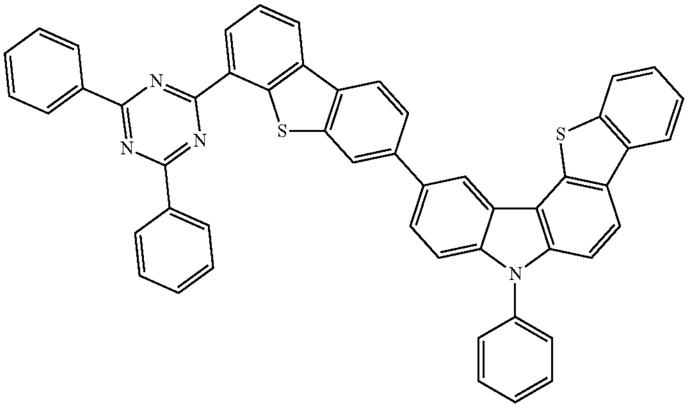

TABLE 4-continued
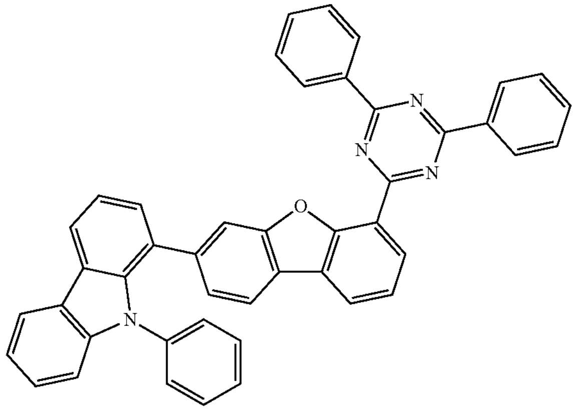 [SMILES: c1ccc(-c2nc(-c3ccccc3)nc(-c3cccc4c3oc3cc(-c5cccc6c7ccccc7n(-c7ccccc7)c56)ccc34)n2)cc1]
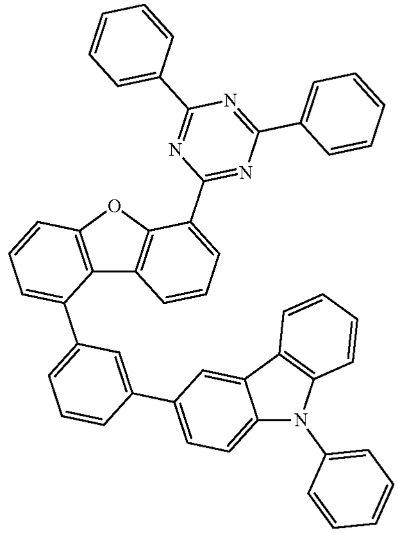 [SMILES: c1ccc(-c2nc(-c3ccccc3)nc(-c3cccc4c3oc3cccc(-c5cccc(-c6ccc7c(c6)c6ccccc6n7-c6ccccc6)c5)c34)n2)cc1]
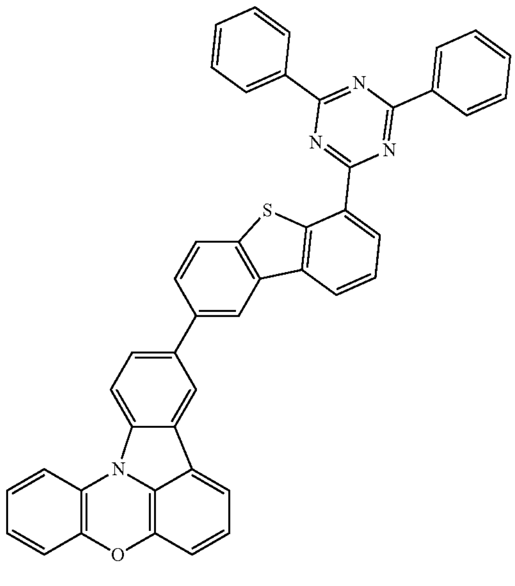 [SMILES: c1ccc(-c2nc(-c3ccccc3)nc(-c3cccc4c3sc3ccc(-c5ccc6c(c5)c5cccc7c5n6-c5ccccc5O7)cc34)n2)cc1]

TABLE 4-continued
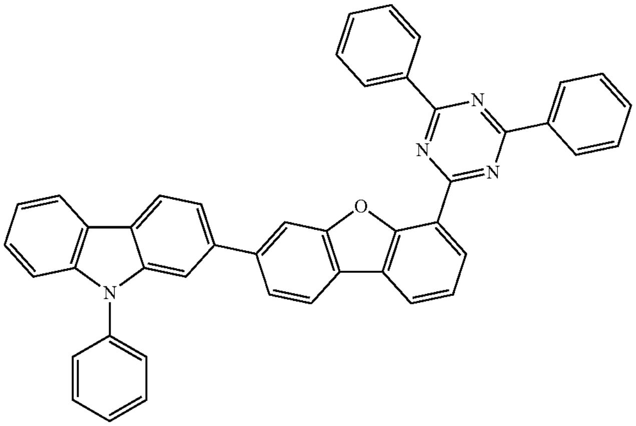 [SMILES: c1ccc(-c2nc(-c3ccccc3)nc(-c3cccc4c3oc3cc(-c5ccc6c7ccccc7n(-c7ccccc7)c6c5)ccc34)n2)cc1]
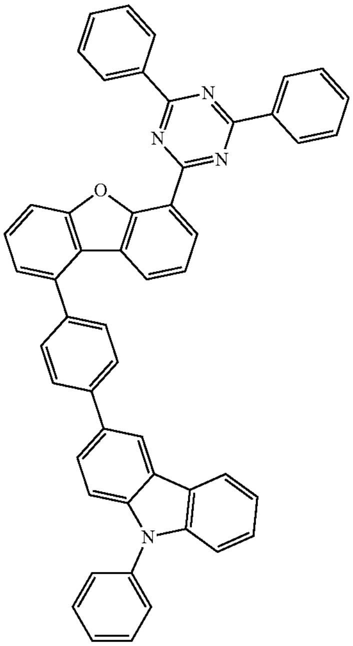 [SMILES: c1ccc(-c2nc(-c3ccccc3)nc(-c3cccc4c3oc3cccc(-c5ccc(-c6ccc7c(c6)c6ccccc6n7-c6ccccc6)cc5)c34)n2)cc1]
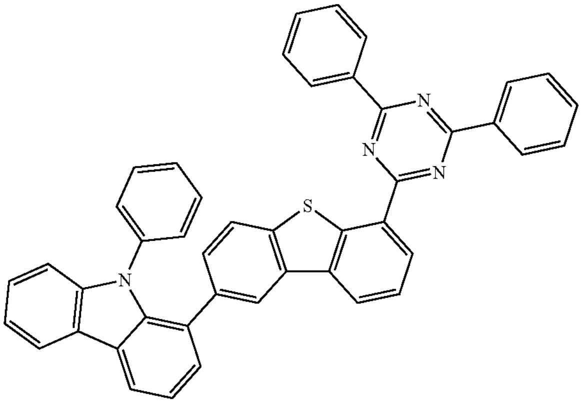 [SMILES: c1ccc(-c2nc(-c3ccccc3)nc(-c3cccc4c3sc3ccc(-c5cccc6c7ccccc7n(-c7ccccc7)c56)cc34)n2)cc1]

TABLE 4-continued
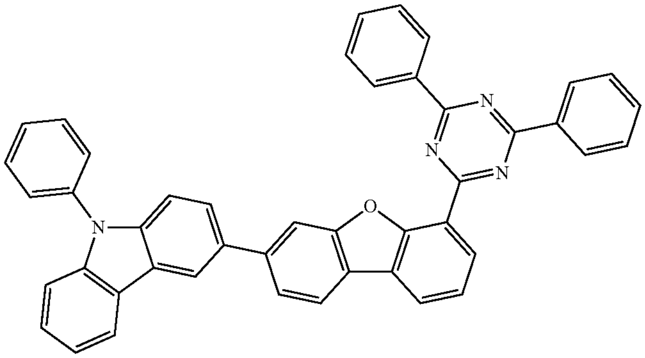 [SMILES: c1ccc(-c2nc(-c3ccccc3)nc(-c3cccc4c3oc3cc(-c5ccc6c(c5)c5ccccc5n6-c5ccccc5)ccc34)n2)cc1]
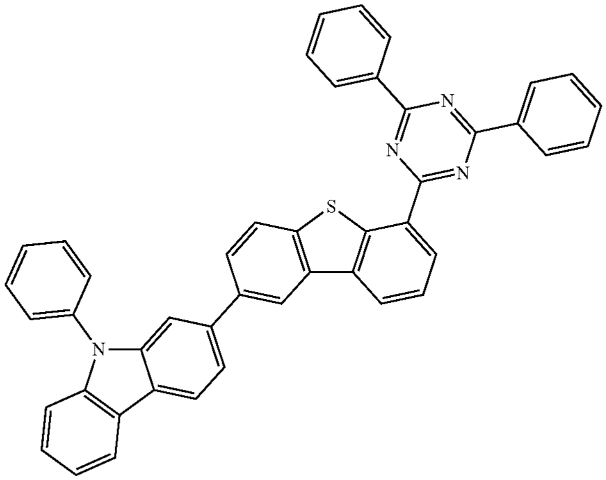
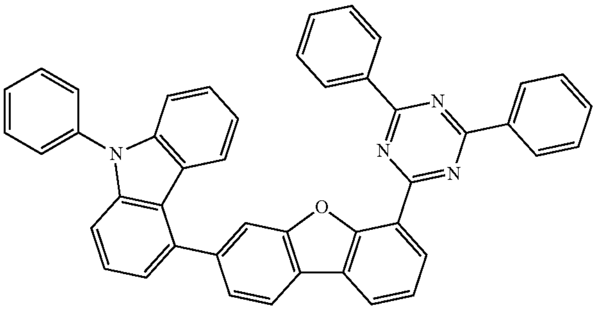

TABLE 4-continued
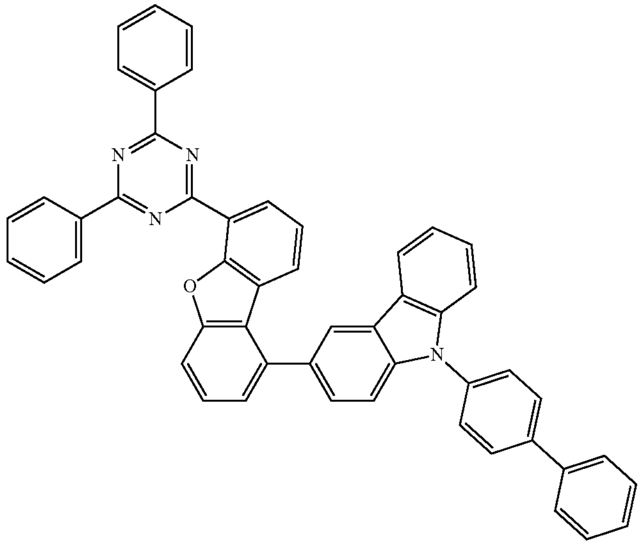 [SMILES: c1ccc(-c2ccc(-n3c4ccccc4c4cc(-c5cccc6oc7c(-c8nc(-c9ccccc9)nc(-c9ccccc9)n8)cccc7c56)ccc43)cc2)cc1]
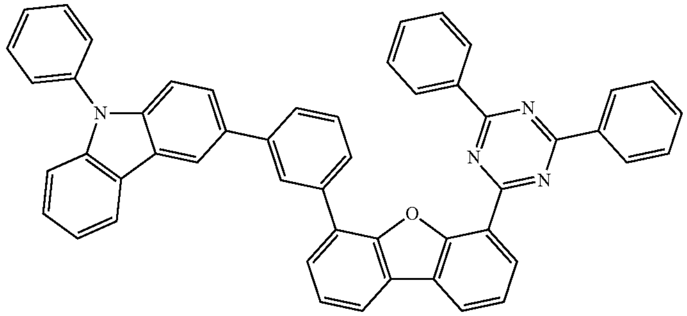 [SMILES: c1ccc(-c2nc(-c3ccccc3)nc(-c3cccc4c3oc3c(-c5cccc(-c6ccc7c(c6)c6ccccc6n7-c6ccccc6)c5)cccc34)n2)cc1]
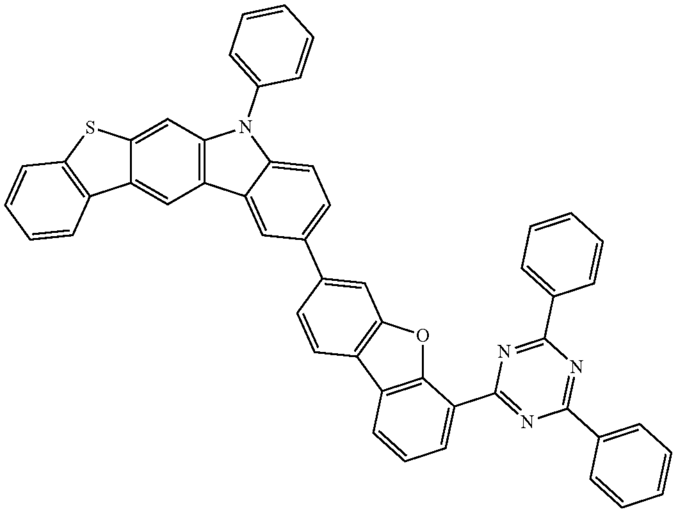

TABLE 4-continued
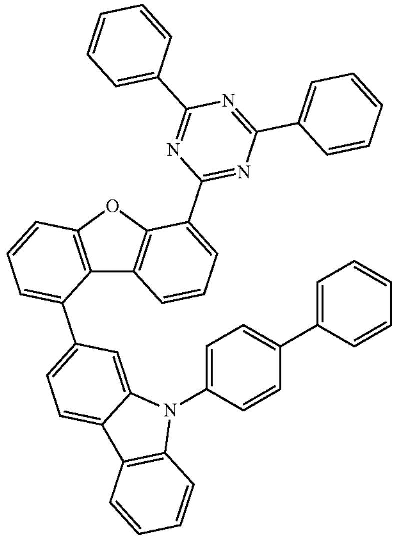 [SMILES: c1ccc(-c2ccc(-n3c4ccccc4c4ccc(-c5cccc6oc7c(-c8nc(-c9ccccc9)nc(-c9ccccc9)n8)cccc7c56)cc43)cc2)cc1]
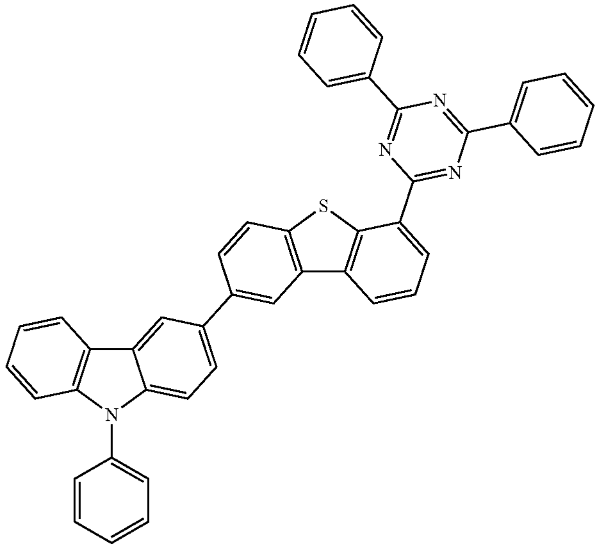 [SMILES: c1ccc(-c2nc(-c3ccccc3)nc(-c3cccc4c3sc3ccc(-c5ccc6c(c5)c5ccccc5n6-c5ccccc5)cc34)n2)cc1]
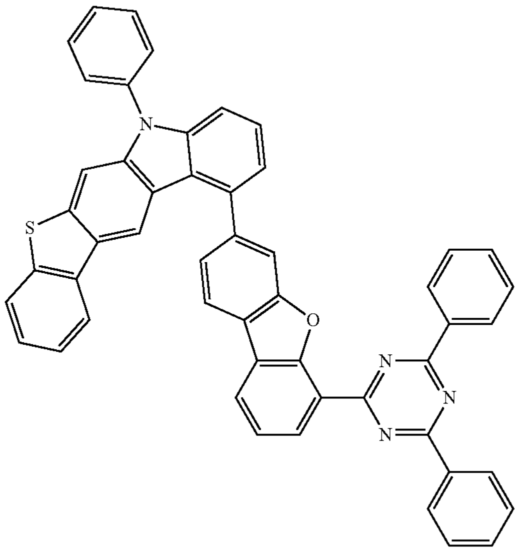

TABLE 4-continued
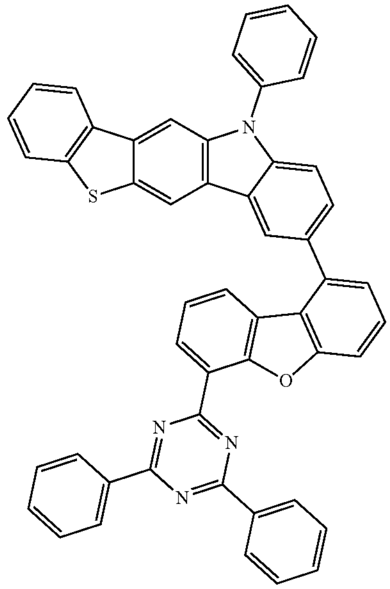 [SMILES: c1ccc(-c2nc(-c3ccccc3)nc(-c3cccc4c3oc3cccc(-c5ccc6c(c5)c5cc7sc8ccccc8c7cc5n6-c5ccccc5)c34)n2)cc1]
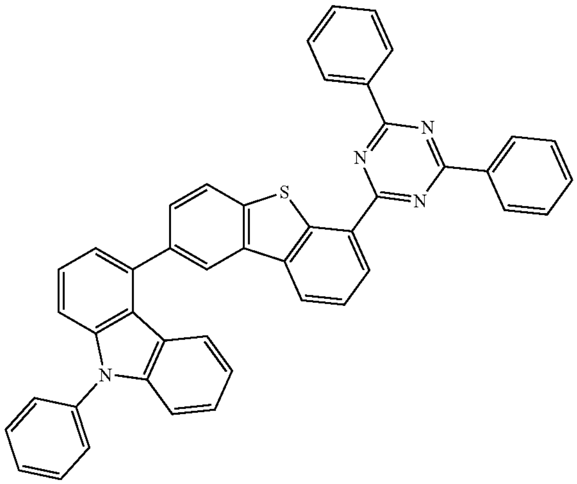 [SMILES: c1ccc(-c2nc(-c3ccccc3)nc(-c3cccc4c3sc3ccc(-c5cccc6c5c5ccccc5n6-c5ccccc5)cc34)n2)cc1]
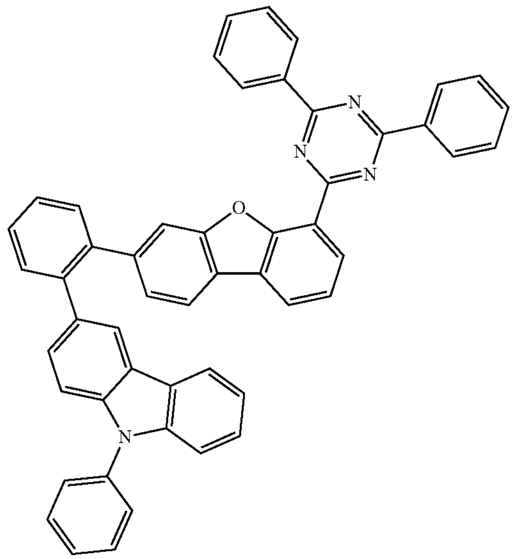 [SMILES: c1ccc(-c2nc(-c3ccccc3)nc(-c3cccc4c3oc3cc(-c5ccccc5-c5ccc6c(c5)c5ccccc5n6-c5ccccc5)ccc34)n2)cc1]

TABLE 4-continued
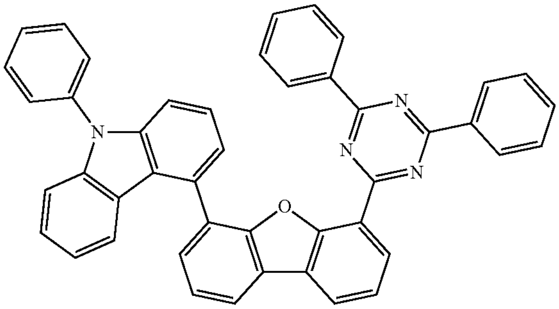 [SMILES: c1ccc(-c2nc(-c3ccccc3)nc(-c3cccc4c3oc3c(-c5cccc6c5c5ccccc5n6-c5ccccc5)cccc34)n2)cc1]
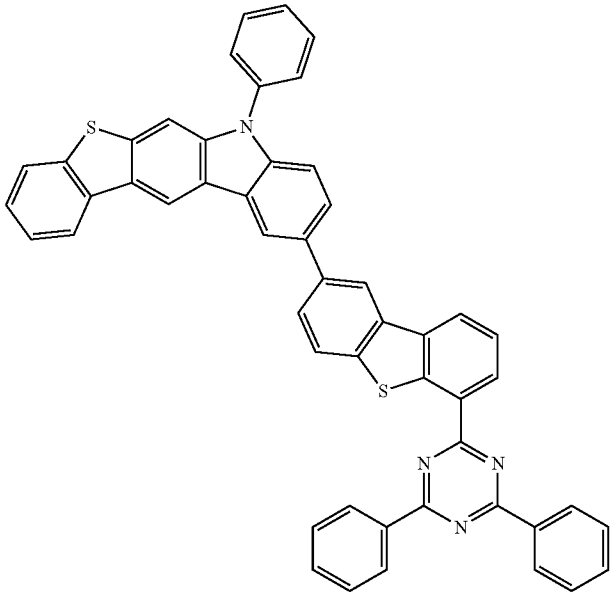
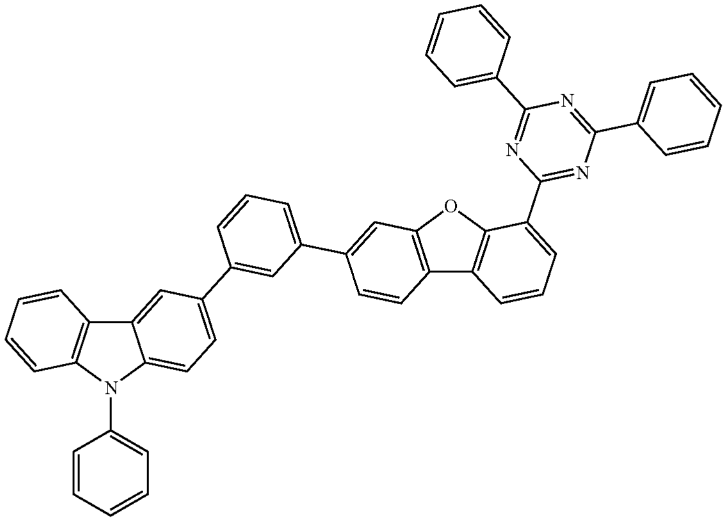 [SMILES: c1ccc(-c2nc(-c3ccccc3)nc(-c3cccc4c3oc3cc(-c5cccc(-c6ccc7c(c6)c6ccccc6n7-c6ccccc6)c5)ccc34)n2)cc1]

TABLE 4-continued
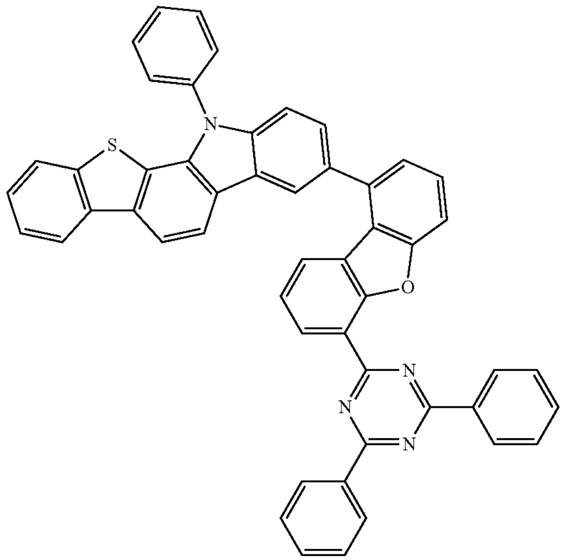 [SMILES: c1ccc(-c2nc(-c3ccccc3)nc(-c3cccc4c3oc3cccc(-c5ccc6c(c5)c5ccc7c8ccccc8sc7c5n6-c5ccccc5)c34)n2)cc1]
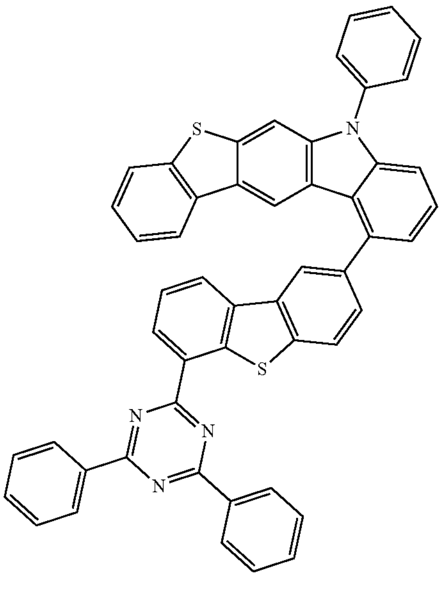 [SMILES: c1ccc(-c2nc(-c3ccccc3)nc(-c3cccc4c3sc3ccc(-c5cccc6c5c5cc7c(cc5n6-c5ccccc5)sc5ccccc57)cc34)n2)cc1]

TABLE 4-continued
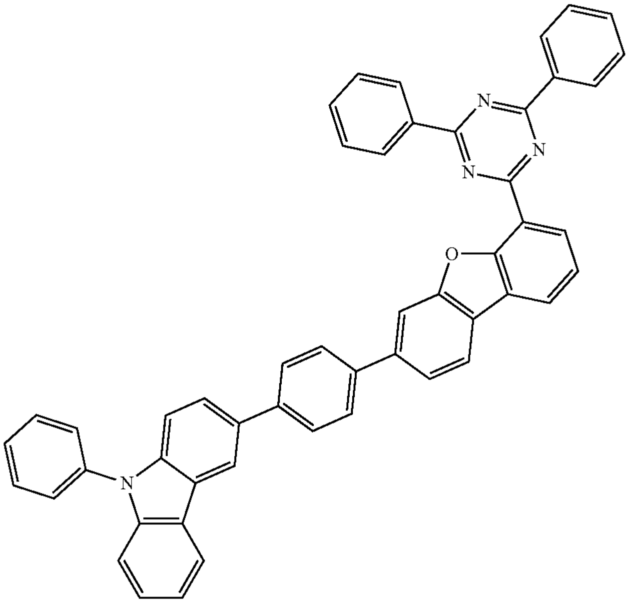 [SMILES: c1ccc(-c2nc(-c3ccccc3)nc(-c3cccc4c3oc3cc(-c5ccc(-c6ccc7c(c6)c6ccccc6n7-c6ccccc6)cc5)ccc34)n2)cc1]
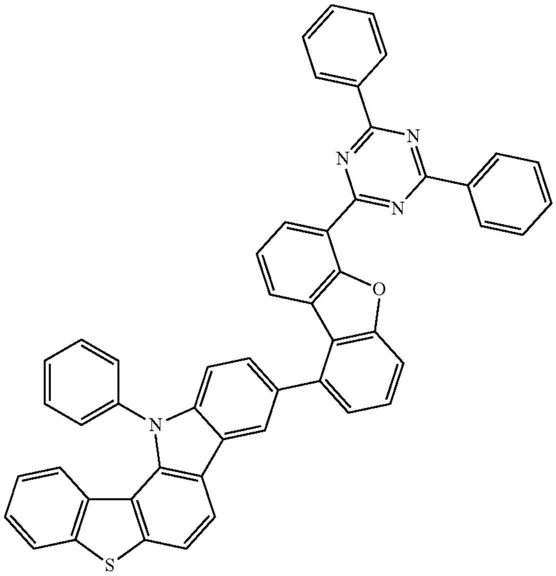 [SMILES: c1ccc(-c2nc(-c3ccccc3)nc(-c3cccc4c3oc3cccc(-c5ccc6c(c5)c5ccc7sc8ccccc8c7c5n6-c5ccccc5)c34)n2)cc1]
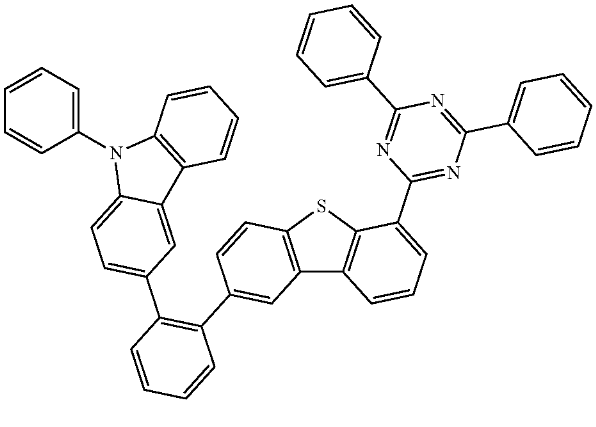 [SMILES: c1ccc(-c2nc(-c3ccccc3)nc(-c3cccc4c3sc3ccc(-c5ccccc5-c5ccc6c(c5)c5ccccc5n6-c5ccccc5)cc34)n2)cc1]

TABLE 4-continued
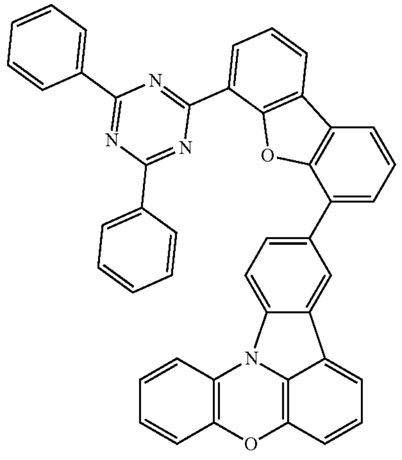 [SMILES: c1ccc(-c2nc(-c3ccccc3)nc(-c3cccc4c3oc3c(-c5ccc6c(c5)c5cccc7c5n6-c5ccccc5O7)cccc34)n2)cc1]
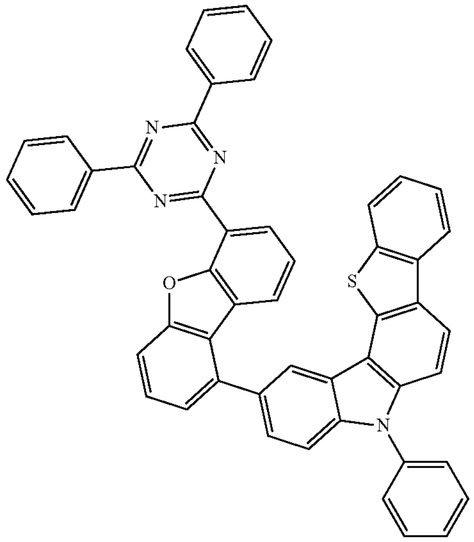
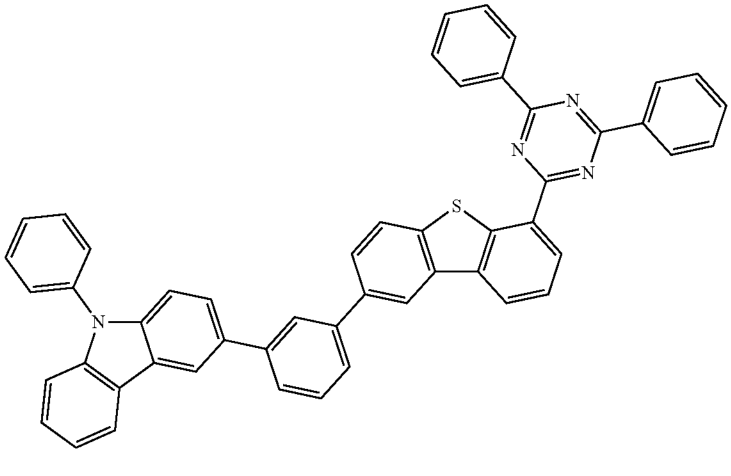 [SMILES: c1ccc(-c2nc(-c3ccccc3)nc(-c3cccc4c3sc3ccc(-c5cccc(-c6ccc7c(c6)c6ccccc6n7-c6ccccc6)c5)cc34)n2)cc1]

TABLE 4-continued
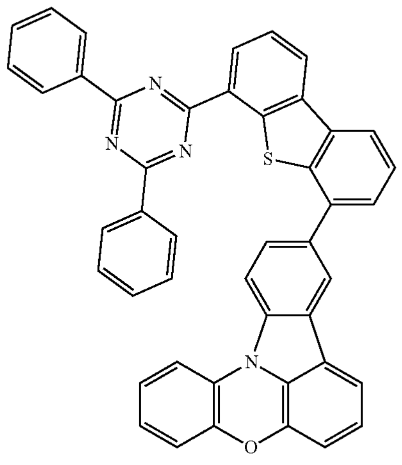 [SMILES: c1ccc(-c2nc(-c3ccccc3)nc(-c3cccc4c3sc3c(-c5ccc6c(c5)c5cccc7c5n6-c5ccccc5O7)cccc34)n2)cc1]
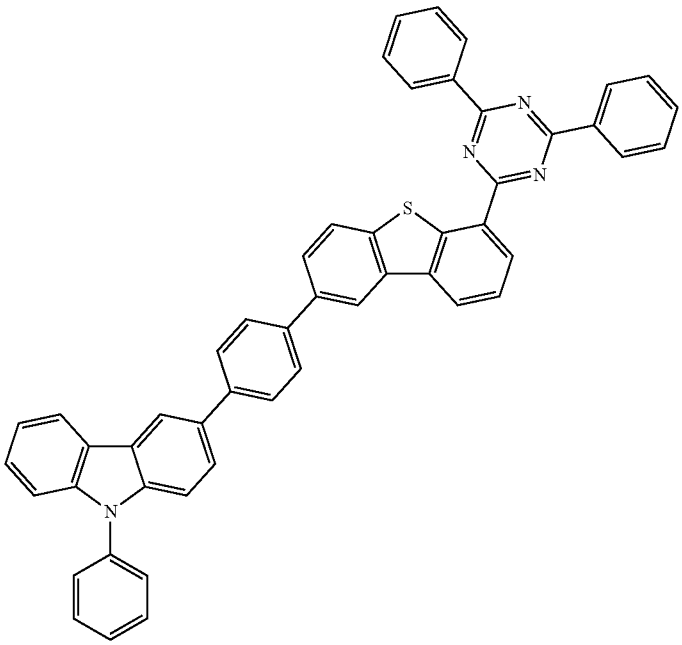 [SMILES: c1ccc(-c2nc(-c3ccccc3)nc(-c3cccc4c3sc3ccc(-c5ccc(-c6ccc7c(c6)c6ccccc6n7-c6ccccc6)cc5)cc34)n2)cc1]
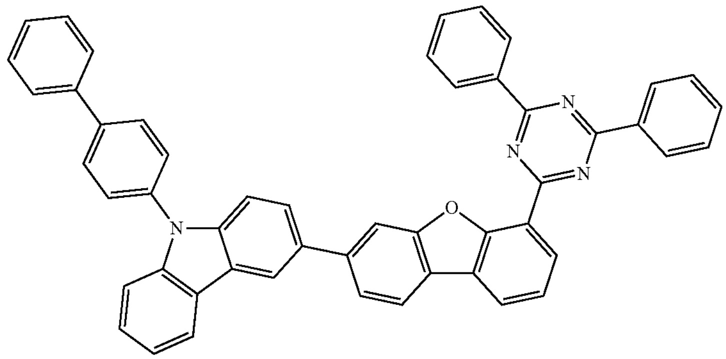 [SMILES: c1ccc(-c2ccc(-n3c4ccccc4c4cc(-c5ccc6c(c5)oc5c(-c7nc(-c8ccccc8)nc(-c8ccccc8)n7)cccc56)ccc43)cc2)cc1]

TABLE 4-continued
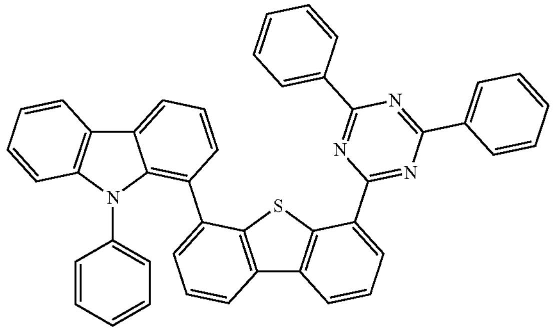 [SMILES: c1ccc(-c2nc(-c3ccccc3)nc(-c3cccc4c3sc3c(-c5cccc6c7ccccc7n(-c7ccccc7)c56)cccc34)n2)cc1]
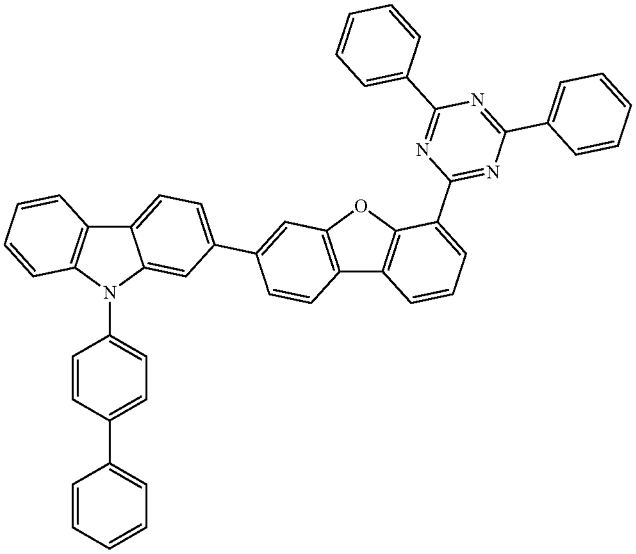
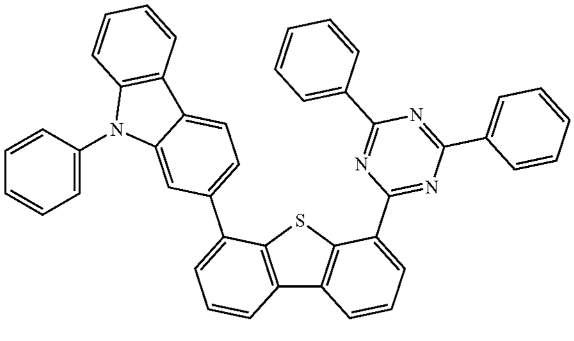

TABLE 4-continued
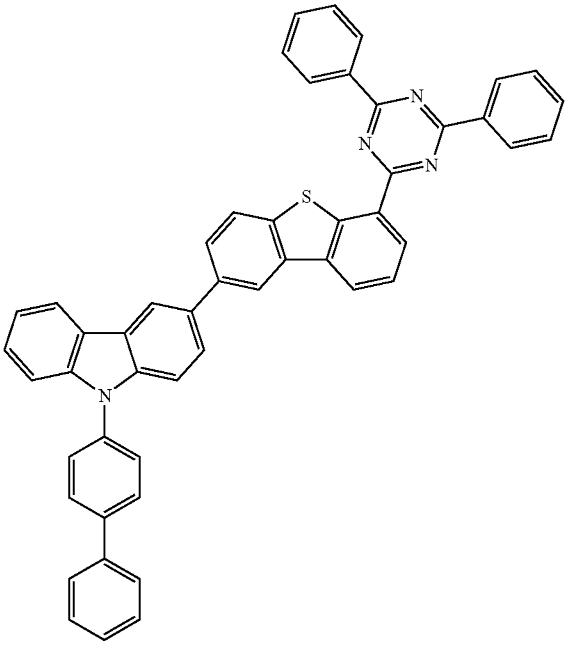 [SMILES: c1ccc(-c2ccc(-n3c4ccccc4c4cc(-c5ccc6sc7c(-c8nc(-c9ccccc9)nc(-c9ccccc9)n8)cccc7c6c5)ccc43)cc2)cc1]
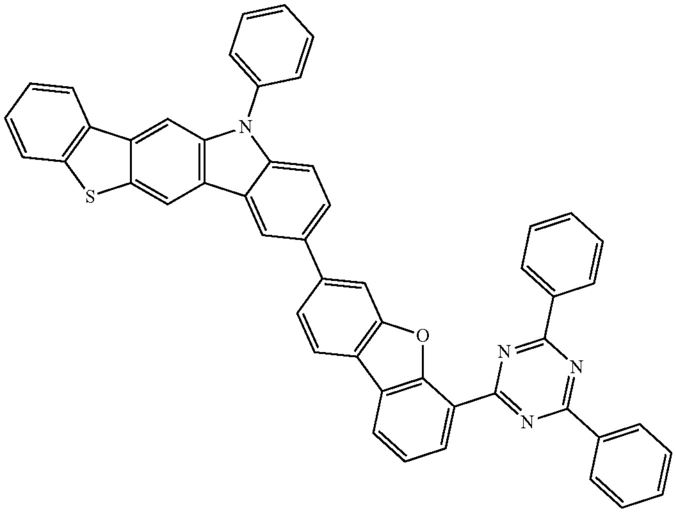
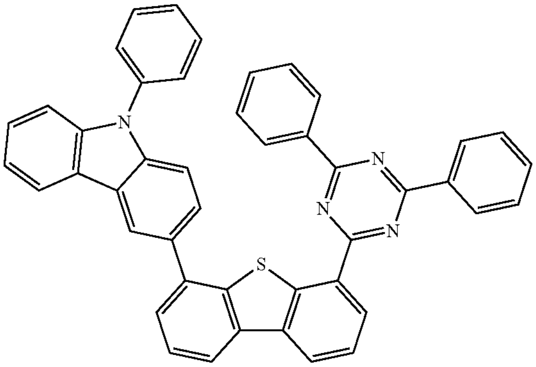 [SMILES: c1ccc(-c2nc(-c3ccccc3)nc(-c3cccc4c3sc3c(-c5ccc6c(c5)c5ccccc5n6-c5ccccc5)cccc34)n2)cc1]

TABLE 4-continued
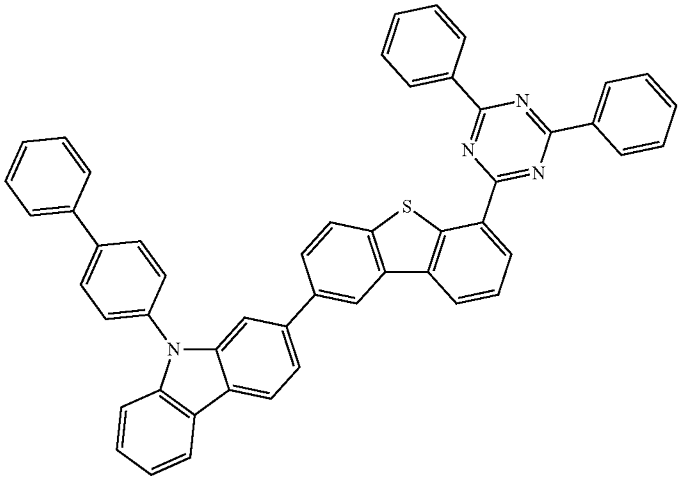
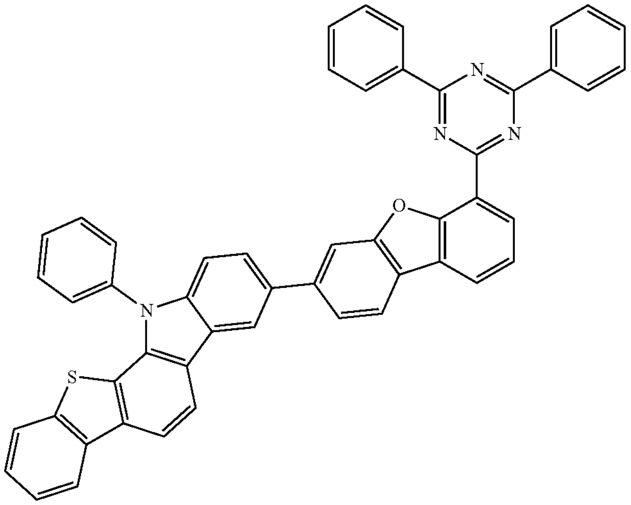 [SMILES: c1ccc(-c2nc(-c3ccccc3)nc(-c3cccc4c3oc3cc(-c5ccc6c(c5)c5ccc7c8ccccc8sc7c5n6-c5ccccc5)ccc34)n2)cc1]
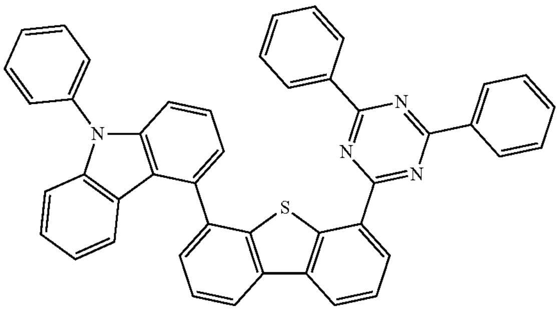

TABLE 4-continued
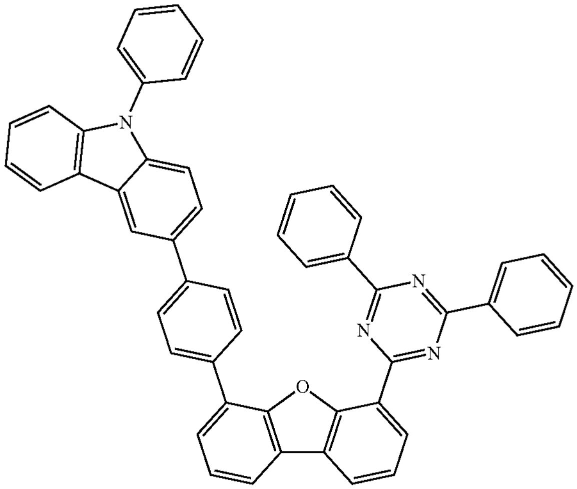 [SMILES: c1ccc(-c2nc(-c3ccccc3)nc(-c3cccc4c3oc3c(-c5ccc(-c6ccc7c(c6)c6ccccc6n7-c6ccccc6)cc5)cccc34)n2)cc1]
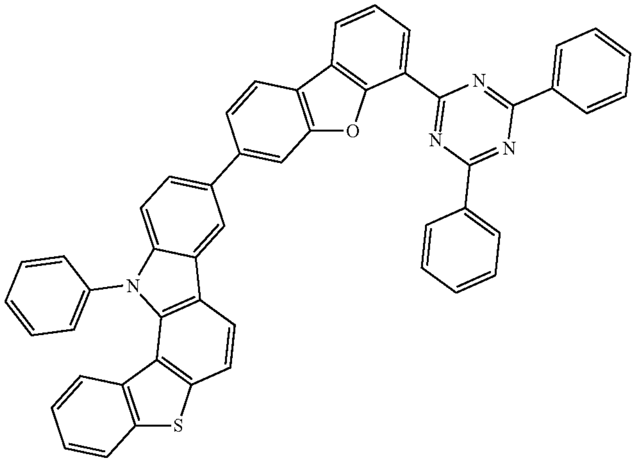 [SMILES: c1ccc(-c2nc(-c3ccccc3)nc(-c3cccc4c3oc3cc(-c5ccc6c(c5)c5ccc7sc8ccccc8c7c5n6-c5ccccc5)ccc34)n2)cc1]
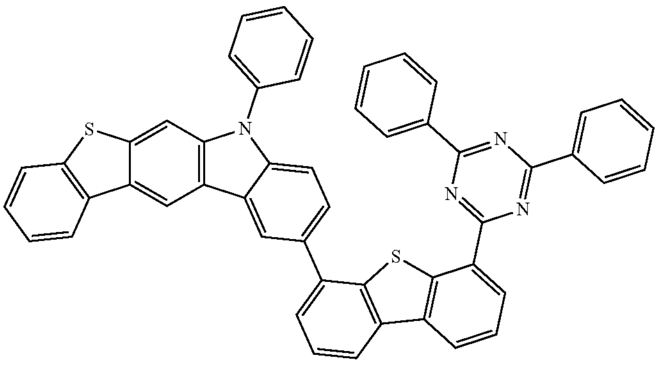

TABLE 4-continued
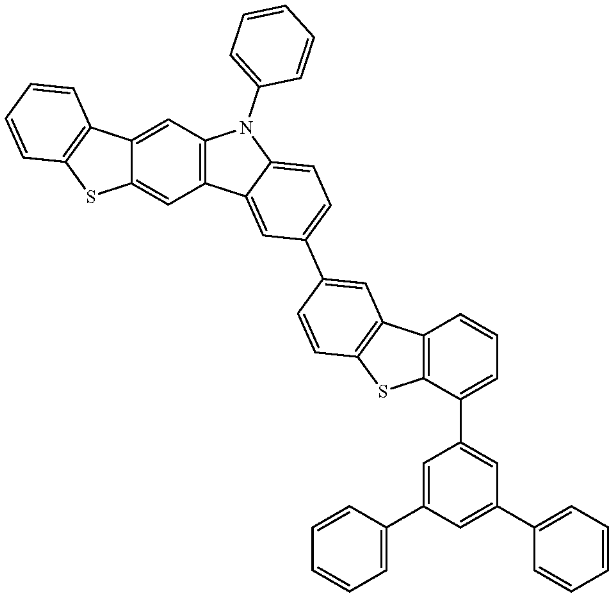 [SMILES: c1ccc(-c2cc(-c3ccccc3)cc(-c3cccc4c3sc3ccc(-c5ccc6c(c5)c5cc7sc8ccccc8c7cc5n6-c5ccccc5)cc34)c2)cc1]
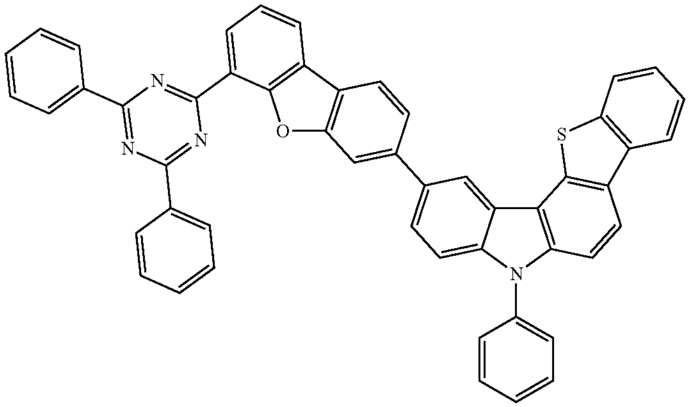 [SMILES: c1ccc(-c2nc(-c3ccccc3)nc(-c3cccc4c3oc3cc(-c5ccc6c(c5)c5c7sc8ccccc8c7ccc5n6-c5ccccc5)ccc34)n2)cc1]
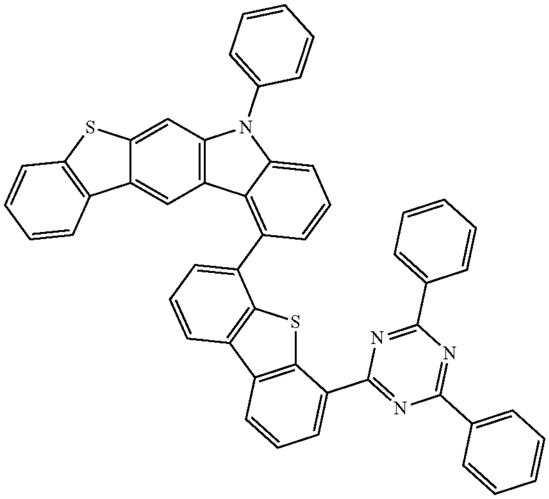 [SMILES: c1ccc(-c2nc(-c3ccccc3)nc(-c3cccc4c3sc3c(-c5cccc6c5c5cc7c(cc5n6-c5ccccc5)sc5ccccc57)cccc34)n2)cc1]

TABLE 4-continued
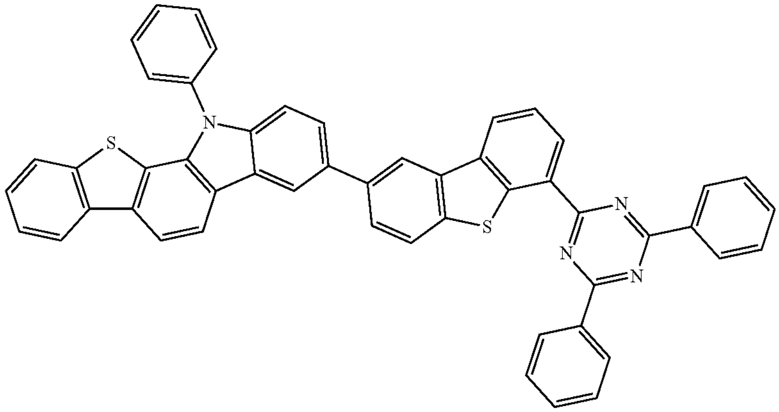 [SMILES: c1ccc(-c2nc(-c3ccccc3)nc(-c3cccc4c3sc3ccc(-c5ccc6c(c5)c5ccc7c8ccccc8sc7c5n6-c5ccccc5)cc34)n2)cc1]
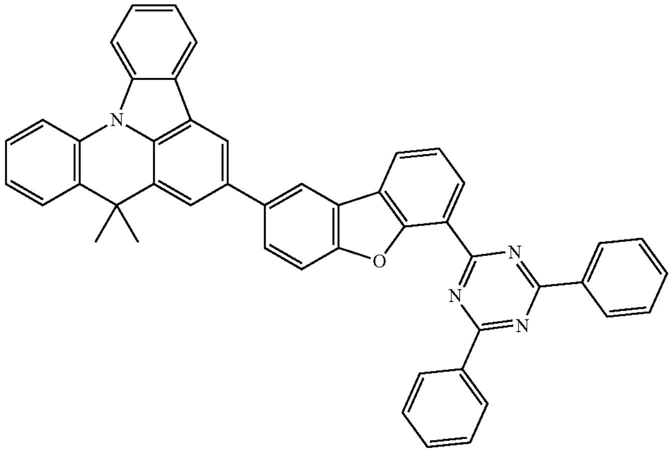 [SMILES: CC1(C)c2ccccc2-n2c3ccccc3c3cc(-c4ccc5oc6c(-c7nc(-c8ccccc8)nc(-c8ccccc8)n7)cccc6c5c4)cc1c32]
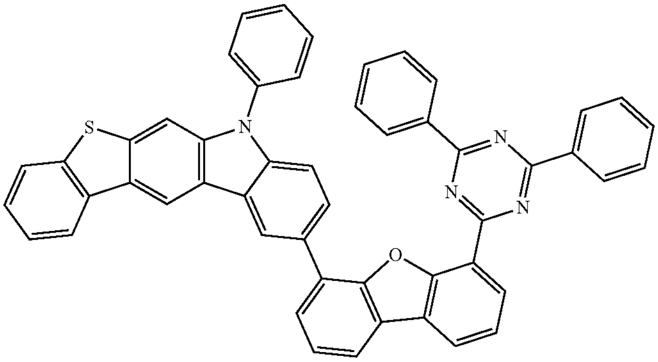 [SMILES: c1ccc(-c2nc(-c3ccccc3)nc(-c3cccc4c3oc3c(-c5ccc6c(c5)c5cc7c(cc5n6-c5ccccc5)sc5ccccc57)cccc34)n2)cc1]
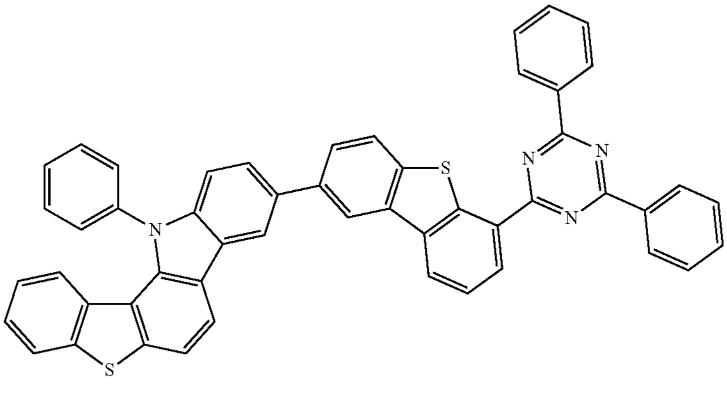 [SMILES: c1ccc(-c2nc(-c3ccccc3)nc(-c3cccc4c3sc3ccc(-c5ccc6c(c5)c5ccc7sc8ccccc8c7c5n6-c5ccccc5)cc34)n2)cc1]

TABLE 4-continued
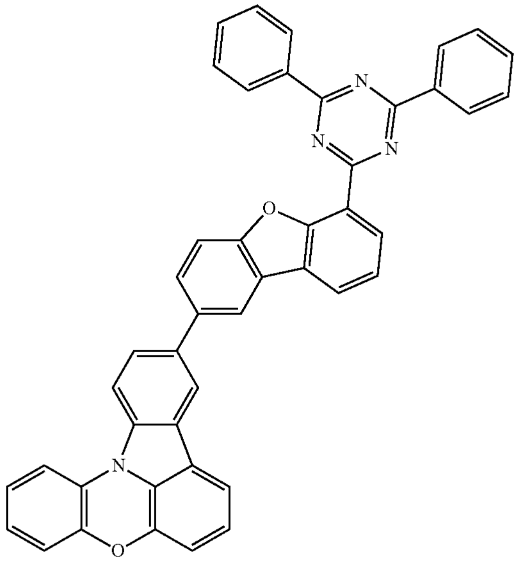
68
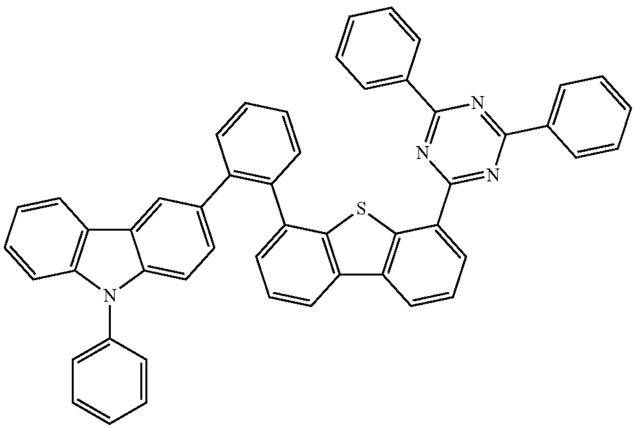 [SMILES: c1ccc(-c2nc(-c3ccccc3)nc(-c3cccc4c3sc3c(-c5ccccc5-c5ccc6c(c5)c5ccccc5n6-c5ccccc5)cccc34)n2)cc1]
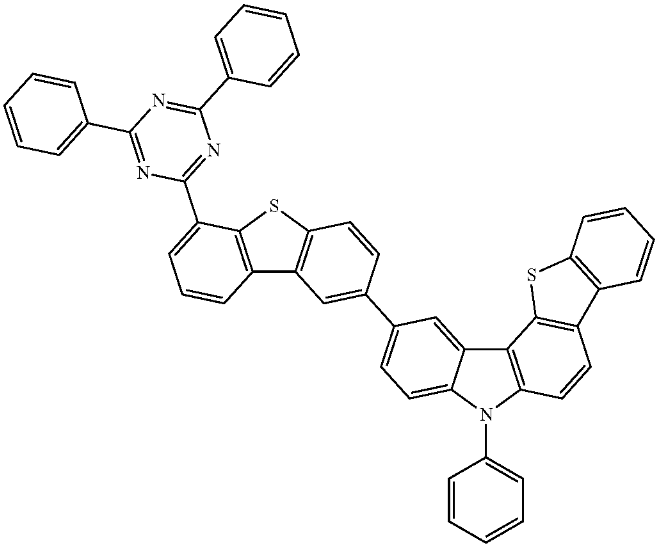 [SMILES: c1ccc(-c2nc(-c3ccccc3)nc(-c3cccc4c3sc3ccc(-c5ccc6c(c5)c5c7sc8ccccc8c7ccc5n6-c5ccccc5)cc34)n2)cc1]

TABLE 4-continued
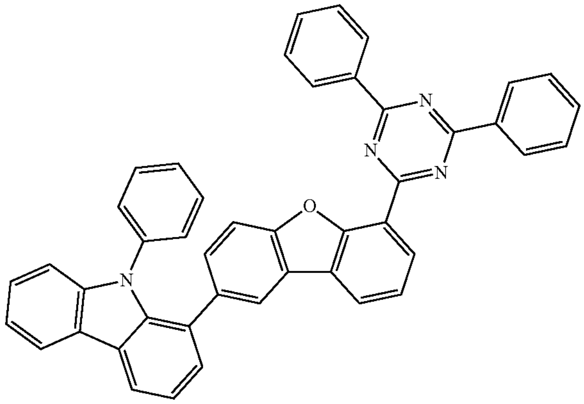
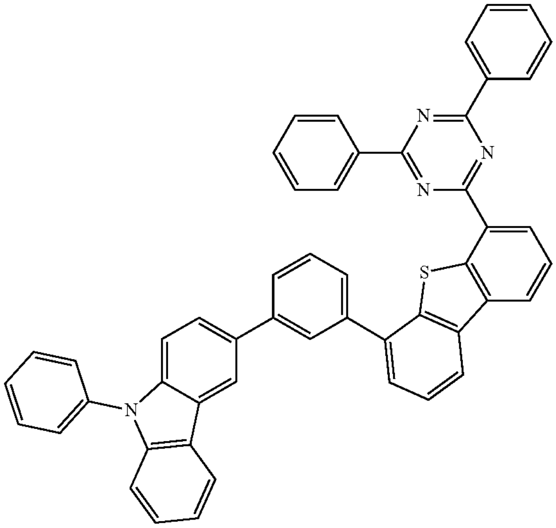 [SMILES: c1ccc(-c2nc(-c3ccccc3)nc(-c3cccc4c3sc3c(-c5cccc(-c6ccc7c(c6)c6ccccc6n7-c6ccccc6)c5)cccc34)n2)cc1]
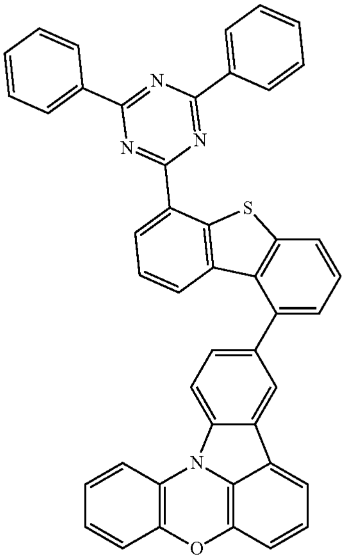 [SMILES: c1ccc(-c2nc(-c3ccccc3)nc(-c3cccc4c3sc3cccc(-c5ccc6c(c5)c5cccc7c5n6-c5ccccc5O7)c34)n2)cc1]

TABLE 4-continued
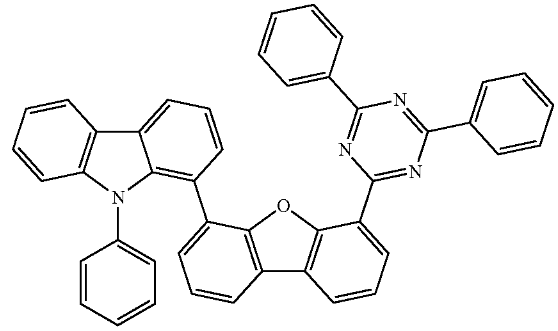
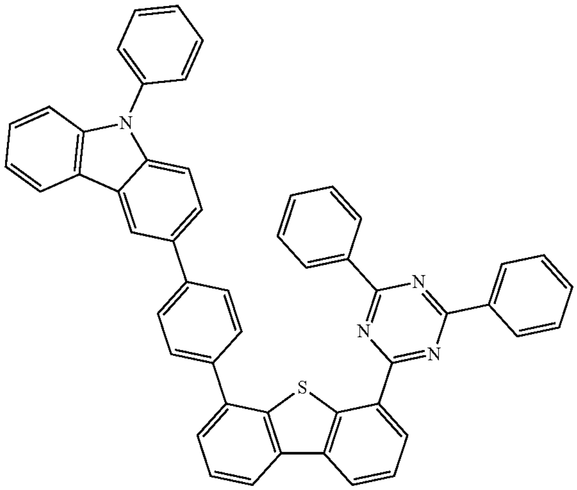
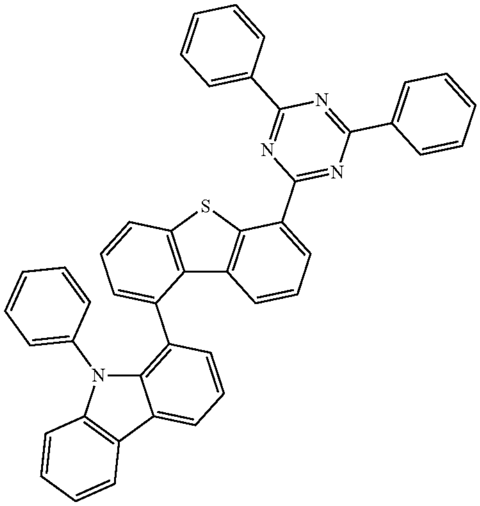

TABLE 4-continued
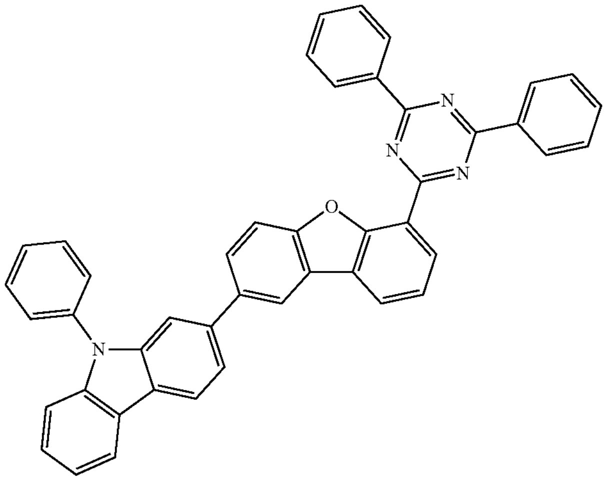 [SMILES: c1ccc(-c2nc(-c3ccccc3)nc(-c3cccc4c3oc3ccc(-c5ccc6c7ccccc7n(-c7ccccc7)c6c5)cc34)n2)cc1]
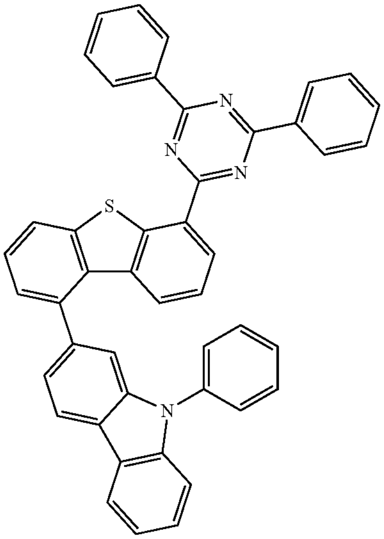
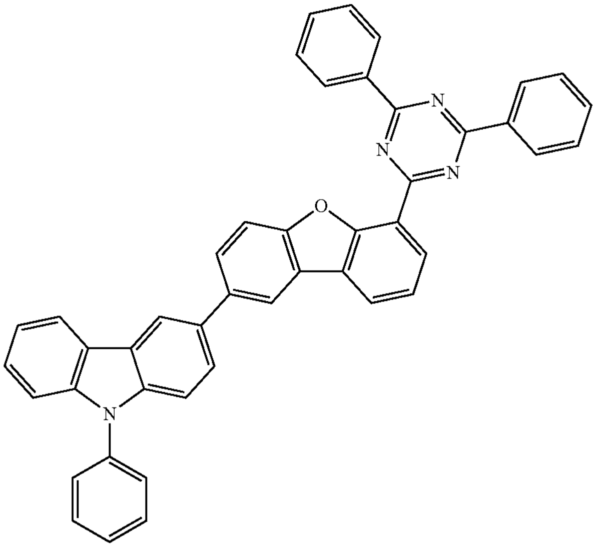

TABLE 4-continued
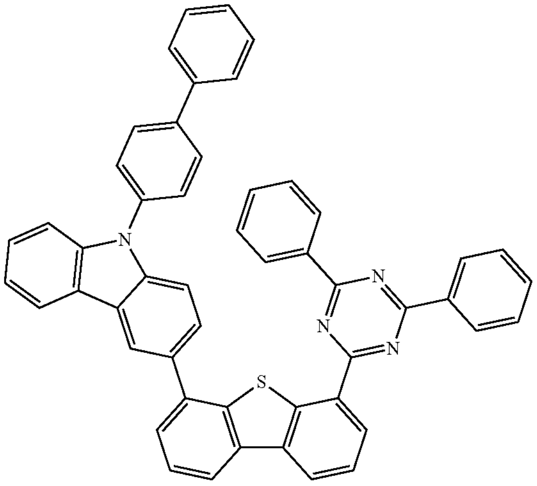 [SMILES: c1ccc(-c2ccc(-n3c4ccccc4c4cc(-c5cccc6c5sc5c(-c7nc(-c8ccccc8)nc(-c8ccccc8)n7)cccc56)ccc43)cc2)cc1]
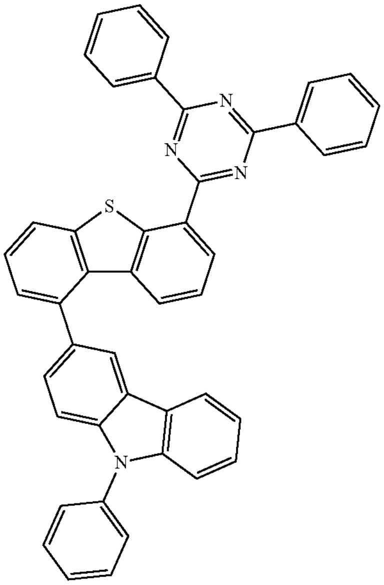 [SMILES: c1ccc(-c2nc(-c3ccccc3)nc(-c3cccc4c3sc3cccc(-c5ccc6c(c5)c5ccccc5n6-c5ccccc5)c34)n2)cc1]
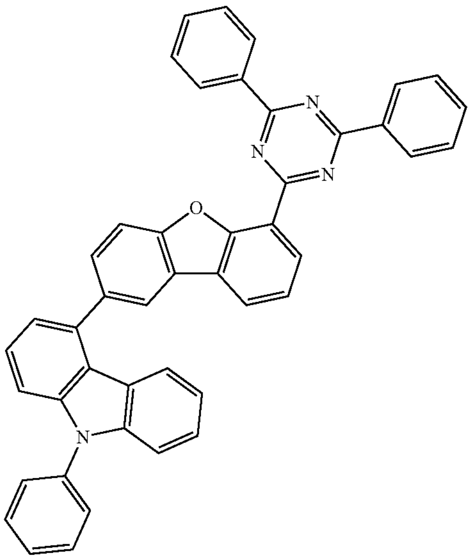 [SMILES: c1ccc(-c2nc(-c3ccccc3)nc(-c3cccc4c3oc3ccc(-c5cccc6c5c5ccccc5n6-c5ccccc5)cc34)n2)cc1]

TABLE 4-continued
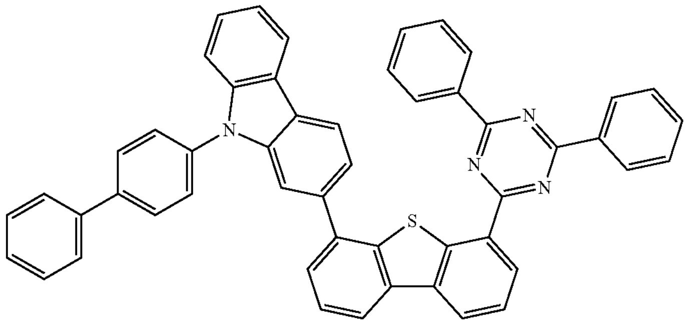 [SMILES: c1ccc(-c2ccc(-n3c4ccccc4c4ccc(-c5cccc6c5sc5c(-c7nc(-c8ccccc8)nc(-c8ccccc8)n7)cccc56)cc43)cc2)cc1]
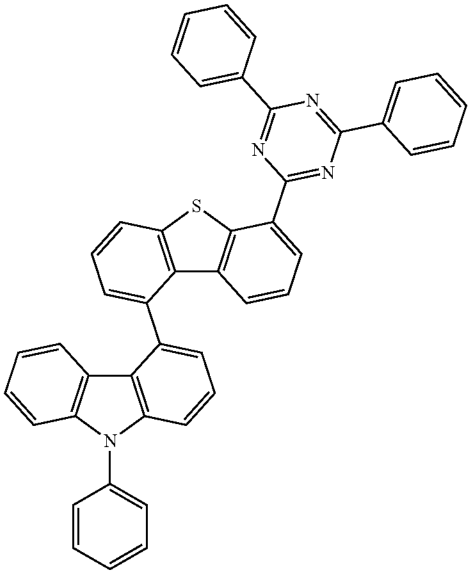
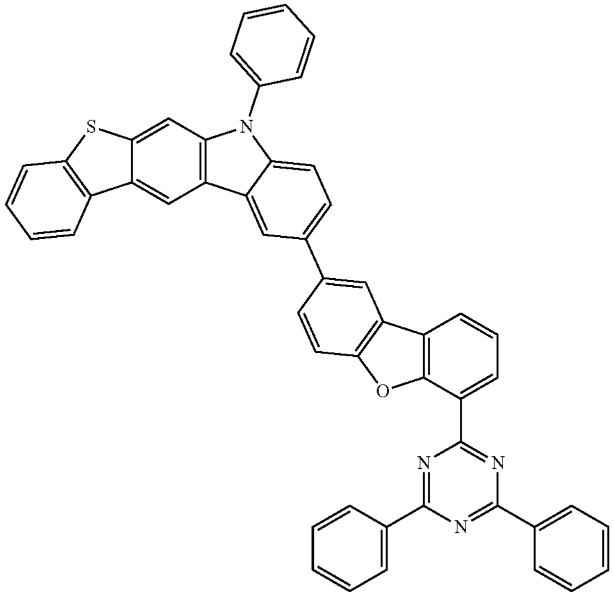 [SMILES: c1ccc(-c2nc(-c3ccccc3)nc(-c3cccc4c3oc3ccc(-c5ccc6c(c5)c5cc7c(cc5n6-c5ccccc5)sc5ccccc57)cc34)n2)cc1]

TABLE 4-continued
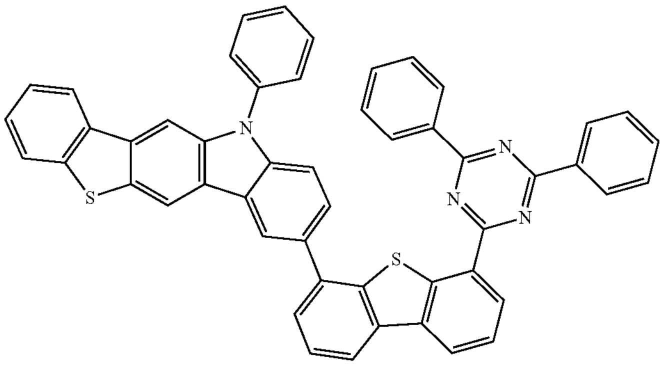 [SMILES: c1ccc(-c2nc(-c3ccccc3)nc(-c3cccc4c3sc3c(-c5ccc6c(c5)c5cc7sc8ccccc8c7cc5n6-c5ccccc5)cccc34)n2)cc1]
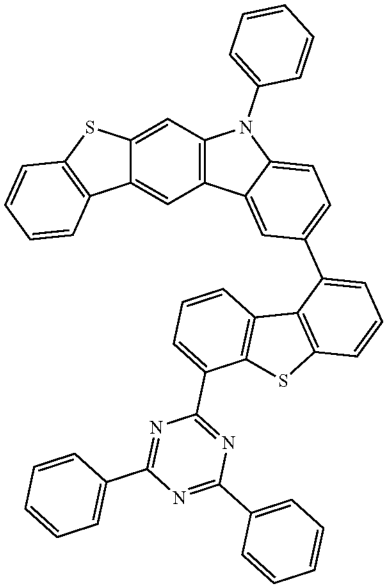 [SMILES: c1ccc(-c2nc(-c3ccccc3)nc(-c3cccc4c3sc3cccc(-c5ccc6c(c5)c5cc7c(cc5n6-c5ccccc5)sc5ccccc57)c34)n2)cc1]
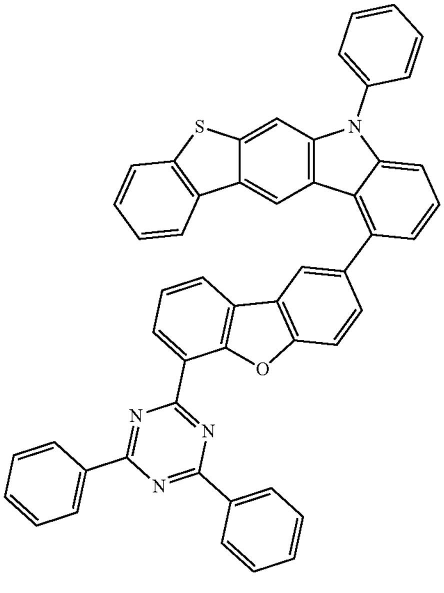 [SMILES: c1ccc(-c2nc(-c3ccccc3)nc(-c3cccc4c3oc3ccc(-c5cccc6c5c5cc7c(cc5n6-c5ccccc5)sc5ccccc57)cc34)n2)cc1]

TABLE 4-continued
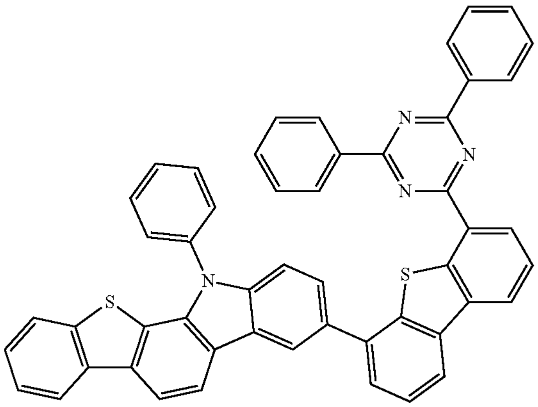
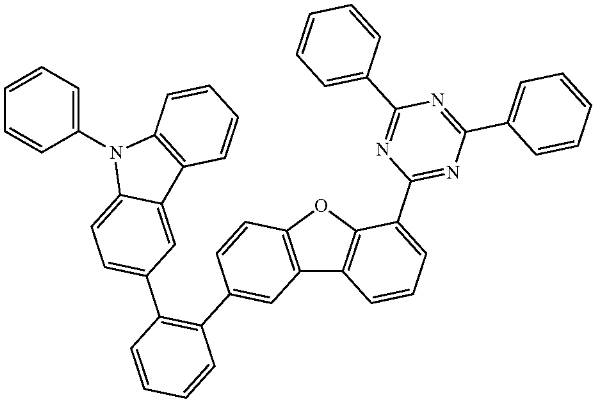
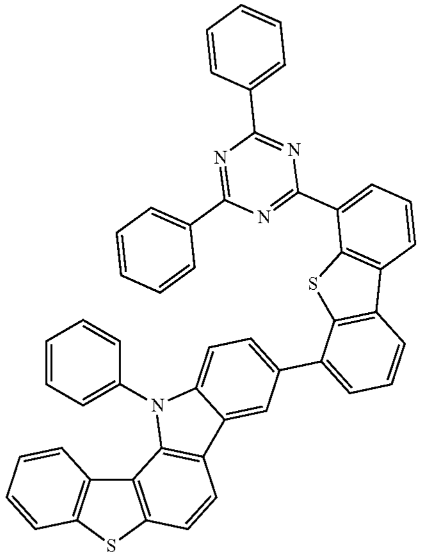

TABLE 4-continued
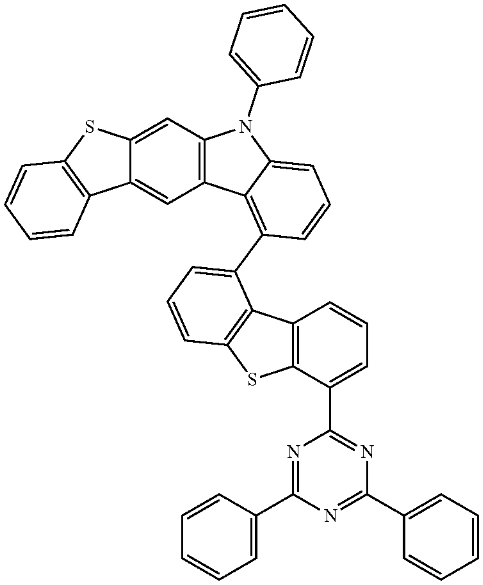 [SMILES: c1ccc(-c2nc(-c3ccccc3)nc(-c3cccc4c3sc3cccc(-c5cccc6c5c5cc7c(cc5n6-c5ccccc5)sc5ccccc57)c34)n2)cc1]
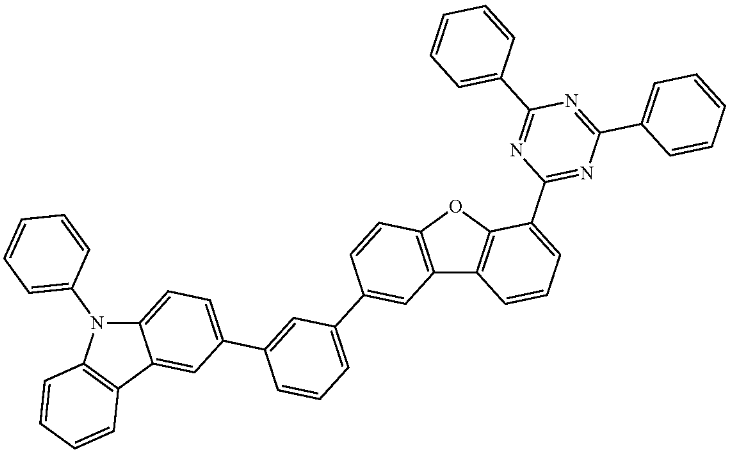
70
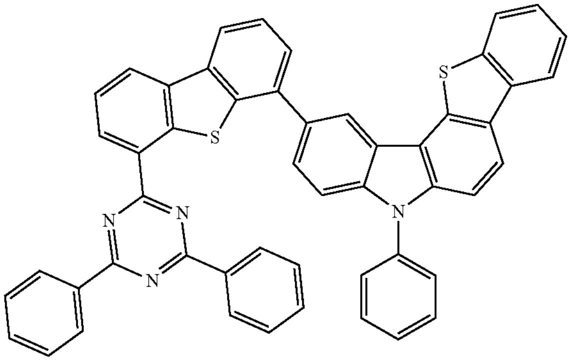

TABLE 4-continued
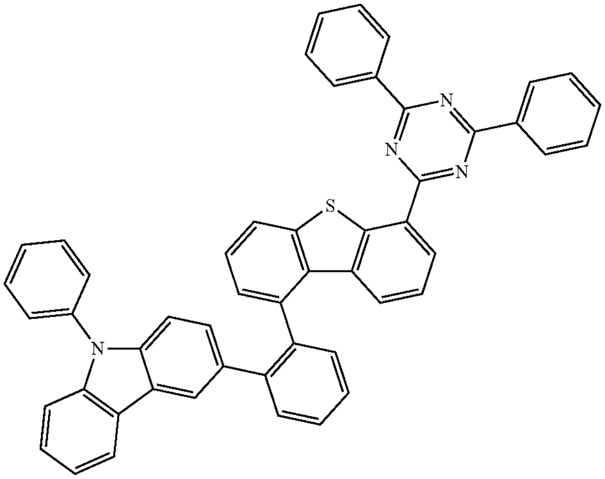 [SMILES: c1ccc(-c2nc(-c3ccccc3)nc(-c3cccc4c3sc3cccc(-c5ccccc5-c5ccc6c(c5)c5ccccc5n6-c5ccccc5)c34)n2)cc1]
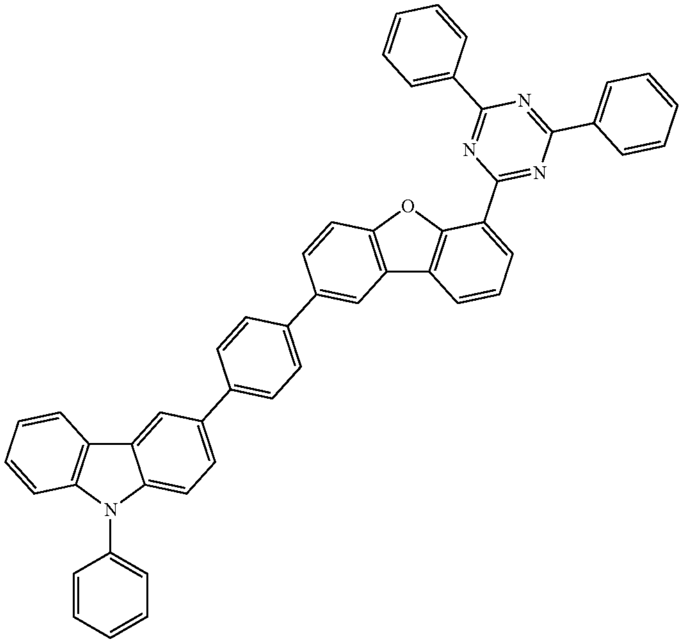 [SMILES: c1ccc(-c2nc(-c3ccccc3)nc(-c3cccc4c3oc3ccc(-c5ccc(-c6ccc7c(c6)c6ccccc6n7-c6ccccc6)cc5)cc34)n2)cc1]
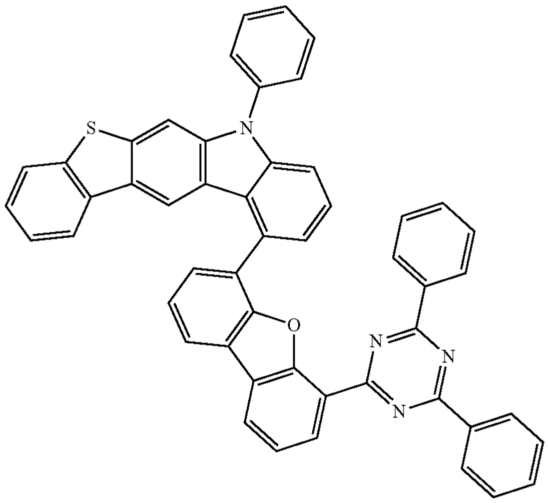 [SMILES: c1ccc(-c2nc(-c3ccccc3)nc(-c3cccc4c3oc3c(-c5cccc6c5c5cc7c(cc5n6-c5ccccc5)sc5ccccc57)cccc34)n2)cc1]

TABLE 4-continued
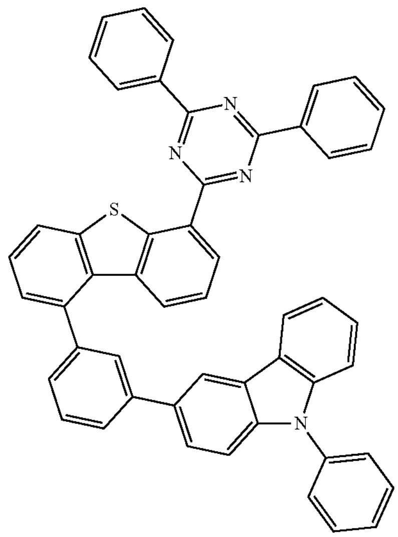 [SMILES: c1ccc(-c2nc(-c3ccccc3)nc(-c3cccc4c3sc3cccc(-c5cccc(-c6ccc7c(c6)c6ccccc6n7-c6ccccc6)c5)c34)n2)cc1]
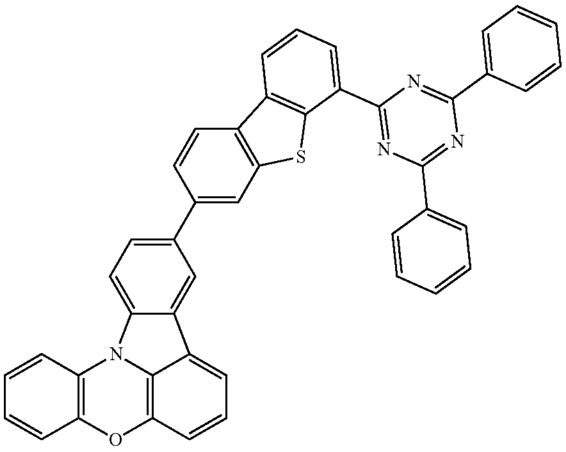 [SMILES: c1ccc(-c2nc(-c3ccccc3)nc(-c3cccc4c3sc3cc(-c5ccc6c(c5)c5cccc7c5n6-c5ccccc5O7)ccc34)n2)cc1]
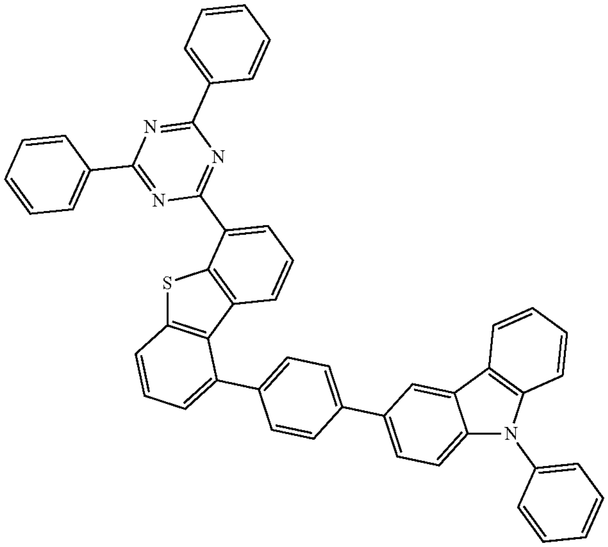 [SMILES: c1ccc(-c2nc(-c3ccccc3)nc(-c3cccc4c3sc3cccc(-c5ccc(-c6ccc7c(c6)c6ccccc6n7-c6ccccc6)cc5)c34)n2)cc1]

TABLE 4-continued
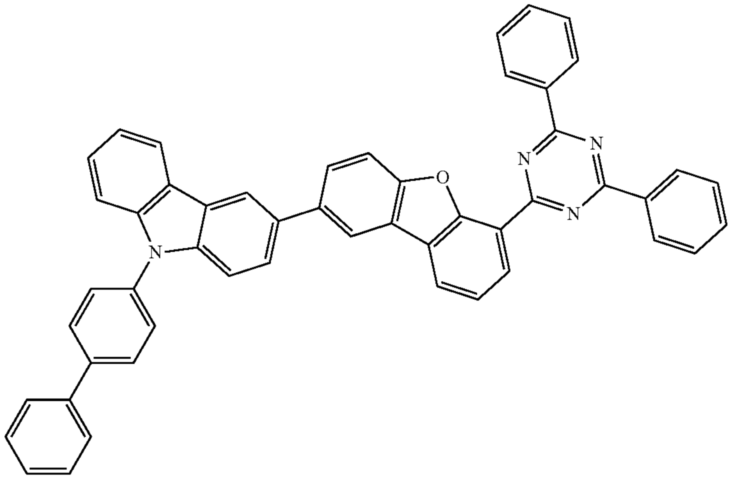
71
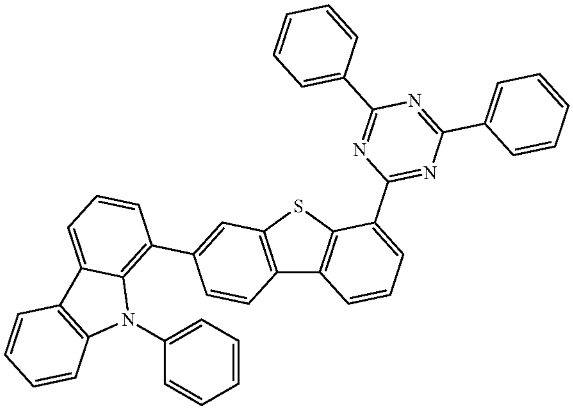
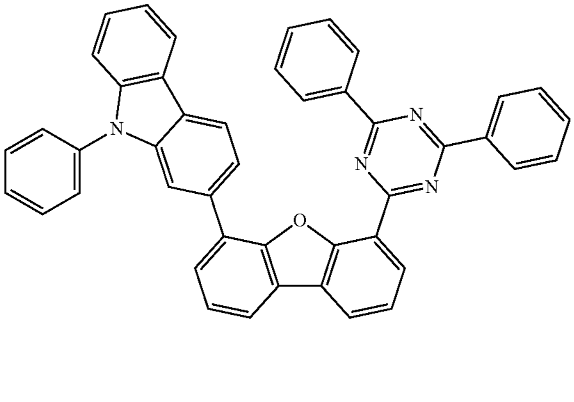 [SMILES: c1ccc(-c2nc(-c3ccccc3)nc(-c3cccc4c3oc3c(-c5ccc6c7ccccc7n(-c7ccccc7)c6c5)cccc34)n2)cc1]

TABLE 4-continued
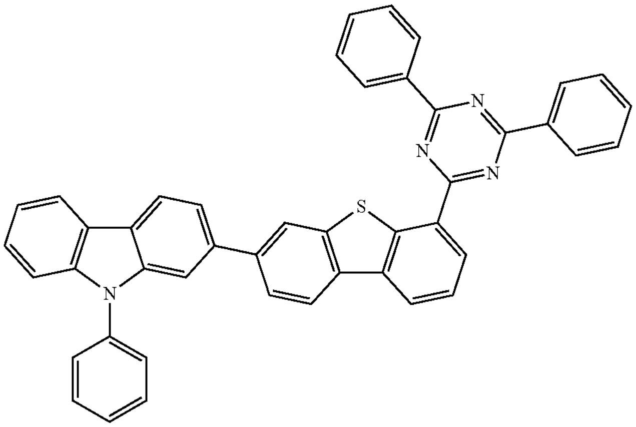 [SMILES: c1ccc(-c2nc(-c3ccccc3)nc(-c3cccc4c3sc3cc(-c5ccc6c7ccccc7n(-c7ccccc7)c6c5)ccc34)n2)cc1]
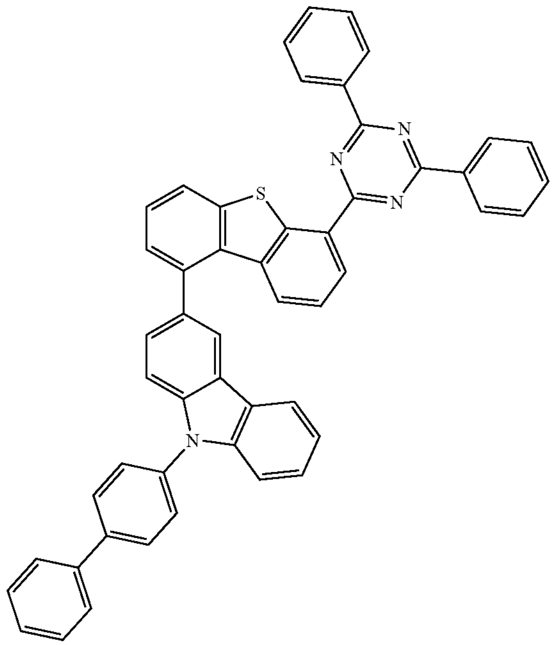 [SMILES: c1ccc(-c2ccc(-n3c4ccccc4c4cc(-c5cccc6sc7c(-c8nc(-c9ccccc9)nc(-c9ccccc9)n8)cccc7c56)ccc43)cc2)cc1]
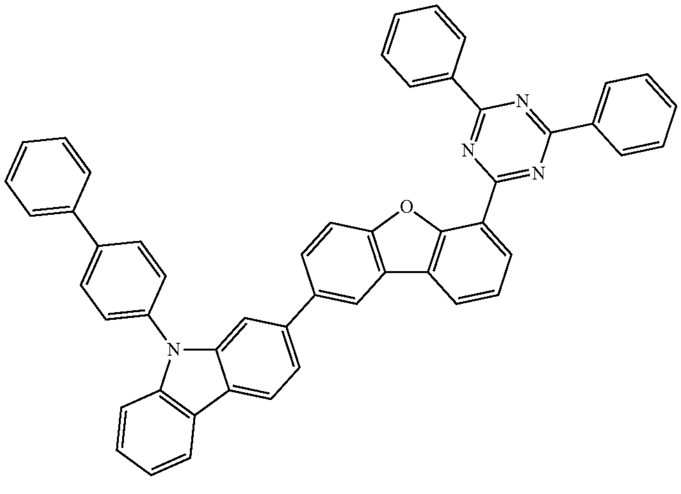 [SMILES: c1ccc(-c2ccc(-n3c4ccccc4c4ccc(-c5ccc6oc7c(-c8nc(-c9ccccc9)nc(-c9ccccc9)n8)cccc7c6c5)cc43)cc2)cc1]

TABLE 4-continued
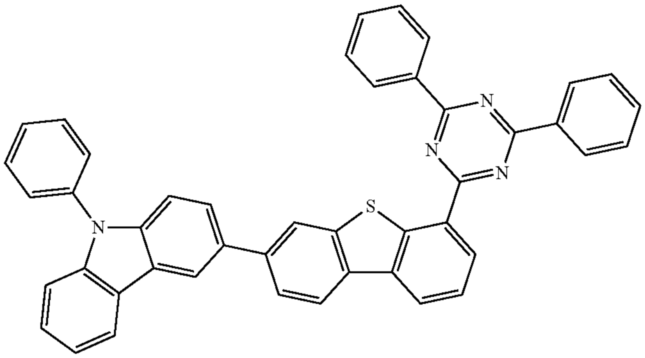
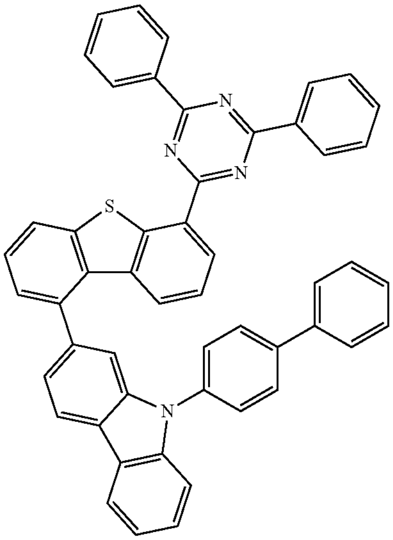
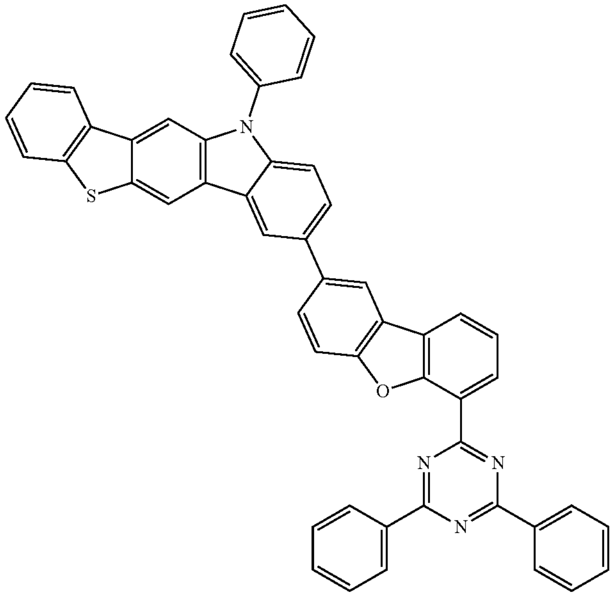 [SMILES: c1ccc(-c2nc(-c3ccccc3)nc(-c3cccc4c3oc3ccc(-c5ccc6c(c5)c5cc7sc8ccccc8c7cc5n6-c5ccccc5)cc34)n2)cc1]

TABLE 4-continued
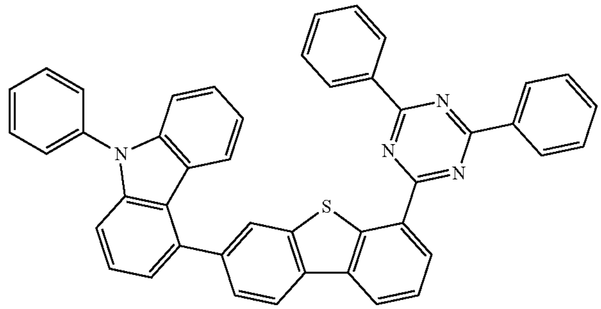
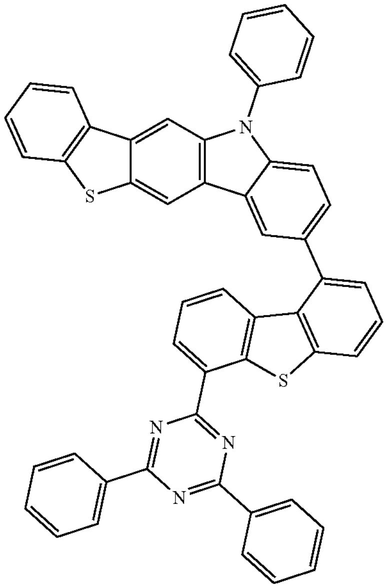
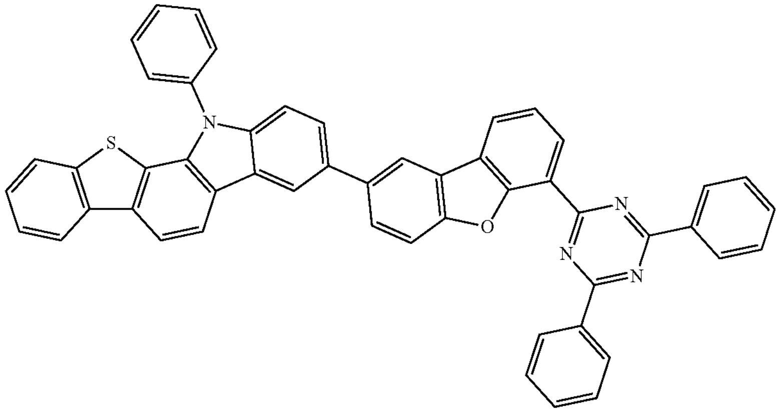

TABLE 4-continued
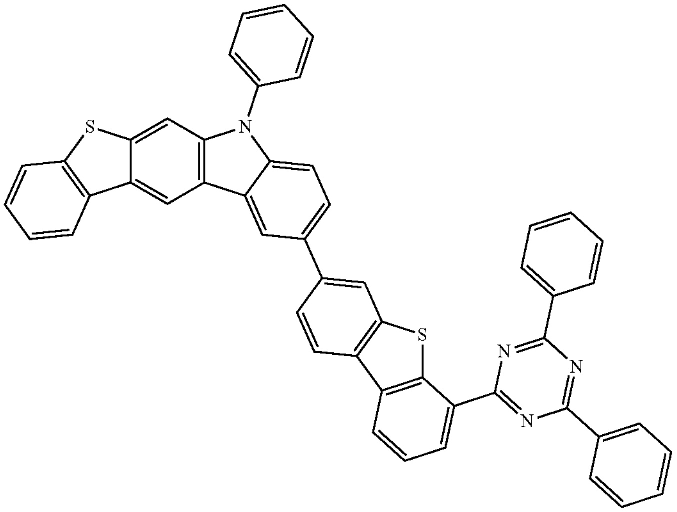 [SMILES: c1ccc(-c2nc(-c3ccccc3)nc(-c3cccc4c3sc3cc(-c5ccc6c(c5)c5cc7c(cc5n6-c5ccccc5)sc5ccccc57)ccc34)n2)cc1]
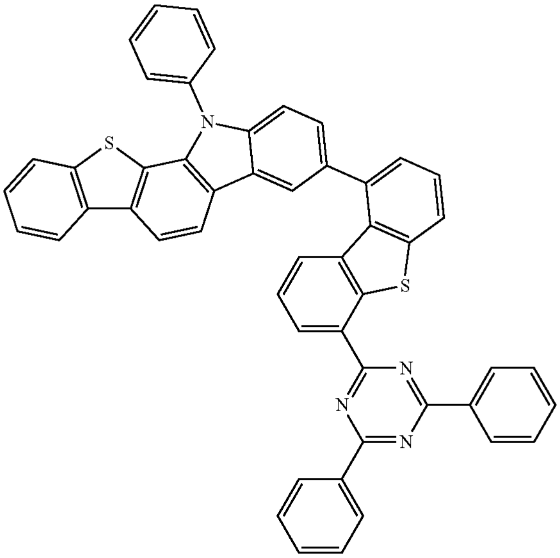 [SMILES: c1ccc(-c2nc(-c3ccccc3)nc(-c3cccc4c3sc3cccc(-c5ccc6c(c5)c5ccc7c8ccccc8sc7c5n6-c5ccccc5)c34)n2)cc1]
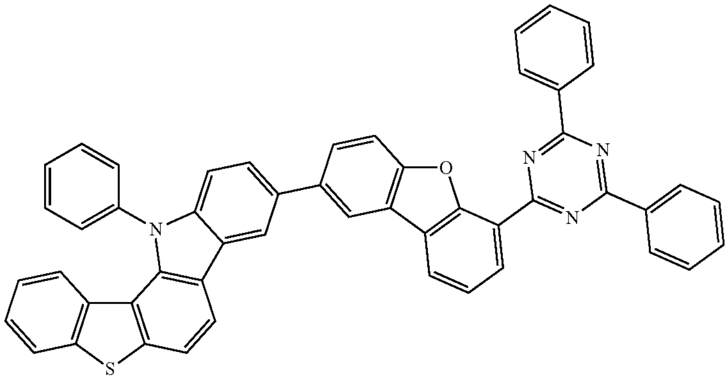 [SMILES: c1ccc(-c2nc(-c3ccccc3)nc(-c3cccc4c3oc3ccc(-c5ccc6c(c5)c5ccc7sc8ccccc8c7c5n6-c5ccccc5)cc34)n2)cc1]

TABLE 4-continued
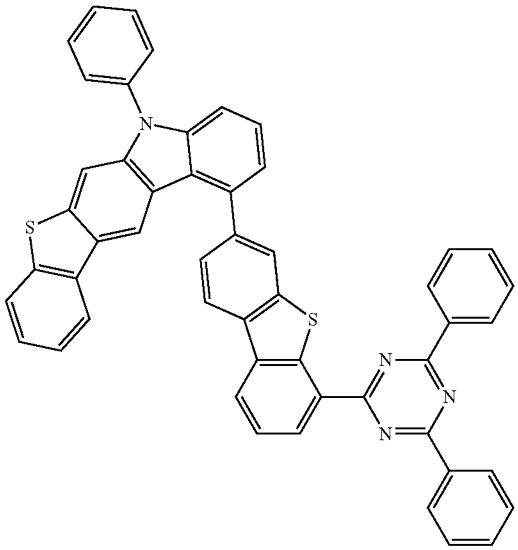 [SMILES: c1ccc(-c2nc(-c3ccccc3)nc(-c3cccc4c3sc3cc(-c5cccc6c5c5cc7c(cc5n6-c5ccccc5)sc5ccccc57)ccc34)n2)cc1]
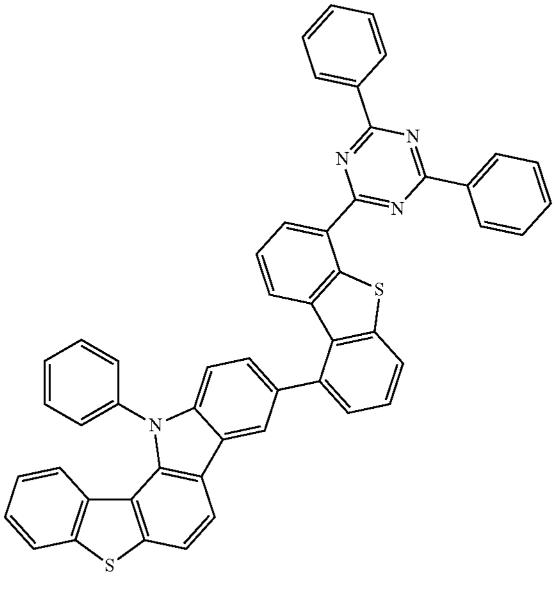

TABLE 4-continued
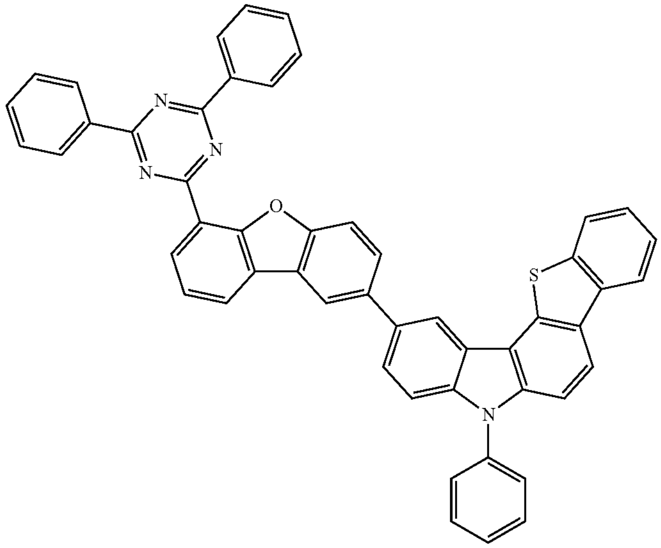
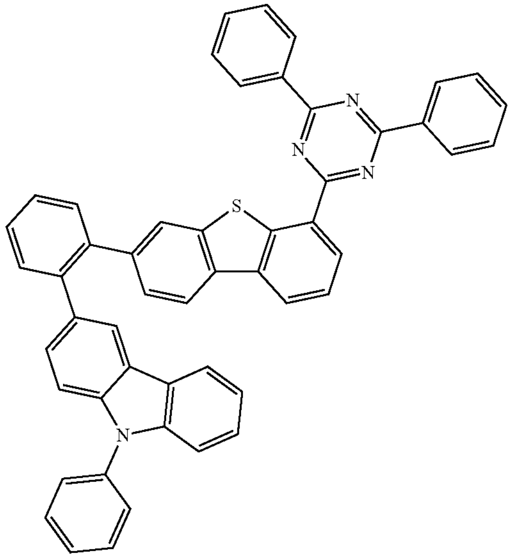 [SMILES: c1ccc(-c2nc(-c3ccccc3)nc(-c3cccc4c3sc3cc(-c5ccccc5-c5ccc6c(c5)c5ccccc5n6-c5ccccc5)ccc34)n2)cc1]
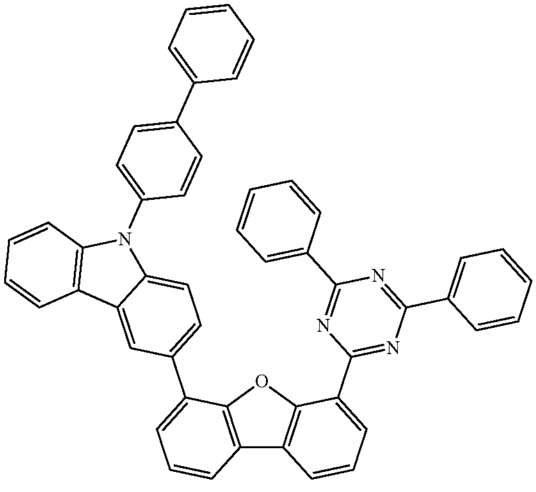

TABLE 4-continued
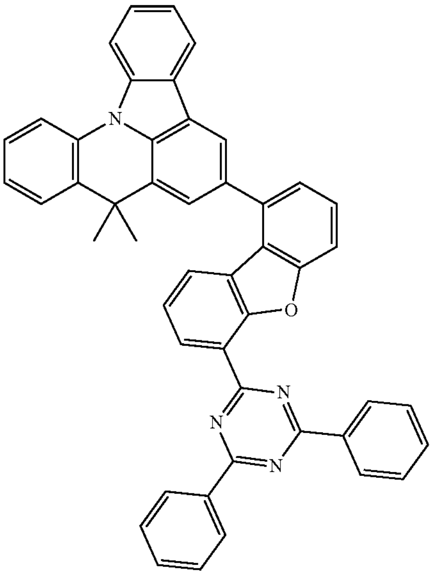 [SMILES: CC1(C)c2ccccc2-n2c3ccccc3c3cc(-c4cccc5oc6c(-c7nc(-c8ccccc8)nc(-c8ccccc8)n7)cccc6c45)cc1c32]
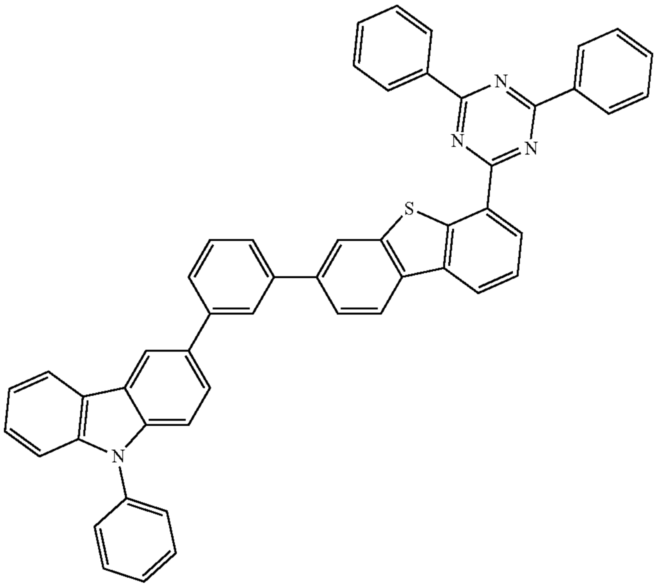 [SMILES: c1ccc(-c2nc(-c3ccccc3)nc(-c3cccc4c3sc3cc(-c5cccc(-c6ccc7c(c6)c6ccccc6n7-c6ccccc6)c5)ccc34)n2)cc1]

TABLE 4-continued
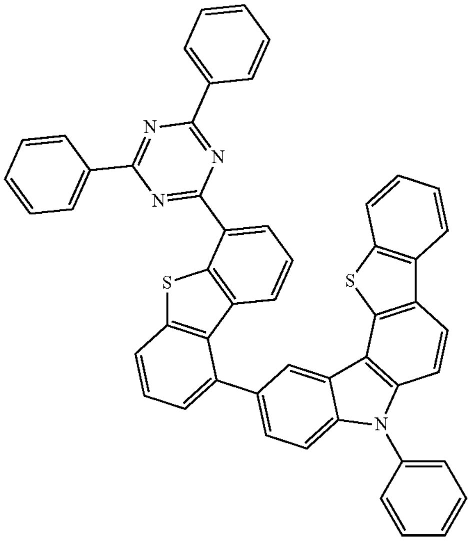
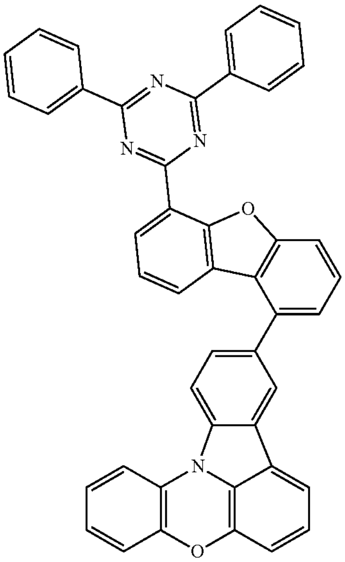 [SMILES: c1ccc(-c2nc(-c3ccccc3)nc(-c3cccc4c3oc3cccc(-c5ccc6c(c5)c5cccc7c5n6-c5ccccc5O7)c34)n2)cc1]

TABLE 4-continued
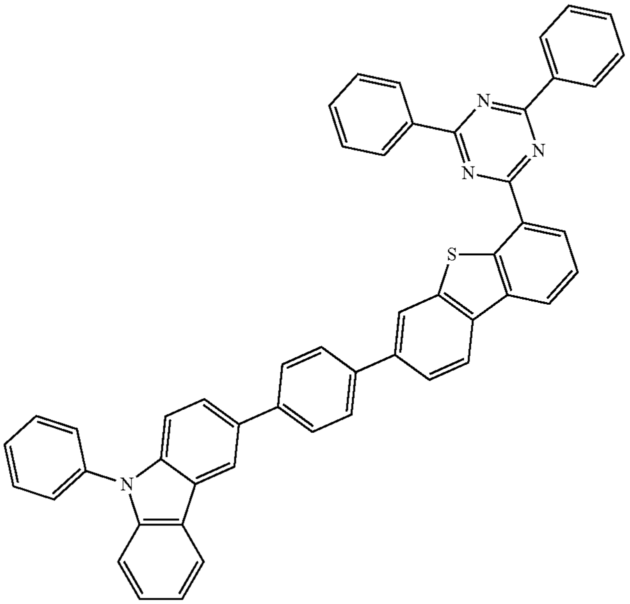 [SMILES: c1ccc(-c2nc(-c3ccccc3)nc(-c3cccc4c3sc3cc(-c5ccc(-c6ccc7c(c6)c6ccccc6n7-c6ccccc6)cc5)ccc34)n2)cc1]
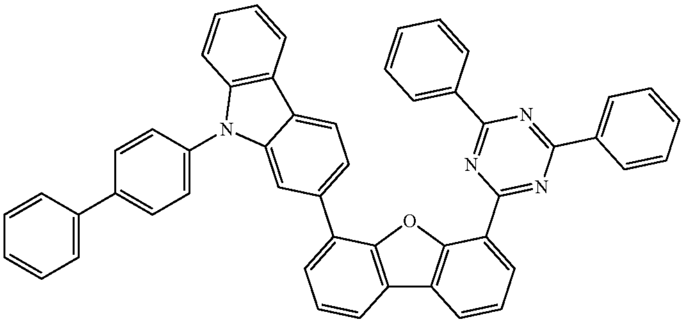 [SMILES: c1ccc(-c2ccc(-n3c4ccccc4c4ccc(-c5cccc6c5oc5c(-c7nc(-c8ccccc8)nc(-c8ccccc8)n7)cccc56)cc43)cc2)cc1]
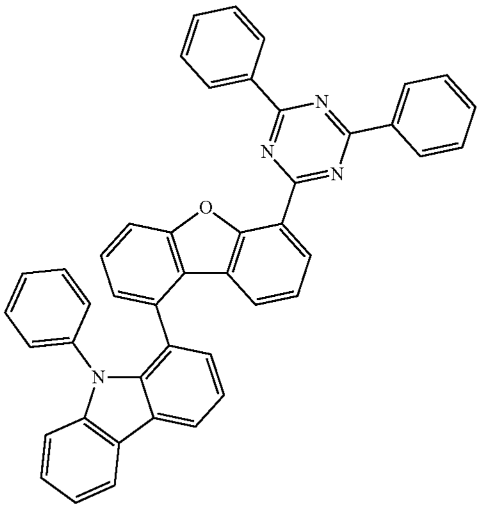

TABLE 4-continued
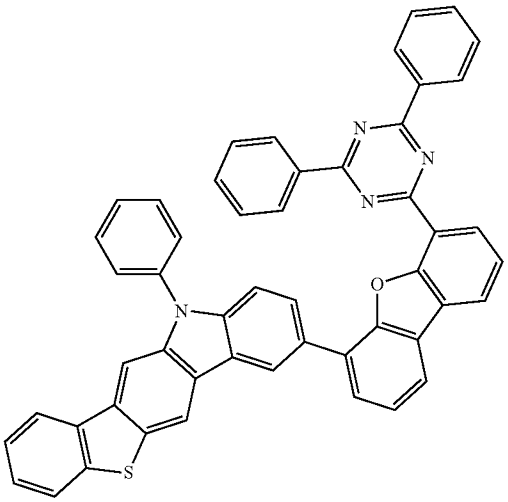 [SMILES: c1ccc(-c2nc(-c3ccccc3)nc(-c3cccc4c3oc3c(-c5ccc6c(c5)c5cc7sc8ccccc8c7cc5n6-c5ccccc5)cccc34)n2)cc1]
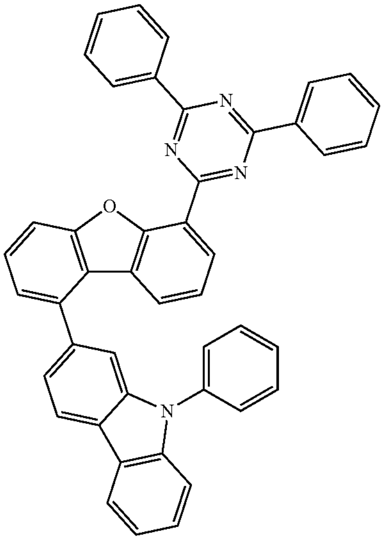 [SMILES: c1ccc(-c2nc(-c3ccccc3)nc(-c3cccc4c3oc3cccc(-c5ccc6c7ccccc7n(-c7ccccc7)c6c5)c34)n2)cc1]

TABLE 4-continued
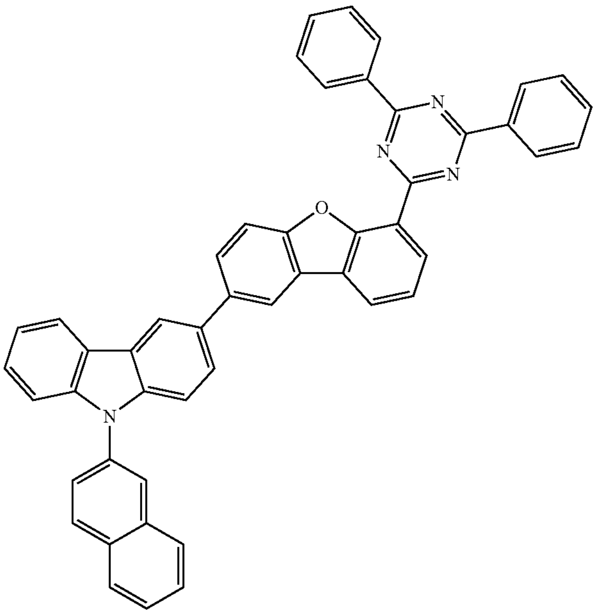
72
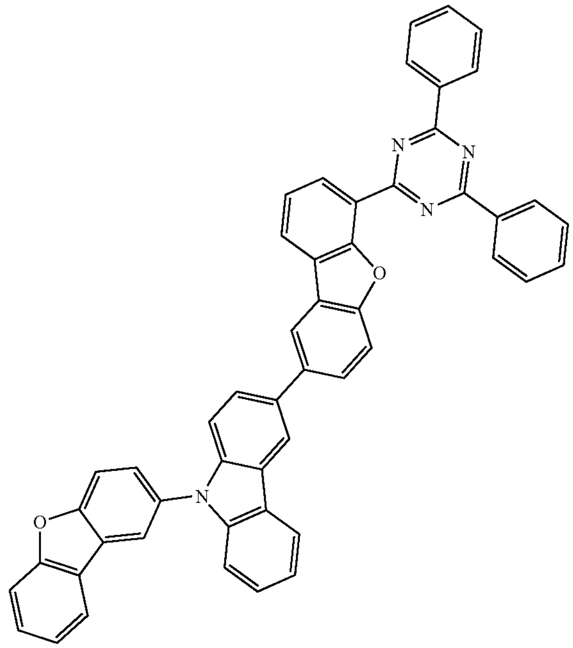
73

TABLE 4-continued
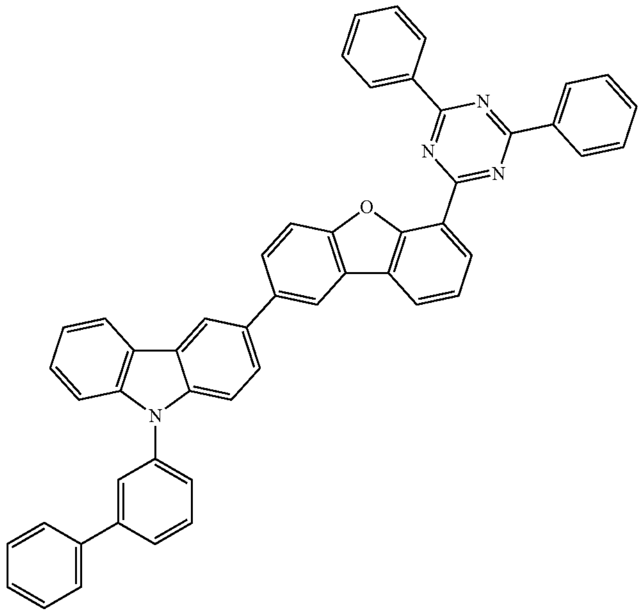
74
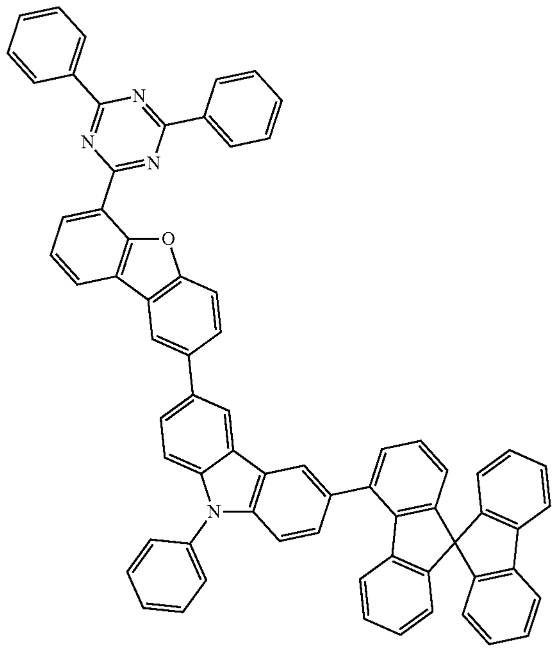
75

TABLE 4-continued
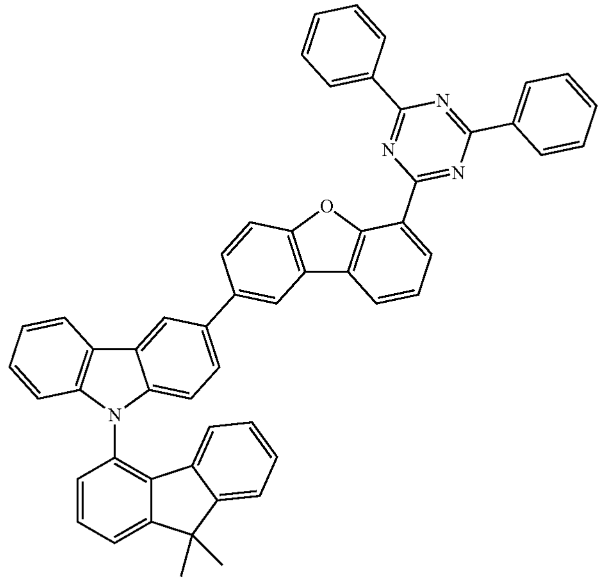
76
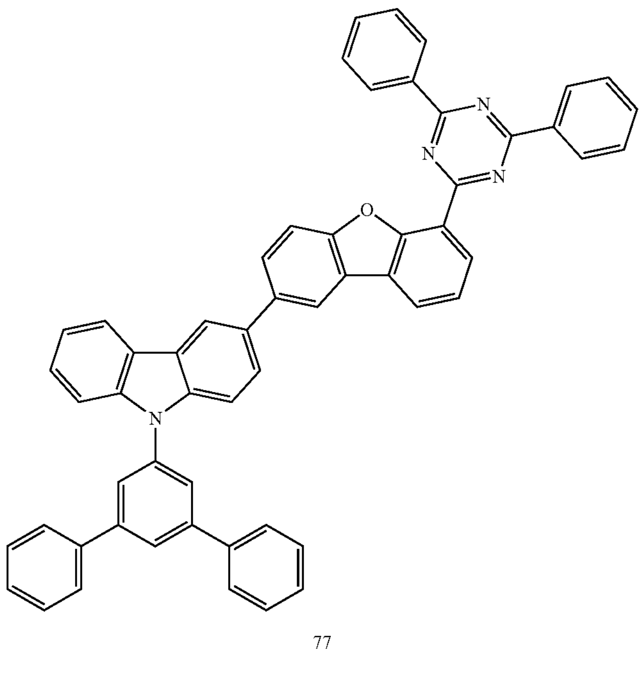 [SMILES: c1ccc(-c2cc(-c3ccccc3)cc(-n3c4ccccc4c4cc(-c5ccc6oc7c(-c8nc(-c9ccccc9)nc(-c9ccccc9)n8)cccc7c6c5)ccc43)c2)cc1]
77

TABLE 4-continued
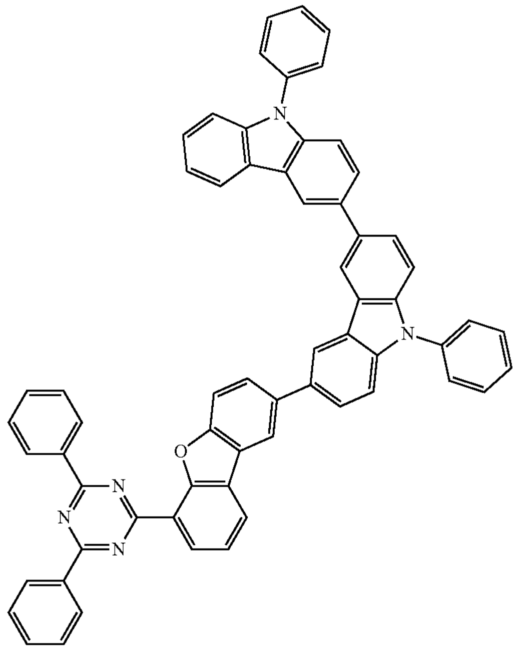
78
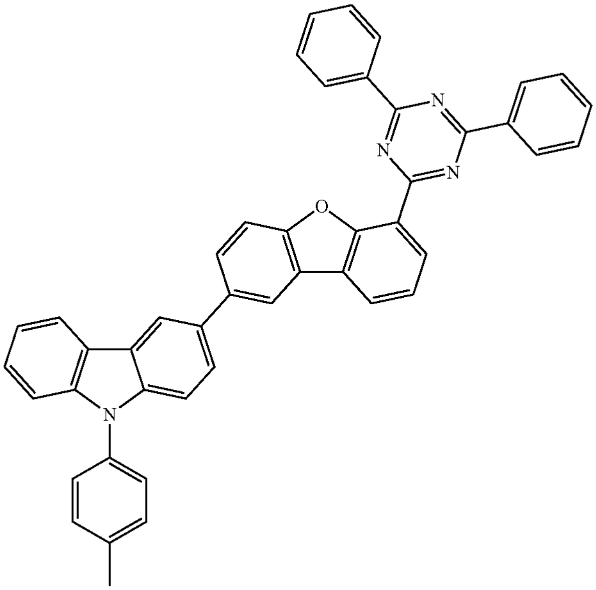
79

TABLE 4-continued
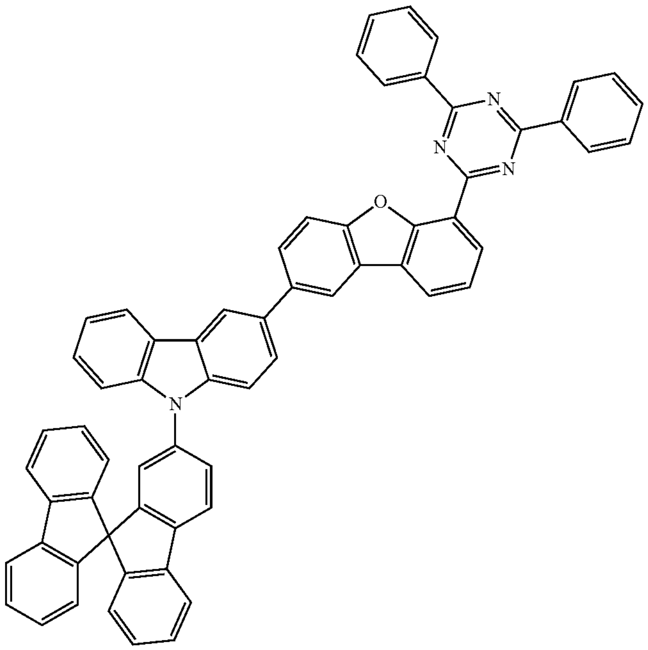
80
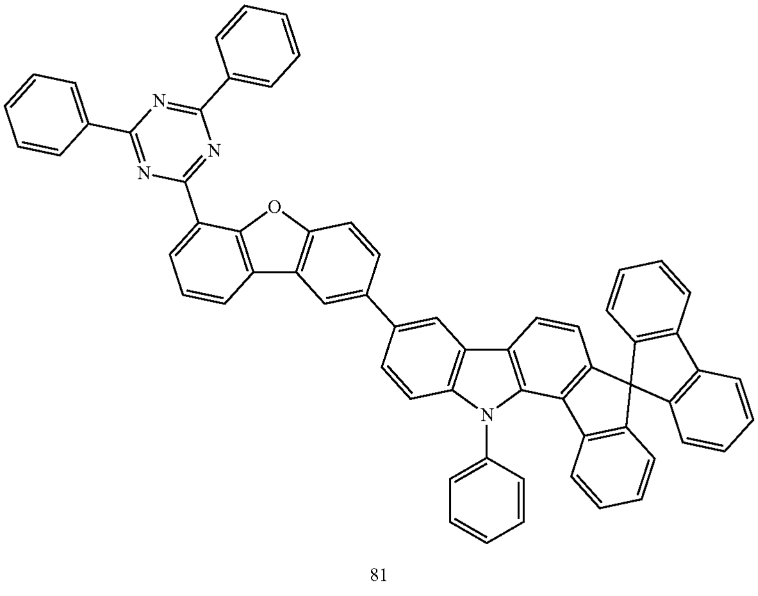 [SMILES: c1ccc(-c2nc(-c3ccccc3)nc(-c3cccc4c3oc3ccc(-c5ccc6c(c5)c5ccc7c(c5n6-c5ccccc5)-c5ccccc5C75c6ccccc6-c6ccccc65)cc34)n2)cc1]
81

TABLE 4-continued
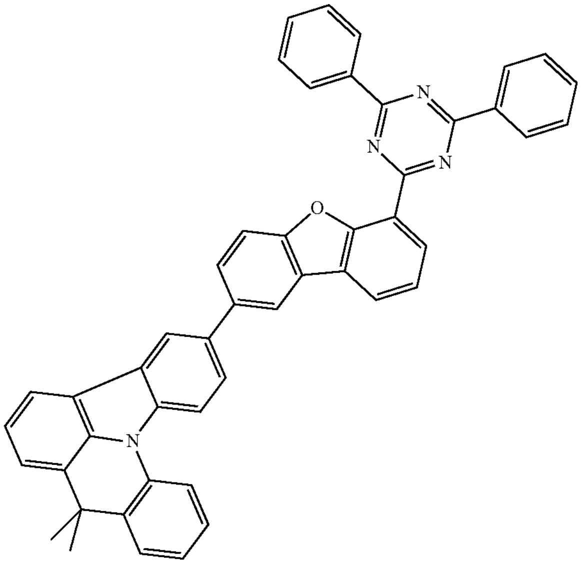
82
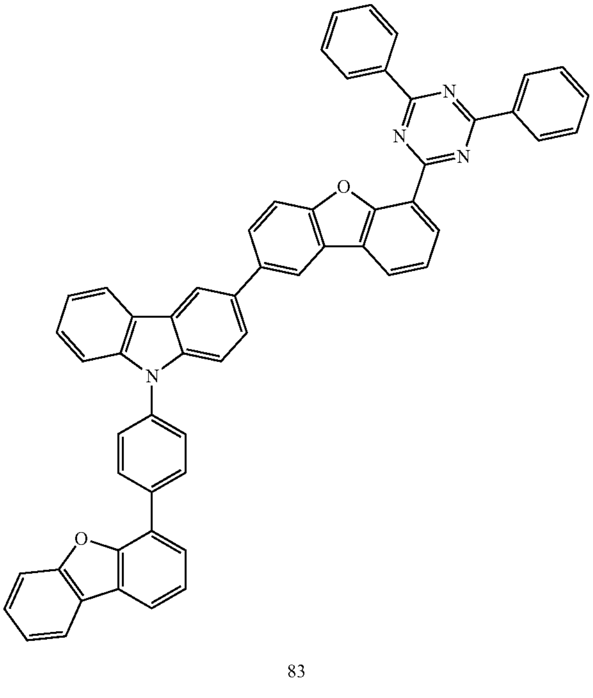 [SMILES: c1ccc(-c2nc(-c3ccccc3)nc(-c3cccc4c3oc3ccc(-c5ccc6c(c5)c5ccccc5n6-c5ccc(-c6cccc7c6oc6ccccc67)cc5)cc34)n2)cc1]
83

TABLE 4-continued
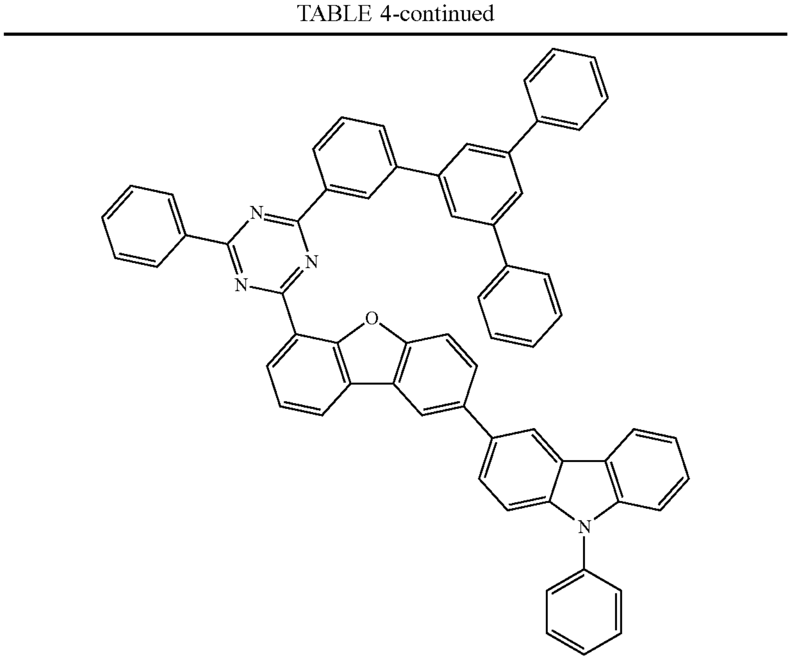
84
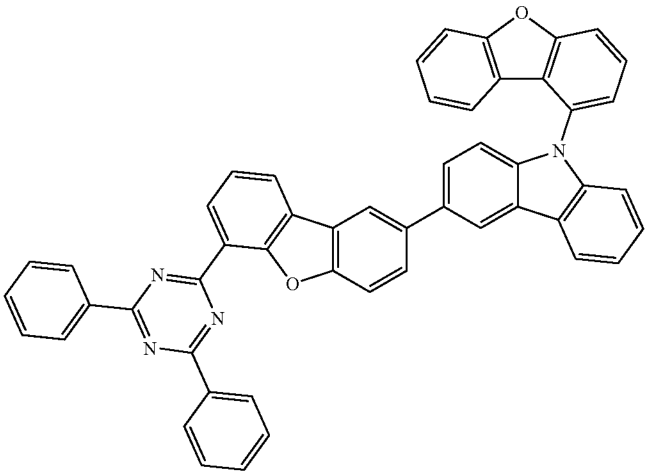
85
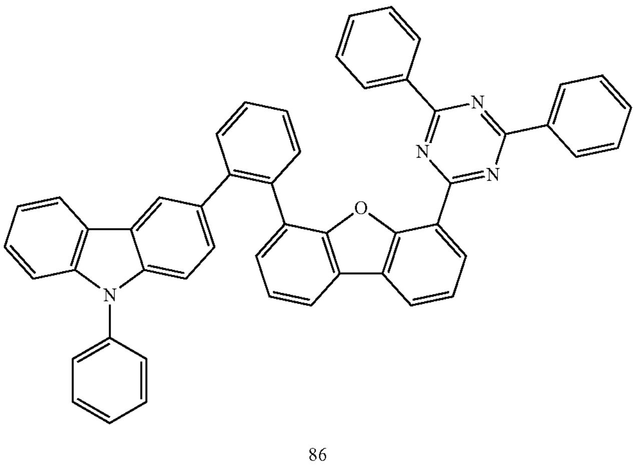 [SMILES: c1ccc(-c2nc(-c3ccccc3)nc(-c3cccc4c3oc3c(-c5ccccc5-c5ccc6c(c5)c5ccccc5n6-c5ccccc5)cccc34)n2)cc1]
86

TABLE 4-continued
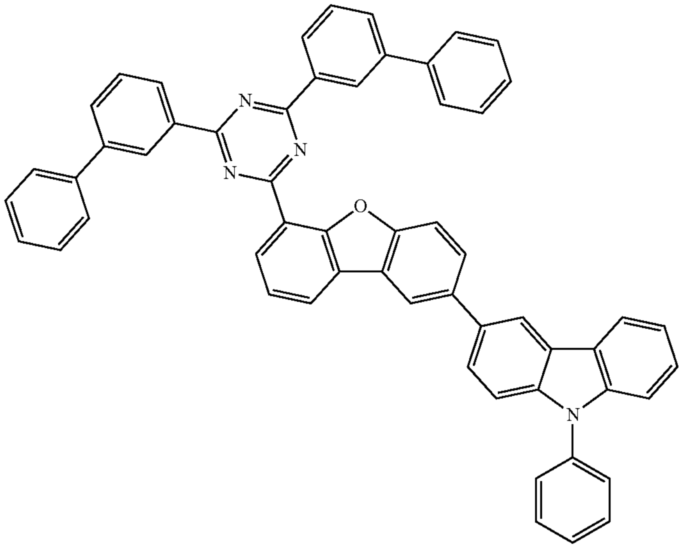
87
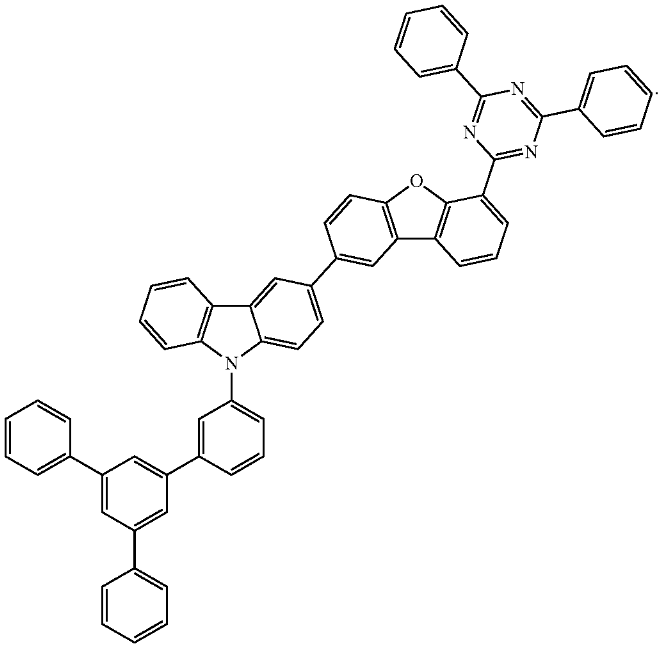
88

Particularly suitable compounds of the formula (1), (1b), (1e), (1f), (1g), (1h) or (1i) which are selected in accordance with the invention are compounds 1 to 21 in Table 5. Very particularly suitable compounds for the composition according to the invention are compounds of the formula (1b) or (1i), where L has one of the preferably mentioned or particularly preferably mentioned meanings.
TABLE 5
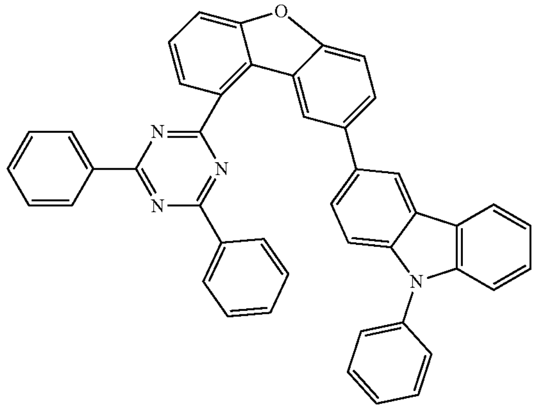
1
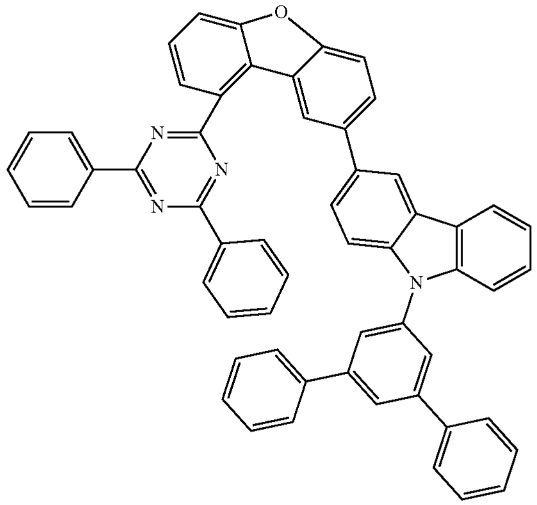
2

TABLE 5-continued
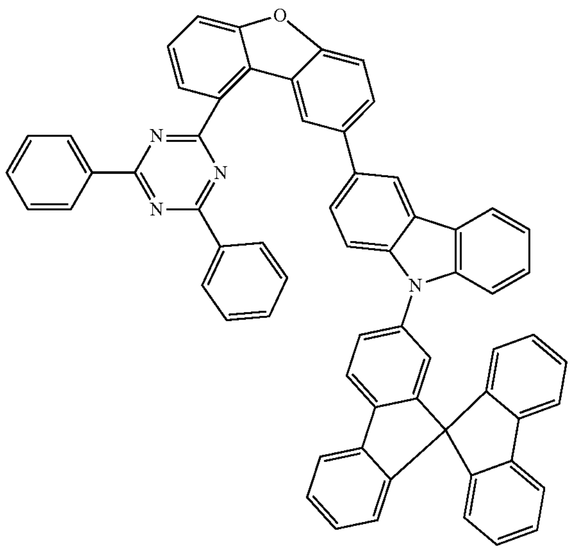
3
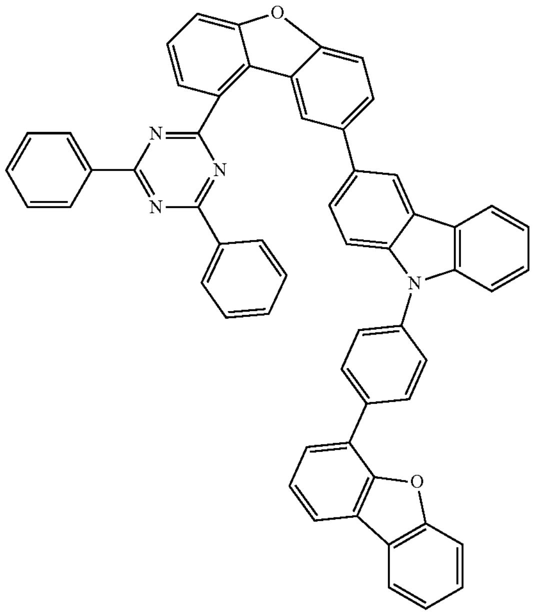
4

TABLE 5-continued
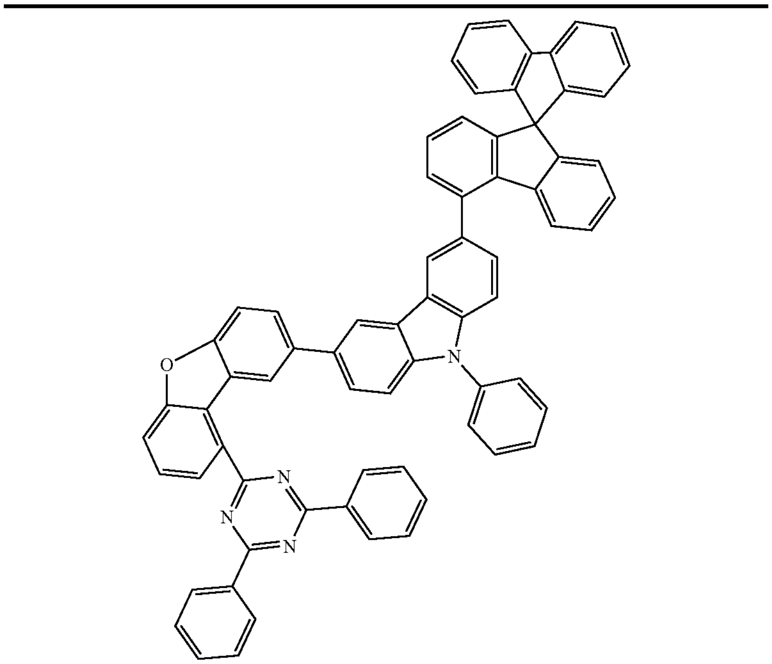
5
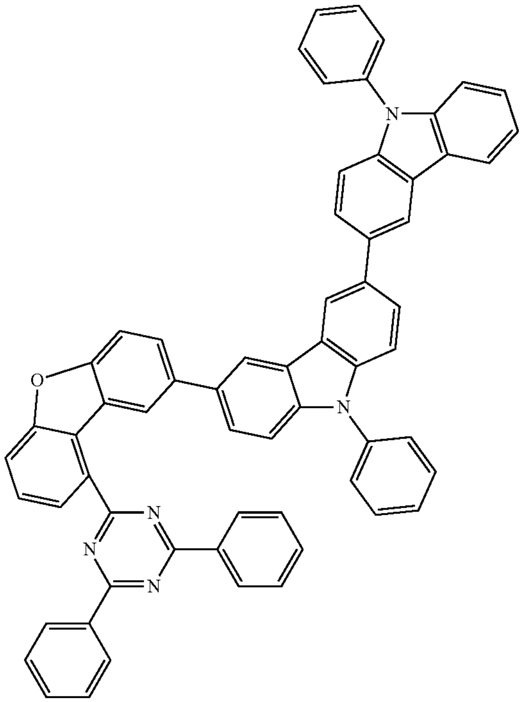
6

TABLE 5-continued
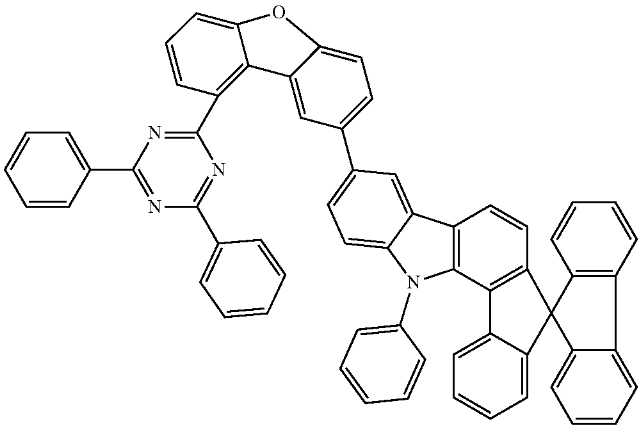
7
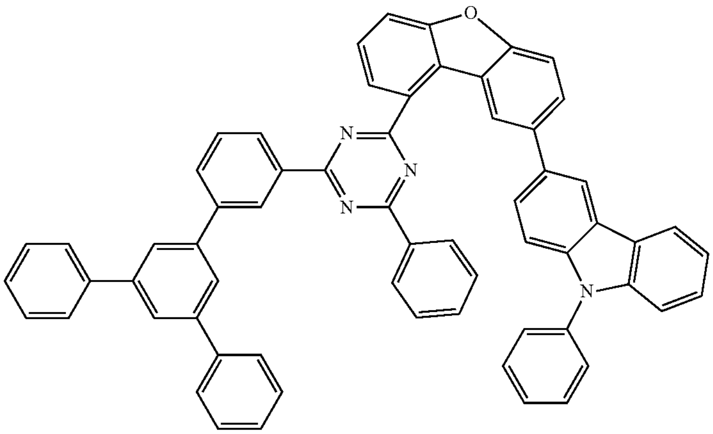
8
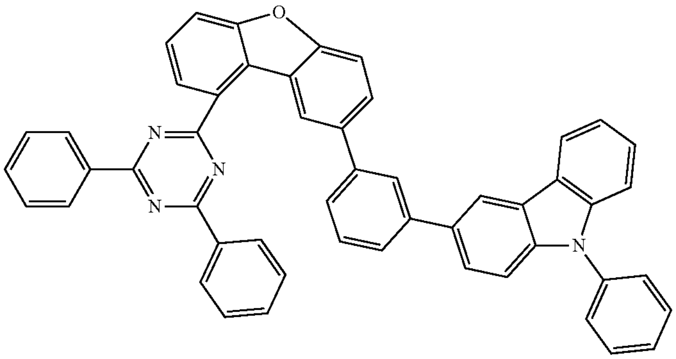
9

TABLE 5-continued
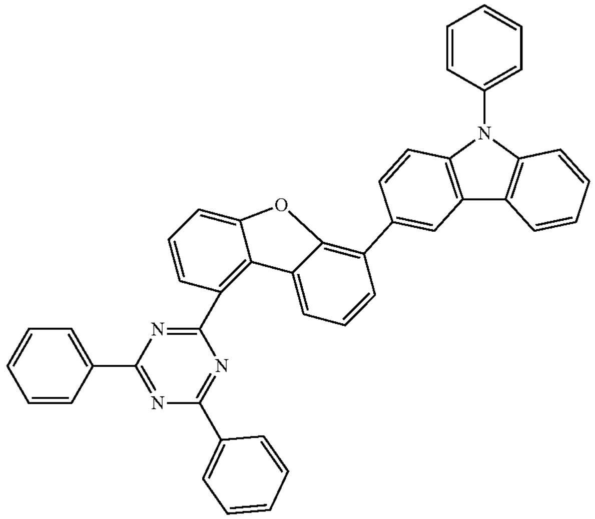
10
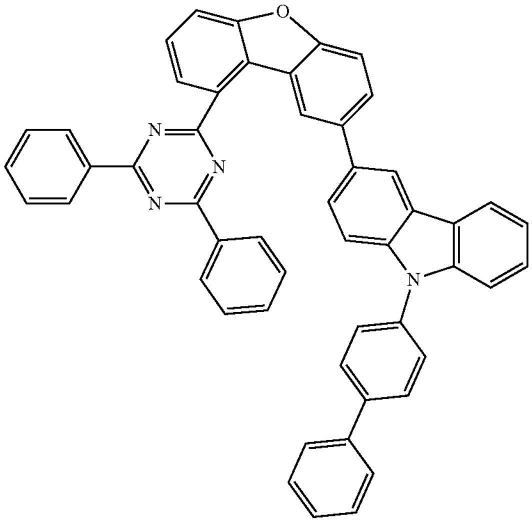
11
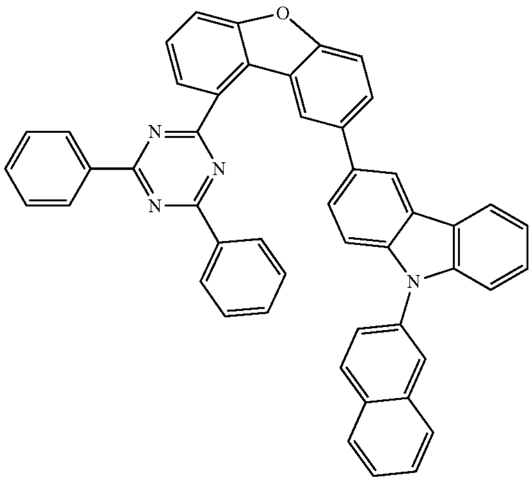
12

TABLE 5-continued
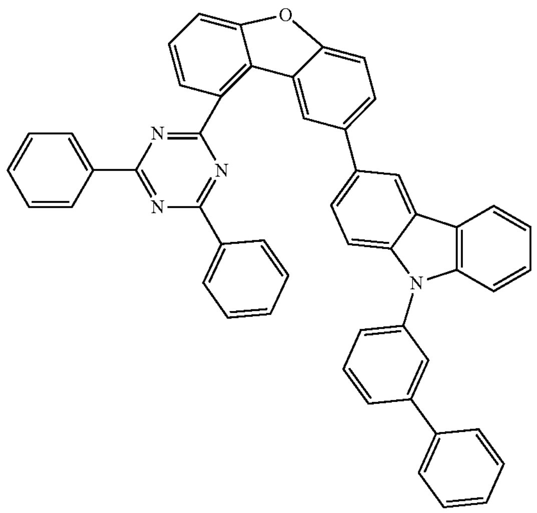
13
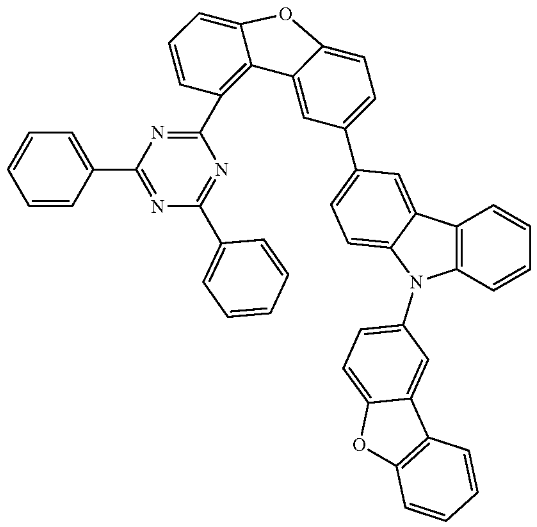
14
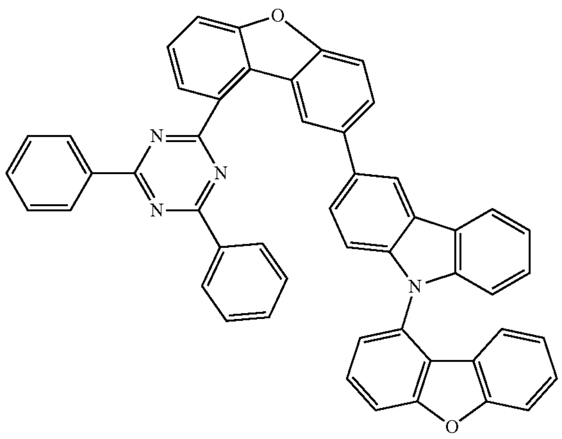
15

TABLE 5-continued
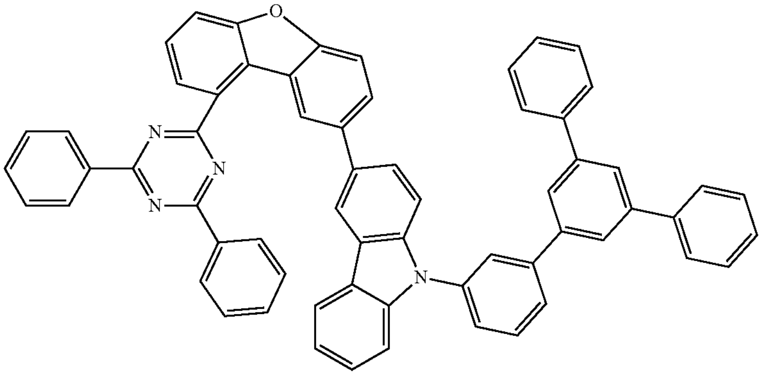
16
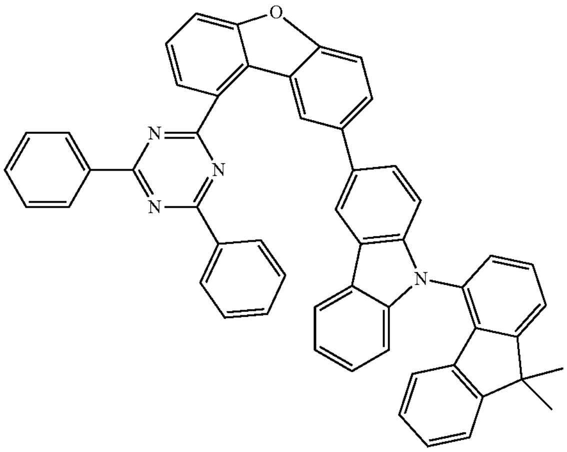
17
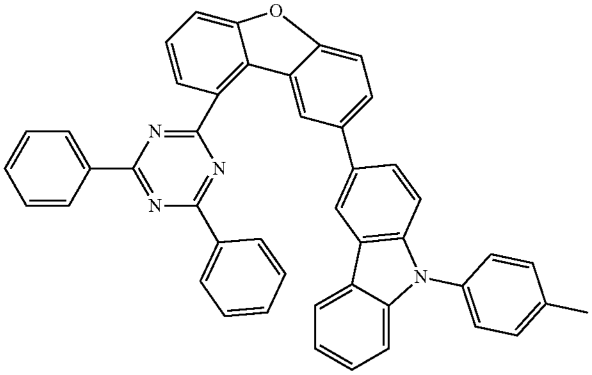
18

TABLE 5-continued
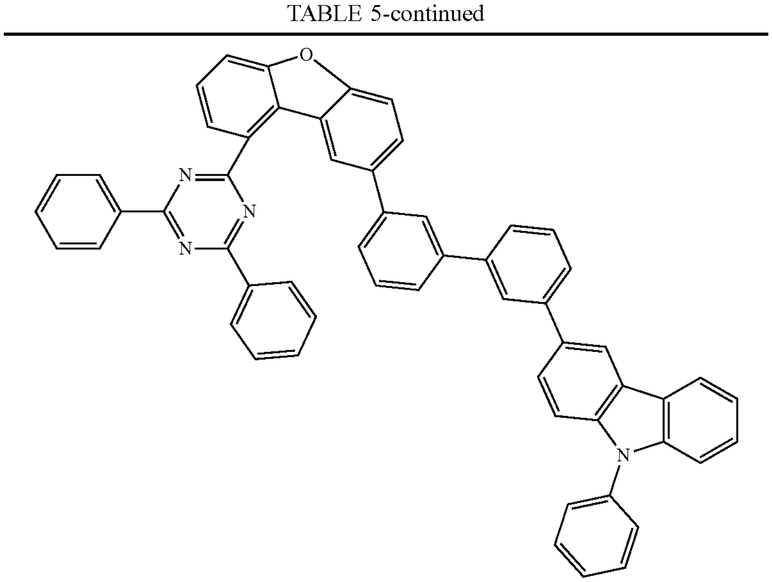
19
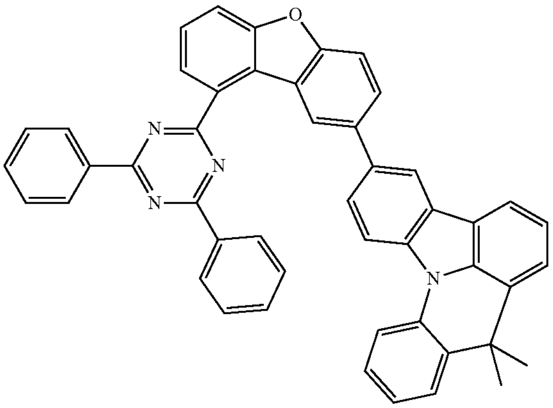
20
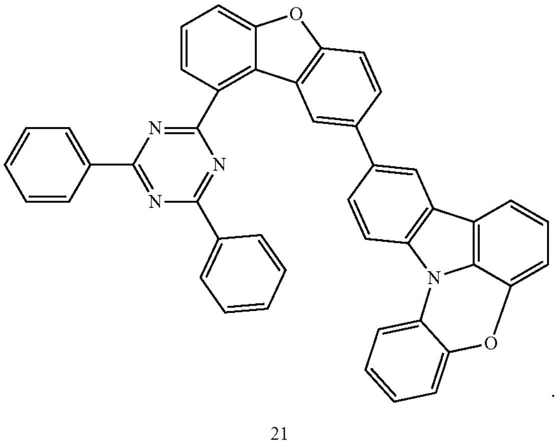 [SMILES: c1ccc(-c2nc(-c3ccccc3)nc(-c3cccc4oc5ccc(-c6ccc7c(c6)c6cccc8c6n7-c6ccccc6O8)cc5c34)n2)cc1]
21

Particularly suitable compounds of the formula (1), (1a), (1e), (1f), (1g), (1h) or (1j) which are selected in accordance with the invention are compounds 23 to 44 in Table 6.
TABLE 6
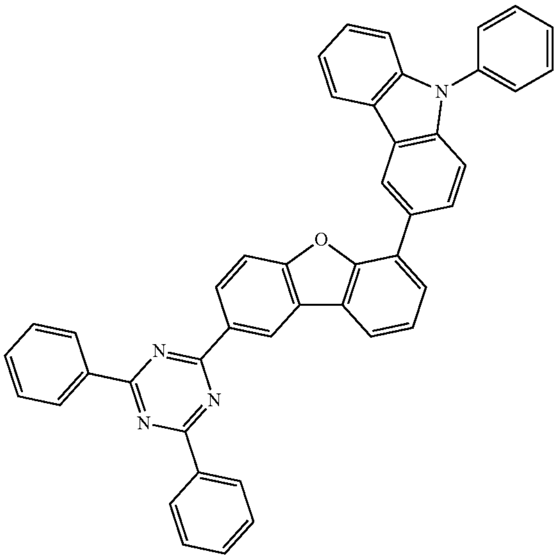
23
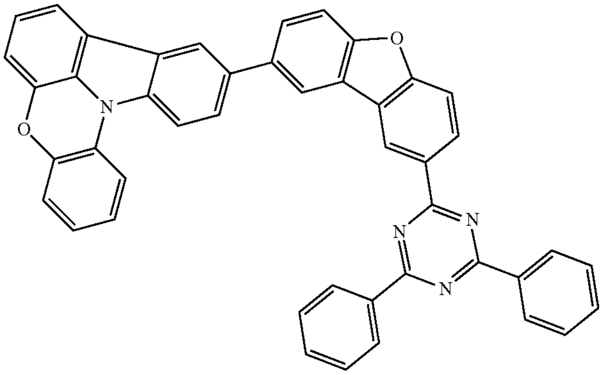
24
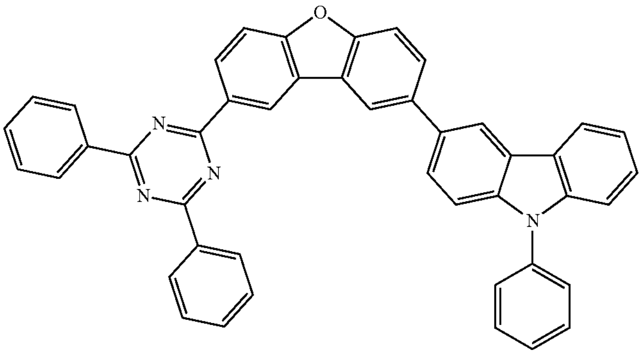
25

TABLE 6-continued
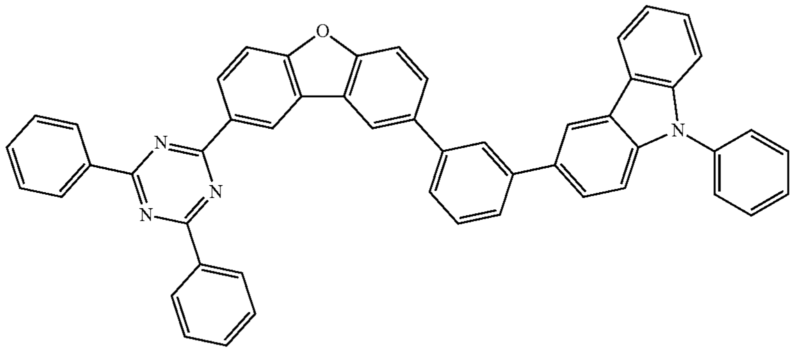
26
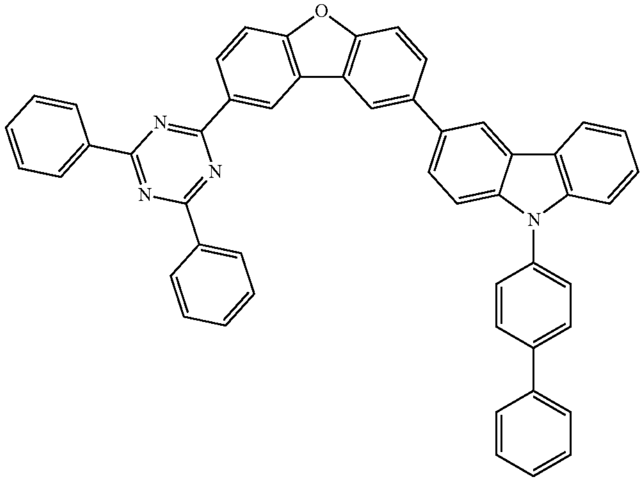
27
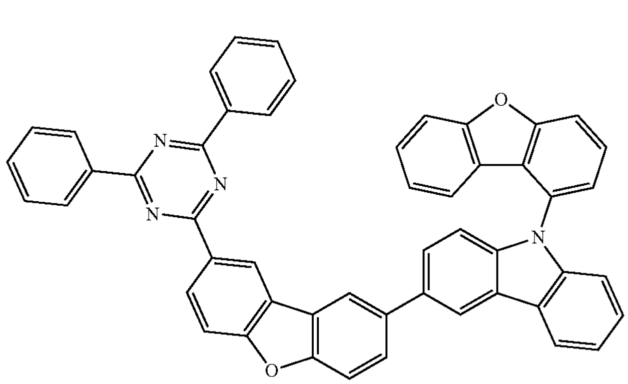
28

TABLE 6-continued
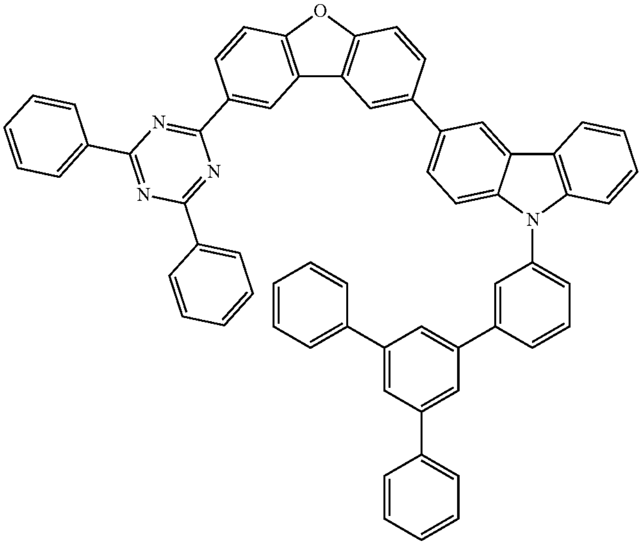
29
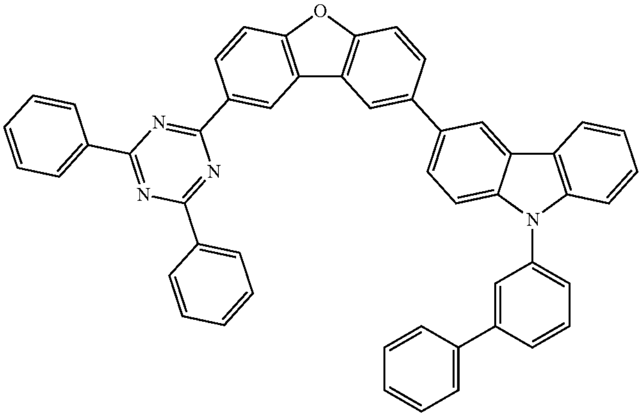
30
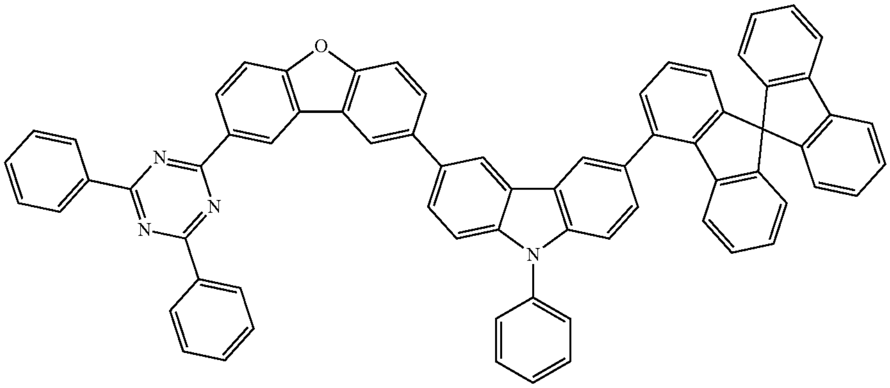
31

TABLE 6-continued
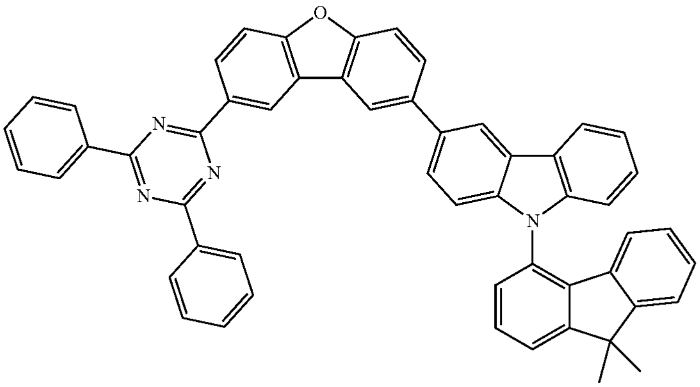
32
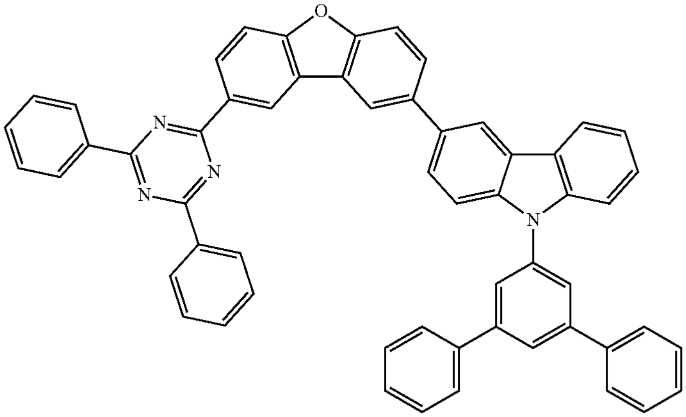
33
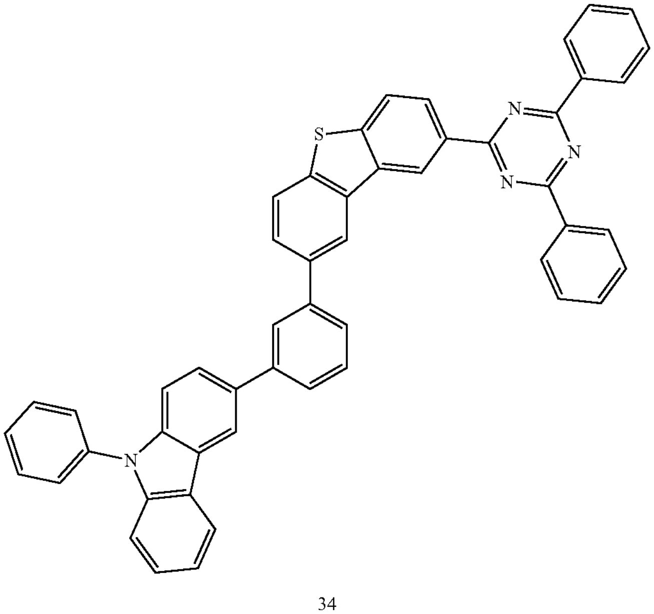
34

TABLE 6-continued
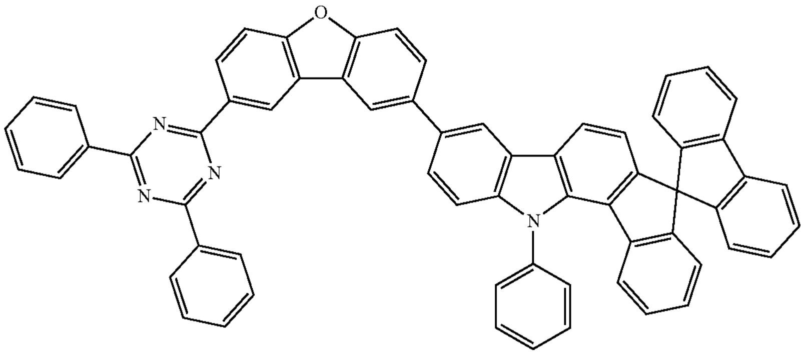
37
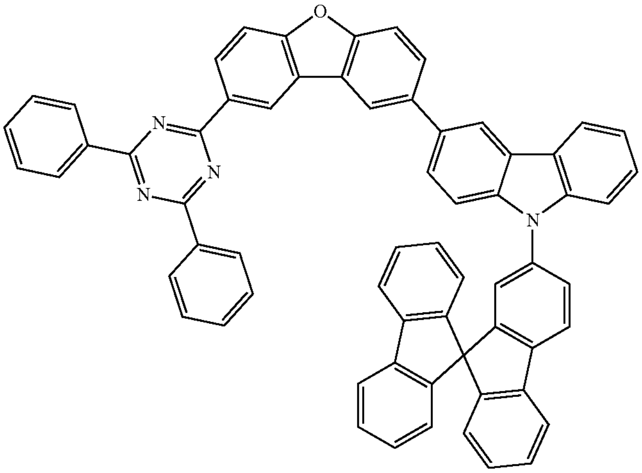
36
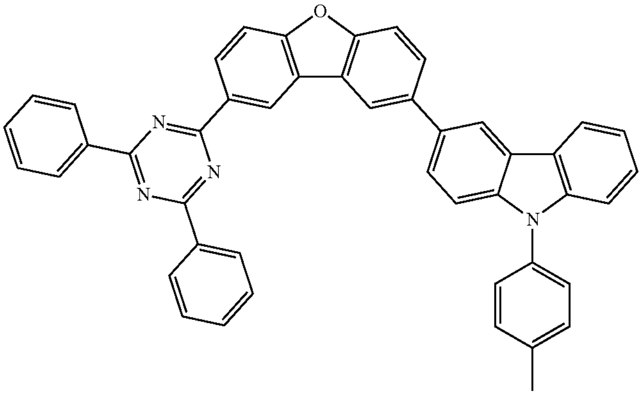 [SMILES: c1ccc(-c2nc(-c3ccccc3)nc(-c3ccc4oc5ccc(-c6ccc7c(c6)c6ccccc6n7-c6ccccc6)cc5c4c3)n2)cc1]
35

TABLE 6-continued
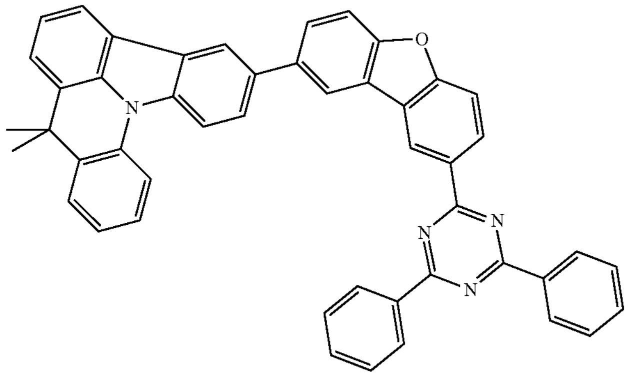
38
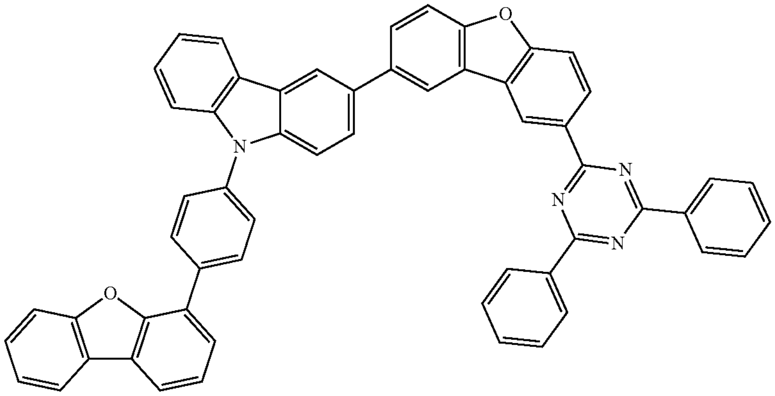
39
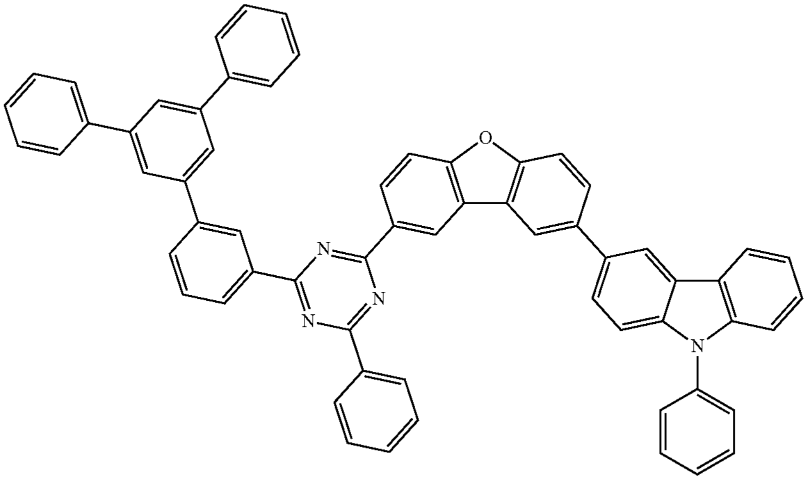
40

TABLE 6-continued
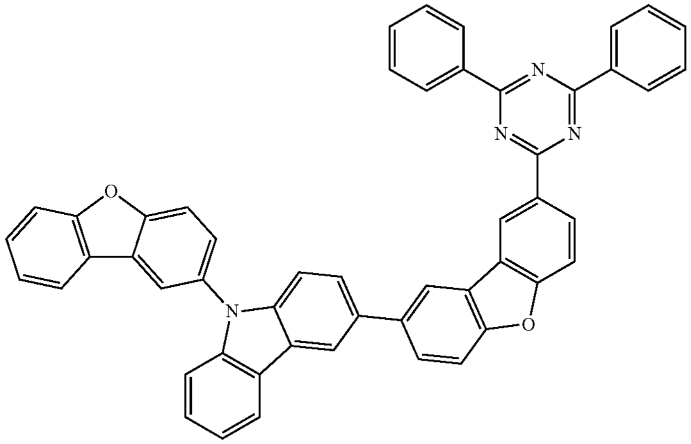
41
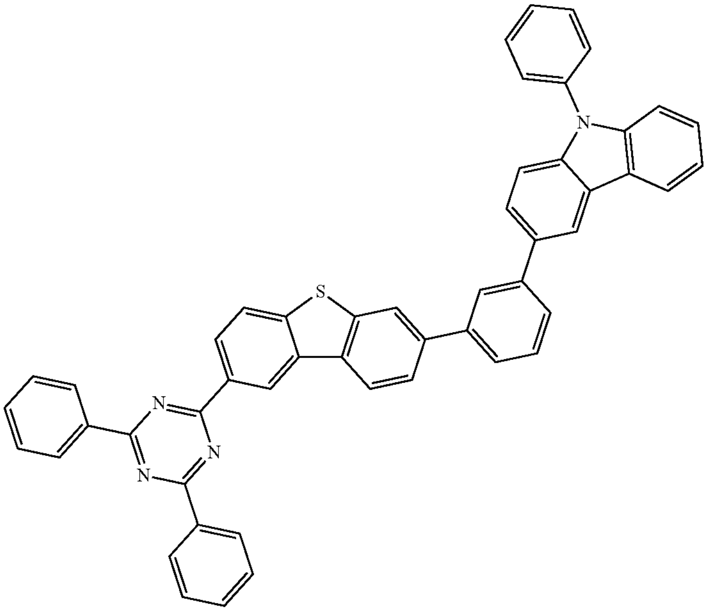
42
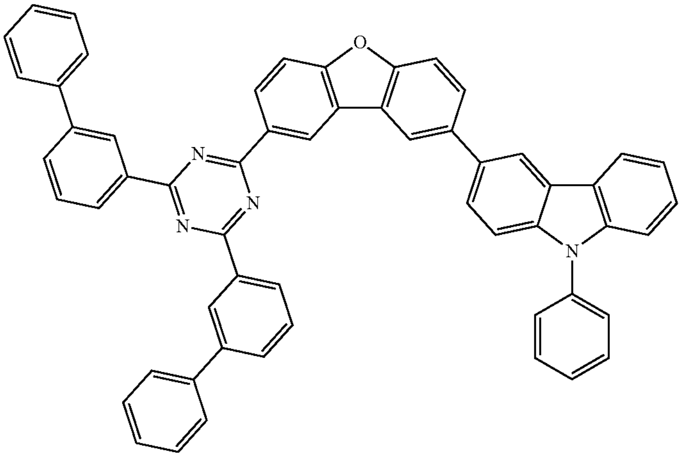
43

TABLE 6-continued
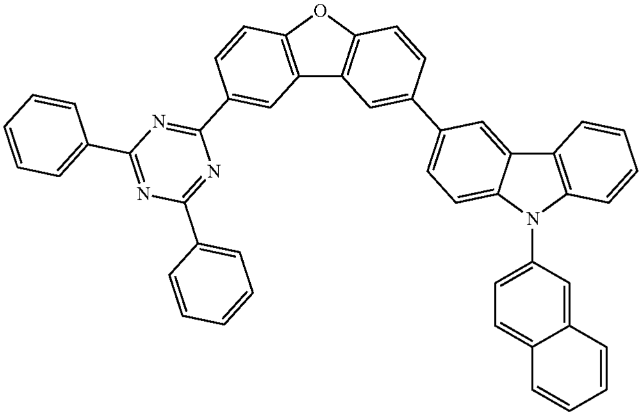
44
Particularly suitable compounds of the formula (1), (1d), (1e), (1f), (1g), (1h) or (1k) which are selected in accordance with the invention are compounds 45 to 66 in Table 7.
TABLE 7
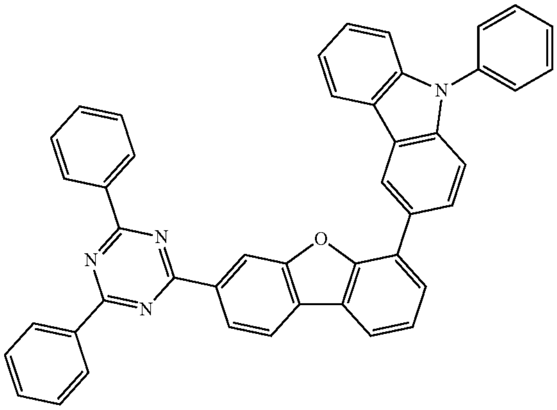
45
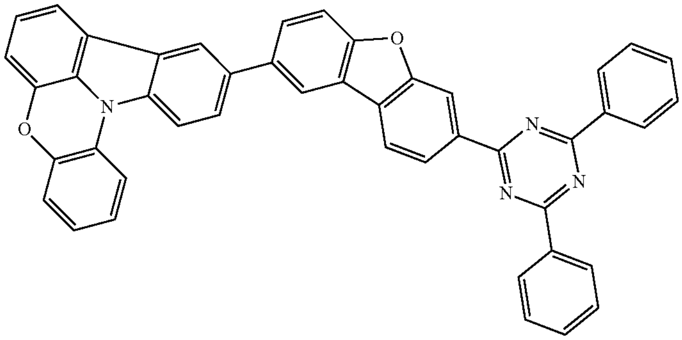
46

TABLE 7-continued
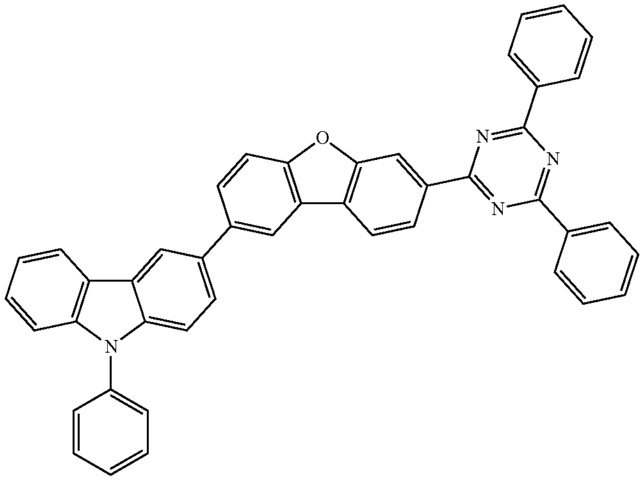
47
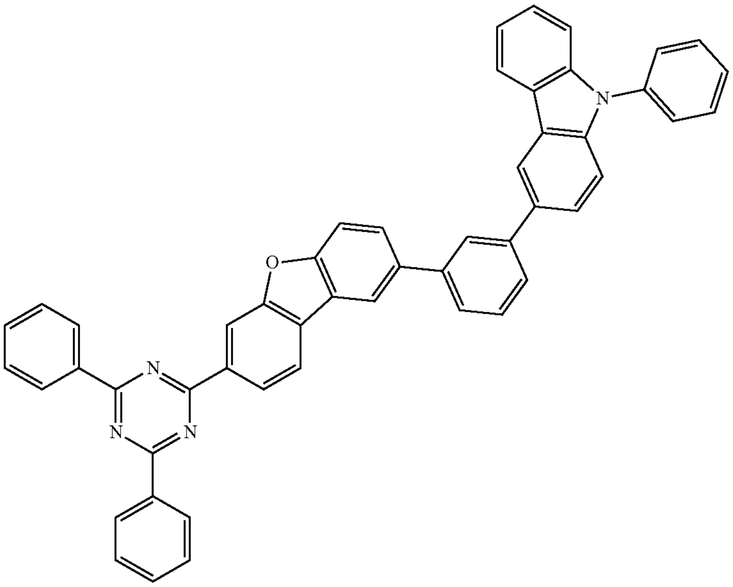
48

TABLE 7-continued
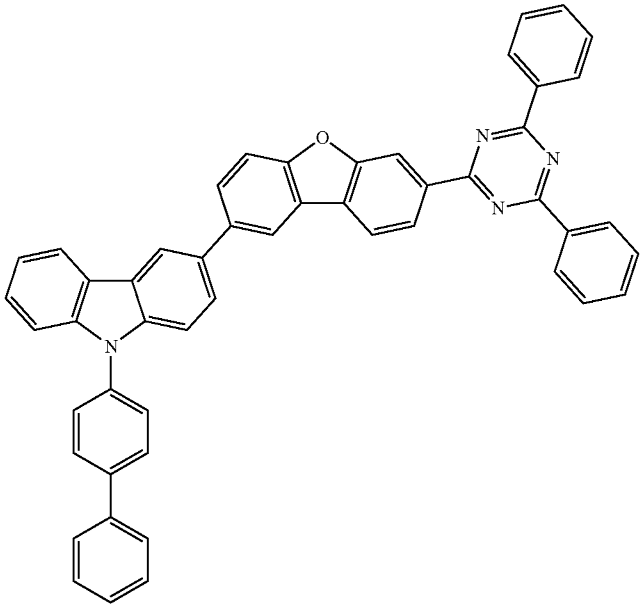
49
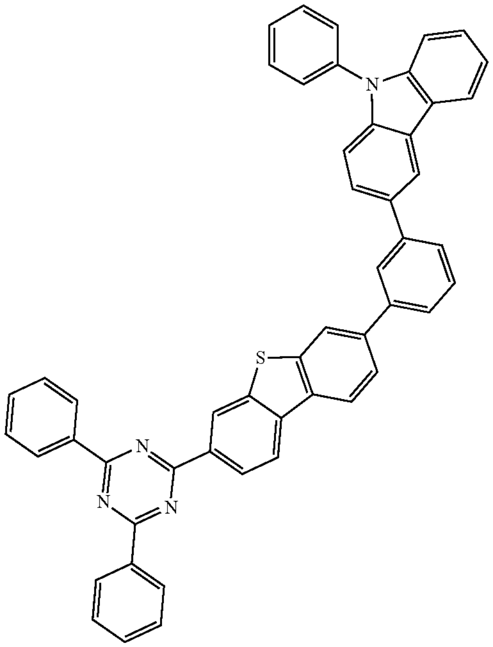
50

TABLE 7-continued
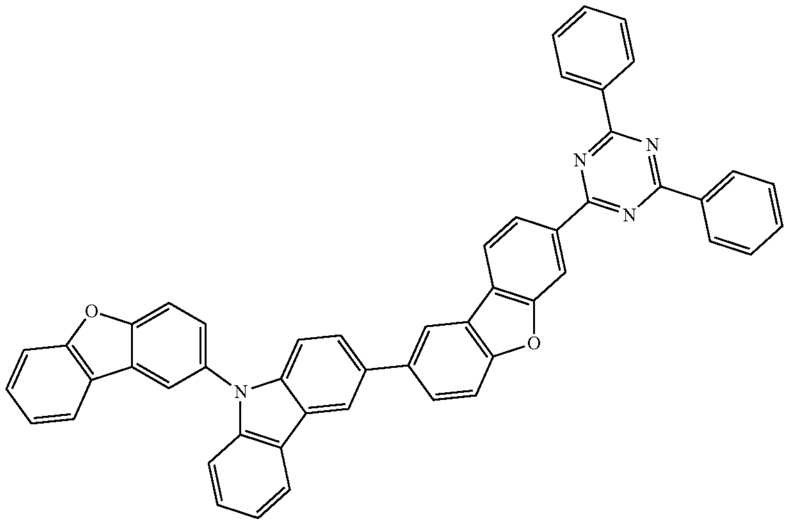
51
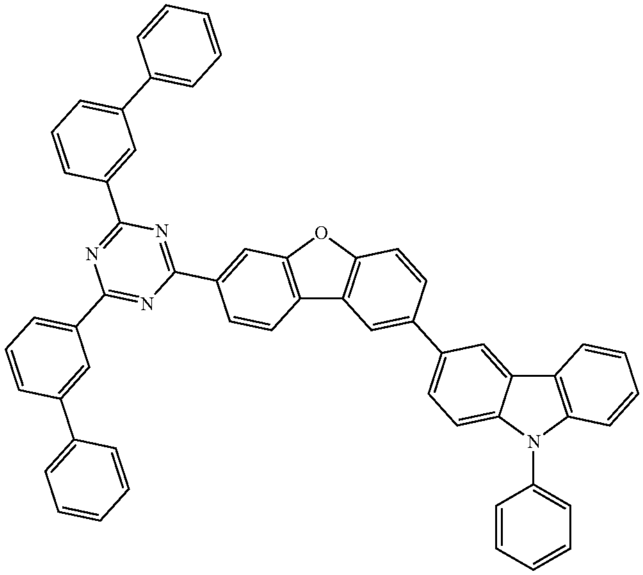
52
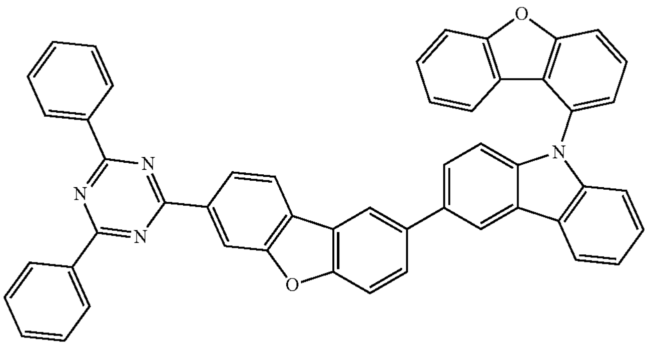
53

TABLE 7-continued
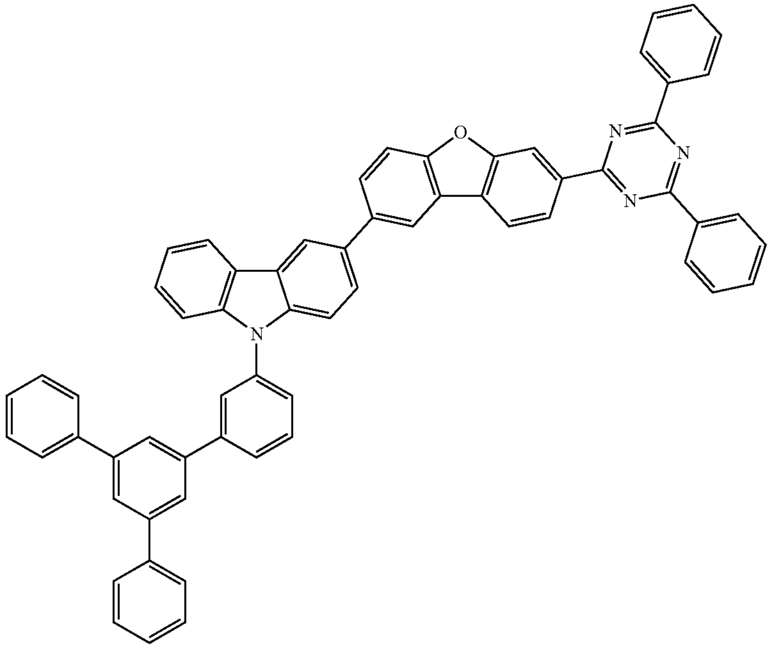
54
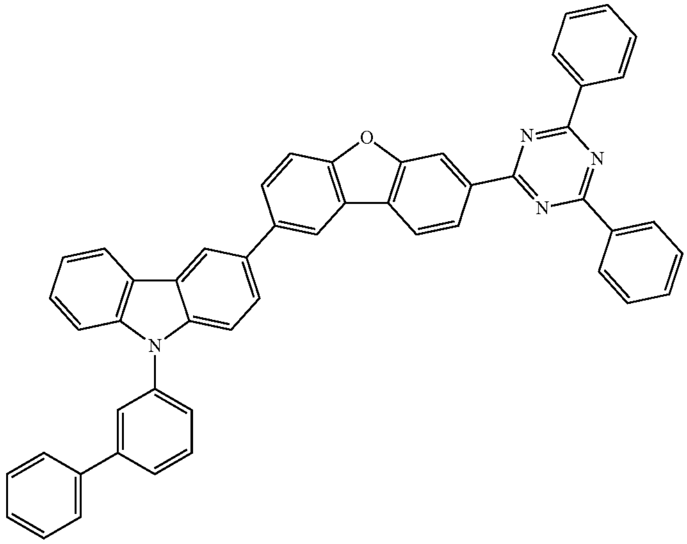
55

TABLE 7-continued
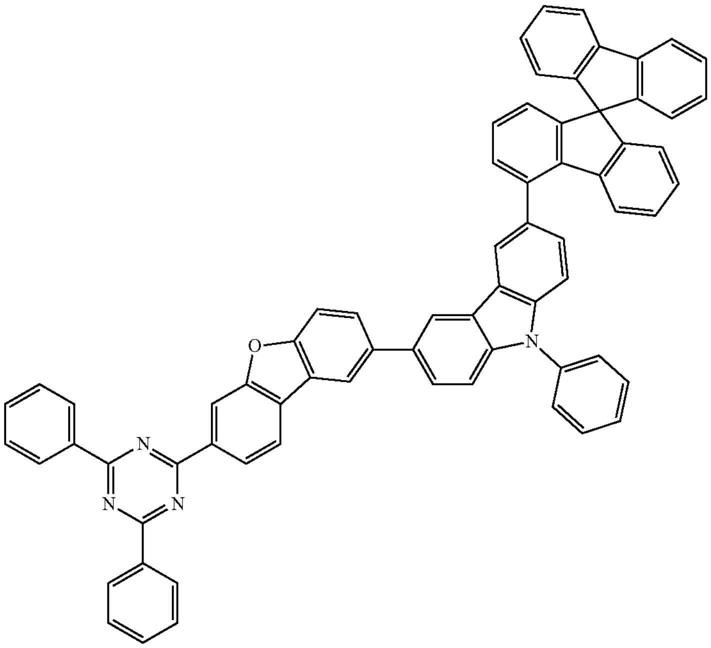
56
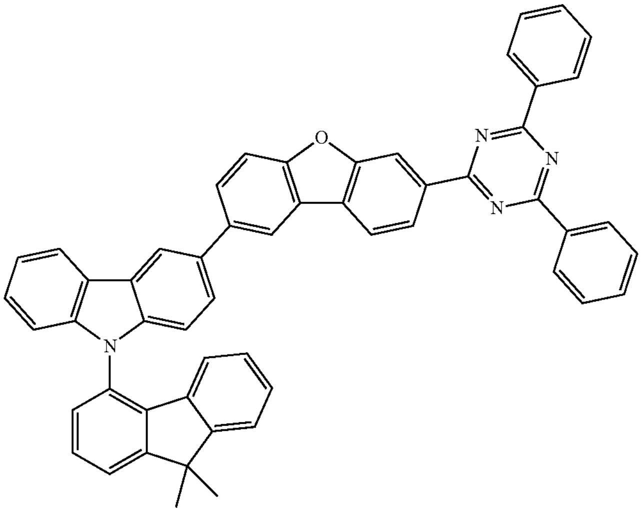
57

TABLE 7-continued
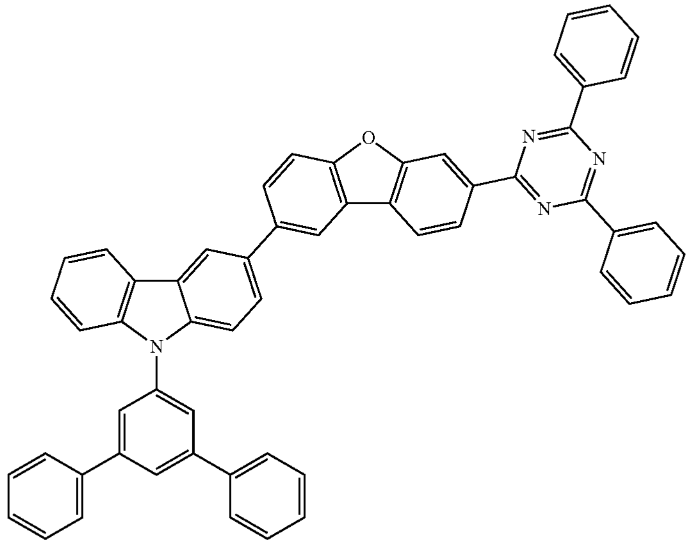
58
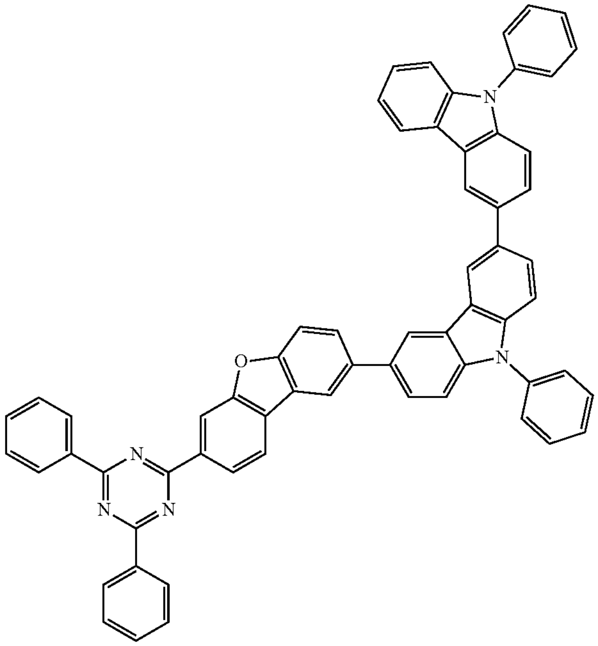
59

TABLE 7-continued
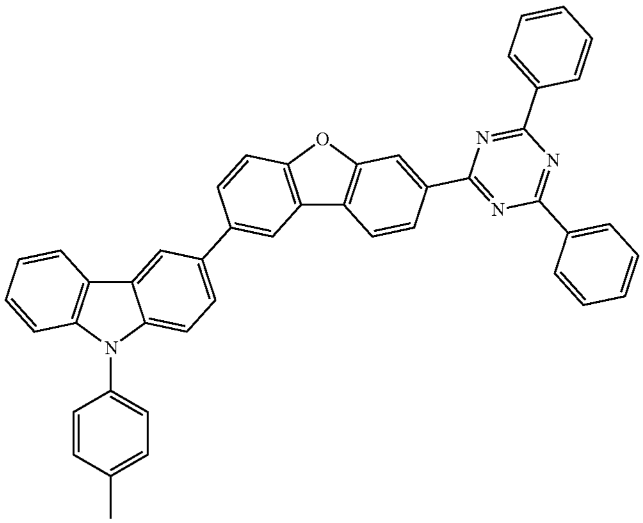 [SMILES: c1ccc(-c2nc(-c3ccccc3)nc(-c3ccc4c(c3)oc3ccc(-c5ccc6c(c5)c5ccccc5n6-c5ccccc5)cc34)n2)cc1]
60
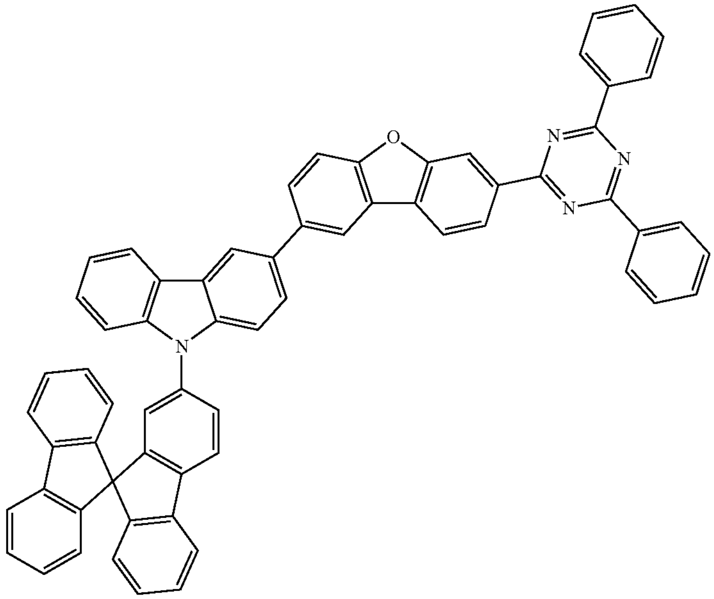
61

TABLE 7-continued
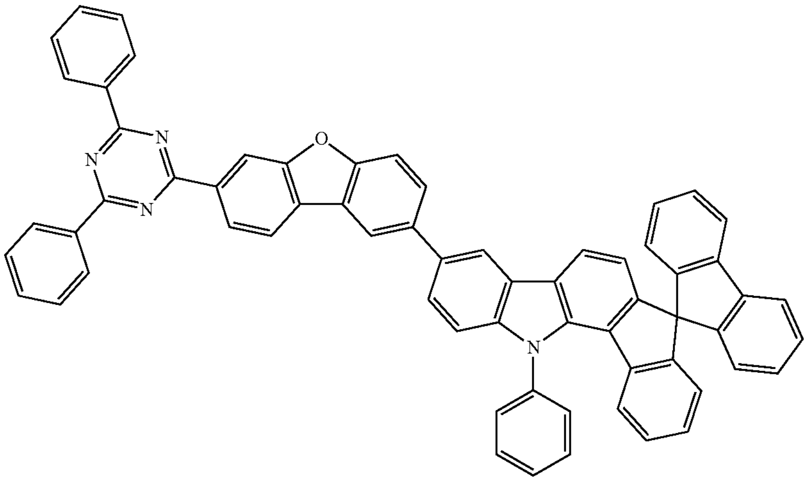
62
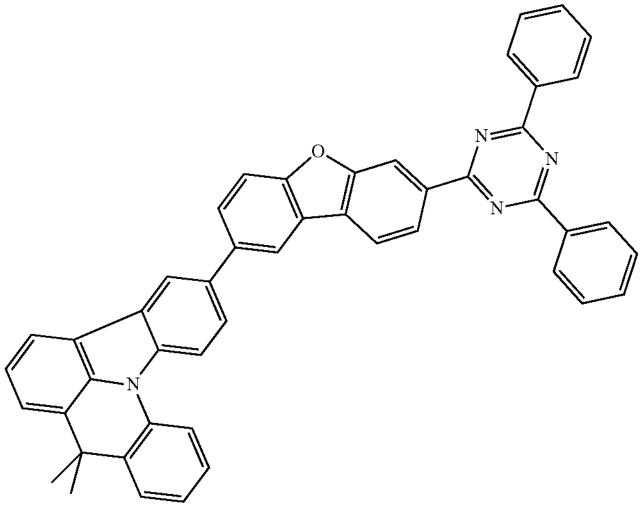
65

TABLE 7-continued
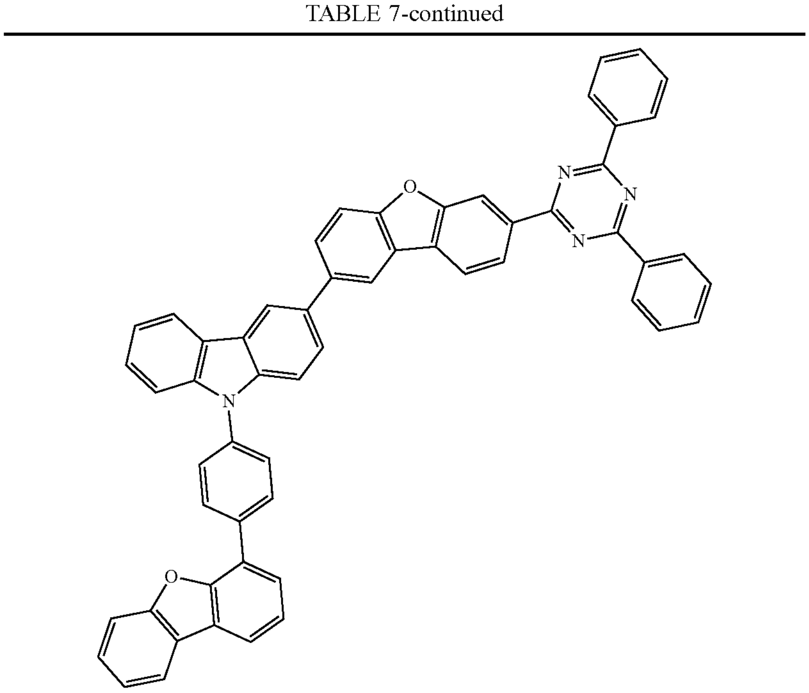
64
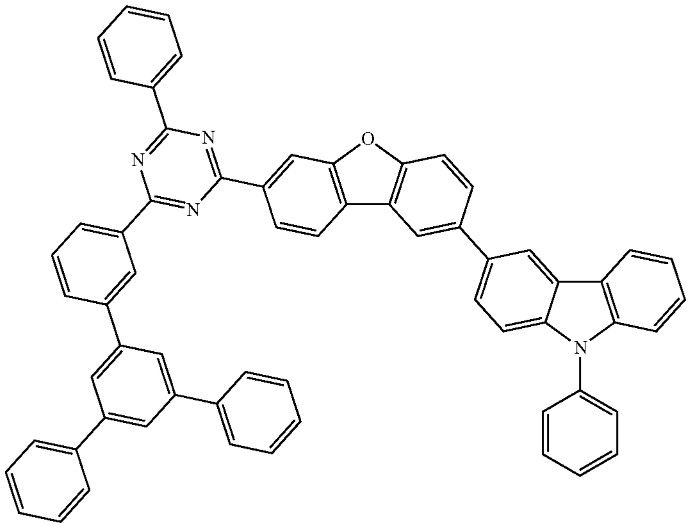
63

TABLE 7-continued
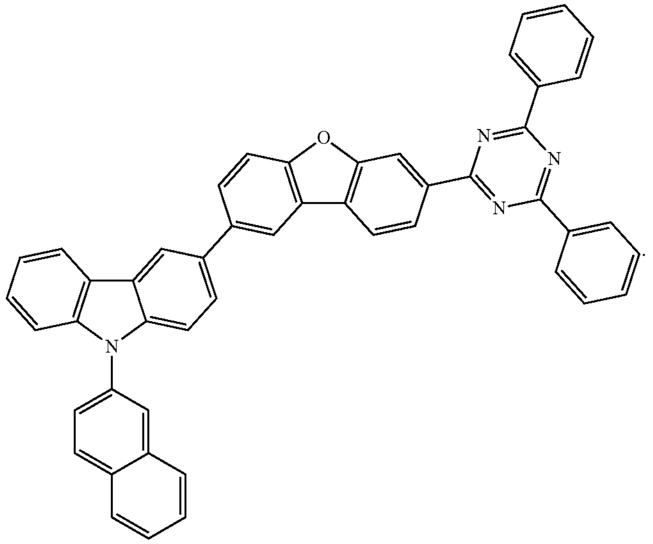
66
Particularly suitable compounds of the formula (1), (1c), (1e), (1f), (1g), (1h) or (1l) which are selected in accordance with the invention are compounds 67 to 88 in Table 8.
TABLE 8
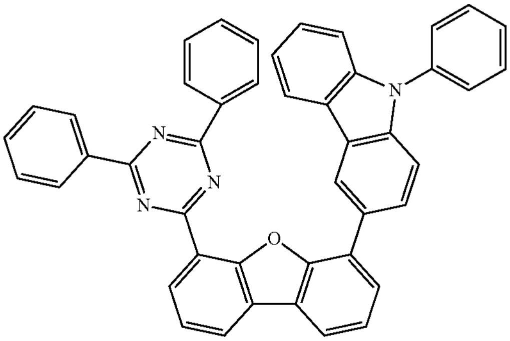
67
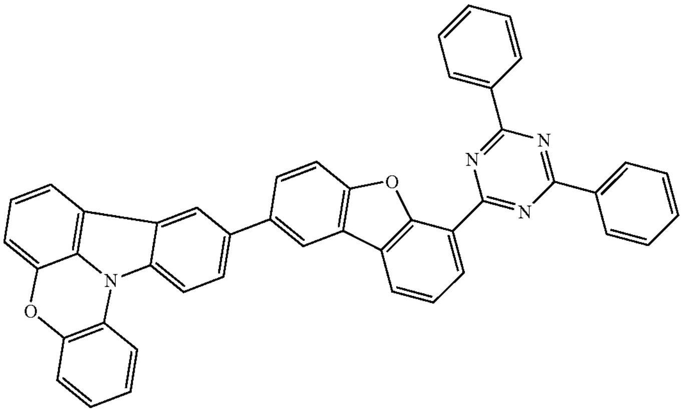
68

TABLE 8-continued
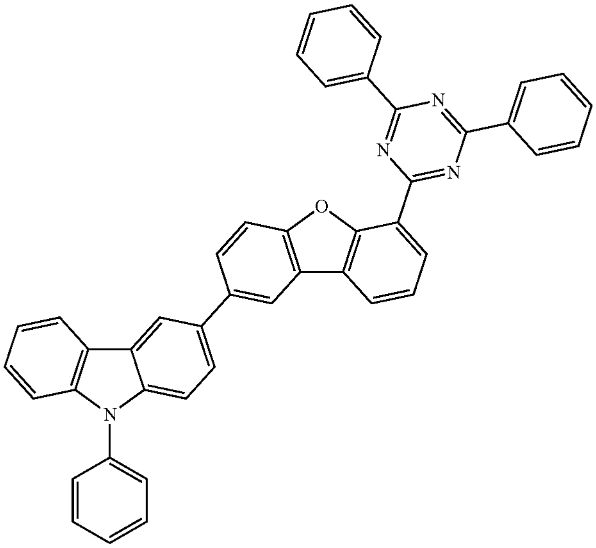
69
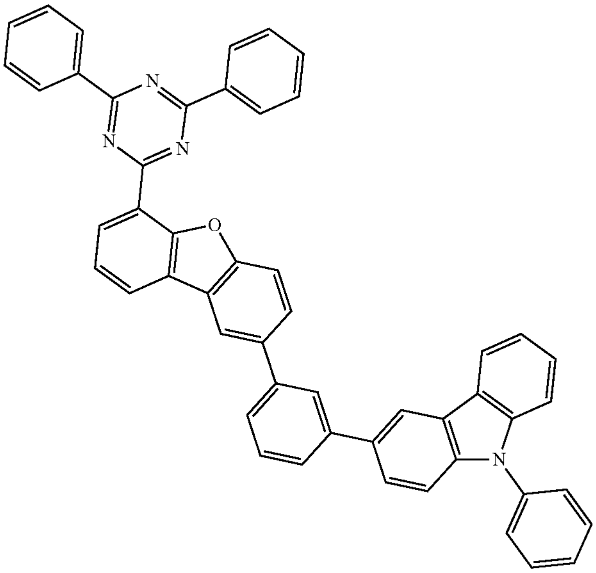
70

TABLE 8-continued
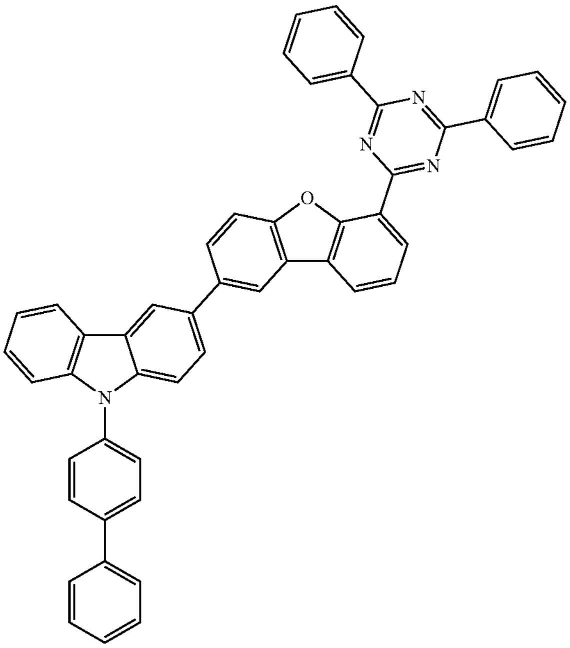
71
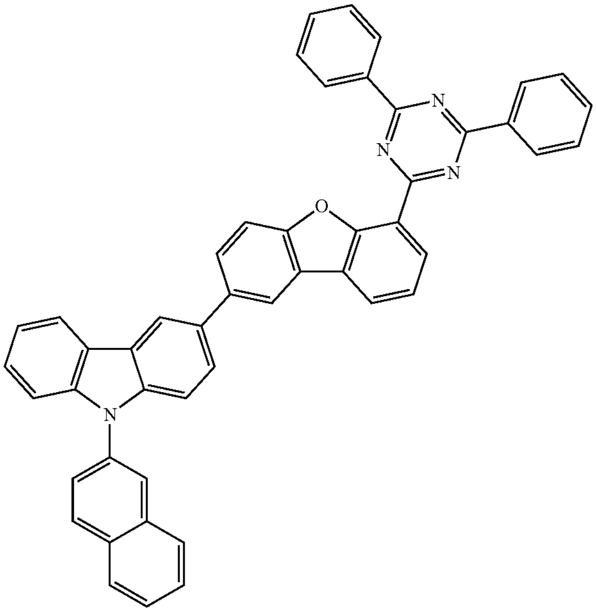
72

TABLE 8-continued
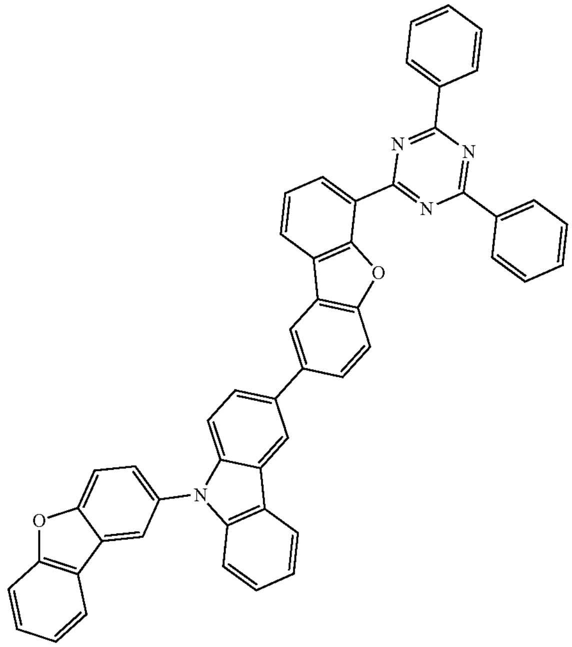
73
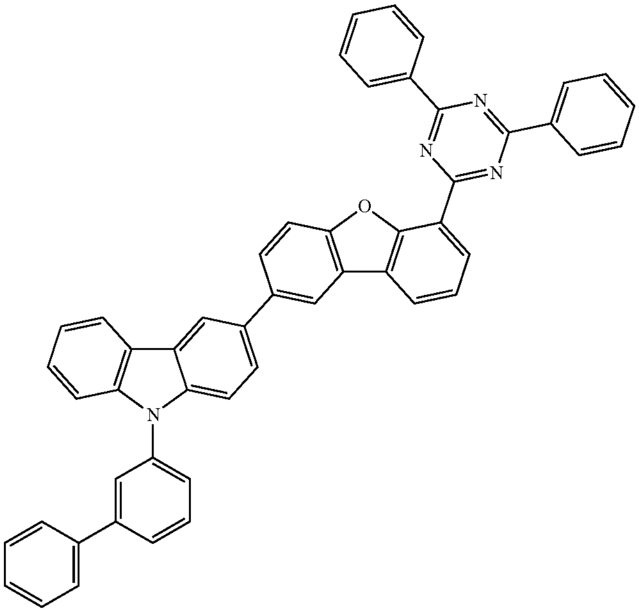
74

TABLE 8-continued
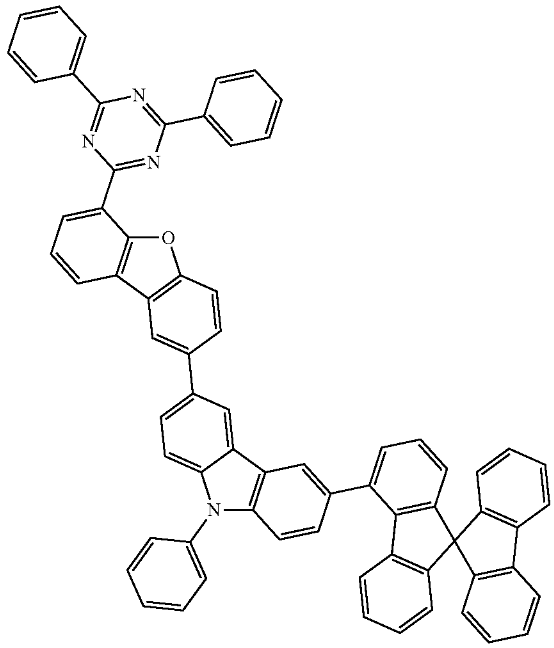
75
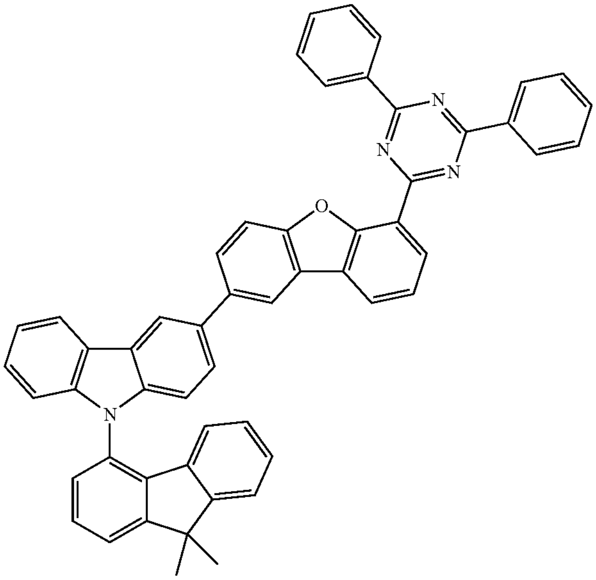
76

TABLE 8-continued
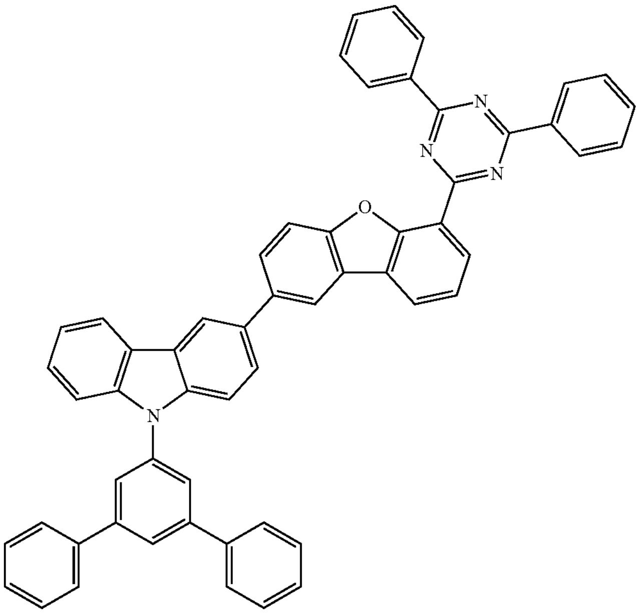
77
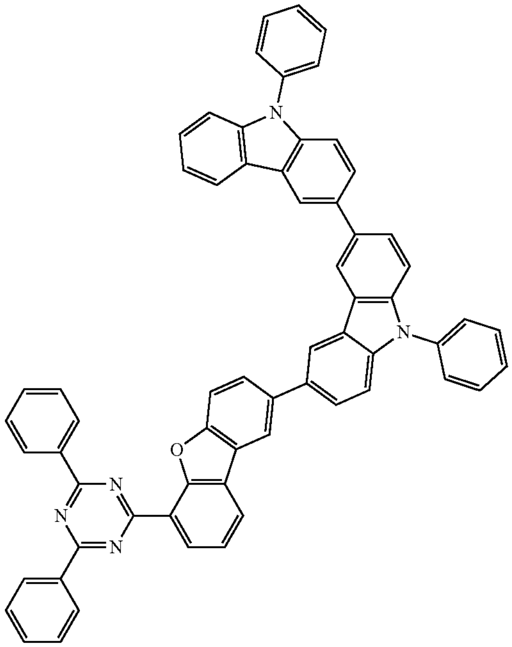
78

TABLE 8-continued
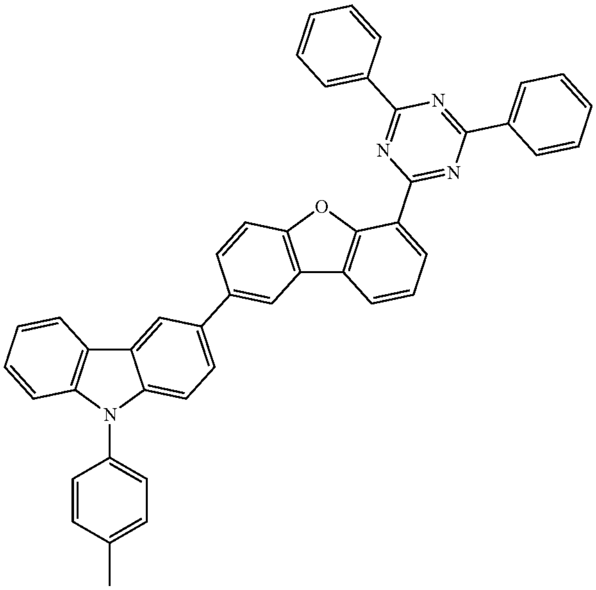 [SMILES: c1ccc(-c2nc(-c3ccccc3)nc(-c3cccc4c3oc3ccc(-c5ccc6c(c5)c5ccccc5n6-c5ccccc5)cc34)n2)cc1]
79
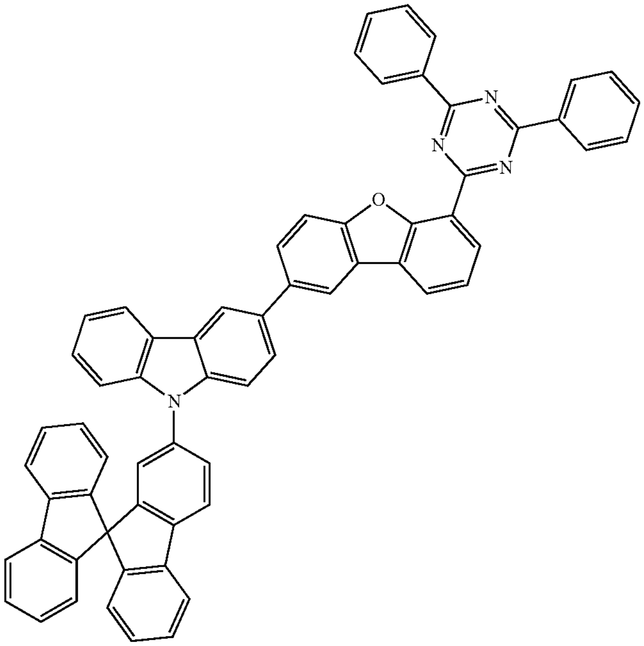
80

TABLE 8-continued
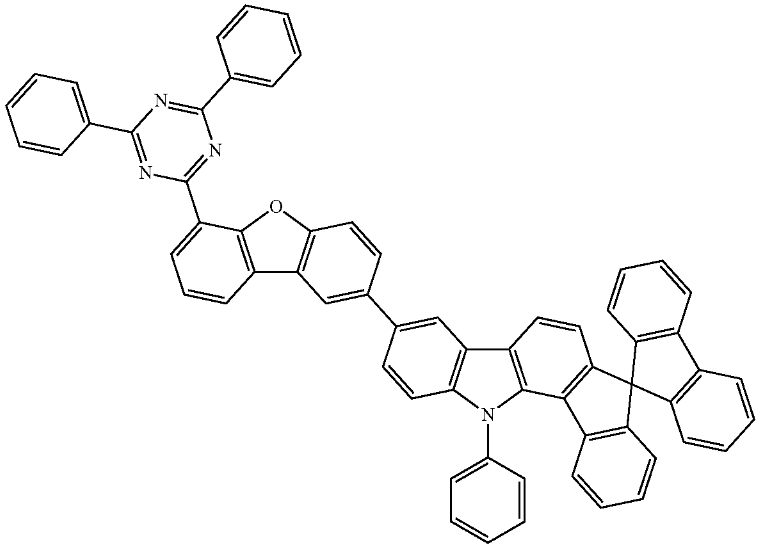
81
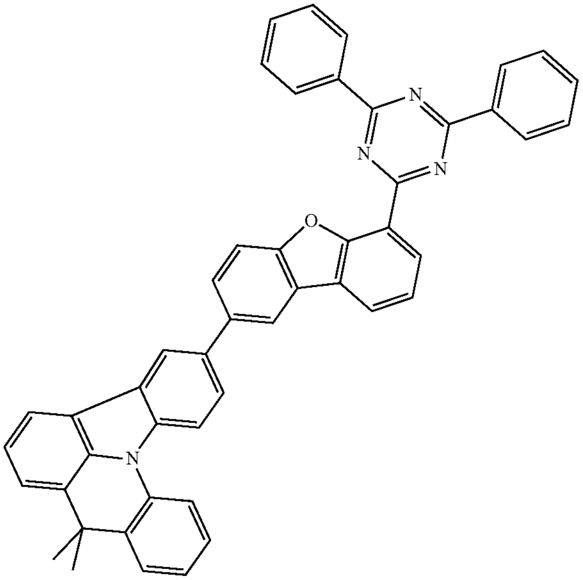
82

TABLE 8-continued
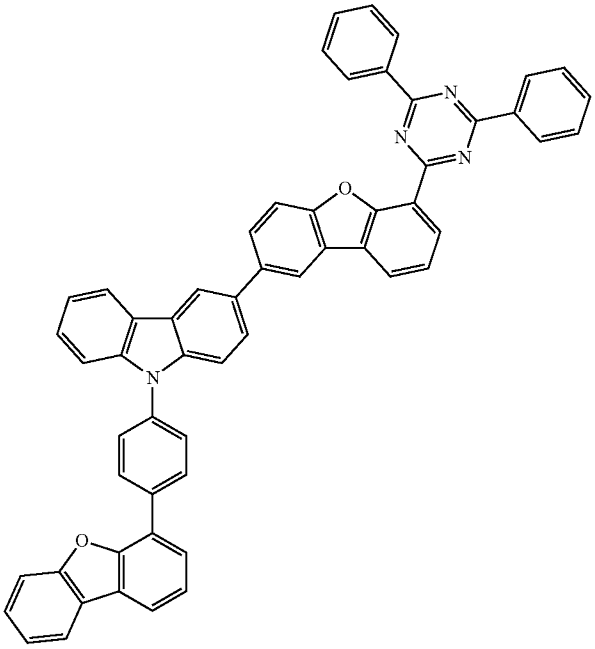
83
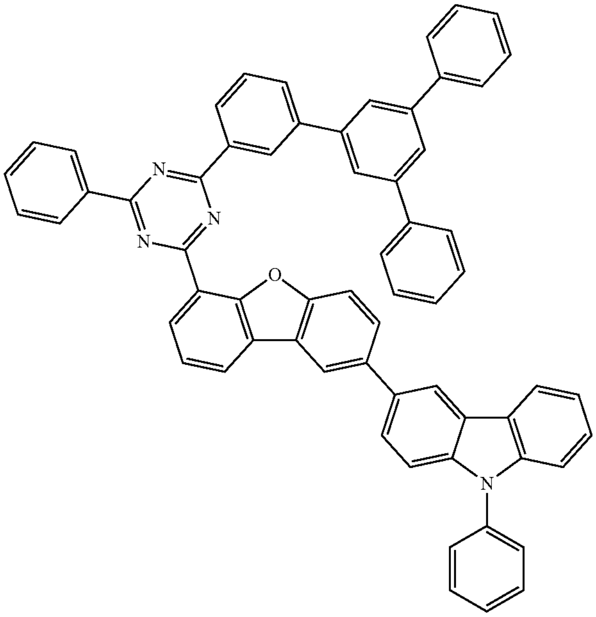
84

TABLE 8-continued
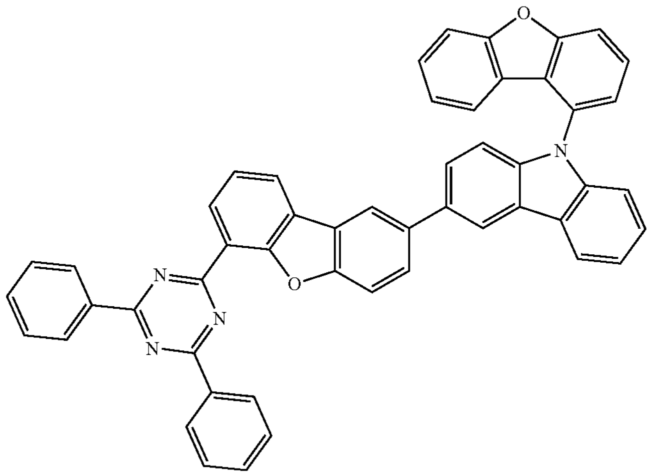
85
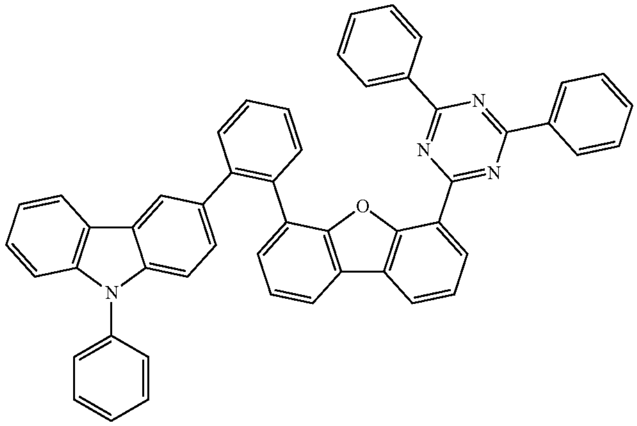
86
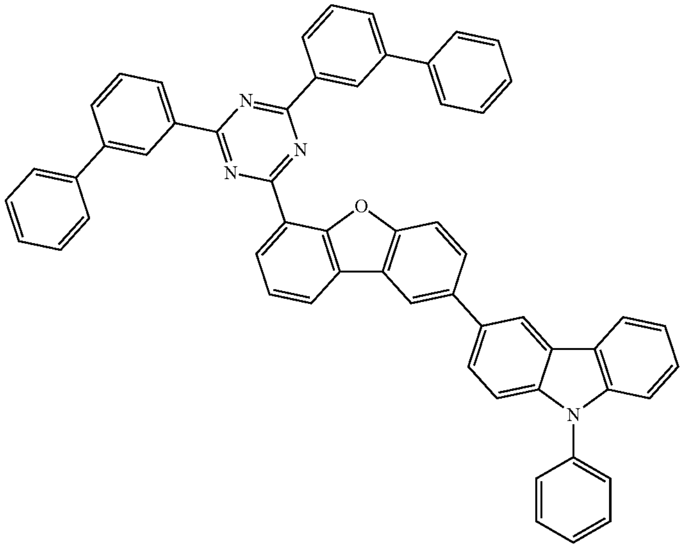
87

TABLE 8-continued

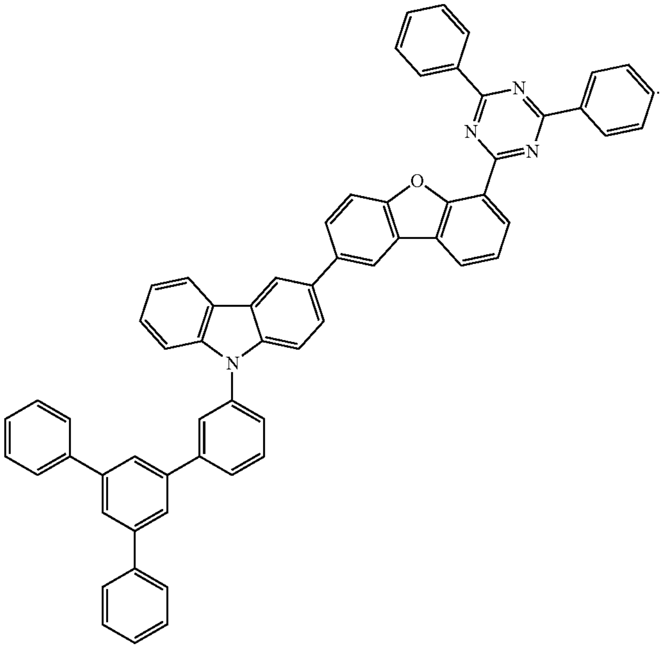

88

The preparation of the compounds of the formula (1) or the preferred compounds of the formulae (1a) to (11) and compounds 1 to 88 is known to the person skilled in the art. The compounds can be prepared by synthesis steps known to the person skilled in the art, such as, for example, halogenation, preferably bromination, and a subsequent organometallic coupling reaction, for example Suzuki coupling, Heck coupling or Hartwig-Buchwald coupling. The preparation of the compounds of the formula (1) or the preferred compounds of the formulae (1 a) to (11) and compounds 1 to 88 is known, in particular, from WO 2015/169412, in particular page 63 and the synthesis examples on pages 77 to 114, and WO 2011/057706, in particular the synthesis examples on pages 92-94.

The preparation of the compounds of the formula (1) or (11) can be carried out in accordance with Scheme 1 below, where X, Y, $Ar_1$, $Ar_2$ and $Ar_3$ have one of the meanings indicated above and R in Scheme 1 denotes an alkyl group having 1 to 4 C atoms.

Scheme 1

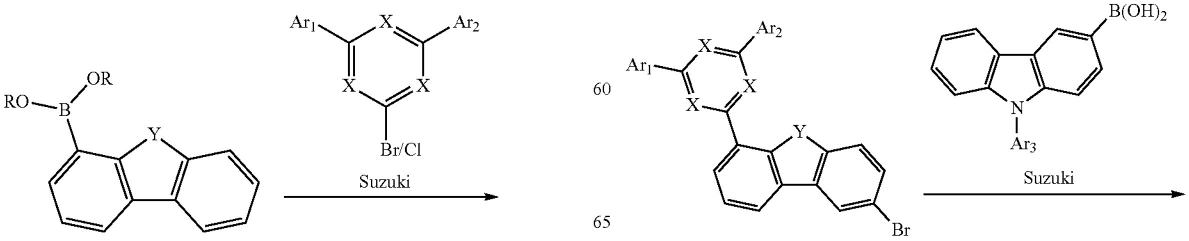

-continued

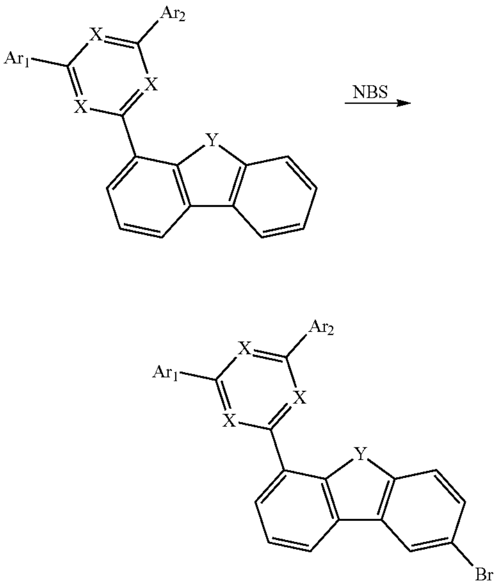

-continued

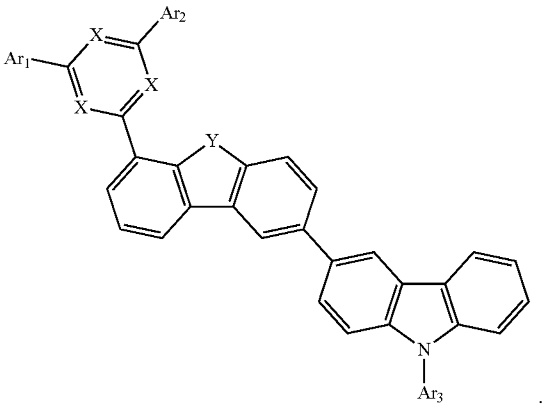

The preparation of the compounds of the formula (1) or (1 k) can be carried out in accordance with Scheme 2 below, where X, Y, $Ar_1$, $Ar_2$ and $Ar_3$ have one of the meanings indicated above and R in Scheme 2 denotes an alkyl group having 1 to 4 C atoms.

Scheme 2

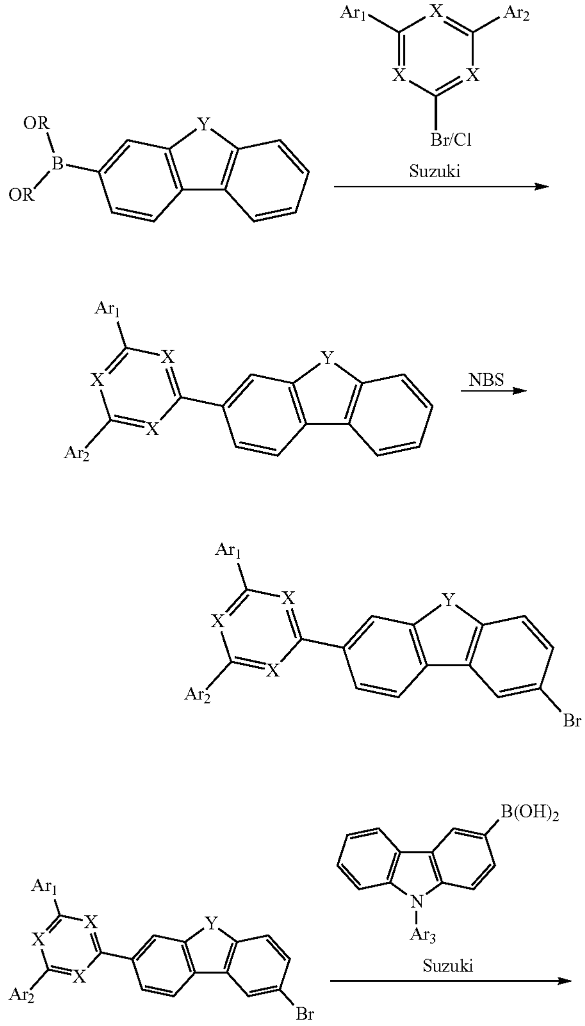

-continued

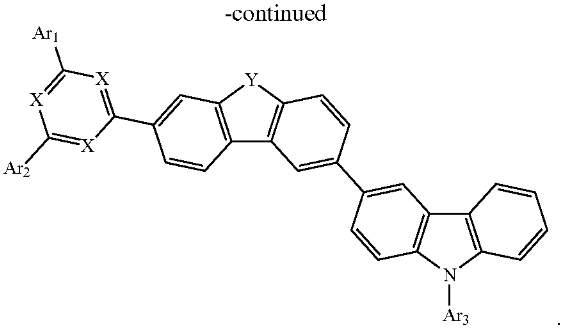

The preparation of the compounds of the formula (1) or (1j) can be carried out in accordance with Scheme 3 below, where X, Y, $Ar_1$, $Ar_2$ and $Ar_3$ have one of the meanings indicated above and R in Scheme 3 denotes an alkyl group having 1 to 4 C atoms.

Scheme 3

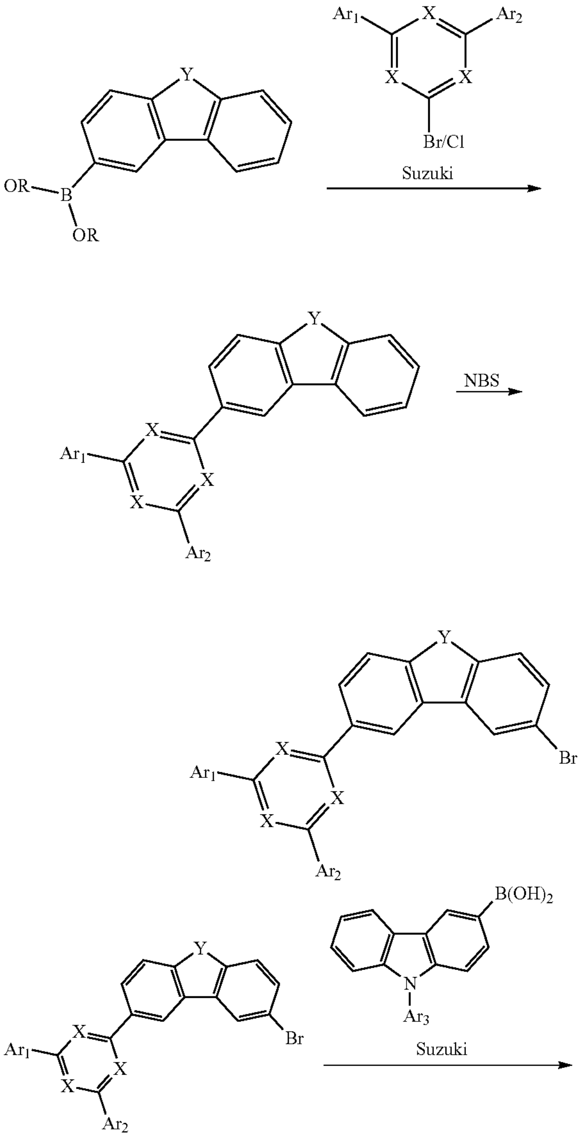

-continued

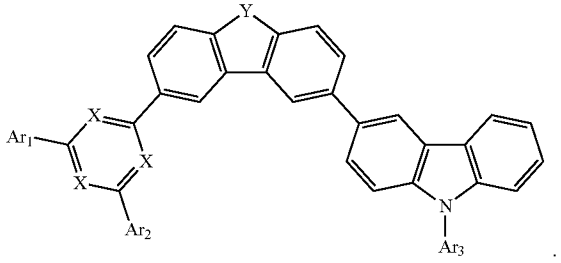

-continued

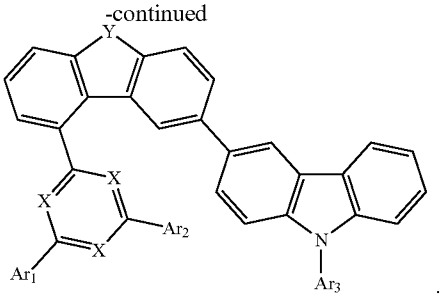

The preparation of the compounds of the formula (1) or (1i) can be carried out in accordance with Scheme 4 below, where X, Y, $Ar_1$, $Ar_2$ and $Ar_3$ have one of the meanings indicated above and R in Scheme 4 denotes an alkyl group having 1 to 4 C atoms. The preparation of the compounds of the formula (1), (1b) or (1i) can likewise be carried out in accordance with Scheme 5 below, where X, Y, $Ar_1$, $Ar_2$ and $Ar_3$ have one of the meanings indicated above.

Scheme 4

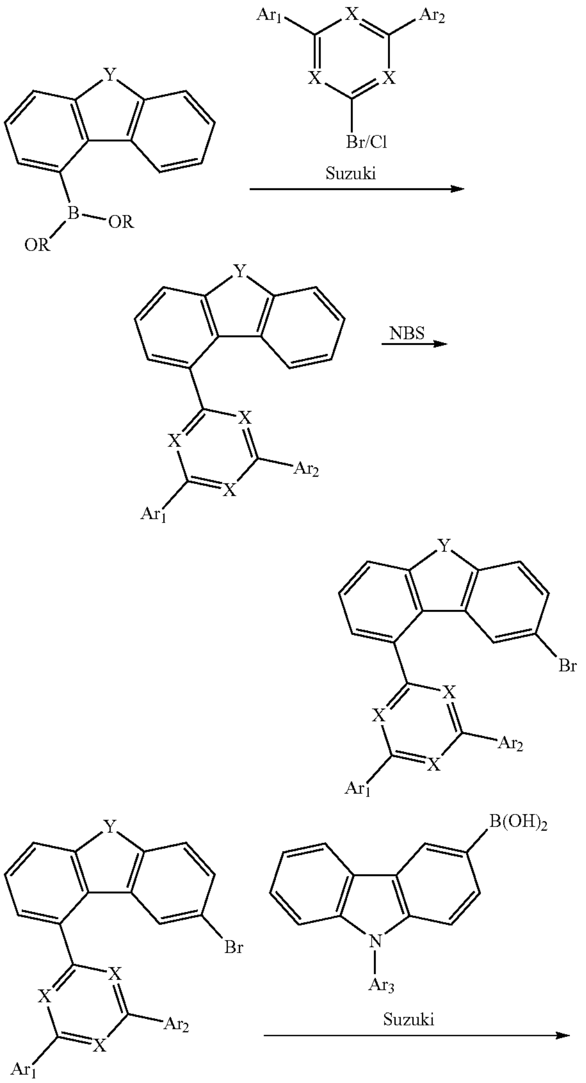

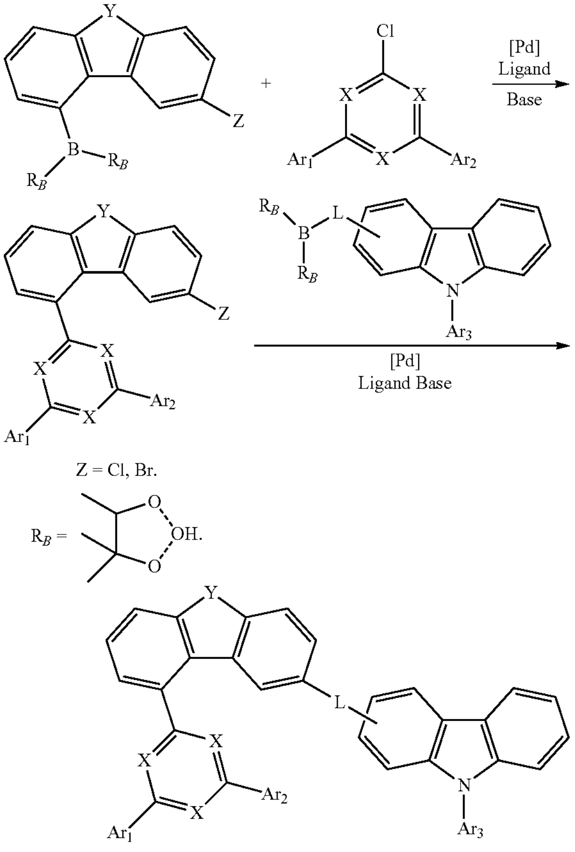

Hole-Transporting Hosts of the Formula (2):

In an embodiment of the invention, compounds of the formula (2), as described above, are selected which are used in the composition with compounds of the formula (1), (1a), (1b), (1c), (1d), (1e), (1f), (1g), (1h), (1i), (1j), (1k) and (1l), as described or preferably described above, or with compounds 1 to 88.

The symbol $X_2$ in compounds of the formula (2) preferably stands twice for N, particularly preferably once for N, and the remaining groups $X_2$ then stand for $CR^1$, where $R^1$ in each case, independently of one another, has a meaning indicated above or preferably indicated below. $X_2$ in compounds of the formula (2) is very particularly preferably $CR^1$.

Compounds of the formula (2) in which $X_2$ on each occurrence, identically or differently, denotes $CR^1$ are represented by the formula (2a), formula (2a)

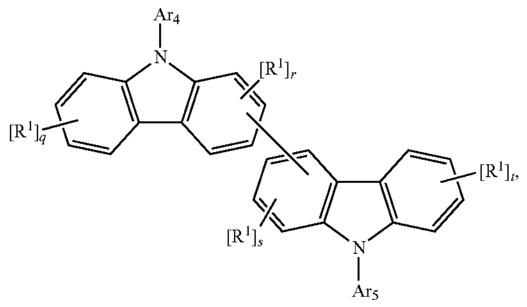

where $R^1$, $Ar_4$ and $Ar_5$ have a meaning given above or a preferred meaning described below and q and t in each case, independently of one another, denote 0, 1, 2, 3 or 4 and r and s in each case, independently of one another, denote 0, 1, 2 or 3.

In compounds of the formula (2a), H is excluded from the definition of the substituents $R^1$. This exclusion applies correspondingly to all formulae below in which q, t, s and r occur.

The invention accordingly furthermore relates to a composition, as described above, where the compound of the formula (2) corresponds to the compound of the formula (2a).

In a preferred embodiment of the compounds of the formula (2) or (2a), the two carbazoles are in each case linked to one another in position 3. This embodiment is represented by the compounds of the formula (2b), formula (2b)

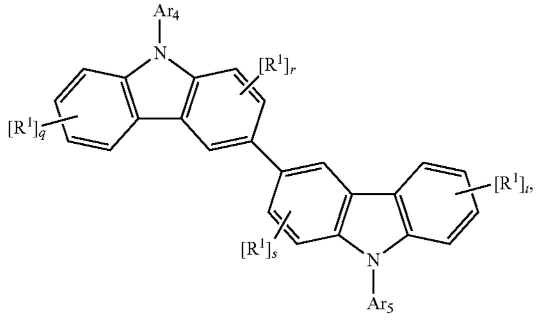

where $R^1$, $Ar_4$ and $Ar_5$ have a meaning given above or a preferred meaning described below and q and t in each case, independently of one another, denote 0, 1, 2, 3 or 4 and r and s in each case, independently of one another, denote 0, 1, 2 or 3.

The invention accordingly furthermore relates to a composition, as described above, where the compound of the formula (2) corresponds to the compound of the formula (2b).

In compounds of the formula (2), (2a) or (2b), q is preferably 0, 1 or 2, where $R^1$ has a meaning indicated above or a meaning indicated below. q is particularly preferably 0 or 1. q is very particularly preferably 0.

If q is greater than 0 in compounds of the formula (2), (2a) or (2b), the substituent $R^1$ is preferably selected on each occurrence, identically or differently, from the group consisting of D, F, an alkyl group having 1 to 40 C atoms or an aromatic or heteroaromatic ring system having 5 to 40 aromatic ring atoms, which may be substituted by one or more radicals $R^2$. The aromatic or heteroaromatic ring system having 5 to 40 aromatic ring atoms in this $R^1$ is preferably derived from benzene, dibenzofuran, dibenzothiophene, 9-phenylcarbazole, biphenyl or terphenyl, which may be substituted by one or more radicals $R^2$. The preferred position of the substituent(s) $[R^1]_q$ is position 1, 2, 3 or 4 or a combination of positions 1 and 4 or 1 and 3, particularly preferably 1 and 3, 2 or 3, very particularly preferably 3, where $R^1$ has one of the preferred meanings indicated above and q is greater than 0. Particularly preferred substituents $R^4$ in $[R^1]_q$ are phenyl and biphenyl.

In compounds of the formula (2), (2a) or (2b), r is preferably 0, 1 or 2, where $R^1$ has a meaning indicated above or a meaning indicated below. r is particularly preferably 0 or 1, very particularly preferably 0.

If r is greater than 0 in compounds of the formula (2), (2a) or (2b), the substituent $R^1$ is preferably selected on each occurrence, identically or differently, from the group consisting of D, F, an alkyl group having 1 to 40 C atoms or an aromatic or heteroaromatic ring system having 5 to 40 aromatic ring atoms, which may be substituted by one or more radicals $R^2$. The aromatic or heteroaromatic ring system having 5 to 40 aromatic ring atoms in this $R^1$ is preferably derived from benzene, dibenzofuran, dibenzothiophene, 9-phenylcarbazole, biphenyl and terphenyl, which may be substituted by one or more radicals $R^2$. The preferred position of the substituent(s) $[R^1]_r$ is position 1 or 2, particularly preferably 1, where $R^1$ has one of the preferred meanings indicated above and r is greater than 0. Particularly preferred substituents $R^1$ in $[R^1]_r$ are phenyl, 9-phenylcarbazole and 9H-carbazol-9-yl.

In compounds of the formula (2), (2a) or (2b), s is preferably 0, 1 or 2, where $R^1$ has a meaning indicated above for a meaning indicated below. s is particularly preferably 0 or 1, very particularly preferably 0.

If s is greater than 0 in compounds of the formula (2), (2a) or (2b), the substituent $R^1$ is preferably selected on each occurrence, identically or differently, from the group consisting of D, F, an alkyl group having 1 to 40 C atoms or an aromatic or heteroaromatic ring system having 5 to 40 aromatic ring atoms, which may be substituted by one or more radicals $R^2$. The aromatic or heteroaromatic ring system having 5 to 40 aromatic ring atoms in this $R^1$ is preferably derived from benzene, dibenzofuran, dibenzothiophene, 9-phenylcarbazole, biphenyl or terphenyl, which may be substituted by one or more radicals $R^2$. The preferred position of the substituent(s) $[R^1]_s$ is position 1 or 2, particularly preferably 1, where $R^1$ has one of the preferred meanings indicated above and s is greater than 0. Particularly preferred substituents $R^1$ in $[R^1]_r$ are phenyl, 9-phenylcarbazole and 9H-carbazol-9-yl.

In compounds of the formula (2), (2a) or (2b), t is preferably 0, 1 or 2, where $R^1$ has a meaning indicated above or a meaning indicated below. t is particularly preferably 0 or 1. t is very particularly preferably 0.

If t is greater than 0 in compounds of the formula (2), (2a) or (2b), the substituent $R^1$ is preferably selected on each occurrence, identically or differently, from the group consisting of D, F, an alkyl group having 1 to 40 C atoms or an aromatic or heteroaromatic ring system having 5 to 40 aromatic ring atoms, which may be substituted by one or more radicals $R^2$. The aromatic or heteroaromatic ring system having 5 to 40 aromatic ring atoms in this $R^1$ is preferably derived from benzene, dibenzofuran, dibenzothiophene, 9-phenylcarbazole, biphenyl or terphenyl, which may be substituted by one or more radicals $R^2$. The preferred position of the substituent(s) $[R^1]_q$ is position 1, 2, 3 or 4 or a combination of positions 1 and 4, 1 and 3, 1 and 2 and 3 and 4, particularly preferably 1 and 3, 2 or 3, very particularly preferably 2 or 3, where $R^1$ has one of the preferred meanings indicated above and t is greater than 0. Particularly preferred substituents $R^1$ in $[R^1]_t$ are phenyl, biphenyl and terphenyl.

The substituent $R^2$ is preferably selected on each occurrence, identically or differently, from the group consisting of D, F, Cl, Br, I, CN, $NO_2$, $N(Ar)_2$, $NH_2$, $N(R^3)_2$, C(=O)Ar, C(=O)H, C(=O)$R^3$, P(=O)$(Ar)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, which may in each case be substituted by one or more radicals $R^3$, or is an aromatic or heteroaromatic ring system having 5 to 60 aromatic ring atoms, which may in each case be substituted by one or more radicals $R^3$, or is an aryloxy or heteroaryloxy group having 5 to 60 aromatic ring atoms, which may be substituted by one or more radicals $R^3$. The substituent $R^2$ is particularly preferably on its occurrence an aromatic or heteroaromatic ring system, as described above, preferably selected from the group carbazole, 9-phenylcarbazole, dibenzofuran, dibenzothiophene, fluorene, terphenyl or spirobifluorene, very particularly preferably derived from a dibenzofuran.

In the case of the substitution of one of the substituents $R^2$, as described above, by a substituent $R^3$, the meanings of $R^3$ as described above or preferably described apply.

In compounds of the formula (2), (2a) or (2b), as described above, $Ar_4$ and $Ar_5$ are in each case, independently of one another, an aromatic ring system having 6 to 40 aromatic ring atoms or a heteroaromatic ring system having 10 to 40 aromatic ring atoms, which may be substituted by one or more radicals $R^3$, with the proviso that $Ar_4$ and $Ar_5$ are not simultaneously phenyl. Due to the condition indicated, the composition according to the invention differs from the composition of WO 2015/169412.

If compounds of the formula (1f), (1h) and (1i) are used in accordance with the invention with a compound of the formula (2), (2a) or (2b) and L in compounds of the formula (1f), (1h) and (1i) does not denote a single bond, then both $Ar_4$ and $Ar_5$ can denote phenyl in addition to the definition indicated above.

In the case of the heteroaromatic ring systems having 10 to 40 C atoms, which may be substituted by one or more of the substituents $R^3$, electron-rich ring systems are particularly preferred, where the ring system which is optionally substituted by $R^3$ preferably contains in total only one N atom or the ring system which is optionally substituted by $R^3$ contains in total one or more O and/or S atoms.

In compounds of the formula (2), (2a) or (2b) or preferably described compounds of the formula (2), (2a) or (2b), $Ar_4$ and $Ar_5$ are preferably selected from the aromatic or heteroaromatic ring systems Ar-1 to Ar-22, as described above, where the comments regarding the groups $R^{\#}$, $Y^3$ and $R^3$ also apply, with the proviso that $Ar_4$ and $Ar_5$ are not simultaneously phenyl and preferably with the condition that a heteroaromatic ring system represented by Ar-12, Ar-13, Ar-14, Ar-15, Ar-20 and Ar-21 which is optionally substituted by $R^3$ contains in total only one N atom.

If compounds of the formula (1f), (1h) and (1i) are used in accordance with the invention with a compound of the formula (2), (2a) or (2b) and L in compounds of the formula (1f), (1h) and (1i) does not denote a single bond, then both $Ar_4$ and $Ar_5$ can denote phenyl in addition to the definition indicated above.

In a preferred embodiment of the invention, compounds of the formula (2), (2a) or (2b) are selected in which one of the substituents $Ar_4$ and $Ar_5$ denotes an aromatic ring system having 6 to 40 aromatic ring atoms or a heteroaromatic ring system having 10 to 40 aromatic ring atoms, which may be substituted by one or more radicals $R^3$, and the other substituent denotes an aromatic ring system having 6 to 40 aromatic ring atoms, which may be substituted by one or more radicals $R^3$, with the proviso that $Ar_4$ and $Ar_5$ are not simultaneously phenyl. This proviso does not apply to compounds of the formulae (1f), (1h) or (1i) in which L does not denote a single bond, as described above.

The invention accordingly furthermore relates to a composition, as described above or as preferably described, where one of the substituents $Ar_4$ and $Ar_5$ in compounds of the formula (2) or (2a) or (2b) denotes an aromatic ring system having 6 to 40 aromatic ring atoms or a heteroaromatic ring system having 10 to 40 aromatic ring atoms, which may be substituted by one or more radicals $R^3$, and the other substituent denotes an aromatic ring system having 6 to 40 aromatic ring atoms, which may be substituted by one or more radicals $R^3$, with the proviso that $Ar_4$ and $Ar_5$ are not simultaneously phenyl.

In this embodiment, it is preferred if one substituent $Ar_4$ or $Ar_5$ corresponds to one of structures Ar-1 to Ar-22, as described above or as preferably described, and the other substituent corresponds to one of structures Ar-1 to Ar-11 or Ar-16 to Ar-19 or Ar-22, with the proviso that $Ar_4$ and $Ar_5$ are not simultaneously phenyl and preferably with the condition that a heteroaromatic ring system represented by Ar-12, Ar-13, Ar-14, Ar-15, Ar-20 and Ar-21 which is optionally substituted by $R^3$ contains in total only one N atom.

In a particularly preferred embodiment of the invention, compounds of the formula (2), (2a) or (2b) are selected in which the substituents $Ar_4$ and $Ar_5$ in each case, independently of one another, denote an aromatic ring system having 6 to 40 aromatic ring atoms, which may be substituted by one or more radicals $R^3$, with the proviso that $Ar_4$ and $Ar_5$ are not simultaneously phenyl.

The substituents $R^3$, when present in this embodiment, are preferably aromatic and do not contain a heteroatom if $Ar_4$ and $Ar_5$ denote an aromatic ring system having 6 to 40 ring atoms.

The invention accordingly furthermore relates to a composition, as described above or as preferably described, where the substituents $Ar_4$ and $Ar_5$ in compounds of the formula (2) or (2a) or (2b) in each case, independently of one another, denote an aromatic ring system having 6 to 40 aromatic ring atoms, which may be substituted by one or more radicals $R^3$, with the proviso that $Ar_4$ and $Ar_5$ are not simultaneously phenyl.

In this embodiment, it is preferred if both substituents $Ar_4$ and $Ar_5$ in each case, independently of one another, correspond to one of structures Ar-1 to Ar-11 or Ar-16 to Ar-19 or Ar-22, as described above or as preferably described, with the proviso that $Ar_4$ and $Ar_5$ are not simultaneously phenyl and preferably with the condition that the substituent $R^3$ in an aromatic ring system which is optionally substituted by $R^3$ is selected so that it does not contain a heteroatom.

Examples of suitable compounds of the formula (2), (2a) or (2b) which are selected in accordance with the invention are the structures shown below in Table 9.

TABLE 9
| Structure | CAS number |
|---|---|
| 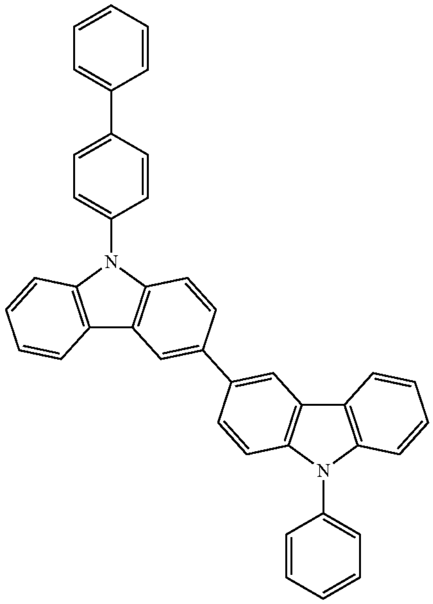 89 | CAS-1454567-05-5 |
| 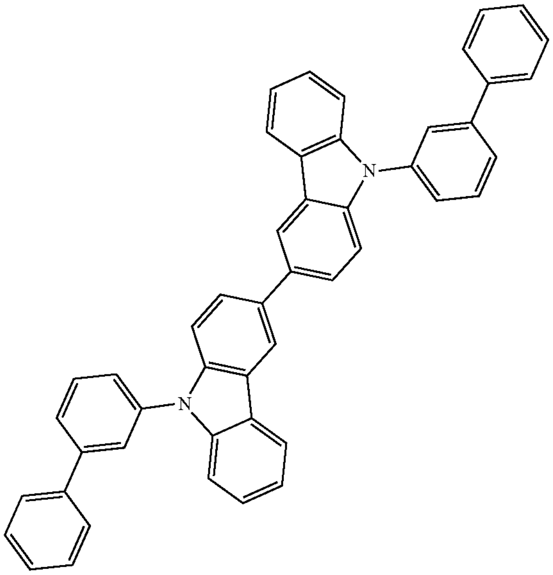 90 | CAS-1352040-89-1 |

TABLE 9-continued
| Structure | CAS number |
| --- | --- |
| 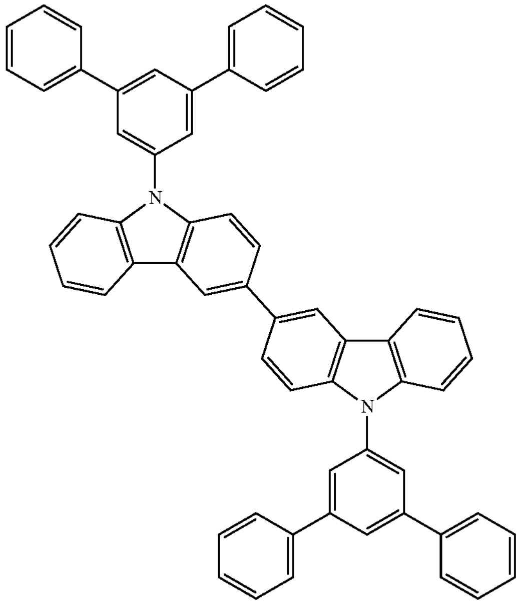 [SMILES: c1ccc(-c2cc(-c3ccccc3)cc(-n3c4ccccc4c4cc(-c5ccc6c(c5)c5ccccc5n6-c5cc(-c6ccccc6)cc(-c6ccccc6)c5)ccc43)c2)cc1] | CAS-1336889-25-8 |
| 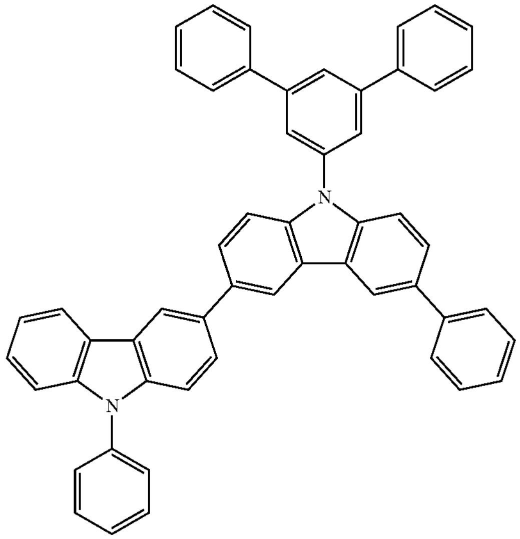 [SMILES: c1ccc(-c2cc(-c3ccccc3)cc(-n3c4ccc(-c5ccccc5)cc4c4cc(-c5ccc6c(c5)c5ccccc5n6-c5ccccc5)ccc43)c2)cc1] | CAS-18005544-05-1 |

TABLE 9-continued
| Structure | CAS number |
|---|---|
| 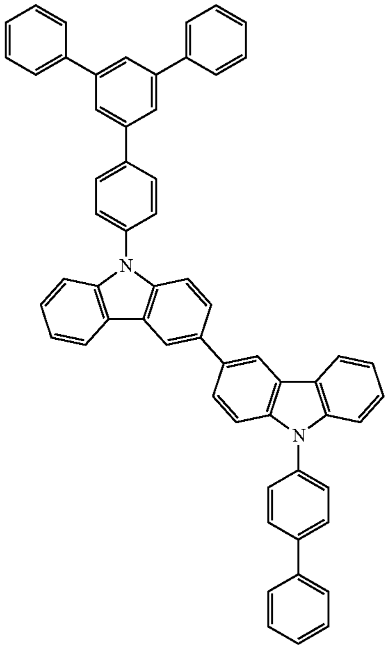 [SMILES: c1ccc(-c2ccc(-n3c4ccccc4c4cc(-c5ccc6c(c5)c5ccccc5n6-c5ccc(-c6cc(-c7ccccc7)cc(-c7ccccc7)c6)cc5)ccc43)cc2)cc1] | CAS-1800544-08-4 |
| 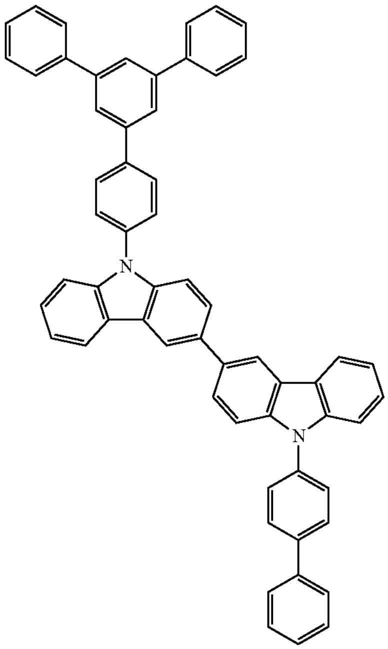 [SMILES: c1ccc(-c2ccc(-n3c4ccccc4c4cc(-c5ccc6c(c5)c5ccccc5n6-c5ccc(-c6cc(-c7ccccc7)cc(-c7ccccc7)c6)cc5)ccc43)cc2)cc1] | CAS-1800544-08-4 |

TABLE 9-continued
| Structure | CAS number |
|---|---|
| 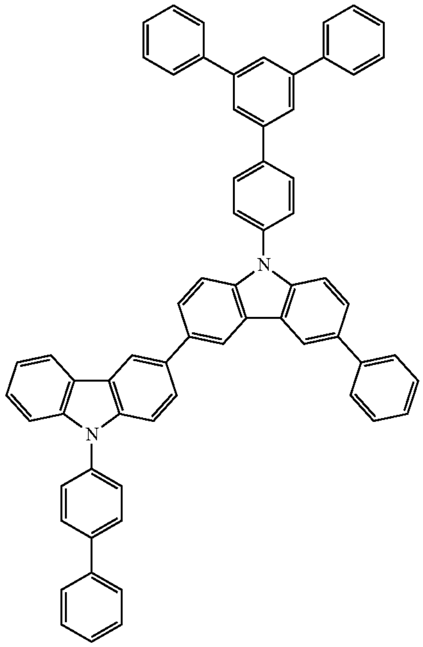 [SMILES: c1ccc(-c2ccc(-n3c4ccccc4c4cc(-c5ccc6c(c5)c5cc(-c7ccccc7)ccc5n6-c5ccc(-c6cc(-c7ccccc7)cc(-c7ccccc7)c6)cc5)ccc43)cc2)cc1] | CAS-1800544-09-5 |
| 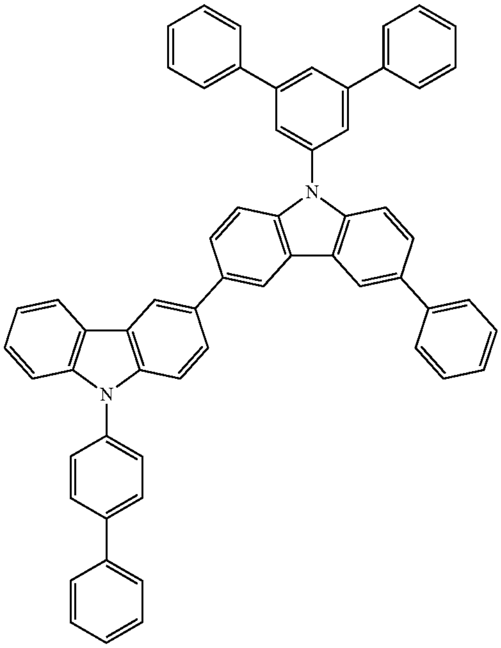 [SMILES: c1ccc(-c2ccc(-n3c4ccccc4c4cc(-c5ccc6c(c5)c5cc(-c7ccccc7)ccc5n6-c5cc(-c6ccccc6)cc(-c6ccccc6)c5)ccc43)cc2)cc1] | CAS-1800544-10-8 |

TABLE 9-continued
| Structure | CAS number |
| --- | --- |
| 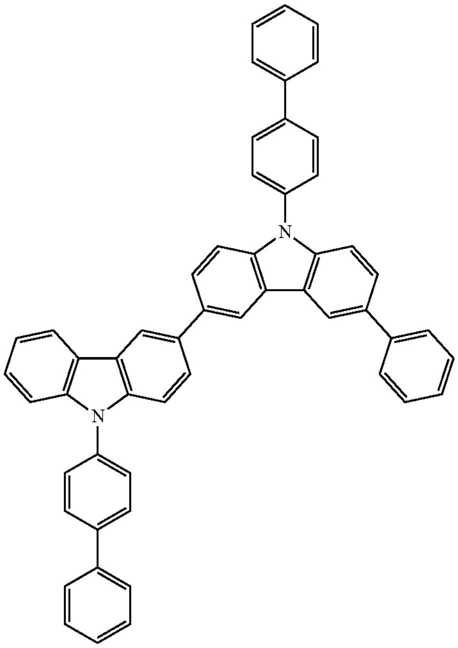 [SMILES: c1ccc(-c2ccc(-n3c4ccccc4c4cc(-c5ccc6c(c5)c5cc(-c7ccccc7)ccc5n6-c5ccc(-c6ccccc6)cc5)ccc43)cc2)cc1] | CAS-1800544-11-9 |
| 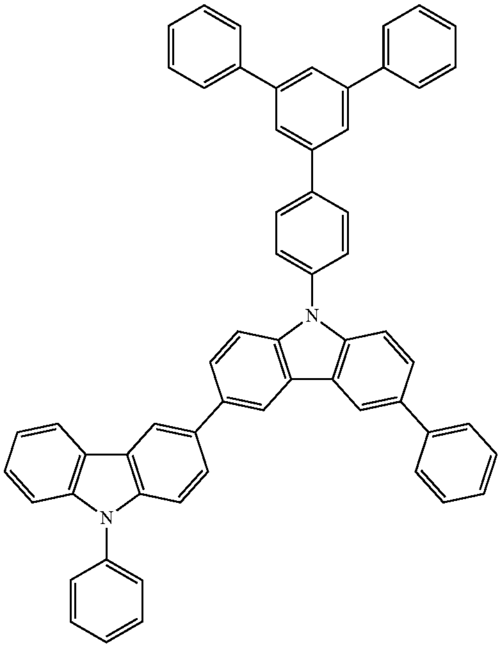 [SMILES: c1ccc(-c2cc(-c3ccccc3)cc(-c3ccc(-n4c5ccc(-c6ccccc6)cc5c5cc(-c6ccc7c(c6)c6ccccc6n7-c6ccccc6)ccc54)cc3)c2)cc1] | CAS-1800544-04-0 |

TABLE 9-continued
| Structure | CAS number |
| --- | --- |
| 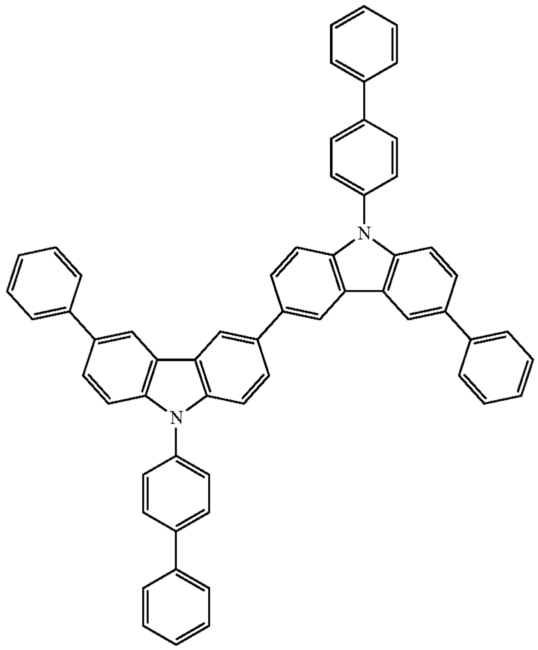 [SMILES: c1ccc(-c2ccc(-n3c4ccc(-c5ccccc5)cc4c4cc(-c5ccc6c(c5)c5cc(-c7ccccc7)ccc5n6-c5ccc(-c6ccccc6)cc5)ccc43)cc2)cc1] | CAS-1842320-52-8 |
| 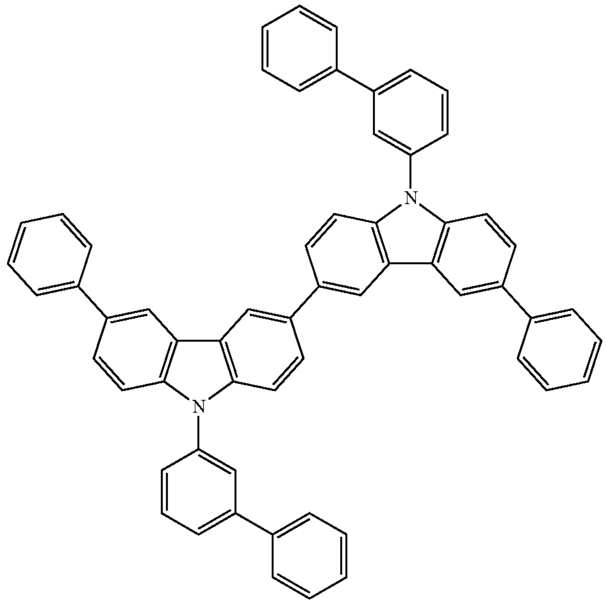 [SMILES: c1ccc(-c2cccc(-n3c4ccc(-c5ccccc5)cc4c4cc(-c5ccc6c(c5)c5cc(-c7ccccc7)ccc5n6-c5cccc(-c6ccccc6)c5)ccc43)c2)cc1] | CAS-1842320-53-9 |

TABLE 9-continued
| Structure | CAS number |
| --- | --- |
| 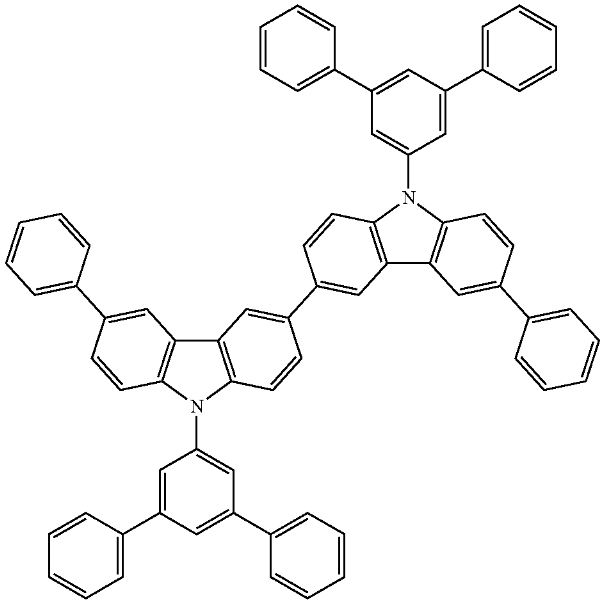 [SMILES: c1ccc(-c2cc(-c3ccccc3)cc(-n3c4ccc(-c5ccccc5)cc4c4cc(-c5ccc6c(c5)c5cc(-c7ccccc7)ccc5n6-c5cc(-c6ccccc6)cc(-c6ccccc6)c5)ccc43)c2)cc1] | CAS-1842320-54-0 |
| 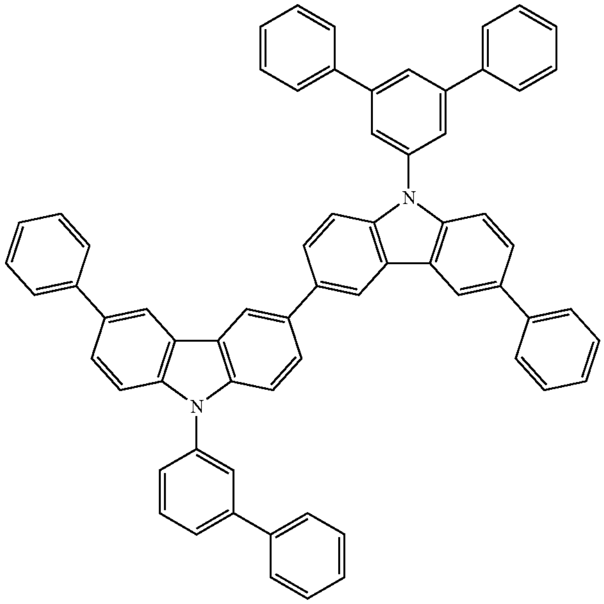 [SMILES: c1ccc(-c2cccc(-n3c4ccc(-c5ccccc5)cc4c4cc(-c5ccc6c(c5)c5cc(-c7ccccc7)ccc5n6-c5cc(-c6ccccc6)cc(-c6ccccc6)c5)ccc43)c2)cc1] | CAS-1842320-55-1 |

TABLE 9-continued
| Structure | CAS number |
| --- | --- |
| 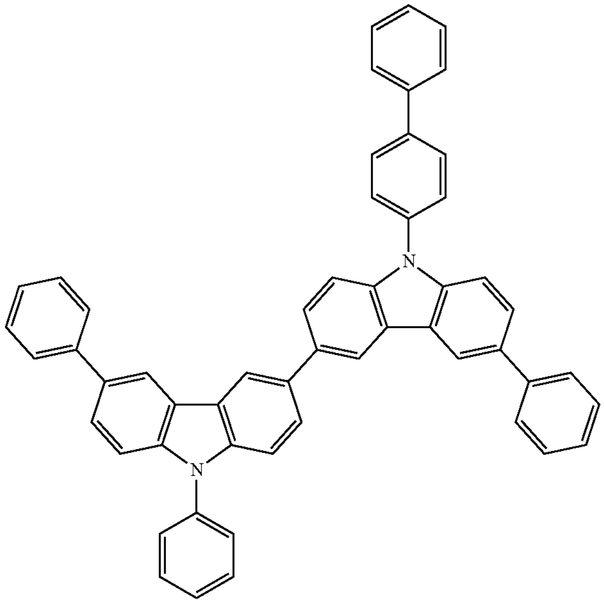 [SMILES: c1ccc(-c2ccc(-n3c4ccc(-c5ccccc5)cc4c4cc(-c5ccc6c(c5)c5cc(-c7ccccc7)ccc5n6-c5ccccc5)ccc43)cc2)cc1] | CAS-1842320-56-2 |
| 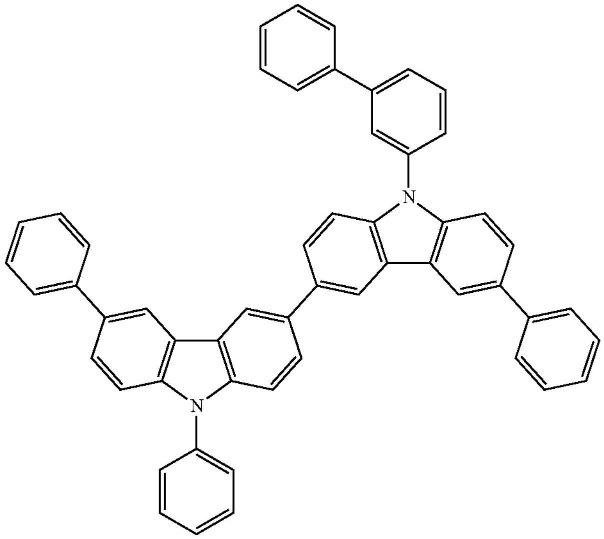 [SMILES: c1ccc(-c2cccc(-n3c4ccc(-c5ccccc5)cc4c4cc(-c5ccc6c(c5)c5cc(-c7ccccc7)ccc5n6-c5ccccc5)ccc43)c2)cc1] | CAS-1842320-57-3 |

TABLE 9-continued
| Structure | CAS number |
|---|---|
| 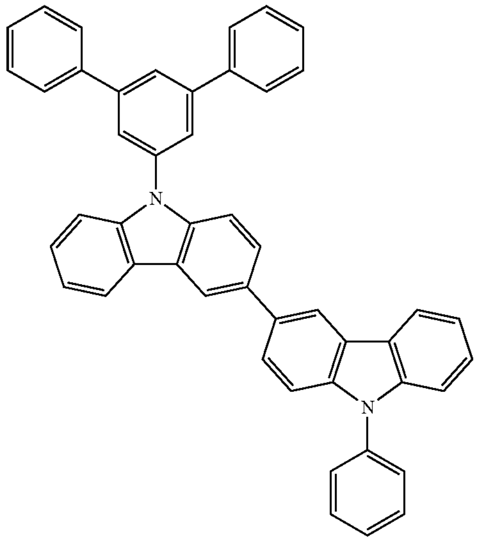 [SMILES: c1ccc(-c2cc(-c3ccccc3)cc(-n3c4ccccc4c4cc(-c5ccc6c(c5)c5ccccc5n6-c5ccccc5)ccc43)c2)cc1] | CAS-1410876-33-3 |
| 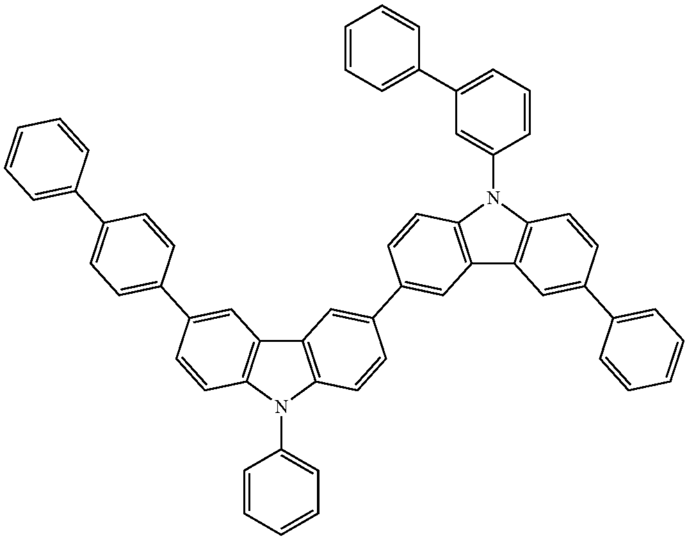 [SMILES: c1ccc(-c2ccc(-c3ccc4c(c3)c3cc(-c5ccc6c(c5)c5cc(-c7ccccc7)ccc5n6-c5cccc(-c6ccccc6)c5)ccc3n4-c3ccccc3)cc2)cc1] | CAS-1842320-58-4 |

TABLE 9-continued
| Structure | CAS number |
| --- | --- |
| 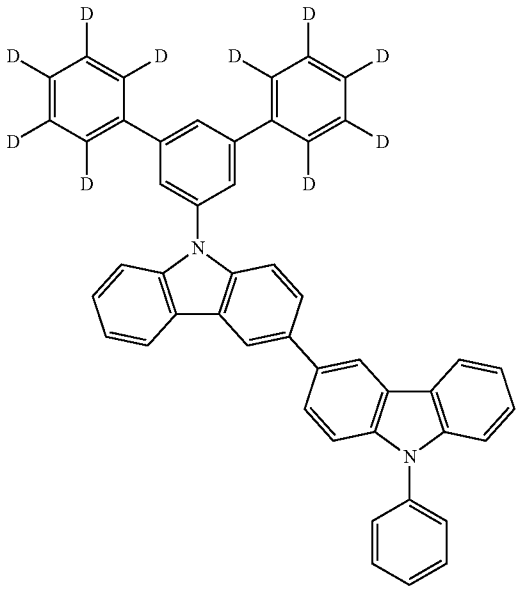 [SMILES: [2H]c1c([2H])c([2H])c(-c2cc(-c3c([2H])c([2H])c([2H])c([2H])c3[2H])cc(-n3c4ccccc4c4cc(-c5ccc6c(c5)c5ccccc5n6-c5ccccc5)ccc43)c2)c([2H])c1[2H]] | CAS-1410876-47-9 |
| 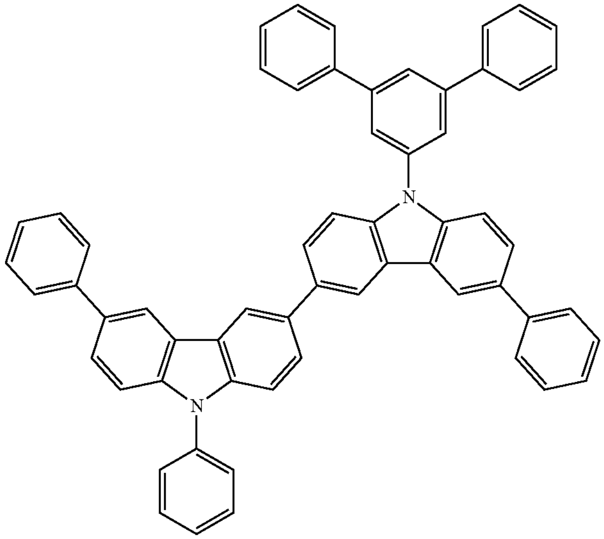 [SMILES: c1ccc(-c2cc(-c3ccccc3)cc(-n3c4ccc(-c5ccccc5)cc4c4cc(-c5ccc6c(c5)c5cc(-c7ccccc7)ccc5n6-c5ccccc5)ccc43)c2)cc1] | CAS-1842320-59-5 |

TABLE 9-continued
| Structure | CAS number |
|---|---|
| 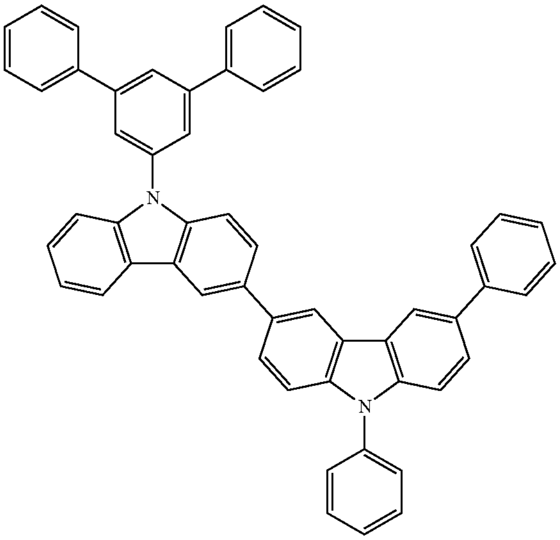 [SMILES: c1ccc(-c2cc(-c3ccccc3)cc(-n3c4ccccc4c4cc(-c5ccc6c(c5)c5cc(-c7ccccc7)ccc5n6-c5ccccc5)ccc43)c2)cc1] | CAS-1848256-38-1 |
| 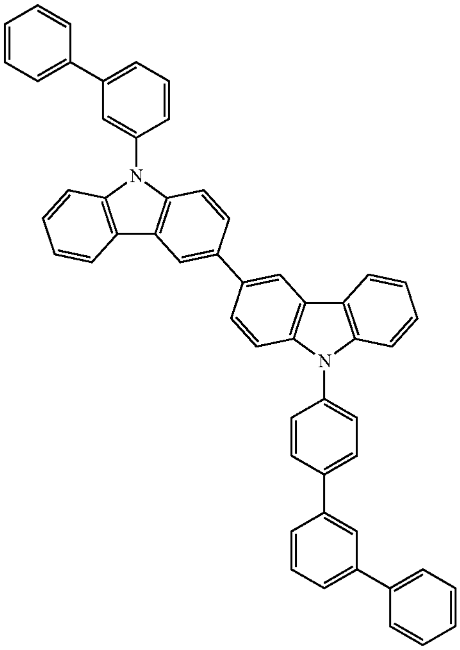 [SMILES: c1ccc(-c2cccc(-c3ccc(-n4c5ccccc5c5cc(-c6ccc7c(c6)c6ccccc6n7-c6cccc(-c7ccccc7)c6)ccc54)cc3)c2)cc1] | CAS-1865661-14-8 |

TABLE 9-continued
| Structure | CAS number |
| --- | --- |
| 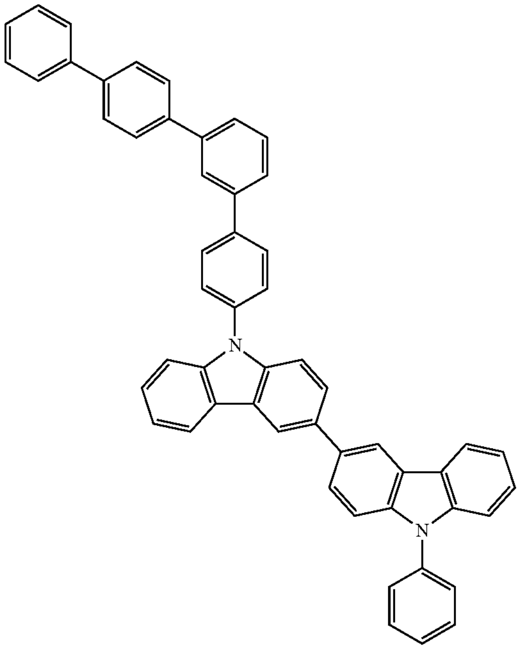 [SMILES: c1ccc(-c2ccc(-c3cccc(-c4ccc(-n5c6ccccc6c6cc(-c7ccc8c(c7)c7ccccc7n8-c7ccccc7)ccc65)cc4)c3)cc2)cc1] | CAS-1870867-25-6 |
| 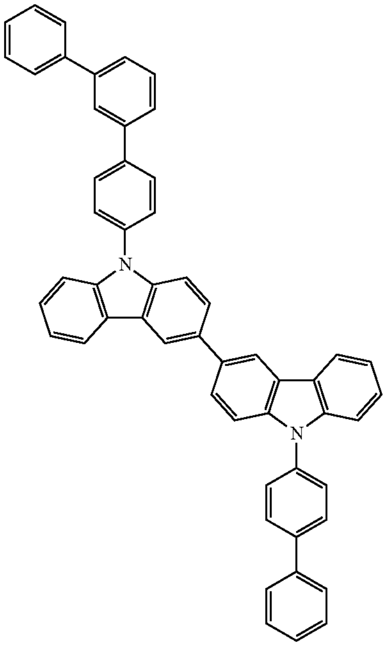 [SMILES: c1ccc(-c2ccc(-n3c4ccccc4c4cc(-c5ccc6c(c5)c5ccccc5n6-c5ccc(-c6cccc(-c7ccccc7)c6)cc5)ccc43)cc2)cc1] | CAS-1884707-32-7 |

TABLE 9-continued
| Structure | CAS number |
| --- | --- |
| 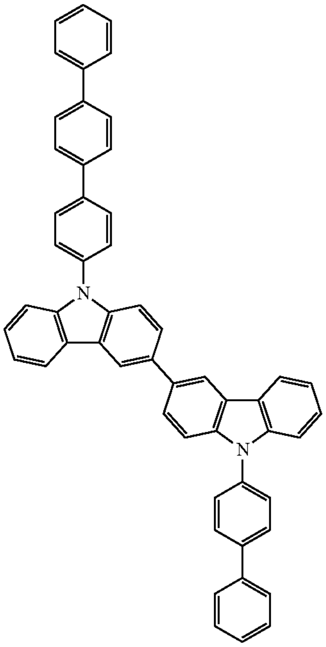 [SMILES: c1ccc(-c2ccc(-c3ccc(-n4c5ccccc5c5cc(-c6ccc7c(c6)c6ccccc6n7-c6ccc(-c7ccccc7)cc6)ccc54)cc3)cc2)cc1] | CAS-1889262-88-7 |
| 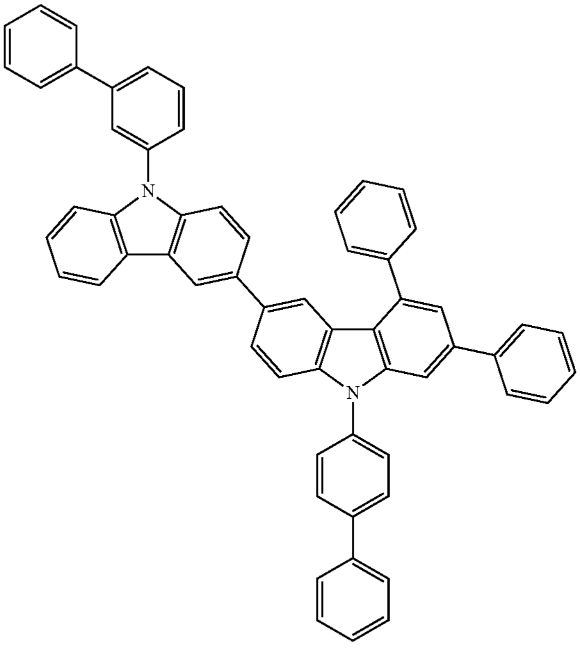 [SMILES: c1ccc(-c2ccc(-n3c4ccc(-c5ccc6c(c5)c5ccccc5n6-c5cccc(-c6ccccc6)c5)cc4c4c(-c5ccccc5)cc(-c5ccccc5)cc43)cc2)cc1] | CAS-2018307-89-4 |

TABLE 9-continued
| Structure | CAS number |
| --- | --- |
| 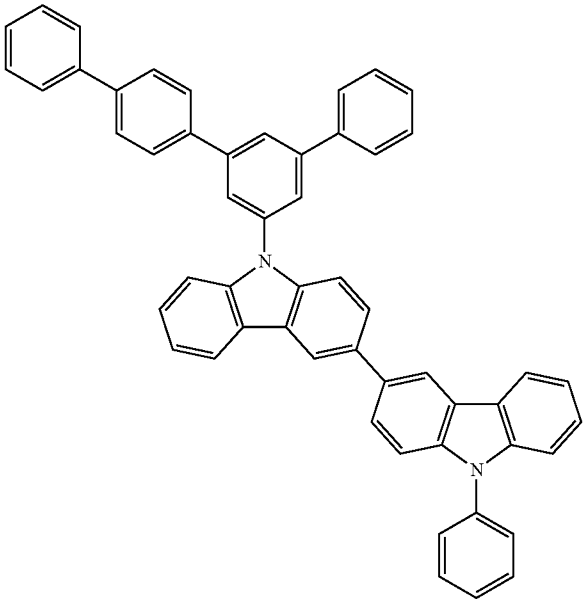 [SMILES: c1ccc(-c2ccc(-c3cc(-c4ccccc4)cc(-n4c5ccccc5c5cc(-c6ccc7c(c6)c6ccccc6n7-c6ccccc6)ccc54)c3)cc2)cc1] | CAS-1454655-29-8 |
| 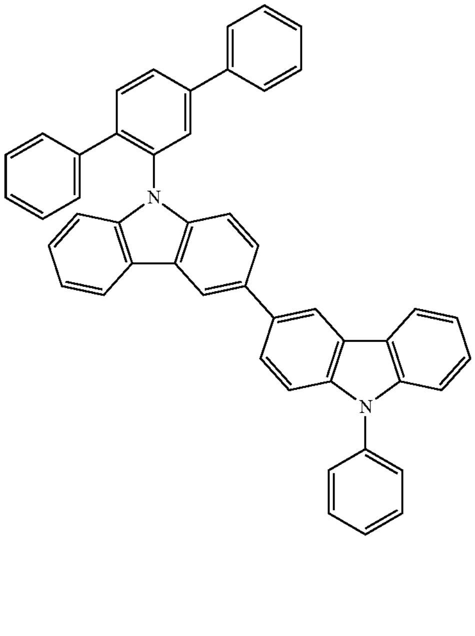 [SMILES: c1ccc(-c2ccc(-c3ccccc3)c(-n3c4ccccc4c4cc(-c5ccc6c(c5)c5ccccc5n6-c5ccccc5)ccc43)c2)cc1] | CAS-1454655-33-4 |

TABLE 9-continued
| Structure | CAS number |
|---|---|
| 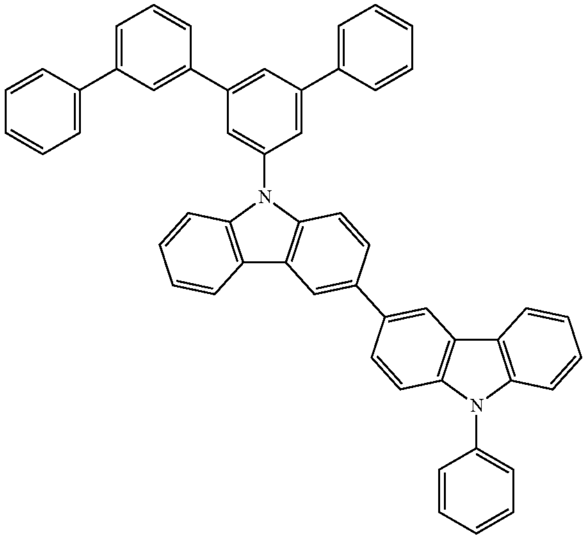 [SMILES: c1ccc(-c2cccc(-c3cc(-c4ccccc4)cc(-n4c5ccccc5c5cc(-c6ccc7c(c6)c6ccccc6n7-c6ccccc6)ccc54)c3)c2)cc1] | CAS-1454660-22-0 |
| 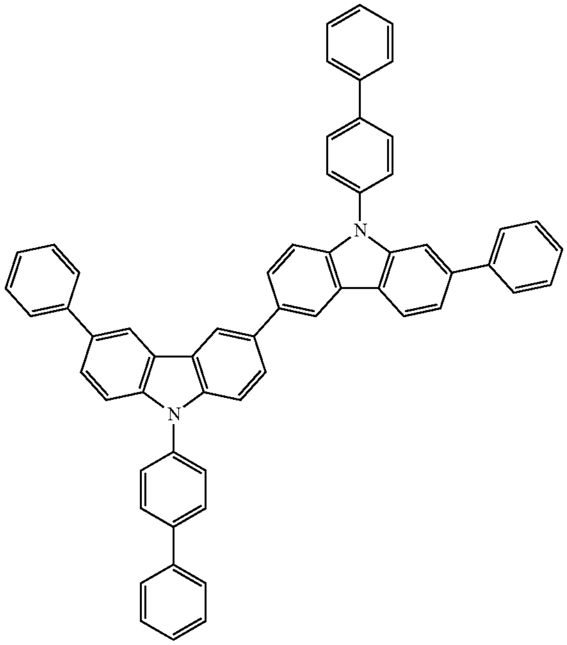 [SMILES: c1ccc(-c2ccc(-n3c4ccc(-c5ccccc5)cc4c4cc(-c5ccc6c(c5)c5ccc(-c7ccccc7)cc5n6-c5ccc(-c6ccccc6)cc5)ccc43)cc2)cc1] | CAS-1907663-27-7 |

TABLE 9-continued
| Structure | CAS number |
| --- | --- |
| 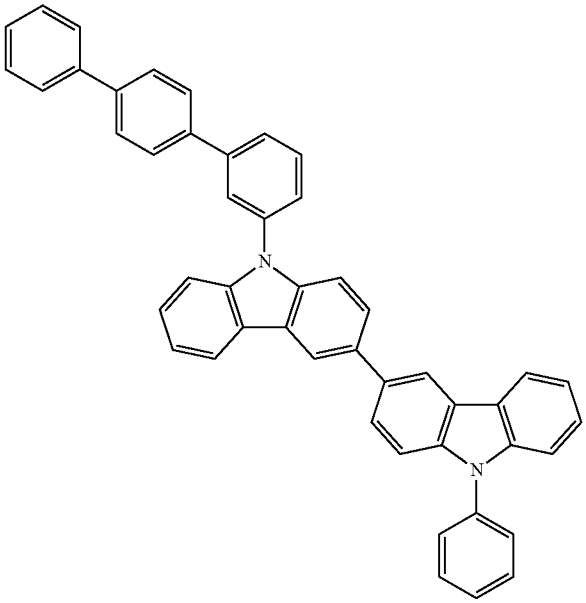 [SMILES: c1ccc(-c2ccc(-c3cccc(-n4c5ccccc5c5cc(-c6ccc7c(c6)c6ccccc6n7-c6ccccc6)ccc54)c3)cc2)cc1] | CAS-1548581-24-3 |
| 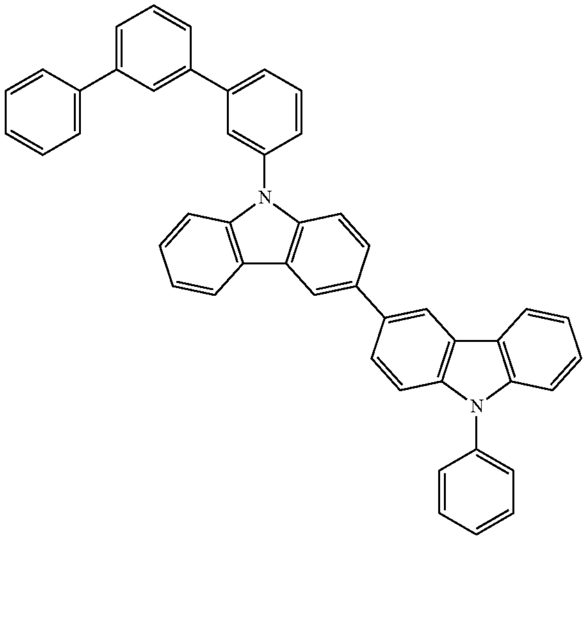 [SMILES: c1ccc(-c2cccc(-c3cccc(-n4c5ccccc5c5cc(-c6ccc7c(c6)c6ccccc6n7-c6ccccc6)ccc54)c3)c2)cc1] | CAS-1548581-27-6 |

TABLE 9-continued
| Structure | CAS number |
| --- | --- |
| 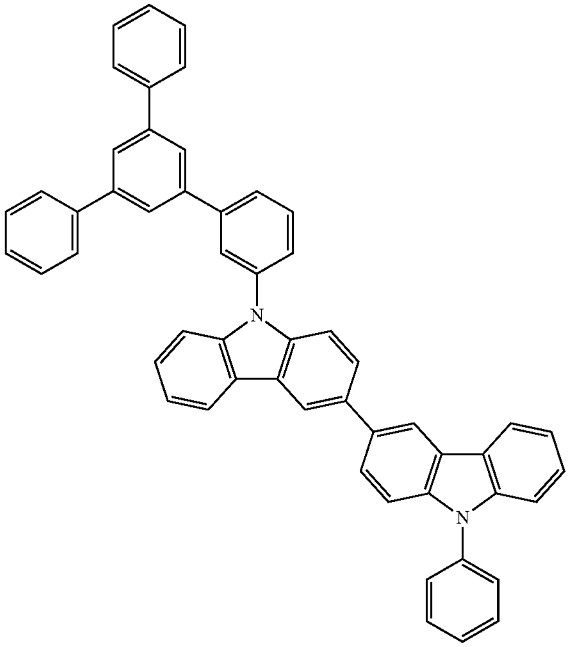 [SMILES: c1ccc(-c2cc(-c3ccccc3)cc(-c3cccc(-n4c5ccccc5c5cc(-c6ccc7c(c6)c6ccccc6n7-c6ccccc6)ccc54)c3)c2)cc1] | CAS-1548581-29-8 |
| 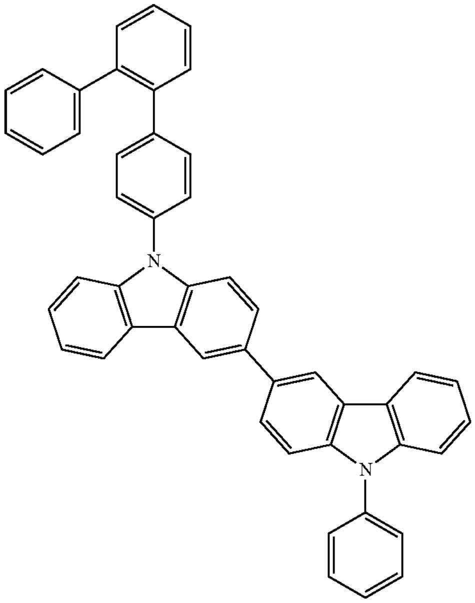 [SMILES: c1ccc(-c2ccccc2-c2ccc(-n3c4ccccc4c4cc(-c5ccc6c(c5)c5ccccc5n6-c5ccccc5)ccc43)cc2)cc1] | CAS-1548581-37-8 |

TABLE 9-continued
| Structure | CAS number |
| --- | --- |
| 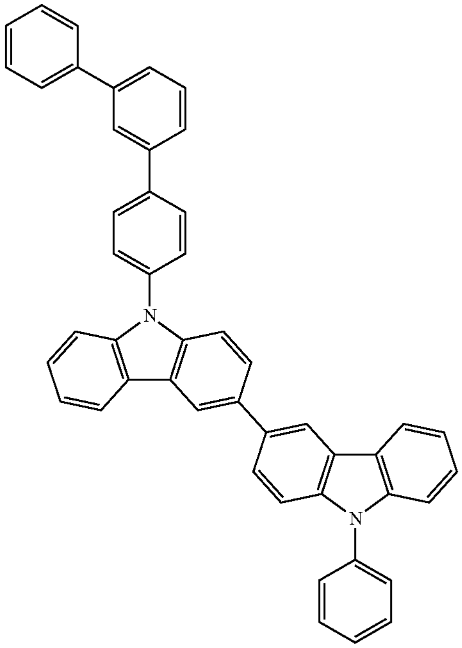 [SMILES: c1ccc(-c2cccc(-c3ccc(-n4c5ccccc5c5cc(-c6ccc7c(c6)c6ccccc6n7-c6ccccc6)ccc54)cc3)c2)cc1] | CAS-1548581-40-3 |
| 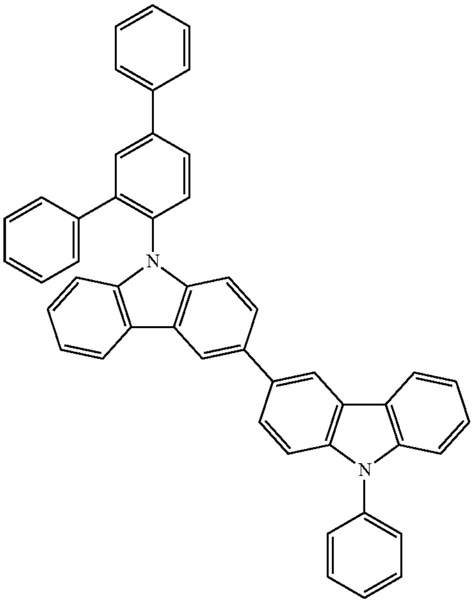 [SMILES: c1ccc(-c2ccc(-n3c4ccccc4c4cc(-c5ccc6c(c5)c5ccccc5n6-c5ccccc5)ccc43)c(-c3ccccc3)c2)cc1] | CAS-1943719-62-7 |

TABLE 9-continued
| Structure | CAS number |
|---|---|
| 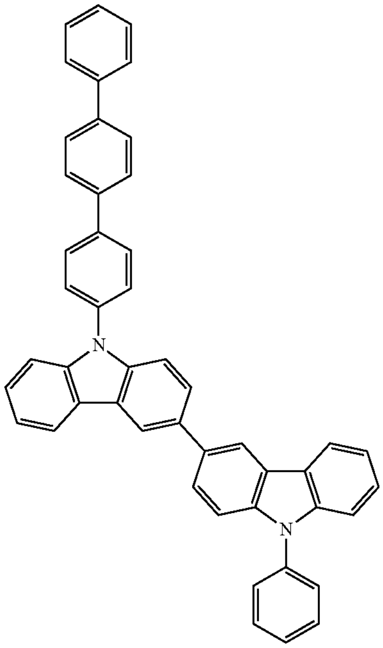 [SMILES: c1ccc(-c2ccc(-c3ccc(-n4c5ccccc5c5cc(-c6ccc7c(c6)c6ccccc6n7-c6ccccc6)ccc54)cc3)cc2)cc1] | CAS-1548581-42-5 |
| 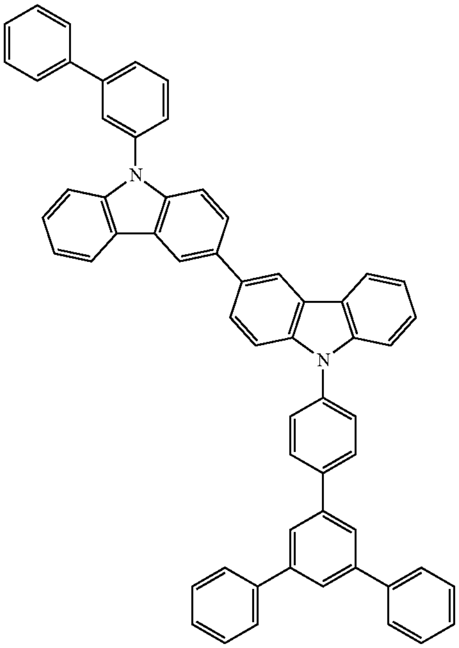 [SMILES: c1ccc(-c2cc(-c3ccccc3)cc(-c3ccc(-n4c5ccccc5c5cc(-c6ccc7c(c6)c6ccccc6n7-c6cccc(-c7ccccc7)c6)ccc54)cc3)c2)cc1] | CAS-1942079-50-6 |

TABLE 9-continued
| Structure | CAS number |
| --- | --- |
| 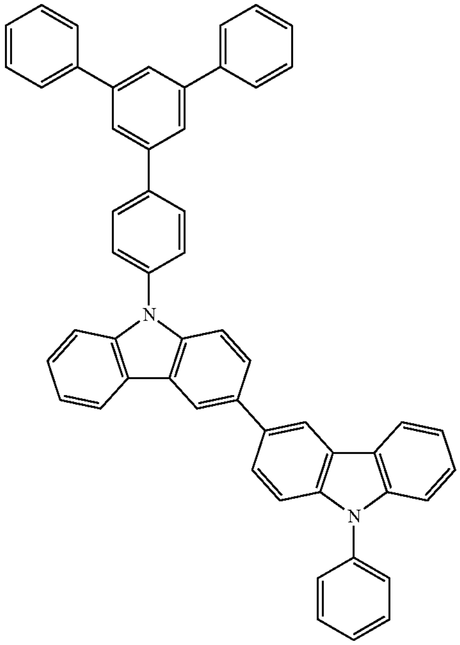 [SMILES: c1ccc(-c2cc(-c3ccccc3)cc(-c3ccc(-n4c5ccccc5c5cc(-c6ccc7c(c6)c6ccccc6n7-c6ccccc6)ccc54)cc3)c2)cc1] | CAS-1548581-44-7 |
| 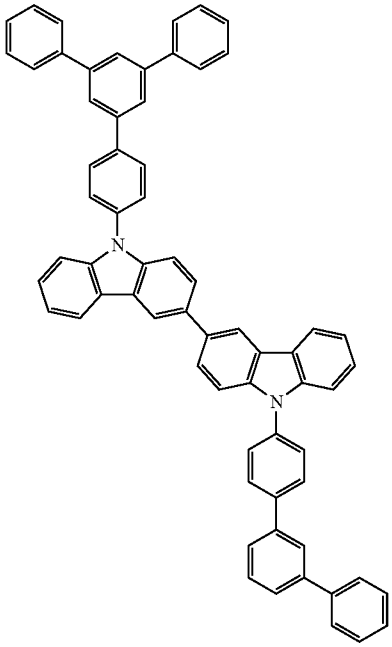 [SMILES: c1ccc(-c2cccc(-c3ccc(-n4c5ccccc5c5cc(-c6ccc7c(c6)c6ccccc6n7-c6ccc(-c7cc(-c8ccccc8)cc(-c8ccccc8)c7)cc6)ccc54)cc3)c2)cc1] | CAS-1942079-51-7 |

TABLE 9-continued
| Structure | CAS number |
|---|---|
| 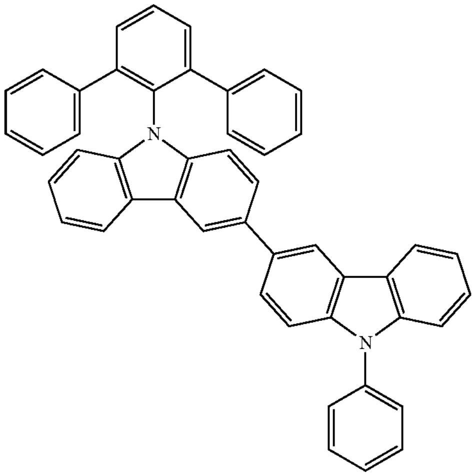 [SMILES: c1ccc(-c2cccc(-c3ccccc3)c2-n2c3ccccc3c3cc(-c4ccc5c(c4)c4ccccc4n5-c4ccccc4)ccc32)cc1] | CAS-1943719-63-8 |
| 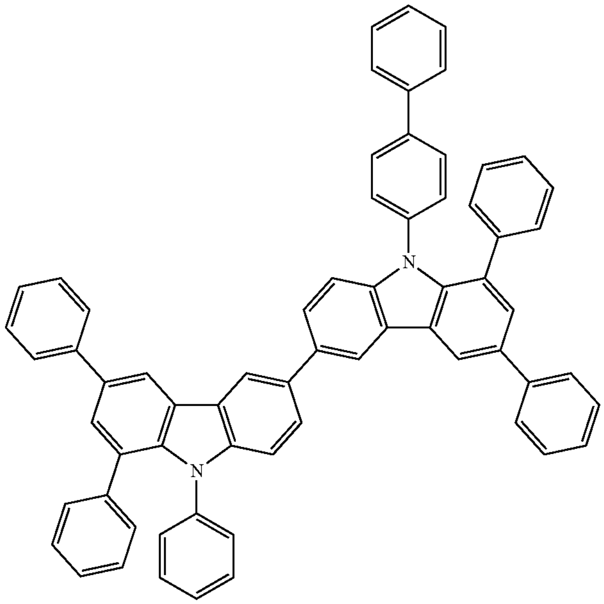 [SMILES: c1ccc(-c2ccc(-n3c4ccc(-c5ccc6c(c5)c5cc(-c7ccccc7)cc(-c7ccccc7)c5n6-c5ccccc5)cc4c4cc(-c5ccccc5)cc(-c5ccccc5)c43)cc2)cc1] | CAS-1955476-12-6 |

TABLE 9-continued
| Structure | CAS number |
|---|---|
| 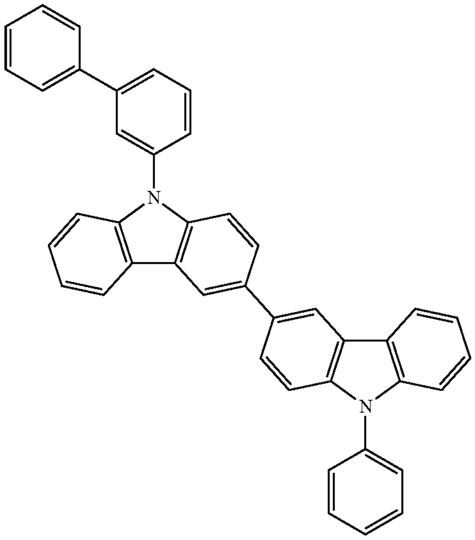<br>96 | CAS-1619966-75-4 |
| 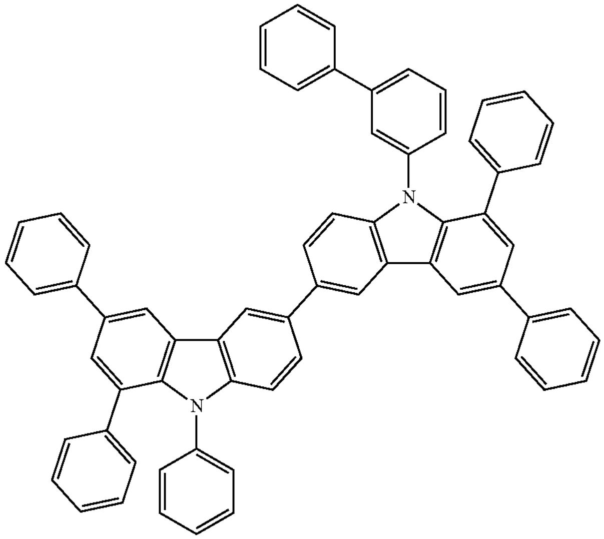 [SMILES: c1ccc(-c2cccc(-n3c4ccc(-c5ccc6c(c5)c5cc(-c7ccccc7)cc(-c7ccccc7)c5n6-c5ccccc5)cc4c4cc(-c5ccccc5)cc(-c5ccccc5)c43)c2)cc1] | CAS-1955476-13-7 |

TABLE 9-continued
| Structure | CAS number |
| --- | --- |
| 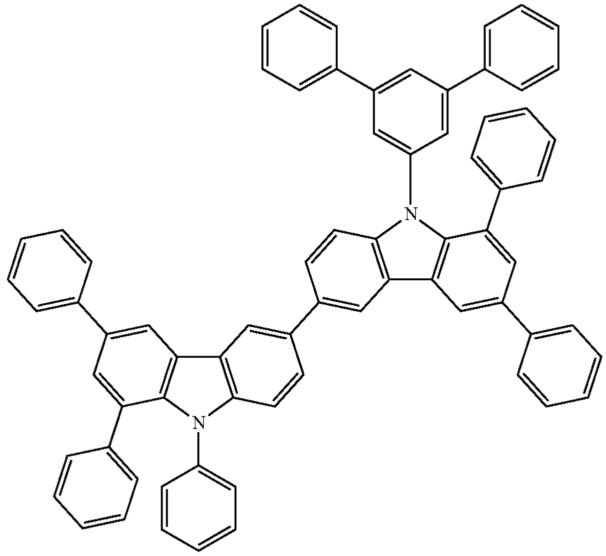 [SMILES: c1ccc(-c2cc(-c3ccccc3)cc(-n3c4ccc(-c5ccc6c(c5)c5cc(-c7ccccc7)cc(-c7ccccc7)c5n6-c5ccccc5)cc4c4cc(-c5ccccc5)cc(-c5ccccc5)c43)c2)cc1] | CAS-1955476-15-9 |
| 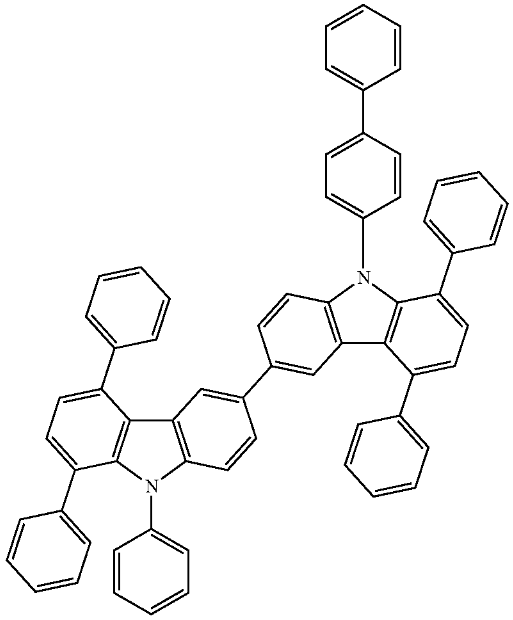 [SMILES: c1ccc(-c2ccc(-n3c4ccc(-c5ccc6c(c5)c5c(-c7ccccc7)ccc(-c7ccccc7)c5n6-c5ccccc5)cc4c4c(-c5ccccc5)ccc(-c5ccccc5)c43)cc2)cc1] | CAS-1955476-28-4 |

TABLE 9-continued
| Structure | CAS number |
|---|---|
| 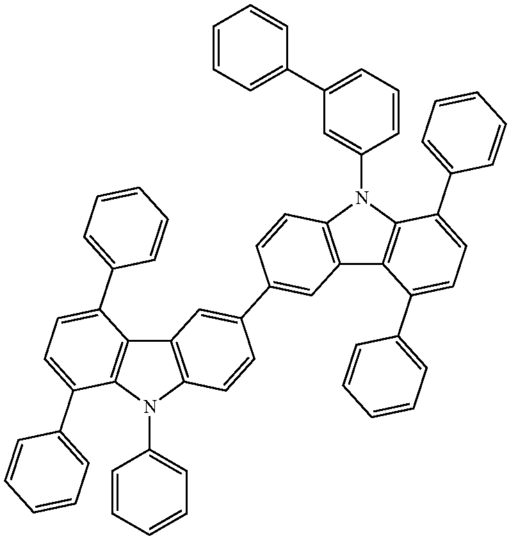 [SMILES: c1ccc(-c2cccc(-n3c4ccc(-c5ccc6c(c5)c5c(-c7ccccc7)ccc(-c7ccccc7)c5n6-c5ccccc5)cc4c4c(-c5ccccc5)ccc(-c5ccccc5)c43)c2)cc1] | CAS-1955476-30-8 |
| 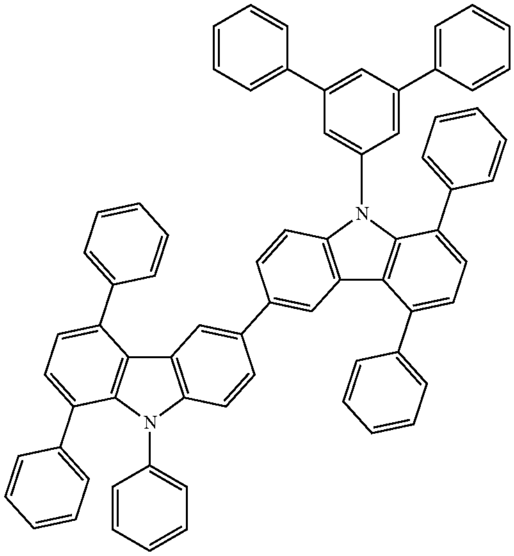 [SMILES: c1ccc(-c2cc(-c3ccccc3)cc(-n3c4ccc(-c5ccc6c(c5)c5c(-c7ccccc7)ccc(-c7ccccc7)c5n6-c5ccccc5)cc4c4c(-c5ccccc5)ccc(-c5ccccc5)c43)c2)cc1] | CAS-1955476-32-0 |

TABLE 9-continued
| Structure | CAS number |
|---|---|
| 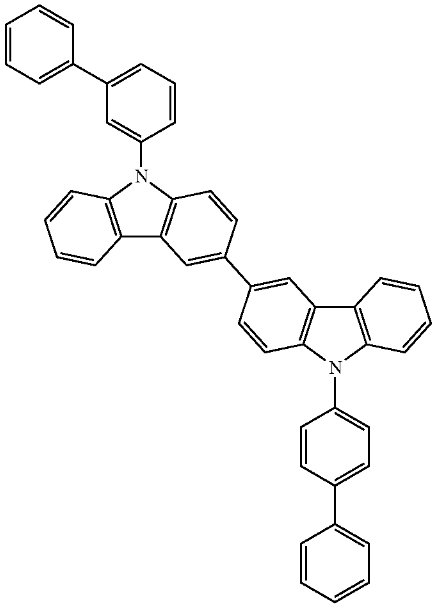<br>91 | CAS-1643479-47-3 |
| 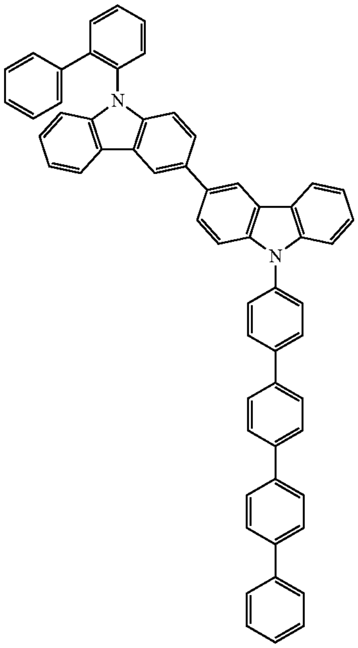 [SMILES: c1ccc(-c2ccc(-c3ccc(-c4ccc(-n5c6ccccc6c6cc(-c7ccc8c(c7)c7ccccc7n8-c7ccccc7-c7ccccc7)ccc65)cc4)cc3)cc2)cc1] | CAS-1973498-04-2 |

TABLE 9-continued
| Structure | CAS number |
|---|---|
| 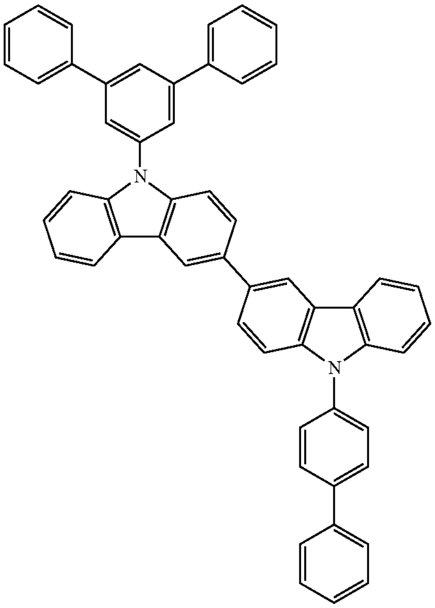 92 | CAS-1643479-49-5 |
| 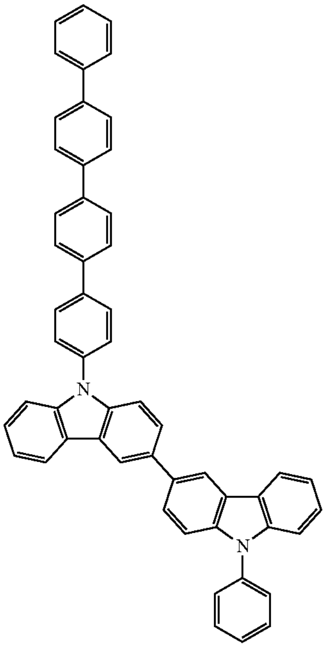 [SMILES: c1ccc(-c2ccc(-c3ccc(-c4ccc(-n5c6ccccc6c6cc(-c7ccc8c(c7)c7ccccc7n8-c7ccccc7)ccc65)cc4)cc3)cc2)cc1] | CAS-1973498-03-1 |

TABLE 9-continued
| Structure | CAS number |
|---|---|
| 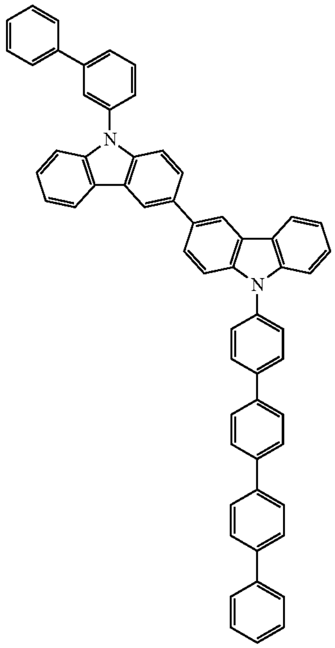 [SMILES: c1ccc(-c2ccc(-c3ccc(-c4ccc(-n5c6ccccc6c6cc(-c7ccc8c(c7)c7ccccc7n8-c7cccc(-c8ccccc8)c7)ccc65)cc4)cc3)cc2)cc1] | CAS-1973498-05-3 |
| 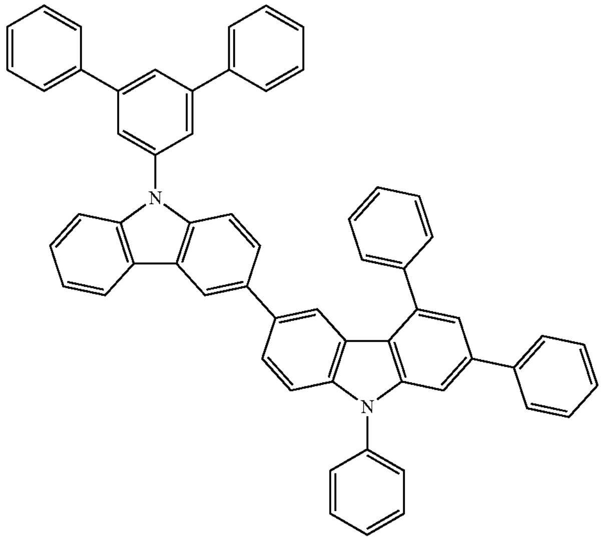 [SMILES: c1ccc(-c2cc(-c3ccccc3)cc(-n3c4ccccc4c4cc(-c5ccc6c(c5)c5c(-c7ccccc7)cc(-c7ccccc7)cc5n6-c5ccccc5)ccc43)c2)cc1] | CAS-2018307-36-1 |

TABLE 9-continued
| Structure | CAS number |
| --- | --- |
| 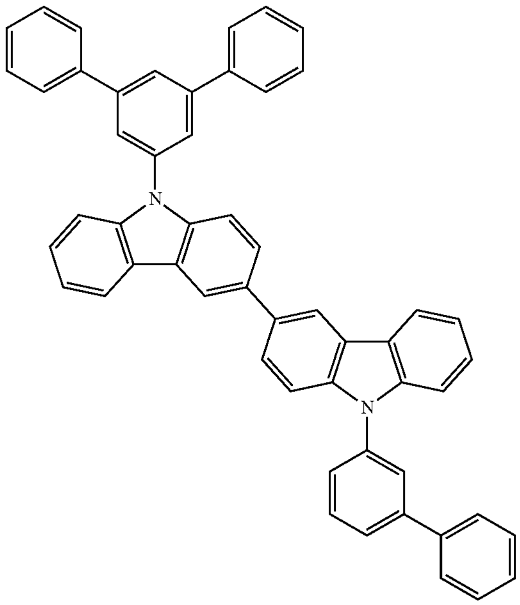 [SMILES: c1ccc(-c2cccc(-n3c4ccccc4c4cc(-c5ccc6c(c5)c5ccccc5n6-c5cc(-c6ccccc6)cc(-c6ccccc6)c5)ccc43)c2)cc1] | CAS-1643479-56-4 |
| 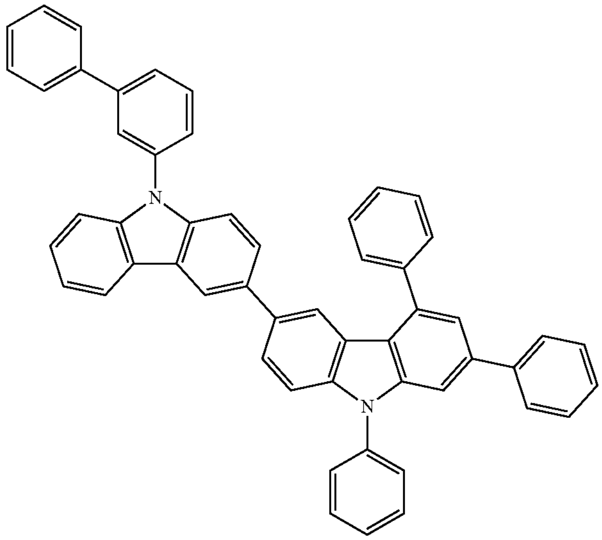 [SMILES: c1ccc(-c2cccc(-n3c4ccccc4c4cc(-c5ccc6c(c5)c5c(-c7ccccc7)cc(-c7ccccc7)cc5n6-c5ccccc5)ccc43)c2)cc1] | CAS-2018307-35-0 |

TABLE 9-continued
| Structure | CAS number |
|---|---|
| 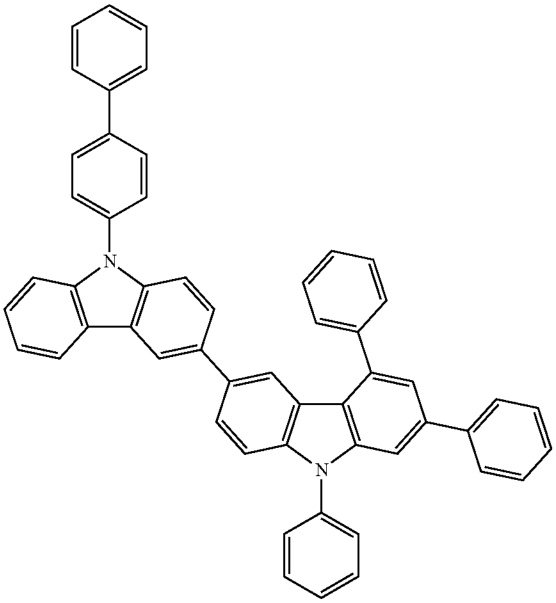 [SMILES: c1ccc(-c2ccc(-n3c4ccccc4c4cc(-c5ccc6c(c5)c5c(-c7ccccc7)cc(-c7ccccc7)cc5n6-c5ccccc5)ccc43)cc2)cc1] | CAS-2018307-37-2 |
| 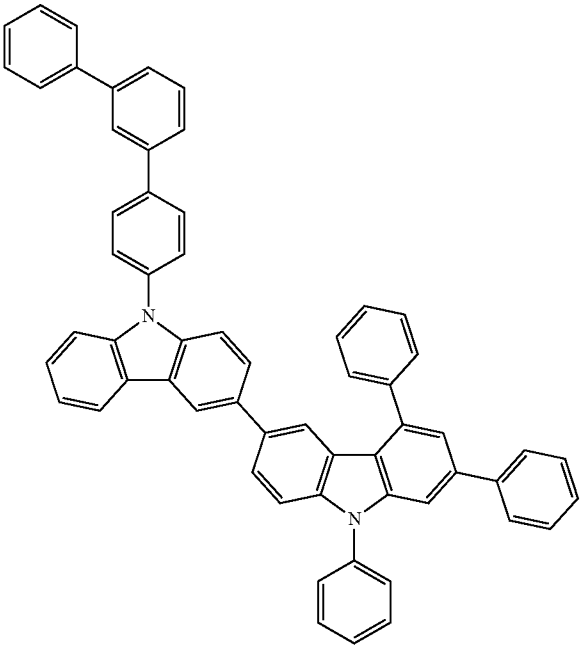 [SMILES: c1ccc(-c2cccc(-c3ccc(-n4c5ccccc5c5cc(-c6ccc7c(c6)c6c(-c8ccccc8)cc(-c8ccccc8)cc6n7-c6ccccc6)ccc54)cc3)c2)cc1] | CAS-2018307-38-3 |

TABLE 9-continued
| Structure | CAS number |
| --- | --- |
| 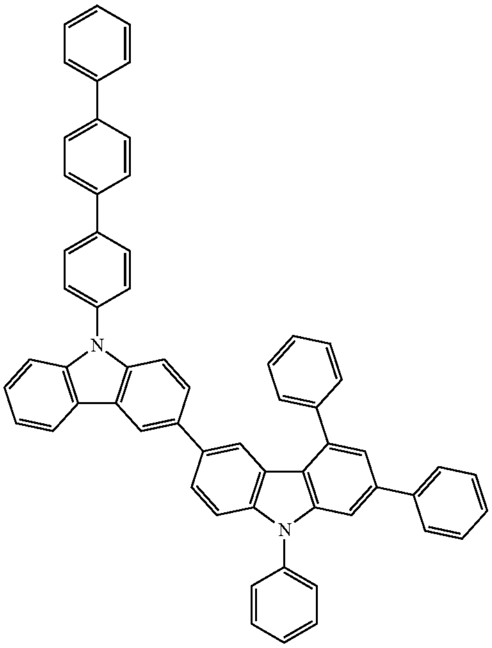 [SMILES: c1ccc(-c2ccc(-c3ccc(-n4c5ccccc5c5cc(-c6ccc7c(c6)c6c(-c8ccccc8)cc(-c8ccccc8)cc6n7-c6ccccc6)ccc54)cc3)cc2)cc1] | CAS-2018307-39-4 |
| 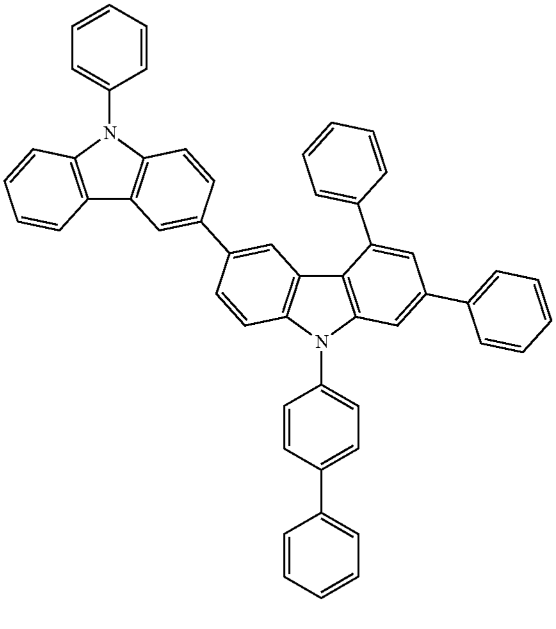 [SMILES: c1ccc(-c2ccc(-n3c4ccc(-c5ccc6c(c5)c5ccccc5n6-c5ccccc5)cc4c4c(-c5ccccc5)cc(-c5ccccc5)cc43)cc2)cc1] | CAS-2018307-77-0 |

TABLE 9-continued
| Structure | CAS number |
| --- | --- |
| 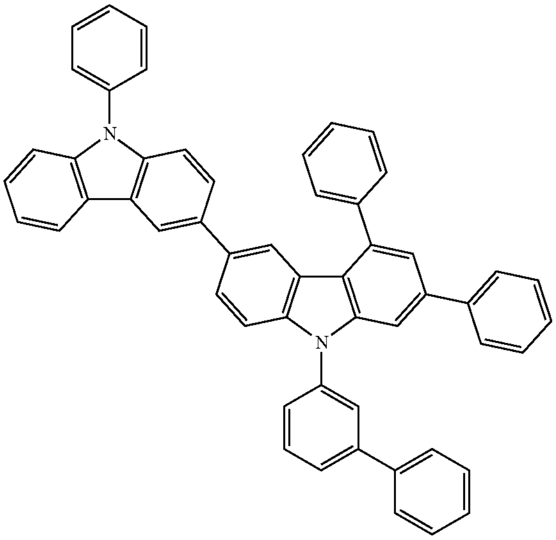 [SMILES: c1ccc(-c2cccc(-n3c4ccc(-c5ccc6c(c5)c5ccccc5n6-c5ccccc5)cc4c4c(-c5ccccc5)cc(-c5ccccc5)cc43)c2)cc1] | CAS-2108307-78-1 |
| 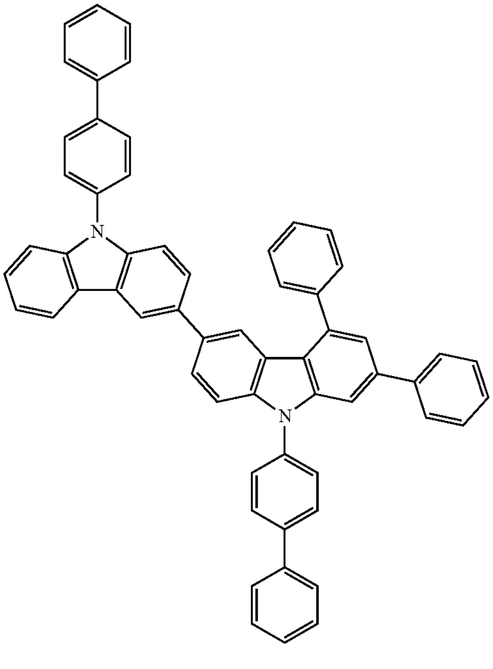 [SMILES: c1ccc(-c2ccc(-n3c4ccccc4c4cc(-c5ccc6c(c5)c5c(-c7ccccc7)cc(-c7ccccc7)cc5n6-c5ccc(-c6ccccc6)cc5)ccc43)cc2)cc1] | CAS-2018307-90-7 |

TABLE 9-continued
| Structure | CAS number |
| --- | --- |
| 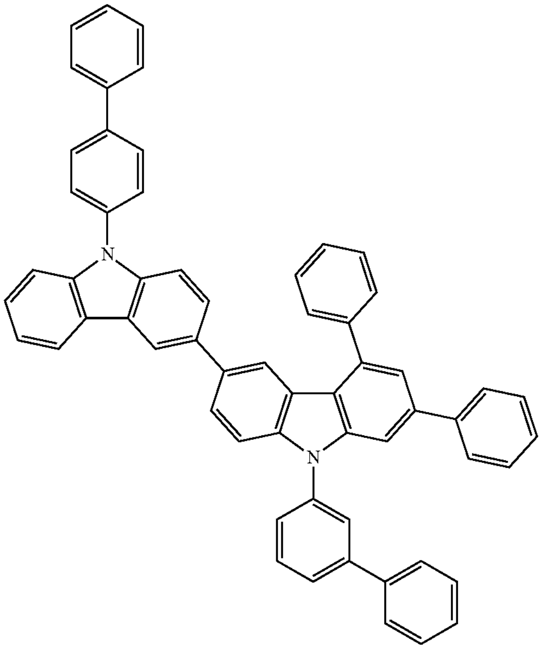 [SMILES: c1ccc(-c2ccc(-n3c4ccccc4c4cc(-c5ccc6c(c5)c5c(-c7ccccc7)cc(-c7ccccc7)cc5n6-c5cccc(-c6ccccc6)c5)ccc43)cc2)cc1] | CAS-2018307-91-8 |
| 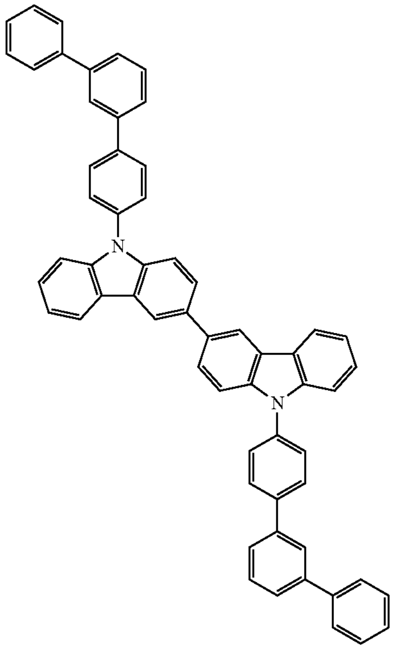 [SMILES: c1ccc(-c2cccc(-c3ccc(-n4c5ccccc5c5cc(-c6ccc7c(c6)c6ccccc6n7-c6ccc(-c7cccc(-c8ccccc8)c7)cc6)ccc54)cc3)c2)cc1] | CAS-1799958-74-9 |

TABLE 9-continued
| Structure | CAS number |
|---|---|
| 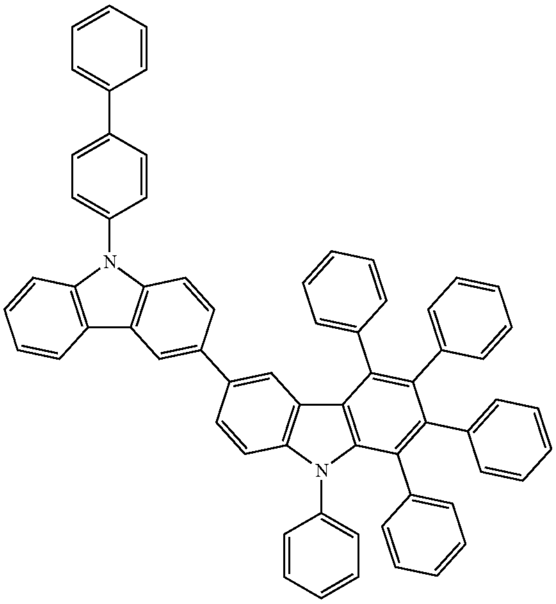 [SMILES: c1ccc(-c2ccc(-n3c4ccccc4c4cc(-c5ccc6c(c5)c5c(-c7ccccc7)c(-c7ccccc7)c(-c7ccccc7)c(-c7ccccc7)c5n6-c5ccccc5)ccc43)cc2)cc1] | CAS-2052160-86-6 |
| 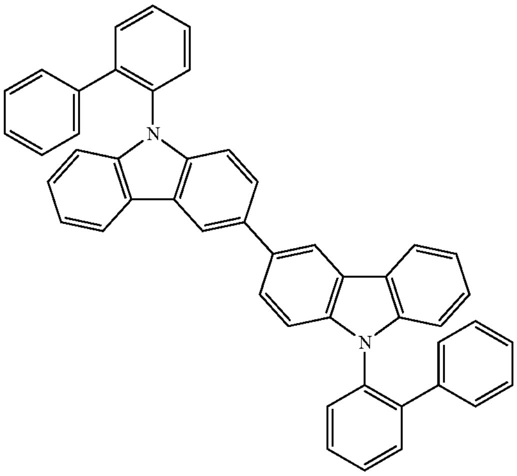 [SMILES: c1ccc(-c2ccccc2-n2c3ccccc3c3cc(-c4ccc5c(c4)c4ccccc4n5-c4ccccc4-c4ccccc4)ccc32)cc1] | CAS-1799958-79-4 |
| 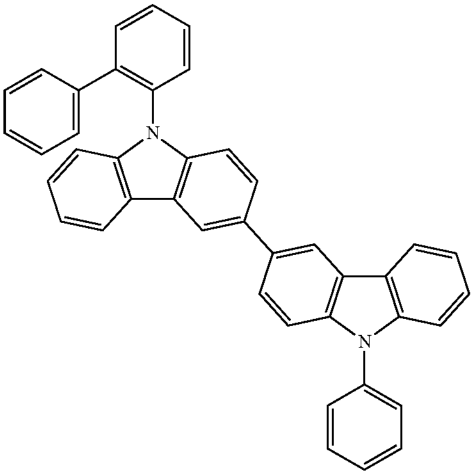 [SMILES: c1ccc(-c2ccccc2-n2c3ccccc3c3cc(-c4ccc5c(c4)c4ccccc4n5-c4ccccc4)ccc32)cc1] | CAS-1799958-76-1 |

TABLE 9-continued
| Structure | CAS number |
| --- | --- |
| 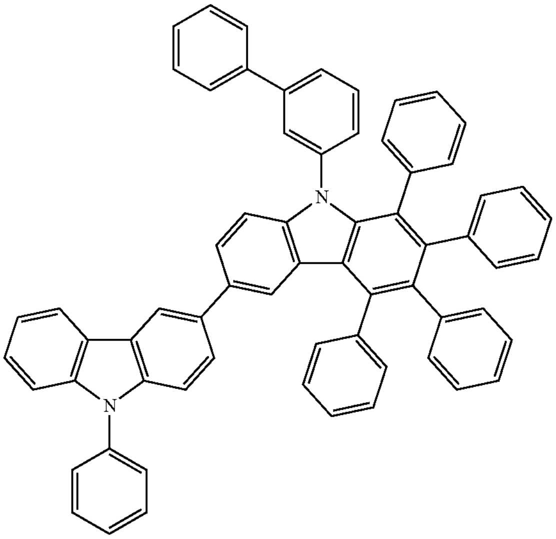 [SMILES: c1ccc(-c2cccc(-n3c4ccc(-c5ccc6c(c5)c5ccccc5n6-c5ccccc5)cc4c4c(-c5ccccc5)c(-c5ccccc5)c(-c5ccccc5)c(-c5ccccc5)c43)c2)cc1] | CAS-2052160-91-3 |
| 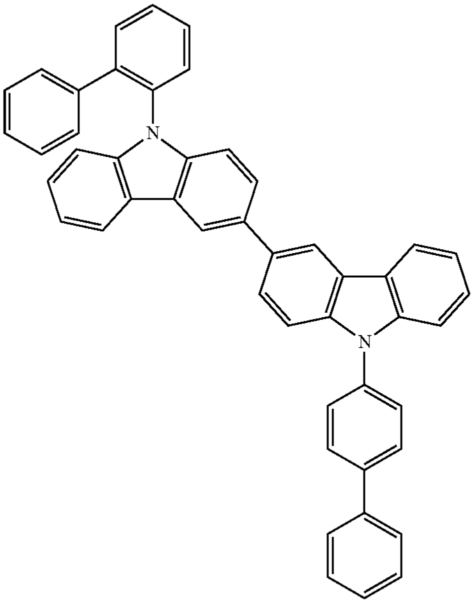 [SMILES: c1ccc(-c2ccc(-n3c4ccccc4c4cc(-c5ccc6c(c5)c5ccccc5n6-c5ccccc5-c5ccccc5)ccc43)cc2)cc1] | CAS-1799958-77-2 |

TABLE 9-continued
| Structure | CAS number |
| --- | --- |
| 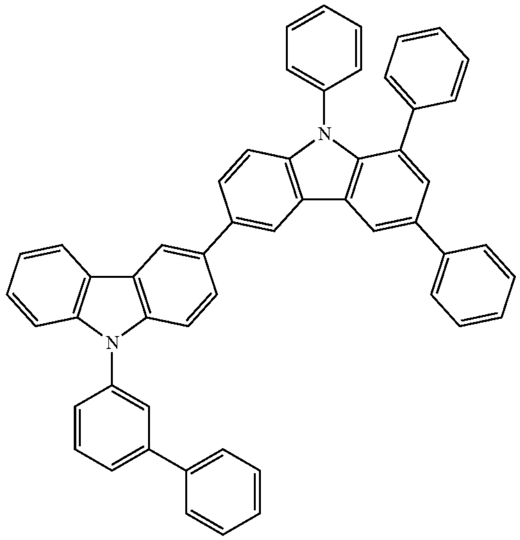 [SMILES: c1ccc(-c2cccc(-n3c4ccccc4c4cc(-c5ccc6c(c5)c5cc(-c7ccccc7)cc(-c7ccccc7)c5n6-c5ccccc5)ccc43)c2)cc1] | CAS-2055858-40-1 |
| 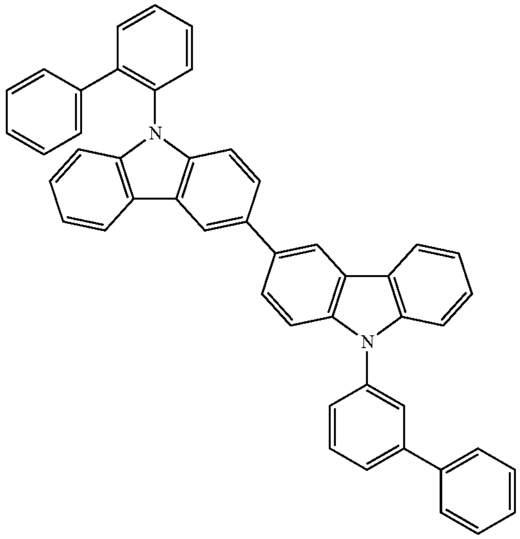 | CAS-1799958-78-3 |

TABLE 9-continued
| Structure | CAS number |
| --- | --- |
| 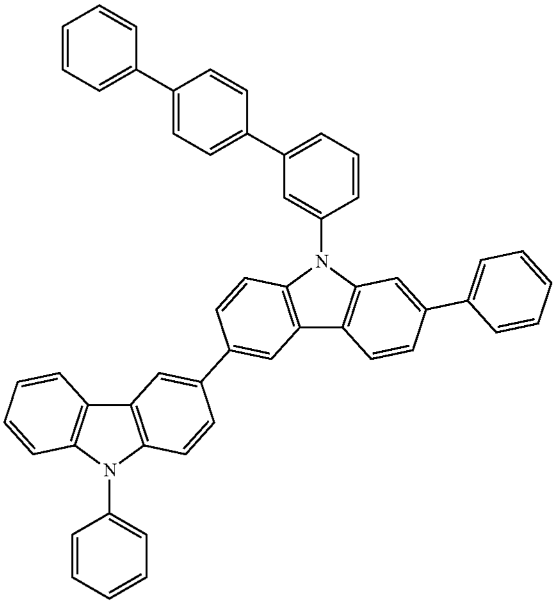 [SMILES: c1ccc(-c2ccc(-c3cccc(-n4c5ccc(-c6ccc7c(c6)c6ccccc6n7-c6ccccc6)cc5c5ccc(-c6ccccc6)cc54)c3)cc2)cc1] | CAS-2057418-19-4 |
| 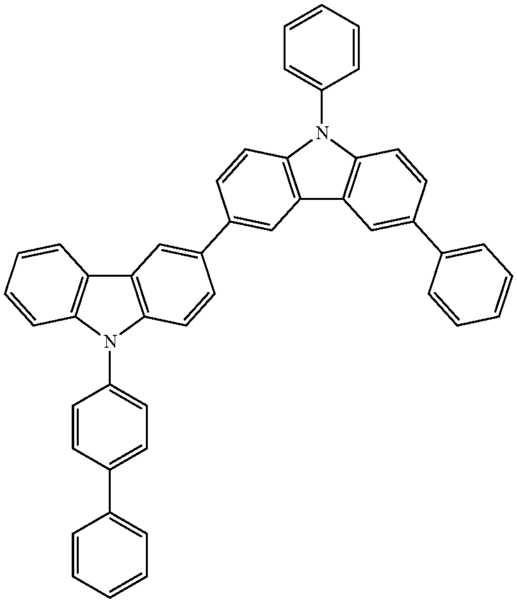 [SMILES: c1ccc(-c2ccc(-n3c4ccccc4c4cc(-c5ccc6c(c5)c5cc(-c7ccccc7)ccc5n6-c5ccccc5)ccc43)cc2)cc1] | CAS-1799958-99-8 |

TABLE 9-continued
| Structure | CAS number |
| --- | --- |
| 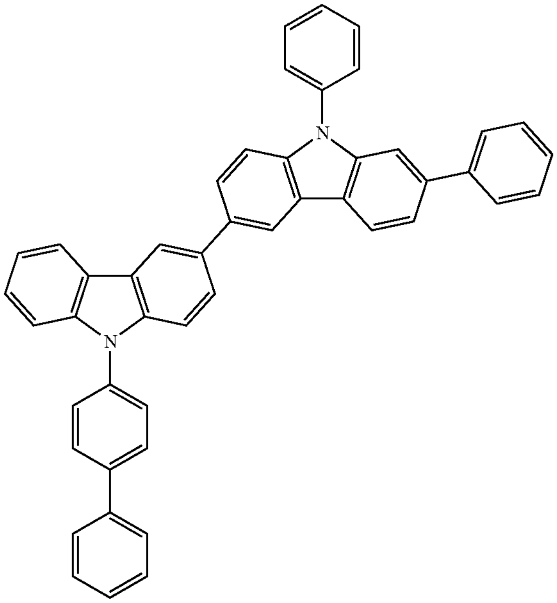 [SMILES: c1ccc(-c2ccc(-n3c4ccccc4c4cc(-c5ccc6c(c5)c5ccc(-c7ccccc7)cc5n6-c5ccccc5)ccc43)cc2)cc1] | CAS-1799959-01-5 |
| 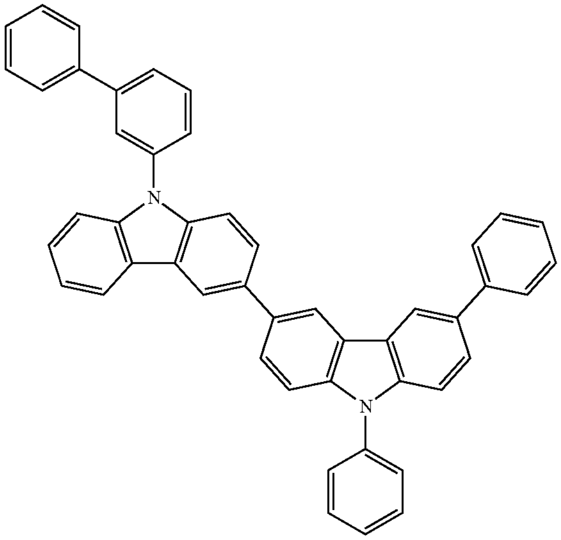 [SMILES: c1ccc(-c2cccc(-n3c4ccccc4c4cc(-c5ccc6c(c5)c5cc(-c7ccccc7)ccc5n6-c5ccccc5)ccc43)c2)cc1] | CAS-1799959-03-7 |

TABLE 9-continued
| Structure | CAS number |
|---|---|
| 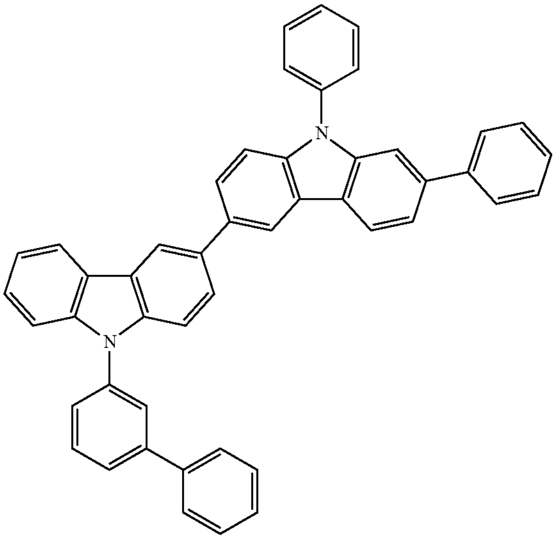 [SMILES: c1ccc(-c2cccc(-n3c4ccccc4c4cc(-c5ccc6c(c5)c5ccc(-c7ccccc7)cc5n6-c5ccccc5)ccc43)c2)cc1] | CAS-1799959-05-9 |
| 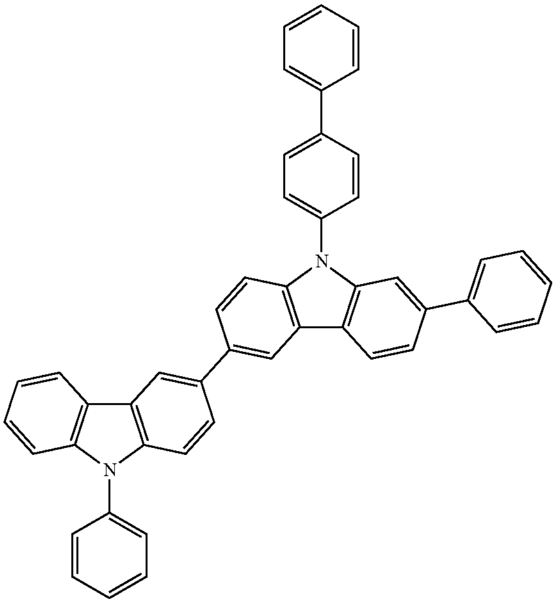 [SMILES: c1ccc(-c2ccc(-n3c4ccc(-c5ccc6c(c5)c5ccccc5n6-c5ccccc5)cc4c4ccc(-c5ccccc5)cc43)cc2)cc1] | CAS-1799959-07-1 |

TABLE 9-continued
| Structure | CAS number |
| --- | --- |
| 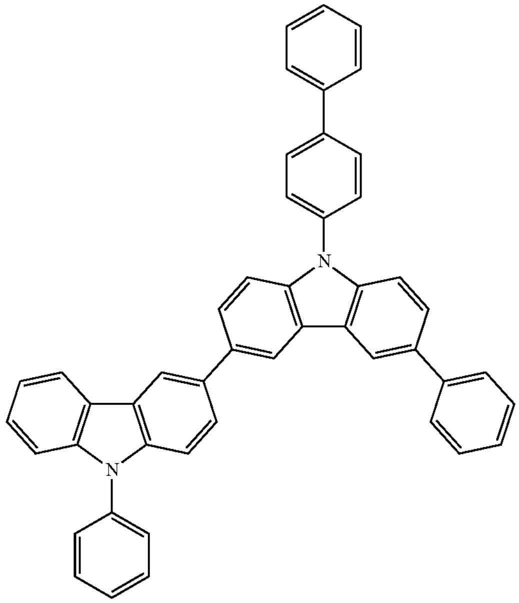 [SMILES: c1ccc(-c2ccc(-n3c4ccc(-c5ccccc5)cc4c4cc(-c5ccc6c(c5)c5ccccc5n6-c5ccccc5)ccc43)cc2)cc1] | CAS-1799959-09-3 |
| 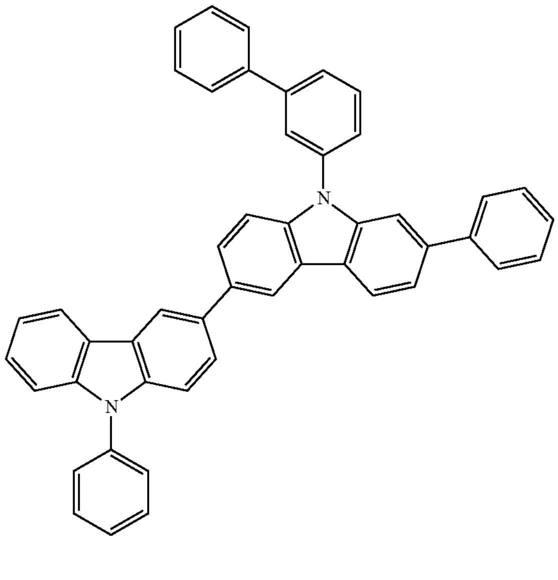 [SMILES: c1ccc(-c2cccc(-n3c4ccc(-c5ccc6c(c5)c5ccccc5n6-c5ccccc5)cc4c4ccc(-c5ccccc5)cc43)c2)cc1] | CAS-1799959-11-7 |

TABLE 9-continued
| Structure | CAS number |
| --- | --- |
| 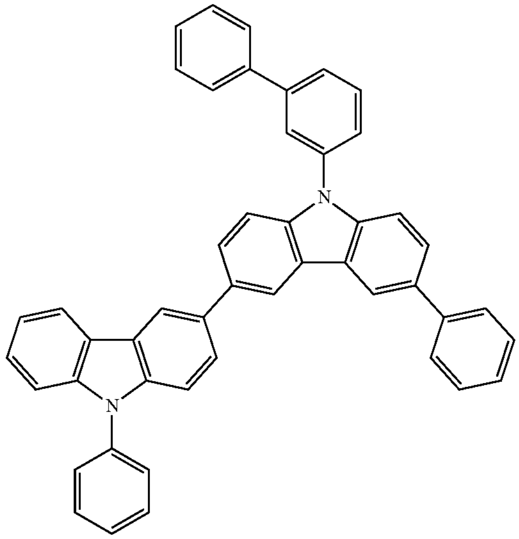 [SMILES: c1ccc(-c2cccc(-n3c4ccc(-c5ccccc5)cc4c4cc(-c5ccc6c(c5)c5ccccc5n6-c5ccccc5)ccc43)c2)cc1] | CAS-1799959-13-9 |
| 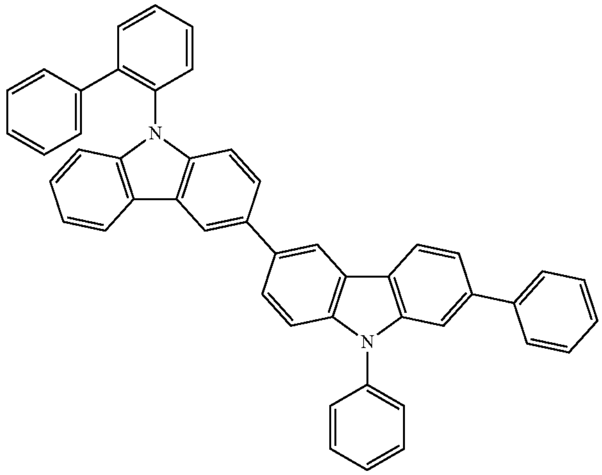 [SMILES: c1ccc(-c2ccc3c4cc(-c5ccc6c(c5)c5ccccc5n6-c5ccccc5-c5ccccc5)ccc4n(-c4ccccc4)c3c2)cc1] | CAS-2085318-61-9 |

TABLE 9-continued
| Structure | CAS number |
| --- | --- |
| 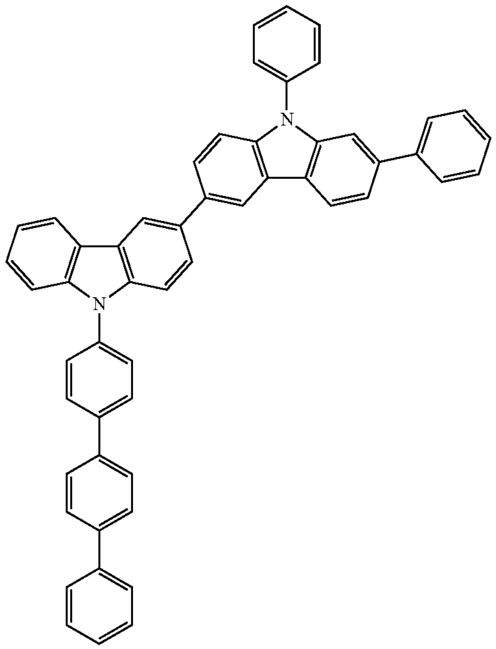 [SMILES: c1ccc(-c2ccc(-c3ccc(-n4c5ccccc5c5cc(-c6ccc7c(c6)c6ccc(-c8ccccc8)cc6n7-c6ccccc6)ccc54)cc3)cc2)cc1] | CAS-2085318-62-1 |
| 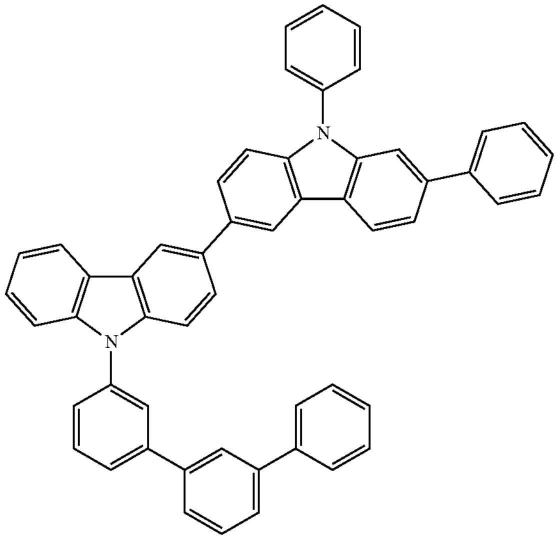 [SMILES: c1ccc(-c2cccc(-c3cccc(-n4c5ccccc5c5cc(-c6ccc7c(c6)c6ccc(-c8ccccc8)cc6n7-c6ccccc6)ccc54)c3)c2)cc1] | CAS-2085318-64-3 |

TABLE 9-continued
| Structure | CAS number |
| --- | --- |
| 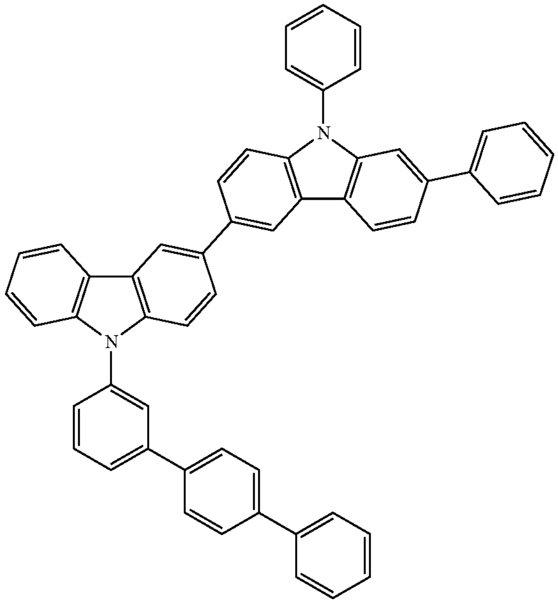 [SMILES: c1ccc(-c2ccc(-c3cccc(-n4c5ccccc5c5cc(-c6ccc7c(c6)c6ccc(-c8ccccc8)cc6n7-c6ccccc6)ccc54)c3)cc2)cc1] | CAS-2085318-63-2 |
| 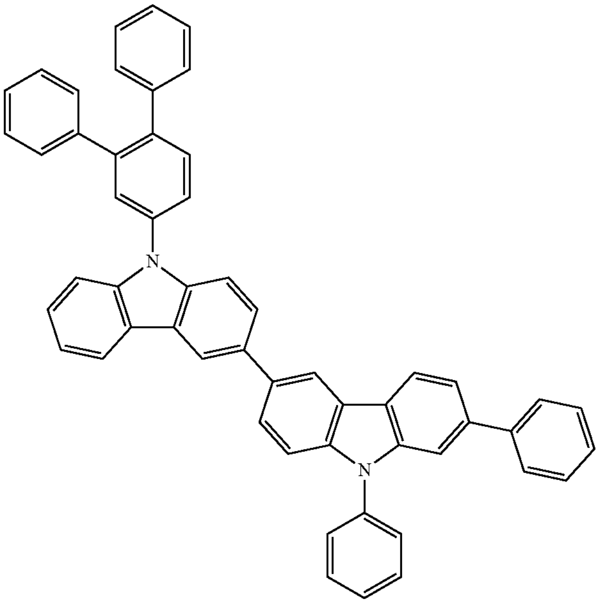 [SMILES: c1ccc(-c2ccc3c4cc(-c5ccc6c(c5)c5ccccc5n6-c5ccc(-c6ccccc6)c(-c6ccccc6)c5)ccc4n(-c4ccccc4)c3c2)cc1] | CAS-2085318-66-5 |

TABLE 9-continued
| Structure | CAS number |
| --- | --- |
| 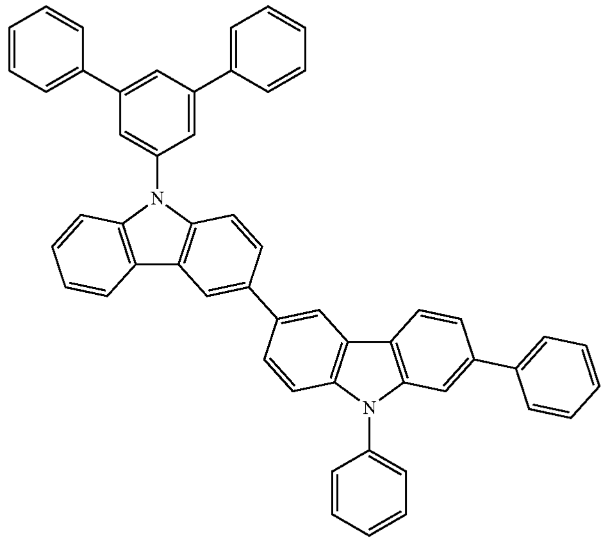 [SMILES: c1ccc(-c2cc(-c3ccccc3)cc(-n3c4ccccc4c4cc(-c5ccc6c(c5)c5ccc(-c7ccccc7)cc5n6-c5ccccc5)ccc43)c2)cc1] | CAS-2085318-65-4 |
| 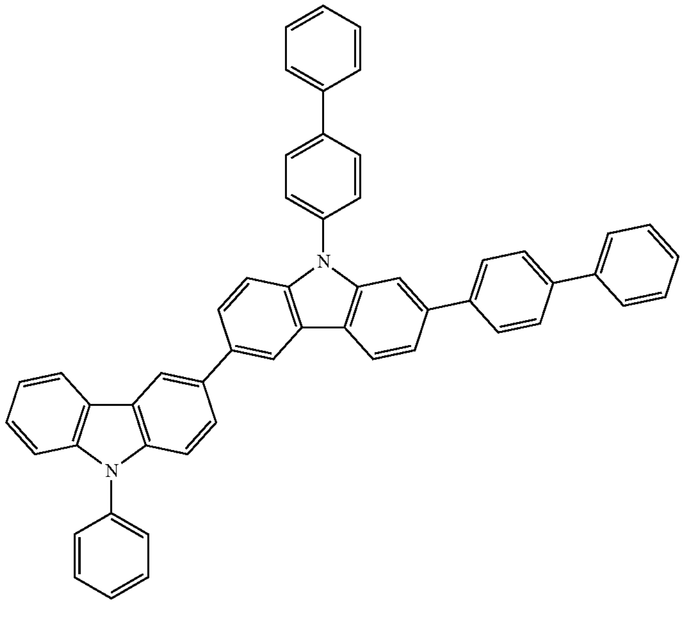 [SMILES: c1ccc(-c2ccc(-c3ccc4c5cc(-c6ccc7c(c6)c6ccccc6n7-c6ccccc6)ccc5n(-c5ccc(-c6ccccc6)cc5)c4c3)cc2)cc1] | CAS-2085318-77-8 |

TABLE 9-continued
| Structure | CAS number |
| --- | --- |
| 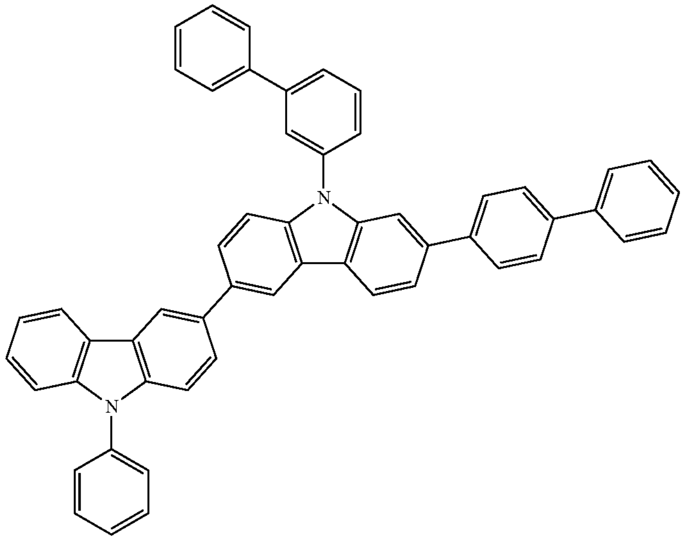 [SMILES: c1ccc(-c2ccc(-c3ccc4c5cc(-c6ccc7c(c6)c6ccccc6n7-c6ccccc6)ccc5n(-c5cccc(-c6ccccc6)c5)c4c3)cc2)cc1] | CAS-2085318-78-9 |
| 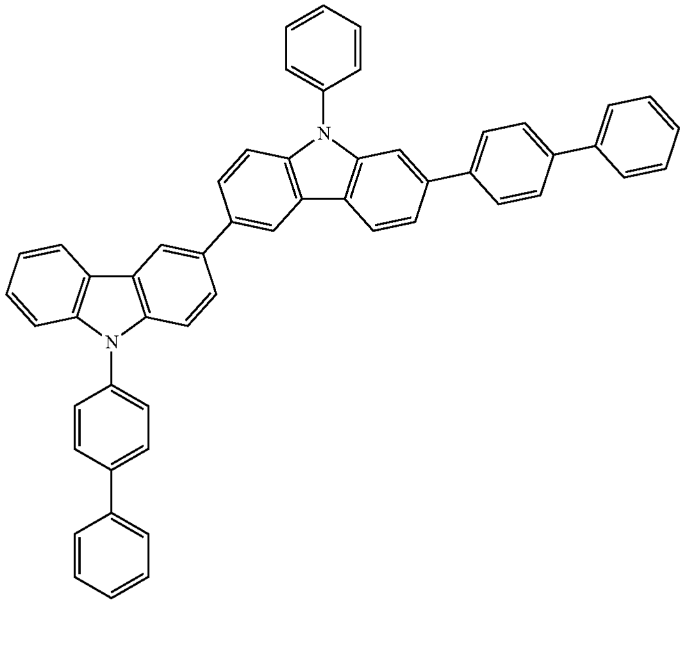 [SMILES: c1ccc(-c2ccc(-c3ccc4c5cc(-c6ccc7c(c6)c6ccccc6n7-c6ccc(-c7ccccc7)cc6)ccc5n(-c5ccccc5)c4c3)cc2)cc1] | CAS-2085318-79-0 |

TABLE 9-continued
| Structure | CAS number |
|---|---|
| 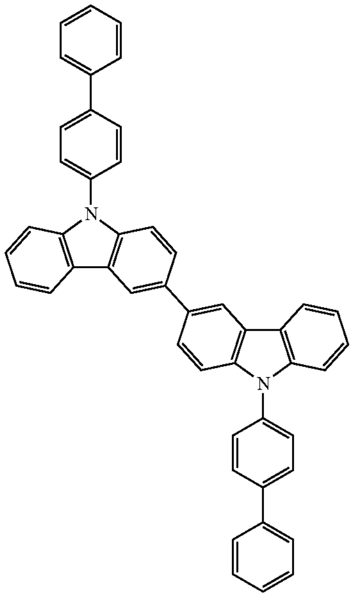 94 | CAS-57102-51-9 |
| 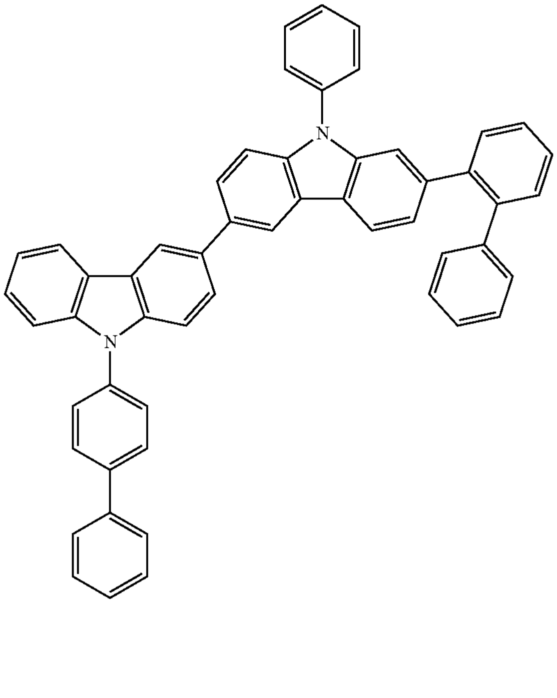 [SMILES: c1ccc(-c2ccc(-n3c4ccccc4c4cc(-c5ccc6c(c5)c5ccc(-c7ccccc7-c7ccccc7)cc5n6-c5ccccc5)ccc43)cc2)cc1] | CAS-2085318-81-4 |

TABLE 9-continued
| Structure | CAS number |
| --- | --- |
| 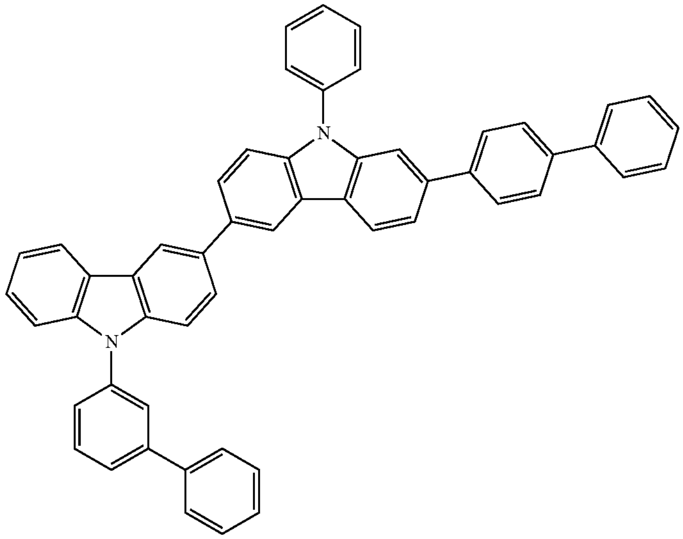 [SMILES: c1ccc(-c2ccc(-c3ccc4c5cc(-c6ccc7c(c6)c6ccccc6n7-c6cccc(-c7ccccc7)c6)ccc5n(-c5ccccc5)c4c3)cc2)cc1] | CAS-2085318-80-3 |
| 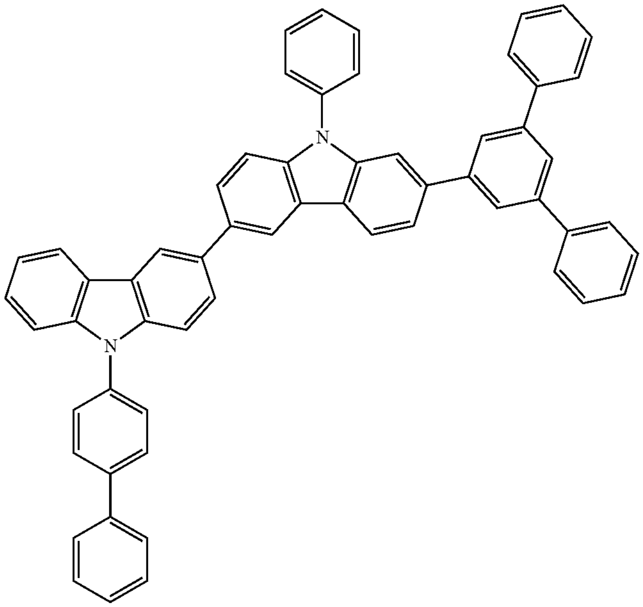 [SMILES: c1ccc(-c2ccc(-n3c4ccccc4c4cc(-c5ccc6c(c5)c5ccc(-c7cc(-c8ccccc8)cc(-c8ccccc8)c7)cc5n6-c5ccccc5)ccc43)cc2)cc1] | CAS-2085318-83-6 |

TABLE 9-continued
| Structure | CAS number |
| --- | --- |
| 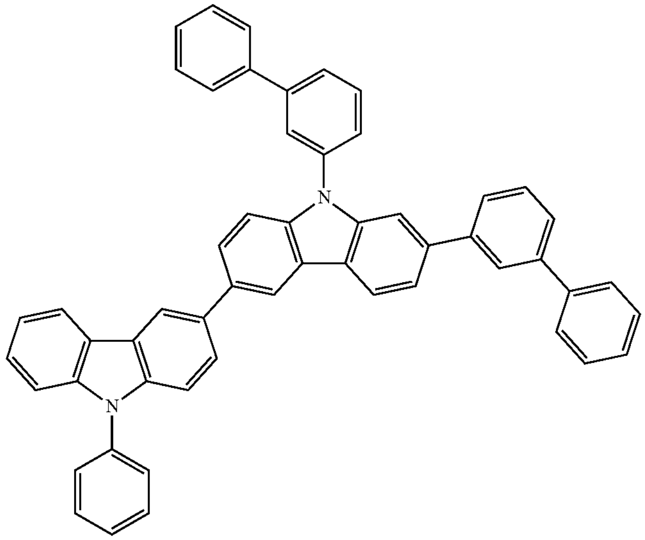 [SMILES: c1ccc(-c2cccc(-c3ccc4c5cc(-c6ccc7c(c6)c6ccccc6n7-c6ccccc6)ccc5n(-c5cccc(-c6ccccc6)c5)c4c3)c2)cc1] | CAS-2085318-82-5 |
| 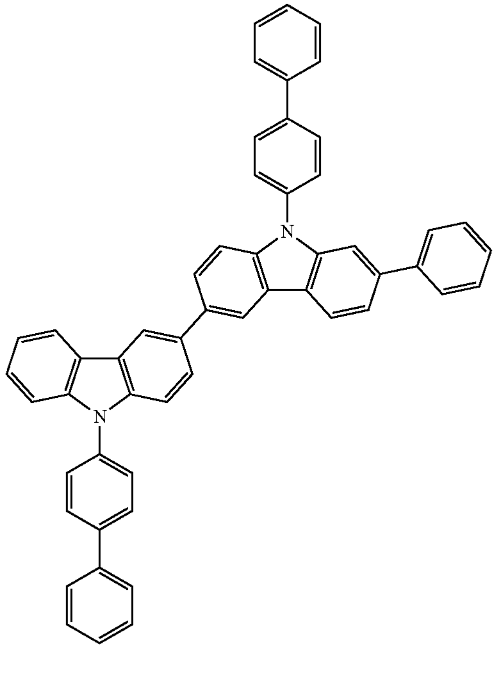 [SMILES: c1ccc(-c2ccc(-n3c4ccccc4c4cc(-c5ccc6c(c5)c5ccc(-c7ccccc7)cc5n6-c5ccc(-c6ccccc6)cc5)ccc43)cc2)cc1] | CAS-2085318-88-1 |

TABLE 9-continued
| Structure | CAS number |
|---|---|
| 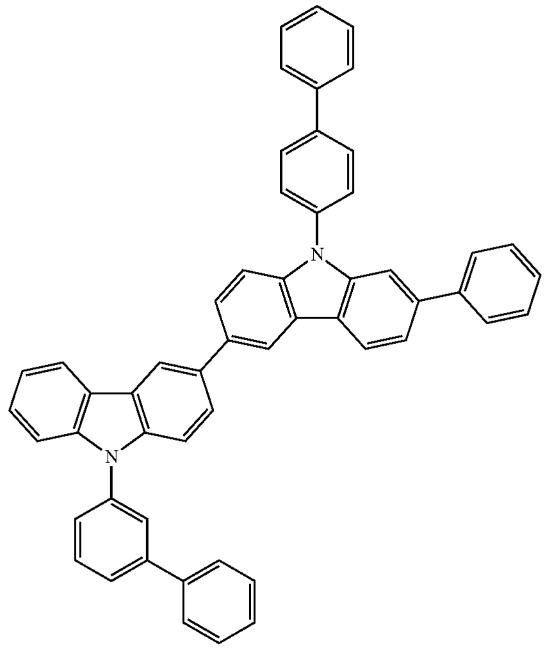 [SMILES: c1ccc(-c2ccc(-n3c4ccc(-c5ccc6c(c5)c5ccccc5n6-c5cccc(-c6ccccc6)c5)cc4c4ccc(-c5ccccc5)cc43)cc2)cc1] | CAS-2085318-87-0 |
| 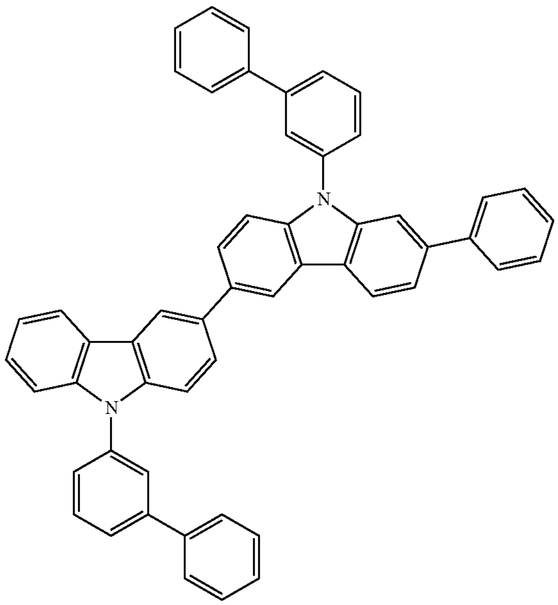 [SMILES: c1ccc(-c2cccc(-n3c4ccccc4c4cc(-c5ccc6c(c5)c5ccc(-c7ccccc7)cc5n6-c5cccc(-c6ccccc6)c5)ccc43)c2)cc1] | CAS-2085316-92-7 |

TABLE 9-continued
| Structure | CAS number |
|---|---|
| 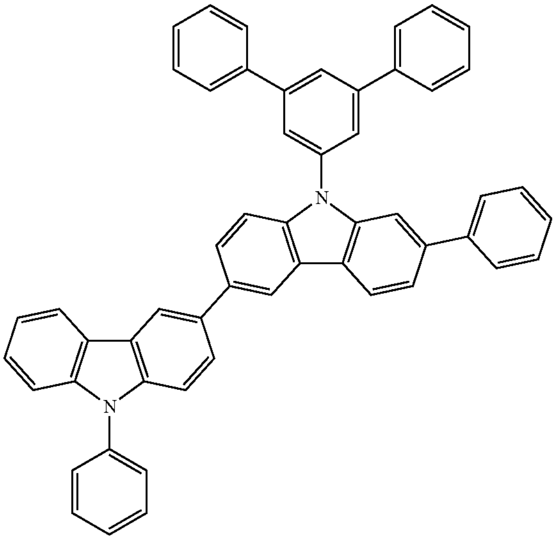 [SMILES: c1ccc(-c2cc(-c3ccccc3)cc(-n3c4ccc(-c5ccc6c(c5)c5ccccc5n6-c5ccccc5)cc4c4ccc(-c5ccccc5)cc43)c2)cc1] | CAS-2085318-89-2 |
| 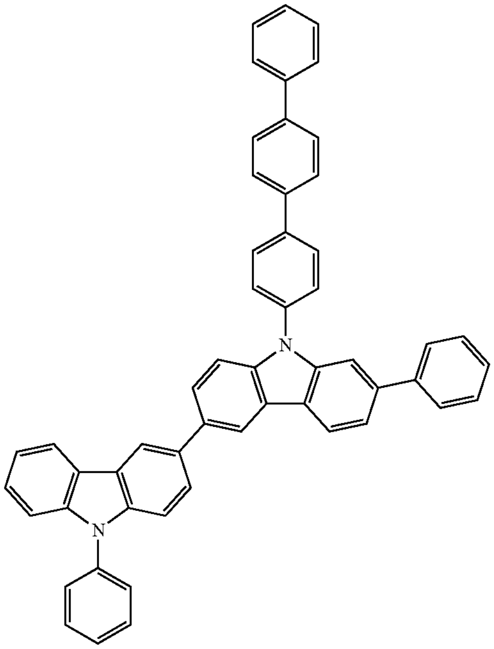 [SMILES: c1ccc(-c2ccc(-c3ccc(-n4c5ccc(-c6ccc7c(c6)c6ccccc6n7-c6ccccc6)cc5c5ccc(-c6ccccc6)cc54)cc3)cc2)cc1] | CAS-2085318-94-9 |

TABLE 9-continued
| Structure | CAS number |
| --- | --- |
| 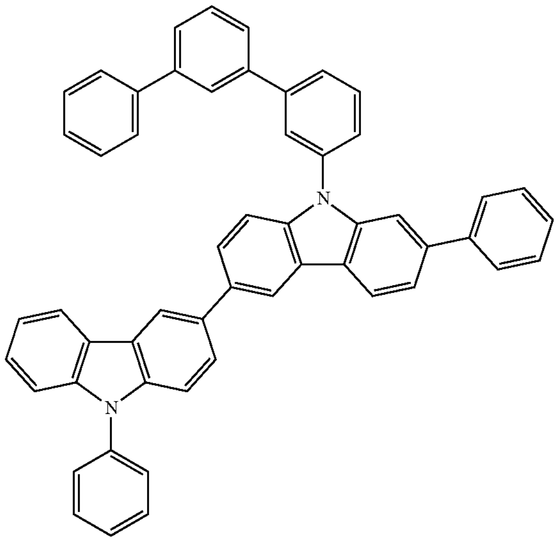 [SMILES: c1ccc(-c2cccc(-c3cccc(-n4c5ccc(-c6ccc7c(c6)c6ccccc6n7-c6ccccc6)cc5c5ccc(-c6ccccc6)cc54)c3)c2)cc1] | CAS-2085318-93-8 |
| 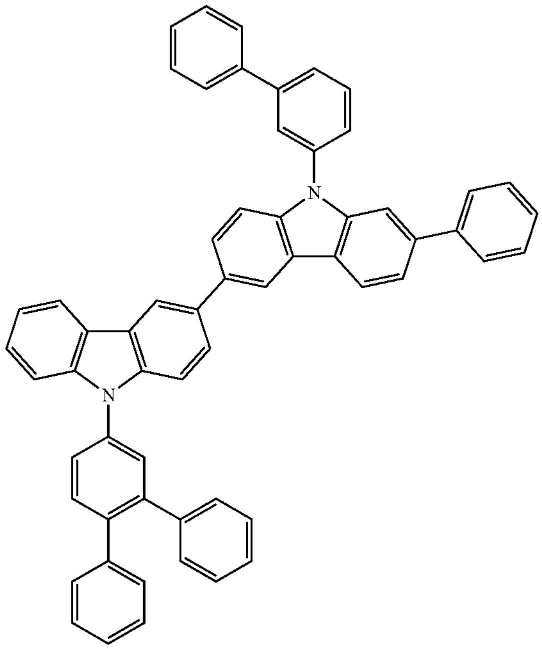 [SMILES: c1ccc(-c2cccc(-n3c4ccc(-c5ccc6c(c5)c5ccccc5n6-c5ccc(-c6ccccc6)c(-c6ccccc6)c5)cc4c4ccc(-c5ccccc5)cc43)c2)cc1] | CAS-2085318-98-3 |

TABLE 9-continued
| Structure | CAS number |
| --- | --- |
| 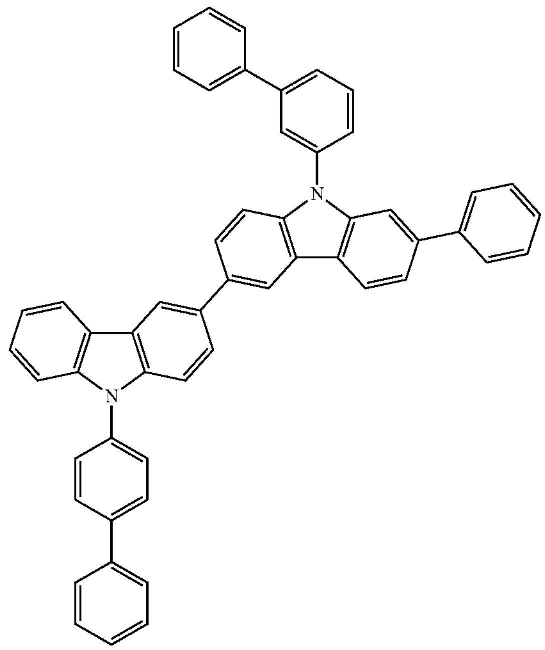 [SMILES: c1ccc(-c2ccc(-n3c4ccccc4c4cc(-c5ccc6c(c5)c5ccc(-c7ccccc7)cc5n6-c5cccc(-c6ccccc6)c5)ccc43)cc2)cc1] | CAS-2085318-97-2 |
| 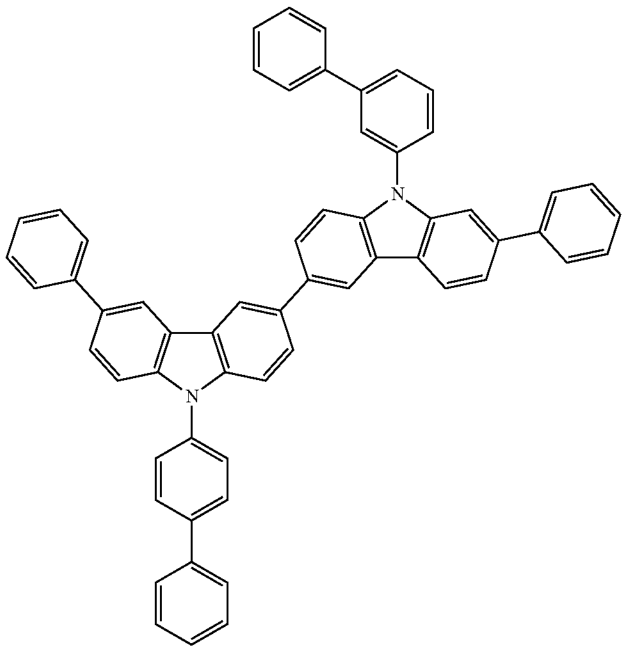 [SMILES: c1ccc(-c2ccc(-n3c4ccc(-c5ccccc5)cc4c4cc(-c5ccc6c(c5)c5ccc(-c7ccccc7)cc5n6-c5cccc(-c6ccccc6)c5)ccc43)cc2)cc1] | CAS-2085319-00-0 |

TABLE 9-continued
| Structure | CAS number |
| --- | --- |
| 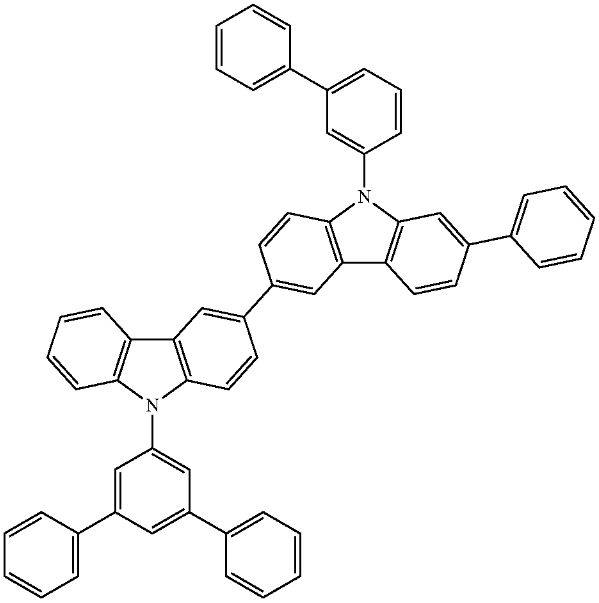 [SMILES: c1ccc(-c2cccc(-n3c4ccc(-c5ccc6c(c5)c5ccccc5n6-c5cc(-c6ccccc6)cc(-c6ccccc6)c5)cc4c4ccc(-c5ccccc5)cc43)c2)cc1] | CAS-2085318-99-4 |
| 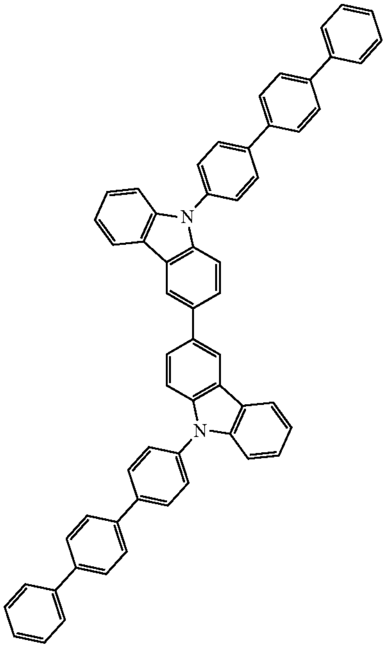 [SMILES: c1ccc(-c2ccc(-c3ccc(-n4c5ccccc5c5cc(-c6ccc7c(c6)c6ccccc6n7-c6ccc(-c7ccc(-c8ccccc8)cc7)cc6)ccc54)cc3)cc2)cc1] | CAS-251316-80-0 |

TABLE 9-continued
| Structure | CAS number |
| --- | --- |
| 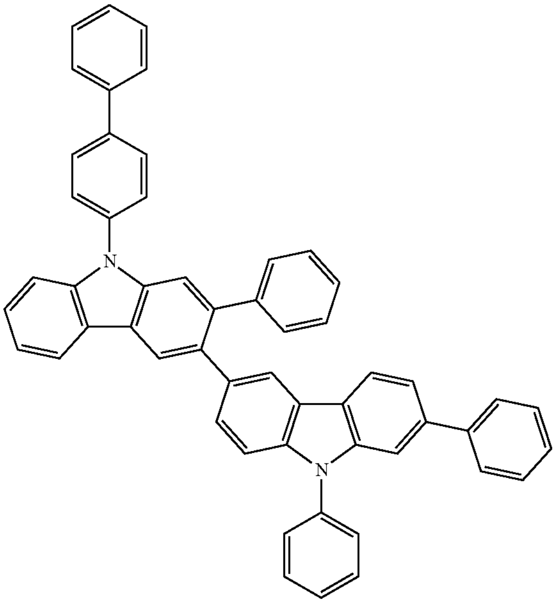 [SMILES: c1ccc(-c2ccc(-n3c4ccccc4c4cc(-c5ccc6c(c5)c5ccc(-c7ccccc7)cc5n6-c5ccccc5)c(-c5ccccc5)cc43)cc2)cc1] | CAS-2085319-17-9 |
| 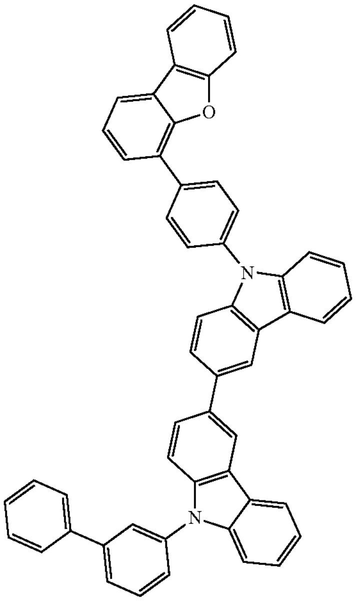 | |
| 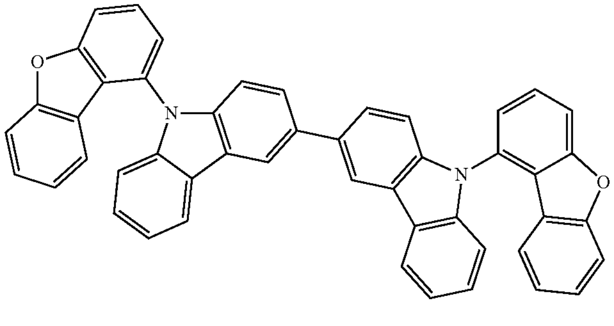 [SMILES: c1ccc2c(c1)oc1cccc(-n3c4ccccc4c4cc(-c5ccc6c(c5)c5ccccc5n6-c5cccc6oc7ccccc7c56)ccc43)c12] | CAS-1427160-09-5 |

TABLE 9-continued
| Structure | CAS number |
| --- | --- |
| 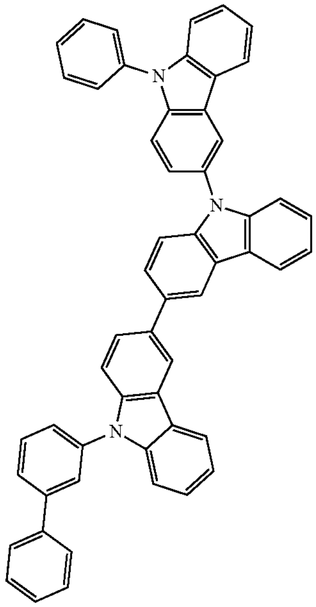 97 | CAS-1643479-72-4 |
| 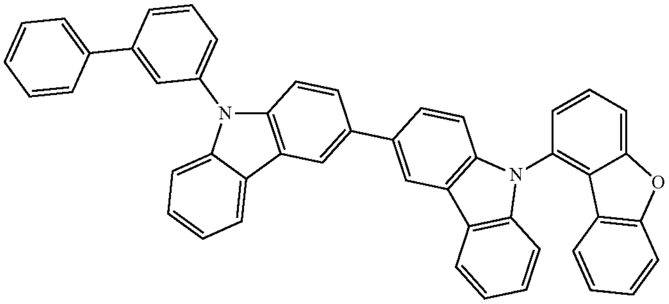 98 | |
| 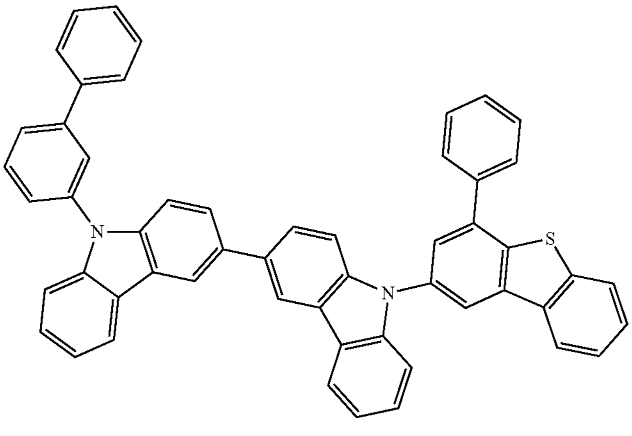 99 | |

TABLE 9-continued
| Structure | CAS number |
| --- | --- |
| 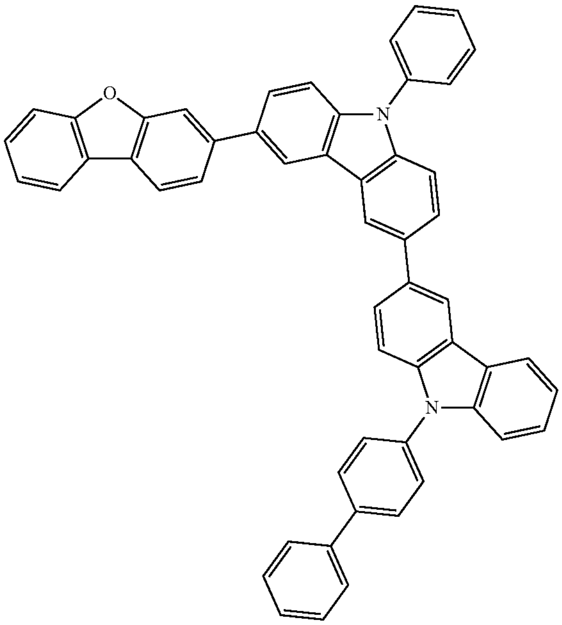 | CAS-1799959-65-1 |
| 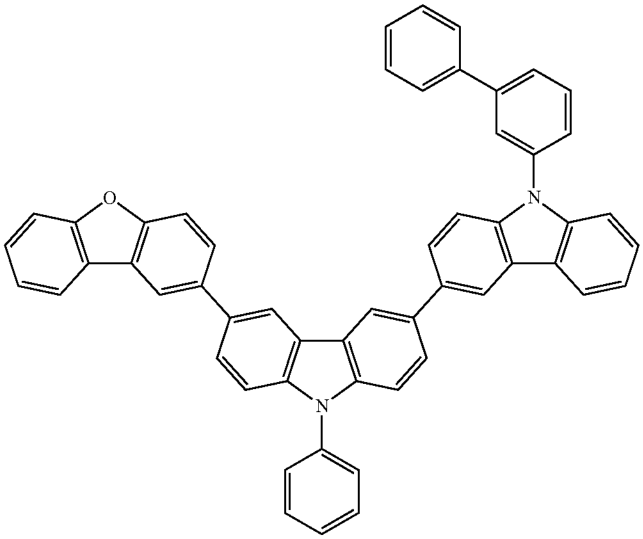 [SMILES: c1ccc(-c2cccc(-n3c4ccccc4c4cc(-c5ccc6c(c5)c5cc(-c7ccc8oc9ccccc9c8c7)ccc5n6-c5ccccc5)ccc43)c2)cc1] | CAS-1799959-74-2 |
| 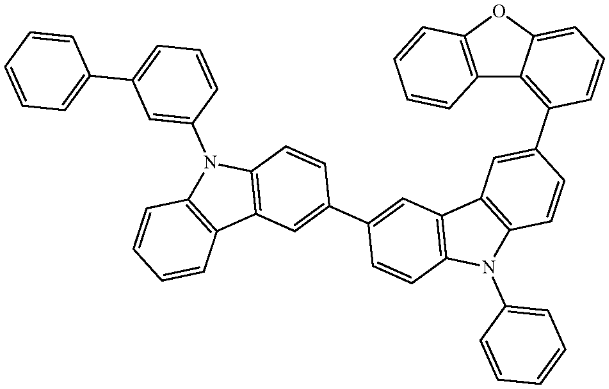 | CAS-1799959-75-3 |

TABLE 9-continued
| Structure | CAS number |
| --- | --- |
| 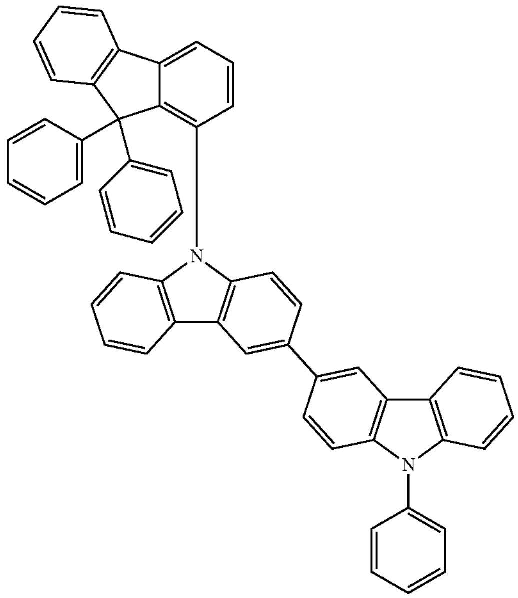 [SMILES: c1ccc(-n2c3ccccc3c3cc(-c4ccc5c(c4)c4ccccc4n5-c4cccc5c4C(c4ccccc4)(c4ccccc4)c4ccccc4-5)ccc32)cc1] | CAS-1799960-24-9 |
| 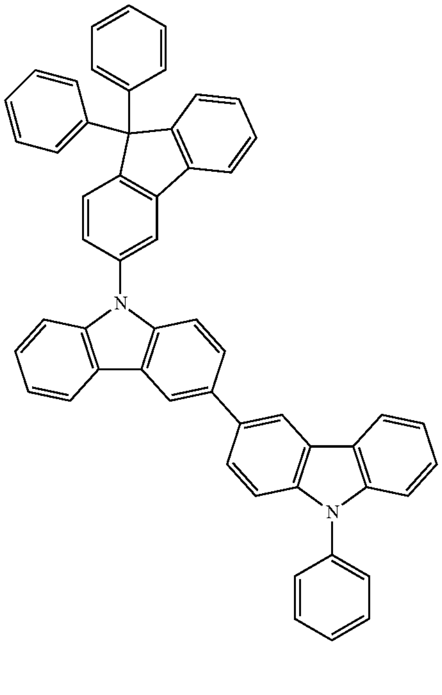 [SMILES: c1ccc(-n2c3ccccc3c3cc(-c4ccc5c(c4)c4ccccc4n5-c4ccc5c(c4)-c4ccccc4C5(c4ccccc4)c4ccccc4)ccc32)cc1] | CAS-1799960-25-0 |

TABLE 9-continued
| Structure | CAS number |
| --- | --- |
| 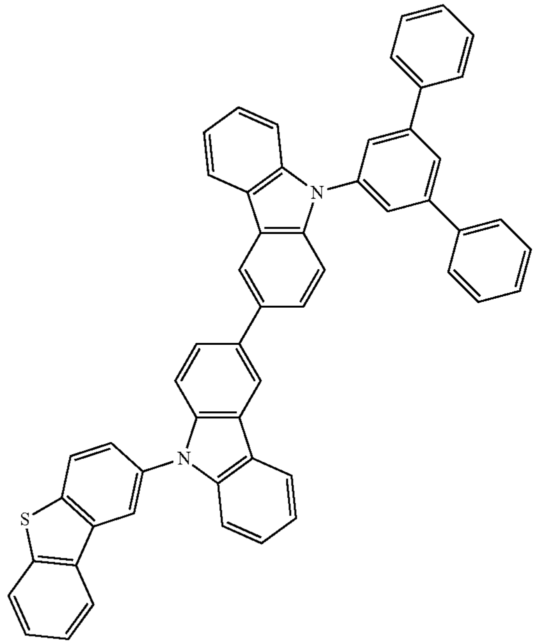 [SMILES: c1ccc(-c2cc(-c3ccccc3)cc(-n3c4ccccc4c4cc(-c5ccc6c(c5)c5ccccc5n6-c5ccc6sc7ccccc7c6c5)ccc43)c2)cc1] | CAS-1340668-17-8 |
| 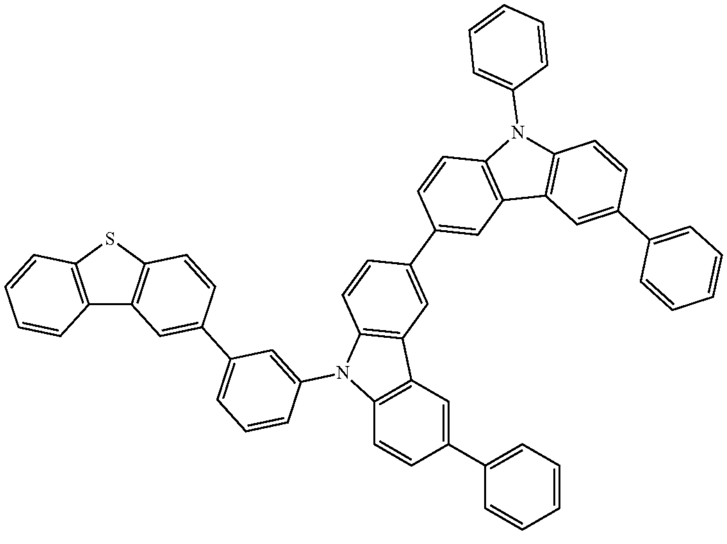 [SMILES: c1ccc(-c2ccc3c(c2)c2cc(-c4ccc5c(c4)c4cc(-c6ccccc6)ccc4n5-c4cccc(-c5ccc6sc7ccccc7c6c5)c4)ccc2n3-c2ccccc2)cc1] | CAS-1340668-19-0 |

TABLE 9-continued
| Structure | CAS number |
| --- | --- |
| 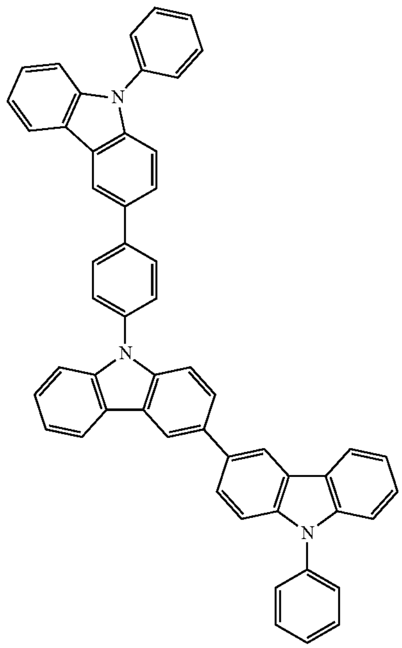 [SMILES: c1ccc(-n2c3ccccc3c3cc(-c4ccc(-n5c6ccccc6c6cc(-c7ccc8c(c7)c7ccccc7n8-c7ccccc7)ccc65)cc4)ccc32)cc1] | CAS-1289556-24-6 |
| 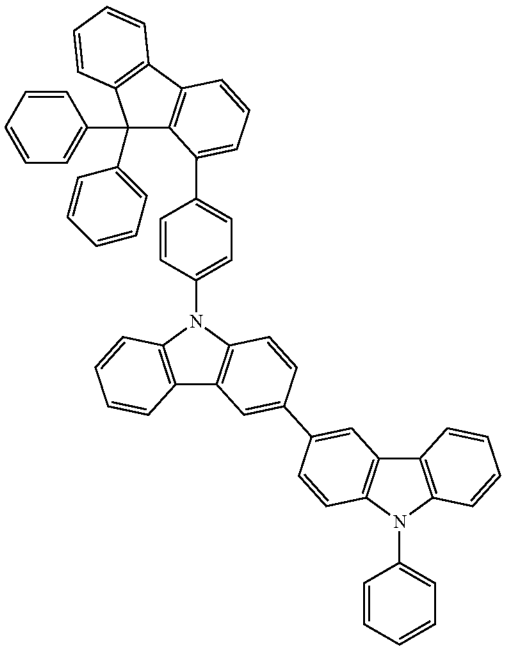 [SMILES: c1ccc(-n2c3ccccc3c3cc(-c4ccc5c(c4)c4ccccc4n5-c4ccc(-c5cccc6c5C(c5ccccc5)(c5ccccc5)c5ccccc5-6)cc4)ccc32)cc1] | CAS-1799960-56-7 |

TABLE 9-continued
| Structure | CAS number |
|---|---|
| 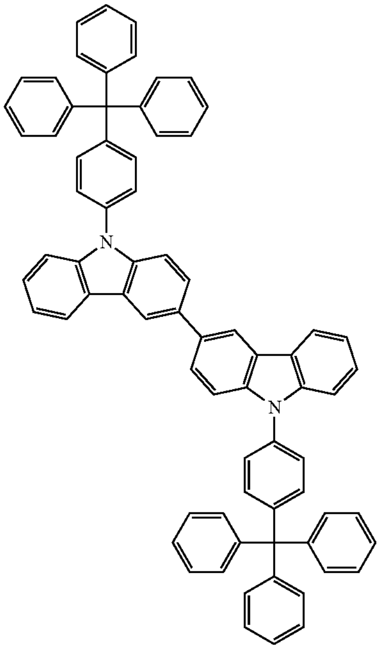 [SMILES: c1ccc(C(c2ccccc2)(c2ccccc2)c2ccc(-n3c4ccccc4c4cc(-c5ccc6c(c5)c5ccccc5n6-c5ccc(C(c6ccccc6)(c6ccccc6)c6ccccc6)cc5)ccc43)cc2)cc1] | CAS-1336889-27-0 |
| 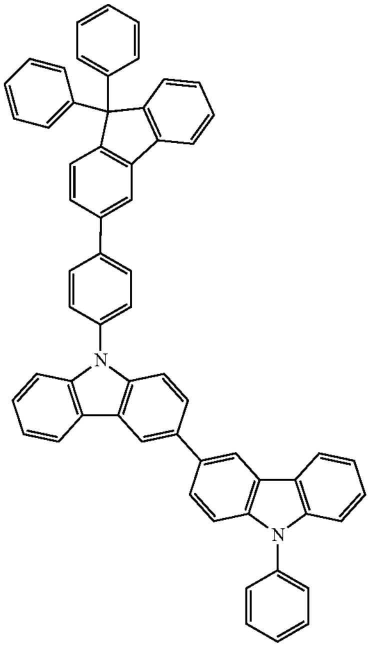 [SMILES: c1ccc(-n2c3ccccc3c3cc(-c4ccc5c(c4)c4ccccc4n5-c4ccc(-c5ccc6c(c5)-c5ccccc5C6(c5ccccc5)c5ccccc5)cc4)ccc32)cc1] | CAS-1799960-58-9 |

TABLE 9-continued
| Structure | CAS number |
| --- | --- |
| 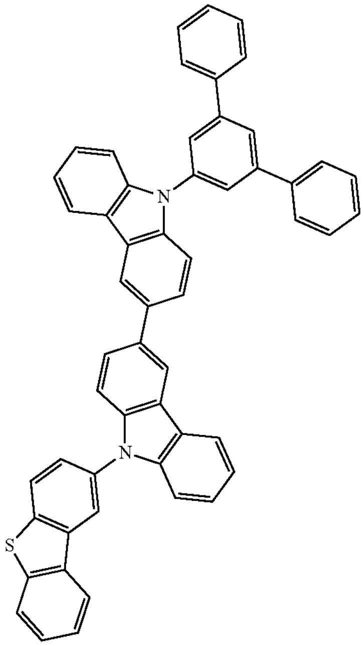 [SMILES: c1ccc(-c2cc(-c3ccccc3)cc(-n3c4ccccc4c4cc(-c5ccc6c(c5)c5ccccc5n6-c5ccc6sc7ccccc7c6c5)ccc43)c2)cc1] | CAS-1340668-17-8 |
| 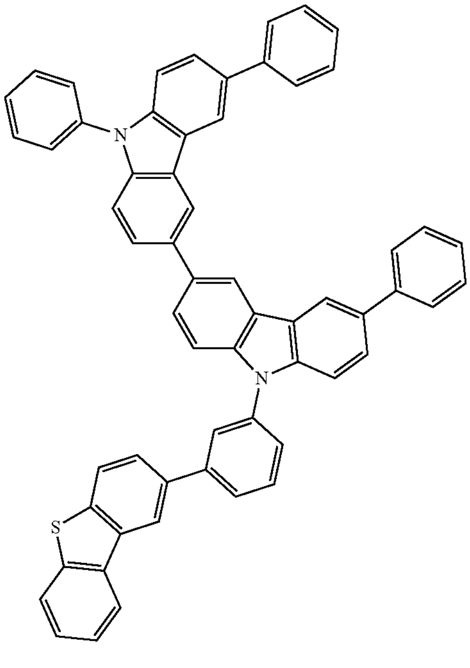 [SMILES: c1ccc(-c2ccc3c(c2)c2cc(-c4ccc5c(c4)c4cc(-c6ccccc6)ccc4n5-c4cccc(-c5ccc6sc7ccccc7c6c5)c4)ccc2n3-c2ccccc2)cc1] | CAS-1340668-19-0 |

TABLE 9-continued
| Structure | CAS number |
|---|---|
| 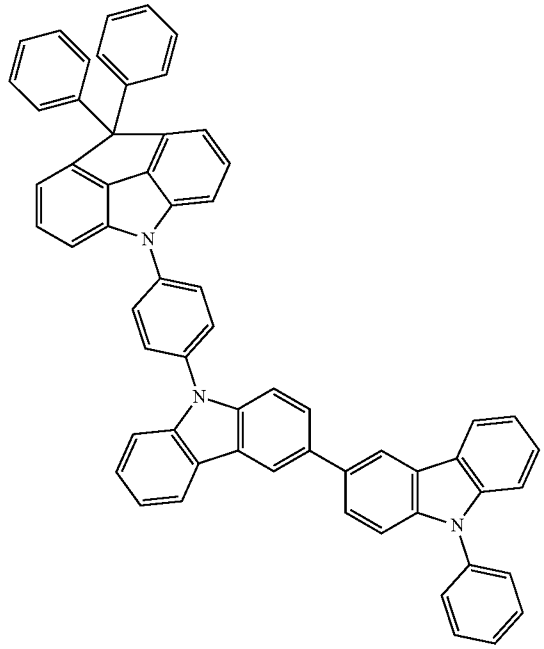 [SMILES: c1ccc(-n2c3ccccc3c3cc(-c4ccc5c(c4)c4ccccc4n5-c4ccc(-n5c6cccc7c6c6c(cccc65)C7(c5ccccc5)c5ccccc5)cc4)ccc32)cc1] | CAS-1812208-18-6 |
| 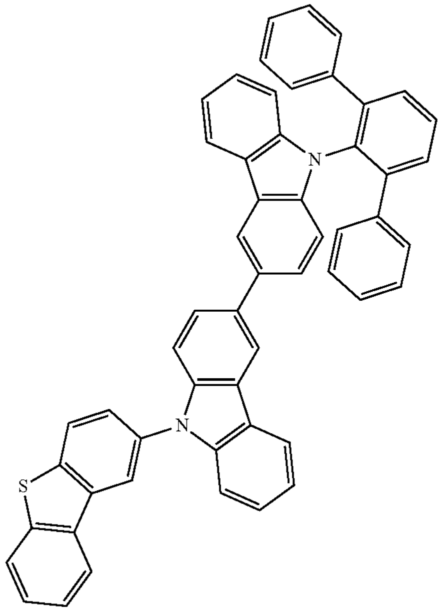 [SMILES: c1ccc(-c2cccc(-c3ccccc3)c2-n2c3ccccc3c3cc(-c4ccc5c(c4)c4ccccc4n5-c4ccc5sc6ccccc6c5c4)ccc32)cc1] | CAS-1340668-35-0 |

TABLE 9-continued
| Structure | CAS number |
| --- | --- |
| 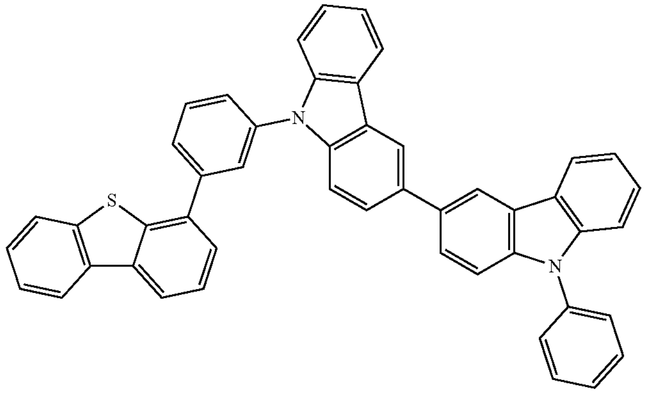 [SMILES: c1ccc(-n2c3ccccc3c3cc(-c4ccc5c(c4)c4ccccc4n5-c4cccc(-c5cccc6c5sc5ccccc56)c4)ccc32)cc1] | CAS-1340668-37-2 |
| 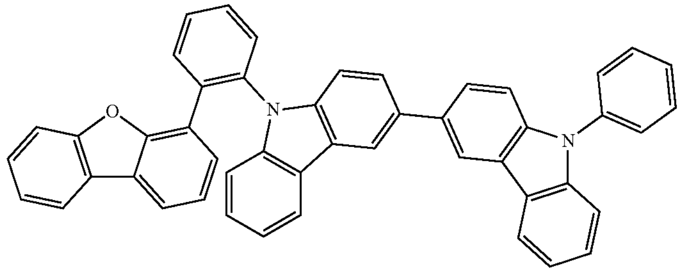 | CAS-1830334-82-1 |
| 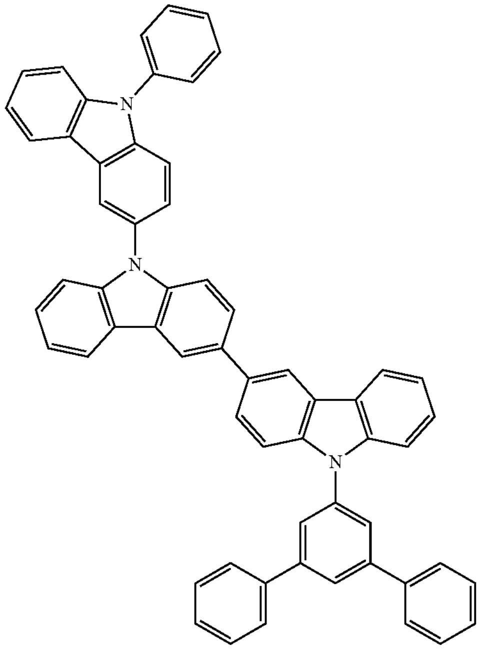 [SMILES: c1ccc(-c2cc(-c3ccccc3)cc(-n3c4ccccc4c4cc(-c5ccc6c(c5)c5ccccc5n6-c5ccc6c(c5)c5ccccc5n6-c5ccccc5)ccc43)c2)cc1] | CAS-1340669-19-3 |

TABLE 9-continued
| Structure | CAS number |
| --- | --- |
| 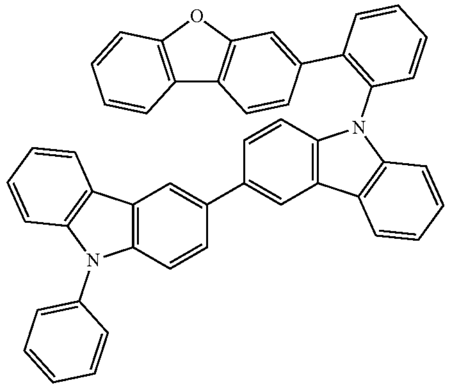 [SMILES: c1ccc(-n2c3ccccc3c3cc(-c4ccc5c(c4)c4ccccc4n5-c4ccccc4-c4ccc5c(c4)oc4ccccc45)ccc32)cc1] | CAS-1830334-85-4 |
| 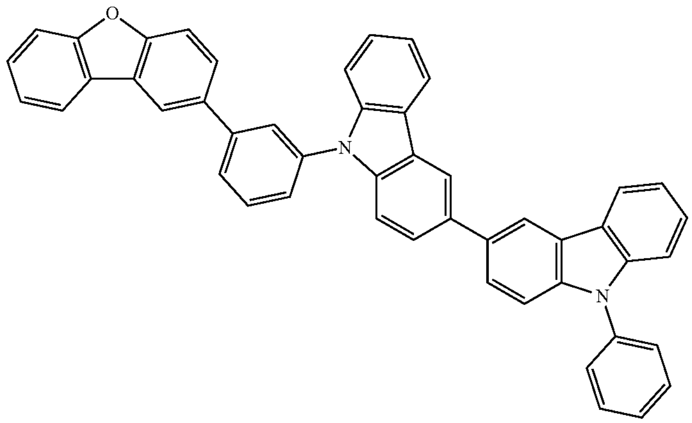 [SMILES: c1ccc(-n2c3ccccc3c3cc(-c4ccc5c(c4)c4ccccc4n5-c4cccc(-c5ccc6oc7ccccc7c6c5)c4)ccc32)cc1] | CAS-1830334-94-5 |
| 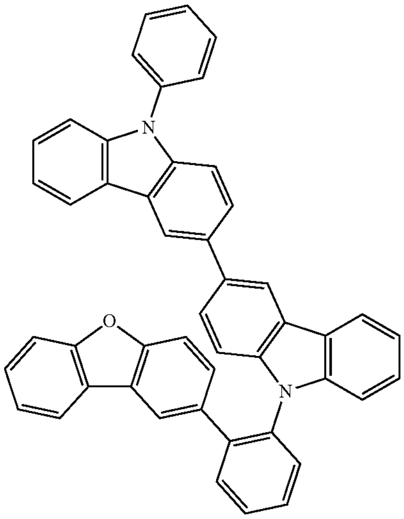 [SMILES: c1ccc(-n2c3ccccc3c3cc(-c4ccc5c(c4)c4ccccc4n5-c4ccccc4-c4ccc5oc6ccccc6c5c4)ccc32)cc1] | CAS-1830334-88-7 |

TABLE 9-continued
| Structure | CAS number |
|---|---|
| 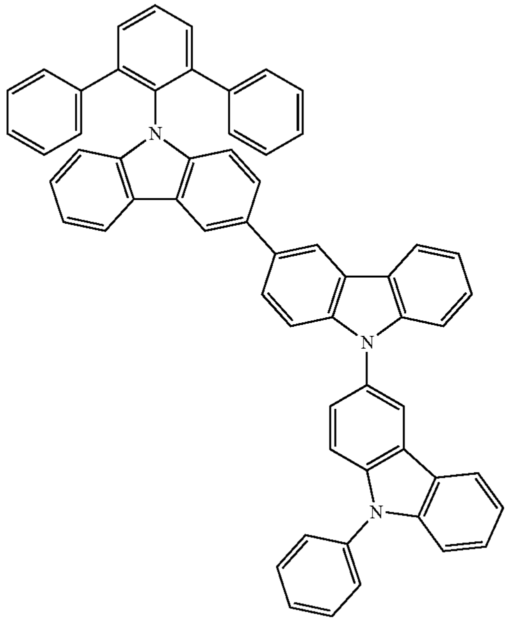 [SMILES: c1ccc(-c2cccc(-c3ccccc3)c2-n2c3ccccc3c3cc(-c4ccc5c(c4)c4ccccc4n5-c4ccc5c(c4)c4ccccc4n5-c4ccccc4)ccc32)cc1] | CAS-1340669-32-0 |
| 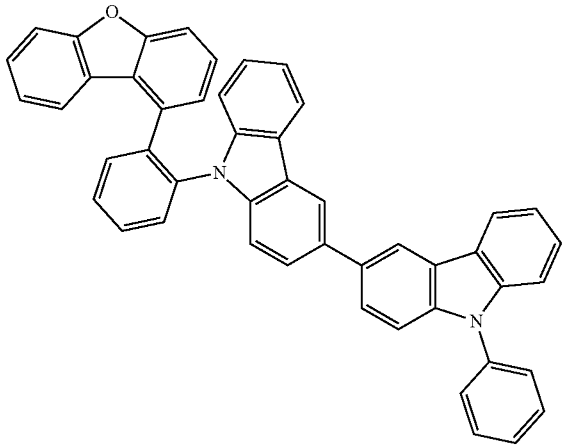 | CAS-1830334-90-1 |
| 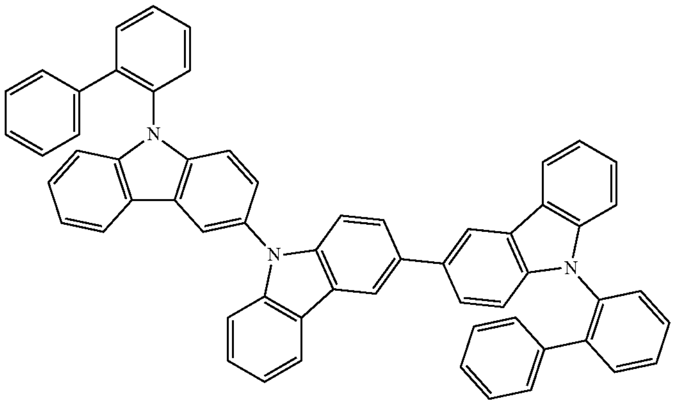 [SMILES: c1ccc(-c2ccccc2-n2c3ccccc3c3cc(-c4ccc5c(c4)c4ccccc4n5-c4ccc5c(c4)c4ccccc4n5-c4ccccc4-c4ccccc4)ccc32)cc1] | CAS-1340669-33-1 |

TABLE 9-continued
| Structure | CAS number |
|---|---|
| 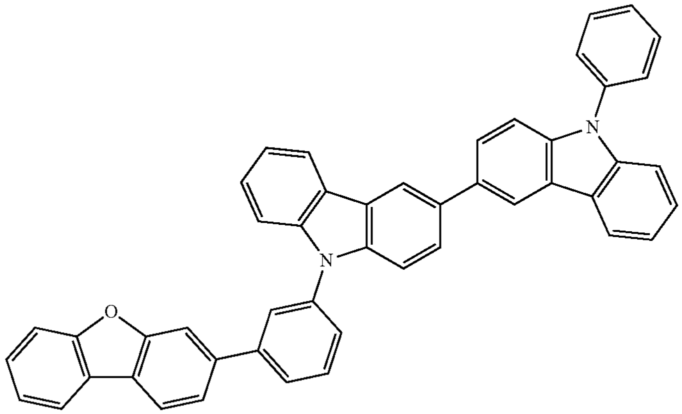 | CAS-1830334-91-2 |
| 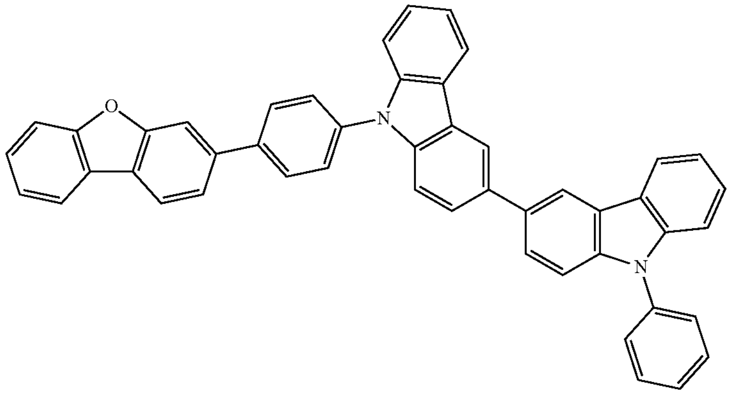 [SMILES: c1ccc(-n2c3ccccc3c3cc(-c4ccc5c(c4)c4ccccc4n5-c4ccc(-c5ccc6c(c5)oc5ccccc56)cc4)ccc32)cc1] | CAS-1830335-02-8 |
| 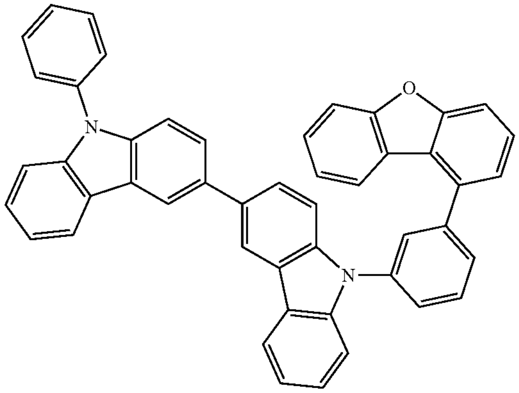 [SMILES: c1ccc(-n2c3ccccc3c3cc(-c4ccc5c(c4)c4ccccc4n5-c4cccc(-c5cccc6oc7ccccc7c56)c4)ccc32)cc1] | CAS-1830334-97-8 |
| 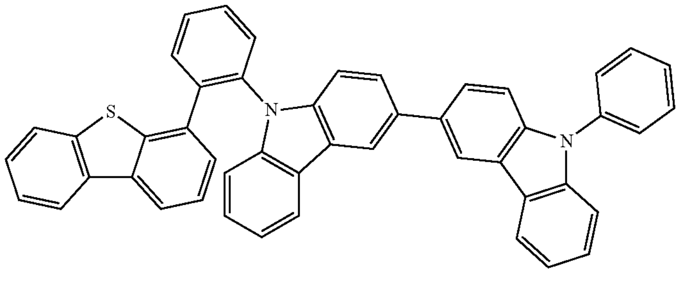 [SMILES: c1ccc(-n2c3ccccc3c3cc(-c4ccc5c(c4)c4ccccc4n5-c4ccccc4-c4cccc5c4sc4ccccc45)ccc32)cc1] | CAS-1830335-71-1 |

TABLE 9-continued
| Structure | CAS number |
| --- | --- |
| 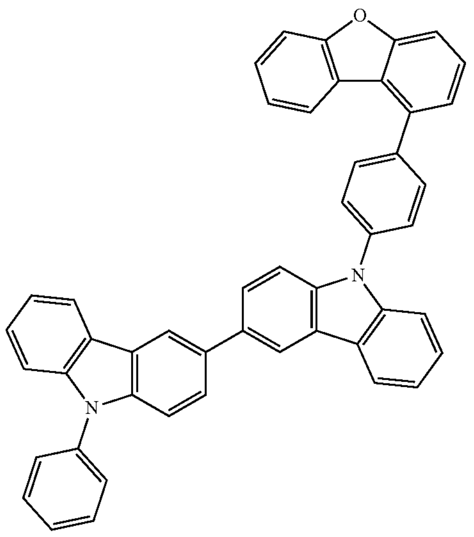 [SMILES: c1ccc(-n2c3ccccc3c3cc(-c4ccc5c(c4)c4ccccc4n5-c4ccc(-c5cccc6oc7ccccc7c56)cc4)ccc32)cc1] | CAS-1830335-07-3 |
| 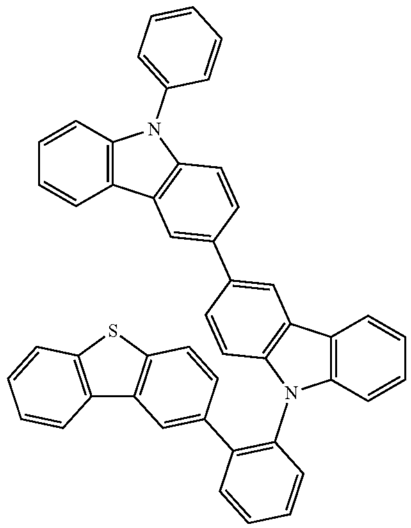 [SMILES: c1ccc(-n2c3ccccc3c3cc(-c4ccc5c(c4)c4ccccc4n5-c4ccccc4-c4ccc5sc6ccccc6c5c4)ccc32)cc1] | CAS-1830335-76-6 |
| 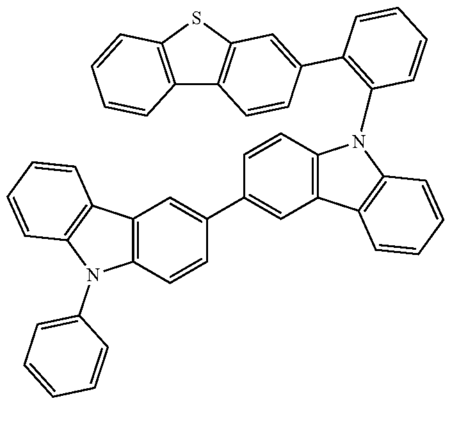 [SMILES: c1ccc(-n2c3ccccc3c3cc(-c4ccc5c(c4)c4ccccc4n5-c4ccccc4-c4ccc5c(c4)sc4ccccc45)ccc32)cc1] | CAS-1830335-72-2 |

TABLE 9-continued
| Structure | CAS number |
| --- | --- |
| 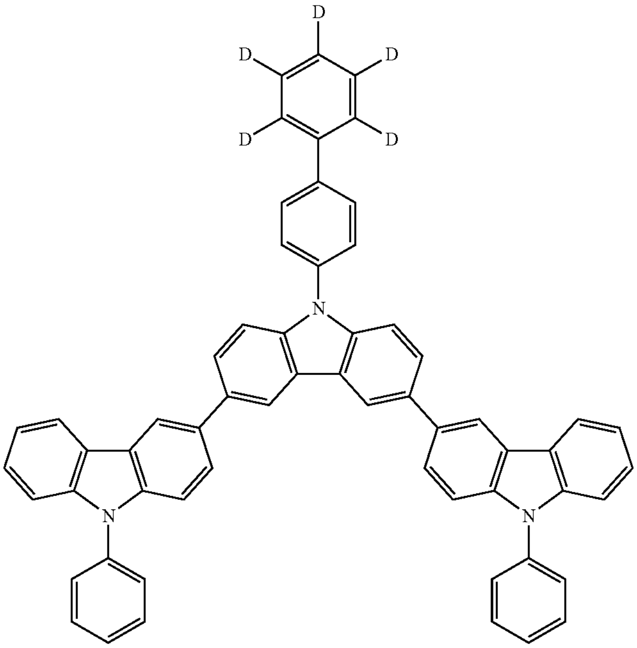 [SMILES: [2H]c1c([2H])c([2H])c(-c2ccc(-n3c4ccc(-c5ccc6c(c5)c5ccccc5n6-c5ccccc5)cc4c4cc(-c5ccc6c(c5)c5ccccc5n6-c5ccccc5)ccc43)cc2)c([2H])c1[2H]] | CAS-1354054-11-7 |
| 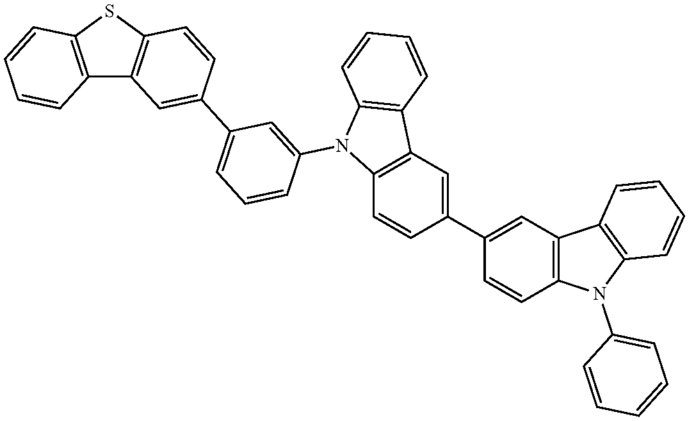 | CAS-1830335-85-7 |
| 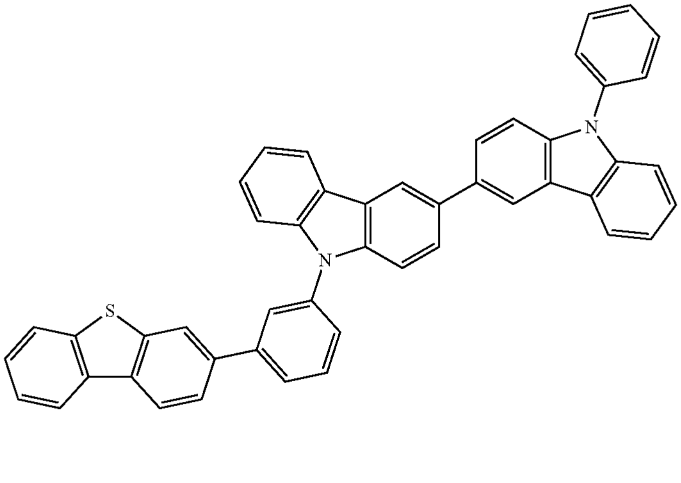 | CAS-1830335082-4 |

TABLE 9-continued
| Structure | CAS number |
| --- | --- |
| 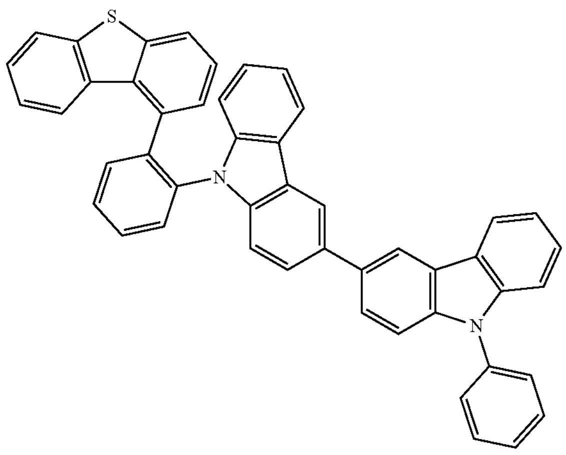 [SMILES: c1ccc(-n2c3ccccc3c3cc(-c4ccc5c(c4)c4ccccc4n5-c4ccccc4-c4cccc5sc6ccccc6c45)ccc32)cc1] | CAS-1830335-79-9 |
| 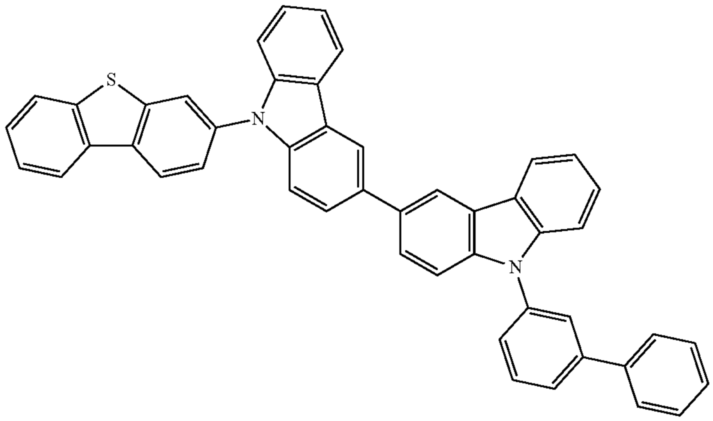 [SMILES: c1ccc(-c2cccc(-n3c4ccccc4c4cc(-c5ccc6c(c5)c5ccccc5n6-c5ccc6c(c5)sc5ccccc56)ccc43)c2)cc1] | CAS-1830339-40-6 |
| 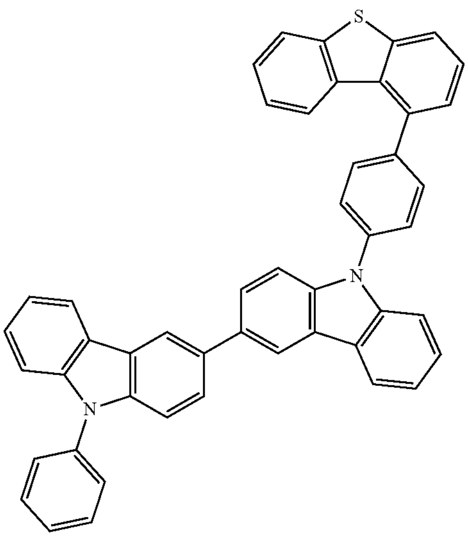 [SMILES: c1ccc(-n2c3ccccc3c3cc(-c4ccc5c(c4)c4ccccc4n5-c4ccc(-c5cccc6sc7ccccc7c56)cc4)ccc32)cc1] | CAS-1830335-95-9 |

TABLE 9-continued
| Structure | CAS number |
| --- | --- |
| 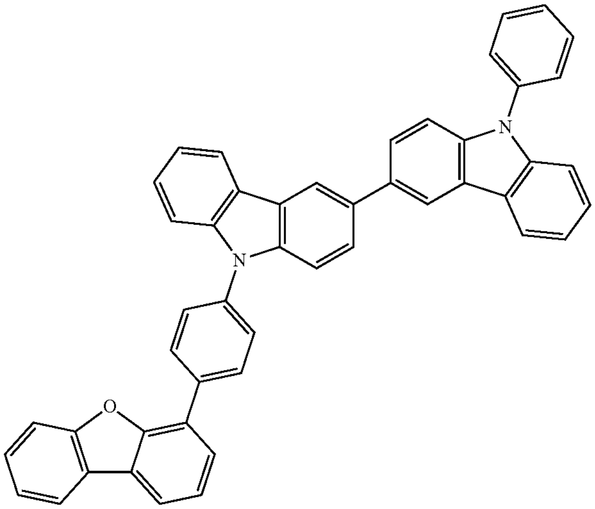 | CAS-1377150-35-0 |
| 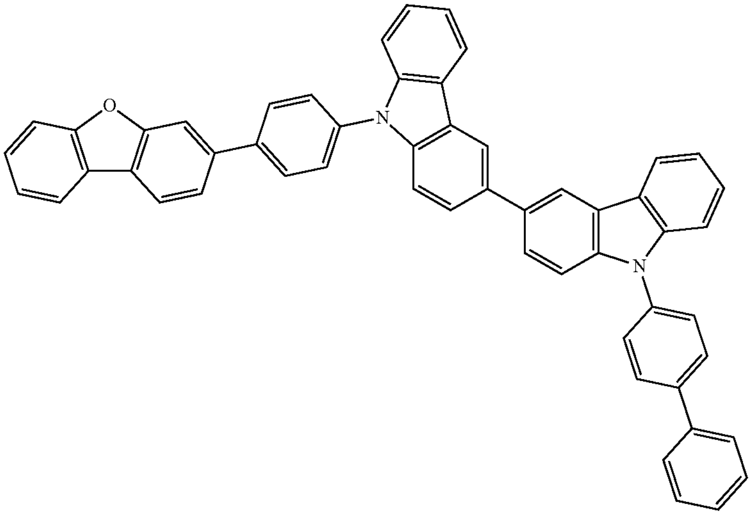 [SMILES: c1ccc(-c2ccc(-n3c4ccccc4c4cc(-c5ccc6c(c5)c5ccccc5n6-c5ccc(-c6ccc7c(c6)oc6ccccc67)cc5)ccc43)cc2)cc1] | CAS-1830339-41-7 |
| 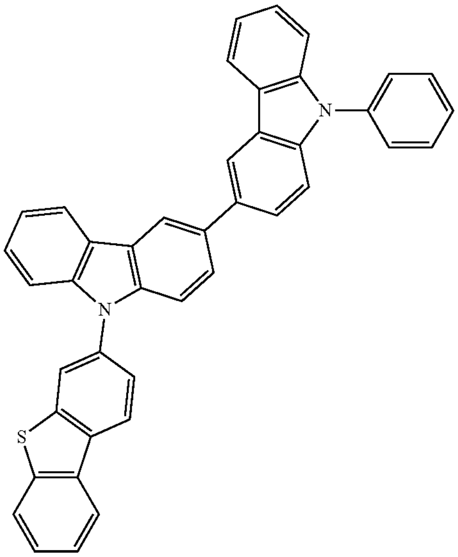 [SMILES: c1ccc(-n2c3ccccc3c3cc(-c4ccc5c(c4)c4ccccc4n5-c4ccc5c(c4)sc4ccccc45)ccc32)cc1] | CAS-1830335-90-4 |

TABLE 9-continued
| Structure | CAS number |
|---|---|
| 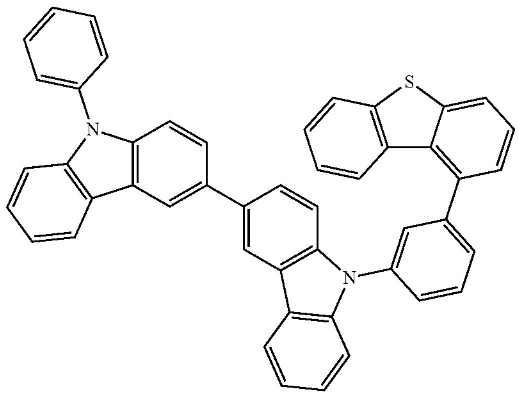 [SMILES: c1ccc(-n2c3ccccc3c3cc(-c4ccc5c(c4)c4ccccc4n5-c4cccc(-c5cccc6sc7ccccc7c56)c4)ccc32)cc1] | CAS-1830335-87-9 |
| 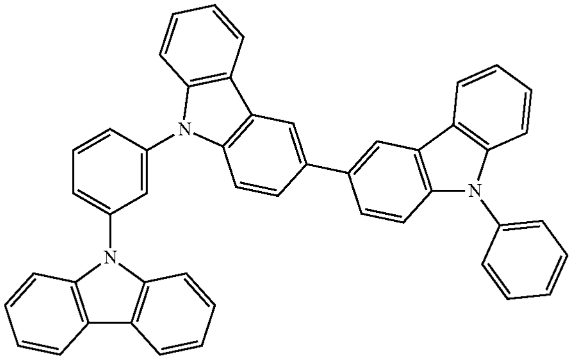 [SMILES: c1ccc(-n2c3ccccc3c3cc(-c4ccc5c(c4)c4ccccc4n5-c4cccc(-n5c6ccccc6c6ccccc65)c4)ccc32)cc1] | CAS-1399855-37-8 |
| 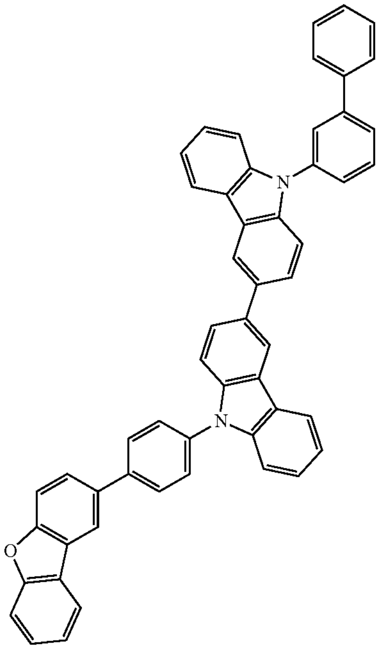 [SMILES: c1ccc(-c2cccc(-n3c4ccccc4c4cc(-c5ccc6c(c5)c5ccccc5n6-c5ccc(-c6ccc7oc8ccccc8c7c6)cc5)ccc43)c2)cc1] | CAS-1830339-42-8 |

TABLE 9-continued
| Structure | CAS number |
|---|---|
| 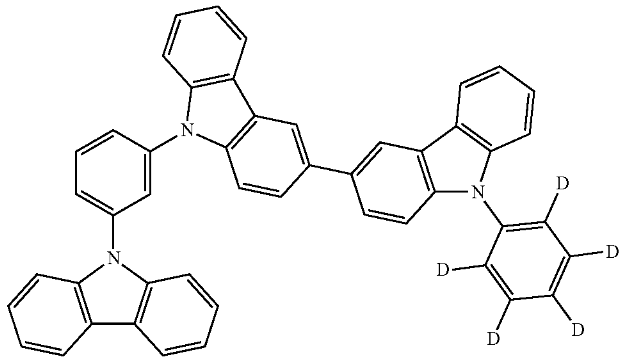 [SMILES: [2H]c1c([2H])c([2H])c(-n2c3ccccc3c3cc(-c4ccc5c(c4)c4ccccc4n5-c4cccc(-n5c6ccccc6c6ccccc65)c4)ccc32)c([2H])c1[2H]] | CAS-1399855-38-9 |
| 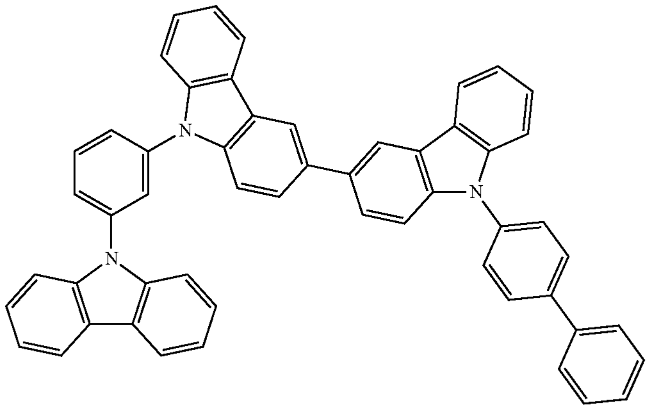 [SMILES: c1ccc(-c2ccc(-n3c4ccccc4c4cc(-c5ccc6c(c5)c5ccccc5n6-c5cccc(-n6c7ccccc7c7ccccc76)c5)ccc43)cc2)cc1] | CAS-1399855-39-0 |
| 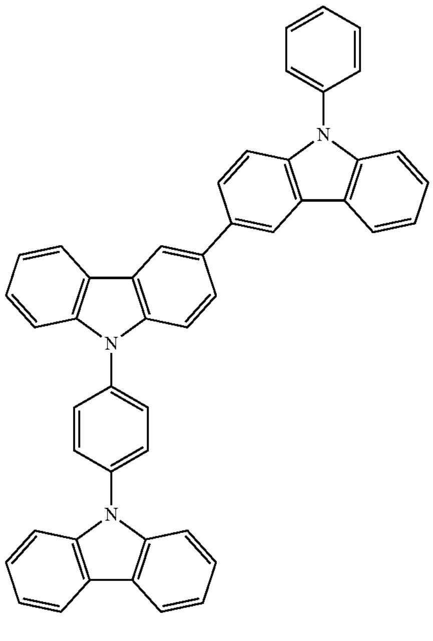 [SMILES: c1ccc(-n2c3ccccc3c3cc(-c4ccc5c(c4)c4ccccc4n5-c4ccc(-n5c6ccccc6c6ccccc65)cc4)ccc32)cc1] | CAS-1399855-46-9 |

TABLE 9-continued
| Structure | CAS number |
| --- | --- |
| 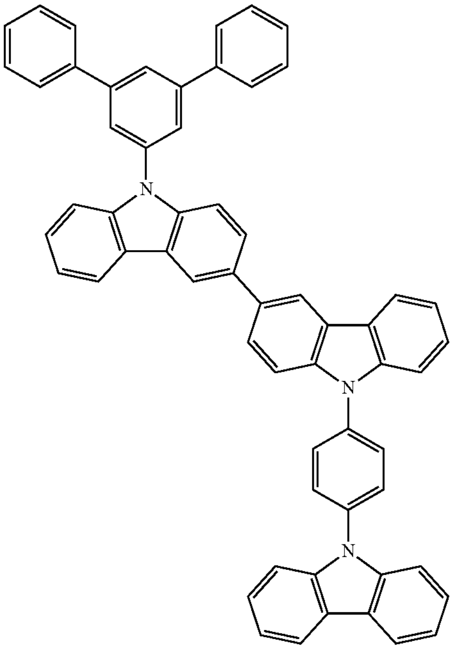 [SMILES: c1ccc(-c2cc(-c3ccccc3)cc(-n3c4ccccc4c4cc(-c5ccc6c(c5)c5ccccc5n6-c5ccc(-n6c7ccccc7c7ccccc76)cc5)ccc43)c2)cc1] | CAS-1399855-47-0 |
| 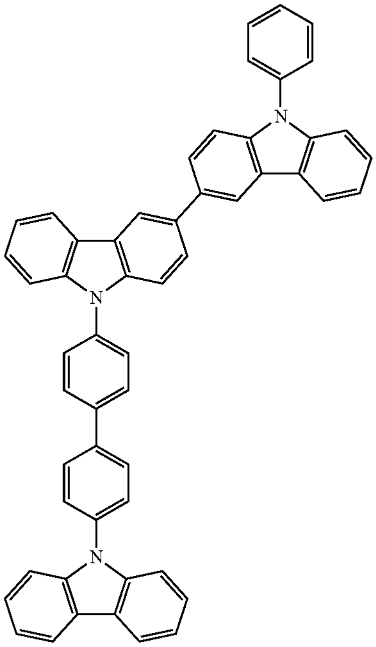 [SMILES: c1ccc(-n2c3ccccc3c3cc(-c4ccc5c(c4)c4ccccc4n5-c4ccc(-c5ccc(-n6c7ccccc7c7ccccc76)cc5)cc4)ccc32)cc1] | CAS-1413936-92-1 |

TABLE 9-continued
| Structure | CAS number |
| --- | --- |
| 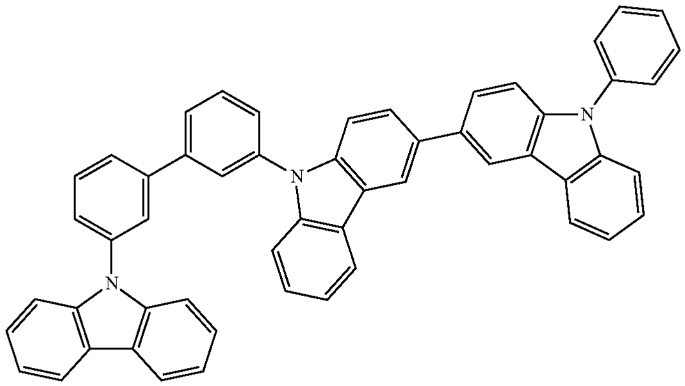 [SMILES: c1ccc(-n2c3ccccc3c3cc(-c4ccc5c(c4)c4ccccc4n5-c4cccc(-c5cccc(-n6c7ccccc7c7ccccc76)c5)c4)ccc32)cc1] | CAS-1413936-95-4 |
| 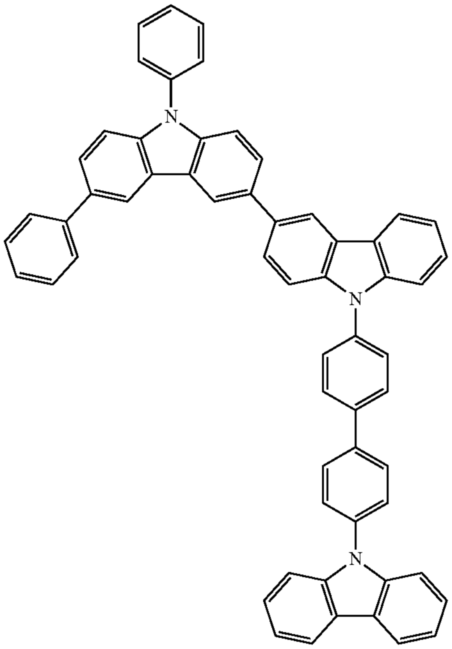 [SMILES: c1ccc(-c2ccc3c(c2)c2cc(-c4ccc5c(c4)c4ccccc4n5-c4ccc(-c5ccc(-n6c7ccccc7c7ccccc76)cc5)cc4)ccc2n3-c2ccccc2)cc1] | CAS-1413936-96-5 |

TABLE 9-continued
| Structure | CAS number |
|---|---|
| 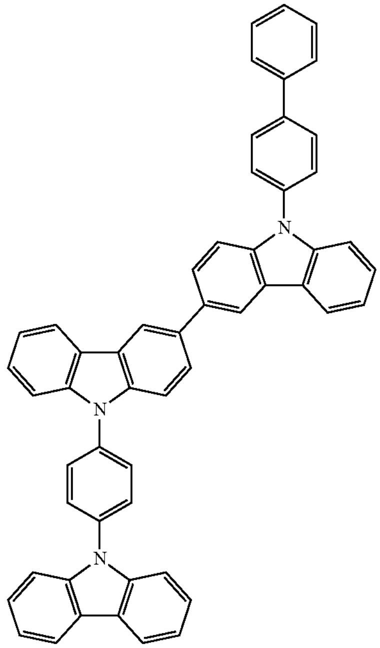 [SMILES: c1ccc(-c2ccc(-n3c4ccccc4c4cc(-c5ccc6c(c5)c5ccccc5n6-c5ccc(-n6c7ccccc7c7ccccc76)cc5)ccc43)cc2)cc1] | CAS-1413936-97-6 |
| 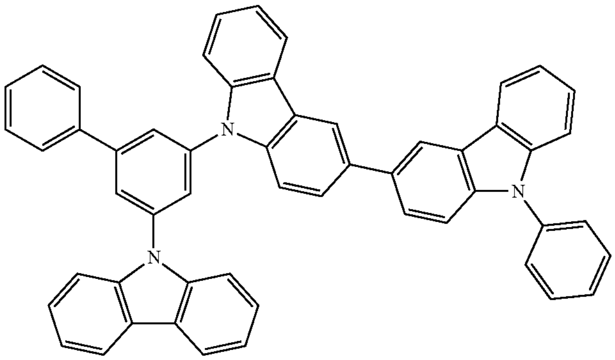 [SMILES: c1ccc(-c2cc(-n3c4ccccc4c4ccccc43)cc(-n3c4ccccc4c4cc(-c5ccc6c(c5)c5ccccc5n6-c5ccccc5)ccc43)c2)cc1] | CAS-1413937-08-2 |
| 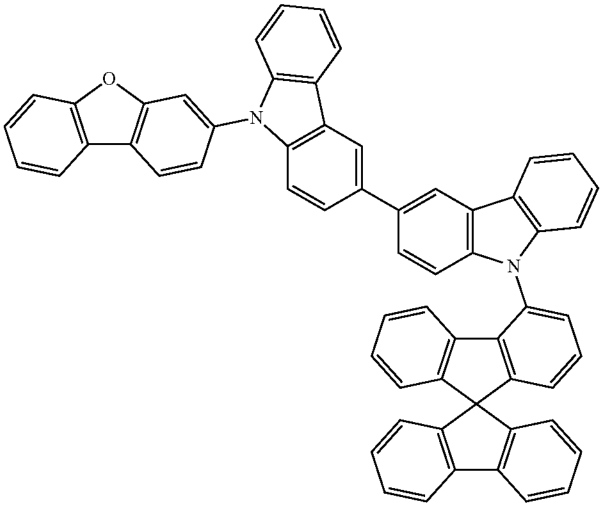 [SMILES: c1ccc2c(c1)-c1ccccc1C21c2ccccc2-c2c(-n3c4ccccc4c4cc(-c5ccc6c(c5)c5ccccc5n6-c5ccc6c(c5)oc5ccccc56)ccc43)cccc21] | CAS-1890157-92-2 |

TABLE 9-continued
| Structure | CAS number |
| --- | --- |
| 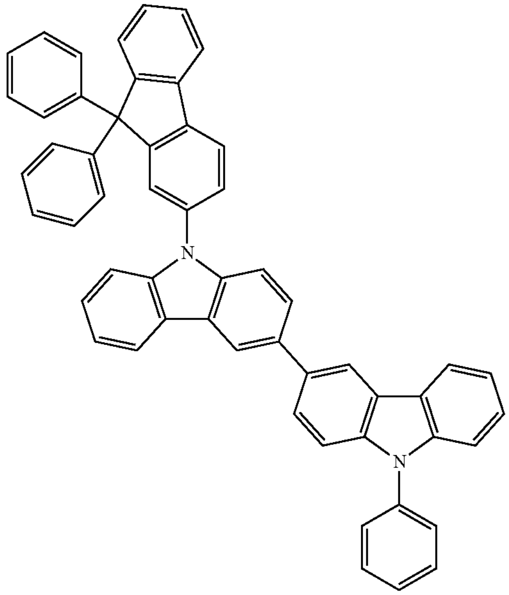 [SMILES: c1ccc(-n2c3ccccc3c3cc(-c4ccc5c(c4)c4ccccc4n5-c4ccc5c(c4)C(c4ccccc4)(c4ccccc4)c4ccccc4-5)ccc32)cc1] | CAS-1415348-93-4 |
| 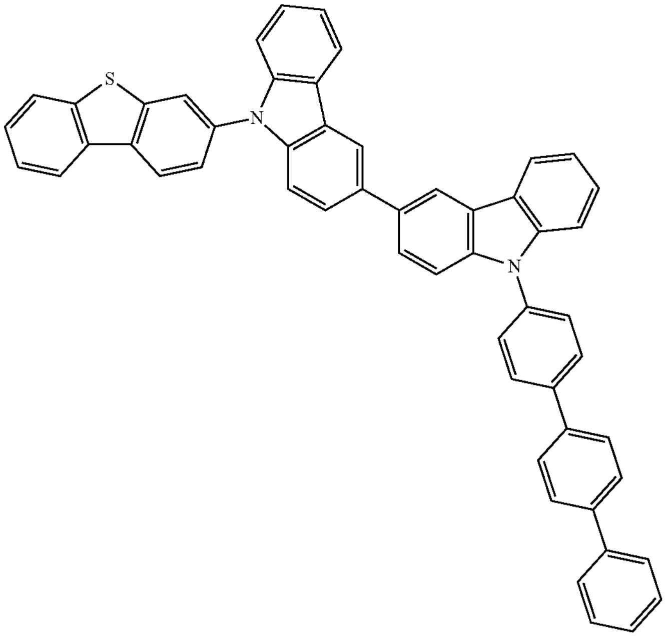 [SMILES: c1ccc(-c2ccc(-c3ccc(-n4c5ccccc5c5cc(-c6ccc7c(c6)c6ccccc6n7-c6ccc7c(c6)sc6ccccc67)ccc54)cc3)cc2)cc1] | CAS-1889262-89-8 |
| 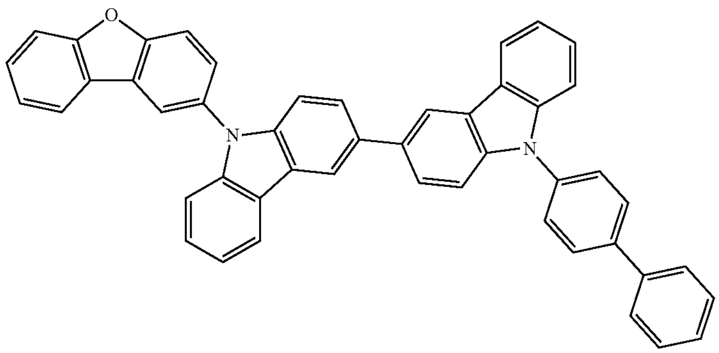 [SMILES: c1ccc(-c2ccc(-n3c4ccccc4c4cc(-c5ccc6c(c5)c5ccccc5n6-c5ccc6oc7ccccc7c6c5)ccc43)cc2)cc1] | CAS-1415348-99-0 |

TABLE 9-continued
| Structure | CAS number |
|---|---|
| 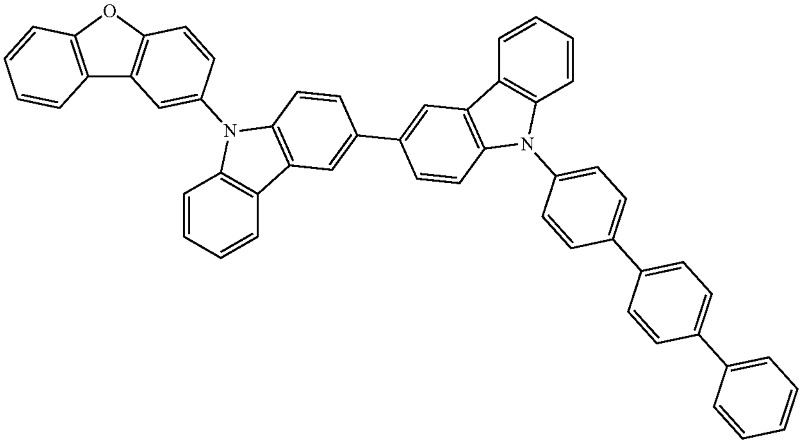 [SMILES: c1ccc(-c2ccc(-c3ccc(-n4c5ccccc5c5cc(-c6ccc7c(c6)c6ccccc6n7-c6ccc7oc8ccccc8c7c6)ccc54)cc3)cc2)cc1] | CAS-1890156-90-7 |
| 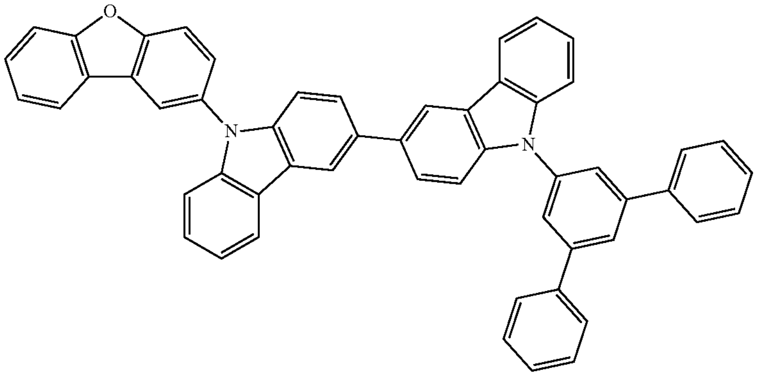 [SMILES: c1ccc(-c2cc(-c3ccccc3)cc(-n3c4ccccc4c4cc(-c5ccc6c(c5)c5ccccc5n6-c5ccc6oc7ccccc7c6c5)ccc43)c2)cc1] | CAS-1415349-00-6 |
| 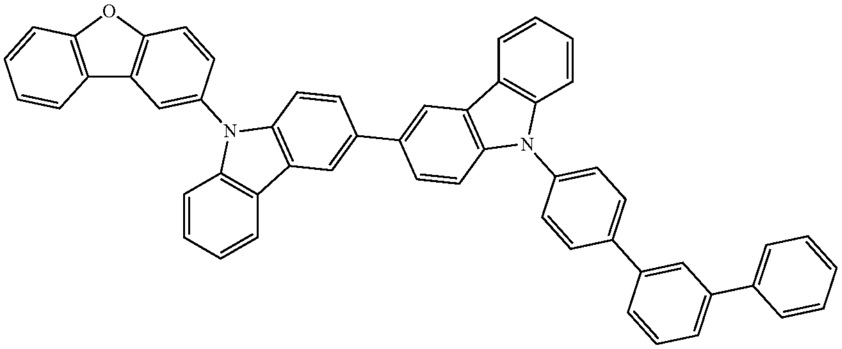 [SMILES: c1ccc(-c2cccc(-c3ccc(-n4c5ccccc5c5cc(-c6ccc7c(c6)c6ccccc6n7-c6ccc7oc8ccccc8c7c6)ccc54)cc3)c2)cc1] | CAS-1890156-91-8 |
| 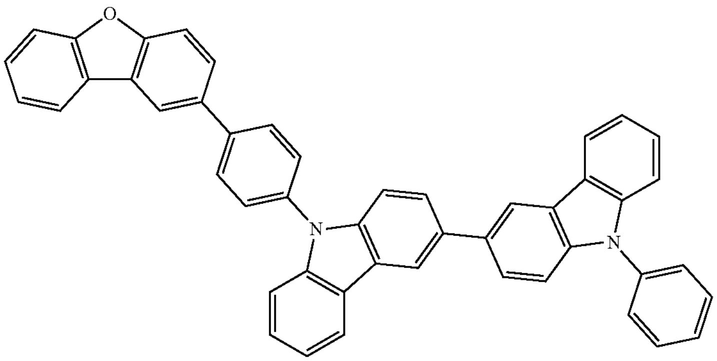 | CAS-1415349-01-7 |

TABLE 9-continued
| Structure | CAS number |
|---|---|
| 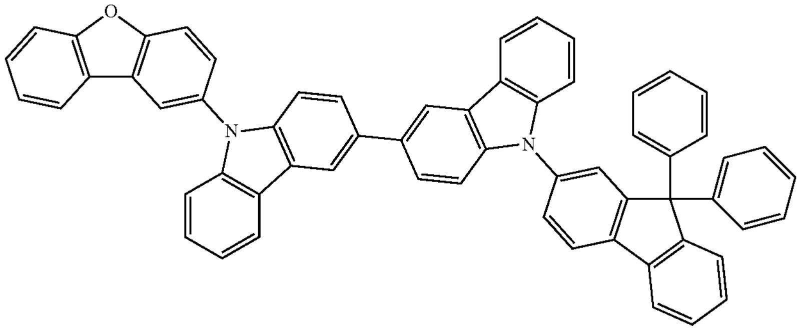 [SMILES: c1ccc(C2(c3ccccc3)c3ccccc3-c3ccc(-n4c5ccccc5c5cc(-c6ccc7c(c6)c6ccccc6n7-c6ccc7oc8ccccc8c7c6)ccc54)cc32)cc1] | CAS-1890157-12-6 |
| 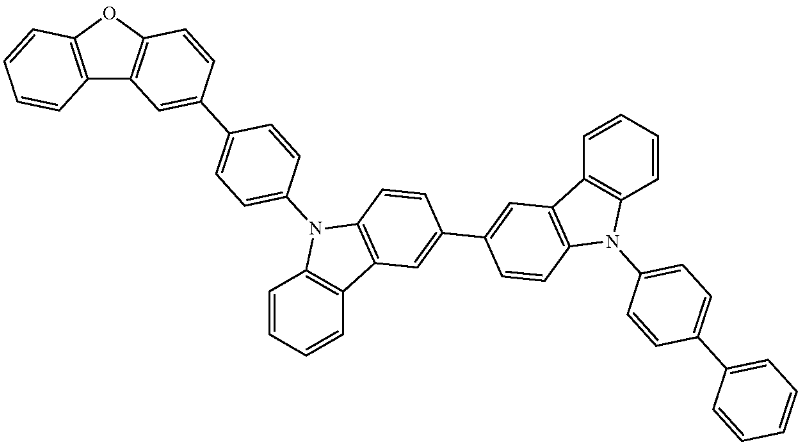 [SMILES: c1ccc(-c2ccc(-n3c4ccccc4c4cc(-c5ccc6c(c5)c5ccccc5n6-c5ccc(-c6ccc7oc8ccccc8c7c6)cc5)ccc43)cc2)cc1] | CAS-1415349-02-8 |
| 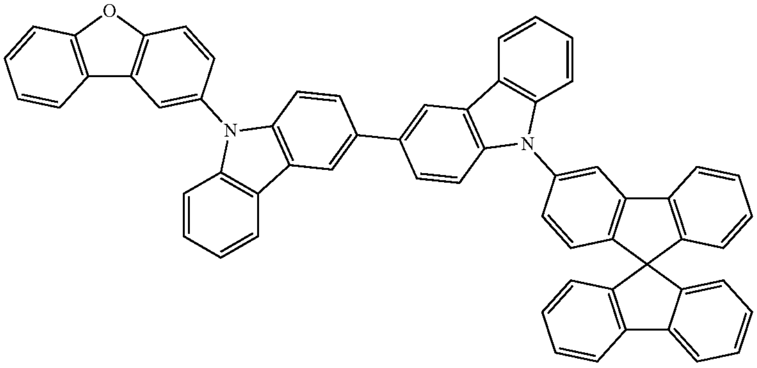 [SMILES: c1ccc2c(c1)-c1ccccc1C21c2ccccc2-c2cc(-n3c4ccccc4c4cc(-c5ccc6c(c5)c5ccccc5n6-c5ccc6oc7ccccc7c6c5)ccc43)ccc21] | CAS-1890157-13-7 |

TABLE 9-continued
| Structure | CAS number |
|---|---|
| 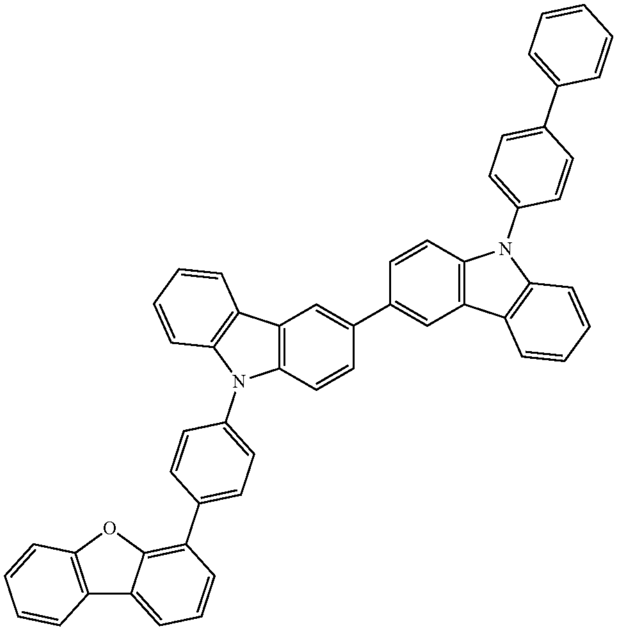 [SMILES: c1ccc(-c2ccc(-n3c4ccccc4c4cc(-c5ccc6c(c5)c5ccccc5n6-c5ccc(-c6cccc7c6oc6ccccc67)cc5)ccc43)cc2)cc1] | CAS-1415349-03-9 |
| 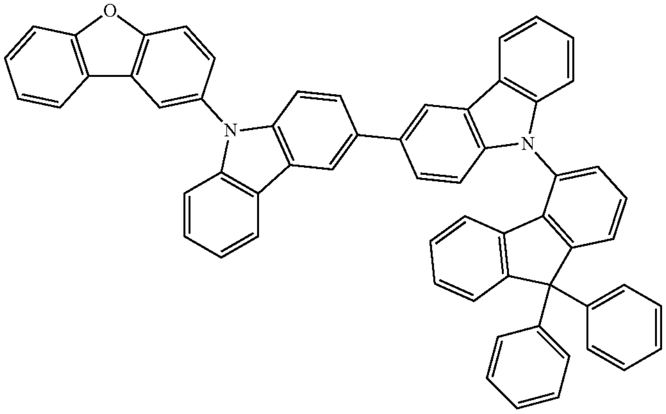 [SMILES: c1ccc(C2(c3ccccc3)c3ccccc3-c3c(-n4c5ccccc5c5cc(-c6ccc7c(c6)c6ccccc6n7-c6ccc7oc8ccccc8c7c6)ccc54)cccc32)cc1] | CAS-1890157-14-8 |
| 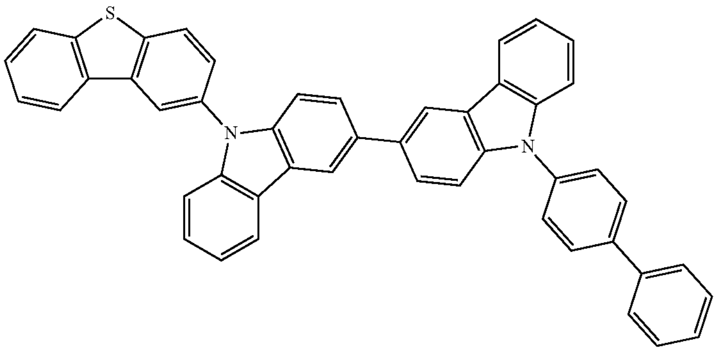 [SMILES: c1ccc(-c2ccc(-n3c4ccccc4c4cc(-c5ccc6c(c5)c5ccccc5n6-c5ccc6sc7ccccc7c6c5)ccc43)cc2)cc1] | CAS-1415349-04-0 |

TABLE 9-continued
| Structure | CAS number |
| --- | --- |
| 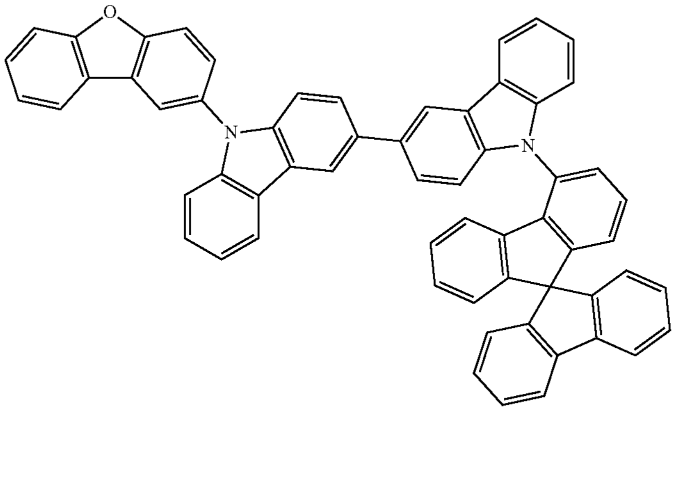 [SMILES: c1ccc2c(c1)-c1ccccc1C21c2ccccc2-c2c(-n3c4ccccc4c4cc(-c5ccc6c(c5)c5ccccc5n6-c5ccc6oc7ccccc7c6c5)ccc43)cccc21] | CAS-1890157-37-5 |
| 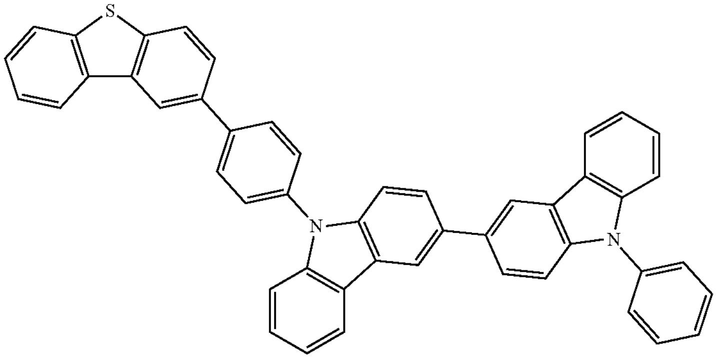 [SMILES: c1ccc(-n2c3ccccc3c3cc(-c4ccc5c(c4)c4ccccc4n5-c4ccc(-c5ccc6sc7ccccc7c6c5)cc4)ccc32)cc1] | CAS-1415349-05-1 |
| 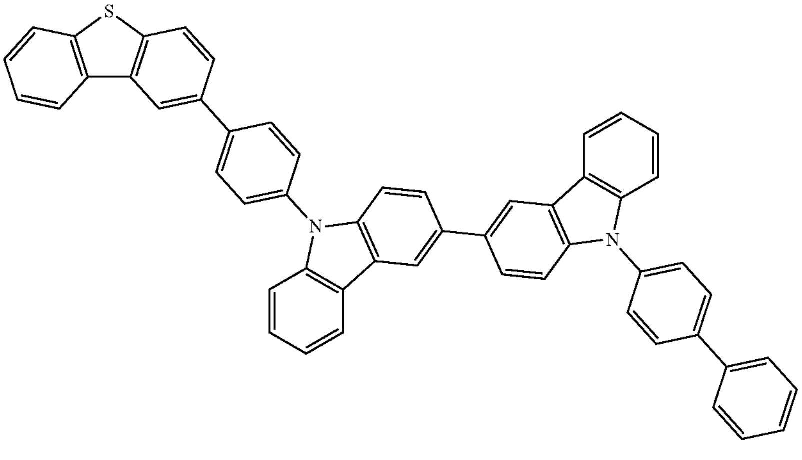 | CAS-1415349-06-2 |

TABLE 9-continued
| Structure | CAS number |
| --- | --- |
| 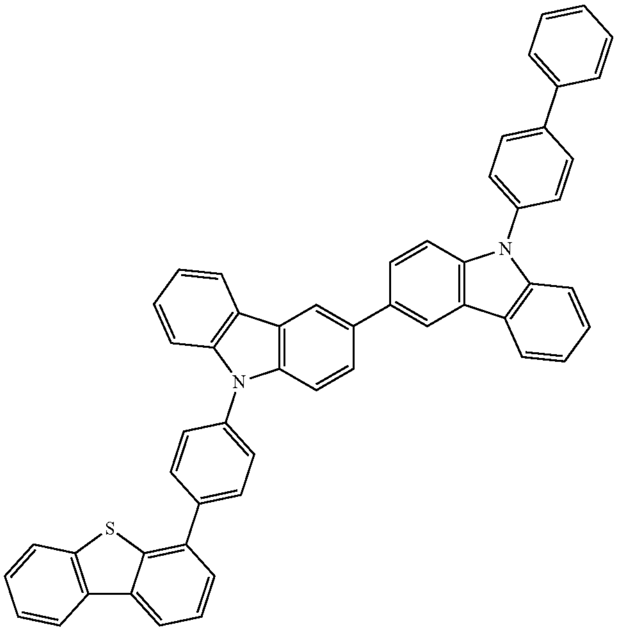 | CAS-1415349-07-3 |
| 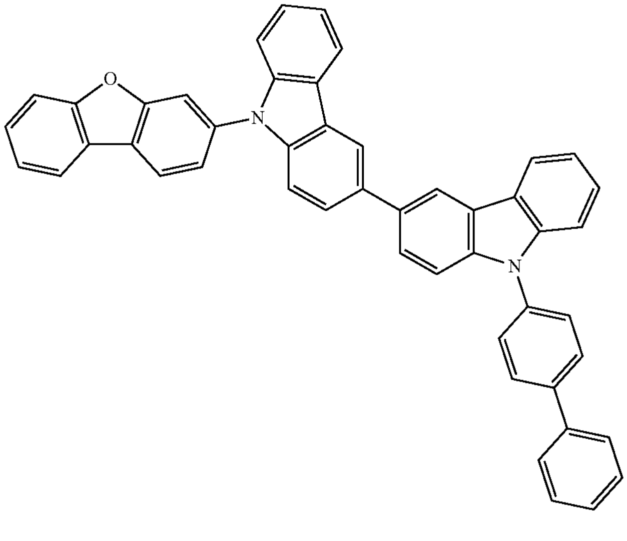 [SMILES: c1ccc(-c2ccc(-n3c4ccccc4c4cc(-c5ccc6c(c5)c5ccccc5n6-c5ccc6c(c5)oc5ccccc56)ccc43)cc2)cc1] | CAS-1890157-41-1 |

TABLE 9-continued
| Structure | CAS number |
| --- | --- |
| 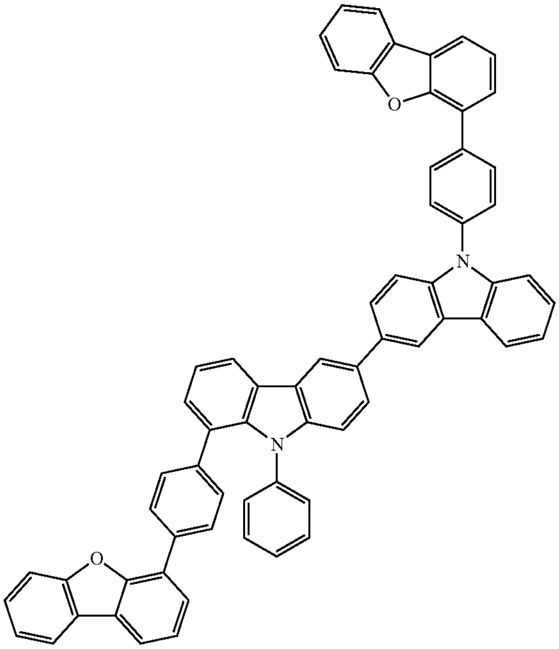 [SMILES: c1ccc(-n2c3ccc(-c4ccc5c(c4)c4ccccc4n5-c4ccc(-c5cccc6c5oc5ccccc56)cc4)cc3c3cccc(-c4ccc(-c5cccc6c5oc5ccccc56)cc4)c32)cc1] | CAS-1415422-76-2 |
| 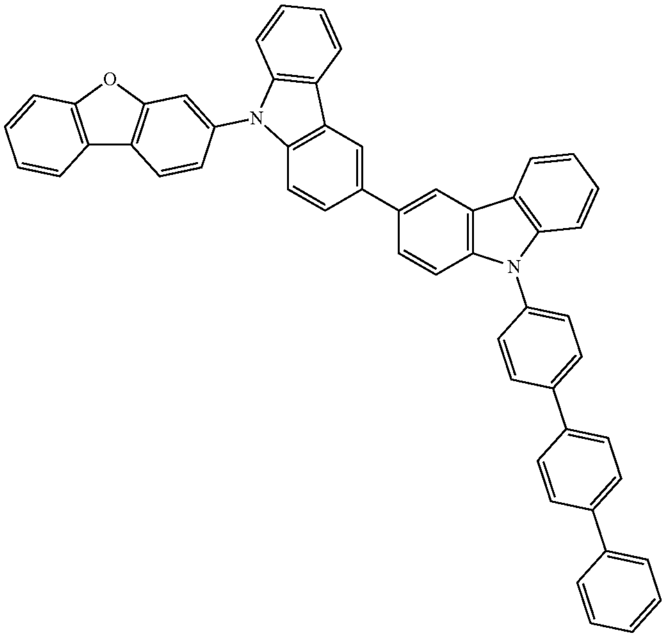 [SMILES: c1ccc(-c2ccc(-c3ccc(-n4c5ccccc5c5cc(-c6ccc7c(c6)c6ccccc6n7-c6ccc7c(c6)oc6ccccc67)ccc54)cc3)cc2)cc1] | CAS-1890157-42-2 |

TABLE 9-continued
| Structure | CAS number |
|---|---|
| 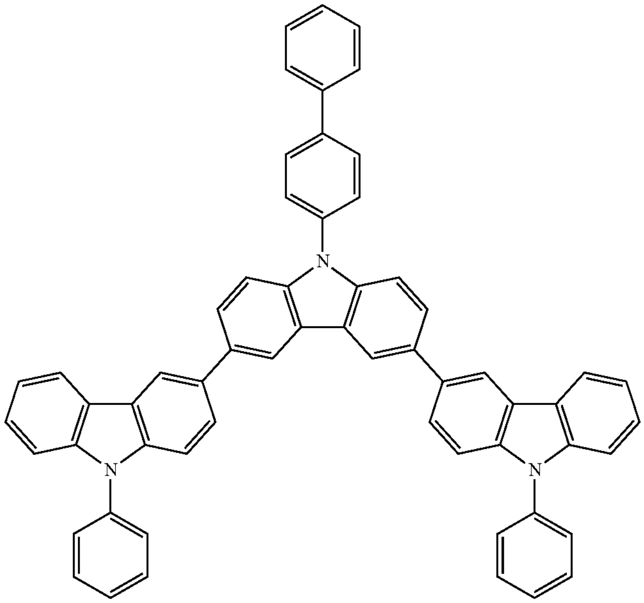 [SMILES: c1ccc(-c2ccc(-n3c4ccc(-c5ccc6c(c5)c5ccccc5n6-c5ccccc5)cc4c4cc(-c5ccc6c(c5)c5ccccc5n6-c5ccccc5)ccc43)cc2)cc1] | CAS-1422451-46-4 |
| 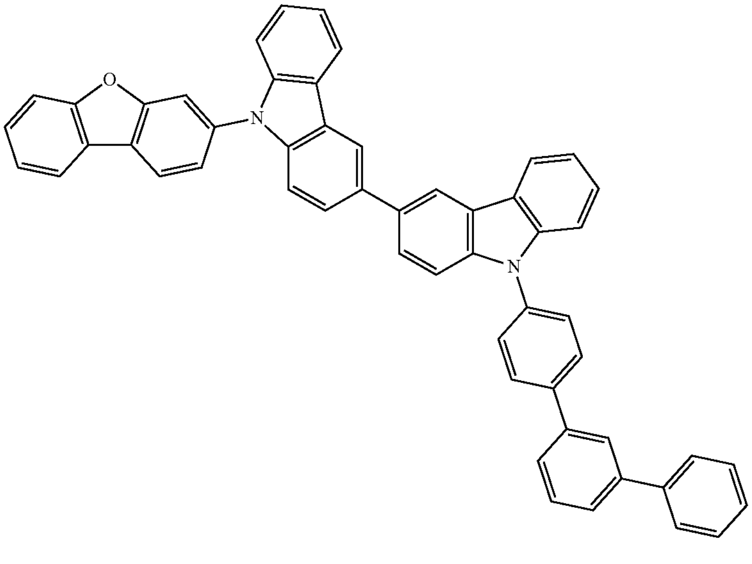 [SMILES: c1ccc(-c2cccc(-c3ccc(-n4c5ccccc5c5cc(-c6ccc7c(c6)c6ccccc6n7-c6ccc7c(c6)oc6ccccc67)ccc54)cc3)c2)cc1] | CAS-1890157-43-3 |

TABLE 9-continued
| Structure | CAS number |
|---|---|
| 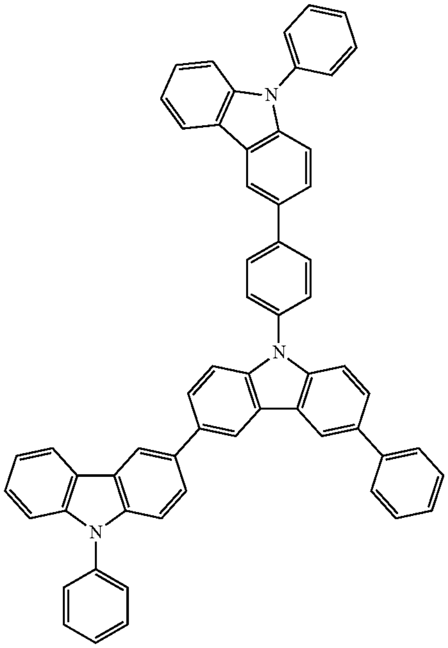 [SMILES: c1ccc(-c2ccc3c(c2)c2cc(-c4ccc5c(c4)c4ccccc4n5-c4ccccc4)ccc2n3-c2ccc(-c3ccc4c(c3)c3ccccc3n4-c3ccccc3)cc2)cc1] | CAS-1422451-48-6 |
| 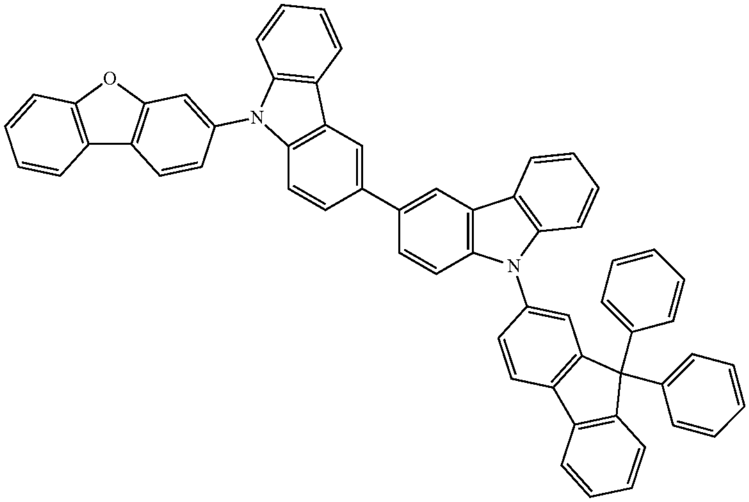 [SMILES: c1ccc(C2(c3ccccc3)c3ccccc3-c3ccc(-n4c5ccccc5c5cc(-c6ccc7c(c6)c6ccccc6n7-c6ccc7c(c6)oc6ccccc67)ccc54)cc32)cc1] | CAS-1890157-64-8 |

TABLE 9-continued
| Structure | CAS number |
|---|---|
| 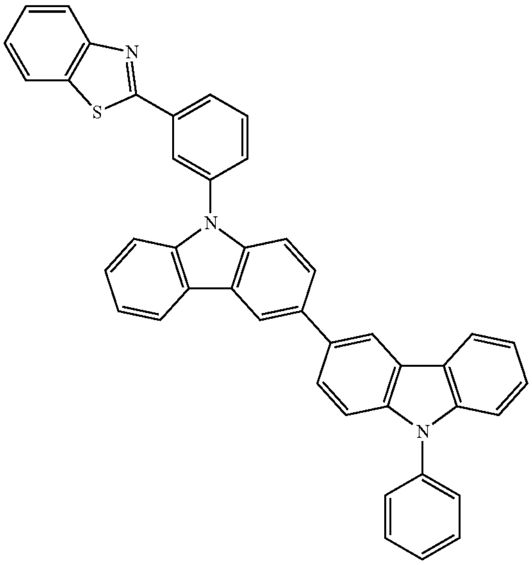 [SMILES: c1ccc(-n2c3ccccc3c3cc(-c4ccc5c(c4)c4ccccc4n5-c4cccc(-c5nc6ccccc6s5)c4)ccc32)cc1] | CAS-1445952-53-3 |
| 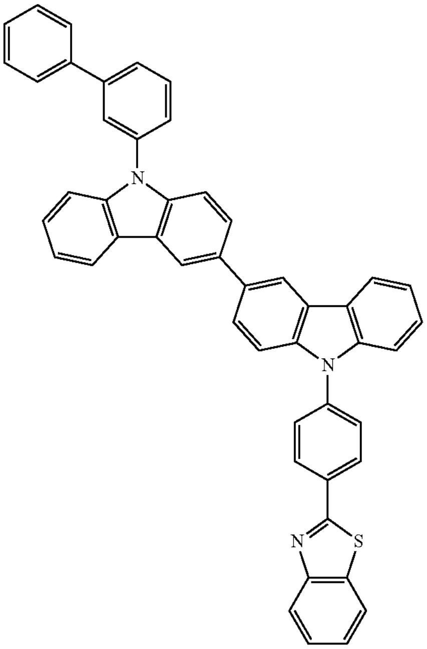 [SMILES: c1ccc(-c2cccc(-n3c4ccccc4c4cc(-c5ccc6c(c5)c5ccccc5n6-c5ccc(-c6nc7ccccc7s6)cc5)ccc43)c2)cc1] | CAS-1445952-58-8 |

TABLE 9-continued
| Structure | CAS number |
|---|---|
| 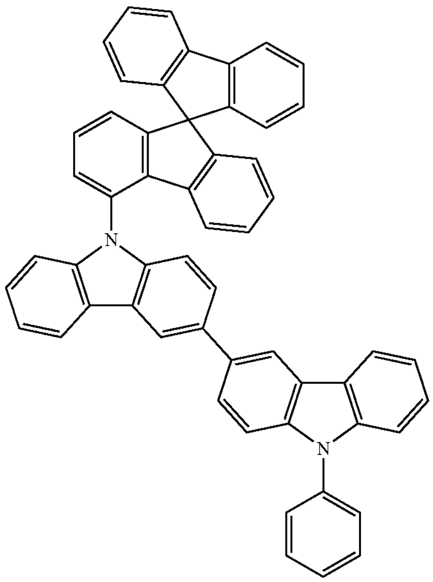 [SMILES: c1ccc(-n2c3ccccc3c3cc(-c4ccc5c(c4)c4ccccc4n5-c4cccc5c4-c4ccccc4C54c5ccccc5-c5ccccc54)ccc32)cc1] | CAS-1450933-86-4 |
| 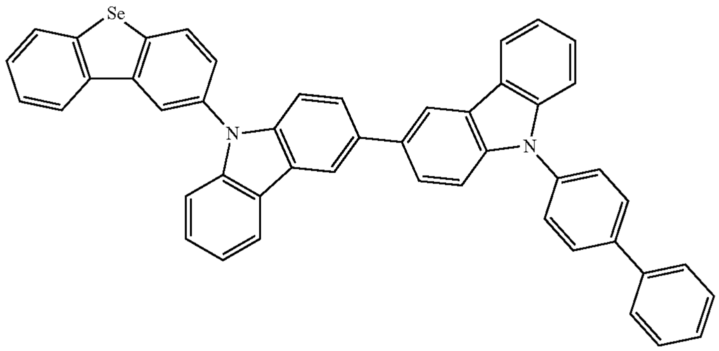 [SMILES: c1ccc(-c2ccc(-n3c4ccccc4c4cc(-c5ccc6c(c5)c5ccccc5n6-c5ccc6[se]c7ccccc7c6c5)ccc43)cc2)cc1] | CAS-1894194-07-0 |
| 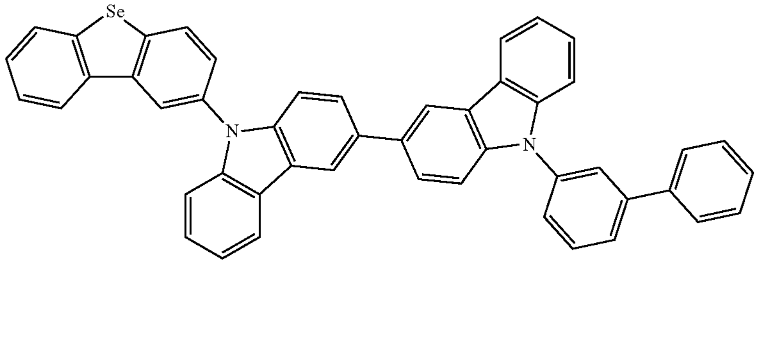 [SMILES: c1ccc(-c2cccc(-n3c4ccccc4c4cc(-c5ccc6c(c5)c5ccccc5n6-c5ccc6[se]c7ccccc7c6c5)ccc43)c2)cc1] | CAS-1894194-09-2 |

TABLE 9-continued
| Structure | CAS number |
| --- | --- |
| 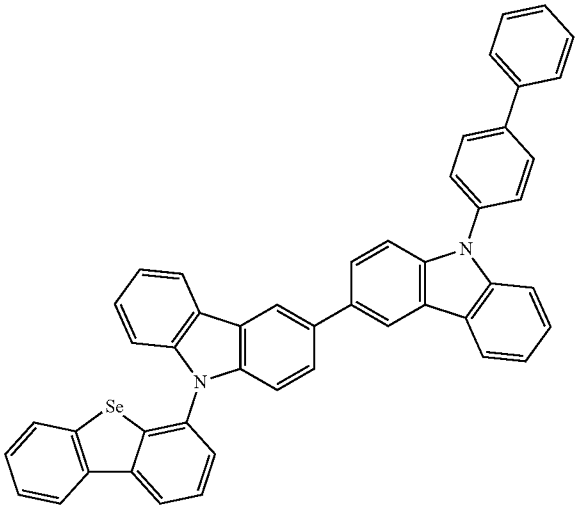 | CAS-1894194-08-1 |
| 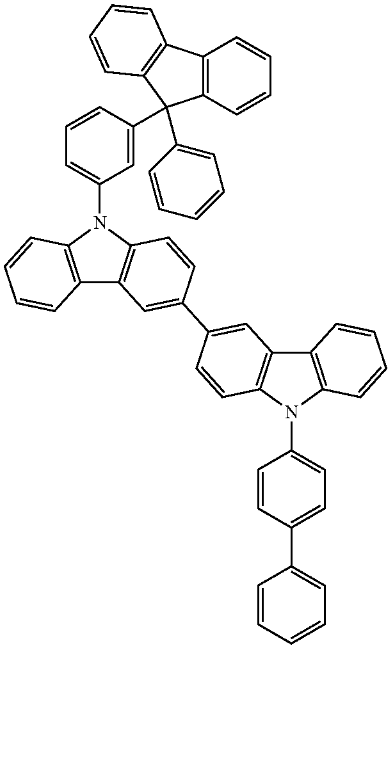 [SMILES: c1ccc(-c2ccc(-n3c4ccccc4c4cc(-c5ccc6c(c5)c5ccccc5n6-c5cccc(C6(c7ccccc7)c7ccccc7-c7ccccc76)c5)ccc43)cc2)cc1] | CAS-1919031-93-8 |

TABLE 9-continued
| Structure | CAS number |
| --- | --- |
| 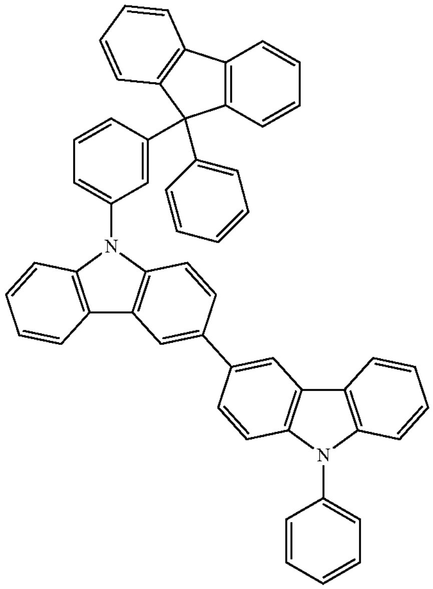 [SMILES: c1ccc(-n2c3ccccc3c3cc(-c4ccc5c(c4)c4ccccc4n5-c4cccc(C5(c6ccccc6)c6ccccc6-c6ccccc65)c4)ccc32)cc1] | CAS-1919031-92-7 |
| 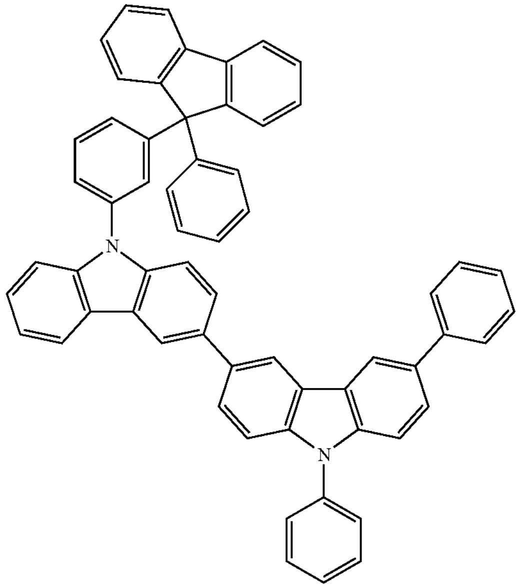 [SMILES: c1ccc(-c2ccc3c(c2)c2cc(-c4ccc5c(c4)c4ccccc4n5-c4cccc(C5(c6ccccc6)c6ccccc6-c6ccccc65)c4)ccc2n3-c2ccccc2)cc1] | CAS-1919031-95-0 |

TABLE 9-continued
| Structure | CAS number |
| --- | --- |
| 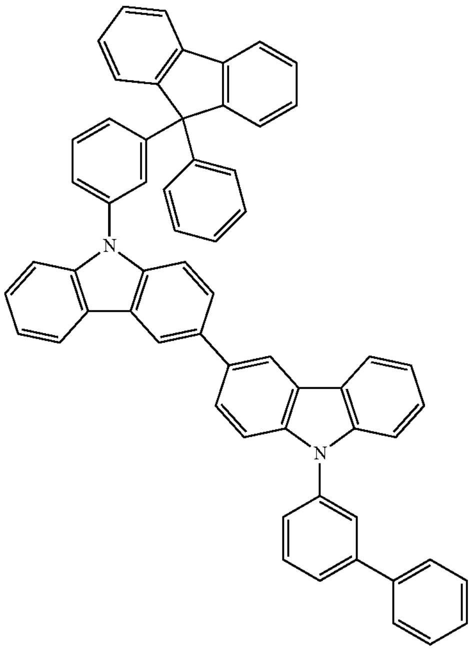 [SMILES: c1ccc(-c2cccc(-n3c4ccccc4c4cc(-c5ccc6c(c5)c5ccccc5n6-c5cccc(C6(c7ccccc7)c7ccccc7-c7ccccc76)c5)ccc43)c2)cc1] | CAS-1919031-94-9 |
| 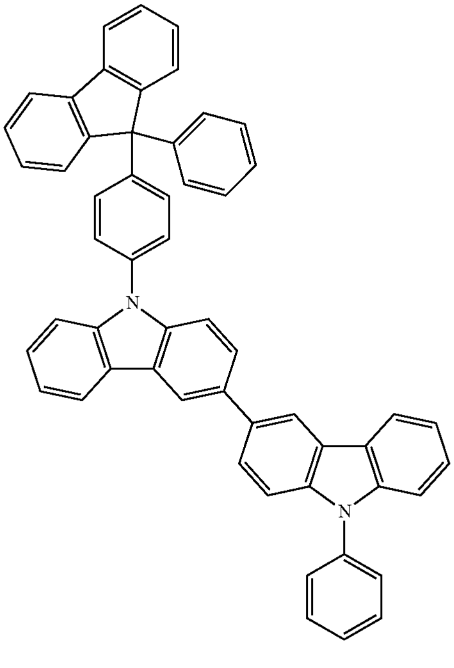 [SMILES: c1ccc(-n2c3ccccc3c3cc(-c4ccc5c(c4)c4ccccc4n5-c4ccc(C5(c6ccccc6)c6ccccc6-c6ccccc65)cc4)ccc32)cc1] | CAS-1919031-97-2 |

TABLE 9-continued
| Structure | CAS number |
|---|---|
| 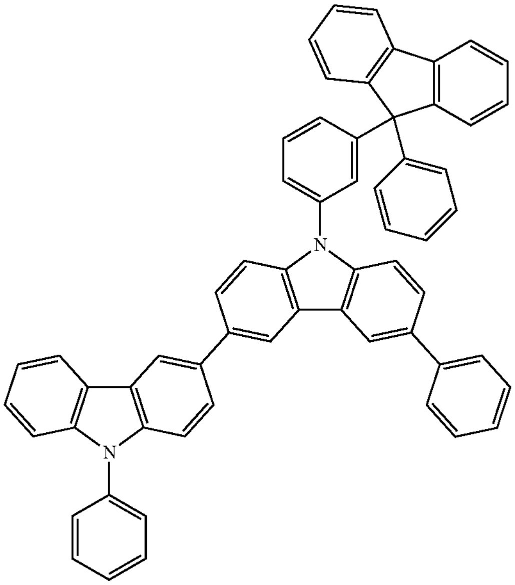 [SMILES: c1ccc(-c2ccc3c(c2)c2cc(-c4ccc5c(c4)c4ccccc4n5-c4ccccc4)ccc2n3-c2cccc(C3(c4ccccc4)c4ccccc4-c4ccccc43)c2)cc1] | CAS-1919031-96-1 |
| 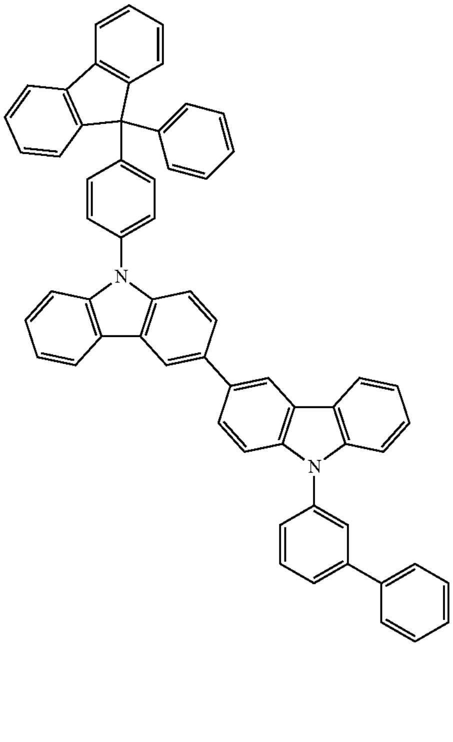 [SMILES: c1ccc(-c2cccc(-n3c4ccccc4c4cc(-c5ccc6c(c5)c5ccccc5n6-c5ccc(C6(c7ccccc7)c7ccccc7-c7ccccc76)cc5)ccc43)c2)cc1] | CAS-1919031-99-4 |

TABLE 9-continued
| Structure | CAS number |
| --- | --- |
| 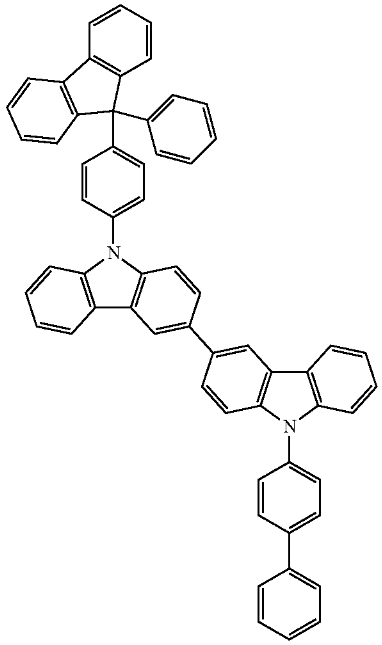 [SMILES: c1ccc(-c2ccc(-n3c4ccccc4c4cc(-c5ccc6c(c5)c5ccccc5n6-c5ccc(C6(c7ccccc7)c7ccccc7-c7ccccc76)cc5)ccc43)cc2)cc1] | CAS-1919031-98-3 |
| 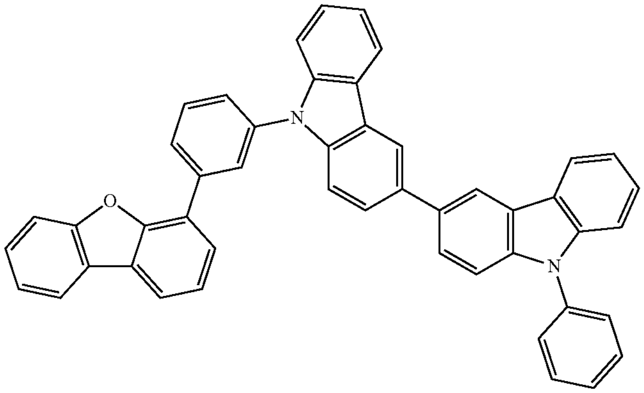 [SMILES: c1ccc(-n2c3ccccc3c3cc(-c4ccc5c(c4)c4ccccc4n5-c4cccc(-c5cccc6c5oc5ccccc56)c4)ccc32)cc1] | CAS-1598389-98-0 |
| 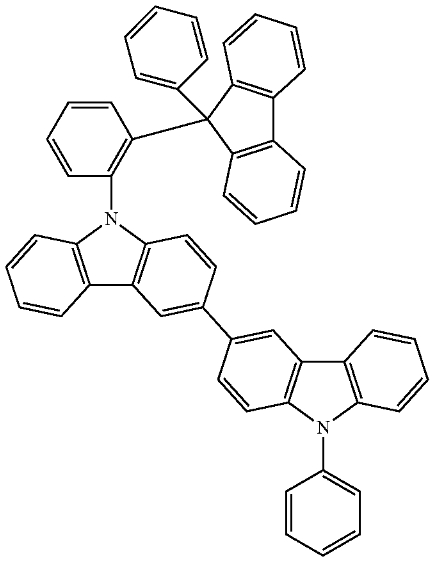 [SMILES: c1ccc(-n2c3ccccc3c3cc(-c4ccc5c(c4)c4ccccc4n5-c4ccccc4C4(c5ccccc5)c5ccccc5-c5ccccc54)ccc32)cc1] | CAS-1919032-02-2 |

TABLE 9-continued
| Structure | CAS number |
| --- | --- |
| 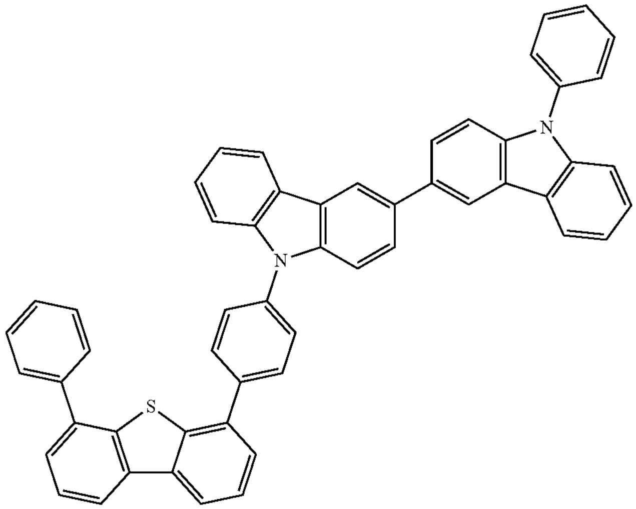 | CAS-1604034-14-1 |
| 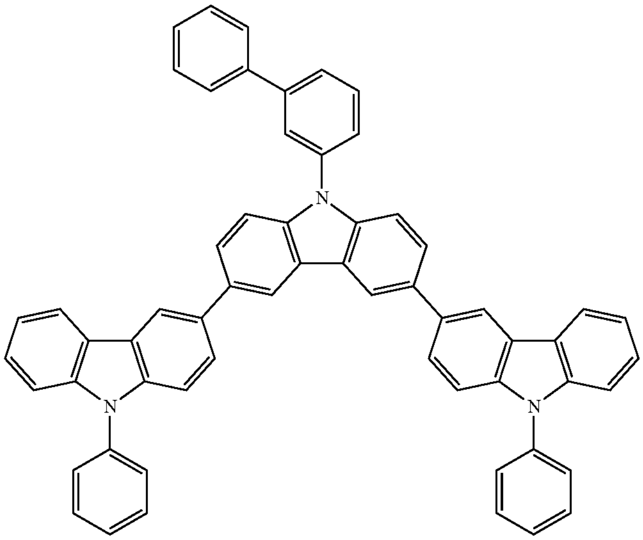 [SMILES: c1ccc(-c2cccc(-n3c4ccc(-c5ccc6c(c5)c5ccccc5n6-c5ccccc5)cc4c4cc(-c5ccc6c(c5)c5ccccc5n6-c5ccccc5)ccc43)c2)cc1] | CAS-1943719-67-2 |
| 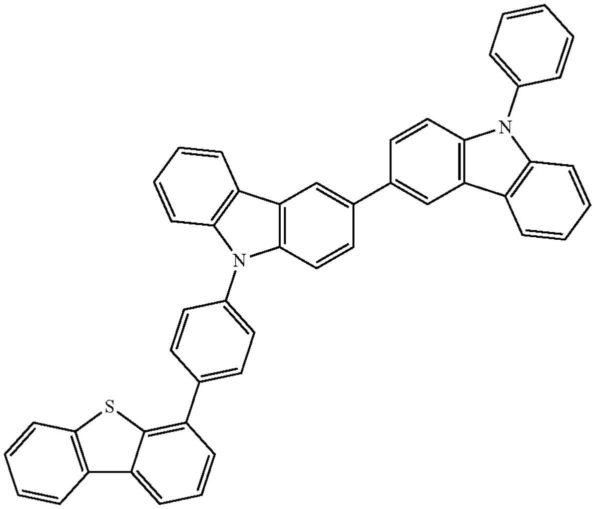 [SMILES: c1ccc(-n2c3ccccc3c3cc(-c4ccc5c(c4)c4ccccc4n5-c4ccc(-c5cccc6c5sc5ccccc56)cc4)ccc32)cc1] | CAS-1604034-02-7 |

TABLE 9-continued
| Structure | CAS number |
| --- | --- |
| 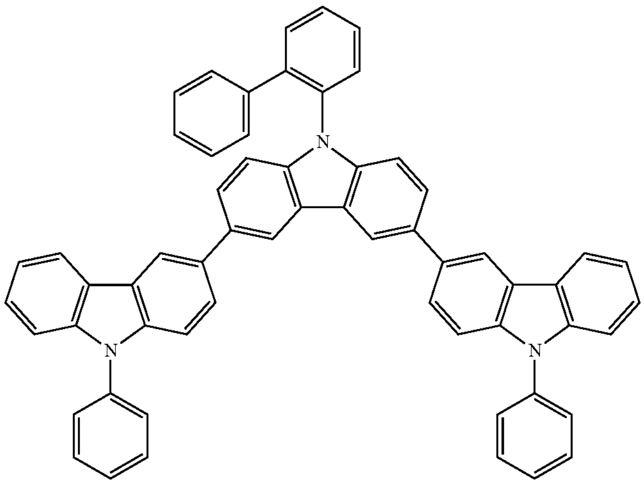 [SMILES: c1ccc(-c2ccccc2-n2c3ccc(-c4ccc5c(c4)c4ccccc4n5-c4ccccc4)cc3c3cc(-c4ccc5c(c4)c4ccccc4n5-c4ccccc4)ccc32)cc1] | CAS-1943719-70-7 |
| 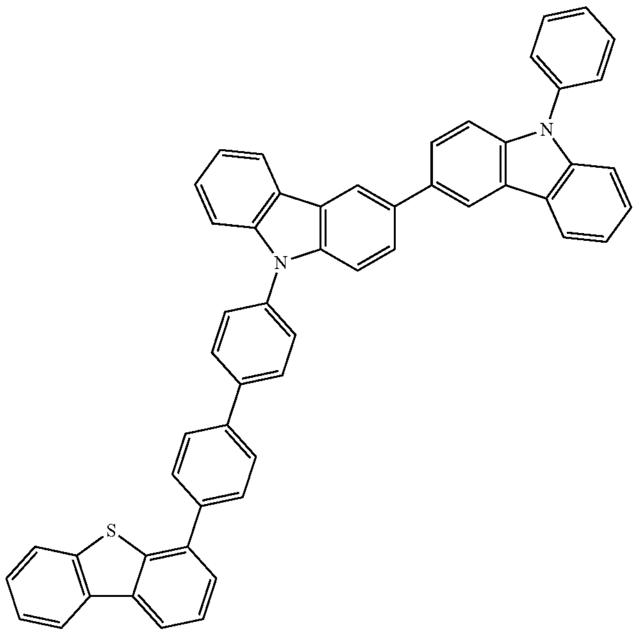 [SMILES: c1ccc(-n2c3ccccc3c3cc(-c4ccc5c(c4)c4ccccc4n5-c4ccc(-c5ccc(-c6cccc7c6sc6ccccc67)cc5)cc4)ccc32)cc1] | CAS-1604034-07-2 |

TABLE 9-continued
| Structure | CAS number |
| --- | --- |
| 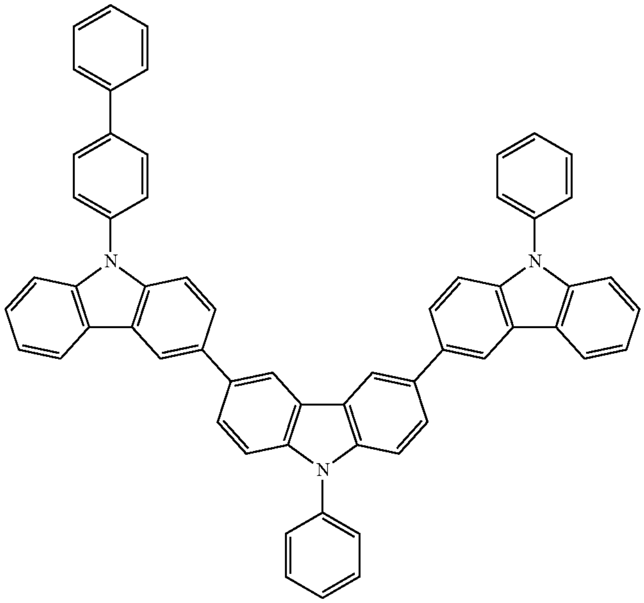 [SMILES: c1ccc(-c2ccc(-n3c4ccccc4c4cc(-c5ccc6c(c5)c5cc(-c7ccc8c(c7)c7ccccc7n8-c7ccccc7)ccc5n6-c5ccccc5)ccc43)cc2)cc1] | CAS-1943719-71-8 |
| 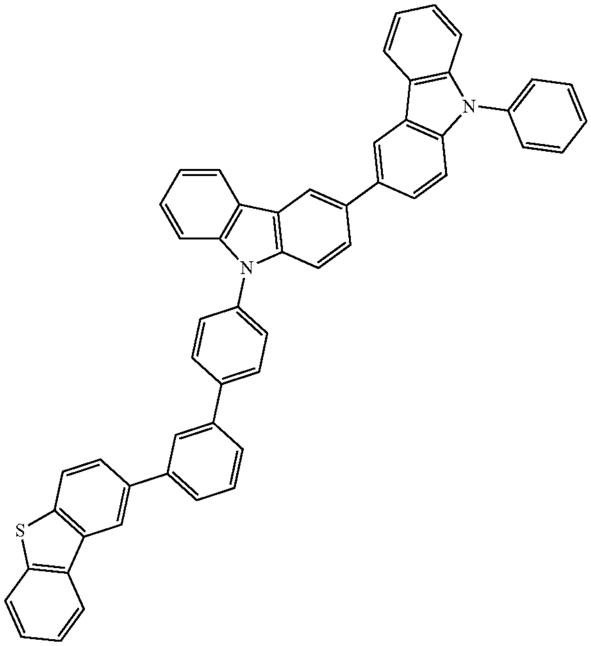 [SMILES: c1ccc(-n2c3ccccc3c3cc(-c4ccc5c(c4)c4ccccc4n5-c4ccc(-c5cccc(-c6ccc7sc8ccccc8c7c6)c5)cc4)ccc32)cc1] | CAS-1604034-12-9 |

TABLE 9-continued
| Structure | CAS number |
|---|---|
| 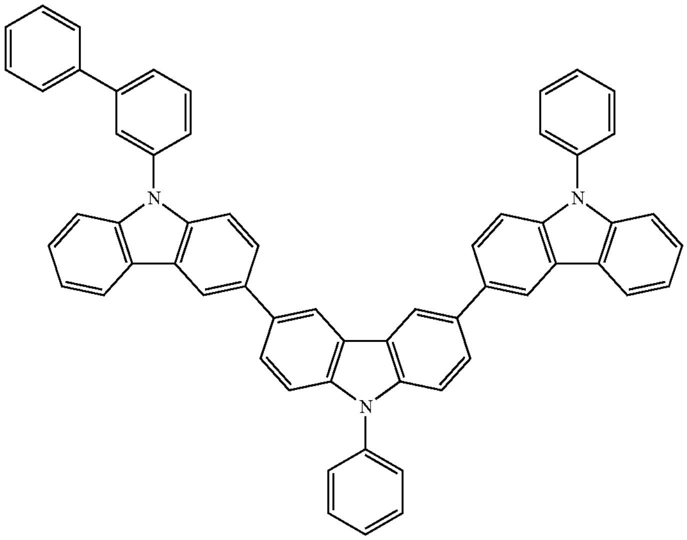 [SMILES: c1ccc(-c2cccc(-n3c4ccccc4c4cc(-c5ccc6c(c5)c5cc(-c7ccc8c(c7)c7ccccc7n8-c7ccccc7)ccc5n6-c5ccccc5)ccc43)c2)cc1] | CAS-1943719-72-9 |
| 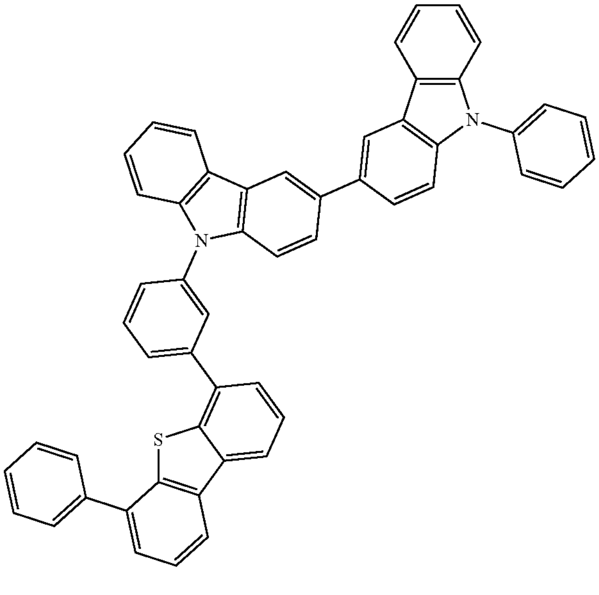 [SMILES: c1ccc(-c2cccc3c2sc2c(-c4cccc(-n5c6ccccc6c6cc(-c7ccc8c(c7)c7ccccc7n8-c7ccccc7)ccc65)c4)cccc23)cc1] | CAS-1622931-00-3 |

TABLE 9-continued
| Structure | CAS number |
|---|---|
| 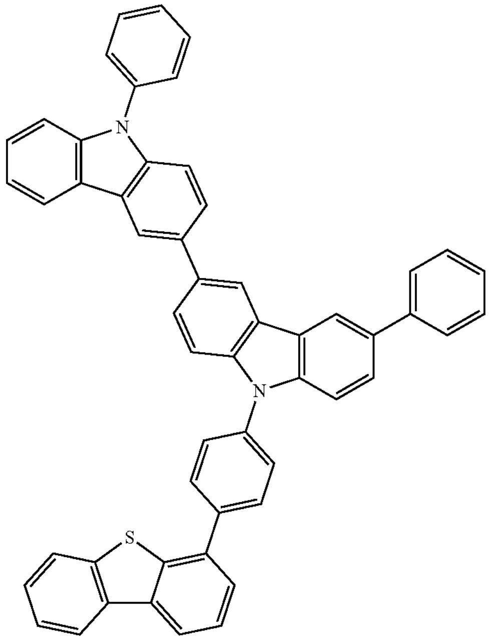 [SMILES: c1ccc(-c2ccc3c(c2)c2cc(-c4ccc5c(c4)c4ccccc4n5-c4ccccc4)ccc2n3-c2ccc(-c3cccc4c3sc3ccccc34)cc2)cc1] | CAS-1604034-15-2 |
| 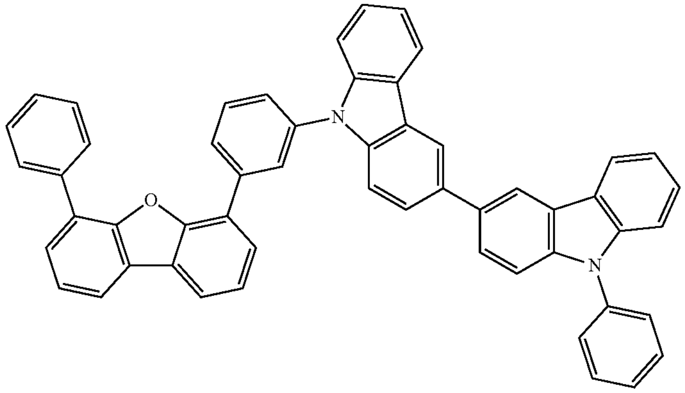 [SMILES: c1ccc(-c2cccc3c2oc2c(-c4cccc(-n5c6ccccc6c6cc(-c7ccc8c(c7)c7ccccc7n8-c7ccccc7)ccc65)c4)cccc23)cc1] | CAS-1622931-01-4 |
| 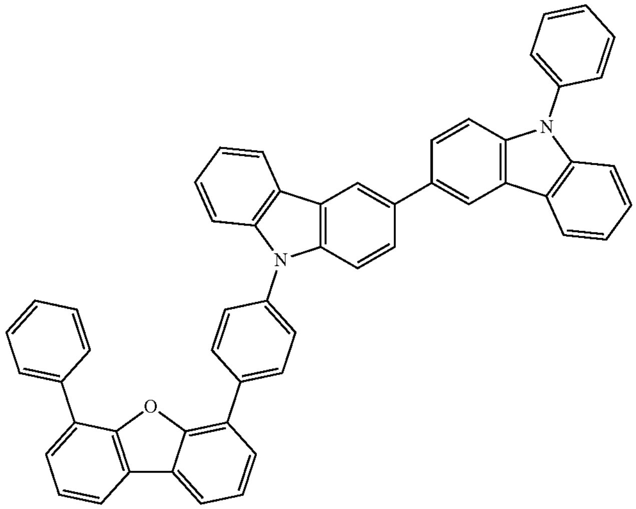 | CAS-1622931-04-7 |

TABLE 9-continued
| Structure | CAS number |
| --- | --- |
| 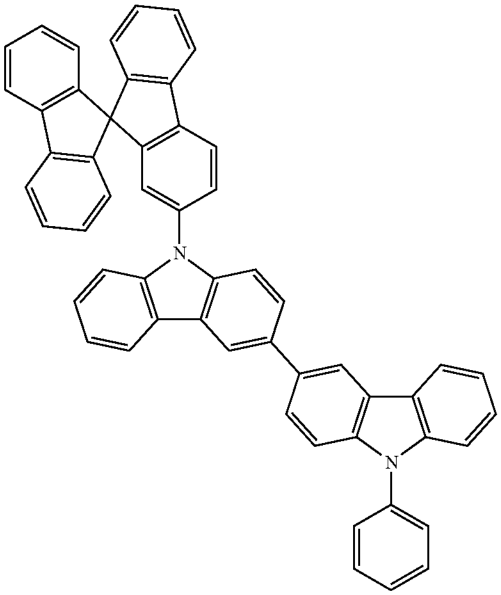 [SMILES: c1ccc(-n2c3ccccc3c3cc(-c4ccc5c(c4)c4ccccc4n5-c4ccc5c(c4)C4(c6ccccc6-c6ccccc64)c4ccccc4-5)ccc32)cc1] | CAS-1630029-28-5 |
| 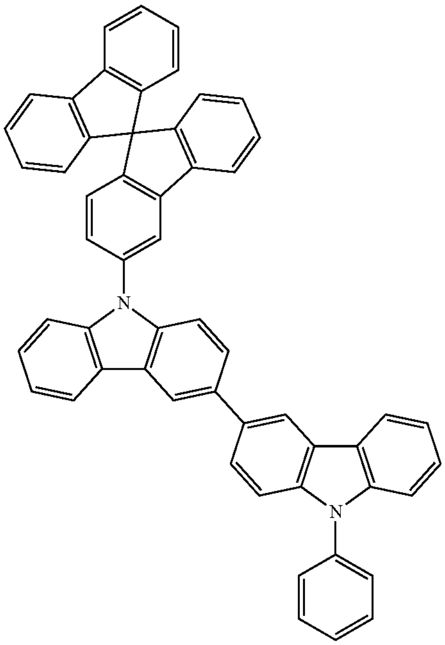 [SMILES: c1ccc(-n2c3ccccc3c3cc(-c4ccc5c(c4)c4ccccc4n5-c4ccc5c(c4)-c4ccccc4C54c5ccccc5-c5ccccc54)ccc32)cc1] | CAS-1630029-29-6 |

TABLE 9-continued
| Structure | CAS number |
|---|---|
| 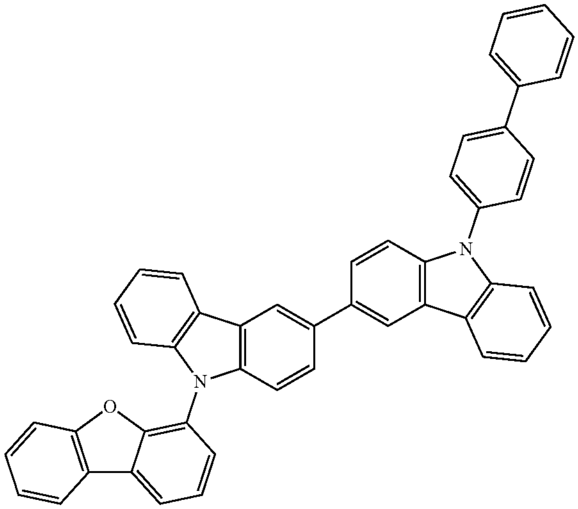 | CAS-1643479-51-9 |
| 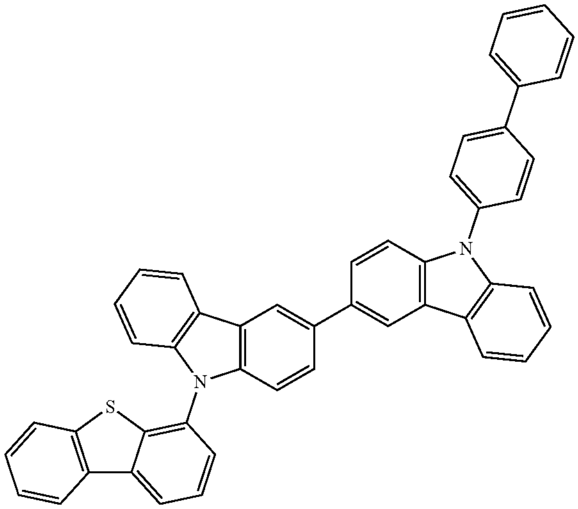 [SMILES: c1ccc(-c2ccc(-n3c4ccccc4c4cc(-c5ccc6c(c5)c5ccccc5n6-c5cccc6c5sc5ccccc56)ccc43)cc2)cc1] | CAS-1643479-52-0 |

TABLE 9-continued
| Structure | CAS number |
| --- | --- |
| 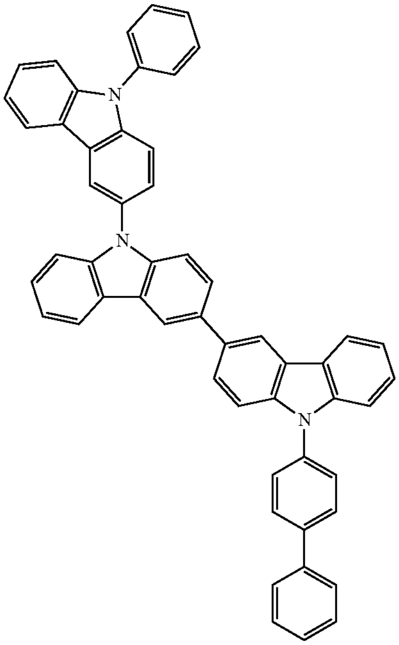 [SMILES: c1ccc(-c2ccc(-n3c4ccccc4c4cc(-c5ccc6c(c5)c5ccccc5n6-c5ccc6c(c5)c5ccccc5n6-c5ccccc5)ccc43)cc2)cc1] | CAS-1643479-54-2 |
| 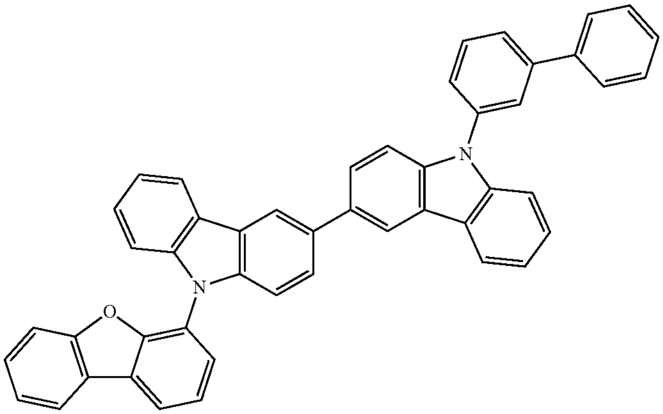 | CAS-1643479-59-7 |
| 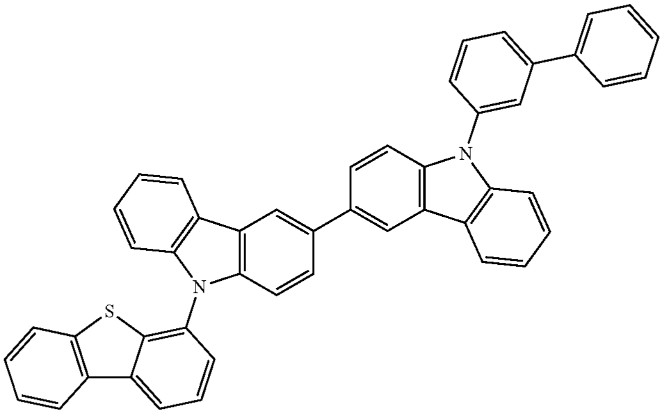 [SMILES: c1ccc(-c2cccc(-n3c4ccccc4c4cc(-c5ccc6c(c5)c5ccccc5n6-c5cccc6c5sc5ccccc56)ccc43)c2)cc1] | CAS-1643479-62-2 |

TABLE 9-continued
| Structure | CAS number |
| --- | --- |
| 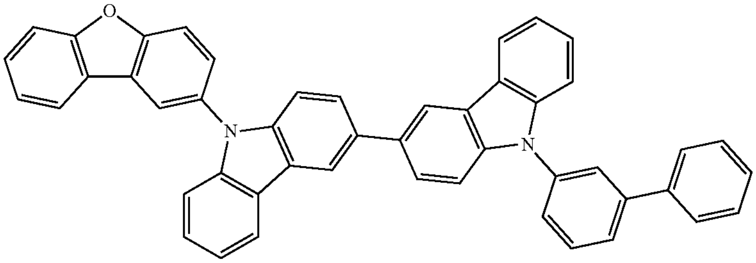 101 | CAS-1643479-68-8 |
| 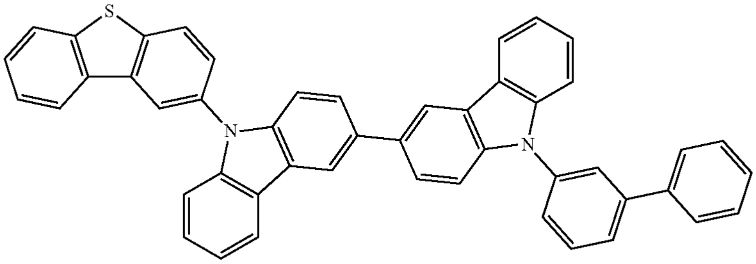 [SMILES: c1ccc(-c2cccc(-n3c4ccccc4c4cc(-c5ccc6c(c5)c5ccccc5n6-c5ccc6sc7ccccc7c6c5)ccc43)c2)cc1] | CAS-1643479-69-9 |
| 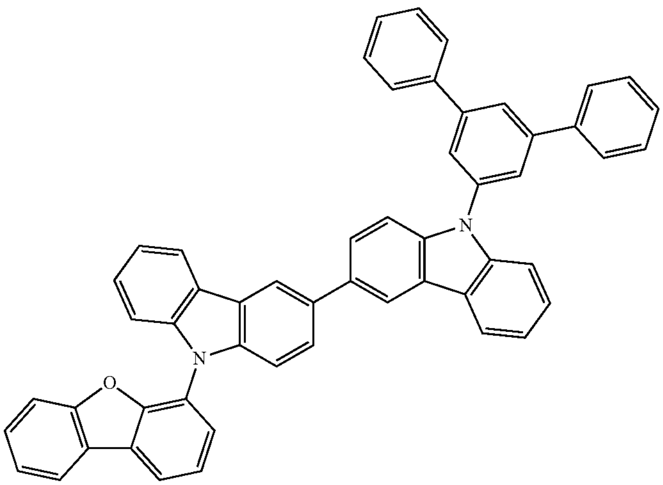 [SMILES: c1ccc(-c2cc(-c3ccccc3)cc(-n3c4ccccc4c4cc(-c5ccc6c(c5)c5ccccc5n6-c5cccc6c5oc5ccccc56)ccc43)c2)cc1] | CAS-1643479-74-6 |

TABLE 9-continued
| Structure | CAS number |
| --- | --- |
| 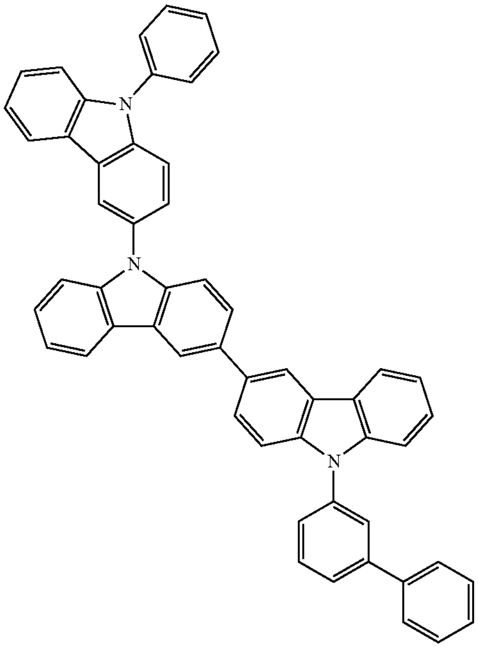 [SMILES: c1ccc(-c2cccc(-n3c4ccccc4c4cc(-c5ccc6c(c5)c5ccccc5n6-c5ccc6c(c5)c5ccccc5n6-c5ccccc5)ccc43)c2)cc1] | CAS-1643479-72-4 |
| 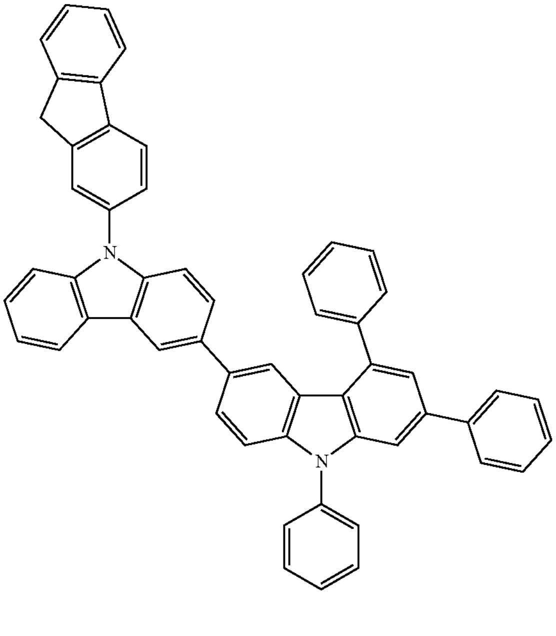 [SMILES: c1ccc(-c2cc(-c3ccccc3)c3c4cc(-c5ccc6c(c5)c5ccccc5n6-c5ccc6c(c5)Cc5ccccc5-6)ccc4n(-c4ccccc4)c3c2)cc1] | CAS-2018307-43-0 |

TABLE 9-continued
| Structure | CAS number |
| --- | --- |
| 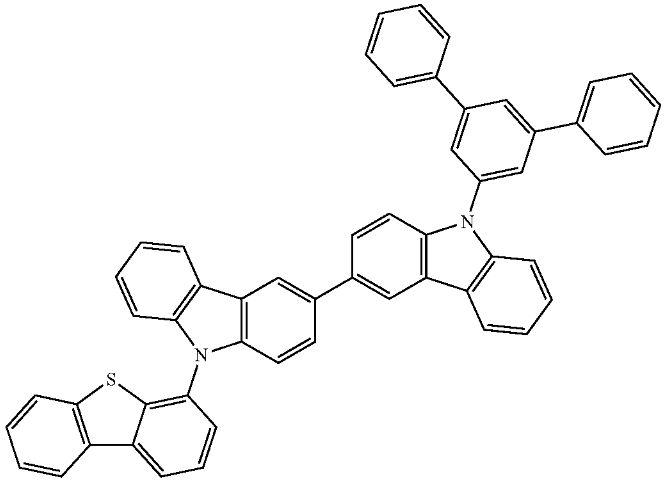 [SMILES: c1ccc(-c2cc(-c3ccccc3)cc(-n3c4ccccc4c4cc(-c5ccc6c(c5)c5ccccc5n6-c5cccc6c5sc5ccccc56)ccc43)c2)cc1] | CAS-1643479-75-7 |
| 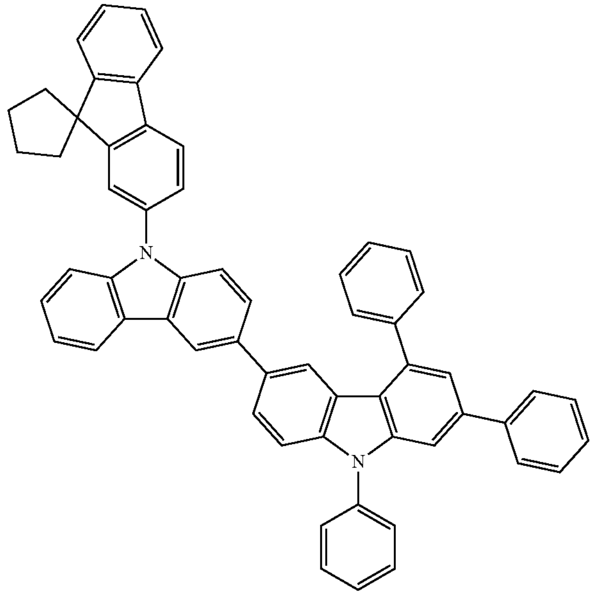 [SMILES: c1ccc(-c2cc(-c3ccccc3)c3c4cc(-c5ccc6c(c5)c5ccccc5n6-c5ccc6c(c5)C5(CCCC5)c5ccccc5-6)ccc4n(-c4ccccc4)c3c2)cc1] | CAS-2018307-47-4 |

TABLE 9-continued
| Structure | CAS number |
| --- | --- |
| 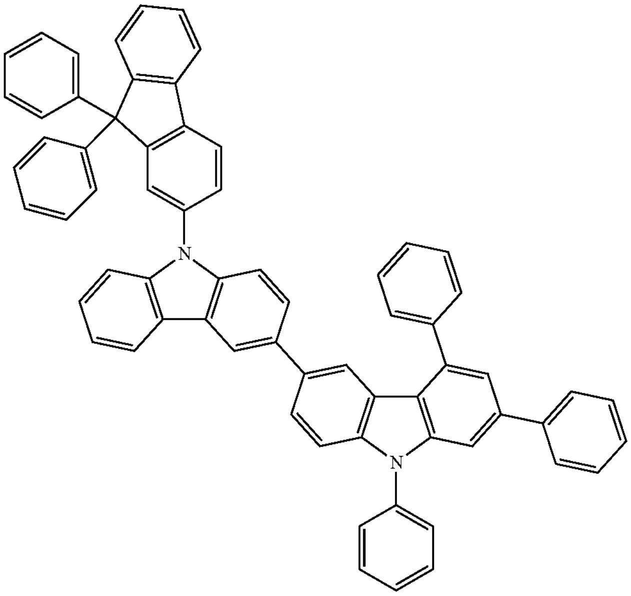 [SMILES: c1ccc(-c2cc(-c3ccccc3)c3c4cc(-c5ccc6c(c5)c5ccccc5n6-c5ccc6c(c5)C(c5ccccc5)(c5ccccc5)c5ccccc5-6)ccc4n(-c4ccccc4)c3c2)cc1] | CAS-2018307-50-9 |
| 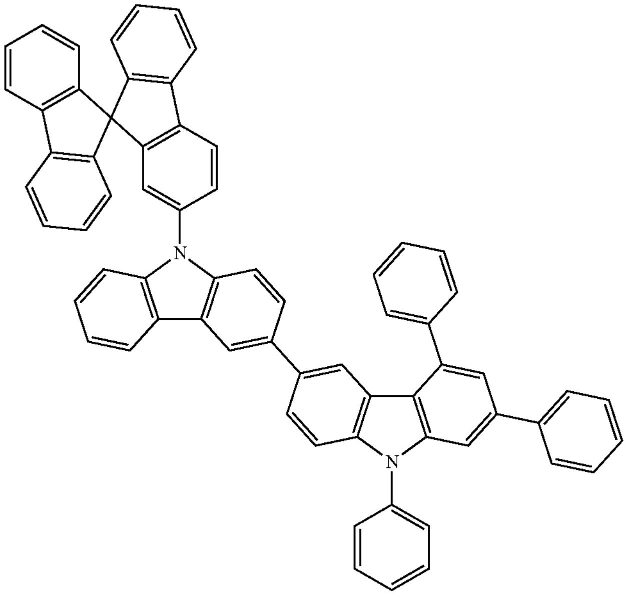 [SMILES: c1ccc(-c2cc(-c3ccccc3)c3c4cc(-c5ccc6c(c5)c5ccccc5n6-c5ccc6c(c5)C5(c7ccccc7-c7ccccc75)c5ccccc5-6)ccc4n(-c4ccccc4)c3c2)cc1] | CAS-2018307-49-6 |

TABLE 9-continued
| Structure | CAS number |
| --- | --- |
| 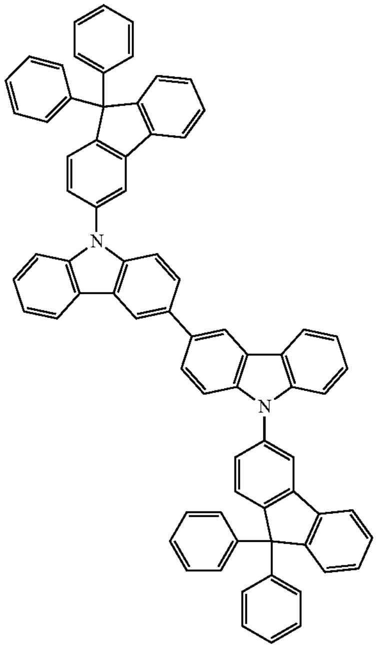 [SMILES: c1ccc(C2(c3ccccc3)c3ccccc3-c3cc(-n4c5ccccc5c5cc(-c6ccc7c(c6)c6ccccc6n7-c6ccc7c(c6)-c6ccccc6C7(c6ccccc6)c6ccccc6)ccc54)ccc32)cc1] | CAS-1656982-30-7 |
| 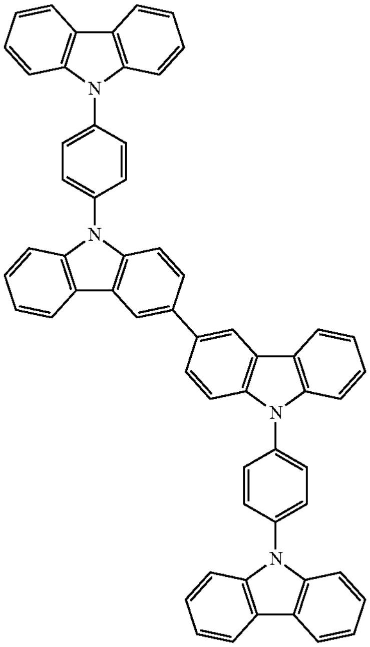 [SMILES: c1ccc2c(c1)c1ccccc1n2-c1ccc(-n2c3ccccc3c3cc(-c4ccc5c(c4)c4ccccc4n5-c4ccc(-n5c6ccccc6c6ccccc65)cc4)ccc32)cc1] | CAS-1680184-58-0 |

TABLE 9-continued
| Structure | CAS number |
| --- | --- |
| 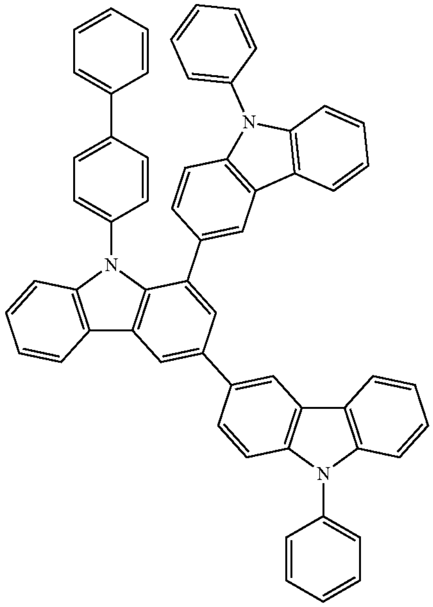 [SMILES: c1ccc(-c2ccc(-n3c4ccccc4c4cc(-c5ccc6c(c5)c5ccccc5n6-c5ccccc5)cc(-c5ccc6c(c5)c5ccccc5n6-c5ccccc5)c43)cc2)cc1] | CAS-1704071-12-4 |
| 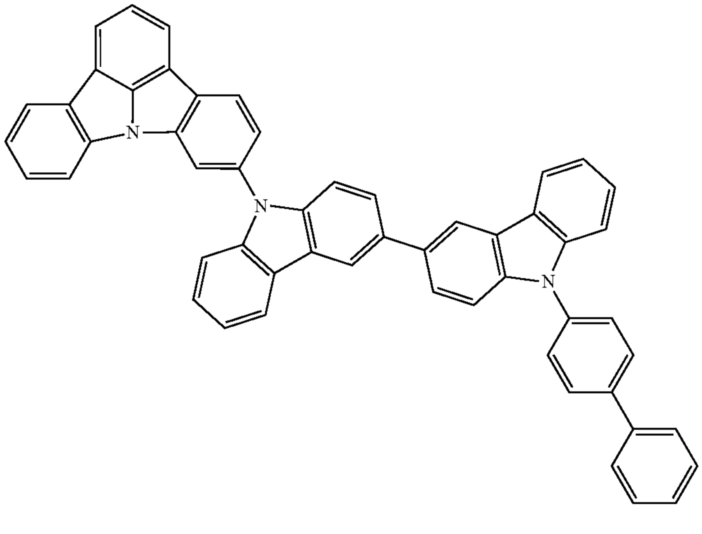 [SMILES: c1ccc(-c2ccc(-n3c4ccccc4c4cc(-c5ccc6c(c5)c5ccccc5n6-c5ccc6c7cccc8c9ccccc9n(c6c5)c87)ccc43)cc2)cc1] | CAS-1799483-56-9 |

TABLE 9-continued
| Structure | CAS number |
|---|---|
| 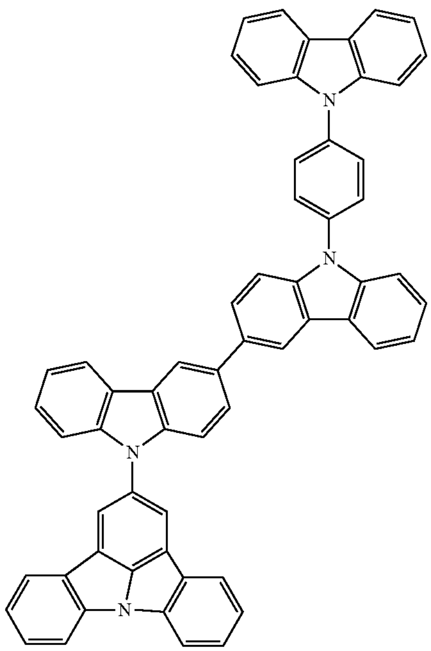 [SMILES: c1ccc2c(c1)c1ccccc1n2-c1ccc(-n2c3ccccc3c3cc(-c4ccc5c(c4)c4ccccc4n5-c4cc5c6ccccc6n6c7ccccc7c(c4)c56)ccc32)cc1] | CAS-1799519-35-9 |
| 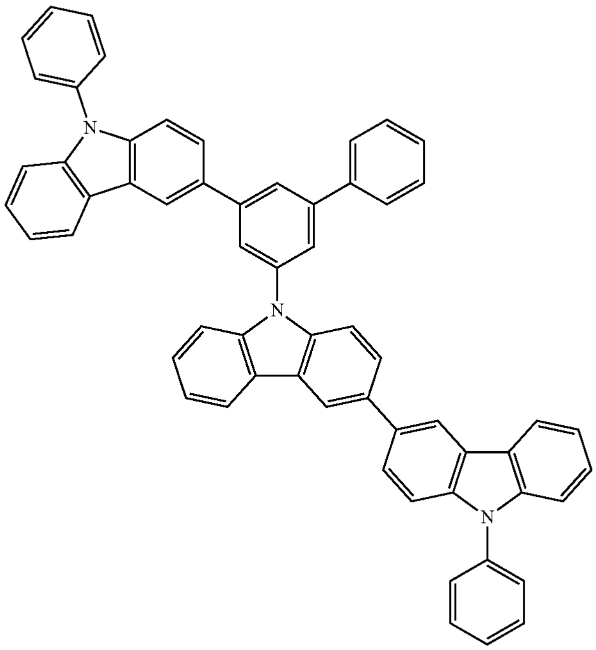 [SMILES: c1ccc(-c2cc(-c3ccc4c(c3)c3ccccc3n4-c3ccccc3)cc(-n3c4ccccc4c4cc(-c5ccc6c(c5)c5ccccc5n6-c5ccccc5)ccc43)c2)cc1] | CAS-1799678-37-7 |

TABLE 9-continued
| Structure | CAS number |
|---|---|
| 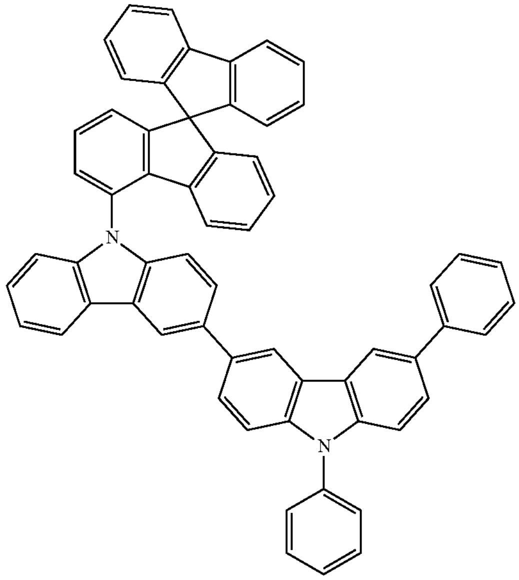 [SMILES: c1ccc(-c2ccc3c(c2)c2cc(-c4ccc5c(c4)c4ccccc4n5-c4cccc5c4-c4ccccc4C54c5ccccc5-c5ccccc54)ccc2n3-c2ccccc2)cc1] | CAS-2073116-97-7 |
| 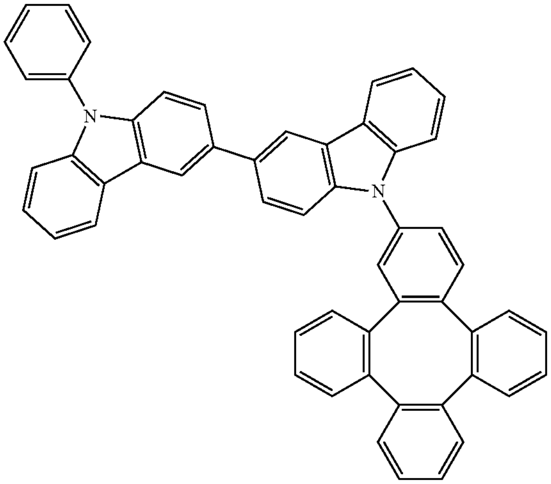 [SMILES: c1ccc(-n2c3ccccc3c3cc(-c4ccc5c(c4)c4ccccc4n5-c4ccc5c(c4)-c4ccccc4-c4ccccc4-c4ccccc4-5)ccc32)cc1] | CAS-2048236-10-6 |
| 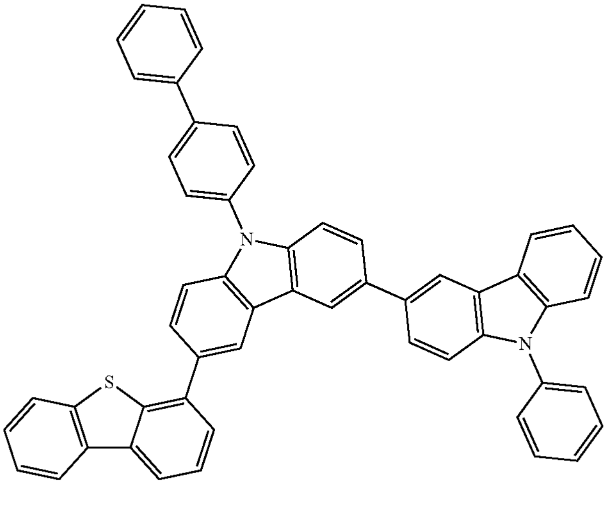 | CAS-1799959-20-8 |

TABLE 9-continued
| Structure | CAS number |
|---|---|
| 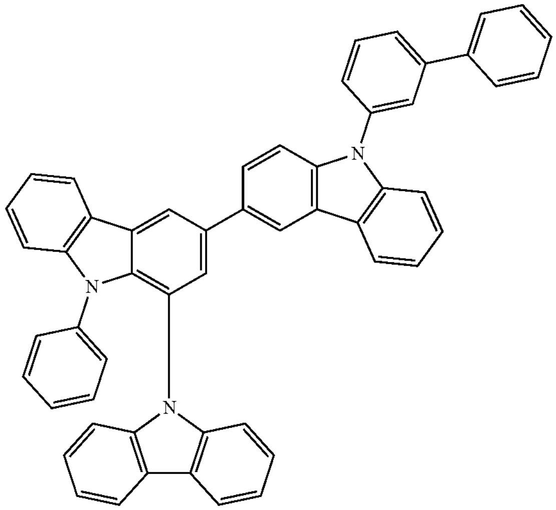 [SMILES: c1ccc(-c2cccc(-n3c4ccccc4c4cc(-c5cc(-n6c7ccccc7c7ccccc76)c6c(c5)c5ccccc5n6-c5ccccc5)ccc43)c2)cc1] | CAS-1704071-30-6 |
| 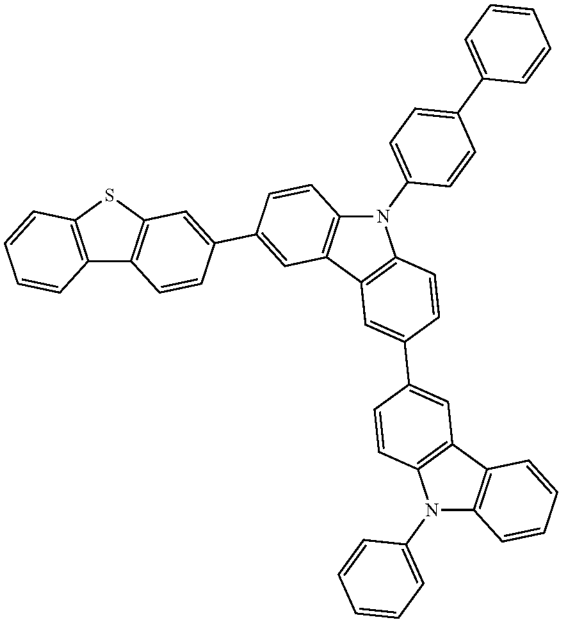 [SMILES: c1ccc(-c2ccc(-n3c4ccc(-c5ccc6c(c5)sc5ccccc56)cc4c4cc(-c5ccc6c(c5)c5ccccc5n6-c5ccccc5)ccc43)cc2)cc1] | CAS-1799959-21-9 |

TABLE 9-continued
| Structure | CAS number |
| --- | --- |
| 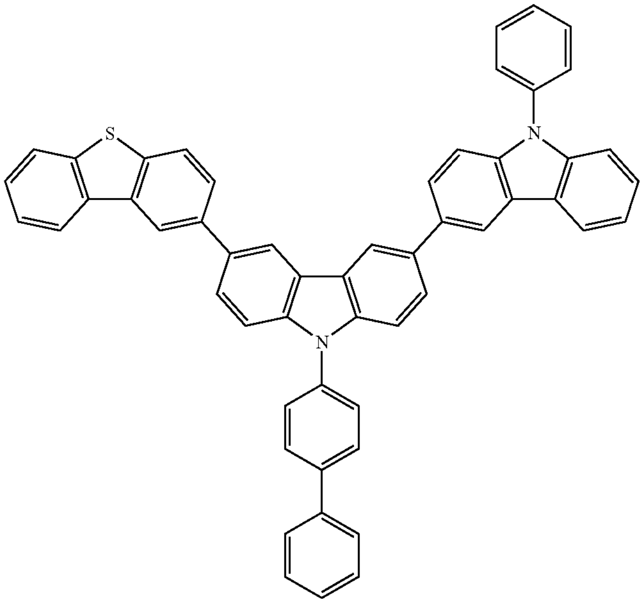 [SMILES: c1ccc(-c2ccc(-n3c4ccc(-c5ccc6sc7ccccc7c6c5)cc4c4cc(-c5ccc6c(c5)c5ccccc5n6-c5ccccc5)ccc43)cc2)cc1] | CAS-1799959-22-0 |
| 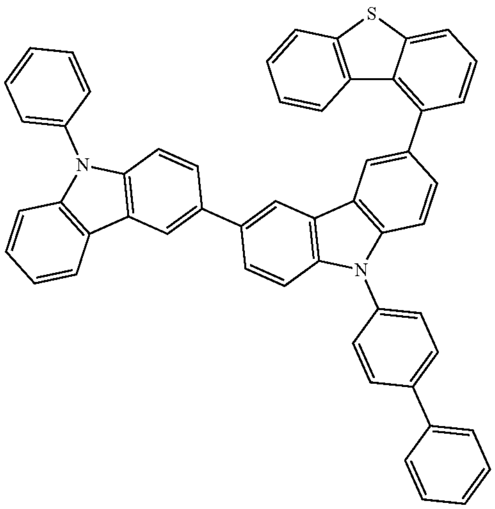 [SMILES: c1ccc(-c2ccc(-n3c4ccc(-c5ccc6c(c5)c5ccccc5n6-c5ccccc5)cc4c4cc(-c5cccc6sc7ccccc7c56)ccc43)cc2)cc1] | CAS-1799959-23-1 |
| 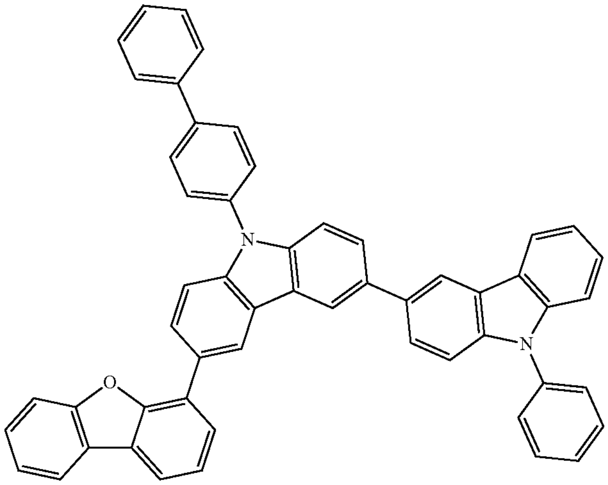 [SMILES: c1ccc(-c2ccc(-n3c4ccc(-c5ccc6c(c5)c5ccccc5n6-c5ccccc5)cc4c4cc(-c5cccc6c5oc5ccccc56)ccc43)cc2)cc1] | CAS-1799959-24-2 |

TABLE 9-continued
| Structure | CAS number |
| --- | --- |
| 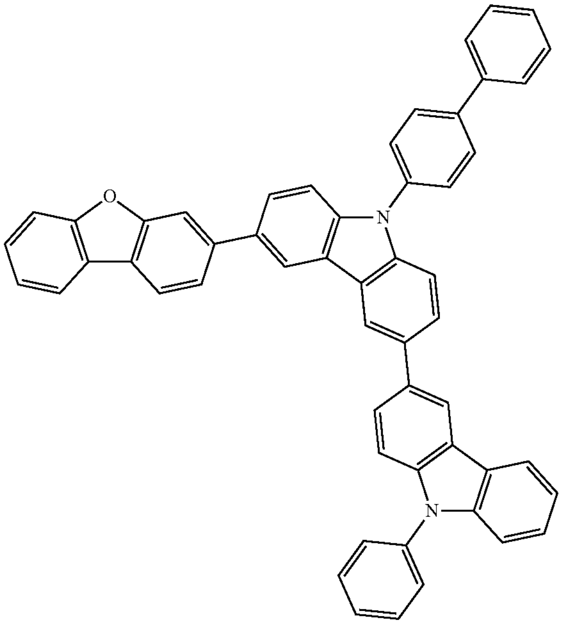 [SMILES: c1ccc(-c2ccc(-n3c4ccc(-c5ccc6c(c5)oc5ccccc56)cc4c4cc(-c5ccc6c(c5)c5ccccc5n6-c5ccccc5)ccc43)cc2)cc1] | CAS-1799959-25-3 |
| 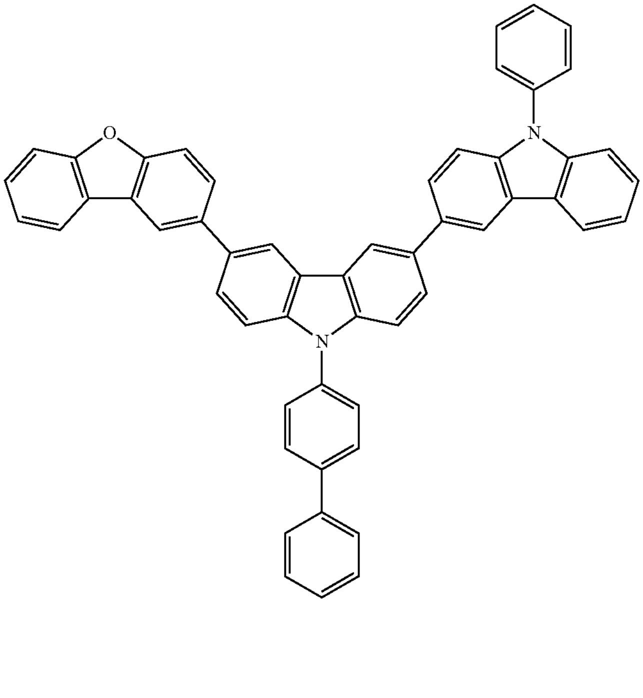 | CAS-1799959-26-4 |

TABLE 9-continued
| Structure | CAS number |
|---|---|
| 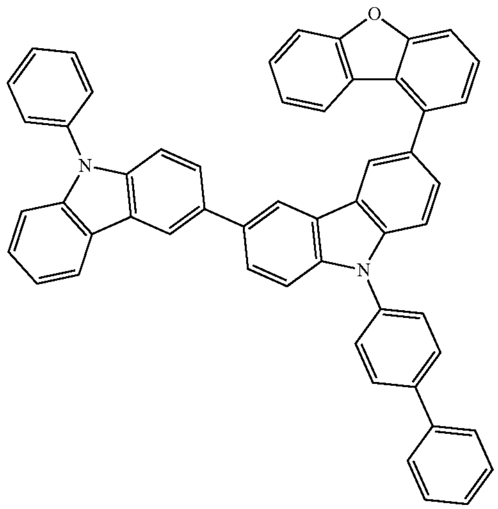 [SMILES: c1ccc(-c2ccc(-n3c4ccc(-c5ccc6c(c5)c5ccccc5n6-c5ccccc5)cc4c4cc(-c5cccc6oc7ccccc7c56)ccc43)cc2)cc1] | CAS-1799959-27-5 |
| 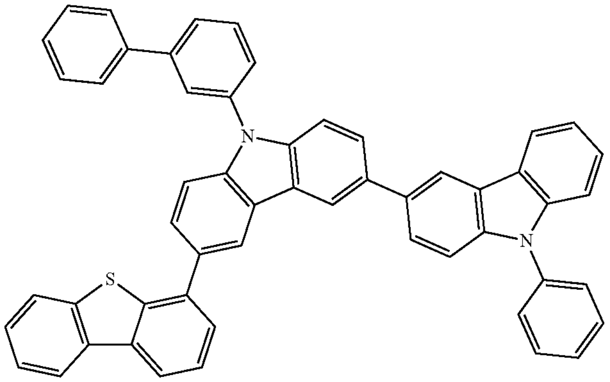 | CAS-1799959-28-6 |
| 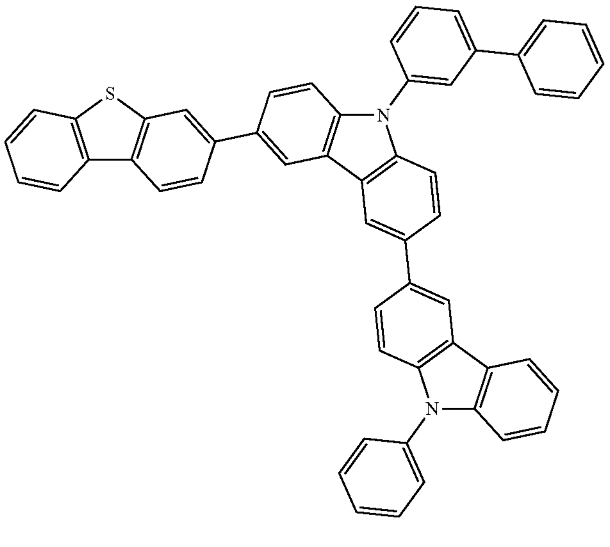 | CAS-1799959-29-7 |

TABLE 9-continued
| Structure | CAS number |
| --- | --- |
| 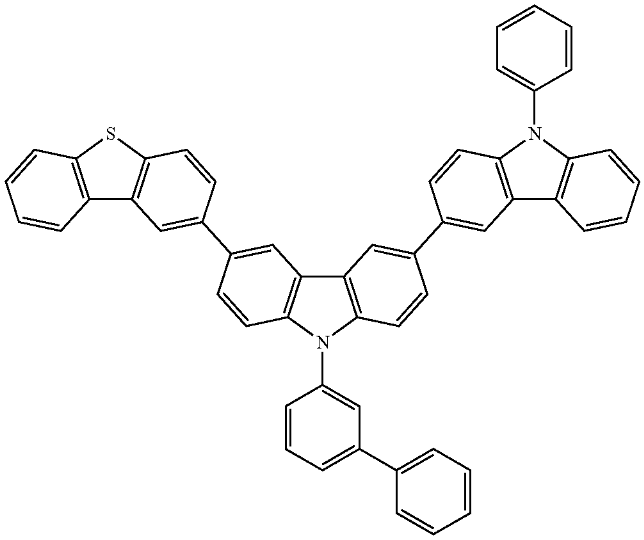 [SMILES: c1ccc(-c2cccc(-n3c4ccc(-c5ccc6sc7ccccc7c6c5)cc4c4cc(-c5ccc6c(c5)c5ccccc5n6-c5ccccc5)ccc43)c2)cc1] | CAS-1799959-30-0 |
| 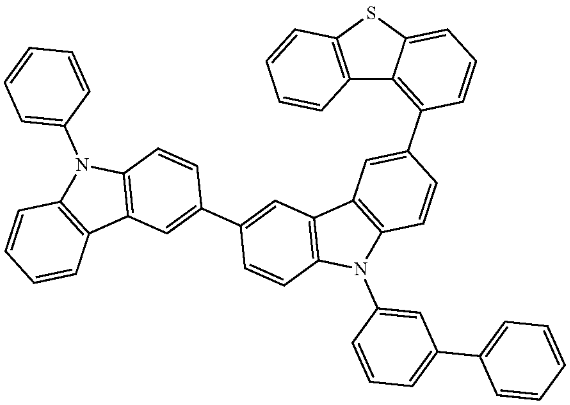 [SMILES: c1ccc(-c2cccc(-n3c4ccc(-c5ccc6c(c5)c5ccccc5n6-c5ccccc5)cc4c4cc(-c5cccc6sc7ccccc7c56)ccc43)c2)cc1] | CAS-1799959-31-1 |
| 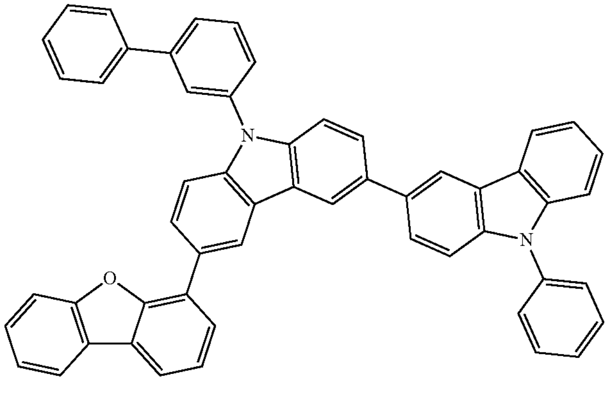 [SMILES: c1ccc(-c2cccc(-n3c4ccc(-c5ccc6c(c5)c5ccccc5n6-c5ccccc5)cc4c4cc(-c5cccc6c5oc5ccccc56)ccc43)c2)cc1] | CAS-1799959-32-2 |

TABLE 9-continued
| Structure | CAS number |
|---|---|
| 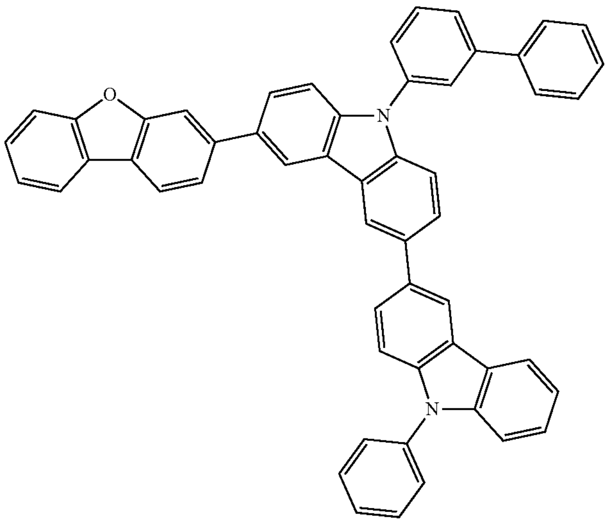 | CAS-1799959-33-3 |
| 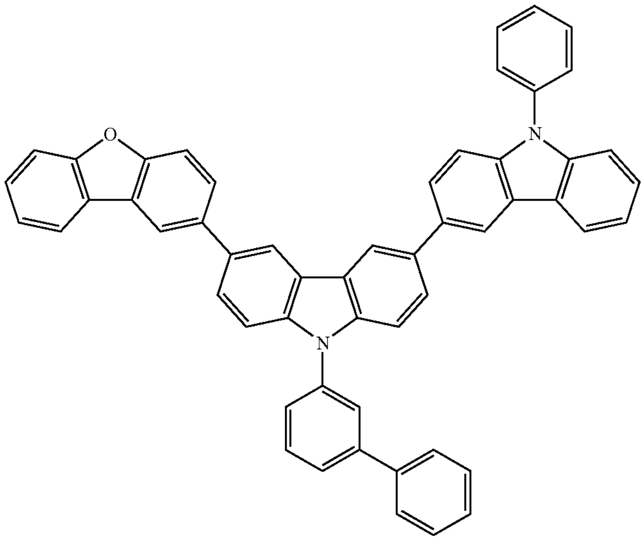 [SMILES: c1ccc(-c2cccc(-n3c4ccc(-c5ccc6oc7ccccc7c6c5)cc4c4cc(-c5ccc6c(c5)c5ccccc5n6-c5ccccc5)ccc43)c2)cc1] | CAS-1799959-34-4 |
| 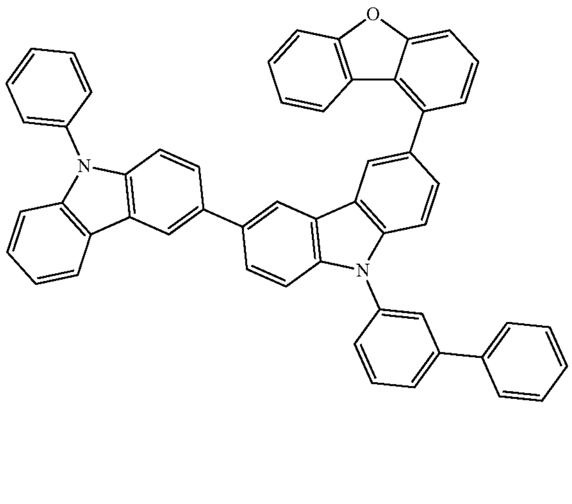 [SMILES: c1ccc(-c2cccc(-n3c4ccc(-c5ccc6c(c5)c5ccccc5n6-c5ccccc5)cc4c4cc(-c5cccc6oc7ccccc7c56)ccc43)c2)cc1] | CAS-1799959-35-5 |

TABLE 9-continued
| Structure | CAS number |
|---|---|
| 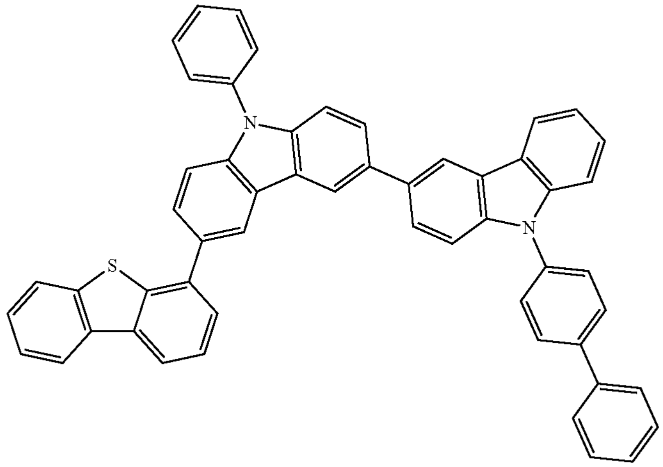 [SMILES: c1ccc(-c2ccc(-n3c4ccccc4c4cc(-c5ccc6c(c5)c5cc(-c7cccc8c7sc7ccccc78)ccc5n6-c5ccccc5)ccc43)cc2)cc1] | CAS-1799959-60-6 |
| 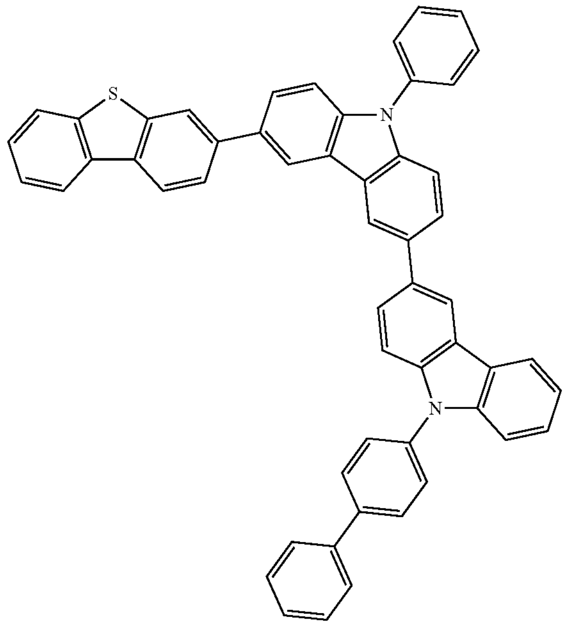 [SMILES: c1ccc(-c2ccc(-n3c4ccccc4c4cc(-c5ccc6c(c5)c5cc(-c7ccc8c(c7)sc7ccccc78)ccc5n6-c5ccccc5)ccc43)cc2)cc1] | CAS-1799959-61-7 |

TABLE 9-continued
| Structure | CAS number |
|---|---|
| 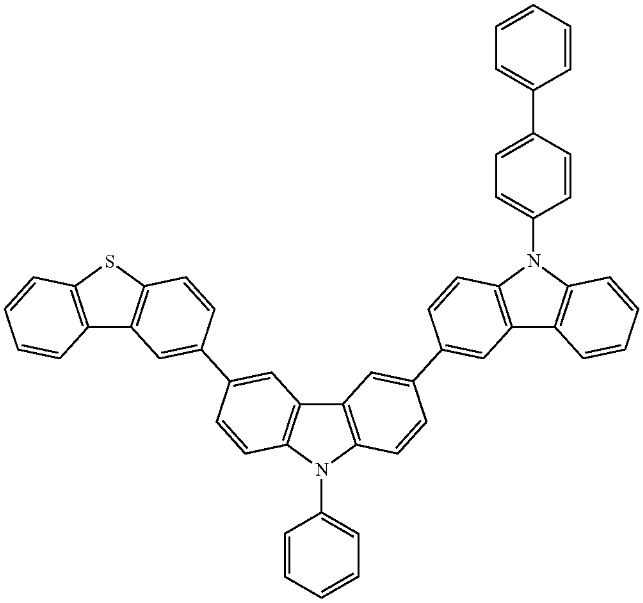 [SMILES: c1ccc(-c2ccc(-n3c4ccccc4c4cc(-c5ccc6c(c5)c5cc(-c7ccc8sc9ccccc9c8c7)ccc5n6-c5ccccc5)ccc43)cc2)cc1] | CAS-1799959-62-8 |
| 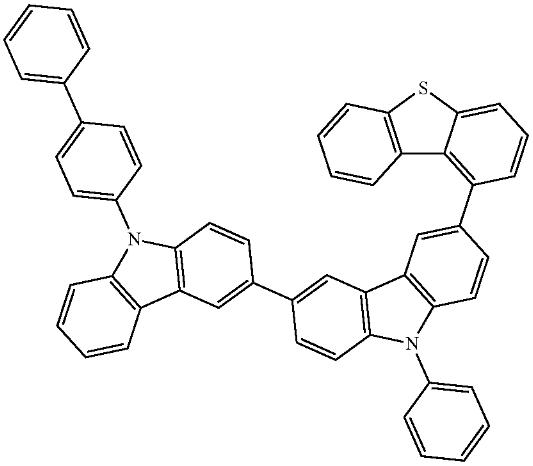 [SMILES: c1ccc(-c2ccc(-n3c4ccccc4c4cc(-c5ccc6c(c5)c5cc(-c7cccc8sc9ccccc9c78)ccc5n6-c5ccccc5)ccc43)cc2)cc1] | CAS-1799959-63-9 |
| 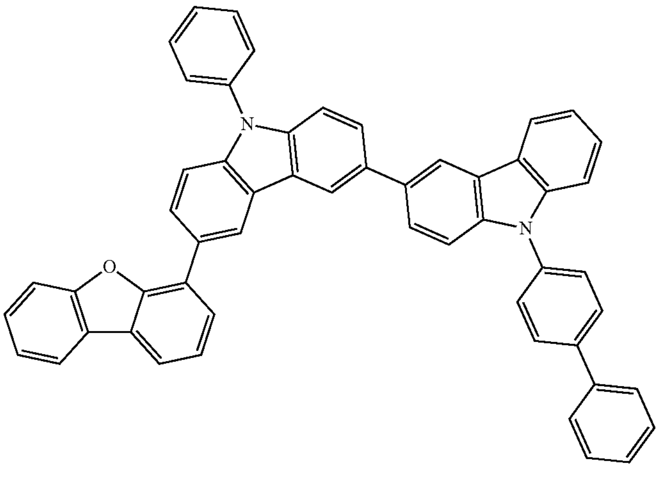 [SMILES: c1ccc(-c2ccc(-n3c4ccccc4c4cc(-c5ccc6c(c5)c5cc(-c7cccc8c7oc7ccccc78)ccc5n6-c5ccccc5)ccc43)cc2)cc1] | CAS-1799959-64-0 |

TABLE 9-continued
| Structure | CAS number |
| --- | --- |
| 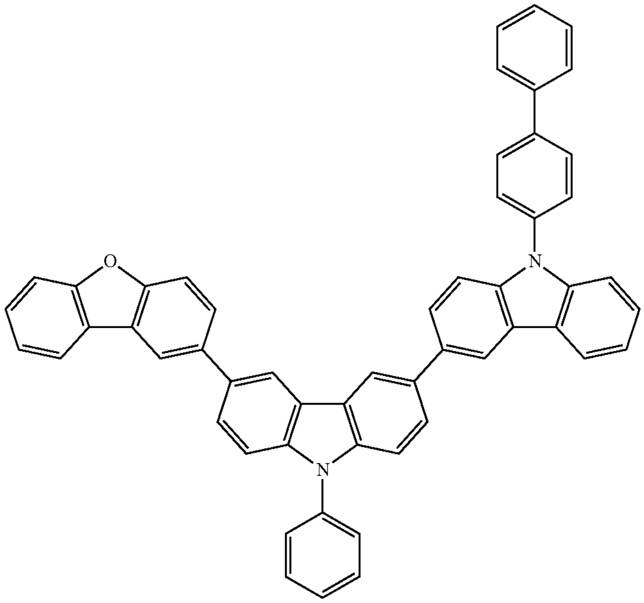 | CAS-1799959-66-2 |
| 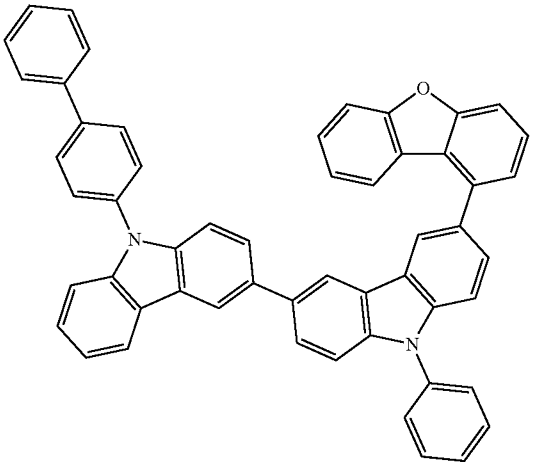 [SMILES: c1ccc(-c2ccc(-n3c4ccccc4c4cc(-c5ccc6c(c5)c5cc(-c7cccc8oc9ccccc9c78)ccc5n6-c5ccccc5)ccc43)cc2)cc1] | CAS-1799959-67-3 |
| 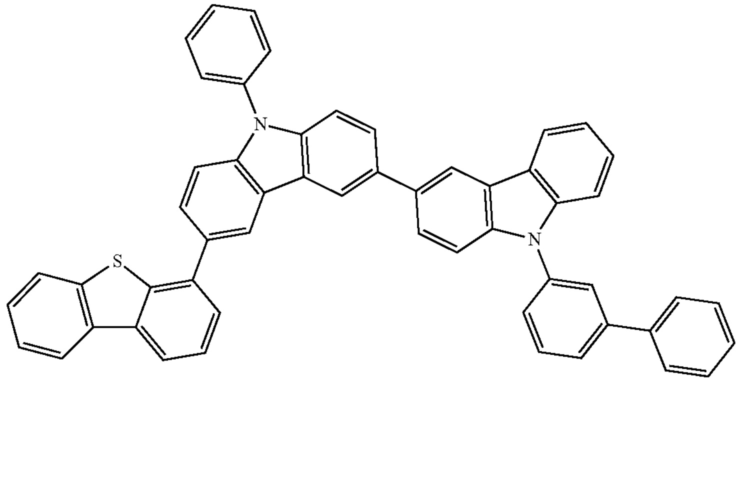 [SMILES: c1ccc(-c2cccc(-n3c4ccccc4c4cc(-c5ccc6c(c5)c5cc(-c7cccc8c7sc7ccccc78)ccc5n6-c5ccccc5)ccc43)c2)cc1] | CAS-1799959-68-4 |

TABLE 9-continued
| Structure | CAS number |
|---|---|
| 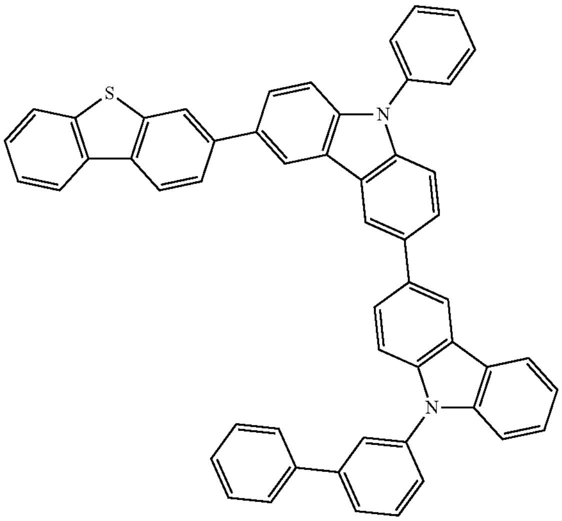 [SMILES: c1ccc(-c2cccc(-n3c4ccccc4c4cc(-c5ccc6c(c5)c5cc(-c7ccc8c(c7)sc7ccccc78)ccc5n6-c5ccccc5)ccc43)c2)cc1] | CAS-1799959-69-5 |
| 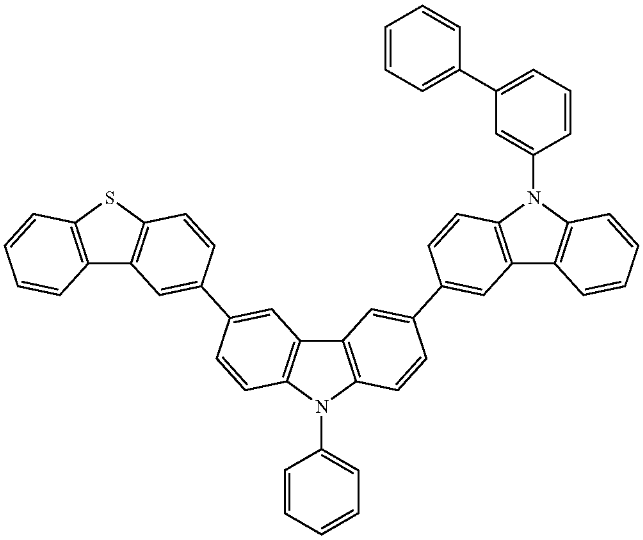 | CAS-1799959-70-8 |
| 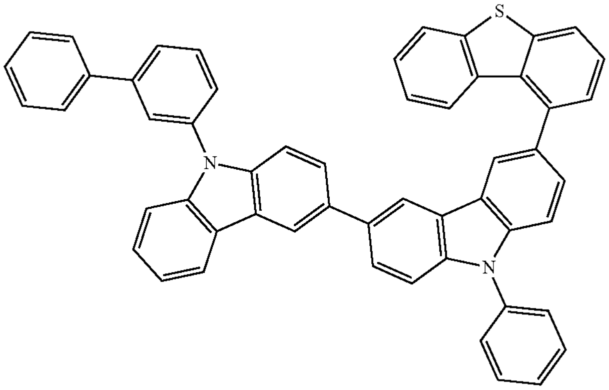 [SMILES: c1ccc(-c2cccc(-n3c4ccccc4c4cc(-c5ccc6c(c5)c5cc(-c7cccc8sc9ccccc9c78)ccc5n6-c5ccccc5)ccc43)c2)cc1] | CAS-1799959-71-9 |

TABLE 9-continued
| Structure | CAS number |
| --- | --- |
| 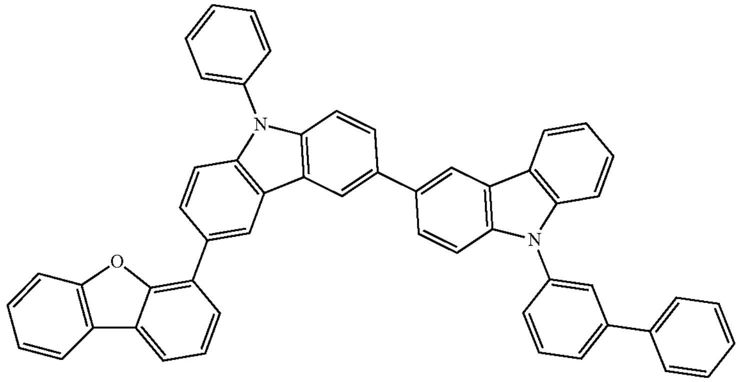 [SMILES: c1ccc(-c2cccc(-n3c4ccccc4c4cc(-c5ccc6c(c5)c5cc(-c7cccc8c7oc7ccccc78)ccc5n6-c5ccccc5)ccc43)c2)cc1] | CAS-1799959-72-0 |
| 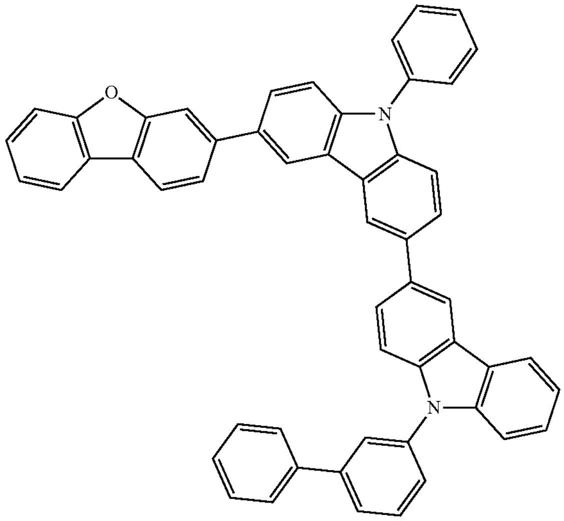 [SMILES: c1ccc(-c2cccc(-n3c4ccccc4c4cc(-c5ccc6c(c5)c5cc(-c7ccc8c(c7)oc7ccccc78)ccc5n6-c5ccccc5)ccc43)c2)cc1] | CAS-1799959-73-1 |
| 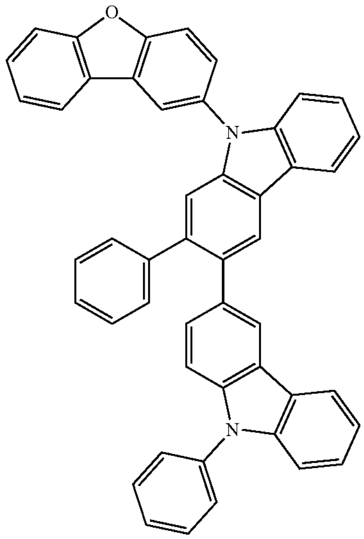 [SMILES: c1ccc(-c2cc3c(cc2-c2ccc4c(c2)c2ccccc2n4-c2ccccc2)c2ccccc2n3-c2ccc3oc4ccccc4c3c2)cc1] | CAS-1428635-33-9 |

TABLE 9-continued
| Structure | CAS number |
| --- | --- |
| 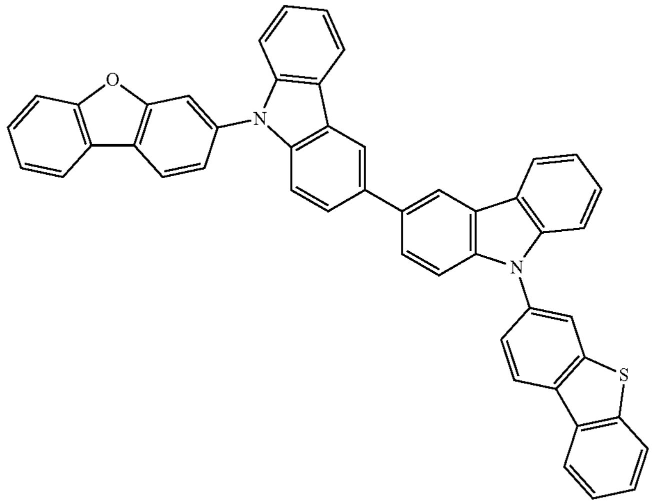 | CAS-1890157-93-3 |
| 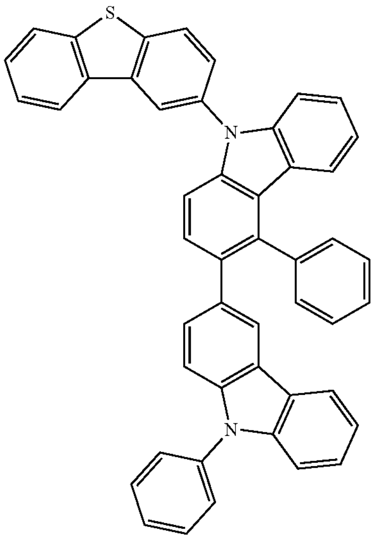 | CAS-1428635-40-8 |
| 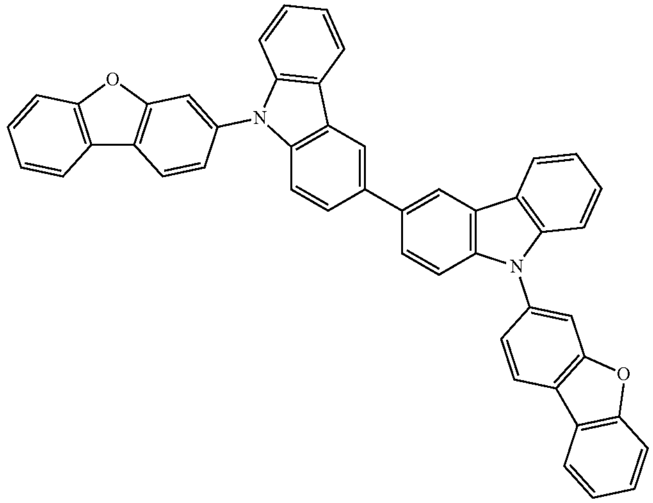 [SMILES: c1ccc2c(c1)oc1cc(-n3c4ccccc4c4cc(-c5ccc6c(c5)c5ccccc5n6-c5ccc6c(c5)sc5ccccc56)ccc43)ccc12] | CAS-1890157-94-4 |

TABLE 9-continued
| Structure | CAS number |
| --- | --- |
| 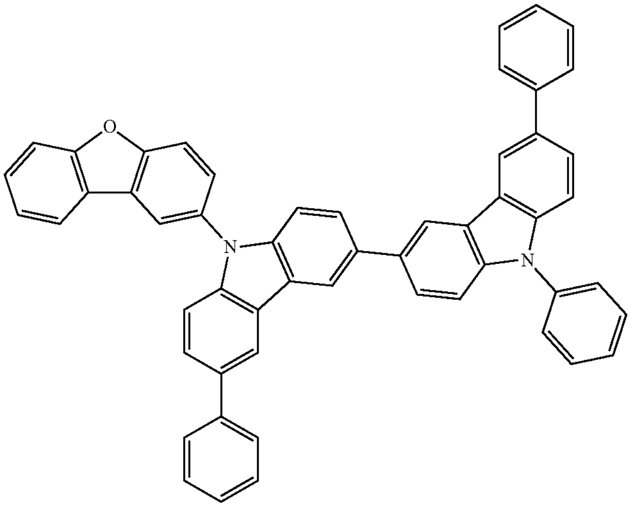 [SMILES: c1ccc(-c2ccc3c(c2)c2cc(-c4ccc5c(c4)c4cc(-c6ccccc6)ccc4n5-c4ccc5oc6ccccc6c5c4)ccc2n3-c2ccccc2)cc1] | CAS-1431151-34-6 |
| 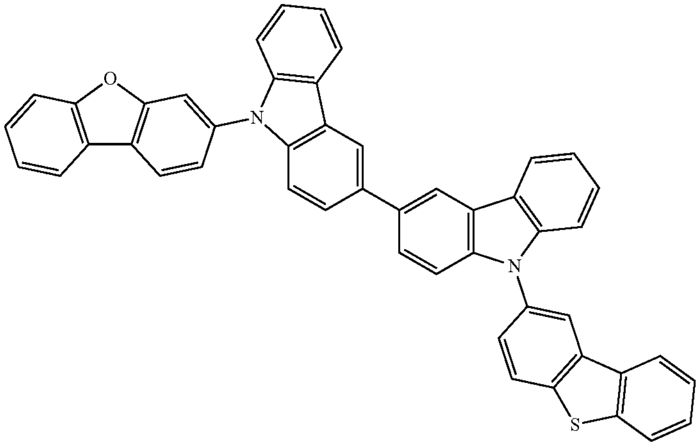 [SMILES: c1ccc2c(c1)oc1cc(-n3c4ccccc4c4cc(-c5ccc6c(c5)c5ccccc5n6-c5ccc6sc7ccccc7c6c5)ccc43)ccc12] | CAS-1890157-95-5 |
| 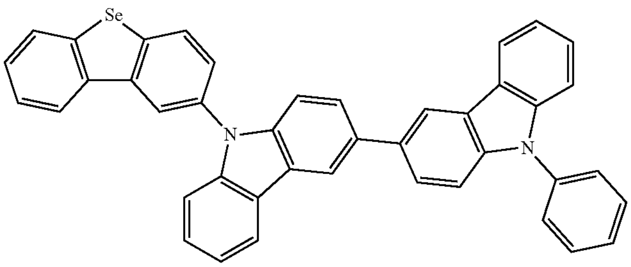 [SMILES: c1ccc(-n2c3ccccc3c3cc(-c4ccc5c(c4)c4ccccc4n5-c4ccc5[se]c6ccccc6c5c4)ccc32)cc1] | CAS-1894193-99-7 |

TABLE 9-continued
| Structure | CAS number |
|---|---|
| 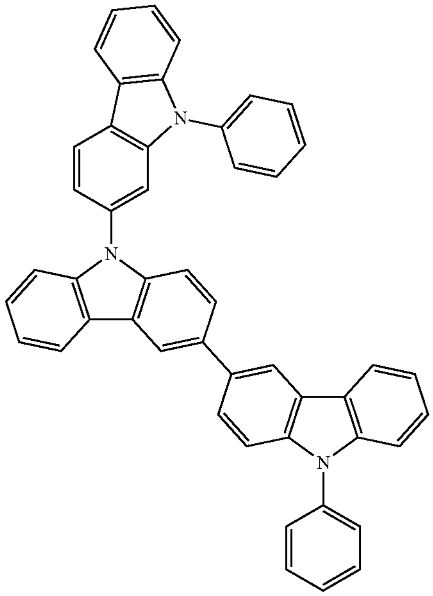 [SMILES: c1ccc(-n2c3ccccc3c3cc(-c4ccc5c(c4)c4ccccc4n5-c4ccc5c6ccccc6n(-c6ccccc6)c5c4)ccc32)cc1] | CAS-1894193-97-5 |
| 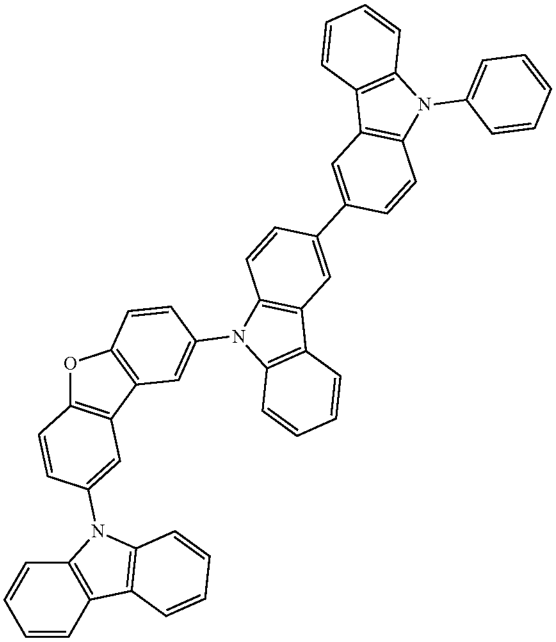 [SMILES: c1ccc(-n2c3ccccc3c3cc(-c4ccc5c(c4)c4ccccc4n5-c4ccc5oc6ccc(-n7c8ccccc8c8ccccc87)cc6c5c4)ccc32)cc1] | CAS-1446411-07-9 |
| 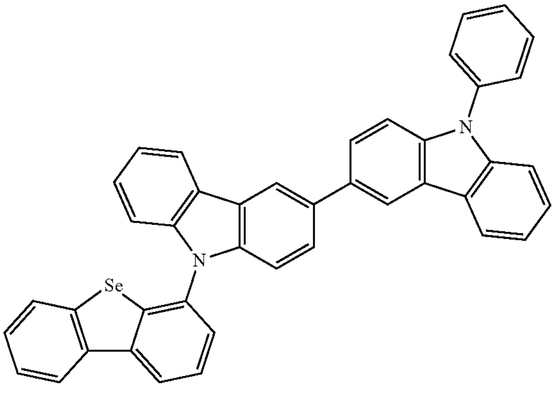 [SMILES: c1ccc(-n2c3ccccc3c3cc(-c4ccc5c(c4)c4ccccc4n5-c4cccc5c4[se]c4ccccc45)ccc32)cc1] | CAS-1894194-03-6 |

TABLE 9-continued
| Structure | CAS number |
|---|---|
| 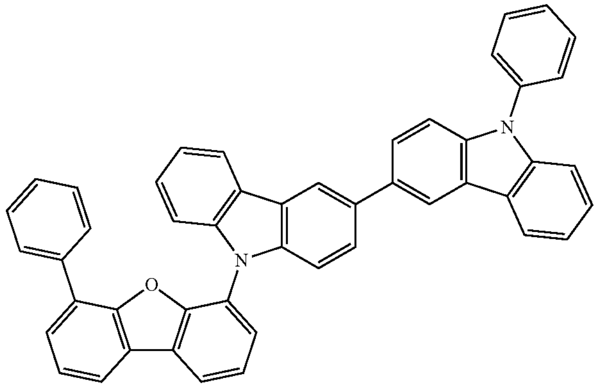 [SMILES: c1ccc(-c2cccc3c2oc2c(-n4c5ccccc5c5cc(-c6ccc7c(c6)c6ccccc6n7-c6ccccc6)ccc54)cccc23)cc1] | CAS-1894194-10-5 |
| 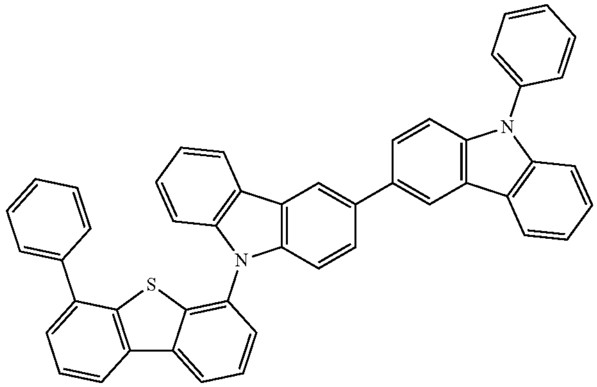 [SMILES: c1ccc(-c2cccc3c2sc2c(-n4c5ccccc5c5cc(-c6ccc7c(c6)c6ccccc6n7-c6ccccc6)ccc54)cccc23)cc1] | CAS-1894194-11-6 |
| 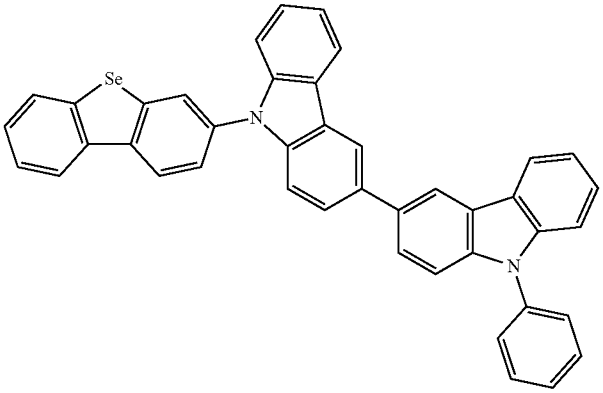 [SMILES: c1ccc(-n2c3ccccc3c3cc(-c4ccc5c(c4)c4ccccc4n5-c4ccc5c(c4)[se]c4ccccc45)ccc32)cc1] | CAS-1894194-16-1 |

TABLE 9-continued
| Structure | CAS number |
| --- | --- |
| 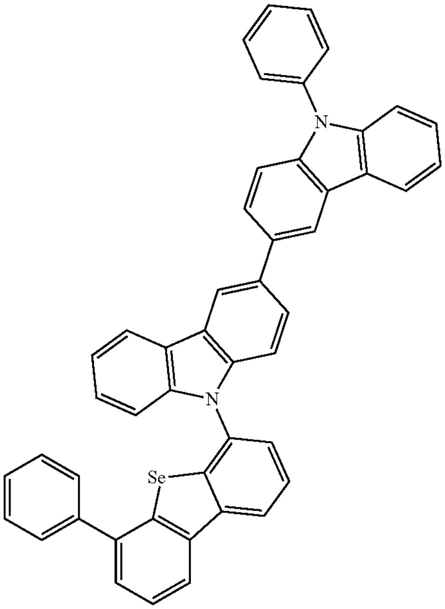 [SMILES: c1ccc(-c2cccc3c2[se]c2c(-n4c5ccccc5c5cc(-c6ccc7c(c6)c6ccccc6n7-c6ccccc6)ccc54)cccc23)cc1] | CAS-1894194-12-7 |
| 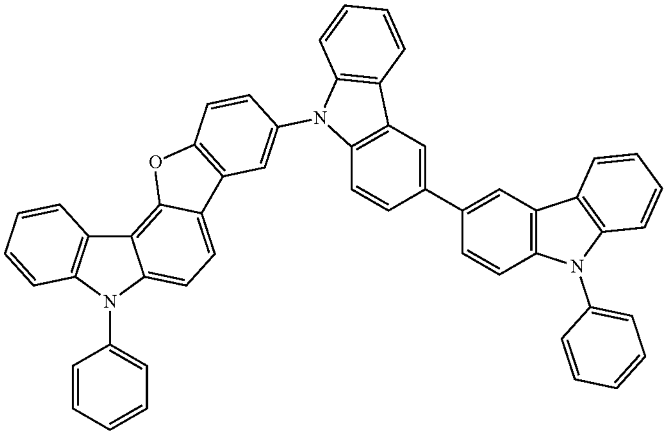 [SMILES: c1ccc(-n2c3ccccc3c3cc(-c4ccc5c(c4)c4ccccc4n5-c4ccc5oc6c(ccc7c6c6ccccc6n7-c6ccccc6)c5c4)ccc32)cc1] | CAS-1497337-43-5 |
| 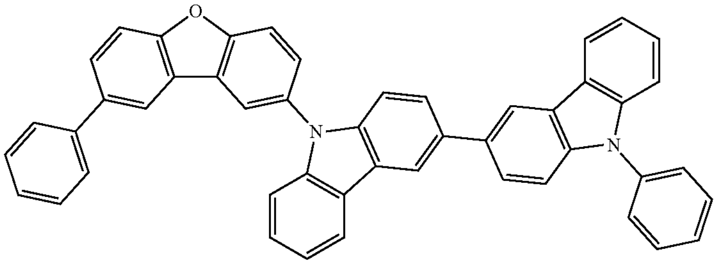 [SMILES: c1ccc(-c2ccc3oc4ccc(-n5c6ccccc6c6cc(-c7ccc8c(c7)c7ccccc7n8-c7ccccc7)ccc65)cc4c3c2)cc1] | CAS-1499917-70-2 |

TABLE 9-continued
| Structure | CAS number |
|---|---|
| 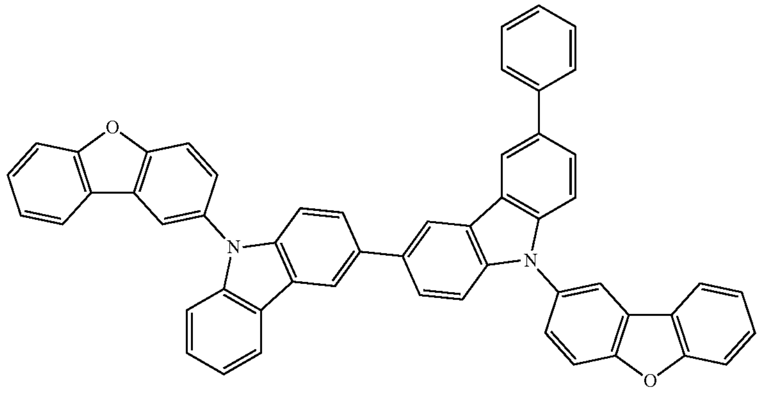 [SMILES: c1ccc(-c2ccc3c(c2)c2cc(-c4ccc5c(c4)c4ccccc4n5-c4ccc5oc6ccccc6c5c4)ccc2n3-c2ccc3oc4ccccc4c3c2)cc1] | CAS-1588866-10-7 |
| 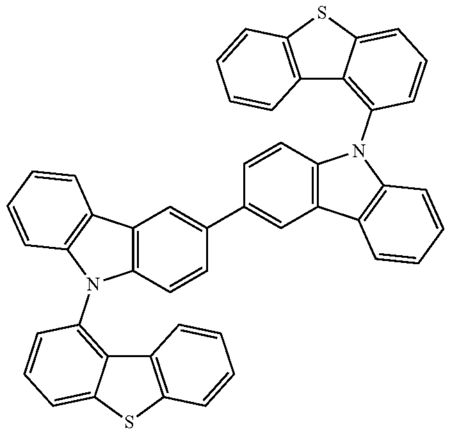 [SMILES: c1ccc2c(c1)sc1cccc(-n3c4ccccc4c4cc(-c5ccc6c(c5)c5ccccc5n6-c5cccc6sc7ccccc7c56)ccc43)c12] | CAS-1934252-94-4 |
| 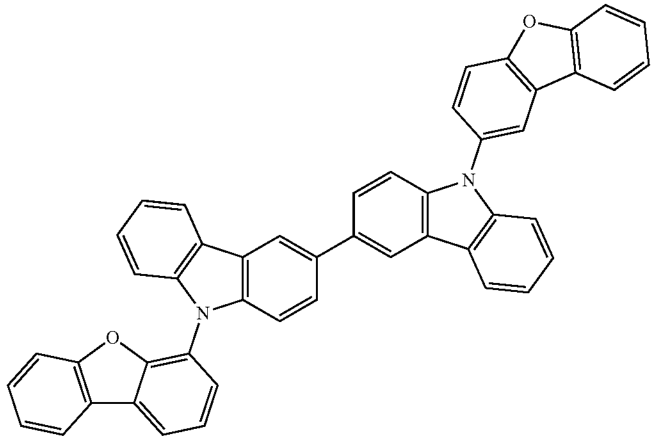 [SMILES: c1ccc2c(c1)oc1ccc(-n3c4ccccc4c4cc(-c5ccc6c(c5)c5ccccc5n6-c5cccc6c5oc5ccccc56)ccc43)cc12] | CAS-1598389-99-1 |

TABLE 9-continued
| Structure | CAS number |
|---|---|
| 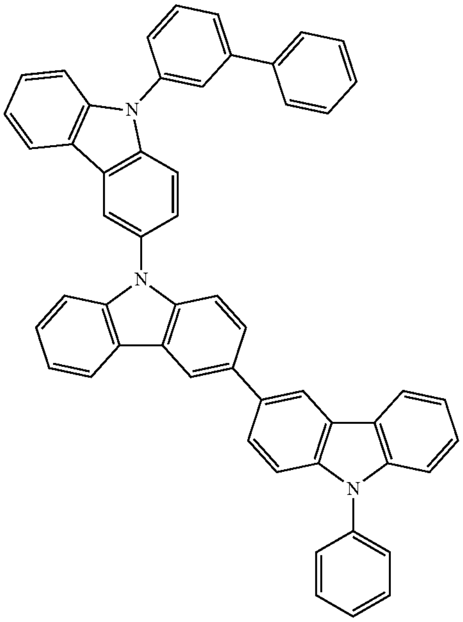 [SMILES: c1ccc(-c2cccc(-n3c4ccccc4c4cc(-n5c6ccccc6c6cc(-c7ccc8c(c7)c7ccccc7n8-c7ccccc7)ccc65)ccc43)c2)cc1] | CAS-1943719-77-4 |
| 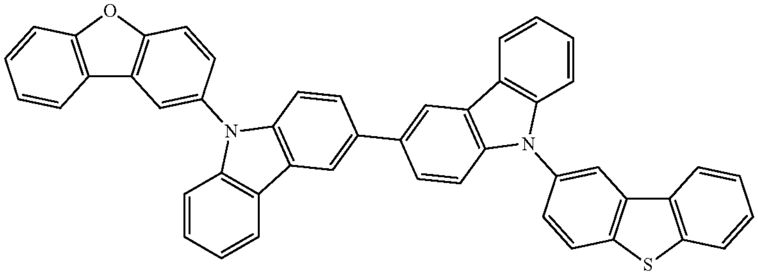 [SMILES: c1ccc2c(c1)oc1ccc(-n3c4ccccc4c4cc(-c5ccc6c(c5)c5ccccc5n6-c5ccc6sc7ccccc7c6c5)ccc43)cc12] | CAS-1613752-14-9 |
| 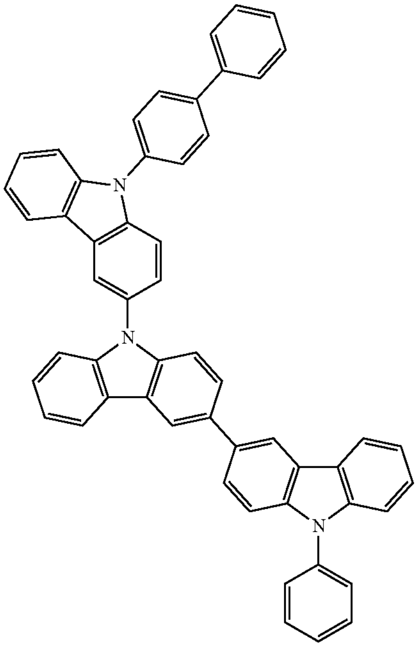 [SMILES: c1ccc(-c2ccc(-n3c4ccccc4c4cc(-n5c6ccccc6c6cc(-c7ccc8c(c7)c7ccccc7n8-c7ccccc7)ccc65)ccc43)cc2)cc1] | CAS-1943719-78-5 |

TABLE 9-continued
| Structure | CAS number |
| --- | --- |
| 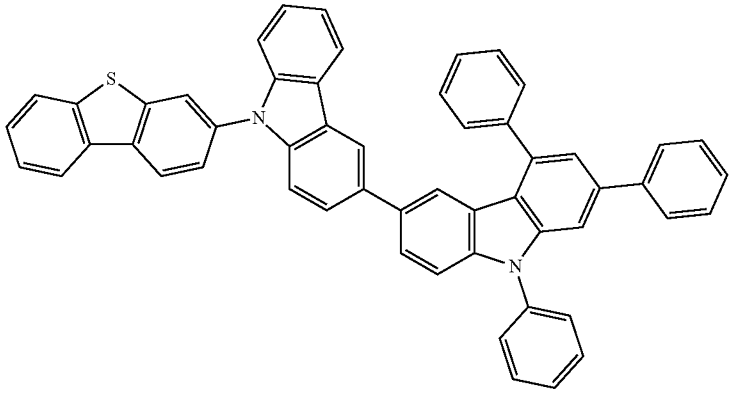 [SMILES: c1ccc(-c2cc(-c3ccccc3)c3c4cc(-c5ccc6c(c5)c5ccccc5n6-c5ccc6c(c5)oc5ccccc56)ccc4n(-c4ccccc4)c3c2)cc1] | CAS-2018307-45-2 |
| 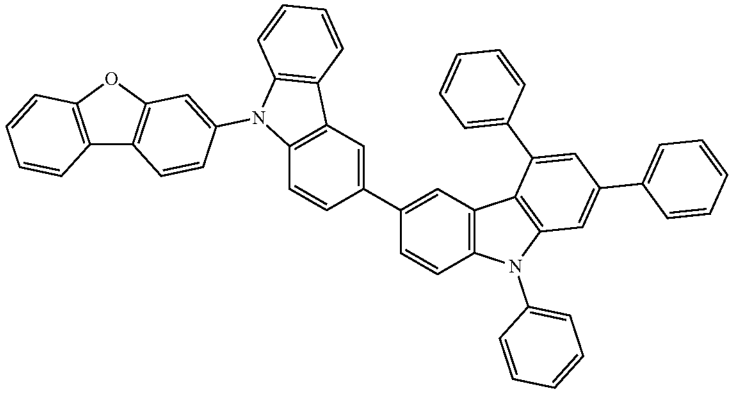 | CAS-2018307-44-1 |
| 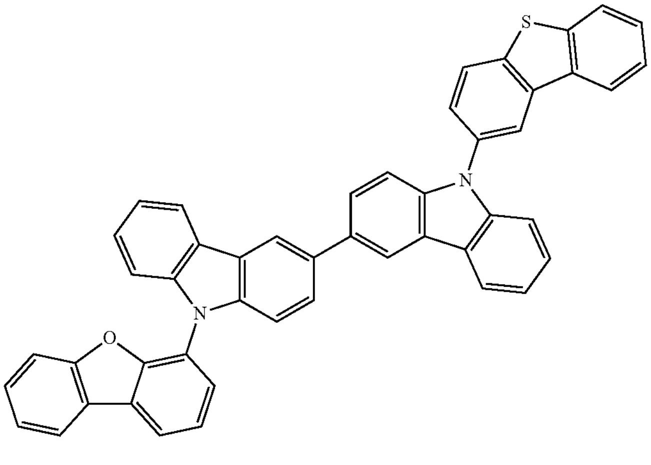 [SMILES: c1ccc2c(c1)oc1c(-n3c4ccccc4c4cc(-c5ccc6c(c5)c5ccccc5n6-c5ccc6sc7ccccc7c6c5)ccc43)cccc12] | CAS-1643479-80-4 |

TABLE 9-continued
| Structure | CAS number |
|---|---|
| 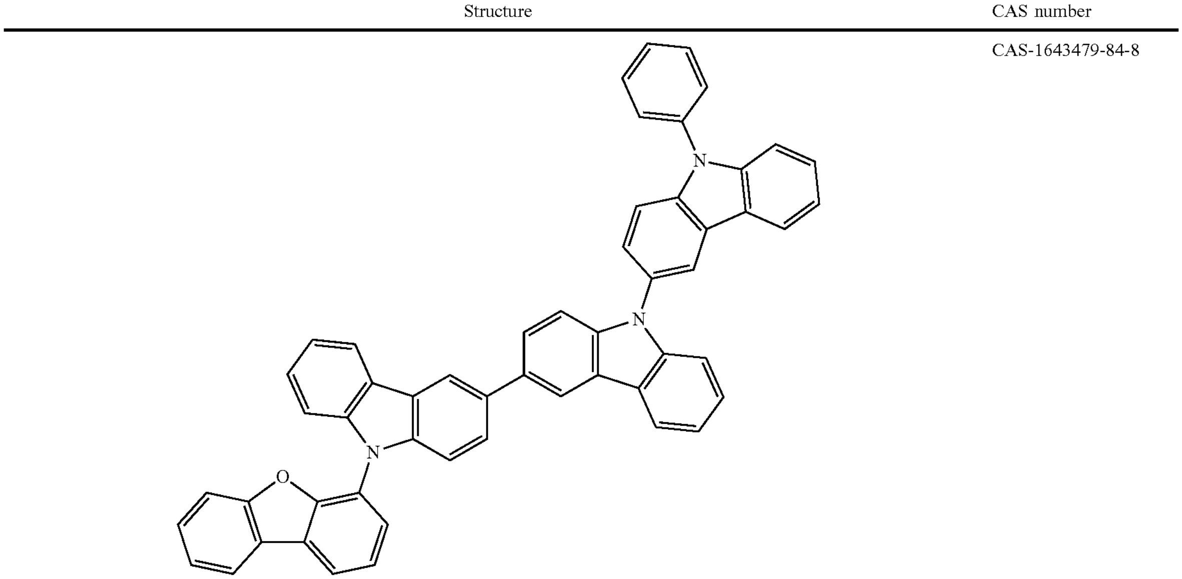 | CAS-1643479-84-8 |
| 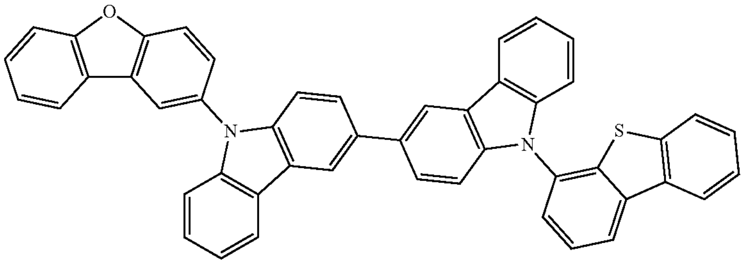 [SMILES: c1ccc2c(c1)oc1ccc(-n3c4ccccc4c4cc(-c5ccc6c(c5)c5ccccc5n6-c5cccc6c5sc5ccccc56)ccc43)cc12] | CAS-1643479-88-2 |
| 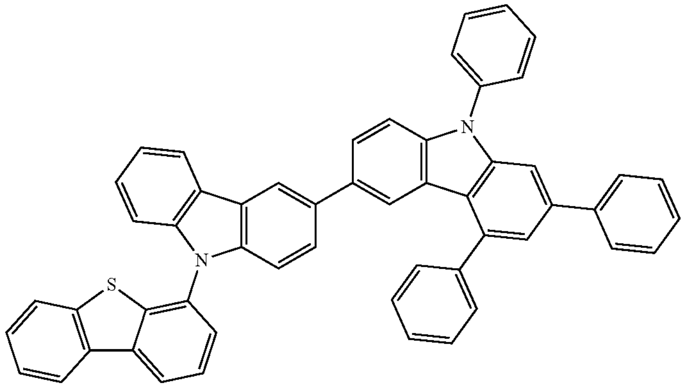 [SMILES: c1ccc(-c2cc(-c3ccccc3)c3c4cc(-c5ccc6c(c5)c5ccccc5n6-c5cccc6c5sc5ccccc56)ccc4n(-c4ccccc4)c3c2)cc1] | CAS-2018307-52-1 |
| 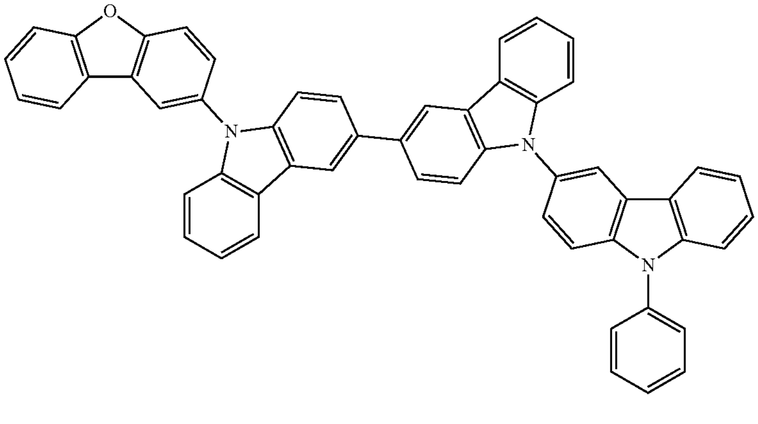 [SMILES: c1ccc(-n2c3ccccc3c3cc(-n4c5ccccc5c5cc(-c6ccc7c(c6)c6ccccc6n7-c6ccc7oc8ccccc8c7c6)ccc54)ccc32)cc1] | CAS-1643480-02-7 |

TABLE 9-continued
| Structure | CAS number |
| --- | --- |
| 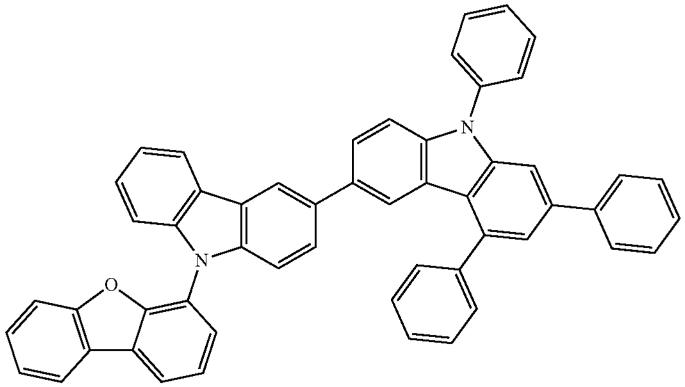 [SMILES: c1ccc(-c2cc(-c3ccccc3)c3c4cc(-c5ccc6c(c5)c5ccccc5n6-c5cccc6c5oc5ccccc56)ccc4n(-c4ccccc4)c3c2)cc1] | CAS-2018307-51-0 |
| 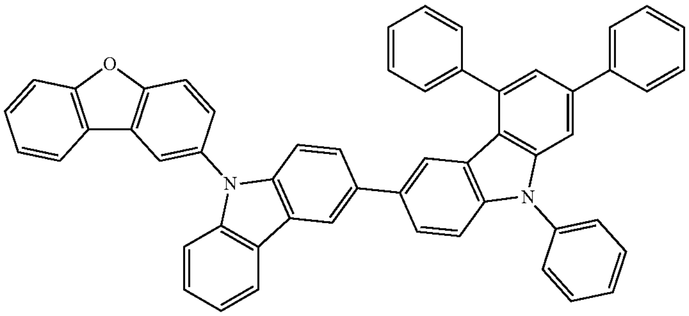 | CAS-2018307-53-2 |
| 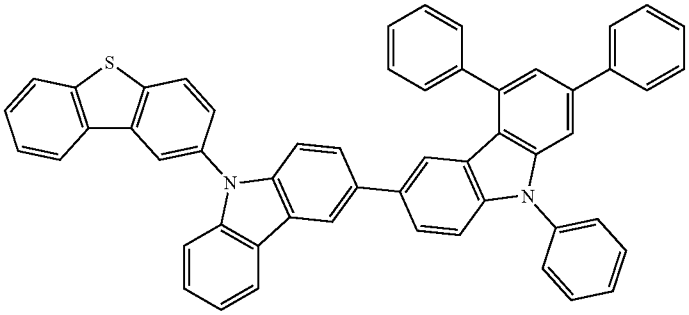 [SMILES: c1ccc(-c2cc(-c3ccccc3)c3c4cc(-c5ccc6c(c5)c5ccccc5n6-c5ccc6oc7ccccc7c6c5)ccc4n(-c4ccccc4)c3c2)cc1] | CAS-2018307-54-3 |

TABLE 9-continued
| Structure | CAS number |
|---|---|
| 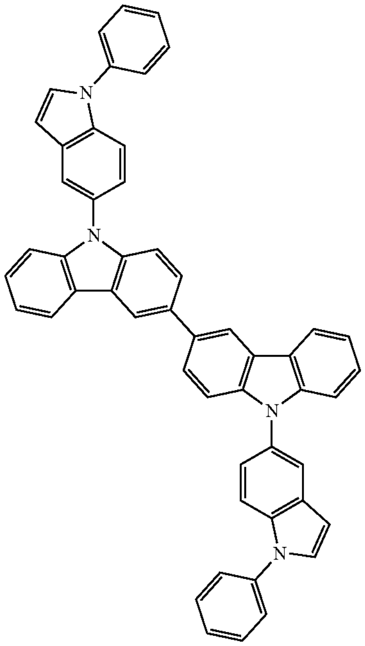 [SMILES: c1ccc(-n2ccc3cc(-n4c5ccccc5c5cc(-c6ccc7c(c6)c6ccccc6n7-c6ccc7c(ccn7-c7ccccc7)c6)ccc54)ccc32)cc1] | CAS-1656982-32-9 |
| 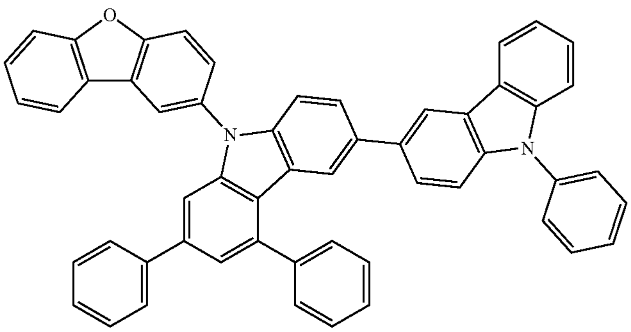 [SMILES: c1ccc(-c2cc(-c3ccccc3)c3c4cc(-c5ccc6c(c5)c5ccccc5n6-c5ccccc5)ccc4n(-c4ccc5oc6ccccc6c5c4)c3c2)cc1] | CAS-2018307-80-5 |
| 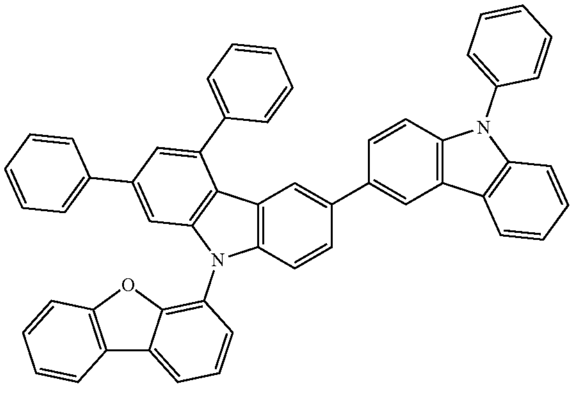 [SMILES: c1ccc(-c2cc(-c3ccccc3)c3c4cc(-c5ccc6c(c5)c5ccccc5n6-c5ccccc5)ccc4n(-c4cccc5c4oc4ccccc45)c3c2)cc1] | CAS-2018307-79-2 |

TABLE 9-continued
| Structure | CAS number |
| --- | --- |
| 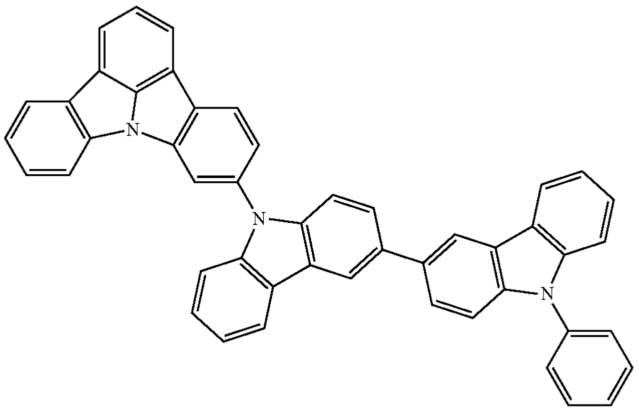 [SMILES: c1ccc(-n2c3ccccc3c3cc(-c4ccc5c(c4)c4ccccc4n5-c4ccc5c6cccc7c8ccccc8n(c5c4)c76)ccc32)cc1] | CAS-1799483-31-0 |
| 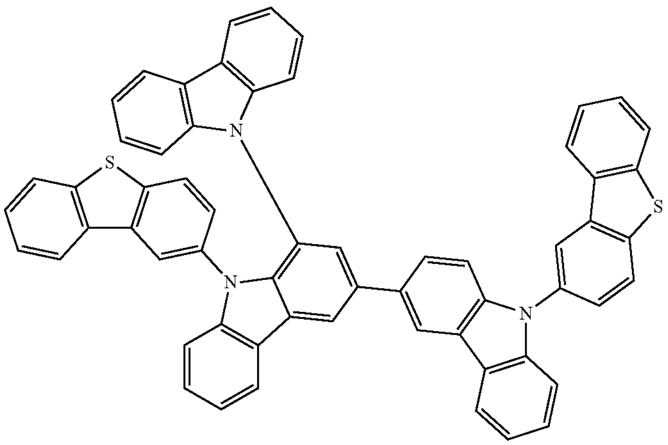 [SMILES: c1ccc2c(c1)sc1ccc(-n3c4ccccc4c4cc(-c5cc(-n6c7ccccc7c7ccccc76)c6c(c5)c5ccccc5n6-c5ccc6sc7ccccc7c6c5)ccc43)cc12] | CAS-1704071-33-9 |
| 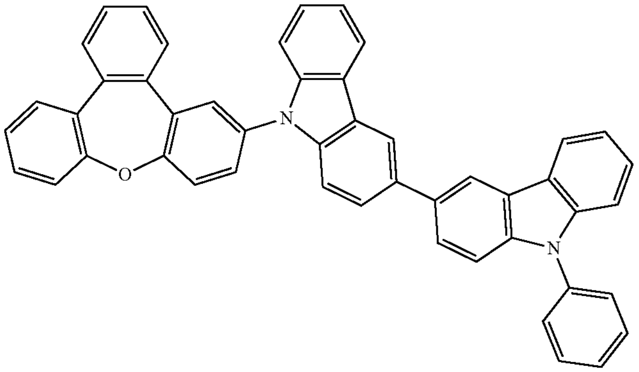 [SMILES: c1ccc(-n2c3ccccc3c3cc(-c4ccc5c(c4)c4ccccc4n5-c4ccc5c(c4)-c4ccccc4-c4ccccc4O5)ccc32)cc1] | CAS-1792238-01-7 |

TABLE 9-continued
| Structure | CAS number |
|---|---|
| 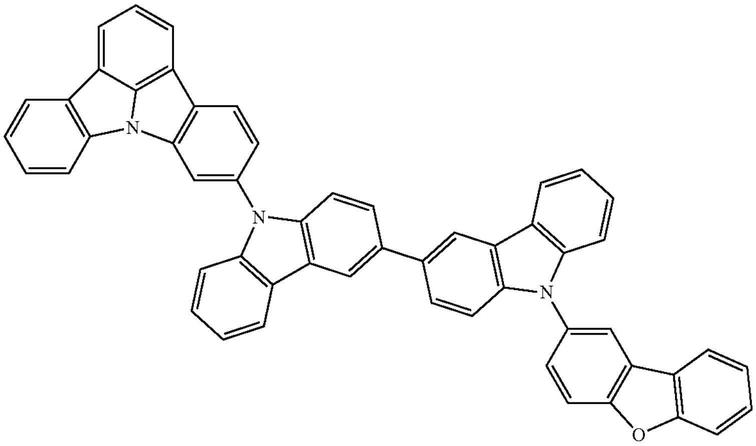 [SMILES: c1ccc2c(c1)oc1ccc(-n3c4ccccc4c4cc(-c5ccc6c(c5)c5ccccc5n6-c5ccc6c7cccc8c9ccccc9n(c6c5)c87)ccc43)cc12] | CAS-1799483-43-4 |
| 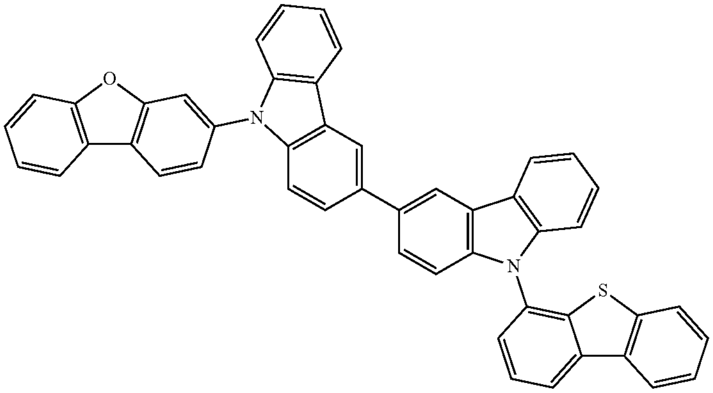 [SMILES: c1ccc2c(c1)oc1cc(-n3c4ccccc4c4cc(-c5ccc6c(c5)c5ccccc5n6-c5cccc6c5sc5ccccc56)ccc43)ccc12] | CAS-2020391-63-1 |
| 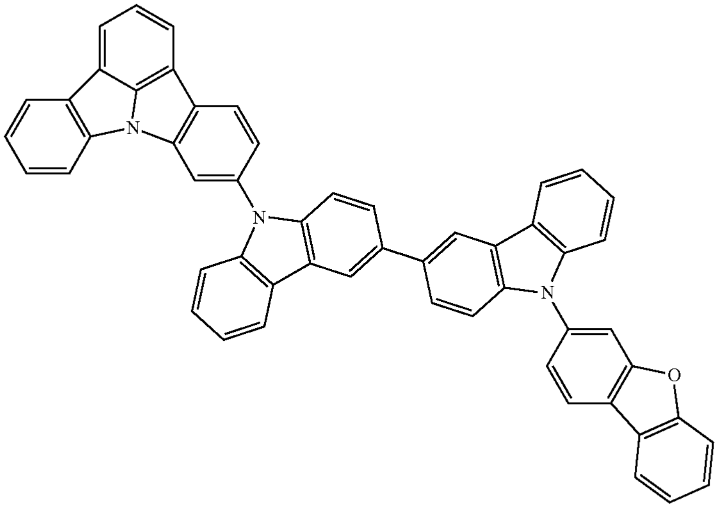 [SMILES: c1ccc2c(c1)oc1cc(-n3c4ccccc4c4cc(-c5ccc6c(c5)c5ccccc5n6-c5ccc6c7cccc8c9ccccc9n(c6c5)c87)ccc43)ccc12] | CAS-1799483-44-5 |

TABLE 9-continued
| Structure | CAS number |
| --- | --- |
| 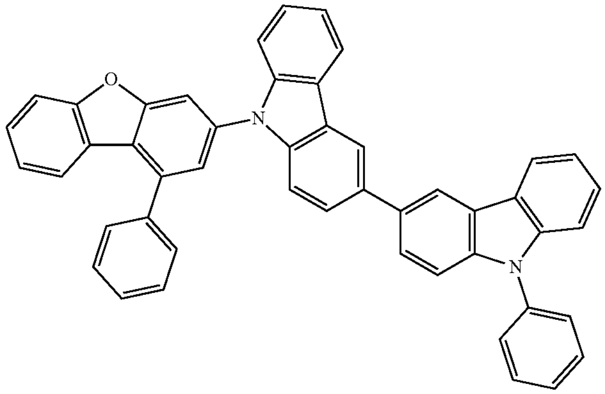 [SMILES: c1ccc(-c2cc(-n3c4ccccc4c4cc(-c5ccc6c(c5)c5ccccc5n6-c5ccccc5)ccc43)cc3oc4ccccc4c23)cc1] | CAS-2020391-71-1 |
| 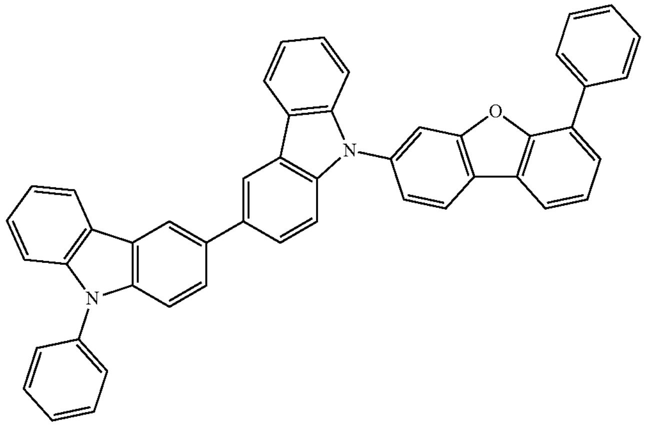 [SMILES: c1ccc(-c2cccc3c2oc2cc(-n4c5ccccc5c5cc(-c6ccc7c(c6)c6ccccc6n7-c6ccccc6)ccc54)ccc23)cc1] | CAS-2020391-73-3 |
| 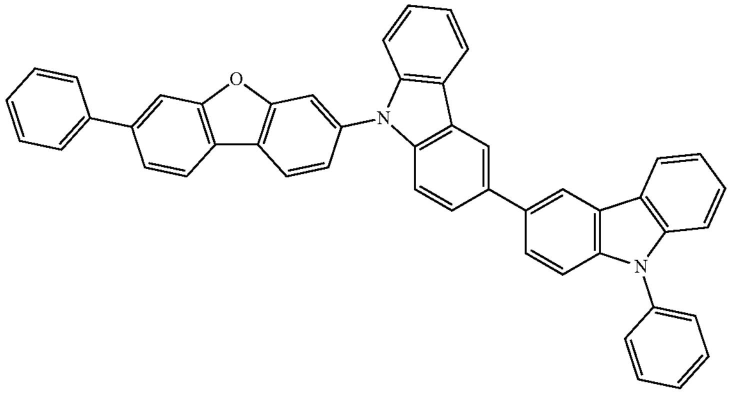 [SMILES: c1ccc(-c2ccc3c(c2)oc2cc(-n4c5ccccc5c5cc(-c6ccc7c(c6)c6ccccc6n7-c6ccccc6)ccc54)ccc23)cc1] | CAS-2020391-72-2 |

TABLE 9-continued
| Structure | CAS number |
| --- | --- |
| 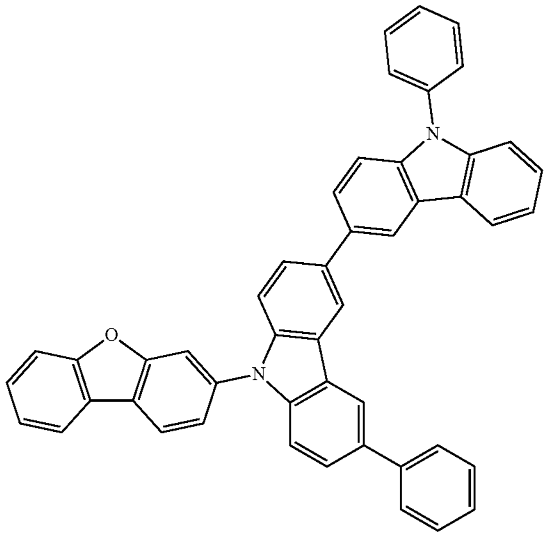 [SMILES: c1ccc(-c2ccc3c(c2)c2cc(-c4ccc5c(c4)c4ccccc4n5-c4ccccc4)ccc2n3-c2ccc3c(c2)oc2ccccc23)cc1] | CAS-2020391-75-5 |
| 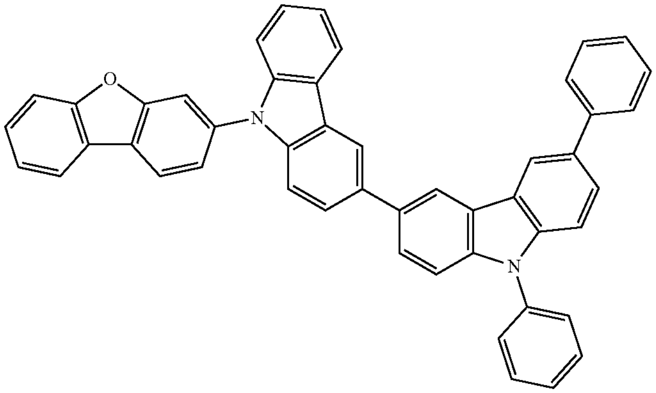 [SMILES: c1ccc(-c2ccc3c(c2)c2cc(-c4ccc5c(c4)c4ccccc4n5-c4ccc5c(c4)oc4ccccc45)ccc2n3-c2ccccc2)cc1] | CAS-2020391-74-4 |
| 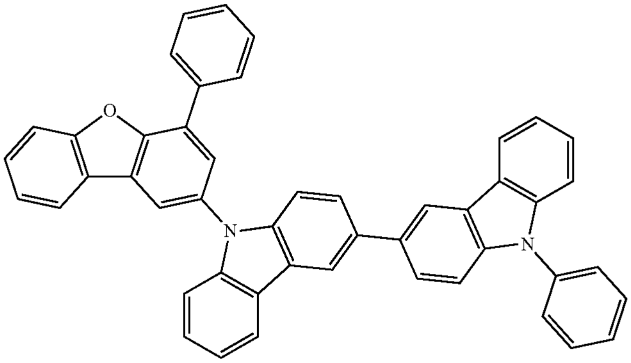 [SMILES: c1ccc(-c2cc(-n3c4ccccc4c4cc(-c5ccc6c(c5)c5ccccc5n6-c5ccccc5)ccc43)cc3c2oc2ccccc23)cc1] | CAS-2079874-13-6 |

TABLE 9-continued
| Structure | CAS number |
|---|---|
| 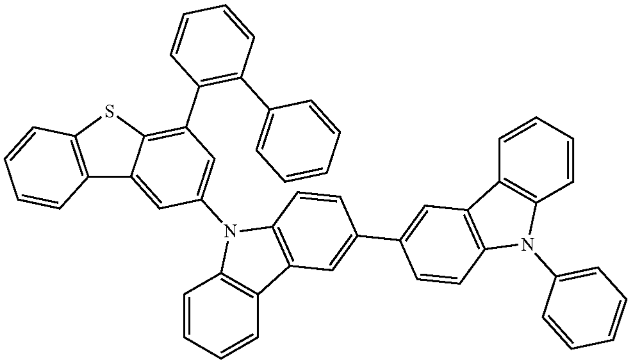 [SMILES: c1ccc(-c2ccccc2-c2cc(-n3c4ccccc4c4cc(-c5ccc6c(c5)c5ccccc5n6-c5ccccc5)ccc43)cc3c2sc2ccccc23)cc1] | CAS-2075738-96-2 |
| 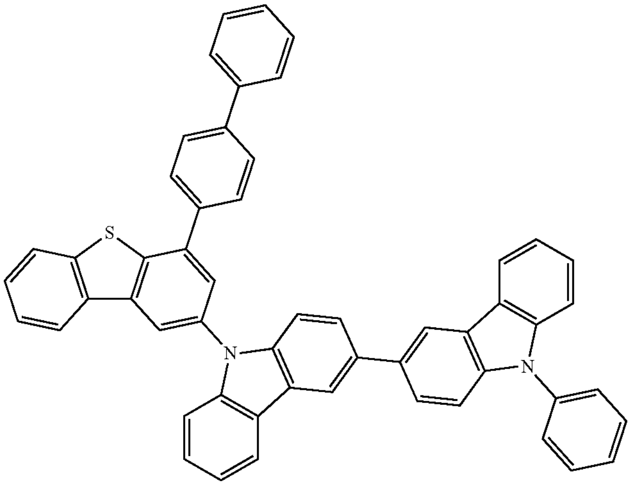 [SMILES: c1ccc(-c2ccc(-c3cc(-n4c5ccccc5c5cc(-c6ccc7c(c6)c6ccccc6n7-c6ccccc6)ccc54)cc4c3sc3ccccc34)cc2)cc1] | CAS-2075738-98-4 |
| 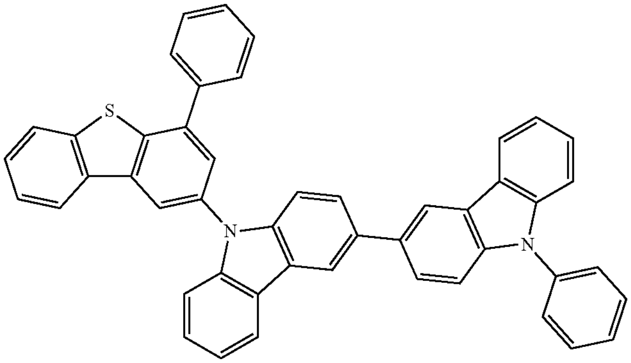 | CAS-2075738-97-3 |
| 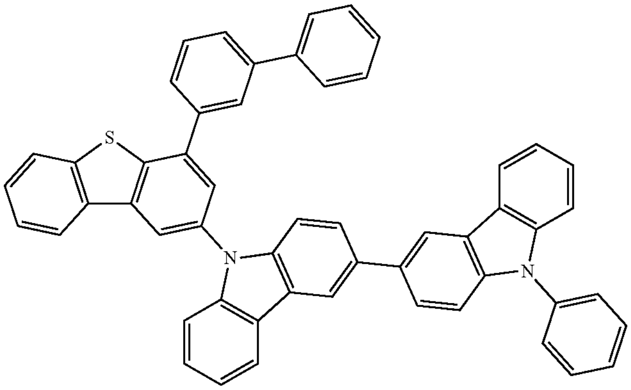 [SMILES: c1ccc(-c2cccc(-c3cc(-n4c5ccccc5c5cc(-c6ccc7c(c6)c6ccccc6n7-c6ccccc6)ccc54)cc4c3sc3ccccc34)c2)cc1] | CAS-2075738-99-5 |

TABLE 9-continued
| Structure | CAS number |
| --- | --- |
| 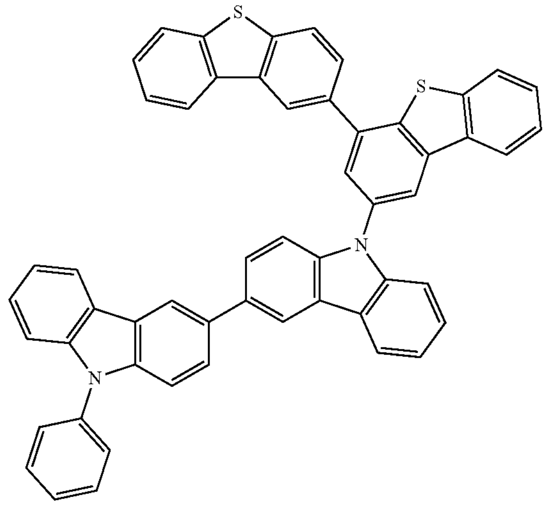 [SMILES: c1ccc(-n2c3ccccc3c3cc(-c4ccc5c(c4)c4ccccc4n5-c4cc(-c5ccc6sc7ccccc7c6c5)c5sc6ccccc6c5c4)ccc32)cc1] | CAS-2075739-04-5 |
| 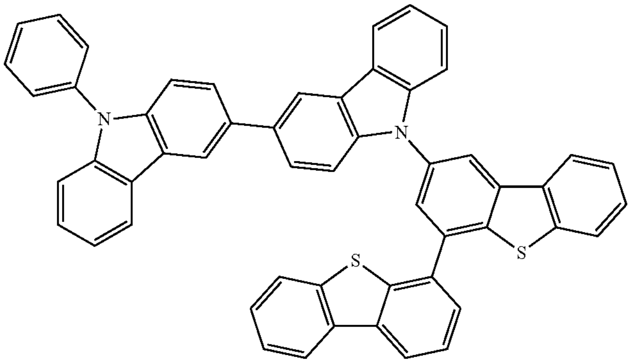 [SMILES: c1ccc(-n2c3ccccc3c3cc(-c4ccc5c(c4)c4ccccc4n5-c4cc(-c5cccc6c5sc5ccccc56)c5sc6ccccc6c5c4)ccc32)cc1] | CAS-2075739-05-6 |
| 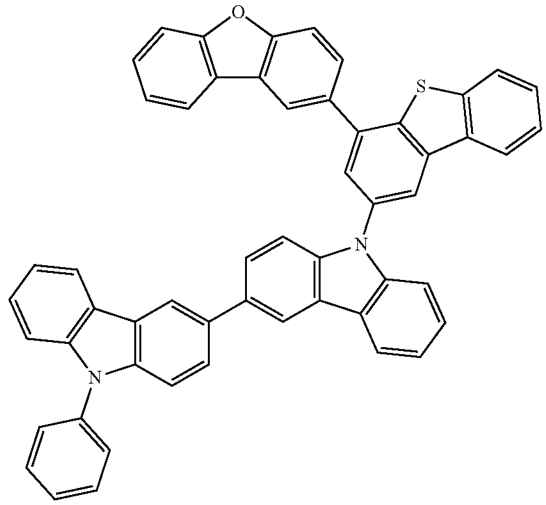 | CAS-2075739-06-7 |

TABLE 9-continued
| Structure | CAS number |
|---|---|
| 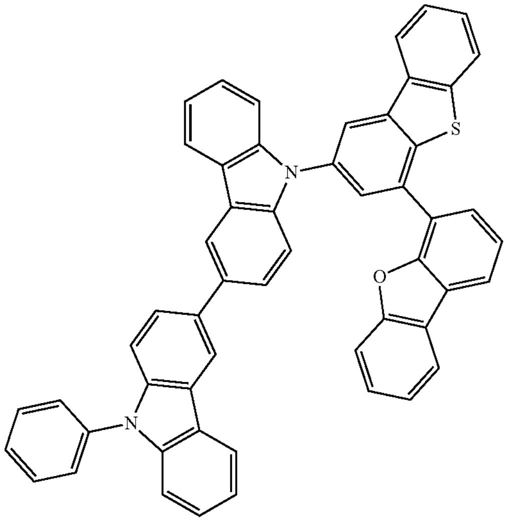 [SMILES: c1ccc(-n2c3ccccc3c3cc(-c4ccc5c(c4)c4ccccc4n5-c4cc(-c5cccc6c5oc5ccccc56)c5sc6ccccc6c5c4)ccc32)cc1] | CAS-2075739-07-8. |
| 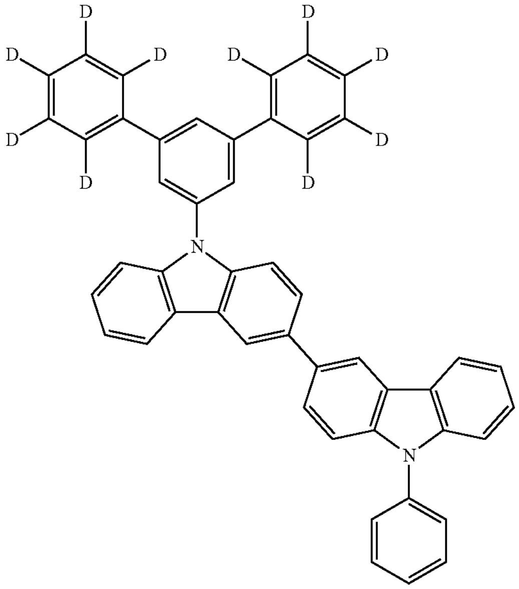 [SMILES: [2H]c1c([2H])c([2H])c(-c2cc(-c3c([2H])c([2H])c([2H])c([2H])c3[2H])cc(-n3c4ccccc4c4cc(-c5ccc6c(c5)c5ccccc5n6-c5ccccc5)ccc43)c2)c([2H])c1[2H]] | |

TABLE 9-continued
| Structure | CAS number |
| --- | --- |
| 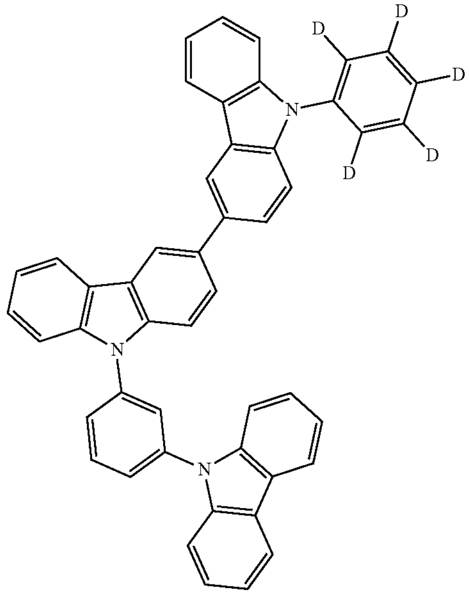 [SMILES: [2H]c1c([2H])c([2H])c(-n2c3ccccc3c3cc(-c4ccc5c(c4)c4ccccc4n5-c4cccc(-n5c6ccccc6c6ccccc65)c4)ccc32)c([2H])c1[2H]] | |
| 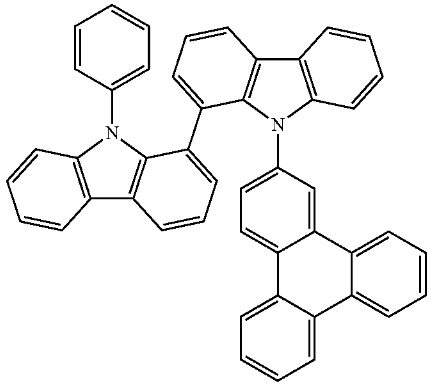 [SMILES: c1ccc(-n2c3ccccc3c3cccc(-c4cccc5c6ccccc6n(-c6ccc7c8ccccc8c8ccccc8c7c6)c45)c32)cc1] | |
| 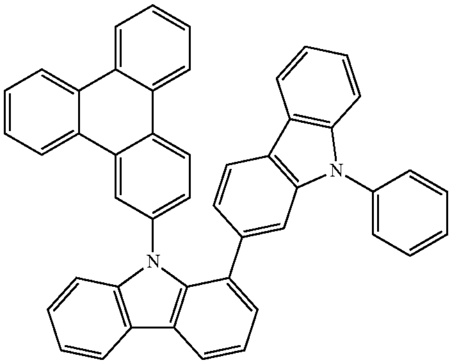 [SMILES: c1ccc(-n2c3ccccc3c3ccc(-c4cccc5c6ccccc6n(-c6ccc7c8ccccc8c8ccccc8c7c6)c45)cc32)cc1] | |

TABLE 9-continued
| Structure | CAS number |
| --- | --- |
| 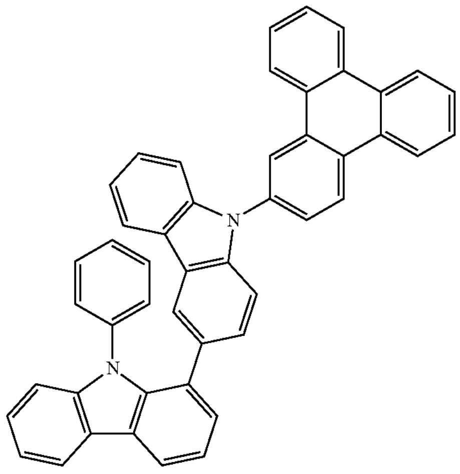 [SMILES: c1ccc(-n2c3ccccc3c3cccc(-c4ccc5c(c4)c4ccccc4n5-c4ccc5c6ccccc6c6ccccc6c5c4)c32)cc1] | |
| 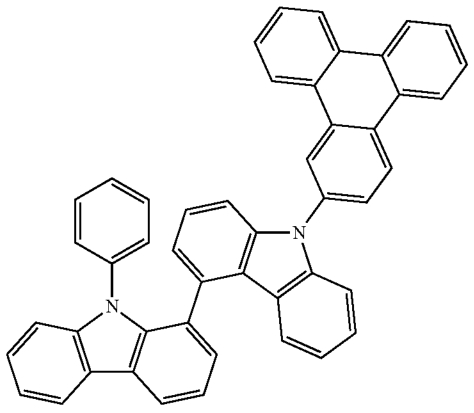 [SMILES: c1ccc(-n2c3ccccc3c3cccc(-c4cccc5c4c4ccccc4n5-c4ccc5c6ccccc6c6ccccc6c5c4)c32)cc1] | |
| 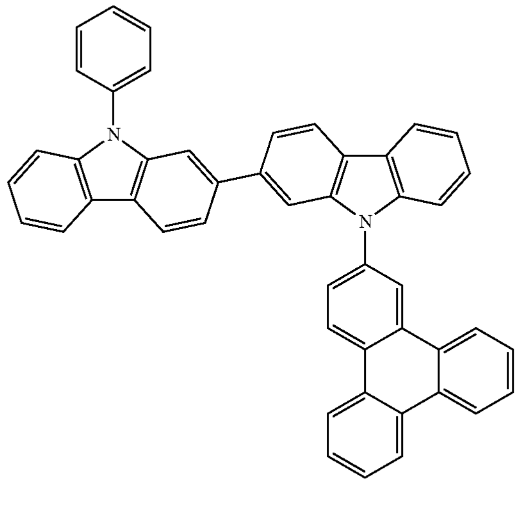 [SMILES: c1ccc(-n2c3ccccc3c3ccc(-c4ccc5c6ccccc6n(-c6ccc7c8ccccc8c8ccccc8c7c6)c5c4)cc32)cc1] | |

TABLE 9-continued
| Structure | CAS number |
| --- | --- |
| 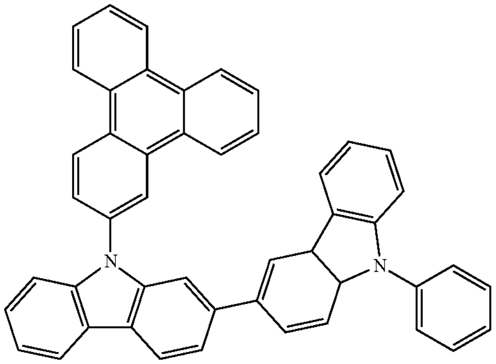 [SMILES: C1=CC2C(C=C1c1ccc3c4ccccc4n(-c4ccc5c6ccccc6c6ccccc6c5c4)c3c1)c1ccccc1N2c1ccccc1] | |
| 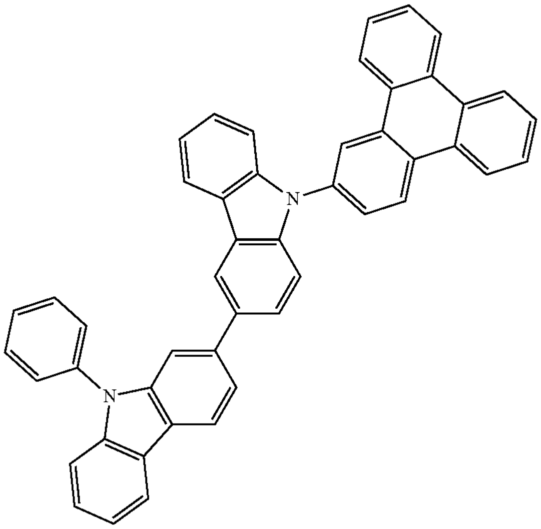 [SMILES: c1ccc(-n2c3ccccc3c3ccc(-c4ccc5c(c4)c4ccccc4n5-c4ccc5c6ccccc6c6ccccc6c5c4)cc32)cc1] | |
| 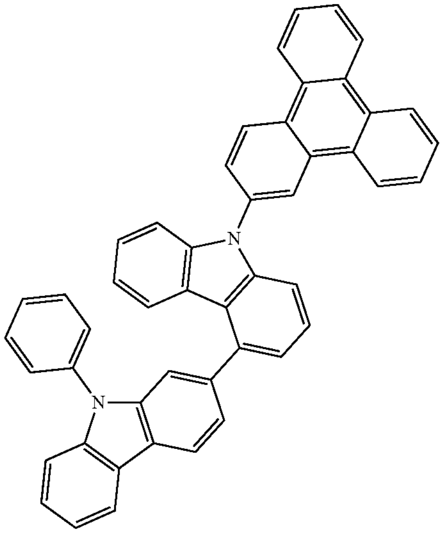 [SMILES: c1ccc(-n2c3ccccc3c3ccc(-c4cccc5c4c4ccccc4n5-c4ccc5c6ccccc6c6ccccc6c5c4)cc32)cc1] | |

TABLE 9-continued
| Structure | CAS number |
| --- | --- |
| 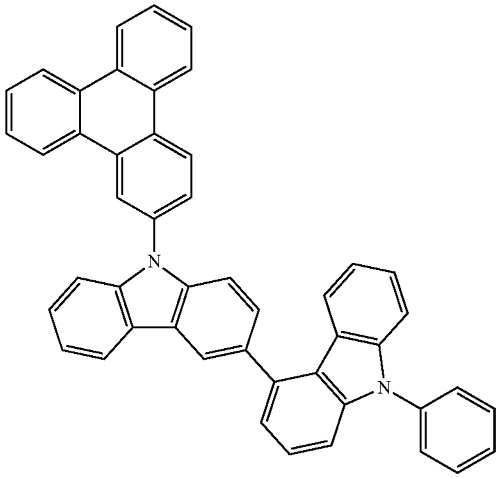 [SMILES: c1ccc(-n2c3ccccc3c3c(-c4ccc5c(c4)c4ccccc4n5-c4ccc5c6ccccc6c6ccccc6c5c4)cccc32)cc1] | |
| 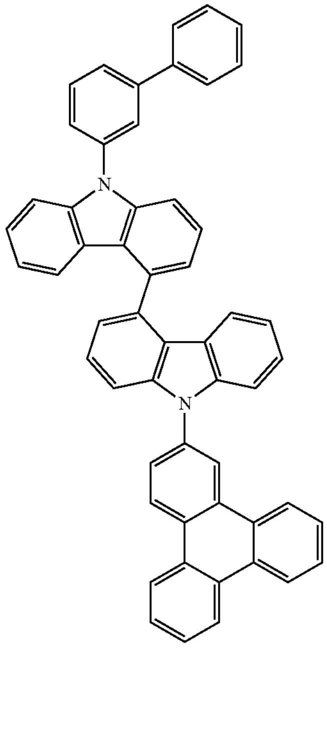 [SMILES: c1ccc(-c2cccc(-n3c4ccccc4c4c(-c5cccc6c5c5ccccc5n6-c5ccc6c7ccccc7c7ccccc7c6c5)cccc43)c2)cc1] | |

TABLE 9-continued

| Structure | CAS number |
| --- | --- |
| 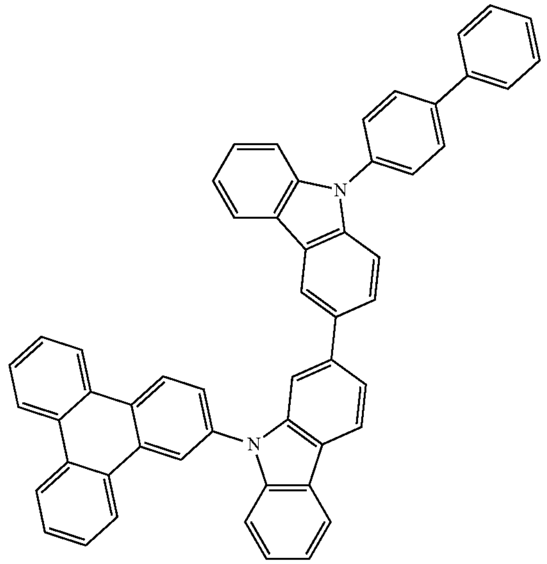 [SMILES: c1ccc(-c2ccc(-n3c4ccccc4c4cc(-c5ccc6c7ccccc7n(-c7ccc8c9ccccc9c9ccccc9c8c7)c6c5)ccc43)cc2)cc1] | |
| 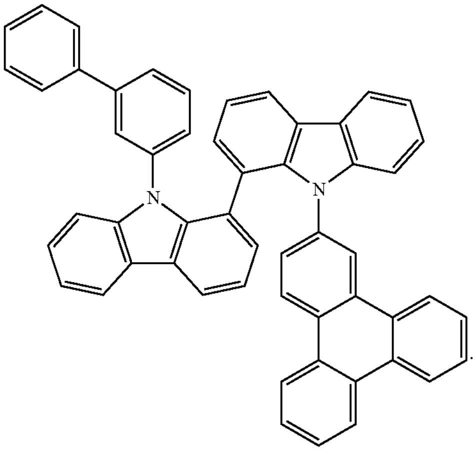 [SMILES: c1ccc(-c2cccc(-n3c4ccccc4c4cccc(-c5cccc6c7ccccc7n(-c7ccc8c9ccccc9c9ccccc9c8c7)c56)c43)c2)cc1] | |

Particularly suitable examples of compounds of the formula (2), (2a) or (2b) which are selected in accordance with the invention are compounds 89 to 101, as described above.

The preparation of the compounds of the formula (2) or the preferred compounds of the formula (2a) and (2b) and the compounds from Table 9 is known to the person skilled in the art. The compounds can be prepared by synthesis steps known to the Derson skilled in the art, such as, for example, halogenation, preferably bromination, and a subsequent organometallic coupling reaction, for example Suzuki coupling, Heck coupling or Hartwig-Buchwald coupling. Some of the biscarbazoles of the formula (2) are commercially available.

The compounds of the formula (2) or the preferred compounds of the formula (2a) and (2b) can be prepared, for example, in accordance with Scheme 6 or Scheme 7.

Scheme 6, for the preparation of asymmetrical biscarbazoles of the formula (2), (2a) or (2b):

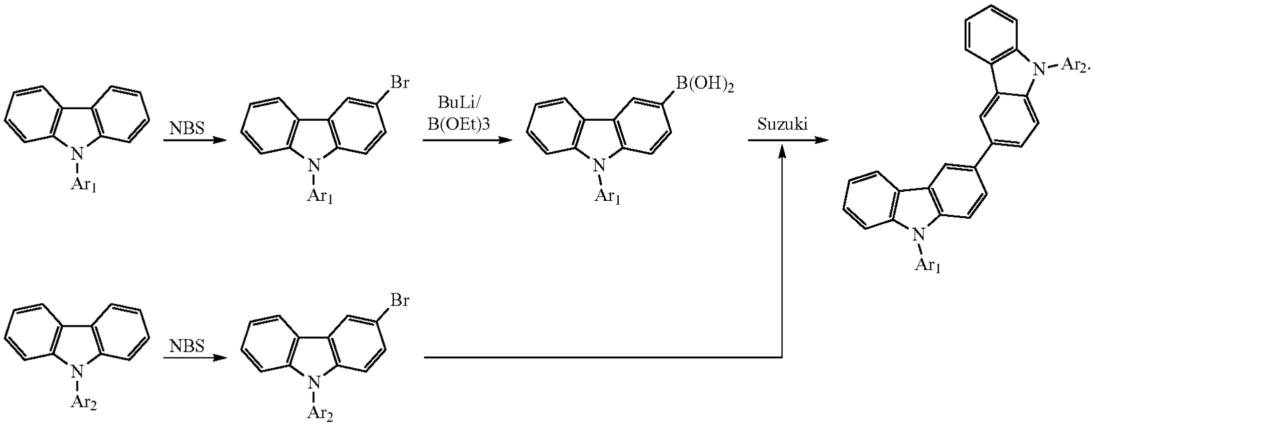

Scheme 7, for the preparation of symmetrical biscarbazoles of the formula (2), (2a) or (2b) ($Ar_1$ and $Ar_2$ are identical and abbreviated to $Ar_1$ in the scheme):

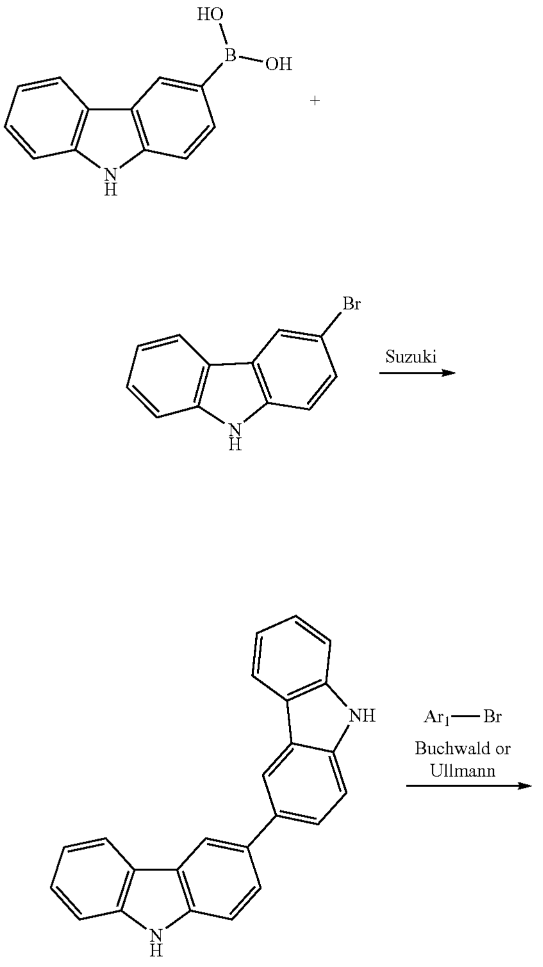

-continued

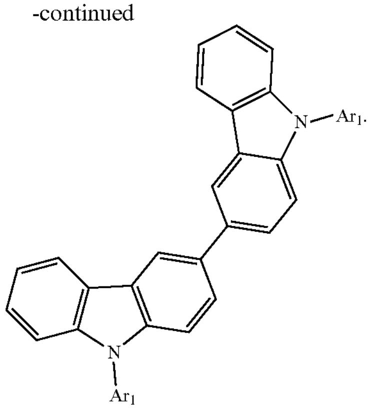

Further details on the syntheses and further literature citations are described in the experimental part.

The above-mentioned host materials of the formulae (1), (1a) to (11) and the preferably described embodiments thereof or the compounds from Tables 1 to 8 can in accordance with the invention be combined as desired with the said host materials of the formulae (2), (2a) and (2b) and preferably described embodiments thereof or the compounds from Table 9.

Particularly preferred mixtures of the host materials of the formula (1) with the host materials of the formula (2) for the compositions according to the invention are obtained by combination of compounds 1 to 88 from Tables 5 to 8 with the compounds from Table 9.

Very particularly preferred mixtures M1 to M279 of the host materials of the formula (1) with the host materials of the formula (2) are obtained by combination of compounds 1 to 21 from Table 5 with compounds 89 to 101 from Table 9, as shown below in Table 10.

TABLE 10

| | | |
|---|---|---|
| M1 | 1 | 89 (CAS-1454567-05-5) |
| M2 | 1 | 90 (CAS-1352040-89-1) |
| M3 | 1 | 91 (CAS-1643479-47-3) |

TABLE 10-continued

| | | |
|---|---|---|
| M4 | 1 | 92 (CAS-1643479-49-5) |
| M5 | 1 | 93 (CAS-1799958-78-3) |
| M6 | 1 | 94 (CAS-57102-51-9) |
| M7 | 1 | 95 |
| M8 | 1 | 96 (CAS-1427160-09-5) |
| M9 | 1 | 97 (CAS-1643479-72-4) |
| M10 | 1 | 98 |
| M11 | 1 | 99 |
| M12 | 1 | 100 (CAS-1643479-59-7) |
| M13 | 1 | 101 (CAS-1643479-68-8) |
| M14 | 2 | 89 (CAS-1454567-05-5) |
| M15 | 2 | 90 (CAS-1352040-89-1) |
| M16 | 2 | 91 (CAS-1643479-47-3) |
| M17 | 2 | 92 (CAS-1643479-49-5) |
| M18 | 2 | 93 (CAS-1799958-78-3) |
| M19 | 2 | 94 (CAS-57102-51-9) |
| M20 | 2 | 95 |
| M21 | 2 | 96 (CAS-1427160-09-5) |
| M22 | 2 | 97 (CAS-1643479-72-4) |
| M23 | 2 | 98 |
| M24 | 2 | 99 |
| M25 | 2 | 100 (CAS-1643479-59-7) |
| M26 | 2 | 101 (CAS-1643479-68-8) |
| M27 | 3 | 89 (CAS-1454567-05-5) |
| M28 | 3 | 90 (CAS-1352040-89-1) |
| M29 | 3 | 91 (CAS-1643479-47-3) |
| M30 | 3 | 92 (CAS-1643479-49-5) |
| M31 | 3 | 93 (CAS-1799958-78-3) |
| M32 | 3 | 94 (CAS-57102-51-9) |
| M33 | 3 | 95 |
| M34 | 3 | 96 (CAS-1427160-09-5) |
| M35 | 3 | 97 (CAS-1643479-72-4) |
| M36 | 3 | 98 |
| M37 | 3 | 99 |
| M38 | 3 | 100 (CAS-1643479-59-7) |
| M39 | 3 | 101 (CAS-1643479-68-8) |
| M40 | 4 | 22 (CAS-1454567-05-5) |
| M41 | 4 | 90 (CAS-1352040-89-1) |
| M42 | 4 | 91 (CAS-1643479-47-3) |
| M43 | 4 | 92 (CAS-1643479-49-5) |
| M44 | 4 | 93 (CAS-1799958-78-3) |
| M45 | 4 | 94 (CAS-57102-51-9) |
| M46 | 4 | 95 |
| M47 | 4 | 96 (CAS-1427160-09-5) |
| M48 | 4 | 97 (CAS-1643479-72-4) |

TABLE 10-continued

| | | |
|---|---|---|
| M49 | 4 | 98 |
| M50 | 4 | 99 |
| M51 | 4 | 100 (CAS-1643479-59-7) |
| M52 | 4 | 101 (CAS-1643479-68-8) |
| M53 | 5 | 89 (CAS-1454567-05-5) |
| M54 | 5 | 90 (CAS-1352040-89-1) |
| M55 | 5 | 91 (CAS-1643479-47-3) |
| M56 | 5 | 92 (CAS-1643479-49-5) |
| M57 | 5 | 93 (CAS-1799958-78-3) |
| M58 | 5 | 94 (CAS-57102-51-9) |
| M59 | 5 | 95 |
| M60 | 5 | 96 (CAS-1427160-09-5) |
| M61 | 5 | 97 (CAS-1643479-72-4) |
| M62 | 5 | 98 |
| M64 | 5 | 99 |
| M65 | 5 | 100 (CAS-1643479-59-7) |
| M66 | 5 | 101 (CAS-1643479-68-8) |
| M67 | 6 | 22 (CAS-1454567-05-5) |
| M68 | 6 | 90 (CAS-1352040-89-1) |
| M69 | 6 | 91 (CAS-1643479-47-3) |
| M70 | 6 | 92 (CAS-1643479-49-5) |
| M71 | 6 | 93 (CAS-1799958-78-3) |
| M72 | 6 | 94 (CAS-57102-51-9) |
| M73 | 6 | 95 |
| M74 | 6 | 96 (CAS-1427160-09-5) |
| M75 | 6 | 97 (CAS-1643479-72-4) |
| M76 | 6 | 98 |
| M77 | 6 | 99 |
| M78 | 6 | 100 (CAS-1643479-59-7) |
| M79 | 6 | 101 (CAS-1643479-68-8) |
| M80 | 7 | 89 (CAS-1454567-05-5) |
| M81 | 7 | 90 (CAS-1352040-89-1) |
| M82 | 7 | 91 (CAS-1643479-47-3) |
| M83 | 7 | 92 (CAS-1643479-49-5) |
| M84 | 7 | 93 (CAS-1799958-78-3) |
| M85 | 7 | 94 (CAS-57102-51-9) |
| M86 | 7 | 95 |
| M87 | 7 | 96 (CAS-1427160-09-5) |
| M88 | 7 | 97 (CAS-1643479-72-4) |
| M89 | 7 | 98 |
| M90 | 7 | 99 |
| M91 | 7 | 100 (CAS-1643479-59-7) |
| M92 | 7 | 101 (CAS-1643479-68-8) |
| M93 | 8 | 22 (CAS-1454567-05-5) |
| M94 | 8 | 90 (CAS-1352040-89-1) |

TABLE 10-continued

| | | |
|---|---|---|
| M95 | 8 | 91 (CAS-1643479-47-3) |
| M96 | 8 | 92 (CAS-1643479-49-5) |
| M97 | 8 | 93 (CAS-1799958-78-3) |
| M98 | 8 | 94 (CAS-57102-51-9) |
| M99 | 8 | 95 |
| M100 | 8 | 96 (CAS-1427160-09-5) |
| M101 | 8 | 97 (CAS-1643479-72-4) |
| M102 | 8 | 98 |
| M103 | 8 | 99 |
| M104 | 8 | 100 (CAS-1643479-59-7) |
| M105 | 8 | 101 (CAS-1643479-68-8) |
| M106 | 9 | 89 (CAS-1454567-05-5) |
| M107 | 9 | 90 (CAS-1352040-89-1) |
| M108 | 9 | 91 (CAS-1643479-47-3) |
| M109 | 9 | 92 (CAS-1643479-49-5) |
| M110 | 9 | 93 (CAS-1799958-78-3) |
| M111 | 9 | 94 (CAS-57102-51-9) |
| M112 | 9 | 95 |
| M113 | 9 | 96 (CAS-1427160-09-5) |
| M114 | 9 | 97 (CAS-1643479-72-4) |
| M115 | 9 | 98 |
| M116 | 9 | 99 |
| M117 | 9 | 100 (CAS-1643479-59-7) |
| M118 | 9 | 101 (CAS-1643479-68-8) |
| M119 | 10 | 89 (CAS-1454567-05-5) |
| M120 | 10 | 90 (CAS-1352040-89-1) |
| M121 | 10 | 91 (CAS-1643479-47-3) |
| M122 | 10 | 92 (CAS-1643479-49-5) |
| M123 | 10 | 93 (CAS-1799958-78-3) |
| M124 | 10 | 94 (CAS-57102-51-9) |
| M125 | 10 | 95 |
| M126 | 10 | 96 (CAS-1427160-09-5) |
| M127 | 10 | 97 (CAS-1643479-72-4) |
| M128 | 10 | 98 |
| M129 | 10 | 99 |
| M130 | 10 | 100 (CAS-1643479-59-7) |
| M131 | 10 | 101 (CAS-1643479-68-8) |
| M132 | 11 | 89 (CAS-1454567-05-5) |
| M133 | 11 | 90 (CAS-1352040-89-1) |
| M134 | 11 | 91 (CAS-1643479-47-3) |
| M135 | 11 | 92 (CAS-1643479-49-5) |
| M136 | 11 | 93 (CAS-1799958-78-3) |
| M137 | 11 | 94 (CAS-57102-51-9) |
| M138 | 11 | 95 |
| M139 | 11 | 96 (CAS-1427160-09-5) |

TABLE 10-continued

| | | |
|---|---|---|
| M140 | 11 | 97 (CAS-1643479-72-4) |
| M141 | 11 | 98 |
| M142 | 11 | 99 |
| M143 | 11 | 100 (CAS-1643479-59-7) |
| M144 | 11 | 101 (CAS-1643479-68-8) |
| M145 | 12 | 89 (CAS-1454567-05-5) |
| M146 | 12 | 90 (CAS-1352040-89-1) |
| M147 | 12 | 91 (CAS-1643479-47-3) |
| M148 | 12 | 92 (CAS-1643479-49-5) |
| M149 | 12 | 93 (CAS-1799958-78-3) |
| M150 | 12 | 94 (CAS-57102-51-9) |
| M151 | 12 | 95 |
| M152 | 12 | 96 CAS-1427160-09-5) |
| M153 | 12 | 97 (CAS-1643479-72-4) |
| M154 | 12 | 98 |
| M155 | 12 | 99 |
| M156 | 12 | 100 (CAS-1643479-59-7) |
| M157 | 12 | 101 (CAS-1643479-68-8) |
| M158 | 13 | 89 (CAS-1454567-05-5) |
| M159 | 13 | 90 (CAS-1352040-89-1) |
| M160 | 13 | 91 (CAS-1643479-47-3) |
| M161 | 13 | 92 (CAS-1643479-49-5) |
| M162 | 13 | 93 (CAS-1799958-78-3) |
| M163 | 13 | 94 (CAS-57102-51-9) |
| M164 | 13 | 95 |
| M165 | 13 | 96 (CAS-1427160-09-5) |
| M166 | 13 | 97 (CAS-1643479-72-4) |
| M167 | 13 | 98 |
| M168 | 13 | 99 |
| M169 | 13 | 100 (CAS-1643479-59-7) |
| M170 | 13 | 101 (CAS-1643479-68-8) |
| M171 | 14 | 89 (CAS-1454567-05-5) |
| M172 | 14 | 90 (CAS-1352040-89-1) |
| M173 | 14 | 91 (CAS-1643479-47-3) |
| M174 | 14 | 92 (CAS-1643479-49-5) |
| M175 | 14 | 93 (CAS-1799958-78-3) |
| M176 | 14 | 94 (CAS-57102-51-9) |
| M177 | 14 | 95 |
| M178 | 14 | 96 (CAS-1427160-09-5) |
| M179 | 14 | 97 (CAS-1643479-72-4) |
| M180 | 14 | 98 |
| M181 | 14 | 99 |
| M182 | 14 | 100 (CAS-1643479-59-7) |
| M183 | 14 | 101 (CAS-1643479-68-8) |
| M184 | 15 | 89 (CAS-1454567-05-5) |

TABLE 10-continued

| | | |
|---|---|---|
| M185 | 15 | 90 (CAS-1352040-89-1) |
| M186 | 15 | 91 (CAS-1643479-47-3) |
| M187 | 15 | 92 (CAS-1643479-49-5) |
| M188 | 15 | 93 (CAS-1799958-78-3) |
| M189 | 15 | 94 (CAS-57102-51-9) |
| M190 | 15 | 95 |
| M191 | 15 | 96 (CAS-1427160-09-5) |
| M192 | 15 | 97 (CAS-1643479-72-4) |
| M193 | 15 | 98 |
| M194 | 15 | 99 |
| M195 | 15 | 100 (CAS-1643479-59-7) |
| M196 | 15 | 101 (CAS-1643479-68-8) |
| M197 | 16 | 89 (CAS-1454567-05-5) |
| M198 | 16 | 90 (CAS-1352040-89-1) |
| M199 | 16 | 91 (CAS-1643479-47-3) |
| M200 | 16 | 92 (CAS-1643479-49-5) |
| M201 | 16 | 93 (CAS-1799958-78-3) |
| M202 | 16 | 94 (CAS-57102-51-9) |
| M203 | 16 | 95 |
| M204 | 16 | 96 (CAS-1427160-09-5) |
| M205 | 16 | 97 (CAS-1643479-72-4) |
| M206 | 16 | 98 |
| M207 | 16 | 99 |
| M208 | 16 | 100 (CAS-1643479-59-7) |
| M209 | 16 | 101 (CAS-1643479-68-8) |
| M210 | 17 | 89 (CAS-1454567-05-5) |
| M211 | 17 | 90 (CAS-1352040-89-1) |
| M212 | 17 | 91 (CAS-1643479-47-3) |
| M218 | 17 | 92 (CAS-1643479-49-5) |
| M219 | 17 | 93 (CAS-1799958-78-3) |
| M220 | 17 | 94 (CAS-57102-51-9) |
| M221 | 17 | 95 |
| M222 | 17 | 96 (CAS-1427160-09-5) |
| M223 | 17 | 97 (CAS-1643479-72-4) |
| M224 | 17 | 98 |
| M225 | 17 | 99 |
| M226 | 17 | 100 (CAS-1643479-59-7) |
| M227 | 17 | 101 (CAS-1643479-68-8) |
| M228 | 18 | 89 (CAS-1454567-05-5) |
| M229 | 18 | 90 (CAS-1352040-89-1) |
| M230 | 18 | 91 (CAS-1643479-47-3) |
| M231 | 18 | 92 (CAS-1643479-49-5) |
| M232 | 18 | 93 (CAS-1799958-78-3) |
| M233 | 18 | 94 (CAS-57102-51-9) |
| M234 | 18 | 95 |

TABLE 10-continued

| | | |
|---|---|---|
| M235 | 18 | 96 (CAS-1427160-09-5) |
| M236 | 18 | 97 (CAS-1643479-72-4) |
| M237 | 18 | 98 |
| M238 | 18 | 99 |
| M239 | 18 | 100 (CAS-1643479-59-7) |
| M240 | 18 | 101 (CAS-1643479-68-8) |
| M241 | 19 | 89 (CAS-1454567-05-5) |
| M242 | 19 | 90 (CAS-1352040-89-1) |
| M243 | 19 | 91 (CAS-1643479-47-3) |
| M244 | 19 | 92 (CAS-1643479-49-5) |
| M245 | 19 | 93 (CAS-1799958-78-3) |
| M246 | 19 | 94 (CAS-57102-51-9) |
| M247 | 19 | 95 |
| M248 | 19 | 96 (CAS-1427160-09-5) |
| M249 | 19 | 97 (CAS-1643479-72-4) |
| M250 | 19 | 98 |
| M251 | 19 | 99 |
| M252 | 19 | 100 (CAS-1643479-59-7) |
| M253 | 19 | 101 (CAS-1643479-68-8) |
| M254 | 20 | 89 (CAS-1454567-05-5) |
| M255 | 20 | 90 (CAS-1352040-89-1) |
| M256 | 20 | 91 (CAS-1643479-47-3) |
| M257 | 20 | 92 (CAS-1643479-49-5) |
| M258 | 20 | 93 (CAS-1799958-78-3) |
| M259 | 20 | 94 (CAS-57102-51-9) |
| M260 | 20 | 95 |
| M261 | 20 | 96 (CAS-1427160-09-5) |
| M262 | 20 | 97 (CAS-1643479-72-4) |
| M263 | 20 | 98 |
| M264 | 20 | 99 |
| M265 | 20 | 100 (CAS-1643479-59-7) |
| M266 | 20 | 101 (CAS-1643479-68-8) |
| M267 | 21 | 89 (CAS-1454567-05-5) |
| M268 | 21 | 90 (CAS-1352040-89-1) |
| M269 | 21 | 91 (CAS-1643479-47-3) |
| M270 | 21 | 92 (CAS-1643479-49-5) |
| M271 | 21 | 93 (CAS-1799958-78-3) |
| M272 | 21 | 94 (CAS-57102-51-9) |
| M273 | 21 | 95 |
| M274 | 21 | 96 (CAS-1427160-09-5) |
| M275 | 21 | 97 (CAS-1643479-72-4) |
| M276 | 21 | 98 |
| M277 | 21 | 99 |
| M278 | 21 | 100 (CAS-1643479-59-7) |
| M279 | 21 | 101 (CAS-1643479-68-8) |

Very particularly preferred mixtures M280 to M565 of the host materials of the formula (1) with the host materials of the formula (2) are obtained by combination of compounds 23 to 44 from Table 6 with compounds 89 to 101 from Table 9, as shown below in Table 11.

TABLE 11

| | | | | | |
|---|---|---|---|---|---|
| M280 | 23 | 89 (CAS-1454567-05-5) | M281 | 23 | 90 (CAS-1352040-89-1) |
| M282 | 23 | 91 (CAS-1643479-47-3) | M283 | 23 | 92 (CAS-1643479-49-5) |
| M284 | 23 | 93 (CAS-1799958-78-3) | M285 | 23 | 94 (CAS-57102-51-9) |
| M286 | 23 | 95 | M287 | 23 | 96 (CAS-1427160-09-5) |
| M288 | 23 | 97 (CAS-1643479-72-4) | M289 | 23 | 98 |
| M290 | 23 | 99 | M291 | 23 | 100 (CAS-1643479-59-7) |
| M292 | 23 | 101 (CAS-1643479-68-8) | | | |
| M293 | 24 | 89 (CAS-1454567-05-5) | M294 | 24 | 90 (CAS-1352040-89-1) |
| M295 | 24 | 91 (CAS-1643479-47-3) | M296 | 24 | 92 (CAS-1643479-49-5) |
| M297 | 24 | 93 (CAS-1799958-78-3) | M298 | 24 | 94 (CAS-57102-51-9) |
| M299 | 24 | 95 | M300 | 24 | 96 (CAS-1427160-09-5) |
| M301 | 24 | 97 (CAS-1643479-72-4) | M302 | 24 | 98 |
| M303 | 24 | 99 | M304 | 24 | 100 (CAS-1643479-59-7) |
| M305 | 24 | 101 (CAS-1643479-68-8) | | | |
| M306 | 25 | 89 (CAS-1454567-05-5) | M307 | 25 | 90 (CAS-1352040-89-1) |
| M308 | 25 | 91 (CAS-1643479-47-3) | M309 | 25 | 92 (CAS-1643479-49-5) |
| M310 | 25 | 93 (CAS-1799958-78-3) | M311 | 25 | 94 (CAS-57102-51-9) |
| M312 | 25 | 95 | M313 | 25 | 96 (CAS-1427160-09-5) |
| M314 | 25 | 97 (CAS-1643479-72-4) | M315 | 25 | 98 |
| M316 | 25 | 99 | M317 | 25 | 100 (CAS-1643479-59-7) |
| M318 | 25 | 101 (CAS-1643479-68-8) | | | |
| M319 | 26 | 22 (CAS-1454567-05-5) | M320 | 26 | 90 (CAS-1352040-89-1) |
| M321 | 26 | 91 (CAS-1643479-47-3) | M322 | 26 | 92 (CAS-1643479-49-5) |
| M323 | 26 | 93 (CAS-1799958-78-3) | M324 | 26 | 94 (CAS-57102-51-9) |
| M325 | 26 | 95 | M326 | 26 | 96 (CAS-1427160-09-5) |
| M327 | 26 | 97 (CAS-1643479-72-4) | M328 | 26 | 98 |
| M329 | 26 | 99 | M330 | 26 | 100 (CAS-1643479-59-7) |
| M331 | 26 | 101 (CAS-1643479-68-8) | | | |
| M332 | 27 | 89 (CAS-1454567-05-5) | M333 | 27 | 90 (CAS-1352040-89-1) |
| M334 | 27 | 91 (CAS-1643479-47-3) | M335 | 27 | 92 (CAS-1643479-49-5) |
| M336 | 27 | 93 (CAS-1799958-78-3) | M337 | 27 | 94 (CAS-57102-51-9) |
| M338 | 27 | 95 | M339 | 27 | 96 (CAS-1427160-09-5) |
| M340 | 27 | 97 (CAS-1643479-72-4) | M341 | 27 | 98 |
| M342 | 27 | 99 | M343 | 27 | 100 (CAS-1643479-59-7) |
| M344 | 27 | 101 (CAS-1643479-68-8) | | | |
| M345 | 28 | 22 (CAS-1454567-05-5) | M346 | 28 | 90 (CAS-1352040-89-1) |

TABLE 11-continued

| | | | | | |
|---|---|---|---|---|---|
| M347 | 28 | 91 (CAS-1643479-47-3) | M348 | 28 | 92 (CAS-1643479-49-5) |
| M349 | 28 | 93 (CAS-1799958-78-3) | M350 | 28 | 94 (CAS-57102-51-9) |
| M351 | 28 | 95 | M352 | 28 | 96 (CAS-1427160-09-5) |
| M353 | 28 | 97 (CAS-1643479-72-4) | M354 | 28 | 98 |
| M355 | 28 | 99 | M356 | 28 | 100 (CAS-1643479-59-7) |
| M357 | 28 | 101 (CAS-1643479-68-8) | | | |
| M358 | 29 | 89 (CAS-1454567-05-5) | M359 | 29 | 90 (CAS-1352040-89-1) |
| M360 | 29 | 91 (CAS-1643479-47-3) | M361 | 29 | 92 CAS-1643479-49-5) |
| M362 | 29 | 93 (CAS-1799958-78-3) | M363 | 29 | 94 (CAS-57102-51-9) |
| M364 | 29 | 95 | M365 | 29 | 96 (CAS-1427160-09-5) |
| M366 | 29 | 97 (CAS-1643479-72-4) | M367 | 29 | 98 |
| M368 | 29 | 99 | M369 | 29 | 100 (CAS-1643479-59-7) |
| M370 | 29 | 101 (CAS-1643479-68-8) | | | |
| M371 | 30 | 22 (CAS-1454567-05-5) | M372 | 30 | 90 (CAS-1352040-89-1) |
| M373 | 30 | 91 (CAS-1643479-47-3) | M374 | 30 | 92 (CAS-1643479-49-5) |
| M375 | 30 | 93 (CAS-1799958-78-3) | M376 | 30 | 94 (CAS-57102-51-9) |
| M377 | 30 | 95 | M378 | 30 | 96 (CAS-1427160-09-5) |
| M379 | 30 | 97 (CAS-1643479-72-4) | M380 | 30 | 98 |
| M381 | 30 | 99 | M382 | 30 | 100 (CAS-1643479-59-7) |
| M383 | 30 | 101 (CAS-1643479-68-8) | | | |
| M384 | 31 | 89 (CAS-1454567-05-5) | M385 | 31 | 90 (CAS-1352040-89-1) |
| M386 | 31 | 91 (CAS-1643479-47-3) | M387 | 31 | 92 (CAS-1643479-49-5) |
| M388 | 31 | 93 (CAS-1799958-78-3) | M389 | 31 | 94 (CAS-57102-51-9) |
| M390 | 31 | 95 | M391 | 31 | 96 (CAS-1427160-09-5) |
| M392 | 31 | 97 (CAS-1643479-72-4) | M393 | 31 | 98 |
| M394 | 31 | 99 | M395 | 31 | 100 (CAS-1643479-59-7) |
| M396 | 31 | 101 (CAS-1643479-68-8) | | | |
| M397 | 32 | 89 (CAS-1454567-05-5) | M398 | 32 | 90 (CAS-1352040-89-1) |
| M399 | 32 | 91 (CAS-1643479-47-3) | M400 | 32 | 92 (CAS-1643479-49-5) |
| M401 | 32 | 93 (CAS-1799958-78-3) | M402 | 32 | 94 (CAS-57102-51-9) |
| M403 | 32 | 95 | M404 | 32 | 96 (CAS-1427160-09-5) |
| M405 | 32 | 97 (CAS-1643479-72-4) | M406 | 32 | 98 |
| M407 | 32 | 99 | M408 | 32 | 100 (CAS-1643479-59-7) |
| M409 | 32 | 101 (CAS-1643479-68-8) | | | |
| M410 | 33 | 89 (CAS-1454567-05-5) | M411 | 33 | 90 (CAS-1352040-89-1) |
| M412 | 33 | 91 (CAS-1643479-47-3) | M413 | 33 | 92 (CAS-1643479-49-5) |
| M414 | 33 | 93 (CAS-1799958-78-3) | M415 | 33 | 94 (CAS-57102-51-9) |
| M416 | 33 | 95 | M417 | 33 | 96 (CAS-1427160-09-5) |
| M418 | 33 | 97 (CAS-1643479-72-4) | M419 | 33 | 98 |
| M420 | 33 | 99 | M421 | 33 | 100 (CAS-1643479-59-7) |

TABLE 11-continued

| | | | | | |
|---|---|---|---|---|---|
| M422 | 33 | 101 (CAS-1643479-68-8) | | | |
| M423 | 34 | 89 (CAS-1454567-05-5) | M424 | 34 | 90 (CAS-1352040-89-1) |
| M425 | 34 | 91 (CAS-1643479-47-3) | M426 | 34 | 92 (CAS-1643479-49-5) |
| M427 | 34 | 193 (CAS-1799958-78-3) | M428 | 34 | 94 (CAS-57102-51-9) |
| M429 | 34 | 95 | M430 | 34 | 96 (CAS-1427160-09-5) |
| M431 | 34 | 97 (CAS-1643479-72-4) | M432 | 34 | 98 |
| M433 | 34 | 99 | M434 | 34 | 100 (CAS-1643479-59-7) |
| M435 | 34 | 101 (CAS-1643479-68-8) | | | |
| M436 | 35 | 89 (CAS-1454567-05-5) | M437 | 35 | 90 (CAS-1352040-89-1) |
| M438 | 35 | 91 (CAS-1643479-47-3) | M439 | 35 | 92 (CAS-1643479-49-5) |
| M440 | 35 | 93 (CAS-1799958-78-3) | M441 | 35 | 94 (CAS-57102-51-9) |
| M442 | 35 | 95 | M443 | 35 | 96 (CAS-1427160-09-5) |
| M444 | 35 | 97 (CAS-1643479-72-4) | M445 | 35 | 98 |
| M446 | 35 | 99 | M447 | 35 | 100 (CAS-1643479-59-7) |
| M448 | 35 | 101 (CAS-1643479-68-8) | | | |
| M449 | 36 | 89 (CAS-1454567-05-5) | M450 | 36 | 90 (CAS-1352040-89-1) |
| M451 | 36 | 91 (CAS-1643479-47-3) | M452 | 36 | 92 (CAS-1643479-49-5) |
| M453 | 36 | 93 (CAS-1799958-78-3) | M454 | 36 | 94 (CAS-57102-51-9) |
| M455 | 36 | 95 | M456 | 36 | 96 (CAS-1427160-09-5) |
| M457 | 36 | 97 (CAS-1643479-72-4) | M458 | 36 | 98 |
| M459 | 36 | 99 | M460 | 36 | 100 (CAS-1643479-59-7) |
| M461 | 36 | 101 (CAS-1643479-68-8) | | | |
| M462 | 37 | 89 (CAS-1454567-05-5) | M463 | 37 | 90 (CAS-1352040-89-1) |
| M464 | 37 | 91 (CAS-1643479-47-3) | M465 | 37 | 92 (CAS-1643479-49-5) |
| M466 | 37 | 93 (CAS-1799958-78-3) | M467 | 37 | 94 (CAS-57102-51-9) |
| M468 | 37 | 95 | M469 | 37 | 96 (CAS-1427160-09-5) |
| M470 | 37 | 97 (CAS-1643479-72-4) | M471 | 37 | 98 |
| M472 | 37 | 99 | M473 | 37 | 100 (CAS-1643479-59-7) |
| M474 | 37 | 101 (CAS-1643479-68-8) | | | |
| M475 | 38 | 89 (CAS-1454567-05-5) | M476 | 38 | 90 (CAS-1352040-89-1) |
| M477 | 38 | 91 (CAS-1643479-47-3) | M478 | 38 | 92 (CAS-1643479-49-5) |
| M479 | 38 | 93 (CAS-1799958-78-3) | M480 | 38 | 94 (CAS-57102-51-9) |
| M481 | 38 | 95 | M482 | 38 | 96 (CAS-1427160-09-5) |
| M483 | 38 | 97 (CAS-1643479-72-4) | M484 | 38 | 98 |
| M485 | 38 | 99 | M486 | 38 | 100 (CAS-1643479-59-7) |
| M487 | 38 | 101 (CAS-1643479-68-8) | | | |
| M488 | 39 | 89 (CAS-1454567-05-5) | M489 | 39 | 90 (CAS-1352040-89-1) |
| M490 | 39 | 91 (CAS-1643479-47-3) | M491 | 39 | 92 (CAS-1643479-49-5) |
| M492 | 39 | 93 (CAS-1799958-78-3) | M493 | 39 | 94 (CAS-57102-51-9) |
| M494 | 39 | 95 | M495 | 39 | 96 (CAS-1427160-09-5) |

TABLE 11-continued

| | | | | | |
|---|---|---|---|---|---|
| M496 | 39 | 97 (CAS-1643479-72-4) | M497 | 39 | 98 |
| M498 | 39 | 99 | M499 | 39 | 100 (CAS-1643479-59-7) |
| M500 | 39 | 101 (CAS-1643479-68-8) | | | |
| M501 | 40 | 89 (CAS-1454567-05-5) | M502 | 40 | 90 (CAS-1352040-89-1) |
| M503 | 40 | 91 (CAS-1643479-47-3) | M504 | 40 | 92 (CAS-1643479-49-5) |
| M505 | 40 | 93 (CAS-1799958-78-3) | M506 | 40 | 94 (CAS-57102-51-9) |
| M507 | 40 | 95 | M508 | 40 | 96 (CAS-1427160-09-5) |
| M509 | 40 | 97 (CAS-1643479-72-4) | M510 | 40 | 98 |
| M511 | 40 | 99 | M512 | 40 | 100 (CAS-1643479-59-7) |
| M513 | 40 | 101 (CAS-1643479-68-8) | | | |
| M514 | 41 | 89 (CAS-1454567-05-5) | M515 | 41 | 90 (CAS-1352040-89-1) |
| M516 | 41 | 91 (CAS-1643479-47-3) | M517 | 41 | 92 (CAS-1643479-49-5) |
| M518 | 41 | 93 (CAS-1799958-78-3) | M519 | 41 | 94 (CAS-57102-51-9) |
| M520 | 41 | 95 | M521 | 41 | 96 (CAS-1427160-09-5) |
| M522 | 41 | 97 (CAS-1643479-72-4) | M523 | 41 | 98 |
| M524 | 41 | 99 | M525 | 41 | 100 (CAS-1643479-59-7) |
| M526 | 41 | 101 (CAS-1643479-68-8) | | | |
| M527 | 42 | 89 (CAS-1454567-05-5) | M528 | 42 | 90 (CAS-1352040-89-1) |
| M529 | 42 | 91 (CAS-1643479-47-3) | M530 | 42 | 92 (CAS-1643479-49-5) |
| M531 | 42 | 93 (CAS-1799958-78-3) | M532 | 42 | 94 (CAS-57102-51-9) |
| M533 | 42 | 95 | M534 | 42 | 96 (CAS-1427160-09-5) |
| M535 | 42 | 97 (CAS-1643479-72-4) | M536 | 42 | 98 |
| M537 | 42 | 99 | M538 | 42 | 100 (CAS-1643479-59-7) |
| M539 | 42 | 101 (CAS-1643479-68-8) | | | |
| M540 | 43 | 89 (CAS-1454567-05-5) | M541 | 43 | 90 (CAS-1352040-89-1) |
| M542 | 43 | 91 (CAS-1643479-47-3) | M543 | 43 | 92 (CAS-1643479-49-5) |
| M544 | 43 | 93 (CAS-1799958-78-3) | M545 | 43 | 94 (CAS-57102-51-9) |
| M546 | 43 | 95 | M547 | 43 | 96 (CAS-1427160-09-5) |
| M548 | 43 | 97 (CAS-1643479-72-4) | M549 | 43 | 98 |
| M550 | 43 | 99 | M551 | 43 | 100 (CAS-1643479-59-7) |
| M552 | 43 | 101 (CAS-1643479-68-8) | | | |
| M553 | 44 | 89 (CAS-1454567-05-5) | M554 | 44 | 90 (CAS-1352040-89-1) |
| M555 | 44 | 91 (CAS-1643479-47-3) | M556 | 44 | 92 (CAS-1643479-49-5) |
| M557 | 44 | 93 (CAS-1799958-78-3) | M558 | 44 | 94 (CAS-57102-51-9) |
| M559 | 44 | 95 | M560 | 44 | 96 (CAS-1427160-09-5) |
| M561 | 44 | 97 (CAS-1643479-72-4) | M562 | 44 | 98 |
| M563 | 44 | 99 | M564 | 44 | 100 (CAS-1643479-59-7) |
| M565 | 44 | 101 (CAS-1643479-68-8). | | | |

Very particularly preferred mixtures M566 to M851 of the host materials of the formula (1) with the host materials of the formula (2) are obtained by combination of compounds 45 to 66 from Table 7 with compounds 89 to 101 from Table 9, as shown below in Table 12.

TABLE 12

| | | | | | |
|---|---|---|---|---|---|
| M566 | 45 | 89 (CAS-1454567-05-5) | M567 | 45 | 90 (CAS-1352040-89-1) |
| M568 | 45 | 91 (CAS-1643479-47-3) | M569 | 45 | 92 (CAS-1643479-49-5) |
| M570 | 45 | 93 (CAS-1799958-78-3) | M571 | 45 | 94 (CAS-57102-51-9) |
| M572 | 45 | 95 | M573 | 45 | 96 (CAS-1427160-09-5) |
| M574 | 45 | 97 (CAS-1643479-72-4) | M575 | 45 | 98 |
| M576 | 45 | 99 | M577 | 45 | 100 (CAS-1643479-59-7) |
| M578 | 45 | 101 (CAS-1643479-68-8) | | | |
| M579 | 46 | 89 (CAS-1454567-05-5) | M580 | 46 | 90 (CAS-1352040-89-1) |
| M581 | 46 | 91 (CAS-1643479-47-3) | M582 | 46 | 92 (CAS-1643479-49-5) |
| M583 | 46 | 93 (CAS-1799958-78-3) | M584 | 46 | 94 (CAS-57102-51-9) |
| M585 | 46 | 95 | M586 | 46 | 96 (CAS-1427160-09-5) |
| M587 | 46 | 97 (CAS-1643479-72-4) | M588 | 46 | 98 |
| M589 | 46 | 99 | M590 | 46 | 100 (CAS-1643479-59-7) |
| M591 | 46 | 101 (CAS-1643479-68-8) | | | |
| M592 | 47 | 89 (CAS-1454567-05-5) | M593 | 47 | 90 (CAS-1352040-89-1) |
| M594 | 47 | 91 (CAS-1643479-47-3) | M595 | 47 | 92 (CAS-1643479-49-5) |
| M596 | 47 | 93 (CAS-1799958-78-3) | M597 | 47 | 94 (CAS-57102-51-9) |
| M598 | 47 | 95 | M599 | 47 | 96 (CAS-1427160-09-5) |
| M600 | 47 | 97 (CAS-1643479-72-4) | M601 | 47 | 98 |
| M602 | 47 | 99 | M603 | 47 | 100 (CAS-1643479-59-7) |
| M604 | 47 | 101 (CAS-1643479-68-8) | | | |
| M605 | 48 | 22 (CAS-1454567-05-5) | M606 | 48 | 90 (CAS-1352040-89-1) |
| M607 | 48 | 91 (CAS-1643479-47-3) | M608 | 48 | 92 (CAS-1643479-49-5) |
| M609 | 48 | 93 (CAS-1799958-78-3) | M610 | 48 | 94 (CAS-57102-51-9) |
| M611 | 48 | 95 | M612 | 48 | 96 (CAS-1427160-09-5) |
| M613 | 48 | 97 (CAS-1643479-72-4) | M614 | 48 | 98 |
| M615 | 48 | 99 | M616 | 48 | 100 (CAS-1643479-59-7) |
| M617 | 48 | 101 (CAS-1643479-68-8) | | | |
| M618 | 49 | 89 (CAS-1454567-05-5) | M619 | 49 | 90 (CAS-1352040-89-1) |
| M620 | 49 | 91 (CAS-1643479-47-3) | M621 | 49 | 92 (CAS-1643479-49-5) |
| M622 | 49 | 93 (CAS-1799958-78-3) | M623 | 49 | 94 (CAS-57102-51-9) |
| M624 | 49 | 95 | M625 | 49 | 96 (CAS-1427160-09-5) |
| M626 | 49 | 97 (CAS-1643479-72-4) | M627 | 49 | 98 |
| M628 | 49 | 99 | M629 | 49 | 100 (CAS-1643479-59-7) |
| M630 | 49 | 101 (CAS-1643479-68-8) | | | |
| M631 | 50 | 22 (CAS-1454567-05-5) | M632 | 50 | 90 (CAS-1352040-89-1) |
| M633 | 50 | 91 (CAS-1643479-47-3) | M634 | 50 | 92 (CAS-1643479-49-5) |
| M635 | 50 | 93 (CAS-1799958-78-3) | M636 | 50 | 94 (CAS-57102-51-9) |

TABLE 12-continued

| | | | | | |
|---|---|---|---|---|---|
| M637 | 50 | 95 | M638 | 50 | 96 (CAS-1427160-09-5) |
| M639 | 50 | 97 (CAS-1643479-72-4) | M640 | 50 | 98 |
| M641 | 50 | 99 | M642 | 50 | 100 (CAS-1643479-59-7) |
| M643 | 50 | 101 (CAS-1643479-68-8) | | | |
| M644 | 51 | 89 (CAS-1454567-05-5) | M645 | 51 | 90 (CAS-1352040-89-1) |
| M646 | 51 | 91 (CAS-1643479-47-3) | M647 | 51 | 92 (CAS-1643479-49-5) |
| M648 | 51 | 93 (CAS-1799958-78-3) | M649 | 51 | 94 (CAS-57102-51-9) |
| M650 | 51 | 95 | M651 | 51 | 96 (CAS-1427160-09-5) |
| M652 | 51 | 97 (CAS-1643479-72-4) | M653 | 51 | 98 |
| M654 | 51 | 99 | M655 | 51 | 100 (CAS-1643479-59-7) |
| M656 | 51 | 101 (CAS-1643479-68-8) | | | |
| M657 | 52 | 22 (CAS-1454567-05-5) | M658 | 52 | 90 (CAS-1352040-89-1) |
| M659 | 52 | 91 (CAS-1643479-47-3) | M660 | 52 | 92 (CAS-1643479-49-5) |
| M661 | 52 | 93 (CAS-1799958-78-3) | M662 | 52 | 94 (CAS-57102-51-9) |
| M663 | 52 | 95 | M664 | 52 | 96 (CAS-1427160-09-5) |
| M665 | 52 | 97 (CAS-1643479-72-4) | M666 | 52 | 98 |
| M667 | 52 | 99 | M668 | 52 | 100 (CAS-1643479-59-7) |
| M669 | 52 | 101 (CAS-1643479-68-8) | | | |
| M670 | 53 | 89 (CAS-1454567-05-5) | M671 | 53 | 90 (CAS-1352040-89-1) |
| M672 | 53 | 91 (CAS-1643479-47-3) | M673 | 53 | 92 (CAS-1643479-49-5) |
| M674 | 53 | 93 (CAS-1799958-78-3) | M675 | 53 | 94 (CAS-57102-51-9) |
| M676 | 53 | 95 | M677 | 53 | 94 (CAS-1427160-09-5) |
| M678 | 53 | 97 (CAS-1643479-72-4) | M679 | 53 | 98 |
| M680 | 53 | 99 | M681 | 53 | 100 (CAS-1643479-59-7) |
| M682 | 53 | 101 (CAS-1643479-68-8) | | | |
| M683 | 54 | 89 (CAS-1454567-05-5) | M684 | 54 | 90 (CAS-1352040-89-1) |
| M685 | 54 | 91 (CAS-1643479-47-3) | M686 | 54 | 92 (CAS-1643479-49-5) |
| M687 | 54 | 93 (CAS-1799958-78-3) | M688 | 54 | 94 (CAS-57102-51-9) |
| M689 | 54 | 95 | M690 | 54 | 96 (CAS-1427160-09-5) |
| M691 | 54 | 97 (CAS-1643479-72-4) | M692 | 54 | 98 |
| M693 | 54 | 99 | M694 | 54 | 100 (CAS-1643479-59-7) |
| M695 | 54 | 101 (CAS-1643479-68-8) | | | |
| M696 | 55 | 89 (CAS-1454567-05-5) | M697 | 55 | 90 (CAS-1352040-89-1) |
| M698 | 55 | 91 (CAS-1643479-47-3) | M699 | 55 | 92 (CAS-1643479-49-5) |
| M700 | 55 | 93 (CAS-1799958-78-3) | M701 | 55 | 94 (CAS-57101-51-9) |
| M702 | 55 | 95 | M703 | 55 | 96 (CAS-1427160-09-5) |
| M704 | 55 | 97 (CAS-1643479-72-4) | M705 | 55 | 98 |
| M706 | 55 | 99 | M707 | 55 | 100 (CAS-1643479-59-7) |
| M708 | 55 | 101 (CAS-1643479-68-8) | | | |
| M709 | 56 | 89 (CAS-1454567-05-5) | M710 | 56 | 90 (CAS-1352040-89-1) |

TABLE 12-continued

| | | | | | |
|---|---|---|---|---|---|
| M711 | 56 | 91 (CAS-1643479-47-3) | M712 | 56 | 92 (CAS-1643479-49-5) |
| M713 | 56 | 93 (CAS-1799958-78-3) | M714 | 56 | 94 (CAS-57102-51-9) |
| M715 | 56 | 95 | M716 | 56 | 96 (CAS-1427160-09-5) |
| M717 | 56 | 97 (CAS-1643479-72-4} | M718 | 56 | 98 |
| M719 | 56 | 99 | M720 | 56 | 100 (CAS-1643479-59-7) |
| M721 | 56 | 101 (CAS-1643479-68-8) | | | |
| M722 | 57 | 89 (CAS-1454567-05-5) | M723 | 57 | 90 (CAS-1352040-89-1) |
| M724 | 57 | 91 (CAS-1643479-47-3) | M725 | 57 | 92 (CAS-1643479-49-5) |
| M726 | 57 | 93 95 | M727 | 57 | 94 (CAS-57102-51-9) |
| M728 | 57 | (CAS-1799958-78-3) | M729 | 57 | 96 (CAS-1427160-09-5) |
| M730 | 57 | 97 (CAS-1643479-72-4) | M731 | 57 | 98 |
| M732 | 57 | 99 | M733 | 57 | 100 (CAS-1643479-59-7) |
| M734 | 57 | 101 (CAS-1643479-68-8) | | | |
| M735 | 58 | 89 (CAS-1454567-05-5) | M736 | 58 | 90 (CAS-1352040-89-1) |
| M737 | 58 | 91 (CAS-1643479-47-3) | M738 | 58 | 92 |
| M739 | 58 | 93 (CAS-1799958-78-3) | M740 | 58 | 94 (CAS-57101-51-9) |
| M741 | 58 | 95 | M742 | 58 | 96 (CAS-1427160-09-5) |
| M743 | 58 | 97 (CAS-1643479-72-4) | M744 | 58 | 98 |
| M745 | 58 | 99 | M746 | 58 | 100 (CAS-1643479-59-7) |
| M747 | 58 | 101 (CAS-1643479-68-8) | | | |
| M748 | 59 | 89 (CAS-1454567-05-5) | M749 | 59 | 90 (CAS-1352040-89-1) |
| M750 | 59 | 91 (CAS-1643479-47-3) | M751 | 59 | 92 (CAS-1643479-49-5) |
| M752 | 59 | 93 (CAS-1799958-78-3) | M753 | 59 | 94 (CAS-57102-51-9) |
| M754 | 59 | 95 | M755 | 59 | 96 (CAS-1427160-09-5) |
| M756 | 59 | 97 (CAS-1643479-72-4) | M757 | 59 | 98 |
| M758 | 59 | 99 | M759 | 59 | 100 (CAS-1643479-59-7) |
| M760 | 59 | 101 (CAS-1643479-68-8) | | | |
| M761 | 60 | 89 (CAS-1454567-05-5) | M762 | 60 | 90 (CAS-1352040-89-1) |
| M763 | 60 | 91 (CAS-1643479-47-3) | M764 | 60 | 92 (CAS-1643479-49-5) |
| M765 | 60 | 93 (CAS-1799958-78-3) | M766 | 60 | 94 (CAS-57102-51-9) |
| M767 | 60 | 95 | M768 | 60 | 96 98 |
| M769 | 60 | 97 (CAS-1643479-72-4) | M770 | 60 | (CAS-1427160-09-5) |
| M771 | 60 | 99 | M772 | 60 | 100 (CAS-1643479-59-7) |
| M773 | 60 | 101 (CAS-1643479-68-8) | | | |
| M774 | 61 | 89 (CAS-1454567-05-5) | M775 | 61 | 90 (CAS-1352040-89-1) |
| M776 | 61 | 91 (CAS-1643479-47-3) | M777 | 61 | 92 (CAS-1643479-49-5) |
| M778 | 61 | 93 (CAS-1799958-78-3) | M779 | 61 | 94 (CAS-57102-51-9) |
| M780 | 61 | 95 | M781 | 61 | 96 (CAS-1427160-09-5) |
| M782 | 61 | 97 (CAS-1643479-72-4) | M783 | 61 | 98 |
| M784 | 61 | 99 | M785 | 61 | 100 (CAS-1643479-59-7) |
| M786 | 61 | 101 (CAS-1643479-68-8)) | | | |
| M787 | 62 | 89 (CAS-1454567-05-5) | M788 | 62 | 90 (CAS-1352040-89-1) |
| M789 | 62 | 91 (CAS-1643479-47-3) | M790 | 62 | 92 (CAS-1643479-49-5) |
| M791 | 62 | 93 (CAS-1799958-78-3) | M792 | 62 | 94 (CAS-57102-51-9) |
| M793 | 62 | 95 | M794 | 62 | 96 (CAS-1427160-09-5) |
| M795 | 62 | 97 (CAS-1643479-72-4) | M796 | 62 | 98 |
| M797 | 62 | 99 | M798 | 62 | 100 (CAS-1643479-59-7) |
| M799 | 62 | 101 (CAS-1643479-68-8) | | | |
| M800 | 63 | 89 (CAS-1454567-05-5) | M801 | 63 | 90 (CAS-1352040-89-1) |
| M802 | 63 | 91 (CAS-1643479-47-3) | M803 | 63 | 92 (CAS-1643479-49-5) |
| M804 | 63 | 93 (CAS-1799958-78-3) | M805 | 63 | 94 (CAS-57102-51-9) |
| M806 | 63 | 95 | M807 | 63 | 96 (CAS-1427160-09-5) |
| M808 | 63 | 97 (CAS-1643479-72-4) | M809 | 63 | 98 |
| M810 | 63 | 99 | M811 | 63 | 100 (CAS-1643479-59-7) |
| M812 | 63 | 101 (CAS-1643479-68-8) | | | |
| M813 | 64 | 89 (CAS-1454567-05-5) | M814 | 64 | 90 (CAS-1352040-89-1) |
| M815 | 64 | 91 (CAS-1643479-47-3) | M816 | 64 | 92 (CAS-1643479-49-5) |
| M817 | 64 | 93 (CAS-1799958-78-3) | M818 | 64 | 94 (CAS-57102-51-9) |
| M819 | 64 | 95 | M820 | 64 | 96 (CAS-1427160-09-5) |
| M821 | 64 | 97 (CAS-1643479-72-4) | M822 | 64 | 98 |
| M823 | 64 | 99 | M824 | 64 | 100 (CAS-1643479-59-7) |
| M825 | 64 | 101 (CAS-1643479-68-8) | | | |
| M826 | 65 | 89 (CAS-1454567-05-5) | M827 | 65 | 90 (CAS-1352040-89-1) |
| M828 | 65 | 91 (CAS-1643479-47-3) | M829 | 65 | 92 (CAS-1643479-49-5) |
| M830 | 65 | 93 (CAS-1799958-78-3) | M831 | 65 | 94 (CAS-57102-51-9) |
| M832 | 65 | 95 | M833 | 65 | 96 (CAS-1427160-09-5) |
| M834 | 65 | 97 (CAS-1643479-72-4) | M835 | 65 | 98 |
| M836 | 65 | 99 | M837 | 65 | 100 (CAS-1643479-59-7) |
| M838 | 65 | 101 (CAS-1643479-68-8) | | | |
| M839 | 66 | 89 (CAS-1454567-05-5) | M840 | 66 | 90 (CAS-1352040-89-1) |
| M841 | 66 | 91 (CAS-1643479-47-3) | M842 | 66 | 92 (CAS-1643479-49-5) |
| M843 | 66 | 93 (CAS-1799958-78-3) | M844 | 66 | 94 (CAS-57102-51-9) |
| M845 | 66 | 95 | M846 | 66 | 96 (CAS-1427160-09-5) |
| M847 | 66 | 97 (CAS-1643479-72-4) | M848 | 66 | 98 |
| M849 | 66 | 99 | M850 | 66 | 100 (CAS-1643479-59-7) |
| M851 | 66 | 101 (CAS-1643479-68-8). | | | |

Very particularly preferred mixtures M852 to M1137 of the host materials of the formula (1) with the host materials of the formula (2) are obtained by combination of compounds 67 to 88 from Table 8 with compounds 89 to 101 from Table 9, as shown below in Table 13.

TABLE 13

| | | | | | |
|---|---|---|---|---|---|
| M852 | 67 | 89 (CAS-1454567-05-5) | M853 | 67 | 90 (CAS-135204.0-89-1) |
| M854 | 67 | 91 (CAS-1643479-47-3) | M855 | 67 | 92 (CAS-1643479-49-5) |
| M856 | 67 | 93 (CAS-1799958-78-3) | M857 | 67 | 94 (CAS-57102-51-9) |
| M858 | 67 | 95 | M859 | 67 | 96 (CAS-1427160-09-5) |
| M860 | 67 | 97 (CAS-1643479-72-4) | M861 | 67 | 98 |
| M862 | 67 | 99 | M863 | 67 | 100 (CAS-1643479-59-7) |
| M864 | 67 | 101 (CAS-1643479-68-8) | | | |
| M865 | 68 | 89 (CAS-1454567-05-5) | M866 | 68 | 90 (CAS-1352040-89-1) |
| M867 | 68 | 91 (CAS-1643479-47-3) | M868 | 68 | 92 (CAS-1643479-49-5) |
| M869 | 68 | 93 (CAS-1799958-78-3) | M870 | 68 | 94 (CAS-57102-51-9) |
| M871 | 68 | 95 | M872 | 68 | 94 (CAS-1427160-09-5) |
| M873 | 68 | 97 (CAS-1643479-72-4) | M874 | 68 | 98 |
| M875 | 68 | 99 | M876 | 68 | 100 (CAS-1643479-59-7) |
| M877 | 68 | 101 (CAS-1643479-68-8) | | | |
| M878 | 69 | 89 (CAS-1454567-05-5) | M879 | 69 | 90 (CAS-1352040-89-1) |
| M880 | 69 | 91 (CAS-1643479-47-3) | M881 | 69 | 92 (CAS-1643479-49-5) |
| M882 | 69 | 93 (CAS-1799958-78-3) | M883 | 69 | 94 (CAS-57102-51-9) |
| M884 | 69 | 95 | M885 | 69 | 96 (CAS-1427160-09-5) |
| M886 | 69 | 97 (CAS-1643479-72-4) | M887 | 69 | 98 |
| M888 | 69 | 99 | M889 | 69 | 100 (CAS-1643479-59-7) |
| M890 | 69 | 101 (CAS-1643479-68-8) | | | |
| M891 | 70 | 22 (CAS-1454567-05-5) | M892 | 70 | 90 (CAS-1352040-89-1) |
| M893 | 70 | 91 (CAS-1643479-47-3) | M894 | 70 | 92 (CAS-1643479-49-5) |
| M895 | 70 | 93 (CAS-1799958-78-3) | M896 | 70 | 94 (CAS-57102-51-9) |
| M897 | 70 | 95 | M898 | 70 | 96 (CAS-1427160-09-5) |
| M899 | 70 | 97 (CAS-1643479-72-4) | M900 | 70 | 98 |
| M901 | 70 | 99 | M902 | 70 | 100 (CAS-1643479-59-7) |
| M903 | 70 | 101 (CAS-1643479-68-8) | | | |
| M904 | 71 | 89 (CAS-1454567-05-5) | M905 | 71 | 90 (CAS-1352040-89-1) |
| M906 | 71 | 91 (CAS-1643479-47-3) | M907 | 71 | 92 (CAS-1643479-49-5) |
| M908 | 71 | 93 (CAS-1799958-78-3) | M909 | 71 | 94 (CAS-57102-51-9) |
| M910 | 71 | 95 | M911 | 71 | 96 (CAS-1427160-09-5) |
| M912 | 71 | 97 (CAS-1643479-72-4) | M913 | 71 | 98 |
| M914 | 71 | 99 | M915 | 71 | 100 (CAS-1643479-59-7) |
| M916 | 71 | 101 (CAS-1643479-68-8) | | | |
| M917 | 72 | 22 (CAS-1454567-05-5) | M918 | 72 | 90 (CAS-1352040-89-1) |
| M919 | 72 | 91 (CAS-1643479-47-3) | M920 | 72 | 92 (CAS-1643479-49-5) |
| M921 | 72 | 93 (CAS-1799958-78-3) | M922 | 72 | 94 (CAS-57102-51-9) |
| M923 | 72 | 95 | M924 | 72 | 96 (CAS-1427160-09-5) |
| M925 | 72 | 97 (CAS-1643479-72-4) | M926 | 72 | 98 |

TABLE 13-continued

| | | | | | |
|---|---|---|---|---|---|
| M927 | 72 | 99 | M928 | 72 | 100 (CAS-1643479-59-7) |
| M929 | 72 | 101 (CAS-1643479-68-8) | | | |
| M930 | 73 | 89 (CAS-1454567-05-5) | M931 | 73 | 90 (CAS-1352040-89-1) |
| M932 | 73 | 91 (CAS-1643479-47-3) | M933 | 73 | 92 (CAS-1643479-49-5) |
| M934 | 73 | 93 (CAS-1799958-78-3) | M935 | 73 | 94 (CAS-57102-51-9) |
| M936 | 73 | 95 | M937 | 73 | 96 (CAS-1427160-09-5) |
| M938 | 73 | 97 (CAS-1643479-72-4) | M939 | 73 | 98 |
| M940 | 73 | 99 | M941 | 73 | 100 (CAS-1643479-59-7) |
| M942 | 73 | 101 (CAS-1643479-68-8) | | | |
| M943 | 74 | 22 (CAS-1454567-05-5) | M944 | 74 | 90 (CAS-1352040-89-1) |
| M945 | 74 | 91 (CAS-1643479-47-3) | M946 | 74 | 92 (CAS-1643479-49-5) |
| M947 | 74 | 93 (CAS-1799958-78-3) | M948 | 74 | 94 (CAS-57102-51-9) |
| M949 | 74 | 95 | M950 | 74 | 96 (CAS-1427160-09-5) |
| M951 | 74 | 97 (CAS-1643479-72-4) | M952 | 74 | 98 |
| M953 | 74 | 99 | M954 | 74 | 100 (CAS-1643479-59-7) |
| M955 | 74 | 101 (CAS-1643479-68-8) | | | |
| M956 | 75 | 89 (CAS-1454567-05-5) | M957 | 75 | 90 (CAS-1352040-89-1) |
| M958 | 75 | 91 (CAS-1643479-47-3) | M959 | 75 | 92 (CAS-1643479-49-5) |
| M960 | 75 | 93 (CAS-1799958-78-3) | M961 | 75 | 94 (CAS-57102-51-9) |
| M962 | 75 | 95 | M963 | 75 | 96 (CAS-1427160-09-5) |
| M964 | 75 | 97 (CAS-1643479-72-4) | M965 | 75 | 98 |
| M966 | 75 | 99 | M967 | 75 | 100 (CAS-1643479-59-7) |
| M968 | 75 | 101 (CAS-1643479-68-8) | | | |
| M969 | 76 | 89 (CAS-1454567-05-5) | M970 | 76 | 90 (CAS-1352040-89-1) |
| M971 | 76 | 91 (CAS-1643479-47-3) | M972 | 76 | 92 (CAS-1643479-49-5) |
| M973 | 76 | 93 (CAS-1799958-78-3) | M974 | 76 | 94 (CAS-57102-51-9) |
| M975 | 76 | 95 | M976 | 76 | 96 (CAS-1427160-09-5) |
| M977 | 76 | 97 (CAS-1643479-72-4) | M978 | 76 | 98 |
| M979 | 76 | 99 | M980 | 76 | 100 (CAS-1643479-59-7) |
| M981 | 76 | 101 (CAS-1643479-68-8) | | | |
| M982 | 77 | 89 (CAS-1454567-05-5) | M983 | 77 | 90 (CAS-1352040-89-1) |
| M984 | 77 | 91 (CAS-1643479-47-3) | M985 | 77 | 92 (CAS-1643479-49-5) |
| M986 | 77 | 93 (CAS-1799958-78-3) | M987 | 77 | 94 (CAS-57102-51-9) |
| M988 | 77 | 95 | M989 | 77 | 96 (CAS-1427160-09-5) |
| M990 | 77 | 97 (CAS-1643479-72-4) | M991 | 77 | 98 |
| M992 | 77 | 99 | M993 | 77 | 100 (CAS-1643479-59-7) |
| M994 | 77 | 101 (CAS-1643479-68-8) | | | |
| M995 | 78 | 89 (CAS-1454567-05-5) | M996 | 78 | 90 (CAS-1352040-89-1) |
| M997 | 78 | 91 (CAS-1643479-47-3) | M998 | 78 | 92 (CAS-1643479-49-5) |
| M999 | 78 | 93 (CAS-1799958-78-3) | M1000 | 78 | 94 (CAS-57102-51-9) |

TABLE 13-continued

| | | | | | |
|---|---|---|---|---|---|
| M1001 | 78 | 95 | M1002 | 78 | 96 (CAS-1427160-09-5) |
| M1003 | 78 | 97 (CAS-1643479-72-4) | M1004 | 78 | 98 |
| M1005 | 78 | 99 | M1006 | 78 | 100 (CAS-1643479-59-7) |
| M1007 | 78 | 101 (CAS-1643479-68-8) | | | |
| M1008 | 79 | 89 (CAS-1454567-05-5) | M1009 | 79 | 90 (CAS-1352040-89-1) |
| M1010 | 79 | 91 (CAS-1643479-47-3) | M1011 | 79 | 92 (CAS-1643479-49-5) |
| M1012 | 79 | 93 (CAS-1799958-78-3) | M1013 | 79 | 94 (CAS-57102-51-9) |
| M1014 | 79 | 95 | M1015 | 79 | 96 (CAS-1427160-09-5) |
| M1016 | 79 | 97 (CAS-1643479-72-4) | M1017 | 79 | 98 |
| M1018 | 79 | 99 | M1019 | 79 | 100 (CAS-1643479-59-7) |
| M1020 | 79 | 101 (CAS-1643479-68-8) | | | |
| M1021 | 80 | 89 (CAS-1454567-05-5) | M1022 | 80 | 90 (CAS-1352040-89-1) |
| M1023 | 80 | 91 (CAS-1643479-47-3) | M1024 | 80 | 92 (CAS-1643479-49-5) |
| M1025 | 80 | 93 (CAS-1799958-78-3) | M1026 | 80 | 94 (CAS-57102-51-9) |
| M1027 | 80 | 95 | M1028 | 80 | 96 (CAS-1427160-09-5) |
| M1029 | 80 | 97 (CAS-1643479-72-4) | M1030 | 80 | 98 |
| M1031 | 80 | 99 | M1032 | 80 | 100 (CAS-1643479-59-7) |
| M1033 | 80 | 101 (CAS-1643479-68-8) | | | |
| M1034 | 81 | 89 (CAS-1454567-05-5) | M1035 | 81 | 90 (CAS-1352040-89-1) |
| M1036 | 81 | 91 (CAS-1643479-47-3) | M1037 | 81 | 92 (CAS-1643479-49-5) |
| M1038 | 81 | 93 (CAS-1799958-78-3) | M1039 | 81 | 94 (CAS-57102-51-9) |
| M1040 | 81 | 95 | M1041 | 81 | 96 (CAS-1427160-09-5) |
| M1042 | 81 | 97 (CAS-1643479-72-4) | M1043 | 81 | 98 |
| M1044 | 81 | 99 | M1045 | 81 | 100 (CAS-1643479-59-7) |
| M1046 | 81 | 101 (CAS-1643479-68-8) | | | |
| M1047 | 82 | 89 (CAS-1454567-05-5) | M1048 | 82 | 90 (CAS-1352040-89-1) |
| M1049 | 82 | 91 (CAS-1643479-47-3) | M1050 | 82 | 92 (CAS-1643479-49-5) |
| M1051 | 82 | 93 (CAS-1799958-78-3) | M1052 | 82 | 94 (CAS-57102-51-9) |
| M1053 | 82 | 95 | M1054 | 82 | 96 (CAS-1427160-09-5) |
| M1055 | 82 | 97 (CAS-1643479-72-4) | M1056 | 82 | 98 |
| M1057 | 82 | 99 | M1058 | 82 | 100 (CAS-1643479-59-7) |
| M1059 | 82 | 101 (CAS-1643479-68-8) | | | |
| M1060 | 83 | 89 (CAS-1454567-05-5) | M1061 | 83 | 90 (CAS-1352040-89-1) |
| M1062 | 83 | 91 (CAS-1643479-47-3) | M1063 | 83 | 92 (CAS-1643479-49-5) |
| M1064 | 83 | 93 (CAS-1799958-78-3) | M1065 | 83 | 94 (CAS-57102-51-9) |
| M1066 | 83 | 95 | M1067 | 83 | 96 (CAS-1427160-09-5) |
| M1068 | 83 | 97 (CAS-1643479-72-4) | M1069 | 83 | 98 |
| M1070 | 83 | 99 | M1071 | 83 | 100 (CAS-1643479-59-7) |
| M1072 | 83 | 101 (CAS-1643479-68-8) | | | |
| M1073 | 84 | 89 (CAS-1454567-05-5) | M1074 | 84 | 90 (CAS-1352040-89-1) |
| M1075 | 84 | 91 (CAS-1643479-47-3) | M1076 | 84 | 92 (CAS-1643479-49-5) |
| M1077 | 84 | 93 (CAS-1799958-78-3) | M1078 | 84 | 94 (CAS-57102-51-9) |
| M1079 | 84 | 95 | M1080 | 84 | 96 (CAS-1427160-09-5) |
| M1081 | 84 | 97 (CAS-1643479-72-4) | M1082 | 84 | 98 |
| M1083 | 84 | 99 | M1084 | 84 | 100 (CAS-1643479-59-7) |
| M1085 | 84 | 101 (CAS-1643479-68-8) | | | |
| M1086 | 85 | 89 (CAS-1454567-05-5) | M1087 | 85 | 90 (CAS-1352040-89-1) |
| M1088 | 85 | 91 (CAS-1643479-47-3) | M1089 | 85 | 92 (CAS-1643479-49-5) |
| M1090 | 85 | 93 (CAS-1799958-78-3) | M1091 | 85 | 94 (CAS-57102-51-9) |
| M1092 | 85 | 95 | M1093 | 85 | 96 (CAS-1427160-09-5) |
| M1094 | 85 | 97 (CAS-1643479-72-4) | M1095 | 85 | 98 |
| M1096 | 85 | 99 | M1097 | 85 | 100 (CAS-1643479-59-7) |
| M1098 | 85 | 101 (CAS-1643479-68-8) | | | |
| M1099 | 86 | 89 (CAS-1454567-05-5) | M1100 | 86 | 90 (CAS-1352040-89-1) |
| M1101 | 86 | 91 (CAS-1643479-47-3) | M1102 | 86 | 92 (CAS-1643479-49-5) |
| M1103 | 86 | 93 (CAS-1799958-78-3) | M1104 | 86 | 94 (CAS-57102-51-9) |
| M1105 | 86 | 95 | M1106 | 86 | 96 (CAS-1427160-09-5) |
| M1107 | 86 | 97 (CAS-1643479-72-4) | M1108 | 86 | 98 |
| M1109 | 86 | 99 | M1110 | 86 | 100 (CAS-1643479-59-7) |
| M1111 | 86 | 101 (CAS-1643479-68-8) | | | |
| M1112 | 87 | 89 (CAS-1454567-05-5) | M1113 | 87 | 90 (CAS-1352040-89-1) |
| M1114 | 87 | 91 (CAS-1643479-47-3) | M1115 | 87 | 92 (CAS-1643479-49-5) |
| M1116 | 87 | 93 (CAS-1799958-78-3) | M1117 | 87 | 94 (CAS-57102-51-9) |
| M1118 | 87 | 95 | M1119 | 87 | 96 (CAS-1427160-09-5) |
| M1120 | 87 | 97 (CAS-1643479-72-4) | M1121 | 87 | 98 |
| M1122 | 87 | 99 | M1123 | 87 | 100 (CAS-1643479-59-7) |
| M1124 | 87 | 101 (CAS-1643479-68-8) | | | |
| M1125 | 88 | 89 (CAS-1454567-05-5) | M1126 | 88 | 90 (CAS-1352040-89-1) |
| M1127 | 88 | 91 (CAS-1643479-47-3) | M1128 | 88 | 92 (CAS-1643479-49-5) |
| M1129 | 88 | 93 (CAS-1799958-78-3) | M1130 | 88 | 94 (CAS-57102-51-9) |
| M1131 | 88 | 95 | M1132 | 88 | 96 (CAS-1427160-09-5) |
| M1133 | 88 | 97 (CAS-1643479-72-4) | M1134 | 88 | 98 |
| M1135 | 88 | 99 | M1136 | 88 | 100 (CAS-1643479-59-7) |
| M1137 | 88 | 101 (CAS-1643479-68-8). | | | |

The concentration of the electron-transporting host of the formula (1), as described or preferably described above, in the composition according to the invention is in the range from 5% by weight to 90% by weight, preferably in the range from 10% by weight to 85% by weight, more preferably in the range from 20% by weight to 85% by weight, even more preferably in the range from 30% by weight to 80% by weight, very particularly preferably in the range from 20% by weight to 60% by weight and most preferably in the range from 30% by weight to 50% by weight, based on the entire composition.

The concentration of the hole-transporting host of the formula (2), as described above or as preferably described, in the composition is in the range from 10% by weight to 95% by weight, preferably in the range from 15% by weight to 90% by weight, more preferably in the range from 15% by weight to 80% by weight, even more preferably in the range from 20% by weight to 70% by weight, very particularly preferably in the range from 40% by weight to 80% by weight and most preferably in the range from 50% by weight to 70% by weight, based on the entire composition.

The concentration of the hole-transporting host of the formula (2), as described above or as preferably described, in the emitting layer is preferably in the range from 40% to 45% by volume, based on all constituents of the emitting layer; the concentration of the electron-transporting host of the formula (1), as described above or as preferably described, in the emitting layer is preferably in the range from 40% to 45% by volume, based on all constituents of the emitting layer.

In the case of emitter concentrations of less than 10% by volume in the emitting layer, the proportion by volume of the hole-transporting compounds of the formula (2) is preferably higher than the proportion by volume of the electron-transporting compounds of the formula (1), as described or preferably described above, based on all constituents of the emitting layer. The proportion by volume of the hole-transporting compounds of the formula (2), as described or preferably described above, in this embodiment is preferably 65 to 75%, based on all constituents of the emitting layer.

In a further preferred embodiment, the composition according to the invention may also comprise further compounds, in particular organic functional materials, besides at least one compound of the formula (1), as described above or as preferably described, as electron-transporting host or electron-transporting matrix material, and at least one compound of the formula (2), as described above or as preferably described, as hole-transporting host or as hole-transporting matrix material. The composition in this embodiment preferably forms an organic layer in an electronic device, as described below.

The present invention therefore also relates to a composition which, besides the above-mentioned materials, also comprises at least one further compound selected from the group consisting of hole-injection materials, hole-transport materials, hole-blocking materials, wide bandgap materials, fluorescent emitters, phosphorescent emitters, host materials, electron-blocking materials, electron-transport materials and electron-injection materials, n-dopants and p-dopants. The person skilled in the art is presented with absolutely no difficulties in selecting these from a multiplicity of materials known to him.

n-Dopants herein are taken to mean reducing agents, i.e. electron donors. Preferred examples of n-dopants are $W(hpp)_4$ and other electron-rich metal complexes in accordance with WO 2005/086251 A2, P═N compounds (for example WO 2012/175535 A1, WO 2012/175219 A1), naphthylenecarbodiimides (for example WO 2012/168358 A1), fluorenes (for example WO 2012/031735 A1), free radicals and diradicals (for example EP 1837926 A1, WO 2007/107306 A1), pyridines (for example EP 2452946 A1, EP 2463927 A1), N-heterocyclic compounds (for example WO 2009/000237 A1) and acridines as well as phenazines (for example US 2007/145355 A1).

p-Dopants herein are taken to mean oxidants, i.e. electron acceptors. Preferred examples of p-dopants are $F_4$-TCNQ, $F_6$-TNAP, NDP-2 (Novaled), NDP-9 (Novaled), quinones (for example EP 1538684 A1, WO 2006/081780 A1, WO 2009/003455 A1, WO 2010/097433 A1), radialenes (for example EP 1988587 A1, US 2010/102709 A1, EP 2180029 A1, WO 2011/131185 A1, WO 2011134458 A1, US 2012/223296 A1), S-containing transition-metal complexes (for example WO 2007/134873 A1, WO 2008/061517 A2, WO 2008/061518 A2, DE 102008051737 A1, WO 2009/089821 A1, US 2010/096600 A1), bisimidazoles (for example WO 2008/138580 A1), phthalocyanines (for example WO 2008/058525 A2), boratetraazapentalenes (for example WO 2007/115540 A1) fullerenes (for example DE 102010046040 A1) and main-group halides (for example WO 2008/128519 A2).

Wide bandgap material herein is taken to mean a material in the sense of the disclosure of U.S. Pat. No. 7,294,849 which is characterised by a bandgap of at least 3.5 eV, where bandgap is taken to mean the separation between the HOMO and LUMO energy of a material.

The composition according to the invention comprising a bipolar host and an electron-transporting host preferably additionally comprises at least one light-emitting compound or an emitter, where phosphorescent emitters are particularly preferred.

The term phosphorescent emitters typically encompasses compounds in which the light emission takes place through a spin-forbidden transition from an excited state having relatively high spin multiplicity, i.e. a spin state >1, for example through a transition from a triplet state or a state having an even higher spin quantum number, for example a quintet state. This is preferably taken to mean a transition from a triplet state.

Suitable phosphorescent emitters (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescent emitters used are preferably compounds which contain copper, molybdenum, tungsten, rhenium, ruthenium, osmium, rhodium, iridium, palladium, platinum, silver, gold or europium, in particular compounds which contain iridium or platinum. For the purposes of the present invention, all luminescent compounds which contain the above-mentioned metals are regarded as phosphorescent compounds.

In general, suitable phosphorescent complexes are all those as are used in accordance with the prior art for phosphorescent OLEDs and as are known to the person skilled in the art in the area of organic electroluminescent devices.

Examples of the emitters described are revealed by the applications WO 2016/015815, WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094961, WO 2014/094960, WO 2015/036074, WO 2015/104045, WO 2015/117718, WO 2016/015815, WO 2016/124304, WO 2017/032439, WO 2015/036074, WO 2015/117718 and WO 2016/015815.

Preferred examples of phosphorescent emitters are shown in Table 14 below.

TABLE 14
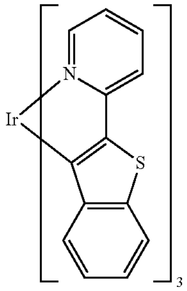
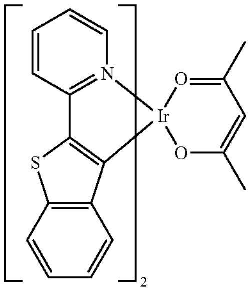
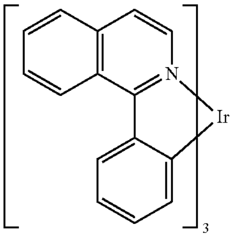
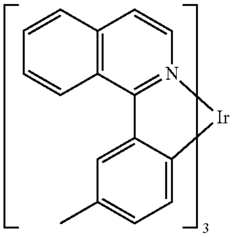
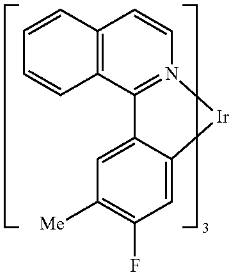
TABLE 14-continued
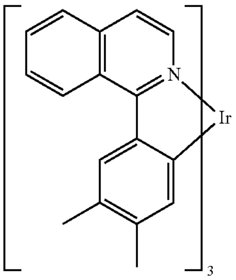
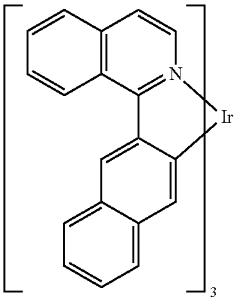
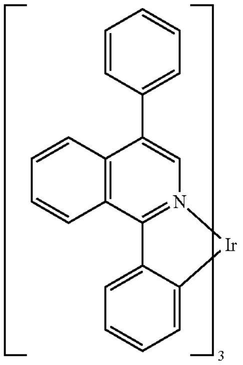
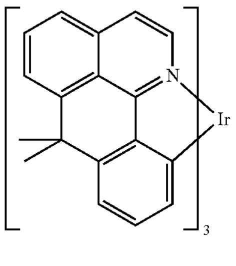
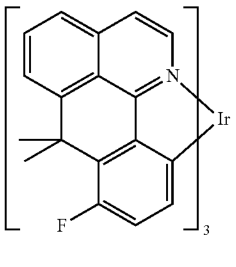

TABLE 14-continued
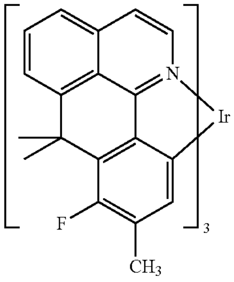
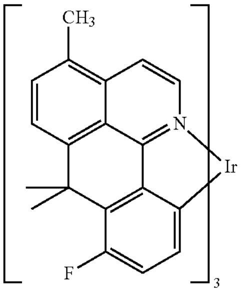
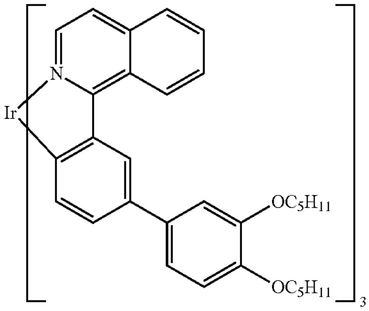
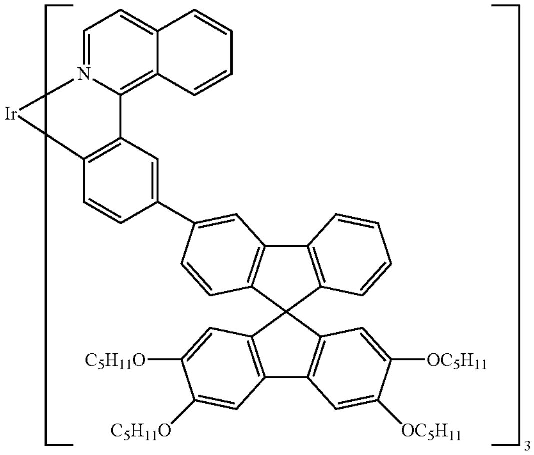
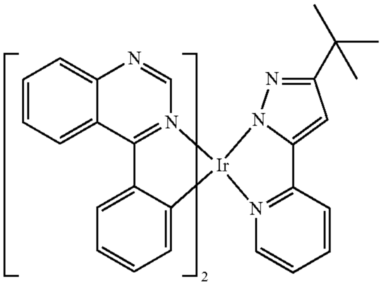
TABLE 14-continued
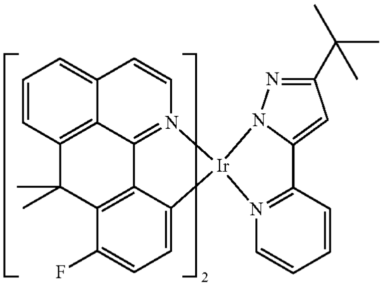
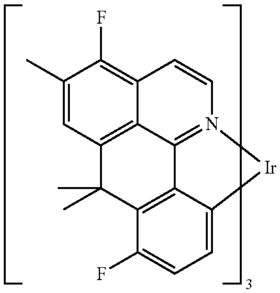
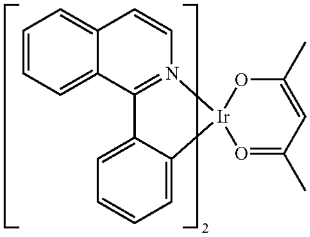
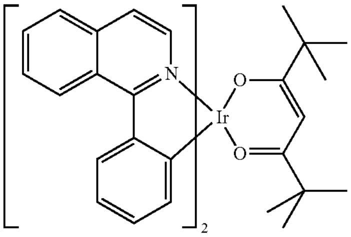
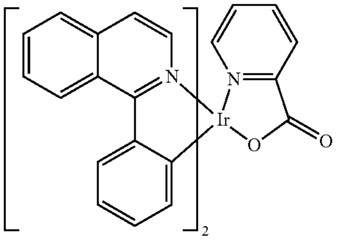
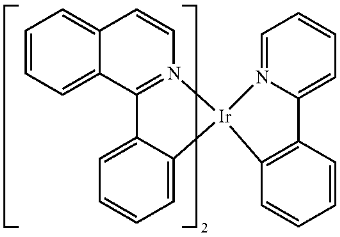

TABLE 14-continued
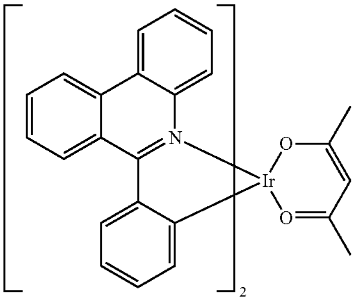
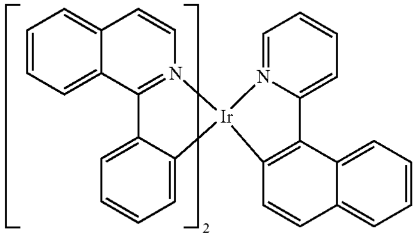
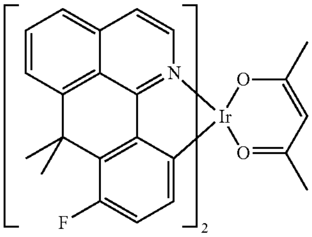
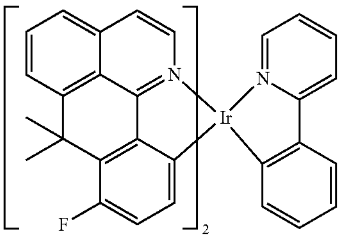
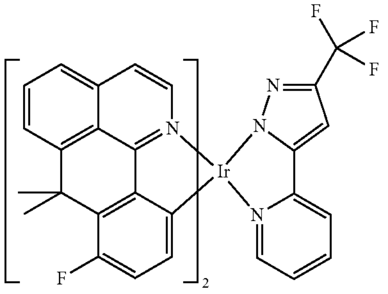
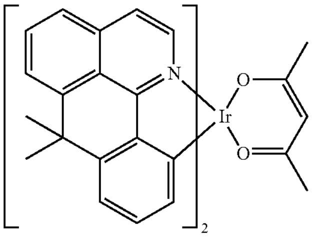
TABLE 14-continued
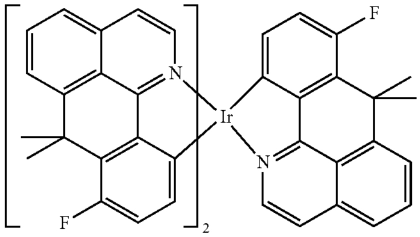
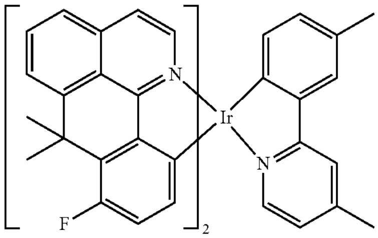
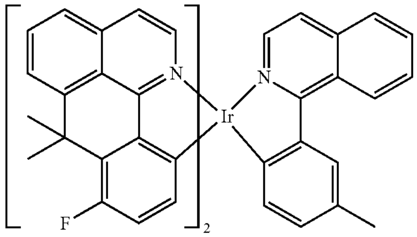
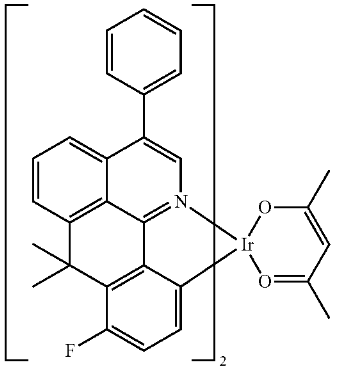
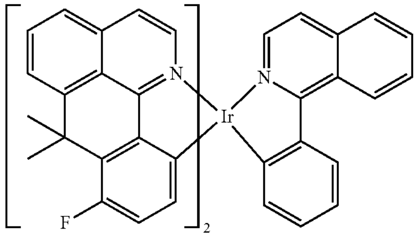
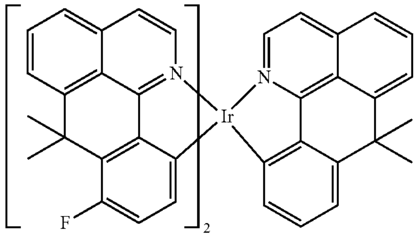

TABLE 14-continued
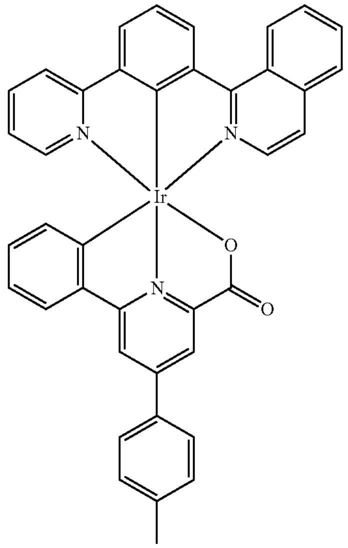
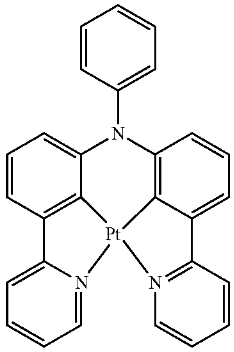
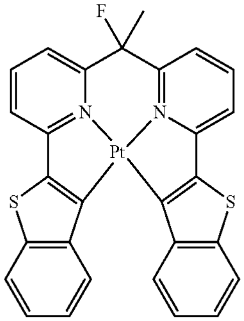
TABLE 14-continued
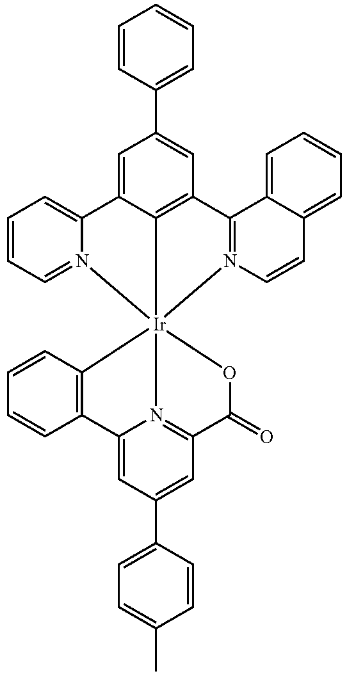
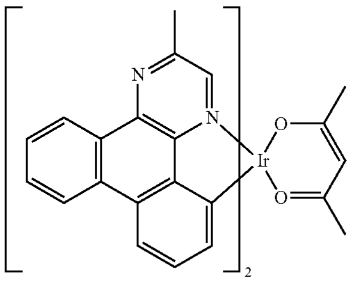
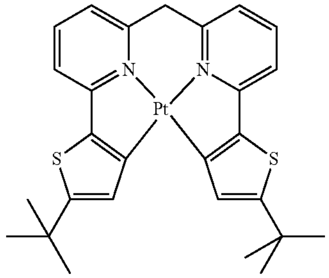
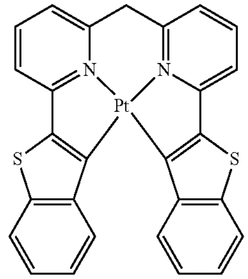

TABLE 14-continued
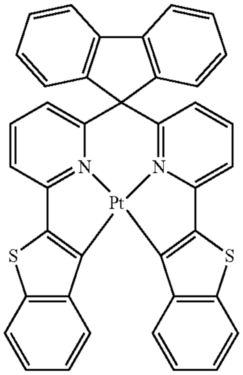
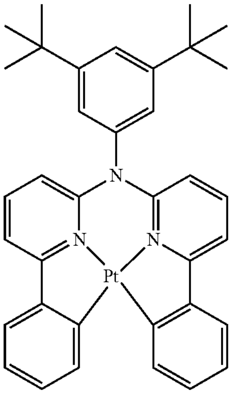
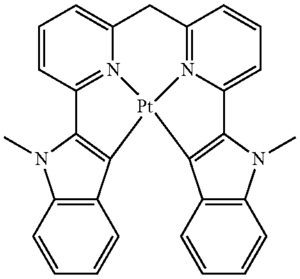
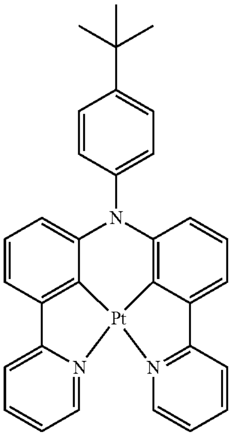
TABLE 14-continued
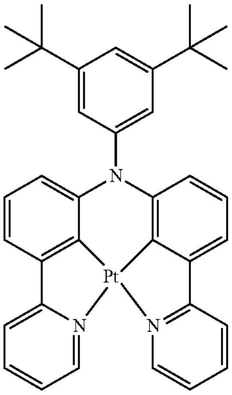
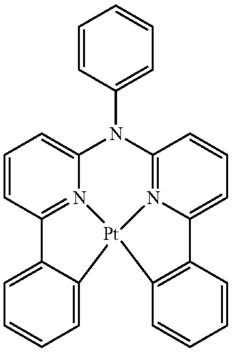
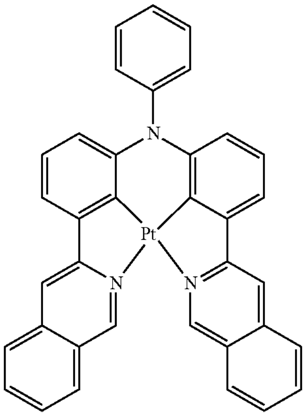
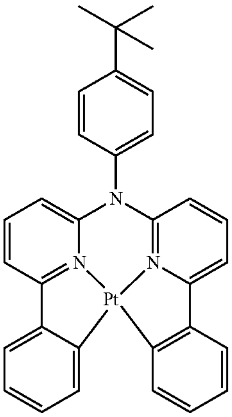

TABLE 14-continued
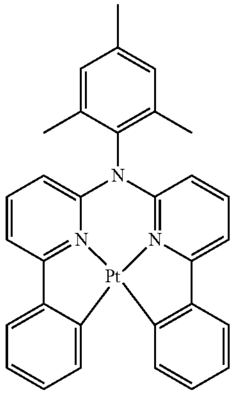
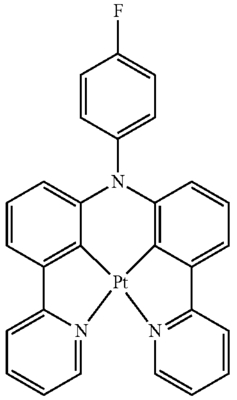
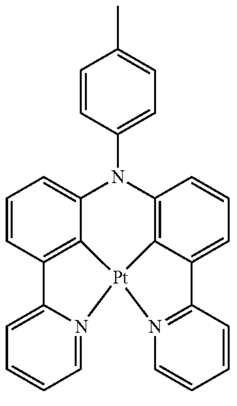
TABLE 14-continued
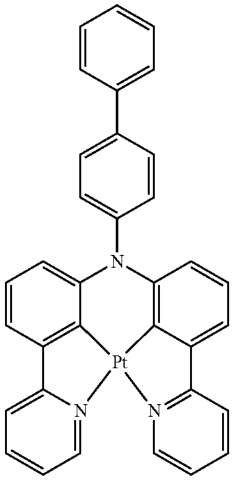
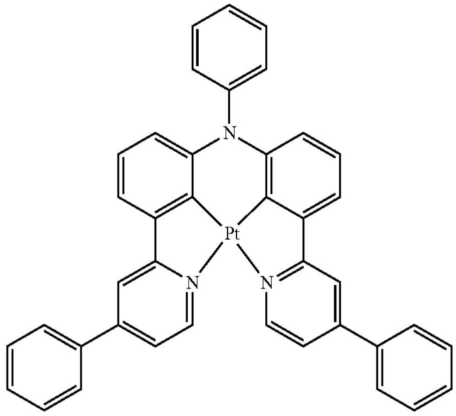
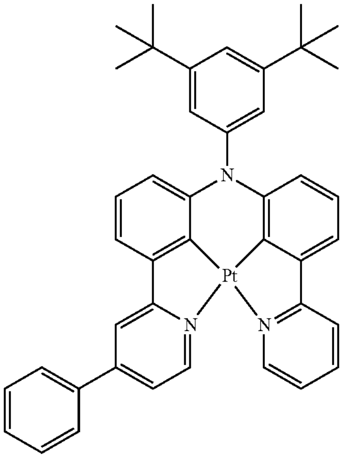

TABLE 14-continued
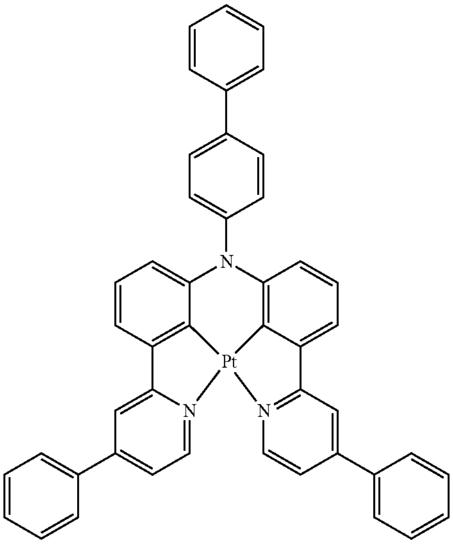
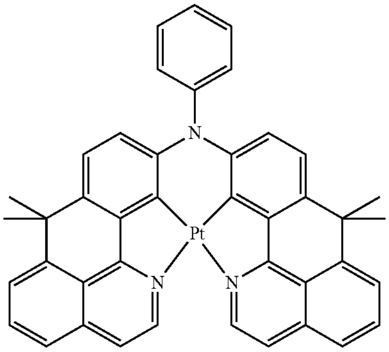
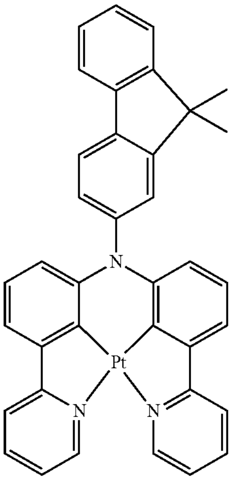
TABLE 14-continued
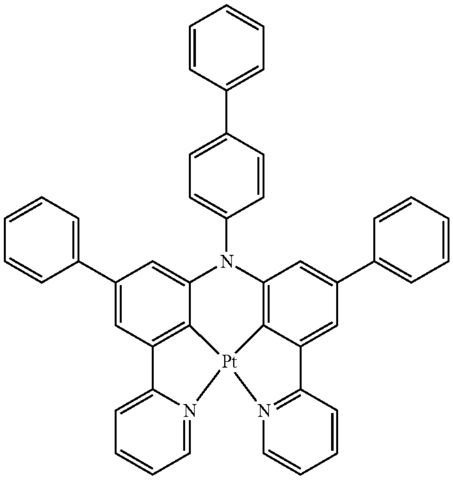
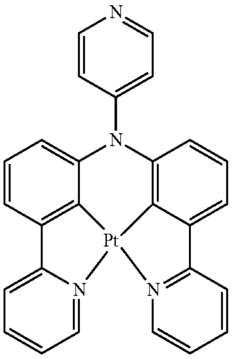
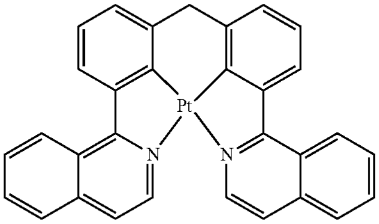
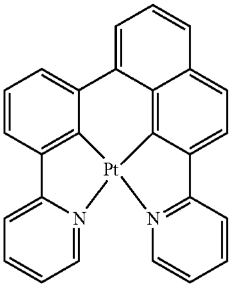

TABLE 14-continued
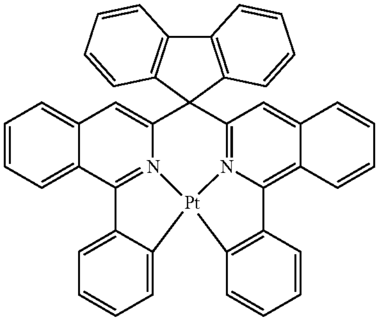
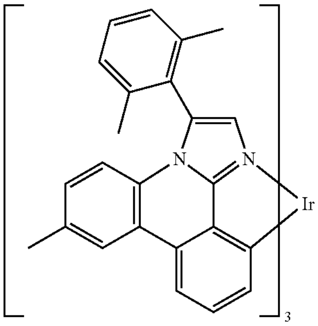
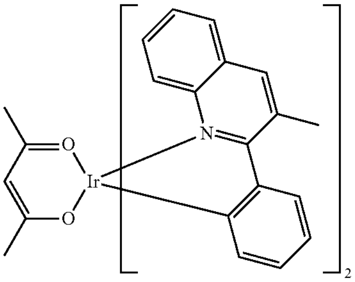
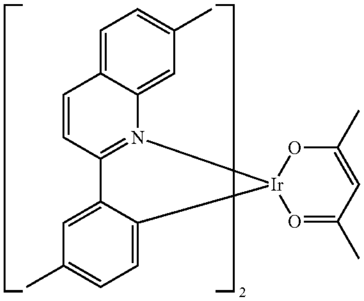
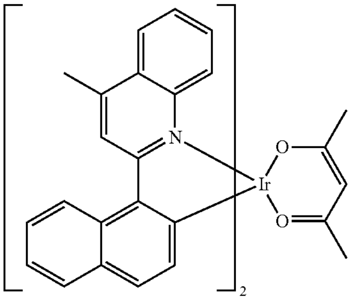
TABLE 14-continued
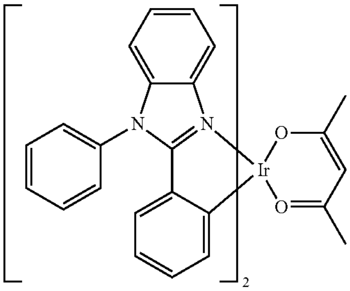
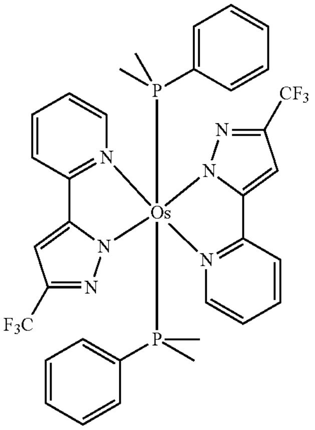
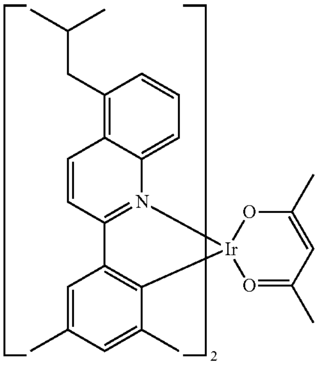
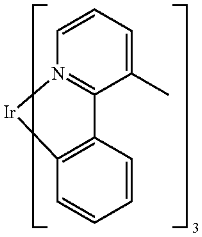
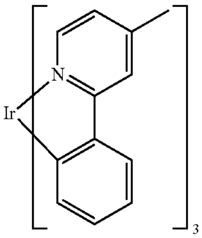

TABLE 14-continued
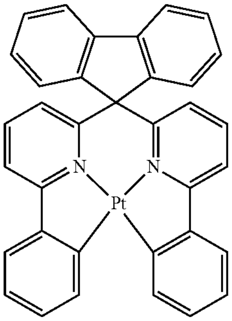
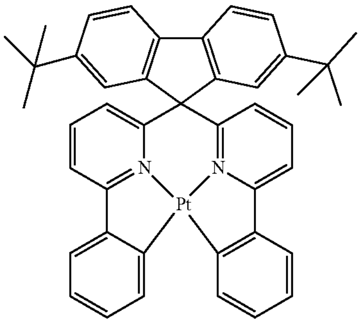
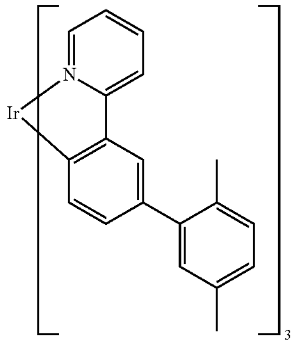
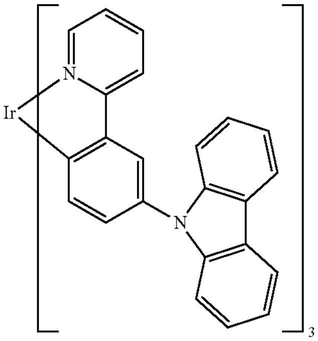
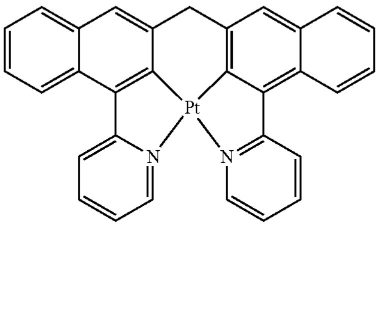
TABLE 14-continued
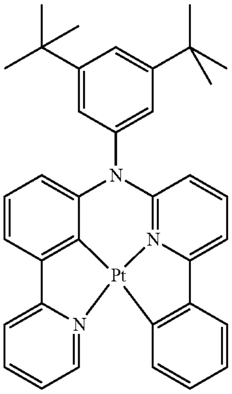
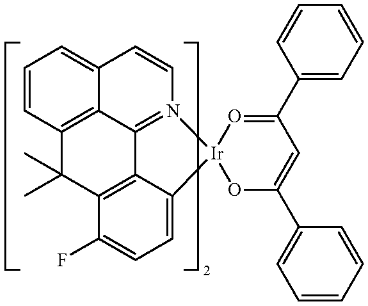
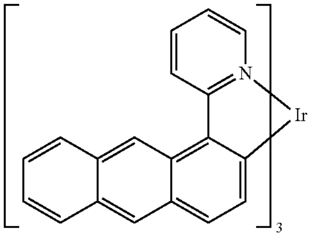
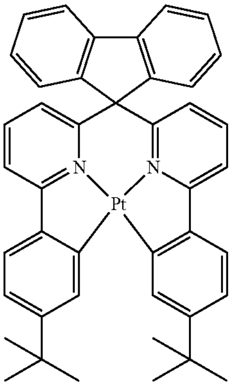

TABLE 14-continued
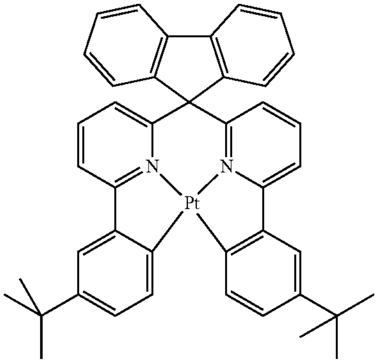
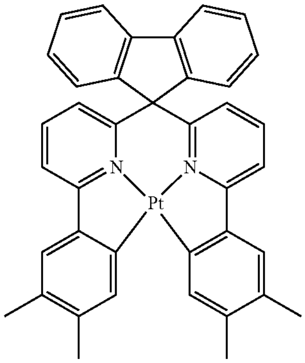
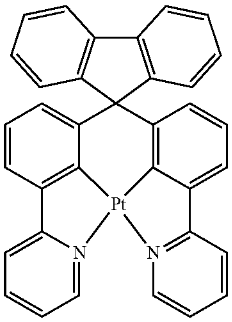
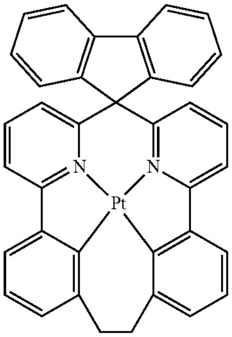
TABLE 14-continued
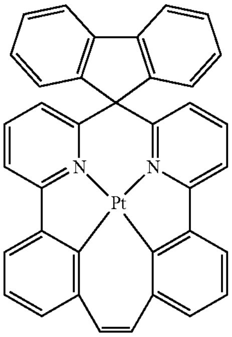
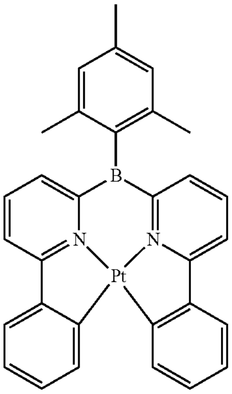
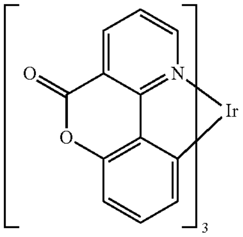
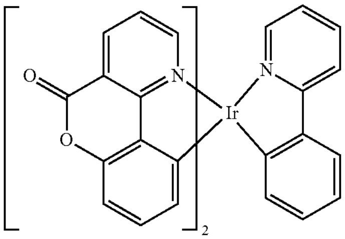
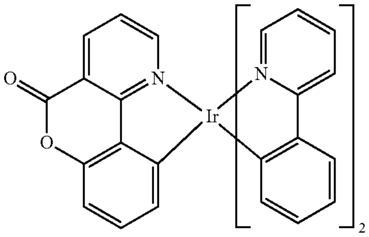

TABLE 14-continued
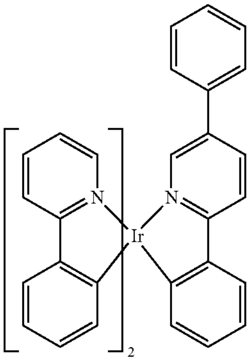
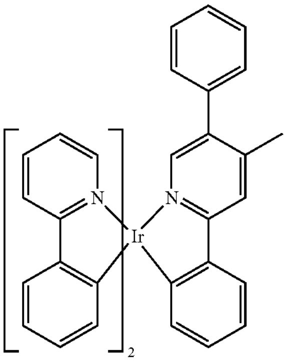
TEG1
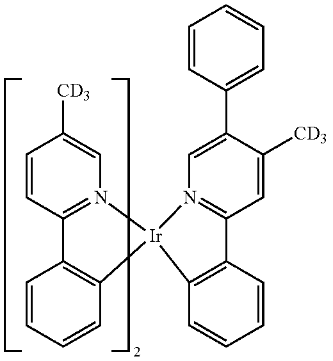
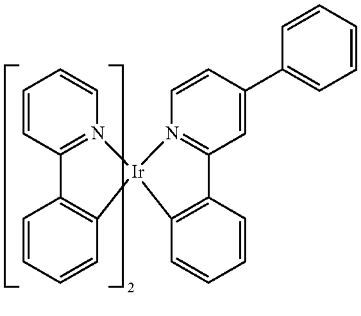
TABLE 14-continued
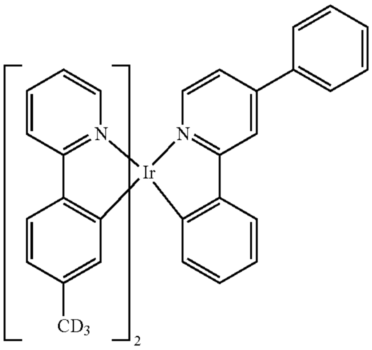
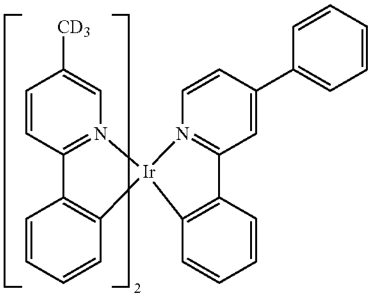
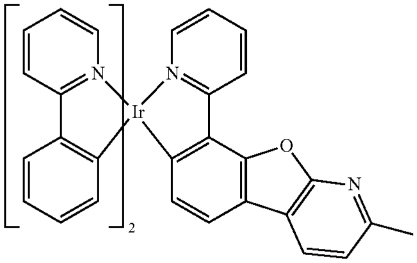
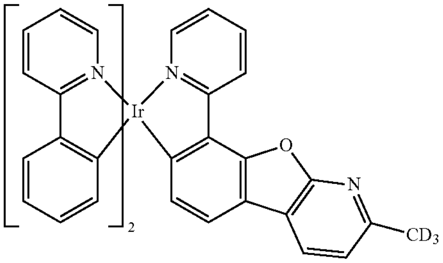
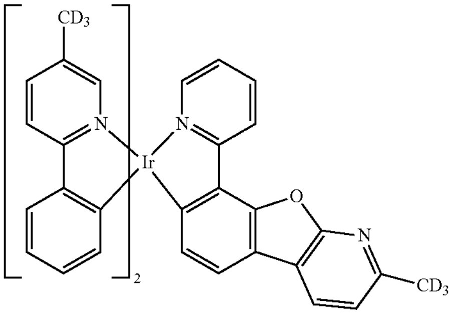

TABLE 14-continued

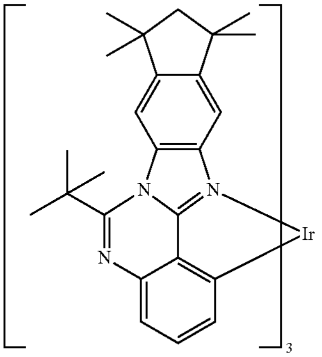

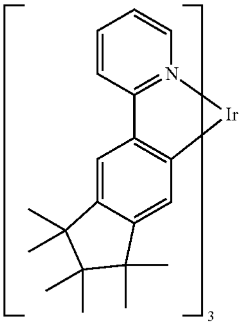

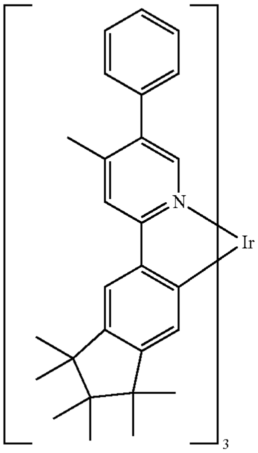

TABLE 14-continued

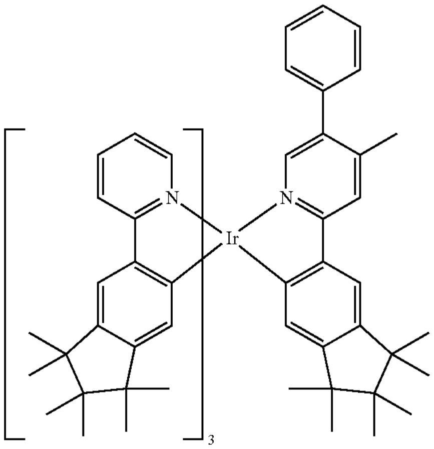

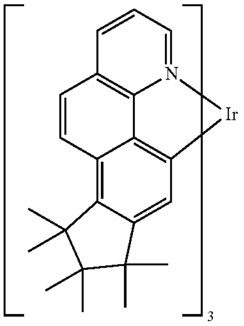

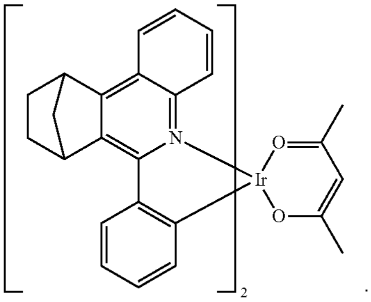

Preferred examples of phosphorescent polypodal emitters are shown in Table 15 below.

TABLE 15

| | | | |
|---|---|---|---|
| CAS-1269508-30-6 | CAS-1989601-68-4 | CAS-1989602-19-8 | CAS-1989602-70-1 |
| CAS-1215692-34-4 | CAS-1989601-69-5 | CAS-1989602-20-1 | CAS-1989602-71-2 |
| CAS-1370364-40-1 | CAS-1989601-70-8 | CAS-1989602-21-2 | CAS-1989602-72-3 |
| CAS-1370364-42-3 | CAS-1989601-71-9 | CAS-1989602-22-3 | CAS-1989602-73-4 |
| CAS-1989600-74-9 | CAS-1989601-72-0 | CAS-1989602-23-4 | CAS-1989602-74-5 |
| CAS-1989600-75-0 | CAS-1989601-73-1 | CAS-1989602-24-5 | CAS-1989602-75-6 |
| CAS-1989600-77-2 | CAS-1989601-74-2 | CAS-1989602-25-6 | CAS-1989602-76-7 |
| CAS-1989600-78-3 | CAS-1989601-75-3 | CAS-1989602-26-7 | CAS-1989602-77-8 |
| CAS-1989600-79-4 | CAS-1989601-76-4 | CAS-1989602-27-8 | CAS-1989602-78-9 |
| CAS-1989600-82-9 | CAS-1989601-77-5 | CAS-1989602-28-9 | CAS-1989602-79-0 |
| CAS-1989600-83-0 | CAS-1989601-78-6 | CAS-1989602-29-0 | CAS-1989602-80-3 |
| CAS-1989600-84-1 | CAS-1989601-79-7 | CAS-1989602-30-3 | CAS-1989602-82-5 |
| CAS-1989600-85-2 | CAS-1989601-80-0 | CAS-1989602-31-4 | CAS-1989602-84-7 |
| CAS-1989600-86-3 | CAS-1989601-81-1 | CAS-1989602-32-5 | CAS-1989602-85-8 |
| CAS-1989600-87-4 | CAS-1989601-82-2 | CAS-1989602-33-6 | CAS-1989602-86-9 |
| CAS-1989600-88-5 | CAS-1989601-83-3 | CAS-1989602-34-7 | CAS-1989602-87-0 |
| CAS-1989600-89-6 | CAS-1989601-84-4 | CAS-1989602-35-8 | CAS-1989602-88-1 |
| CAS-1989601-11-7 | CAS-1989601-85-5 | CAS-1989602-36-9 | CAS-1989604-00-3 |
| CAS-1989601-23-1 | CAS-1989601-86-6 | CAS-1989602-37-0 | CAS-1989604-01-4 |

TABLE 15-continued

| | | | |
|---|---|---|---|
| CAS-1989601-26-4 | CAS-1989601-87-7 | CAS-1989602-38-1 | CAS-1989604-02-5 |
| CAS-1989601-28-6 | CAS-1989601-88-8 | CAS-1989602-39-2 | CAS-1989604-03-6 |
| CAS-1989601-29-7 | CAS-1989601-89-9 | CAS-1989602-40-5 | CAS-1989604-04-7 |
| CAS-1989601-33-3 | CAS-1989601-90-2 | CAS-1989602-41-6 | CAS-1989604-05-8 |
| CAS-1989601-40-2 | CAS-1989601-91-3 | CAS-1989602-42-7 | CAS-1989604-06-9 |
| CAS-1989601-41-3 | CAS-1989601-92-4 | CAS-1989602-43-8 | CAS-1989604-07-0 |
| CAS-1989601-42-4 | CAS-1989601-93-5 | CAS-1989602-44-9 | CAS-1989604-08-1 |
| CAS-1989601-43-5 | CAS-1989601-94-6 | CAS-1989602-45-0 | CAS-1989604-09-2 |
| CAS-1989601-44-6 | CAS-1989601-95-7 | CAS-1989602-46-1 | CAS-1989604-10-5 |
| CAS-1989601-45-7 | CAS-1989601-96-8 | CAS-1989602-47-2 | CAS-1989604-11-6 |
| CAS-1989601-46-8 | CAS-1989601-97-9 | CAS-1989602-48-3 | CAS-1989604-13-8 |
| CAS-1989601-47-9 | CAS-1989601-98-0 | CAS-1989602-49-4 | CAS-1989604-14-9 |
| CAS-1989601-48-0 | CAS-1989601-99-1 | CAS-1989602-50-7 | CAS-1989604-15-0 |
| CAS-1989601-49-1 | CAS-1989602-00-7 | CAS-1989602-51-8 | CAS-1989604-16-1 |
| CAS-1989601-50-4 | CAS-1989602-01-8 | CAS-1989602-52-9 | CAS-1989604-17-2 |
| CAS-1989601-51-5 | CAS-1989602-02-9 | CAS-1989602-53-0 | CAS-1989604-18-3 |
| CAS-1989601-52-6 | CAS-1989602-03-0 | CAS-1989602-54-1 | CAS-1989604-19-4 |
| CAS-1989601-53-7 | CAS-1989602-04-1 | CAS-1989602-55-2 | CAS-1989604-20-7 |
| CAS-1989601-54-8 | CAS-1989602-05-2 | CAS-1989602-56-3 | CAS-1989604-21-8 |
| CAS-1989601-55-9 | CAS-1989602-06-3 | CAS-1989602-57-4 | CAS-1989604-22-9 |
| CAS-1989601-56-0 | CAS-1989602-07-4 | CAS-1989602-58-5 | CAS-1989604-23-0 |
| CAS-1989601-57-1 | CAS-1989602-08-5 | CAS-1989602-59-6 | CAS-1989604-24-1 |
| CAS-1989601-58-2 | CAS-1989602-09-6 | CAS-1989602-60-9 | CAS-1989604-25-2 |
| CAS-1989601-59-3 | CAS-1989602-10-9 | CAS-1989602-61-0 | CAS-1989604-26-3 |
| CAS-1989601-60-6 | CAS-1989602-11-0 | CAS-1989602-62-1 | CAS-1989604-27-4 |
| CAS-1989601-61-7 | CAS-1989602-12-1 | CAS-1989602-63-2 | CAS-1989604-28-5 |
| CAS-1989601-62-8 | CAS-1989602-13-2 | CAS-1989602-64-3 | CAS-1989604-29-6 |
| CAS-1989601-63-9 | CAS-1989602-14-3 | CAS-1989602-65-4 | CAS-1989604-30-9 |
| CAS-1989601-64-0 | CAS-1989602-15-4 | CAS-1989602-66-5 | CAS-1989604-31-0 |
| CAS-1989601-65-1 | CAS-1989602-16-5 | CAS-1989602-67-6 | CAS-1989604-32-1 |
| CAS-1989601-66-2 | CAS-1989602-17-6 | CAS-1989602-68-7 | CAS-1989604-33-2 |
| CAS-1989601-67-3 | CAS-1989602-18-7 | CAS-1989602-69-8 | CAS-1989604-34-3 |
| CAS-1989604-35-4 | CAS-1989604-88-7 | CAS-1989605-52-8 | CAS-1989606-07-6 |
| CAS-1989604-36-5 | CAS-1989604-89-8 | CAS-1989605-53-9 | CAS-1989606-08-7 |
| CAS-1989604-37-6 | CAS-1989604-90-1 | CAS-1989605-54-0 | CAS-1989606-09-8 |
| CAS-1989604-38-7 | CAS-1989604-92-3 | CAS-1989605-55-1 | CAS-1989606-10-1 |
| CAS-1989604-39-8 | CAS-1989604-93-4 | CAS-1989605-56-2 | CAS-1989606-11-2 |
| CAS-1989604-40-1 | CAS-1989604-94-5 | CAS-1989605-57-3 | CAS-1989606-12-3 |
| CAS-1989604-41-2 | CAS-1989604-95-6 | CAS-1989605-58-4 | CAS-1989606-13-4 |
| CAS-1989604-42-3 | CAS-1989604-96-7 | CAS-1989605-59-5 | CAS-1989606-14-5 |
| CAS-1989604-43-4 | CAS-1989604-97-8 | CAS-1989605-61-9 | CAS-1989606-15-6 |
| CAS-1989604-45-6 | CAS-1989605-09-5 | CAS-1989605-62-0 | CAS-1989606-16-7 |
| CAS-1989604-46-7 | CAS-1989605-10-8 | CAS-1989605-63-1 | CAS-1989606-17-8 |
| CAS-1989604-47-8 | CAS-1989605-11-9 | CAS-1989605-64-2 | CAS-1989606-18-9 |
| CAS-1989604-48-9 | CAS-1989605-13-1 | CAS-1989605-65-3 | CAS-1989606-19-0 |
| CAS-1989604-49-0 | CAS-1989605-14-2 | CAS-1989605-66-4 | CAS-1989606-20-3 |
| CAS-1989604-50-3 | CAS-1989605-15-3 | CAS-1989605-67-5 | CAS-1989606-21-4 |
| CAS-1989604-52-5 | CAS-1989605-16-4 | CAS-1989605-68-6 | CAS-1989606-22-5 |
| CAS-1989604-53-6 | CAS-1989605-17-5 | CAS-1989605-69-7 | CAS-1989606-23-6 |
| CAS-1989604-54-7 | CAS-1989605-18-6 | CAS-1989605-70-0 | CAS-1989606-24-7 |
| CAS-1989604-55-8 | CAS-1989605-19-7 | CAS-1989605-71-1 | CAS-1989606-26-9 |
| CAS-1989604-56-9 | CAS-1989605-20-0 | CAS-1989605-72-2 | CAS-1989606-27-0 |
| CAS-1989604-57-0 | CAS-1989605-21-1 | CAS-1989605-73-3 | CAS-1989606-28-1 |
| CAS-1989604-58-1 | CAS-1989605-22-2 | CAS-1989605-74-4 | CAS-1989606-29-2 |
| CAS-1989604-59-2 | CAS-1989605-23-3 | CAS-1989605-75-5 | CAS-1989606-30-5 |
| CAS-1989604-60-5 | CAS-1989605-24-4 | CAS-1989605-76-6 | CAS-1989606-31-6 |
| CAS-1989604-61-6 | CAS-1989605-25-5 | CAS-1989605-77-7 | CAS-1989606-32-7 |
| CAS-1989604-62-7 | CAS-1989605-26-6 | CAS-1989605-78-8 | CAS-1989606-33-8 |
| CAS-1989604-63-8 | CAS-1989605-27-7 | CAS-1989605-79-9 | CAS-1989606-34-9 |
| CAS-1989604-64-9 | CAS-1989605-28-8 | CAS-1989605-81-3 | CAS-1989606-35-0 |
| CAS-1989604-65-0 | CAS-1989605-29-9 | CAS-1989605-82-4 | CAS-1989606-36-1 |
| CAS-1989604-66-1 | CAS-1989605-30-2 | CAS-1989605-83-5 | CAS-1989606-37-2 |
| CAS-1989604-67-2 | CAS-1989605-31-3 | CAS-1989605-84-6 | CAS-1989606-38-3 |
| CAS-1989604-68-3 | CAS-1989605-32-4 | CAS-1989605-85-7 | CAS-1989606-39-4 |
| CAS-1989604-69-4 | CAS-1989605-33-5 | CAS-1989605-86-8 | CAS-1989606-40-7 |
| CAS-1989604-70-7 | CAS-1989605-34-6 | CAS-1989605-87-9 | CAS-1989606-41-8 |
| CAS-1989604-71-8 | CAS-1989605-35-7 | CAS-1989605-88-0 | CAS-1989606-42-9 |
| CAS-1989604-72-9 | CAS-1989605-36-8 | CAS-1989605-89-1 | CAS-1989606-43-0 |
| CAS-1989604-73-0 | CAS-1989605-37-9 | CAS-1989605-90-4 | CAS-1989606-44-1 |
| CAS-1989604-74-1 | CAS-1989605-38-0 | CAS-1989605-91-5 | CAS-1989606-45-2 |
| CAS-1989604-75-2 | CAS-1989605-39-1 | CAS-1989605-92-6 | CAS-1989606-46-3 |
| CAS-1989604-76-3 | CAS-1989605-40-4 | CAS-1989605-93-7 | CAS-1989606-48-5 |
| CAS-1989604-77-4 | CAS-1989605-41-5 | CAS-1989605-94-8 | CAS-1989606-49-6 |
| CAS-1989604-78-5 | CAS-1989605-42-6 | CAS-1989605-95-9 | CAS-1989606-53-2 |
| CAS-1989604-79-6 | CAS-1989605-43-7 | CAS-1989605-96-0 | CAS-1989606-55-4 |
| CAS-1989604-80-9 | CAS-1989605-44-8 | CAS-1989605-97-1 | CAS-1989606-56-5 |
| CAS-1989604-81-0 | CAS-1989605-45-9 | CAS-1989605-98-2 | CAS-1989606-61-2 |
| CAS-1989604-82-1 | CAS-1989605-46-0 | CAS-1989605-99-3 | CAS-1989606-62-3 |
| CAS-1989604-83-2 | CAS-1989605-47-1 | CAS-1989606-00-9 | CAS-1989606-63-4 |
| CAS-1989604-84-3 | CAS-1989605-48-2 | CAS-1989606-01-0 | CAS-1989606-67-8 |

TABLE 15-continued

| | | | |
|---|---|---|---|
| CAS-1989604-85-4 | CAS-1989605-49-3 | CAS-1989606-04-3 | CAS-1989606-69-0 |
| CAS-1989604-86-5 | CAS-1989605-50-6 | CAS-1989606-05-4 | CAS-1989606-70-3 |
| CAS-1989604-87-6 | CAS-1989605-51-7 | CAS-1989606-06-5 | CAS-1989606-74-7 |
| CAS-1989658-39-0 | CAS-2088184-56-7 | CAS-2088185-07-1 | CAS-2088185-66-2 |
| CAS-1989658-41-4 | CAS-2088184-57-8 | CAS-2088185-08-2 | CAS-2088185-67-3 |
| CAS-1989658-43-6 | CAS-2088184-58-9 | CAS-2088185-09-3 | CAS-2088185-68-4 |
| CAS-1989658-47-0 | CAS-2088184-59-0 | CAS-2088185-10-6 | CAS-2088185-69-5 |
| CAS-1989658-49-2 | CAS-2088184-60-3 | CAS-2088185-11-7 | CAS-2088185-70-8 |
| CAS-2088184-07-8 | CAS-2088184-61-4 | CAS-2088185-12-8 | CAS-2088185-71-9 |
| CAS-2088184-08-9 | CAS-2088184-62-5 | CAS-2088185-13-9 | CAS-2088185-72-0 |
| CAS-2088184-09-0 | CAS-2088184-63-6 | CAS-2088185-14-0 | CAS-2088185-73-1 |
| CAS-2088184-10-3 | CAS-2088184-64-7 | CAS-2088185-15-1 | CAS-2088185-74-2 |
| CAS-2088184-11-4 | CAS-2088184-65-8 | CAS-2088185-16-2 | CAS-2088185-75-3 |
| CAS-2088184-13-6 | CAS-2088184-66-9 | CAS-2088185-17-3 | CAS-2088185-76-4 |
| CAS-2088184-14-7 | CAS-2088184-67-0 | CAS-2088185-18-4 | CAS-2088185-77-5 |
| CAS-2088184-15-8 | CAS-2088184-68-1 | CAS-2088185-19-5 | CAS-2088185-78-6 |
| CAS-2088184-16-9 | CAS-2088184-69-2 | CAS-2088185-20-8 | CAS-2088185-79-7 |
| CAS-2088184-17-0 | CAS-2088184-70-5 | CAS-2088185-21-9 | CAS-2088185-80-0 |
| CAS-2088184-18-1 | CAS-2088184-71-6 | CAS-2088185-22-0 | CAS-2088185-81-1 |
| CAS-2088184-19-2 | CAS-2088184-72-7 | CAS-2088185-23-1 | CAS-2088185-82-2 |
| CAS-2088184-20-5 | CAS-2088184-73-8 | CAS-2088185-32-2 | CAS-2088185-83-3 |
| CAS-2088184-21-6 | CAS-2088184-74-9 | CAS-2088185-33-3 | CAS-2088185-84-4 |
| CAS-2088184-22-7 | CAS-2088184-75-0 | CAS-2088185-34-4 | CAS-2088185-85-5 |
| CAS-2088184-23-8 | CAS-2088184-76-1 | CAS-2088185-35-5 | CAS-2088185-86-6 |
| CAS-2088184-24-9 | CAS-2088184-77-2 | CAS-2088185-36-6 | CAS-2088185-87-7 |
| CAS-2088184-25-0 | CAS-2088184-78-3 | CAS-2088185-37-7 | CAS-2088185-88-8 |
| CAS-2088184-26-1 | CAS-2088184-79-4 | CAS-2088185-38-8 | CAS-2088185-89-9 |
| CAS-2088184-27-2 | CAS-2088184-80-7 | CAS-2088185-39-9 | CAS-2088185-90-2 |
| CAS-2088184-28-3 | CAS-2088184-81-8 | CAS-2088185-40-2 | CAS-2088185-91-3 |
| CAS-2088184-29-4 | CAS-2088184-82-9 | CAS-2088185-41-3 | CAS-2088185-92-4 |
| CAS-2088184-30-7 | CAS-2088184-83-0 | CAS-2088185-42-4 | CAS-2088185-93-5 |
| CAS-2088184-32-9 | CAS-2088184-84-1 | CAS-2088185-43-5 | CAS-2088185-94-6 |
| CAS-2088184-34-1 | CAS-2088184-85-2 | CAS-2088185-44-6 | CAS-2088185-95-7 |
| CAS-2088184-35-2 | CAS-2088184-86-3 | CAS-2088185-45-7 | CAS-2088185-96-8 |
| CAS-2088184-36-3 | CAS-2088184-87-4 | CAS-2088185-46-8 | CAS-2088185-97-9 |
| CAS-2088184-37-4 | CAS-2088184-88-5 | CAS-2088185-47-9 | CAS-2088185-98-0 |
| CAS-2088184-38-5 | CAS-2088184-89-6 | CAS-2088185-48-0 | CAS-2088185-99-1 |
| CAS-2088184-39-6 | CAS-2088184-90-9 | CAS-2088185-49-1 | CAS-2088186-00-7 |
| CAS-2088184-40-9 | CAS-2088184-91-0 | CAS-2088185-50-4 | CAS-2088186-01-8 |
| CAS-2088184-41-0 | CAS-2088184-92-1 | CAS-2088185-51-5 | CAS-2088186-02-9 |
| CAS-2088184-42-1 | CAS-2088184-93-2 | CAS-2088185-52-6 | CAS-2088195-88-2 |
| CAS-2088184-43-2 | CAS-2088184-94-3 | CAS-2088185-53-7 | CAS-2088195-89-3 |
| CAS-2088184-44-3 | CAS-2088184-95-4 | CAS-2088185-54-8 | CAS-2088195-90-6 |
| CAS-2088184-45-4 | CAS-2088184-96-5 | CAS-2088185-55-9 | CAS-2088195-91-7 |
| CAS-2088184-46-5 | CAS-2088184-97-6 | CAS-2088185-56-0 | CAS-861806-70-4 |
| CAS-2088184-47-6 | CAS-2088184-98-7 | CAS-2088185-57-1 | CAS-1269508-30-6 |
| CAS-2088184-48-7 | CAS-2088184-99-8 | CAS-2088185-58-2 | |
| CAS-2088184-49-8 | CAS-2088185-00-4 | CAS-2088185-59-3 | |
| CAS-2088184-50-1 | CAS-2088185-01-5 | CAS-2088185-60-6 | |
| CAS-2088184-51-2 | CAS-2088185-02-6 | CAS-2088185-61-7 | |
| CAS-2088184-52-3 | CAS-2088185-03-7 | CAS-2088185-62-8 | |
| CAS-2088184-53-4 | CAS-2088185-04-8 | CAS-2088185-63-9 | |
| CAS-2088184-54-5 | CAS-2088185-05-9 | CAS-2088185-64-0 | |
| CAS-2088184-55-6 | CAS-2088185-06-0 | CAS-2088185-65-1 | |

In the composition according to the invention, each mixture M1, M2, M3, M4, M5, M6, M7, M8, M9, M10, M11, M12, M13, M14, M15, M16, M17, M18, M19, M20, M21, M22, M23, M24, M25, M26, M27, M28, M29, M30, M31, M32, M33, M34, M35, M36, M37, M38, M39, M40, M41, M42, M43, M44, M45, M46, M47, M48, M49, M50, M51, M52, M53, M54, M55, M56, M57, M58, M59, M60, M61, M62, M63, M64, M65, M66, M67, M68, M69, M70, M71, M72, M73, M74, M75, M76, M77, M78, M79, M80, M81, M82, M83, M84, M85, M86, M87, M88, M89, M90, M91, M92, M93, M94, M95, M96, M97, M98, M99, M100, M101, M102, M103, M104, M105, M106, M107, M108, M109, M110, M111, M112, M113, M114, M115, M116, M117, M118, M119, M120, M121, M122, M123, M124, M125, M126, M127, M128, M129, M130, M131, M132, M133, M134, M135, M136, M137, M138, M139, M140, M141, M142, M143, M144, M145, M146, M147, M148, M149, M150, M151, M152, M153, M154, M155, M156, M157, M158, M159, M160, M161, M162, M163, M164, M165, M166, M167, M168, M169, M170, M171, M172, M173, M174, M175, M176, M177, M178, M179, M180, M181, M182, M183, M184, M185, M186, M187, M188, M189, M190, M191, M192, M193, M194, M195, M196, M197, M198, M199, M200, M201, M202, M203, M204, M205, M206, M207, M208, M209, M210, M211, M212, M213, M214, M215, M216, M217, M218, M219, M220, M221, M222, M223, M224, M225, M226, M227, M228, M229, M230, M231, M232, M233, M234, M235, M236, M237, M238, M239, M240, M241, M242, M243, M244, M245, M246, M247, M248, M249, M250, M251, M252, M253, M254, M255, M256, M257, M258, M259, M260, M261, M262, M263, M264, M265, M266, M267, M268, M269, M270, M271, M272, M273, M274, M275, M276, M277, M278, M279, M280, M281, M282, M283, M284, M285, M286, M287, M288, M289, M290, M291, M292, M293, M294, M295, M296, M297, M298, M299, M300, M301, M302, M303, M304, M305, M306, M307, M308, M309, M310, M311, M312, M313, M314, M315, M316, M317, M318, M319, M320, M321, M322, M323, M324, M325, M326, M327, M328, M329, M330, M331, M332, M333, M334, M335, M336, M337, M338, M339, M340, M341, M342, M343, M344, M345, M346, M347, M348, M349, M350, M351, M352, M353, M354, M355, M356, M357, M358, M359, M360, M361, M362, M363, M364, M365, M366, M367, M368, M369, M370, M371, M372, M373, M374, M375, M376, M377, M378, M379, M380, M381, M382, M383, M384, M385, M386, M387, M388, M389, M390, M391, M392, M393, M394, M395, M396, M397, M398, M399, M400, M401, M402, M403, M404, M405, M406, M407, M408, M409, M410, M411, M412, M413, M414, M415, M416, M417, M418, M419, M420, M421, M422, M423, M424, M425, M426, M427, M428, M429, M430, M431, M432, M433, M434, M435, M436, M437, M438, M439, M440, M441, M442, M443, M444, M445, M446, M447, M448, M449, M450, M451, M452, M453, M454, M455, M456, M457, M458, M459, M460, M461, M462, M463, M464, M465, M466, M467, M468, M469, M470, M471, M472, M473, M474, M475, M476, M477, M478, M479, M480, M481, M482, M483, M484, M485, M486, M487, M488, M489, M490, M491, M492, M493, M494, M495, M496, M497, M498, M499, M500, M501, M502, M503, M504, M505, M506, M507, M508, M509, M510, M511, M512, M513, M514, M515, M516, M517, M518, M519, M520, M521, M522, M523, M524, M525, M526, M527, M528, M529, M530, M531, M532, M533, M534, M535, M536, M537, M538, M539, M540, M541, M542, M543, M544, M545, M546, M547, M548, M549, M550, M551, M552, M553, M554, M555, M556, M557, M558, M559, M560, M561, M562, M563, M564, M565, M566, M567, M568, M569, M570, M571, M572, M573, M574, M575, M576, M577, M578, M579, M580, M581, M582, M583, M584, M585, M586, M587, M588, M589, M590, M591, M592, M593, M594, M595, M596, M597, M598, M599, M600, M601, M602, M603, M604, M605, M606, M607, M608, M609, M610, M611, M612, M613, M614, M615, M616, M617, M618, M619, M620, M621, M622, M623, M624, M625, M626, M627, M628, M629, M630, M631, M632, M633, M634, M635, M636, M637, M638, M639, M640, M641, M642, M643, M644, M645, M646, M647, M648, M649, M650, M651, M652, M653, M654, M655, M656, M657, M658, M659, M660, M661, M662, M663, M664, M665, M666, M667, M668, M669, M670, M671, M672, M673, M674, M675, M676, M677, M678, M679, M680, M681, M682, M683, M684, M685, M686, M687, M688, M689, M690, M691, M692, M693, M694, M695, M696, M697, M698, M699, M700, M701, M702, M703, M704, M705, M706, M707, M708, M709, M710, M711, M712, M713, M714, M715, M716, M717, M718, M719, M720, M721, M722, M723, M724, M725, M726, M727, M728, M729, M730, M731, M732, M733, M734, M735, M736, M737, M738, M739, M740, M741, M742, M743, M744, M745, M746, M747, M748, M749, M750, M751, M752, M753, M754, M755, M756, M757, M758, M759, M760, M761, M762, M763, M764, M765, M766, M767, M768, M769, M770, M771, M772, M773, M774, M775, M776, M777, M778, M779, M780, M781, M782, M783, M784, M785, M786, M787, M788, M789, M790, M791, M792, M793, M794, M795, M796, M797, M798, M799, M800, M801, M802, M803, M804, M805, M806, M807, M808, M809, M810, M811, M812, M813, M814, M815, M816, M817, M818, M819, M820, M821, M822, M823, M824, M825, M826, M827, M828, M829, M830, M831, M832, M833, M834, M835, M836, M837, M838, M839, M840, M841, M842, M843, M844, M845, M846, M847, M848, M849, M850, M851, M852, M853, M854, M855, M856, M857, M858, M859, M860, M861, M862, M863, M864, M865, M866, M867, M868, M869, M870, M871, M872, M873, M874, M875, M876, M877, M878, M879, M880, M881, M882, M883, M884, M885, M886, M887, M888, M889, M890, M891, M892, M893, M894, M895, M896, M897, M898, M899, M900, M901, M902, M903, M904, M905, M906, M907, M908, M909, M910, M911, M912, M913, M914, M915, M916, M917, M918, M919, M920, M921, M922, M923, M924, M925, M926, M927, M928, M929, M930, M931, M932, M933, M934, M935, M936, M937, M938, M939, M940, M941, M942, M943, M944, M945, M946, M947, M948, M949, M950, M951, M952, M953, M954, M955, M956, M957, M958, M959, M960, M961, M962, M963, M964, M965, M966, M967, M968, M969, M970, M971, M972, M973, M974, M975, M976, M977, M978, M979, M980, M981, M982, M983, M984, M985, M986, M987, M988, M989, M990, M991, M992, M993, M994, M995, M996, M997, M998, M999, M1000, M1001, M1002, M1003, M1004, M1005, M1006, M1007, M1008, M1009, M1010, M1011, M1012, M1013, M1014, M1015, M1016, M1017, M1018, M1019, M1020, M1021, M1022, M1023, M1024, M1025, M1026, M1027, M1028, M1029, M1030, M1031, M1032, M1033, M1034, M1035, M1036, M1037, M1038, M1039, M1040, M1041, M1042, M1043, M1044, M1045, M1046, M1047, M1048, M1049, M1050, M1051, M1052, M1053, M1054, M1055, M1056, M1057, M1058, M1059, M1060, M1061, M1062, M1063, M1064, M1065, M1066, M1067, M1068, M1069, M1070, M1071, M1072, M1073, M1074, M1075, M1076, M1077, M1078, M1079, M1080, M1081, M1082, M1083, M1084, M1085, M1086, M1087, M1088, M1089, M1090, M1091, M1092, M1093, M1094, M1095, M1096, M1097, M1098, M1099, M1100, M1101, M1102, M1103, M1104, M1105, M1106, M1107, M1108, M1109, M1110, M1111, M1112, M1113, M1114, M1115, M1116, M1117, M1118, M1119, M1120, M1121, M1122, M1123, M1124, M1125, M1126, M1127, M1128, M1129, M1130, M1131, M1132, M1133, M1134, M1135, M1136 or M1137 is preferably combined with a compound from Table 14 or 15.

The composition according to the invention comprising at least one phosphorescent emitter preferably forms an infrared-, yellow-, orange-, red-, green-, blue- or ultraviolet-emitting layer, particularly preferably a yellow- or green-emitting layer and very particularly preferably a green-emitting layer.

A yellow-emitting layer here is taken to mean a layer whose photoluminescence maximum is in the range from 540 to 570 nm. An orange-emitting layer is taken to mean a layer whose photoluminescence maximum is in the range from 570 to 600 nm. A red-emitting layer is taken to mean a layer whose photoluminescence maximum is in the range from 600 to 750 nm. A green-emitting layer is taken to mean a layer whose photoluminescence maximum is in the range from 490 to 540 nm. A blue-emitting layer is taken to mean a layer whose photoluminescence maximum is in the range from 440 to 490 nm. The photoluminescence of the layer is determined here by measurement of the photoluminescence spectrum of the layer having a layer thickness of 50 nm at room temperature, where the layer comprises the composition according to the invention, i.e. comprises emitter and matrix.

The photoluminescence spectrum of the layer is recorded, for example, using a commercially available photoluminescence spectrometer.

The photoluminescence spectrum of the selected emitter is generally measured in oxygen-free solution, 10-5 molar, where the measurement is carried out at room temperature and any solvent in which the selected emitter dissolves in the said concentration is suitable. Particularly suitable solvents are usually toluene or 2-methyl-THF, but also dichloromethane. The measurement is carried out using a commercially available photoluminescence spectrometer. The triplet energy $T_1$ in eV is determined from the photoluminescence spectra of the emitters. Firstly the peak maximum PImax. (in nm) of the photoluminescence spectrum is determined. The peak maximum PImax. (in nm) is then converted into in eV in accordance with: E(T1 in eV)=1240/E(T1 in nm)=1240/PImax. (in nm).

Preferred phosphorescent emitters are accordingly infrared emitters, preferably from Table 14 or 15, whose triplet energy $T_1$ is preferably ~1.9 eV to ~1.0 eV.

Preferred phosphorescent emitters are accordingly red emitters, preferably from Table 14 or 15, whose triplet energy $T_1$ is preferably ~2.1 eV to ~1.9 eV.

Preferred phosphorescent emitters are accordingly yellow emitters, preferably from Table 14 or 15, whose triplet energy $T_1$ is preferably ~2.3 eV to ~2.1 eV.

Preferred phosphorescent emitters are accordingly green emitters, preferably from Table 14 or 15, whose triplet energy $T_1$ is preferably ~2.5 eV to ~2.3 eV.

Preferred phosphorescent emitters are accordingly blue emitters, preferably from Table 14 or 15, whose triplet energy $T_1$ is preferably ~3.1 eV to ~2.5 eV.

Preferred phosphorescent emitters are accordingly ultraviolette Emitter, preferably from Table 14 or 15, whose triplet energy $T_1$ is preferably ~4.0 eV to ~3.1 eV.

Particularly preferred phosphorescent emitters are accordingly green or yellow emitters, preferably from Table 14 or 15, as described above.

Very particularly preferred phosphorescent emitters are accordingly green emitters, preferably from Table 14 or 15, whose triplet energy $T_1$ is preferably ~2.5 eV to ~2.3 eV.

Green emitters, preferably from Table 14 or 15, as described above, are very particularly preferably selected for the composition according to the invention or the emitting layer according to the invention.

Preferred fluorescent emitters are selected from the class of the arylamines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1 position or in the 1,6 position. Further preferred fluorescent emitters are indenofluorenamines or indenofluorenediamines, for example in accordance with WO 2006/108497 or WO 2006/122630, benzoindenofluorenamines or benzoindenofluorenediamines, for example in accordance with WO 2008/006449, and dibenzoindenofluorenamines or dibenzoindenofluorenediamines, for example in accordance with WO 2007/140847, and the indenofluorene derivatives containing condensed aryl groups which are disclosed in WO 2010/012328.

In a further preferred embodiment of the invention, the composition according to the invention is used as a component of mixed-matrix systems. The mixed-matrix systems preferably comprise three or four different matrix materials, particularly preferably three different matrix materials (i.e. a further matrix component in addition to the composition according to the invention). Particularly suitable matrix materials which can be used in combination with the composition according to invention as matrix components of a mixed-matrix system are selected from wide bandgap materials, electron-transport materials (ETMs) and hole-transport materials (HTMs).

Mixed-matrix systems are preferably employed in phosphorescent organic electroluminescent devices. More precise details on mixed-matrix systems are given, inter alia, in the application WO 2010/108579. Particularly suitable matrix materials which can be employed in combination with the composition according to the invention as matrix components of a mixed-matrix system in phosphorescent or fluorescent organic electroluminescent devices are selected from the preferred matrix materials indicated below for phosphorescent emitters or the preferred matrix materials for fluorescent emitters, depending on what type of emitter is employed. The mixed-matrix system is preferably optimised for an emitter from Table 14 or 15.

Suitable further host materials, preferably for fluorescent emitters, besides the composition according to the invention, as described above, particularly preferably comprising a mixture of materials selected from M1 to M1137, are various classes of substance. Preferred further host materials are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, contaning naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, containing anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Suitable further matrix materials, preferably for phosphorescent emitters, besides the composition according to the invention, as described above, particularly preferably comprising a mixture of materials selected from M1 to M1137, are various classes of substance. Preferred further matrix materials are selected from the classes of the aromatic amines, in particular triarylamines, for example in accordance with US 2005/0069729, carbazole derivatives (for example CBP, N,N-biscarbazolylbiphenyl) or compounds in accordance with WO 2005/039246, US 2005/0069729, JP 2004/288381, EP 1205527 or WO 2008/086851, bridged carbazole derivatives, for example in accordance with WO 2011/088877 and WO 2011/128017, indenocarbazole derivatives, for example in accordance with WO 2010/136109 and WO 2011/000455, azacarbazole derivatives, for example in accordance with EP 1617710, EP 1617711, EP 1731584, JP 2005/347160, indolocarbazole derivatives, for example in accordance with WO 2007/063754 or WO 2008/056746, ketones, for example in accordance with WO 2004/093207 or WO 2010/006680, phosphine oxides, sulfoxides and sulfones, for example in accordance with WO 2005/003253, oligophenylenes, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, aluminium complexes, for example BAlq, diazasilole and tetraazasilole derivatives, for example in accordance with WO 2010/054729, diazaphosphole derivatives, for example in accordance with WO 2010/054730, and aluminium complexes, for example BAlQ.

According to an alternative embodiment of the present invention, the composition comprises no further constituents, i.e. functional materials, besides the constituents of electron-transporting host and hole-transporting host. This embodiment involves material mixtures which are used as such for the production of the organic layer. The systems are also known as premix systems, which are used as the sole material source during vapour deposition. This enables the vapour deposition of a layer with more uniform distribution of the components to be achieved in a simple and rapid manner, without precise control of a multiplicity of material sources being necessary.

The invention accordingly furthermore relates to a composition consisting of a compound of the formula (1), (1a) to (11) or a compound selected from 1 to 88 and a compound of the formula (2), (2a), (2b) or a compound selected from 89 to 101.

The composition according to the invention, as described or preferably described above, is suitable for use in an organic electronic device. An organic electronic device here is taken to mean a device which contains at least one layer which comprises at least one organic compound. However, the device may also contain inorganic materials or also layers which are built up entirely from inorganic materials.

The invention accordingly furthermore relates to the use of a composition, as described or preferably described above, in particular a mixture selected from M1 to M1137, in an organic electronic device.

The components or constituents of the compositions can be processed by vapour deposition or from solution. If the compositions are applied from solution, formulations of the composition according to the invention comprising at least one further solvent are necessary. These formulations can be, for example, solutions, dispersions or emulsions. It may be preferred to use mixtures of two or more solvents for this purpose.

The present invention therefore furthermore relates to a formulation comprising a composition according to the invention and at least one solvent.

Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetol, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, hexamethylindane or mixtures of these solvents.

The formulation here may also comprise at least one further organic or inorganic compound which is likewise employed in the electronic device, in particular an emitting compound, in particular a phosphorescent emitter, and/or a further matrix material. Suitable emitting compounds and further matrix materials have already been mentioned above.

The present invention also relates to the use of the composition according to the invention in an organic electronic device, preferably in an electron-transporting and/or emitting layer.

The organic electronic devices is preferably selected from organic integrated circuits (OICs), organic field-effect transistors (OFETs), organic thin-film transistors (OTFTs), organic electroluminescent devices, organic solar cells (OSCs), organic optical detectors and organic photoreceptors, where organic electroluminescent devices are particularly preferred.

Very particularly preferred organic electroluminescent devices for use of the composition according to the invention are organic light-emitting transistors (OLETs), organic field-quench devices (OFQDs), organic light-emitting electrochemical cells (OLECs, LECs, LEECs), organic laser diodes (O-lasers) and organic light-emitting diodes (OLEDs), particularly preferably OLECs and OLEDs and most preferably OLEDs.

The composition according to the invention, as described above or as preferably described, is preferably used in an electronic device in a layer having an electron-transporting function. The layer is preferably an electron-injection layer (EIL), an electron-transport layer (ETL), a hole-blocking layer (HBL) and/or an emission layer (EML), particularly preferably eine ETL, EIL and/or EML. The composition according to the invention is particularly preferably employed in an EML in particular as matrix material.

The present invention therefore still furthermore relates to an organic electronic device which is selected, in particular, from one of the electronic devices mentioned above and which preferably contains the composition according to the invention, as described or preferably described above, in an emission layer (EML), in an electron-transport layer (ETL), in an electron-injection layer (EIL) and/or in a hole-blocking layer (HBL), very preferably in an EML, EIL and/or ETL and very particularly preferably in an EML.

In the case of an emitting layer, this is particularly preferably a phosphorescent layer which is characterised in that, in addition to the composition as described or preferably described above, it comprises a phosphorescent emitter, in particular together with an emitter from Table 14 or 15 or a preferred emitter, as described above.

In a particularly preferred embodiment of the present invention, the electronic device is therefore an organic electroluminescent device, very particularly preferably an organic light-emitting diode (OLED), which contains the composition according to the invention, as described or preferably described above, together with a phosphorescent emitter in the emission layer (EML).

The composition according to the invention in accordance with the preferred embodiments and the emitting compound preferably comprises between 99.9 and 1% by vol., further preferably between 99 and 10% by vol., particularly preferably between 98 and 60% by vol., very particularly preferably between 97 and 80% by vol., of matrix material comprising at least one compound of the formula (1) and at least one compound of the formula (2) in accordance with the preferred embodiments, based on the entire composition comprising emitter and matrix material. Correspondingly, the composition preferably comprises between 0.1 and 99% by vol., further preferably between 1 and 90% by vol., particularly preferably between 2 and 40% by vol., very particularly preferably between 3 and 20% by vol., of the emitter, based on the entire composition comprising emitter and matrix material. If the compounds are processed from solution, the corresponding amounts in % by weight are preferably used instead of the abovementioned amounts in % by vol.

Apart from cathode, anode and the layer comprising the composition according to the invention, an electronic device may also comprise further layers. These are selected, for example, from in each case one or more hole-injection layers, hole-transport layers, hole-blocking layers, emitting layers, electron-transport layers, electron-injection layers, electron-blocking layers, exciton-blocking layers, interlayers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions. However, it should be pointed out that each of these layers does not necessarily have to be present.

The sequence of the layers in an organic electroluminescent device device is preferably the following:

anode/hole-injection layer/hole-transport layer/emitting layer/electron-transport layer/electron-injection layer/cathode.

This sequence of the layers is a preferred sequence.

It should again be pointed out here that not all of the said layers have to be present, and/or that further layers may additionally be present.

An organic electroluminescent device which contains the composition according to the invention according to the invention may comprise a plurality of emitting layers. These emission layers in this case particularly preferably have in total a plurality of emission maxima between 380 nm and 750 nm, resulting overall in white emission, i.e. various emitting compounds which are able to fluoresce or phosphoresce and which emit blue or yellow or orange or red light are used in the emitting layers. Particular preference is given to three-layer systems, i.e. systems having three emitting layers, where the three layers exhibit blue, green and orange or red emission (for the basic structure see, for example, WO 2005/011013). It should be noted that, for the generation of white light, one emitter compound used individually which emits in a broad wavelength range may also be suitable instead of a plurality of emitter compounds emitting in colour.

Suitable charge-transport materials, as can be used in the hole-injection or hole-transport layer or electron-blocking layer or in the electron-transport layer of the organic electroluminescent device according to the invention, are, for example, the compounds disclosed in Y. Shirota et al., Chem. Rev. 2007, 107(4), 953-1010 or other materials as are employed in accordance with the prior art in these layers.

Materials which can be used for the electron-transport layer are all materials as are used in accordance with the prior art as electron-transport materials in the electron-transport layer. Particularly suitable are aluminium complexes, for example $Alq_3$, zirconium complexes, for example $Zrq_4$, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Furthermore suitable materials are derivatives of the above-mentioned compounds, as disclosed in JP 2000/053957, WO 2003/060956, WO 2004/028217, WO 2004/080975 and WO 2010/072300.

Preferred hole-transport materials are, in particular, materials which can be used in a hole-transport, hole-injection or electron-blocking layer, such as indenofluorenamine derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic rings (for example in accordance with U.S. Pat. No. 5,061,569), the amine derivatives disclosed in WO 95/09147, monobenzoindenofluorenamines (for example in accordance with WO 08/006449), dibenzoindenofluorenamines (for example in accordance with WO 07/140847), spirobifluorenamines (for example in accordance with WO 2012/034627 or the as yet unpublished EP 12000929.5), fluorenamines (for example in accordance with WO 2014/015937, WO 2014/015938 and WO 2014/015935), spirodibenzopyranamines (for example in accordance with WO 2013/083216) and dihydroacridine derivatives (for example WO 2012/150001).

Further suitable hole-transport materials are the following compounds:
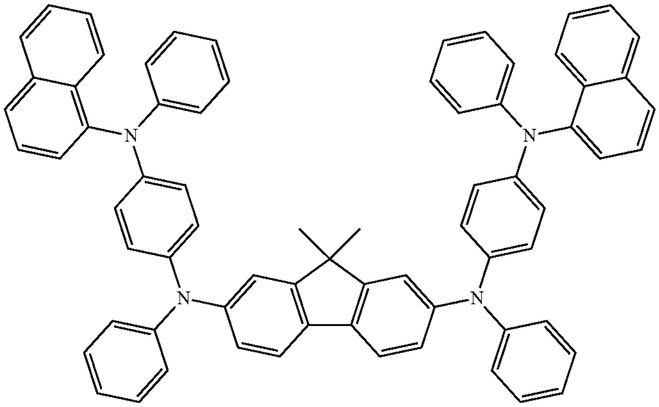
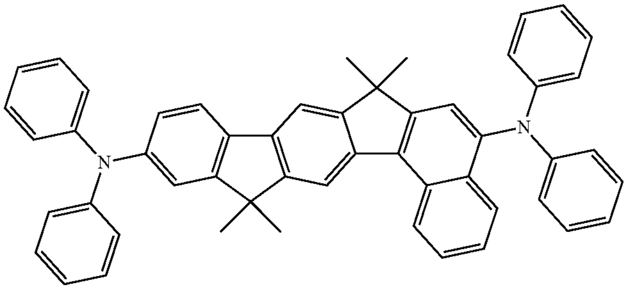
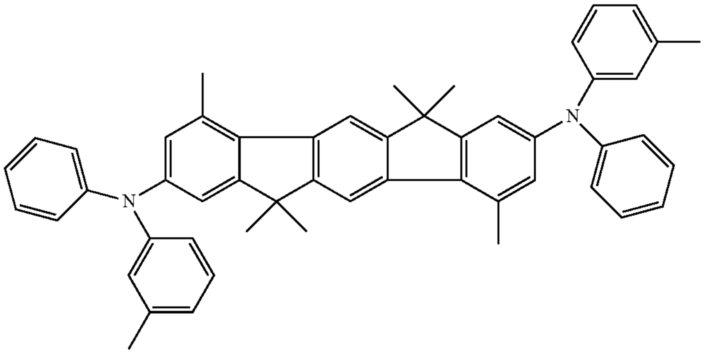
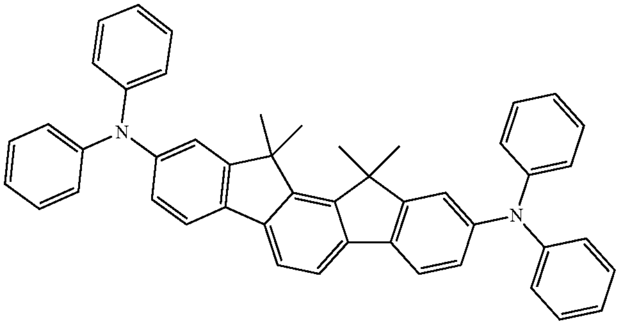
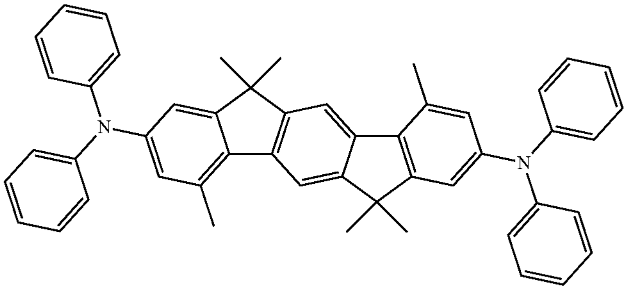

-continued
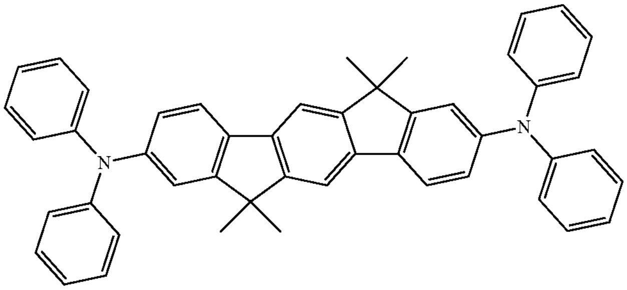
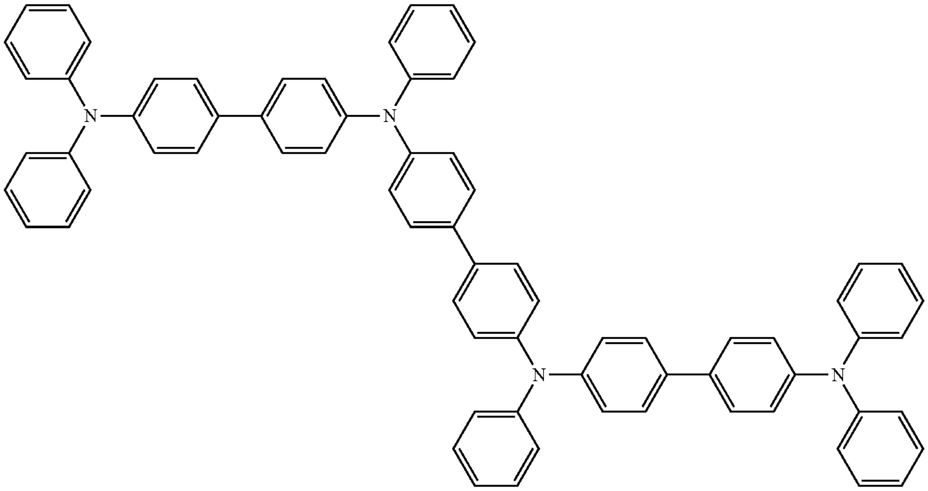
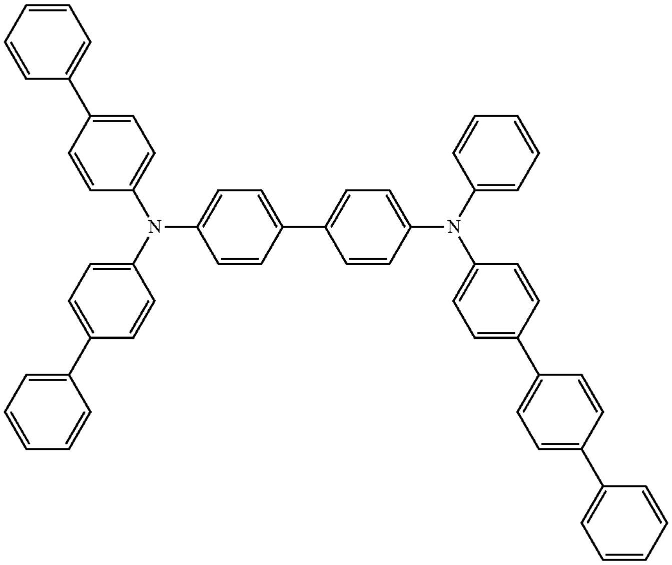

-continued
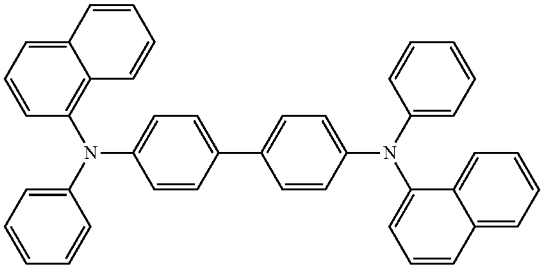
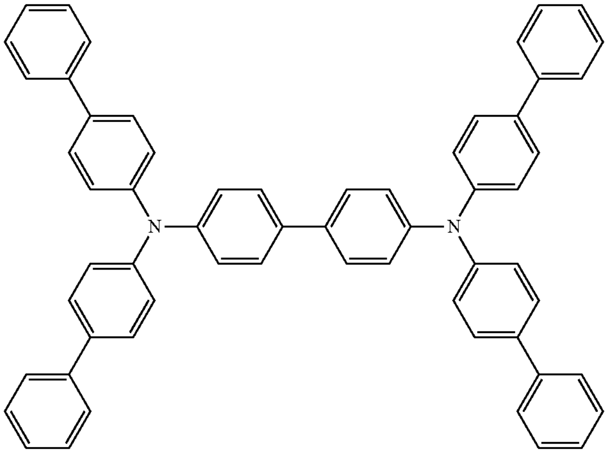
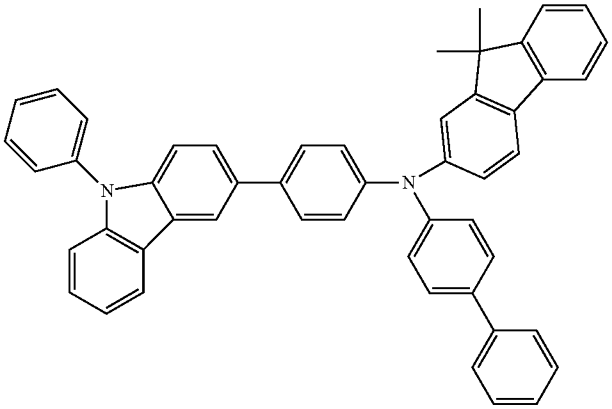
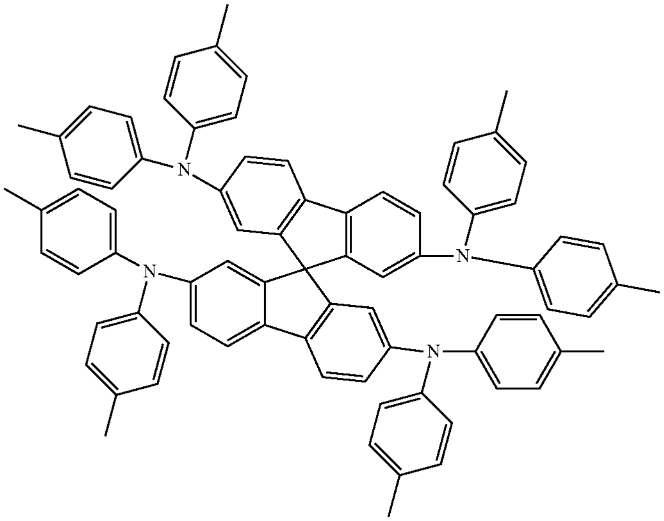
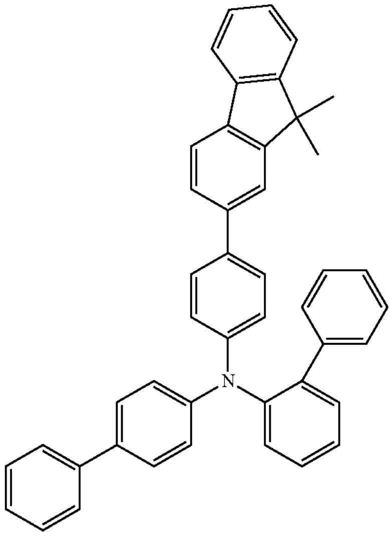

-continued
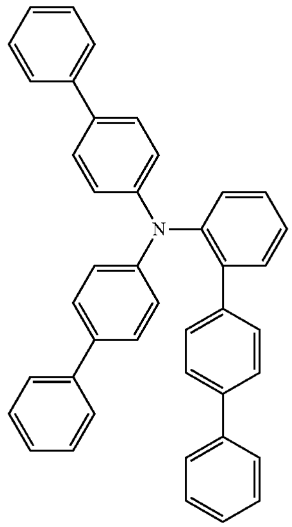
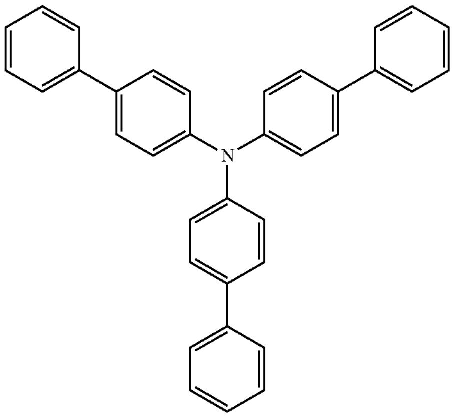
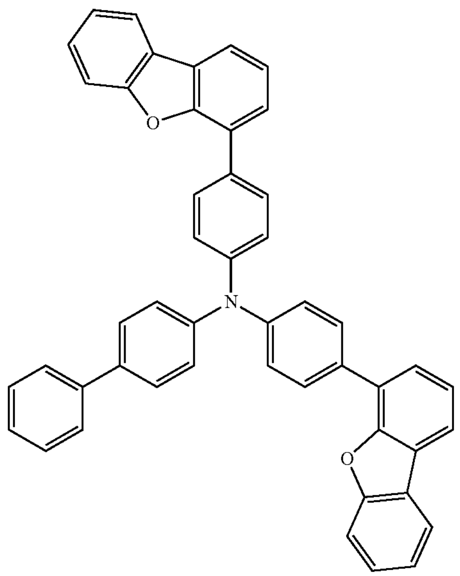
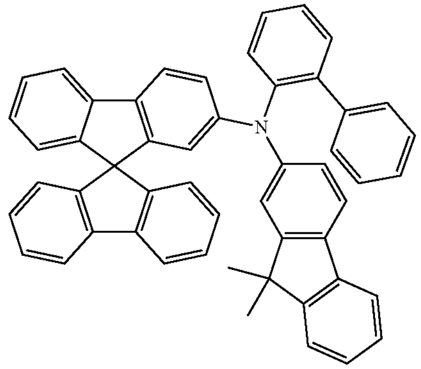
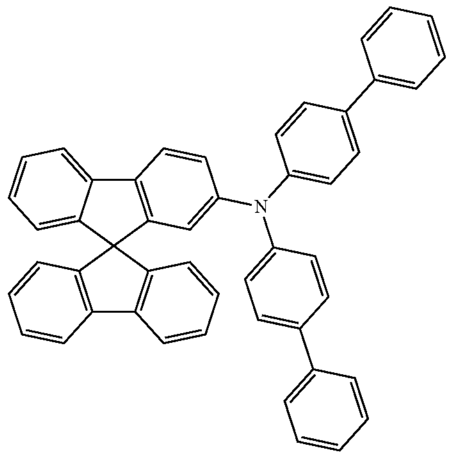
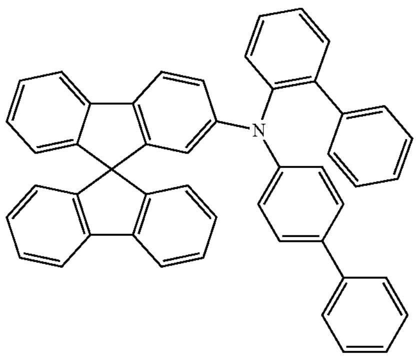

-continued
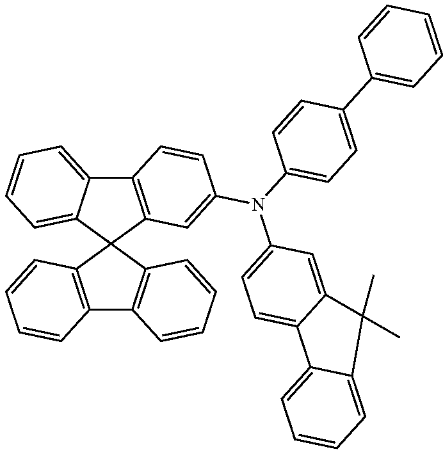
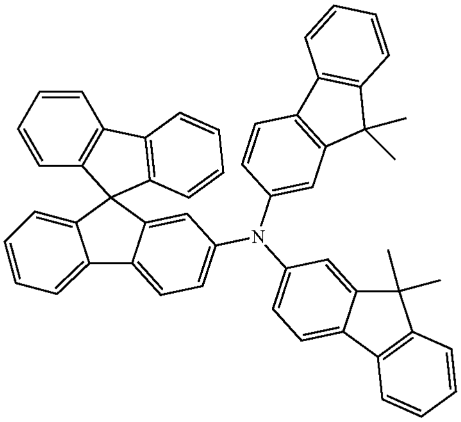
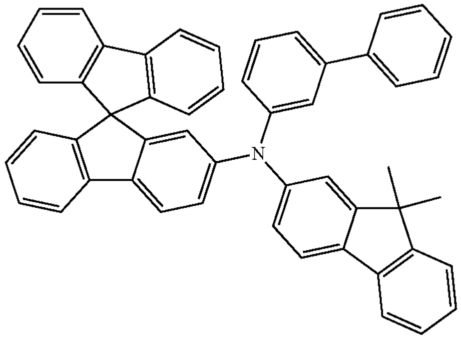
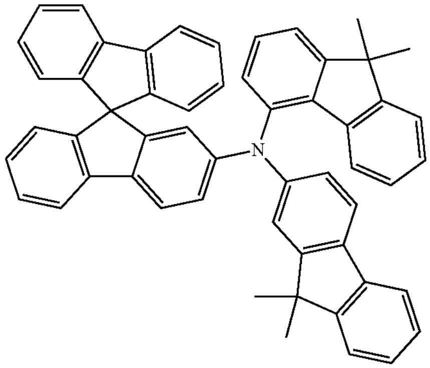
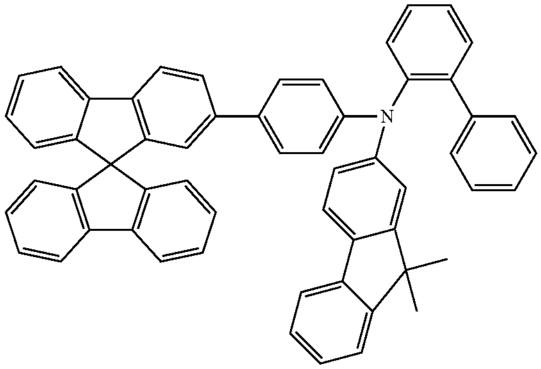
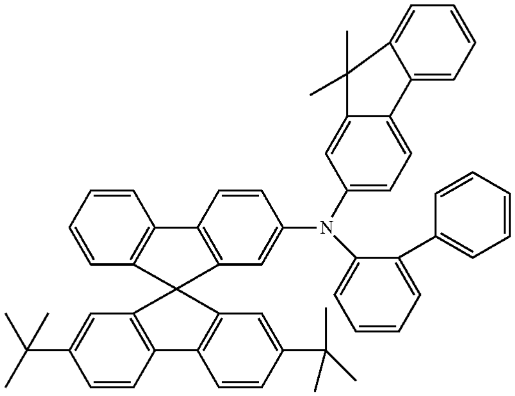
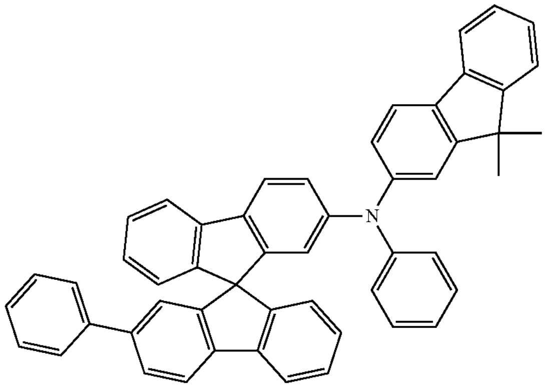
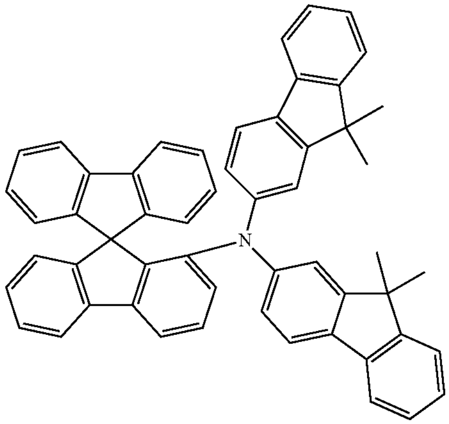

-continued
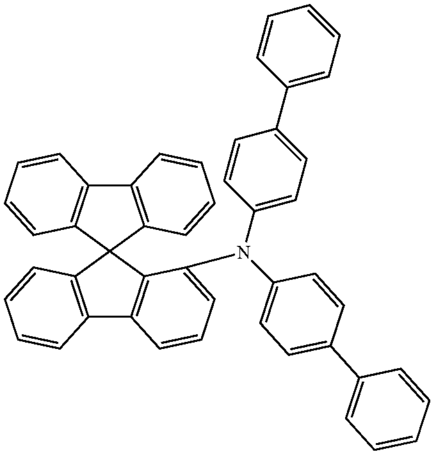
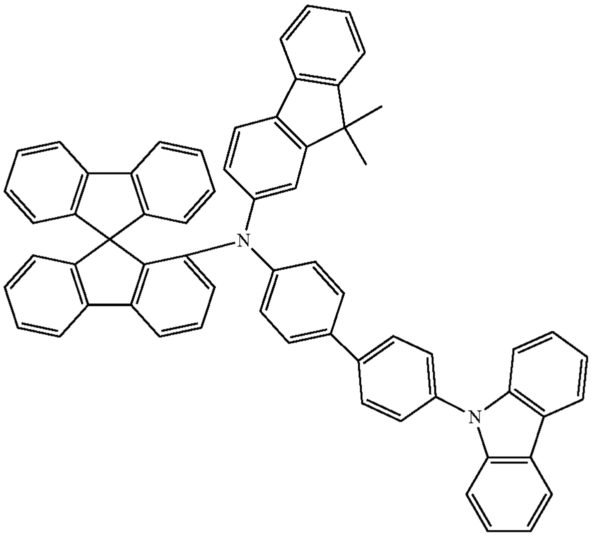
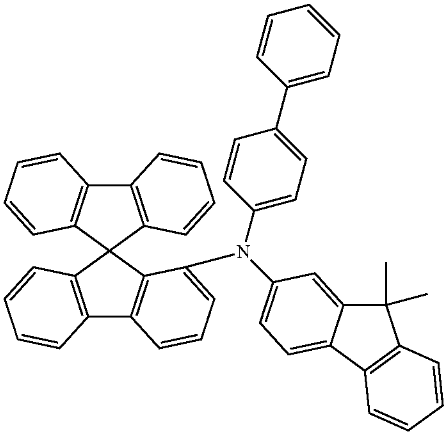
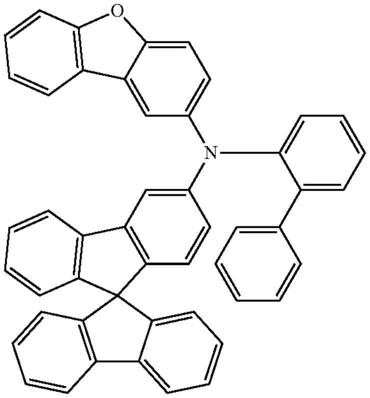
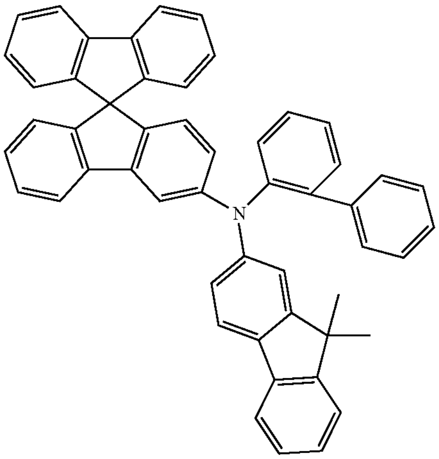
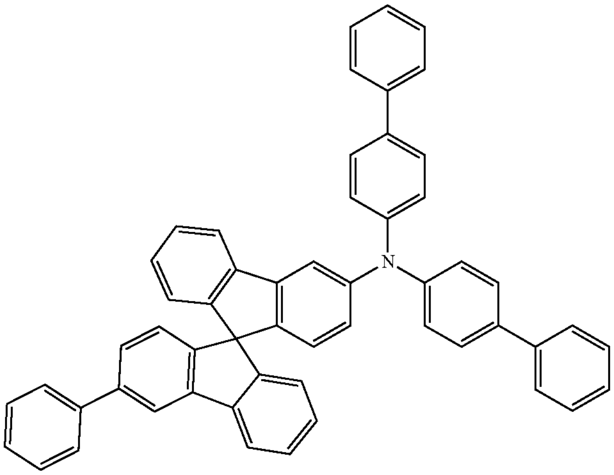

-continued
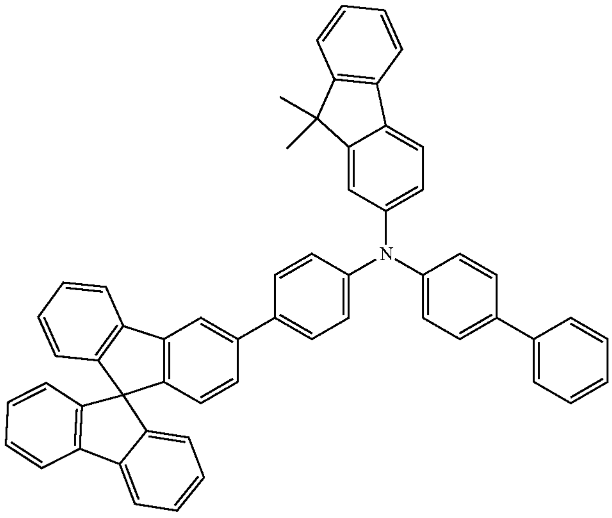
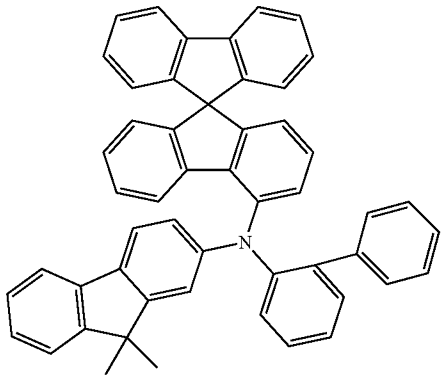
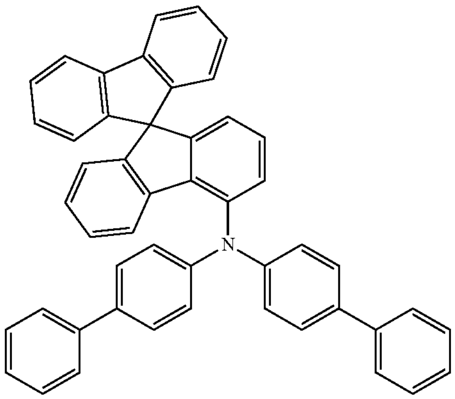
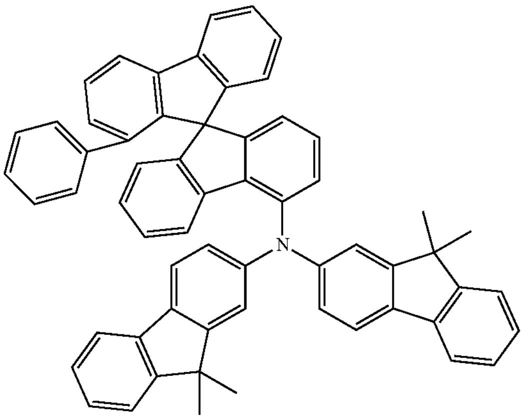
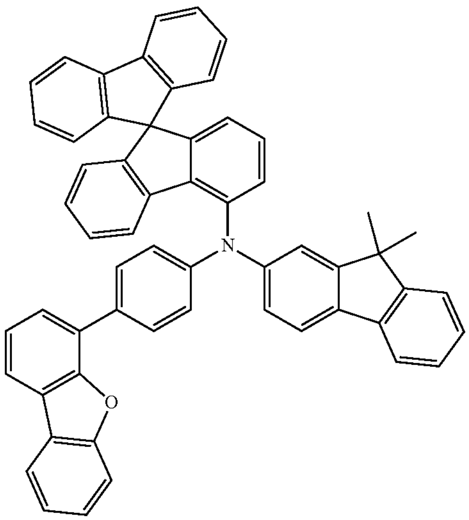
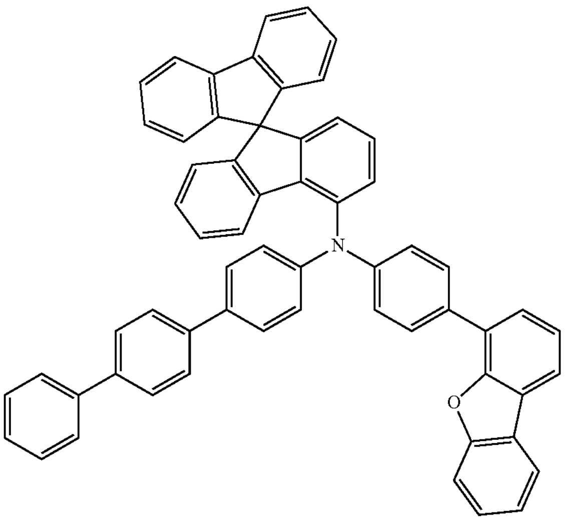

-continued
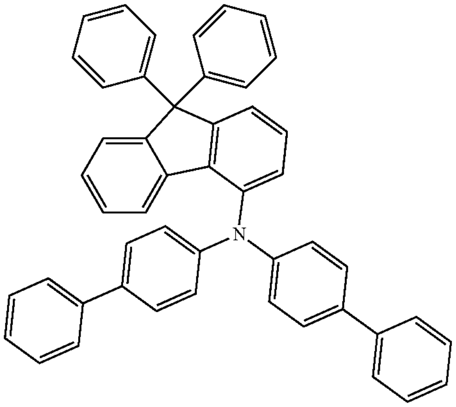
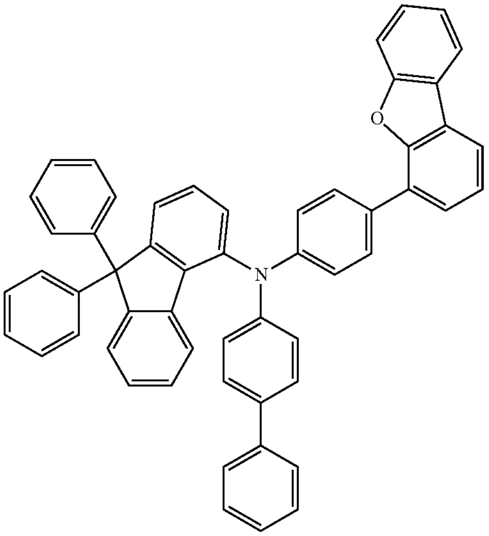
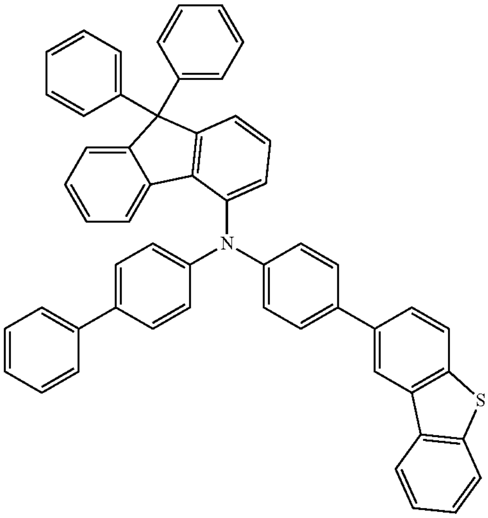
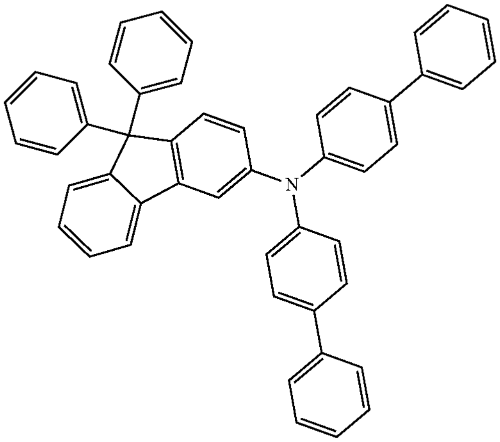
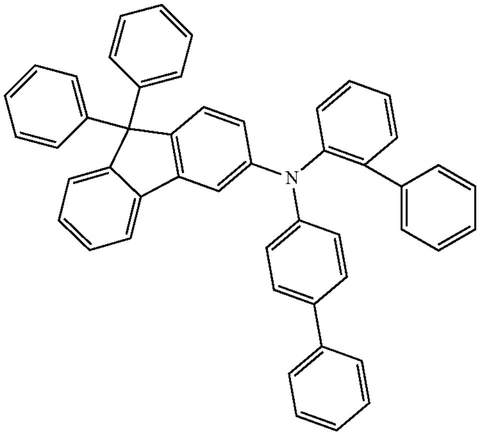
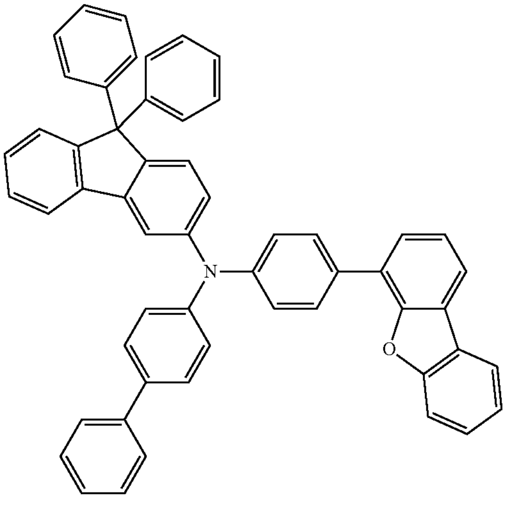

-continued
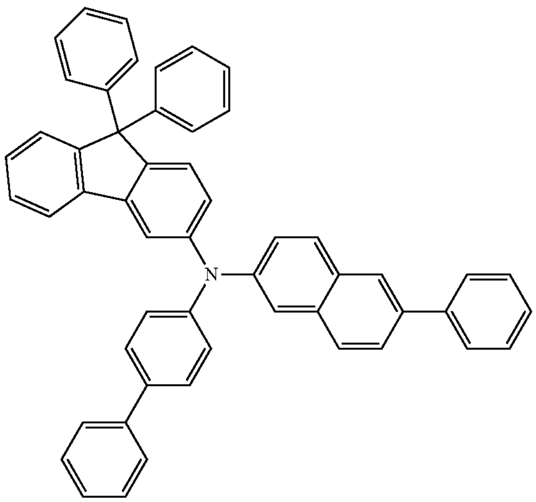
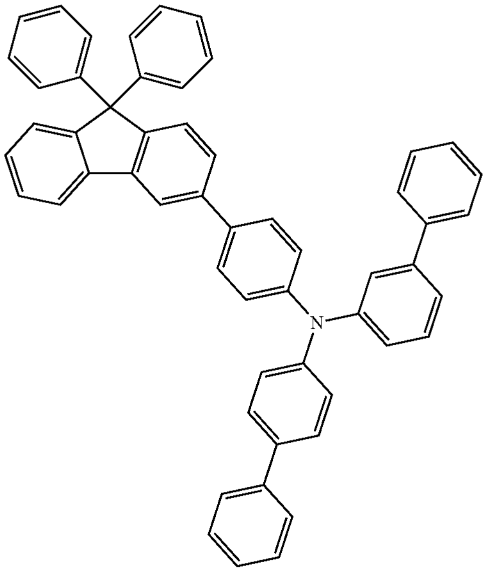
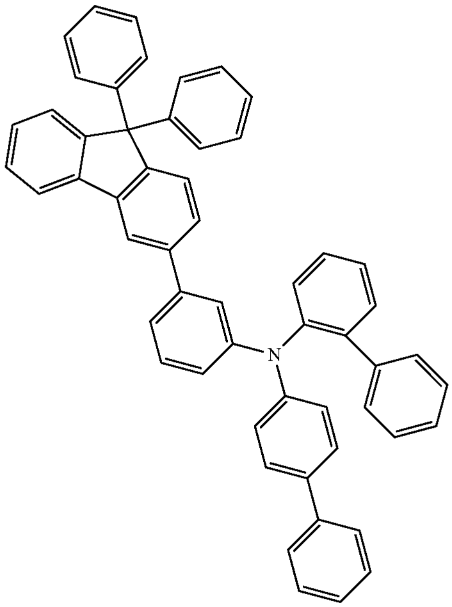
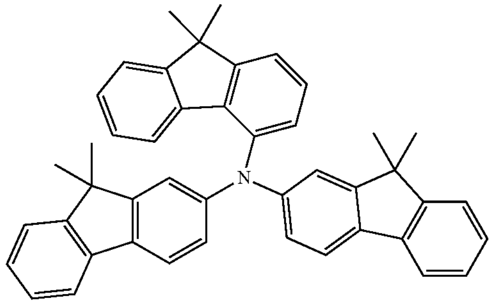
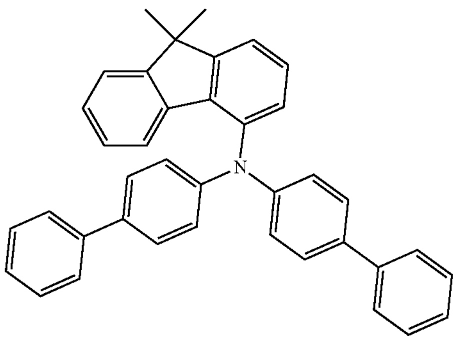
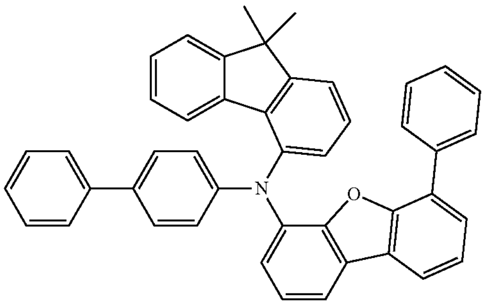

-continued
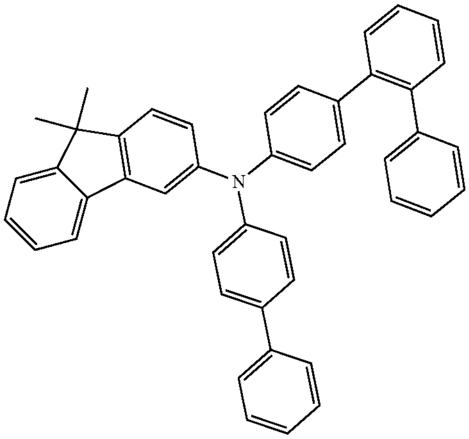
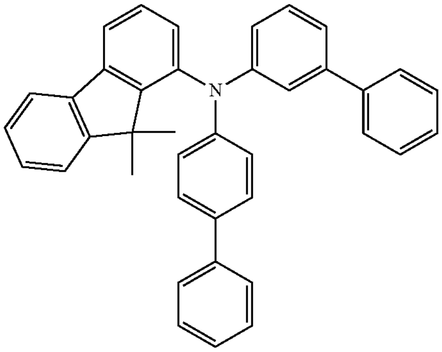
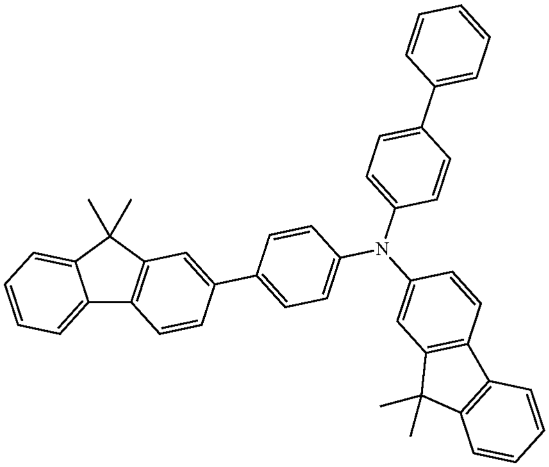
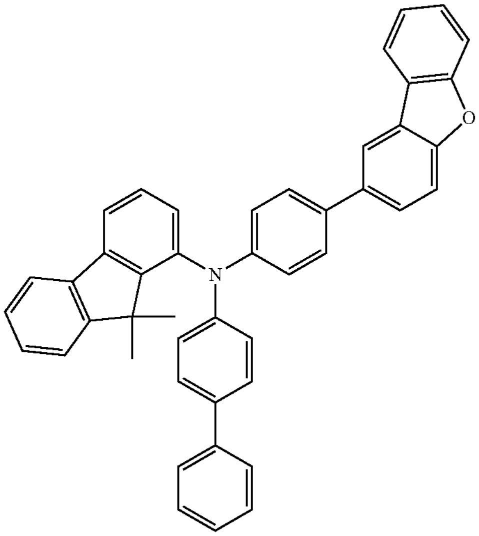
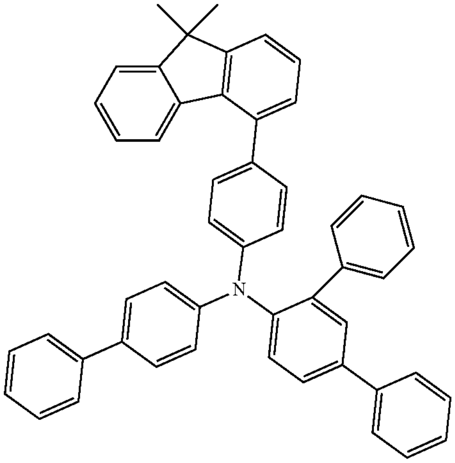
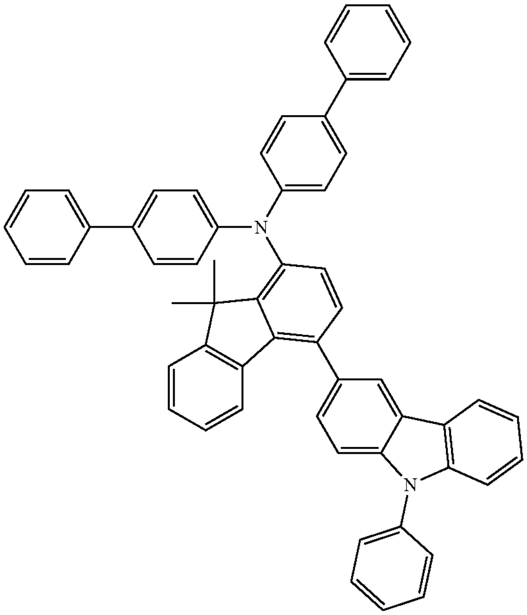

-continued

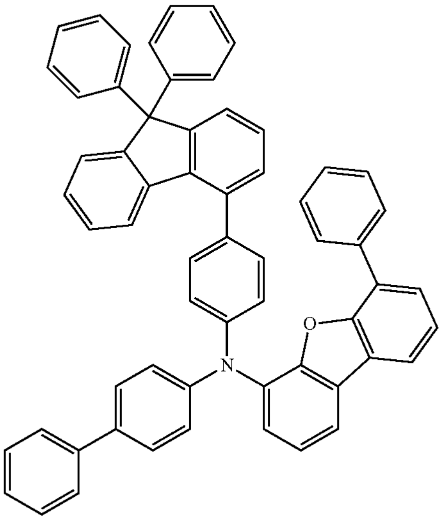

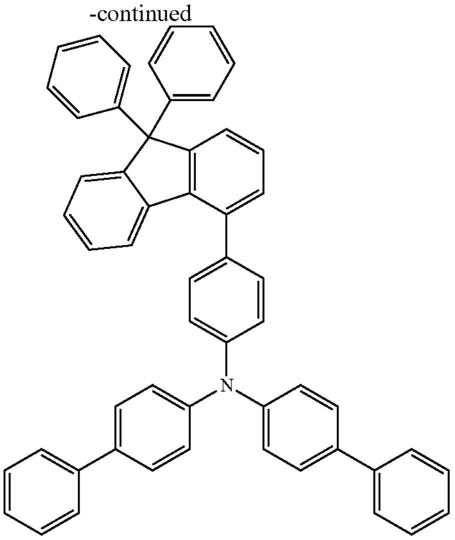

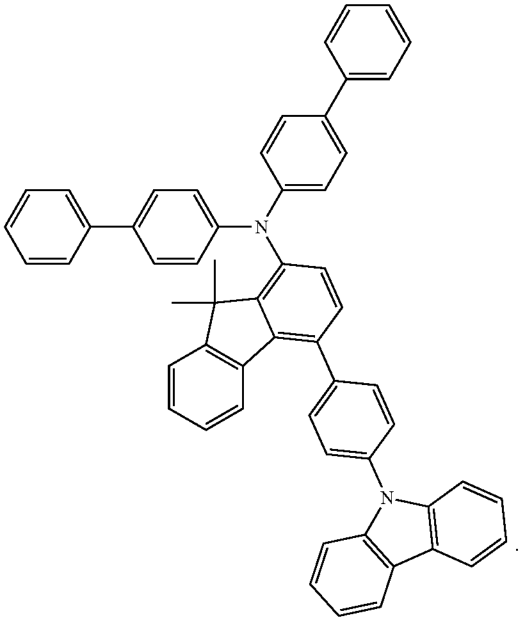

The cathode of electronic devices preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ba/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive doped polymers. Furthermore, the anode may also consist of a plurality of layers, for example of an inner layer of ITO and an outer layer of a metal oxide, preferably tungsten oxide, molybdenum oxide or vanadium oxide.

During production, the organic electronic device is appropriately (depending on the application) structured, provided with contacts and finally sealed, since the lifetime of the devices according to the invention is shortened in the presence of water and/or air.

In a further preferred embodiment, the organic electronic device which contains the composition according to the invention is characterised in that one or more organic layers comprising the compositions according to the invention are applied by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the components of the composition according to the invention are necessary for this purpose. High solubility can be achieved through suitable substitution of the corresponding compounds. Processing from solution has the advantage that the layer comprising the composition according to the invention can be applied very simply and inexpensively. This technique is suitable, in particular, for the mass production of organic electronic devices.

Also possible are hybrid processes, in which, for example, one or more layers are applied from solution and one or more further layers are applied by vapour deposition.

These processes are generally known to the person skilled in the art and can be applied to organic electroluminescent devices.

The invention therefore furthermore relates to a process for the production of an organic electronic device containing a composition according to the invention, as described or preferably described above, characterised in that at least one organic layer comprising a composition according to the invention is applied by gas-phase deposition, in particular by means of a sublimation process and/or by means of an OVPD (organic vapour phase deposition) process and/or with the aid of carrier-gas sublimation, or from solution, in particular by spin coating or by means of a printing process.

In the case of the production of an organic electronic device by means of gas-phase deposition, there are basically two possibilities for how an organic layer which is intended to comprise the composition according to invention and which may comprise a plurality of different constituents can be applied or vapour-deposited onto any desired substrate. On the one hand, the materials used may each be present in one material source and finally evaporated out of the various material sources ("co-evaporation"). On the other hand, the various materials may be premixed and the mixture may be presented in a single material source, from which it is finally evaporated ("premix evaporation"). This enables the vapour-deposition of a layer having a uniform distribution of the components to be achieved in a simple and rapid manner without precise control of a multiplicity of material sources being necessary.

The invention accordingly furthermore relates to a process, characterised in that the at least one compound of the formula (1), as described above or as preferably described, and the at least one compound of the formula (2), as described above or as preferably described, are deposited from the gas phase successively or simultaneously from at least two material sources, optionally with further materials, as described or preferably described above, and form the organic layer.

In a preferred embodiment of the present invention, the at least one organic layer is applied by means of gas-phase deposition, where the constituents of the composition are premixed and evaporated from a single material source.

The invention accordingly furthermore relates to a process, characterised in that the composition according to the invention, as described or preferably described above, is utilised as material source for the gas-phase deposition and forms the organic layer, optionally with further materials.

The invention furthermore relates to a process for the production of an organic electronic device containing a composition according to the invention, as described or preferably described above, characterised in that the formulation according to the invention, as described above, is used in order to apply the organic layer.

The compositions according to the invention or the devices according to the invention are distinguished by the following surprising advantages over the prior art:

The use of the compositions according to the invention in organic electronic devices, in particular in organic electroluminescent devices, and in particular in an OLED or OLE C, leads to significant increases in the lifetime of the devices.

As can be seen in Example 1 indicated below, good voltages and efficiencies can be achieved through the use of compounds in accordance with the prior art, for example compound V1, at average emitter concentrations in the EML of 10%. However, the lifetime of the components is short.

An improvement in the lifetime by a factor greater than 2 with comparable component voltage and comparable or improved component efficiency can be achieved through the combination according to the invention of the compounds of the formula (1), as described above, with compounds of the formula (2), as described above.

This improvement in the lifetime by a factor approximately greater than 2 with comparable component voltage and comparable or improved component efficiency can preferably be achieved through the combination according to the invention of the compounds of the formula (1), as described above, with compounds of the formula (2), as described above, with emitter concentrations of 2 to 15% by weight in the emission layer.

This advantage is demonstrated as representative for compounds of the formula (1) through the use of compound 1 (abbreviated to CbzT1) with the biscarbazole 89 (abbreviated to BisC2) or 90 (abbreviated to BisC3) in Examples E1 and E2 with an emitter concentration of 12%.

Even with a lower emitter concentration of only 7% in the EML, at which the lifetime of an OLED typically drops, the lifetimes achieved of the combinations according to the invention are still significantly improved compared with the prior art. This is demonstrated as representative for compounds of the formula (1) through the use of compound 1 (abbreviated to CbzT1) with the biscarbazole 89 (abbreviated to BisC2) or 90 (abbreviated to BisC3) in Examples E3 and E4 and through the use of compound 9, 13 or 15 with the biscarbazole 91 in Examples E5, E6 and E7 respectively with an emitter concentration of 7%.

Compound 9, representative of compounds of the formulae (1), (1f), (1h) and (1i), in combination with compounds of the formula (2) according to the invention, as described above, shows the best results.

This is likewise demonstrated as representative for compounds of the formula (1) through the use of compound 69 with the biscarbazole 91 in Example E8 with an emitter concentration of 7%.

The difference from the comparative example lies in the electronic structure of the substituents $Ar_4$ and $Ar_5$ in the biscarbazole of the formula (2), which are not simultaneously phenyl. The person skilled in the art could not have foreseen that the higher electronic density of at least one of the substituents $Ar_4$ and $Ar_5$ as an aromatic ring system having 10 to 40 ring atoms, in particular 12 to 40 ring atoms, or as a heteroaromatic electron-rich ring system having 10 to 40 ring atoms causes an improved vapour-deposition behaviour and consequently results in an improvement in the lifetime of electronic devices, in particular OLEDs. The improvement becomes clear since the lifetime is increased compared with the prior art, in particular by a factor of approximately greater than 1.5, in particular by factor of approximately greater than 2, very particularly by a factor of 2 to 3.

Without being tied to the theory, it is thought that the conjugation of the selected substituents $Ar_4$ and $Ar_5$ also has an influence. This is because if phenyl is changed to biphenyl, the conjugation is also improved and the device exhibits the advantageous properties as described above. If biphenyl is changed to a heteroaromatic ring system, such as, for example, a dibenzofuran, dibenzothiophene or carbazole, the system planarises due to the bridging via the O atom, S atom or N atom and the conjugation is additionally improved. The advantages are therefore also achieved on use of electron-rich heteroaromatic ring systems.

The other difference from the prior art lies in the choice of specific compounds of the formula (1) in which the linker L denotes an aromatic ring system having 6 to 18 C atoms, where the lifetime is surprisingly improved once again.

The compositions according to the invention are very highly suitable for use in an emission layer and exhibit improved performance data, in particular for the lifetime, compared with compounds from the prior art, as described above.

The compositions according to the invention can be processed easily and are therefore very highly suitable for mass production in commercial use. The compositions according to the invention can be premixed and vapour-deposited from a single material source, so that an organic layer having a uniform distribution of the components used can be produced in a simple and rapid manner.

These above-mentioned advantages are not accompanied by an impairment of the other electronic properties of an electronic device.

It should be pointed out that variations of the embodiments described in the present invention fall within the scope of this invention. Each feature disclosed in the present invention can, unless this is explicitly excluded, be replaced by alternative features which serve the same, an equivalent or a similar purpose. Thus, each feature disclosed in the present invention is, unless stated otherwise, to be regarded as an example of a generic series or as an equivalent or similar feature.

All features of the present invention can be combined with one another in any way, unless certain features and/or steps are mutually exclusive. This applies, in particular, to preferred features of the present invention. Equally, features of non-essential combinations can be used separately (and not in combination).

The teaching regarding technical action disclosed with the present invention can be abstracted and combined with other examples.

The invention is explained in greater detail by the following examples without wishing to restrict it thereby.

GENERAL METHODS

Determination of Orbital Energies and Electronic States

The HOMO and LUMO energies and the triplet level and singlet levels of the materials are determined via quantum-chemical calculations. To this end, the "Gaussian09, Revision D.01" software package (Gaussian Inc.) is used in the present application. For the calculation of organic substances without metals (denoted by "org." method), firstly a geometry optimisation is carried out using the semi-empirical method AM1 (Gaussian input line "#AM1 opt") with charge 0 and multiplicity 1. This is followed by an energy calculation (single point) for the electronic ground state and triplet level on the basis of the optimised geometry. The TDDFT (time dependent density functional theory) method B3PW91 with the 6-31G(d) base set (Gaussian input line "#B3PW91/6-31G(d) td=(50-50, nstates=4)") is used here (charge 0, multiplicity 1). For organometallic compounds (denoted by "org.-m" method), the geometry is optimised using the Hartree-Fock method and the LanL2 MB base set (Gaussian input line "#HF/LanL2 MB opt") (charge 0, multiplicity 1). The energy calculation is carried out, as described above, analogously to that of the organic substances, with the difference that the "LanL2DZ" base set is used for the metal atom and the "6-31G(d)" base set is used for the ligands (Gaussian input line "#B3PW91/gen pseudo=lanl2 td=(50-50, nstates=4)"). The energy calculation gives the HOMO as the last orbital occupied by two electrons (Alpha occ. eigenvalues) and LUMO as the first unoccupied orbital (alpha virt. eigenvalues) in hartree units, where HEh and LEh stand for the HOMO energy in hartree units and the LUMO energy in hartree units respectively. The HOMO and LUMO values in electron volts calibrated with reference to cyclic voltammetry measurements are determined thereform as follows:

$$HOMO\ (eV)=(HEh*27.212)*0.8308-1.118;$$

$$LUMO\ (eV)=(LEh*27.212)*1.0658-0.5049.$$

The triplet state T1 of a material is defined as the relative excitation energy (in eV) of the triplet state having the lowest energy which arises from the quantum-chemical energy calculation.

The singlet level S1 is defined as the relative excitation energy (in eV) of the singlet state having the second lowest energy which arises from the quantum-chemical energy calculation.

The singlet state of lowest energy is called S0.

The method described herein is independent of the software package used and always gives the same results. Examples of frequently used programs for this purpose are "Gaussian09" (Gaussian Inc.) and Q-Chem 4.1 (Q-Chem, Inc.). In the present application, the "Gaussian09, Revision D.01" software package is used for the calculation of the energies.

Example 1: Production of the OLEDs

The use of the material combinations according to the invention in OLEDs is presented in Examples E1 to E10a below (see Table 16).

Pretreatment for Examples E1-E10a: Glass plates coated with structured ITO (indium tin oxide) in a thickness of 50 nm are, before coating, treated firstly with an oxygen plasma, followed by an argon plasma. These plasma-treated glass plates form the substrates to which the OLEDs are applied.

The OLEDs have basically the following layer structure: substrate/hole-injection layer (HIL)/hole-transport layer (HTL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The precise structure of the OLEDs is shown in Table 16. The materials required for the production of the OLEDs are shown in Table 17. The data of the OLEDs are listed in Table 18. Example V1 is a comparative example in accordance with WO 2015/169412, Examples E1 to E10a show data of OLEDs according to the invention. Examples E5, E10 and E10a show the preferred OLEDs according to the invention.

All materials are applied by thermal vapour deposition in a vacuum chamber. The emission layer here always consists of at least one matrix material (host material), in the sense of the invention at least two matrix materials, and an emitting dopant (emitter), which is admixed with the matrix material or matrix materials in a certain proportion by volume by co-evaporation. An expression such as CbzT1:BisC1:TEG1 (45%:45%:10%) here means that material CbzT1 is present in the layer in a proportion by volume of 45%, BisC1 is present in the layer in a proportion of 45% and TEG1 is present in the layer in a proportion of 10%. Analogously, the electron-transport layer may also consist of a mixture of two materials.

The OLEDs are characterised by standard methods. For this purpose, the electroluminescence spectra, the current efficiency (CE, gemessen in cd/A) and the external quantum efficiency (EQE, measured in %) as a function of the luminous density, calculated from current/voltage/luminous density characteristic lines assuming Lambert emission characteristics, and the lifetime are determined. The electroluminescence spectra are determined at a luminous density of 1000 cd/$m^2$ and the CIE 1931 x and y colour coordinates are calculated therefrom. The term U1000 in Table 18 denotes the voltage required for a luminous density of 1000 cd/$m^2$. CE1000 and EQE1000 denote the current efficiency and external quantum efficiency respectively that are achieved at 1000 cd/$m^2$.

The lifetime LT defines the time after which the luminous density drops from the initial luminous density to a certain proportion L1 on operation at a constant current density $j_0$. An expression L1=80% in Table 18 means that the lifetime indicated in column LT corresponds to the time after which the luminous density drops to 80% of its initial value.

Use of Mixtures According to the Invention in OLEDs

The material combinations according to the invention can be employed in the emission layer in phosphorescent OLEDs. The combination according to the invention of compound CbzT1, corresponding to compound 1, with BisC2 (corresponding to compound 89) or BisC3 (corresponding to compound 90) is employed in Examples E1 to E4 as matrix material in the emission layer. The combination according to the invention of compounds 9, 13 and 15 in each case with compound 91 is employed in Examples E5, E5a, E6, E7, E10 and E10a as matrix material in the emission layer. The combination according to the invention of compound 69 with compound 91 is employed in Example E8 as matrix material in the emission layer.

TABLE 16

Structure of the OLEDs

| Ex. | HIL Thickness | HTL Thickness | EBL Thickness | EML Thickness | HBL Thickness | ETL Thickness | EIL Thickness |
|---|---|---|---|---|---|---|---|
| V1 | HATCN 5 nm | SpMA1 230 nm | SpMA2 20 nm | CbzT1:BisC1:TEG1 (45%:45%:10%) 30 nm | ST2 10 nm | ST2:LiQ (50%:50%) 30 nm | — |
| E1 | HATCN 5 nm | SpMA1 230 nm | SpMA2 20 nm | CbzT1:BisC2:TEG1 (44%:44%:12%) 30 nm | ST2 10 nm | ST2:LiQ (50%:50%) 30 nm | LiQ 1 nm |
| E2 | HATCN 5 nm | SpMA1 230 nm | SpMA2 20 nm | CbzT1:BisC3:TEG1 (44%:44%:12%) 30 nm | ST2 10 nm | ST2:LiQ (50%:50%) 30 nm | LiQ 1 nm |
| E3 | HATCN 5 nm | SpMA1 230 nm | SpMA2 20 nm | CbzT1:BisC2:TEG1 (46%:47%:7%) 30 nm | ST2 10 nm | ST2:LiQ (50%:50%) 30 nm | LiQ 1 nm |
| E4 | HATCN 5 nm | SpMA1 230 nm | SpMA2 20 nm | CbzT1:BisC3:TEG1 (46%:47%:7%) 30 nm | ST2 10 nm | ST2:LiQ (50%:50%) 30 nm | LiQ 1 nm |
| E5 | HATCN 5 nm | SpMA1 230 nm | SpMA2 20 nm | 9:91:TEG1 (23%:70%:7%) 30 nm | ST2 10 nm | ST2:LiQ (50%:50%) 30 nm | LiQ 1 nm |
| E5a | HATCN 5 nm | SpMA1 230 nm | SpMA2 20 nm | 9:91:TEG1 (46%:47%:7%) 30 nm | ST2 10 nm | ST2:LiQ (50%:50%) 30 nm | LiQ 1 nm |
| E6 | HATCN 5 nm | SpMA1 230 nm | SpMA2 20 nm | 13:91:TEG1 (46%:47%:7%) 30 nm | ST2 10 nm | ST2:LiQ (50%:50%) 30 nm | LiQ 1 nm |
| E7 | HATCN 5 nm | SpMA1 230 nm | SpMA2 20 nm | 15:91:TEG1 (46%:47%:7%) 30 nm | ST2 10 nm | ST2:LiQ (50%:50%) 30 nm | LiQ 1 nm |

TABLE 16-continued

| Structure of the OLEDs | | | | | | | |
|---|---|---|---|---|---|---|---|
| Ex. | HIL Thickness | HTL Thickness | EBL Thickness | EML Thickness | HBL Thickness | ETL Thickness | EIL Thickness |
| E8 | HATCN 5 nm | SpMA1 230 nm | SpMA2 20 nm | 69:91:TEG1 (46%:47%:7%) 30 nm | ST2 10 nm | ST2:LiQ (50%:50%) 30 nm | LiQ 1 nm |
| E9 | HATCN 5 nm | SpMA1 230 nm | SpMA2 20 nm | CbzT1:91:TEG1 (46%:47%:7%) 30 nm | ST2 10 nm | ST2:LiQ (50%:50%) 30 nm | LiQ 1 nm |
| E10 | HATCN 5 nm | SpMA1 230 nm | SpMA2 20 nm | 9:91:TEG1 (44%:44%:12%) 30 nm | ST2 10 nm | ST2:LiQ (50%:50%) 30 nm | LiQ 1 nm |
| E10a | HATCN 5 nm | SpMA1 230 nm | SpMA2 20 nm | 9:91:TEG1 (22%:66%:12%) 30 nm | ST2 10 nm | ST2:LiQ (50%:50%) 30 nm | LiQ 1 nm |

TABLE 17

Structural formulae of the materials for OLEDs

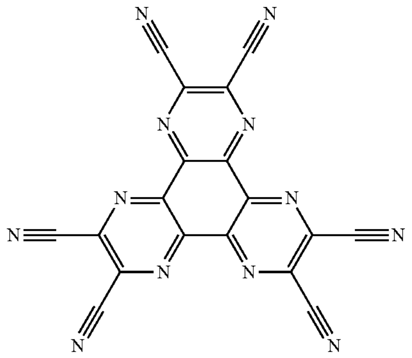

HATCN

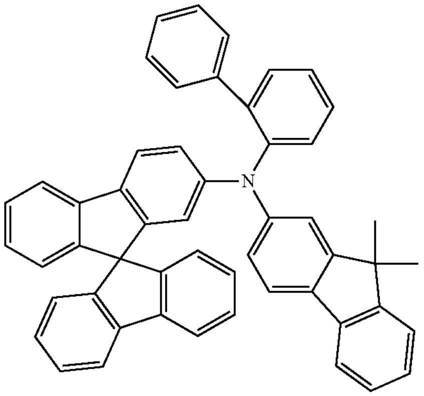

SpMA1

TABLE 17-continued
| Structural formulae of the materials for OLEDs |
| --- |
| 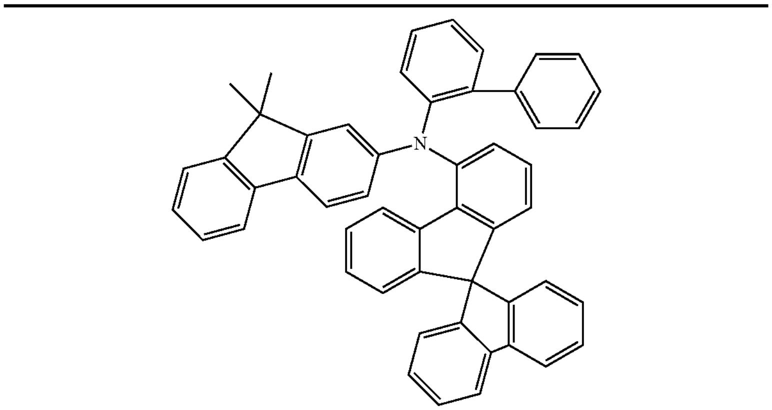 SpMA2 |
| 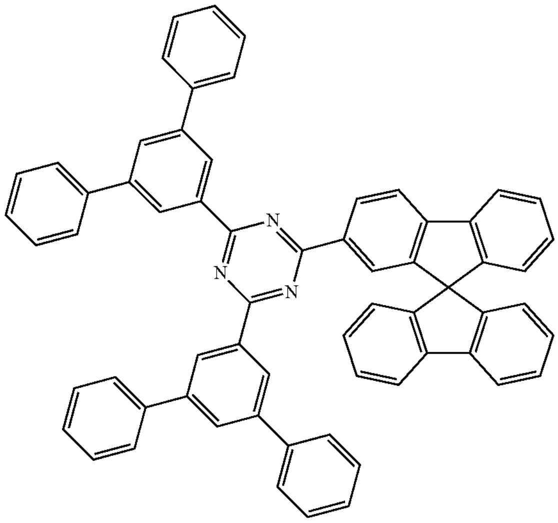 ST2 |
| 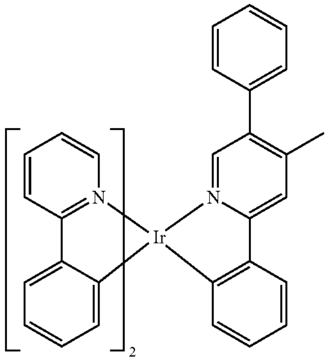 TEG1 |
| 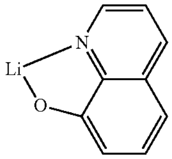 LiQ |

TABLE 17-continued
| Structural formulae of the materials for OLEDs |
| --- |
| 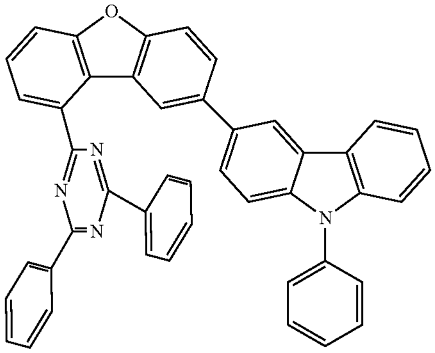 |
| CbzT1 |
| 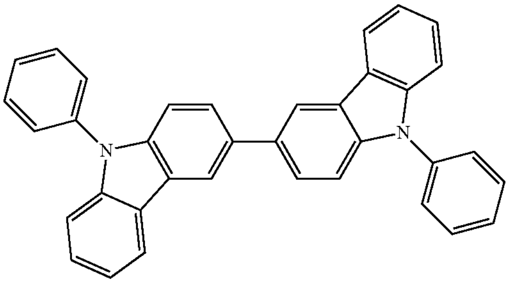 |
| BisC1 |
| 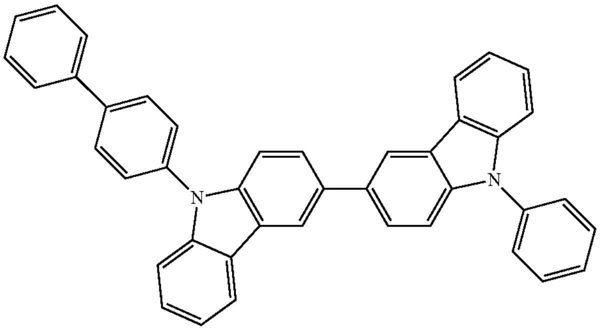 |
| BisC2 |
| 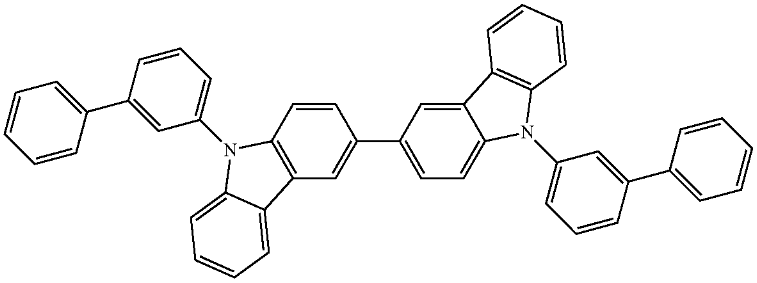 |
| BisC3 |

TABLE 17-continued
| Structural formulae of the materials for OLEDs |
|---|
| 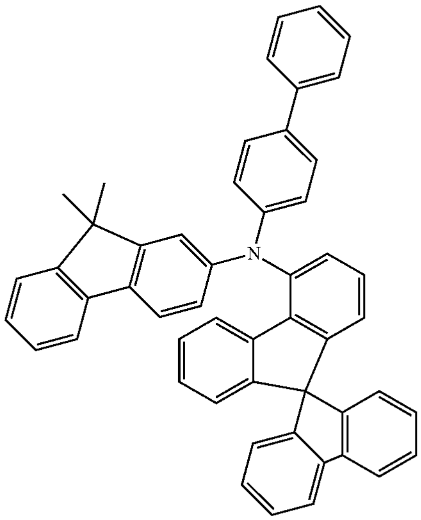 |
| SpMA3 |
| 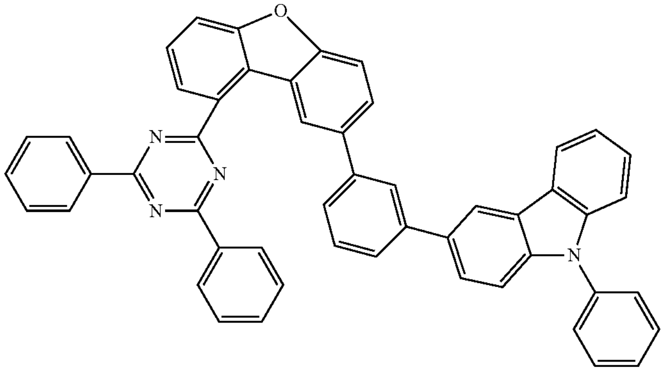 |
| 9 |
| 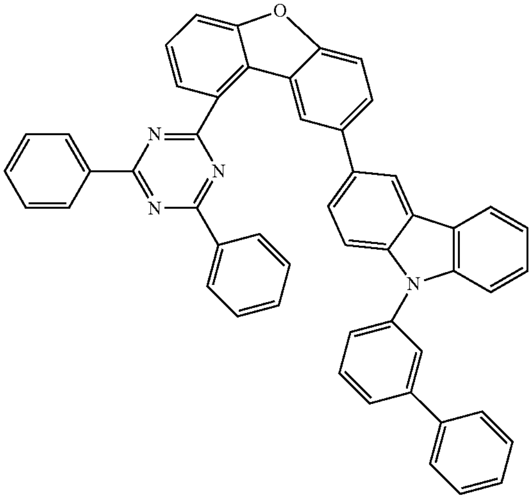 |
| 13 |

TABLE 17-continued
| Structural formulae of the materials for OLEDs |
| --- |
| 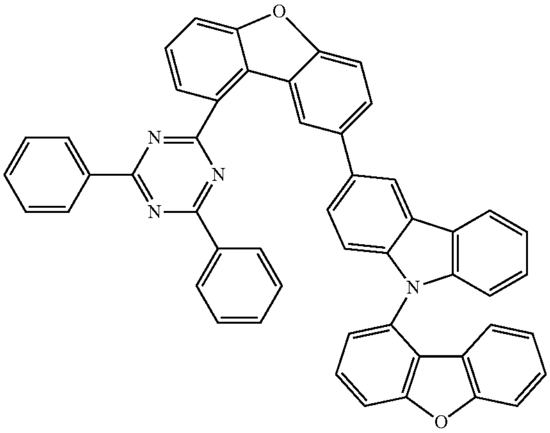 |
| 15 |
| 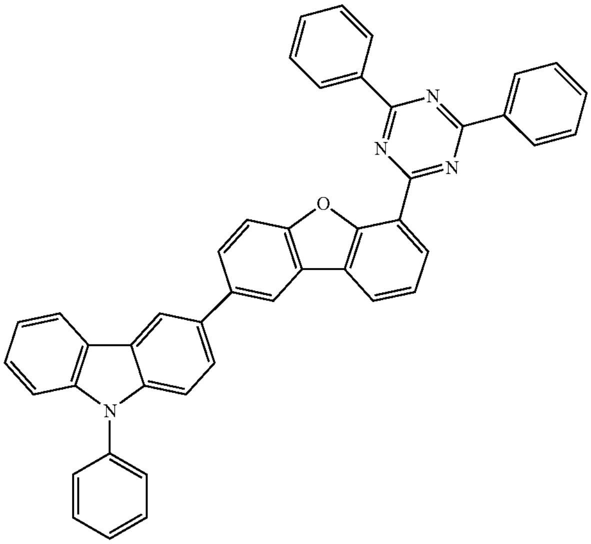 |
| 69 |

TABLE 17-continued

| Structural formulae of the materials for OLEDs |
|---|
| 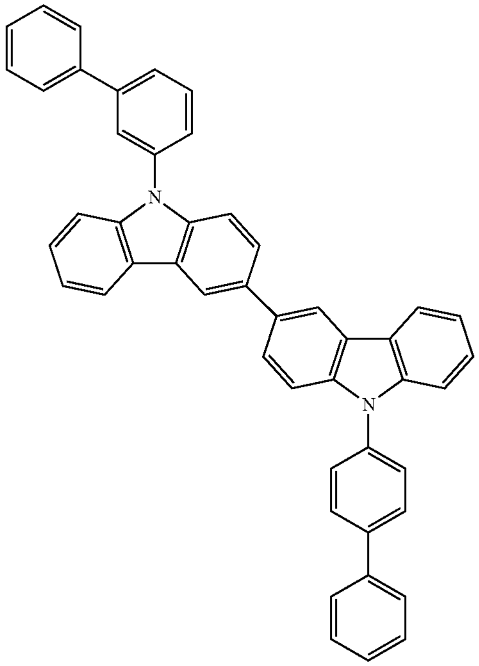 |
| 91 |

TABLE 18

| Data of the OLEDs | | | | | | | |
|---|---|---|---|---|---|---|---|
| Ex. | U1000 (V) | CE1000 (cd/A) | EQE 1000 (%) | CIE x/y at 1000 $cd/m^2$ | $j_0$ ($mA/cm^2$) | L1 (%) | LT (h) |
| V1 | 3.5 | 70 | 18.4 | 0.33/0.63 | 20 | 80 | 370 |
| E1 | 3.2 | 67 | 18.0 | 0.33/0.63 | 20 | 80 | 930 |
| E2 | 3.1 | 69 | 18.8 | 0.32/0.64 | 20 | 80 | 980 |
| E3 | 3.2 | 74 | 20.1 | 0.32/0.63 | 20 | 80 | 650 |
| E4 | 3.2 | 73 | 19.8 | 0.33/0.63 | 20 | 80 | 608 |
| E5 | 3.4 | 69 | 19.0 | 0.31/0.64 | 20 | 80 | 1030 |
| E5a | 3.2 | 75 | 20.5 | 0.31/0.64 | 20 | 80 | 645 |
| E6 | 3.2 | 75 | 20.4 | 0.32/0.64 | 20 | 80 | 850 |
| E7 | 3.2 | 77 | 20.9 | 0.31/0.64 | 20 | 80 | 480 |
| E8 | 3.4 | 79 | 21.5 | 0.31/0.64 | 20 | 80 | 520 |
| E9 | 3.4 | 72 | 19.9 | 0.31/0.64 | 20 | 80 | 620 |
| E10 | 3.2 | 66 | 18.3 | 0.32/0.64 | 20 | 80 | 990 |
| E10a | 3.4 | 60 | 16.5 | 0.31/0.64 | 20 | 80 | 1125 |

Example 2: Synthesis of Compound 1 (CbzT1)

a) 6-Bromo-2-fluoro-2'-methoxybiphenyl

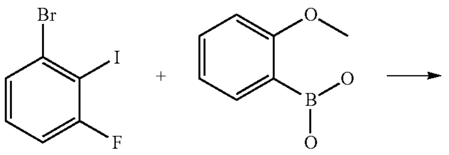

-continued

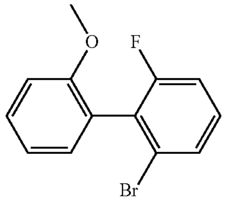

200 g (664 mmol) of 1-bromo-3-fluoro-2-iodobenzene, 101 g (664 mmol) of 2-methoxyphenylboronic acid and 137.5 g (997 mmol) of sodium tetraborate are dissolved in 1000 ml of THF and 600 ml of water and degassed. 9.3 g (13.3 mmol) of bis(triphenylphosphine)palladium(II) chloride and 1 g (20 mmol) of hydrazinium hydroxide are added. The reaction mixture is subsequently stirred at 70° C. under a protective-gas atmosphere for 48 h. Toluene is added to the cooled solution, which is washed a number of times with water, dried and evaporated. The product is purified by column chromatography on silica gel with toluene/heptane (1:2). Yield: 155 g (553 mmol), 83% of theory.

b) 6'-Bromo-2'-fluorobiphenyl-2-ol

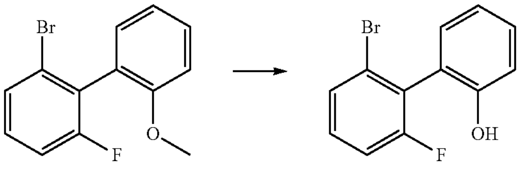 [SMILES: COc1ccccc1-c1c(F)cccc1Br ; Oc1ccccc1-c1c(F)cccc1Br]

112 g (418 mmol) of 6-bromo-2-fluoro-2'-methoxybiphenyl are dissolved in 2 l of dichloromethane and cooled to 5° C. 41.01 ml (431 mmol) of boron tribromide are added dropwise to this solution over the course of 90 min. and stirring is continued overnight. Water is subsequently added slowly to the mixture, the organic phase is washed three times with water, dried over $Na_2SO_4$ and evaporated in a rotary evaporator, and the product is purified by chromatography. Yield: 104 g (397 mmol), 98% of theory.

c) 1-Bromodibenzofuran

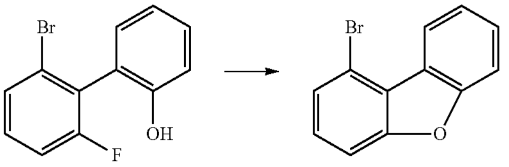 [SMILES: Oc1ccccc1-c1c(F)cccc1Br ; Brc1cccc2oc3ccccc3c12]

111 g (416 mmol) of 6'-bromo-2'-fluorobiphenyl-2-ol are dissolved in 2 l of SeccoSolv® DMF (max. 0.003% of $H_2O$) and cooled to 5° C. 20 g (449 mmol) of sodium hydride (60% suspension in paraffin oil) are added to this solution, stirring is continued for a further 20 min. after the addition is complete, and the mixture is then heated at 100° C. for 45 min. After cooling, 500 ml of ethanol are slowly added to the mixture, the mixture is evaporated in a rotary evaporator, and the product is then purified by chromatography. Yield: 90 g (367 mmol), 88.5% of theory.

d) Dibenzofuran-1-boronic acid

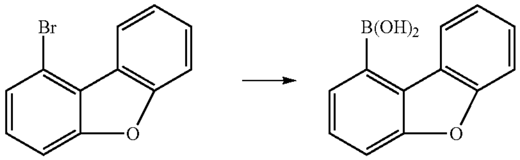 [SMILES: Brc1cccc2oc3ccccc3c12 ; OB(O)c1cccc2oc3ccccc3c12]

180 g (728 mmol) of 1-bromodibenzofuran are dissolved in 1500 ml of dry THE and cooled to −78° C. 305 ml (764 mmol/2.5 M in hexane) of n-butyllithium are added at this temperature over the course of about 5 min., and the mixture is subsequently stirred at −78° C. for a further 2.5 h. 151 g (1456 mmol) of trimethyl borate are added as rapidly as possible at this temperature, and the reaction mixture is allowed to come slowly to room temperature (about 18 h). The reaction solution is washed with water, and the precipitated solid and the organic phase are dried azeotropically with toluene. The crude product is washed by stirring with toluene/methylene chloride at about 40° C. and filtered off with suction. Yield: 146 g (690 mmol), 95% of theory.

e) 2-Dibenzofuran-1-yl-4,6-diphenyl-1,3,5-triazine

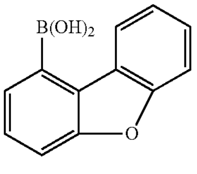

+

-continued

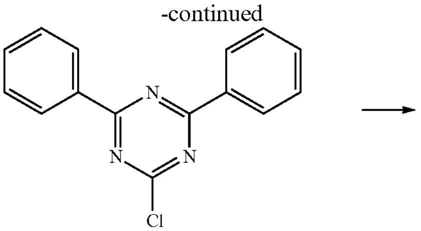

[2842-55-5]

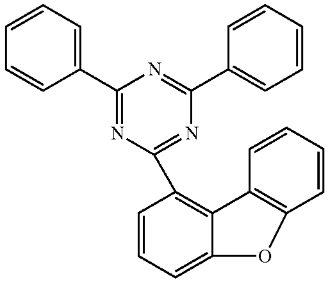

23 g (110.0 mmol) of dibenzofuran-1-boronic acid, 29.5 g (110.0 mmol) of 2-chloro-4,6-diphenyl-1,3,5-triazine and 21 g (210.0 mmol) of sodium carbonate are suspended in 500 ml of ethylene glycol damine ether and 500 ml of water. 913 mg (3.0 mmol) of tri-o-tolylphosphine and then 112 mg (0.5 mmol) of palladium(II) acetate are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene and from dichloromethane/heptane. The yield is 37 g (94 mmol), corresponding to 87% of theory.

f) 2-(8-Bromodibenzofuran-1-yl)-4,6-diphenyl-1,3,5-triazine

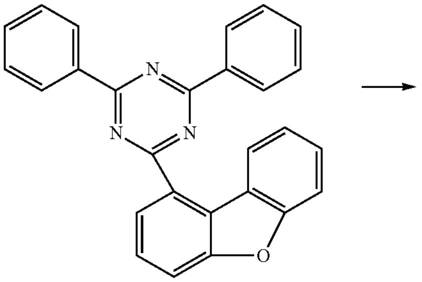

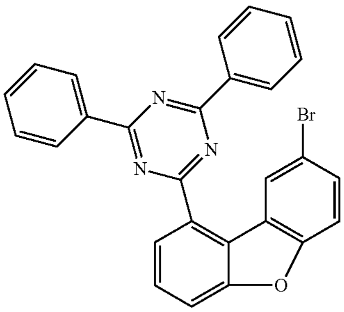

70 g (190.0 mmol) of 2-dibenzofuran-1-yl-4,6-diphenyl-1,3,5-triazine are suspended in 2000 ml of acetic acid (100%) and 2000 ml of sulfuric acid (95-98%). 34 g (190 mmol) of NBS are added in portions to this suspension, and the mixture is stirred in the dark for 2 h. Water/ice is then added, and the solid is separated off and rinsed with ethanol. The residue is recrystallised from toluene. The yield is 80 g (167 mmol), corresponding to 87% of theory.

g) 3-[9-(4,6-Diphenyl-1,3,5-triazin-2-yl)dibenzofuran-2-yl]-9-phenyl-9H-carbazole

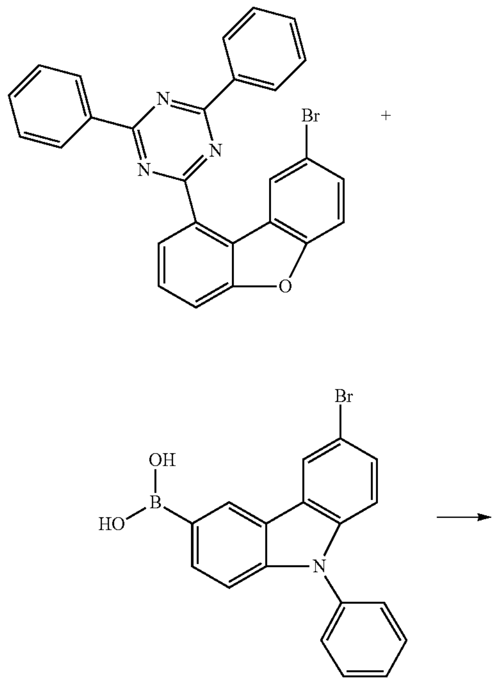

[854952-58-2]

-continued

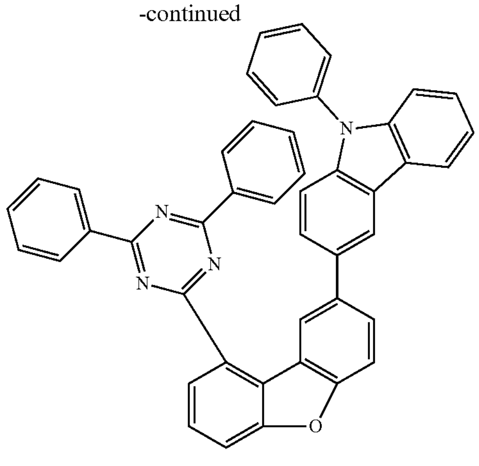

1

75 g (156 mmol) of 2-(8-bromodibenzofuran-1-yl)-4,6-diphenyl-1,3,5-triazine, 50 g (172 mmol) of N-phenylcarbazole-3-boronic acid [854952-58-2] and 36 g (340 mmol) of sodium carbonate are suspended in 1000 ml of ethylene glycol diamine ether and 280 ml of water. 1.8 g (1.5 mmol) of tetrakis(triphenylphosphine)palladium(0) are added to this suspension, and the reaction mixture is heated under reflux for 16 h. After cooling, the organic phase is separated off, filtered through silica gel, washed three times with 200 ml of water and subsequently evaporated to dryness. The product is purified by column chromatography on silica gel with toluene/heptane (1:2) and subsequently sublimed in a high vacuum ($p=5\times10^{-7}$ mbar) (purity 99.9%). The yield is 50 g (78 mmol), corresponding to 50% of theory.

The following compounds can be prepared analogously. The purification here can also be carried out using column chromatography, or other common solvents, such as n-heptane, butanol, acetone, ethyl acetate, acetonitrile, toluene, xylene, dichloromethane, methanol, N,N-dimethylformamide, tetrahydrofuran, ethyl acetate, n-butyl acetate or 1,4-dioxane, can be used for the recrystallisation or hot extraction.

| Starting material 1 | Starting material 2 | Product/Yield |
| --- | --- | --- |
| 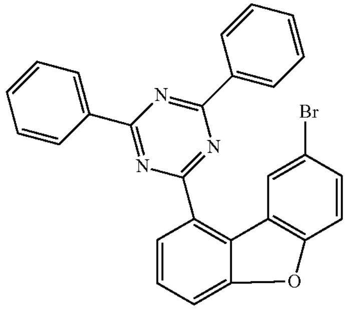 [SMILES: Brc1ccc2oc3cccc(-c4nc(-c5ccccc5)nc(-c5ccccc5)n4)c3c2c1] | 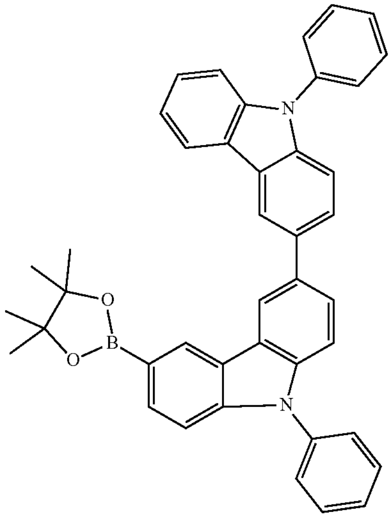 [SMILES: CC1(C)OB(c2ccc3c(c2)c2cc(-c4ccc5c(c4)c4ccccc4n5-c4ccccc4)ccc2n3-c2ccccc2)OC1(C)C] [1572537-61-1] | 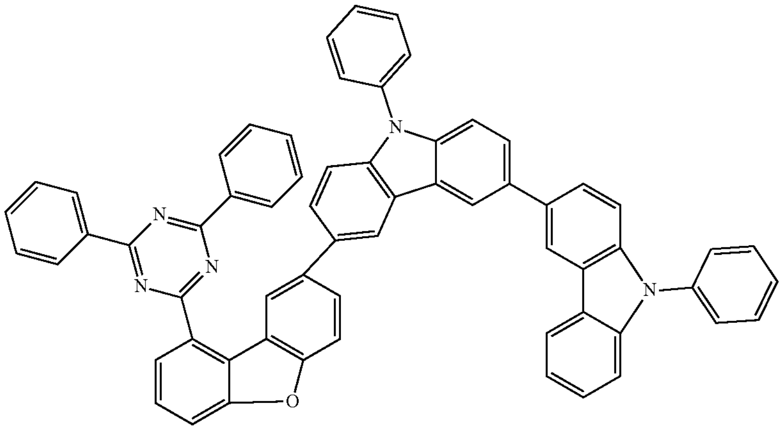 [SMILES: c1ccc(-c2nc(-c3ccccc3)nc(-c3cccc4oc5ccc(-c6ccc7c(c6)c6cc(-c8ccc9c(c8)c8ccccc8n9-c8ccccc8)ccc6n7-c6ccccc6)cc5c34)n2)cc1] 6 61% G1 |
| 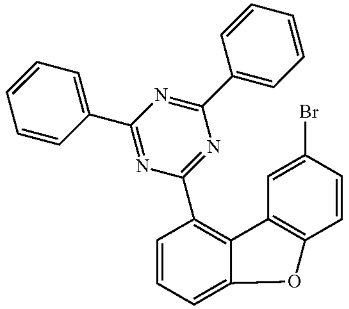 [SMILES: Brc1ccc2oc3cccc(-c4nc(-c5ccccc5)nc(-c5ccccc5)n4)c3c2c1] | 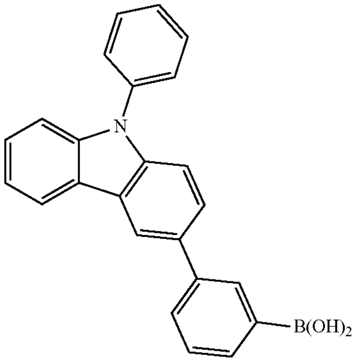 [SMILES: OB(O)c1cccc(-c2ccc3c(c2)c2ccccc2n3-c2ccccc2)c1] 854952-60-6 | 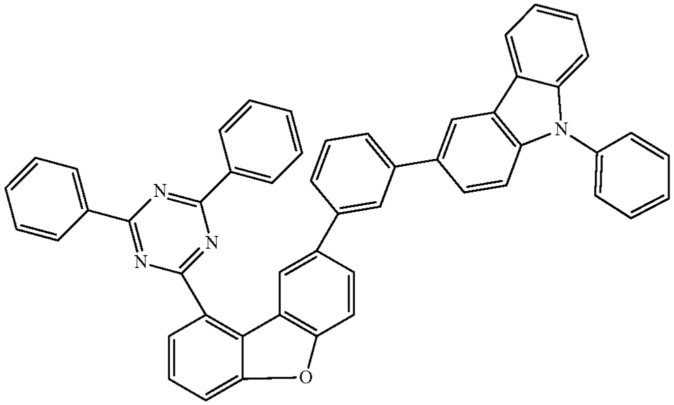 [SMILES: c1ccc(-c2nc(-c3ccccc3)nc(-c3cccc4oc5ccc(-c6cccc(-c7ccc8c(c7)c7ccccc7n8-c7ccccc7)c6)cc5c34)n2)cc1] 9 56% G2 |

-continued
| Starting material 1 | Starting material 2 | Product/Yield |
|---|---|---|
| 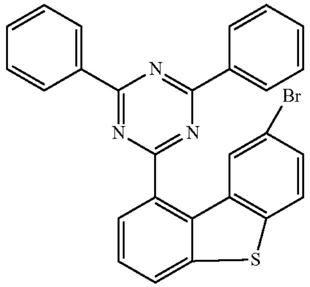 [SMILES: Brc1ccc2sc3cccc(-c4nc(-c5ccccc5)nc(-c5ccccc5)n4)c3c2c1] | 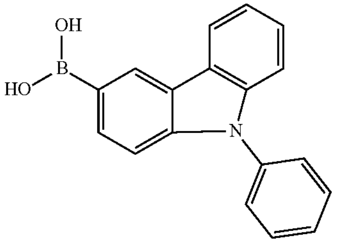 [SMILES: OB(O)c1ccc2c(c1)c1ccccc1n2-c1ccccc1]<br>[854952-58-2] | 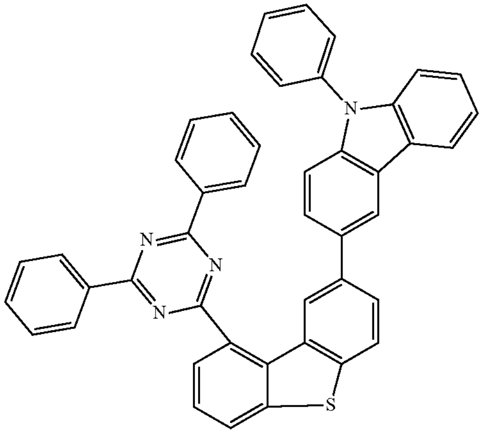 [SMILES: c1ccc(-c2nc(-c3ccccc3)nc(-c3cccc4sc5ccc(-c6ccc7c(c6)c6ccccc6n7-c6ccccc6)cc5c34)n2)cc1]<br>63%<br>G3 |
| 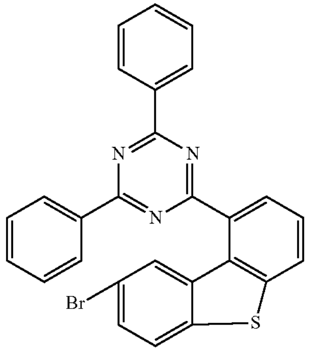 [SMILES: Brc1ccc2sc3cccc(-c4nc(-c5ccccc5)nc(-c5ccccc5)n4)c3c2c1] | 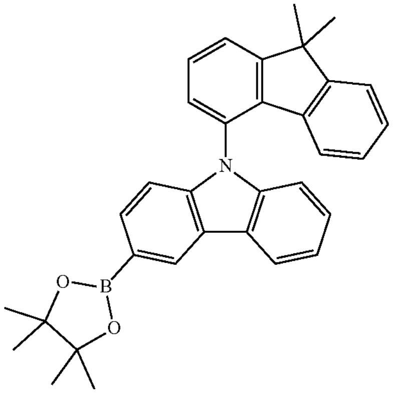 [SMILES: CC1(C)c2ccccc2-c2c(-n3c4ccccc4c4cc(B5OC(C)(C)C(C)(C)O5)ccc43)cccc21]<br>[1802588-7] | 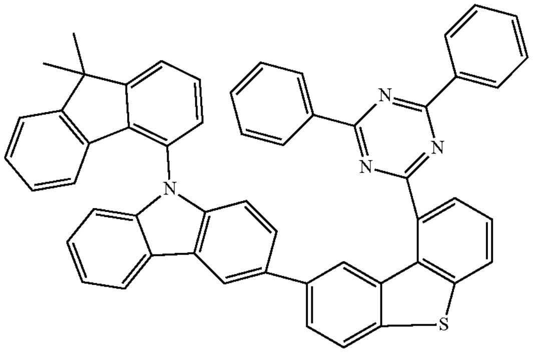 [SMILES: CC1(C)c2ccccc2-c2c(-n3c4ccccc4c4cc(-c5ccc6sc7cccc(-c8nc(-c9ccccc9)nc(-c9ccccc9)n8)c7c6c5)ccc43)cccc21]<br>60%<br>G4 |

-continued
| Starting material 1 | Starting material 2 | Product/Yield |
| --- | --- | --- |
| 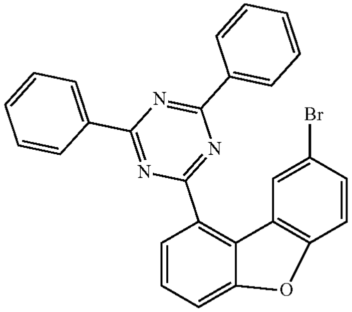 [SMILES: Brc1ccc2oc3cccc(-c4nc(-c5ccccc5)nc(-c5ccccc5)n4)c3c2c1] | 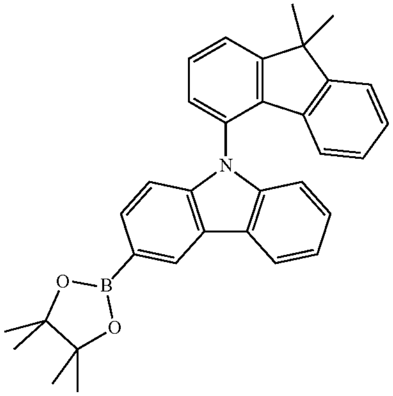 [SMILES: CC1(C)c2ccccc2-c2c(-n3c4ccccc4c4cc(B5OC(C)(C)C(C)(C)O5)ccc43)cccc21] [1802588-7] | 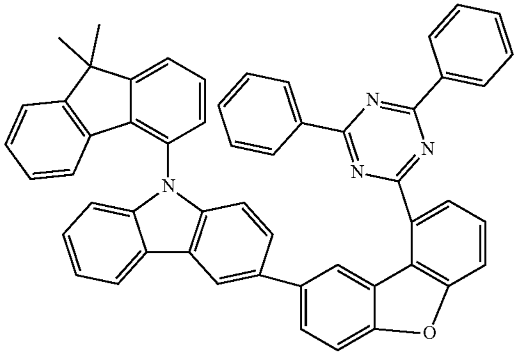 [SMILES: CC1(C)c2ccccc2-c2c(-n3c4ccccc4c4cc(-c5ccc6oc7cccc(-c8nc(-c9ccccc9)nc(-c9ccccc9)n8)c7c6c5)ccc43)cccc21] 17 65% G5 |

-continued
| Starting material 1 | Starting material 2 | Product/Yield |
| --- | --- | --- |
| 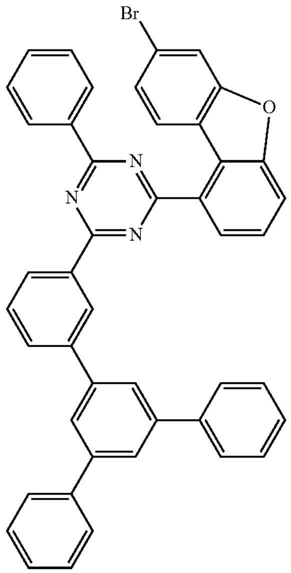 [SMILES: Brc1ccc2c(c1)oc1cccc(-c3nc(-c4ccccc4)nc(-c4cccc(-c5cc(-c6ccccc6)cc(-c6ccccc6)c5)c4)n3)c12] | 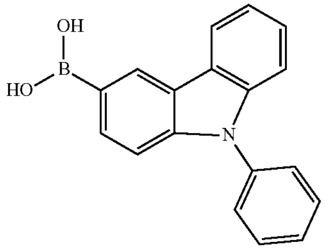 [SMILES: OB(O)c1ccc2c(c1)c1ccccc1n2-c1ccccc1]<br>[854952-58-2] | 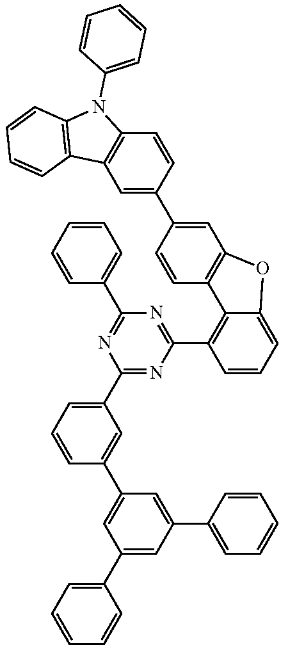 [SMILES: c1ccc(-c2cc(-c3ccccc3)cc(-c3cccc(-c4nc(-c5ccccc5)nc(-c5cccc6oc7cc(-c8ccc9c(c8)c8ccccc8n9-c8ccccc8)ccc7c56)n4)c3)c2)cc1]<br>8<br>54%<br>G6 |

-continued
| Starting material 1 | Starting material 2 | Product/Yield |
|---|---|---|
| 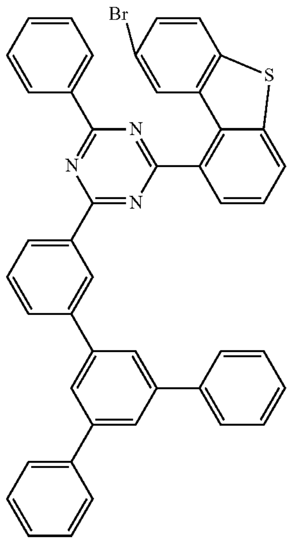 [SMILES: Brc1ccc2sc3cccc(-c4nc(-c5ccccc5)nc(-c5cccc(-c6cc(-c7ccccc7)cc(-c7ccccc7)c6)c5)n4)c3c2c1] | 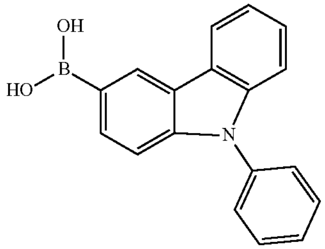 [SMILES: OB(O)c1ccc2c(c1)c1ccccc1n2-c1ccccc1] [854952-58-2] | 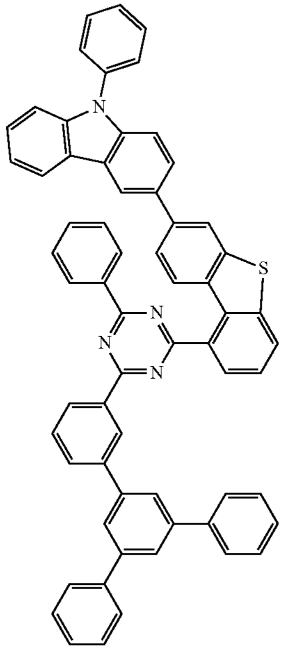 [SMILES: c1ccc(-c2cc(-c3ccccc3)cc(-c3cccc(-c4nc(-c5ccccc5)nc(-c5cccc6sc7cc(-c8ccc9c(c8)c8ccccc8n9-c8ccccc8)ccc7c56)n4)c3)c2)cc1] 59% G7 |

-continued
| Starting material 1 | Starting material 2 | Product/Yield |
| --- | --- | --- |
| 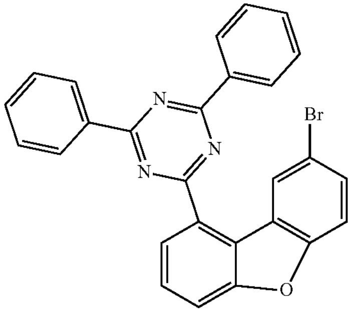 [SMILES: Brc1ccc2oc3cccc(-c4nc(-c5ccccc5)nc(-c5ccccc5)n4)c3c2c1] | 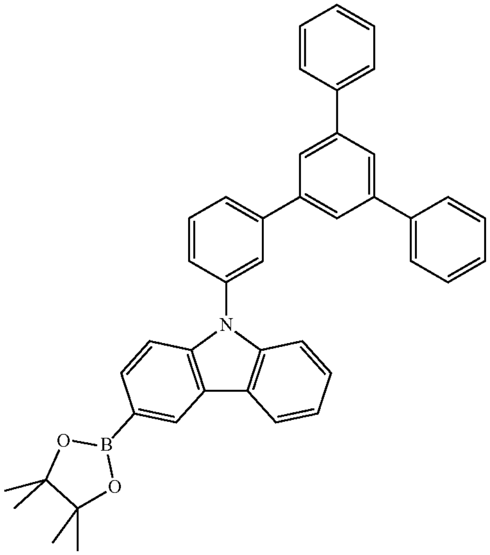 [SMILES: CC1(C)OB(c2ccc3c(c2)c2ccccc2n3-c2cccc(-c3cc(-c4ccccc4)cc(-c4ccccc4)c3)c2)OC1(C)C] [1846559-20-3] | 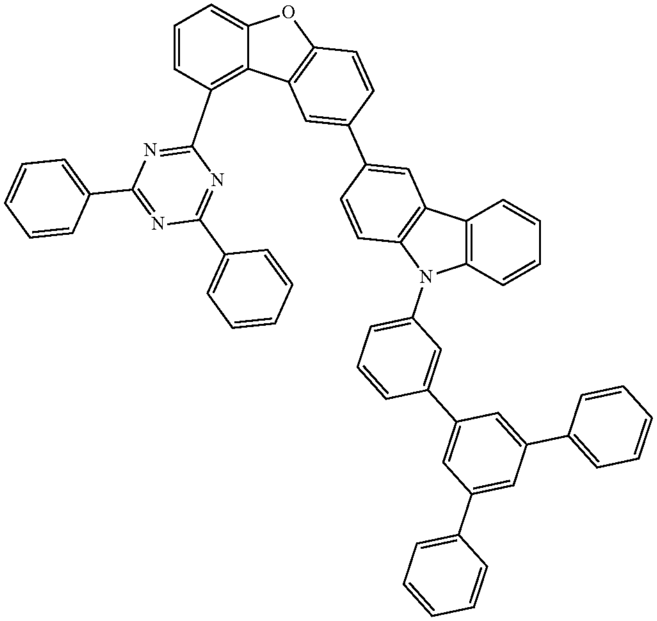 [SMILES: c1ccc(-c2cc(-c3ccccc3)cc(-c3cccc(-n4c5ccccc5c5cc(-c6ccc7oc8cccc(-c9nc(-c%10ccccc%10)nc(-c%10ccccc%10)n9)c8c7c6)ccc54)c3)c2)cc1] 16 60% G8 |

-continued
| Starting material 1 | Starting material 2 | Product/Yield |
|---|---|---|
| 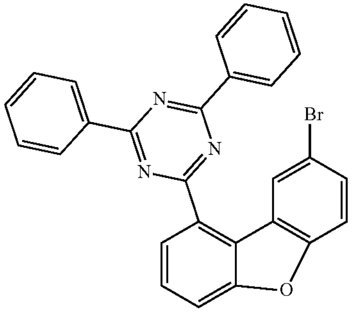 [SMILES: Brc1ccc2oc3cccc(-c4nc(-c5ccccc5)nc(-c5ccccc5)n4)c3c2c1] | 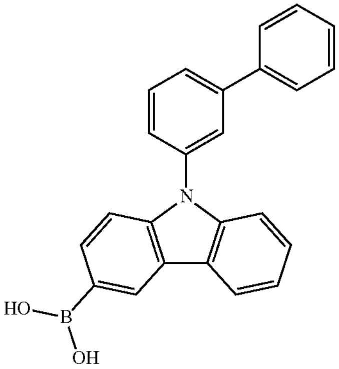 [SMILES: OB(O)c1ccc2c(c1)c1ccccc1n2-c1cccc(-c2ccccc2)c1] [1416814-68-0] | 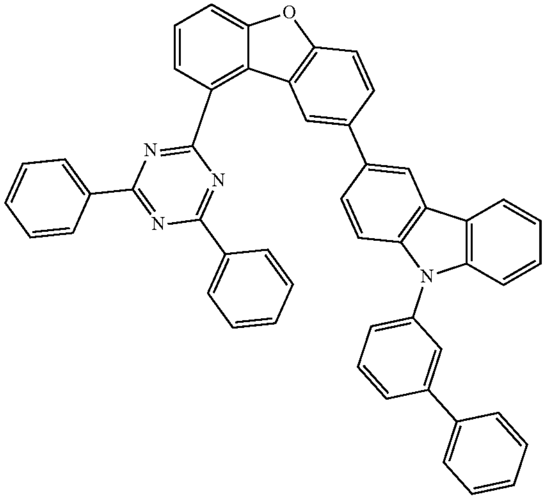 [SMILES: c1ccc(-c2cccc(-n3c4ccccc4c4cc(-c5ccc6oc7cccc(-c8nc(-c9ccccc9)nc(-c9ccccc9)n8)c7c6c5)ccc43)c2)cc1] 13 62% G9 |

-continued
| Starting material 1 | Starting material 2 | Product/Yield |
| --- | --- | --- |
| 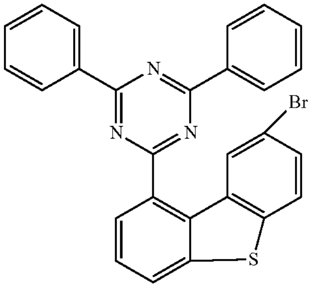 [SMILES: Brc1ccc2sc3cccc(-c4nc(-c5ccccc5)nc(-c5ccccc5)n4)c3c2c1] | 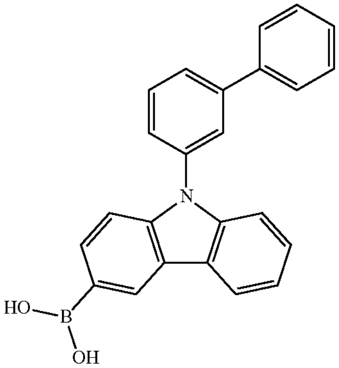 [SMILES: OB(O)c1ccc2c(c1)c1ccccc1n2-c1cccc(-c2ccccc2)c1] [1416814-68-0] | 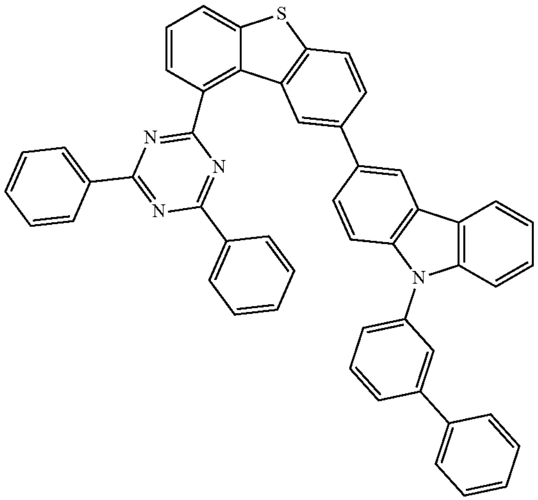 [SMILES: c1ccc(-c2cccc(-n3c4ccccc4c4cc(-c5ccc6sc7cccc(-c8nc(-c9ccccc9)nc(-c9ccccc9)n8)c7c6c5)ccc43)c2)cc1] 54% G10 |

-continued
| Starting material 1 | Starting material 2 | Product/Yield |
| --- | --- | --- |
| 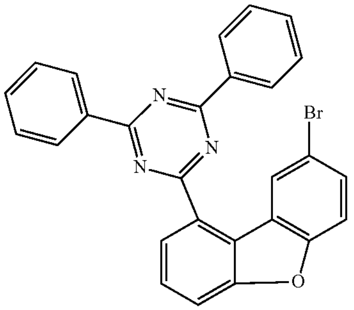 [SMILES: Brc1ccc2oc3cccc(-c4nc(-c5ccccc5)nc(-c5ccccc5)n4)c3c2c1] | 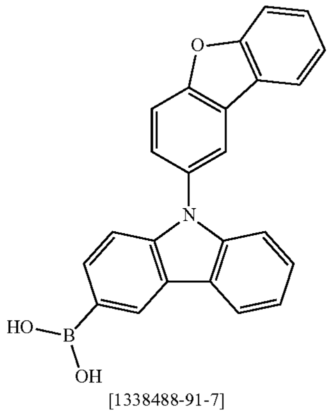 [1338488-91-7] | 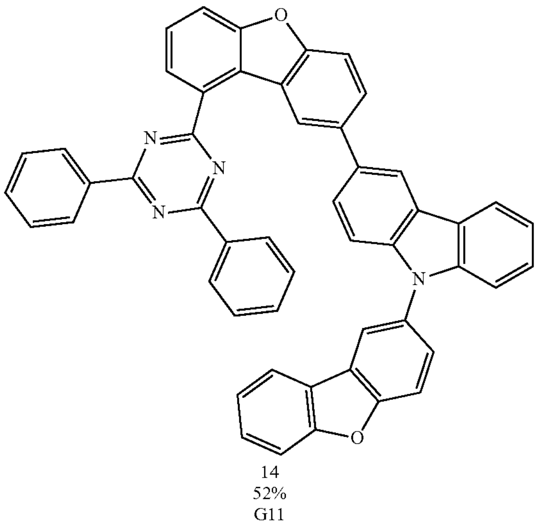 14 52% G11 |

-continued
| Starting material 1 | Starting material 2 | Product/Yield |
|---|---|---|
| 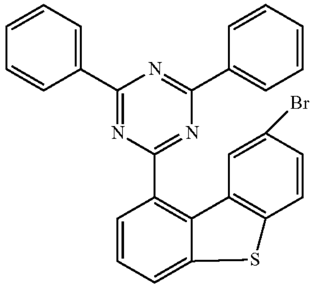 [SMILES: Brc1ccc2sc3cccc(-c4nc(-c5ccccc5)nc(-c5ccccc5)n4)c3c2c1] | 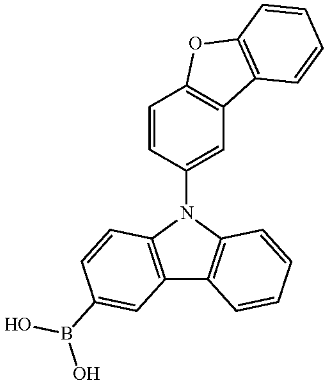 [SMILES: OB(O)c1ccc2c(c1)c1ccccc1n2-c1ccc2oc3ccccc3c2c1] | 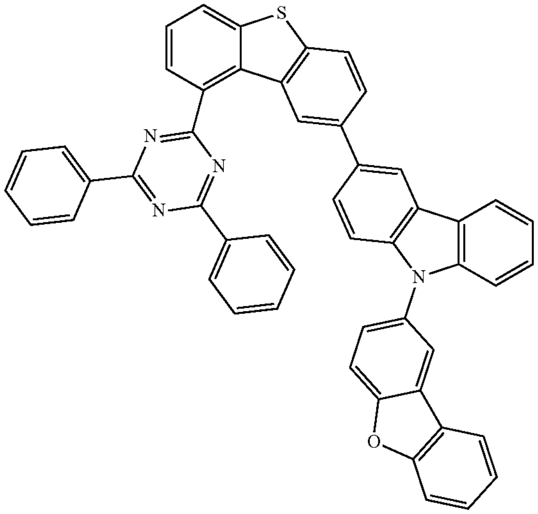 [SMILES: c1ccc(-c2nc(-c3ccccc3)nc(-c3cccc4sc5ccc(-c6ccc7c(c6)c6ccccc6n7-c6ccc7oc8ccccc8c7c6)cc5c34)n2)cc1] 50% G12 |

-continued
| Starting material 1 | Starting material 2 | Product/Yield |
|---|---|---|
| 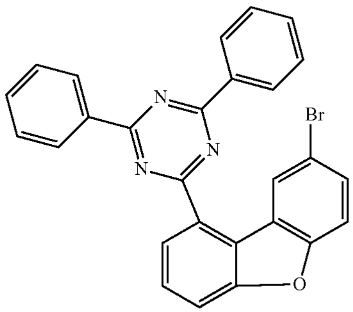 [SMILES: Brc1ccc2oc3cccc(-c4nc(-c5ccccc5)nc(-c5ccccc5)n4)c3c2c1] | 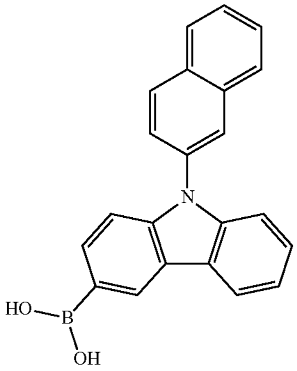 [SMILES: OB(O)c1ccc2c(c1)c1ccccc1n2-c1ccc2ccccc2c1] [1133057-98-3] | 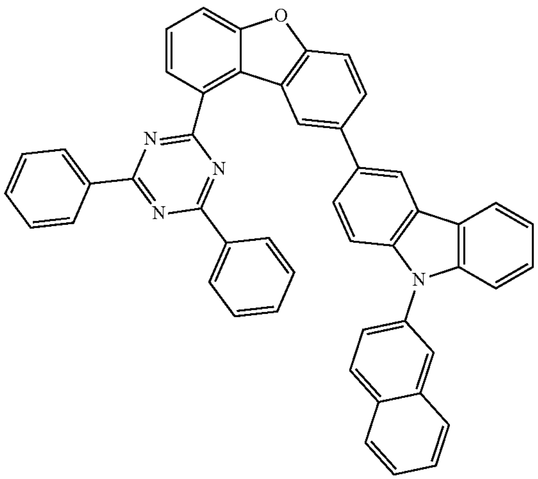 [SMILES: c1ccc(-c2nc(-c3ccccc3)nc(-c3cccc4oc5ccc(-c6ccc7c(c6)c6ccccc6n7-c6ccc7ccccc7c6)cc5c34)n2)cc1] 12 62% G13 |

-continued
| Starting material 1 | Starting material 2 | Product/Yield |
| --- | --- | --- |
| 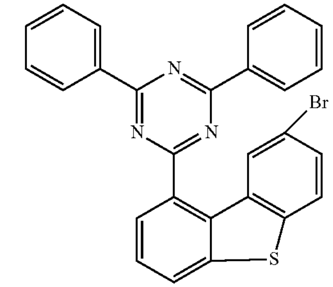 [SMILES: Brc1ccc2sc3cccc(-c4nc(-c5ccccc5)nc(-c5ccccc5)n4)c3c2c1] | 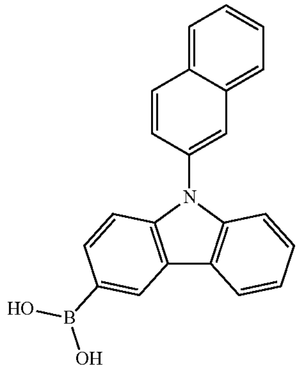 [SMILES: OB(O)c1ccc2c(c1)c1ccccc1n2-c1ccc2ccccc2c1] [1133057-98-3] | 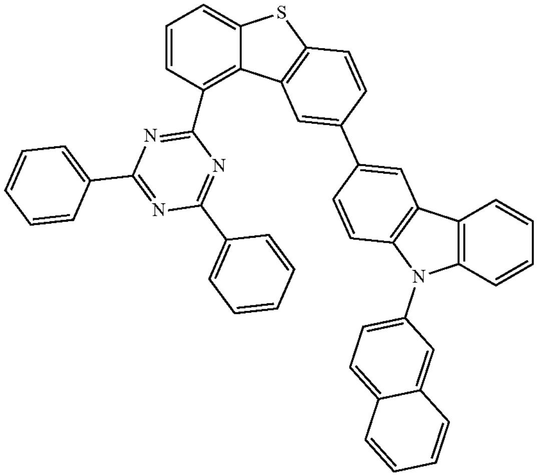 [SMILES: c1ccc(-c2nc(-c3ccccc3)nc(-c3cccc4sc5ccc(-c6ccc7c(c6)c6ccccc6n7-c6ccc7ccccc7c6)cc5c34)n2)cc1] 57% G14 |
| 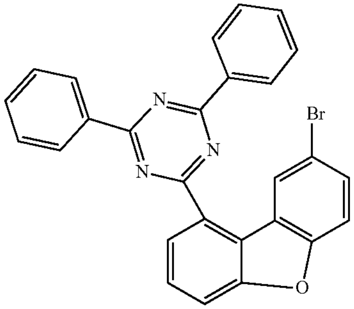 [SMILES: Brc1ccc2oc3cccc(-c4nc(-c5ccccc5)nc(-c5ccccc5)n4)c3c2c1] | 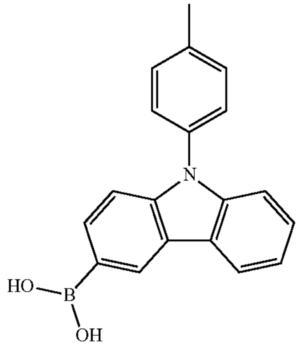 [SMILES: Cc1ccc(-n2c3ccccc3c3cc(B(O)O)ccc32)cc1] [731016-45-8] | 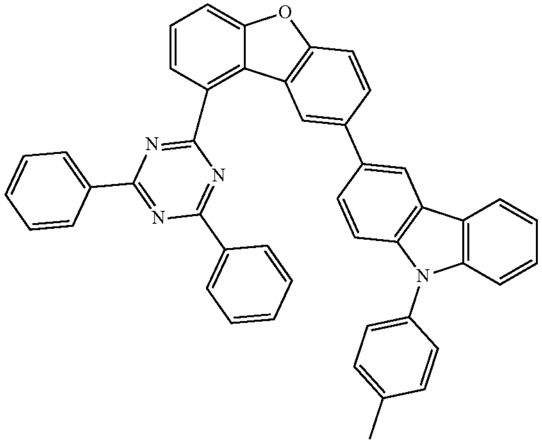 [SMILES: Cc1ccc(-n2c3ccccc3c3cc(-c4ccc5oc6cccc(-c7nc(-c8ccccc8)nc(-c8ccccc8)n7)c6c5c4)ccc32)cc1] 18 62% G15 |

-continued
| Starting material 1 | Starting material 2 | Product/Yield |
|---|---|---|
| 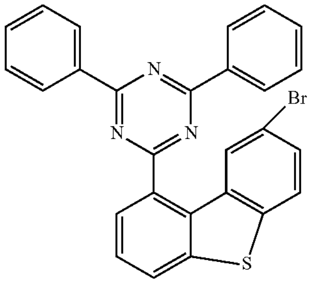 [SMILES: Brc1ccc2sc3cccc(-c4nc(-c5ccccc5)nc(-c5ccccc5)n4)c3c2c1] | 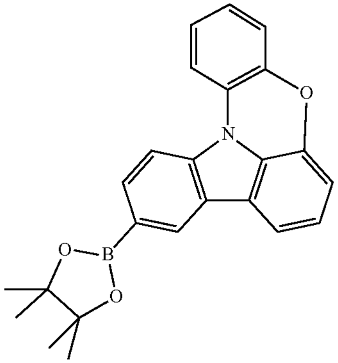 [SMILES: CC1(C)OB(c2ccc3c(c2)c2cccc4c2n3-c2ccccc2O4)OC1(C)C] [1380485-64-2] | 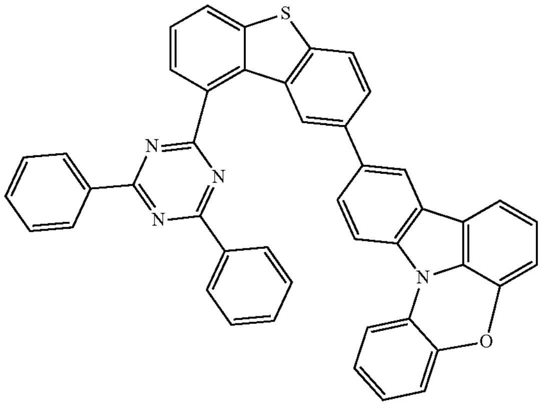 [SMILES: c1ccc(-c2nc(-c3ccccc3)nc(-c3cccc4sc5ccc(-c6ccc7c(c6)c6cccc8c6n7-c6ccccc6O8)cc5c34)n2)cc1] 56% G16 |
| 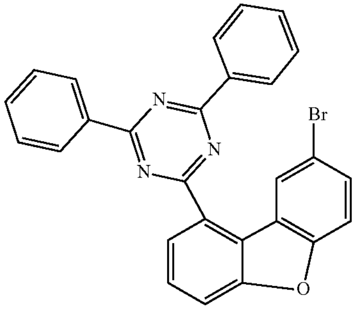 [SMILES: Brc1ccc2oc3cccc(-c4nc(-c5ccccc5)nc(-c5ccccc5)n4)c3c2c1] | 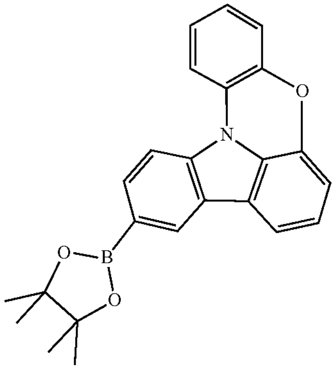 [SMILES: CC1(C)OB(c2ccc3c(c2)c2cccc4c2n3-c2ccccc2O4)OC1(C)C] [1380485-64-2] | 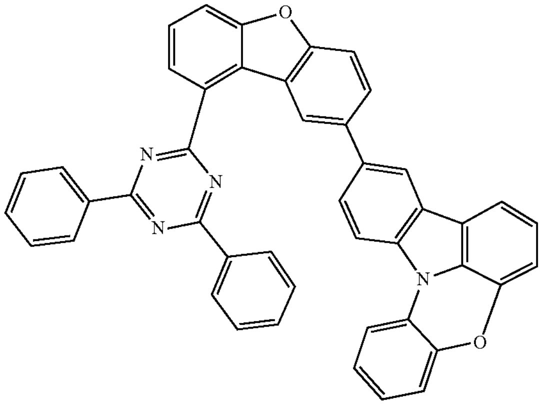 [SMILES: c1ccc(-c2nc(-c3ccccc3)nc(-c3cccc4oc5ccc(-c6ccc7c(c6)c6cccc8c6n7-c6ccccc6O8)cc5c34)n2)cc1] 21 52% G17 |

-continued
| Starting material 1 | Starting material 2 | Product/Yield |
| --- | --- | --- |
| 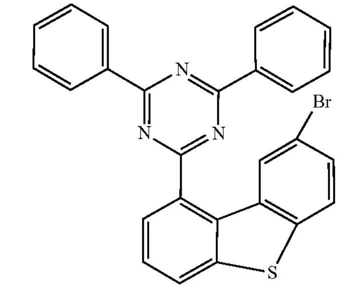 [SMILES: Brc1ccc2sc3cccc(-c4nc(-c5ccccc5)nc(-c5ccccc5)n4)c3c2c1] | 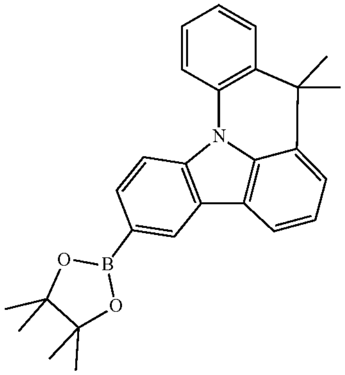 [1456606-40-8] | 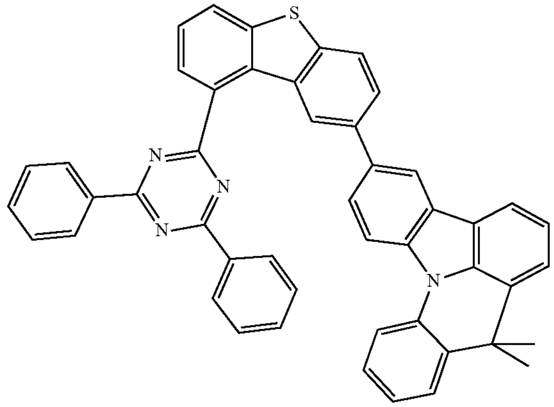 [SMILES: CC1(C)c2ccccc2-n2c3ccc(-c4ccc5sc6cccc(-c7nc(-c8ccccc8)nc(-c8ccccc8)n7)c6c5c4)cc3c3cccc1c32] 55% G18 |
| 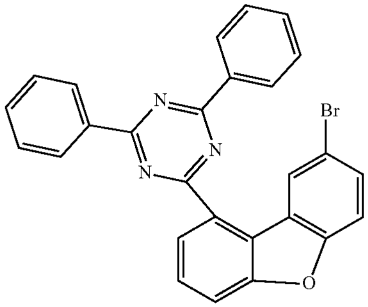 [SMILES: Brc1ccc2oc3cccc(-c4nc(-c5ccccc5)nc(-c5ccccc5)n4)c3c2c1] | 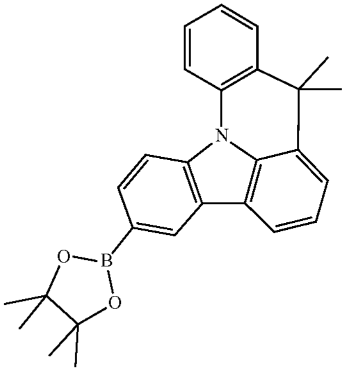 [1456606-40-8] | 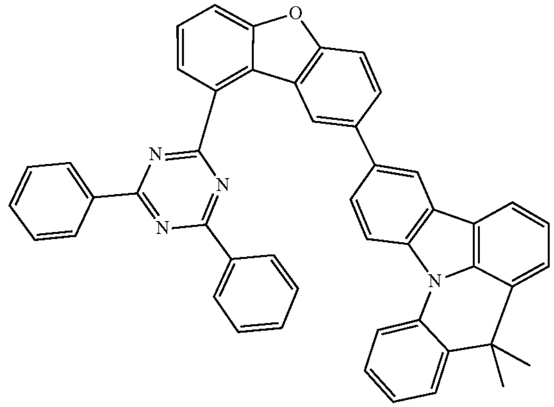 [SMILES: CC1(C)c2ccccc2-n2c3ccc(-c4ccc5oc6cccc(-c7nc(-c8ccccc8)nc(-c8ccccc8)n7)c6c5c4)cc3c3cccc1c32] 20 60% G19 |

-continued
| Starting material 1 | Starting material 2 | Product/Yield |
| --- | --- | --- |
| 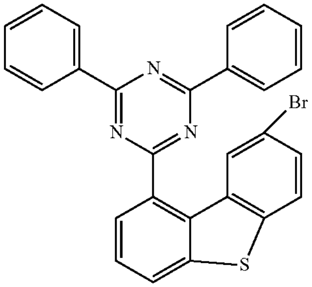 [SMILES: Brc1ccc2sc3cccc(-c4nc(-c5ccccc5)nc(-c5ccccc5)n4)c3c2c1] | 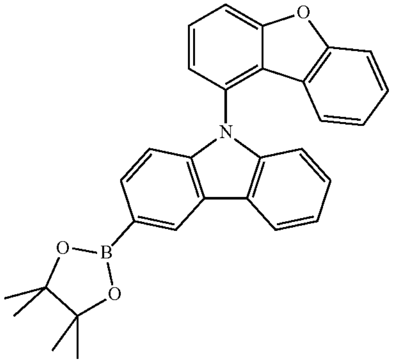 [SMILES: CC1(C)OB(c2ccc3c(c2)c2ccccc2n3-c2cccc3oc4ccccc4c23)OC1(C)C]<br>[1427160-10-8] | 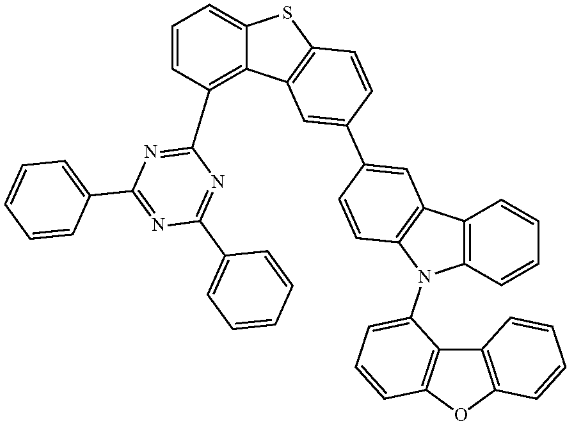 [SMILES: c1ccc(-c2nc(-c3ccccc3)nc(-c3cccc4sc5ccc(-c6ccc7c(c6)c6ccccc6n7-c6cccc7oc8ccccc8c67)cc5c34)n2)cc1]<br>54%<br>G20 |
| 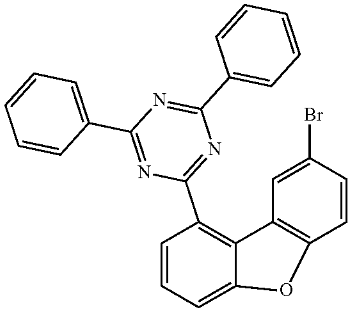 [SMILES: Brc1ccc2oc3cccc(-c4nc(-c5ccccc5)nc(-c5ccccc5)n4)c3c2c1] | 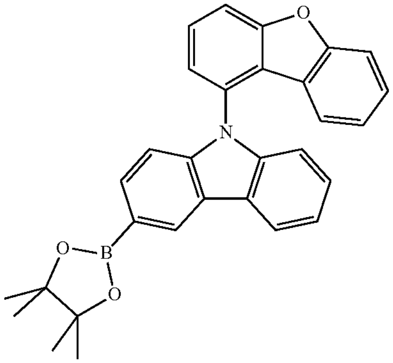 [SMILES: CC1(C)OB(c2ccc3c(c2)c2ccccc2n3-c2cccc3oc4ccccc4c23)OC1(C)C]<br>[1427160-10-8] | 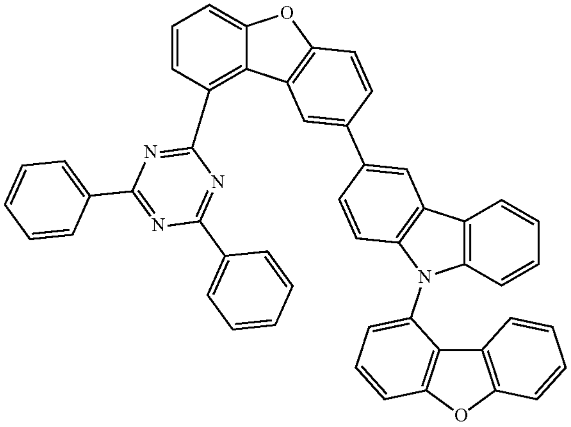 [SMILES: c1ccc(-c2nc(-c3ccccc3)nc(-c3cccc4oc5ccc(-c6ccc7c(c6)c6ccccc6n7-c6cccc7oc8ccccc8c67)cc5c34)n2)cc1]<br>15<br>56%<br>G21 |

-continued
| Starting material 1 | Starting material 2 | Product/Yield |
| --- | --- | --- |
| 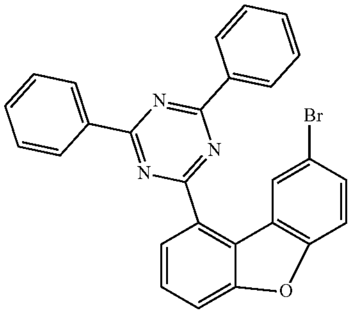 [SMILES: Brc1ccc2oc3cccc(-c4nc(-c5ccccc5)nc(-c5ccccc5)n4)c3c2c1] | 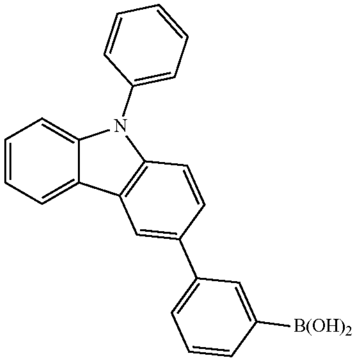 [SMILES: OB(O)c1cccc(-c2ccc3c(c2)c2ccccc2n3-c2ccccc2)c1] [854952-60-6] | 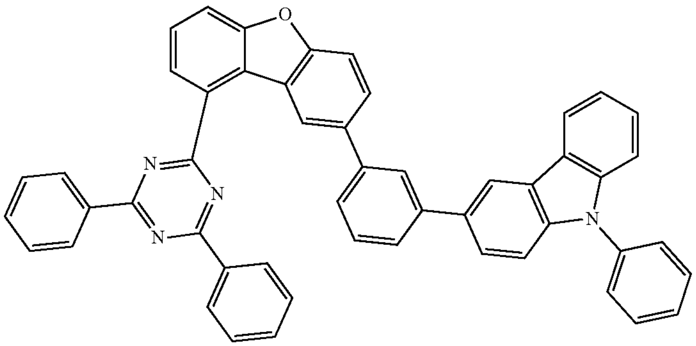 [SMILES: c1ccc(-c2nc(-c3ccccc3)nc(-c3cccc4oc5ccc(-c6cccc(-c7ccc8c(c7)c7ccccc7n8-c7ccccc7)c6)cc5c34)n2)cc1] 9 62% G50 |
| 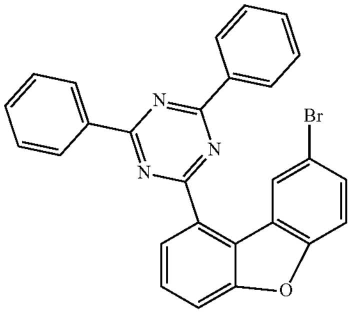 [SMILES: Brc1ccc2oc3cccc(-c4nc(-c5ccccc5)nc(-c5ccccc5)n4)c3c2c1] | 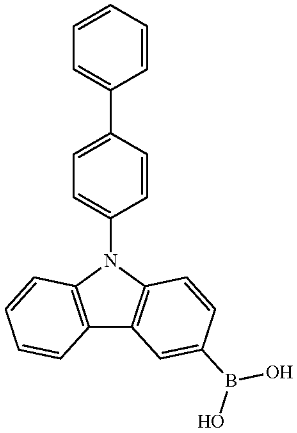 [SMILES: OB(O)c1ccc2c(c1)c1ccccc1n2-c1ccc(-c2ccccc2)cc1] [1028648-22-7] | 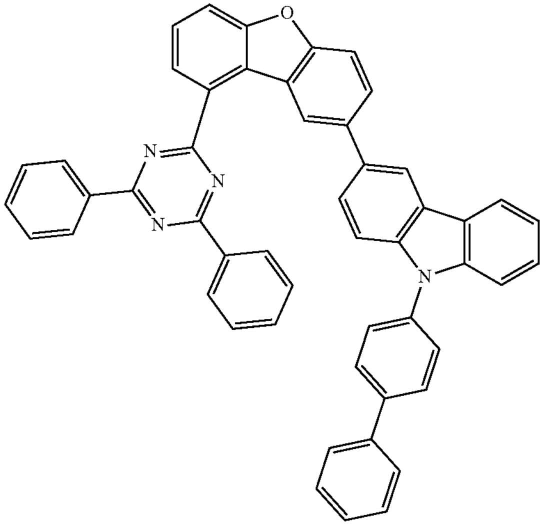 [SMILES: c1ccc(-c2ccc(-n3c4ccccc4c4cc(-c5ccc6oc7cccc(-c8nc(-c9ccccc9)nc(-c9ccccc9)n8)c7c6c5)ccc43)cc2)cc1] 11 66% G51 |

-continued
| Starting material 1 | Starting material 2 | Product/Yield |
|---|---|---|
| 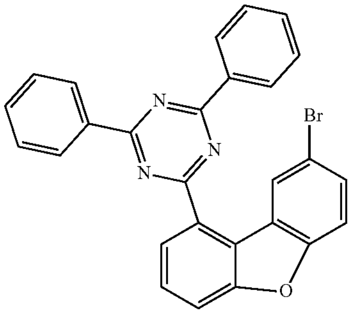 [SMILES: Brc1ccc2oc3cccc(-c4nc(-c5ccccc5)nc(-c5ccccc5)n4)c3c2c1] | 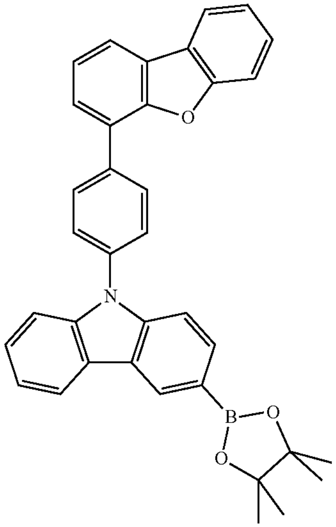 [SMILES: CC1(C)OB(c2ccc3c(c2)c2ccccc2n3-c2ccc(-c3cccc4c3oc3ccccc34)cc2)OC1(C)C] | 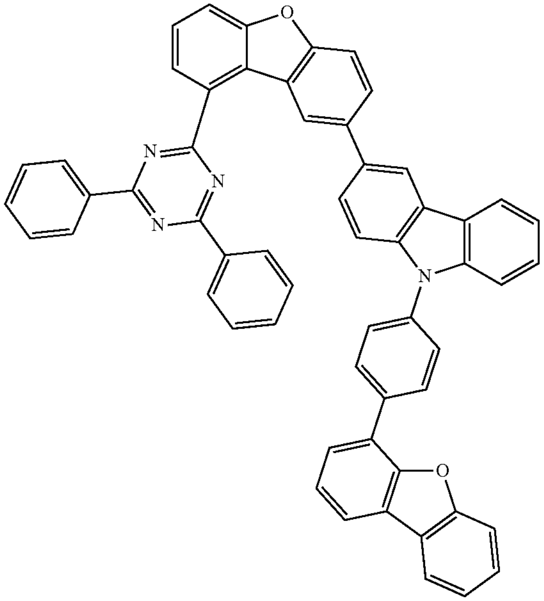 [SMILES: c1ccc(-c2nc(-c3ccccc3)nc(-c3cccc4oc5ccc(-c6ccc7c(c6)c6ccccc6n7-c6ccc(-c7cccc8c7oc7ccccc78)cc6)cc5c34)n2)cc1]<br>4<br>55%<br>G52 |

Example 3: Synthesis of Compounds 89 (BisC2) and 90 (BisC3)

Compound 89 is known from the literature and is prepared analogously to US 20150001488.

Compound 90 is known from the literature and is prepared analogously to Physical Chemistry Chemical Physics, 17(37), 2015, 24468-24474.

Example 4

The following compounds can be prepared analogously to Example 2g). The purification here can also be carried out using column chromatography, or other common solvents, such as n-heptane, butanol, acetone, ethyl acetate, acetonitrile, toluene, xylene, dichloromethane, methanol, N,N-dimethylformamide, tetrahydrofuran, ethyl acetate, n-butyl acetate or 1,4-dioxane, can be used for the recrystallisation or hot extraction.

| Starting material 1 | Starting material 2 | Product/Yield |
|---|---|---|
| 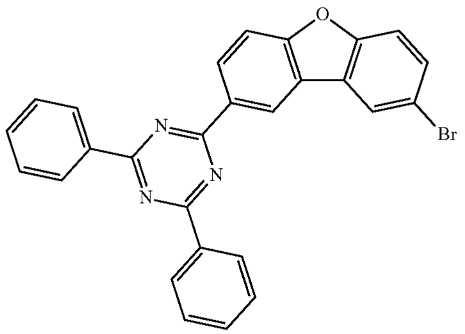 [SMILES: Brc1ccc2oc3ccc(-c4nc(-c5ccccc5)nc(-c5ccccc5)n4)cc3c2c1] [2102445-25-8] | 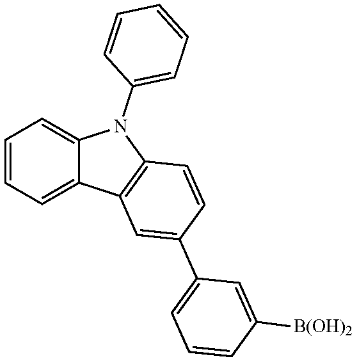 [SMILES: OB(O)c1cccc(-c2ccc3c(c2)c2ccccc2n3-c2ccccc2)c1] [854952-60-6] | 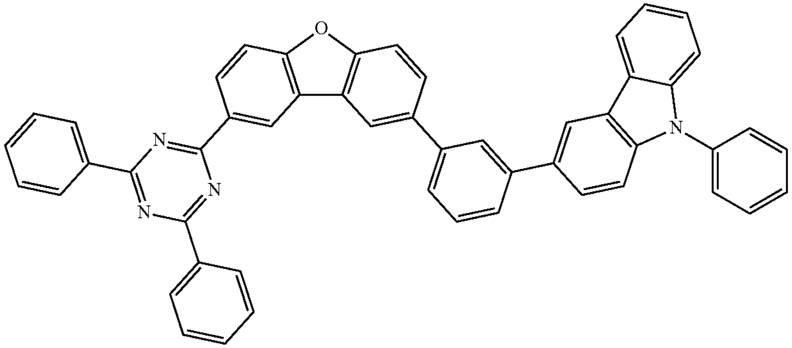 [SMILES: c1ccc(-c2nc(-c3ccccc3)nc(-c3ccc4oc5ccc(-c6cccc(-c7ccc8c(c7)c7ccccc7n8-c7ccccc7)c6)cc5c4c3)n2)cc1] 26 62% G23 |
| 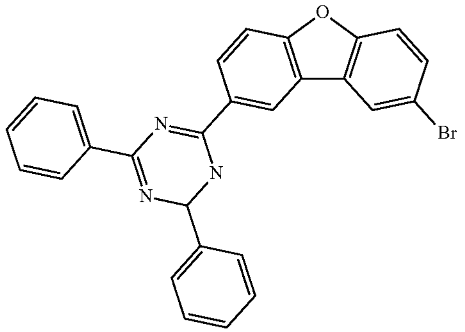 [2102445-25-8] | 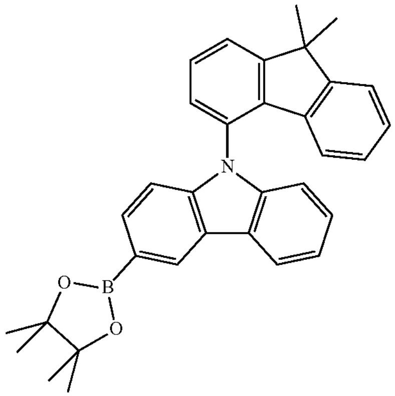 [SMILES: CC1(C)c2ccccc2-c2c(-n3c4ccccc4c4cc(B5OC(C)(C)C(C)(C)O5)ccc43)cccc21] [1802588-7] | 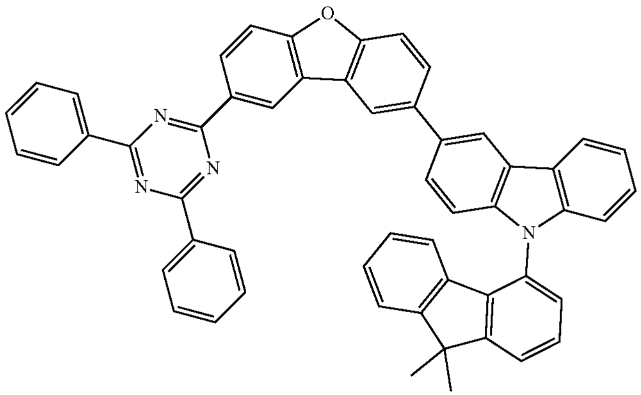 [SMILES: CC1(C)c2ccccc2-c2c(-n3c4ccccc4c4cc(-c5ccc6oc7ccc(-c8nc(-c9ccccc9)nc(-c9ccccc9)n8)cc7c6c5)ccc43)cccc21] 32 67% G24 |

-continued
| Starting material 1 | Starting material 2 | Product/Yield |
| --- | --- | --- |
| 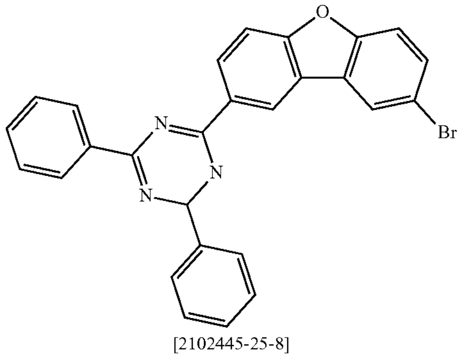 [2102445-25-8] | 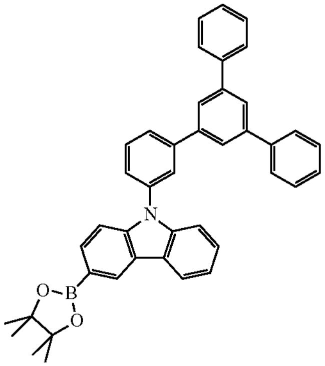 [SMILES: CC1(C)OB(c2ccc3c(c2)c2ccccc2n3-c2cccc(-c3cc(-c4ccccc4)cc(-c4ccccc4)c3)c2)OC1(C)C] [1846559-20-3] | 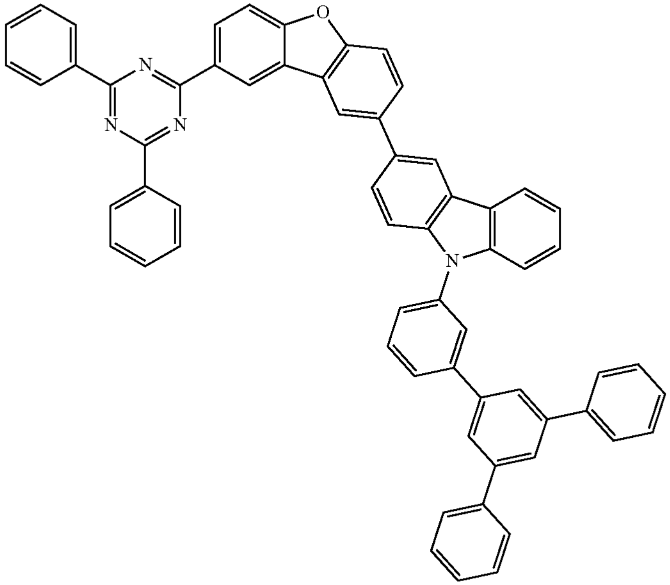 [SMILES: c1ccc(-c2cc(-c3ccccc3)cc(-c3cccc(-n4c5ccccc5c5cc(-c6ccc7oc8ccc(-c9nc(-c%10ccccc%10)nc(-c%10ccccc%10)n9)cc8c7c6)ccc54)c3)c2)cc1] 29 64% G25 |

-continued
| Starting material 1 | Starting material 2 | Product/Yield |
| --- | --- | --- |
| 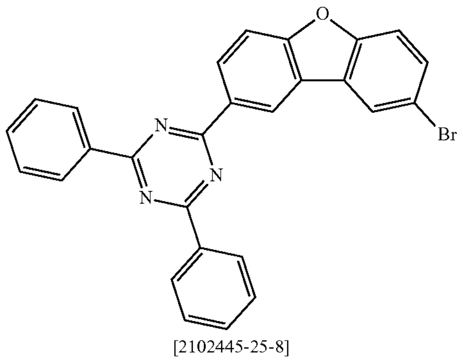 [2102445-25-8] | 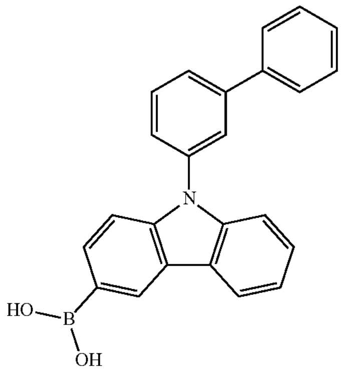 [SMILES: OB(O)c1ccc2c(c1)c1ccccc1n2-c1cccc(-c2ccccc2)c1] [1416814-68-0] | 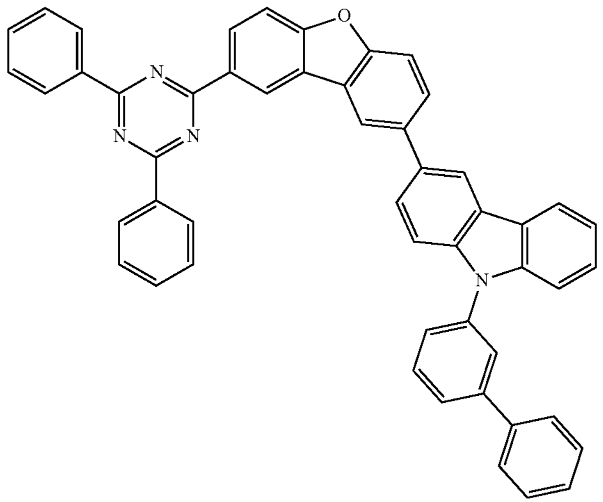 [SMILES: c1ccc(-c2cccc(-n3c4ccccc4c4cc(-c5ccc6oc7ccc(-c8nc(-c9ccccc9)nc(-c9ccccc9)n8)cc7c6c5)ccc43)c2)cc1] 30 58% G26 |

-continued
| Starting material 1 | Starting material 2 | Product/Yield |
| --- | --- | --- |
| 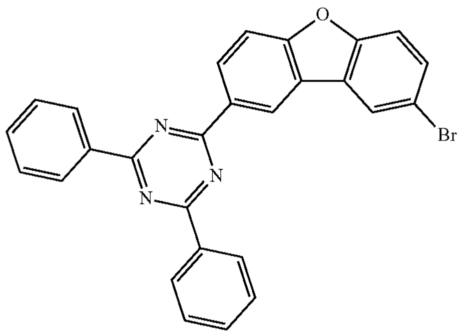 [SMILES: Brc1ccc2oc3ccc(-c4nc(-c5ccccc5)nc(-c5ccccc5)n4)cc3c2c1] [2102445-25-8] | 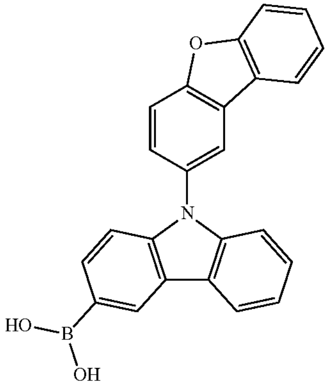 [SMILES: OB(O)c1ccc2c(c1)c1ccccc1n2-c1ccc2oc3ccccc3c2c1] [1338488-91-7] | 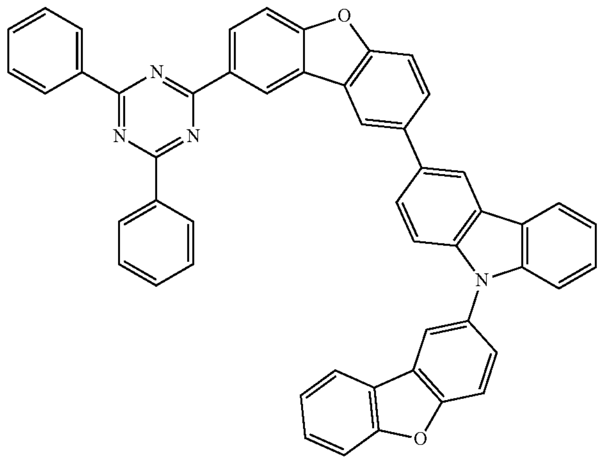 [SMILES: c1ccc(-c2nc(-c3ccccc3)nc(-c3ccc4oc5ccc(-c6ccc7c(c6)c6ccccc6n7-c6ccc7oc8ccccc8c7c6)cc5c4c3)n2)cc1] 41 53% G27 |
| 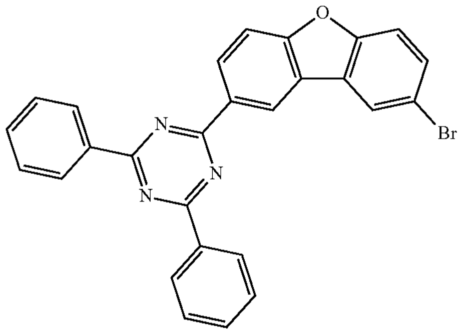 [SMILES: Brc1ccc2oc3ccc(-c4nc(-c5ccccc5)nc(-c5ccccc5)n4)cc3c2c1] [2102445-25-8] | 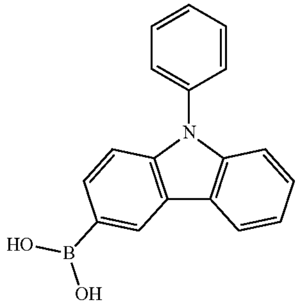 [SMILES: OB(O)c1ccc2c(c1)c1ccccc1n2-c1ccccc1] [854952-58-2] | 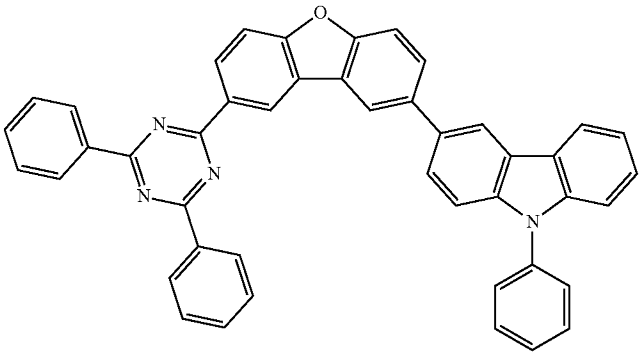 [SMILES: c1ccc(-c2nc(-c3ccccc3)nc(-c3ccc4oc5ccc(-c6ccc7c(c6)c6ccccc6n7-c6ccccc6)cc5c4c3)n2)cc1] 25 70% G28 |

-continued
| Starting material 1 | Starting material 2 | Product/Yield |
|---|---|---|
| 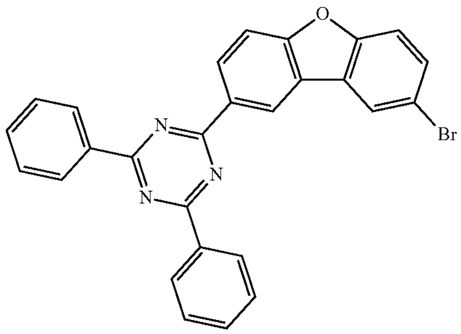 [SMILES: Brc1ccc2oc3ccc(-c4nc(-c5ccccc5)nc(-c5ccccc5)n4)cc3c2c1] [2102445-25-8] | 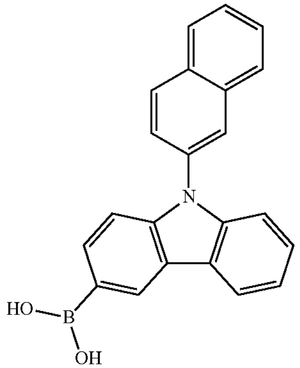 [SMILES: OB(O)c1ccc2c(c1)c1ccccc1n2-c1ccc2ccccc2c1] [1133057-98-3] | 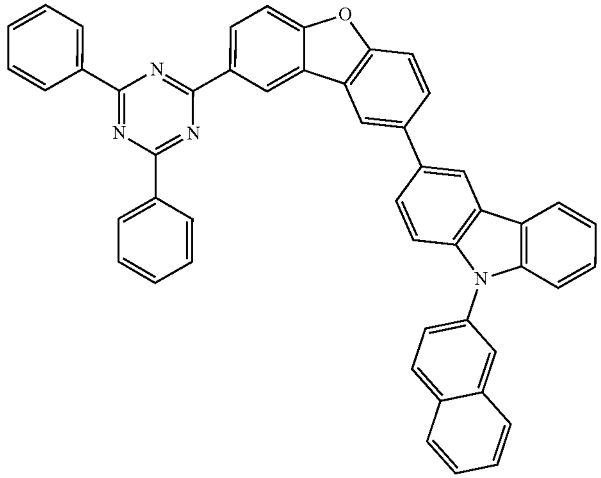 [SMILES: c1ccc(-c2nc(-c3ccccc3)nc(-c3ccc4oc5ccc(-c6ccc7c(c6)c6ccccc6n7-c6ccc7ccccc7c6)cc5c4c3)n2)cc1] 44 59% G29 |
| 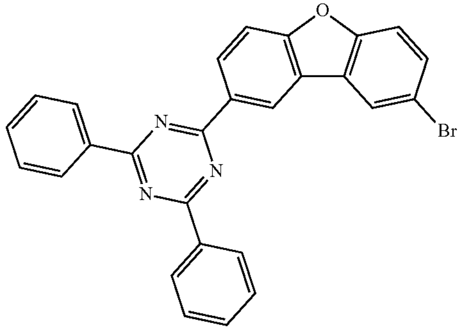 [SMILES: Brc1ccc2oc3ccc(-c4nc(-c5ccccc5)nc(-c5ccccc5)n4)cc3c2c1] [2102445-25-8] | 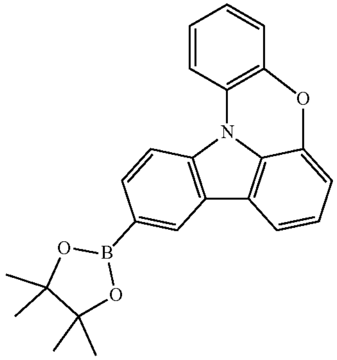 [SMILES: CC1(C)OB(c2ccc3c(c2)c2cccc4c2n3-c2ccccc2O4)OC1(C)C] [1380485-64-2] | 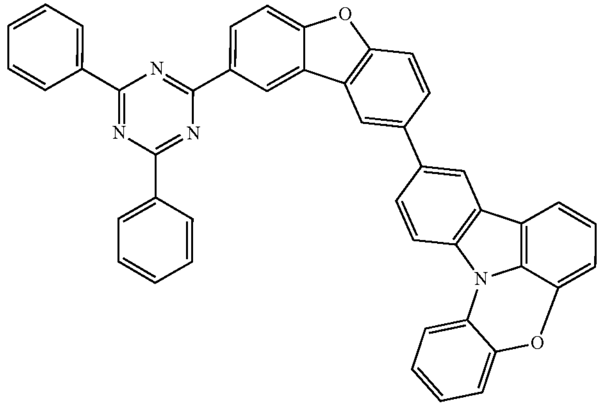 [SMILES: c1ccc(-c2nc(-c3ccccc3)nc(-c3ccc4oc5ccc(-c6ccc7c(c6)c6cccc8c6n7-c6ccccc6O8)cc5c4c3)n2)cc1] 24 68% G30 |

-continued
| Starting material 1 | Starting material 2 | Product/Yield |
|---|---|---|
| 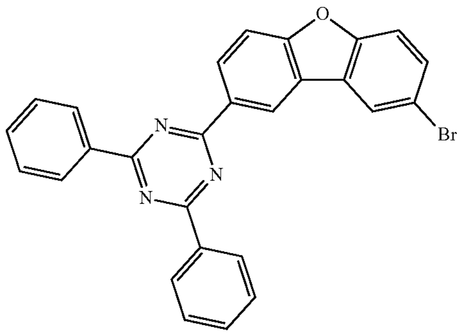 [SMILES: Brc1ccc2oc3ccc(-c4nc(-c5ccccc5)nc(-c5ccccc5)n4)cc3c2c1] [2102445-25-8] | 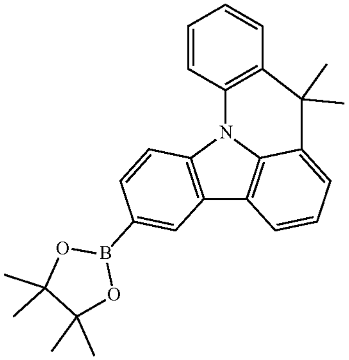 [1456606-40-8] | 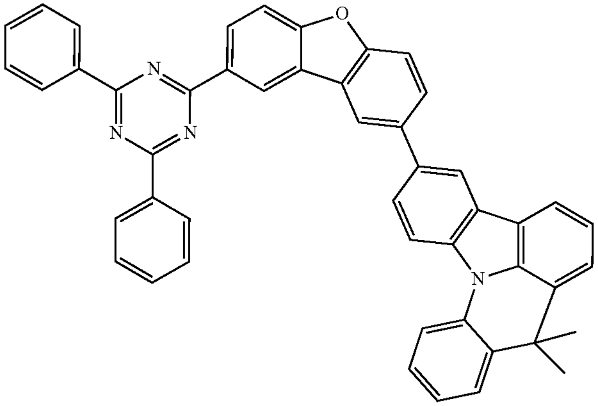 [SMILES: CC1(C)c2ccccc2-n2c3ccc(-c4ccc5oc6ccc(-c7nc(-c8ccccc8)nc(-c8ccccc8)n7)cc6c5c4)cc3c3cccc1c32] 38 53% G31 |
| 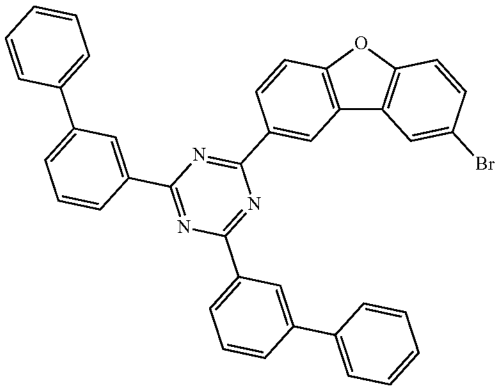 [SMILES: Brc1ccc2oc3ccc(-c4nc(-c5cccc(-c6ccccc6)c5)nc(-c5cccc(-c6ccccc6)c5)n4)cc3c2c1] | 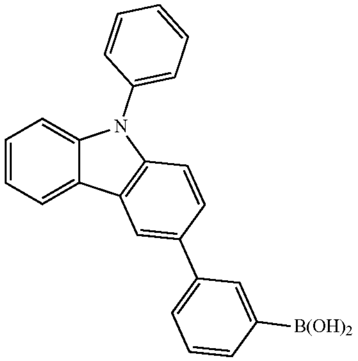 [SMILES: OB(O)c1cccc(-c2ccc3c(c2)c2ccccc2n3-c2ccccc2)c1] [854952-60-6] | 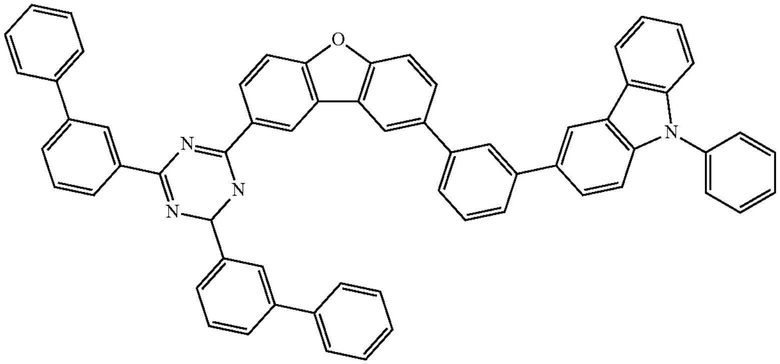 43 50% G32 |

Example 5

A)

Preparation of the bromine intermediate analogously to Example 2f) starting from 2-(dibenzo[b,d]furan-3-yl)-4,6-diphenyl-1,3,5-triazine [1651203-47-2]. Yield 83%.

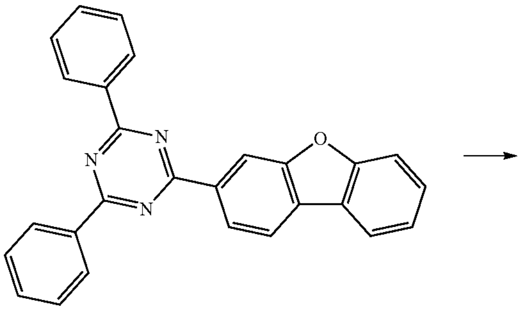

-continued

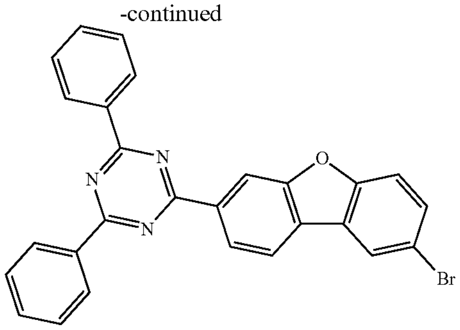

B)

The following compounds can be prepared analogously to Example 2g). The purification here can also be carried out using column chromatography, or other common solvents, such as n-heptane, butanol, acetone, ethyl acetate, acetonitrile, toluene, xylene, dichloromethane, methanol, N,N-dimethylformamide, tetrahydrofuran, ethyl acetate, n-butyl acetate or 1,4-dioxane, can be used for the recrystallisation or hot extraction.

| Starting material 1 | Starting material 2 | Product/Yield |
|---|---|---|
| 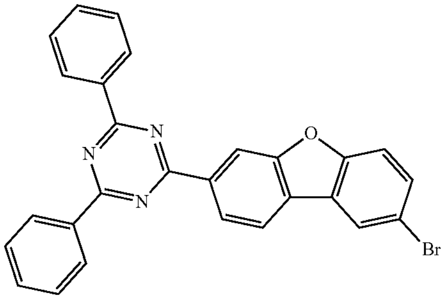 [SMILES: Brc1ccc2oc3cc(-c4nc(-c5ccccc5)nc(-c5ccccc5)n4)ccc3c2c1] | 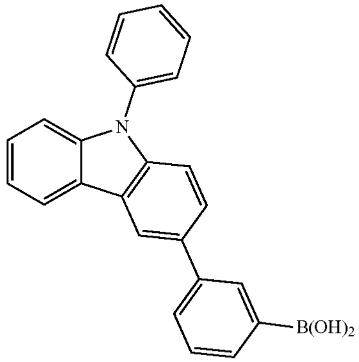 [SMILES: OB(O)c1cccc(-c2ccc3c(c2)c2ccccc2n3-c2ccccc2)c1] [854952-60-6] | 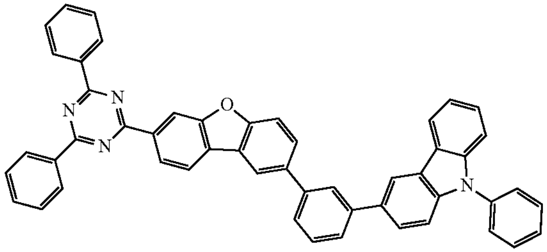 [SMILES: c1ccc(-c2nc(-c3ccccc3)nc(-c3ccc4c(c3)oc3ccc(-c5cccc(-c6ccc7c(c6)c6ccccc6n7-c6ccccc6)c5)cc34)n2)cc1] 48 63% G34 |
| 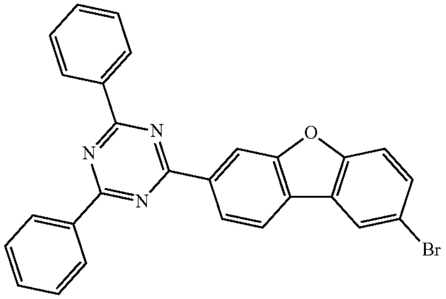 [SMILES: Brc1ccc2oc3cc(-c4nc(-c5ccccc5)nc(-c5ccccc5)n4)ccc3c2c1] | 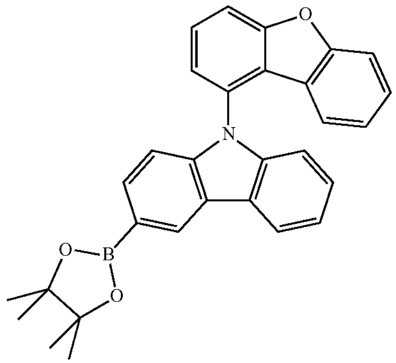 [SMILES: CC1(C)OB(c2ccc3c(c2)c2ccccc2n3-c2cccc3oc4ccccc4c23)OC1(C)C] [1427160-10-8] | 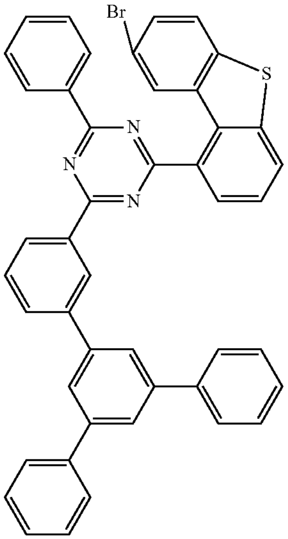 [SMILES: Brc1ccc2sc3cccc(-c4nc(-c5ccccc5)nc(-c5cccc(-c6cc(-c7ccccc7)cc(-c7ccccc7)c6)c5)n4)c3c2c1] 53 56% G35 |

-continued
| Starting material 1 | Starting material 2 | Product/Yield |
| --- | --- | --- |
| 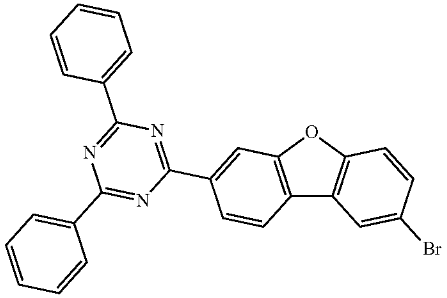 [SMILES: Brc1ccc2oc3cc(-c4nc(-c5ccccc5)nc(-c5ccccc5)n4)ccc3c2c1] | 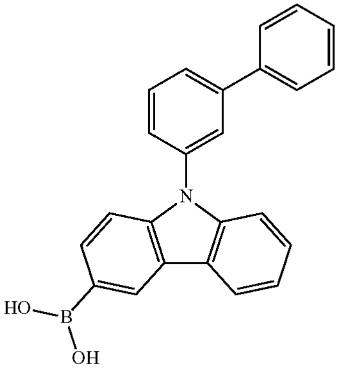 [SMILES: OB(O)c1ccc2c(c1)c1ccccc1n2-c1cccc(-c2ccccc2)c1] [1416814-68-0] | 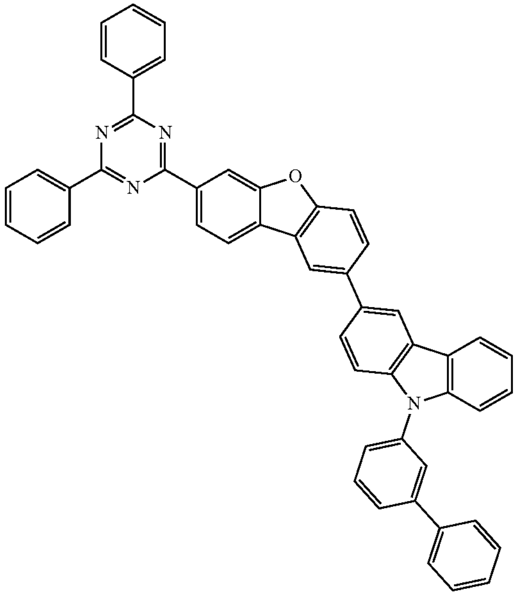 [SMILES: c1ccc(-c2cccc(-n3c4ccccc4c4cc(-c5ccc6oc7cc(-c8nc(-c9ccccc9)nc(-c9ccccc9)n8)ccc7c6c5)ccc43)c2)cc1] 55 66% G36 |

-continued
| Starting material 1 | Starting material 2 | Product/Yield |
|---|---|---|
| 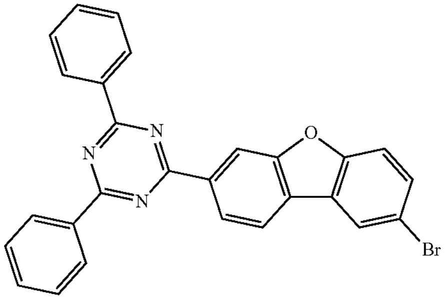 [SMILES: Brc1ccc2oc3cc(-c4nc(-c5ccccc5)nc(-c5ccccc5)n4)ccc3c2c1] | 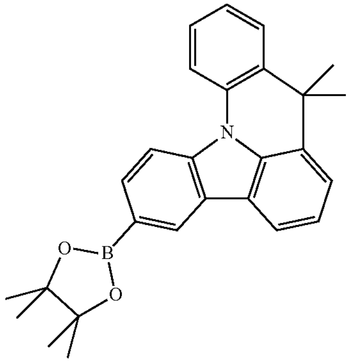 [1456606-40-8] | 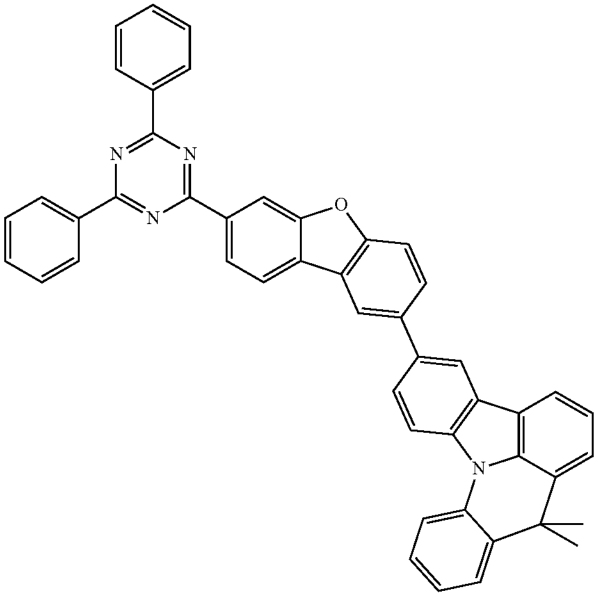 [SMILES: CC1(C)c2ccccc2-n2c3ccc(-c4ccc5oc6cc(-c7nc(-c8ccccc8)nc(-c8ccccc8)n7)ccc6c5c4)cc3c3cccc1c32] 63 58% G37 |

-continued
| Starting material 1 | Starting material 2 | Product/Yield |
| --- | --- | --- |
| 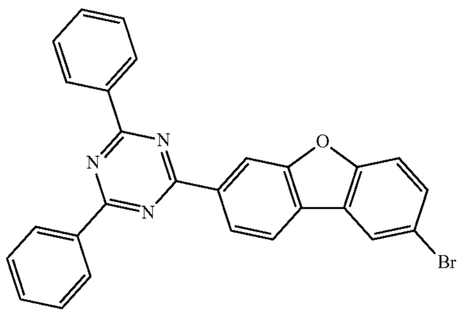 [SMILES: Brc1ccc2oc3cc(-c4nc(-c5ccccc5)nc(-c5ccccc5)n4)ccc3c2c1] | 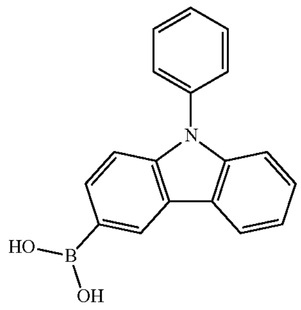 [SMILES: OB(O)c1ccc2c(c1)c1ccccc1n2-c1ccccc1] [854952-58-2] | 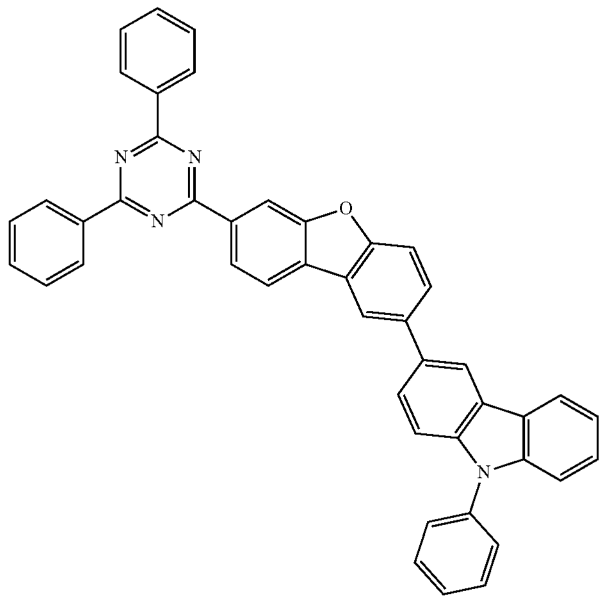 [SMILES: c1ccc(-c2nc(-c3ccccc3)nc(-c3ccc4c(c3)oc3ccc(-c5ccc6c(c5)c5ccccc5n6-c5ccccc5)cc34)n2)cc1] 47 65% G38 |

Example 6

The following compounds can be prepared analogously to Example 2g). The purification here can also be carried out using column chromatography, or other common solvents, such as n-heptane, butanol, acetone, ethyl acetate, acetonitrile, toluene, xylene, dichloromethane, methanol, N,N-dimethylformamide, tetrahydrofuran, ethyl acetate, n-butyl acetate or 1,4-dioxane, can be used for the recrystallisation or hot extraction.

| Starting material 1 | Starting material 2 | Product/Yield |
|---|---|---|
| 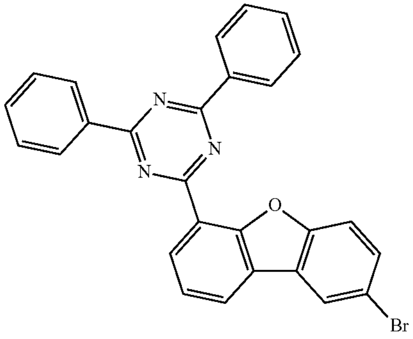 [SMILES: Brc1ccc2oc3c(-c4nc(-c5ccccc5)nc(-c5ccccc5)n4)cccc3c2c1] [1821221-55-9] | 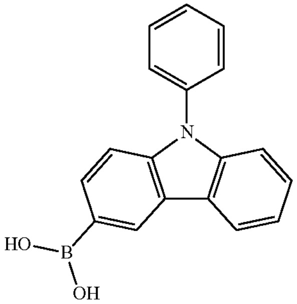 [SMILES: OB(O)c1ccc2c(c1)c1ccccc1n2-c1ccccc1] [854952-58-2] | 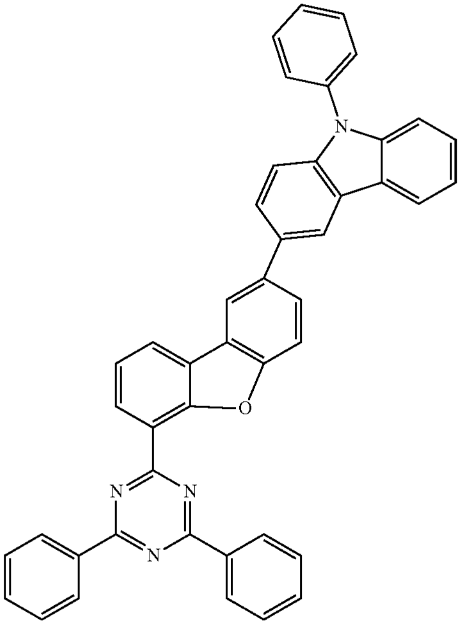 [SMILES: c1ccc(-c2nc(-c3ccccc3)nc(-c3cccc4c3oc3ccc(-c5ccc6c(c5)c5ccccc5n6-c5ccccc5)cc34)n2)cc1] 69 58% G40 |

-continued
| Starting material 1 | Starting material 2 | Product/Yield |
|---|---|---|
| 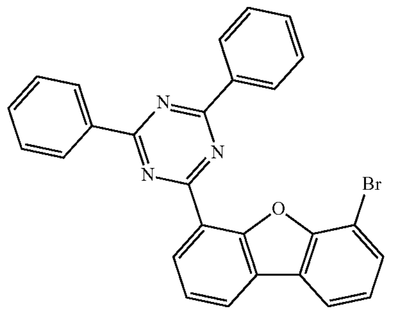 [SMILES: Brc1cccc2c1oc1c(-c3nc(-c4ccccc4)nc(-c4ccccc4)n3)cccc12] [1651196-06-3] | 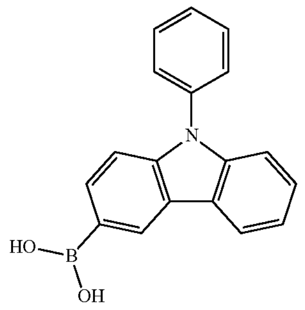 [SMILES: OB(O)c1ccc2c(c1)c1ccccc1n2-c1ccccc1] [854952-58-2] | 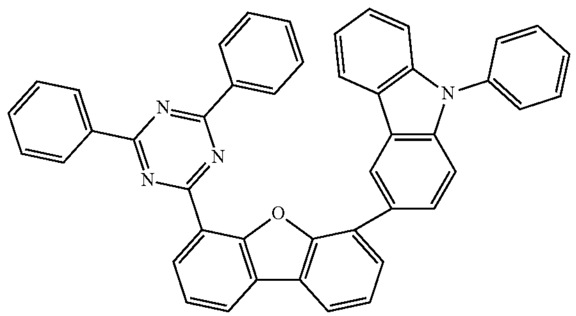 [SMILES: c1ccc(-c2nc(-c3ccccc3)nc(-c3cccc4c3oc3c(-c5ccc6c(c5)c5ccccc5n6-c5ccccc5)cccc34)n2)cc1] 67 49% G41 |
| 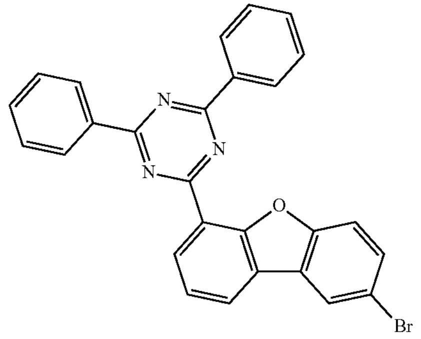 [SMILES: Brc1ccc2oc3c(-c4nc(-c5ccccc5)nc(-c5ccccc5)n4)cccc3c2c1] [1821221-55-9] | 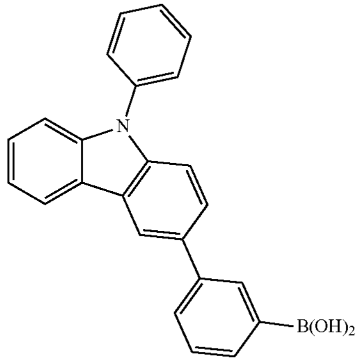 [SMILES: OB(O)c1cccc(-c2ccc3c(c2)c2ccccc2n3-c2ccccc2)c1] [854952-60-6] | 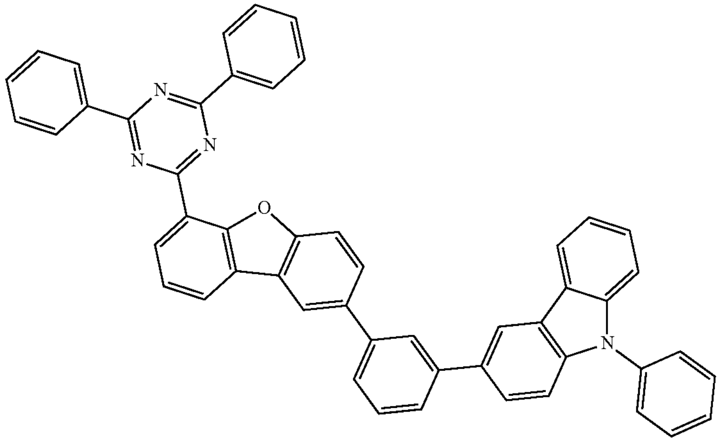 [SMILES: c1ccc(-c2nc(-c3ccccc3)nc(-c3cccc4c3oc3ccc(-c5cccc(-c6ccc7c(c6)c6ccccc6n7-c6ccccc6)c5)cc34)n2)cc1] 70 66% G42 |

-continued
| Starting material 1 | Starting material 2 | Product/Yield |
|---|---|---|
| 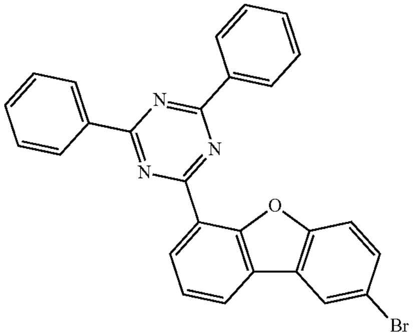 [SMILES: Brc1ccc2oc3c(-c4nc(-c5ccccc5)nc(-c5ccccc5)n4)cccc3c2c1] [1821221-55-9] | 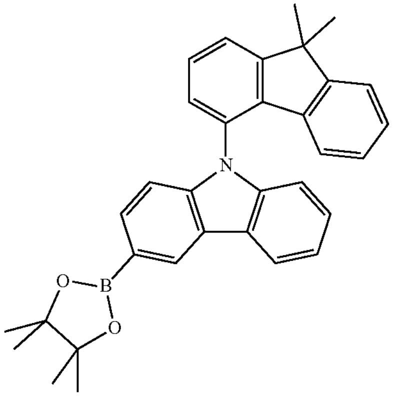 [SMILES: CC1(C)c2ccccc2-c2c(-n3c4ccccc4c4cc(B5OC(C)(C)C(C)(C)O5)ccc43)cccc21] [1802588-7] | 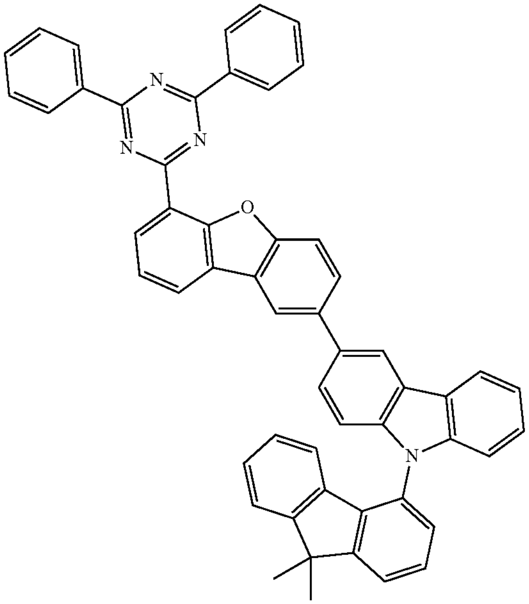 [SMILES: CC1(C)c2ccccc2-c2c(-n3c4ccccc4c4cc(-c5ccc6oc7c(-c8nc(-c9ccccc9)nc(-c9ccccc9)n8)cccc7c6c5)ccc43)cccc21] 76 47% G43 |

-continued
| Starting material 1 | Starting material 2 | Product/Yield |
| --- | --- | --- |
| 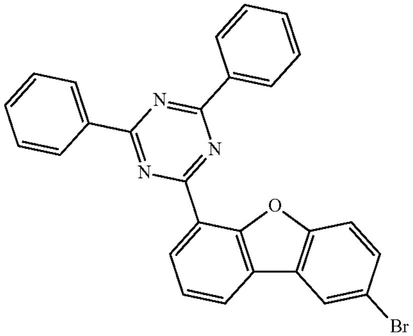 [SMILES: Brc1ccc2oc3c(-c4nc(-c5ccccc5)nc(-c5ccccc5)n4)cccc3c2c1] [1821221-55-9] | 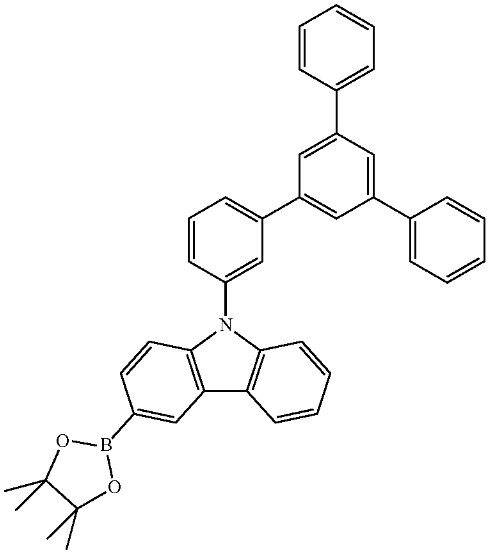 [SMILES: CC1(C)OB(c2ccc3c(c2)c2ccccc2n3-c2cccc(-c3cc(-c4ccccc4)cc(-c4ccccc4)c3)c2)OC1(C)C] [1846559-20-3] | 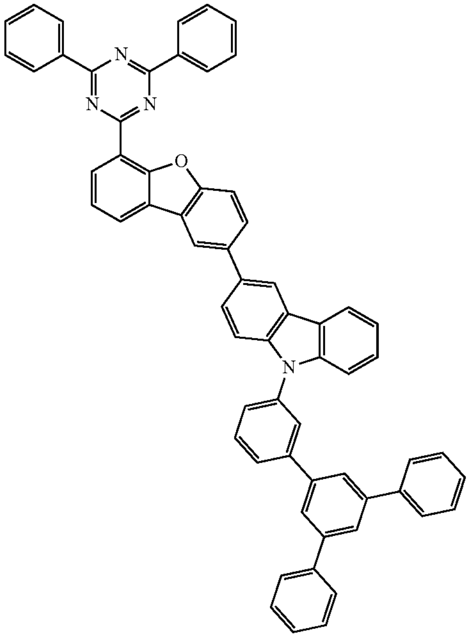 [SMILES: c1ccc(-c2cc(-c3ccccc3)cc(-c3cccc(-n4c5ccccc5c5cc(-c6ccc7oc8c(-c9nc(-c%10ccccc%10)nc(-c%10ccccc%10)n9)cccc8c7c6)ccc54)c3)c2)cc1] 88 51% G44 |

-continued
| Starting material 1 | Starting material 2 | Product/Yield |
|---|---|---|
| 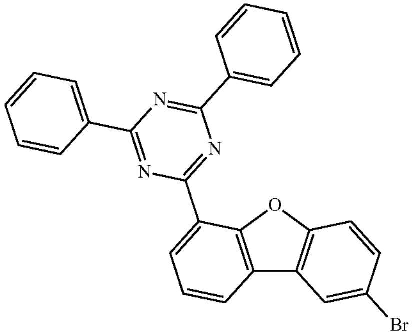 [SMILES: Brc1ccc2oc3c(-c4nc(-c5ccccc5)nc(-c5ccccc5)n4)cccc3c2c1] [1821221-55-9] | 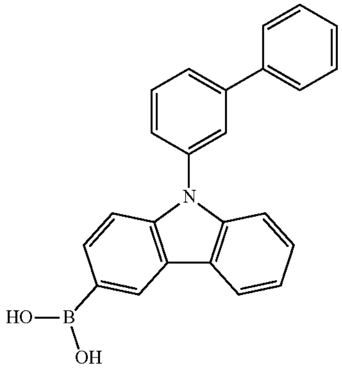 [SMILES: OB(O)c1ccc2c(c1)c1ccccc1n2-c1cccc(-c2ccccc2)c1] [1416814-68-0] | 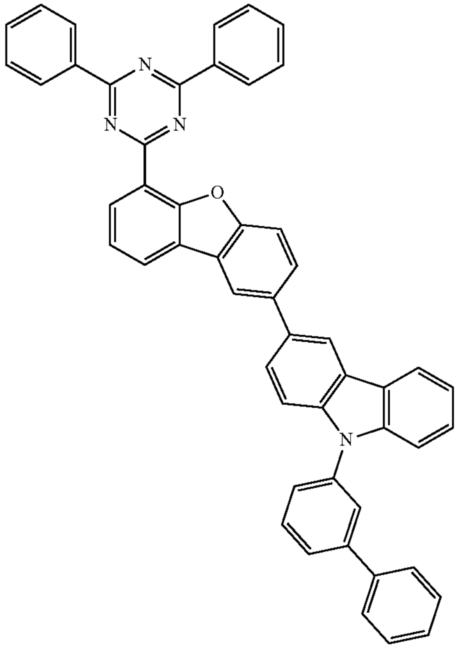 [SMILES: c1ccc(-c2cccc(-n3c4ccccc4c4cc(-c5ccc6oc7c(-c8nc(-c9ccccc9)nc(-c9ccccc9)n8)cccc7c6c5)ccc43)c2)cc1] 74<br>60%<br>G45 |

-continued
| Starting material 1 | Starting material 2 | Product/Yield |
|---|---|---|
| 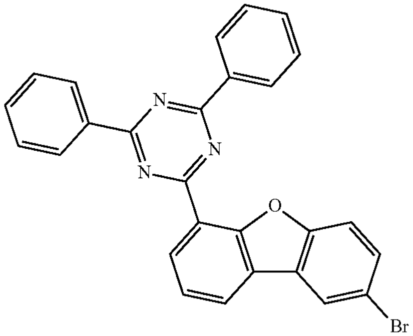 [SMILES: Brc1ccc2oc3c(-c4nc(-c5ccccc5)nc(-c5ccccc5)n4)cccc3c2c1] [1821221-55-9] | 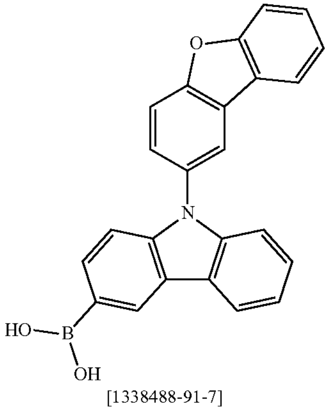 [1338488-91-7] | 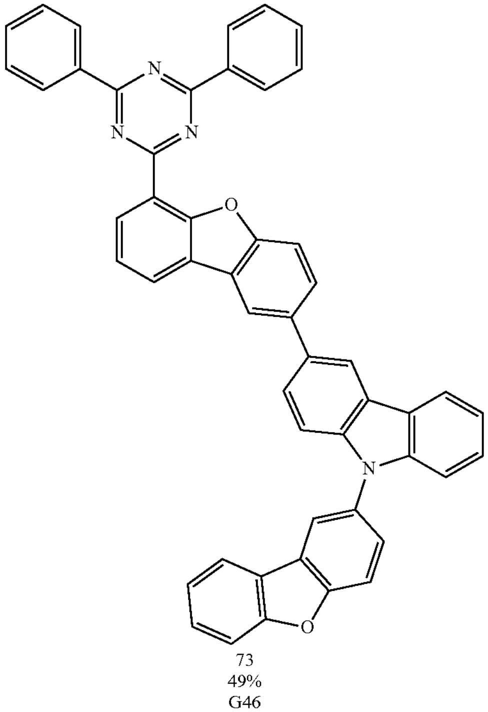 73 49% G46 |

-continued
| Starting material 1 | Starting material 2 | Product/Yield |
| --- | --- | --- |
| 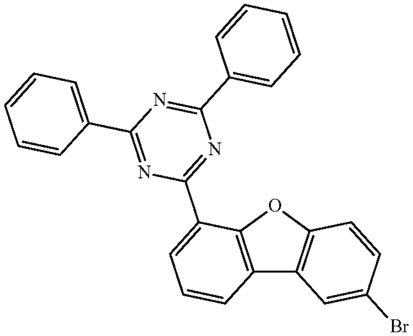 [SMILES: Brc1ccc2oc3c(-c4nc(-c5ccccc5)nc(-c5ccccc5)n4)cccc3c2c1] [1821221-55-9] | 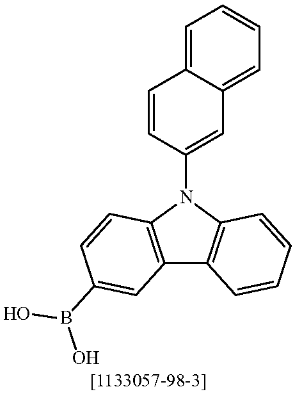 [1133057-98-3] | 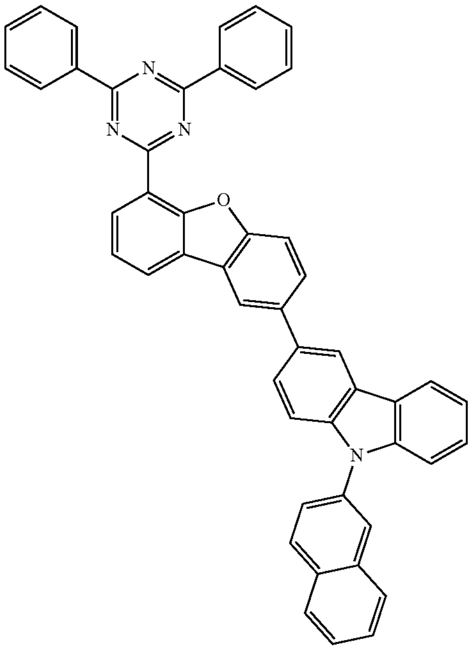 [SMILES: c1ccc(-c2nc(-c3ccccc3)nc(-c3cccc4c3oc3ccc(-c5ccc6c(c5)c5ccccc5n6-c5ccc6ccccc6c5)cc34)n2)cc1] 72 57% G47 |

-continued
| Starting material 1 | Starting material 2 | Product/Yield |
|---|---|---|
| 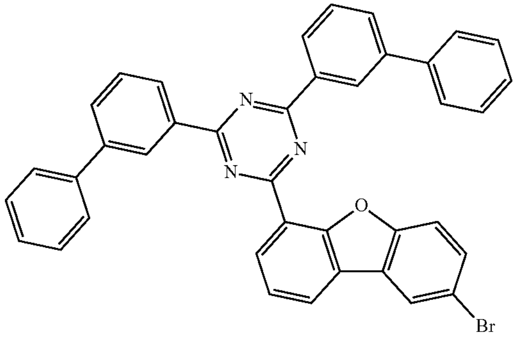 [SMILES: Brc1ccc2oc3c(-c4nc(-c5cccc(-c6ccccc6)c5)nc(-c5cccc(-c6ccccc6)c5)n4)cccc3c2c1] | 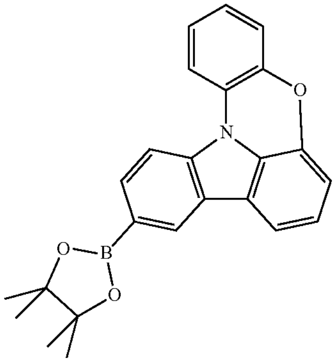 [SMILES: CC1(C)OB(c2ccc3c(c2)c2cccc4c2n3-c2ccccc2O4)OC1(C)C] [1380485-64-2] | 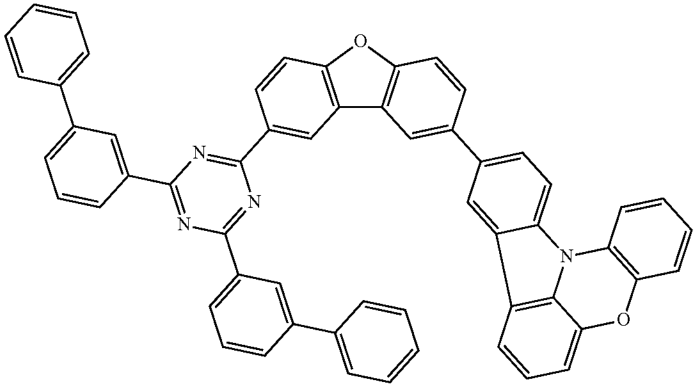 [SMILES: c1ccc(-c2cccc(-c3nc(-c4cccc(-c5ccccc5)c4)nc(-c4ccc5oc6ccc(-c7ccc8c(c7)c7cccc9c7n8-c7ccccc7O9)cc6c5c4)n3)c2)cc1] 68 41% G48 |
| 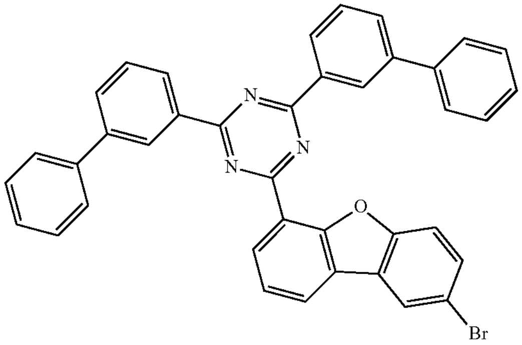 [SMILES: Brc1ccc2oc3c(-c4nc(-c5cccc(-c6ccccc6)c5)nc(-c5cccc(-c6ccccc6)c5)n4)cccc3c2c1] | 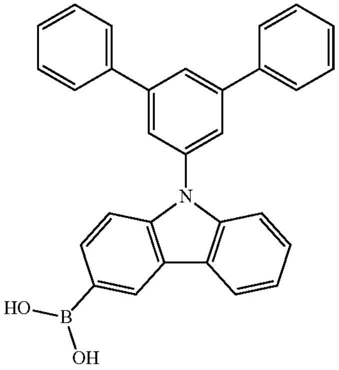 [SMILES: OB(O)c1ccc2c(c1)c1ccccc1n2-c1cc(-c2ccccc2)cc(-c2ccccc2)c1] [1609267-51-7] | 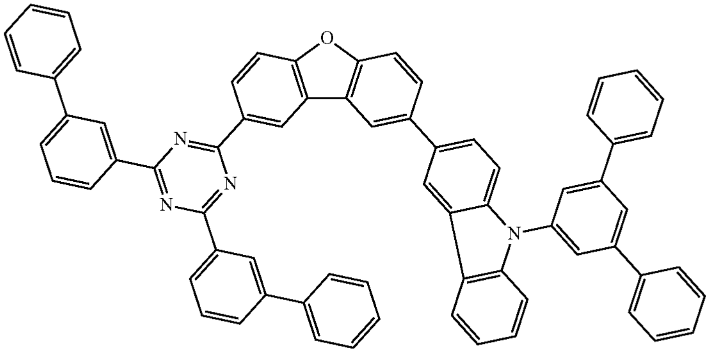 [SMILES: c1ccc(-c2cccc(-c3nc(-c4cccc(-c5ccccc5)c4)nc(-c4ccc5oc6ccc(-c7ccc8c(c7)c7ccccc7n8-c7cc(-c8ccccc8)cc(-c8ccccc8)c7)cc6c5c4)n3)c2)cc1] 77 53% G49 |

The invention claimed is:

1. A composition comprising at least one compound of the formula (1b) or (1c) and at least one compound of the formula (2a)

formula (1b)

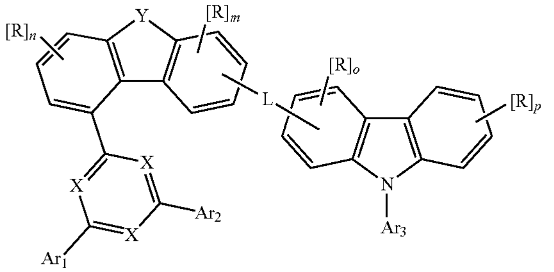

formula (1c)

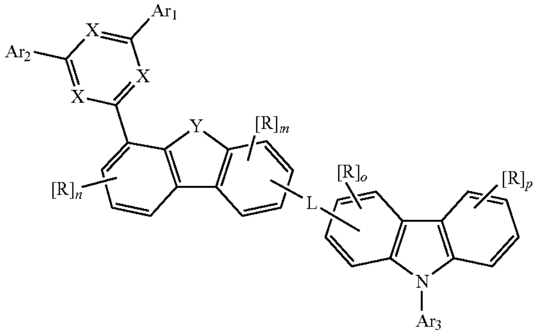

formula (2a)

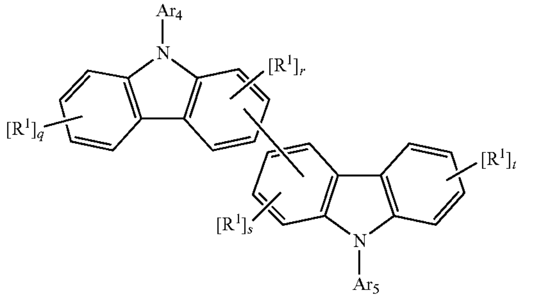

where the following applies to the symbols and indices used:

X is on each occurrence, identically or differently, $CR^0$ or N, with the proviso that at least one group X stands for N;

Y is selected from O or S;

L is on each occurrence, identically or differently a single bond and is linked in position 6 of the dibenzofuran ring or dibenzothiophene ring;

$Ar_1$, $Ar_2$ are in each case, independently of one another on each occurrence, an aryl or heteroaryl group having 5 to 40 aromatic ring atoms, which may be substituted by one or more radicals $R^3$;

$Ar_3$ is an aromatic ring system having 6 to 40 aromatic ring atoms or a heteroaromatic ring system having 10 to 40 aromatic ring atoms, which may be substituted by one or more radicals $R^3$;

$Ar_4$ and $Ar_5$ are in each case, independently of one another, an aromatic ring system having 6 to 40 aromatic ring atoms or a heteroaromatic ring system having 10 to 40 aromatic ring atoms, which may be substituted by one or more radicals $R^3$ with the proviso that $Ar_4$ and $Ar_5$ cannot simultaneously be phenyl;

$R^0$, R, are selected on each occurrence, identically or differently, from the group consisting of H, D, F, Cl, Br, I, CN, $NO_2$, $N(Ar)_2$, $N(R^2)_2$, C(=O)Ar, $C(=O)R^2$, $P(=O)(Ar)_2$, $P(Ar)_2$, $B(Ar)_2$, $Si(Ar)_3$, $Si(R^2)_3$, a straight-chain alkyl, alkoxy or thioalkyl group having 1 to 20 C atoms or a branched or cyclic alkyl, alkoxy or thioalkyl group having 3 to 20 C atoms or an alkenyl group having 2 to 20 C atoms, which may in each case be substituted by one or more radicals $R^2$, where one or more non-adjacent $CH_2$ groups may be replaced by $R^2C{=}CR^2$, $Si(R^2)_2$, C=O, C=S, $C{=}NR^2$, $P(=O)(R^2)$, SO, $SO_2$, $NR^2$, O, S or $CONR^2$ and where one or more H atoms may be replaced by D, F, Cl, Br, I, CN or $NO_2$, an aromatic or heteroaromatic ring system having 5 to 40 aromatic ring atoms, which may in each case be substituted by one or more radicals $R^2$, or an aryloxy or heteroaryloxy group having 5 to 40 aromatic ring atoms, which may be substituted by one or more radicals $R^2$, or an aralkyl or heteroaralkyl group having 5 to 40 aromatic ring atoms, which may be substituted by one or more radicals $R^2$; two substituents $R^0$ and/or R which are bonded to the same carbon atom or to adjacent carbon atoms may optionally form a monocyclic or polycyclic, aliphatic, aromatic or heteroaromatic ring system, which may be substituted by one or more radicals $R^2$;

$R^1$ is selected on each occurrence, identically or differently, from the group consisting of D, F, an alkyl group having 1 to 40 C atoms or an aromatic or heteroaromatic ring system having 5 to 40 aromatic ring atoms, which may be substituted by one or more radicals $R^2$;

$R^2$ is selected on each occurrence, identically or differently, from the group consisting of H, D, F, Cl, Br, I, CN, $NO_2$, $N(Ar)_2$, $NH_2$, $N(R^3)_2$, C(=O)Ar, C(=O)H, $C(=O)R^3$, $P(=O)(Ar)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, which may in each case be substituted by one or more radicals $R^3$, where one or more non-adjacent $CH_2$ groups may be replaced by HC=CH, $R^3C{=}CR^3$, C≡C, $Si(R^3)_2$, $Ge(R^3)_2$, $Sn(R^3)_2$, C=O, C=S, C=Se, $C{=}NR^3$, $P(=O)(R^3)$, SO, $SO_2$, NH, $NR^3$, O, S, CONH or $CONR^3$ and where one or more H atoms may be replaced by D, F, Cl, Br, I, CN or $NO_2$, an aromatic or heteroaromatic ring system having 5 to 60 aromatic ring atoms, which may in each case be substituted by one or more radicals $R^3$, or an aryloxy or heteroaryloxy group having 5 to 60 aromatic ring atoms, which may be substituted by one or more radicals $R^3$, or a combination of these systems, where two or more adjacent substituents $R^2$ may optionally form a monocyclic or polycyclic, aliphatic, aromatic or heteroaromatic ring system, which may be substituted by one or more radicals $R^3$;

$R^3$ is selected on each occurrence, identically or differently, from the group consisting of H, D, F, CN, an aliphatic hydrocarbon radical having 1 to 20 C atoms or an aromatic or heteroaromatic ring system having 5 to 30 aromatic ring atoms, in which one or more H atoms may be replaced by D, F, Cl, Br, I or CN and which may be substituted by one or more alkyl groups, each having 1 to 4 carbon atoms; two or more adjacent substituents $R^3$ may form a mono- or polycyclic, aliphatic ring system with one another;

Ar is on each occurrence, identically or differently, an aromatic or heteroaromatic ring system having 5 to 30 aromatic ring atoms, which may be substituted by one or more non-aromatic radicals $R^3$; two radicals Ar which are bonded to the same N atom, P atom or B atom may also be bridged to one another by a single bond or a bridge selected from $N(R^3)$, $C(R^3)_2$, O or S, and n and m, independently of one another, denote 0, 1, 2 or 3;

p and o in each case, independently of one another, denote 0, 1, 2, or 3;

q and t in each case, independently of one another, denote 0, 1, 2, 3, or 4 and r and s in each case, independently of one another, denote 0, 1, 2, or 3.

2. The composition according to claim 1, wherein the compound of the formula (1b) or (1c) corresponds to the formula (1c).

3. The composition according to claim 1, wherein one of the substituents $Ar_4$ or $Ar_5$ denotes an aromatic ring system having 6 to 40 aromatic ring atoms or a heteroaromatic ring system having 10 to 40 aromatic ring atoms, which may be substituted by one or more radicals $R^3$, and the other substituent denotes an aromatic ring system having 6 to 40 aromatic ring atoms, which may be substituted by one or more radicals $R^3$, with the proviso that $Ar_4$ and $Ar_5$ cannot simultaneously be phenyl.

4. The composition according to claim 1, wherein the substituents $Ar_4$ and $Ar_5$ in each case, independently of one another, denote an aromatic ring system having 6 to 40 aromatic ring atoms, which may be substituted by one or more radicals $R^3$, with the proviso that $Ar_4$ and $Ar_5$ are not simultaneously phenyl.

5. The composition according to claim 1, wherein $Ar_3$ is selected from the aromatic or heteroaromatic ring systems Ar-1 to Ar-22

Ar-1

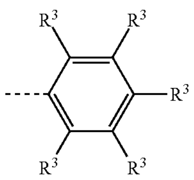

Ar-2

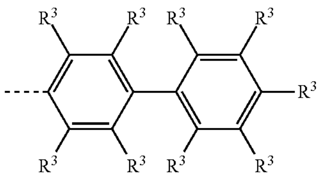

Ar-3

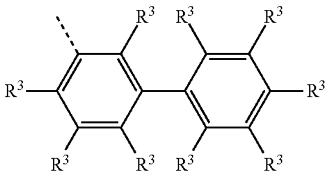

-continued

Ar-4

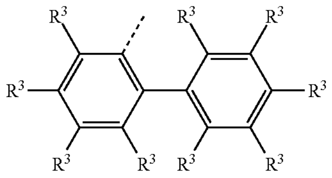

Ar-5

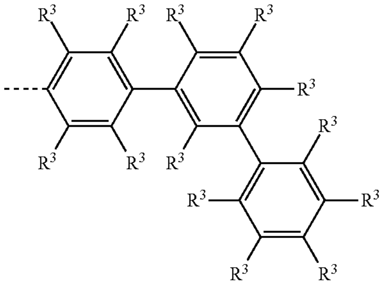

Ar-6

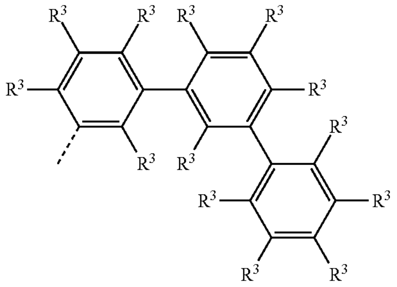

Ar-7

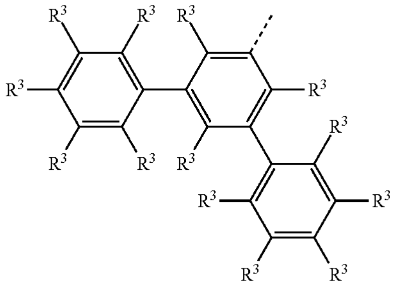

Ar-8

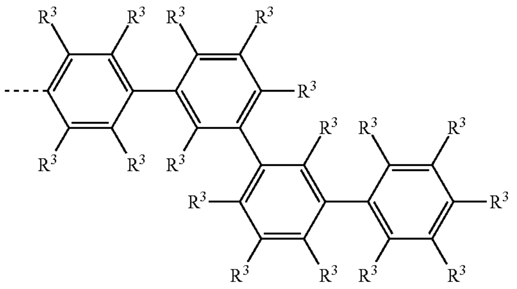

-continued
Ar-9
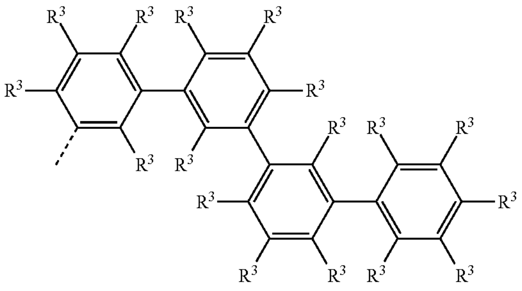
Ar-10
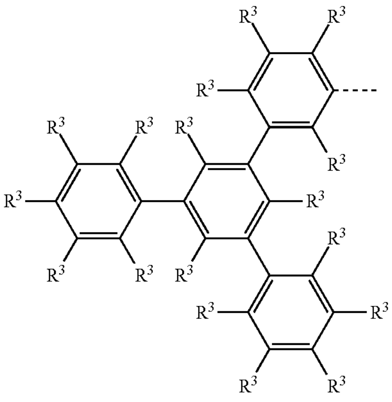
Ar-11
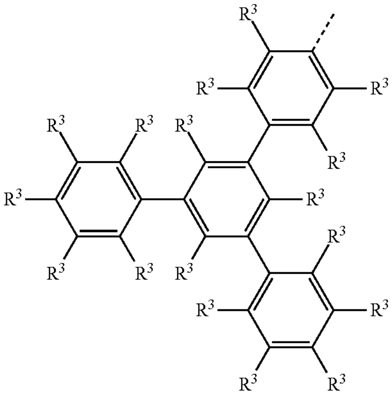
Ar-12
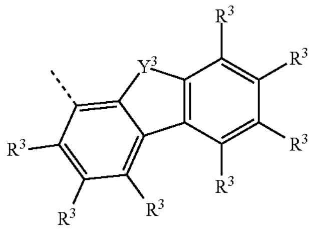
Ar-13
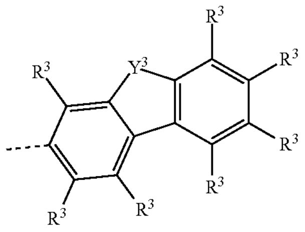
-continued
Ar-14
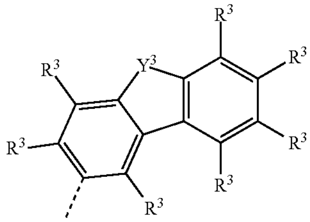
Ar-15
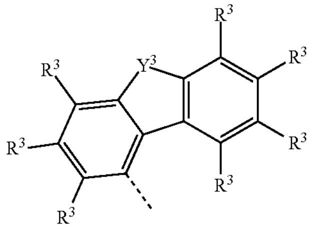
Ar-16
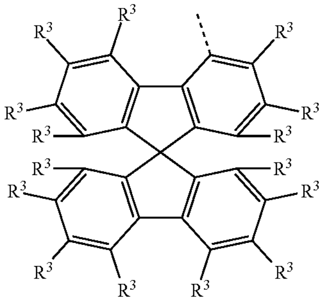
Ar-17
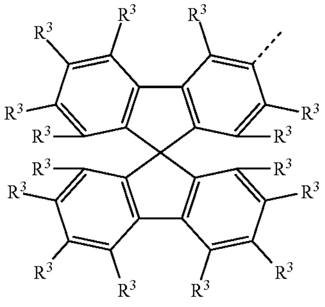
Ar-18
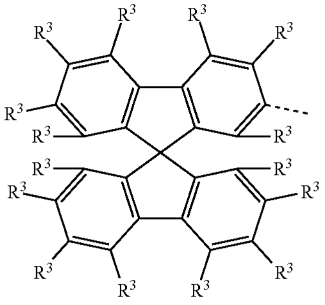

-continued

Ar-19

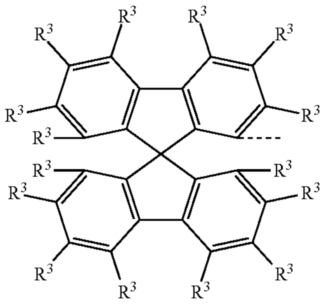

Ar-20

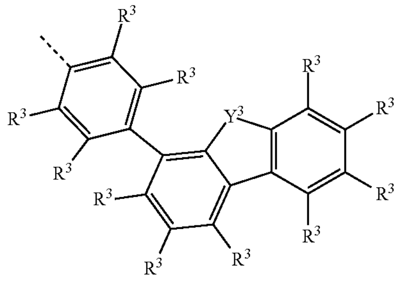

Ar-21

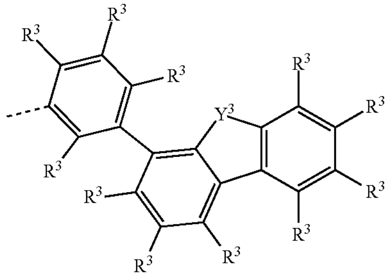

Ar-22

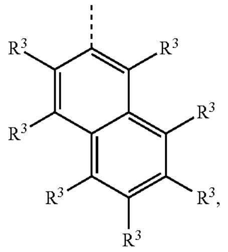

$Y^3$ on each occurrence, identically or differently, denotes O, S or $C(CH_3)_2$;

the dashed bond represents the bond to the N atom, $Ar_4$ and $Ar_5$ are in each case, independently of one another, an aromatic ring system having 6 to 40 aromatic ring atoms or a heteroaromatic ring system having 10 to 40 aromatic ring atoms, which may be substituted by one or more radicals $R^3$, with the proviso that $Ar_4$ and $Ar_5$ cannot simultaneously be phenyl.

6. The composition according to claim 1, wherein the compounds of formula (2a) is selected from the following compounds

89

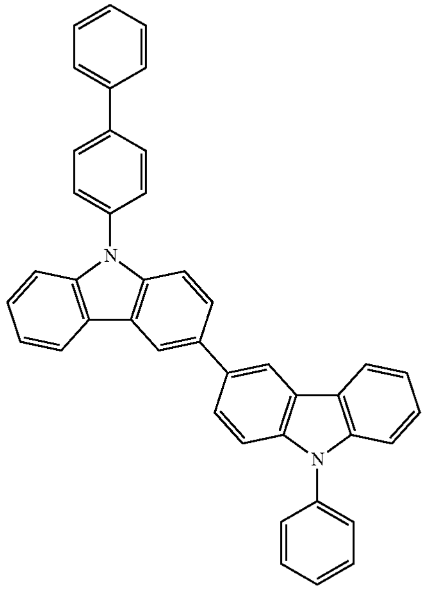

90

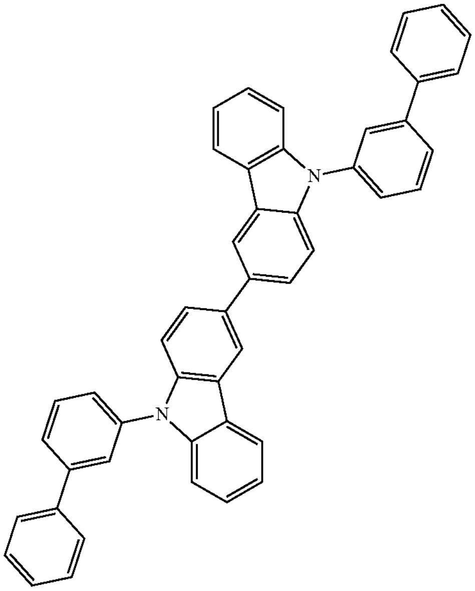

-continued
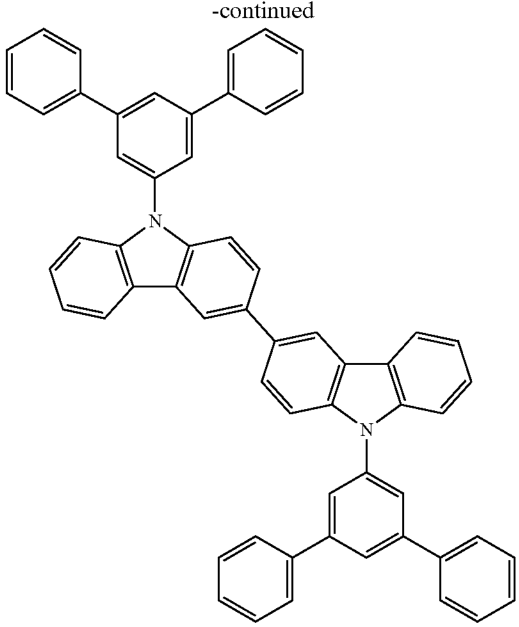
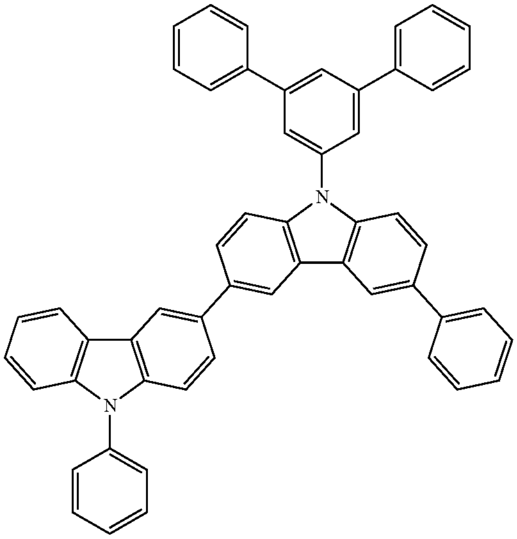
-continued
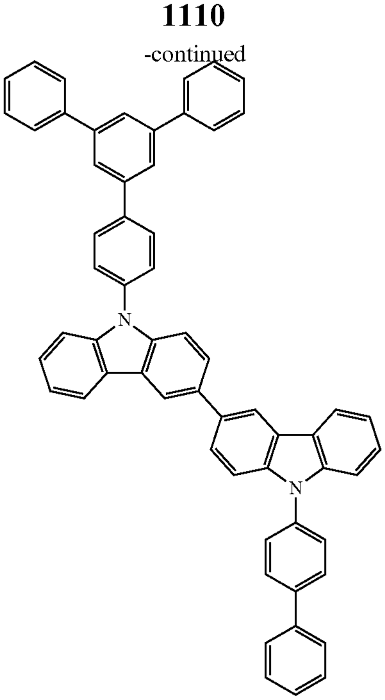
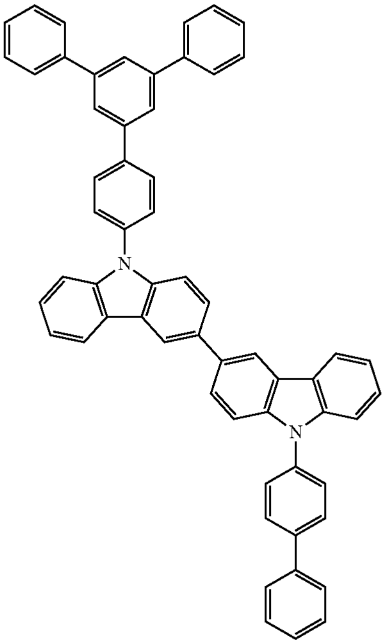

-continued
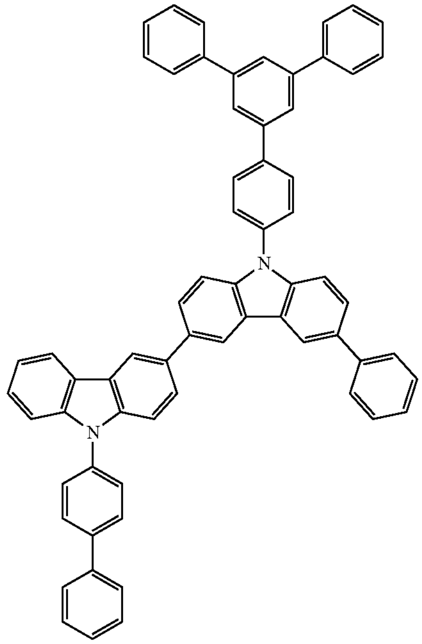
-continued
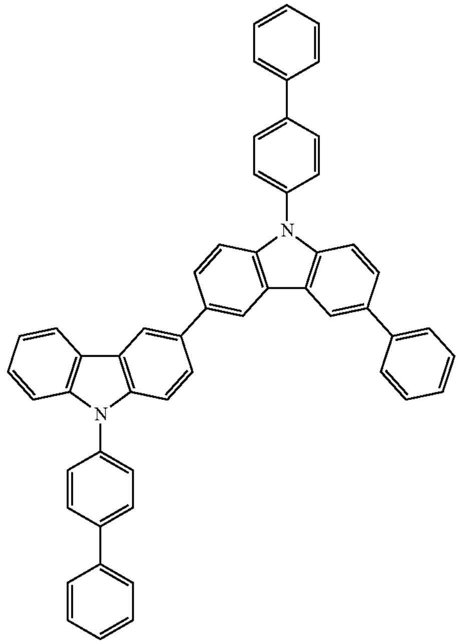
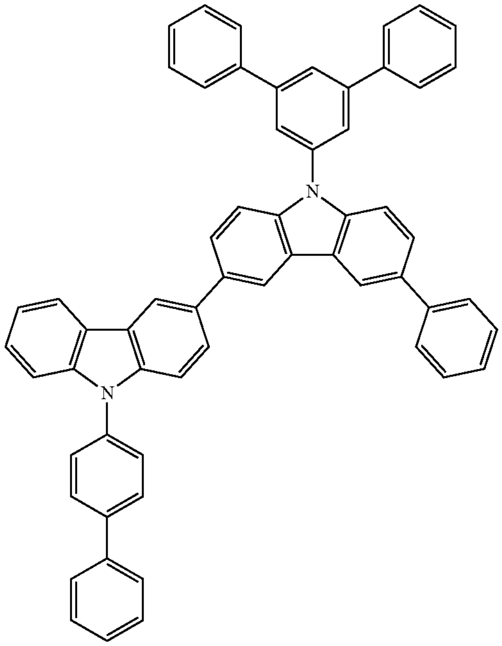
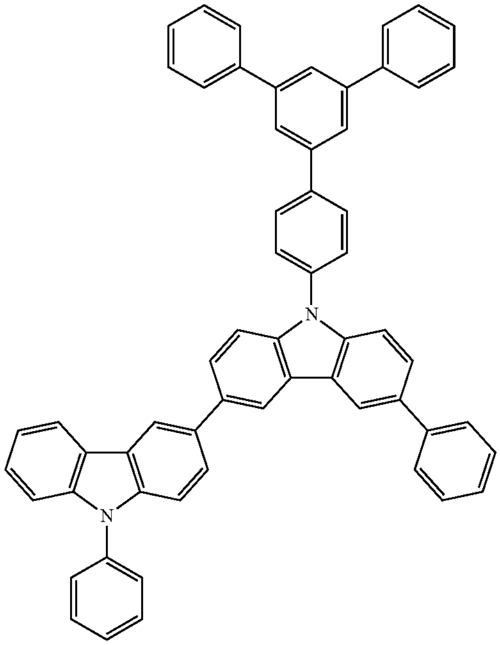

-continued
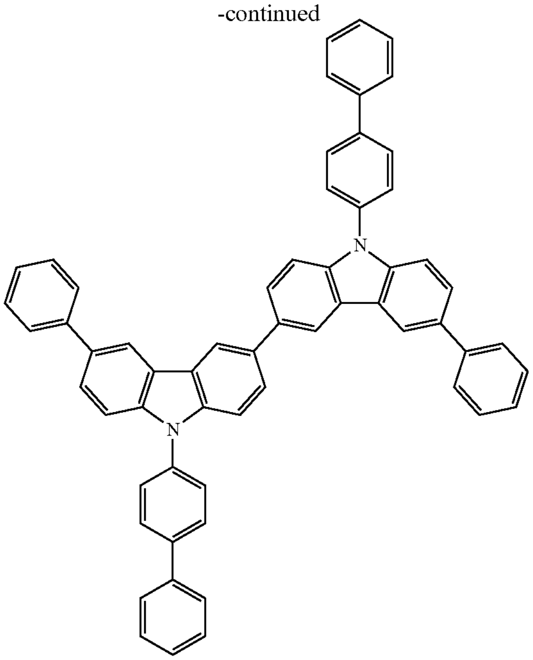
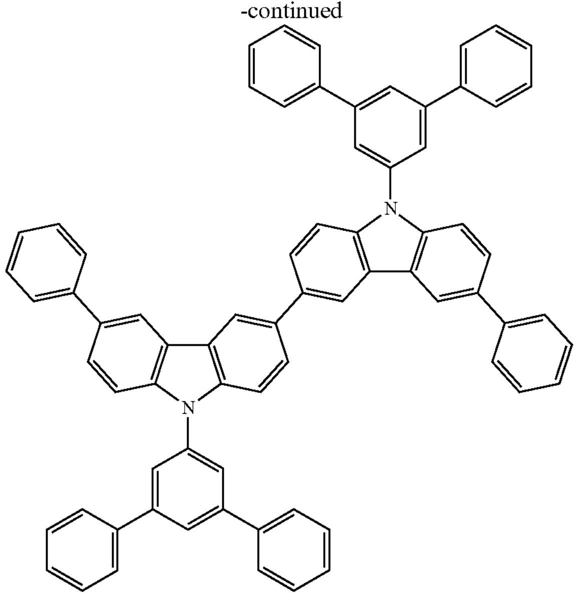
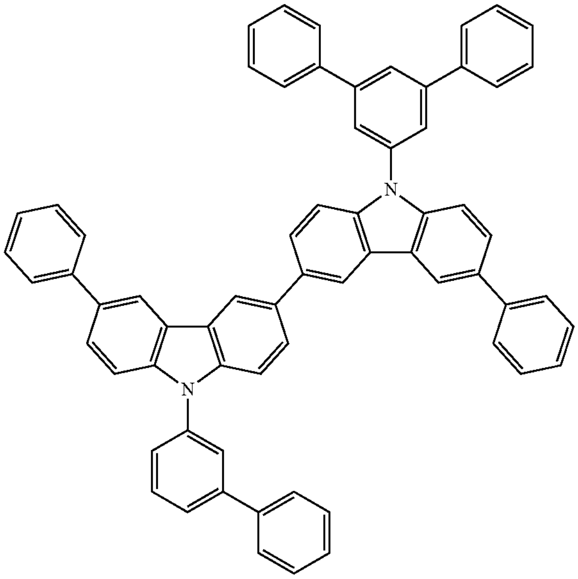
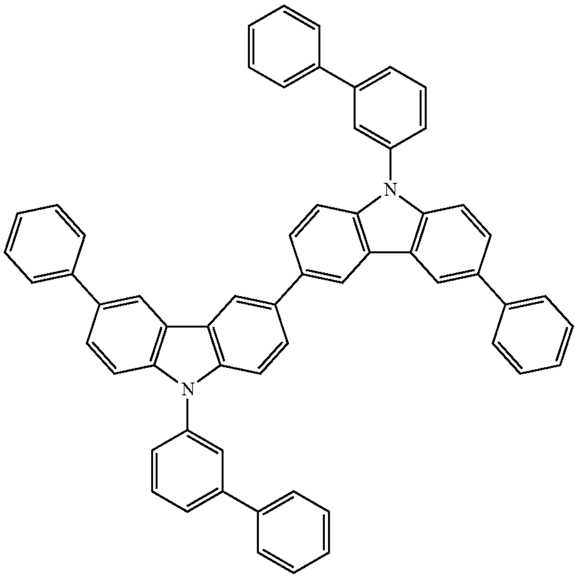
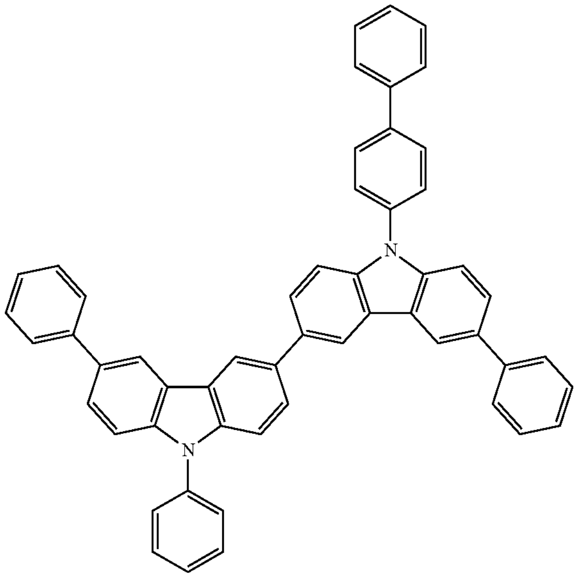

-continued
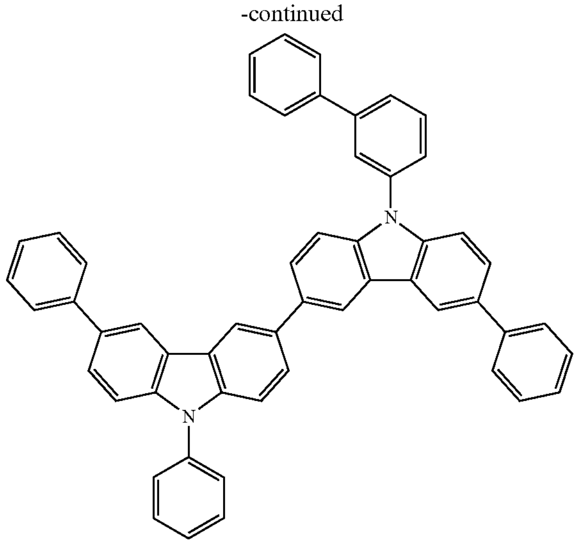
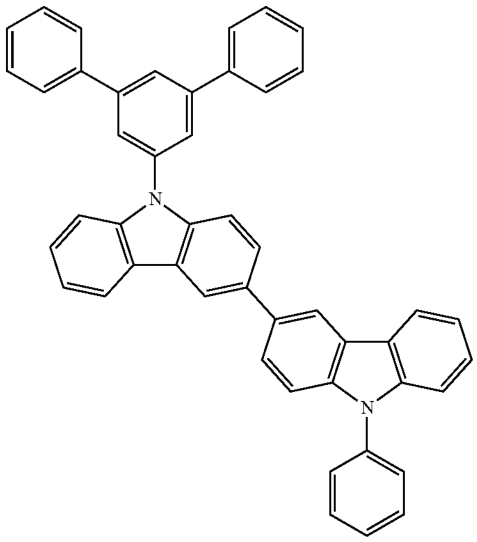
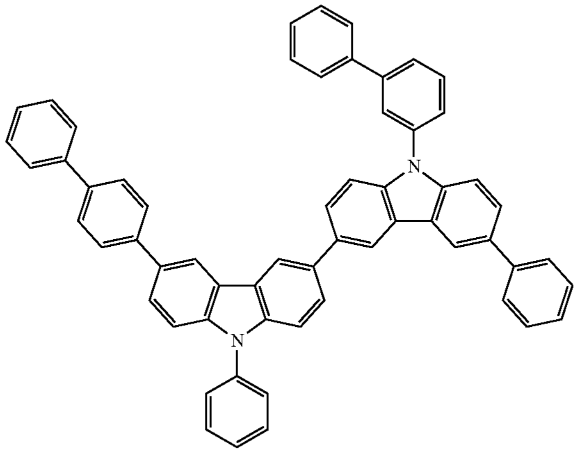
-continued
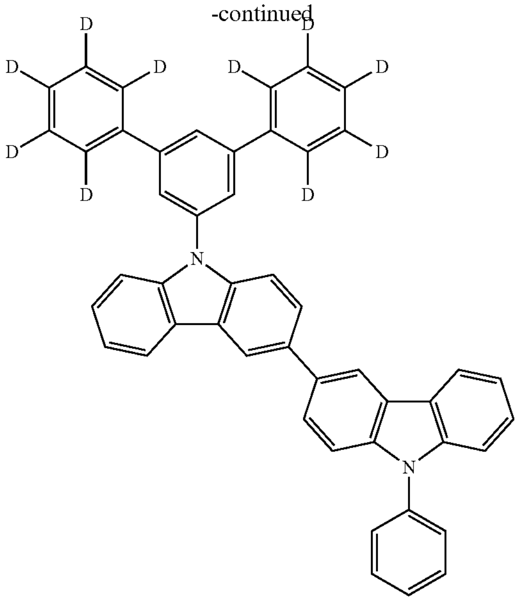
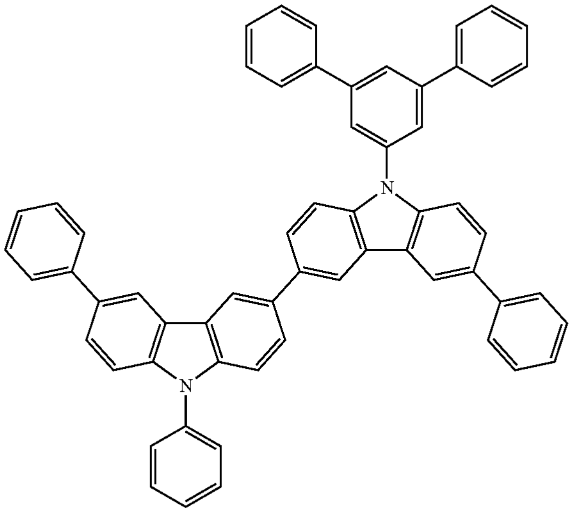
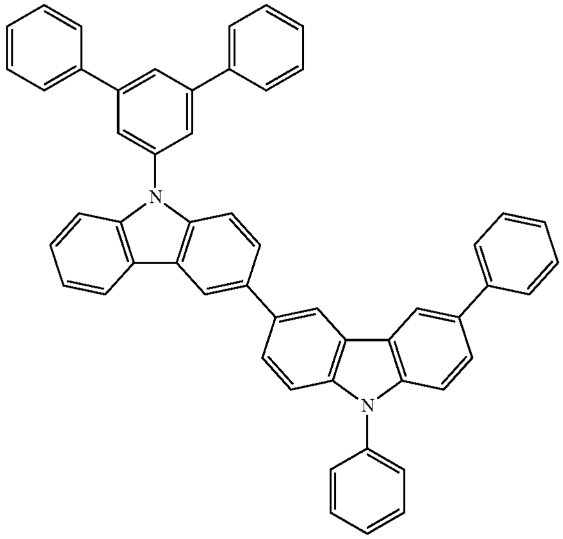

-continued
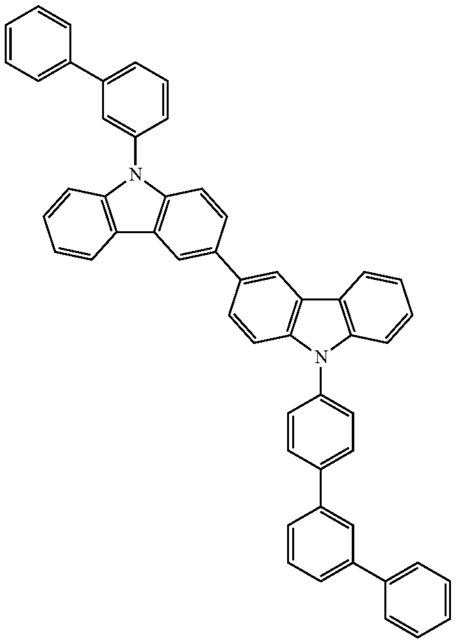
-continued
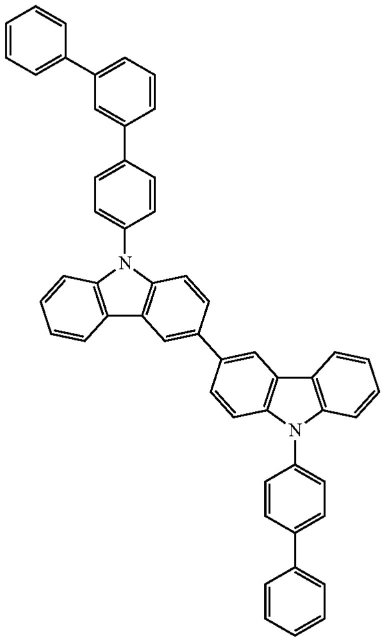
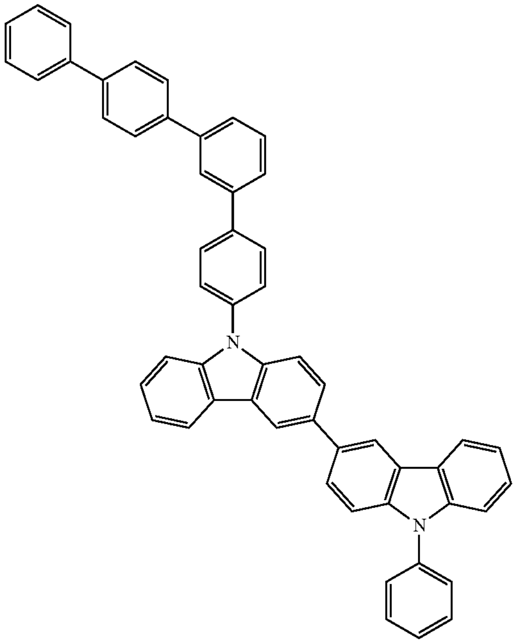
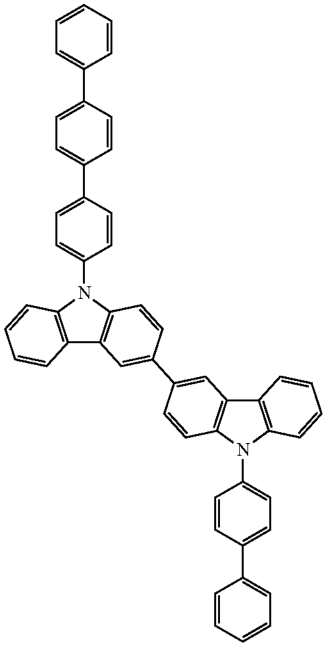

-continued
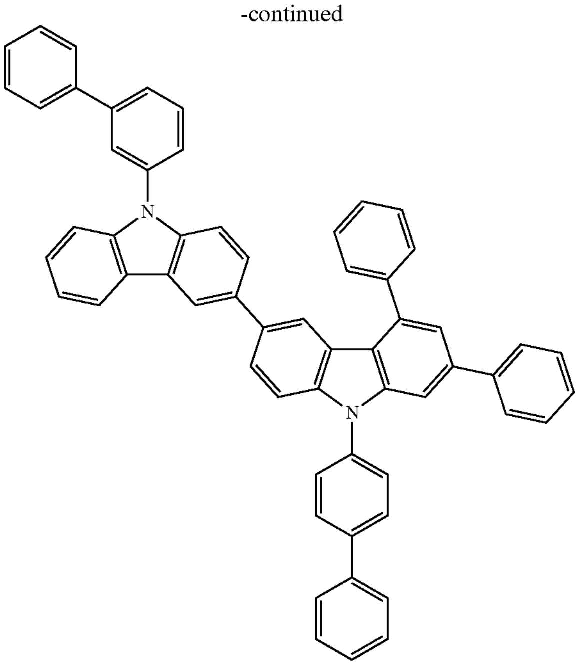
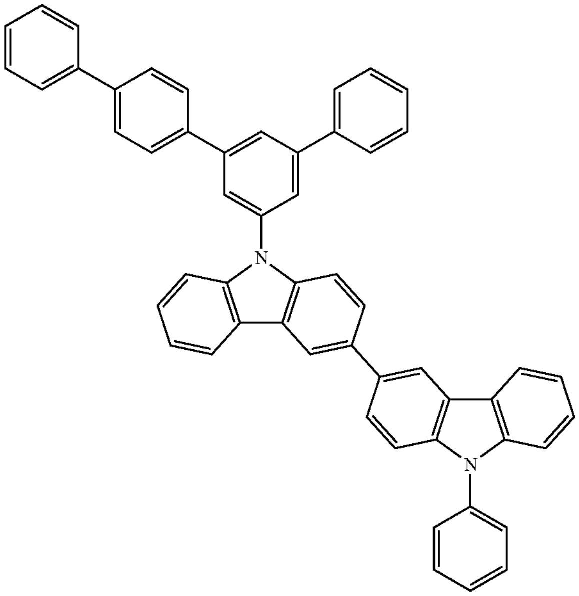
-continued
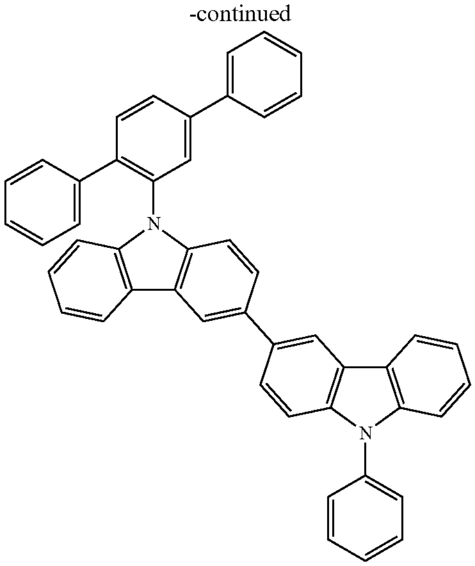
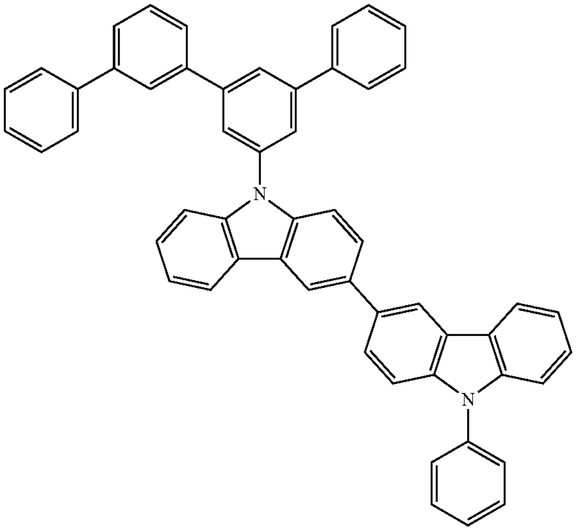
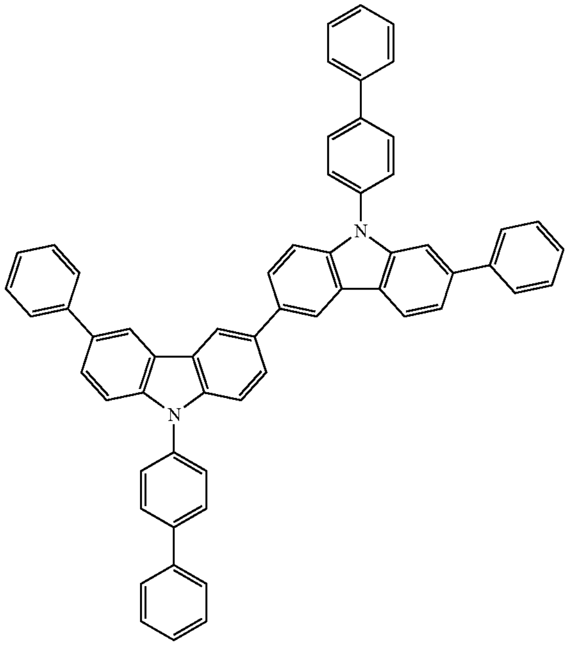

-continued
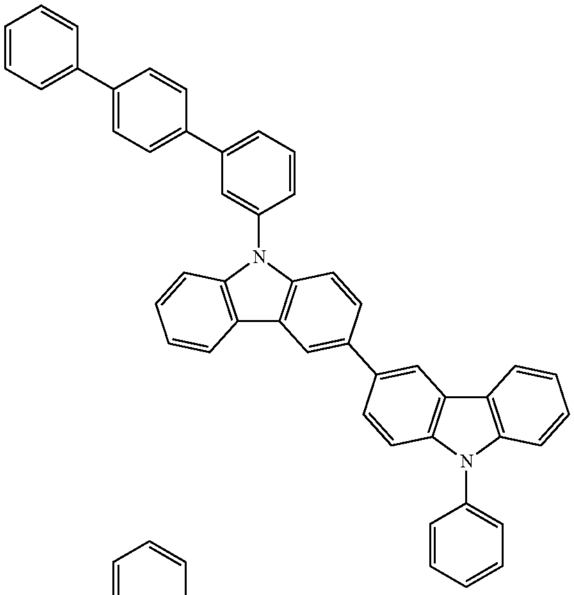
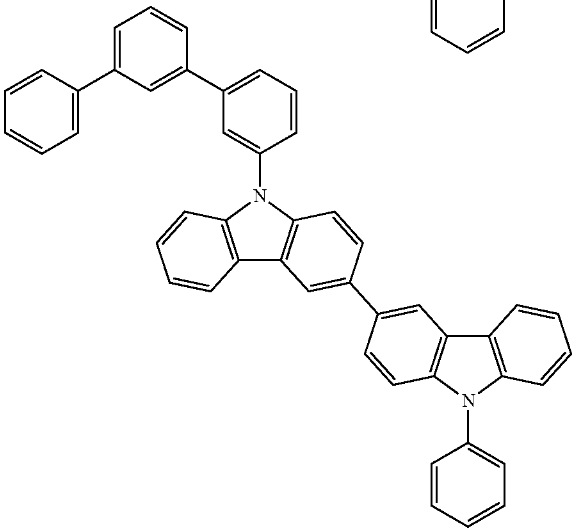
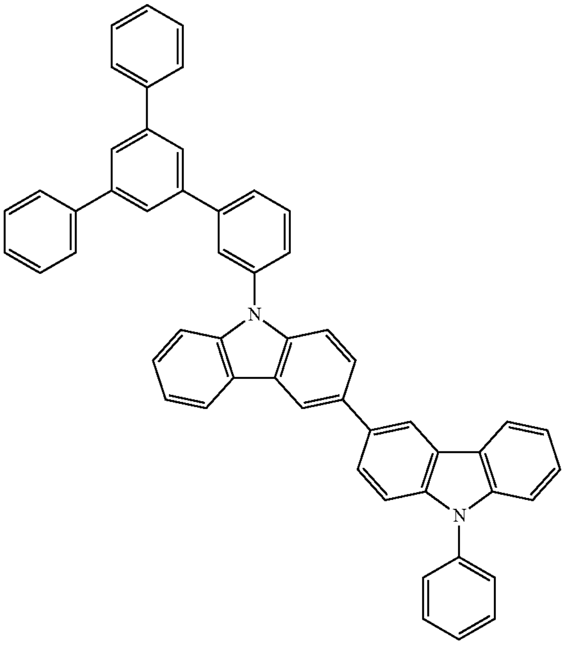
-continued
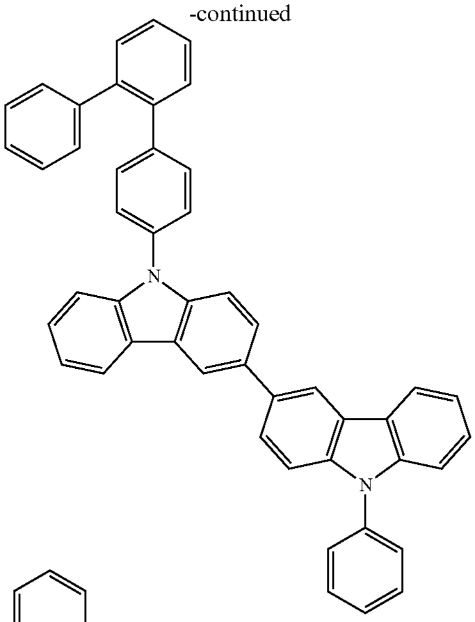
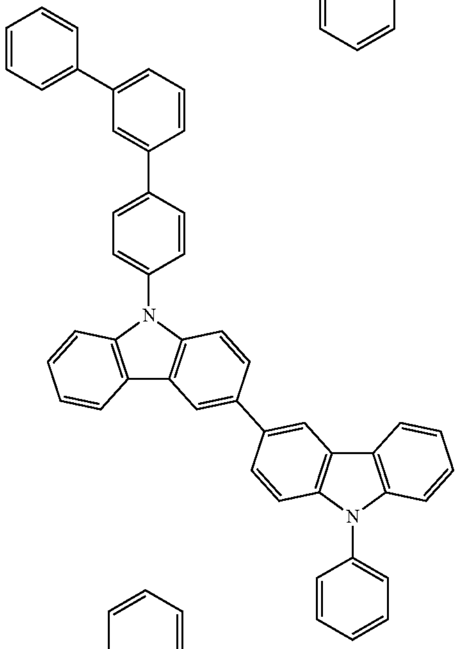
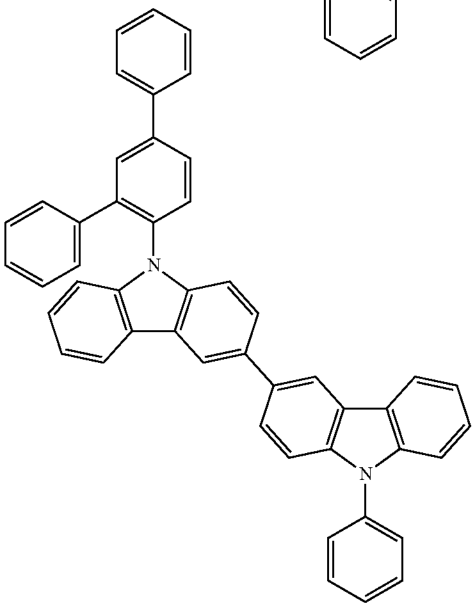

-continued
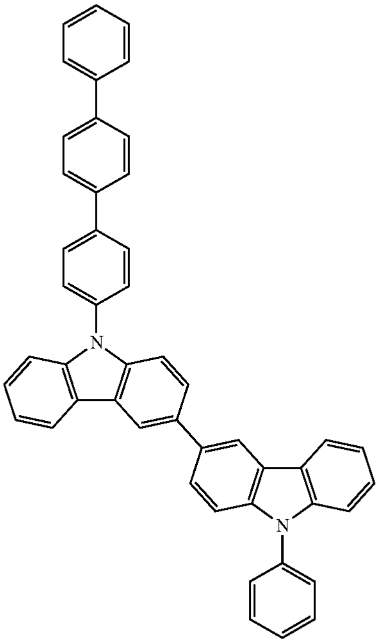
-continued
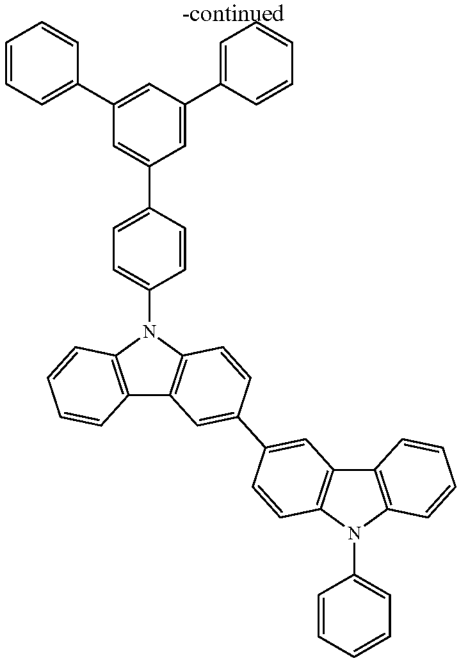
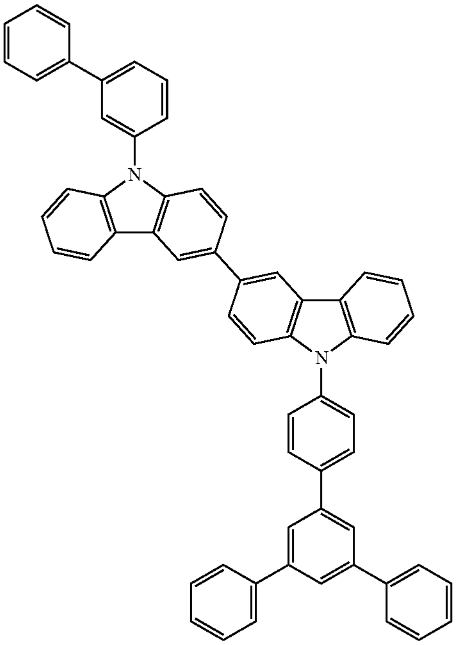
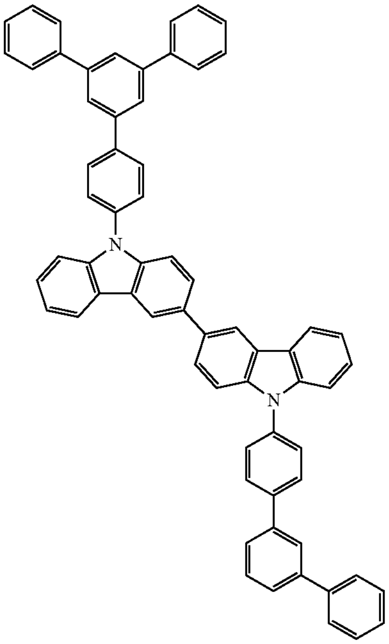

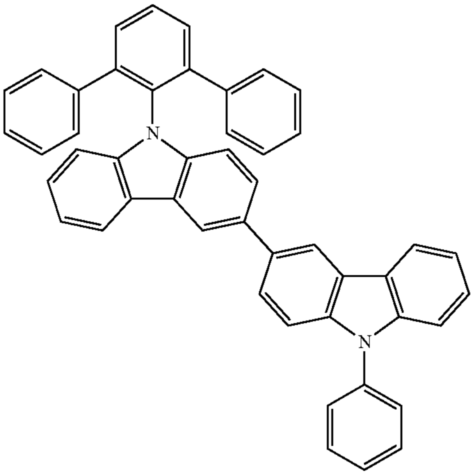
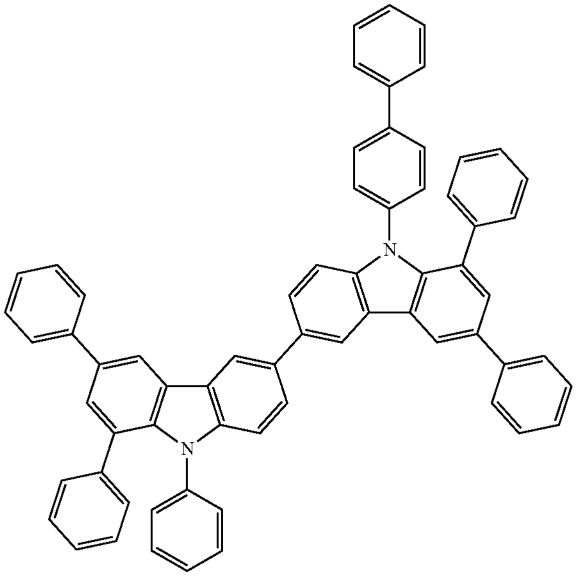
96
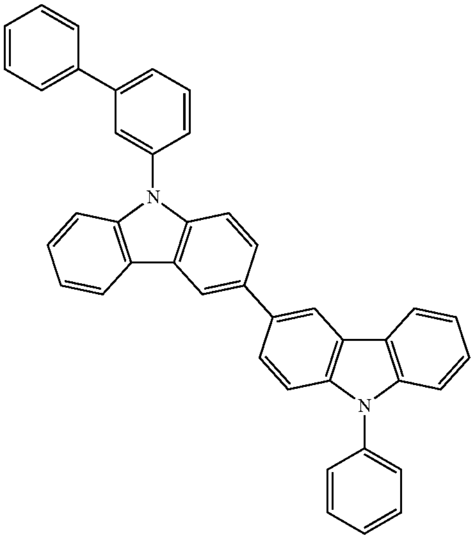
-continued
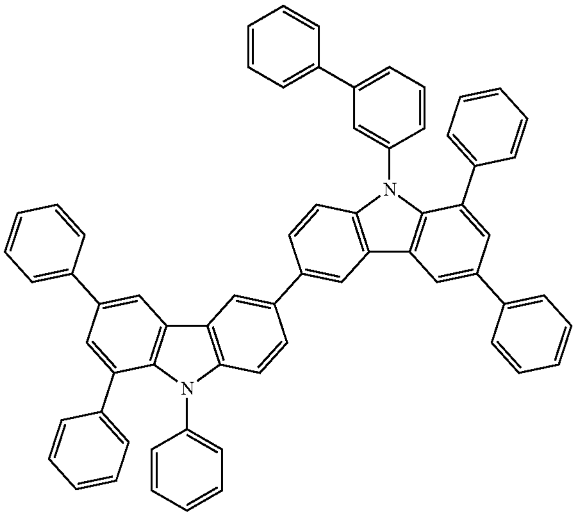
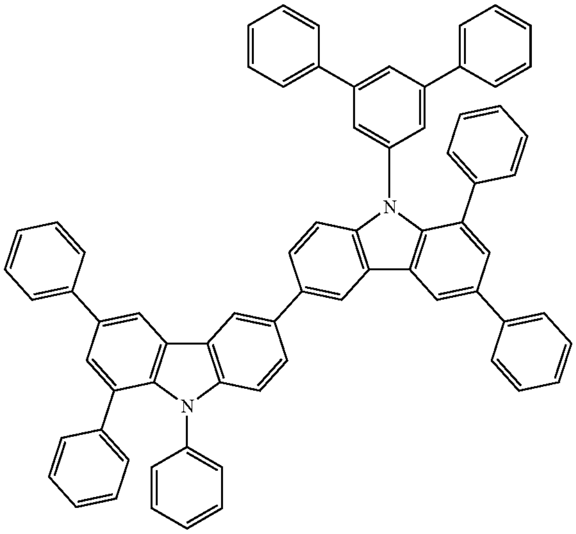
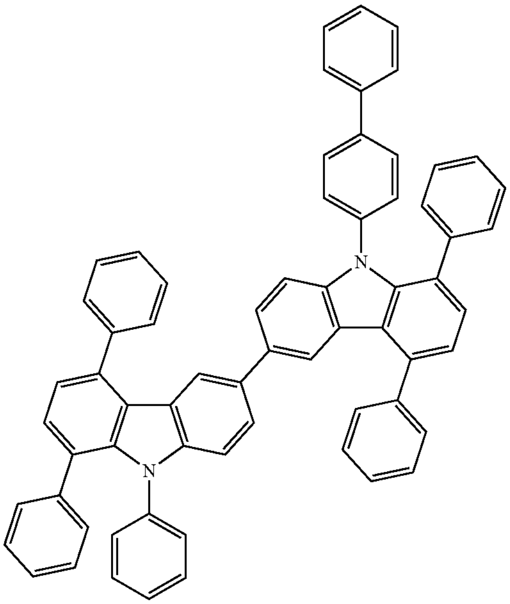

-continued
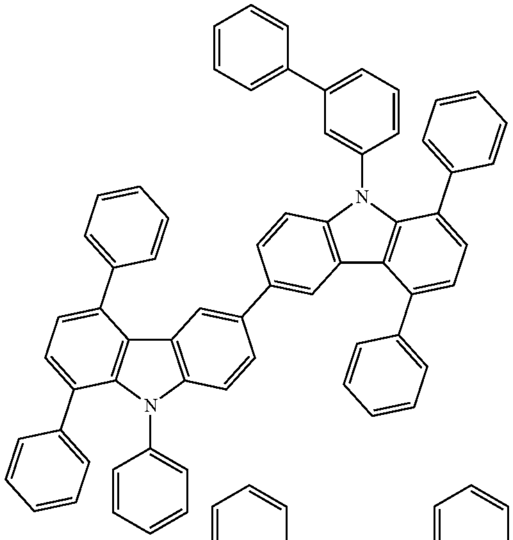
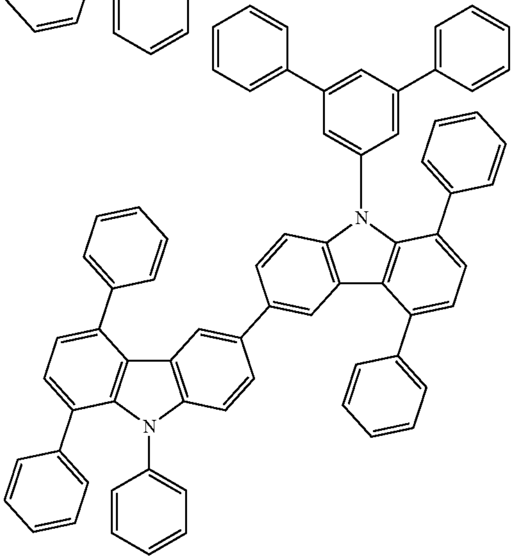
-continued
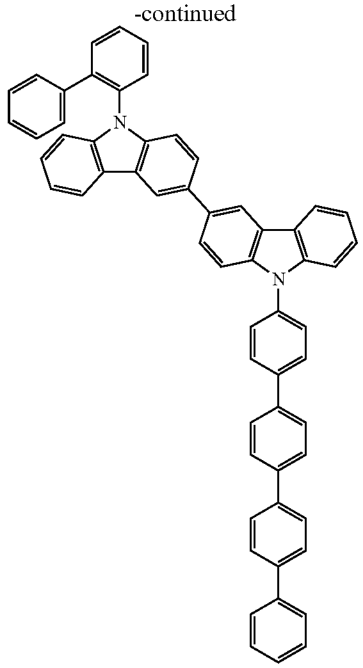
91
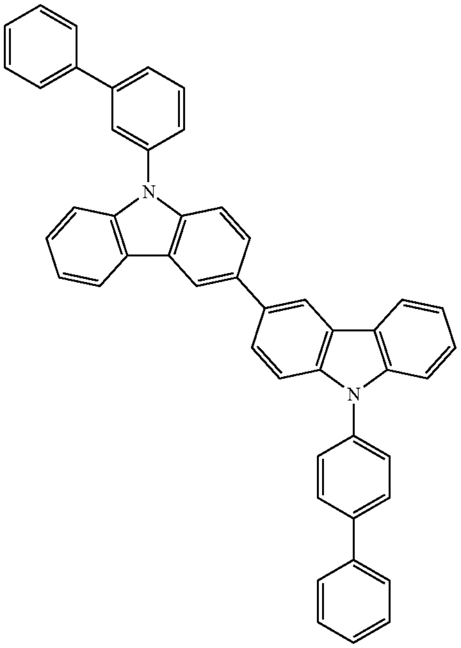
92
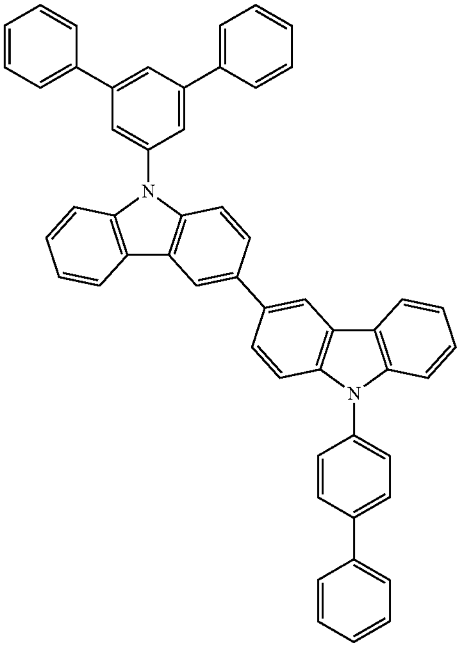

-continued
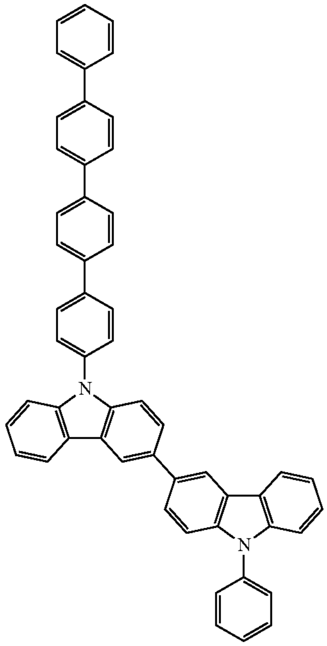
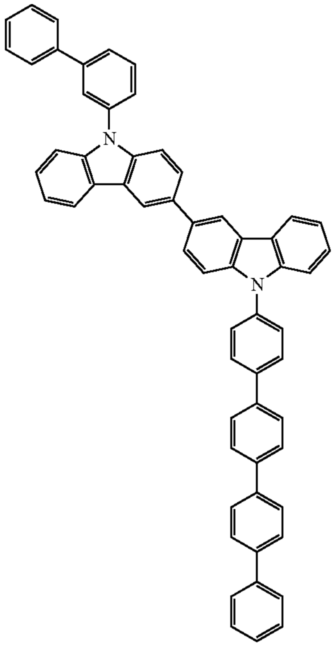
-continued
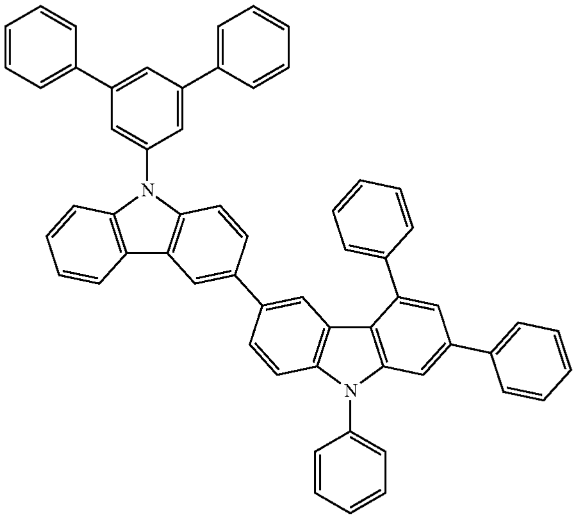
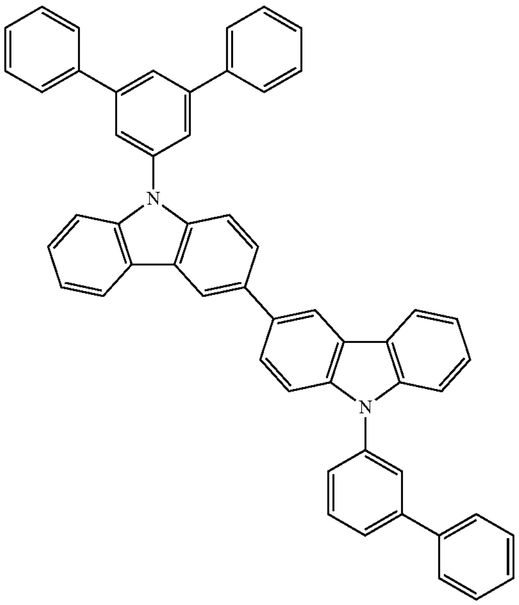
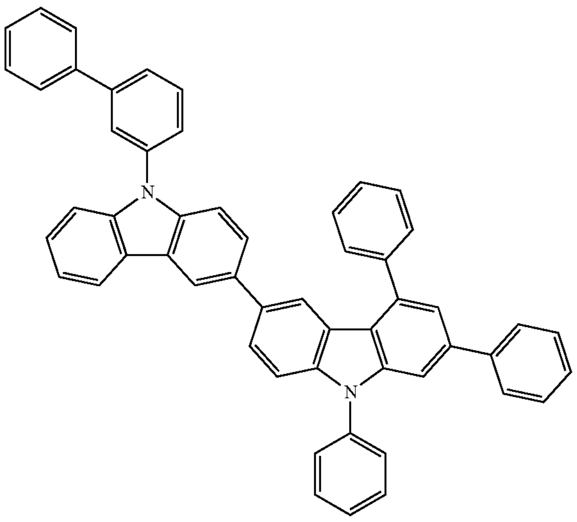

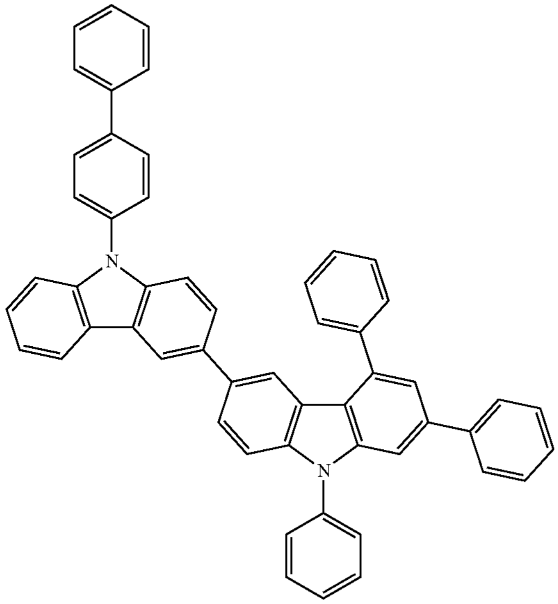
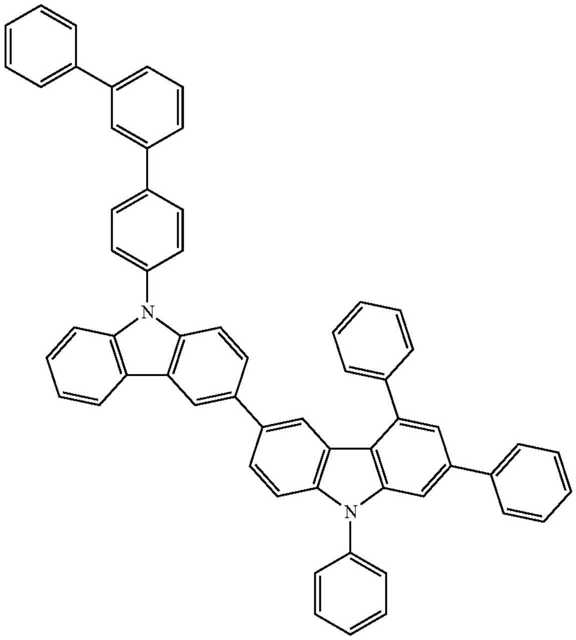
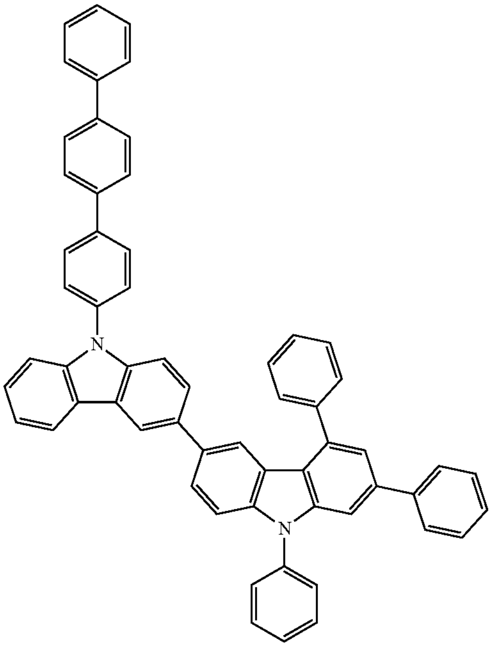
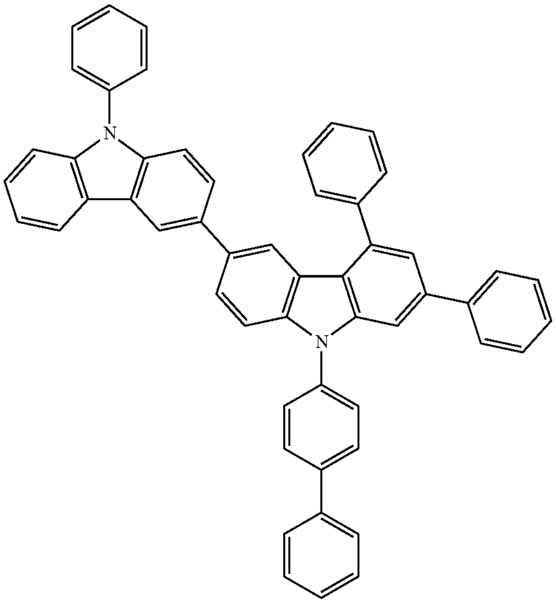

-continued
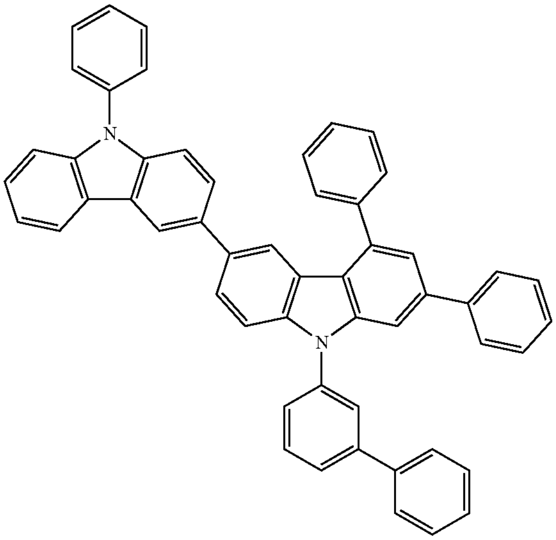
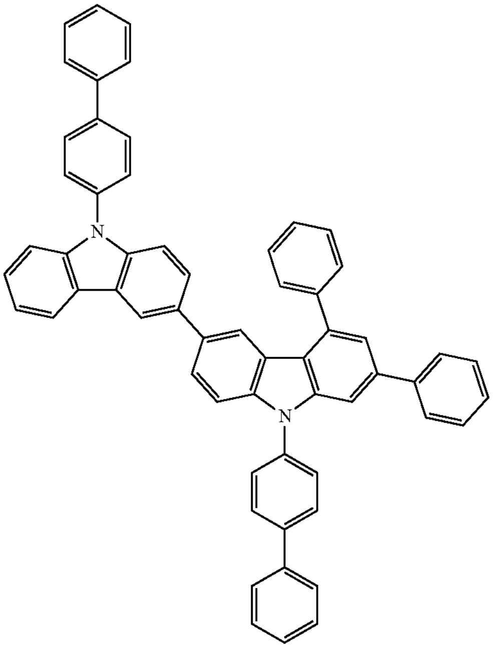
-continued
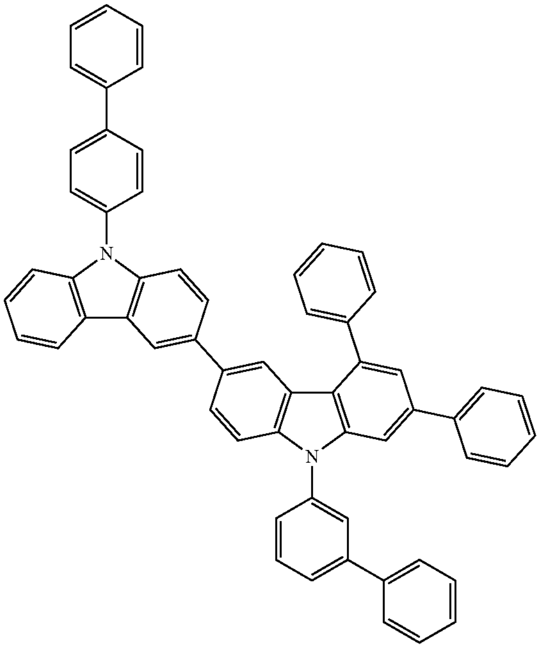
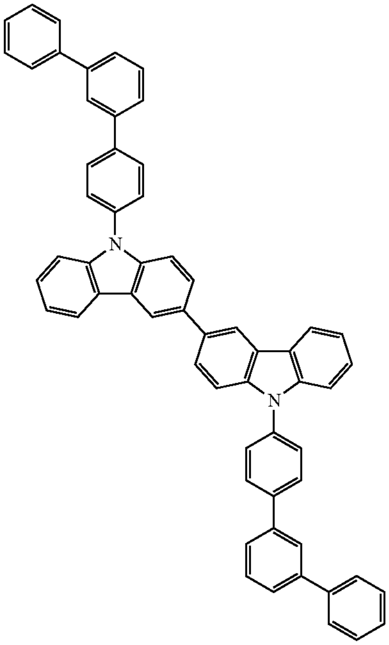

-continued
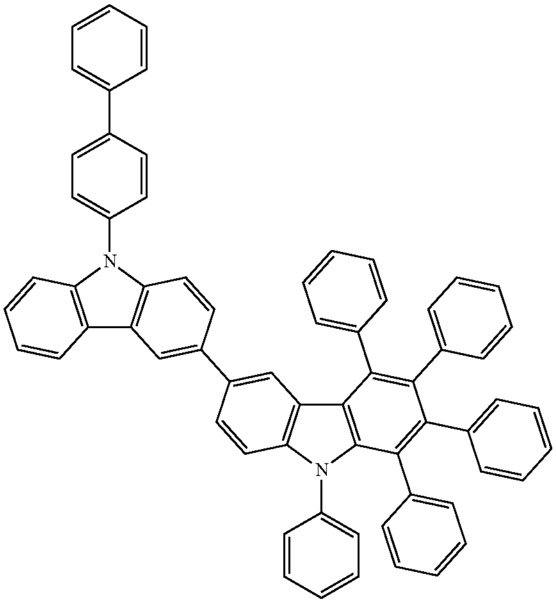
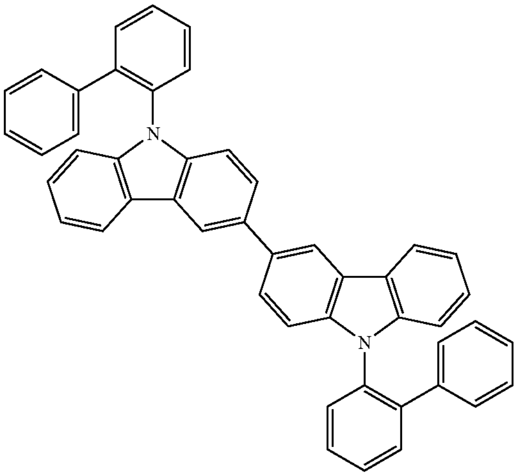
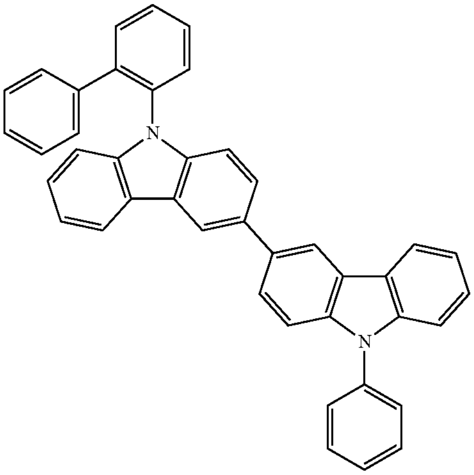
-continued
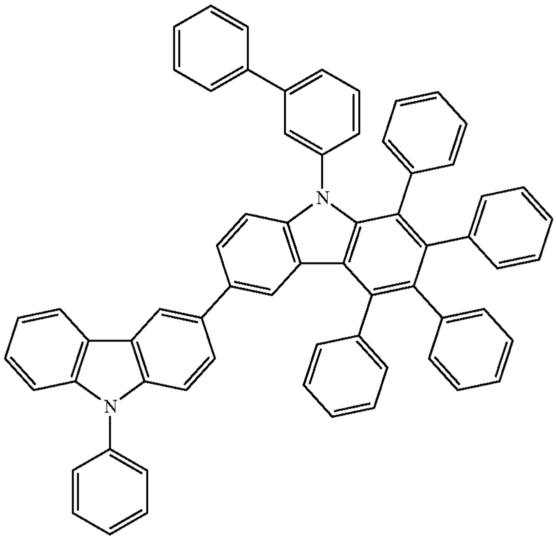
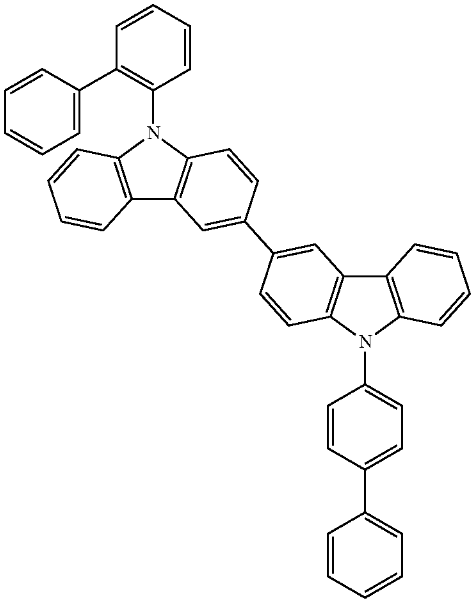
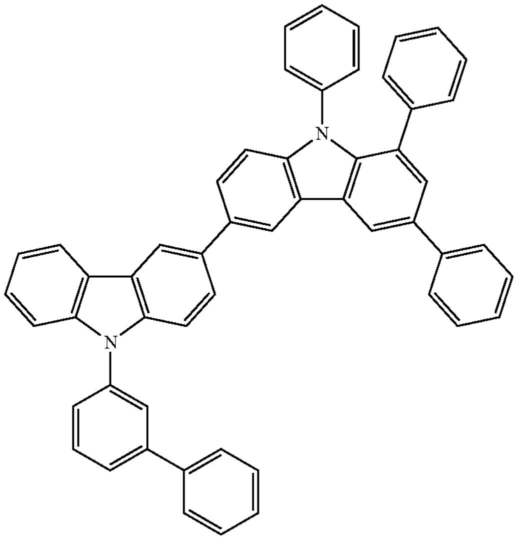

-continued
93
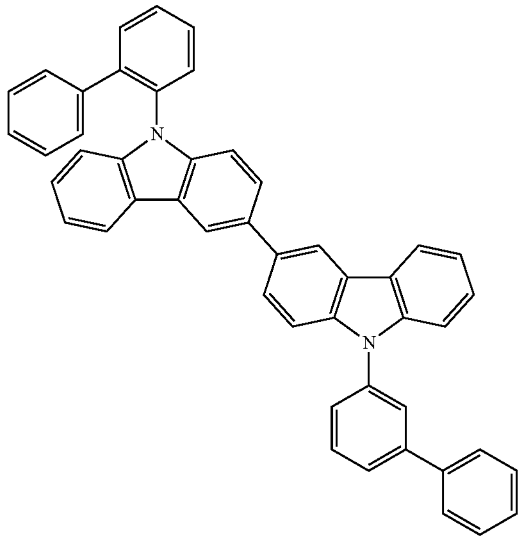
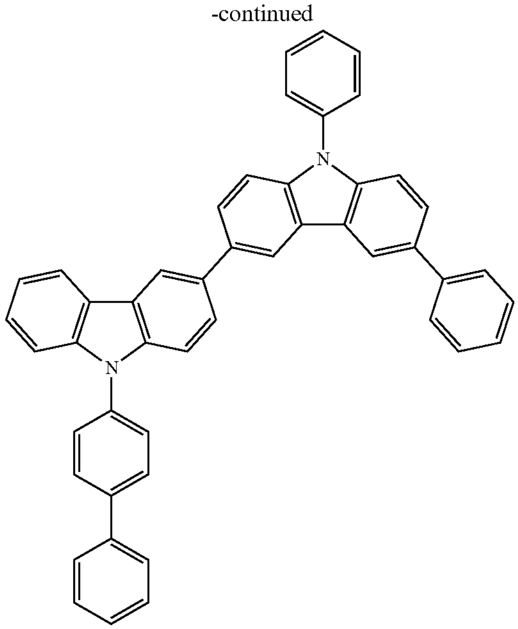
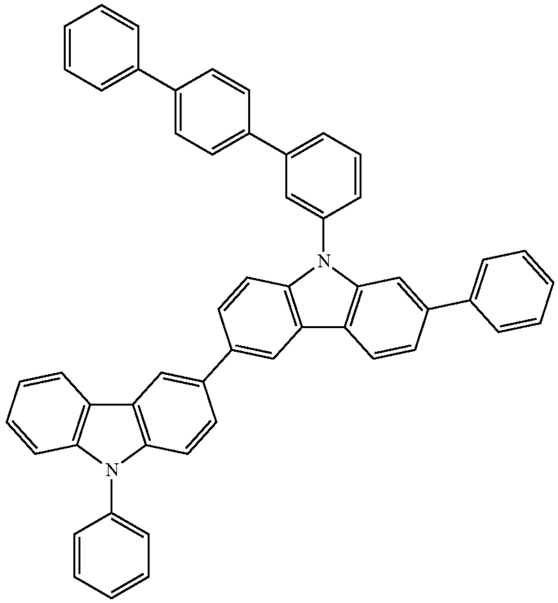
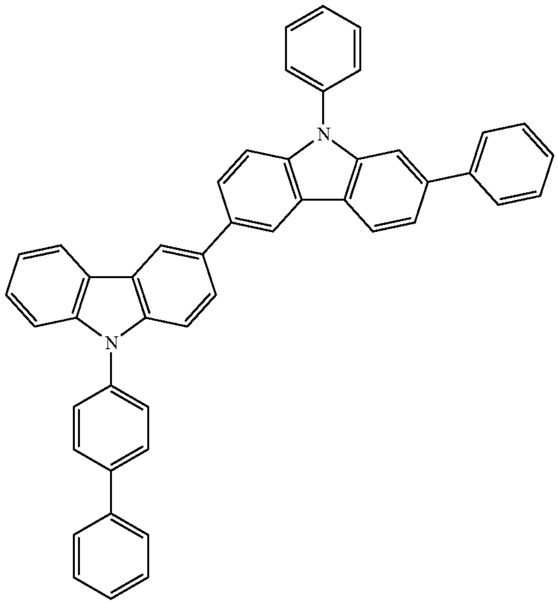

-continued
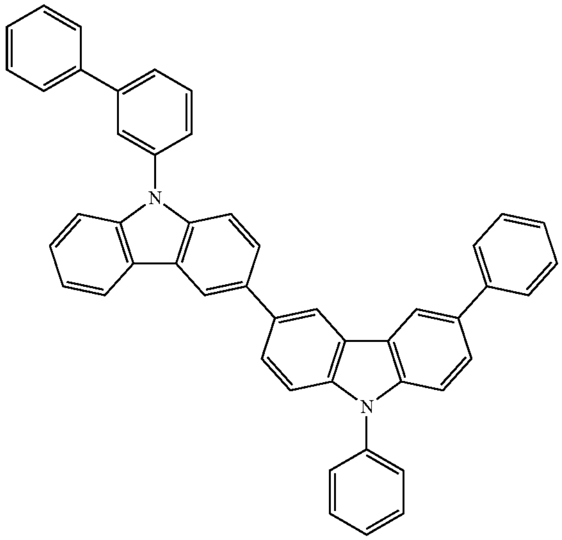
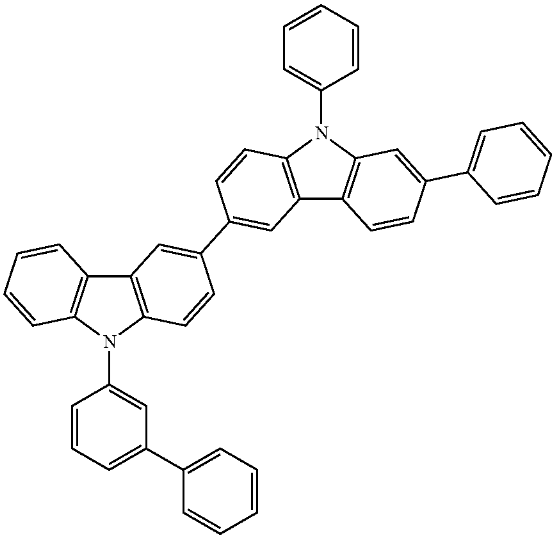
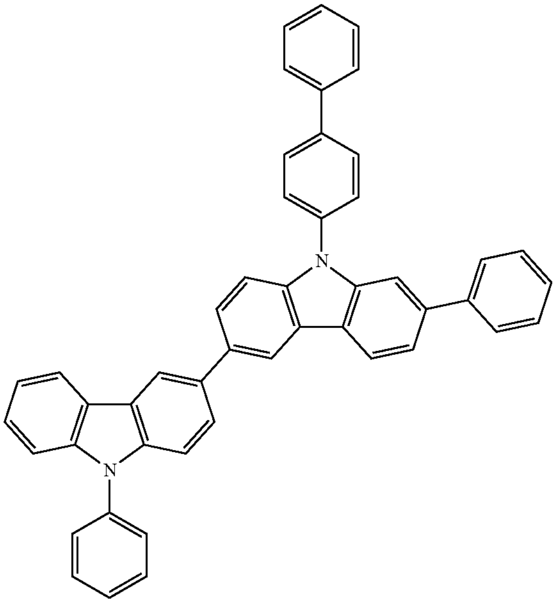
-continued
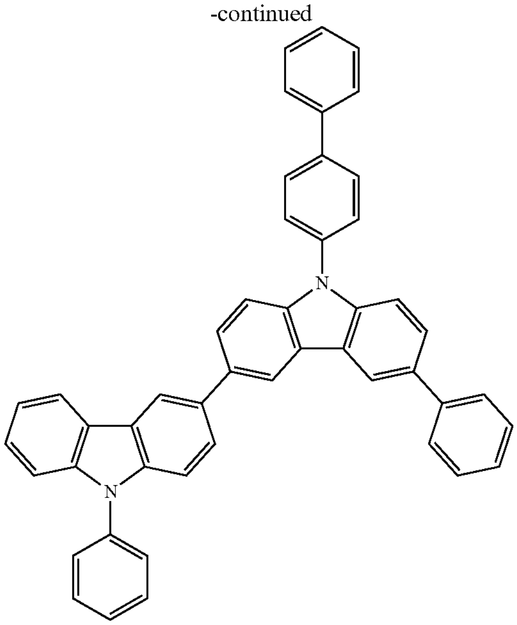
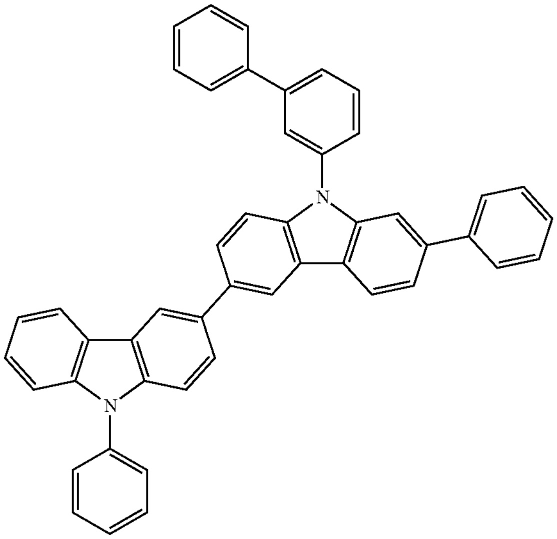
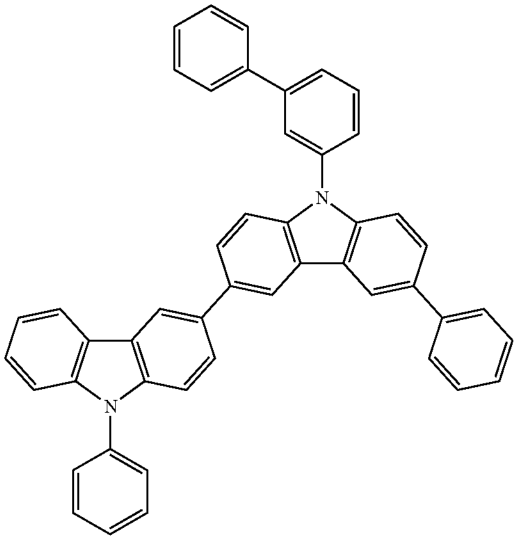

-continued
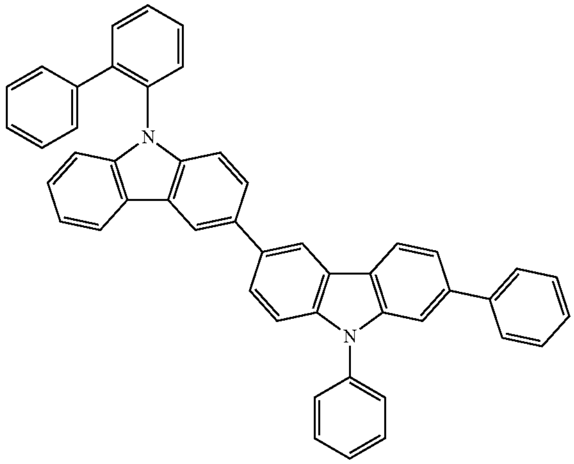
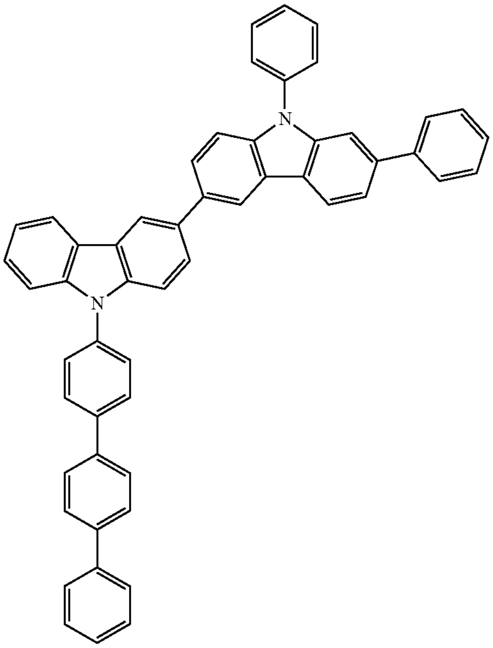
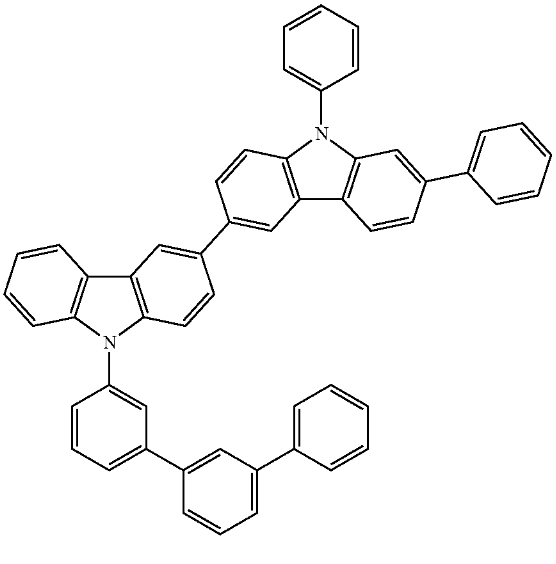
-continued
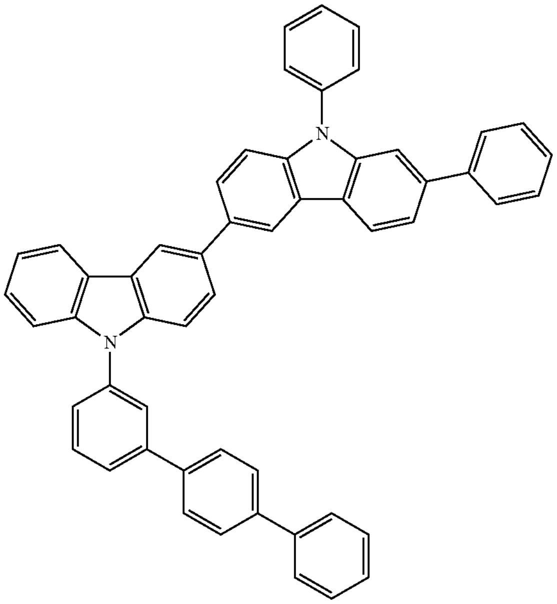
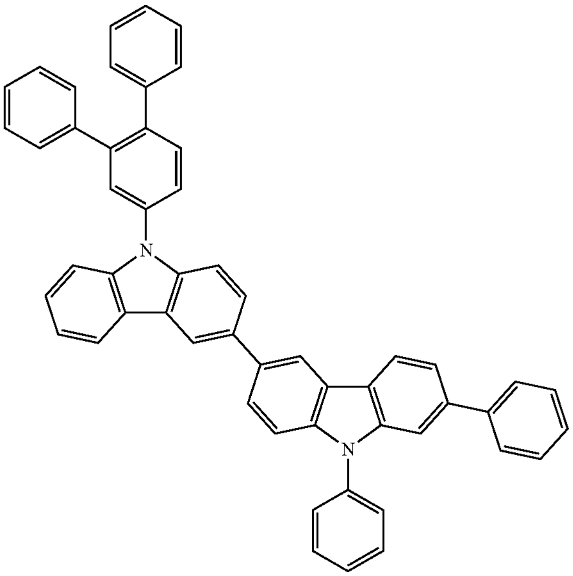
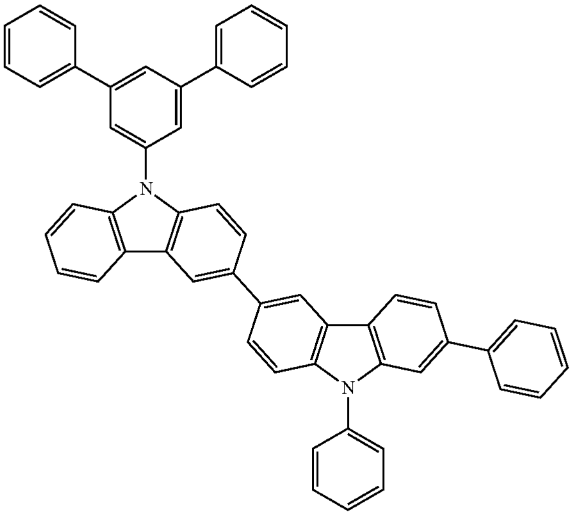

-continued
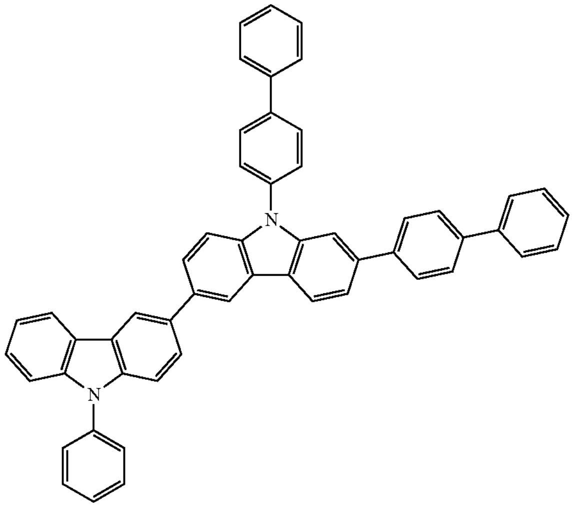
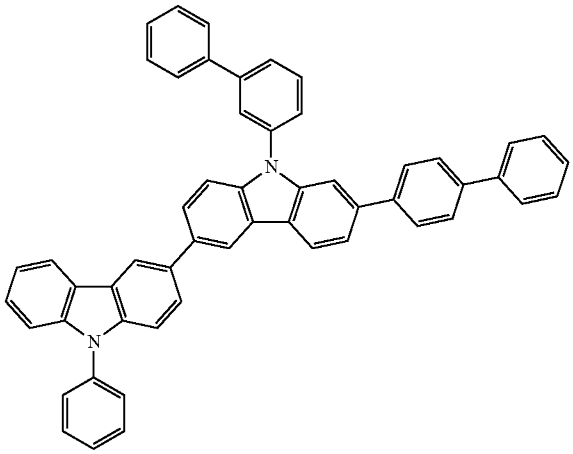
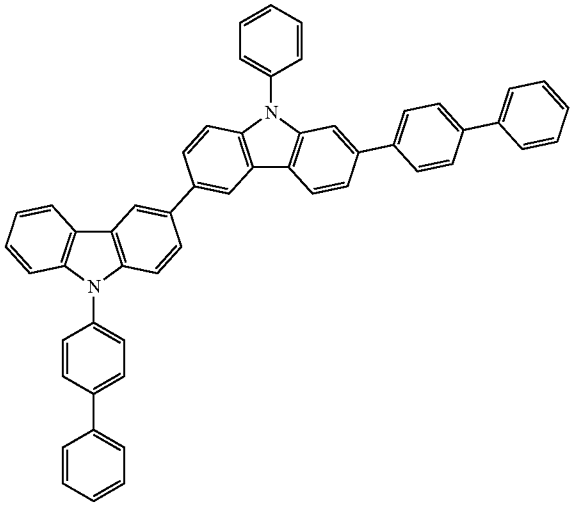
-continued
94
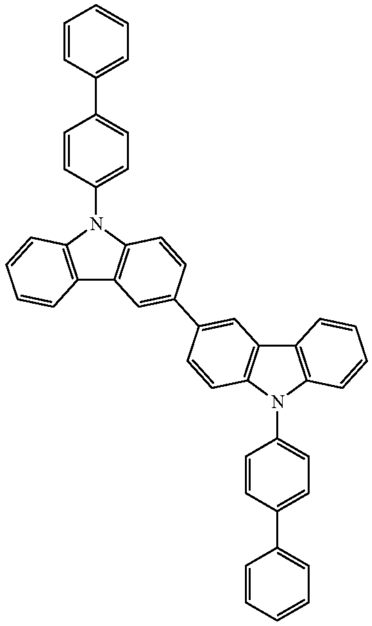
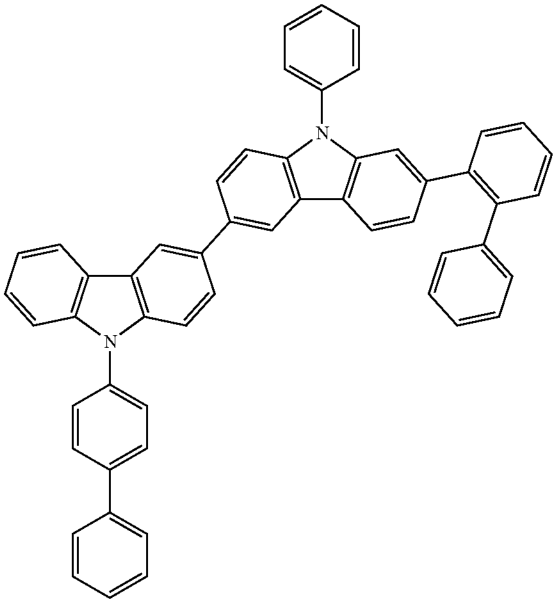
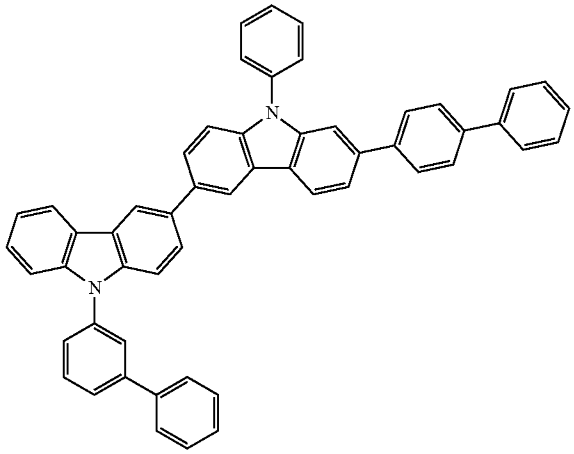

-continued
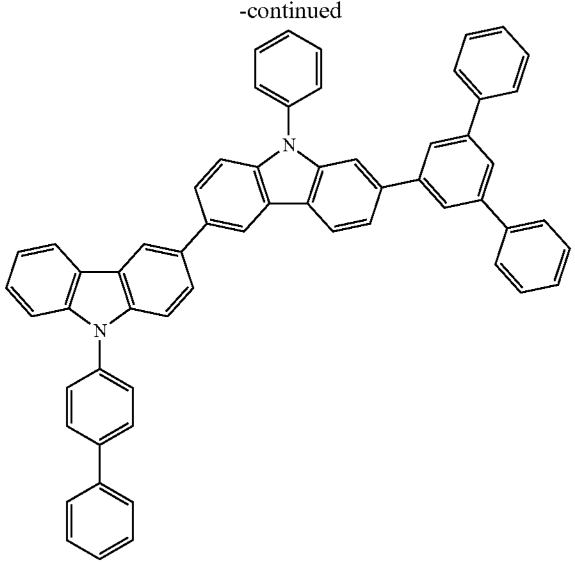
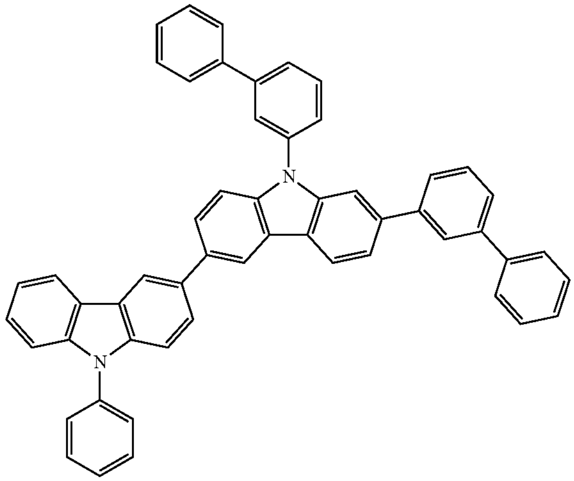
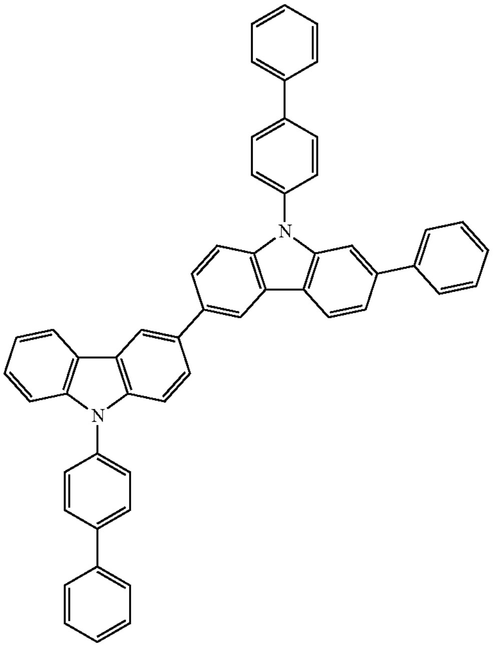
-continued
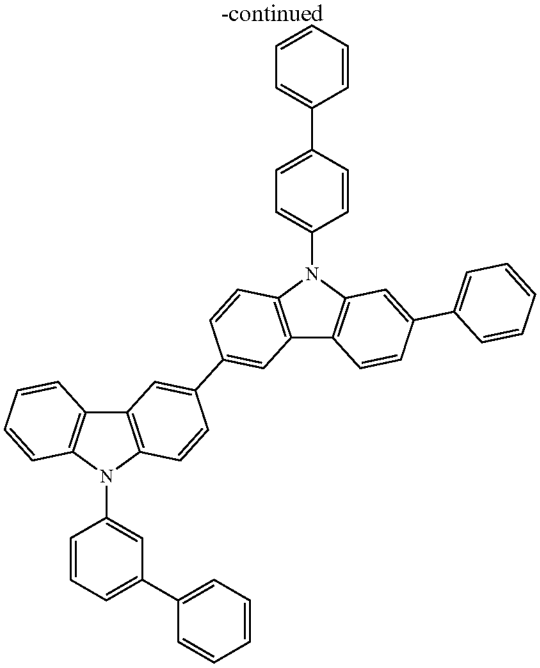
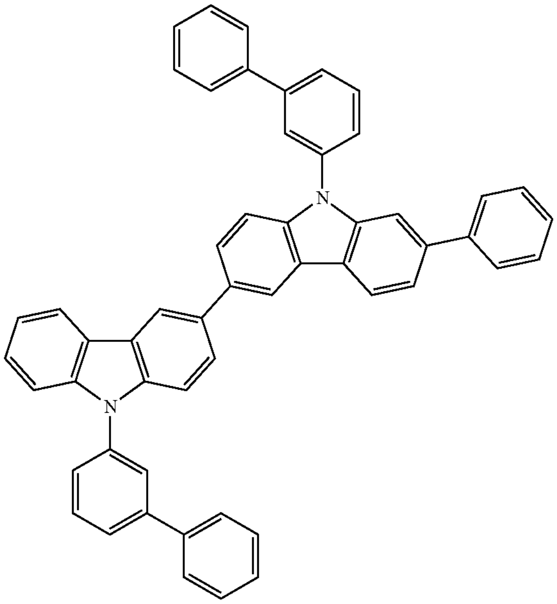

-continued
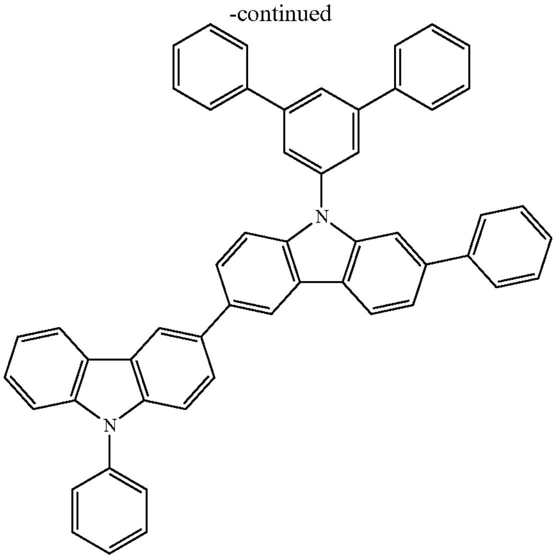
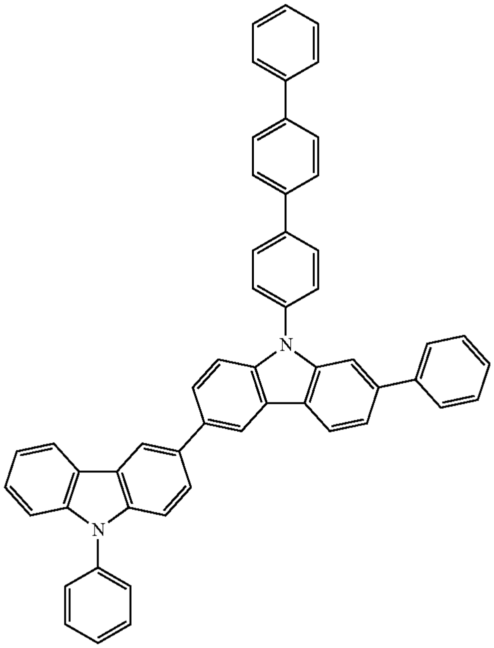
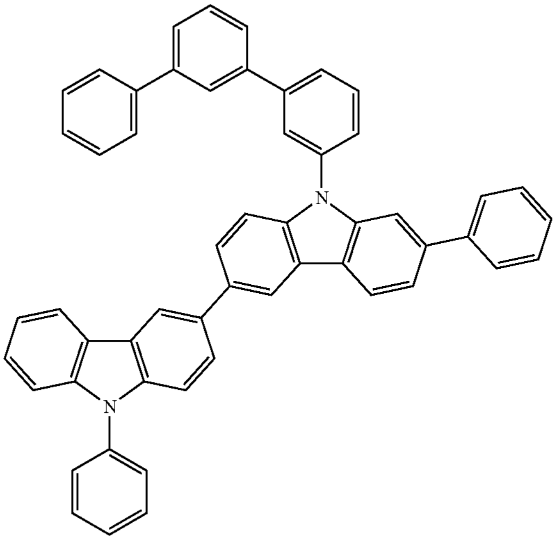
-continued
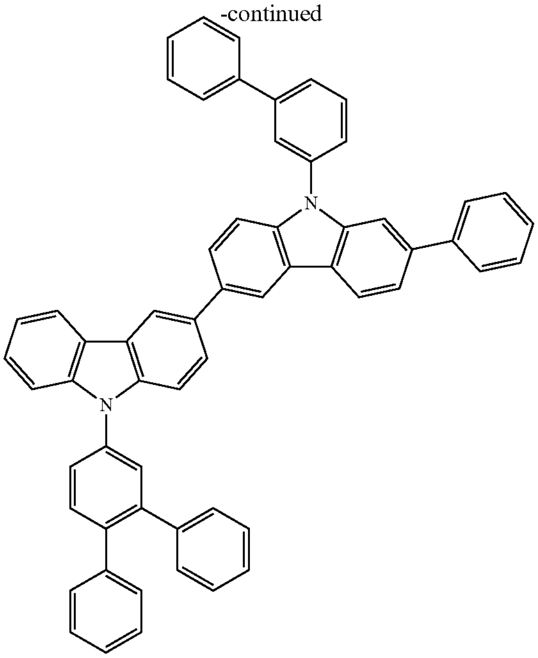
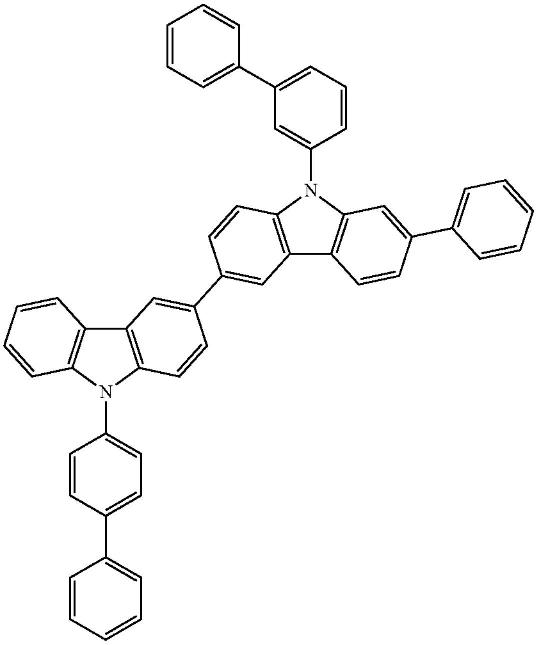

-continued
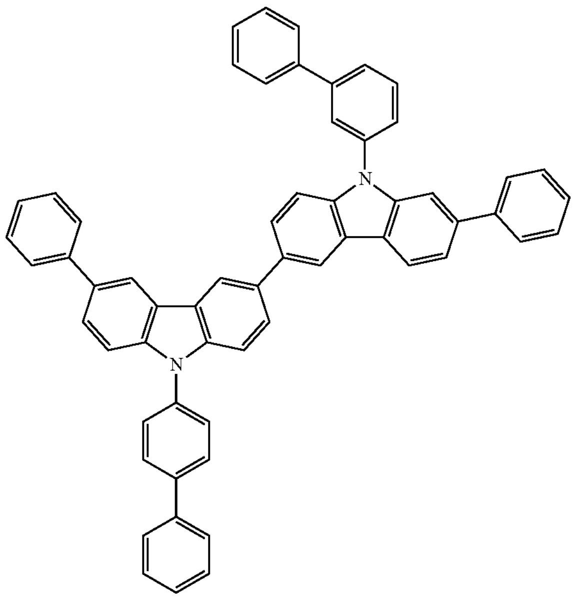
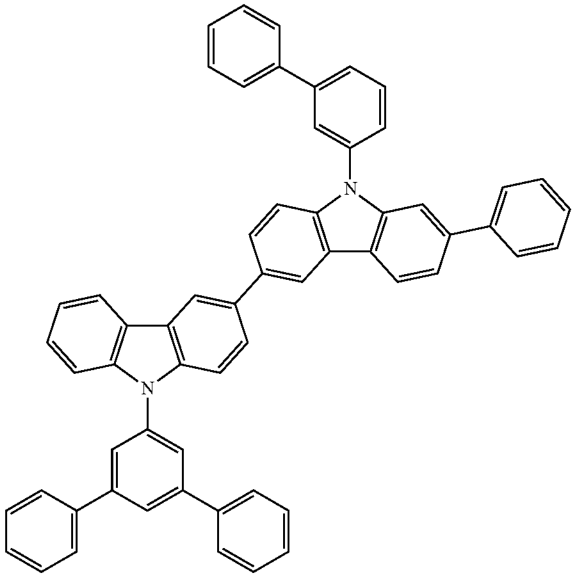
-continued
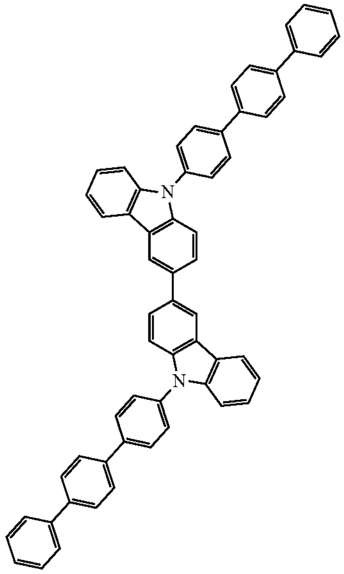
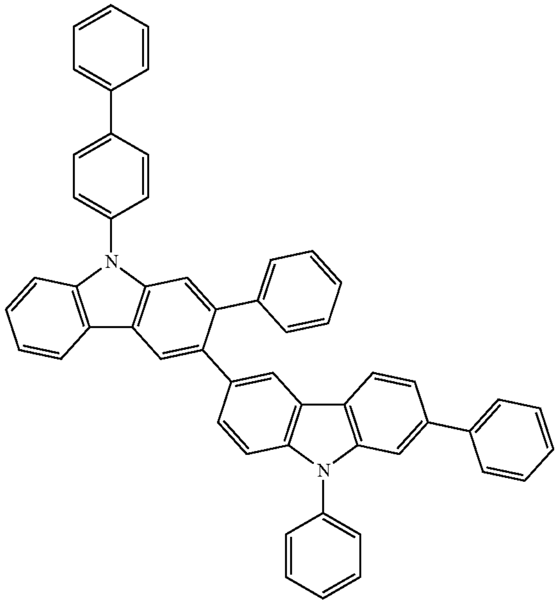

-continued
95
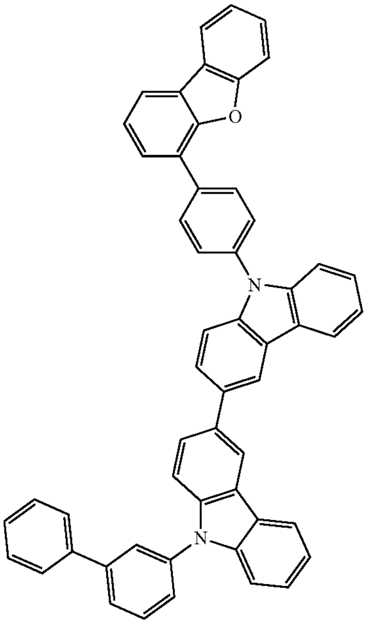
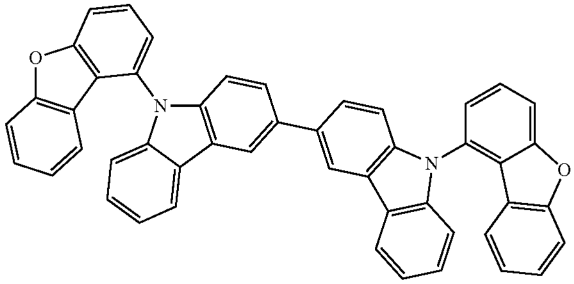
97
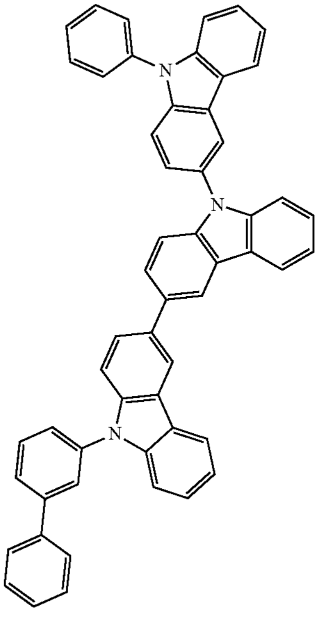
-continued
98
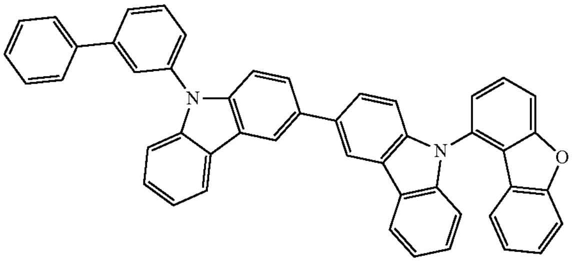
99
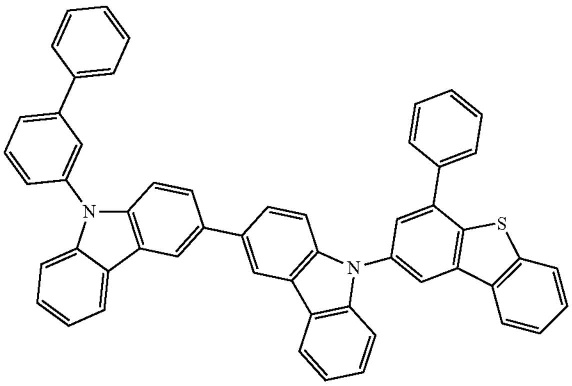
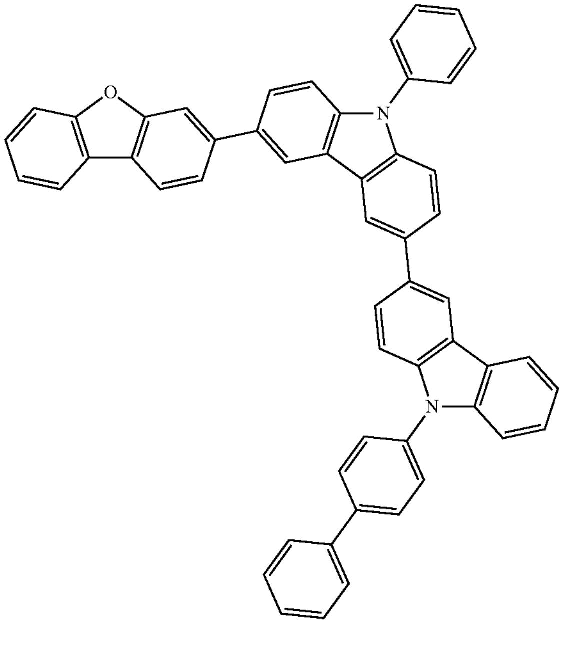

-continued
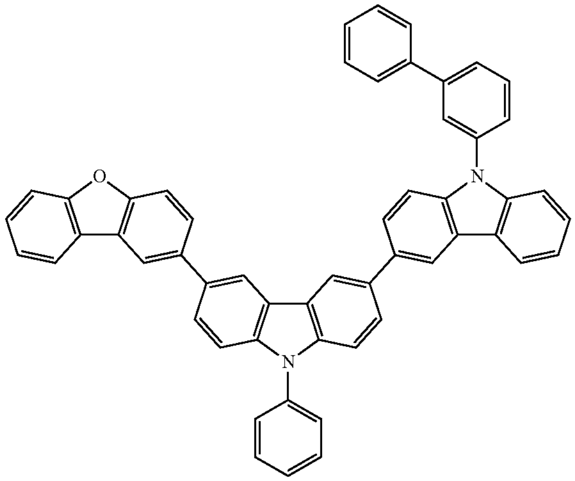
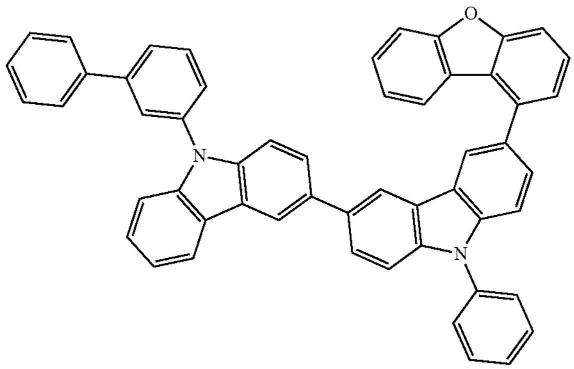
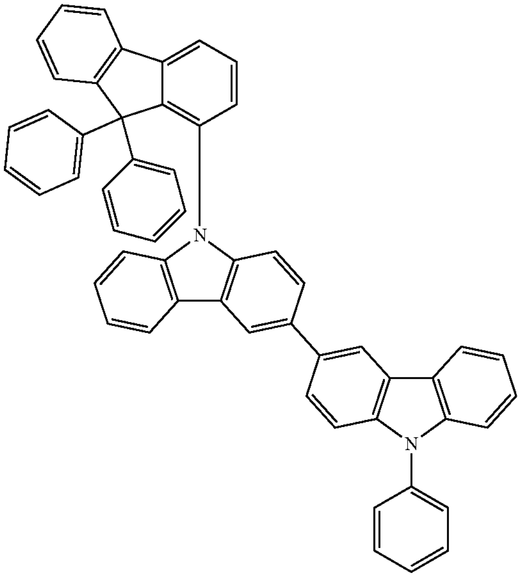
-continued
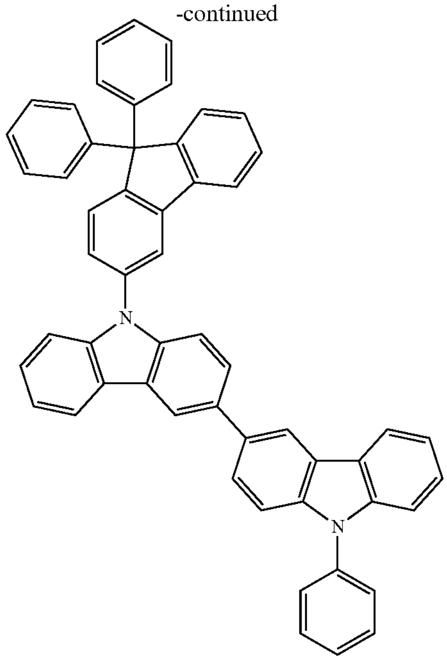
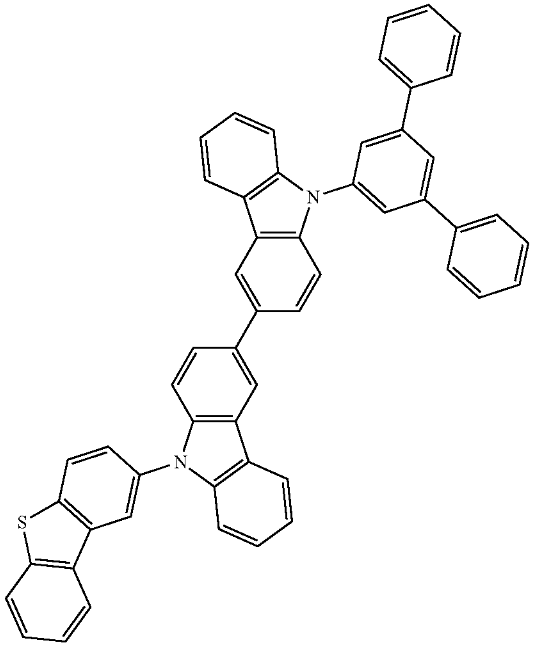

-continued
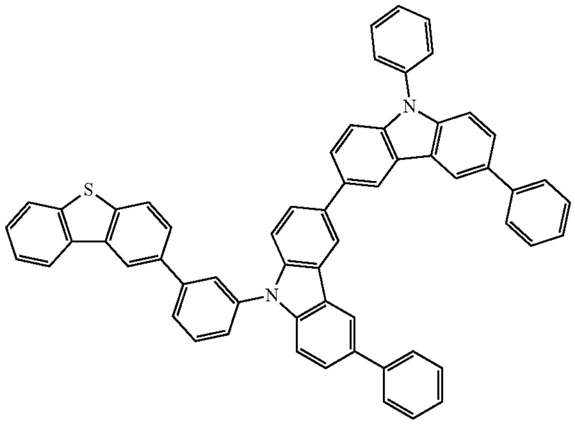
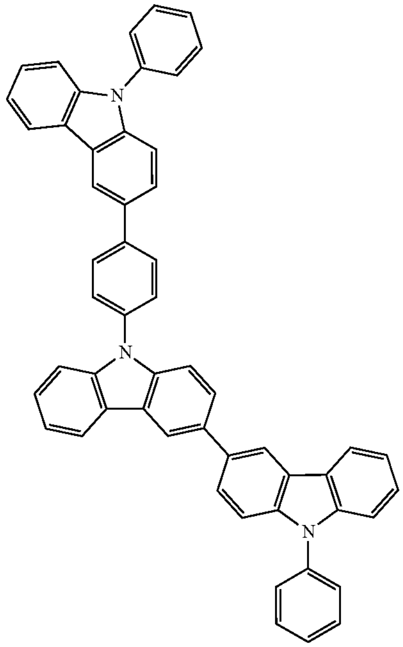
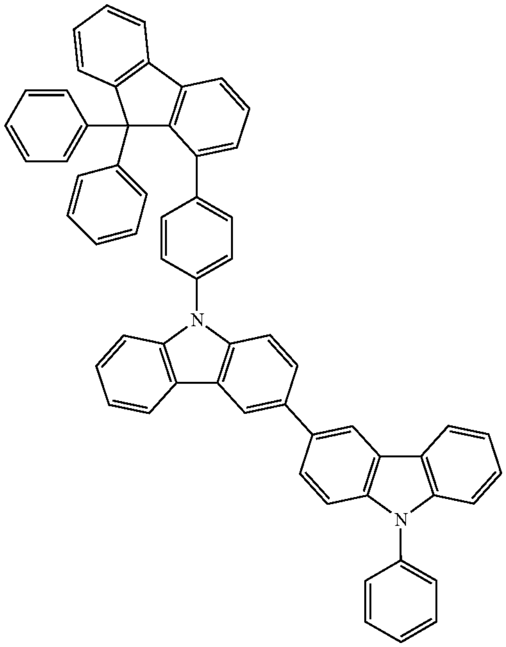
-continued
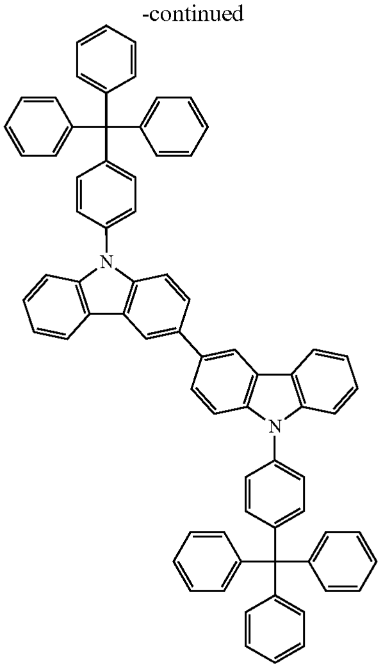
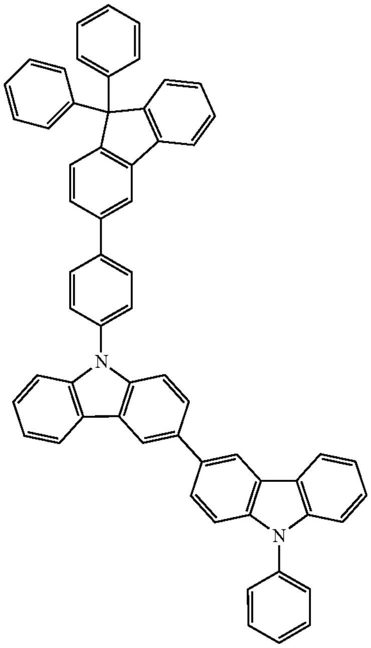

-continued
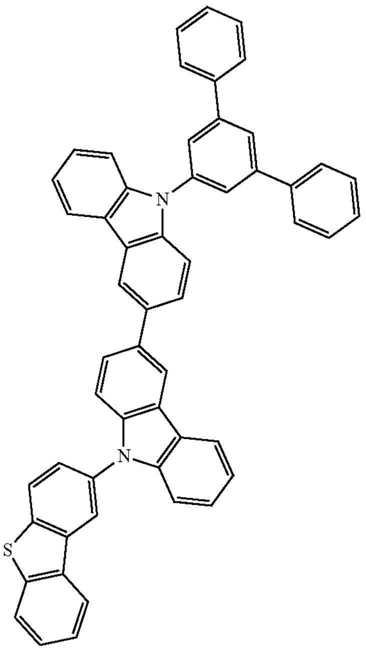
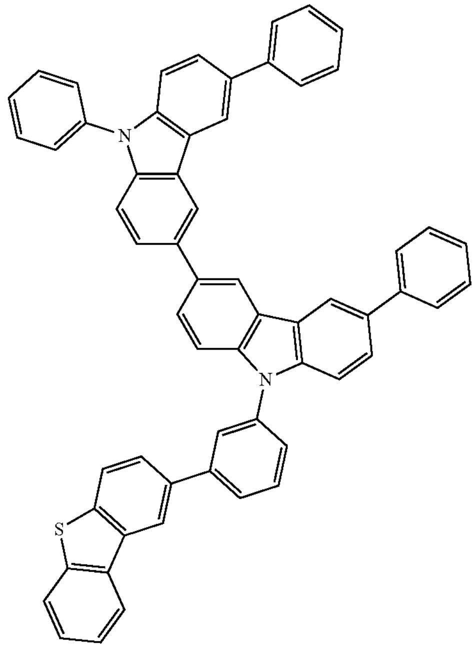
-continued
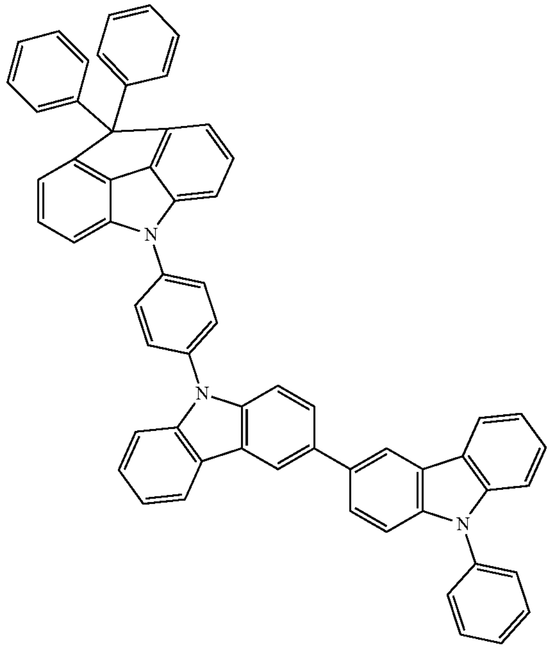
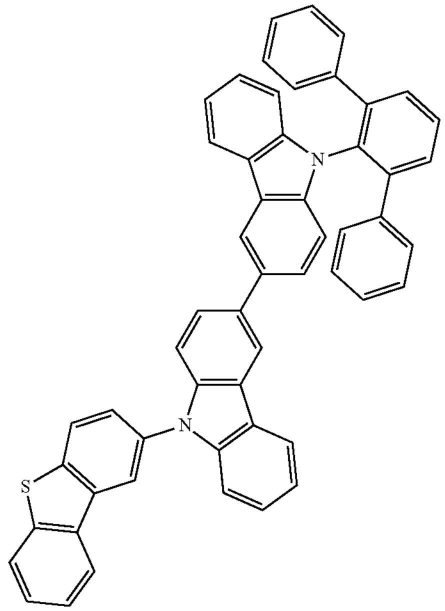
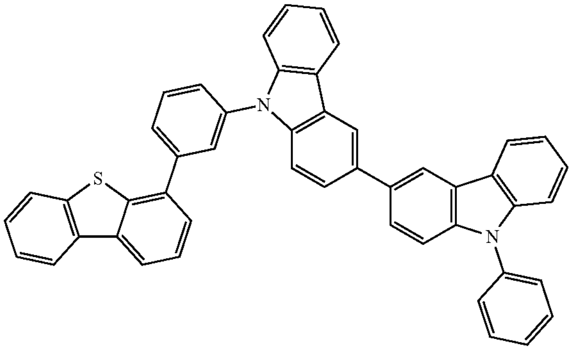

-continued
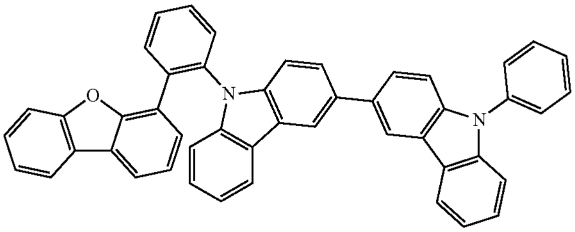
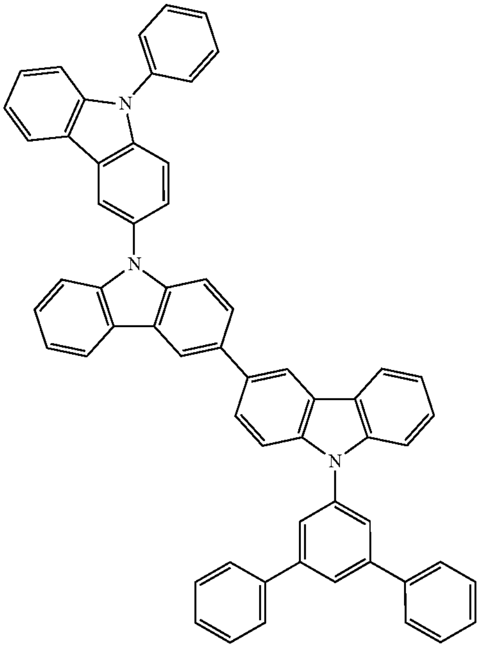
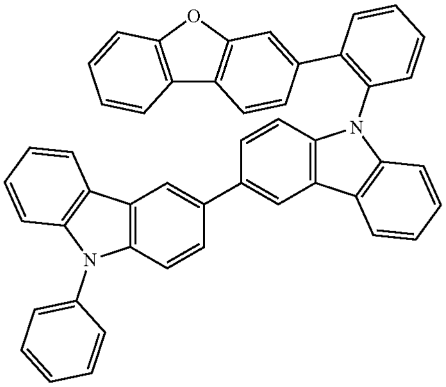
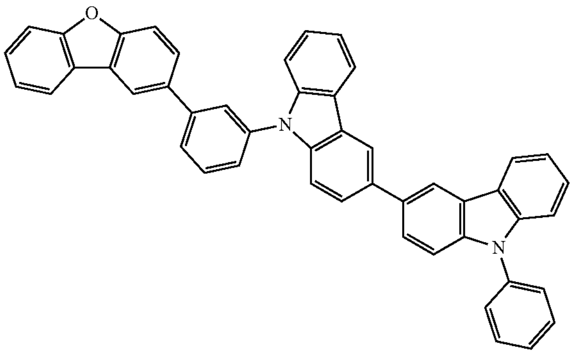
-continued
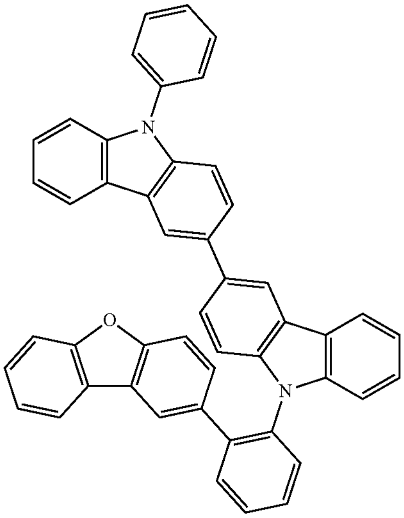
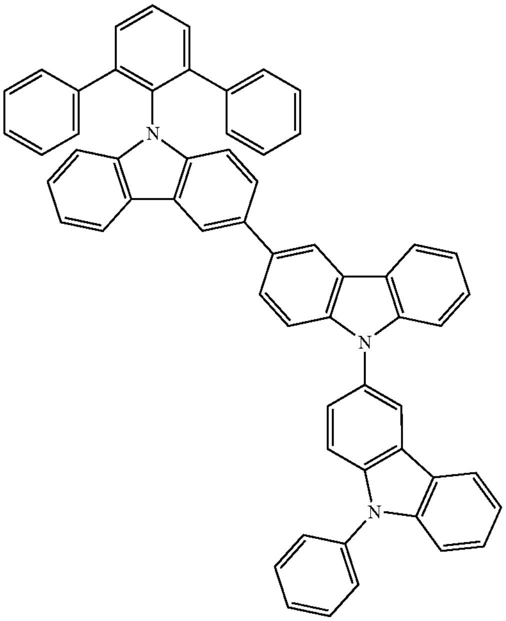
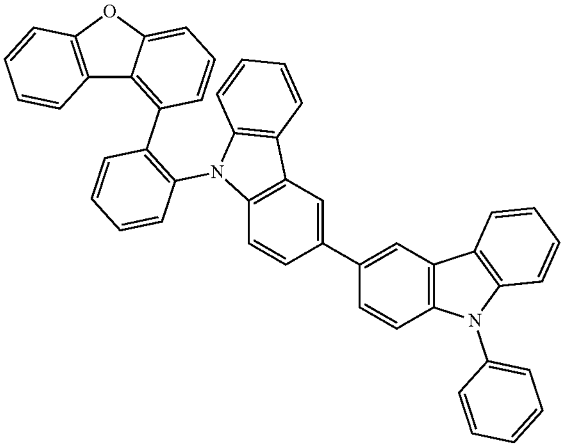

-continued
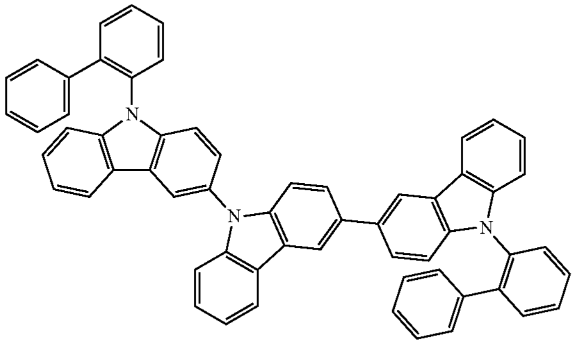
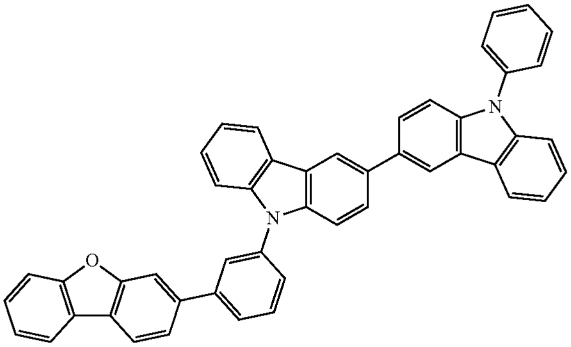
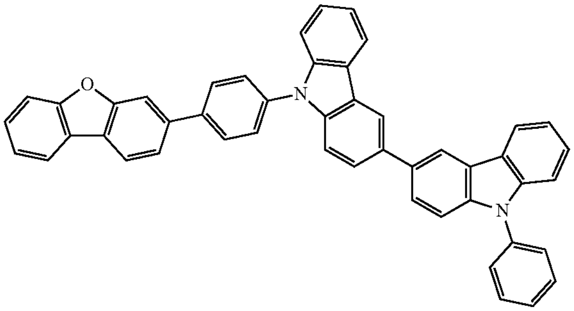
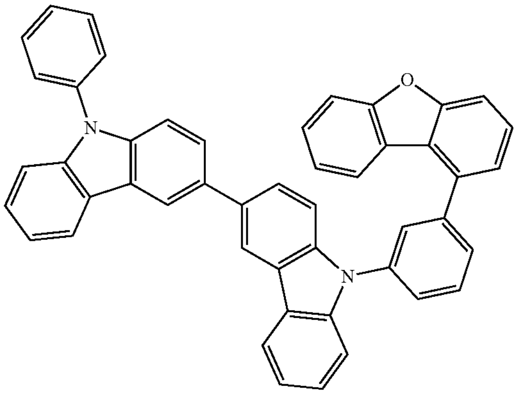
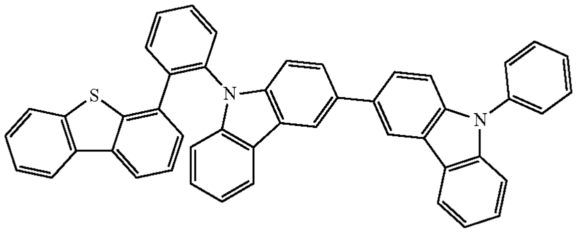
-continued
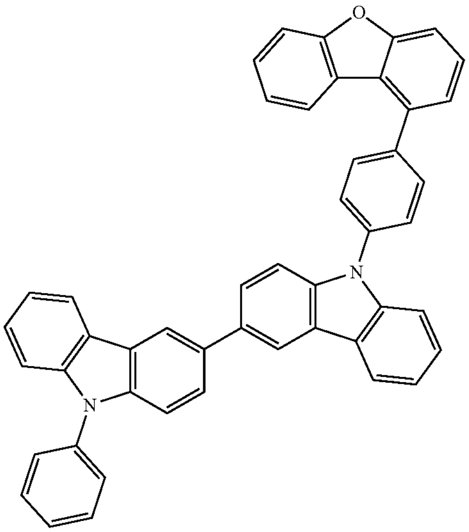
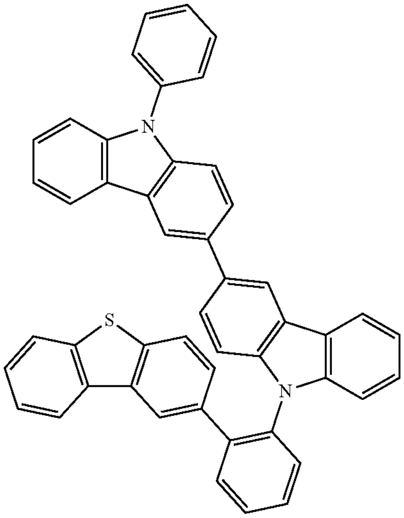
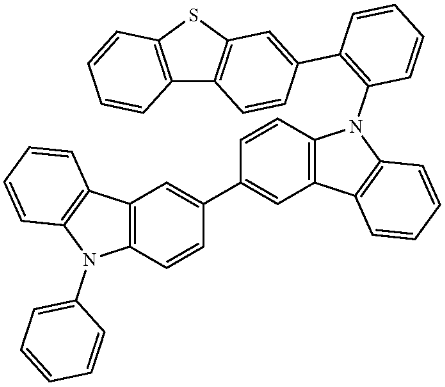

-continued
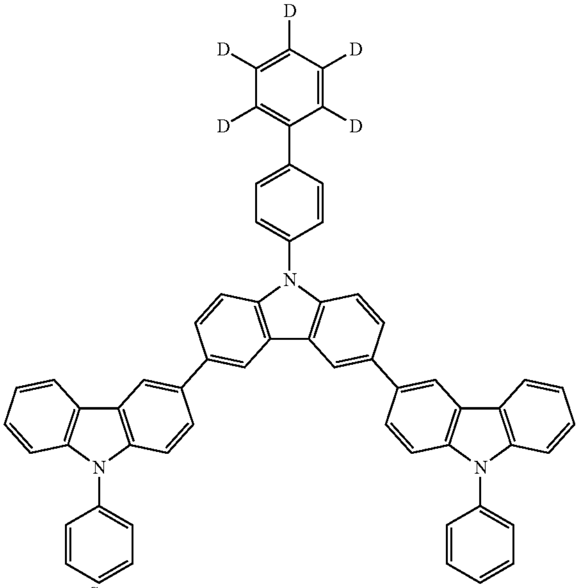
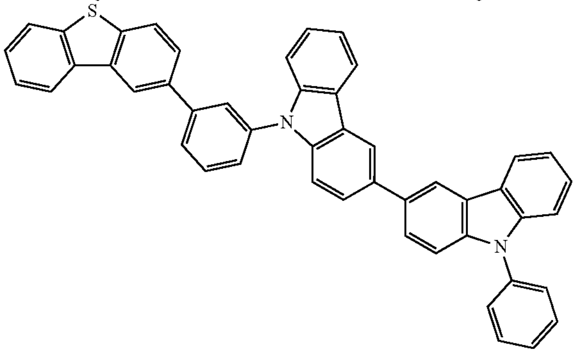
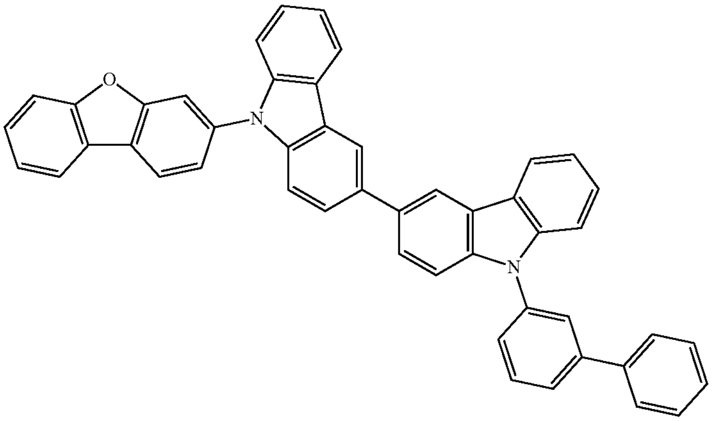
-continued
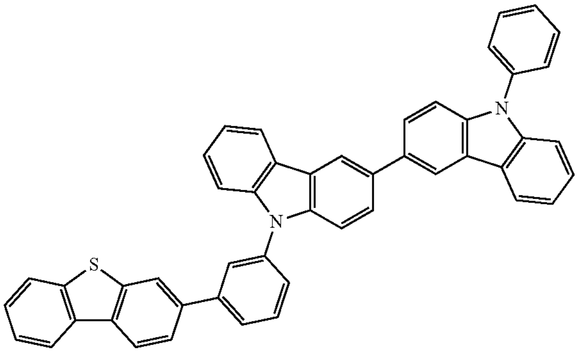
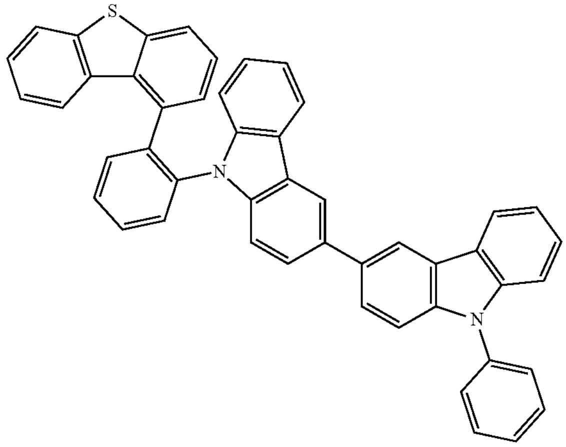
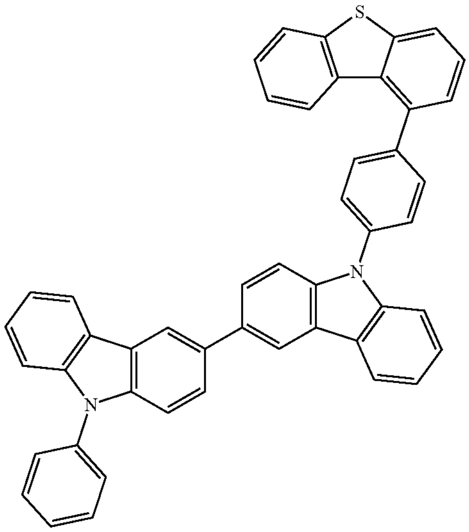

-continued
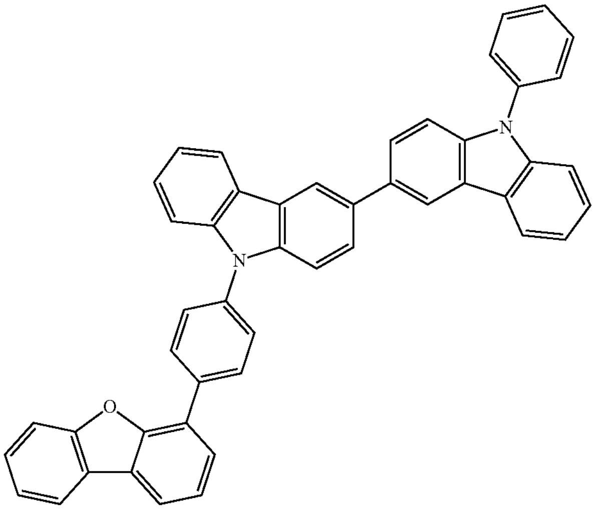
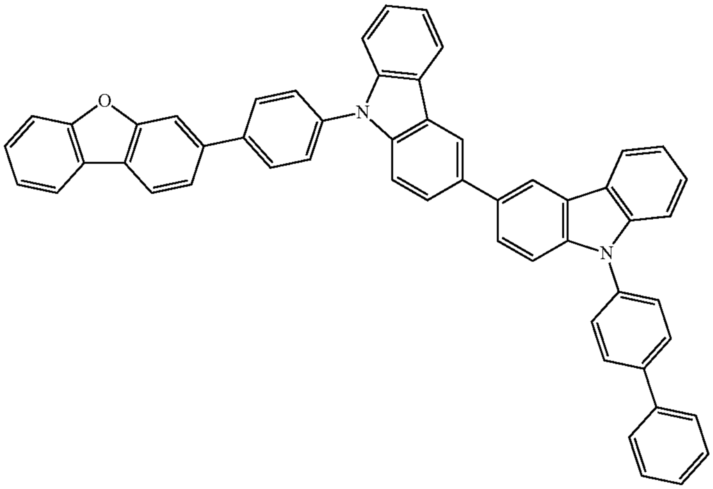
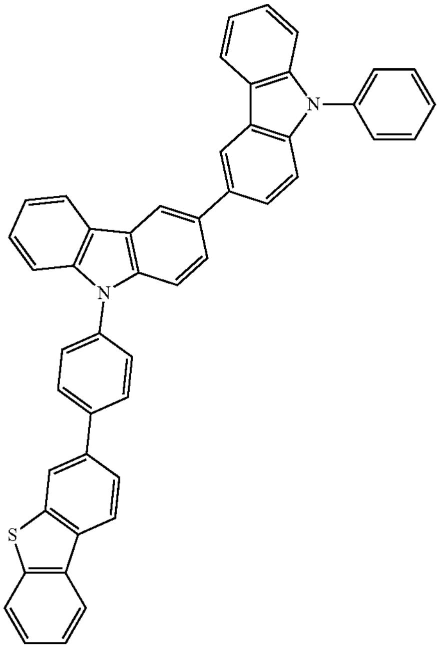
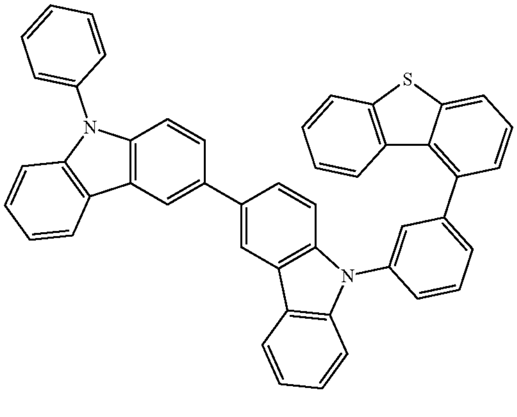
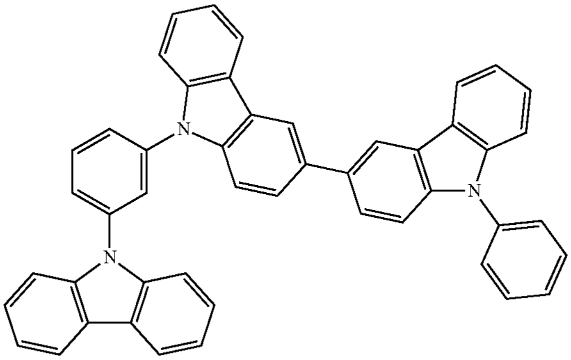

-continued
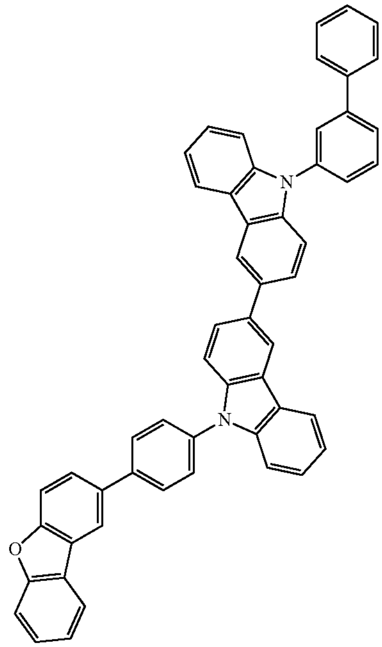
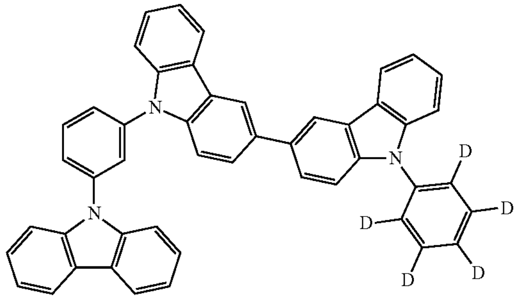
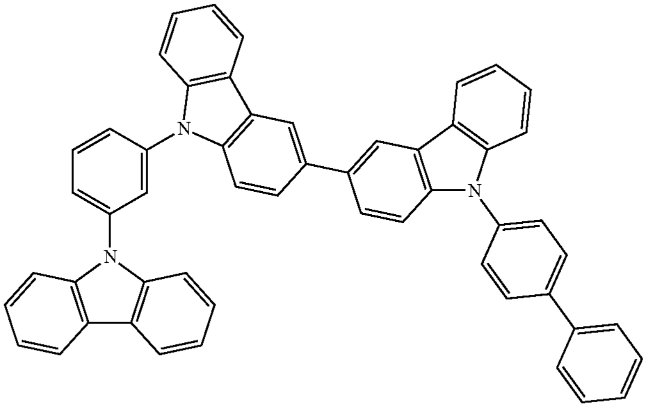
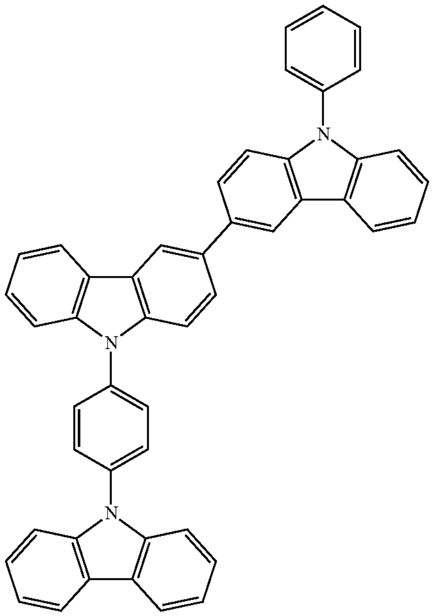

-continued
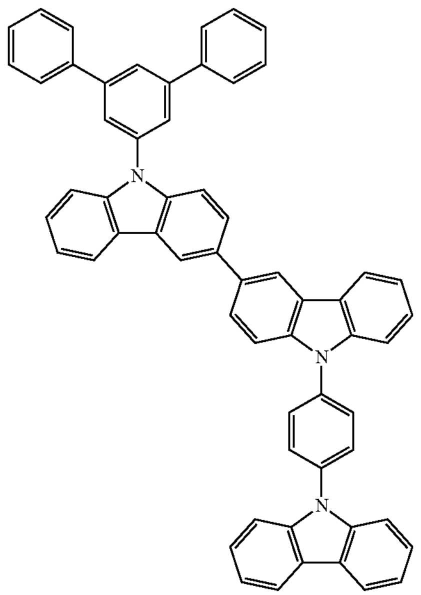
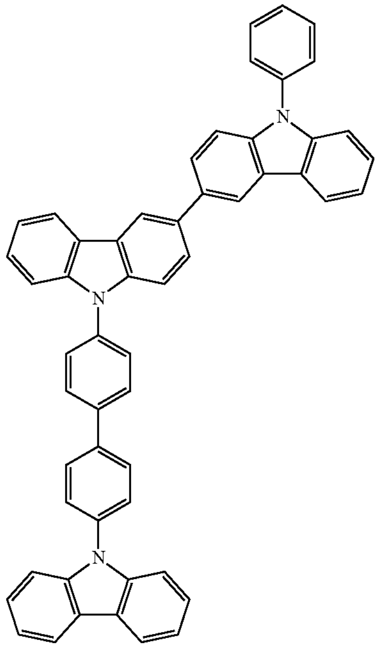
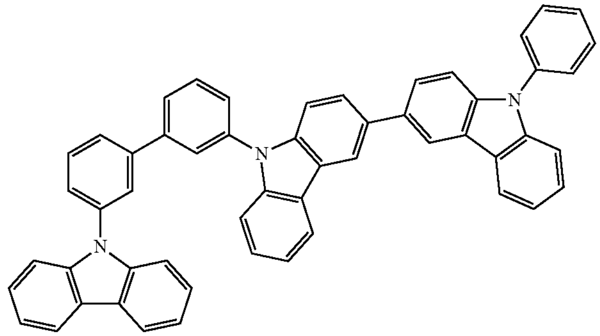
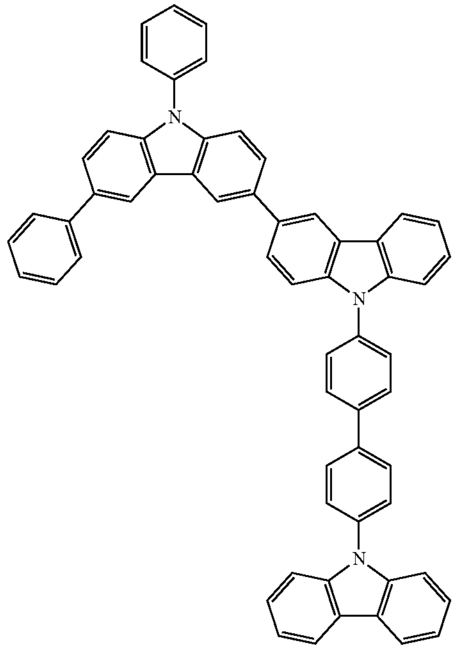

-continued
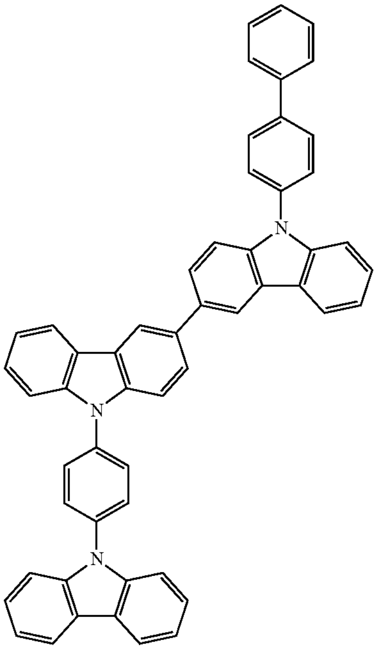
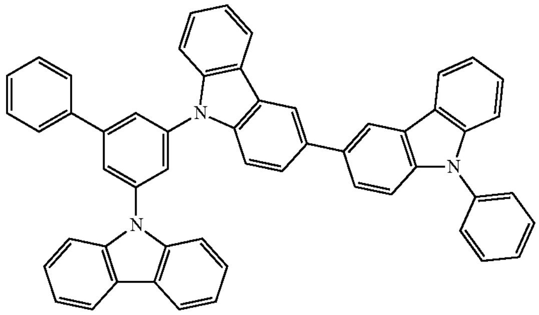
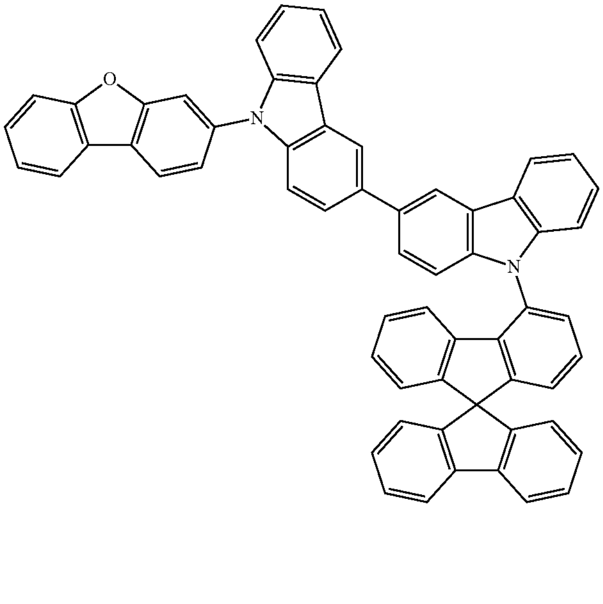
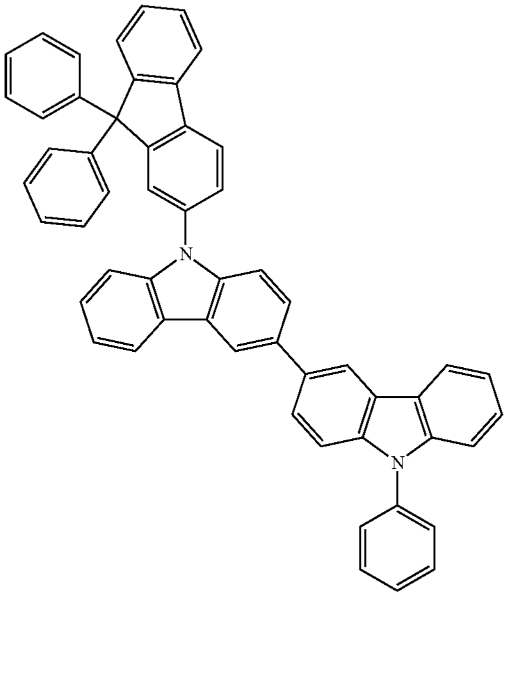

-continued
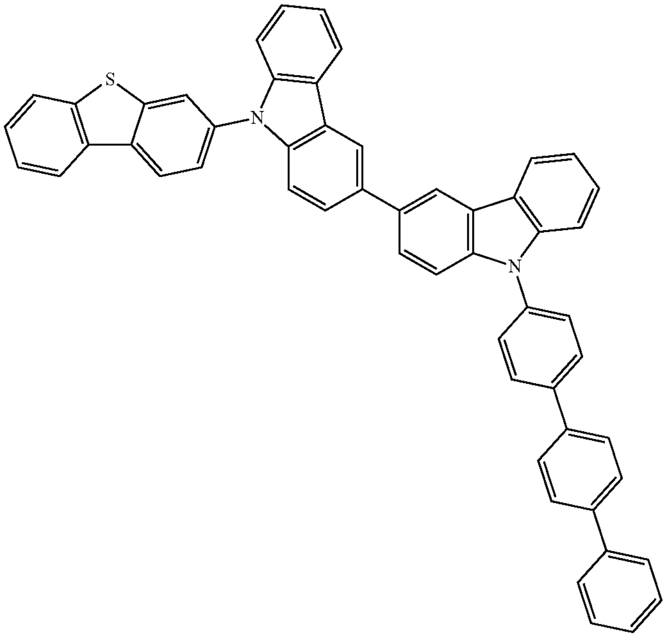
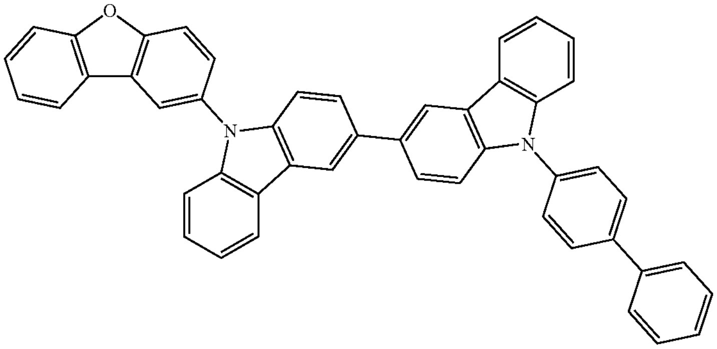
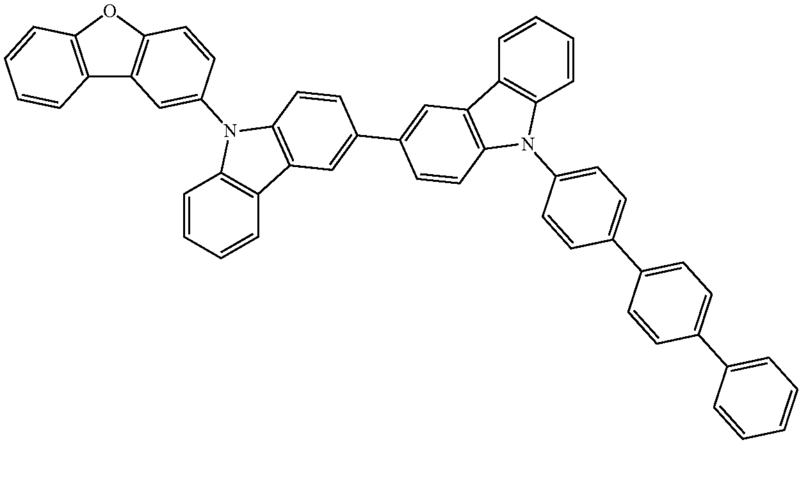

-continued
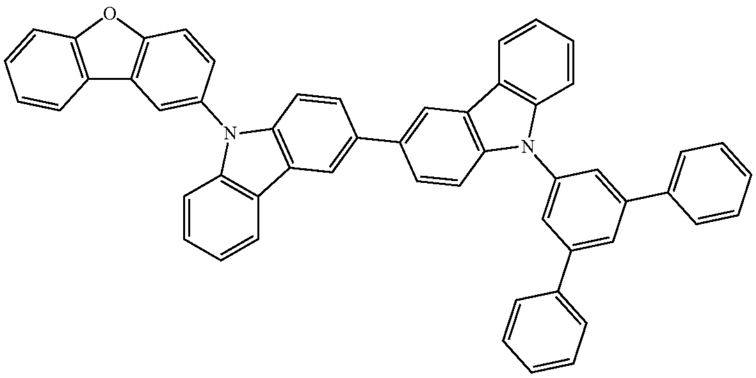
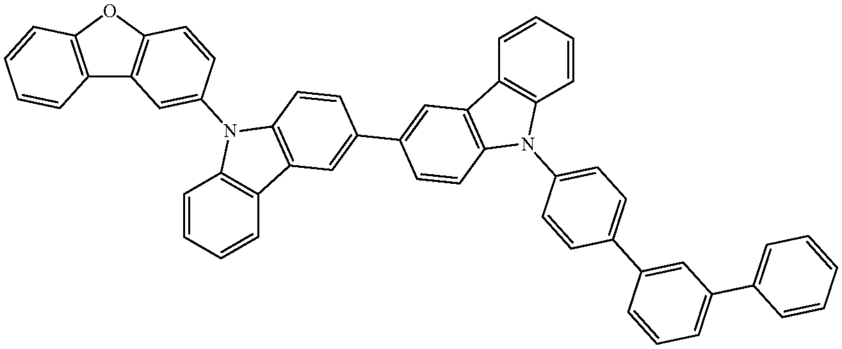
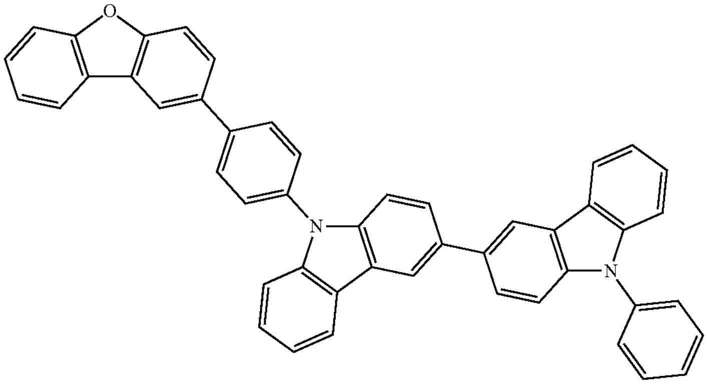
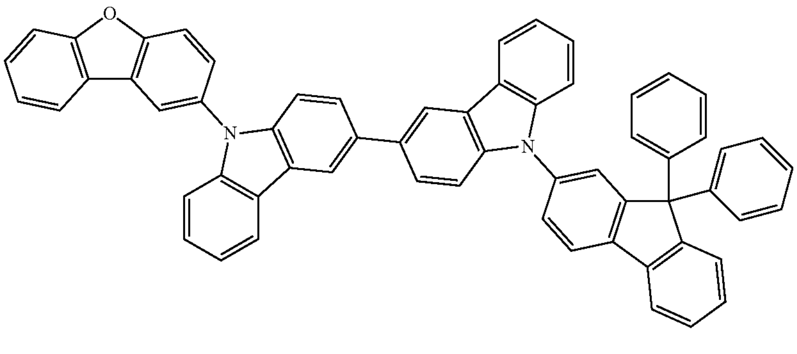

-continued
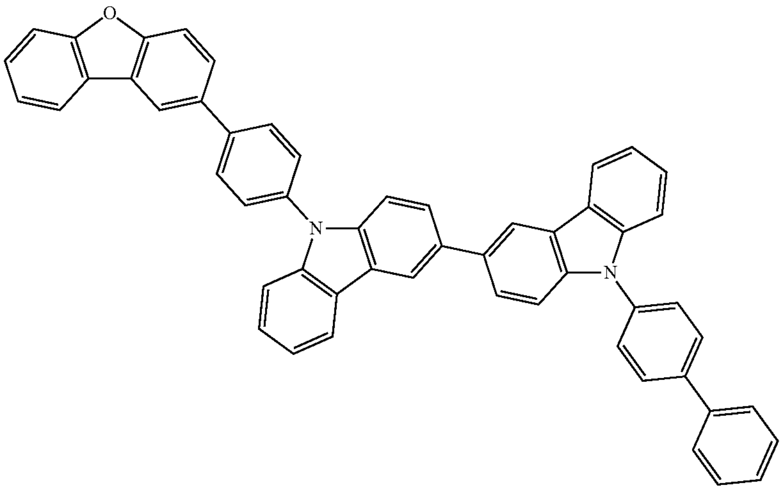
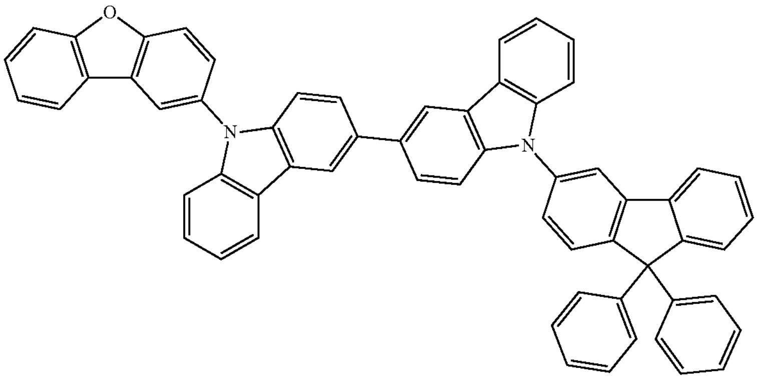
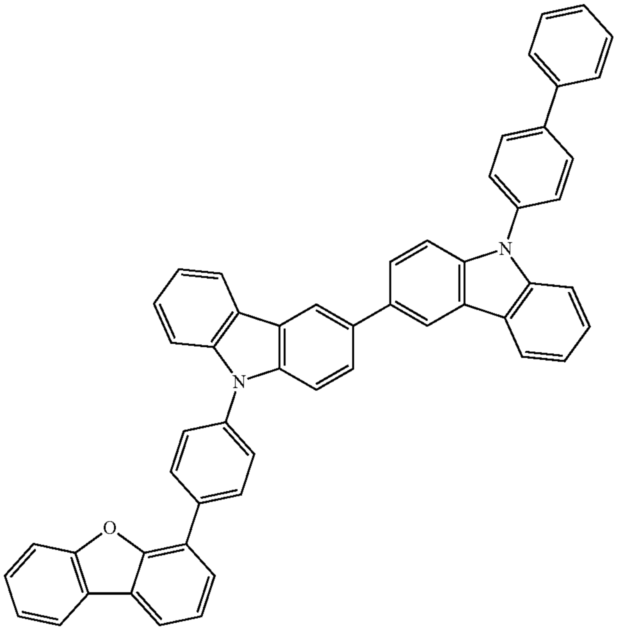

-continued
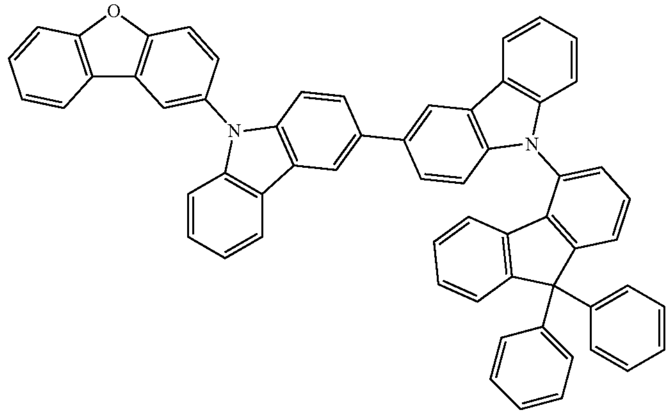
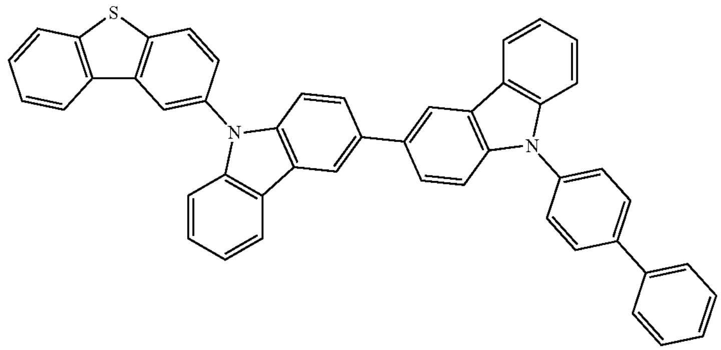
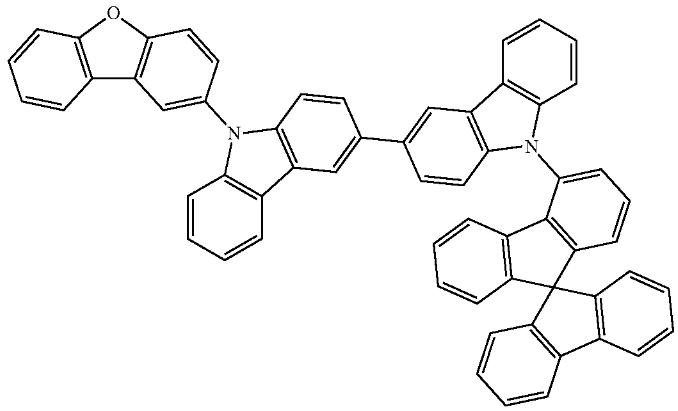
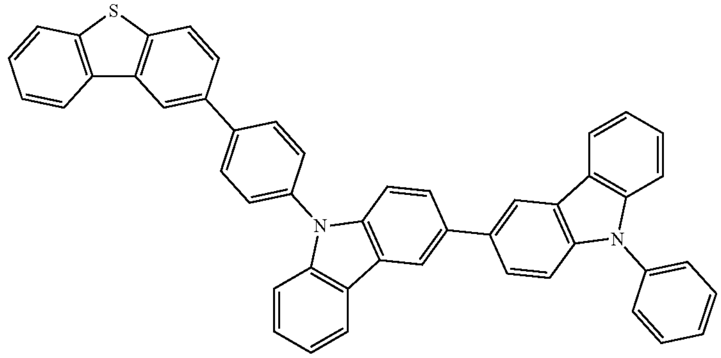

-continued
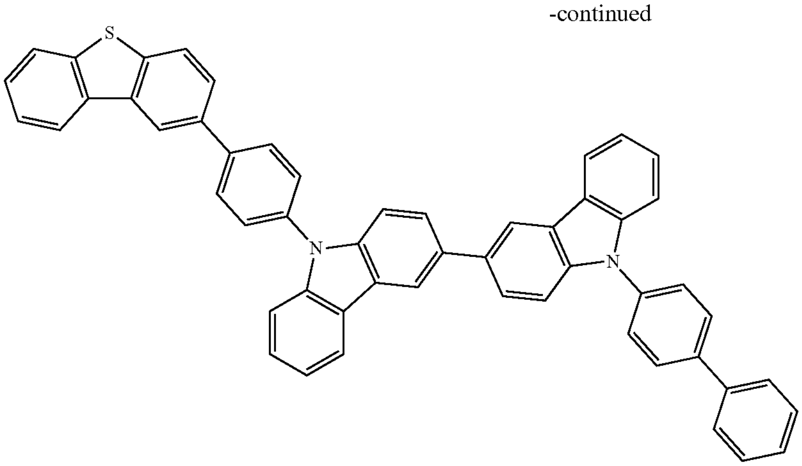
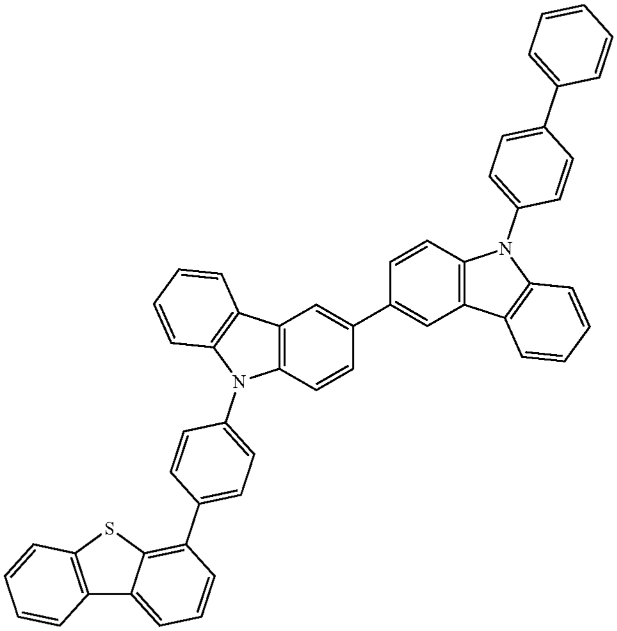
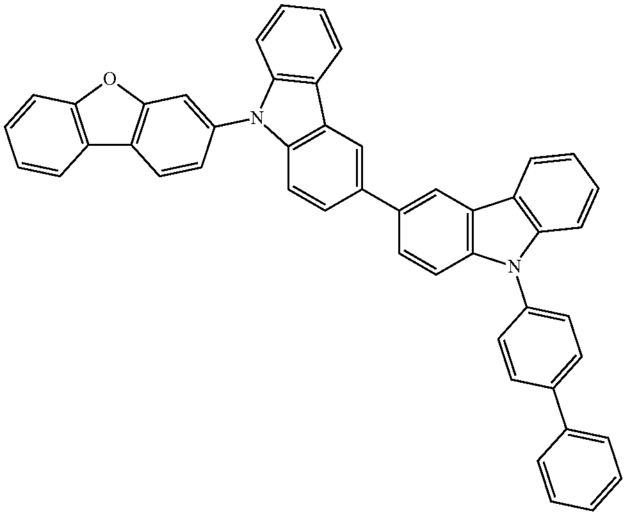

-continued
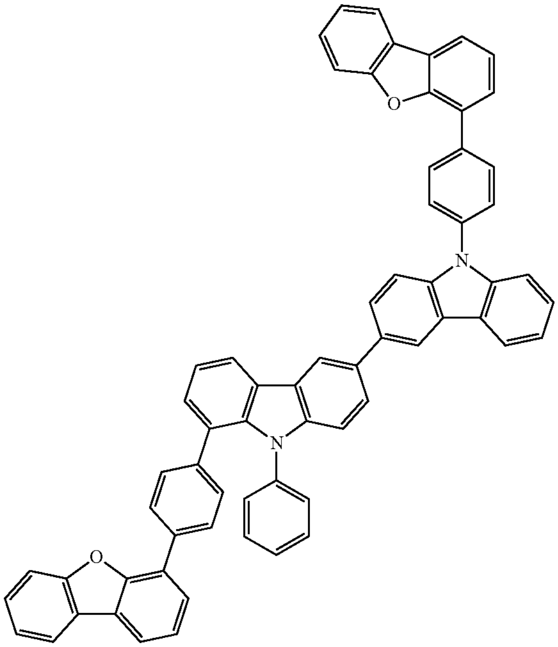
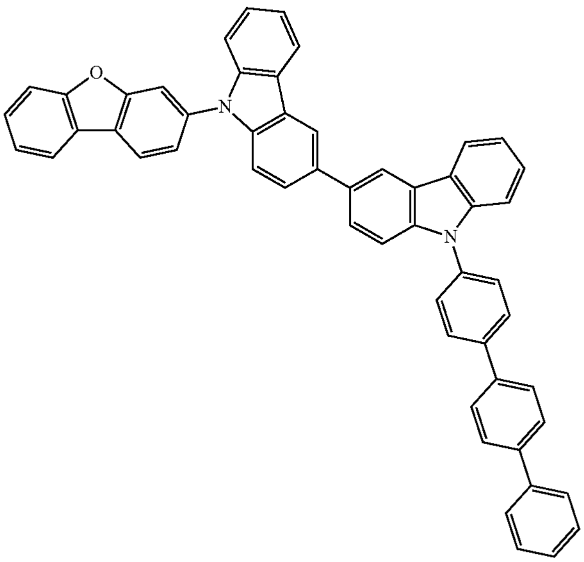
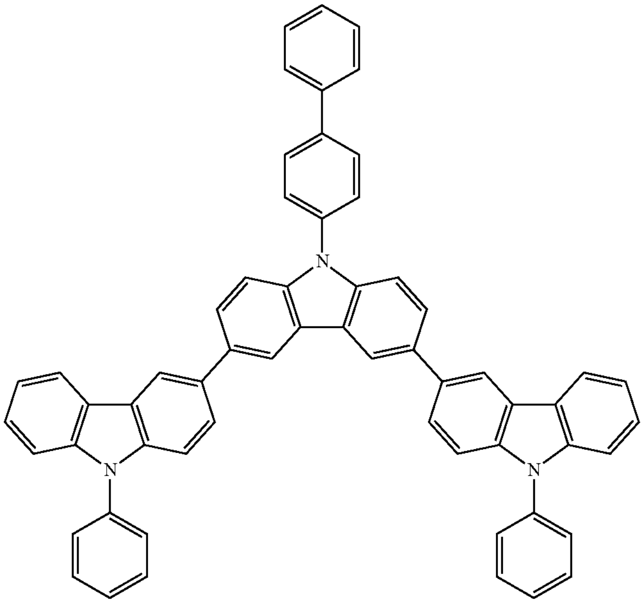

-continued
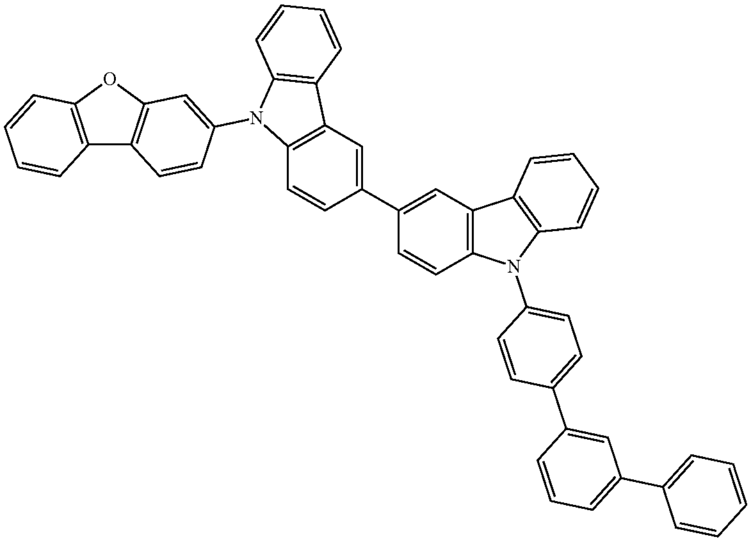
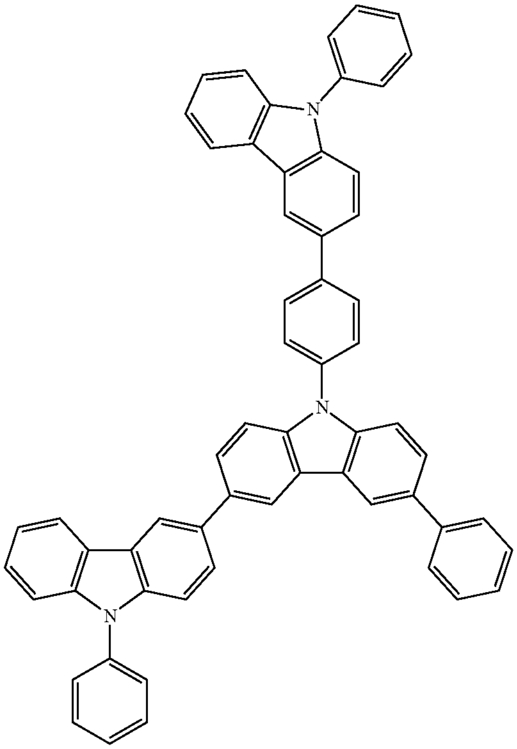

-continued
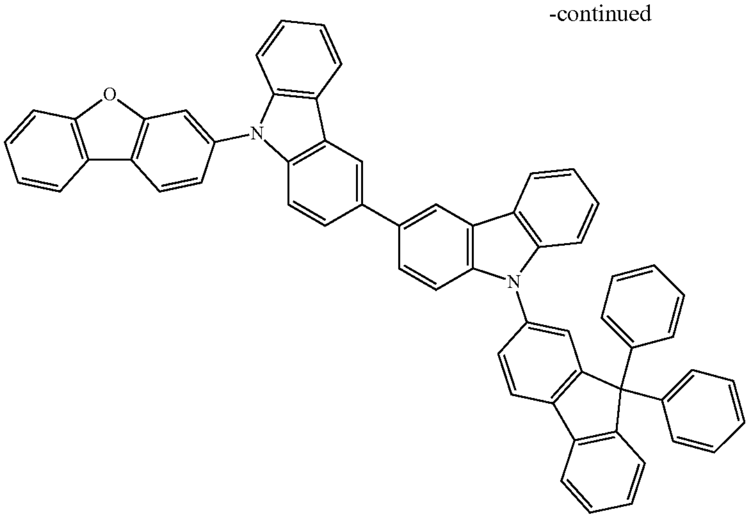
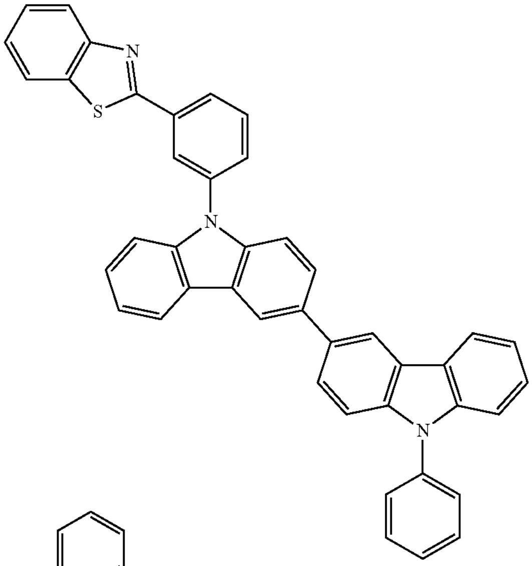
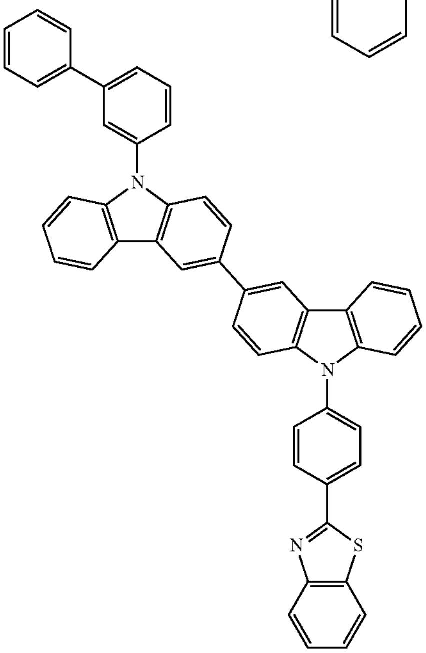
-continued
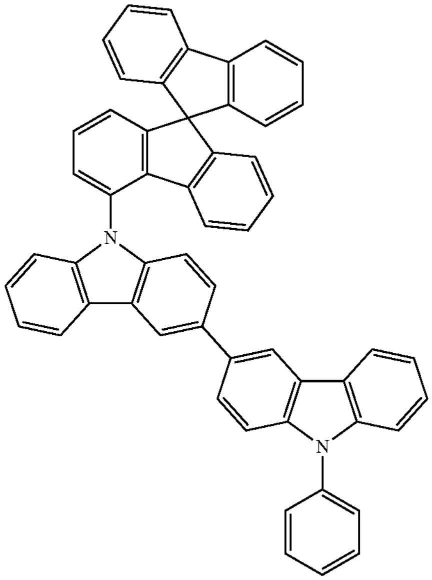
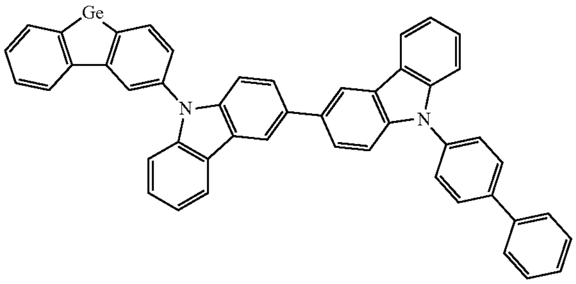
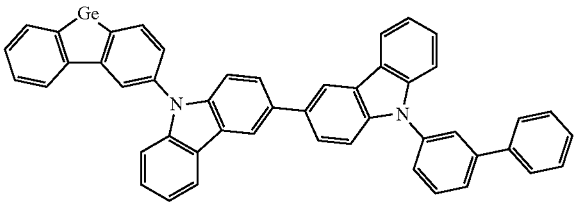

-continued
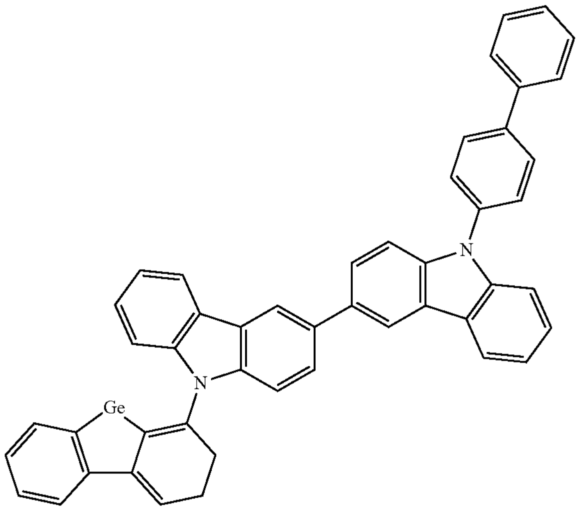
-continued
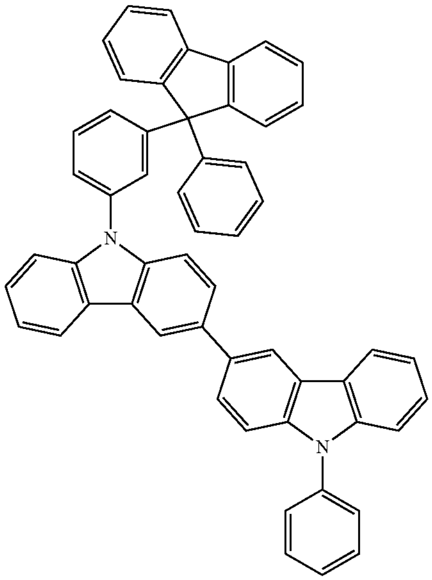
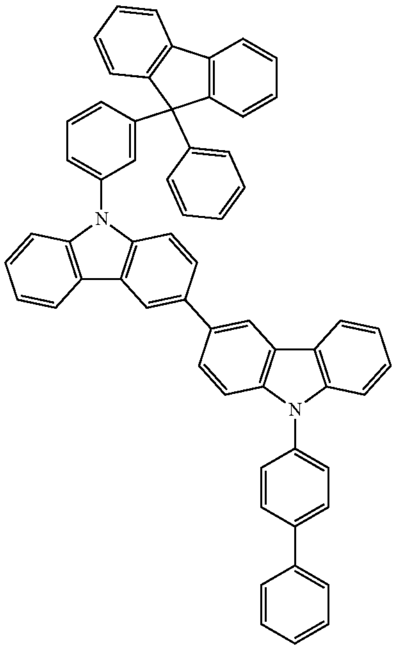
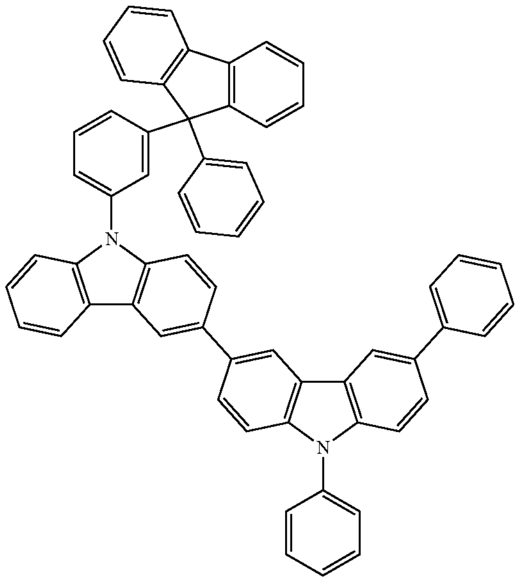

-continued
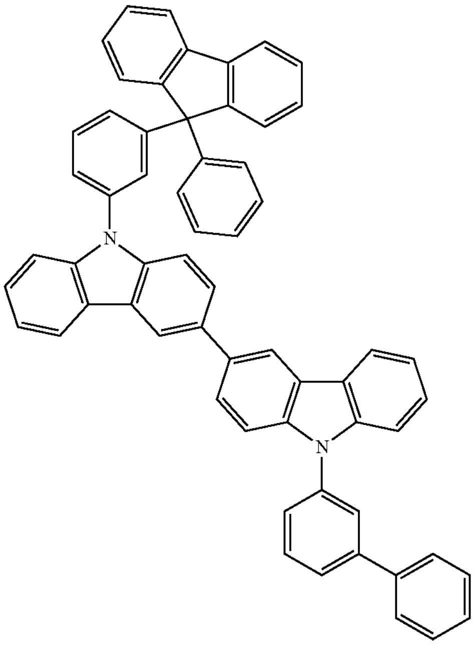
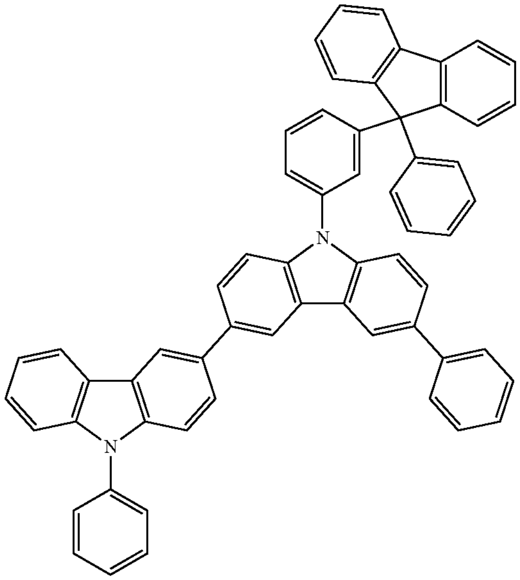
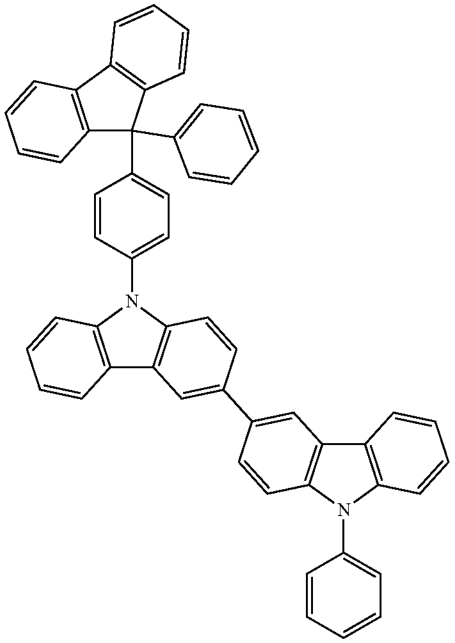
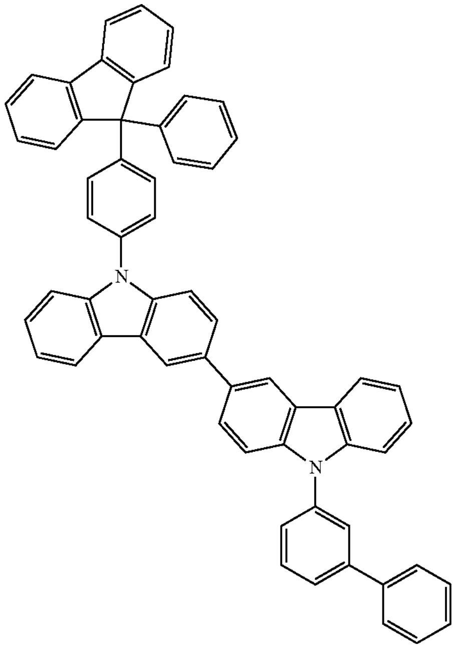

-continued
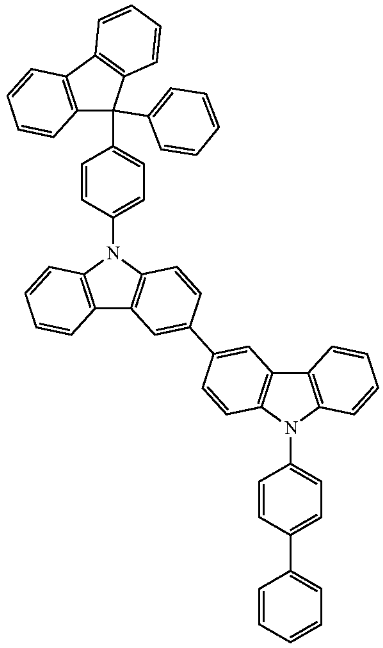
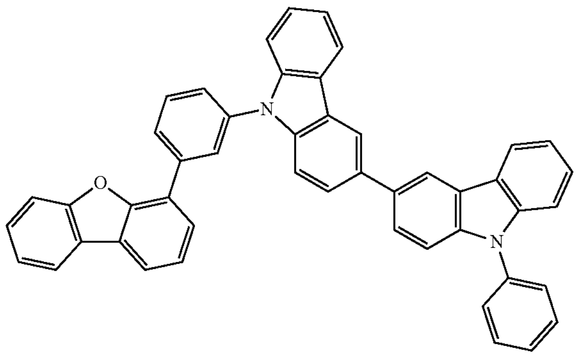
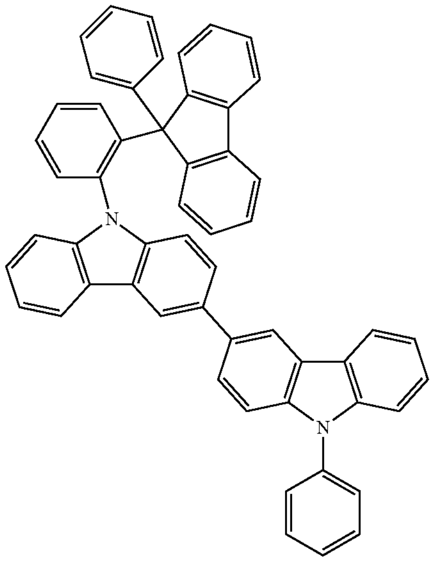
-continued
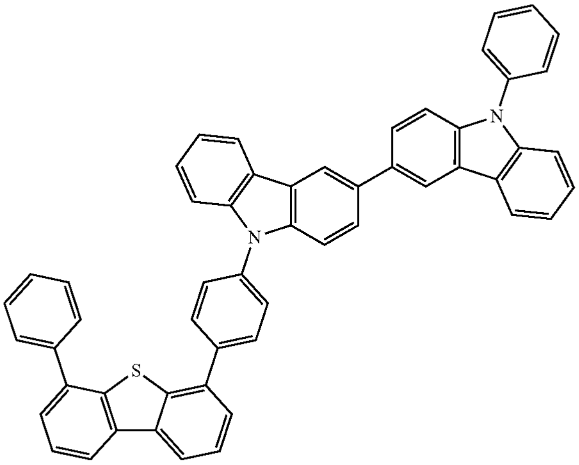
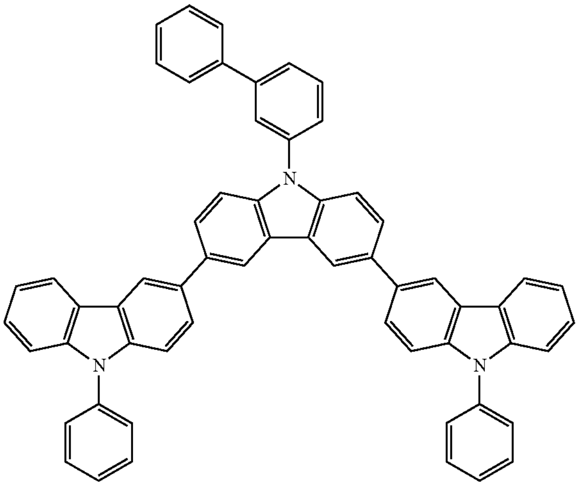
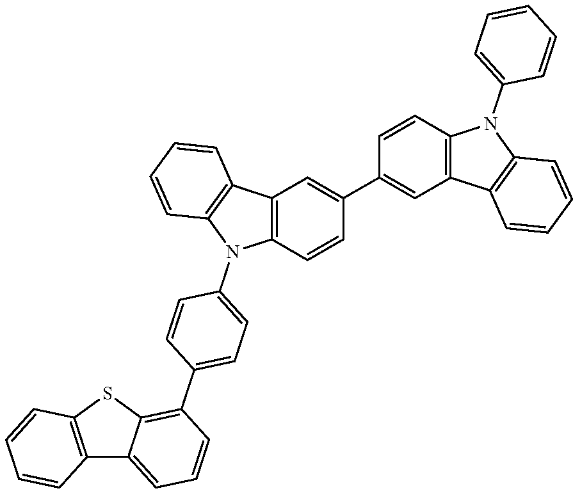

-continued
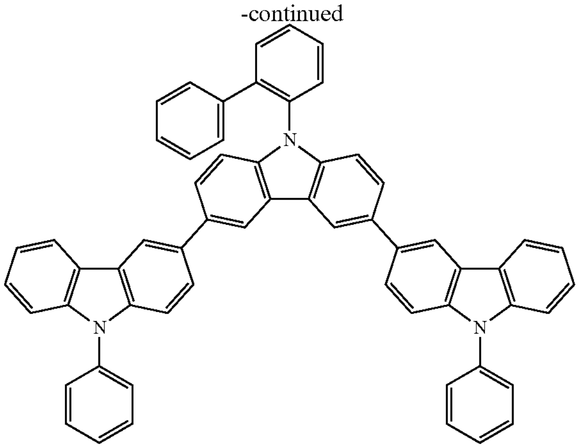
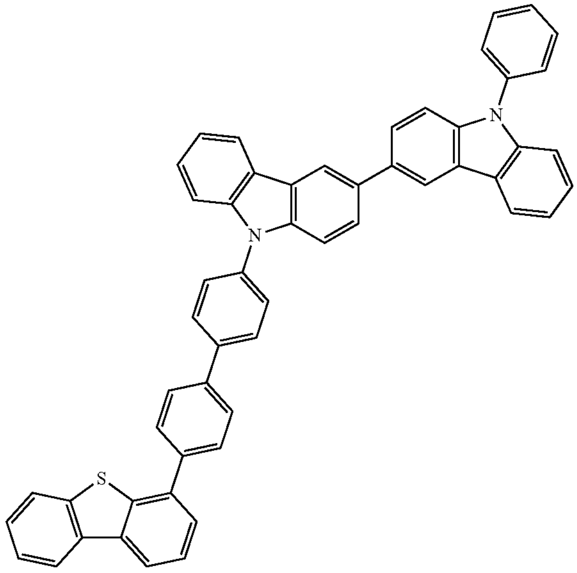
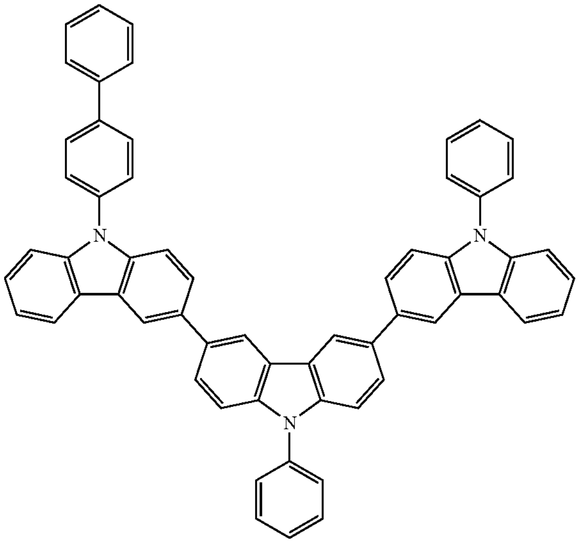
-continued
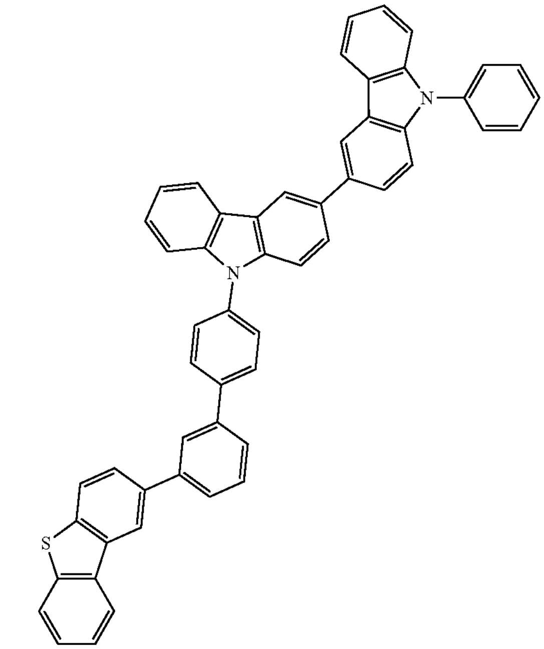
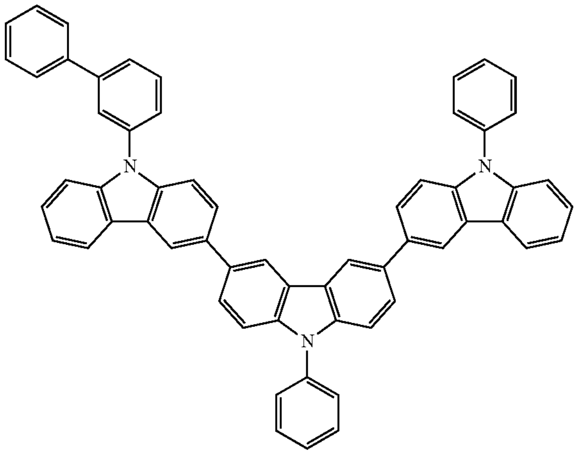
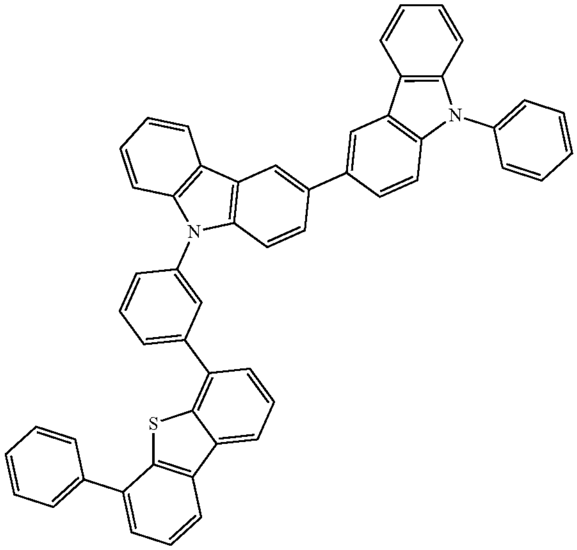

-continued
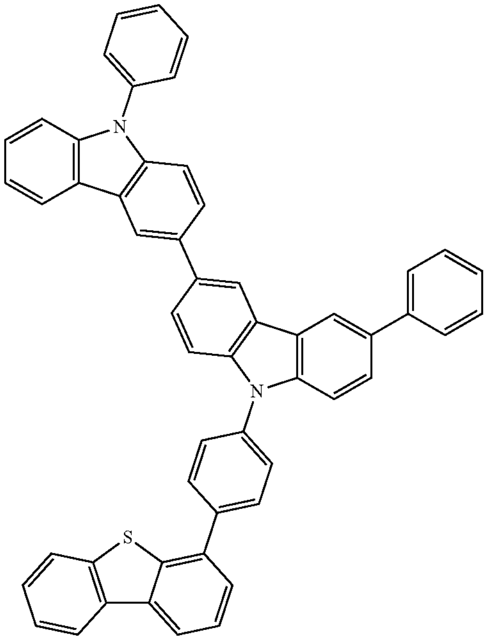
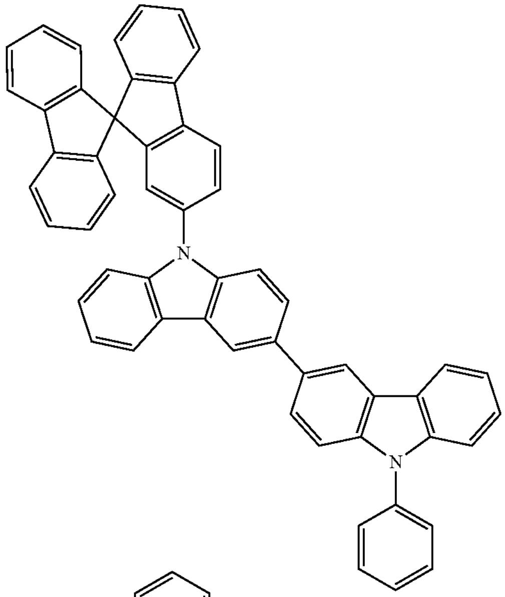
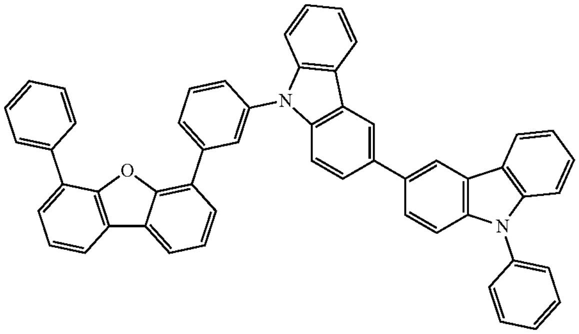
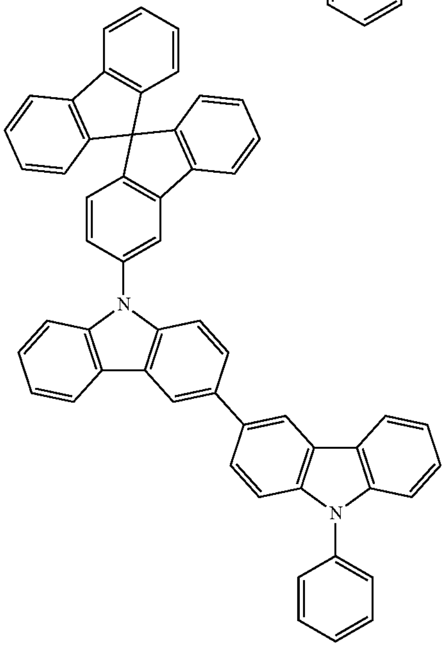
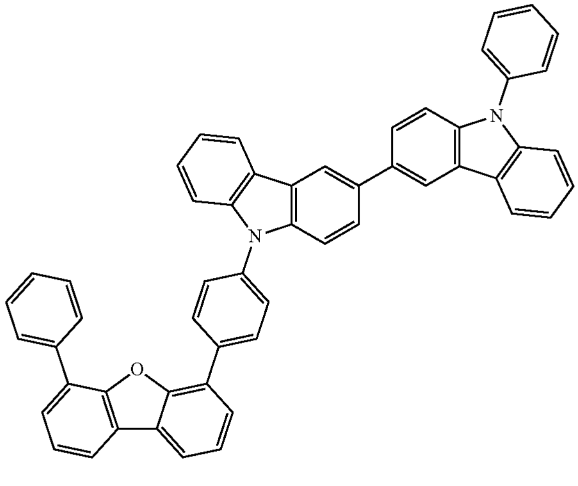
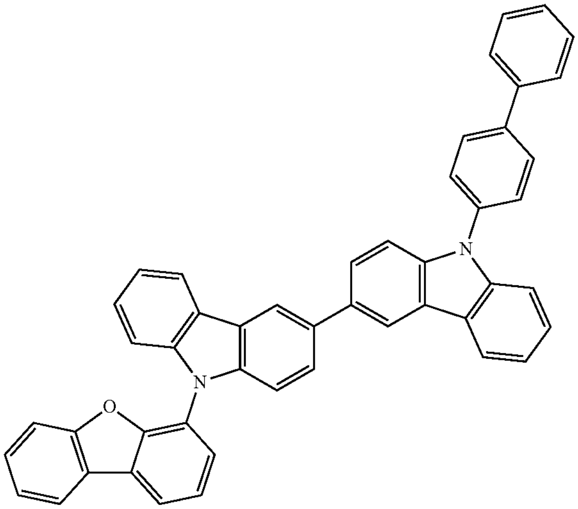

-continued
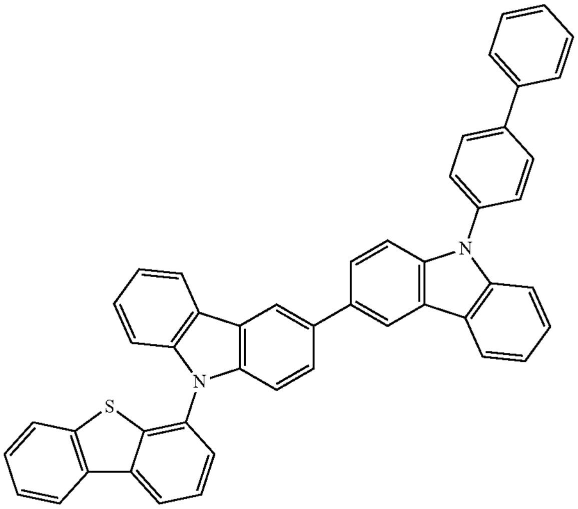
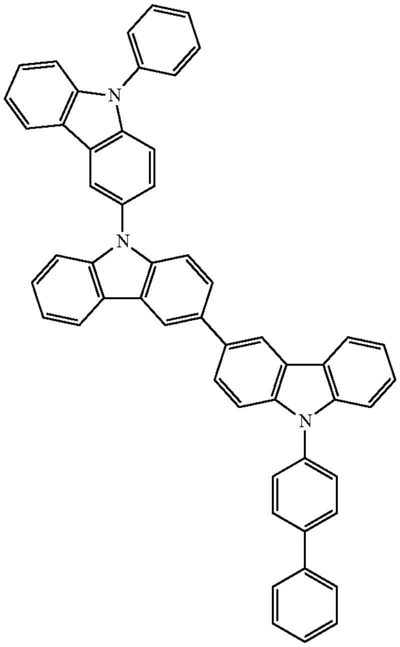
100
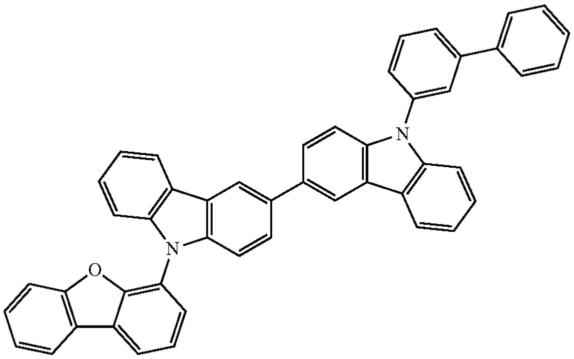
-continued
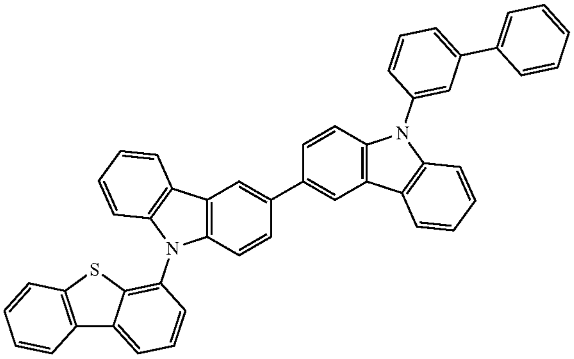
101
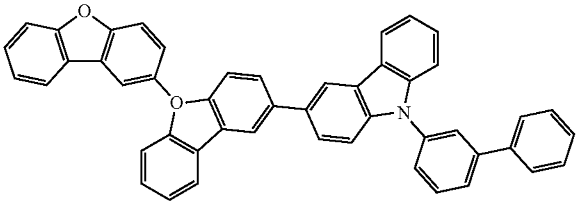
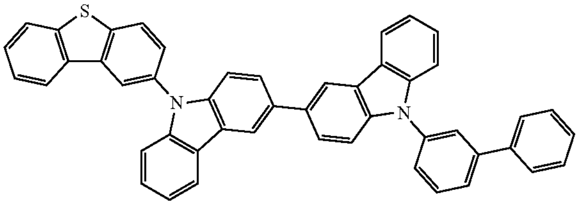
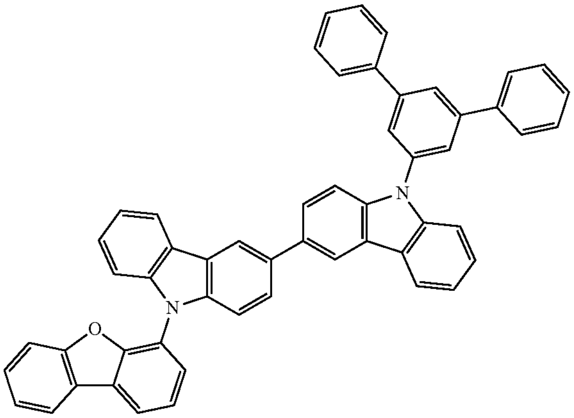

-continued
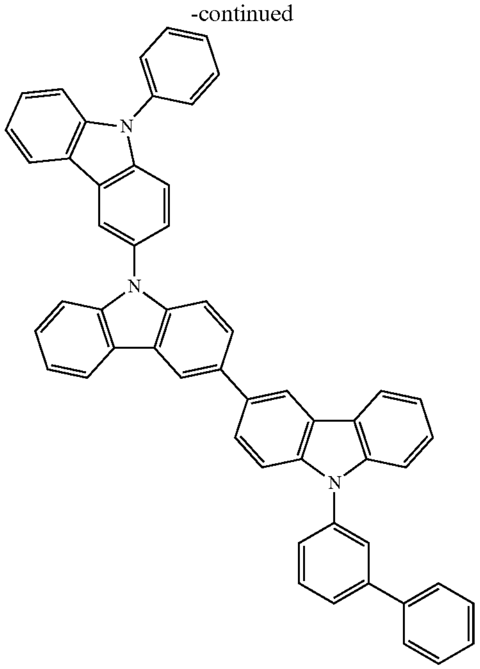
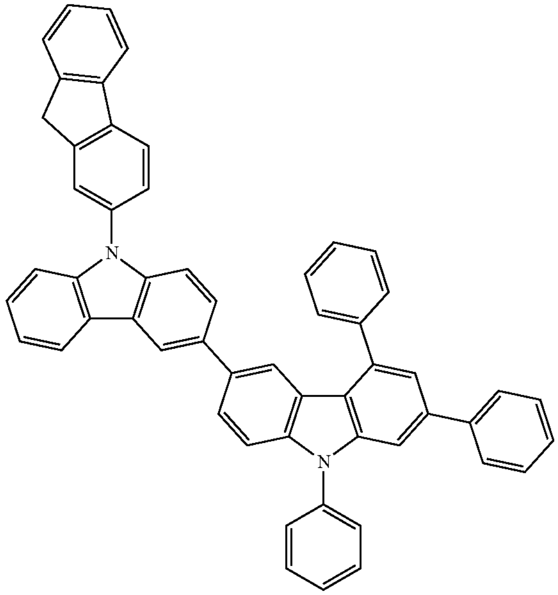
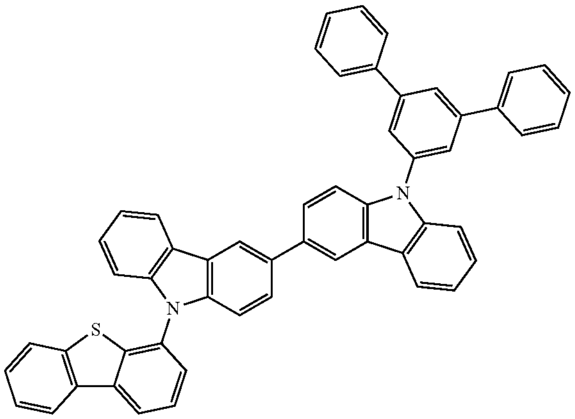
-continued
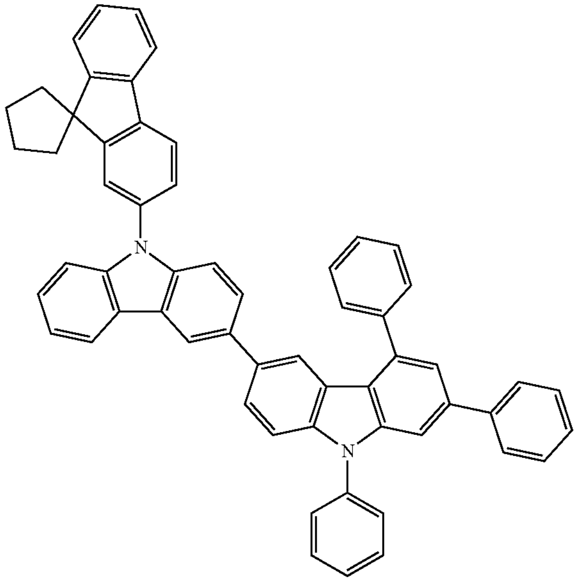
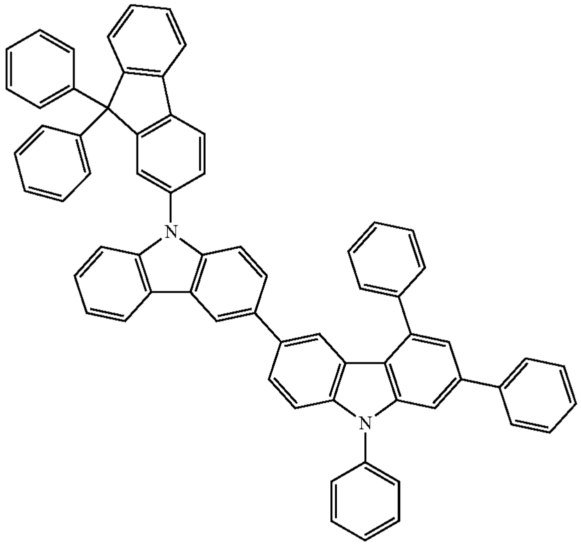
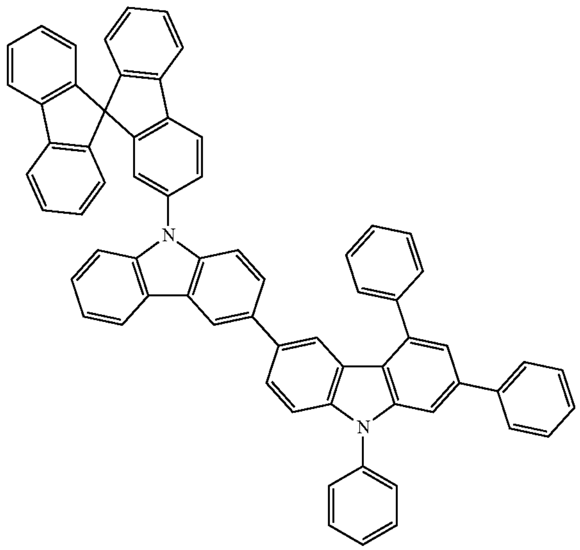

-continued
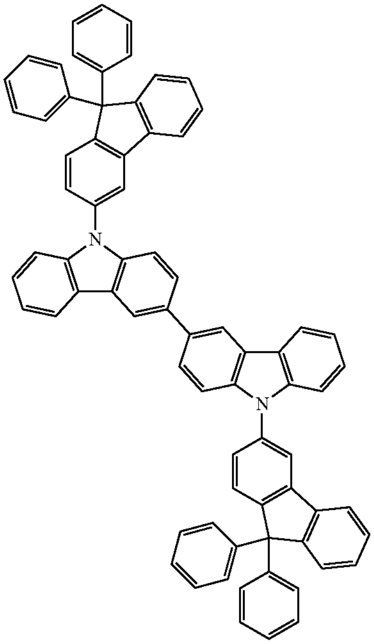
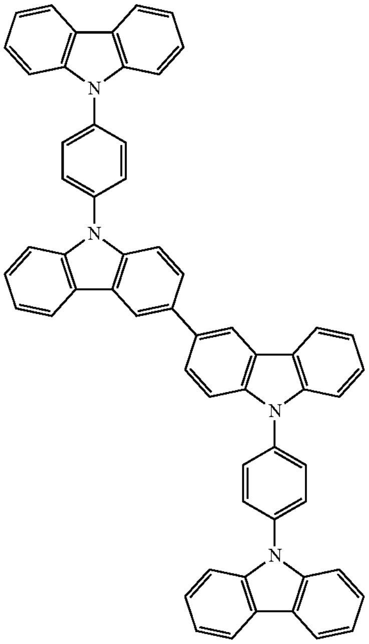
-continued
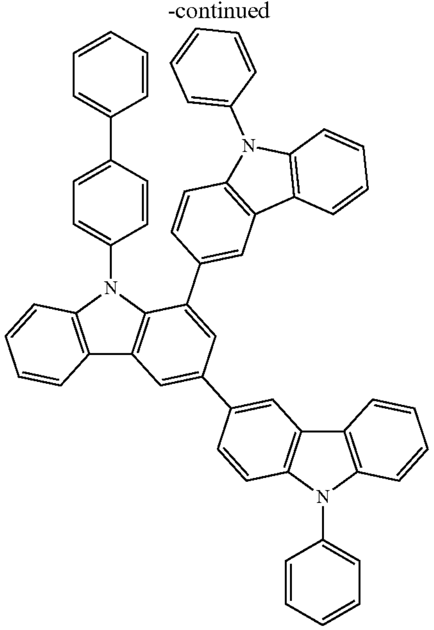
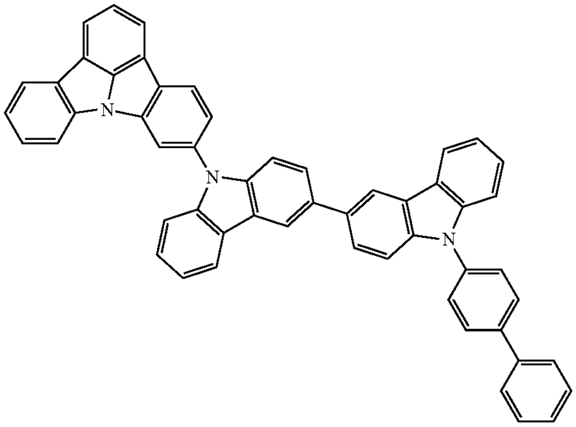
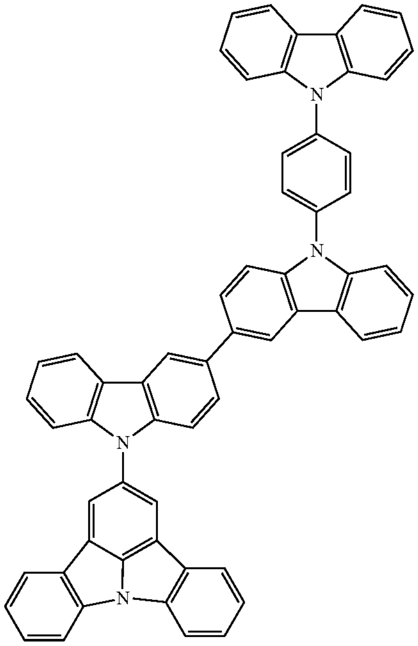

-continued
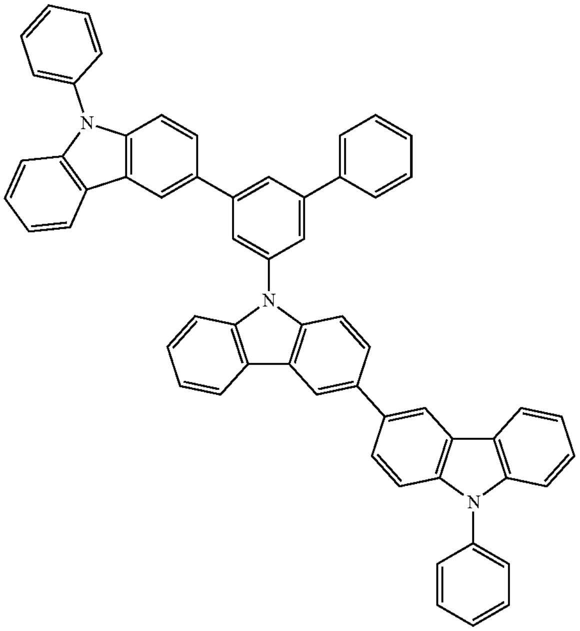
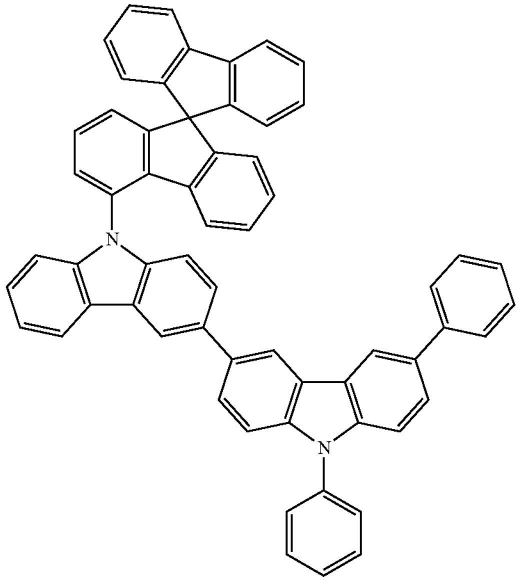
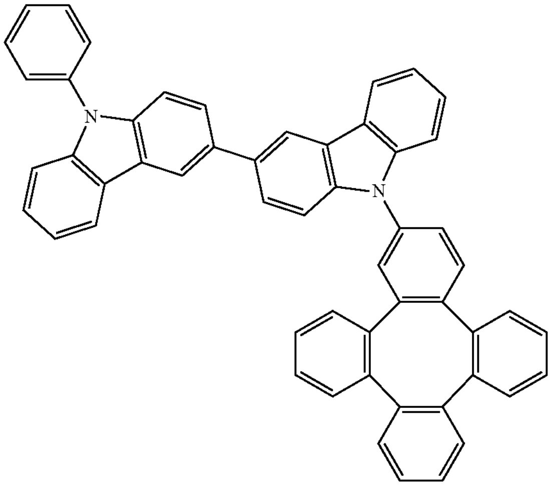
-continued
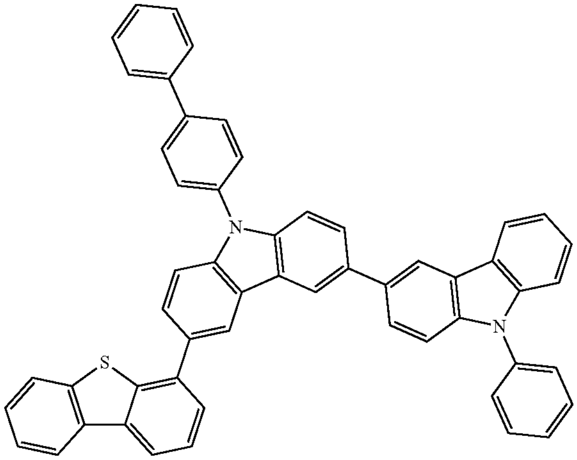
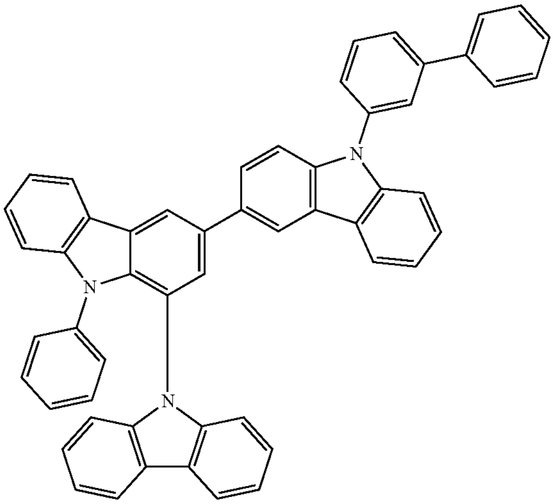
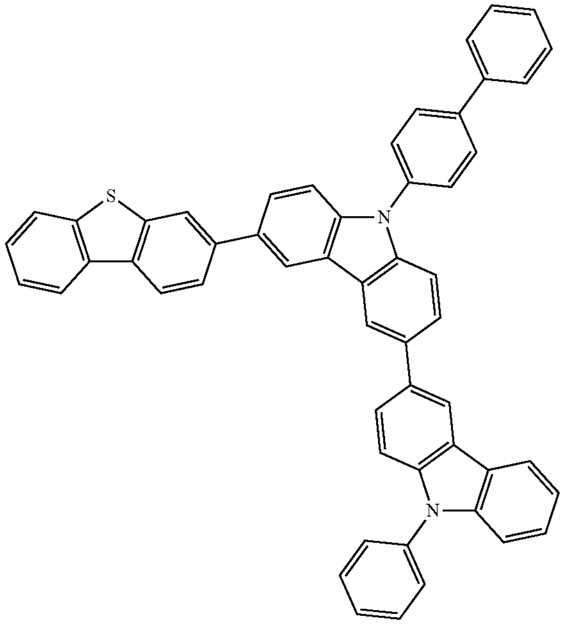

-continued
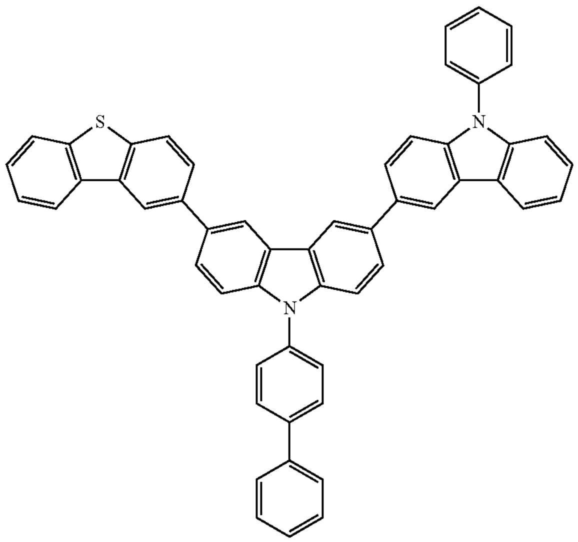
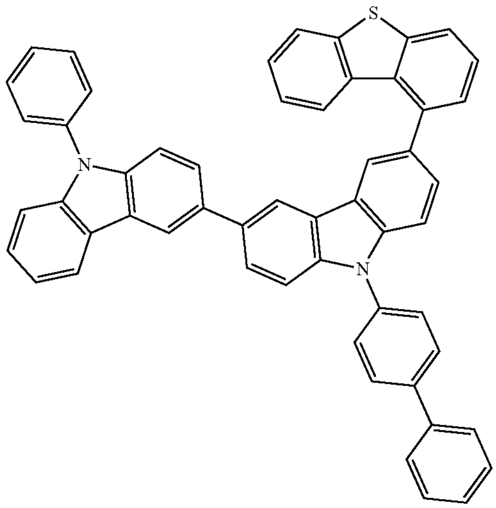
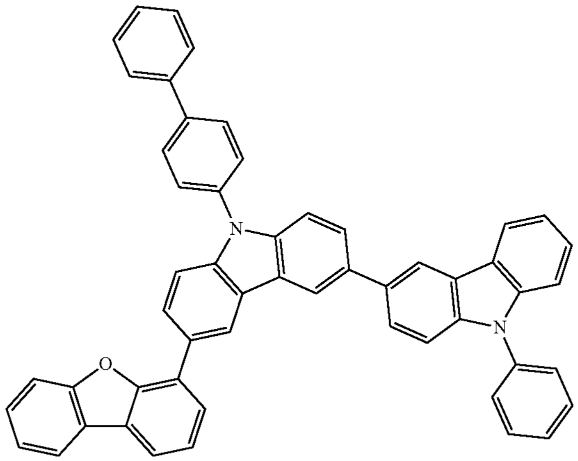
-continued
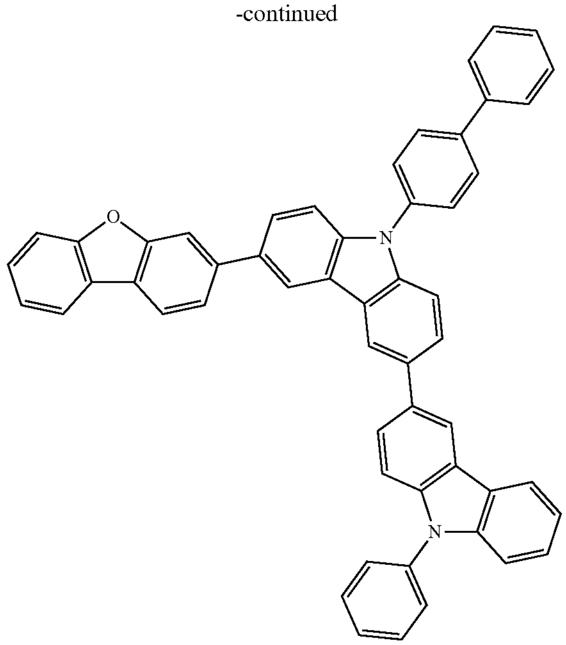
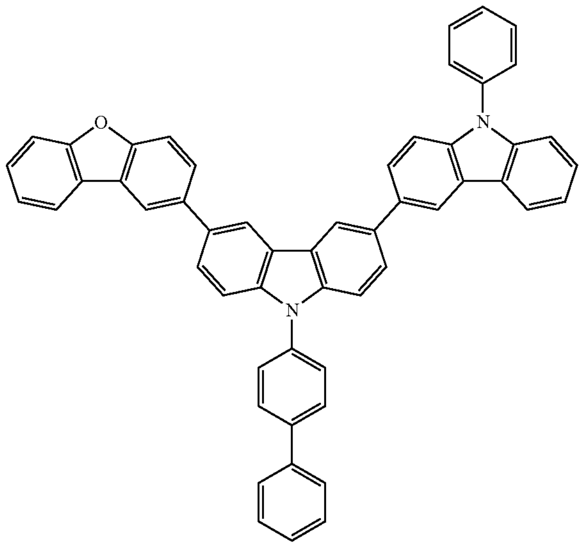
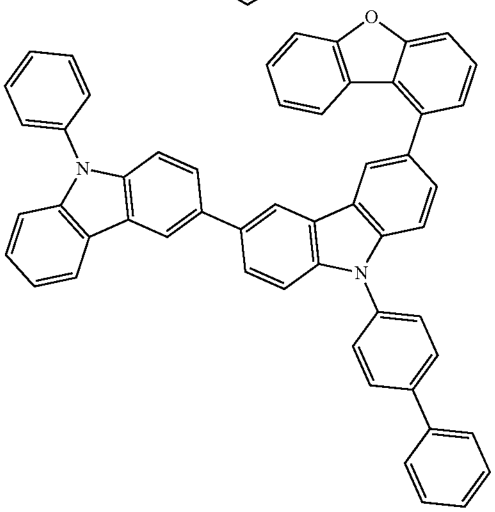

-continued
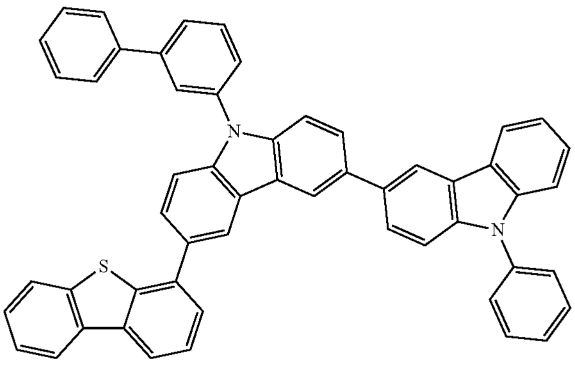
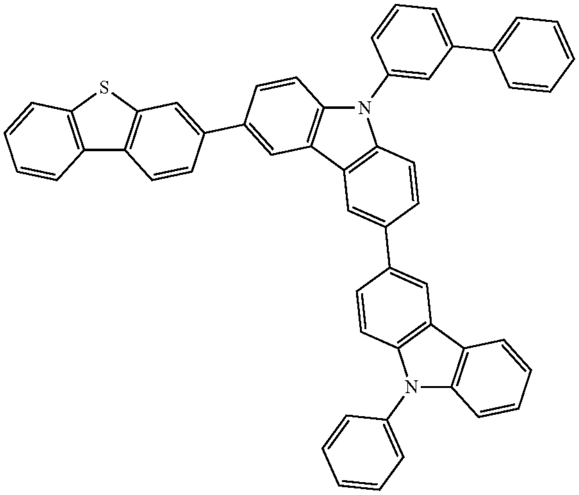
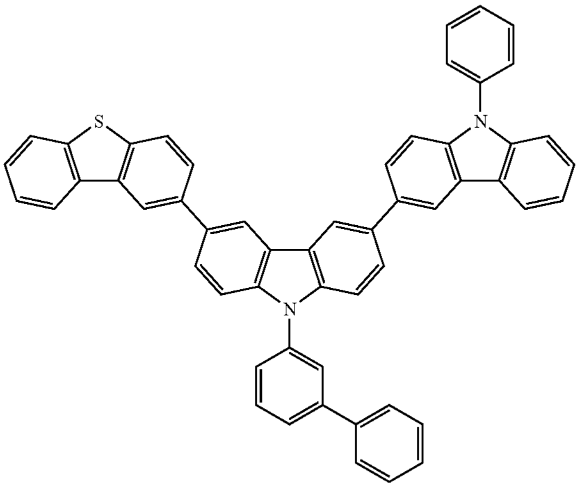
-continued
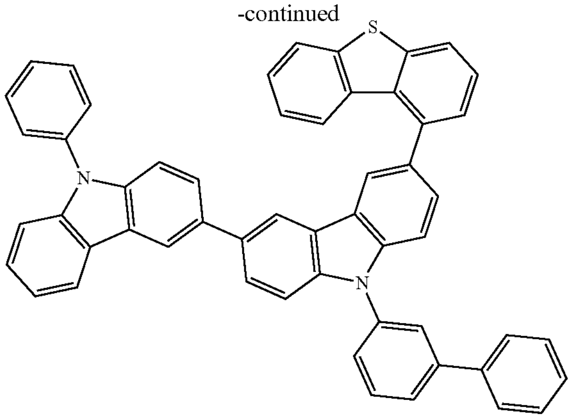
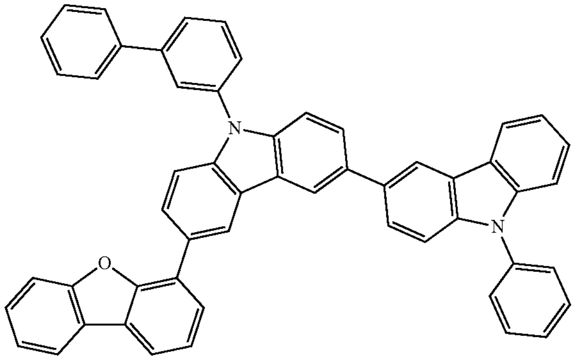
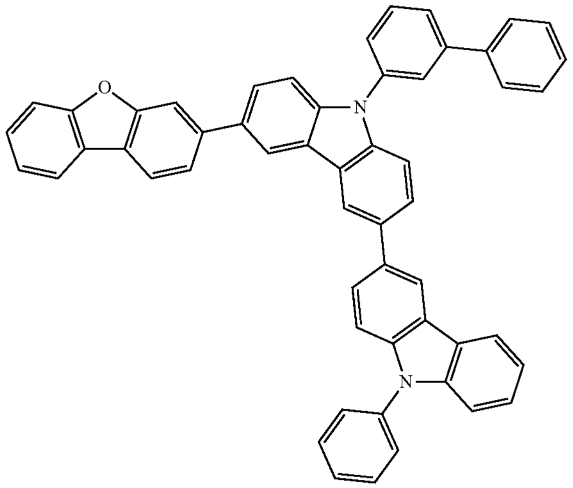
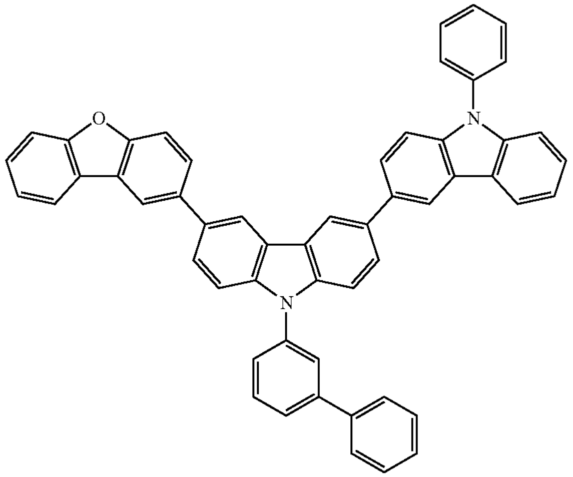

-continued
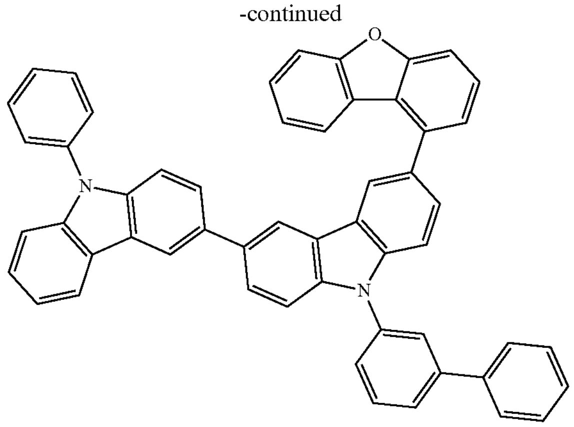
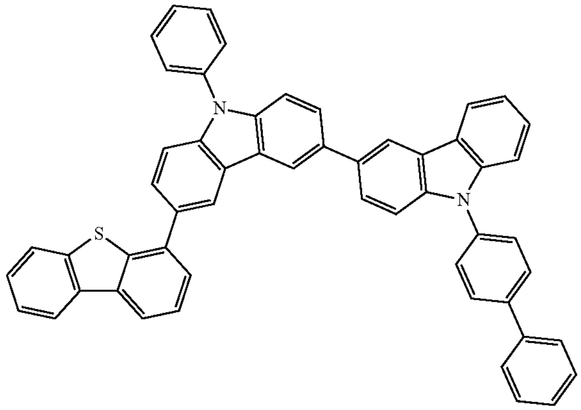
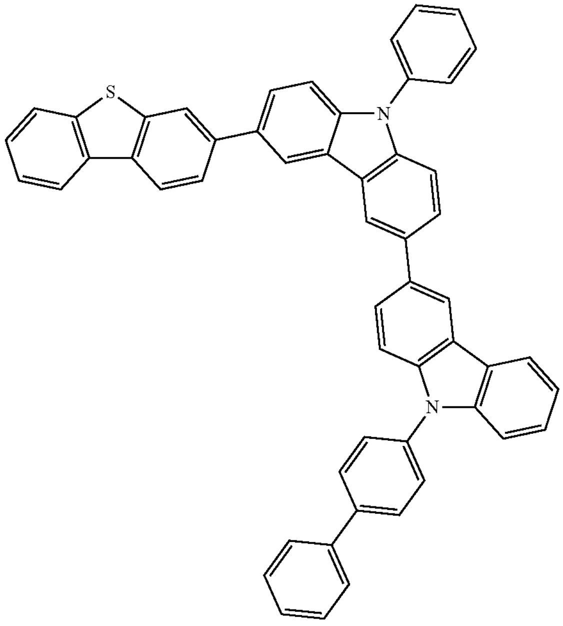
-continued
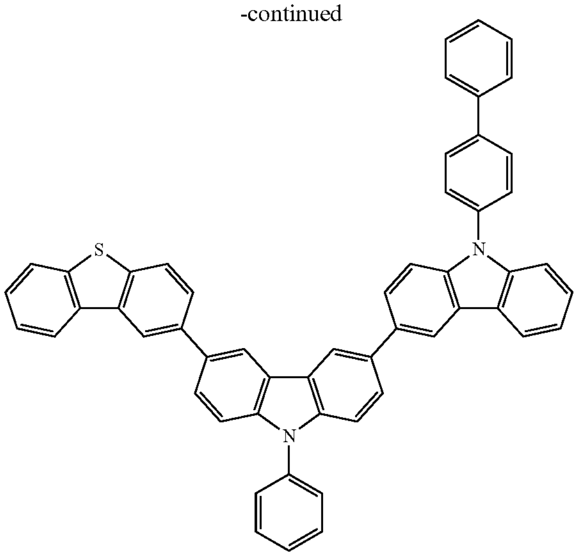
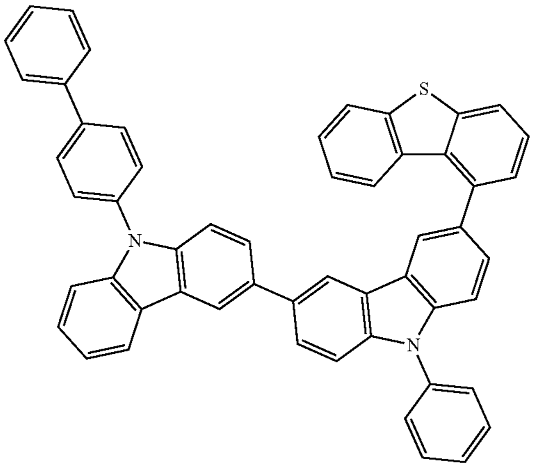
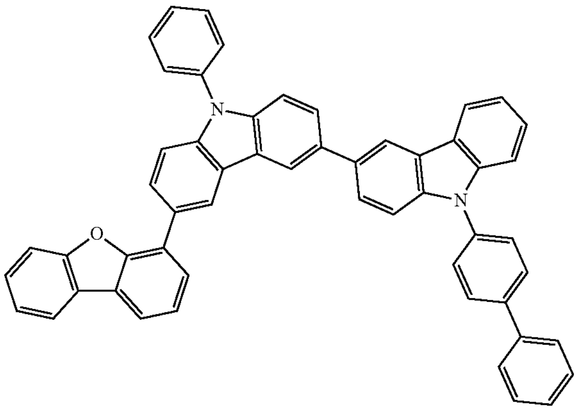

-continued
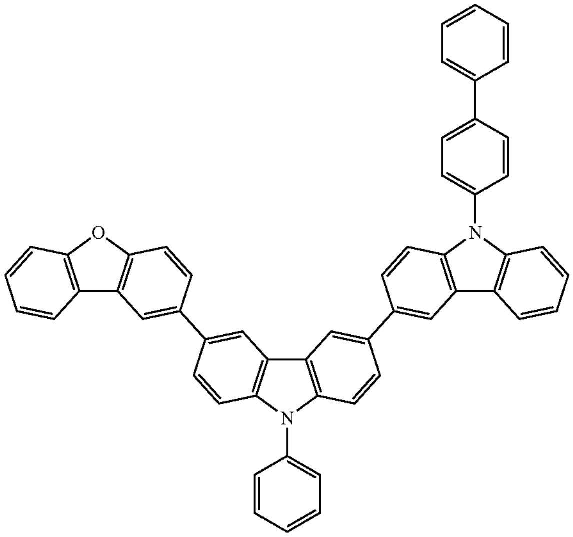
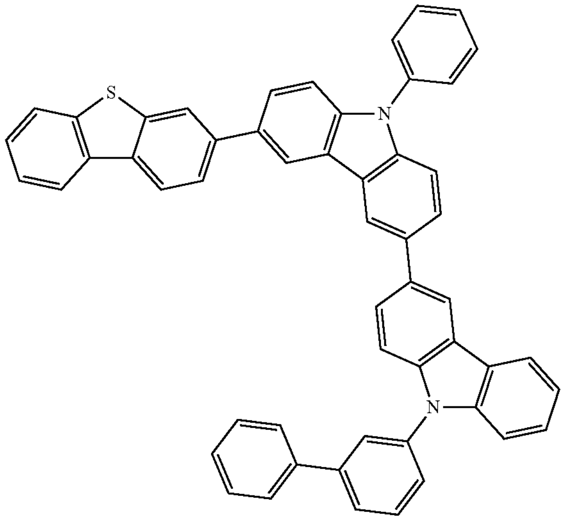
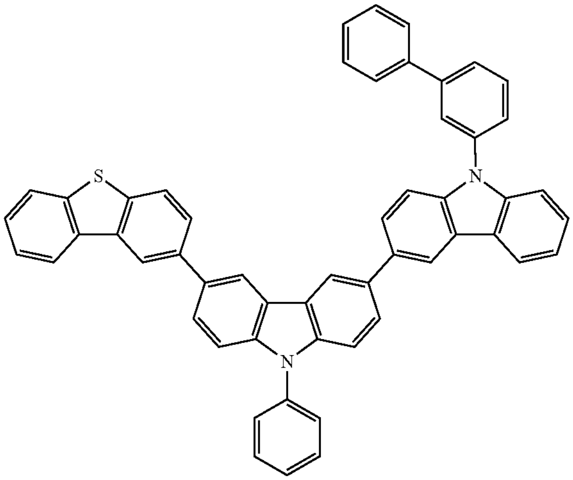
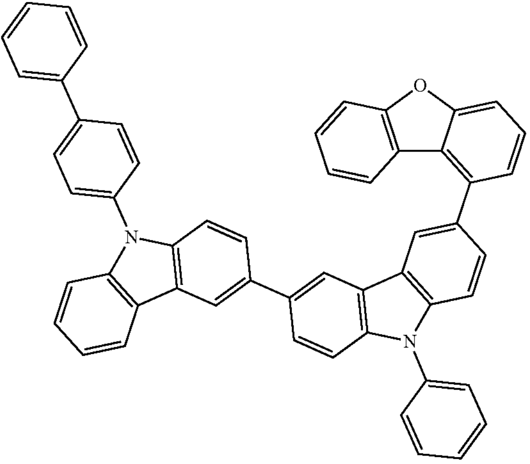
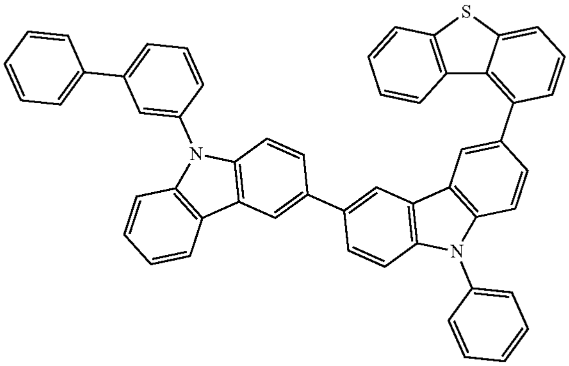
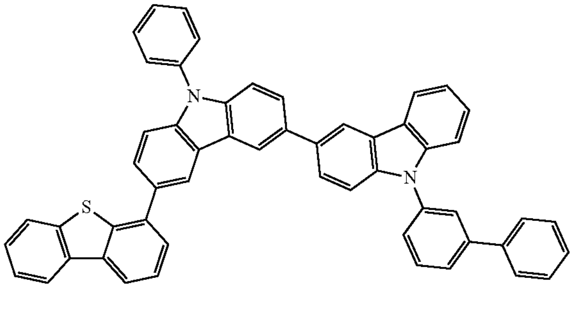
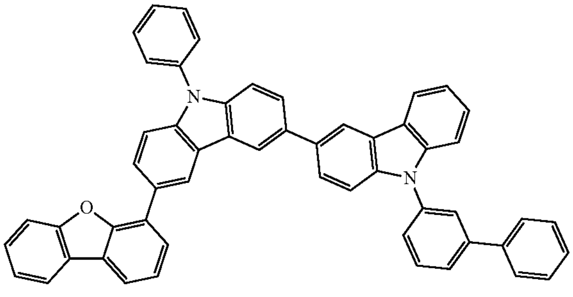

-continued
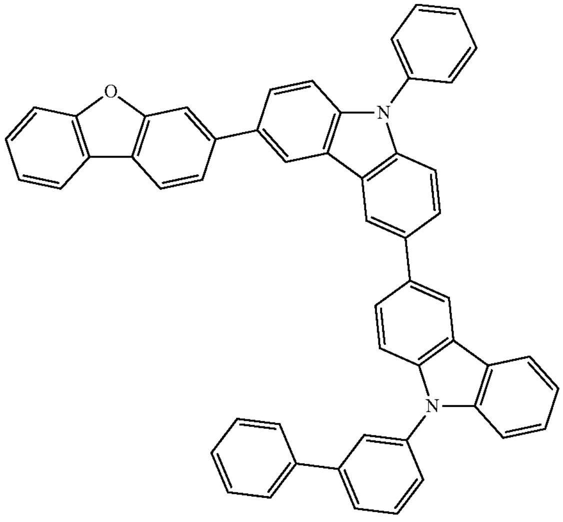
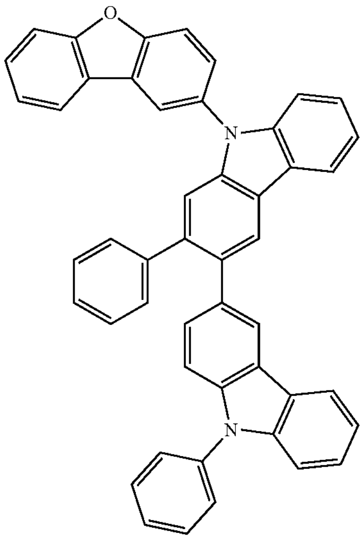
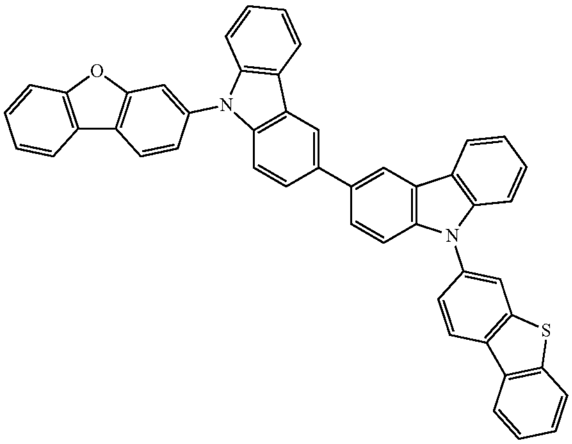
-continued
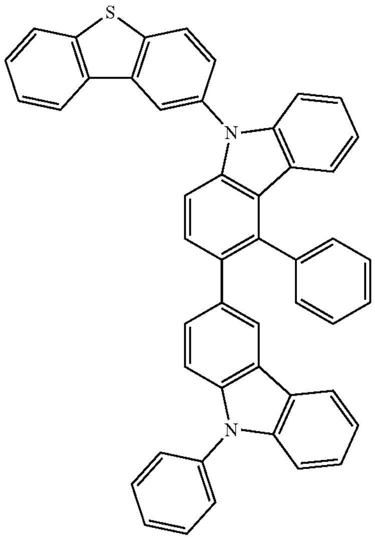
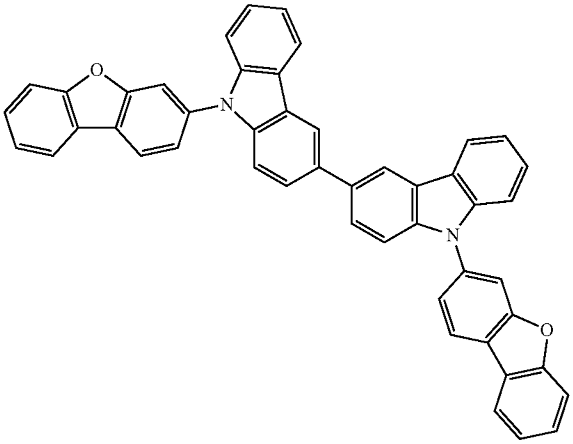
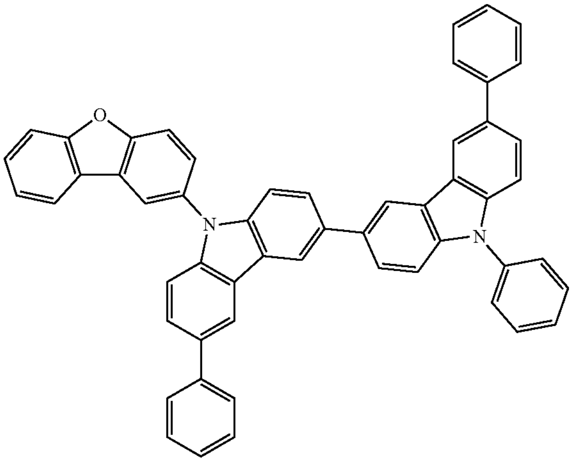

-continued
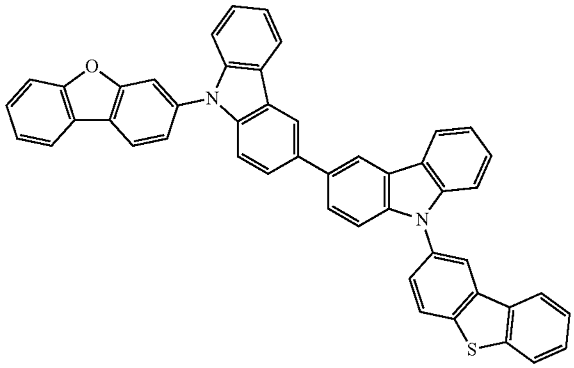
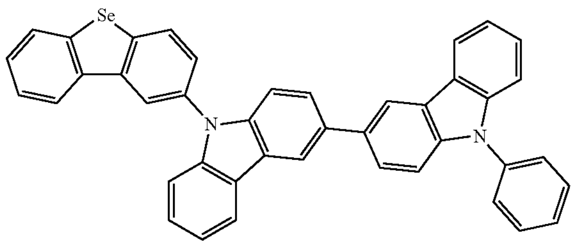
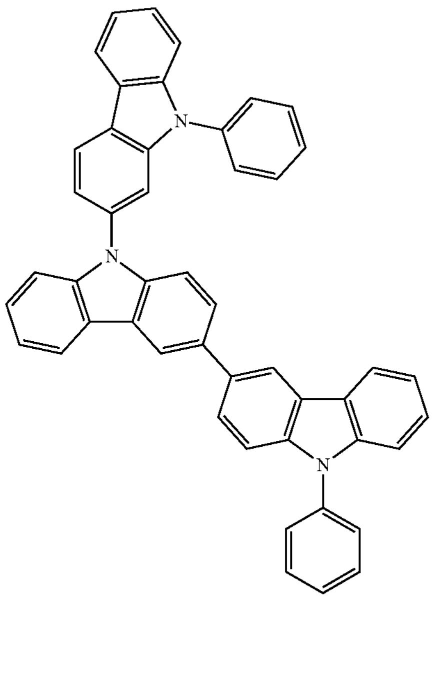
-continued
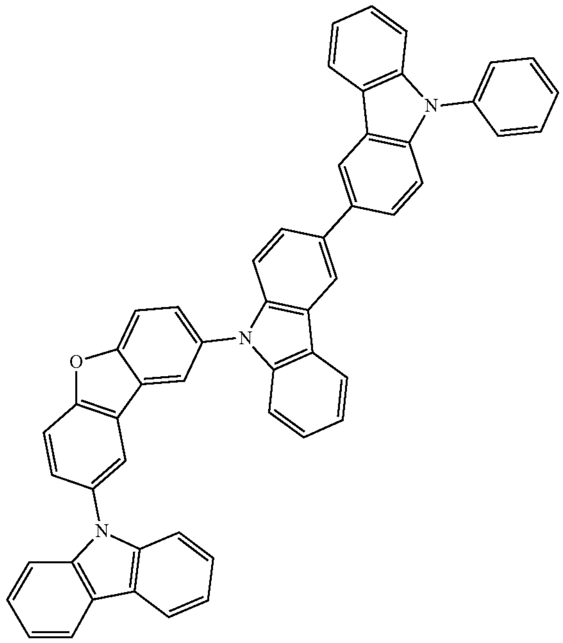
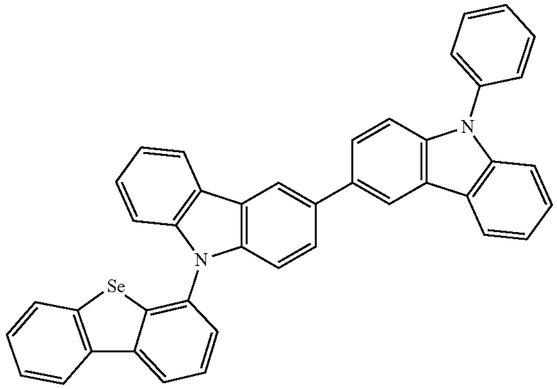
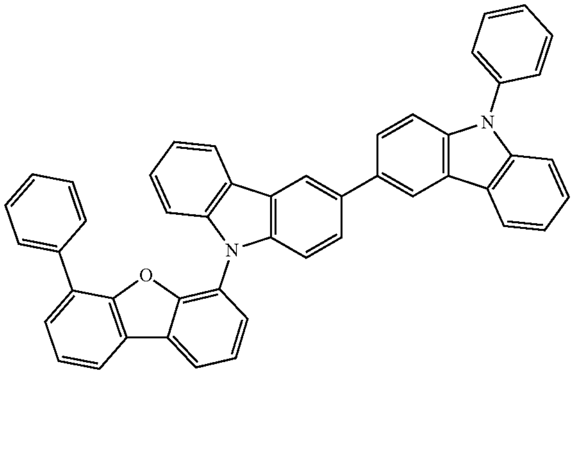

-continued
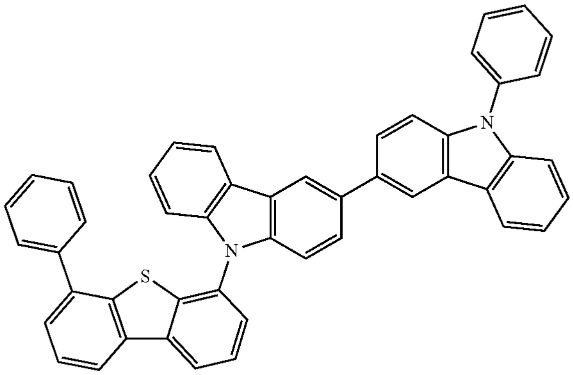
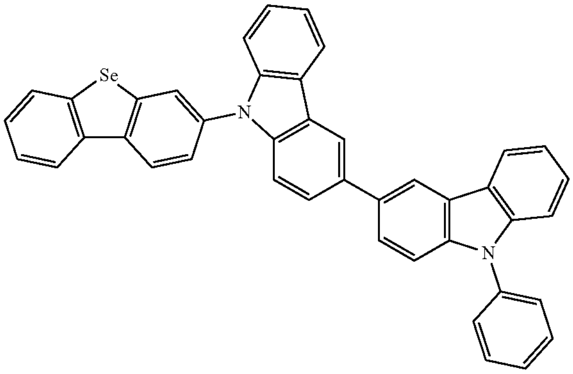
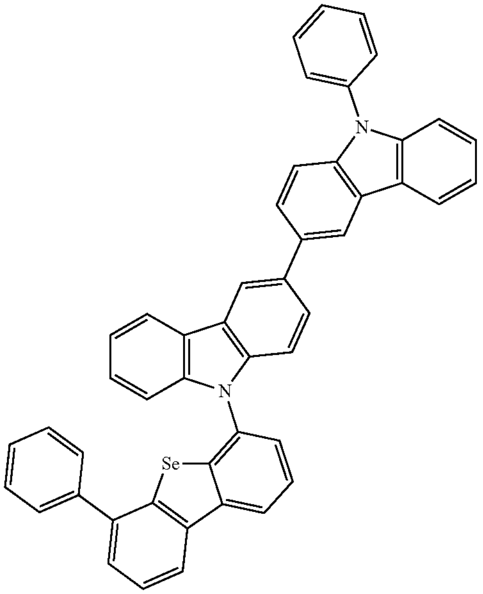
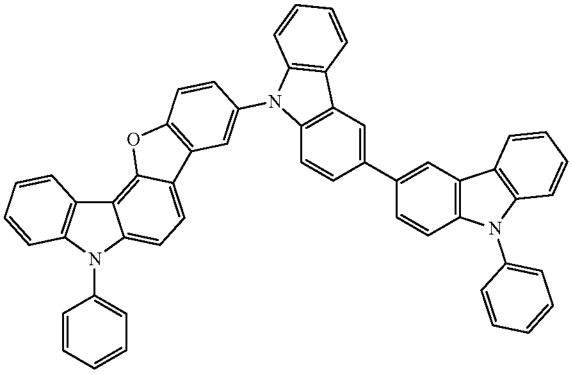
-continued
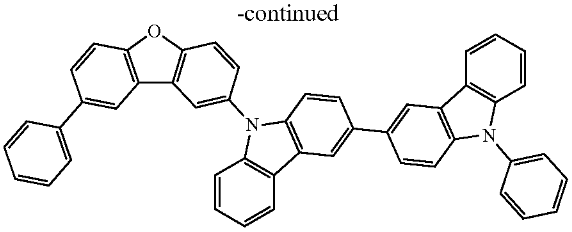
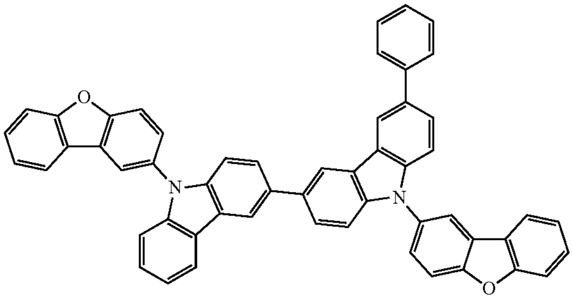
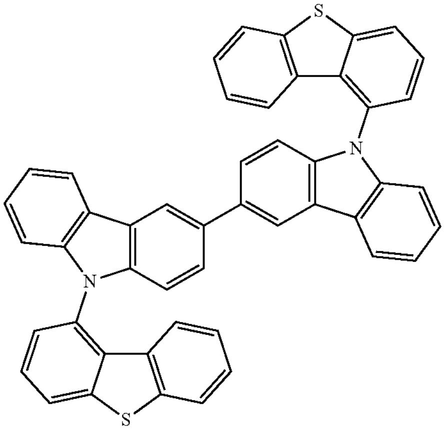
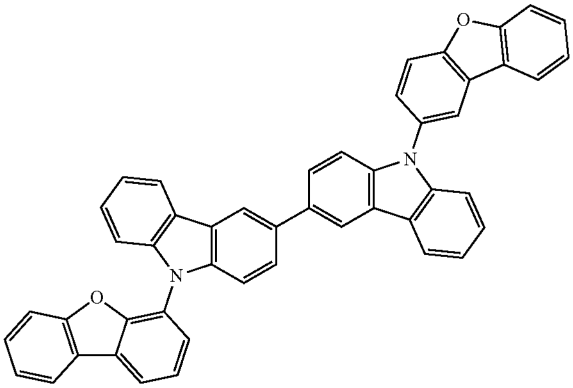

-continued
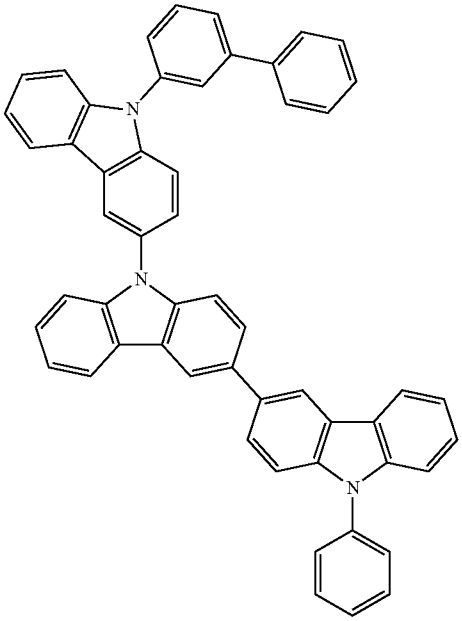
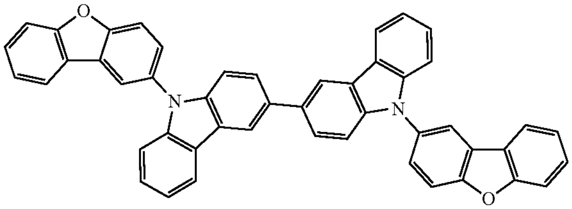
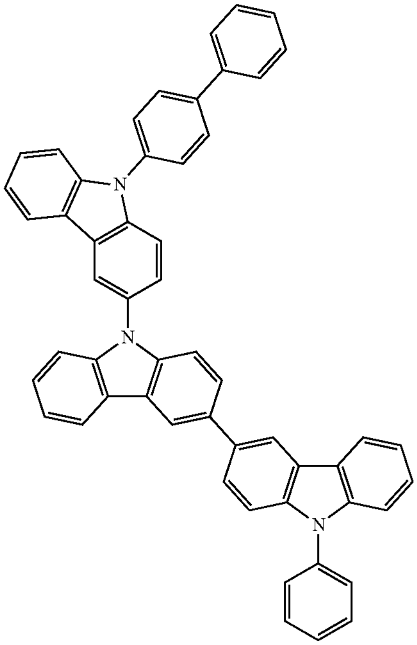
-continued
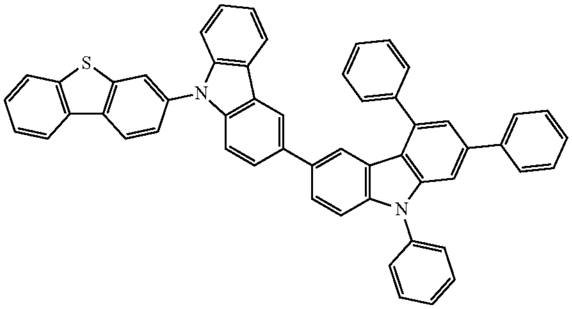
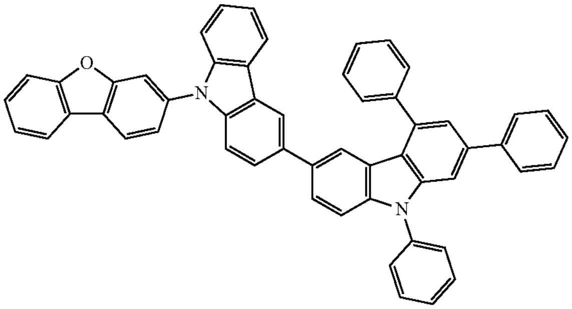
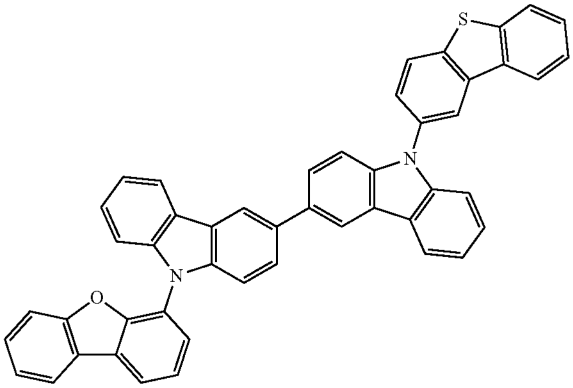
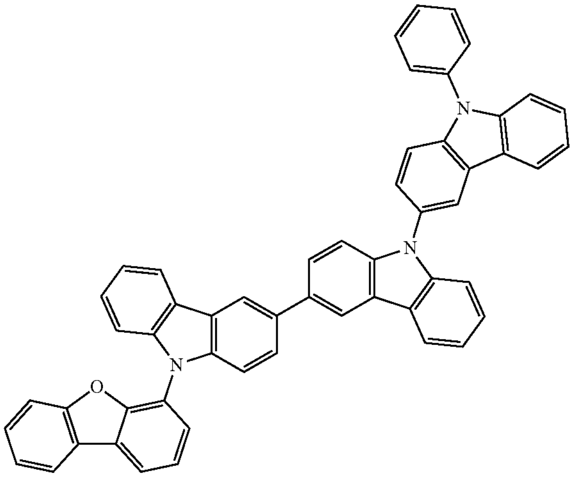
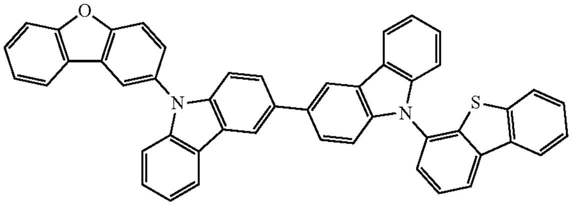

-continued
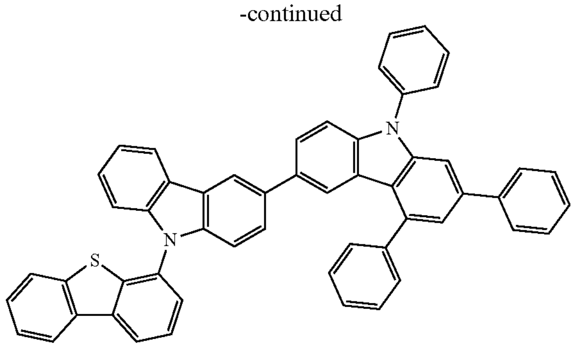
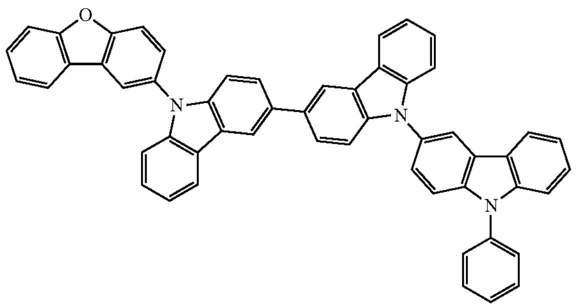
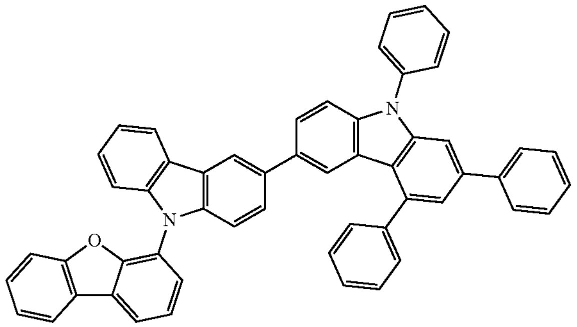
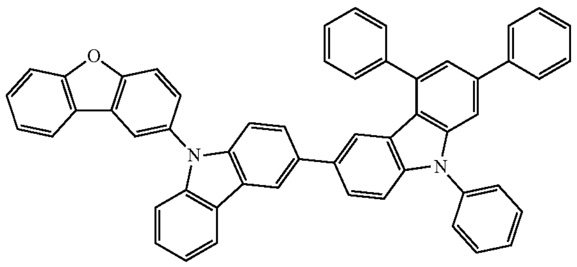
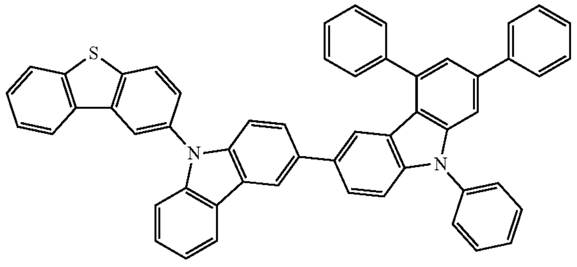
-continued
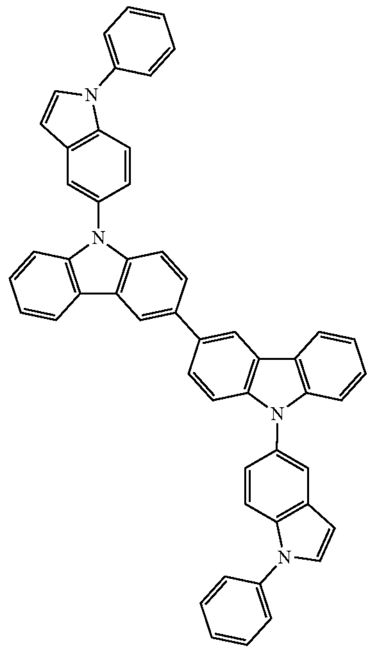
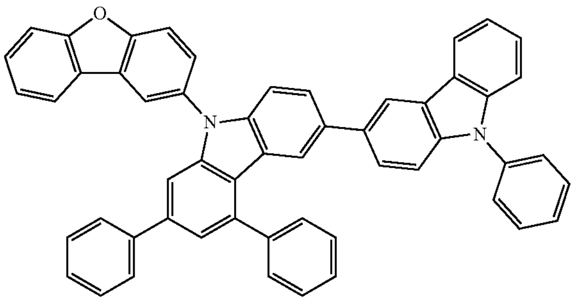
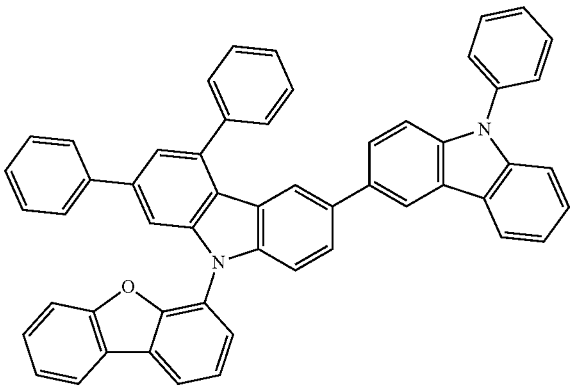
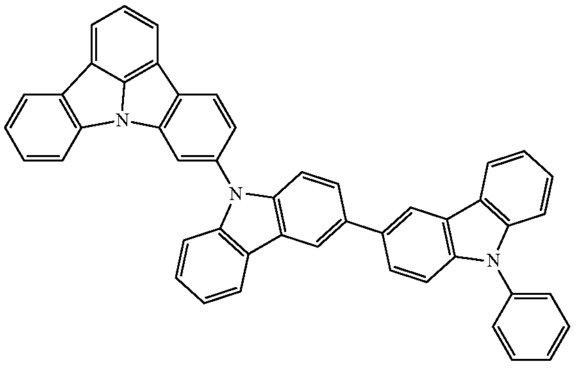

-continued
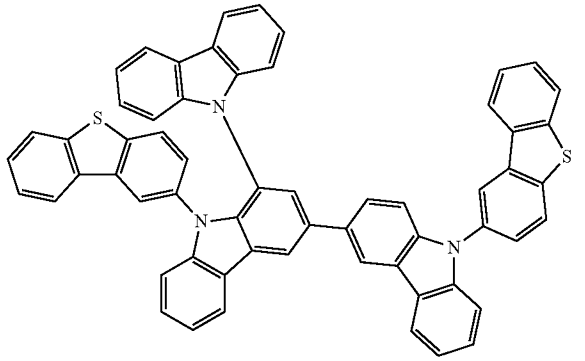
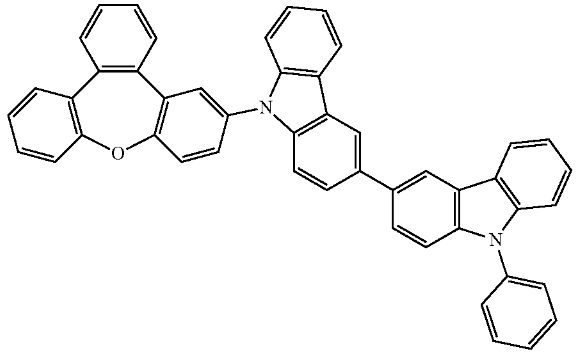
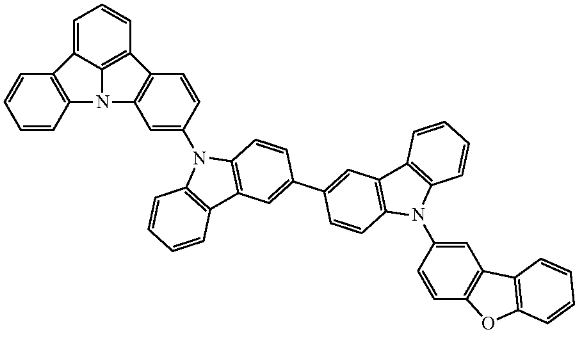
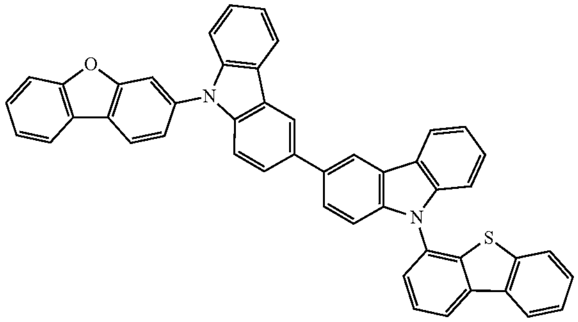
-continued
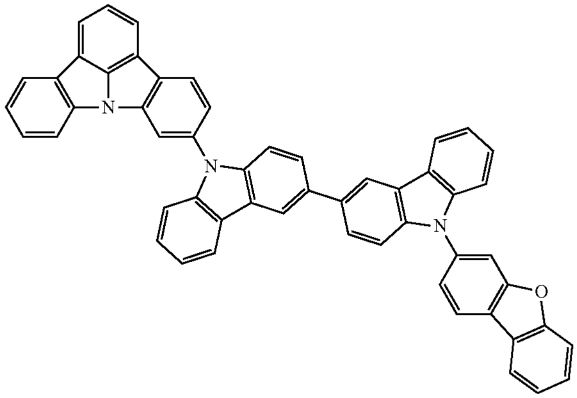
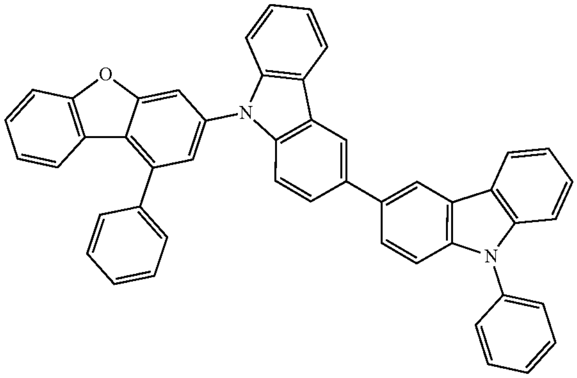
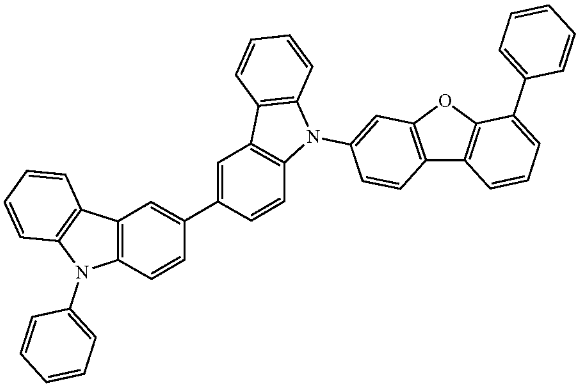
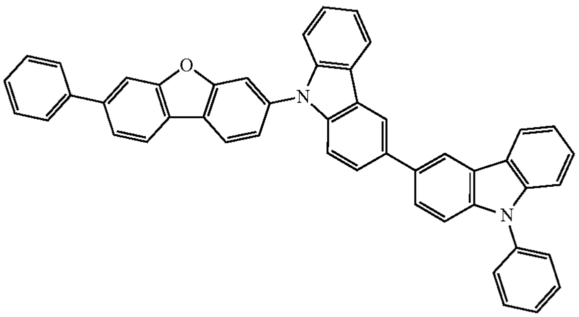

-continued
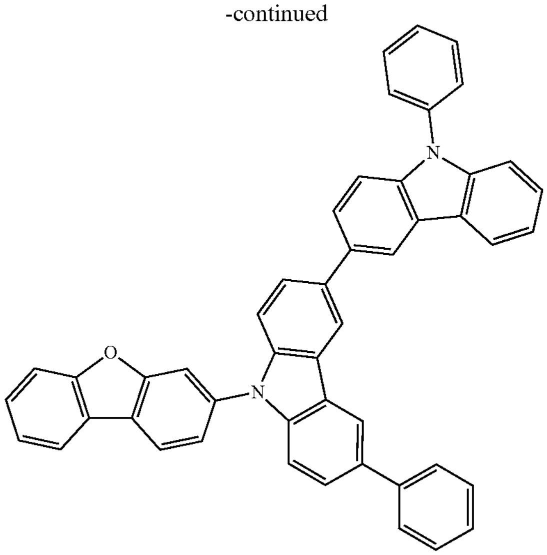
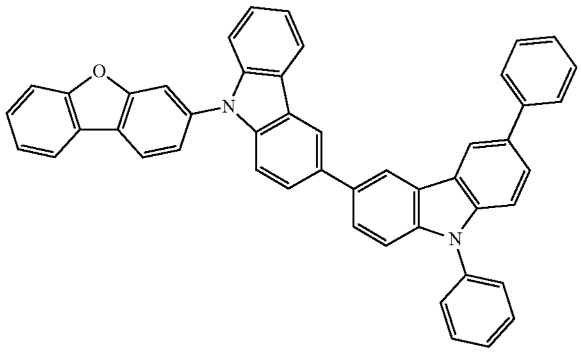
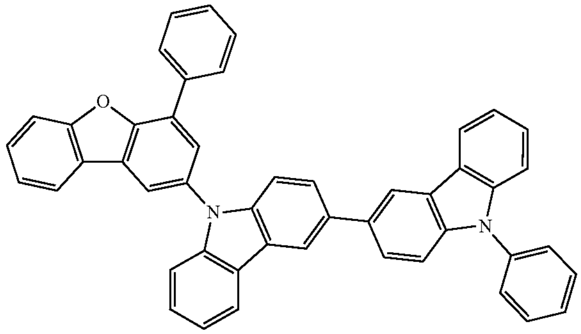
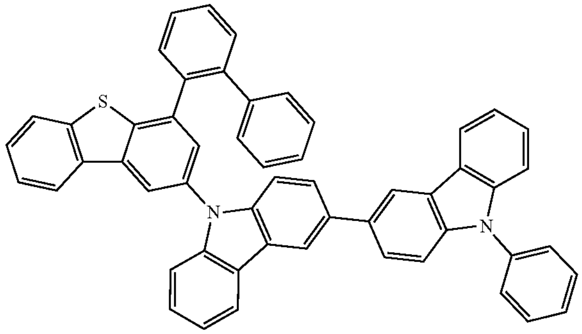
-continued
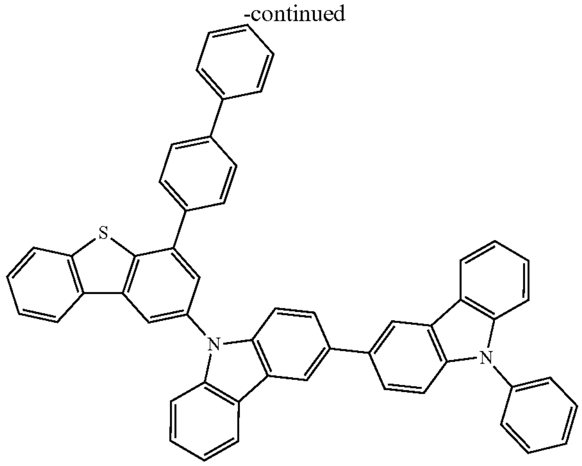
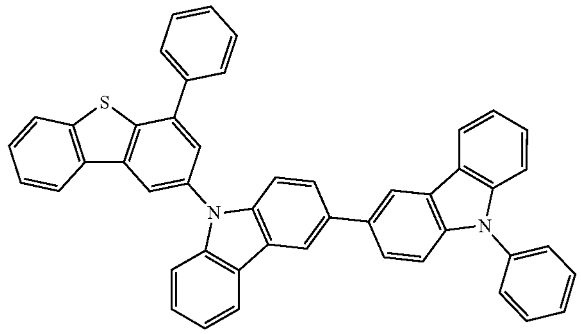
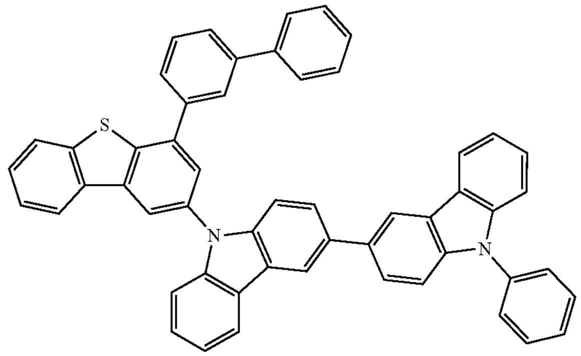
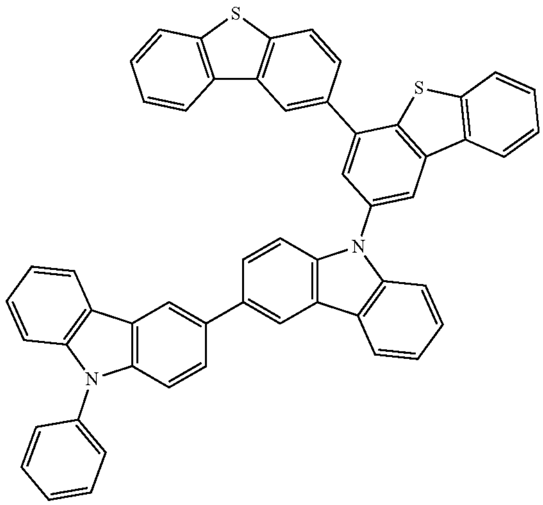

-continued
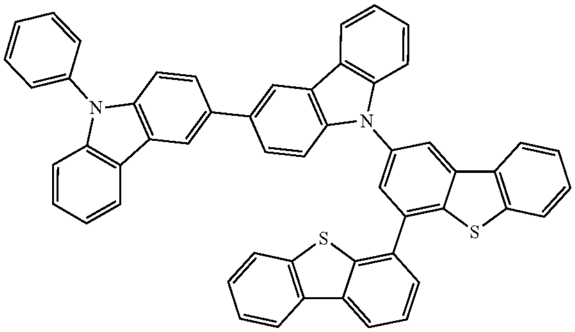
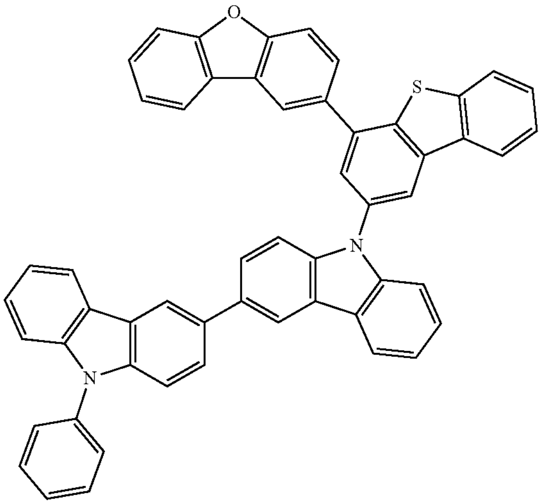
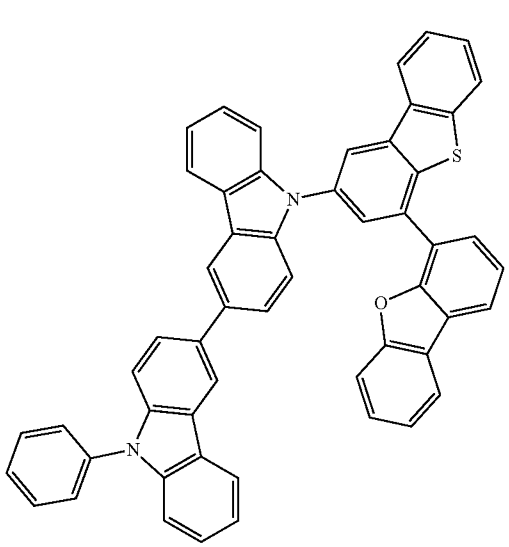
-continued
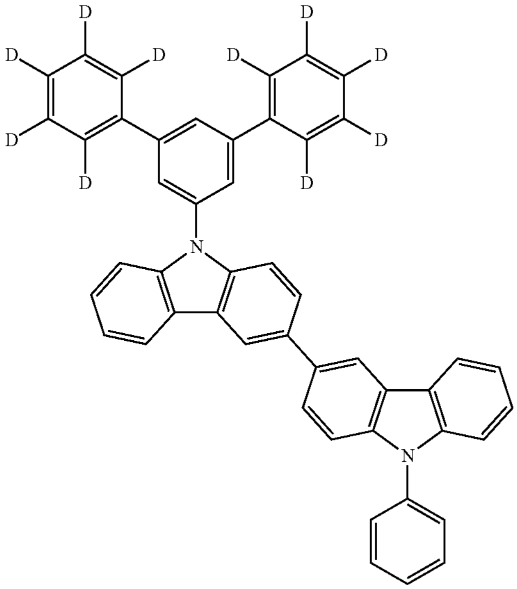
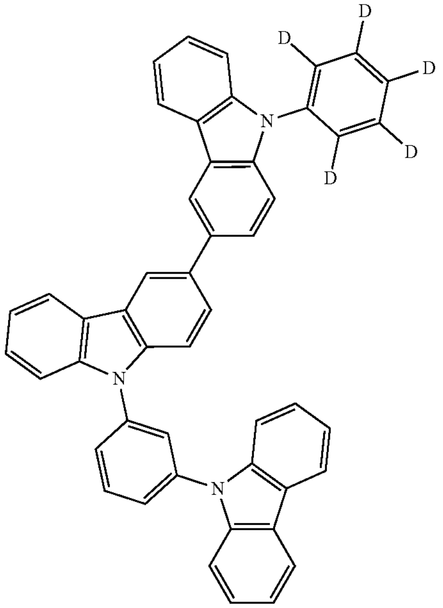
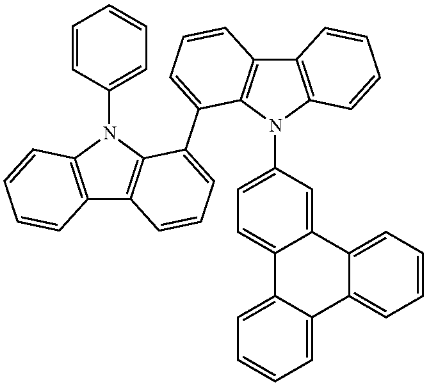

-continued
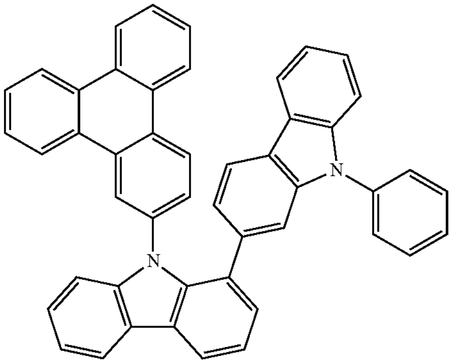
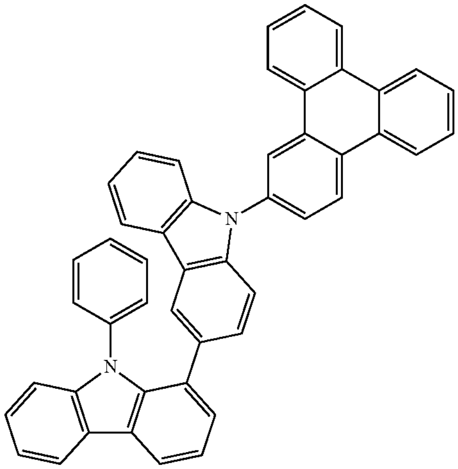
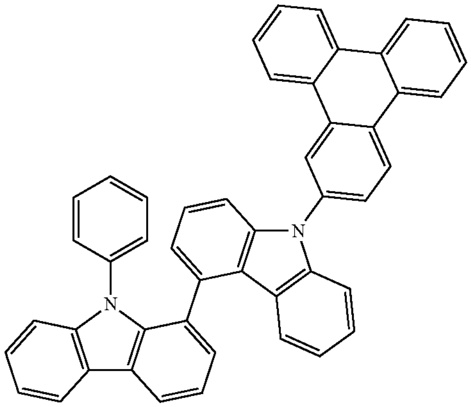
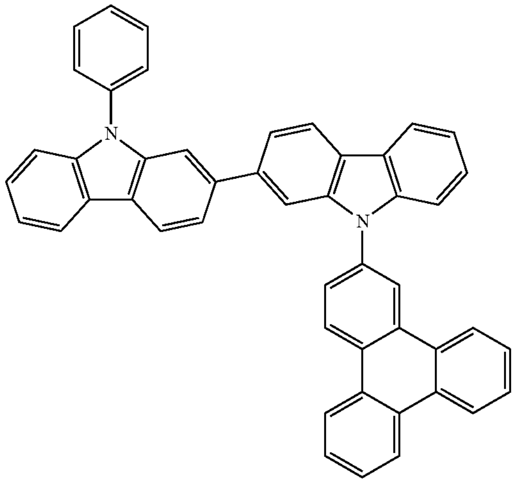
-continued
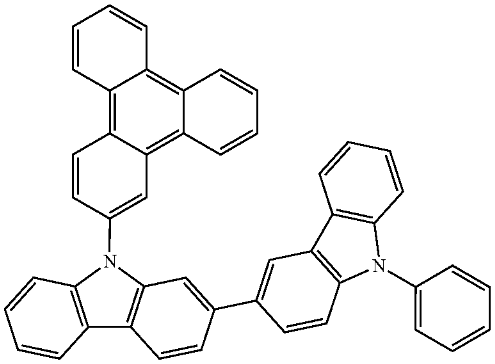
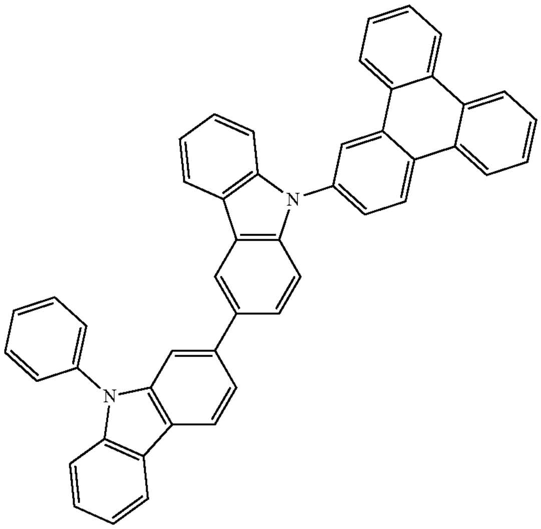
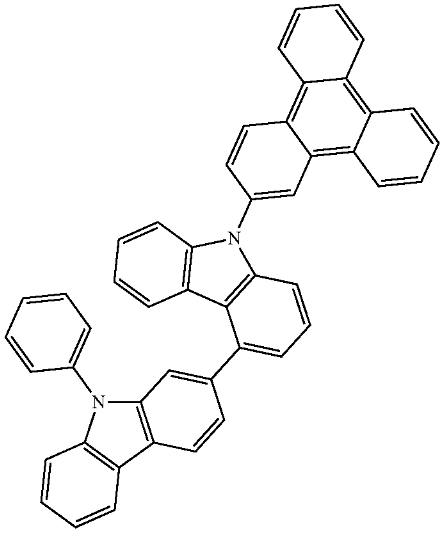

-continued

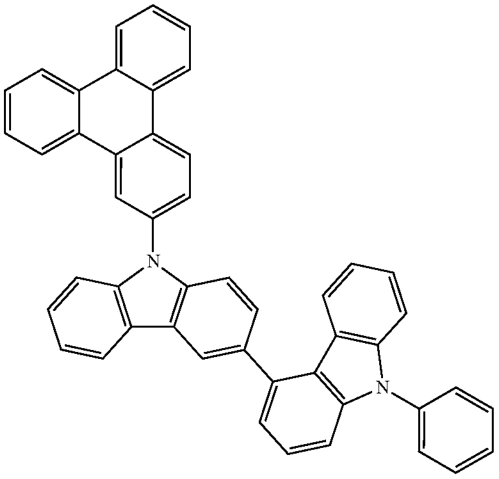

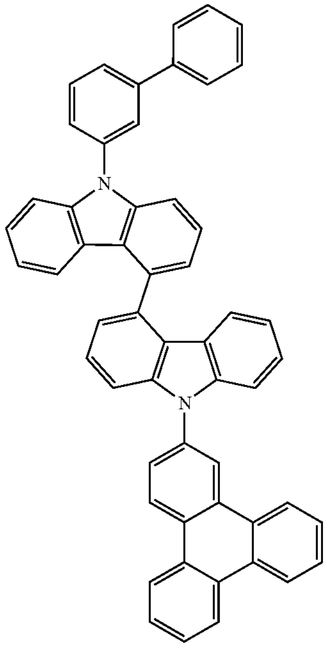

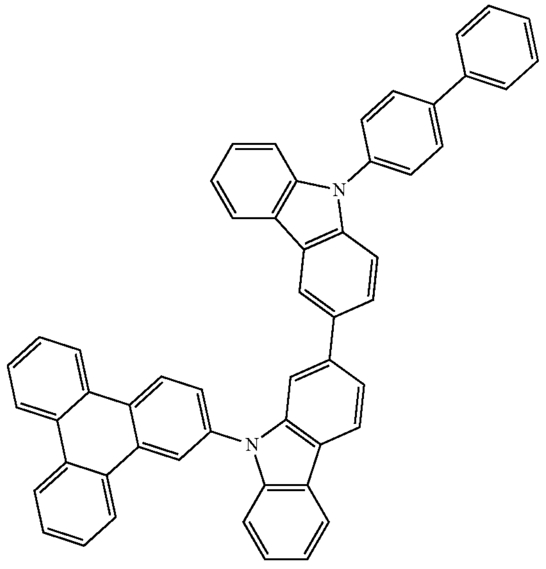

-continued

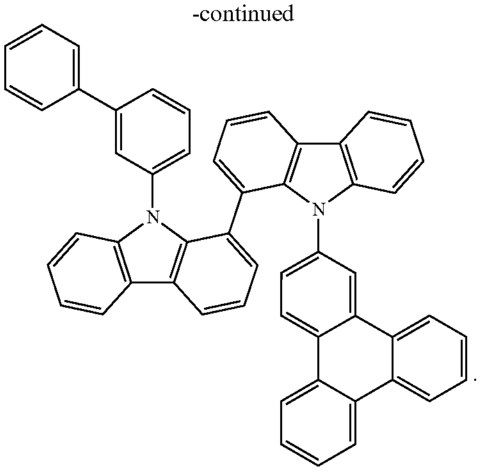

7. The composition according to claim 1, wherein the composition comprises at least one further compound selected from the group consisting of hole-injection materials, hole-transport materials, hole-blocking materials, wide bandgap materials, fluorescent emitters, phosphorescent emitters, host materials, electron-blocking materials, electron-transport materials and electron-injection materials, n-dopants and p-dopants.

8. A formulation comprising the composition according to claim 1 and at least one solvent.

9. An organic electronic device containing at least one composition according to claim 1.

10. The device according to claim 9, wherein the device is selected from the group of organic integrated circuits (OICs), organic field-effect transistors (OFETs), organic thin-film transistors (OTFTs), organic electroluminescent devices, organic solar cells (OSCs), organic optical detectors and organic photoreceptors.

11. The device according to claim 9, wherein the device is an electroluminescent device selected from organic light-emitting transistors (OLETs), organic field-quench devices (OFQDs), organic light-emitting electrochemical cells (OLECs, LECs, LEECs), organic laser diodes (O-lasers) and organic light-emitting diodes (OLEDs).

12. The device according to claim 9, wherein the device contains the composition in an emission layer (EML), in an electron-transport layer (ETL), in an electron-injection layer (EIL) and/or in a hole-blocking layer (HBL).

13. The device according to claim 9, wherein the device contains the composition in the emission layer together with a phosphorescent emitter.

14. A process for the production of a device which comprises, applying at least one organic layer comprising a composition according to claim 1 by gas-phase deposition or from solution.

15. The process according to claim 14, wherein at least one compound of the formula (1) and at least one compound of the formula (2), are deposited from the gas phase successively or simultaneously from at least two material sources, optionally with further materials, and form the organic layer.

16. The process according to claim 14, wherein the composition is utilized as material source for the gas-phase deposition and forms the organic layer.

17. The process according to claim 14, which comprises utilizing a formulation comprising the composition and at least one solvent in order to apply the organic layer.

18. An organic electronic device containing at least one composition according to claim 1.
19. An organic electronic device containing at least one composition according to claim 6.
20. The composition according to claim 1, wherein the compounds of formula (1b) and (1c) is selected from the following compounds
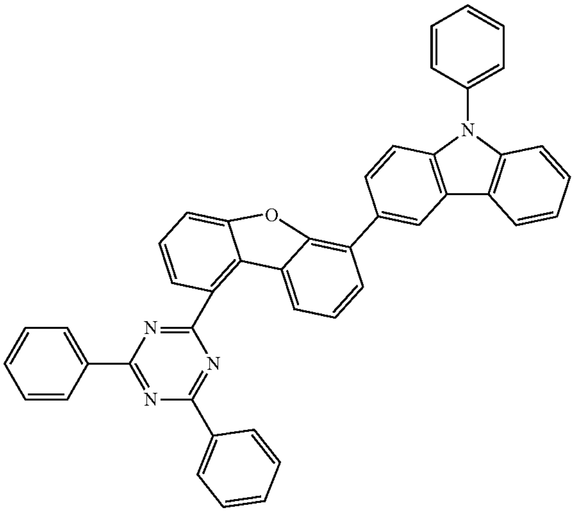
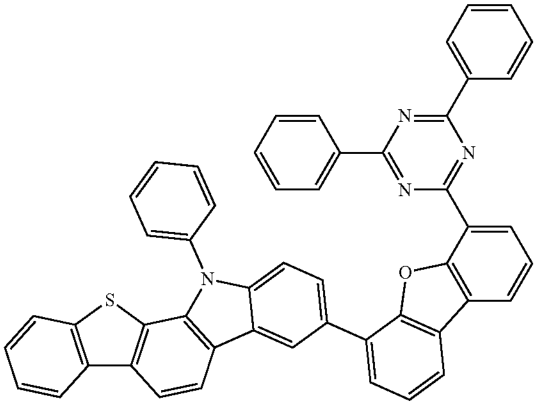
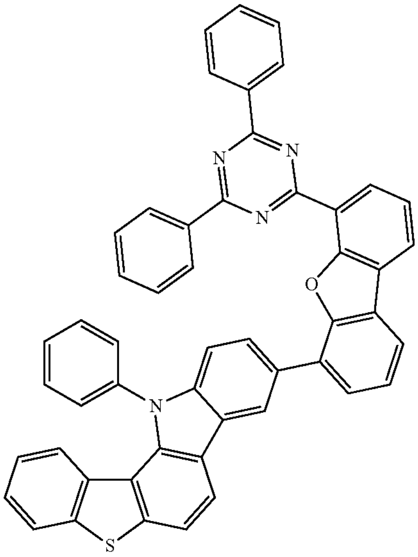
-continued
67
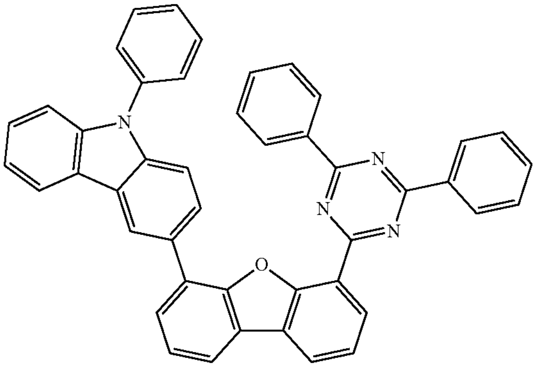
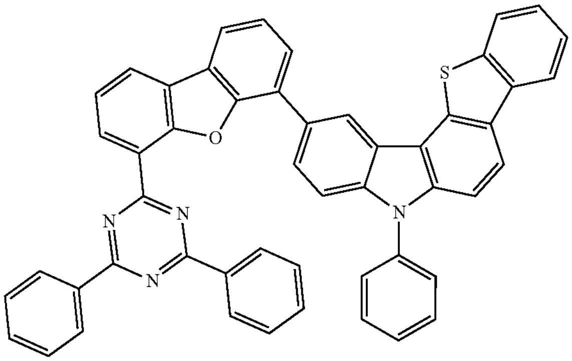
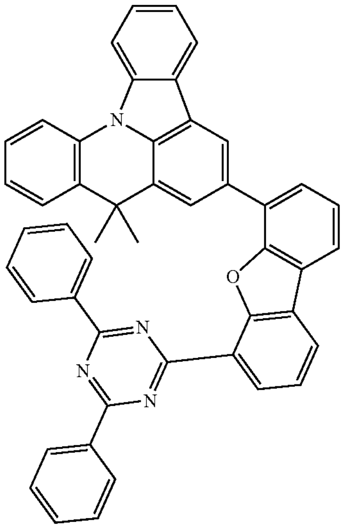

-continued
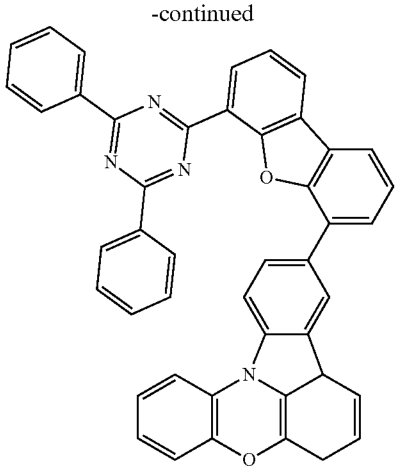
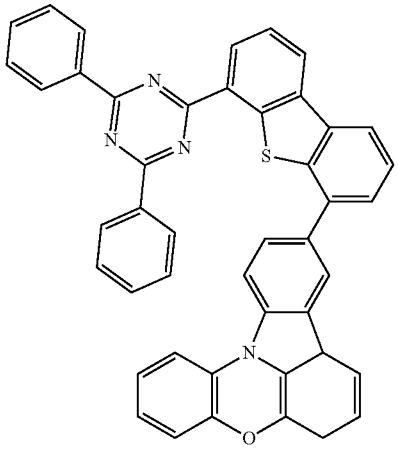
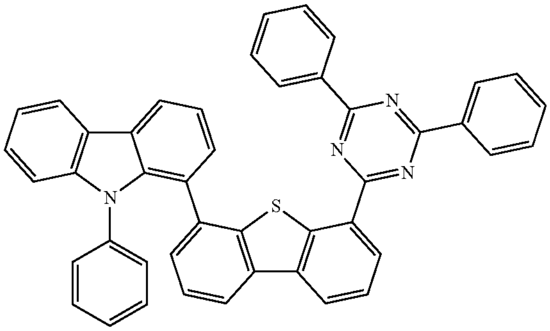
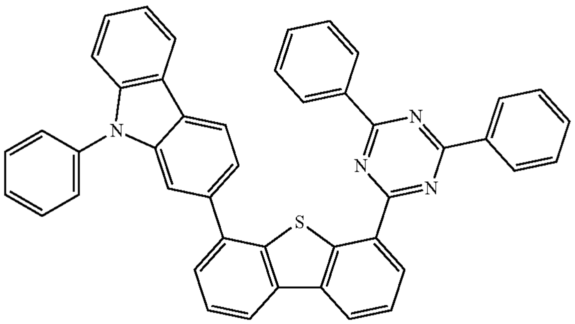
-continued
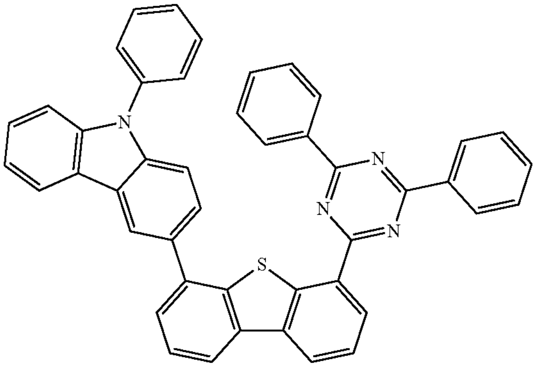
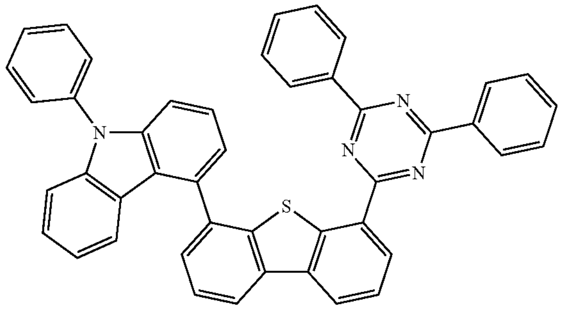
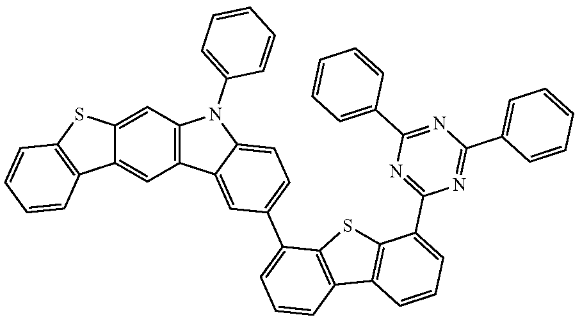
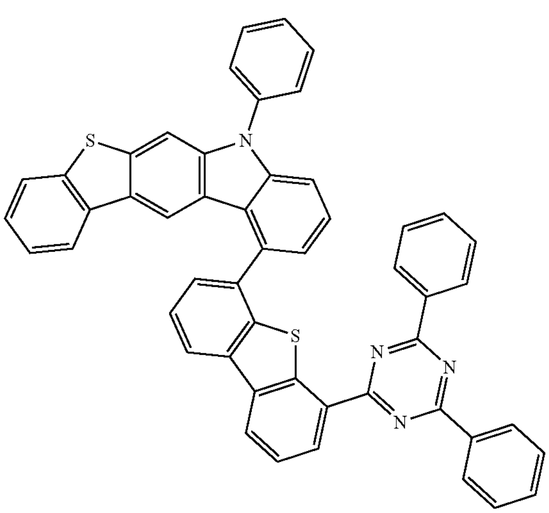

-continued
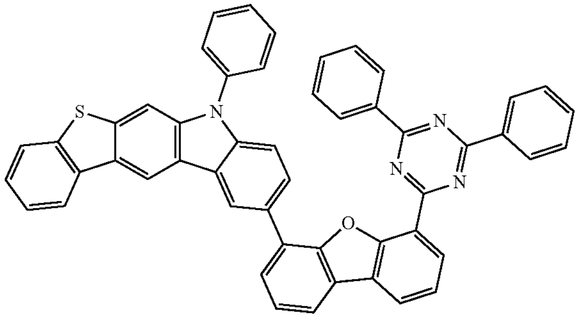
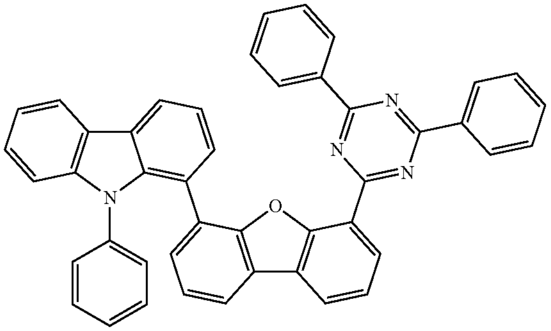
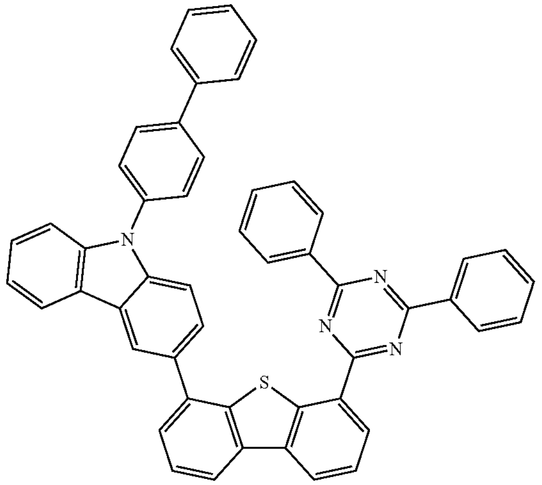
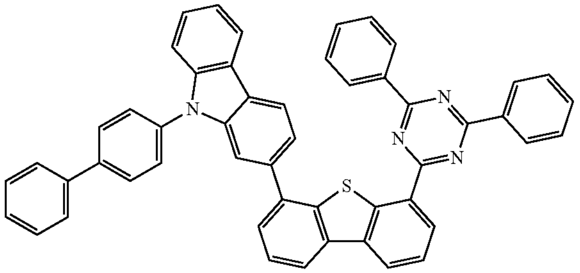
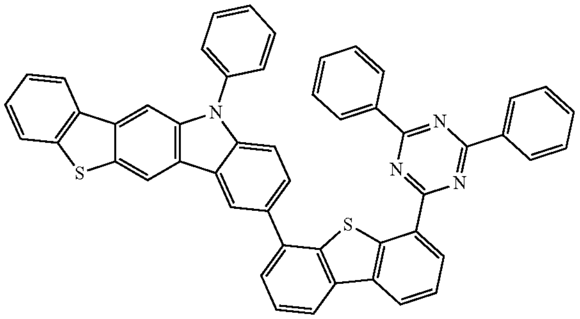
-continued
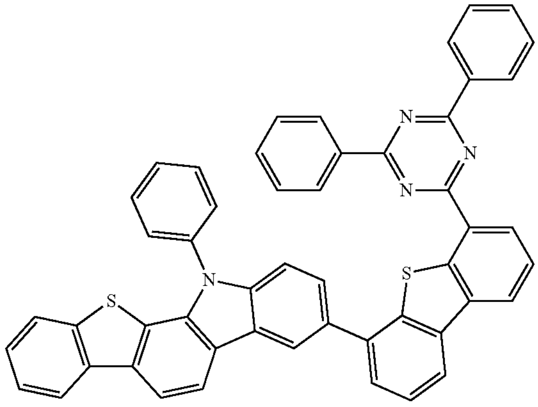
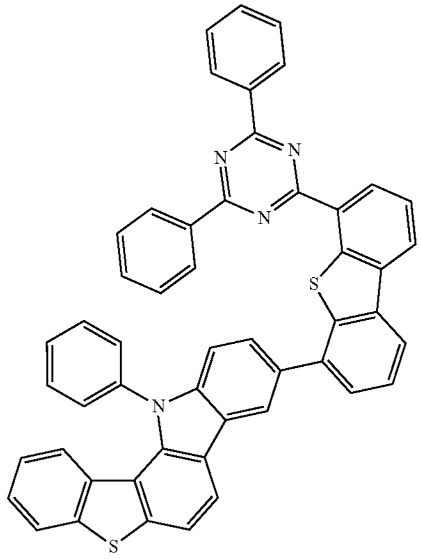
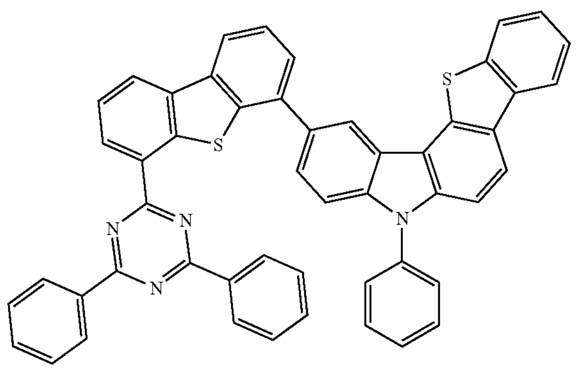

-continued
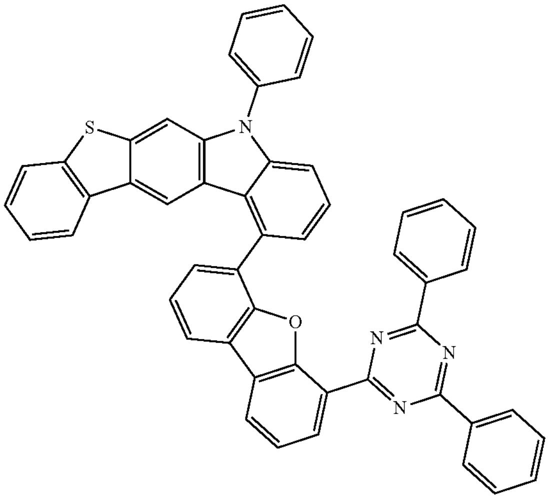
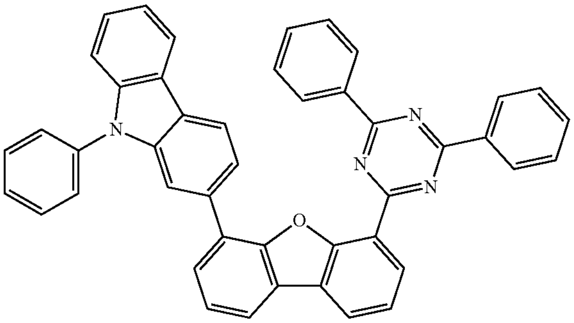
-continued
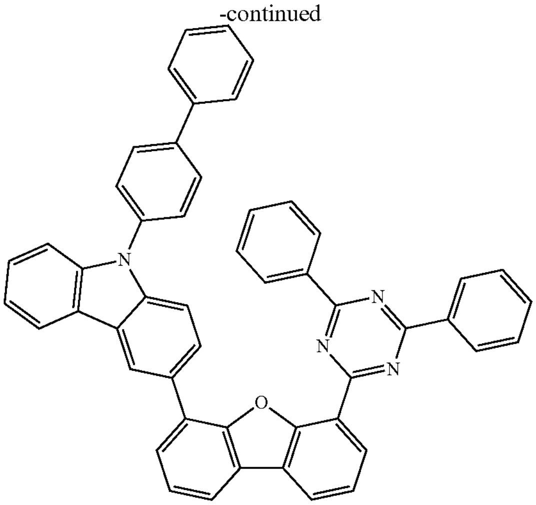
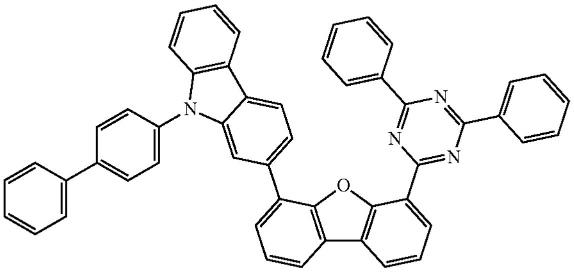
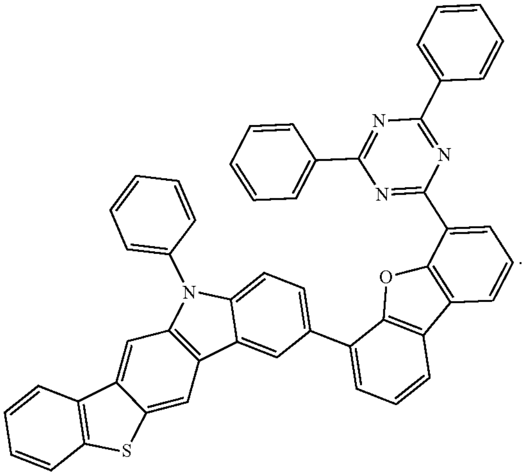
* * * * *